US012583864B2

(12) United States Patent
Tasaki et al.

(10) Patent No.: US 12,583,864 B2
(45) Date of Patent: Mar. 24, 2026

(54) ORGANIC ELECTROLUMINESCENT ELEMENT AND ELECTRONIC DEVICE

(71) Applicant: IDEMITSU KOSAN CO., LTD., Tokyo (JP)

(72) Inventors: Satomi Tasaki, Tokyo (JP); Kazuki Nishimura, Tokyo (JP); Ryoji Maeda, Tokyo (JP); Yuichiro Kawamura, Tokyo (JP); Yuki Nakano, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1050 days.

(21) Appl. No.: 17/642,220

(22) PCT Filed: Sep. 11, 2020

(86) PCT No.: PCT/JP2020/034593

§ 371 (c)(1),
(2) Date: Mar. 10, 2022

(87) PCT Pub. No.: WO2021/049653

PCT Pub. Date: Mar. 18, 2021

(65) Prior Publication Data

US 2022/0348522 A1 Nov. 3, 2022

(30) Foreign Application Priority Data

| | | |
|---|---|---|
| Sep. 13, 2019 | (JP) | 2019-167582 |
| Nov. 26, 2019 | (JP) | 2019-213461 |
| Dec. 27, 2019 | (JP) | 2019-239933 |
| Apr. 1, 2020 | (JP) | 2020-066268 |
| Apr. 15, 2020 | (JP) | 2020-073061 |

(51) Int. Cl.
*C07D 493/04* (2006.01)
*C07C 13/62* (2006.01)
(Continued)

(52) U.S. Cl.
CPC ............ *C07D 493/04* (2013.01); *C07C 13/62* (2013.01); *C07C 15/28* (2013.01); *C07C 15/30* (2013.01); *C07C 15/38* (2013.01); *C07C 255/34* (2013.01); *C07C 255/51* (2013.01); *C07D 211/54* (2013.01); *C07D 231/56* (2013.01);
(Continued)

(58) Field of Classification Search
CPC .. C07D 493/04; C07D 211/54; C07D 231/56; C07D 241/38; C07D 251/24; C07D 307/91; C07D 311/82; C07D 333/76; C07D 403/10; C07D 403/14; C07D 405/10; C07D 405/12; C07D 471/06; C07D 487/06; C07D 491/04; C07D 491/16; C07D 491/22; C07D 495/04; C07D 495/22; C07D 519/00; C07C 13/62; C07C 15/28; C07C 15/30; C07C 15/38; C07C 15/20; C07C 255/34; C07C 255/51; C07C 2603/18; C07C 2603/26; C07C 2603/40; C07C 2603/42; C07C 2603/50; C07C 2603/52; C07C 2603/94; C07F 1/02; C07F 5/027; C07F 7/081; C07F 7/0812; C07F 7/0816; H10K 50/11; H10K 85/40; H10K 85/615; H10K 85/622; H10K 85/623; H10K 85/624; H10K 85/631; H10K 85/633; H10K 85/636; H10K 85/652; H10K 85/654; H10K 85/657; H10K 85/6572; H10K 85/6574; H10K 85/6576; H10K 85/658; H10K 2101/10; H10K 50/13; H10K 2102/351; H10K 85/626; H10K 50/12; H10K 50/15; H10K 50/16; C07B 2200/05; C07B 59/001; C07B 59/002; H05B 33/12

See application file for complete search history.

(56) References Cited

U.S. PATENT DOCUMENTS

| | | | | |
|---|---|---|---|---|
| 11,489,121 | B1 * | 11/2022 | Tasaki | H10K 85/615 |
| 2010/0295444 | A1 | 11/2010 | Kuma et al. | |

(Continued)

FOREIGN PATENT DOCUMENTS

| | | | |
|---|---|---|---|
| CN | 107958959 | A | 4/2018 |
| EP | 1 933 397 | A1 | 6/2008 |

(Continued)

OTHER PUBLICATIONS

Machine translation of JP 2013-157552 (publication date Aug. 2013). (Year: 2013).*

(Continued)

*Primary Examiner* — Dawn L Garrett
(74) *Attorney, Agent, or Firm* — Foley & Lardner LLP

(57) ABSTRACT

An organic EL device includes a first emitting layer and a second emitting layer, in which the first emitting layer contains a first host material, the second emitting layer contains a second host material, the first and the second host material are mutually different, the first emitting layer and the second emitting layer at least contains a compound that emits fluorescence having a main peak wavelength of 500 nm or less, respectively, the compound contained in the first emitting layer and that emits fluorescence having a main peak wavelength of 500 nm or less is the same as or different from the compound contained in the second emitting layer, and a triplet energy $T_1(H1)$ of the first host material and a triplet energy $T_1(H2)$ of the second host material satisfy a numerical formula (Numerical Formula 1), $$T_1(H1)>T_1(H2) \quad \text{(Numerical Formula 1).}$$

23 Claims, 1 Drawing Sheet

(51) Int. Cl.

| | |
|---|---|
| ***C07C 15/28*** | (2006.01) |
| ***C07C 15/30*** | (2006.01) |
| ***C07C 15/38*** | (2006.01) |
| ***C07C 255/34*** | (2006.01) |
| ***C07C 255/51*** | (2006.01) |
| ***C07D 211/54*** | (2006.01) |
| ***C07D 231/56*** | (2006.01) |
| ***C07D 241/38*** | (2006.01) |
| ***C07D 251/24*** | (2006.01) |
| ***C07D 307/91*** | (2006.01) |
| ***C07D 311/82*** | (2006.01) |
| ***C07D 333/76*** | (2006.01) |
| ***C07D 403/10*** | (2006.01) |
| ***C07D 403/14*** | (2006.01) |
| ***C07D 405/10*** | (2006.01) |
| ***C07D 405/12*** | (2006.01) |
| ***C07D 471/06*** | (2006.01) |
| ***C07D 487/06*** | (2006.01) |
| ***C07D 491/04*** | (2006.01) |
| ***C07D 491/16*** | (2006.01) |
| ***C07D 491/22*** | (2006.01) |
| ***C07D 495/04*** | (2006.01) |
| ***C07D 495/22*** | (2006.01) |
| ***C07D 519/00*** | (2006.01) |
| ***C07F 1/02*** | (2006.01) |
| ***C07F 5/02*** | (2006.01) |
| ***C07F 7/08*** | (2006.01) |
| ***H10K 50/11*** | (2023.01) |
| ***H10K 85/40*** | (2023.01) |
| ***H10K 85/60*** | (2023.01) |
| *H10K 101/10* | (2023.01) |

(52) U.S. Cl.

CPC ......... *C07D 241/38* (2013.01); *C07D 251/24* (2013.01); *C07D 307/91* (2013.01); *C07D 311/82* (2013.01); *C07D 333/76* (2013.01); *C07D 403/10* (2013.01); *C07D 403/14* (2013.01); *C07D 405/10* (2013.01); *C07D 405/12* (2013.01); *C07D 471/06* (2013.01); *C07D 487/06* (2013.01); *C07D 491/04* (2013.01); *C07D 491/16* (2013.01); *C07D 491/22* (2013.01); *C07D 495/04* (2013.01); *C07D 495/22* (2013.01); *C07D 519/00* (2013.01); *C07F 1/02* (2013.01); *C07F 5/027* (2013.01); *C07F 7/081* (2013.01); *C07F 7/0812* (2013.01); *C07F 7/0816* (2013.01); *H10K 50/11* (2023.02); *H10K 85/40* (2023.02); *H10K 85/615* (2023.02); *H10K 85/622* (2023.02); *H10K 85/623* (2023.02); *H10K 85/624* (2023.02); *H10K 85/631* (2023.02); *H10K 85/633* (2023.02); *H10K 85/636* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 85/658* (2023.02); *C07B 2200/05* (2013.01); *H10K 2101/10* (2023.02)

(56) References Cited

U.S. PATENT DOCUMENTS

| | | | |
|---|---|---|---|
| 2014/0183500 | A1 | 7/2014 | Ikeda et al. |
| 2015/0053958 | A1 | 2/2015 | Ishisone et al. |
| 2017/0053970 | A1 | 2/2017 | Ishisone et al. |
| 2017/0324043 | A1 | 11/2017 | Ikeda et al. |
| 2017/0338436 | A1 | 11/2017 | Mitsumori et al. |
| 2019/0140027 | A1 | 5/2019 | Ishisone et al. |
| 2019/0280209 | A1 | 9/2019 | Fujita |
| 2019/0348625 | A1 | 11/2019 | Mitsumori et al. |
| 2020/0280012 | A1 | 9/2020 | Mitsumori et al. |
| 2021/0159440 | A1 | 5/2021 | Mitsumori et al. |
| 2021/0327968 | A1 | 10/2021 | Ishisone et al. |
| 2023/0109651 | A1 | 4/2023 | Mitsumori et al. |
| 2024/0164165 | A1 | 5/2024 | Ishisone et al. |

FOREIGN PATENT DOCUMENTS

| | | | |
|---|---|---|---|
| JP | 2007-294261 | A | 11/2007 |
| JP | 2009-016478 | A | 1/2009 |
| JP | 2013-157552 | A | 8/2013 |
| JP | 2014-241315 | A | 12/2014 |
| JP | 2016-214512 | A | 12/2016 |
| JP | 2017-195373 | A | 10/2017 |
| JP | 2020-077628 | A | 5/2020 |
| KR | 10-2019-0011754 | A | 2/2019 |
| WO | WO-2007/138906 | A1 | 12/2007 |
| WO | WO-2010/134350 | A1 | 11/2010 |
| WO | WO-2014/104144 | A1 | 7/2014 |
| WO | WO-2018/206138 | A1 | 11/2018 |

OTHER PUBLICATIONS

Office Action issued in corresponding Korean Patent Application No. 10-2022-7009158 dated Jul. 16, 2024.

International Preliminary Report on Patentability issued in corresponding International Patent Application No. PCT/JP2020/034593 dated Mar. 15, 2022.

Office Action issued in corresponding Chinese Patent Application No. 202080063336.6 dated Jan. 8, 2025.

Kondakova et al., "Highly efficient fluorescent-phosphorescent triplet-harvesting hybrid organic light-emitting diodes," Journal of Applied Physics, vol. 107, No. 1, 2010, pp. 14515-1 to 14515-13.

Mi et al., "Reduction of molecular aggregation and its application to the high-performance blue perylene-doped organic electroluminescent device," Applied Physics Letters, vol. 75, No. 26, Dec. 27, 1999, pp. 4055-4057.

Cho et al., "Highly efficient and stable deep-blue emitting anthracene-derived molecular glass for versatile types of non-doped OLED applications," Journal of Materials Chemistry, vol. 22, 2012, pp. 123-129.

International Searching Authority, "International Search Report," issued in connection with International Patent Application No. PCT/JP2020/034593, dated Nov. 17, 2020.

International Searching Authority, "Written Opinion," issued in connection with International Patent Application No. PCT/JP2020/034593, dated Nov. 17, 2020.

* cited by examiner

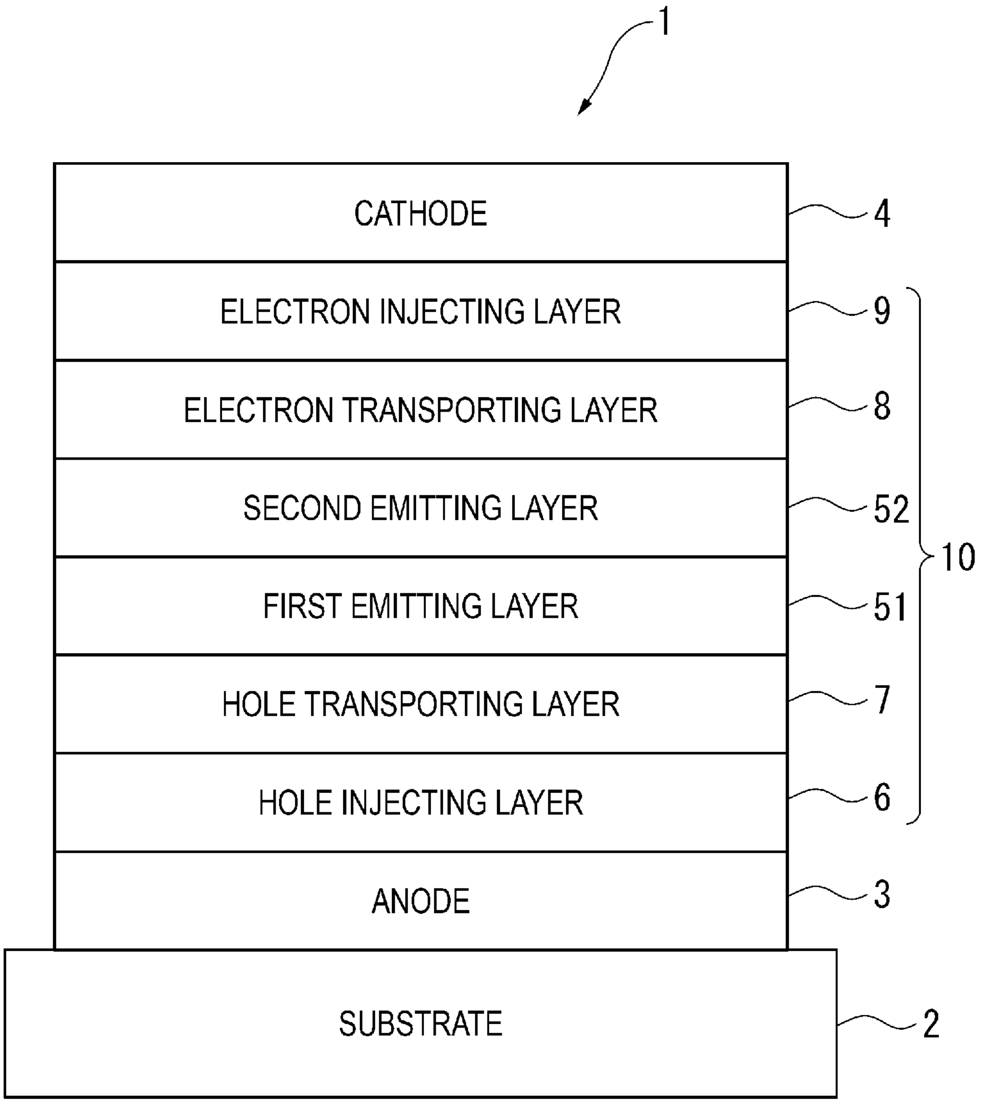
1
CATHODE
4
ELECTRON INJECTING LAYER
9
ELECTRON TRANSPORTING LAYER
8
SECOND EMITTING LAYER
52
10
FIRST EMITTING LAYER
51
HOLE TRANSPORTING LAYER
7
HOLE INJECTING LAYER
6
ANODE
3
SUBSTRATE
2

ORGANIC ELECTROLUMINESCENT ELEMENT AND ELECTRONIC DEVICE

CROSS-REFERENCE TO RELATED APPLICATIONS

The present application claims priority under 37 U.S.C. § 371 to International Patent Application No. PCT/JP2020/034593, filed Sep. 11, 2020, which claims priority to and the benefit of Japanese Patent Application Nos. 2019-167582, filed on Sep. 13, 2019, 2019-213461, filed on Nov. 26, 2019, 2019-239933, filed on Dec. 27, 2019, 2020-066268, filed on Apr. 1, 2020, and 2020-073061, filed on Apr. 15, 2020. The contents of these applications are hereby incorporated by reference in their entireties.

TECHNICAL FIELD

The present invention relates to an organic electroluminescence device and an electronic device.

BACKGROUND ART

An organic electroluminescence device (hereinafter, occasionally referred to as "organic EL device") has found its application in a full-color display for mobile phones, televisions and the like. When a voltage is applied to an organic EL device, holes and electrons are injected from an anode and a cathode, respectively, into an emitting layer. The injected holes and electrons are recombined in the emitting layer to form excitons. Specifically, according to the electron spin statistics theory, singlet excitons and triplet excitons are generated at a ratio of 25%:75%.

For instance, in Patent Literatures 1 to 4 and 6, various studies have been made for compounds to be used for the organic EL device in order to enhance the performance of the organic EL device. In addition, Patent Literature 5 describes a phenomenon where singlet excitons are generated by collision and fusion of two triplet excitons (hereinafter, sometimes referred to as a Triplet-Triplet Fusion (TTF) phenomenon) in order to enhance the performance of the organic EL device.

The performance of the organic EL device is evaluable in terms of, for instance, luminance, emission wavelength, chromaticity, luminous efficiency, drive voltage, and lifetime.

CITATION LIST

Patent Literature(s)

Patent Literature 1: JP 2013-157552 A

Patent Literature 2: JP 2009-016478 A

Patent Literature 3: International Publication No. WO2007/138906

Patent Literature 4: US Patent Application Publication No. 2019/280209

Patent Literature 5: International Publication No. WO2010/134350

Patent Literature 6: JP 2007-294261 A

SUMMARY OF THE INVENTION

Problems to be Solved by the Invention

An object of the invention is to provide an organic electroluminescence device with enhanced performance.

Another object of the invention is to provide an organic electroluminescence device with improved luminous efficiency and an electronic device including the organic electroluminescence device.

Means for Solving the Problems

According to an aspect of the invention, there is provided an organic electroluminescence device including a first emitting layer and a second emitting layer, in which the first emitting layer includes a first host material, the second emitting layer includes a second host material, the first host material and the second host material are mutually different, the first emitting layer at least includes a compound that emits fluorescence having a main peak wavelength of 500 nm or less, the second emitting layer at least includes a compound that emits fluorescence having a main peak wavelength of 500 nm or less, the compound included in the first emitting layer and that emits fluorescence having a main peak wavelength of 500 nm or less is the same as or different from the compound included in the second emitting layer and that emits fluorescence having a main peak wavelength of 500 nm or less, and a triplet energy $T_1(H1)$ of the first host material and a triplet energy $T_1(H2)$ of the second host material satisfy a relationship of a numerical formula (Numerical Formula 1) below, $$T_1(H1)>T_1(H2) \quad \text{(Numerical Formula 1).}$$

According to another aspect of the invention, an electronic device including the organic electroluminescence device according to the above aspect of the invention is provided.

According to the above aspect of the invention, an organic electroluminescence device with enhanced performance can be provided. According to the above aspect of the invention, an organic electroluminescence device with improved luminous efficiency can be provided. According to the above aspect of the invention, an electronic device including the organic electroluminescence device can be provided.

BRIEF DESCRIPTION OF DRAWING(S)

The FIGURE schematically shows an exemplary arrangement of an organic electroluminescence device according to an exemplary embodiment of the invention.

DESCRIPTION OF EMBODIMENT(S)

Definitions

Herein, a hydrogen atom includes isotope having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded with each other to form the ring. When the ring is substituted by a substituent(s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, cross-linking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded to a hydrogen atom(s) or a substituent(s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded to hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and do not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituents Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B) below. (Herein, an unsubstituted aryl group refers to an "unsubstituted aryl group" in a "substituted or unsubstituted aryl group," and a substituted aryl group refers to a "substituted aryl group" in a "substituted or unsubstituted aryl group.") A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A)

a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, a phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, perylenyl group, and a monovalent aryl group derived by removing one hydrogen atom from cyclic structures represented by formulae (TEMP-1) to (TEMP-15) below.

[Formula 1]

(TEMP-1)

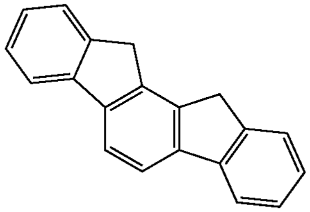

(TEMP-2)

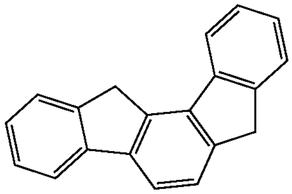

(TEMP-3)

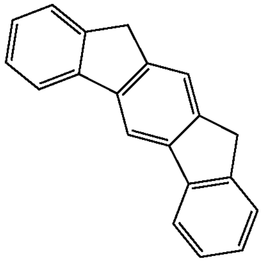

(TEMP-4)

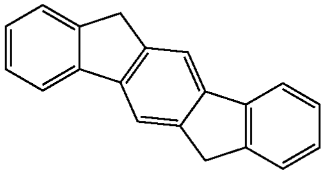

(TEMP-5)

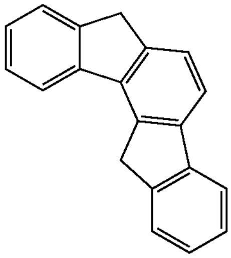

-continued (TEMP-6)

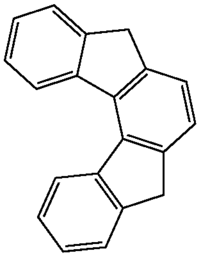

(TEMP-7)

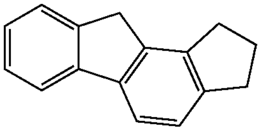

(TEMP-8)

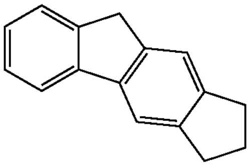

(TEMP-9)

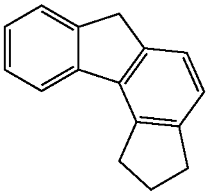

[Formula 2]

(TEMP-10)

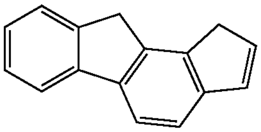

(TEMP-11)

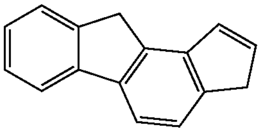

(TEMP-12)

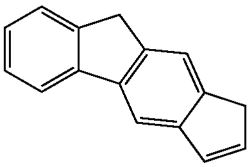

(TEMP-13)

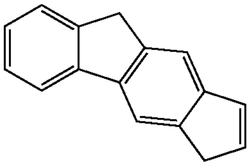

-continued (TEMP-14)

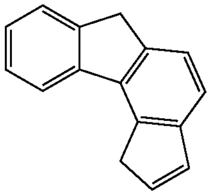

(TEMP-15)

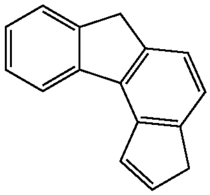

Substituted Aryl Group (Specific Example Group G1B)

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from one of the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B). Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group.") A simply termed "heterocyclic group" herein includes both of an "unsubstituted heterocyclic group" and a "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1)

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2)

furyl group, oxazolyl group, isoxazolyl group, oxadiazolyl group, xanthenyl group, benzofuranyl group, isobenzofuranyl group, a dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3)

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing One Hydrogen Atom from Cyclic Structures Represented by Formulae (TEMP-16) to (TEMP-33) (Specific Example Group G2A4)

[Formula 3]

(TEMP-16)

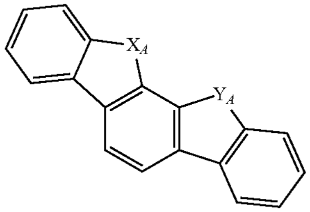

(TEMP-17)

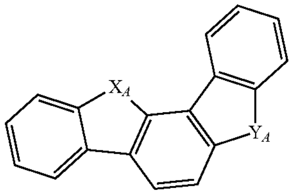

(TEMP-18)

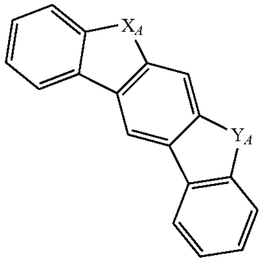

(TEMP-19)

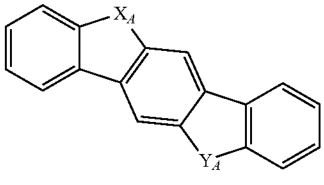

(TEMP-20)

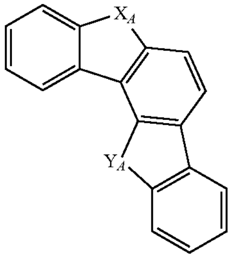

-continued (TEMP-21)

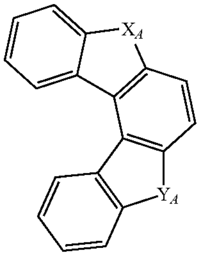

(TEMP-22)

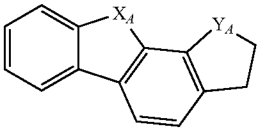

(TEMP-23)

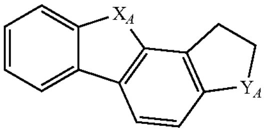

(TEMP-24)

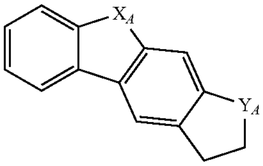

[Formula 4]

(TEMP-25)

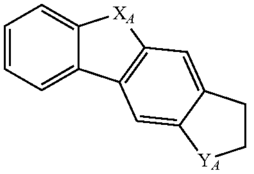

(TEMP-26)

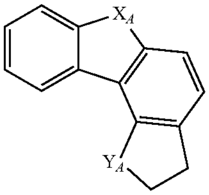

(TEMP-27)

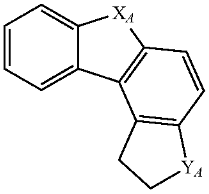

(TEMP-28)

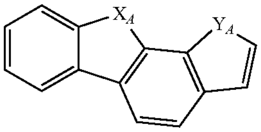

-continued (TEMP-29)

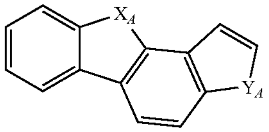

(TEMP-30)

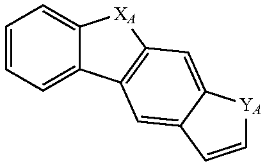

(TEMP-31)

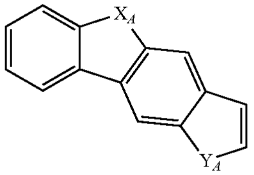

(TEMP-32)

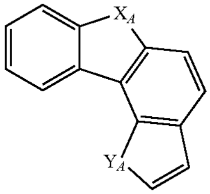

(TEMP-33)

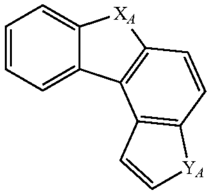

In the formulae (TEMP-16) to (TEMP-33), $X_A$ and $Y_A$ are each independently an oxygen atom, a sulfur atom, NH, or $CH_2$, with a proviso that at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH or $CH_2$.

Substituted Heterocyclic Groups Including Nitrogen Atom (Specific Example Group G2B1)

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, biphenylquinazolinyl group, and biphenylquinazolinyl group.

Substituted Heterocyclic Groups Including Oxygen Atom (Specific Example Group G2B2)

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3)

phenyldibenzothiophenyl group, methyldibenzothiophenyl group, t-butyldibenzothiophenyl group, and monovalent residue of spiro[9H-thioxanthene-9,9'-[9H]fluorene].

Groups Obtained by Substituting at Least One Hydrogen Atom of Monovalent Heterocyclic Group Derived from Cyclic Structures Represented by Formulae (TEMP-16) to (TEMP-33) with Substituent (Specific Example Group G2B4)

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of XA or YA in a form of NH, and a hydrogen atom of one of XA and YA in a form of a methylene group ($CH_2$).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B) below. (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl group" herein includes both of an "unsubstituted alkyl group" and a "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A)

methyl group, ethyl group, n-propyl group, isopropyl group, n-butyl group, isobutyl group, s-butyl group, and t-butyl group.

Substituted Alkyl Group (Specific Example Group G3B)

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl group" herein includes both of an "unsubstituted alkenyl group" and a "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A)

vinyl group, allyl group, 1-butenyl group, 2-butenyl group, and 3-butenyl group.

Substituted Alkenyl Group (Specific Example Group G4B)

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. (Herein, an unsubstituted alkynyl group refers to an "unsubstituted alkynyl group" in a "substituted or unsubstituted alkynyl group.") A simply termed "alkynyl group" herein includes both of an "unsubstituted alkynyl group" and a "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A): Ethynyl Group

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B). (Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group.") A simply termed "cycloalkyl group" herein includes both of an "unsubstituted cycloalkyl group" and a "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A)

cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B 4-methylcyclohexyl group.

Group Represented by —Si($R_{901}$)($R_{902}$)($R_{903}$)

Specific examples (specific example group G7) of the group represented herein by —Si($R_{901}$)($R_{902}$)($R_{903}$) include:

—Si(G1)(G1)(G1); —Si(G1)(G2)(G2); —Si(G1)(G1)(G2); —Si(G2)(G2)(G2); —Si(G3)(G3)(G3); and —Si(G6)(G6)(G6).

Here: G1 represents a "substituted or unsubstituted aryl group" in the specific example group G1;

G2 represents a "substituted or unsubstituted heterocyclic group" in the specific example group G2; G3 represents a "substituted or unsubstituted alkyl group" in the specific example group G3;

G6 represents a "substituted or unsubstituted cycloalkyl group" in the specific example group G6;

a plurality of G1 in —Si(G1)(G1)(G1) are mutually the same or different;

a plurality of G2 in —Si(G1)(G2)(G2) are mutually the same or different;

a plurality of G1 in —Si(G1)(G1)(G2) are mutually the same or different;

a plurality of G2 in —Si(G2)(G2)(G2) are mutually the same or different;

a plurality of G3 in —Si(G3)(G3)(G3) are mutually the same or different; and a plurality of G6 in —Si(G6)(G6)(G6) are mutually the same or different.

Group Represented by —O—($R_{904}$)

Specific examples (specific example group G8) of a group represented by —O—($R_{904}$) herein include: —O(G1); —O(G2); —O(G3); and —O(G6).

Here:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6).

Here:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6).

Here:

G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3;

G6 represents a "substituted or unsubstituted cycloalkyl group" in the specific example group G6;

a plurality of G1 in —N(G1)(G1) are mutually the same or different;

a plurality of G2 in —N(G2)(G2) are mutually the same or different;

a plurality of G3 in —N(G3)(G3) are mutually the same or different; and a plurality of G6 in —N(G6)(G6) are mutually the same or different.

Halogen Atom

Specific examples (specific example group G11) of "halogen atom" mentioned herein include a fluorine atom, chlorine atom, bromine atom, and iodine atom.

Substituted or Unsubstituted Fluoroalkyl Group

The "substituted or unsubstituted fluoroalkyl group" mentioned herein refers to a group derived by substituting at least one hydrogen atom bonded to at least one of carbon atoms forming an alkyl group in the "substituted or unsubstituted alkyl group" with a fluorine atom, and also includes a group (perfluoro group) derived by substituting all of hydrogen atoms bonded to carbon atoms forming the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group

The "substituted or unsubstituted haloalkyl group" mentioned herein refers to a group derived by substituting at least one hydrogen atom bonded to carbon atoms forming the alkyl group in the "substituted or unsubstituted alkyl group" with a halogen atom, and also includes a group derived by substituting all hydrogen atoms bonded to carbon atoms forming the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "unsubstituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 5]

(TEMP-Cz1)

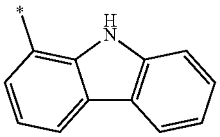

(TEMP-Cz2)

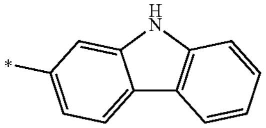

(TEMP-Cz3)

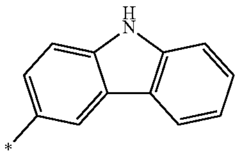

(TEMP-Cz4)

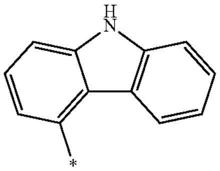

(TEMP-Cz5)

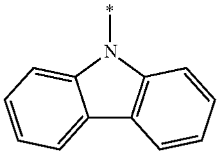

The (9-phenyl)carbazolyl group mentioned herein is, unless otherwise specified herein, specifically a group represented by one of formulae below.

[Formula 6]

(TEMP-Cz6)

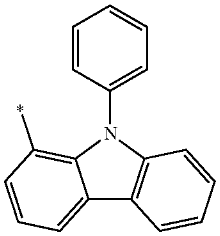

(TEMP-Cz7)

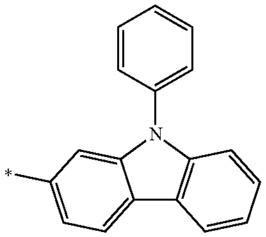

-continued (TEMP-Cz8)

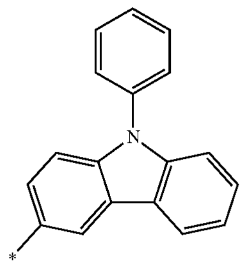

(TEMP-Cz9)

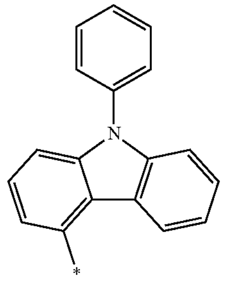

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 7]

(TEMP-34)

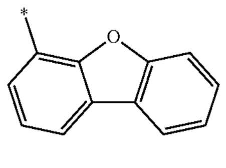

(TEMP-35)

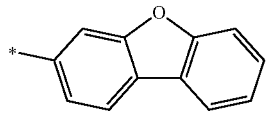

(TEMP-36)

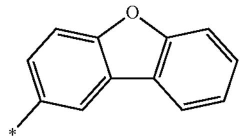

(TEMP-37)

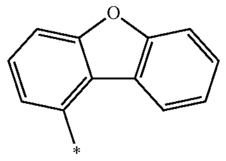

-continued (TEMP-38)

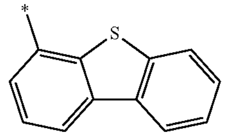

(TEMP-39)

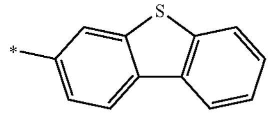

(TEMP-40)

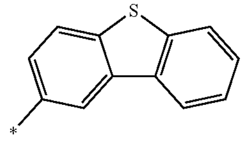

(TEMP-41)

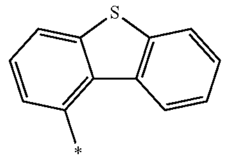

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocycle of the "substituted or unsubstituted heterocyclic group." Specific examples of the "substituted or unsubstituted divalent heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl chain of the "substituted or unsubstituted alkyl group." Specific examples of the "substituted or unsubstituted alkylene group" (specific example group G14) include a divalent group derived by removing one hydrogen atom on an alkyl chain of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

[Formula 8]
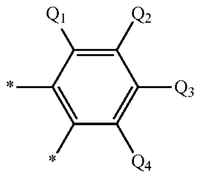
(TEMP-42)
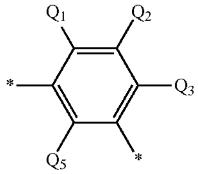
(TEMP-43)
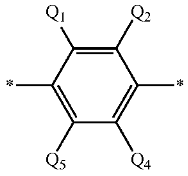
(TEMP-44)
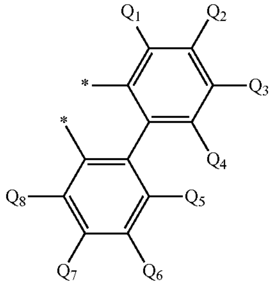
(TEMP-45)
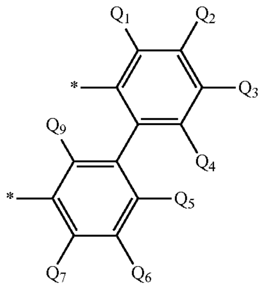
(TEMP-46)
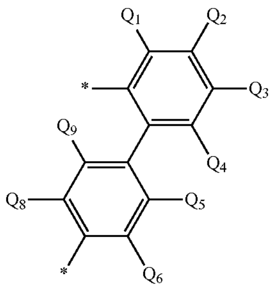
(TEMP-47)
-continued
[Formula 9]
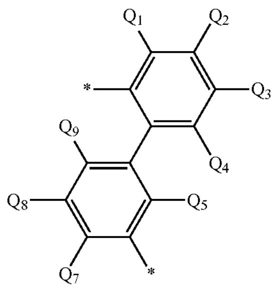
(TEMP-48)
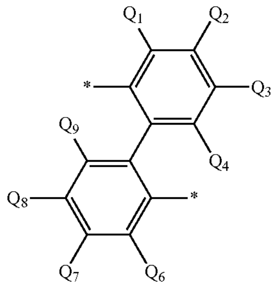
(TEMP-49)
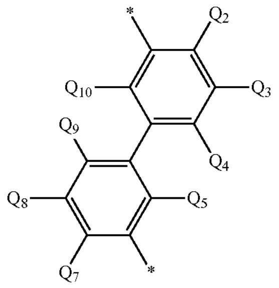
(TEMP-50)
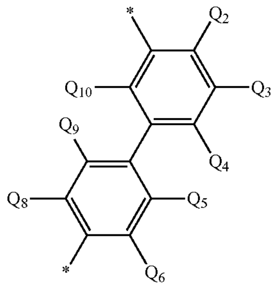
(TEMP-51)
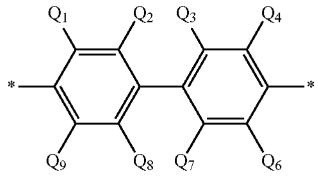
(TEMP-52)
In the formulae (TEMP-42) to (TEMP-52), $Q_1$ to $Q_{10}$ each independently are a hydrogen atom or a substituent.
In the formulae (TEMP-42) to (TEMP-52), * represents a bonding position.

[Formula 10]
(TEMP-53)
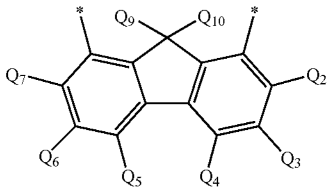
(TEMP-54)
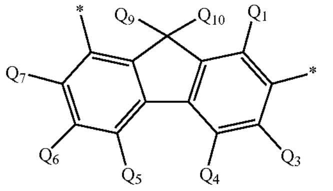
(TEMP-55)
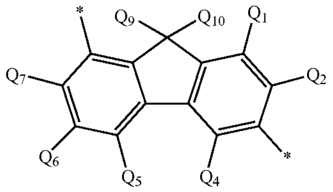
(TEMP-56)
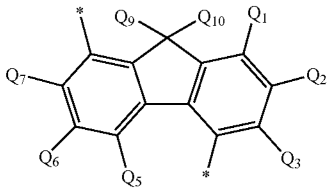
(TEMP-57)
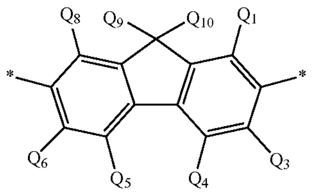
(TEMP-58)
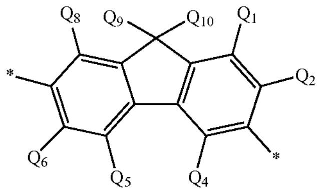
(TEMP-59)
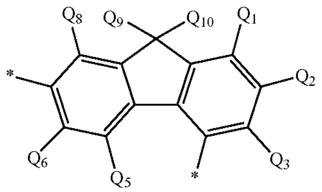
(TEMP-60)
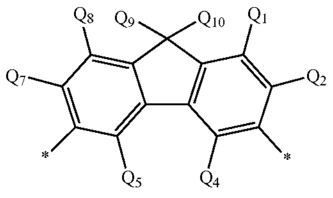
-continued
(TEMP-61)
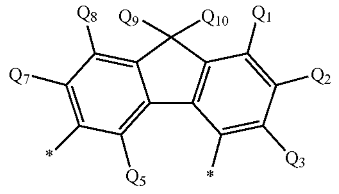
(TEMP-62)
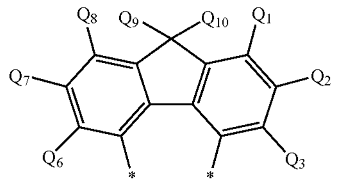
In the formulae (TEMP-53) to (TEMP-62), $Q_1$ to $Q_{10}$ each independently are a hydrogen atom or a substituent.
In the formulae, $Q_9$ and $Q_{10}$ may be mutually bonded through a single bond to form a ring.
In the formulae (TEMP-53) to (TEMP-62), * represents a bonding position.
[Formula 11]
(TEMP-63)
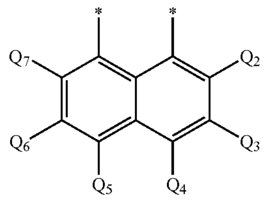
(TEMP-64)
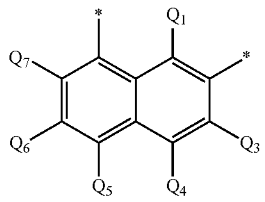
(TEMP-65)
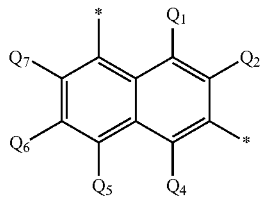
(TEMP-66)
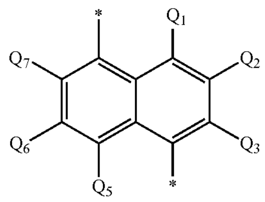

-continued (TEMP-67)

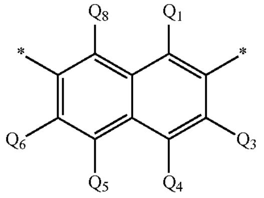

(TEMP-68)

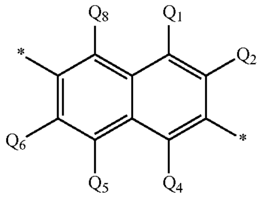

In the formulae (TEMP-63) to (TEMP-68), $Q_1$ to $Q_8$ each independently are a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 12]

(TEMP-69)

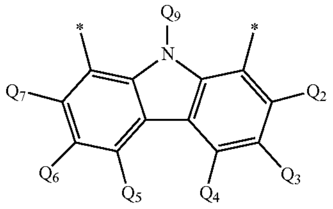

(TEMP-70)

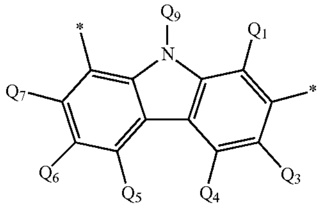

(TEMP-71)

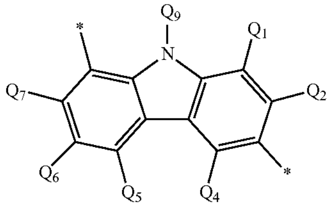

(TEMP-72)

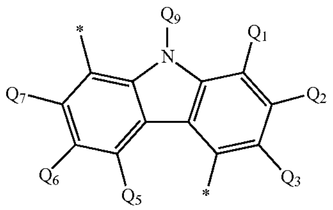

-continued (TEMP-73)

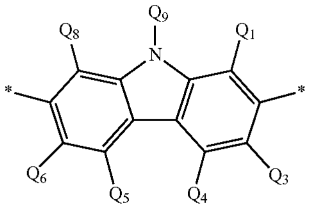

(TEMP-74)

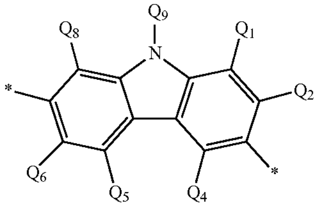

[Formula 13]

(TEMP-75)

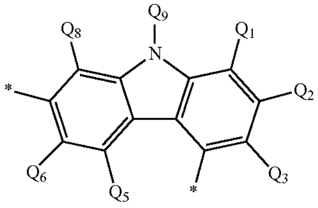

(TEMP-76)

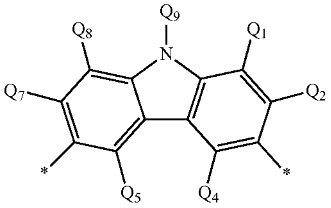

(TEMP-77)

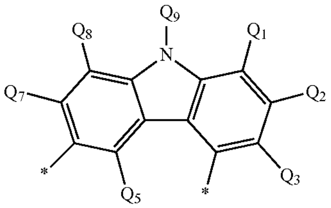

(TEMP-78)

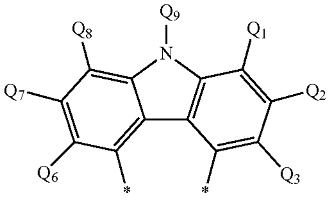

(TEMP-79)

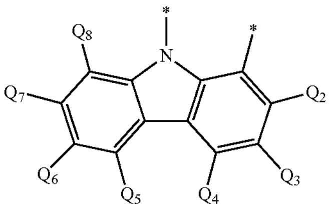

-continued
(TEMP-80)
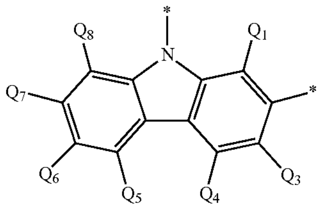
[Formula 14]
(TEMP-81)
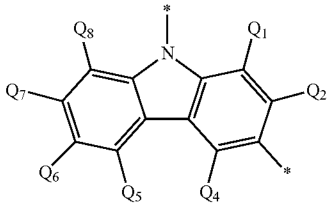
(TEMP-82)
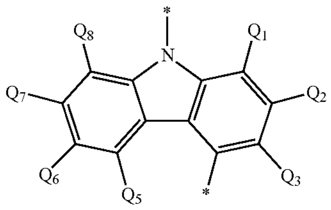
In the formulae (TEMP-69) to (TEMP-82), $Q_1$ to Qs each independently are a hydrogen atom or a substituent.
[Formula 15]
(TEMP-83)
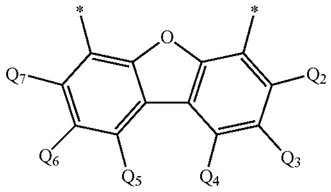
(TEMP-84)
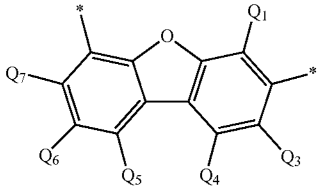
(TEMP-85)
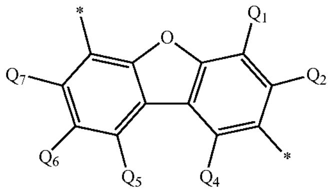
-continued
(TEMP-86)
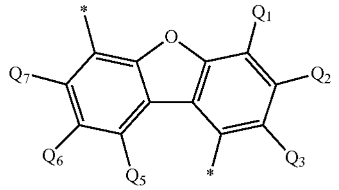
(TEMP-87)
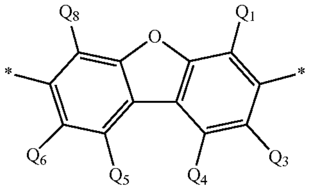
(TEMP-88)
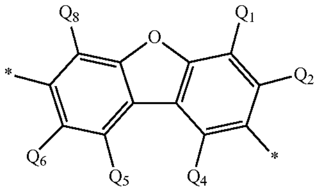
[Formula 16]
(TEMP-89)
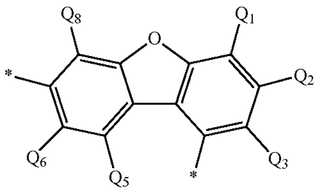
(TEMP-90)
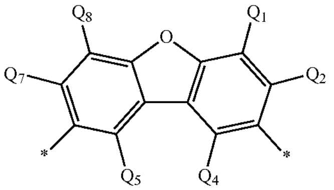
(TEMP-91)
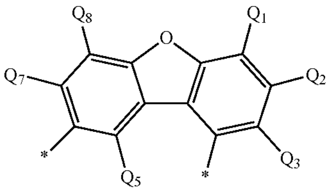
(TEMP-92)
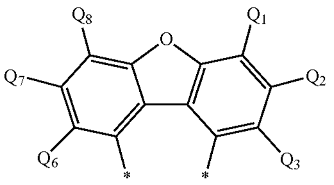

-continued

[Formula 17]

(TEMP-93)

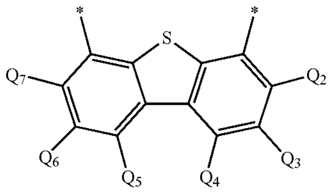

(TEMP-94)

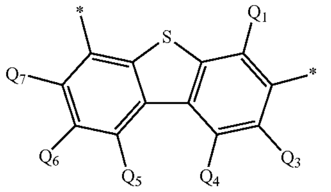

(TEMP-95)

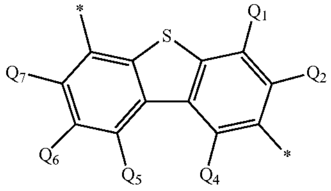

(TEMP-96)

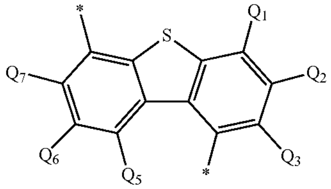

(TEMP-97)

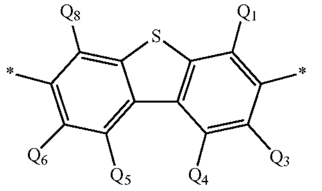

(TEMP-98)

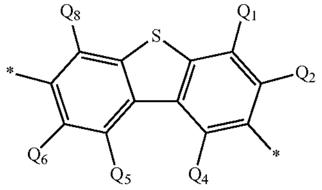

[Formula 18]

(TEMP-99)

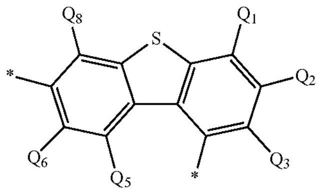

-continued (TEMP-100)

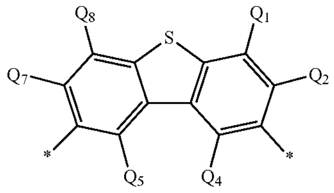

(TEMP-101)

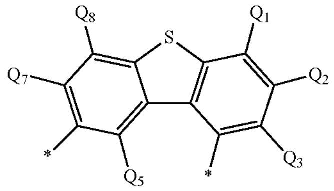

(TEMP-102)

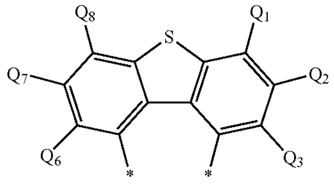

In the formulae (TEMP-83) to (TEMP-102), $Q_1$ to $Q_8$ each independently are a hydrogen atom or a substituent.

The substituent mentioned herein has been described above.

Instance of "Bonded to Form Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

[Formula 19]

(TEMP-103)

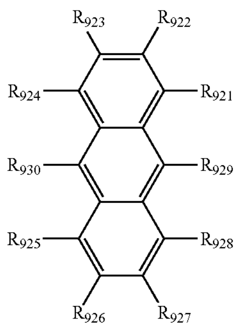

For instance, when "at least one combination of adjacent two or more of $R_{921}$ to $R_{930}$ are mutually bonded to form a ring," the combination of adjacent ones of $R_{921}$ to $R_{930}$ (i.e. the combination at issue) is a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 20]

(TEMP-104)

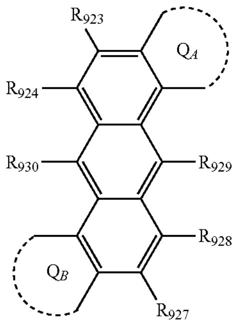

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$ and $R_{923}$ are mutually bonded to form a ring $Q_C$, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring $Q_C$ share $R_{922}$.

[Formula 21]

(TEMP-105)

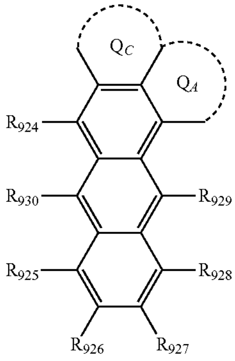

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring $Q_C$ formed in the formula (TEMP-105) are each a "fused ring." The ring $Q_A$ and the ring $Q_C$ in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocycle include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and 8922 shown in the formula (TEMP-104) is a ring formed by a carbon atom of the anthracene skeleton bonded to $R_{921}$, a carbon atom of the anthracene skeleton bonded to $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded to $R_{921}$, a carbon atom of the anthracene skeleton bonded to $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

When the "saturated ring" or the "unsaturated ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance of "bonded to form a ring").

Substituent for Substituted or Unsubstituted Group

In an exemplary embodiment herein, a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms; $R_{901}$ to $R_{907}$ each independently are a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted unsaturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represent a range whose lower limit is the value (AA) recited before "to" and whose upper limit is the value (BB) recited after "to."

First Exemplary Embodiment

Organic Electroluminescence Device

An organic electroluminescence device according to the exemplary embodiment includes a first emitting layer and a second emitting layer, in which the first emitting layer contains a first host material, the second emitting layer contains a second host material, the first host material and the second host material are mutually different, the first emitting layer at least contains a compound that emits fluorescence having a main peak wavelength of 500 nm or less, the second emitting layer at least contains a compound that emits fluorescence having a main peak wavelength of 500 nm or less, the compound that emits fluorescence having a main peak wavelength of 500 nm or less and contained in the first emitting layer is the same as or different from the compound that emits fluorescence having a main peak wavelength of 500 nm or less and contained in the second emitting layer, and a triplet energy $T_1$(H1) of the first host material and a triplet energy $T_1$(H2) of the second host material satisfy a numerical formula (Numerical Formula 1).

$$T_1(H1)>T_1(H2) \quad \text{(Numerical Formula 1)}$$

According to the exemplary embodiment, an organic electroluminescence device with improved luminous efficiency can be provided.

Conventionally, Triplet-Triplet-Annihilation (sometimes referred to as TTA) is known as a technique for enhancing the luminous efficiency of the organic electroluminescence device. TTA is a mechanism in which triplet excitons collide with one another to generate singlet excitons. It should be noted that the TTA mechanism is also occasionally referred to as a TTF mechanism as described in Patent Literature 4.

The TTF phenomenon will be described. Holes injected from an anode and electrons injected from a cathode are recombined in an emitting layer to generate excitons. As for the spin state, as is conventionally known, singlet excitons account for 25% and triplet excitons account for 75%. In a conventionally known fluorescent device, light is emitted when singlet excitons of 25% are relaxed to the ground state. The remaining triplet excitons of 75% are returned to the ground state without emitting light through a thermal deactivation process. Accordingly, the theoretical limit value of the internal quantum efficiency of a conventional fluorescent device is believed to be 25%.

Meanwhile, the behavior of triplet excitons generated within an organic substance has been theoretically examined. According to S. M. Bachilo et al. (J. Phys. Chem. A, 104, 7711 (2000)), assuming that high-order excitons such as quintet excitons are quickly returned to triplet excitons, triplet excitons (hereinafter abbreviated as 3A*) collide with one another with an increase in the density thereof, whereby a reaction shown by the following formula occurs. In the formula, $^1A$ represents the ground state and $^1A^*$ represents the lowest singlet excitons.

$$^3A^*+^3A^*\rightarrow(4/9)^1A+(1/9)^1A^*+(13/9)^3A^*$$

In other words, $5^3A^*\rightarrow4^1A+1A^*$ is satisfied, and it is expected that, among triplet excitons initially generated, which account for 75%, one fifth thereof (i.e., 20%) is changed to singlet excitons. Accordingly, the amount of singlet excitons which contribute to emission is 40%, which is a value obtained by adding 15% (75%×(1/5)=15%) to 25%, which is the amount ratio of initially generated singlet excitons. At this time, a ratio of luminous intensity derived from TTF (TTF ratio) relative to the total luminous intensity is 15/40, i.e., 37.5%. Assuming that singlet excitons are generated by collision of initially generated triplet excitons accounting for 75% (i.e., one singlet exciton is generated from two triplet excitons), a significantly high internal quantum efficiency of 62.5% is obtained, which is a value obtained by adding 37.5% (75%×(½)=37.5%) to 25% (the amount ratio of initially generated singlet excitons). At this time, the TTF ratio is 37.5/62.5=60%.

In the organic electroluminescence device of the exemplary embodiment, it is considered that triplet excitons generated by recombination of holes and electrons in the first emitting layer and present on an interface between the first emitting layer and organic layer(s) in direct contact therewith are not likely to be quenched even under the presence of excessive carriers on the interface between the first emitting layer and the organic layer(s). For instance, the presence of a recombination region locally on an interface between the first emitting layer and a hole transporting layer or an electron blocking layer is considered to cause quenching by excessive electrons. Meanwhile, the presence of a recombination region locally on an interface between the first emitting layer and an electron transporting layer or a hole blocking layer is considered to cause quenching by excessive holes.

The organic EL device of the exemplary embodiment includes at least two emitting layers (i.e., the first emitting layer and the second emitting layer) satisfying a predetermined relationship, in which a triplet energy $T_1$(H1) of the first host material in the first emitting layer and a triplet energy $T_1$(H2) of the second host material in the second emitting layer satisfy the relationship of the above numerical formula (Numerical Formula 1).

By including the first emitting layer and the second emitting layer so as to satisfy the numerical formula (Numerical Formula 1), triplet excitons generated in the first emitting layer can transfer to the second emitting layer without being quenched by excessive carriers and be inhibited from back-transferring from the second emitting layer to the first emitting layer. Consequently, the second emitting layer exhibits the TTF mechanism to efficiently generate singlet excitons, thereby improving luminous efficiency.

Accordingly, the organic electroluminescence device includes, as different regions, the first emitting layer mainly generating triplet excitons and the second emitting layer mainly exhibiting the TTF mechanism using triplet excitons having transferred from the first emitting layer, and a difference in triplet energy is provided by using a compound having a smaller triplet energy than that of the first host material in the first emitting layer as the second host material in the second emitting layer, thereby improving the luminous efficiency.

In the organic EL device according to the exemplary embodiment, the triplet energy $T_1$(H1) of the first host material and the triplet energy $T_1$(H2) of the second host material preferably satisfy a relationship of a numerical formula (Numerical Formula 5) below.

$$T_1(H1)-T_1(H2)>0.03\text{ eV} \quad \text{(Numerical Formula 5)}$$

Herein, the "host material" refers to, for instance, a material that accounts for "50 mass % or more of the layer." Accordingly, for instance, the first emitting layer contains the first host material at 50 mass % or more with respect to a total mass of the first emitting layer. For instance, the second emitting layer contains the second host material at 50 mass % or more with respect to a total mass of the second emitting layer.

Emission Wavelength of Organic EL Device

The organic electroluminescence device of the exemplary embodiment preferably emit light having a main peak wavelength of 500 nm or less when the device is driven.

The organic electroluminescence device of the exemplary embodiment more preferably emits light having a main peak wavelength in a range from 430 nm to 480 nm when the device is driven.

The main peak wavelength of the light emitted from the organic EL device when being driven is measured as follows. Voltage is applied on the organic EL devices such that a current density becomes 10 mA/cm$^2$, where spectral radiance spectrum is measured by a spectroradiometer CS-2000 (manufactured by Konica Minolta, Inc.). A peak wavelength of an emission spectrum, at which the luminous intensity of the resultant spectral radiance spectrum is at the maximum, is measured and defined as the main peak wavelength (unit: nm).

First Emitting Layer

The first emitting layer contains the first host material. The first host material and the second host material contained in the second emitting layer are different compounds.

The first emitting layer at least contains a compound that emits fluorescence having a main peak wavelength of 500 nm or less. This "compound that emits fluorescence having a main peak wavelength of 500 nm or less" may be the first host material or a compound different from the first host material.

In the organic EL device of the exemplary embodiment, it is preferable that the first emitting layer further contains a first dopant material and the first dopant material is a fluorescent compound.

In the organic EL device of the exemplary embodiment, the first dopant material is preferably a compound not including an azine ring structure in a molecule.

In the organic EL device of the exemplary embodiment, the first dopant material is preferably not a boron-containing complex, and the first dopant material is more preferably not a complex.

In the organic EL device of the exemplary embodiment, the first emitting layer preferably does not contain a metal complex. In the organic EL device of the exemplary embodiment, the first emitting layer also preferably does not contain a boron-containing complex.

In the organic EL device of the exemplary embodiment, the first emitting layer preferably does not contain a phosphorescent material (dopant material).

The first emitting layer also preferably does not contain a heavy-metal complex and a phosphorescent rare earth metal complex. Examples of the heavy-metal complex herein include iridium complex, osmium complex, and platinum complex.

In the organic EL device of the exemplary embodiment, the first dopant material is preferably the compound that emits fluorescence having a main peak wavelength of 500 nm or less.

A measurement method of a main peak wavelength of the compound is as follows. A toluene solutions of each of measurement target compounds at a concentration of 5 μmol/L is prepared and put in a quartz cell. An emission spectrum (ordinate axis: emission intensity, abscissa axis: wavelength) of each sample is measured at a normal temperature (300K). The emission spectrum can be measured using a spectrophotometer (machine name: F-7000) manufactured by Hitachi High-Tech Science Corporation. It should be noted that the machine for measuring the emission spectrum is not limited to the machine used herein.

A peak wavelength of the emission spectrum exhibiting the maximum luminous intensity is defined as a main peak wavelength. It should be noted that the main peak wavelength is sometimes referred to as a fluorescence main peak wavelength (FL-peak) herein.

In an emission spectrum of the first dopant material, where a peak exhibiting a maximum luminous intensity is defined as a maximum peak and a height of the maximum peak is defined as 1, heights of other peaks appearing in the emission spectrum are preferably less than 0.6. It should be noted that the peaks in the emission spectrum are defined as local maximum values.

Moreover, in the emission spectrum of the first dopant material, the number of peaks is preferably less than three.

In the organic EL device of the exemplary embodiment, the first emitting layer preferably emits light having a main peak wavelength of 500 nm or less when the device is driven.

The main peak wavelength of light radiated from the organic EL device when being driven is measured by a method described in the section of later-described Examples.

In the organic EL device according to the exemplary embodiment, singlet energy $S_1(H1)$ of the first host material and singlet energy $S_1(D1)$ of the first dopant material preferably satisfy a relationship of the following numerical formula (Numerical Formula 2).

$$S_1(H1)>S_1(D1) \quad \text{(Numerical Formula 2)}$$

The singlet energy $S_1$ means an energy difference between the lowest singlet state and the ground state.

When the first host material and the first dopant material satisfy the relationship of the above numerical formula (Numerical Formula 2), singlet excitons generated on the first host material easily energy-transfer from the first host material to the first dopant material, thereby contributing to fluorescence of the first dopant material.

In the organic EL device according to the exemplary embodiment, the triplet energy $T_1(H1)$ of the first host material and a triplet energy $T_1(D1)$ of the first dopant material preferably satisfy a relationship of the following numerical formula (Numerical Formula 2A).

$$T_1(D1)>T_1(H1) \quad \text{(Numerical Formula 2A)}$$

When the first host material and the first dopant material satisfy the relationship of the numerical formula (Numerical Formula 2A), triplet excitons generated in the first emitting layer are transferred not onto the first dopant material having higher triplet energy but onto the first host material, thereby being easily transferred to the second emitting layer.

The organic EL device of the exemplary embodiment preferably satisfies a relationship of a numerical formula (Numerical Formula 2B) below.

$$T_1(D1)>T_1(H1)>T_1(H2) \quad \text{(Numerical Formula 2B)}$$

Triplet Energy $T_1$

A method of measuring triplet energy $T_1$ is exemplified by a method below.

A measurement target compound is dissolved in EPA (diethylether: isopentane:ethanol=5:5:2 in volume ratio) so as to fall within a range from $10^{-5}$ mol/L to $10^4$ mol/L, and the obtained solution is put in a quartz cell to provide a measurement sample. A phosphorescence spectrum (ordinate axis: phosphorescent luminous intensity, abscissa axis: wavelength) of the measurement sample is measured at a low temperature (77K). A tangent is drawn to the rise of the phosphorescence spectrum close to the short-wavelength region. An energy amount is calculated by a conversion equation (F1) below on a basis of a wavelength value $\lambda_{edge}$ [nm] at an intersection of the tangent and the abscissa axis. The calculated energy amount is defined as triplet energy $T_1$.

$$T_1[\text{eV}]=1239.85/\lambda_{edge} \quad \text{Conversion Equation (F1):}$$

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength region of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted in the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy $S_1$

A method of measuring a singlet energy $S_1$ with use of a solution (occasionally referred to as a solution method) is exemplified by a method below.

A toluene solution of a measurement target compound at a concentration ranging from $10^{-5}$ mol/L to $10^{4}$ mol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum on the long-wavelength side, and a wavelength value fledge (nm) at an intersection of the tangent and the abscissa axis is assigned to a conversion equation (F2) below to calculate singlet energy.

$$S_1[\text{eV}]=1239.85/\lambda_{edge} \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The maximum absorbance of 0.2 or less is not counted as the above-mentioned local maximum absorbance closest to the long-wavelength region.

In the organic EL device of the exemplary embodiment, an electron mobility pH1 of the first host material and an electron mobility pH2 of the second host material preferably satisfy a relationship of a numerical formula (Numerical Formula 6) below.

$$\mu H2>\mu H1 \quad \text{(Numerical Formula 6)}$$

When the first host material and the second host material satisfy the relationship of the numerical formula (Numerical Formula 6), a recombination ability of holes and electrons in the first emitting layer is improved.

The electron mobility can be measured according to impedance spectroscopy.

A measurement target layer having a thickness in a range from 100 nm to 200 nm is held between the anode and the cathode, to which a small alternating voltage of 100 mV or less is applied while a bias DC voltage is applied. A value of an alternating current (absolute value and phase) which flows at this time is measured. This measurement is performed while changing a frequency of the alternating voltage, and complex impedance (Z) is calculated from the current value and the voltage value. A frequency dependency of the imaginary part (ImM) of the modulus M=iωZ (i: imaginary unit, ω: angular frequency) is obtained. The reciprocal number of a frequency ω at which the ImM becomes the maximum is defined as a response time of electrons carried in the measurement target layer. The electron mobility is calculated by the following equation.

$$\text{Electron Mobility}=(\text{Film Thickness of Measurement Target Layer})^2/(\text{Response Time}\cdot\text{Voltage})$$

In the organic EL device of the exemplary embodiment, the first dopant material is preferably contained at more than 1.1 mass % in the first emitting layer. Specifically, the first emitting layer preferably contains the first dopant material at more than 1.1 mass % with respect to a total mass of the first emitting layer, more preferably at more than 1.2 mass % with respect to the total mass of the first emitting layer, further preferably at more than 1.5 mass % with respect to the total mass of the first emitting layer.

The first emitting layer preferably contains the first dopant material at 10 mass % or less with respect to the total mass of the first emitting layer, more preferably at 7 mass % or less with respect to the total mass of the first emitting layer, further preferably at 5 mass % or less with respect to the total mass of the first emitting layer.

In the organic EL device of the exemplary embodiment, the first emitting layer preferably contains the first emitting compound as the first host material at 60 mass % or more with respect to the total mass of the first emitting layer, more preferably at 70 mass % or more with respect to the total mass of the first emitting layer, further preferably at 80 mass % or more with respect to the total mass of the first emitting layer, more further preferably at 90 mass % or more with respect to the total mass of the first emitting layer, still further more preferably at 95 mass % or more with respect to the total mass of the first emitting layer.

The first emitting layer preferably contains the first host material at 99 mass % or less with respect to the total mass of the first emitting layer.

In a case where the first emitting layer contains the first host material and the first dopant material, an upper limit of a total of the content ratios of the first host material and the first dopant material is 100 mass %.

It is not excluded that the first emitting layer of the exemplary embodiment further contains a material(s) other than the first host material and the first dopant material.

The first emitting layer may include a single type of the first host material or may include two or more types of the first host material. The first emitting layer may include a single type of the first dopant material or may include two or more types of the first dopant material.

A film thickness of the first emitting layer of the organic EL device in the exemplary embodiment is preferably 3 nm or more, more preferably 5 nm or more.

The film thickness of the first emitting layer being 3 nm or more is a film thickness enough for causing recombination of holes and electrons in the first emitting layer.

The film thickness of the first emitting layer of the organic EL device in the exemplary embodiment is preferably 15 nm or less, more preferably 10 nm or less. The film thickness of the first emitting layer being 15 nm or less is a film thickness thin enough for transfer of triplet excitons to the second emitting layer.

The film thickness of the first emitting layer of the organic EL device in the exemplary embodiment is more preferably in a range from 3 nm to 15 nm.

Second Emitting Layer

The second emitting layer contains the second host material. The second host material is a different compound from the first host material contained in the first emitting layer.

The second emitting layer at least contains a compound that emits fluorescence having a main peak wavelength of 500 nm or less. This "compound that emits fluorescence having a main peak wavelength of 500 nm or less" may be the second host material or a compound different from the second host material.

A measurement method of the main peak wavelength of the compound is as described above.

In the organic EL device of the exemplary embodiment, it is preferable that the second emitting layer further contains the second dopant material and the second dopant material is a fluorescent compound.

In the organic EL device of the exemplary embodiment, the second dopant material is preferably the compound that emits fluorescence having a main peak wavelength of 500 nm or less.

In the organic EL device of the exemplary embodiment, the second emitting layer preferably emits light having a main peak wavelength of 500 nm or less when the device is driven.

In the organic EL device of the exemplary embodiment, a full width at half maximum of the main peak of the second dopant material is preferably in a range from 1 nm to 20 nm.

In the organic EL device of the exemplary embodiment, a Stokes shift of the second dopant material preferably exceeds 7 nm.

When the Stokes shift of the second dopant material exceeds 7 nm, a reduction in the luminous efficiency due to self-absorption is likely to be inhibited.

The self-absorption is a phenomenon that emitted light is absorbed by the same compound to reduce luminous efficiency. The self-absorption is notably observed in a compound having a small Stokes shift (i.e., a large overlap between an absorption spectrum and a fluorescence spectrum). Accordingly, in order to reduce the self-absorption, it is preferable to use a compound having a large Stokes shift (i.e., a small overlap between the absorption spectrum and the fluorescence spectrum). The Stokes shift can be measured by a method described in Examples.

In the organic EL device of the exemplary embodiment, a triplet energy $T_1$(D2) of the second dopant material and the triplet energy $T_1$(H2) of the second host material preferably satisfy a relationship of a numerical formula (Numerical Formula 3) below.

$$T_1(D2)>T_1(H2) \quad \text{(Numerical Formula 3)}$$

In the organic EL device according to the exemplary embodiment, when the second dopant material and the second host material satisfy the relationship of the numerical formula (Numerical Formula 3), in transfer of triplet excitons generated in the first emitting layer to the second emitting layer, the triplet excitons energy-transfer not to the second dopant material having higher triplet energy but to molecules of the second host material. In addition, triplet excitons generated by recombination of holes and electrons on the second host material do not transfer to the second dopant material having higher triplet energy. Triplet excitons generated by recombination on molecules of the second dopant material quickly energy-transfer to molecules of the second host material.

Triplet excitons in the second host material do not transfer to the second dopant material but efficiently collide with one another on the second host material to generate singlet excitons by the TTF phenomenon.

In the organic EL device of the exemplary embodiment, a singlet energy Si(H2) of the second host material and a singlet energy $S_1$(D2) of the second dopant material preferably satisfy a relationship of a numerical formula (Numerical Formula 4) below.

$$S_1(H2)>S_1(D2) \quad \text{(Numerical Formula 4)}$$

In the organic EL device according to the exemplary embodiment, when the second dopant material and the second host material satisfy the relationship of the numerical formula (Numerical formula 4), due to the singlet energy of the second dopant material being lower than the singlet energy of the second host material, singlet excitons generated by the TTF phenomenon energy-transfer from the second host material to the second dopant material, thereby contributing to fluorescence of the second dopant material.

In the organic EL device of the exemplary embodiment, it is preferable that the second dopant material is a compound not having an azine ring structure in a molecule.

In the organic EL device of the exemplary embodiment, the second dopant material is preferably not a boron-containing complex, and the second dopant material is more preferably not a complex.

In the organic EL device of the exemplary embodiment, it is preferable that the second emitting layer does not contain a metal complex. Further, in the organic EL device of the exemplary embodiment, it is also preferable that the second emitting layer does not contain a boron-containing complex.

In the organic EL device of the exemplary embodiment, it is preferable that the second emitting layer does not contain a phosphorescent material (dopant material).

Further, it is preferable that the second emitting layer does not contain a heavy metal complex and a phosphorescent rare earth metal complex. Examples of the heavy-metal complex herein include iridium complex, osmium complex, and platinum complex.

In the organic EL device of the exemplary embodiment, the second dopant material is preferably contained at more than 1.1 mass % in the second emitting layer. That is, the second emitting layer preferably contains the second dopant material at more than 1.1 mass % with respect to a total mass of the second emitting layer, more preferably at more than 1.2 mass % with respect to the total mass of the second emitting layer, further preferably at more than 1.5 mass % with respect to the total mass of the second emitting layer.

The second emitting layer preferably contains the second dopant material at 10 mass % or less with respect to the total mass of the second emitting layer, more preferably at 7 mass % or less with respect to the total mass of the second emitting layer, further preferably at 5 mass % or less with respect to the total mass of the second emitting layer.

The second emitting layer preferably contains a second compound as the second host material at 60 mass % or more with respect to the total mass of the second emitting layer, more preferably at 70 mass % or more with respect to the total mass of the second emitting layer, further preferably at 80 mass % or more with respect to the total mass of the second emitting layer, further more preferably at 90 mass % or more with respect to the total mass of the second emitting layer, still further preferably at 95 mass % or more with respect to the total mass of the second emitting layer.

The second emitting layer preferably contains the second host material at 99 mass % or less with respect to the total mass of the second emitting layer.

It should be noted that when the second emitting layer contains the second host material and the second dopant material, an upper limit of the total of the respective content ratios of the second host material and the second dopant material is 100 mass %.

It is not excluded that the second emitting layer according to the exemplary embodiment further contains a material(s) other than the second host material and the second dopant material.

The second emitting layer may include a single type of the second host material or may include two or more types of the second host material. The second emitting layer may include a single type of the second dopant material or may include two or more types of the second dopant material.

In the organic EL device according to the exemplary embodiment, the film thickness of the second emitting layer is preferably 5 nm or more, more preferably 15 nm or more. When the film thickness of the second emitting layer is 5 nm or more, it is easy to inhibit triplet excitons having transferred from the first emitting layer to the second emitting layer from returning to the first emitting layer. Further, when the film thickness of the second emitting layer is 5 nm or more, triplet excitons can be sufficiently separated from the recombination portion on the first emitting layer.

In the organic EL device according to the exemplary embodiment, the film thickness of the second emitting layer is preferably 20 nm or less. When the film thickness of the second emitting layer is 20 nm or less, the density of the triplet excitons in the second emitting layer is improved to cause the TTF phenomenon more easily.

In the organic EL device according to the exemplary embodiment, the film thickness of the second emitting layer is preferably in a range from 5 nm to 20 nm.

In the organic EL device of the exemplary embodiment, a triplet energy $T_1$(DX) of the compound contained in the first emitting layer and emitting fluorescence having a main peak wavelength of 500 nm or less or the compound contained in the second emitting layer and emitting fluorescence having a main peak wavelength of 500 nm or less, a triplet energy $T_1$(H1) of the first host material, and a triplet energy $T_1$(H2) of the second host material preferably satisfy a relationship of a numerical formula (Numerical Formula 10) below.

$$2.6\ \text{eV} > T_1(DX) > T_1(H1) > T_1(H2) \quad \text{(Numerical Formula 10)}$$

When the first emitting layer contains the first dopant material, the triplet energy $T_1$(D1) of the first dopant material preferably satisfies a relationship of a numerical formula (Numerical Formula 10A) below.

$$2.6\ \text{eV} > T_1(D1) > T_1(H1) > T_1(H2) \quad \text{(Numerical Formula 10A)}$$

When the second emitting layer contains the second dopant material, the triplet energy $T_1$(D2) of the second dopant material preferably satisfies a relationship of a numerical formula (Numerical Formula 10B) below.

$$2.6\ \text{eV} > T_1(D2) > T_1(H1) > T_1(H2) \quad \text{(Numerical Formula 10B)}$$

In the organic EL device of the exemplary embodiment, the triplet energy $T_1$(DX) of the compound contained in the first emitting layer and emitting fluorescence having a main peak wavelength of 500 nm or less or the compound contained in the second emitting layer and emitting fluorescence having a main peak wavelength of 500 nm or less, and the triplet energy $T_1$(H1) of the first host material preferably satisfy a relationship of a numerical formula (Numerical Formula 11) below.

$$0\ \text{eV} < T_1(DX) - T_1(H1) < 0.6\ \text{eV} \quad \text{(Numerical Formula 11)}$$

When the first emitting layer contains the first dopant material, the triplet energy $T_1$(D1) of the first dopant material preferably satisfies a relationship of a numerical formula (Numerical Formula 11A) below.

$$0\ \text{eV} < T_1(D1) - T_1(H1) < 0.6\ \text{eV} \quad \text{(Numerical Formula 11A)}$$

When the second emitting layer contains the second dopant material, the triplet energy $T_1$(D2) of the second dopant material preferably satisfies a relationship of a numerical formula (Numerical Formula 11B) below.

$$0\ \text{eV} < T_1(D2) - T_1(H2) < 0.8\ \text{eV} \quad \text{(Numerical Formula 11B)}$$

In the organic EL device according to the present exemplary embodiment, the triplet energy $T_1$(H1) of the first host material preferably satisfies a relationship of a numerical formula (Numerical Formula 12) below.

$$T_1(H1) > 2.0\ \text{eV} \quad \text{(Numerical Formula 12)}$$

In the organic EL device according to the present exemplary embodiment, the triplet energy $T_1$(H1) of the first host material also preferably satisfies a relationship of a numerical formula (Numerical Formula 12A) below, or also preferably satisfies a relationship of a numerical formula (Numerical Formula 12B) below.

$$T_1(H1) > 2.10\ \text{eV} \quad \text{(Numerical Formula 12A).}$$

$$T_1(H1) > 2.15\ \text{eV} \quad \text{(Numerical Formula 12B)}$$

In the organic EL device according to the present exemplary embodiment, when the triplet energy $T_1$(H1) of the first host material satisfies the relationship of the numerical formula (Numerical Formula 12A) or the numerical formula (Numerical Formula 12B), triplet excitons generated in the first emitting layer are easily transferred to the second emitting layer, and also easily inhibited from back-transferring from the second emitting layer to the first emitting layer. Consequently, singlet excitons are efficiently generated, thereby improving luminous efficiency.

In the organic EL device according to the present exemplary embodiment, the triplet energy $T_1$(H1) of the first host material also preferably satisfies a relationship of a numerical formula (Numerical Formula 12C) below, or also preferably satisfies a relationship of a numerical formula (Numerical Formula 12D) below.

$$2.08\ \text{eV} > T_1(H1) > 1.87\ \text{eV} \quad \text{(Numerical Formula 12C)}$$

$$2.05\ \text{eV} > T_1(H1) > 1.90\ \text{eV} \quad \text{(Numerical Formula 12D)}$$

In the organic EL device according to the present exemplary embodiment, when the triplet energy $T_1$(H1) of the first host material satisfies the relationship of the numerical formula (Numerical Formula 12C) or the numerical formula (Numerical Formula 12D), energy of the triplet excitons generated in the first emitting layer is reduced, so that the organic EL device is expected to have a longer lifetime.

In the organic EL device of the exemplary embodiment, a triplet energy $T_1$(F1) of the compound contained in the first emitting layer and that emits fluorescence having a main peak wavelength of 500 nm or less also preferably satisfies a relationship of a numerical formula (Numerical Formula 14A) below, or also preferably satisfies a relationship of a numerical formula (Numerical Formula 14B) below.

$$2.60\ \text{eV} > T_1(F1) \quad \text{(Numerical Formula 14A)}$$

$$2.50\ \text{eV} > T_1(F1) \quad \text{(Numerical Formula 14B)}$$

The organic EL device has a longer lifetime by containing the compound that satisfies the numerical formula (Numerical Formula 14A) or the numerical formula (Numerical Formula 14B) in the first emitting layer.

In the organic EL device of the exemplary embodiment, a triplet energy $T_1$(F2) of the compound contained in the second emitting layer and that emits fluorescence having a main peak wavelength of 500 nm or less also preferably satisfies a relationship of a numerical formula (Numerical Formula 14C) below, or also preferably satisfies a relationship of a numerical formula (Numerical Formula 14D) below.

$$2.60\ \text{eV} > T_1(F2) \quad \text{(Numerical Formula 14C)}$$

$$2.50\ \text{eV} > T_1(F2) \quad \text{(Numerical Formula 14D)}$$

The second emitting layer contains the compound that satisfies the relationship of the numerical formula (Numerical Formula 14C) or the numerical formula (Numerical Formula 14D), so that the organic EL device has a longer lifetime.

In the organic EL device according to the present exemplary embodiment, the triplet energy $T_1$(H2) of the second host material preferably satisfies a relationship of a numerical formula (Numerical Formula 13) below.

$$T_1(H2) \geq 1.9\ \text{eV} \quad \text{(Numerical Formula 13).}$$

Additional Layers of Organic EL Device

The organic EL device according to the exemplary embodiment may include one or more organic layer(s) in addition to the first emitting layer and the second emitting layer. Examples of the organic layer include at least one layer selected from the group consisting of a hole injecting layer, a hole transporting layer, an emitting layer, an electron injecting layer, an electron transporting layer, a hole blocking layer, and an electron blocking layer.

In the organic EL device of the exemplary embodiment, the organic layer may consist of the first emitting layer and the second emitting layer, however, may further includes at least one layer selected from the group consisting of a hole injecting layer, a hole transporting layer, an electron injecting layer, an electron transporting layer, a hole blocking layer, and an electron blocking layer.

It is preferable that the organic EL device of the exemplary embodiment further includes an anode and a cathode, the first emitting layer is provided between the anode and the cathode, and the second emitting layer is provided between the first emitting layer and the cathode.

The organic electroluminescence device of the exemplary embodiment also preferably includes the anode, the first emitting layer, the second emitting layer, and the cathode in this order.

Hole Transporting Layer

The organic EL device of the exemplary embodiment preferably includes a hole transporting layer between the anode and the first emitting layer.

Electron Transporting Layer

The organic EL device of the exemplary embodiment preferably includes an electron transporting layer between the second emitting layer and the cathode.

The FIGURE schematically shows an exemplary structure of the organic EL device of the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, a first emitting layer 51, a second emitting layer 52, an electron transporting layer 8, and an electron injecting layer 9, which are sequentially laminated on the anode 3.

It should be noted that the scope of the invention is by no means limited by the arrangement of the organic EL device shown in the FIGURE. In the organic EL device with another arrangement, for instance, the organic layer includes the hole injecting layer, hole transporting layer, second emitting layer, first emitting layer, electron transporting layer, and electron injecting layer which are laminated on the anode in this order from the anode.

The organic EL device according to the exemplary embodiment may further include a third emitting layer.

It is preferable that the third emitting layer contains a third host material; the first host material, the second host material, and the third host material are mutually different, the third emitting layer at least contains a compound that emits fluorescence having a main peak wavelength of 500 nm or less; the compound that is contained in the first emitting layer and emits fluorescence having a main peak wavelength of 500 nm or less, the compound that is contained in the second emitting layer and emits fluorescence having a main peak wavelength of 500 nm or less, and the compound that is contained in the third emitting layer and emits fluorescence having a main peak wavelength of 500 nm or less are mutually the same or different; and a triplet energy $T_1$(H1) of the first host material and a triplet energy $T_1$(H3) of the third host material satisfy a relationship of a numerical formula (Numerical Formula 1A).

$$T_1(H1) > T_1(H3) \quad \text{(Numerical Formula 1A)}$$

When the organic EL device of the exemplary embodiment includes the third emitting layer, a triplet energy $T_1$(H2) of the second host material and a triplet energy $T_1$(H3) of the third host material preferably satisfy a relationship of a numerical formula (Numerical Formula 1B) below.

$$T_1(H2) > T_1(H3) \quad \text{(Numerical Formula 1B)}$$

In the organic EL device of the exemplary embodiment, the first emitting layer and the second emitting layer are preferably in direct contact with each other.

Herein, a layer arrangement that "the first emitting layer and the second emitting layer are in direct contact with each other" can include one of embodiments ($LS_1$), (LS2), and (LS3) below.

($LS_1$) An embodiment in which a region containing both the first host material and the second host material is generated in a process of vapor-depositing the compound of the first emitting layer and vapor-depositing the compound of the second emitting layer, and is present on the interface between the first emitting layer and the second emitting layer.

(LS2) An embodiment in which in a case of containing an emitting compound in the first emitting layer and the second emitting layer, a region containing all of the first host material, the second host material and the emitting compound is generated in a process of vapor-depositing the compound of the first emitting layer and vapor-depositing the compound of the second emitting layer, and is present on the interface between the first emitting layer and the second emitting layer.

(LS3) An embodiment in which in a case of containing an emitting compound in the first emitting layer and the second emitting layer, a region containing the emitting compound, a region containing the first host material or a region containing the second host material is generated in a process of vapor-depositing the compound of the first emitting layer and vapor-depositing the compound of the second emitting layer, and is present on the interface between the first emitting layer and the second emitting layer.

When the organic EL device according to the exemplary embodiment includes the third emitting layer, it is preferable that the first emitting layer and the second emitting layer are in direct contact with each other and the second emitting layer and the third emitting layer are in direct contact with each other.

Herein, a layer arrangement that the second emitting layer and the third emitting layer are in direct contact with each other can include one of embodiments (LS4), (LS5) and (LS6) below.

(LS4) An embodiment in which a region containing both the second host material and the third host material is generated in a process of vapor-depositing the compound of the second emitting layer and vapor-depositing the compound of the third emitting layer, and is present on the interface between the second emitting layer and the third emitting layer.

(LS5) An embodiment in which in a case of containing an emitting compound in the second emitting layer and the third emitting layer, a region containing all of the second host material, the third host material and the emitting compound is generated in a process of vapor-depositing the compound of the second emitting layer and vapor-depositing the compound of the third emitting layer, and is present on the interface between the second emitting layer and the third emitting layer.

(LS6) An embodiment in which in a case of containing an emitting compound in the second emitting layer and the third emitting layer, a region containing the emitting compound, a region containing the second host material or a region containing the third host material is generated in a process of vapor-depositing the compound of the second emitting layer and vapor-depositing the compound of the third emitting layer, and is present on the interface between the second emitting layer and the third emitting layer.

It is also preferable that the organic EL device of the exemplary embodiment further includes a diffusion layer.

When the organic EL device of the exemplary embodiment includes the diffusion layer, it is preferable that the diffusion layer is interposed between the first emitting layer and the second emitting layer.

An arrangement of the organic EL device 1 will be further described. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N, N'-bis(4-butylphenyl)-N, N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N, N'-bis(3-methylphenyl)-N, N'-diphenyl-[1,1'-biphenyl]-4,4'-diamine (abbreviation: TPD), 4-phenyl-4'-(9-phenylfluorene-9-yl) triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ $cm^2/(V{\cdot}s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is suitably usable. The above-described substances mostly have an electron mobility of $10^{-6}$ $cm^2/Vs$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Further, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the present exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

A film thickness of each of the organic layers of the organic EL device in the exemplary embodiment is not limited unless otherwise specified in the above. In general, the thickness preferably ranges from several nanometers to 1 μm because excessively small film thickness is likely to cause defects (e.g. pin holes) and excessively large thickness leads to the necessity of applying high voltage and consequent reduction in efficiency.

First Host Material, Second Host Material, and Third Host Material

In the organic EL device of the exemplary embodiment, examples of the first host material, the second host material, and the third host material includes the first compound represented by a formula (1), formula (1X), formula (12X), formula (13X), formula (14X), formula (15X) or formula (16X) below and the second compound represented by a formula (2) below. Moreover, the first compound is usable as the first host material and the second host material. In this case, the compound represented by the formula (1) or the compound represented by the formula (1X), formula (12X), formula (13X), formula (14X), formula (15X) or formula (16X) which are used as the second host material is sometimes referred to as the second compound for convenience.

First Compound

[Formula 22]

(1)

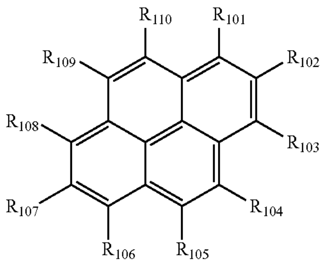

(11)

$*\!-\!(L_{101})_{mx}\!-\!Ar_{101}$

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11) above;

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4 or 5; and when two or more $L_{101}$ are present, two or more $L_{101}$ are mutually the same or different;

when two or more $Ar_{101}$ are present, two or more $Ar_{101}$ are mutually the same or different; and

* in the formula (11) represents a bonding position to a pyrene ring in the formula (1).

In the first compound according to the exemplary embodiment, $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, the group represented by the formula (11) is preferably a group represented by a formula (111) below.

[Formula 23]

(111)

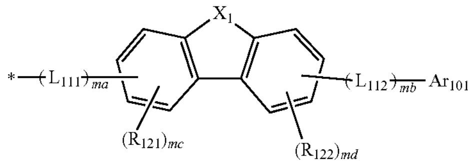

In the formula (111):

$X_1$ is $CR_{123}R1_{24}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$Ar_{101}$ represents the same as $Ar_{101}$ in the formula (11);

$R_{121}$, $R_{122}$, $R_{123}$, $R_{124}$, and $R_{125}$ are each dependently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

md is 3; and three $R_{122}$ are mutually the same or different.

Among positions *1 to *8 of carbon atoms in the cyclic structure represented by a formula (111a) below in the group represented by the formula (111), $L_{111}$ is bonded to one of positions *1 to *4, $R_{121}$ is bonded to three positions of the rest of *1 to *4, $L_{112}$ is bonded to one of positions *5 to *8, and $R_{122}$ is bonded to three positions of the rest of *5 to *8.

[Formula 24]

(111a)

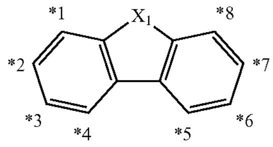

For instance, in the group represented by the formula (111), when $L_{111}$ and $L_{112}$ are bonded to *2 and *7 positions, respectively, of the carbon atom of the cyclic structure represented by the formula (111a), the group represented by the formula (111) is represented by a formula (111b) below.

[Formula 25]

(111b)

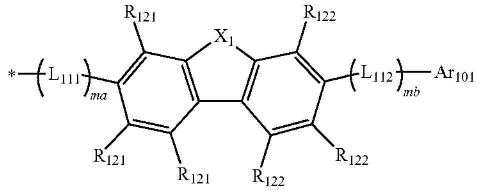

In the formula (111b): $X_1$, $L_{111}$, $L_{112}$, ma, mb, $Ar_{101}$, $R_{121}$, $R_{122}$, $R_{123}$, $R_{124}$, and $R_{125}$ each independently represent the same as $X_1$, $L_{111}$, $L_{112}$, ma, mb, $Ar_{101}$, $R_{121}$, $R_{122}$, $R_{123}$, $R_{124}$, and $R_{125}$ in the formula (111);

a plurality of $R_{121}$ are mutually the same or different; and a plurality of $R_{122}$ are mutually the same or different.

In the organic EL device of the exemplary embodiment, the group represented by the formula (111) is preferably a group represented by the formula (111b).

In the organic EL device according to the exemplary embodiment, it is preferable that ma is 0, 1, or 2, and mb is 0, 1, or 2.

In the organic EL device according to the exemplary embodiment, it is preferable that ma is 0 or 1, and mb is 0 or 1.

In the organic EL device according to the exemplary embodiment, $Ar_{101}$ is preferably a substituted or unsubstituted aryl group having 6 to 50 ring carbon atoms.

In the organic EL device according to the exemplary embodiment, $Ar_{101}$ is preferably a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

In the organic EL device according to the exemplary embodiment, $Ar_{101}$ is also preferably a group represented by a formula (12), a formula (13), or a formula (14) below.

[Formula 26]

(12)

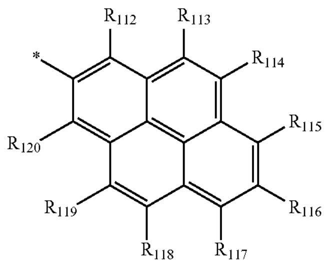

(13)

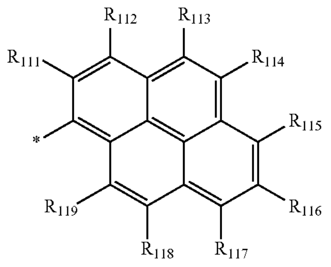

(14)

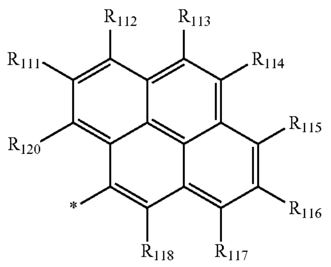

In the formulae (12), (13), and (14):

$R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{124}$, a group represented by —COOR$_{125}$ a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formulae (12), (13) and (14) represents a bonding position to $L_{101}$ in the formula (11) or a bonding position to $L_{112}$ in the formula (111) or (111 b).

In the organic EL device according to the exemplary embodiment, the first compound is preferably represented by a formula (101) below.

[Formula 27]

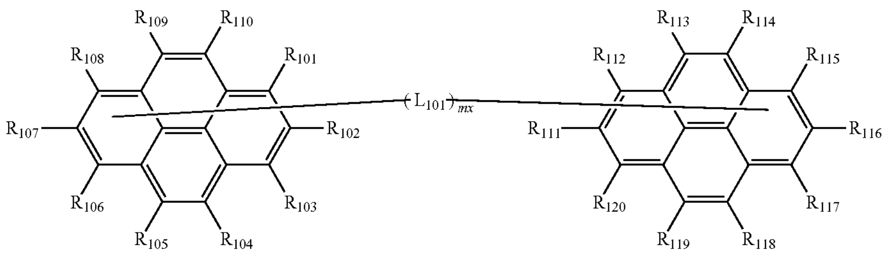

(101)

In the formula (101):

$R_{101}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4 or 5; and when two or more $L_{101}$ are present, the two or more $L_{101}$ are mutually the same or different.

In the organic EL device according to the exemplary embodiment, $L_{101}$ is preferably a single bond or a substituted or unsubstituted arylene group having 6 to 50 ring carbon atoms.

In the organic EL device according to the exemplary embodiment, the first compound is preferably represented by a formula (102) below.

[Formula 28]

(102)

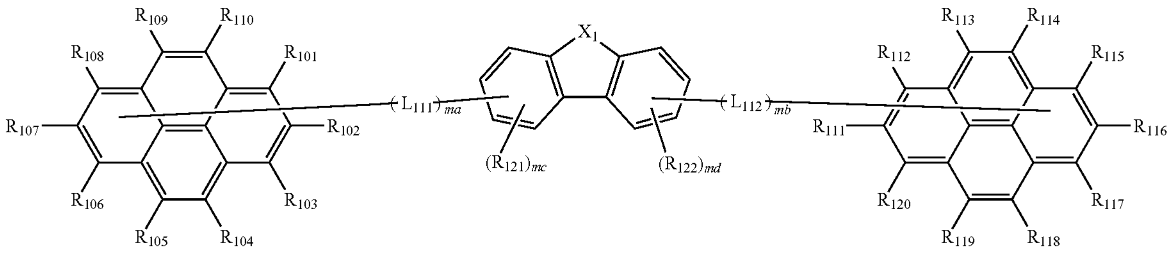

In the formula (102):

$R_{101}$ to $R_{120}$ each independently represent the same as $R_{101}$ to $R_{120}$ of the formula (101);

one of $R_{101}$ to $R_{110}$ represents a bonding position to $L_{111}$, and one of $R_{111}$ to $R_{120}$ represents a bonding position to $L_{112}$;

$X_1$ is $CR_{123}R1_{24}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$R_{121}$, $R_{122}$, $R_{123}$, $R_{124}$, and $R_{125}$ are each dependently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

md is 3; and three $R_{122}$ are mutually the same or different.

In the compound represented by the formula (102), it is preferable that: ma is 0, 1, or 2, and mb is 0, 1, or 2.

In the compound represented by the formula (102), it is preferable that: ma is 0 or 1, and mb is 0 or 1.

In the organic EL device according to the exemplary embodiment, two or more of $R_{101}$ to $R_{110}$ are preferably groups represented by the formula (11).

In the organic EL device according to the exemplary embodiment, it is preferable that two or more of $R_{101}$ to $R_{110}$ are groups represented by the formula (11) and $Ar_{101}$ is a substituted or unsubstituted aryl group having 6 to 50 ring carbon atoms.

In the organic EL device according to the exemplary embodiment, it is preferable that $Ar_{101}$ is not a substituted or unsubstituted pyrenyl group;

$L_{101}$ is not a substituted or unsubstituted pyrenylene group; and the substituted or unsubstituted aryl group having 6 to 50 ring carbon atoms for $R_{101}$ to $R_{110}$ not being the group represented by the formula (11) is not a substituted or unsubstituted pyrenyl group.

In the organic EL device according to the exemplary embodiment, it is preferable that $R_{101}$ to $R_{110}$ not being the group represented by the formula (11) are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that $R_{101}$ to $R_{110}$ not being the group represented by the formula (11) are each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the group represented by the formula (11) are each preferably a hydrogen atom.

Compound Represented by Formula (1X)

In the organic EL device of the exemplary embodiment, the first compound is also preferably represented by a formula (1X) below.

[Formula 29]

(1X)

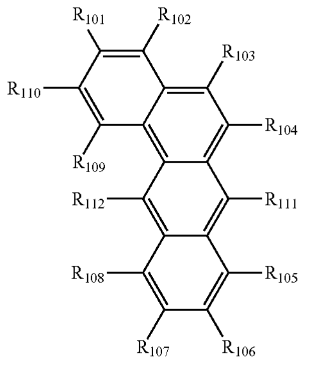

(11X)

In the formula (1X):

$R_{101}$ to $R_{112}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by a formula (11X) above;

at least one of $R_{101}$ to $R_{112}$ is the group represented by the formula (11X);

when a plurality of groups represented by the formula (11X) are present, the plurality of groups represented by the formula (11X) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 1, 2, 3, 4 or 5;

when two or more $L_{101}$ are present, two or more $L_{101}$ are mutually the same or different;

when two or more $Ar_{101}$ are present, two or more $Ar_{101}$ are mutually the same or different; and

* in the formula (11X) represents a bonding position to a benz[a]anthracene ring in the formula (1X).

In the organic EL device of the exemplary embodiment, the group represented by the formula (11X) is preferably a group represented by a formula (111X) below.

[Formula 30]

(111X)

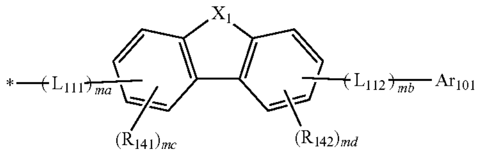

In the formula (111X);

$X_1$ is $CR_{143}R_{144}$, an oxygen atom, a sulfur atom, or $NR_{145}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 1, 2, 3, or 4;

mb is 1, 2, 3, or 4;

ma+mb is 2, 3, or 4;

$Ar_{101}$ represents the same as $Ar_{101}$ in the formula (11);

$R_{141}$, $R_{142}$, $R_{143}$, $R_{144}$, and $R_{145}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{141}$ are mutually the same or different;

md is 3; and three $R_{142}$ are mutually the same or different.

Among positions *1 to *8 of carbon atoms in a cyclic structure represented by a formula (111aX) below in the group represented by the formula (111X), $L_{111}$ is bonded to one of the positions *1 to *4, $R_{141}$ is bonded to each of three positions of the rest of *1 to *4, $L_{112}$ is bonded to one of the positions *5 to *8, and $R_{142}$ is bonded to each of three positions of the rest of *5 to *8.

[Formula 31]

(111aX)

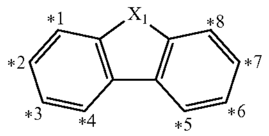

For instance, in the group represented by the formula (111X), when $L_{111}$ is bonded to a carbon atom at *2 in the cyclic structure represented by the formula (111 aX) and $L_{112}$ is bonded to a carbon atom at *7 in the cyclic structure represented by the formula (111aX), the group represented by the formula (111X) is represented by a formula (111bX) below.

[Formula 32]

(111bX)

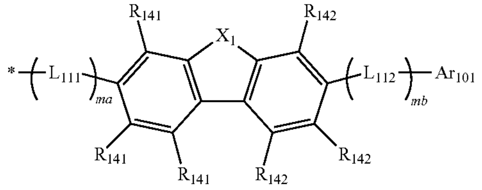

In the formula (111 bX):

$X_1$, $L_{111}$, $L_{112}$, ma, mb, $Ar_{101}$, $R_{141}$, $R_{142}$, $R_{143}$, $R_{144}$ and $R_{145}$ each independently represent the same as $X_1$, $L_{111}$, $L_{112}$, ma, mb, $Ar_{101}$, $R_{141}$, $R_{142}$, $R_{143}$, $R_{144}$ and $R_{145}$ in the formula (111X);

a plurality of $R_{141}$ are mutually the same or different; and a plurality of $R_{142}$ are mutually the same or different.

In the organic EL device of the exemplary embodiment, the group represented by the formula (111X) is preferably a group represented by the formula (111bX).

In the compound represented by the formula (1X), it is preferable that ma is 1 or 2 and mb is 1 or 2.

In the compound represented by the formula (1X), it is preferable that ma is 1 and mb is 1.

In the compound represented by the formula (1X), $Ar_{101}$ is preferably a substituted or unsubstituted aryl group having 6 to 50 ring carbon atoms.

In the compound represented by the formula (1X), $Ar_{101}$ is preferably a substituted or unsubstituted phenyl group, a substituted or unsubstituted naphthyl group, a substituted or unsubstituted biphenyl group, a substituted or unsubstituted terphenyl group, a substituted or unsubstituted benz[a]anthryl group; a substituted or unsubstituted pyrenyl group, a substituted or unsubstituted phenanthryl group, or a substituted or unsubstituted fluorenyl group.

The compound represented by the formula (1X) is also preferably represented by a formula (101X) below.

atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{101}$ is a single bond, a substituted or unsubstituted arylene group having 6 to 50 ring carbon atoms, or a substituted or unsubstituted divalent heterocyclic group having 5 to 50 ring atoms;

[Formula 33]

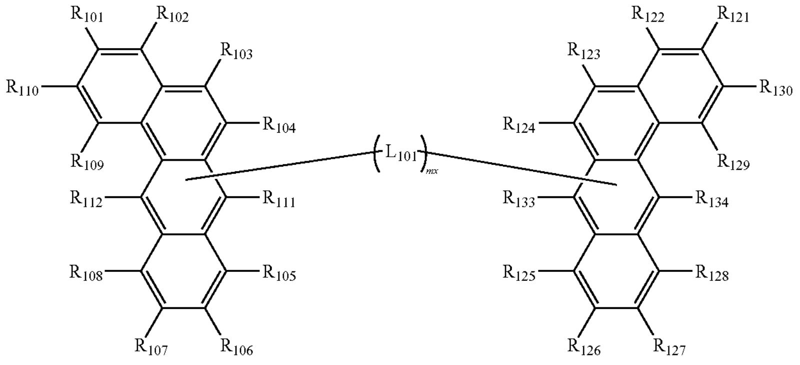

(101X)

In the formula (101X):

one of $R_{111}$ and $R_{112}$ represents a bonding position to $L_{101}$ and one of $R_{133}$ and $R_{134}$ represents a bonding position to $L_{101}$;

$R_{111}$ or $R_{112}$ that is not a bonding position to $R_{101}$ to $R_{110}$, $R_{121}$ to $R_{130}$, and $L_{101}$, and $R_{133}$ or $R_{134}$ that is not a bonding position to $L_{101}$ are each independently a hydrogen atom, a substituted or unsubstituted alkyl group having 1 to 50 carbon atoms, a substituted or unsubstituted haloalkyl group having 1 to 50 carbon mx is 1, 2, 3, 4 or 5; and when two or more $L_{101}$ are present, the two or more $L_{101}$ are mutually the same or different.

In the compound represented by the formula (1X), $L_{101}$ is preferably a single bond or a substituted or unsubstituted arylene group having 6 to 50 ring carbon atoms.

The compound represented by the formula (1X) is also preferably represented by a formula (102X) below.

[Formula 34]

(102X)

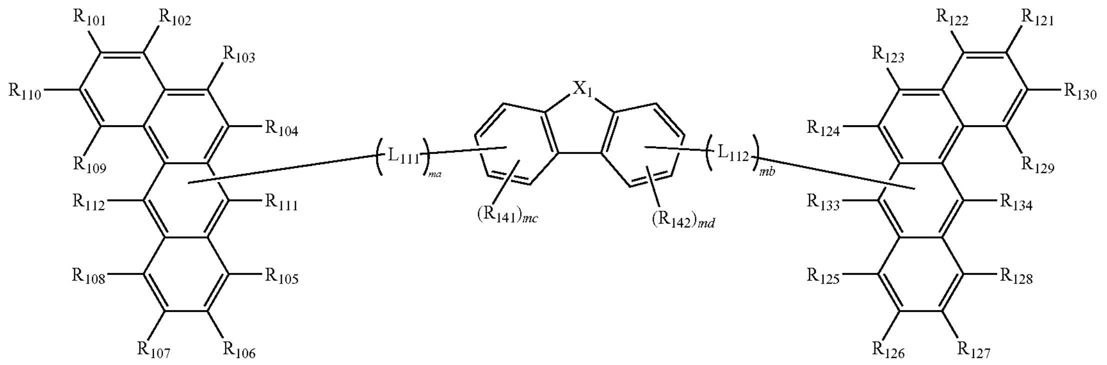

In the formula (102X):

one of $R_{111}$ and $R_{112}$ represents a bonding position to $L_{111}$ and one of $R_{133}$ and $R_{134}$ represents a bonding position to $L_{112}$;

$R_{111}$ or $R_{112}$ that is not a bonding position to $R_{101}$ to $R_{110}$, $R_{121}$ to $R_{130}$, and $L_{111}$, and $R_{133}$ or $R_{134}$ that is not a bonding position to $R_{111}$ or $R_{112}$ and $L_{112}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$X_1$ is $CR_{143}R_{144}$, an oxygen atom, a sulfur atom, or $NR_{145}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 1, 2, 3, or 4;

mb is 1, 2, 3, or 4;

ma+mb is 2, 3, 4, or 5;

$R_{141}$, $R_{142}$, $R_{143}$, $R_{144}$, and $R_{145}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{141}$ are mutually the same or different;

md is 3; and three $R_{142}$ are mutually the same or different.

In the compound represented by the formula (1X), it is preferable that ma is 1 or 2 and mb is 1 or 2 in the formula (102X).

In the compound represented by the formula (1X), it is preferable that ma is 1 and mb is 1 in the formula (102X).

In the compound represented by the formula (1X), the group represented by the formula (11X) is also preferably a group represented by a formula (11AX) or a group represented by a formula (11BX).

[Formula 35]

(11AX)

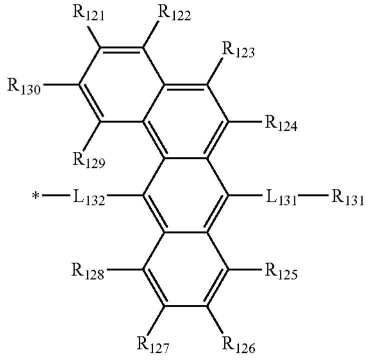

-continued (11BX)

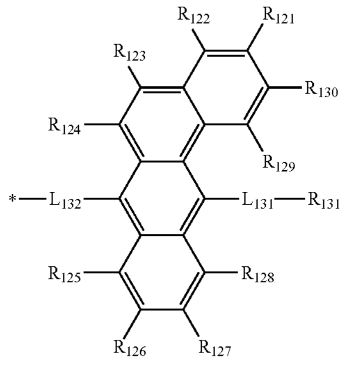

In the formulae (11AX) and (11BX):

$R_{121}$ to $R_{131}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms, when a plurality of groups represented by the formula (11AX) are present, the plurality of groups represented by the formula (11AX) are mutually the same or different;

when a plurality of groups represented by the formula (11BX) are present, the plurality of groups represented by the formula (11BX) are mutually the same or different;

$L_{131}$ and $L_{132}$ are each independently a single bond, a substituted or unsubstituted arylene group having 6 to 50 ring carbon atoms, or a substituted or unsubstituted divalent heterocyclic group having 5 to 50 ring atoms; and

* in the formulae (11AX) and (11BX) each represents a bonding position to a benz[a]anthracene ring in the formula (1X).

The compound represented by the formula (1X) is also preferably represented by a formula (103X).

[Formula 36]

(103X)

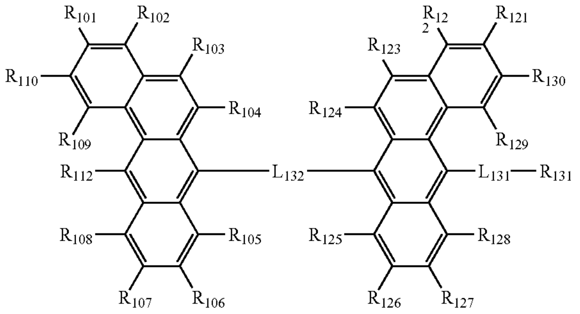

In the formula (103X):

$R_{101}$ to $R_{110}$ and $R_{112}$ respectively represent the same as $R_{101}$ to $R_{110}$ and $R_{112}$ in the formula (1X); and $R_{121}$ to $R_{131}$, $L_{131}$ and $L_{132}$ respectively represent the same as $R_{121}$ to $R_{131}$, $L_{131}$ and $L_{132}$ in the formula (11BX).

In the compound represented by the formula (1X), $L_{131}$ is preferably a substituted or unsubstituted arylene group having 6 to 50 ring carbon atoms.

In the compound represented by the formula (1X), $L_{132}$ is preferably a substituted or unsubstituted arylene group having 6 to 50 ring carbon atoms.

In the compound represented by the formula (1X), two or more of $R_{101}$ to $R_{112}$ are preferably the groups represented by the formula (11).

In the compound represented by the formula (1X), it is preferable that two or more of $R_{101}$ to $R_{112}$ are the groups represented by the formula (11X) and $Ar_{101}$ in the formula (11X) is a substituted or unsubstituted aryl group having 6 to 50 ring carbon atoms.

In the compound represented by the formula (1X), it is also preferable that $Ar_{101}$ is not a substituted or unsubstituted benz[a]anthryl group, $L_{101}$ is not a substituted or unsubstituted benz[a]anthrylene group, and a substituted or unsubstituted aryl group having 6 to 50 ring carbon atoms as $R_{101}$ to $R_{110}$ that are not the group represented by the formula (11X) is not a substituted or unsubstituted benz[a]anthryl group.

In the compound represented by the formula (1X), $R_{101}$ to $R_{112}$ that are not the group represented by the formula (11X) are each independently preferably a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the compound represented by the formula (1X), $R_{101}$ to $R_{112}$ that are not the group represented by the formula (11X) are preferably a hydrogen atom, a substituted or unsubstituted alkyl group having 1 to 50 carbon atoms, or a substituted or unsubstituted cycloalkyl group having 3 to 50 ring carbon atoms.

In the compound represented by the formula (1X), $R_{101}$ to $R_{112}$ that are not the group represented by the formula (11X) are each preferably a hydrogen atom.

Compound Represented by Formula (12X)

In the organic EL device of the exemplary embodiment, the first compound is also preferably the compound represented by the formula (12X).

[Formula 37]

(12X)

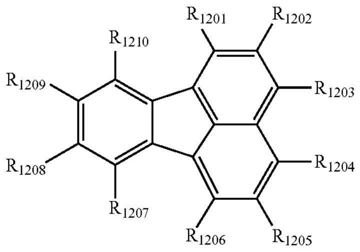

(121)

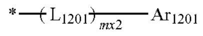

In the formula (12X):

at least one combination of adjacent two or more of $R_{1201}$ to $R_{1210}$ are mutually bonded to form a substituted or unsubstituted monocyclic ring, or mutually bonded to form a substituted or unsubstituted fused ring;

$R_{1201}$ to $R_{1210}$ neither forming the substituted or unsubstituted monocyclic ring nor forming the substituted or unsubstituted fused ring each independently represent a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (121);

a substituent for substituting the substituted or unsubstituted monocyclic ring, a substituent for substituting a substituted or unsubstituted fused ring, and at least one of $R_{1201}$ to $R_{1210}$ are a group represented by the formula (121);

when a plurality of groups represented by the formula (121) are present, the plurality of groups represented by the formula (121) are mutually the same or different;

$L_{1201}$ is a single bond, a substituted or unsubstituted arylene group having 6 to 50 ring carbon atoms, or a substituted or unsubstituted divalent heterocyclic group having 5 to 50 ring atoms; and $Ar_{1201}$ is a substituted or unsubstituted aryl group having 6 to 50 ring carbon atoms, or a substituted or unsubstituted heterocyclic group having 5 to 50 ring atoms;

mx2 is 0, 1, 2, 3, 4, or 5;

when two or more $L_{1201}$ are present, the two or more $L_{1201}$ are mutually the same or different;

when two or more $Ar_{1201}$ are present, the two or more $Ar_{1201}$ are mutually the same or different; and

* in the formula (121) represents a bonding position to a ring represented by the formula (12X).

In the formula (12X), combinations of adjacent two of $R_{1201}$ to $R_{1210}$ refer to a combination of $R_{1201}$ and $R_{1202}$, a combination of $R_{1202}$ and $R_{1203}$, a combination of $R_{1203}$ and $R_{1204}$, a combination of $R_{1204}$ and $R_{1205}$, a combination of $R_{1205}$ and $R_{1206}$, a combination of $R_{1207}$ and $R_{1208}$, a combination of $R_{1208}$ and $R_{1209}$, and a combination of $R_{1209}$ and $R_{1210}$.

Compound Represented by Formula (13X)

In the organic EL device of the exemplary embodiment, the first compound is also preferably a compound represented by a formula (13X).

[Formula 38]

(13X)

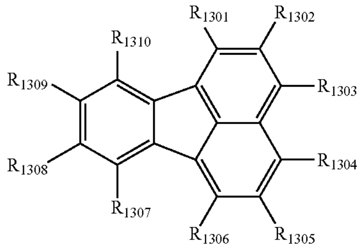

(131)

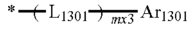

In the formula (13X):

$R_{1301}$ to $R_{1310}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (131);

at least one of $R_{1301}$ to $R_{1310}$ is a group represented by the formula (131);

when a plurality of groups represented by the formula (131) are present, the plurality of groups represented by the formula (131) are mutually the same or different;

$L_{1301}$ is a single bond, a substituted or unsubstituted arylene group having 6 to 50 ring carbon atoms, or a substituted or unsubstituted divalent heterocyclic group having 5 to 50 ring atoms;

$Ar_{1301}$ is a substituted or unsubstituted aryl group having 6 to 50 ring carbon atoms, or a substituted or unsubstituted heterocyclic group having 5 to 50 ring atoms;

mx3 is 0, 1, 2, 3, 4, or 5;

when two or more $L_{1301}$ are present, the two or more $L_{1301}$ are mutually the same or different;

when two or more $Ar_{1301}$ are present, two or more $Ar_{1301}$ are mutually the same or different; and

* in the formula (131) represents a bonding position to a fluoranthene ring in the formula (13X).

In the organic EL device of the exemplary embodiment, combinations of adjacent two or more of $R_{1301}$ to $R_{1310}$ that are not the group represented by the formula (131) are not bonded to each other. In the formula (13X), combinations of adjacent two of $R_{1301}$ to $R_{1310}$ refer to a combination of $R_{1301}$ and $R_{1302}$, a combination of $R_{1302}$ and $R_{1303}$, a combination of $R_{1303}$ and $R_{1304}$, a combination of $R_{1304}$ and $R_{1305}$, a combination of $R_{1305}$ and $R_{1306}$, a combination of $R_{1307}$ and $R_{1308}$, a combination of $R_{1308}$ and $R_{1309}$, and a combination of $R_{1309}$ and $R_{1310}$.

Compound Represented by Formula (14X)

In the organic EL device of the exemplary embodiment, the first compound is also preferably a compound represented by a formula (14X) below.

[Formula 39]

(14X)

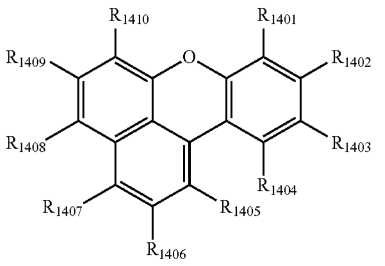

(141)

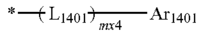

In the formula (14X):

$R_{1401}$ to $R_{1410}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (141);

at least one of $R_{1401}$ to $R_{1410}$ is a group represented by the formula (141);

when a plurality of groups represented by the formula (141) are present, the plurality of groups represented by the formula (141) are mutually the same or different;

$L_{1401}$ is a single bond, a substituted or unsubstituted arylene group having 6 to 50 ring carbon atoms, or a substituted or unsubstituted divalent heterocyclic group having 5 to 50 ring atoms;

$Ar_{1401}$ is a substituted or unsubstituted aryl group having 6 to 50 ring carbon atoms, or a substituted or unsubstituted heterocyclic group having 5 to 50 ring atoms;

mx4 is 0, 1, 2, 3, 4, or 5;

when two or more $L_{1401}$ are present, the two or more $L_{1401}$ are mutually the same or different;

when two or more $Ar_{1401}$ are present, the two or more $Ar_{1401}$ are mutually the same or different; and

* in the formula (141) represents a bonding position to a ring represented by the formula (14X).

Compound Represented by Formula (15X)

In the organic EL device of the exemplary embodiment, the first compound is also preferably a compound represented by a formula (15X) below.

[Formula 40]

(15X)

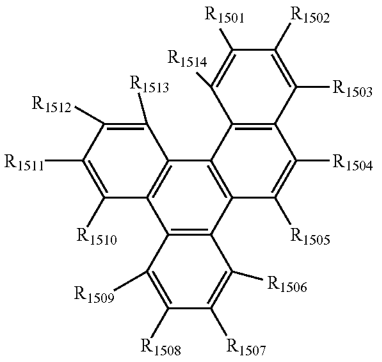

(151)

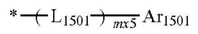

In the formula (15X):

$R_{1501}$ to $R_{1514}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (151);

at least one of $R_{1501}$ to $R_{1514}$ is a group represented by the formula (151);

when a plurality of group represented by the formula (151) are present, the plurality of groups represented by the formula (151) are mutually the same or different;

$L_{1501}$ is a single bond, a substituted or unsubstituted arylene group having 6 to 50 ring carbon atoms, or a substituted or unsubstituted divalent heterocyclic group having 5 to 50 ring atoms;

$Ar_{1501}$ is a substituted or unsubstituted aryl group having 6 to 50 ring carbon atoms, or a substituted or unsubstituted heterocyclic group having 5 to 50 ring atoms;

mx5 is 0, 1, 2, 3, 4, or 5;

when two or more $L_{1501}$ are present, the two or more $L_{1501}$ are mutually the same or different;

when two or more $Ar_{1501}$ are present, the two or more $Ar_{1501}$ are mutually the same or different; and

* in the formula (151) represents a bonding position to a ring represented by the formula (15X).

Compound Represented by Formula (16X)

In the organic EL device of the exemplary embodiment, the first compound is also preferably is a compound represented by a formula (16X) below.

[Formula 41]

(16X)

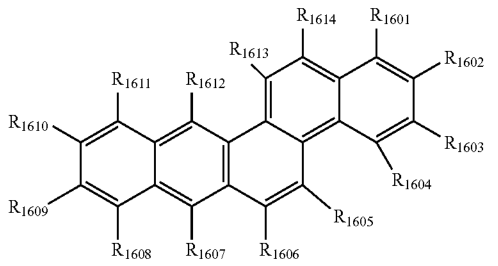

(161)

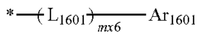

In the formula (16X):

$R_{1601}$ to $R_{1614}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (161);

at least one of $R_{1601}$ to $R_{1614}$ is a group represented by the formula (161);

when a plurality of group represented by the formula (161) are present, the plurality of groups represented by the formula (161) are mutually the same or different;

$L_{1601}$ is a single bond, a substituted or unsubstituted arylene group having 6 to 50 ring carbon atoms, or a substituted or unsubstituted divalent heterocyclic group having 5 to 50 ring atoms;

$Ar_{1601}$ is a substituted or unsubstituted aryl group having 6 to 50 ring carbon atoms, or a substituted or unsubstituted heterocyclic group having 5 to 50 ring atoms;

mx6 is 0, 1, 2, 3, 4, or 5;

when two or more $L_{1601}$ are present, the two or more $L_{1601}$ are mutually the same or different;

when two or more $Ar_{1601}$ are present, the two or more $Ar_{1601}$ are mutually the same or different; and

* in the formula (161) represents a bonding position to a ring represented by the formula (16X).

In the organic EL device of the exemplary embodiment, it is also preferable that the first host material has, in a molecule, a linking structure including a benzene ring and a naphthalene ring linked to each other with a single bond, in which the benzene ring and the naphthalene ring in the linking structure are each independently fused or not fused with a further monocyclic ring or fused ring, and the benzene ring and the naphthalene ring in the linking structure are further linked to each other by cross-linking at at least one site other than the single bond.

Since the first host material has the linking structure including such cross-linking, it can be expected to suppress deterioration in chromaticity of the organic EL device.

The first host material in the above case is only required to have a linking structure as the minimum unit in a molecule, the linking structure including a benzene ring and a naphthalene ring linked to each other with a single bond (referred to as a benzene-naphthalene linking structure in some cases), the linking structure being as represented by a formula (X1) or a formula (X2) below. The benzene ring may be fused with a further monocyclic ring or fused ring, and the naphthalene ring may be fused with a further monocyclic ring or fused ring. For example, also in a case where the first host material has, in a molecule, a linking structure including a naphthalene ring and a naphthalene ring linked to each other with a single bond (referred to as a naphthalene-naphthalene linking structure in some cases) and being as represented by a formula (X3), a formula (X4), or a formula (X5) below, the naphthalene-naphthalene linking structure is regarded as including the benzene-naphthalene linking structure since one of the naphthalene rings includes a benzene ring.

[Formula 42]

(X1)

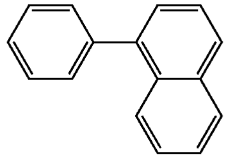

(X2)

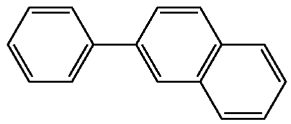

(X3)

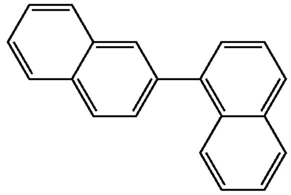

(X4)

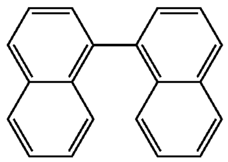

-continued (X5)

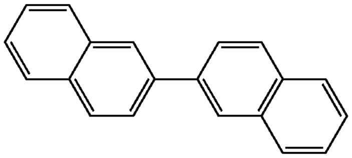

In the organic EL device according to the exemplary embodiment, the cross-linking also preferably includes a double bond. Specifically, the first host material also preferably has a structure in which the benzene ring and the naphthalene ring are further linked to each other at any other site than the single bond by the cross-linking structure including a double bond.

Assuming that the benzene ring and the naphthalene ring in the benzene-naphthalene linking structure are further linked to each other at at least one site other than the single bond by cross-linking, for example, a linking structure (fused ring) represented by a formula (X11) below is obtained in a case of the formula (X1), and a linking structure (fused ring) represented by a formula (X31) below is obtained in a case of the formula (X3).

Assuming that the benzene ring and the naphthalene ring in the benzene-naphthalene linking structure are further linked to each other at any other site than the single bond by crosslinking including a double bond, for example, a linking structure (fused ring) represented by a formula (X12) below is obtained in a case of the formula (X1), a linking structure (fused ring) represented by a formula (X21) or formula (X22) below is obtained in a case of the formula (X2), a linking structure (fused ring) represented by a formula (X41) below is obtained in a case of the formula (X4), and a linking structure (fused ring) represented by a formula (X51) below is obtained in a case of the formula (X5).

Assuming that the benzene ring and the naphthalene ring in the benzene-naphthalene linking structure are further linked to each other at at least one site other than the single bond by cross-linking including a hetero atom (e.g., an oxygen atom), for example, a linking structure (fused ring) represented by a formula (X13) below is obtained in a case of the formula (X1).

[Formula 43]

(X11)

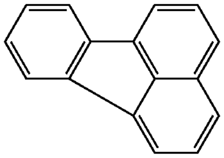

(X12)

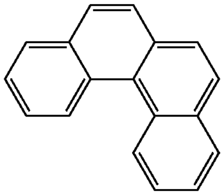

-continued (X13)

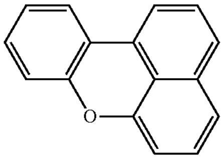

(X21)

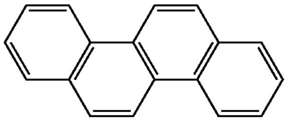

(X22)

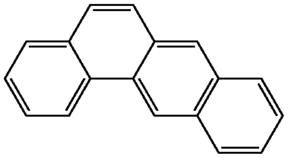

(X31)

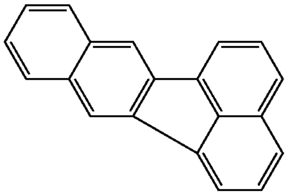

(X41)

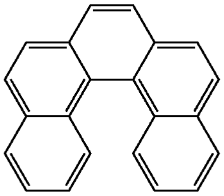

(X51)

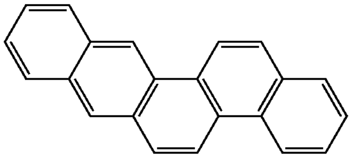

In the organic EL device according to the exemplary embodiment, it is also preferable that: the first host material has, in a molecule, a biphenyl structure in which a first benzene ring and a second benzene ring are linked to each other with a single bond; and the first benzene ring and the second benzene ring in the biphenyl structure are further linked to each other by cross-linking at at least one site other than the single bond.

In the organic EL device according to the exemplary embodiment, it is also preferable that the first benzene ring and the second benzene ring in the biphenyl structure are further linked to each other by the cross-linking at one site other than the single bond. Since the first host material has the biphenyl structure including such cross-linking, it can be expected to inhibit the deterioration in the chromaticity of the organic EL device.

In the organic EL device according to the exemplary embodiment, the cross-linking also preferably includes a double bond.

In the organic EL device according to the exemplary embodiment, it is also preferable that the cross-linking does not include a double bond.

It is also preferable that the first benzene ring and the second benzene ring in the biphenyl structure are further linked to each other by the cross-linking in two sites other than the single bond.

In the organic EL device according to the exemplary embodiment, it is also preferable that the first benzene ring and the second benzene ring in the biphenyl structure are further linked to each other by the cross-linking in two sites other than the single bond and the cross-linking includes no double bond. Since the first host material has the biphenyl structure including such cross-linking, it can be expected to inhibit the deterioration in the chromaticity of the organic EL device.

For example, assuming that the first benzene ring and the second benzene ring in the biphenyl structure represented by a formula (BP1) below are further linked to each other by cross-linking at at least one site other than the single bond, the biphenyl structure is exemplified by linking structures (fused rings) represented by formulae (BP11) to (BP15) below.

[Formula 44]

(BP1)

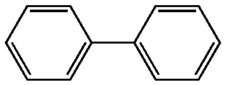

(BP11)

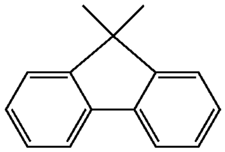

(BP12)

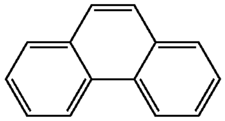

(BP13)

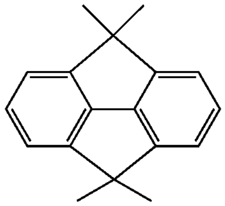

-continued (BP14)

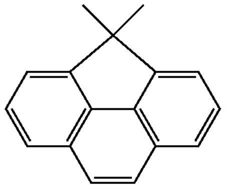

(BP15)

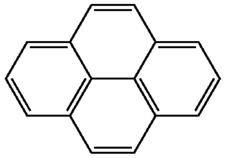

The formula (BP11) represents a linking structure in which the first benzene ring and the second benzene ring are linked to each other at one site other than the single bond by cross-linking including no double bond.

The formula (BP12) represents a linking structure in which the first benzene ring and the second benzene ring are linked to each other at one site other than the single bond by cross-linking including a double bond.

The formula (BP13) represents a linking structure in which the first benzene ring and the second benzene ring are linked to each other at two sites other than the single bond by cross-linking including no double bond.

The formula (BP14) represents a linking structure in which the first benzene ring and the second benzene ring are linked to each other at one of two sites other than the single bond by cross-linking including no double bond while being linked to each other at the other of the two sites other than the single bond by cross-linking including a double bond.

The formula (BP15) represents a linking structure in which the first benzene ring and the second benzene ring are linked to each other at two sites other than the single bond by cross-linking including double bonds.

In the first compound and the second compound, it is preferable that all groups described as "substituted or unsubstituted" groups are "unsubstituted" groups.

Manufacturing Method of First Compound

The first compound can be manufactured by a known method. The first compound can also be manufactured based on a known method through a known alternative reaction using a known material(s) tailored for the target compound.

Specific Examples of First Compound

Specific examples of the first compound include the following compounds. It should however be noted that the invention is not limited by the specific examples of the first compound.

In the specific examples of the compound herein, D represents a deuterium atom, Me represents a methyl group, and tBu represents a tert-butyl group.

[Formula 45]
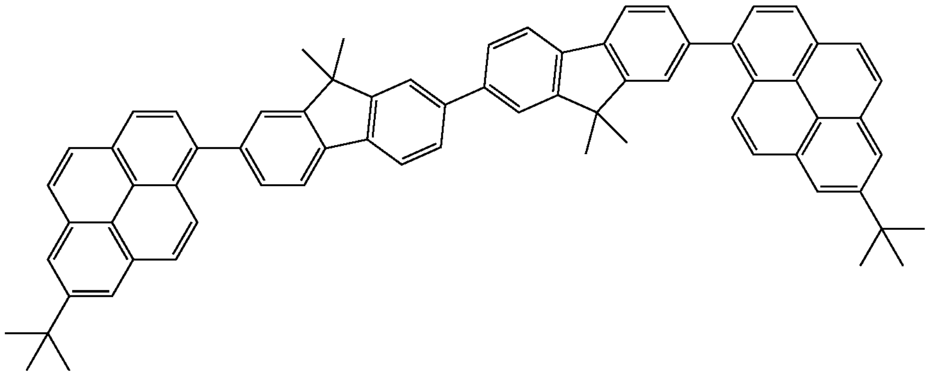
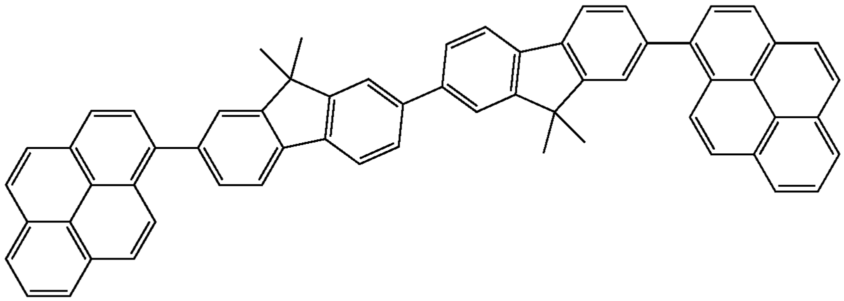
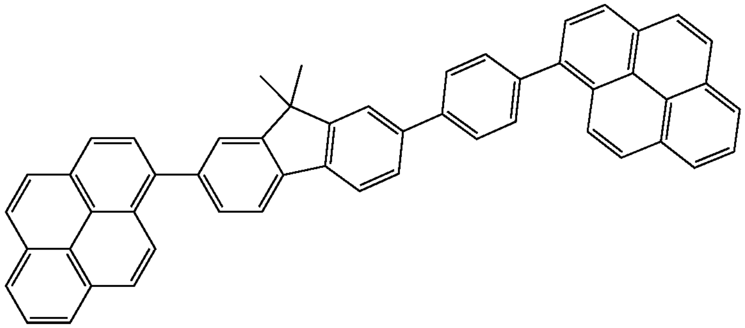
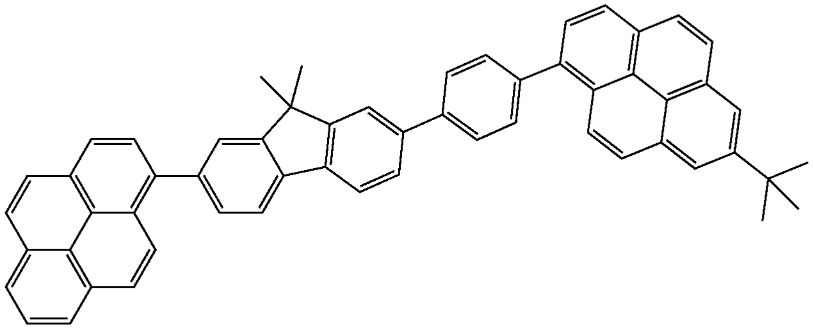
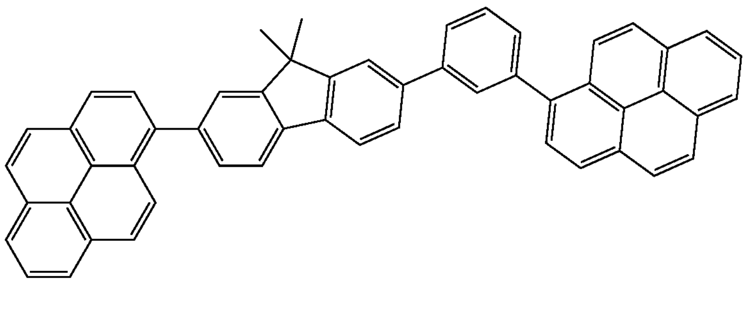

-continued
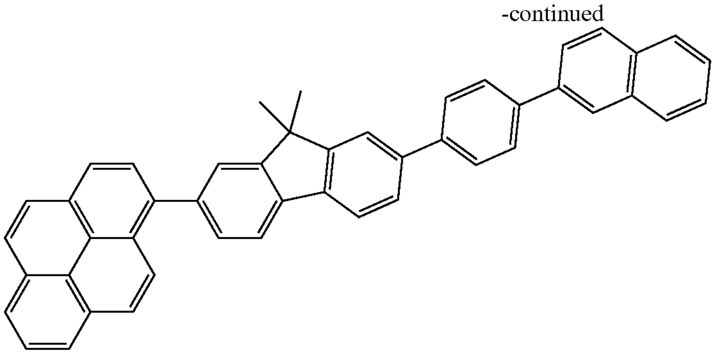
[Formula 46]
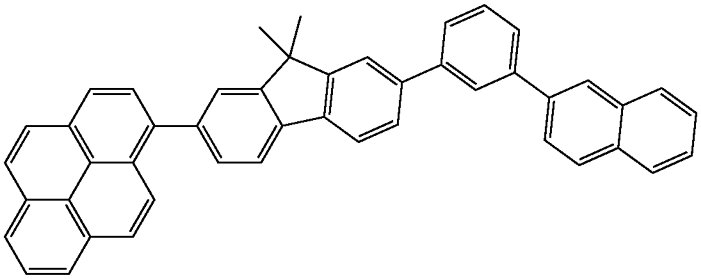
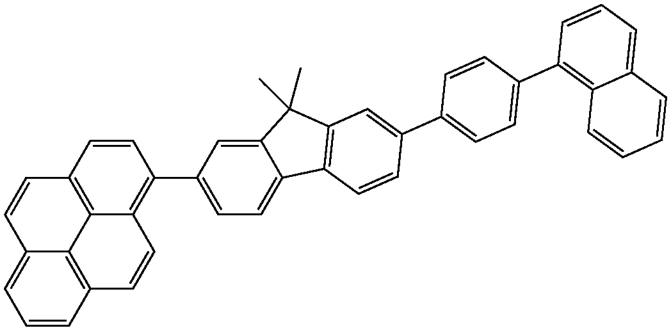
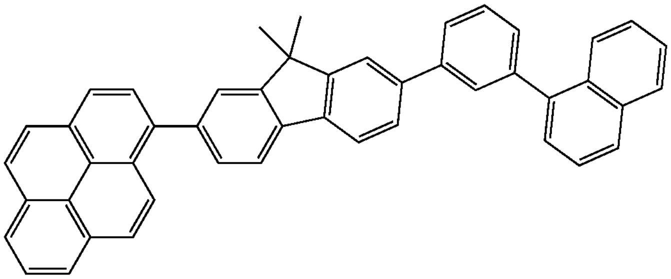
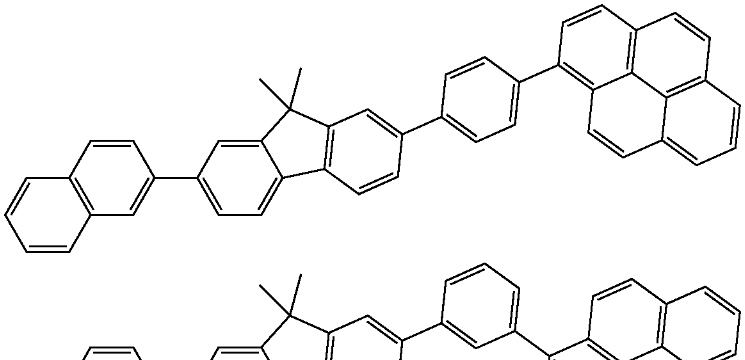
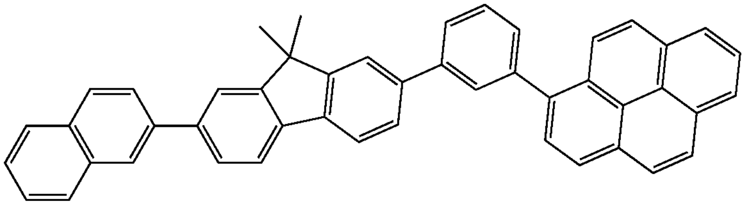

-continued
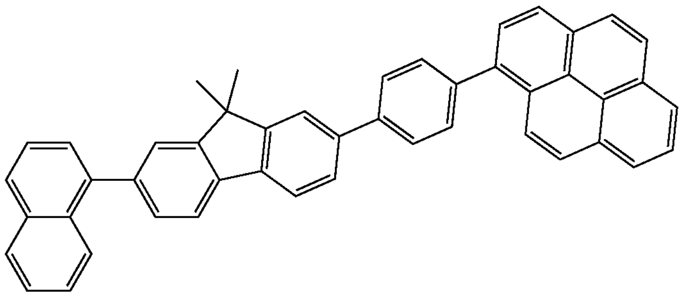
[Formula 47]
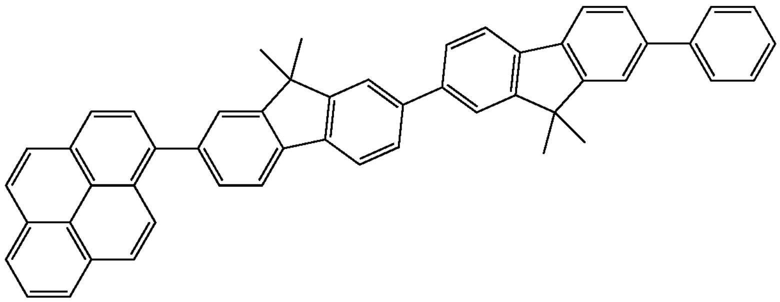
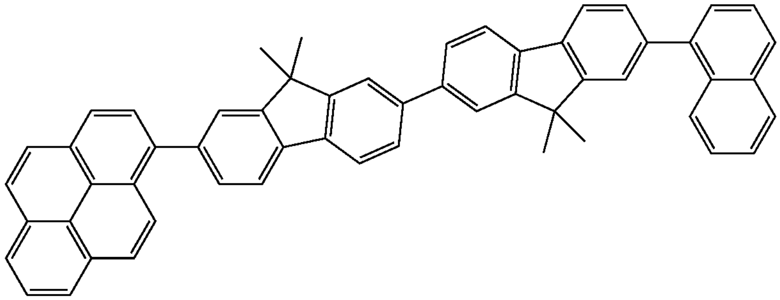
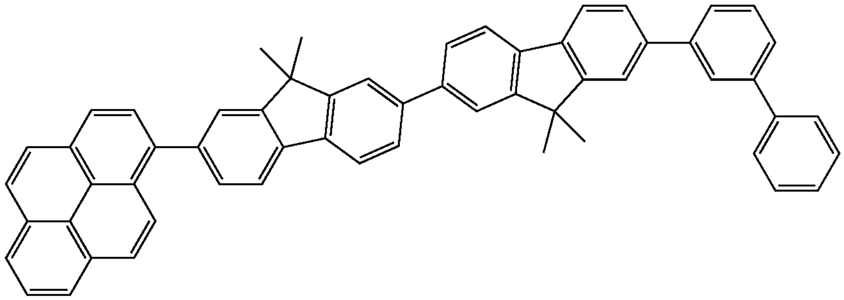
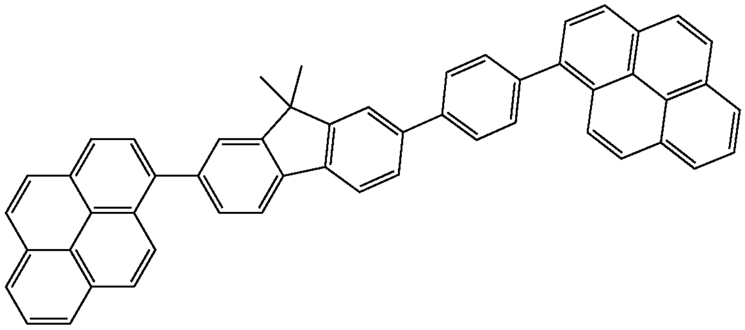

-continued
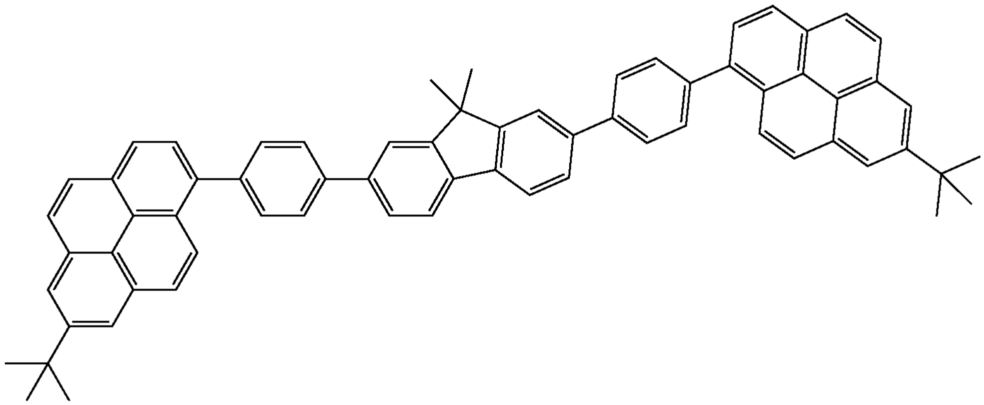
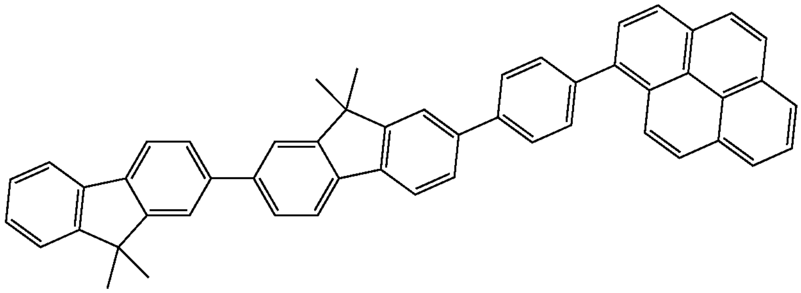
[Formula 48]
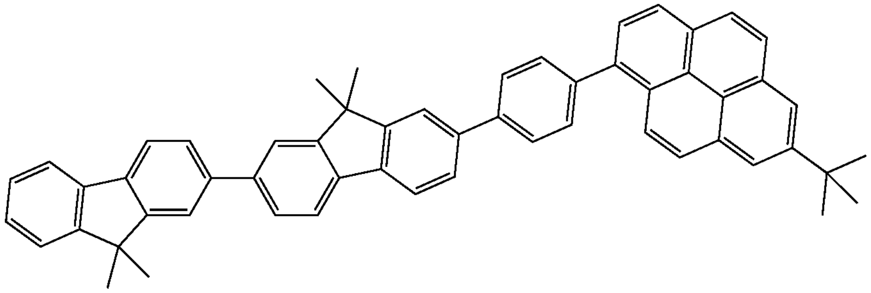
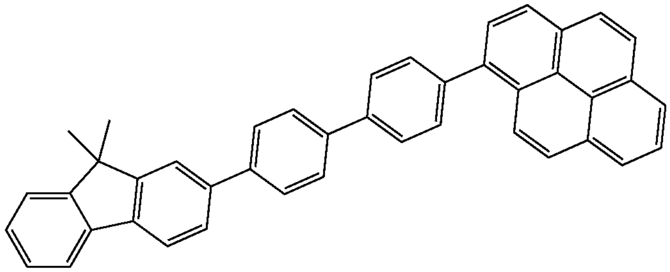
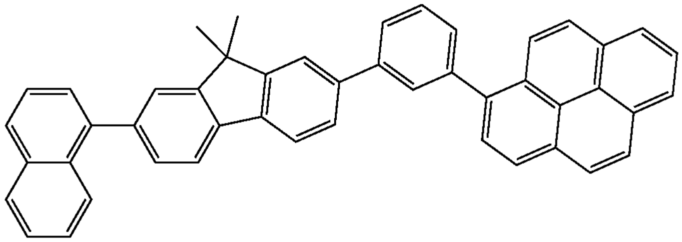

-continued
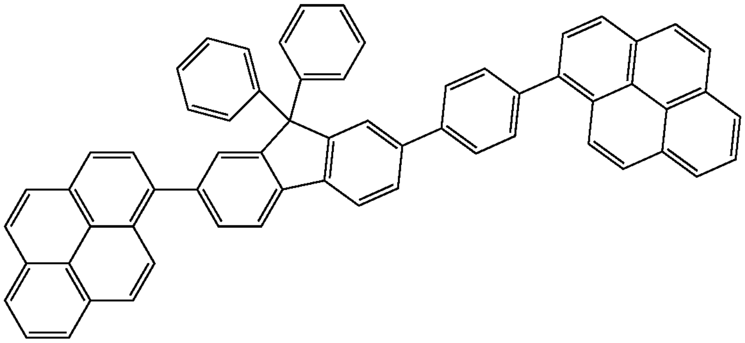
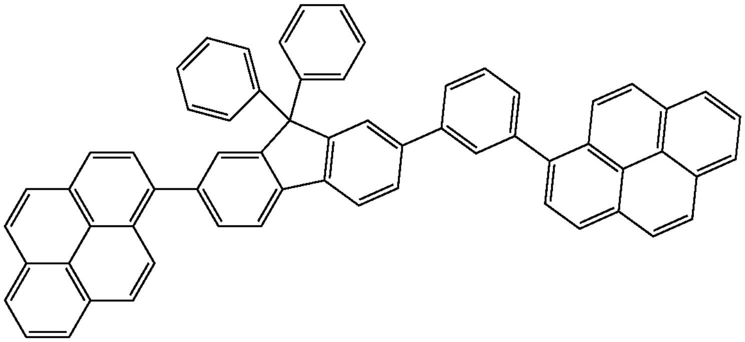
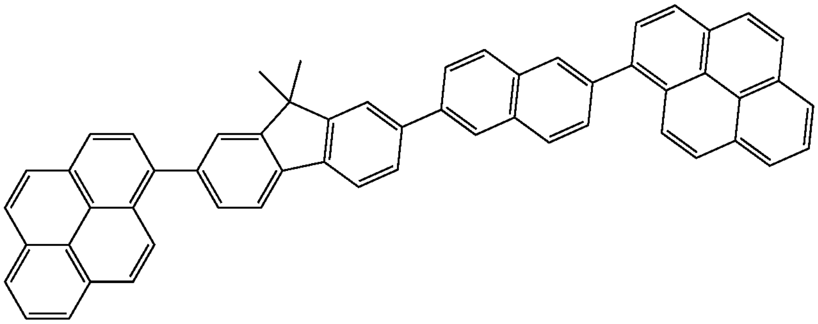
[Formula 49]
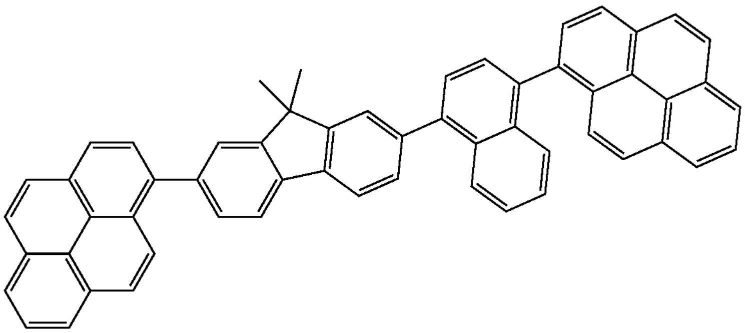
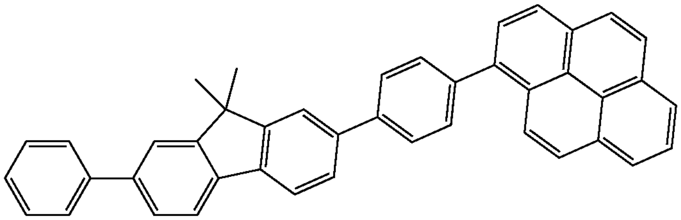

-continued
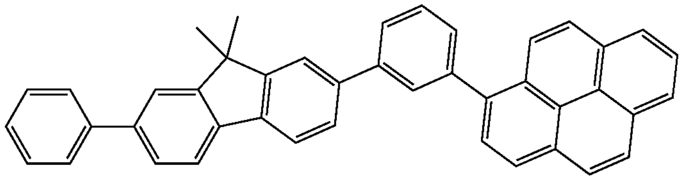
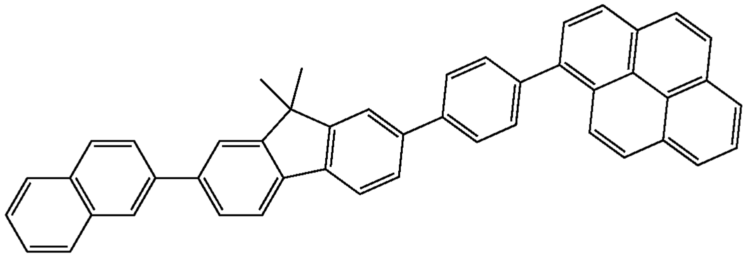
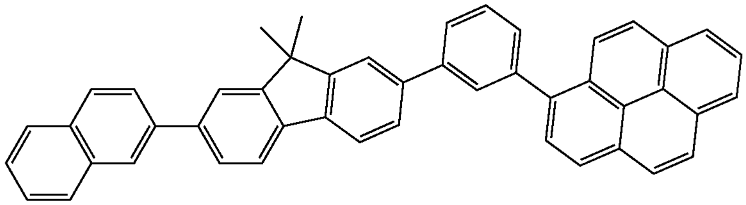
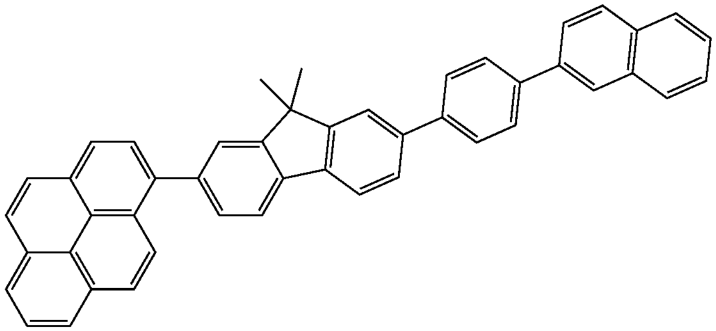
[Formula 50]
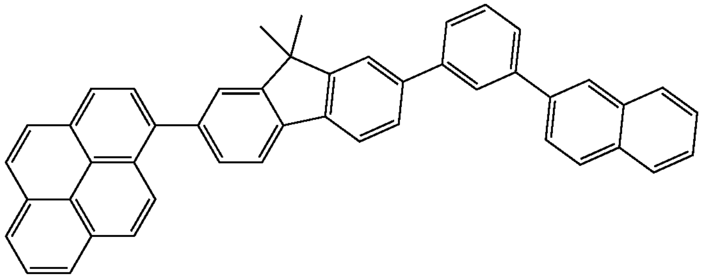
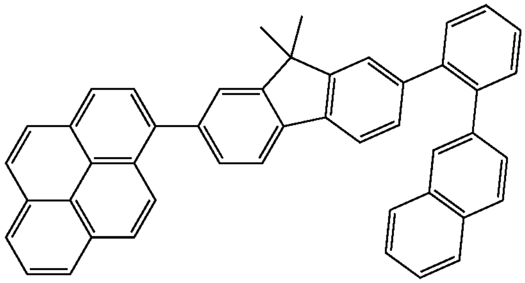

-continued
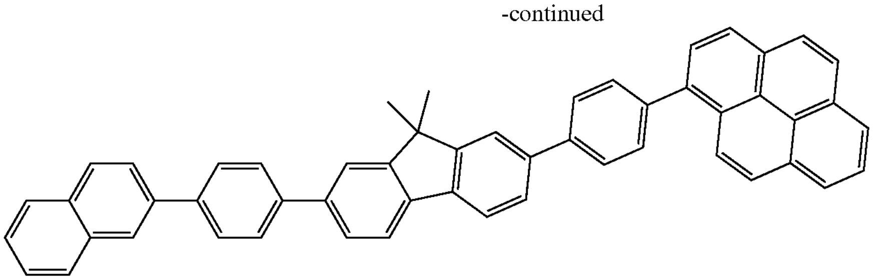
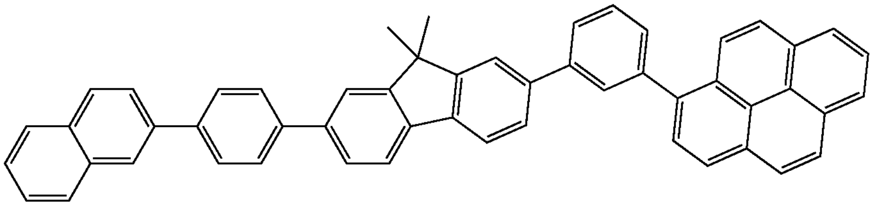
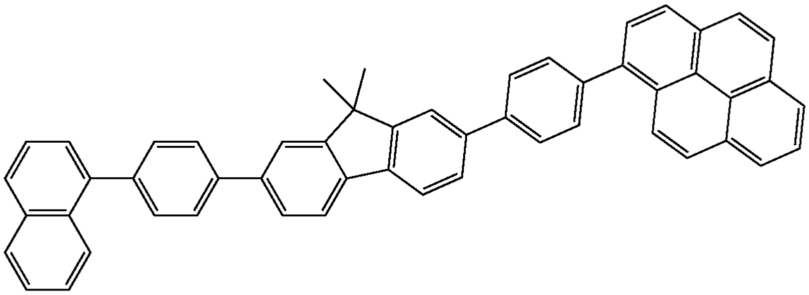
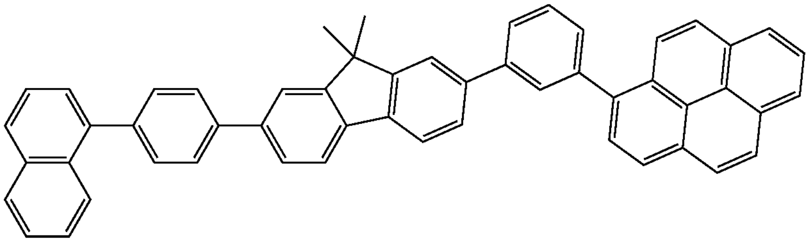
[Formula 51]
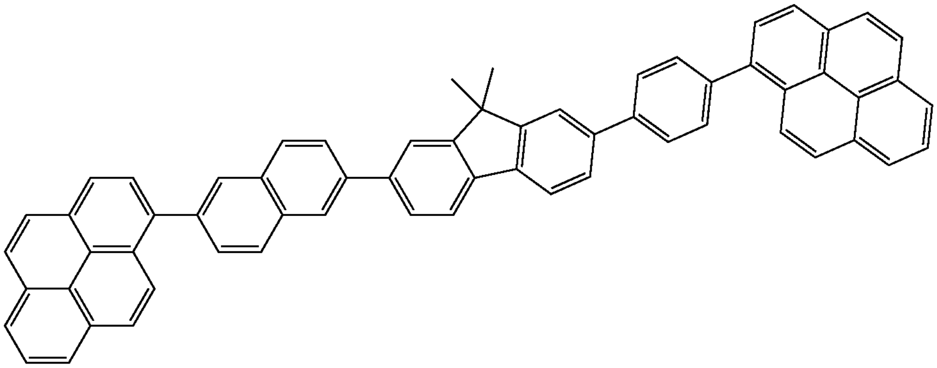
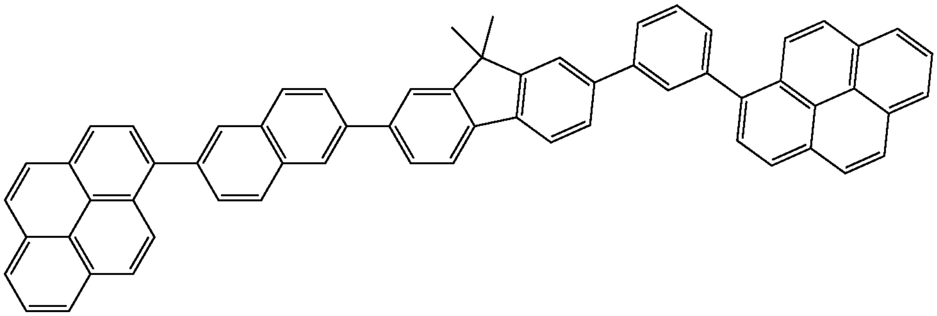

-continued
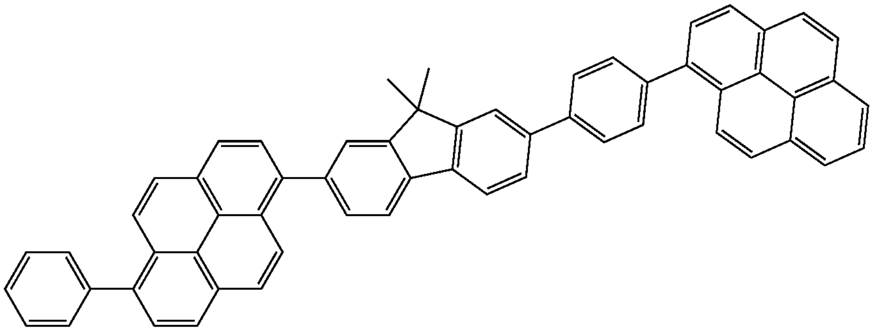
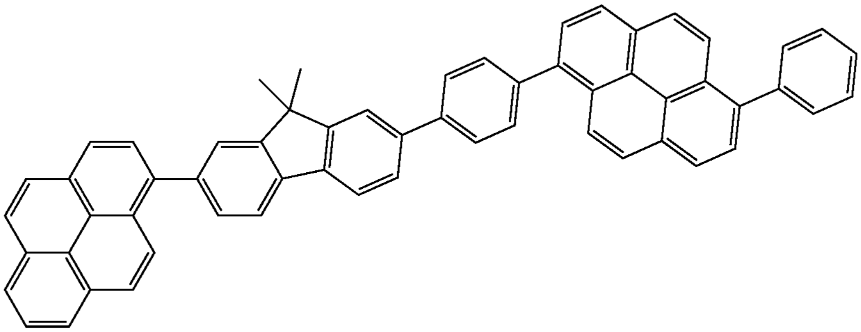
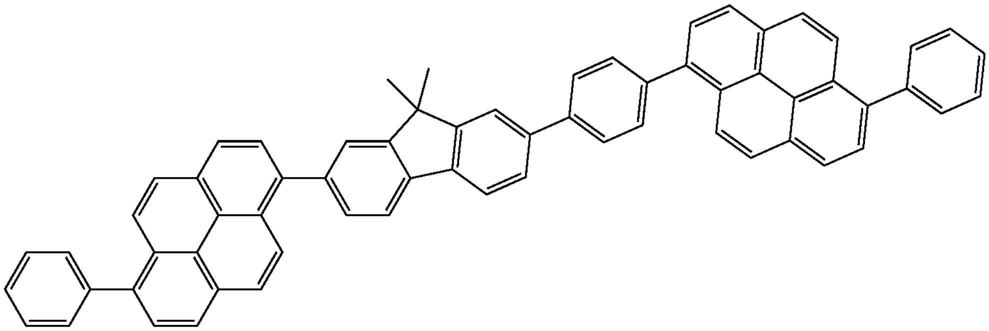
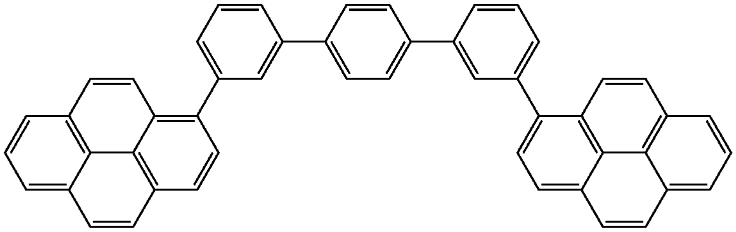
[Formula 52]
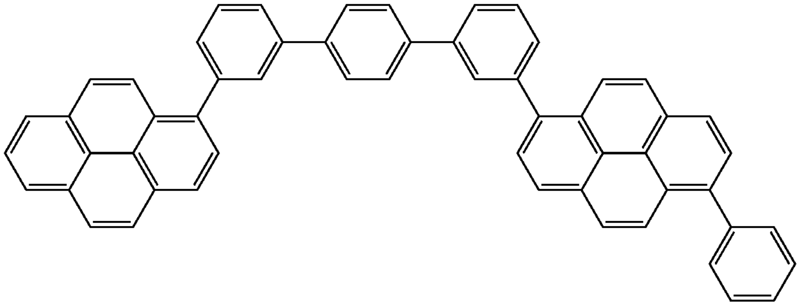

-continued
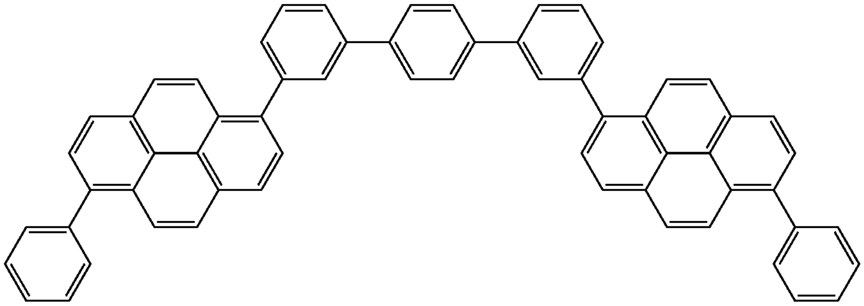
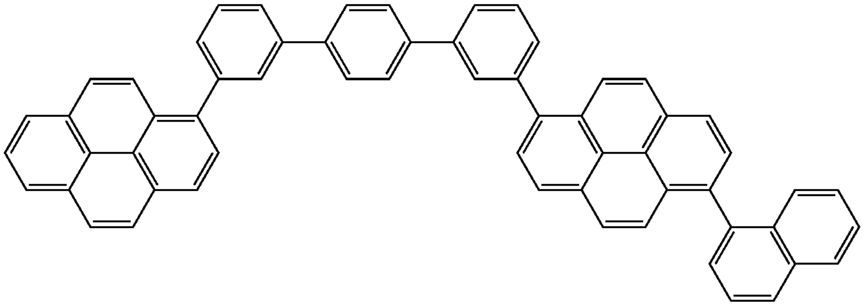
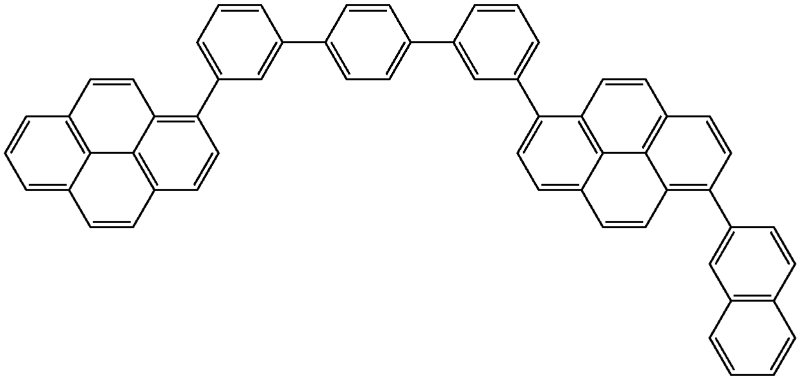
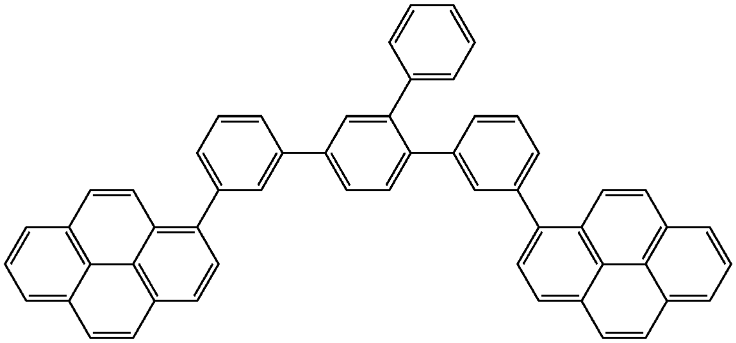

-continued
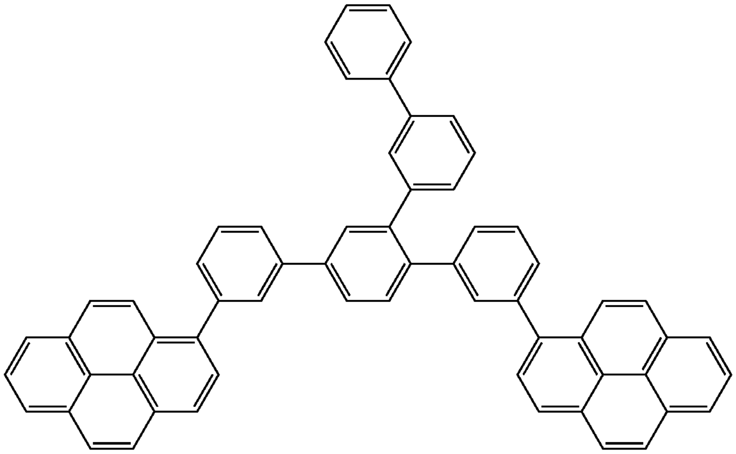
[Formula 53]
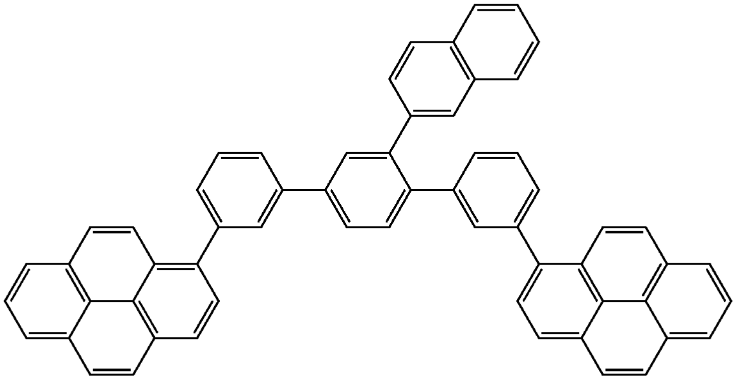
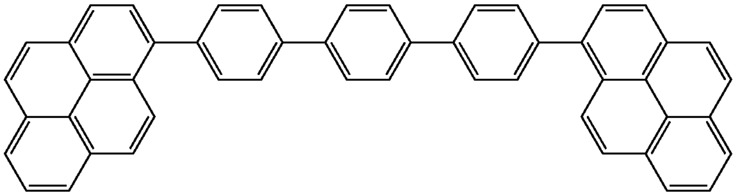
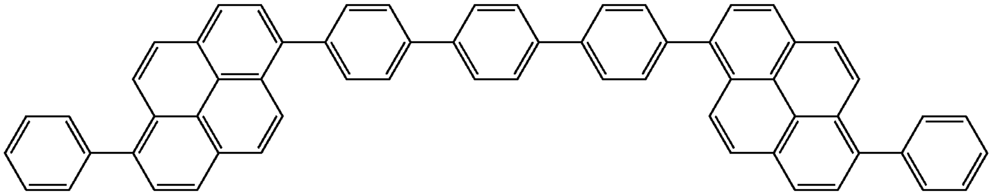
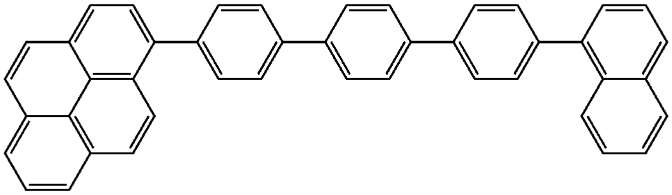
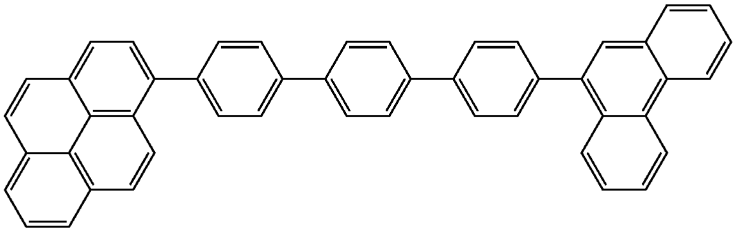

-continued
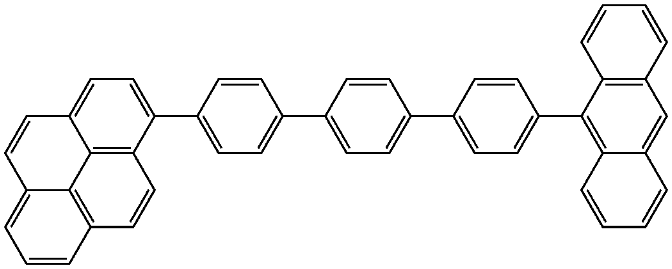
[Formula 54]
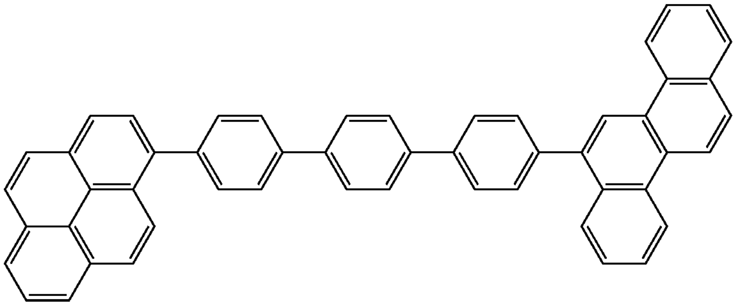
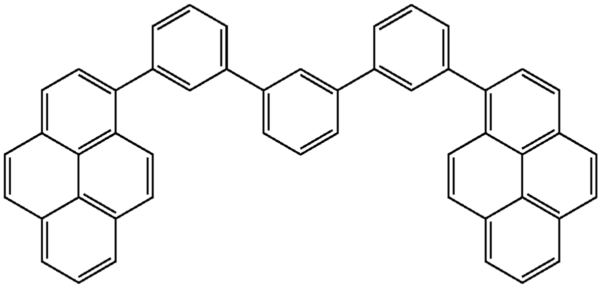
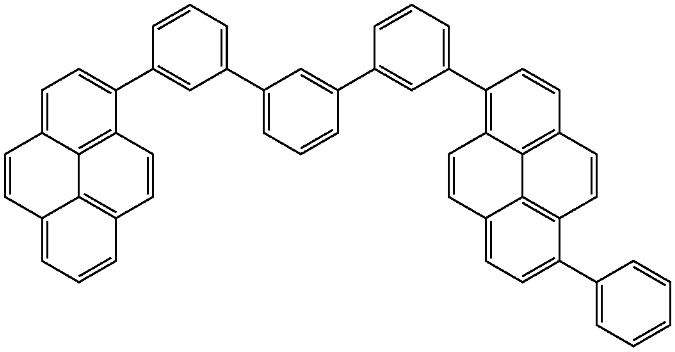
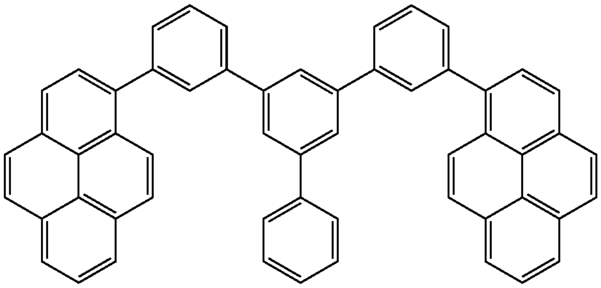

-continued
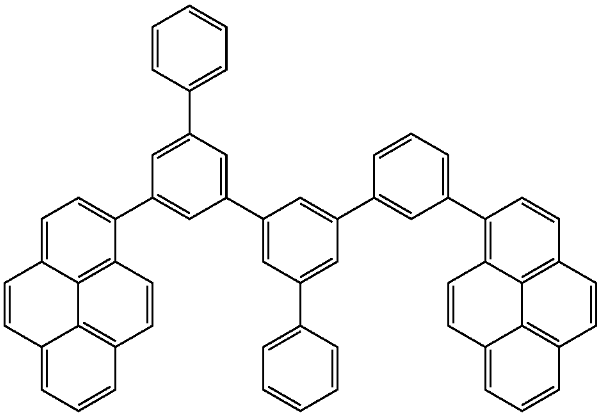
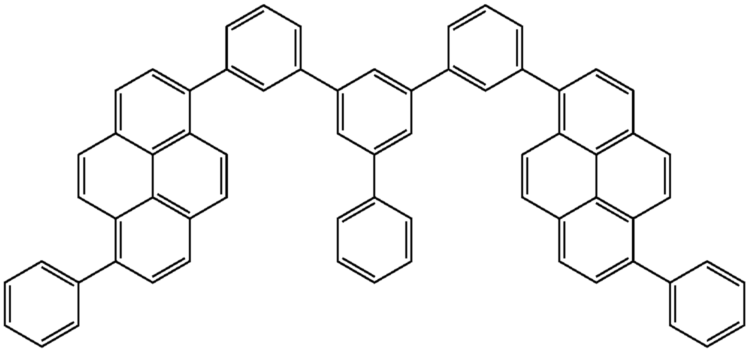
[Formula 55]
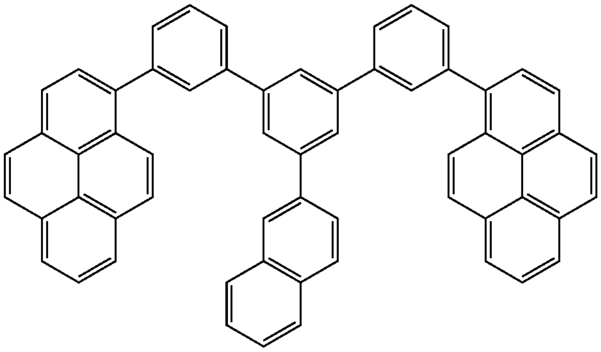
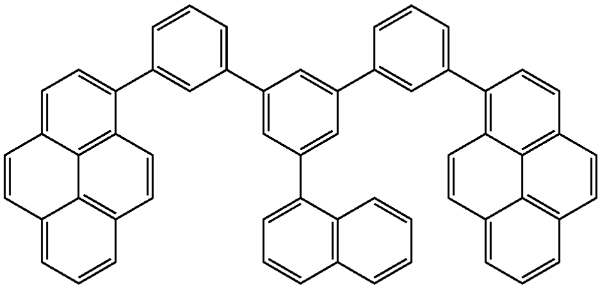
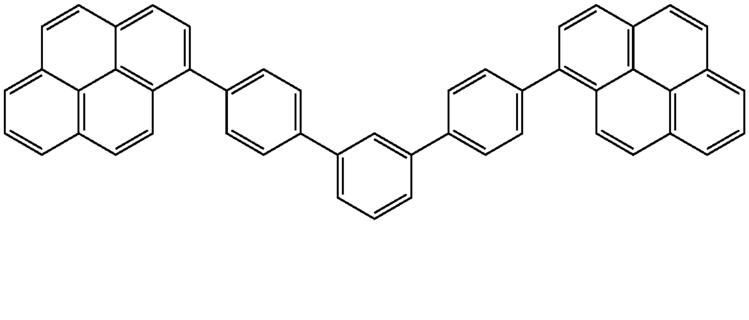

-continued
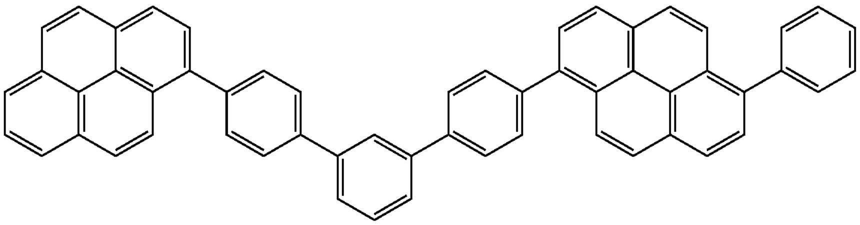
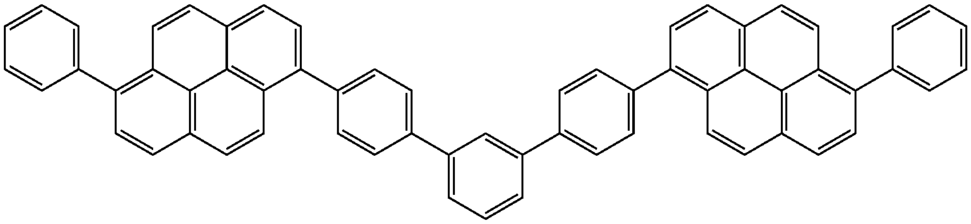
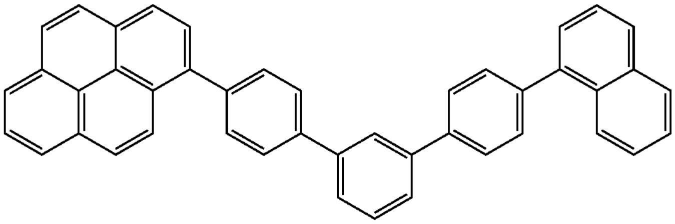
[Formula 56]
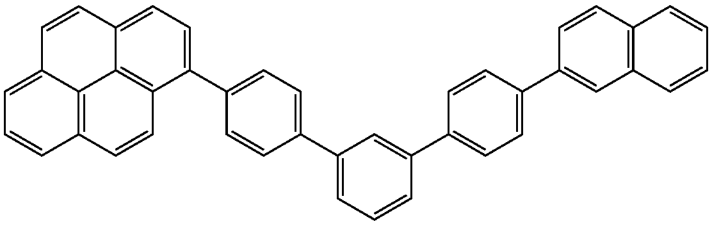
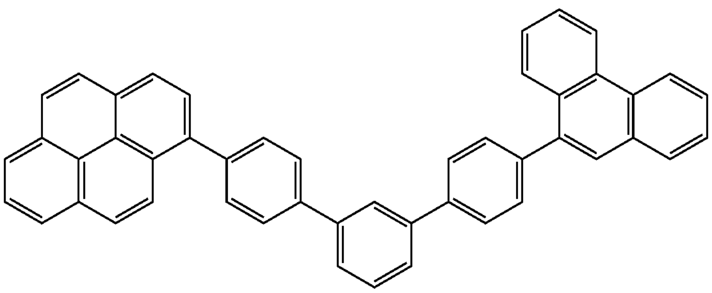
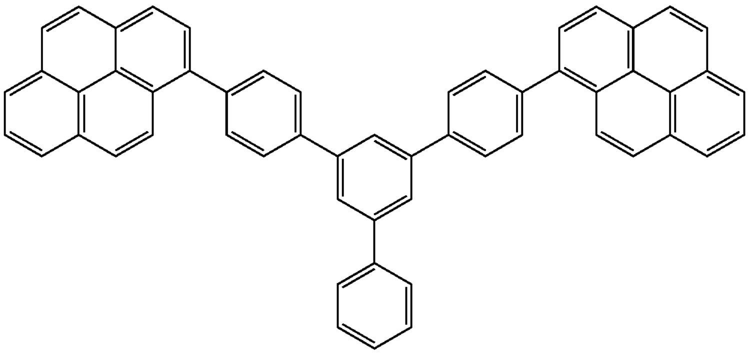

-continued
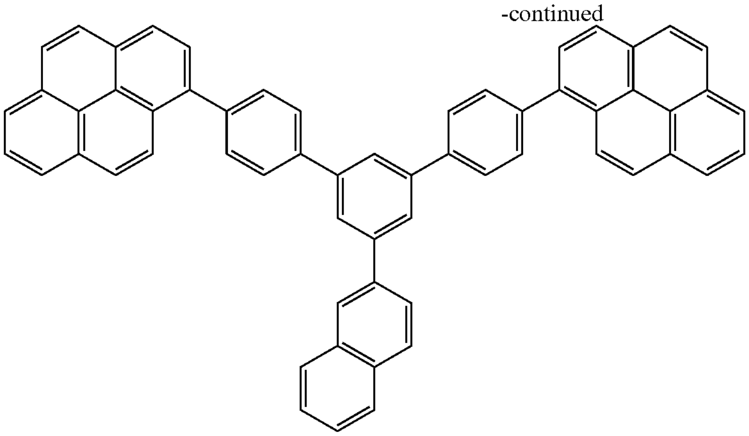
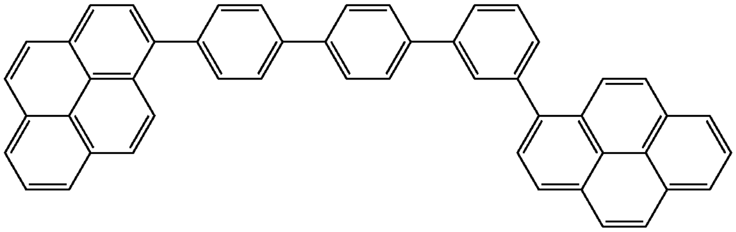
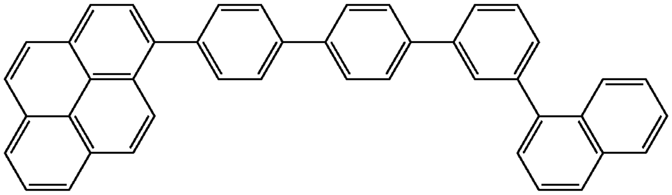
[Formula 57]
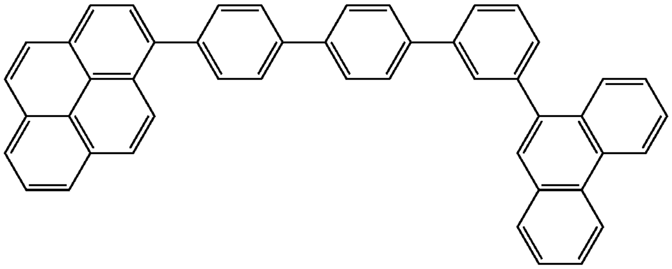
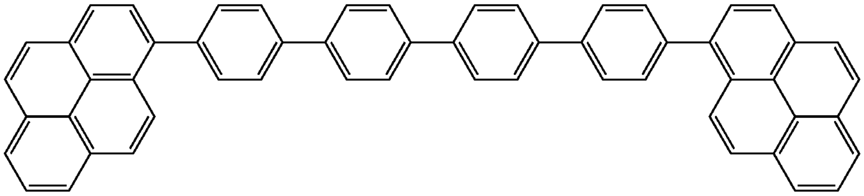
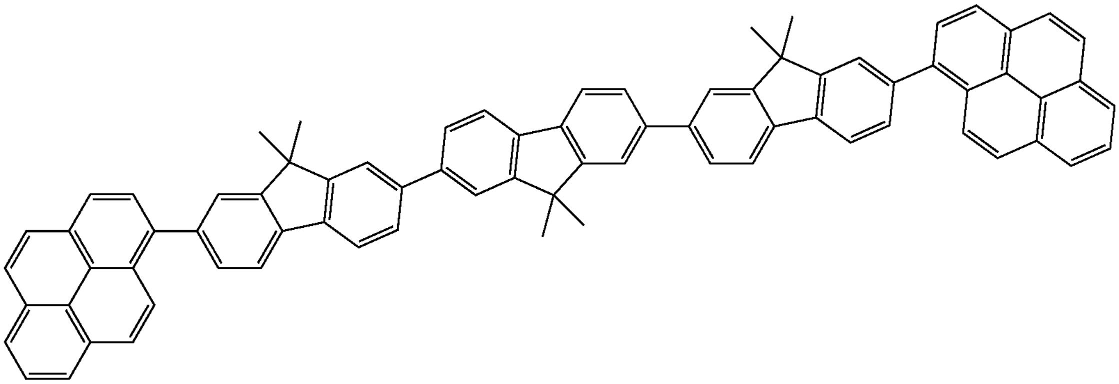

-continued
[Formula 58]
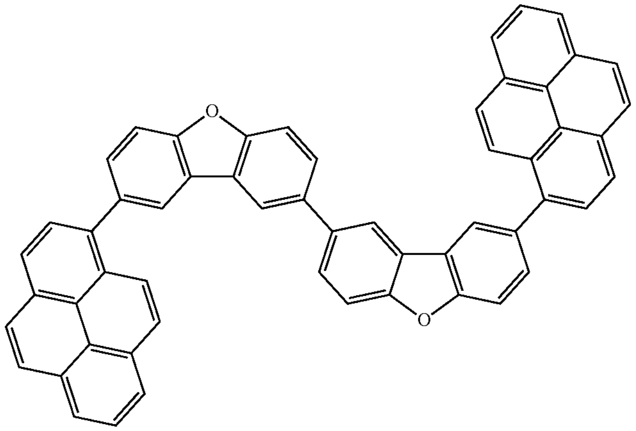
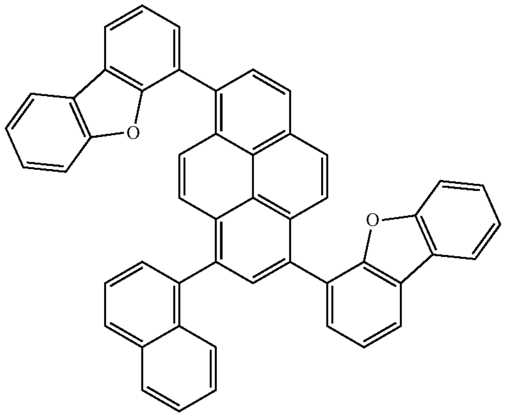
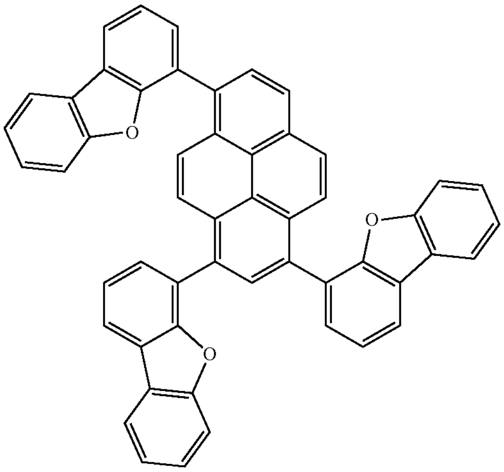
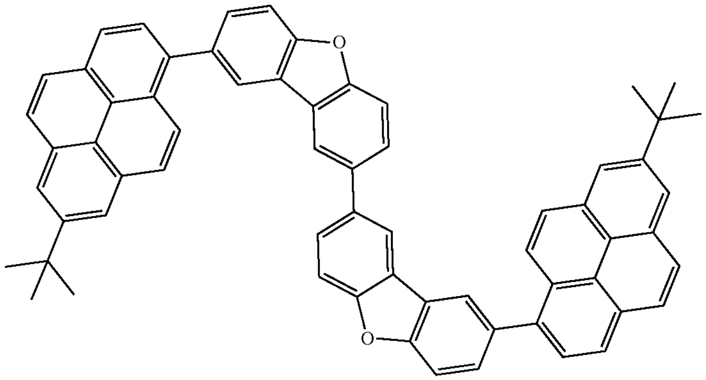
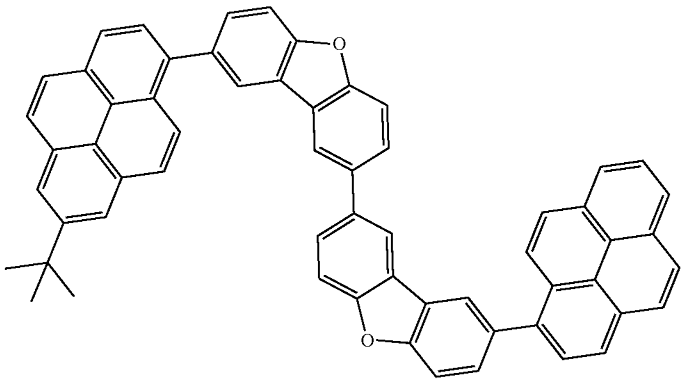

-continued
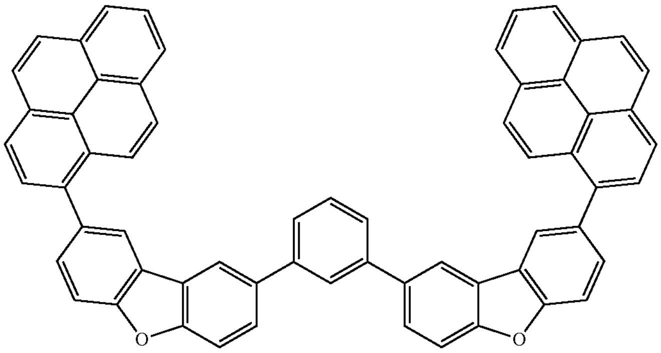
[Formula 59]
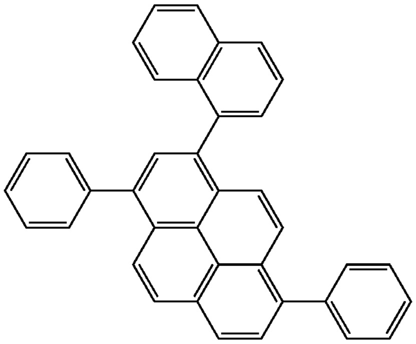
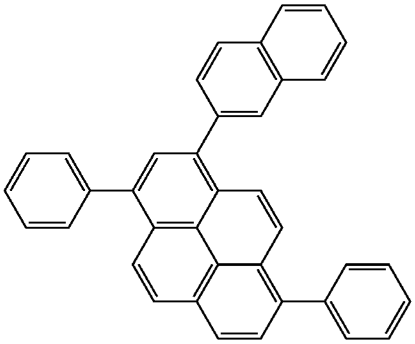
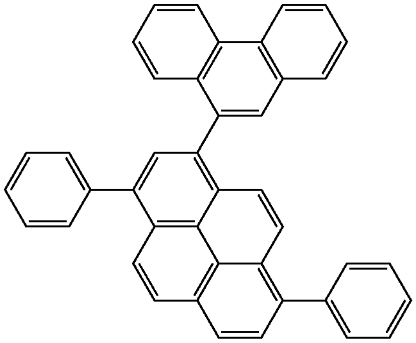
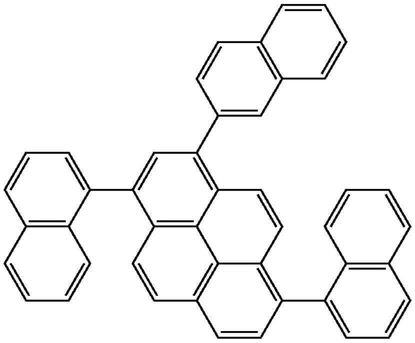
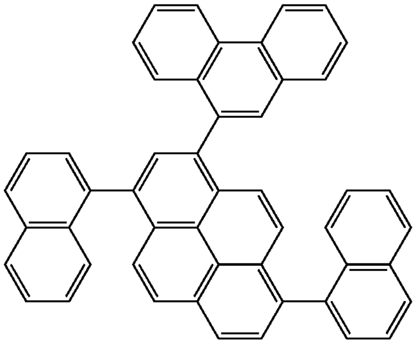
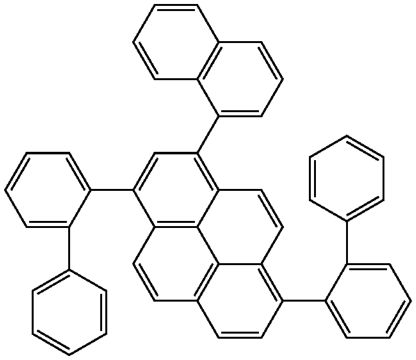

-continued
[Formula 60]
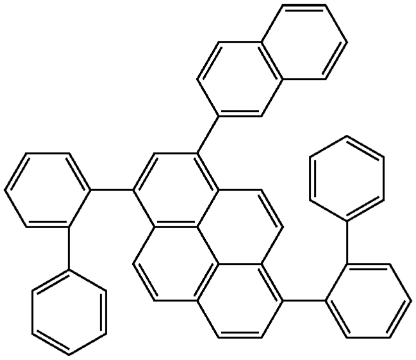
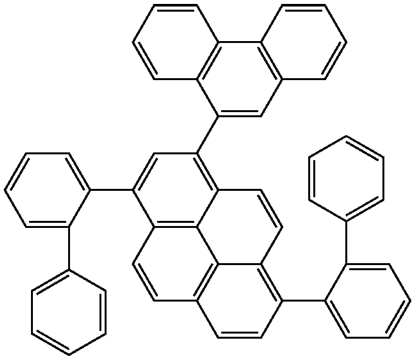
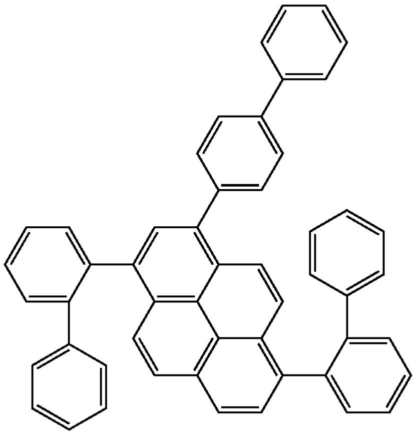
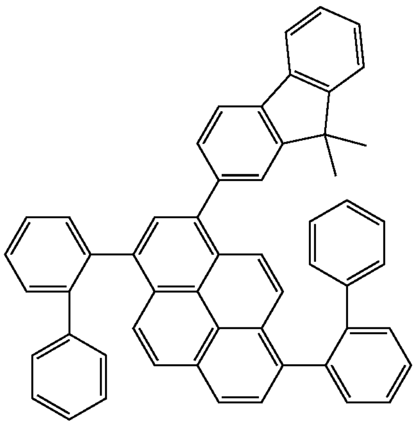
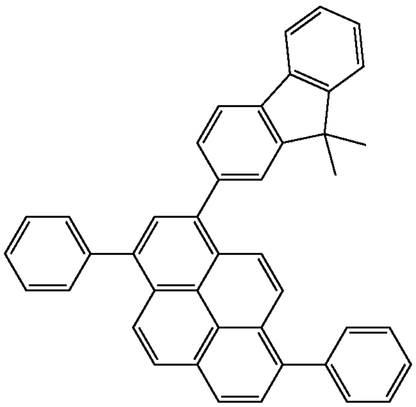
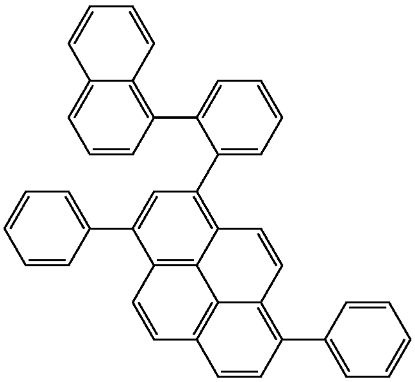
[Formula 61]
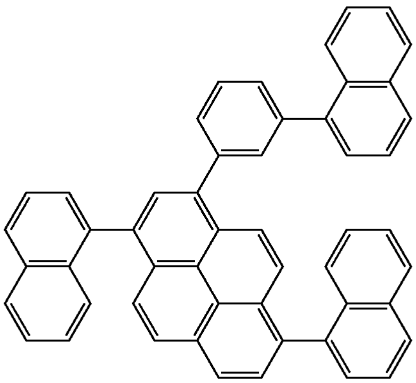
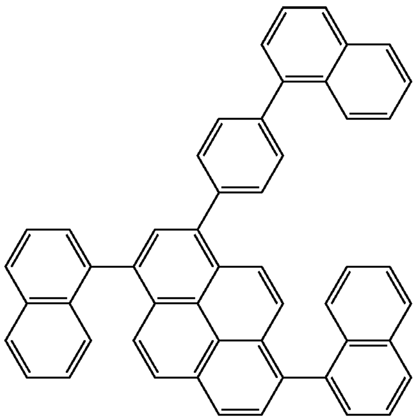

-continued
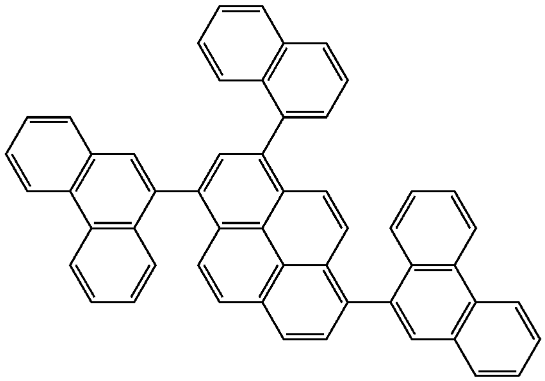
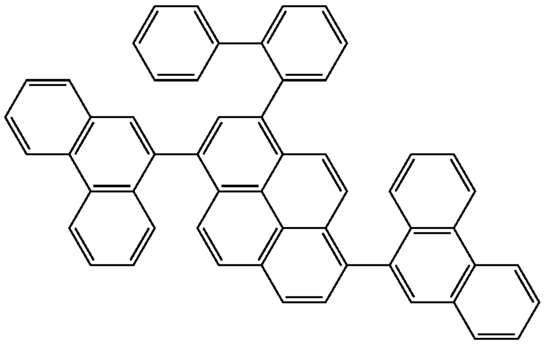
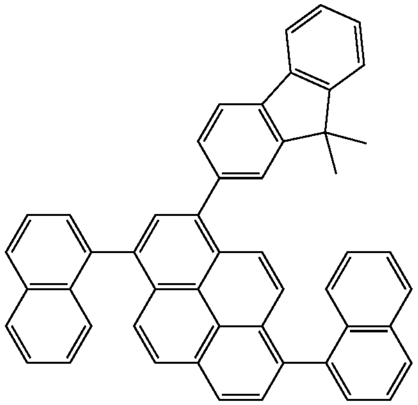
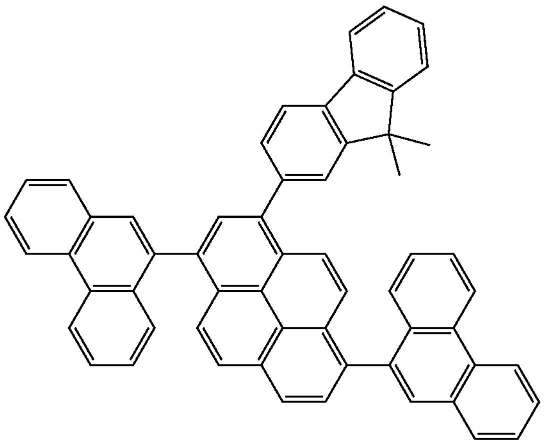
[Formula 62]
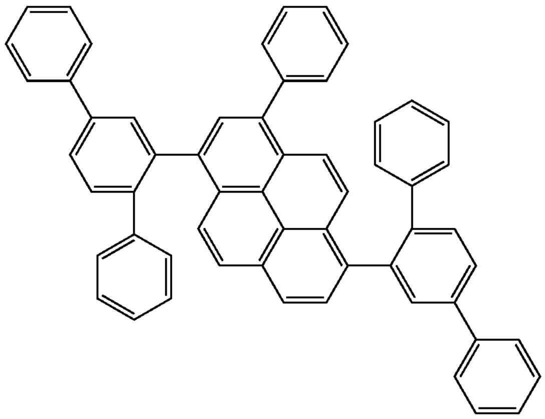
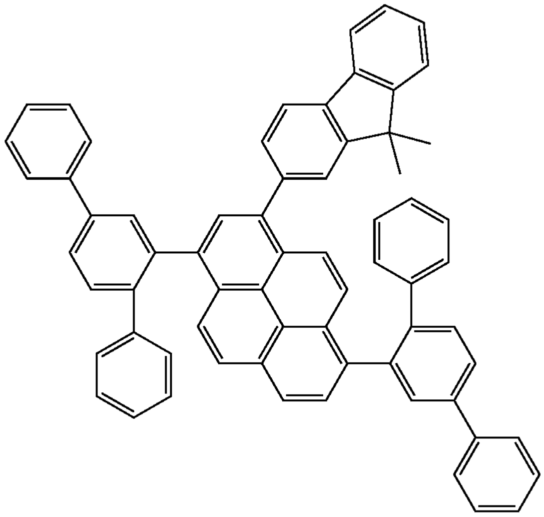

-continued
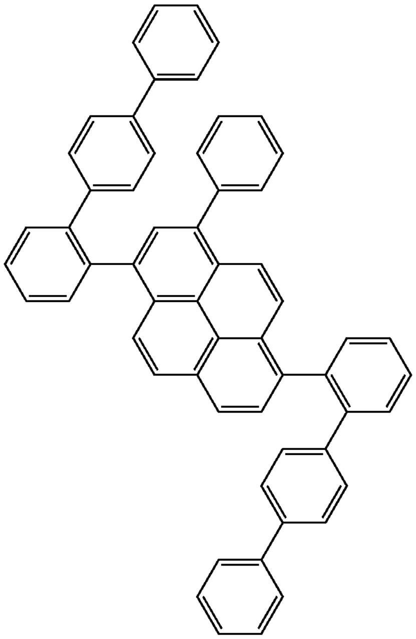
[Formula 63]
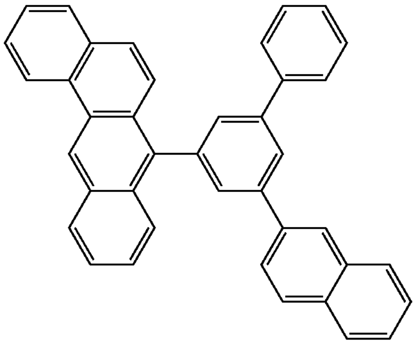
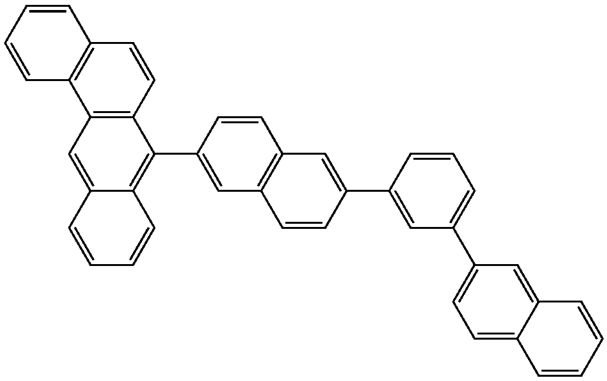
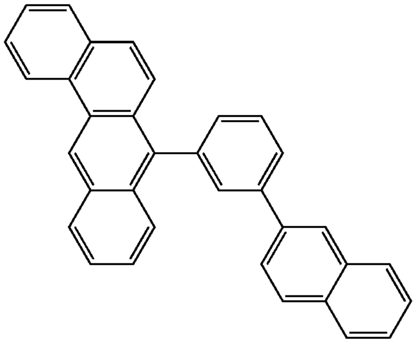
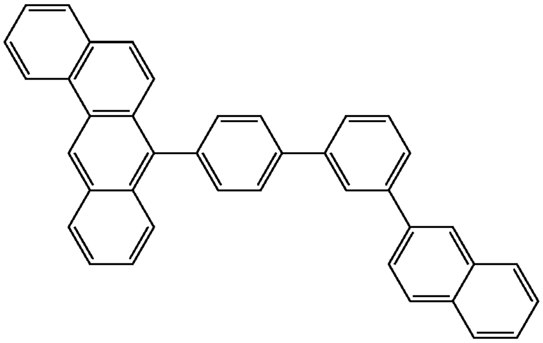

-continued
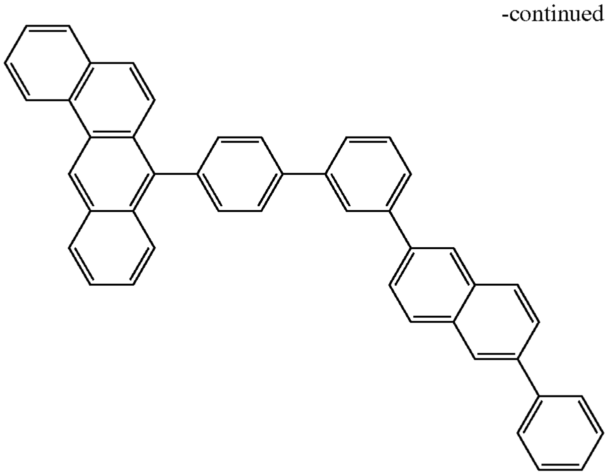
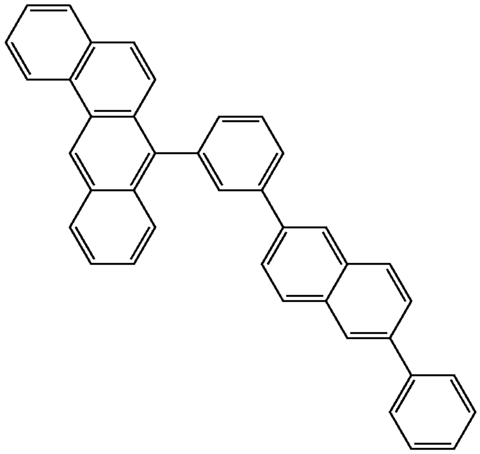
[Formula 64]
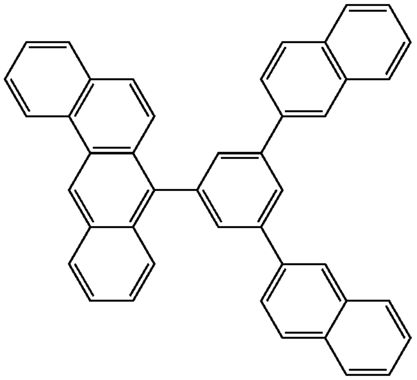
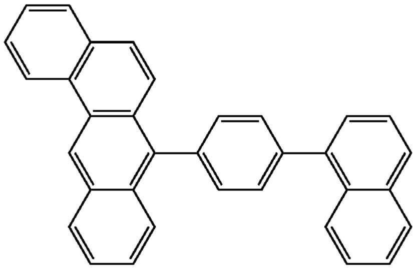
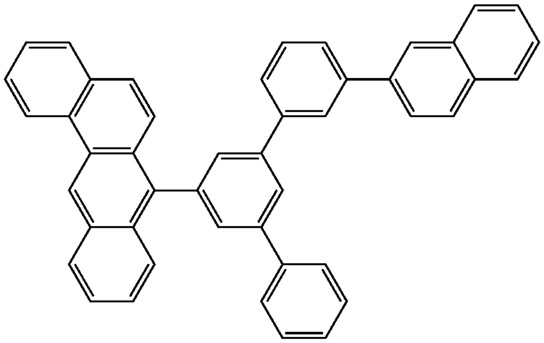
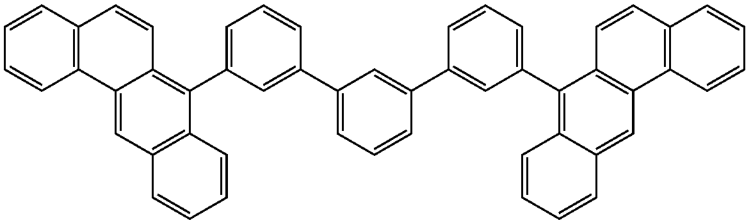
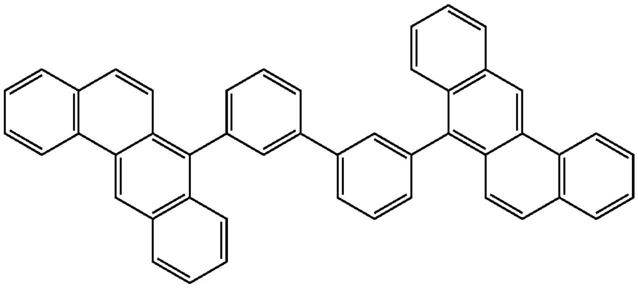

-continued
[Formula 65]
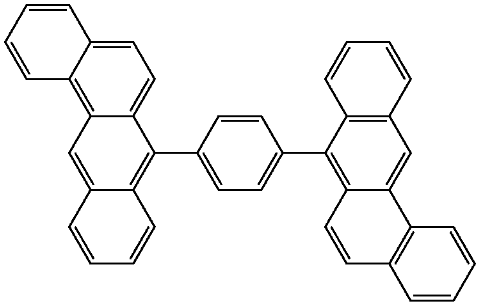
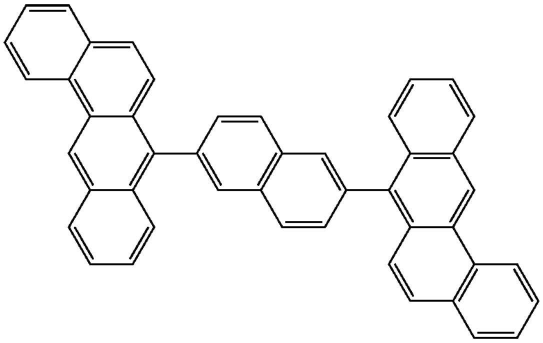
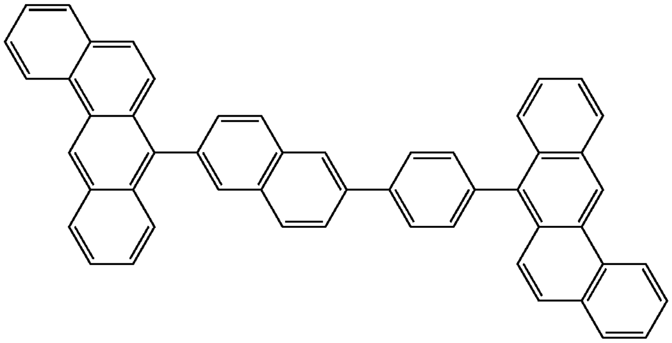
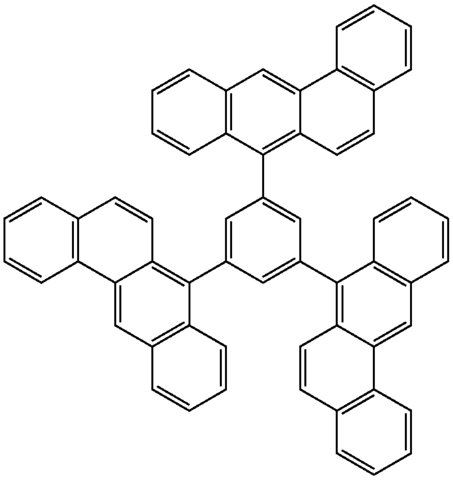
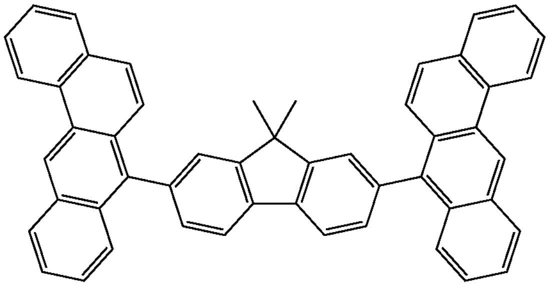
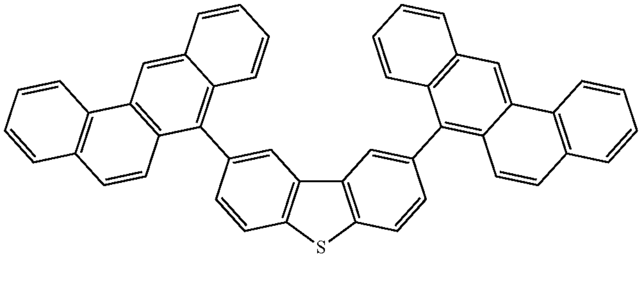

-continued
[Formula 66]
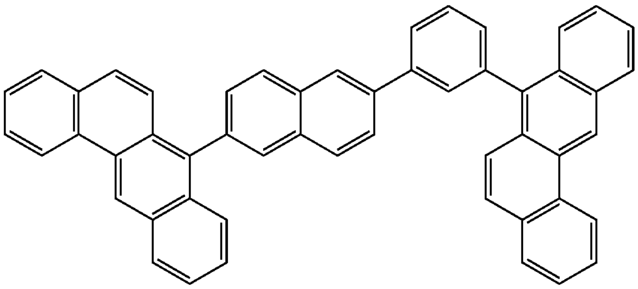
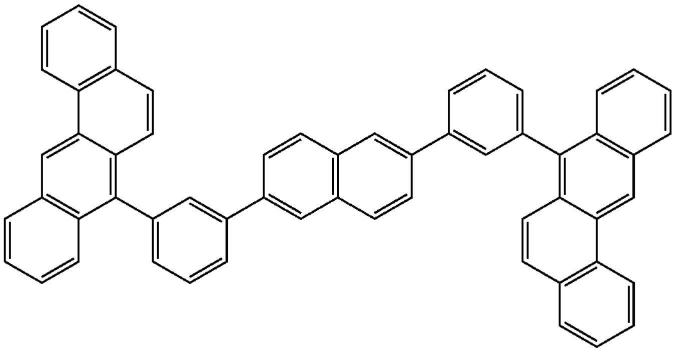
[Formula 67]
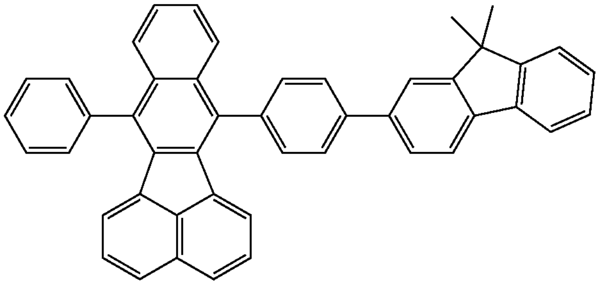
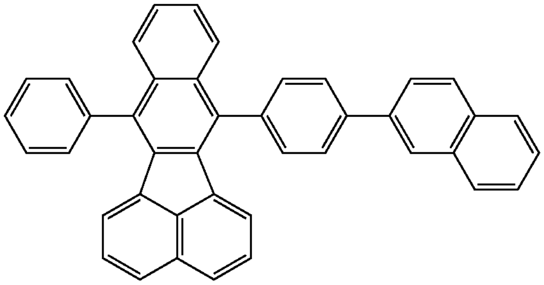
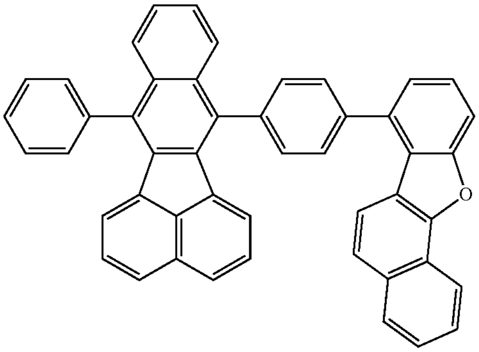
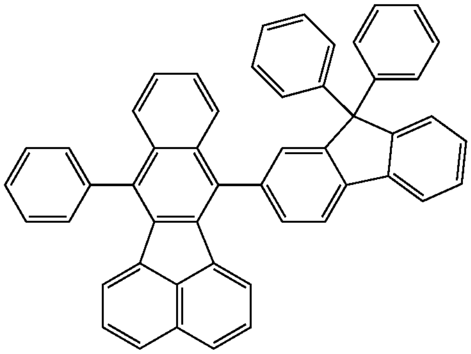
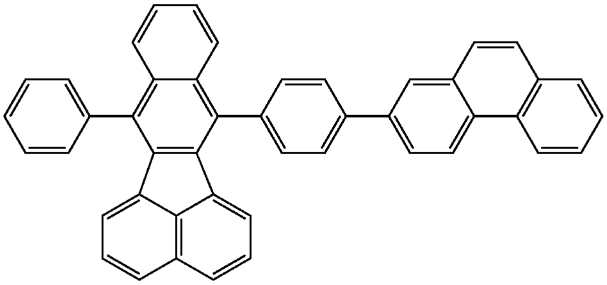

-continued
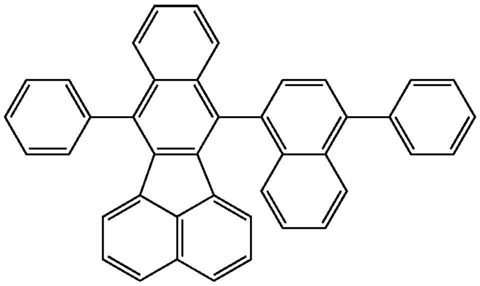
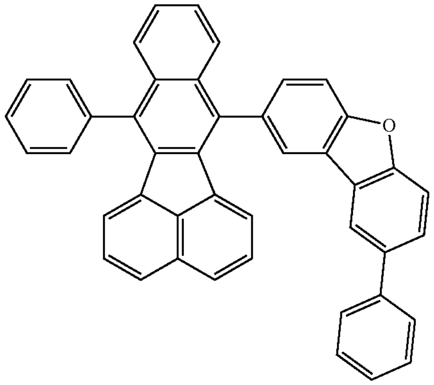
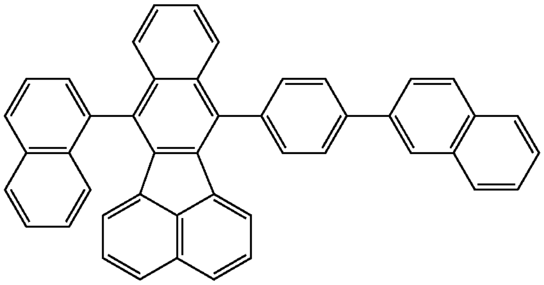
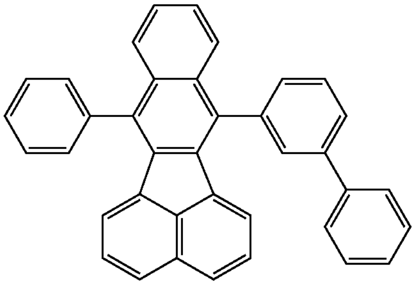
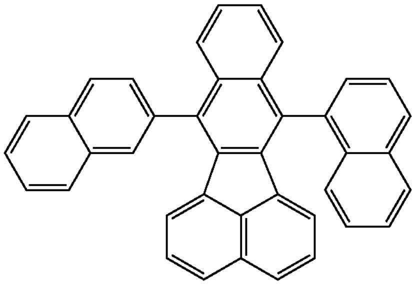
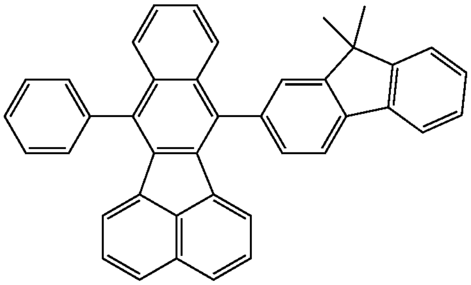
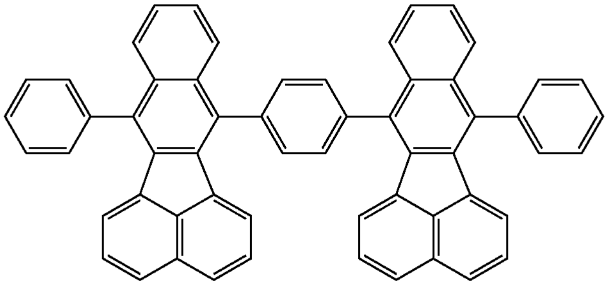
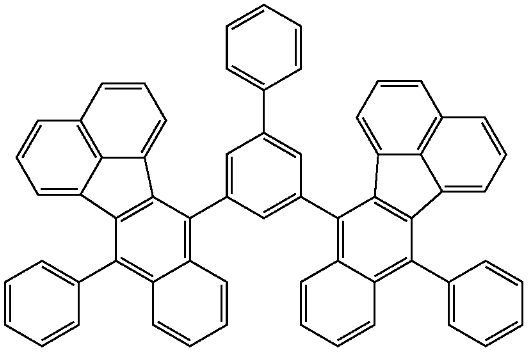
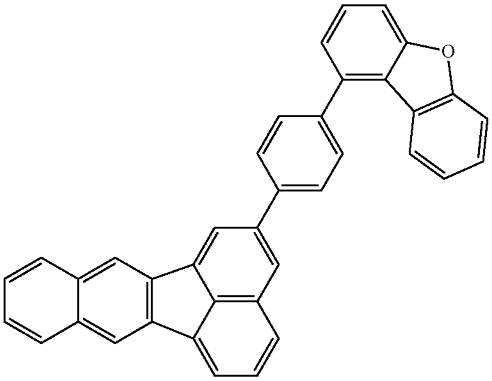

-continued
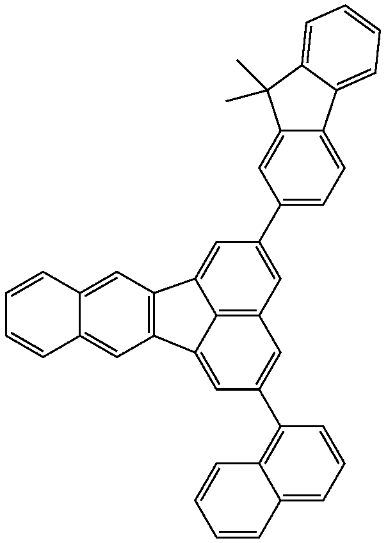
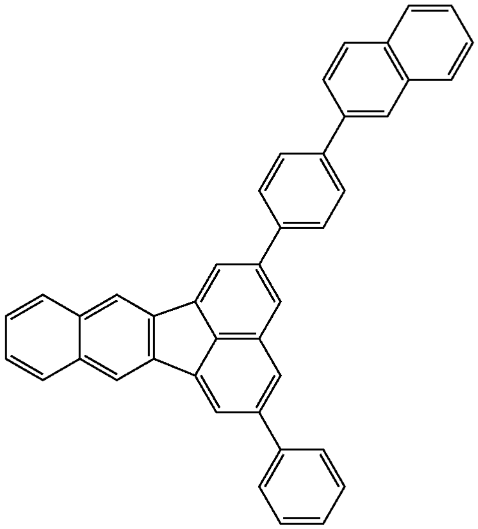
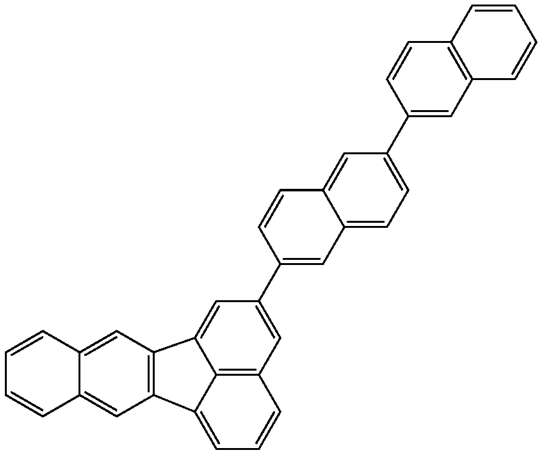
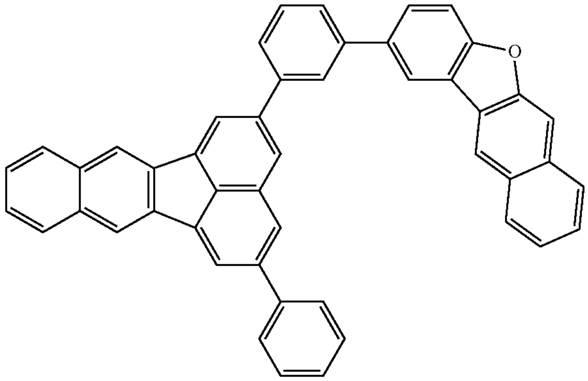
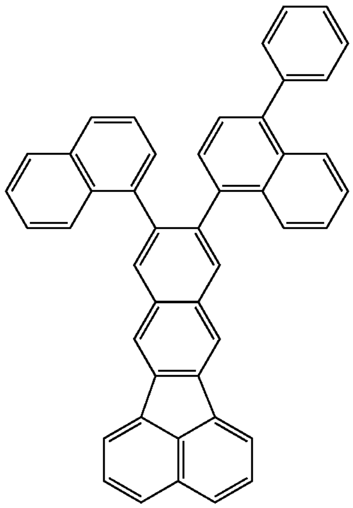
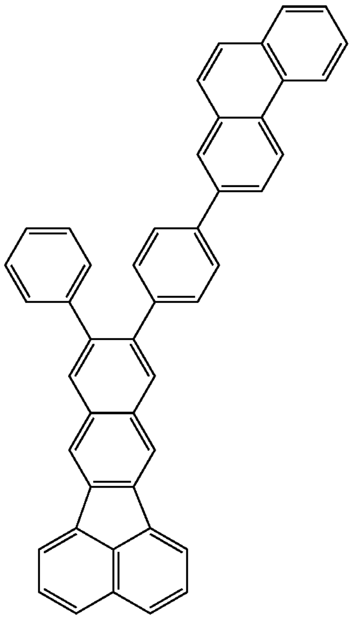

-continued
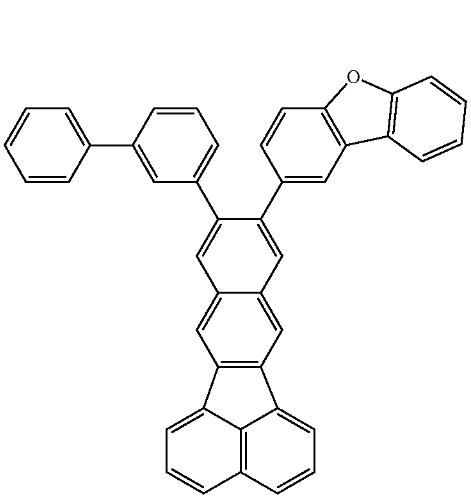
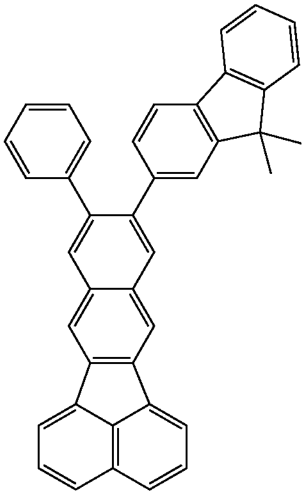
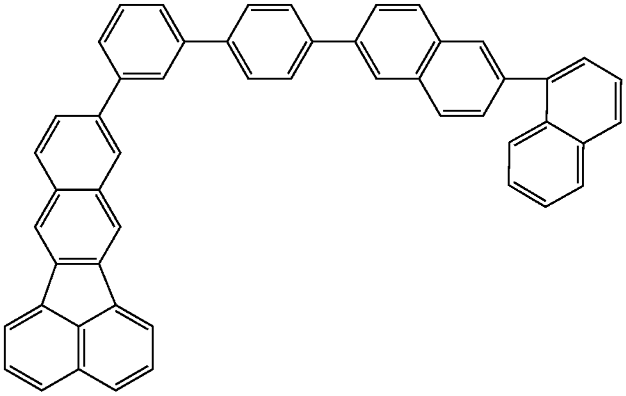
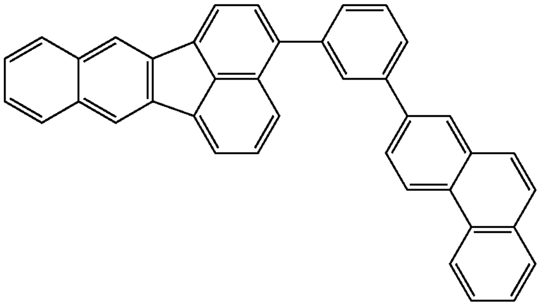
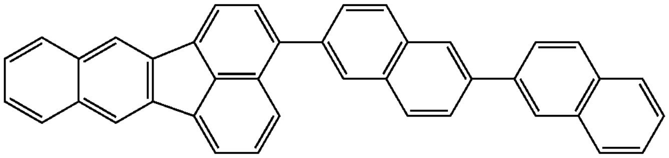
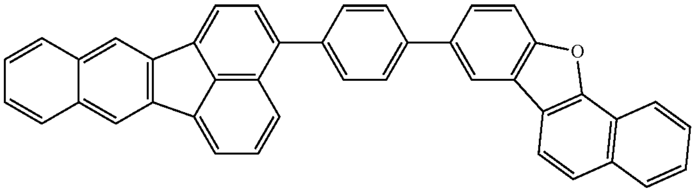

-continued
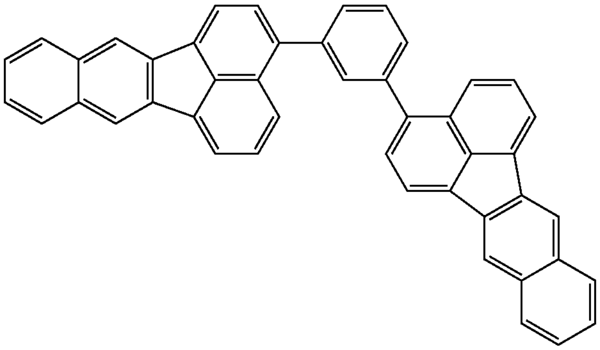
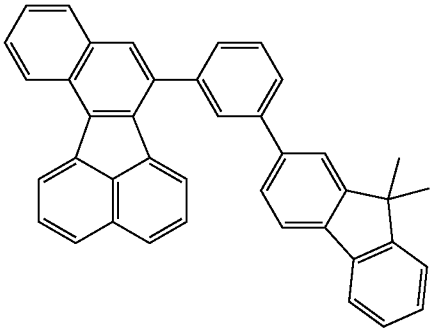
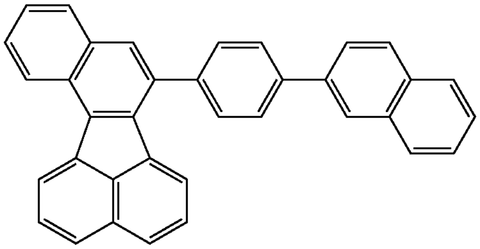
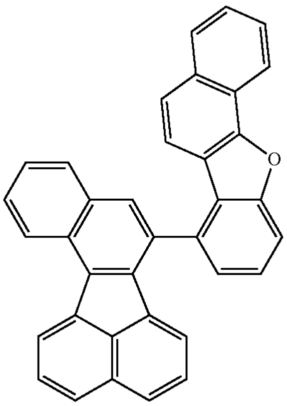
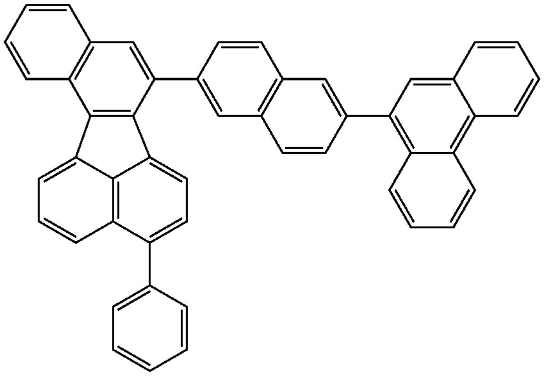
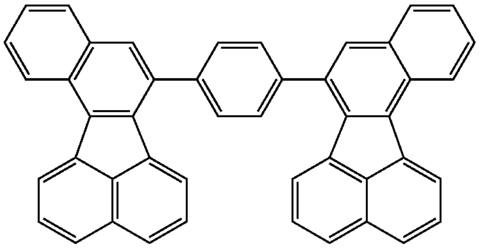
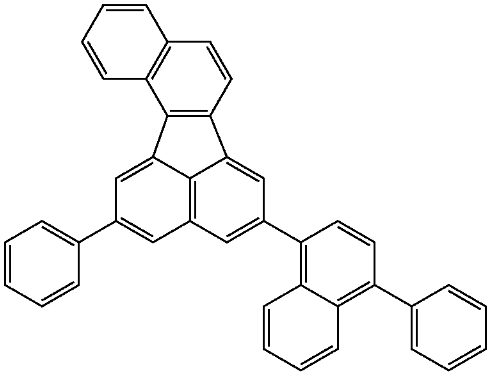
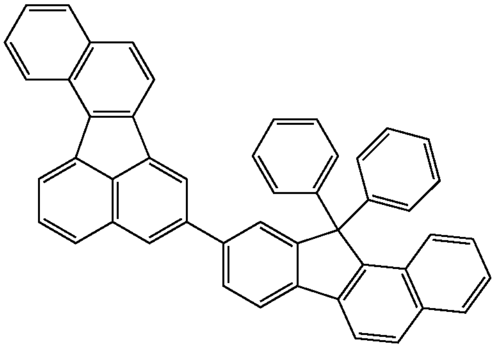

-continued
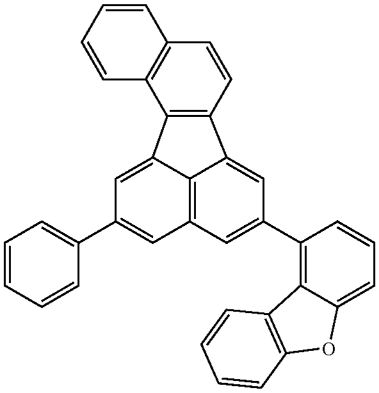
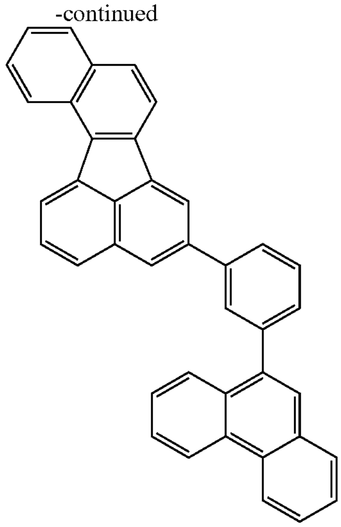
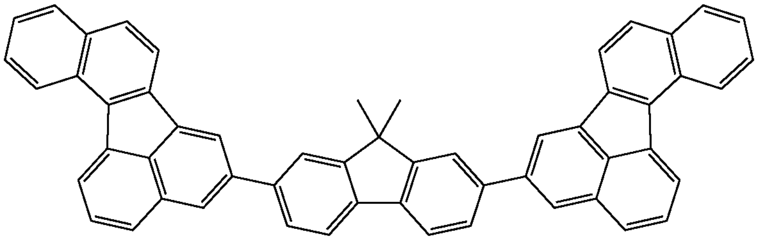
[Formula 68]
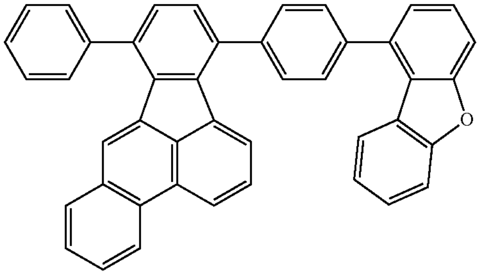
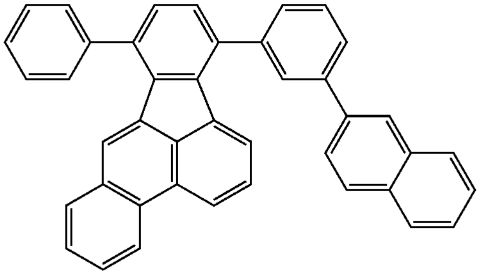
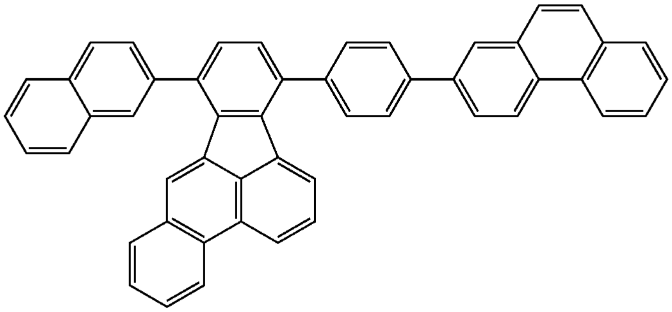
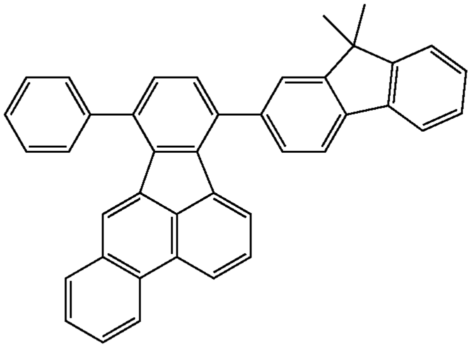
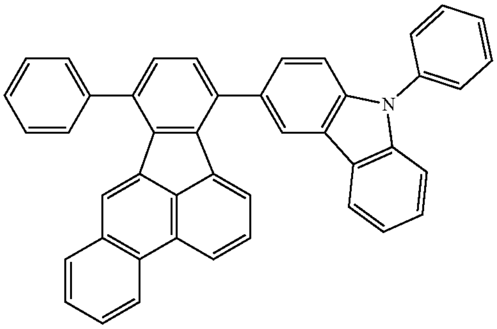

-continued
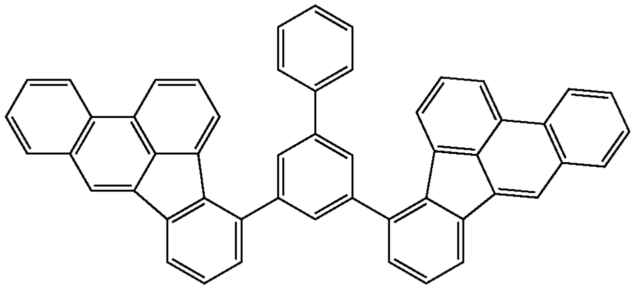
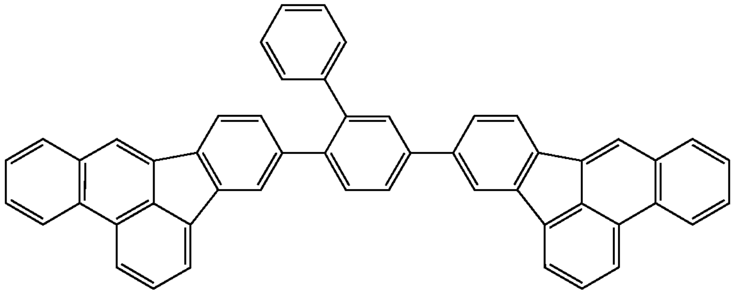
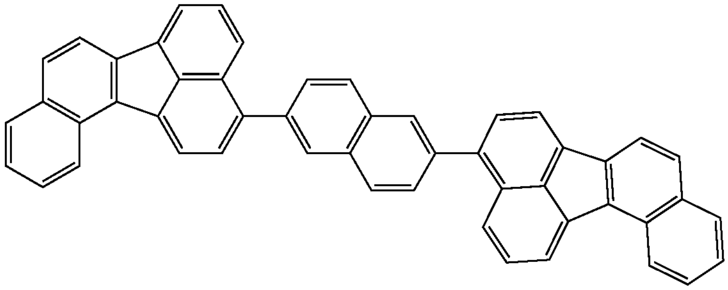
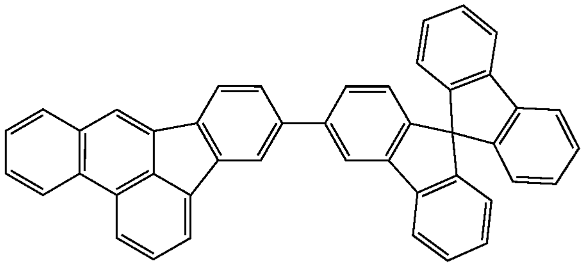
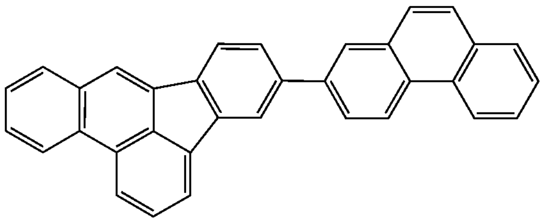
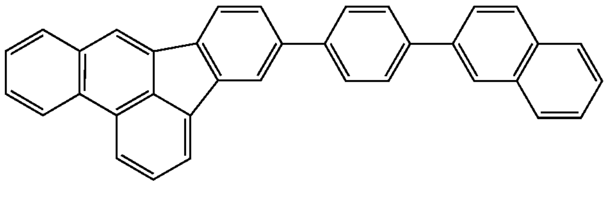

-continued
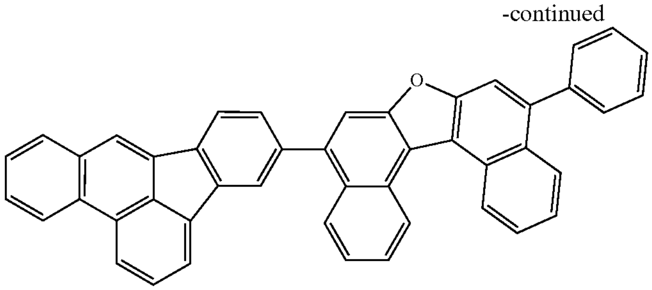
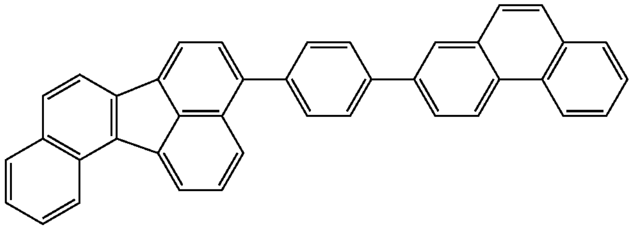
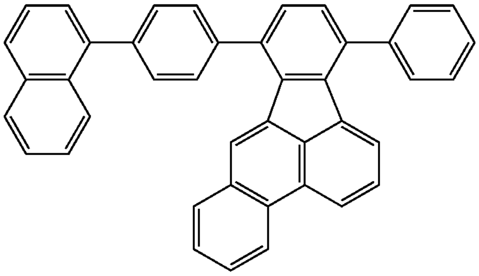
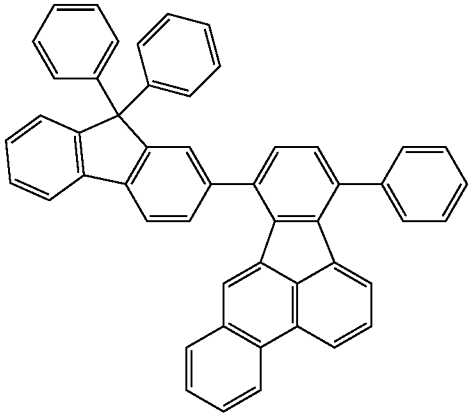
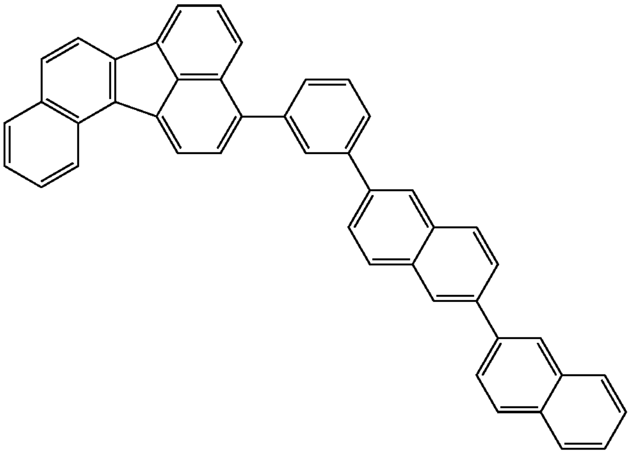
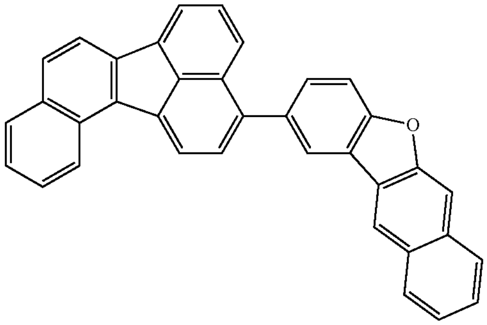
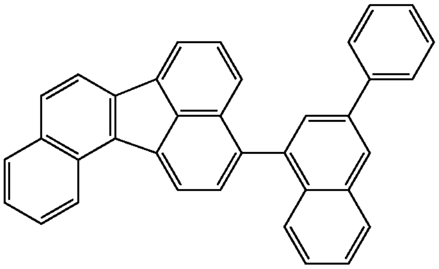
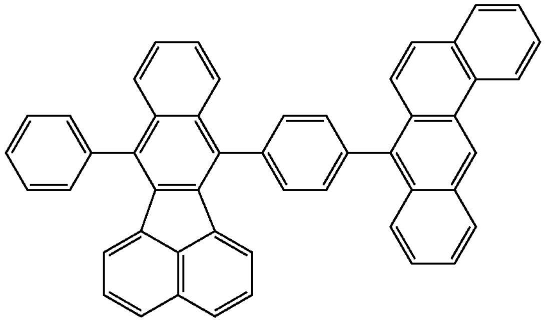
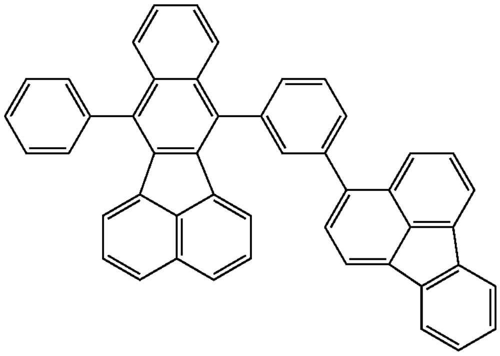

-continued
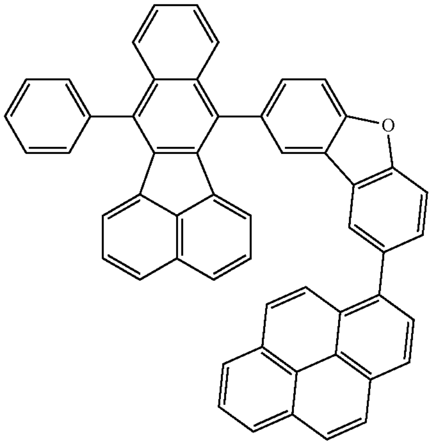
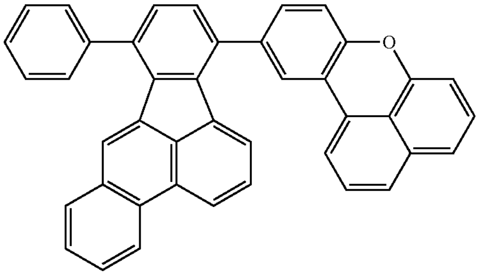
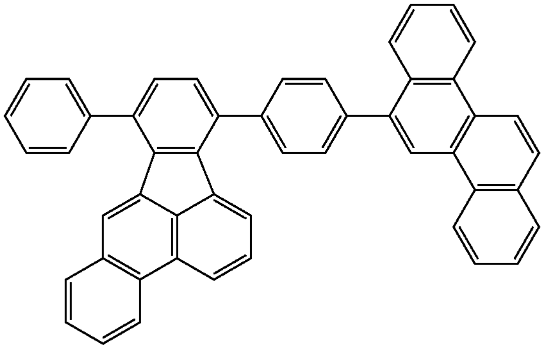
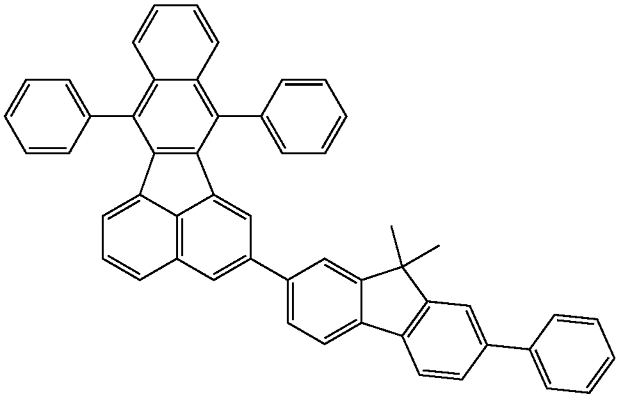
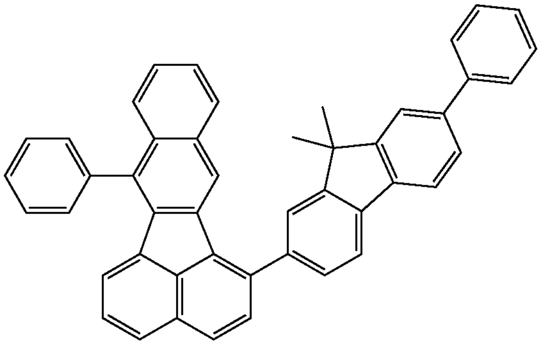
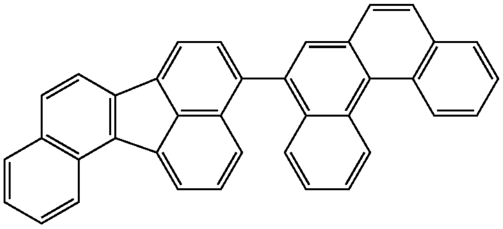

-continued
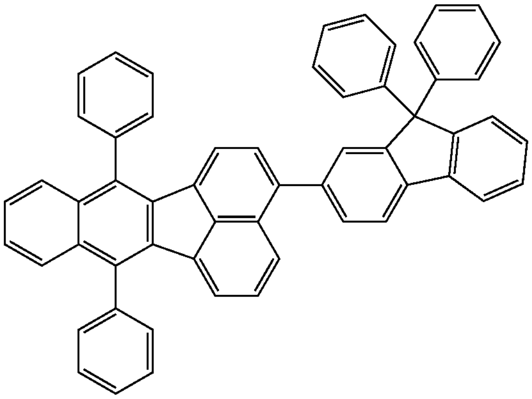
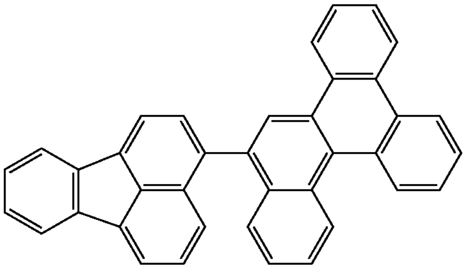
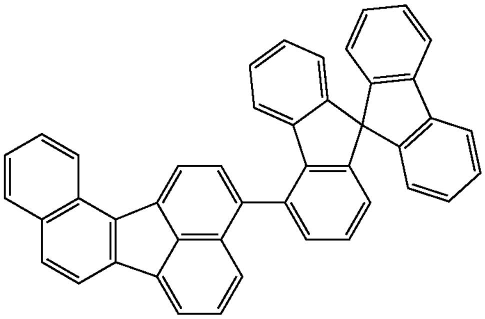
[Formula 69]
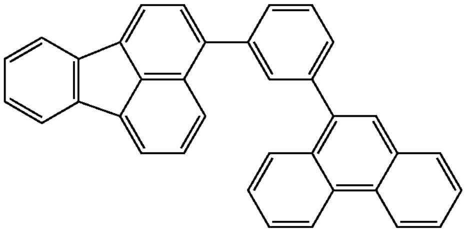
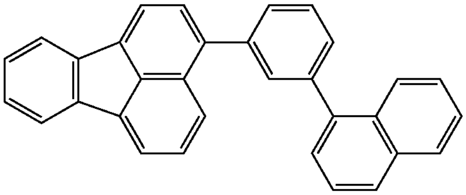
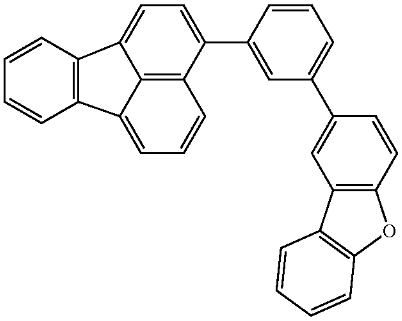
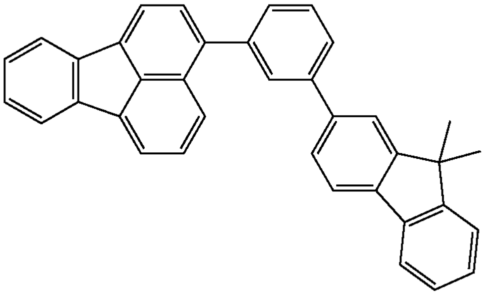
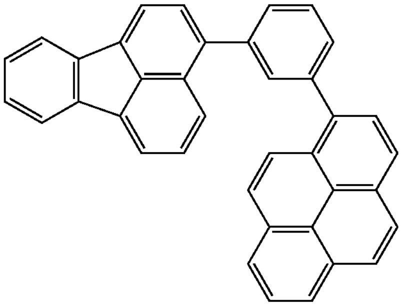
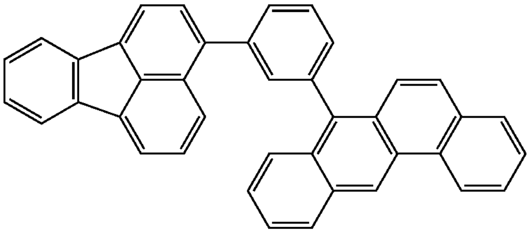

-continued
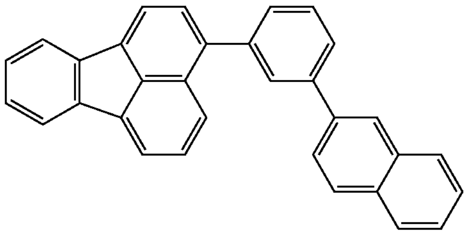
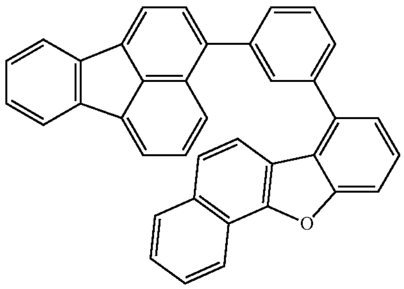
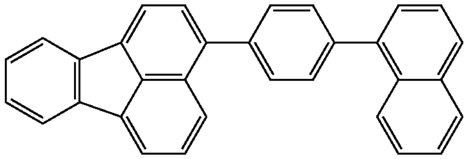
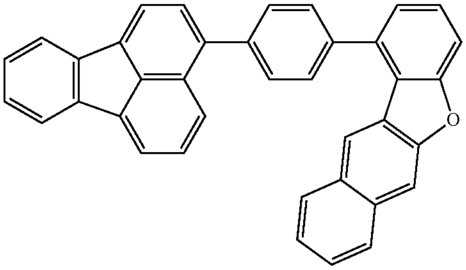
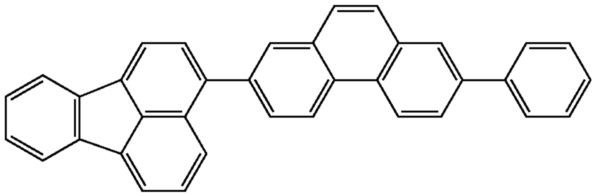
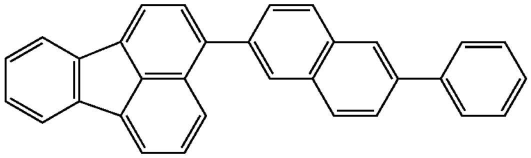
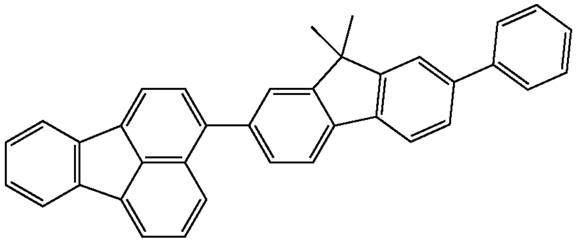
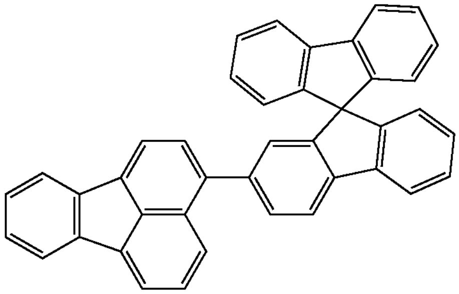
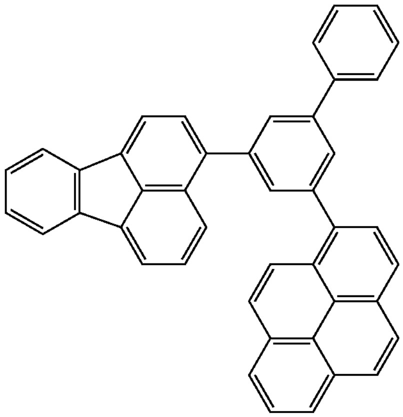
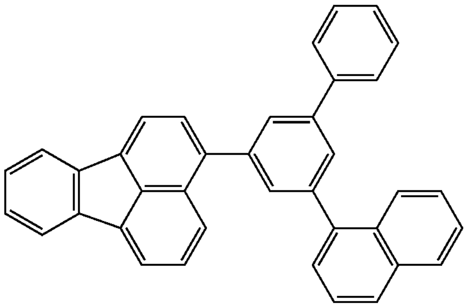

-continued
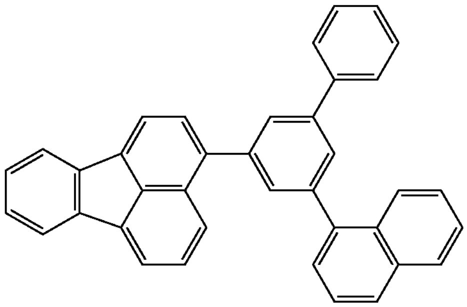
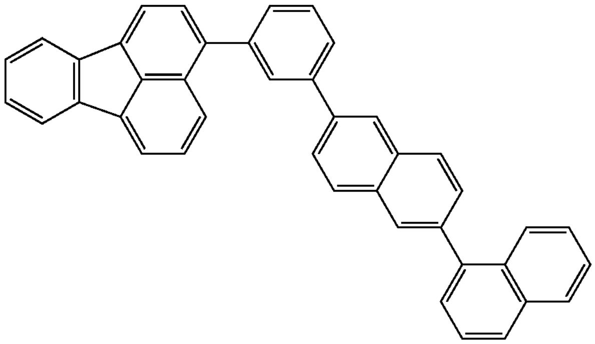
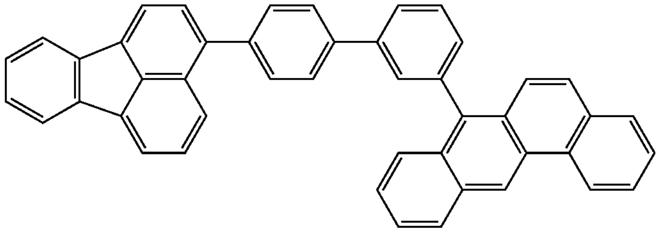
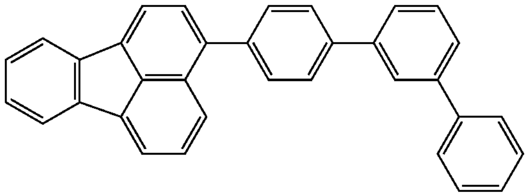
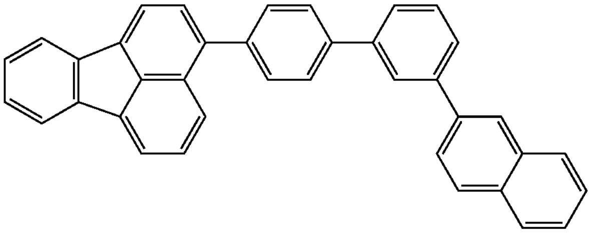
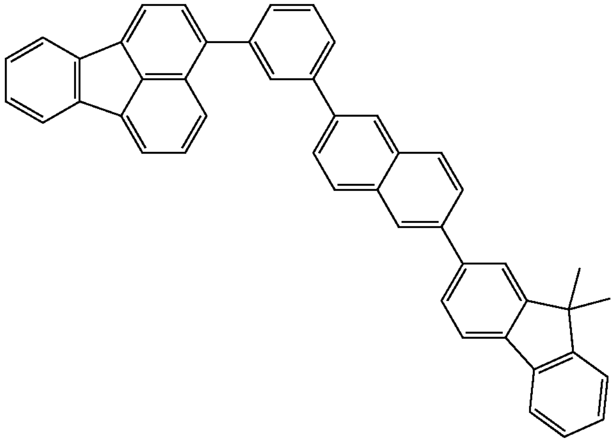
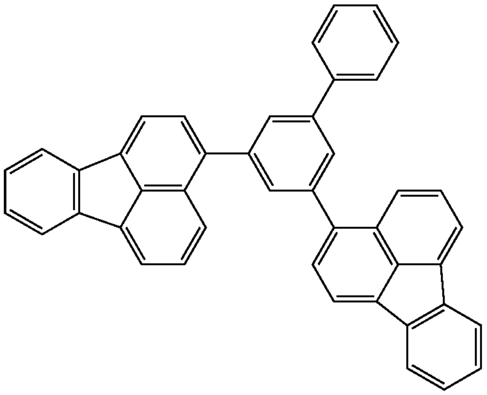
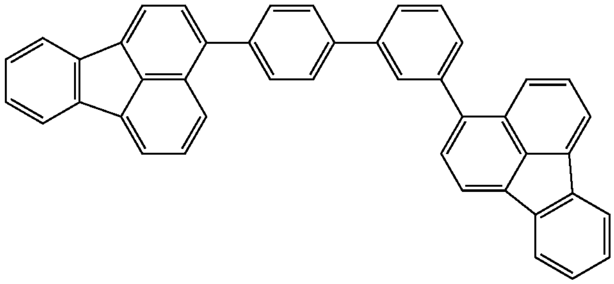
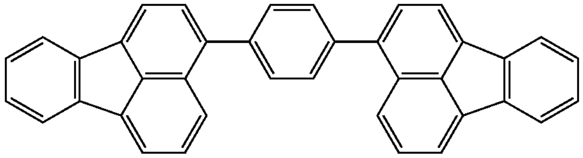

-continued
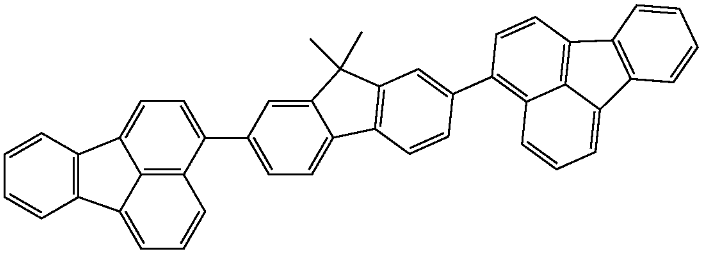
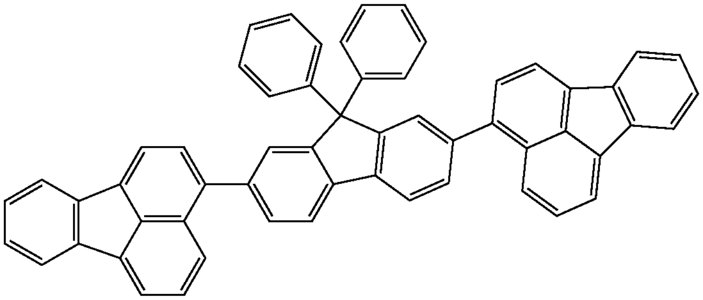
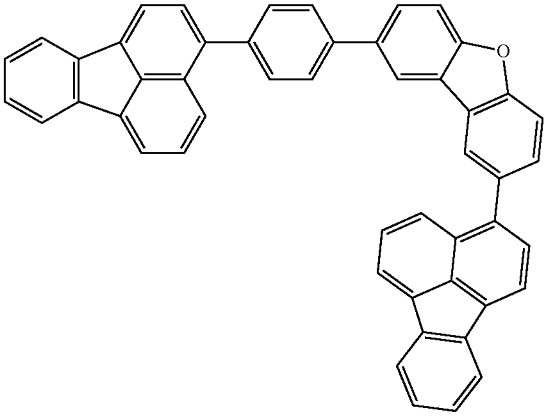
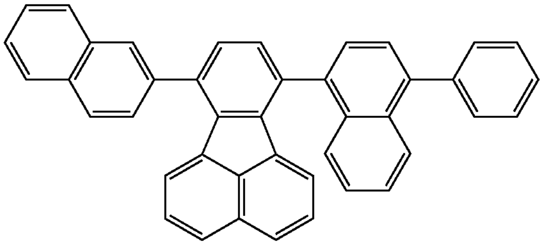
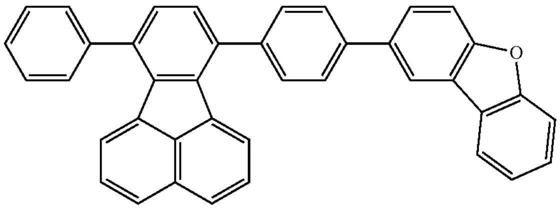
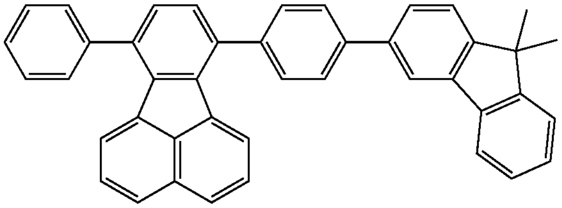
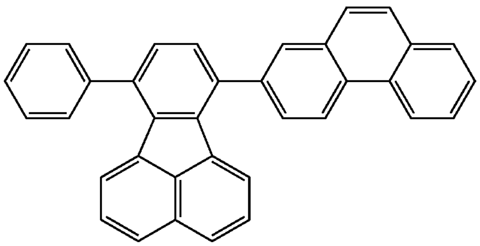
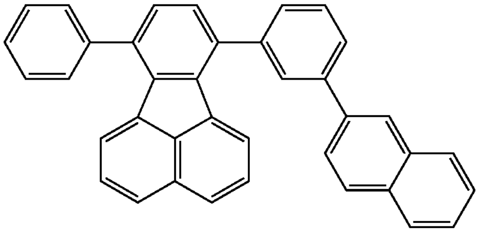
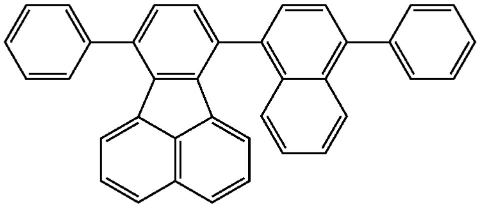
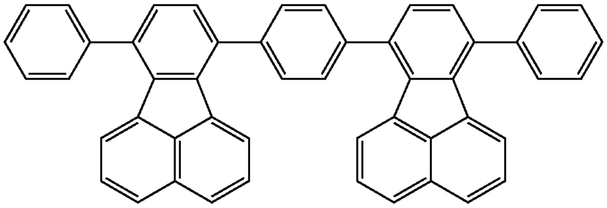

-continued
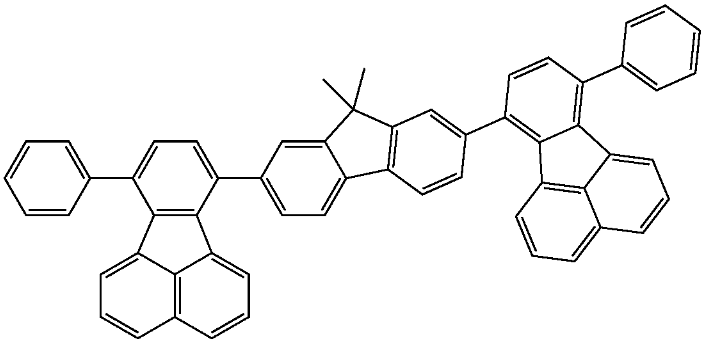
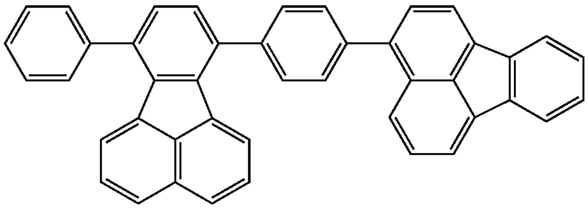
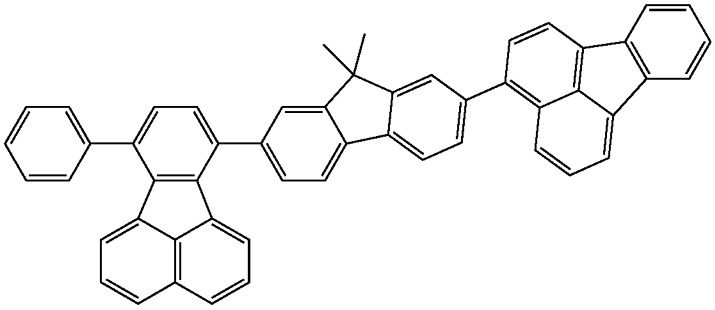
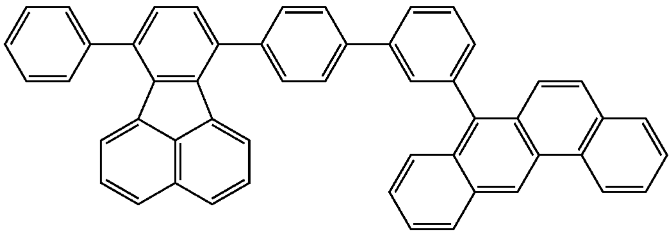
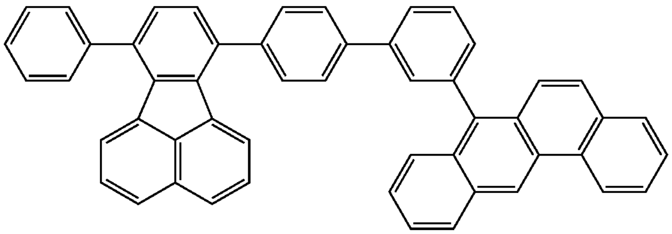
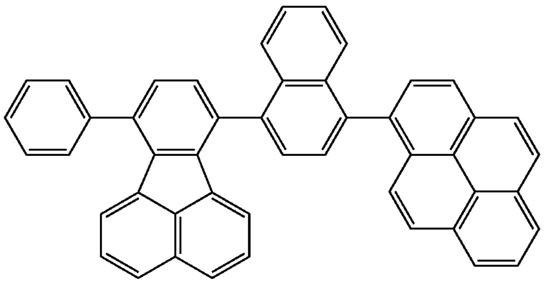
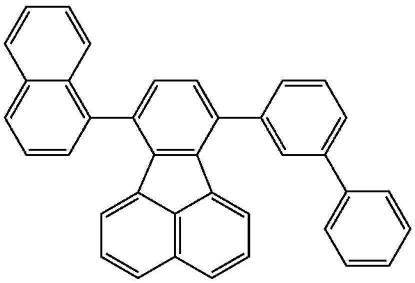

-continued
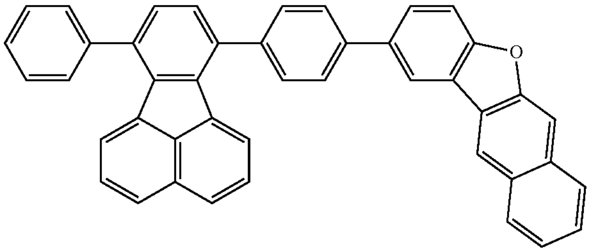
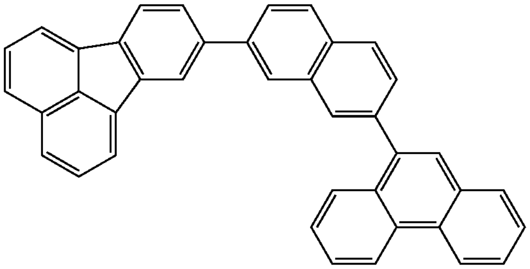
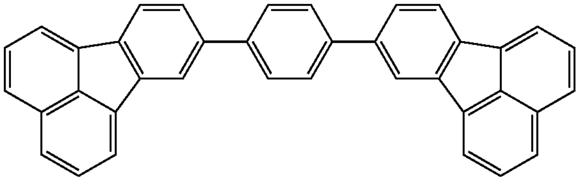
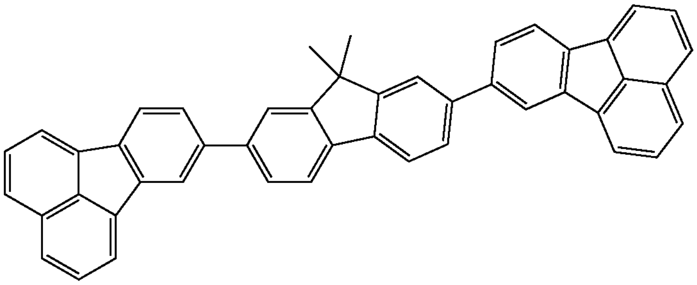
[Formula 70]
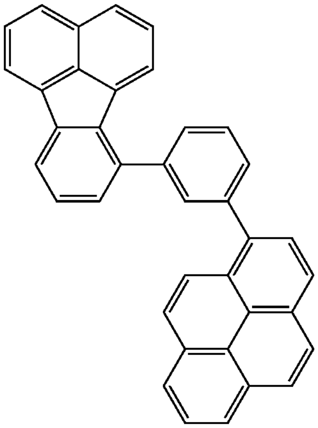
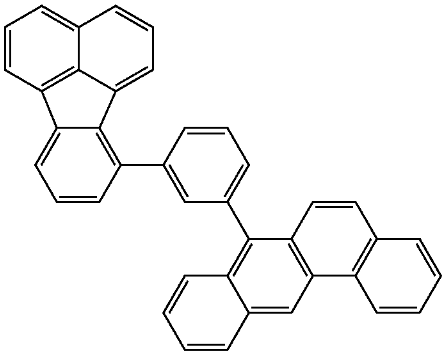
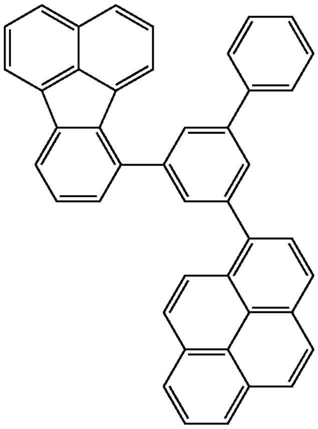
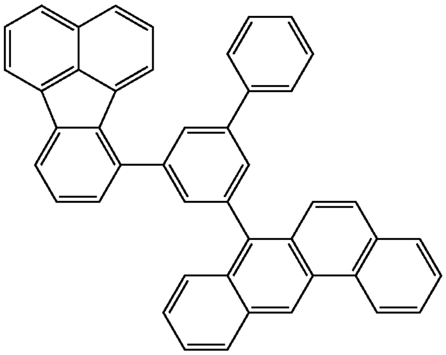

-continued
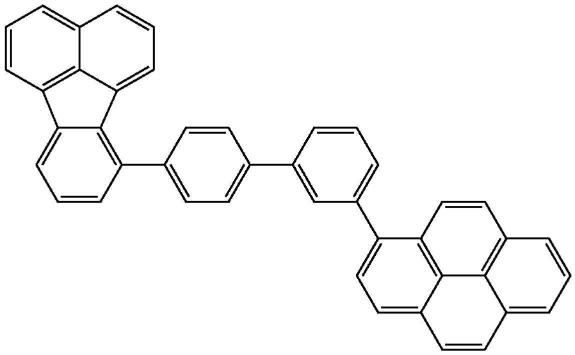
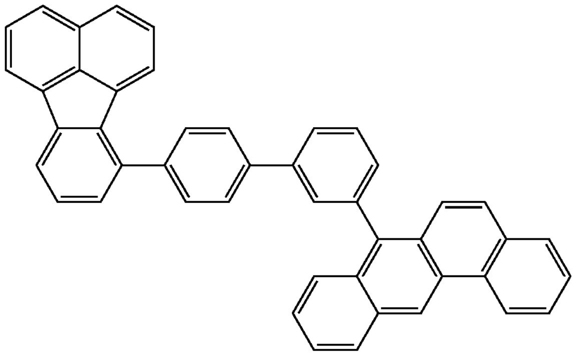
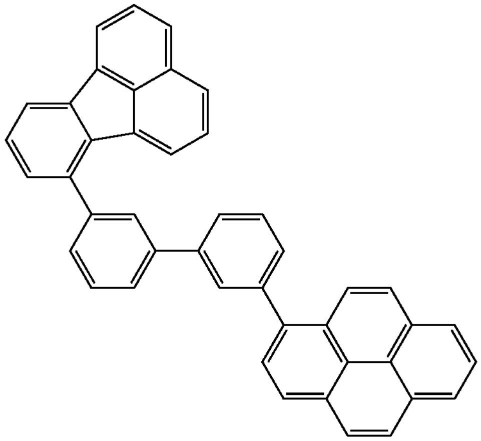
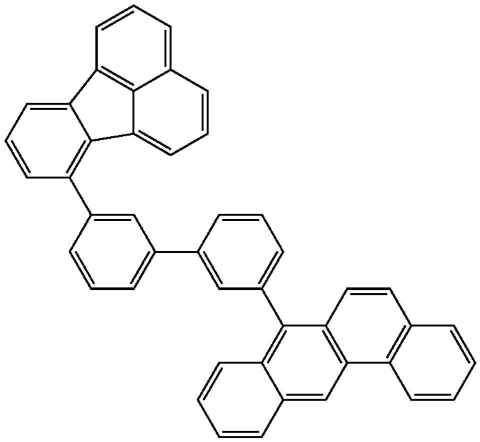
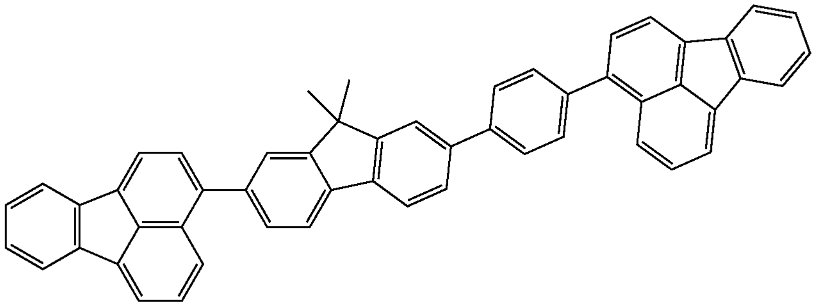

-continued
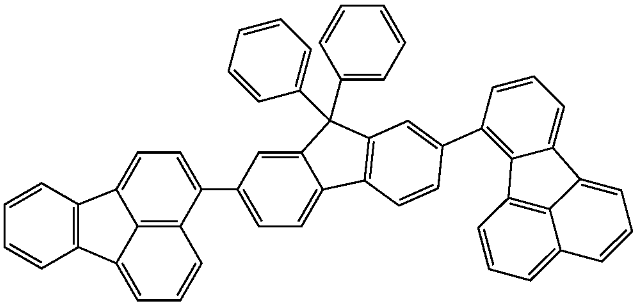
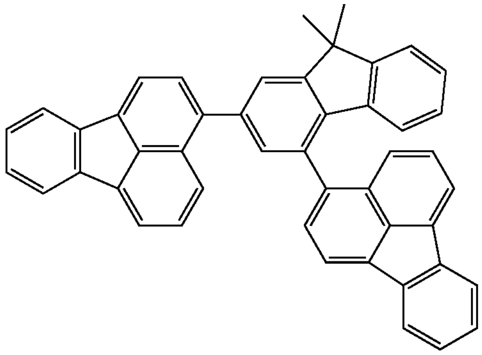
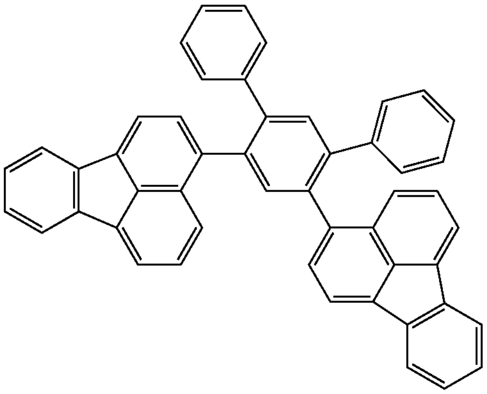
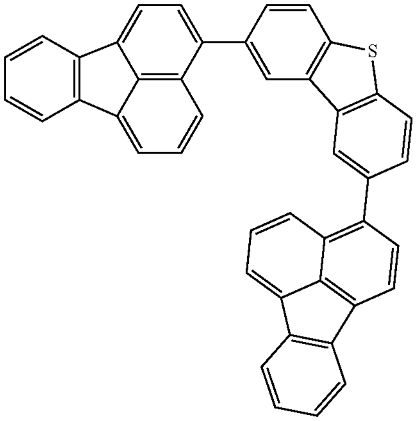
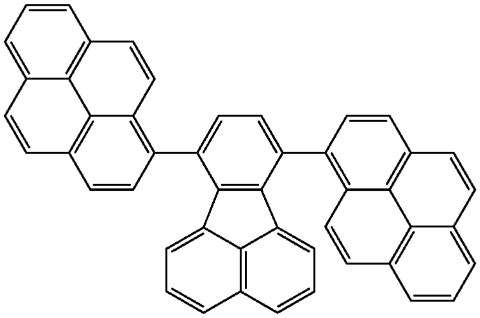
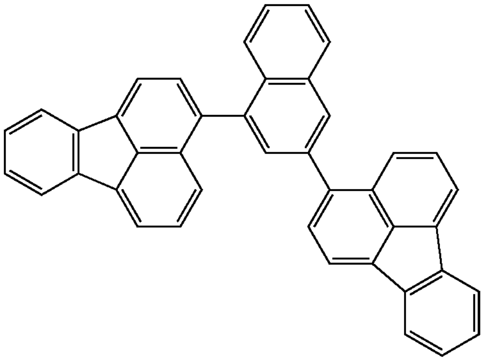
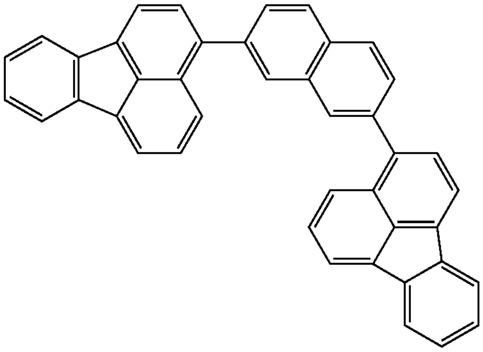
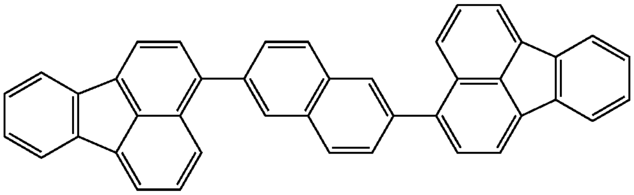

-continued
[Formula 71]
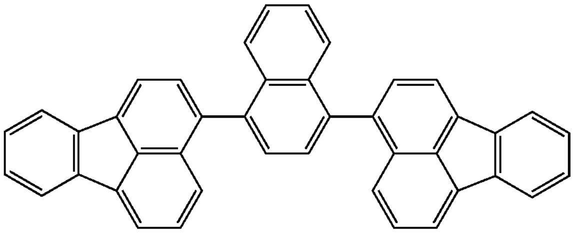
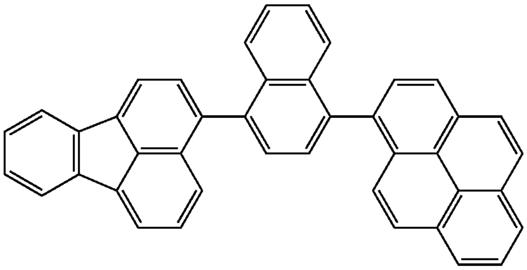
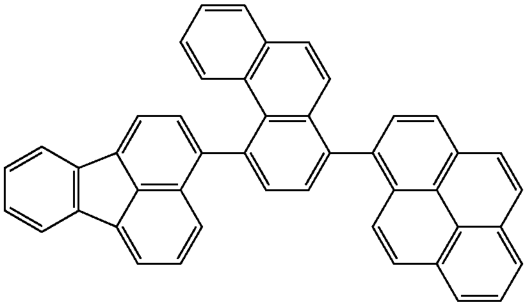
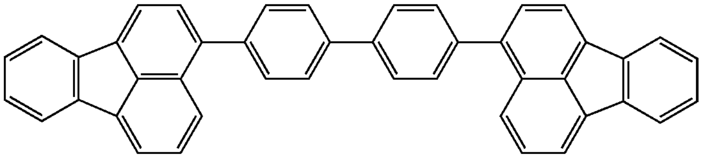
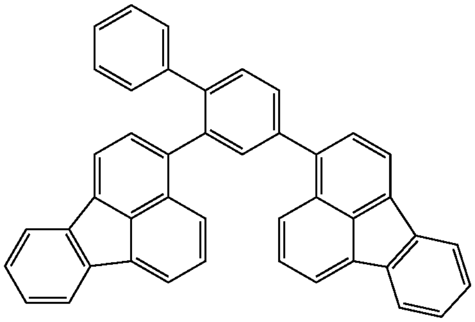
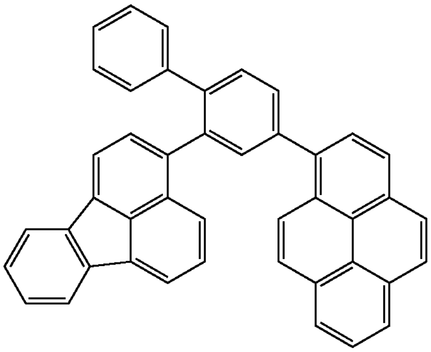
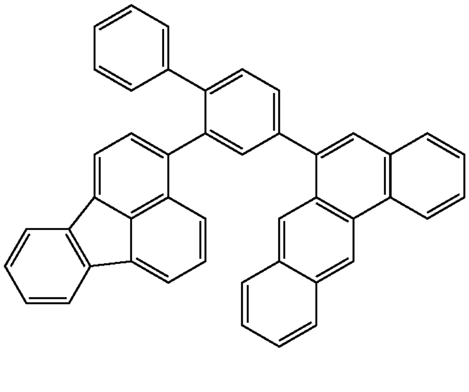
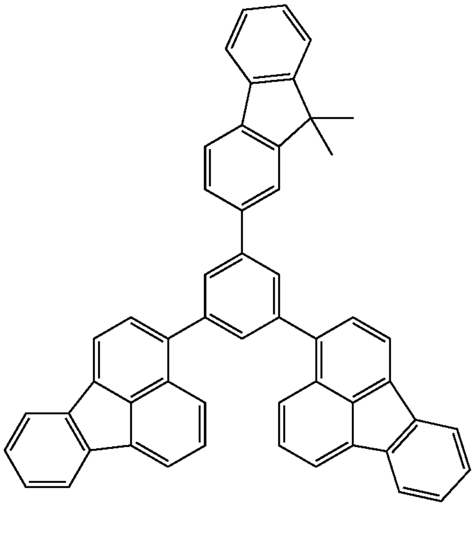

-continued
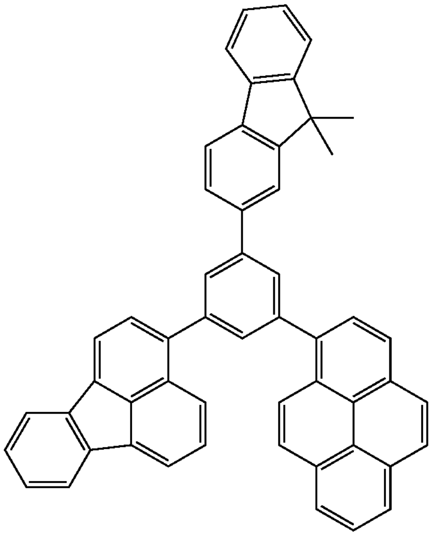
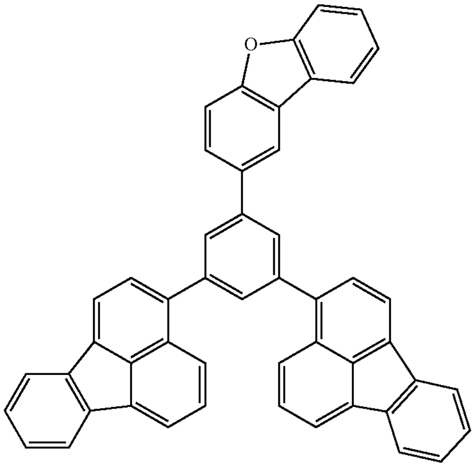
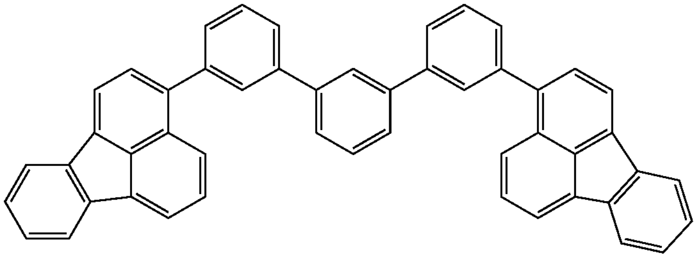
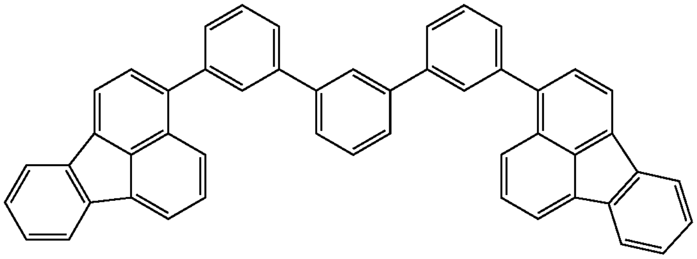
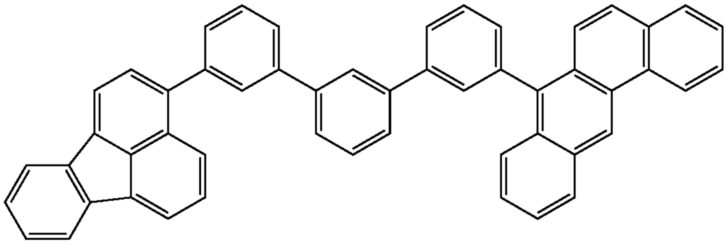
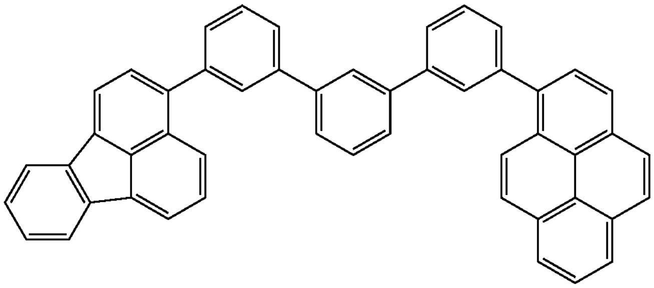

-continued
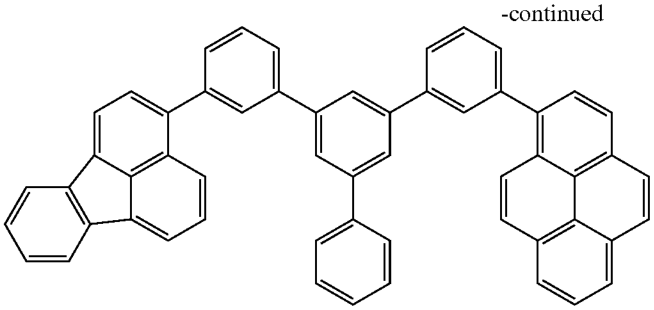
[Formula 72]
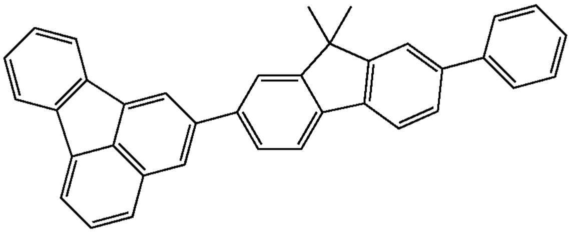
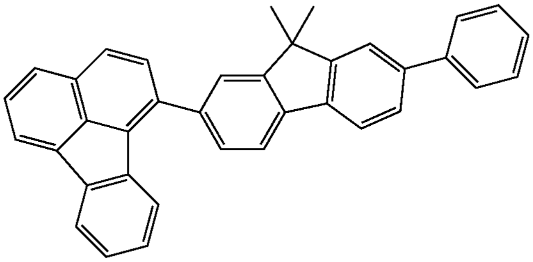
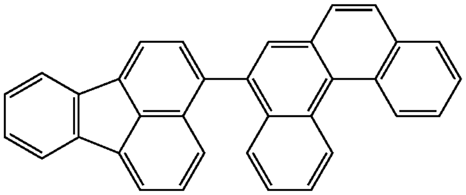
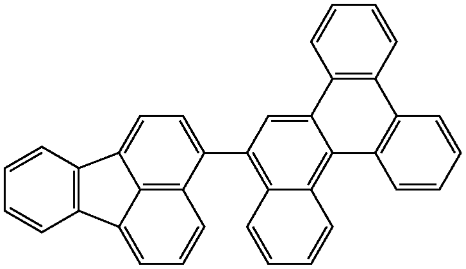
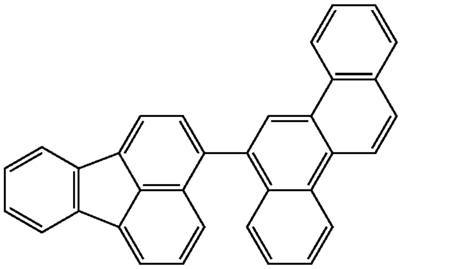
-continued
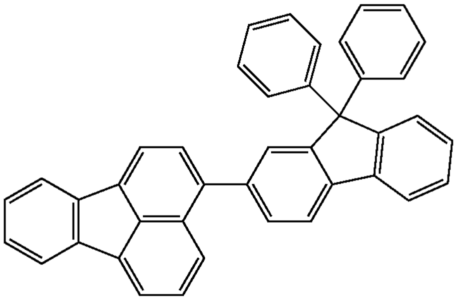
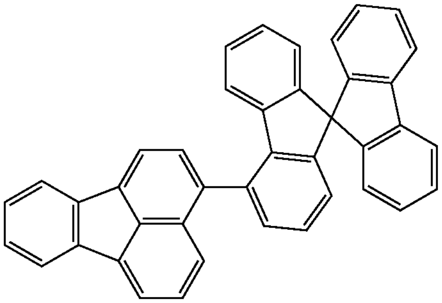
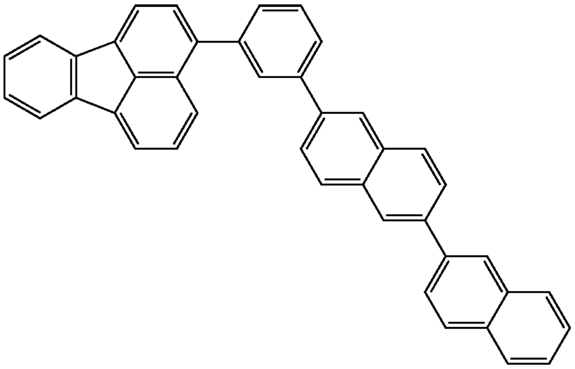
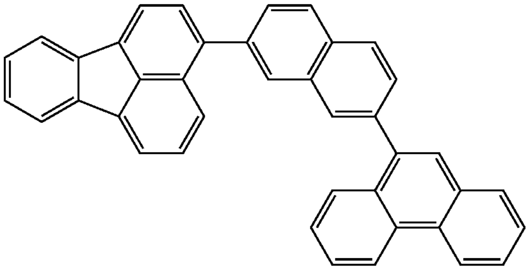

-continued
[Formula 73]
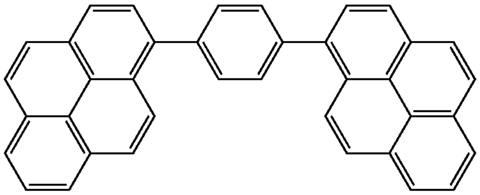
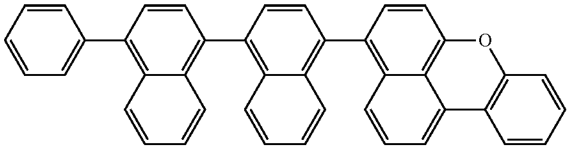
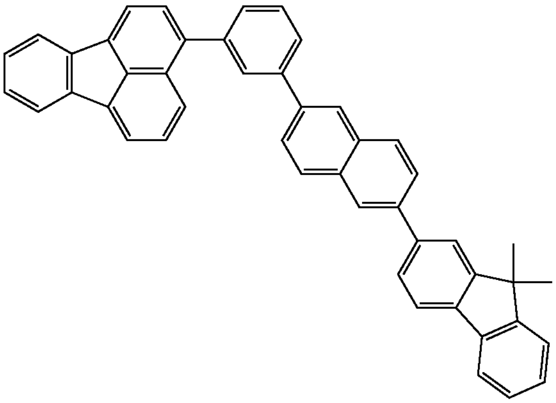
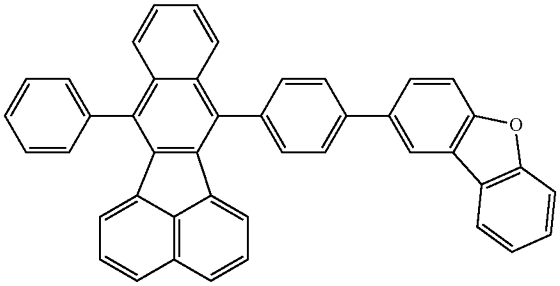
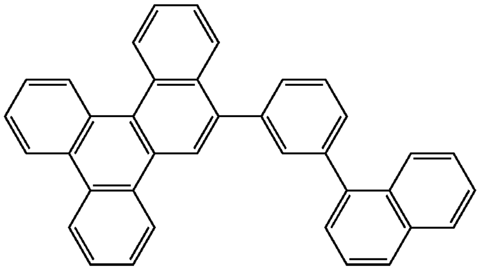
-continued
[Formula 74]
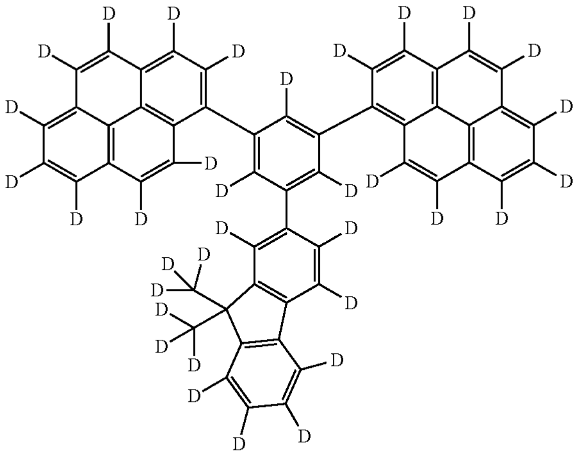
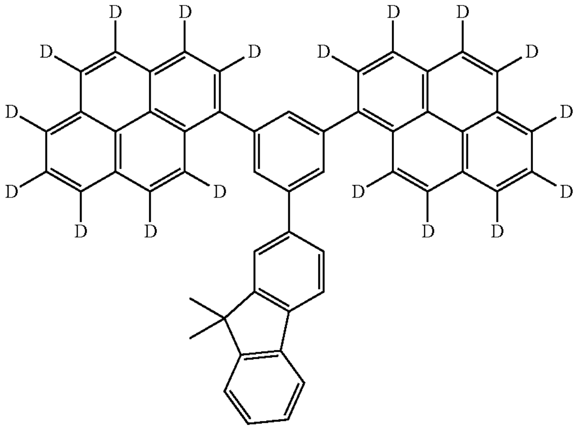
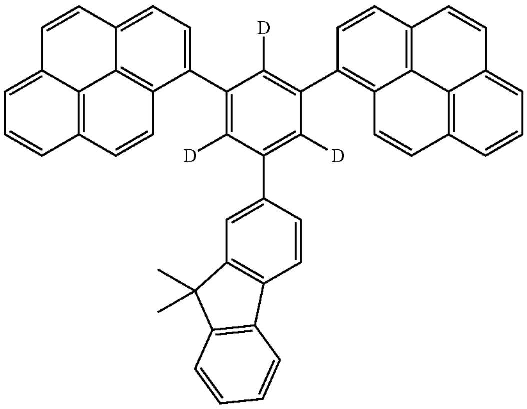

-continued
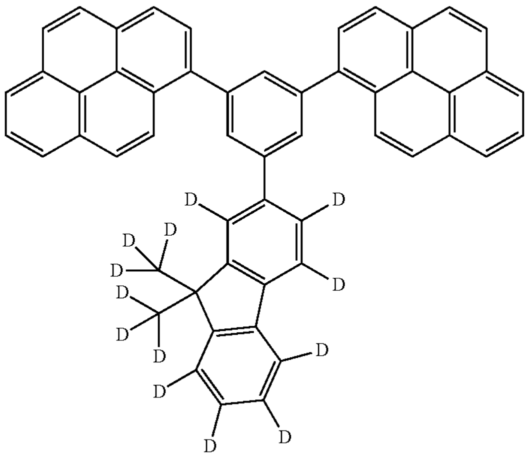
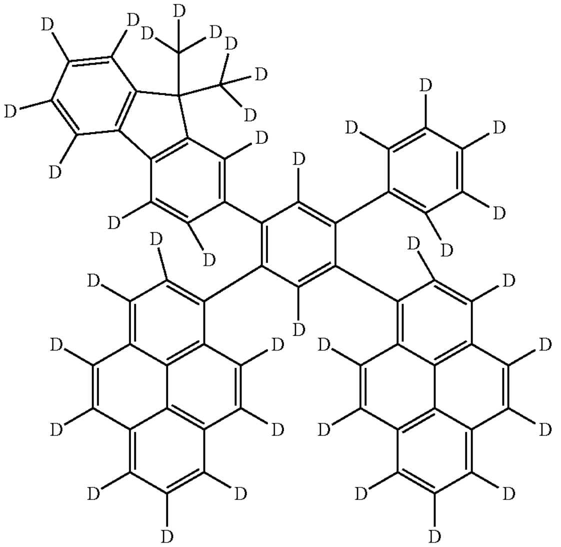
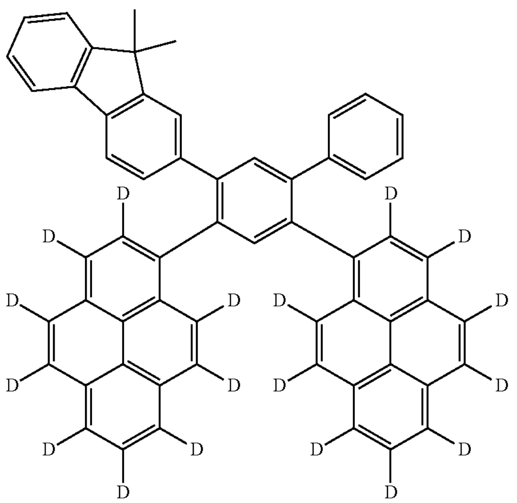
-continued
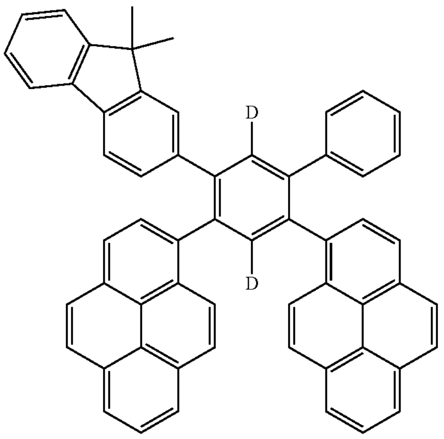
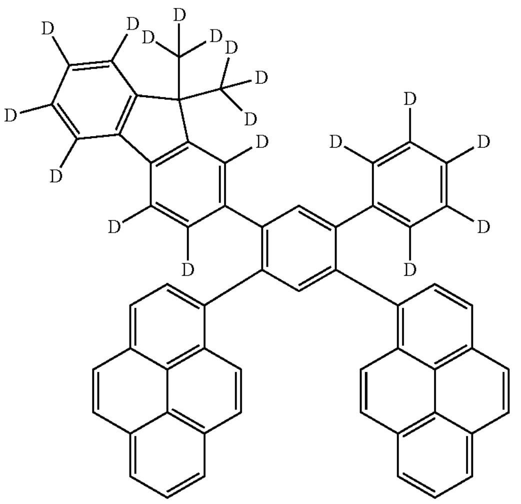
[Formula 75]
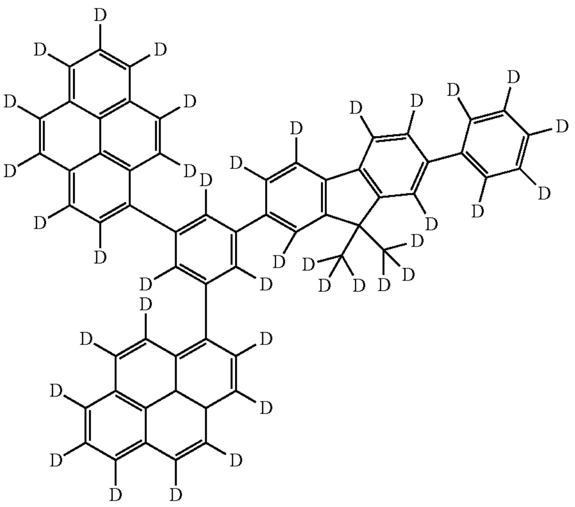

-continued
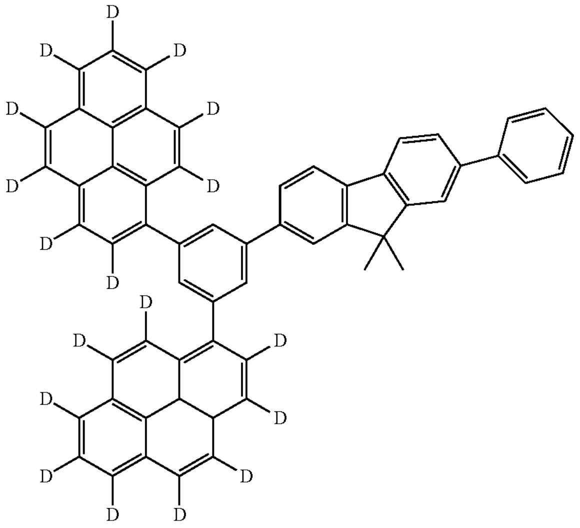
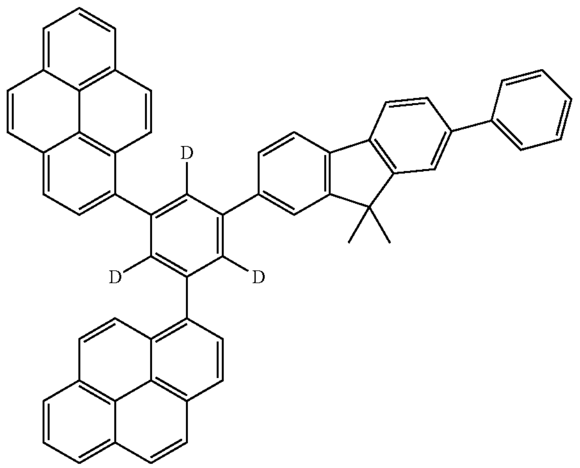
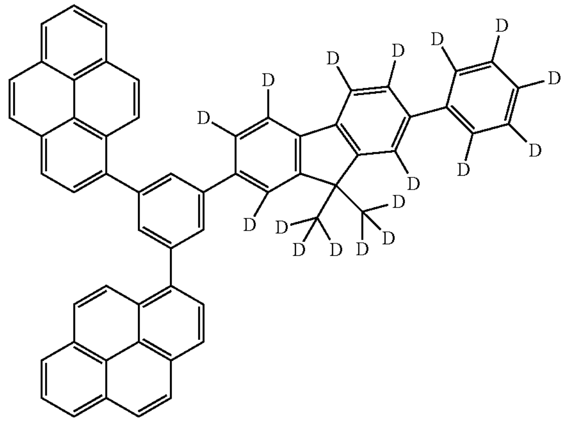
-continued
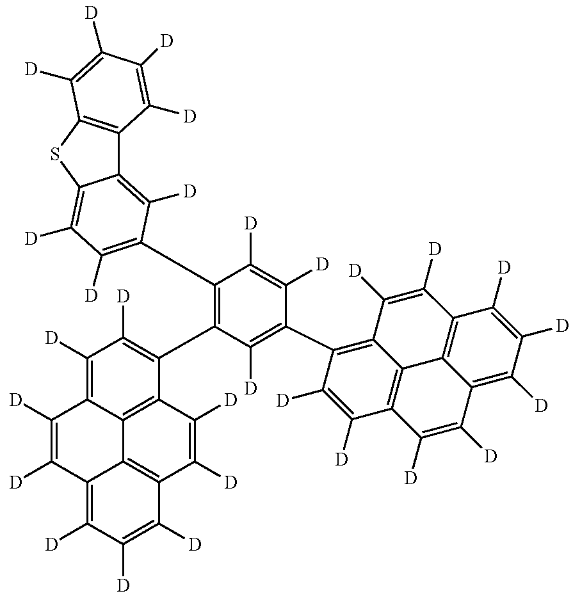
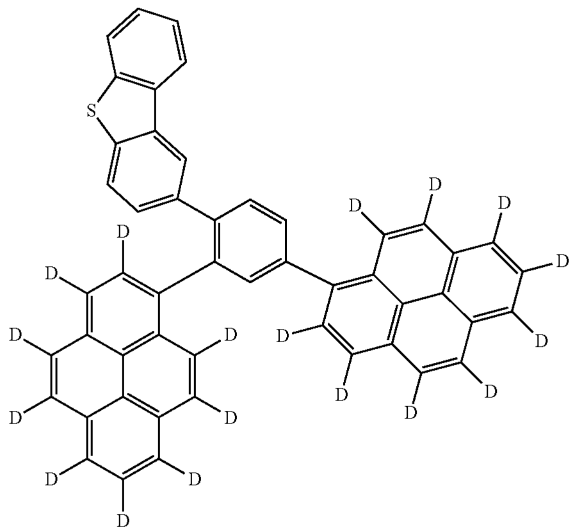
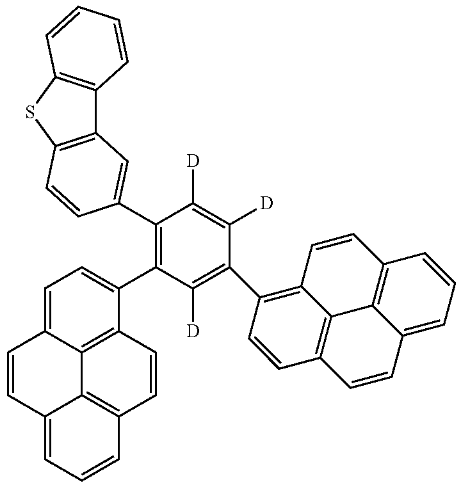

-continued
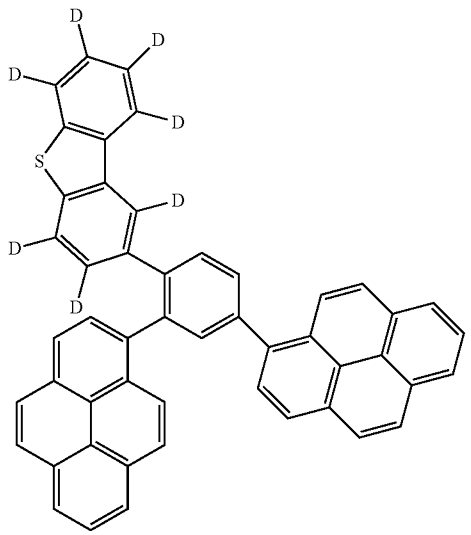
[Formula 76]
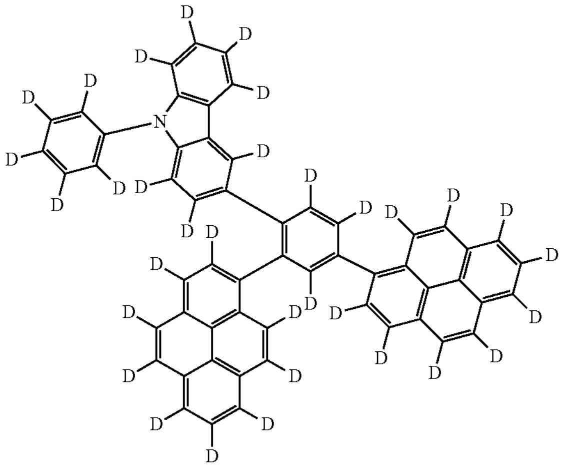
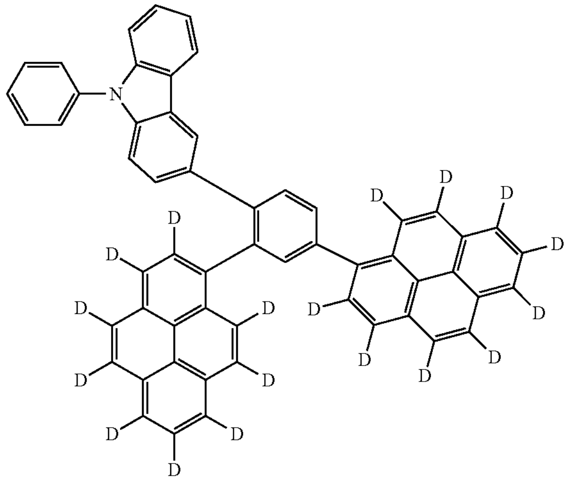
-continued
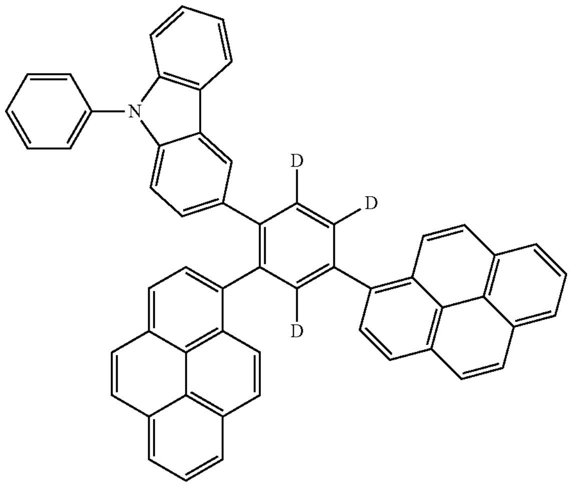
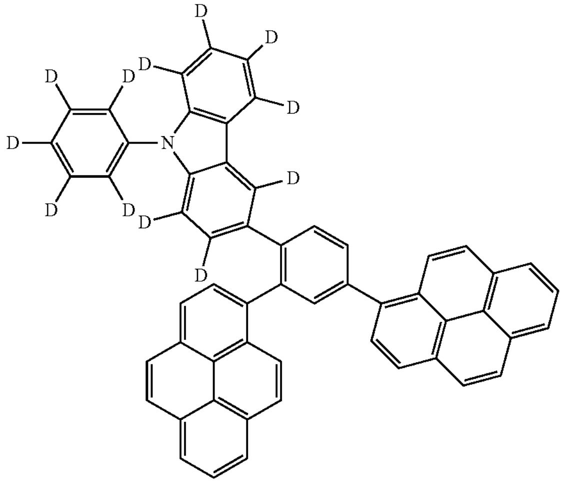
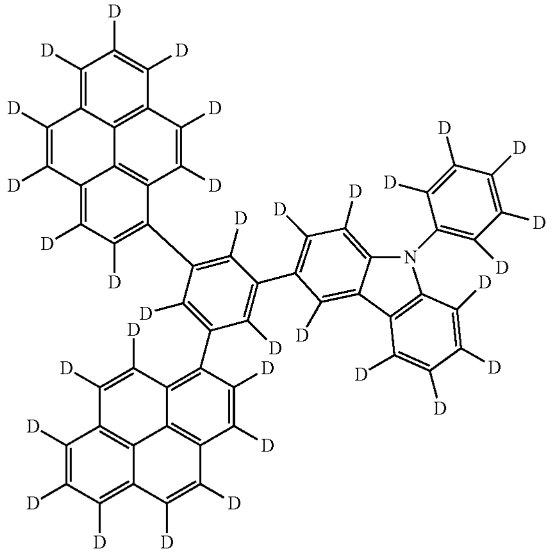

-continued
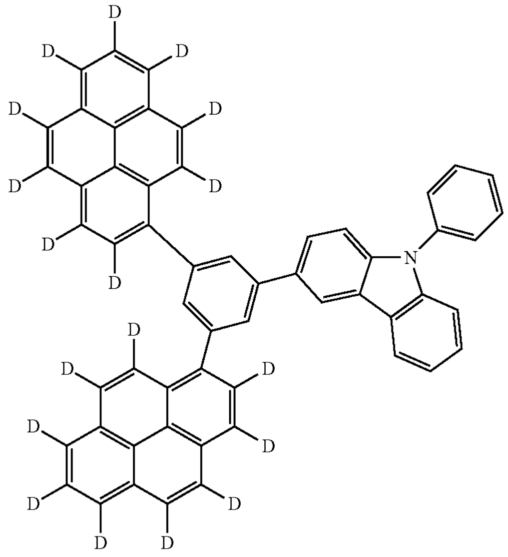
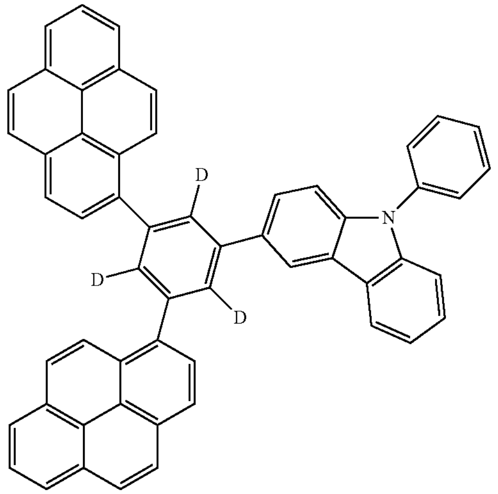
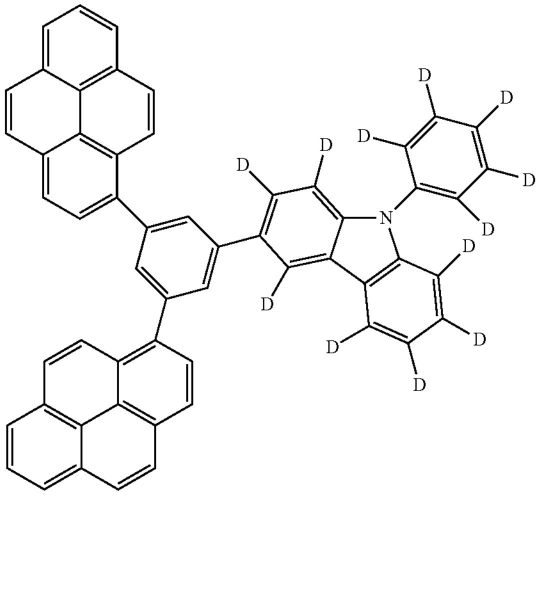
-continued
[Formula 77]
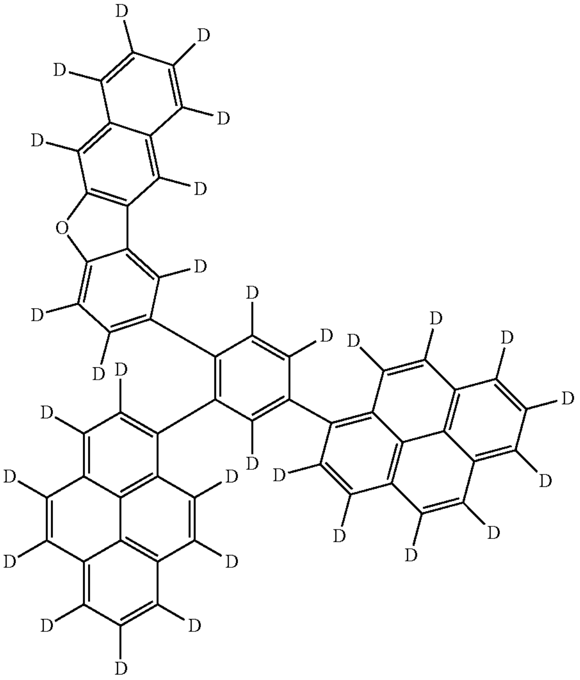
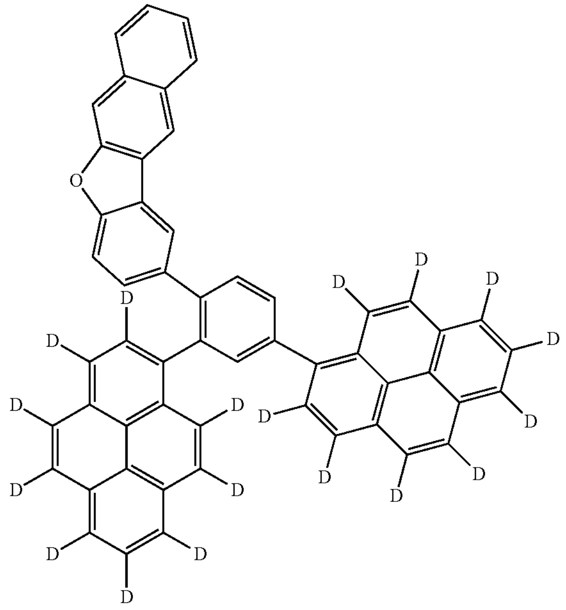

-continued
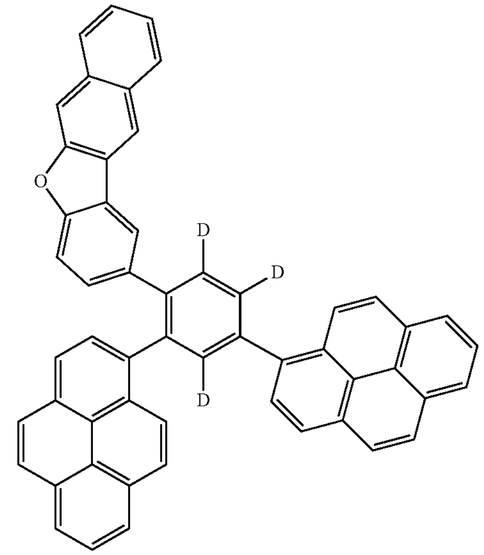
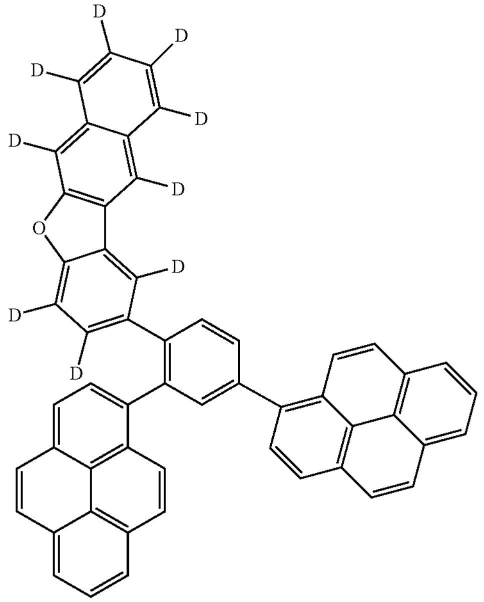
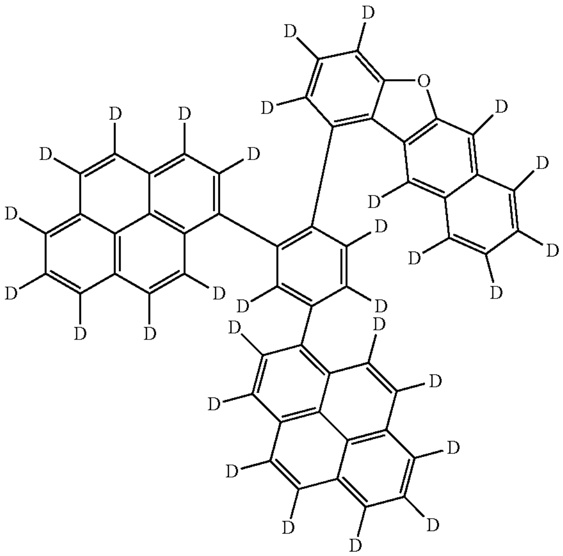
-continued
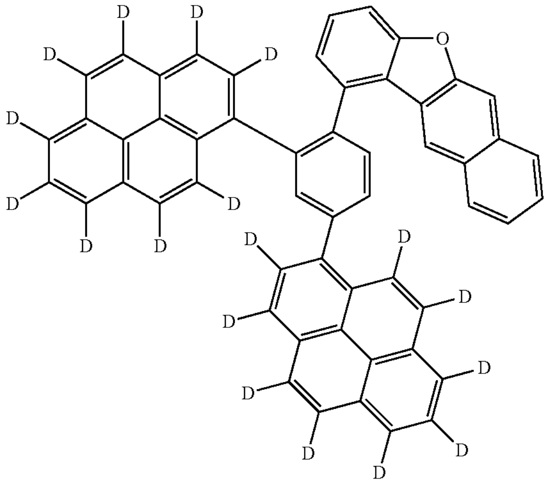
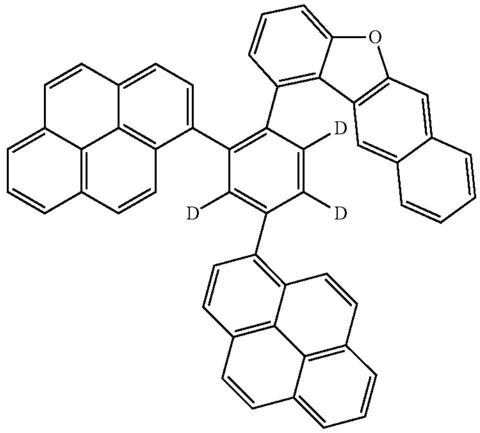
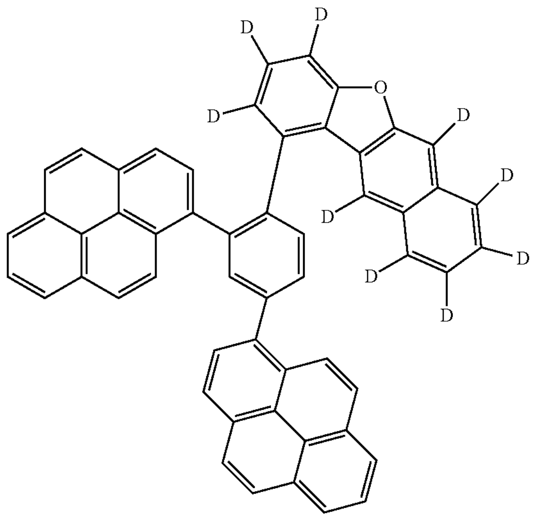

-continued
[Formula 78]
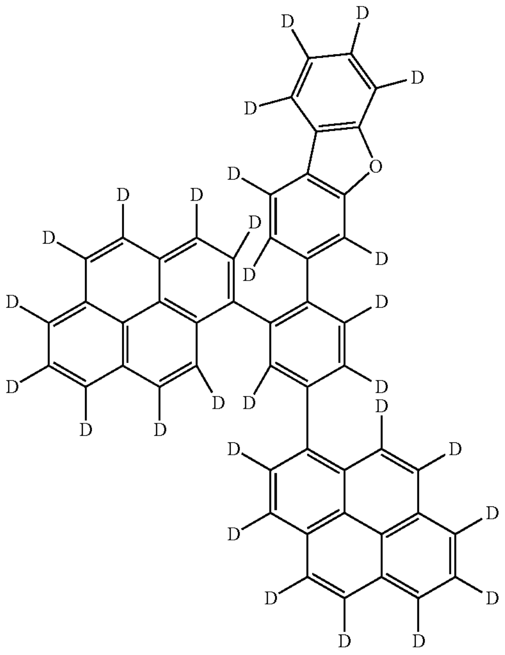
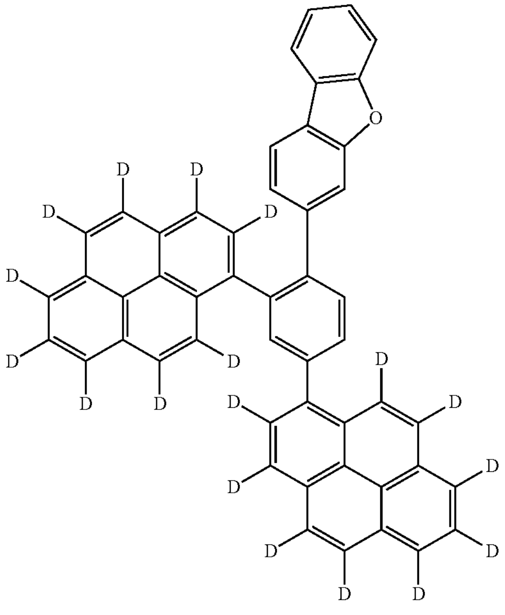
-continued
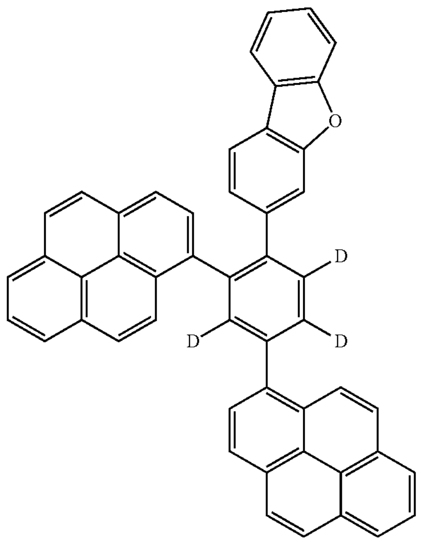
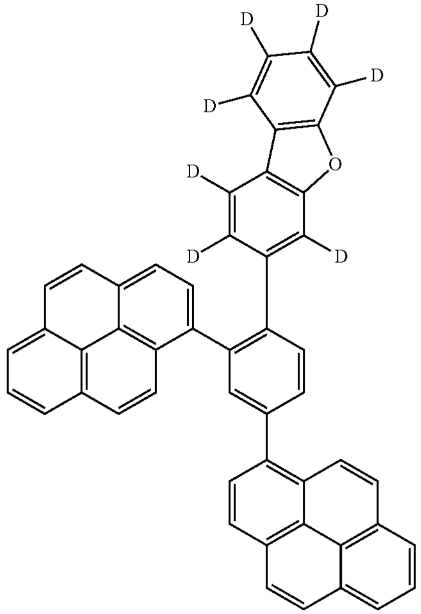
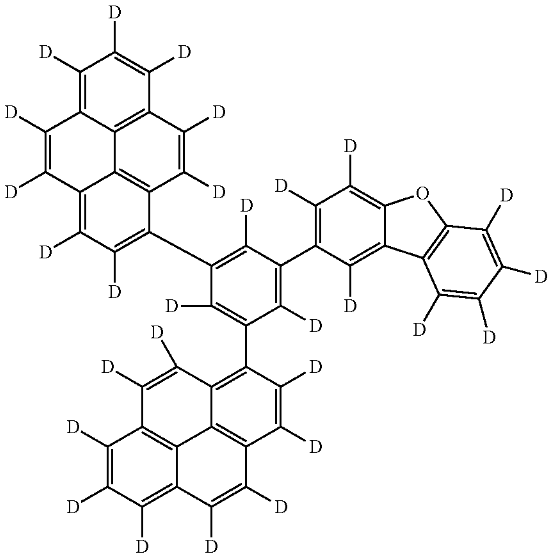

-continued
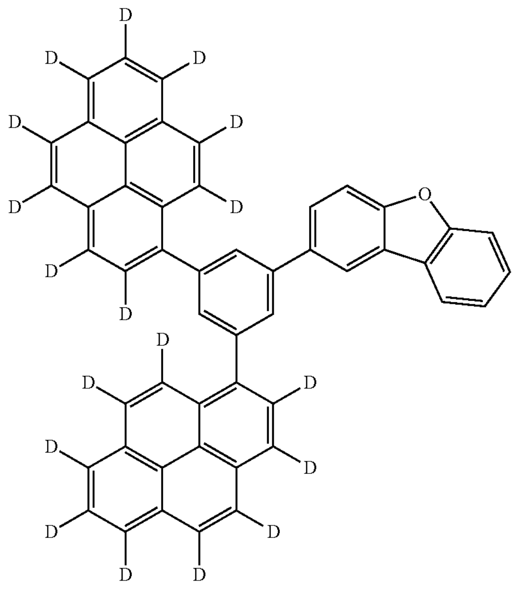
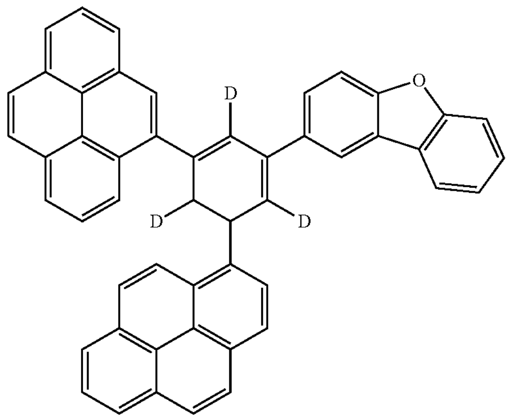
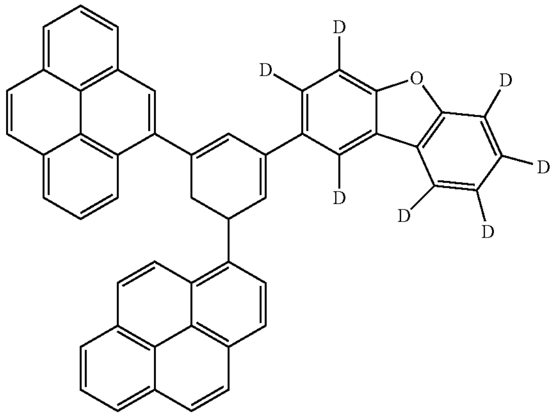
-continued
[Formula 79]
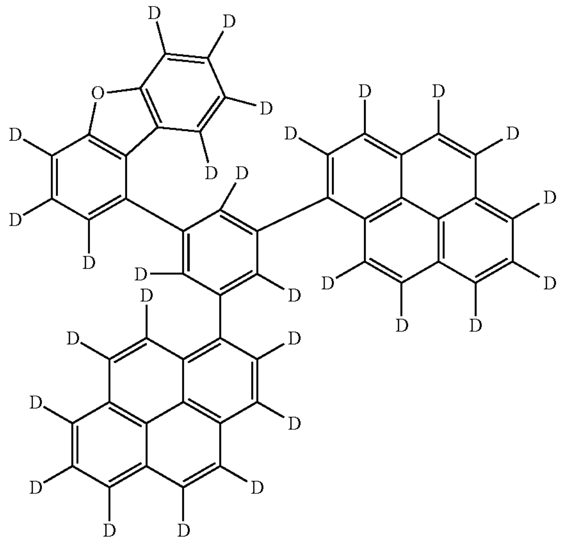
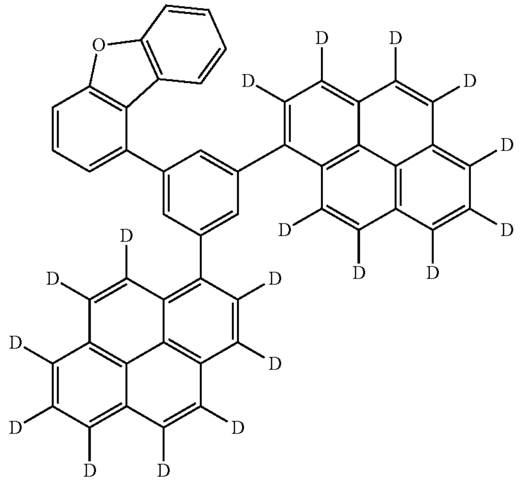
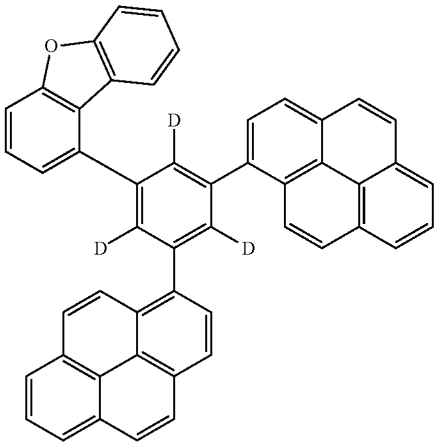

-continued
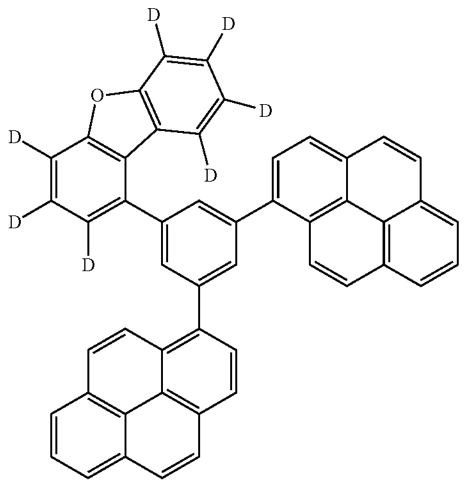
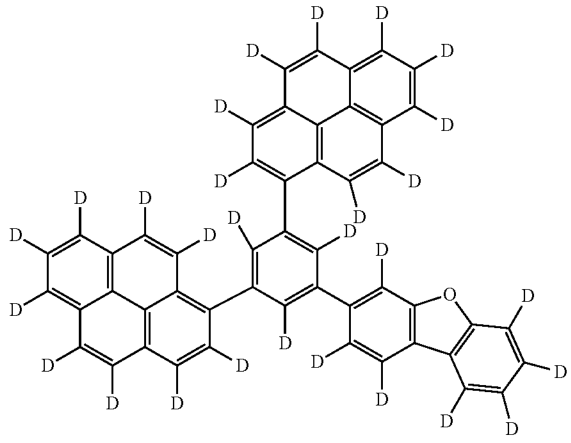
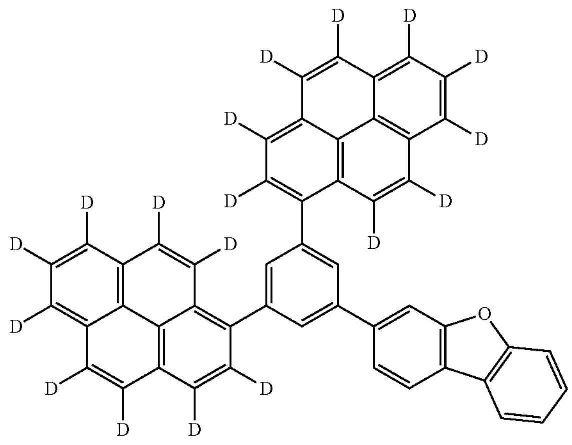
-continued
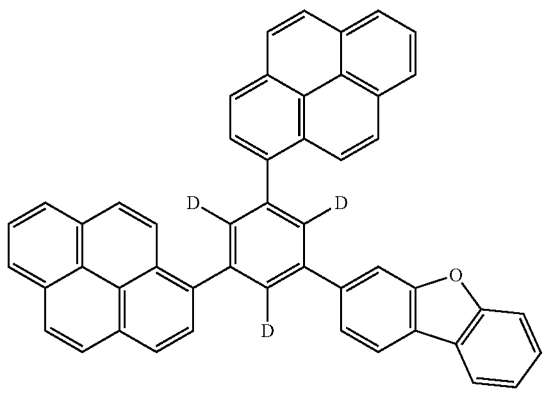
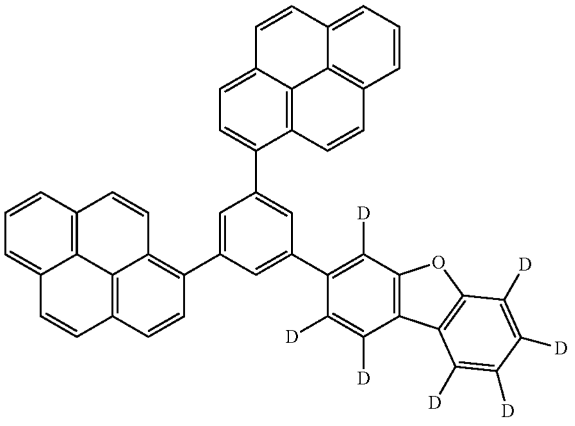
[Formula 80]
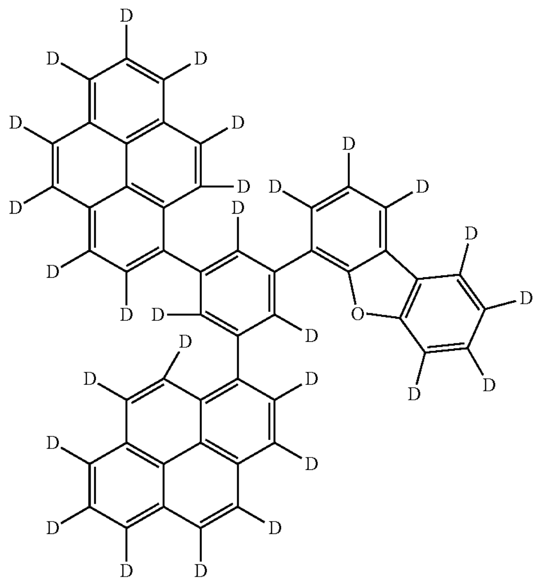

-continued
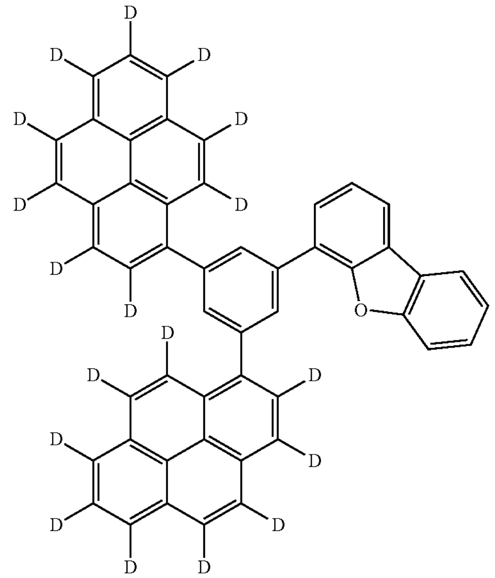
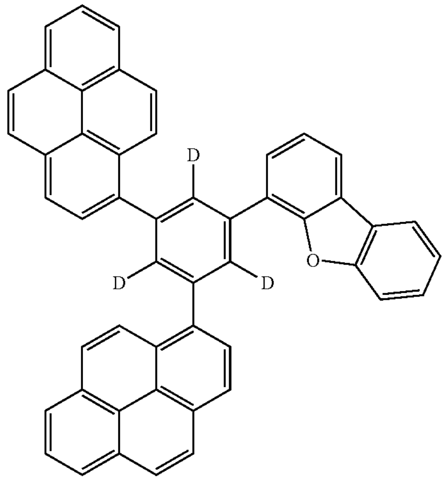
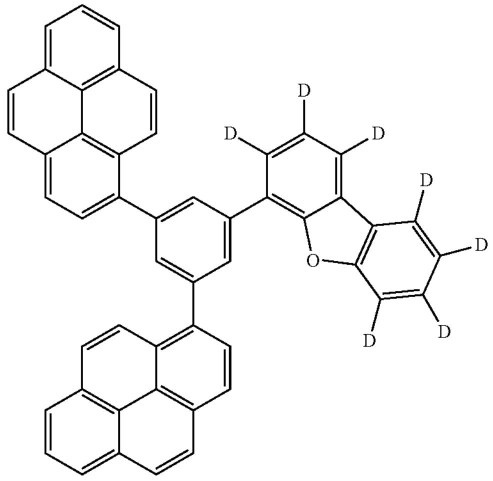
-continued
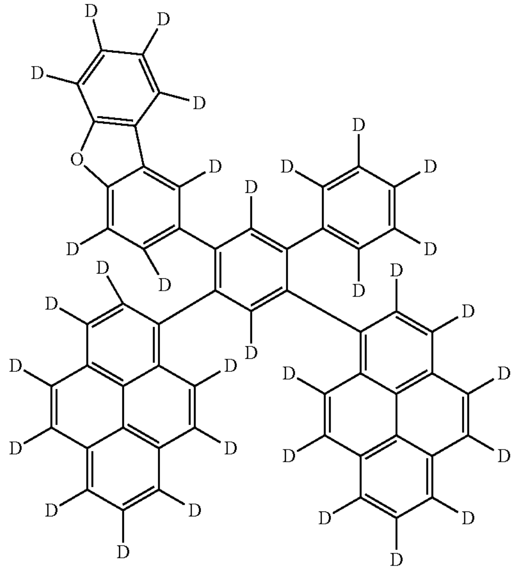
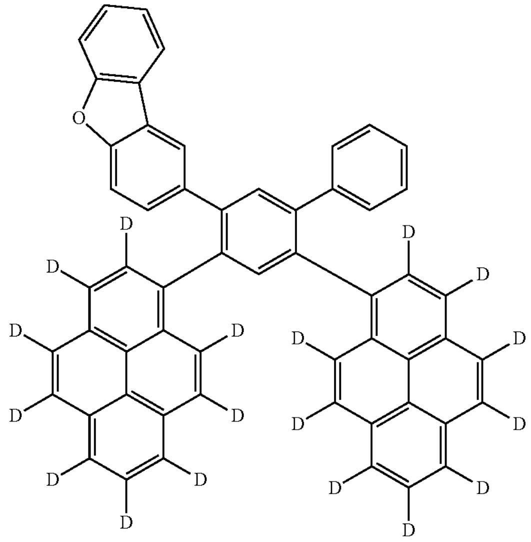
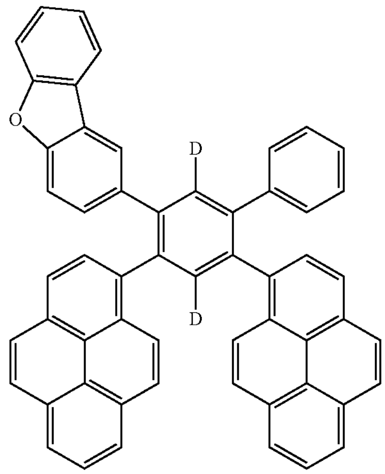

-continued
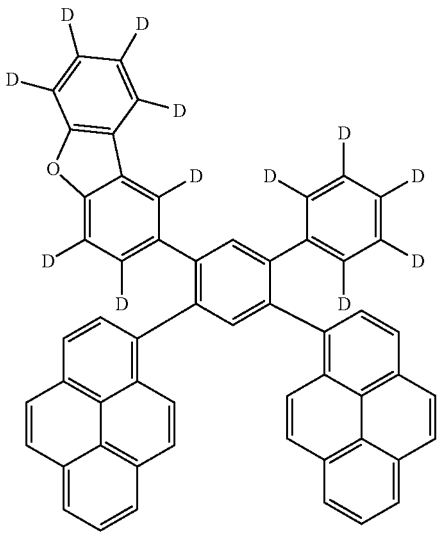
[Formula 81]
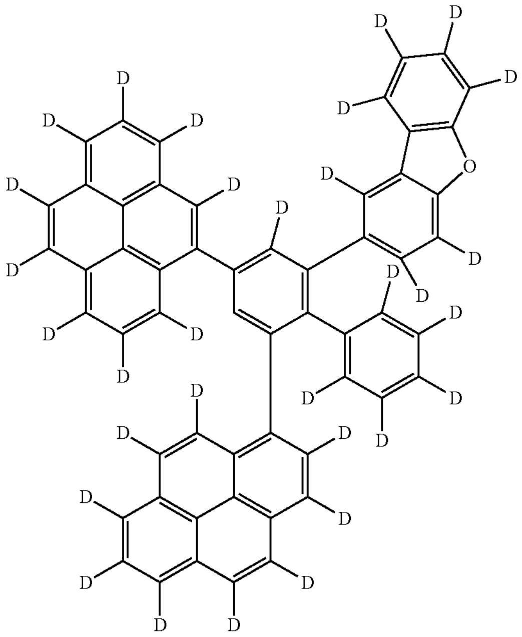
-continued
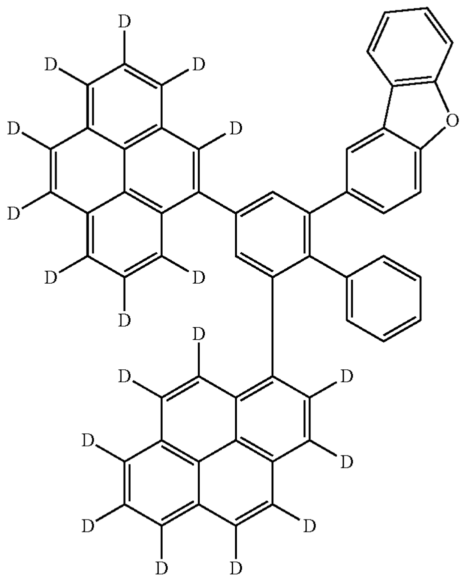
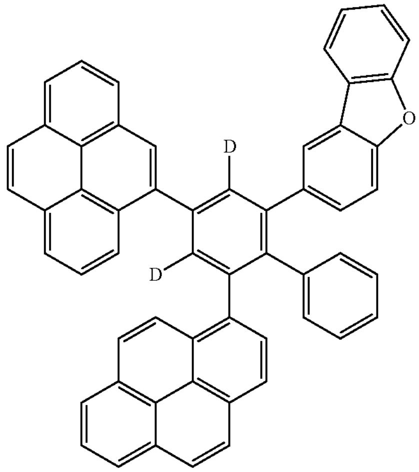
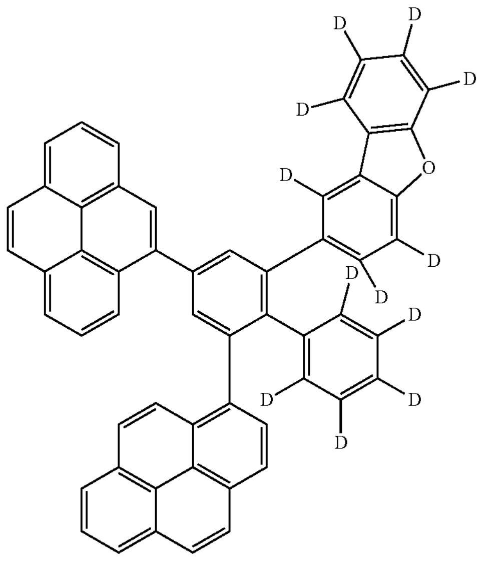

-continued
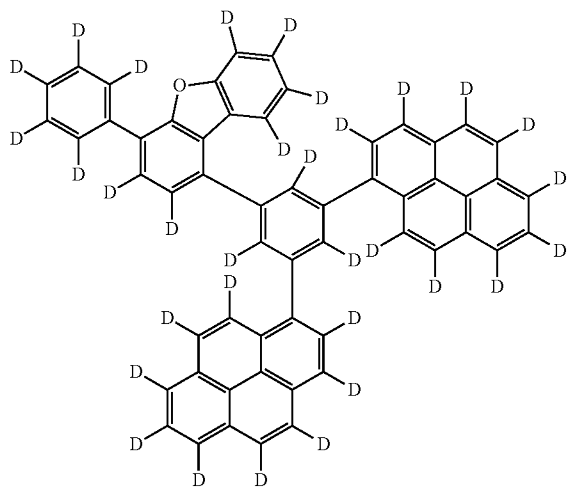
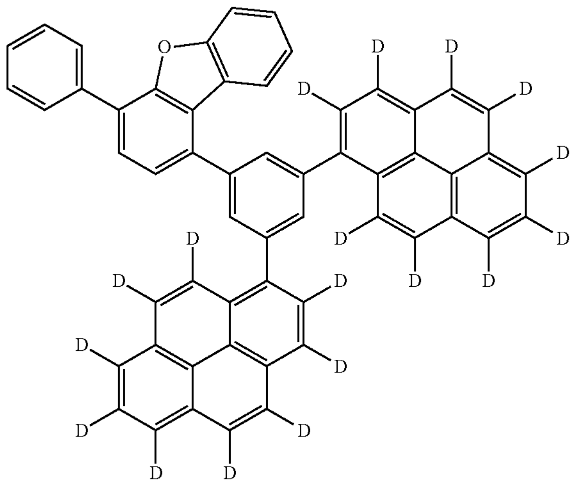
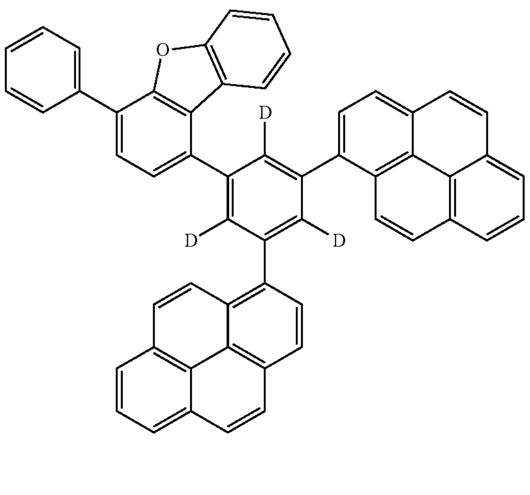
-continued
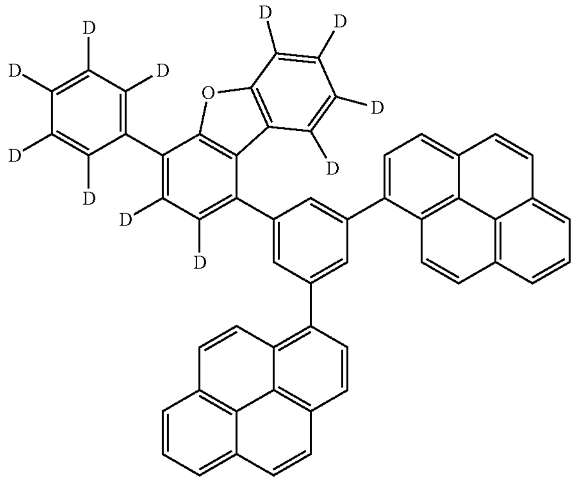
[Formula 82]
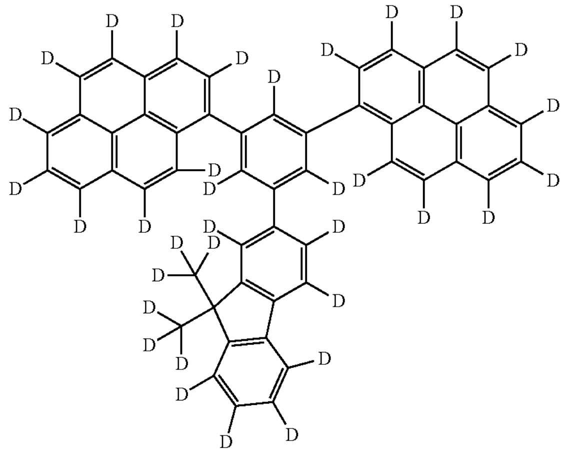
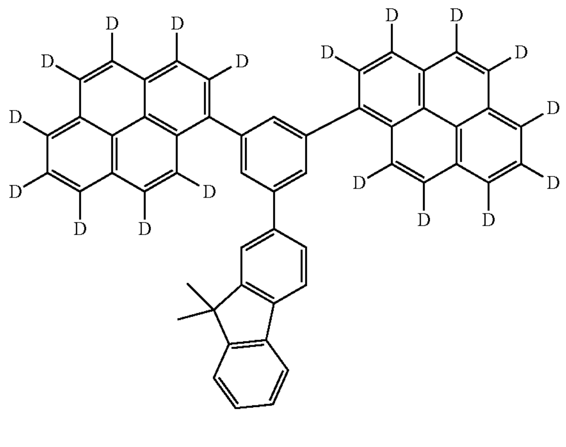

-continued
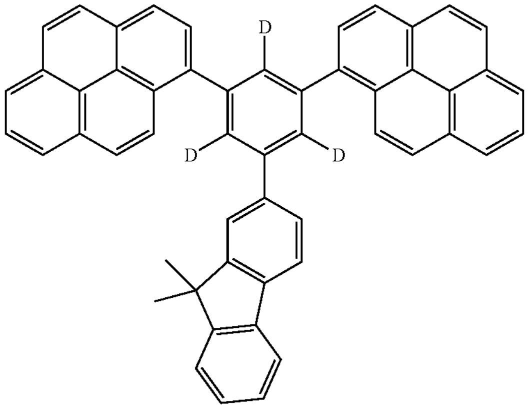
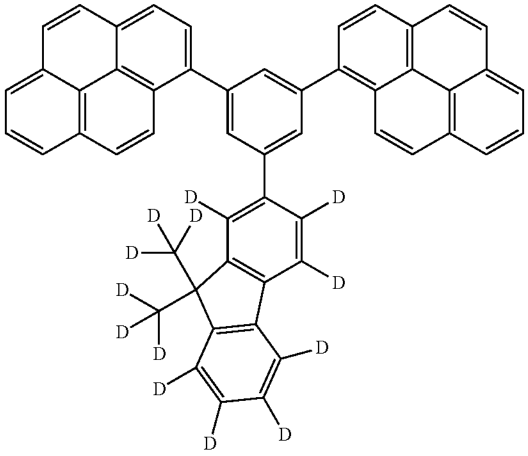
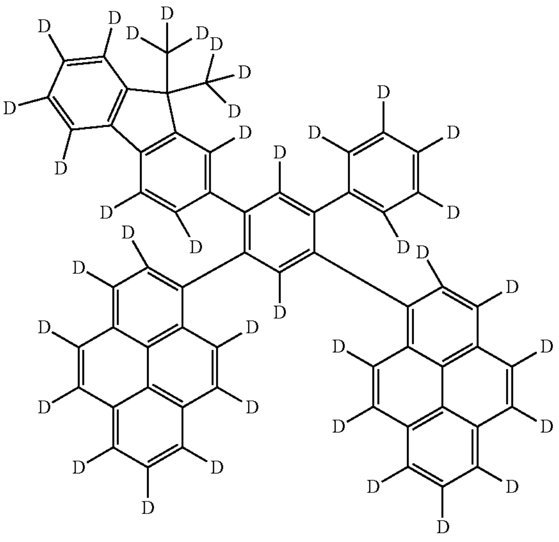
-continued
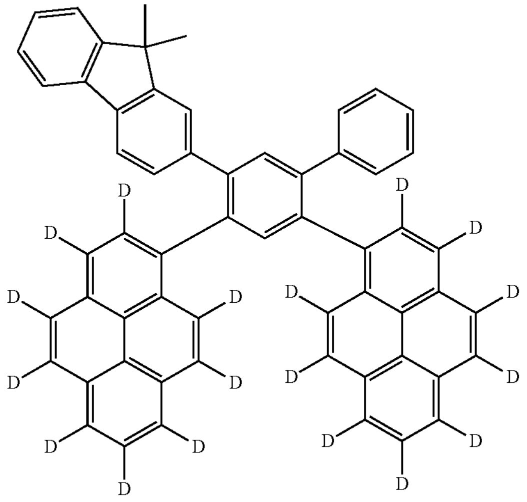
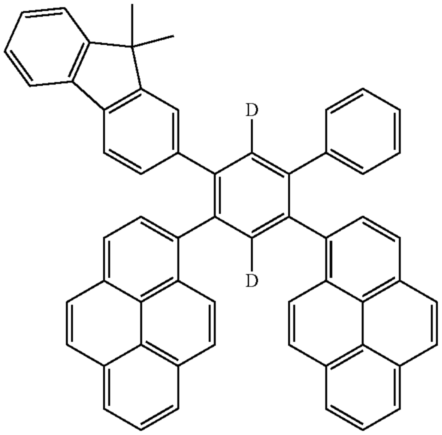
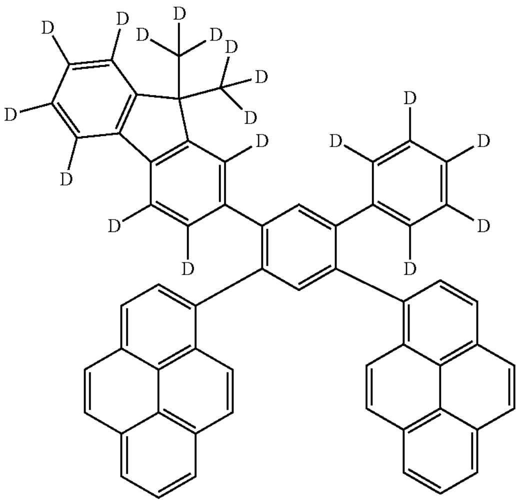

-continued
[Formula 83]
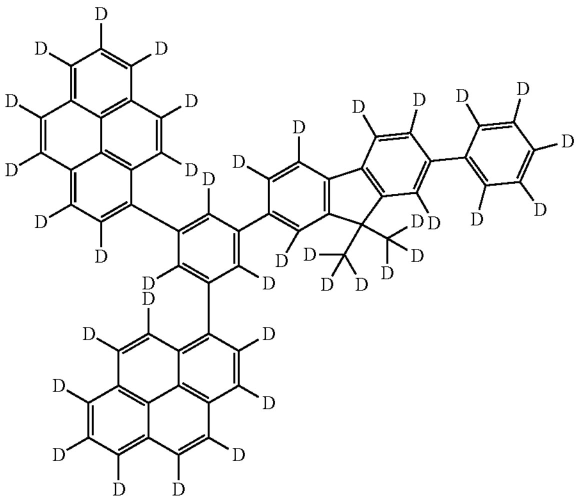
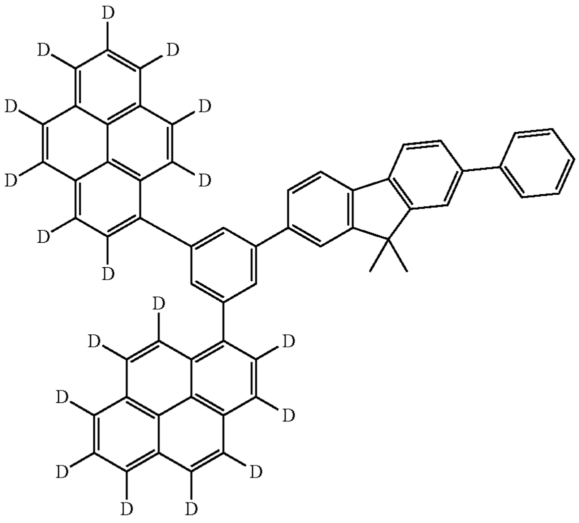
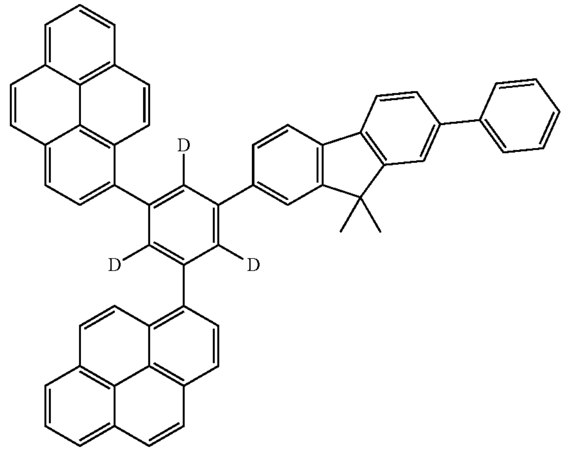
-continued
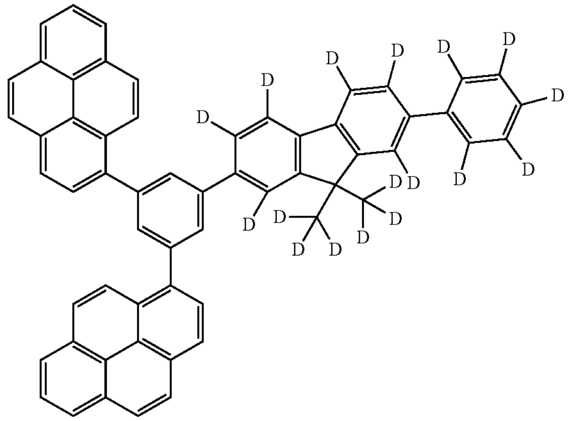
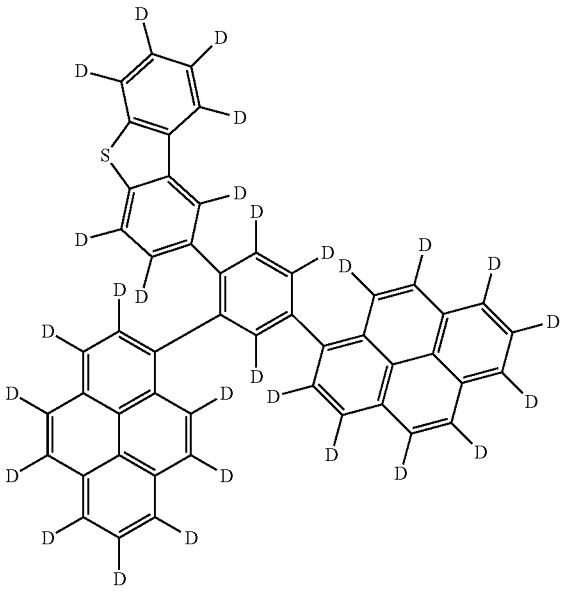
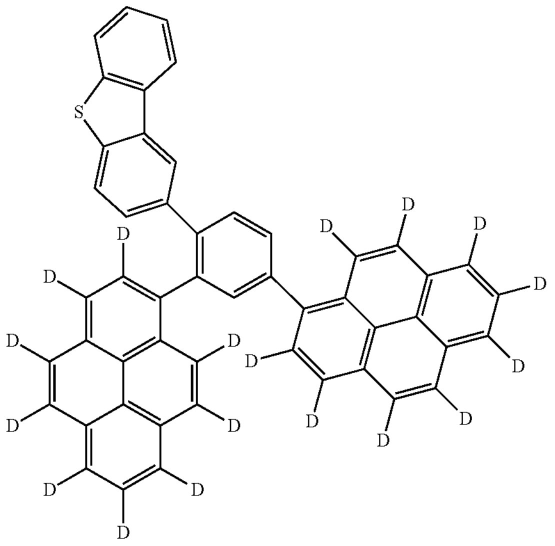

-continued
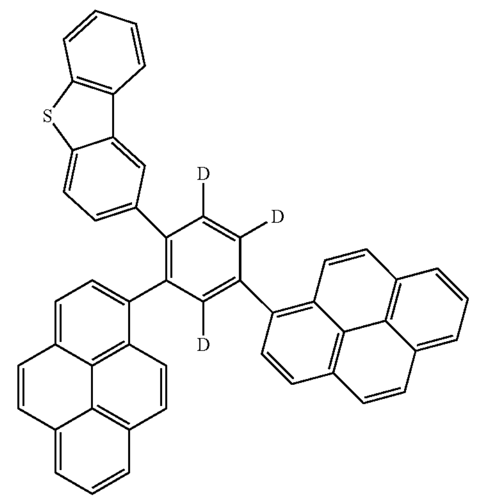
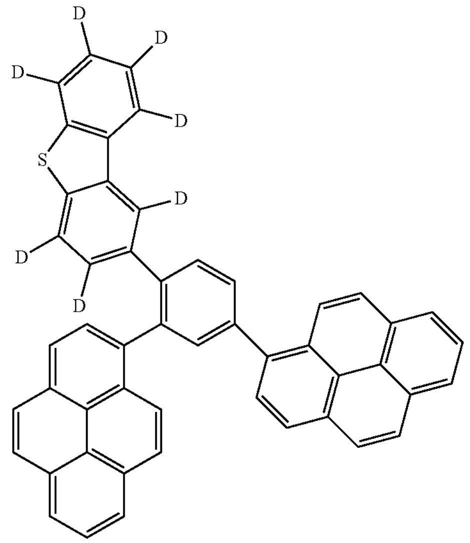
[Formula 84]
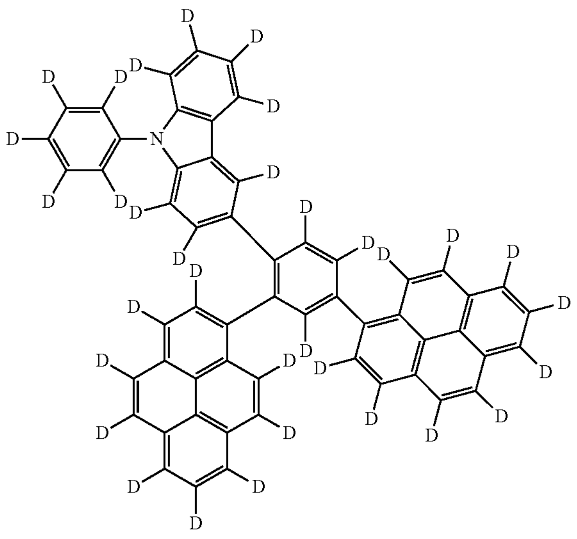
-continued
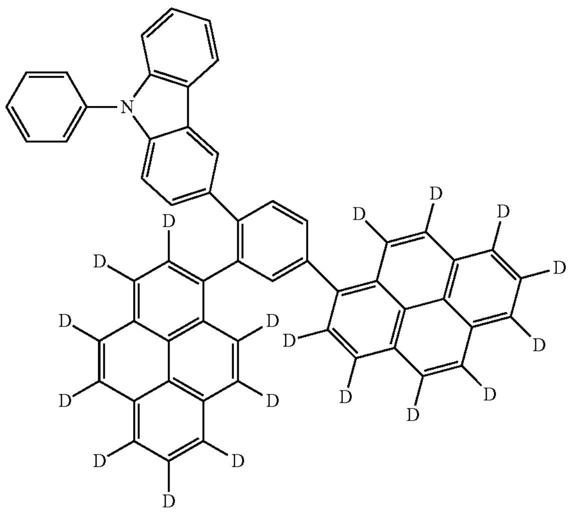
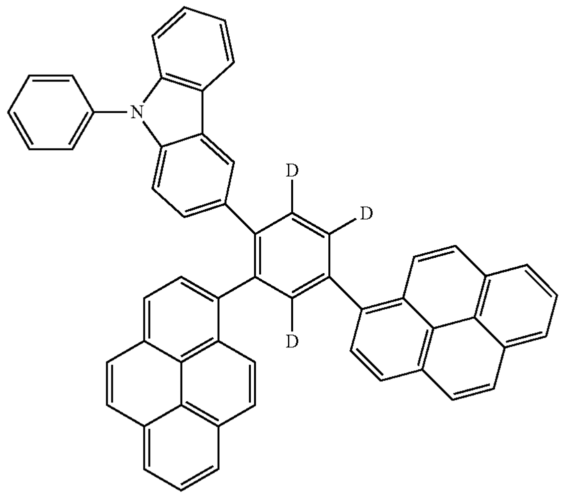
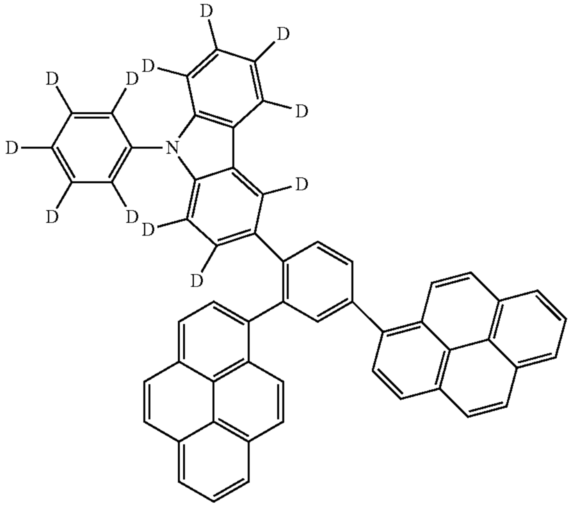

-continued
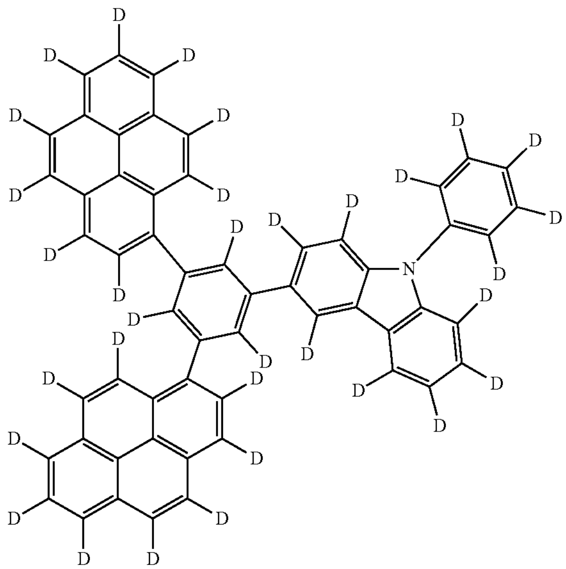
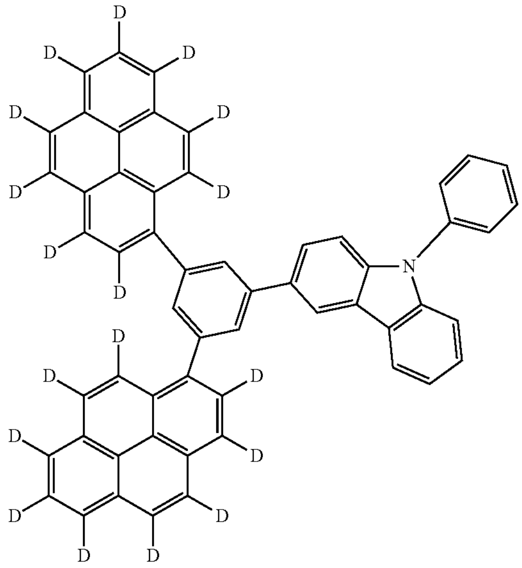
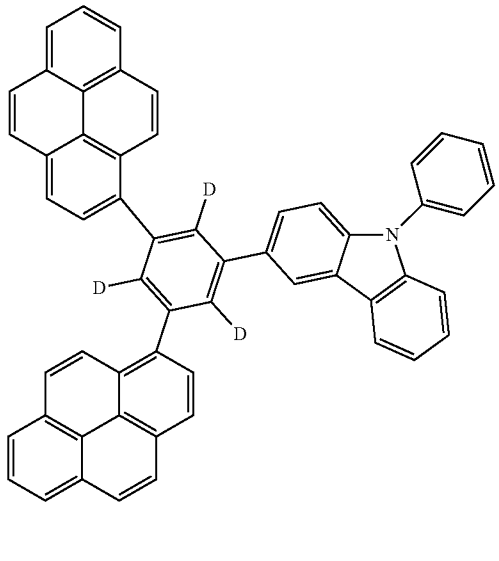
-continued
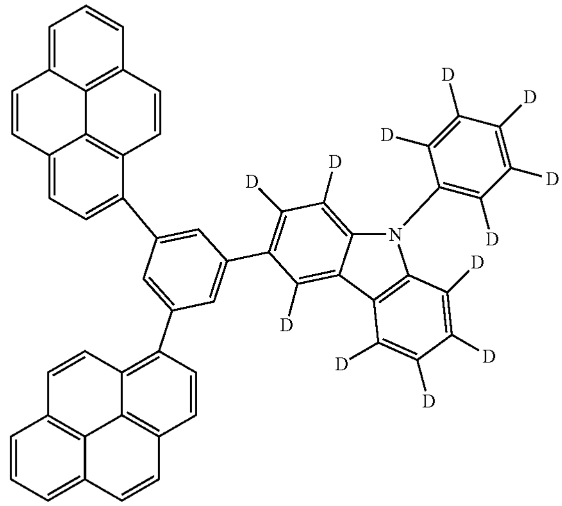
[Formula 85]
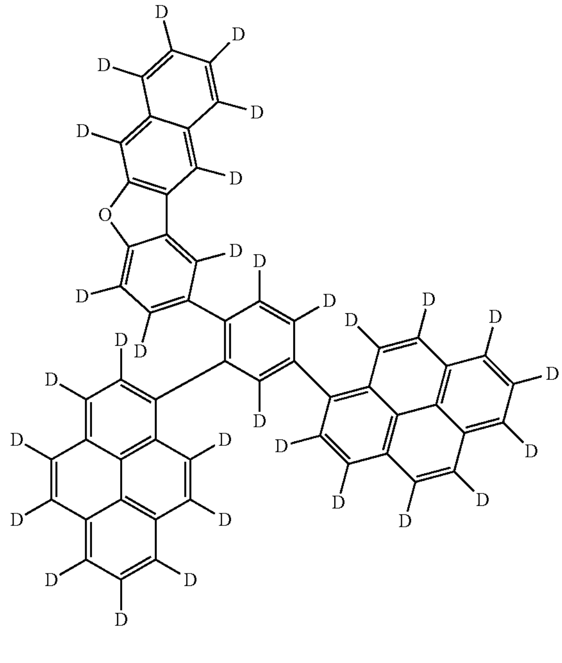

-continued
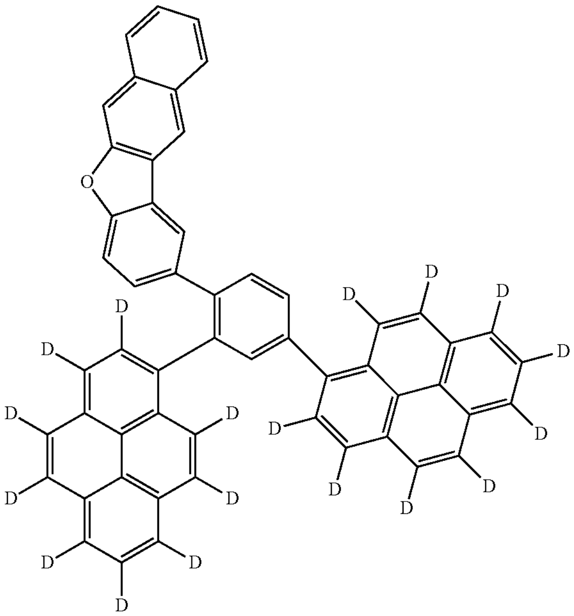
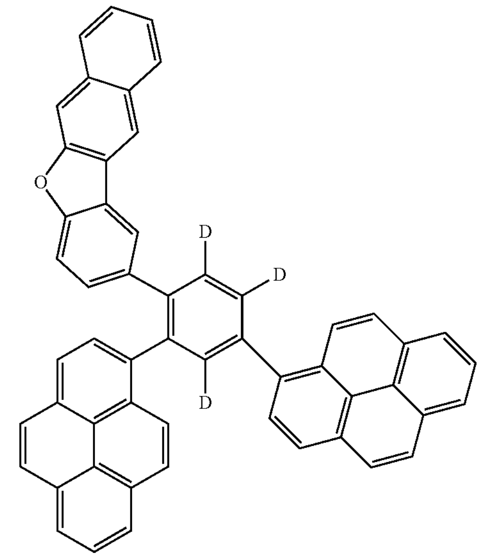
-continued
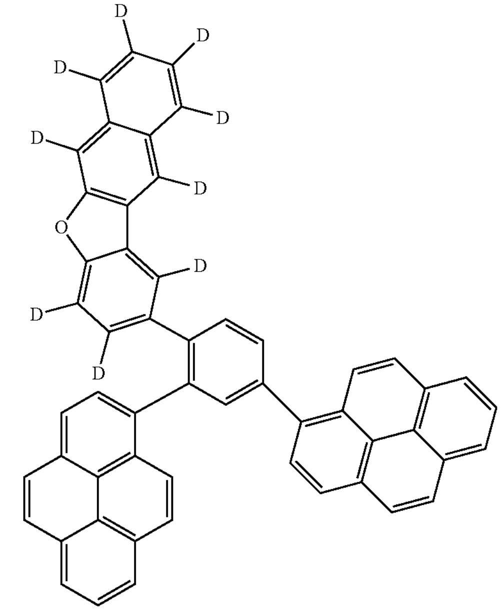
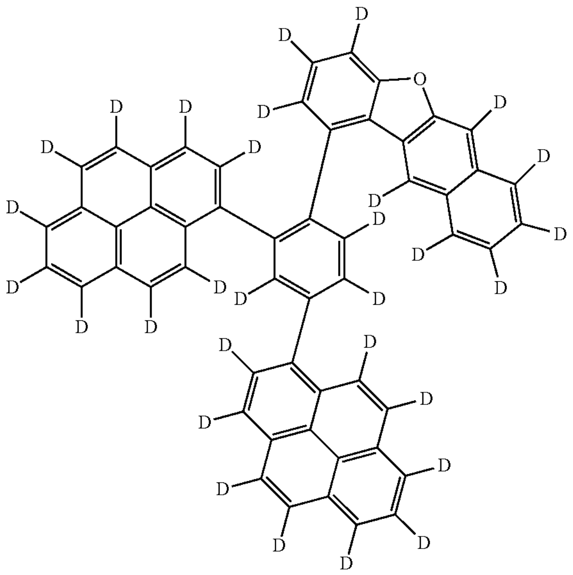
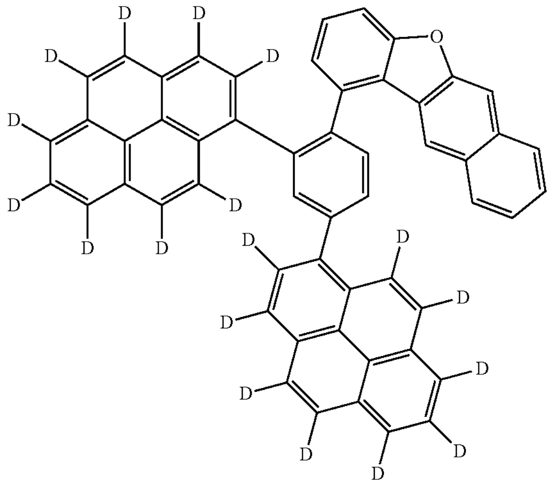

-continued
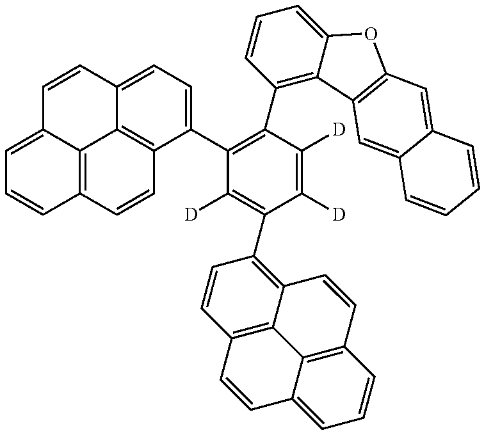
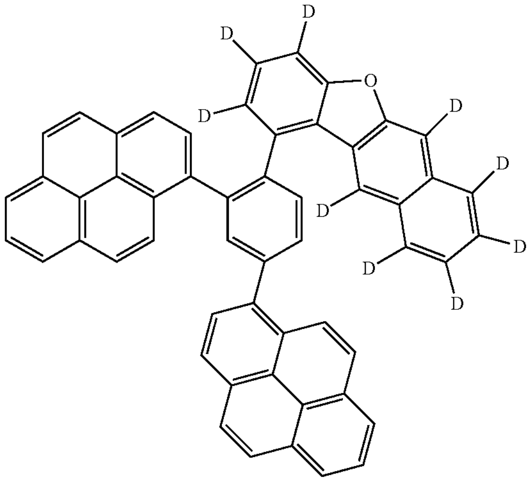
[Formula 86]
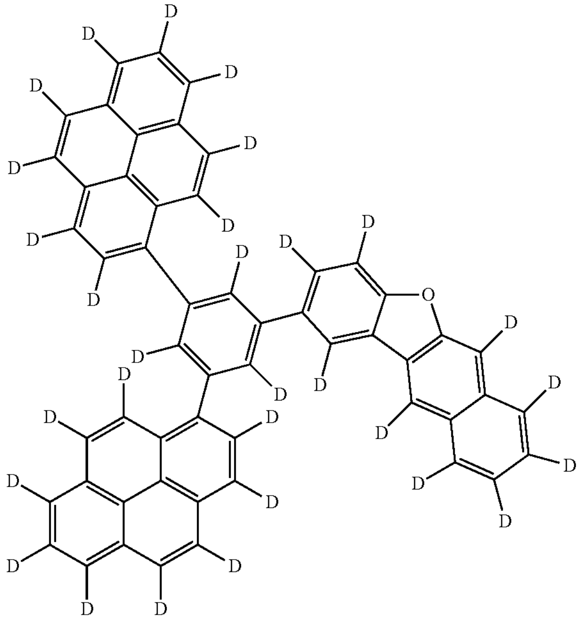
-continued
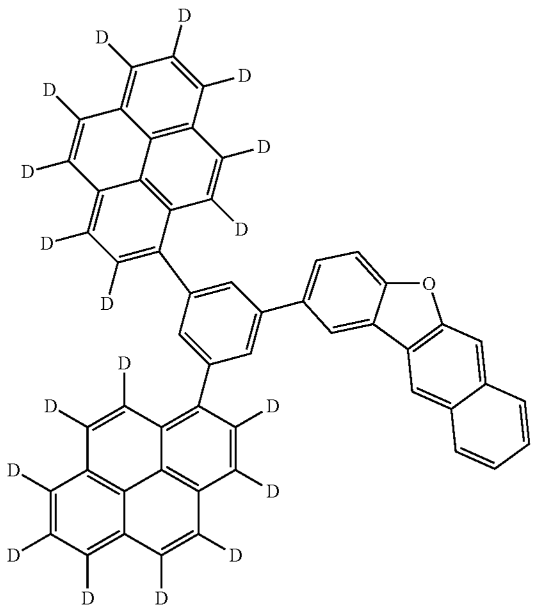
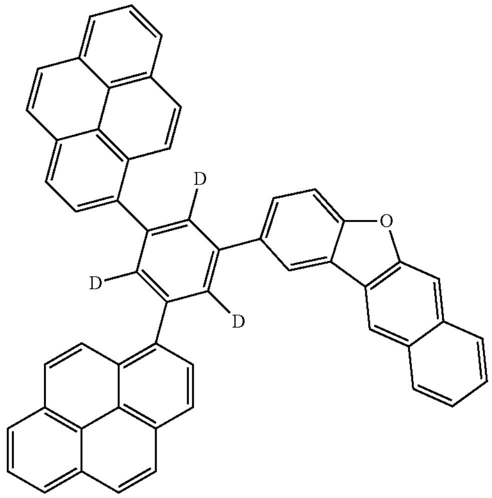
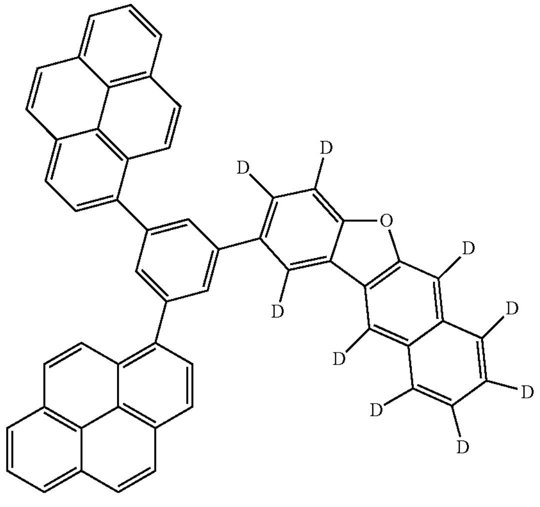

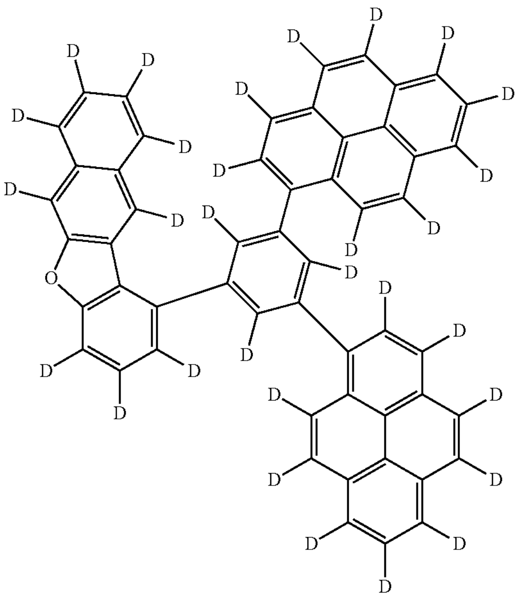
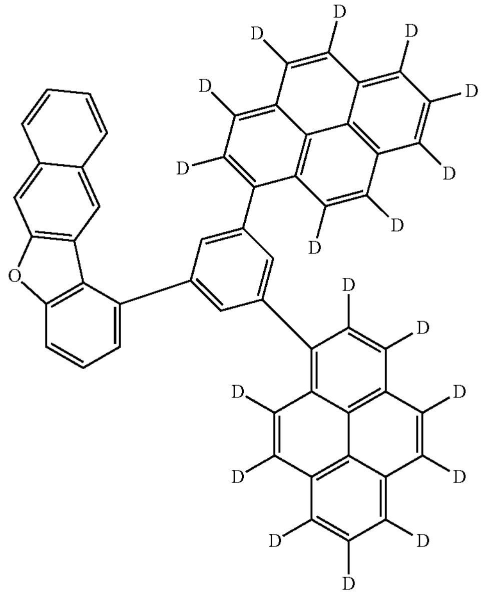
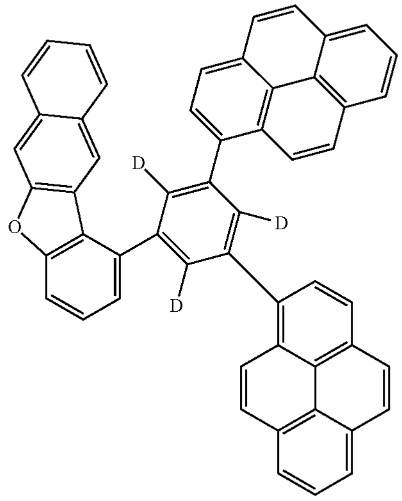
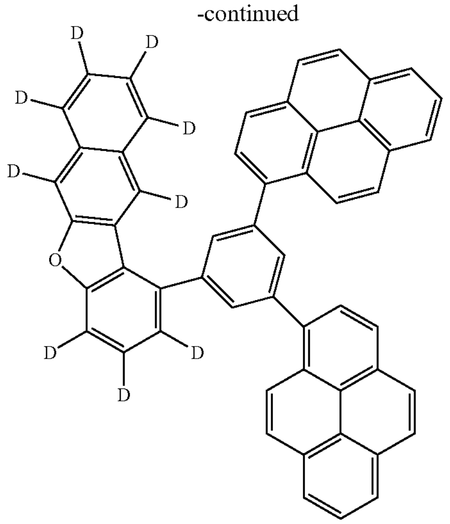
[Formula 87]
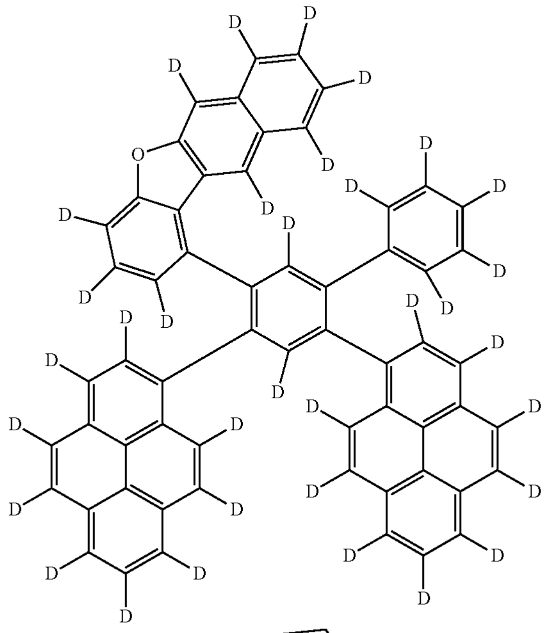
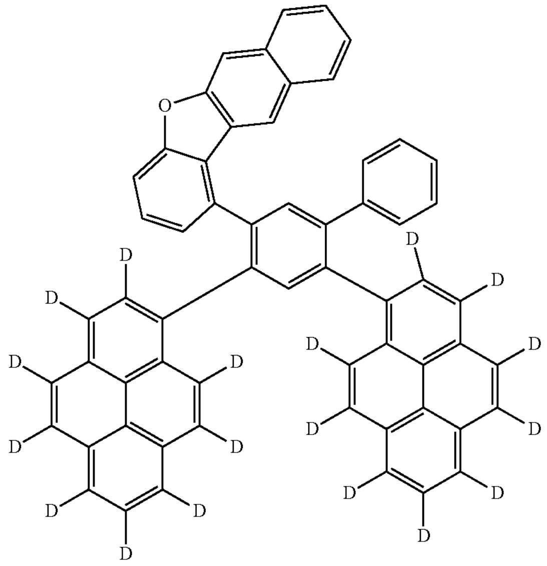

-continued
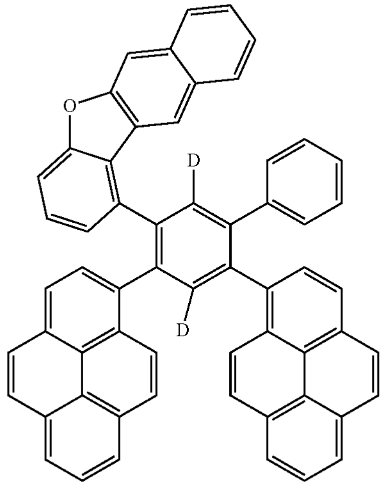
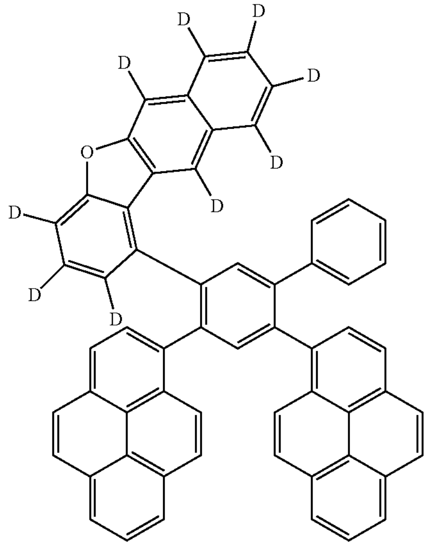
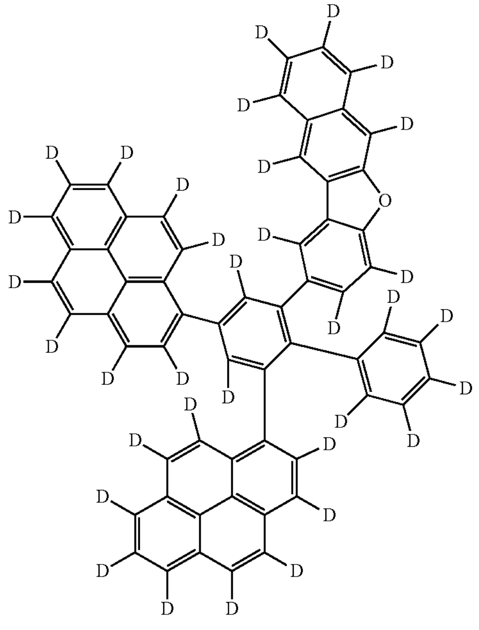
-continued
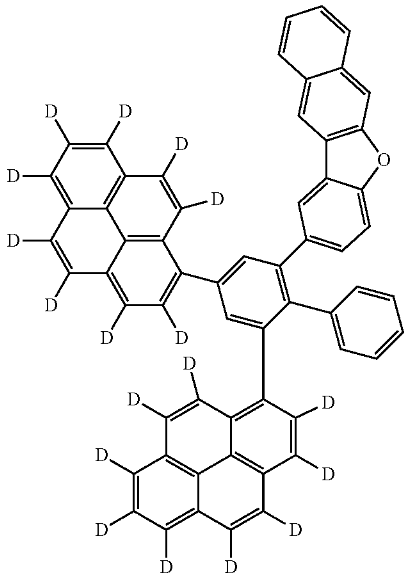
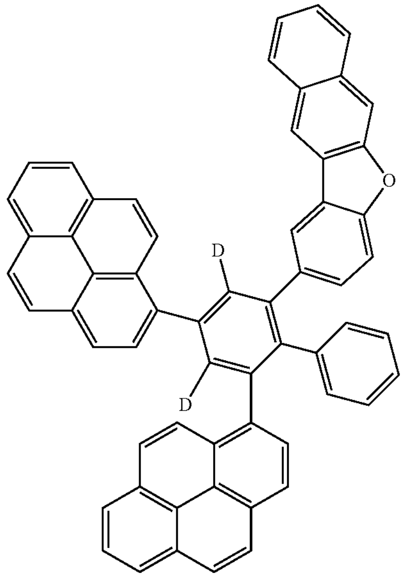

-continued
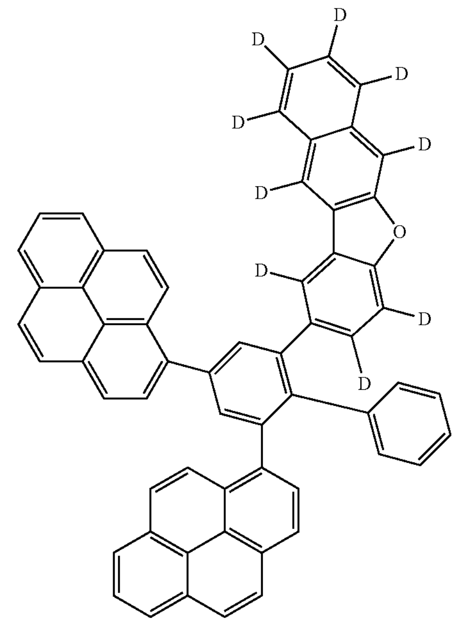
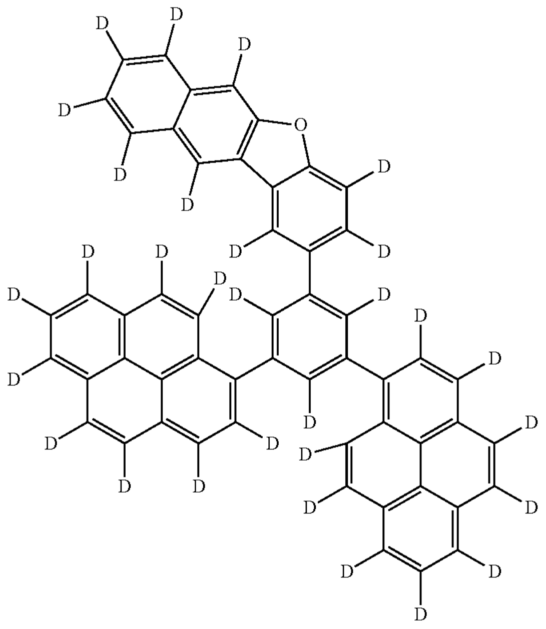
-continued
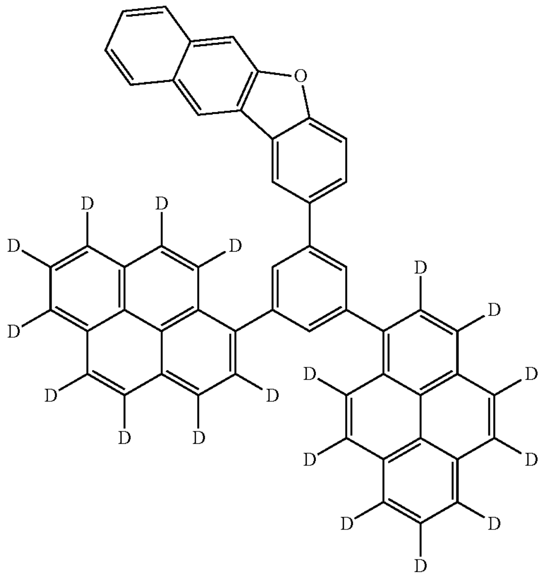
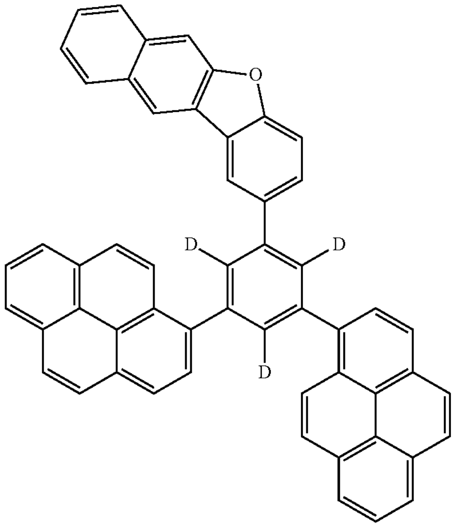
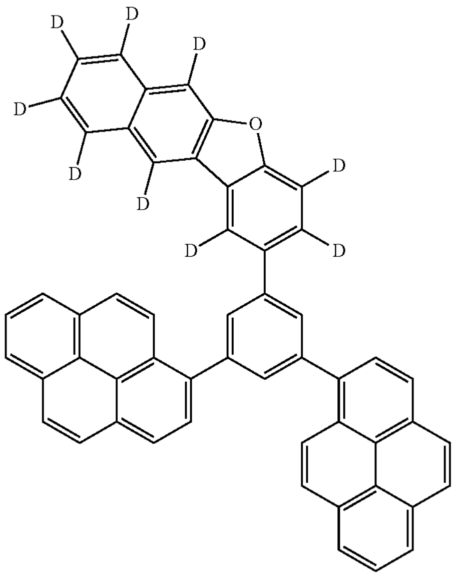

[Formula 88]
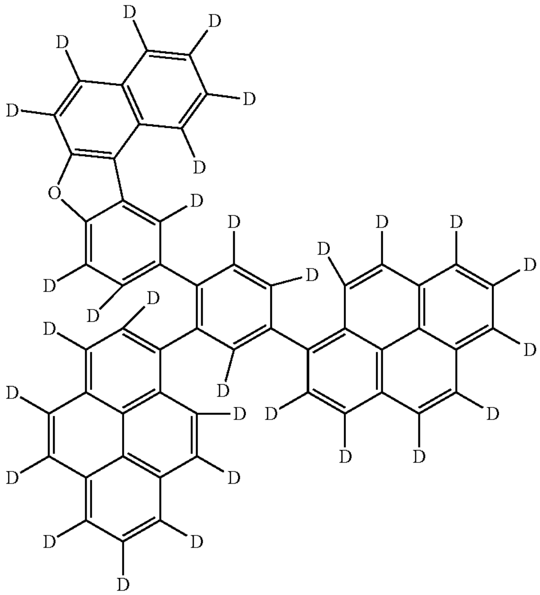
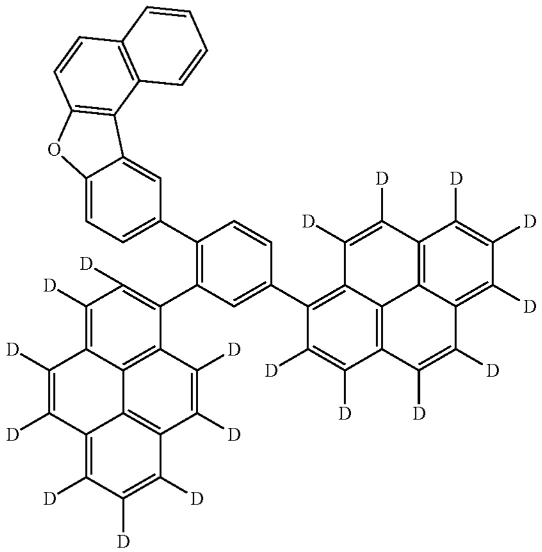
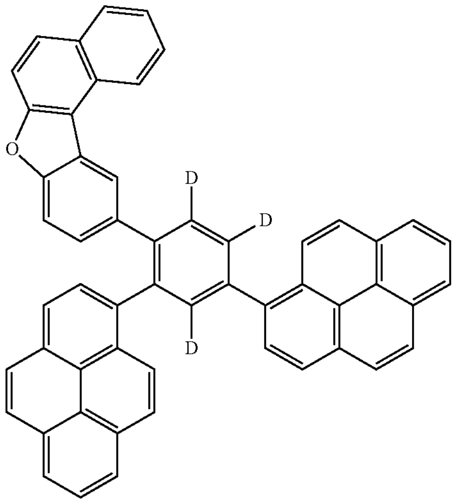
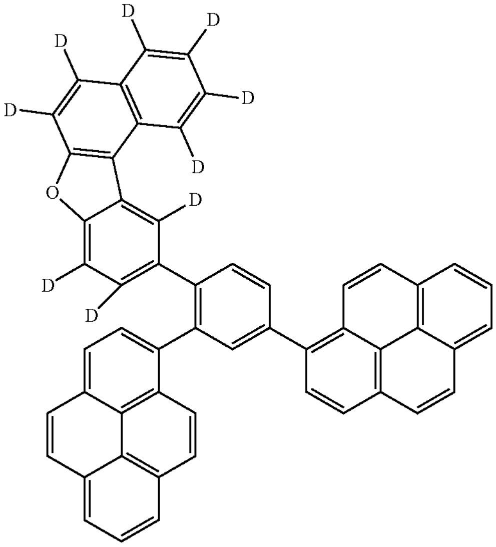

-continued
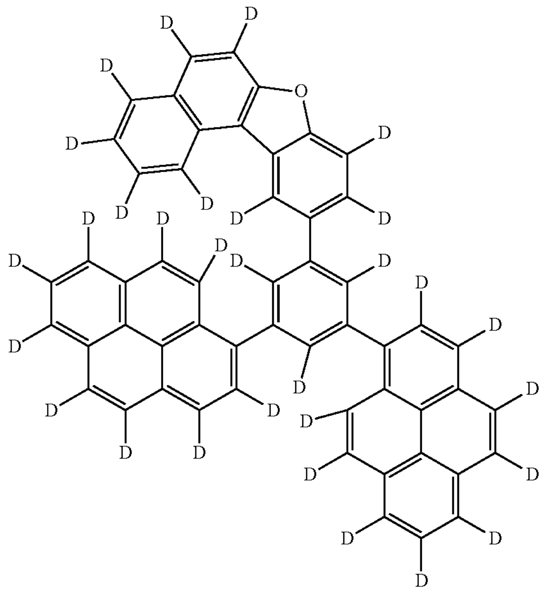
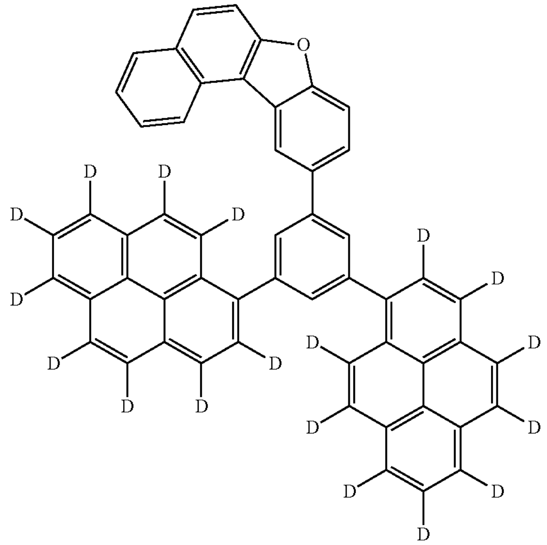
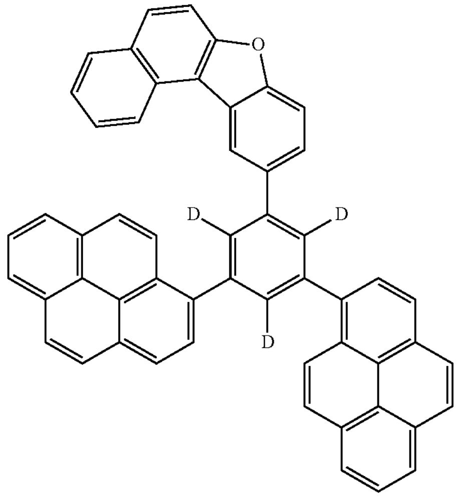
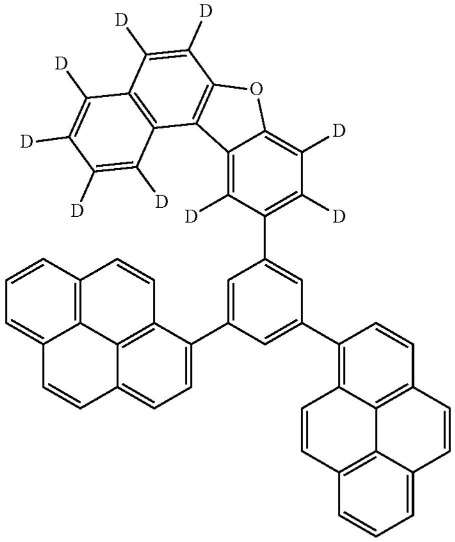

-continued
[Formula 89]
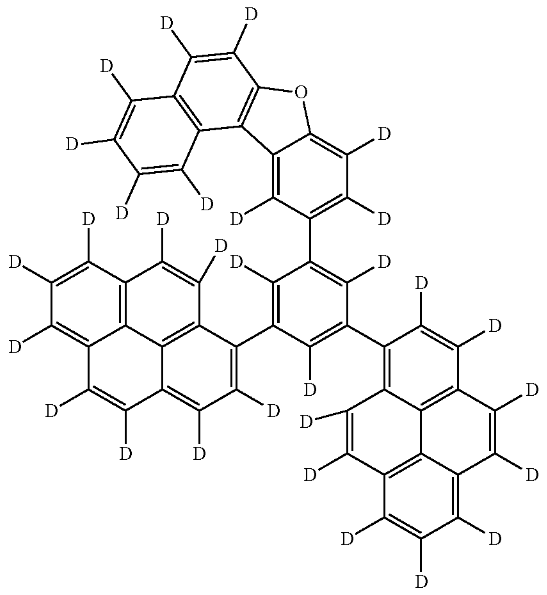
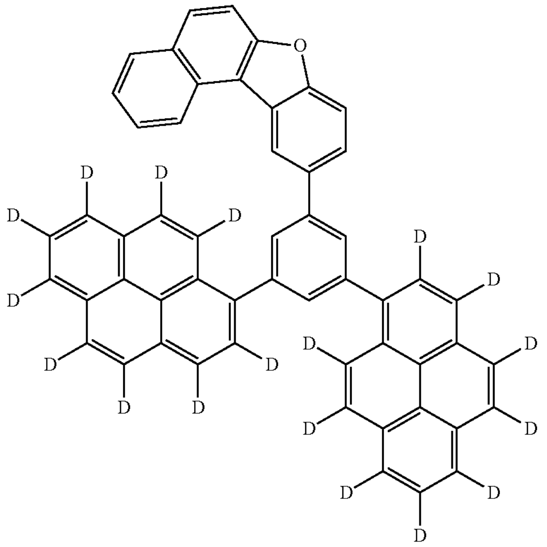
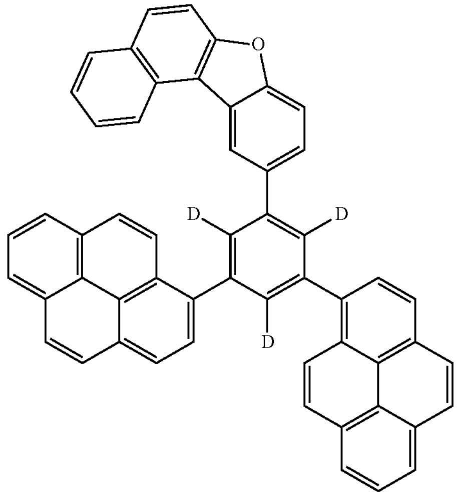
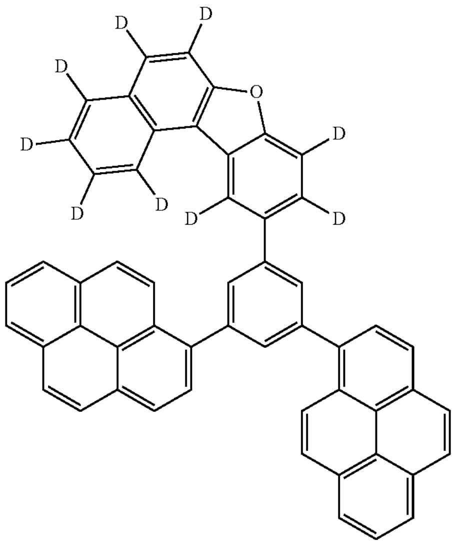

-continued
[Formula 90]
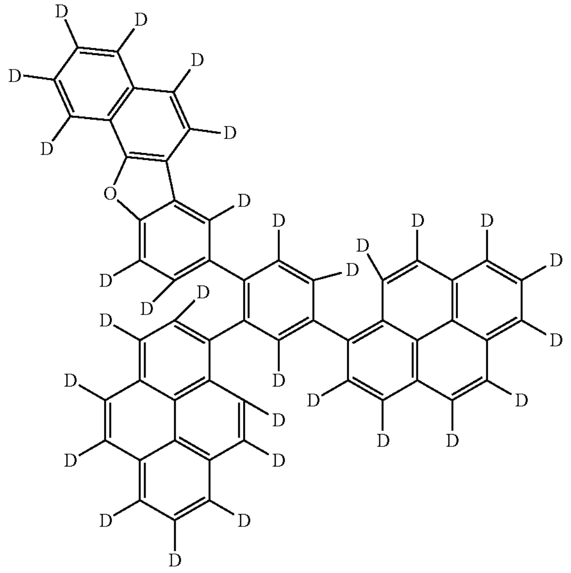
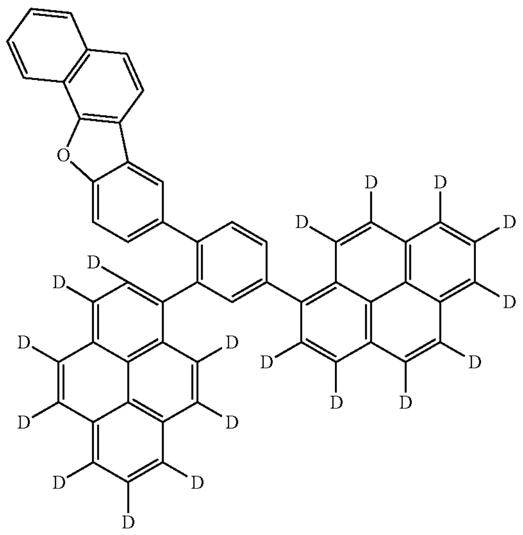
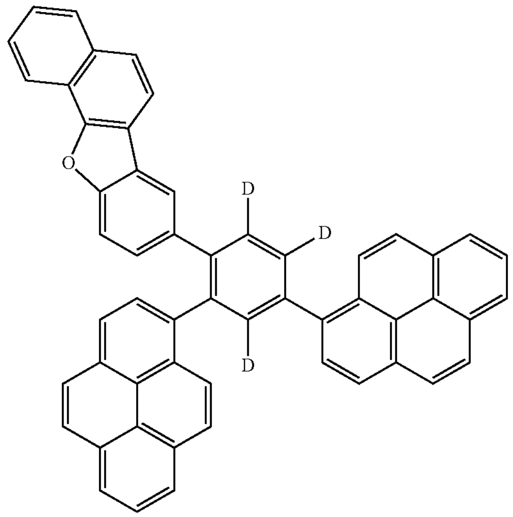
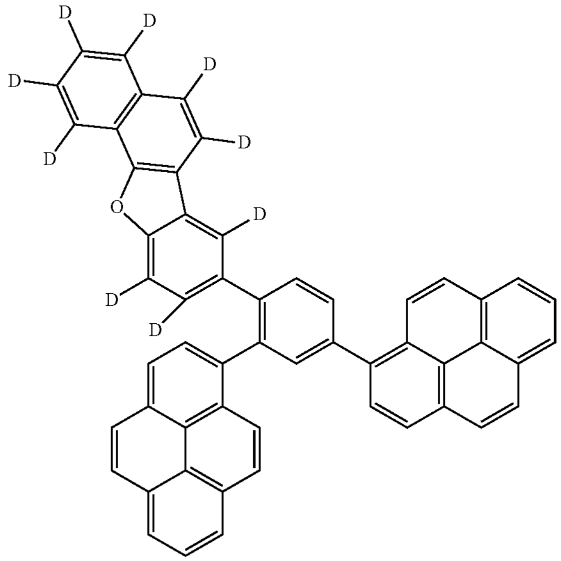

-continued
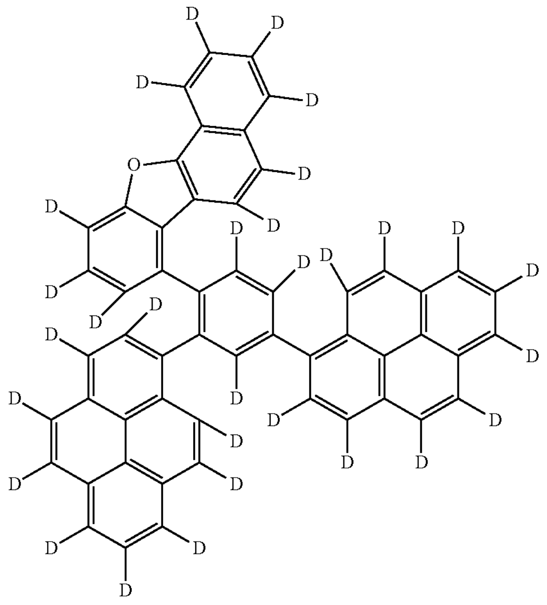
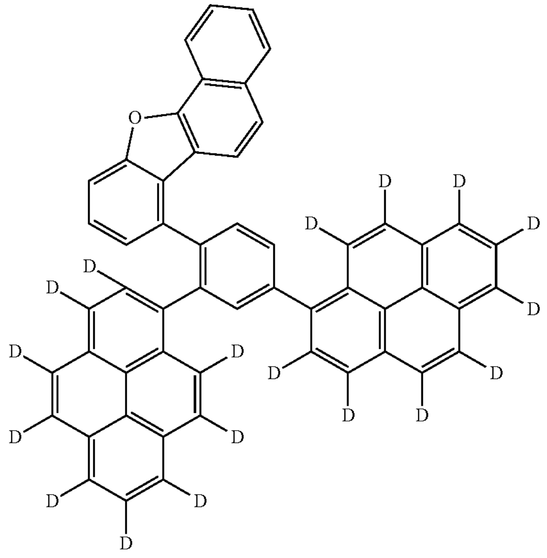
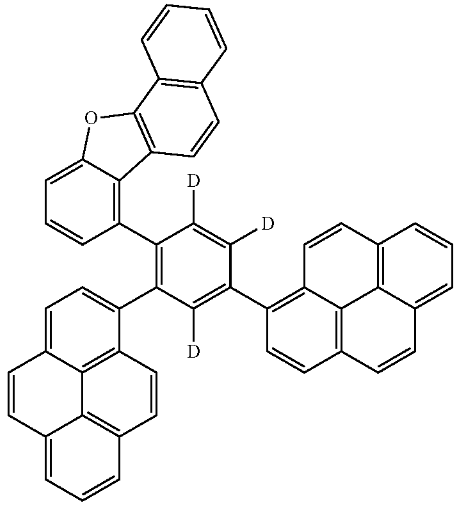
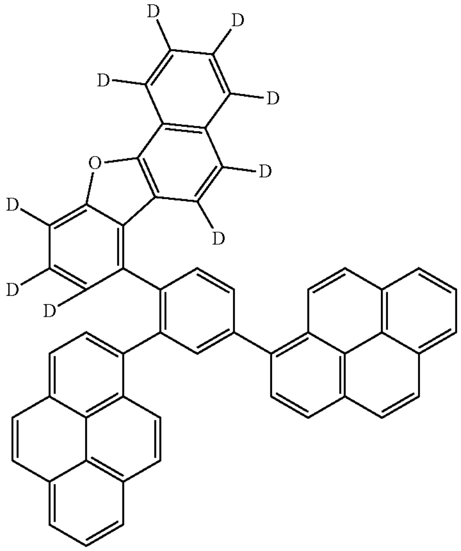

-continued
[Formula 91]
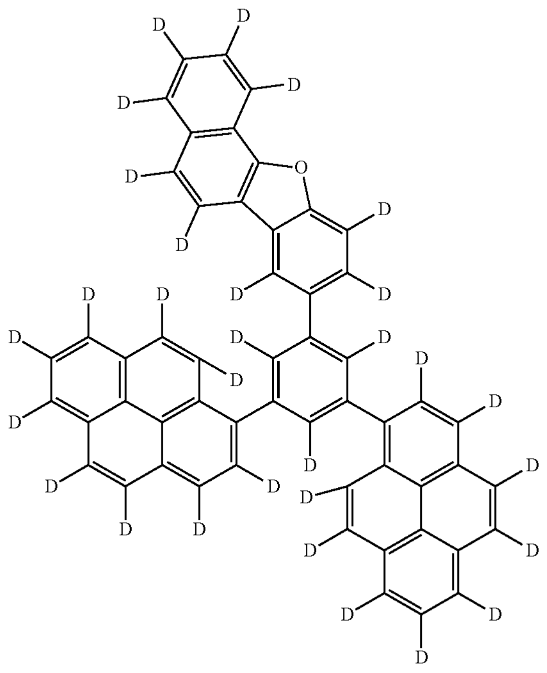
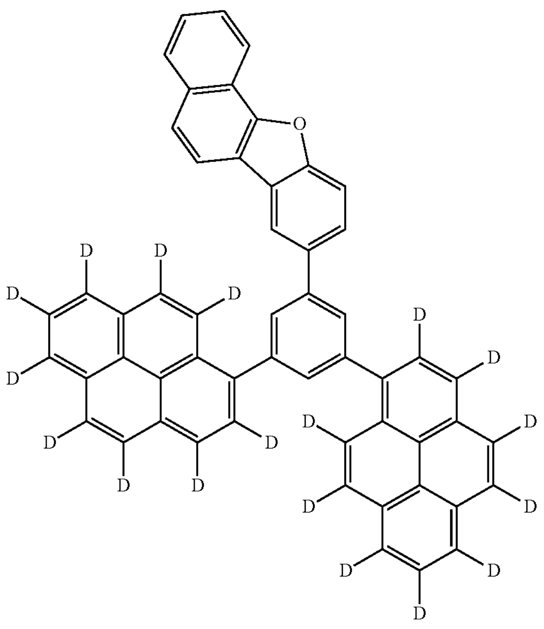
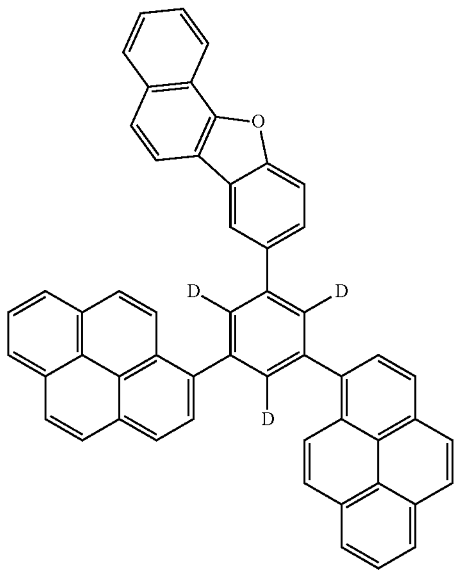
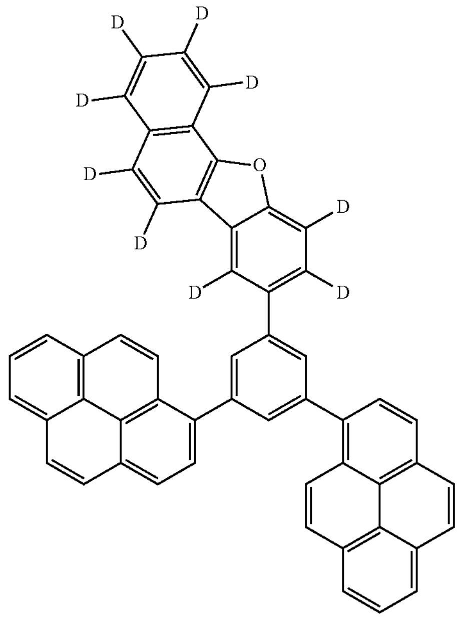

-continued
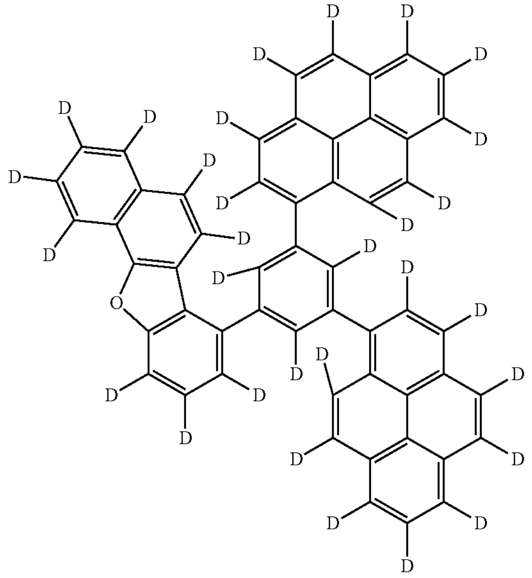
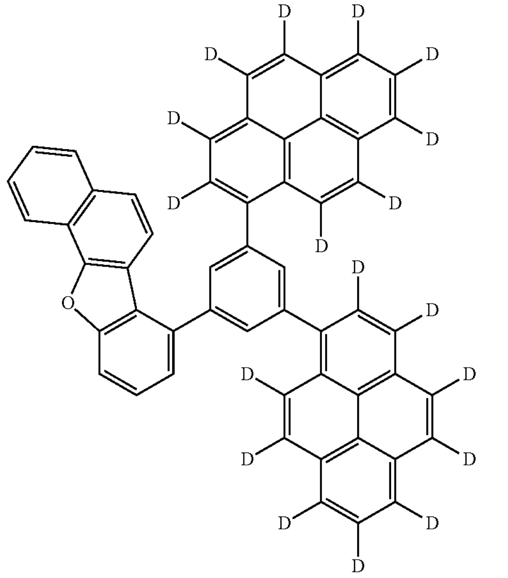
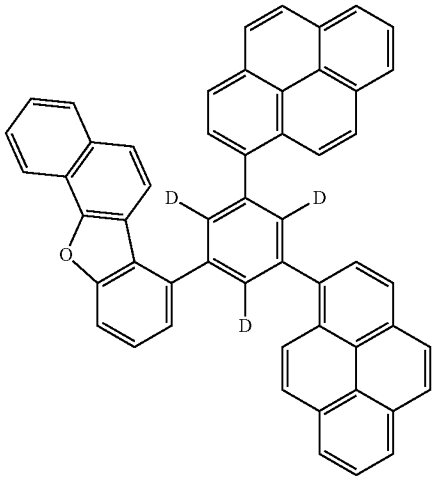
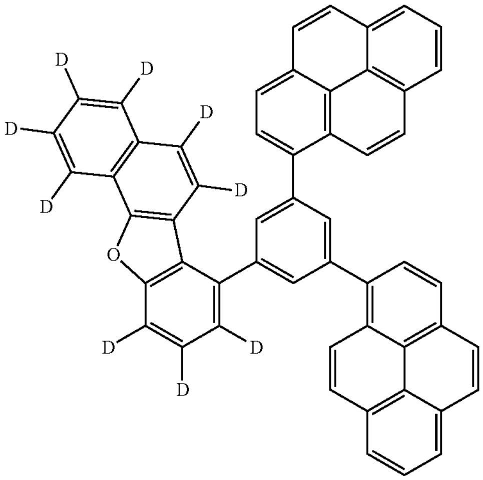
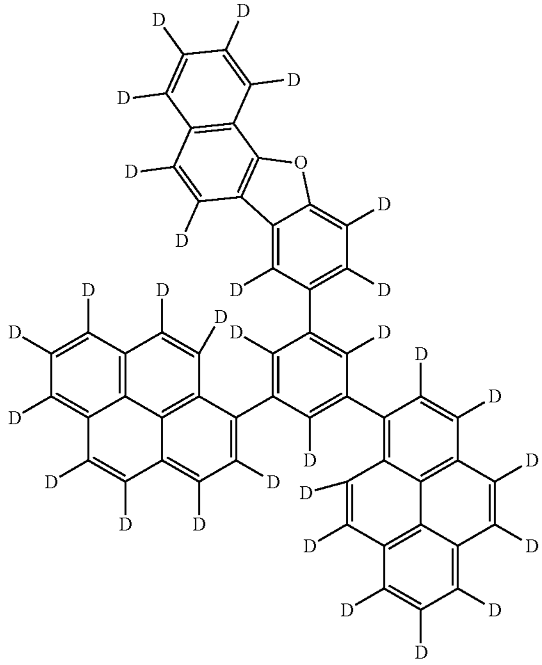
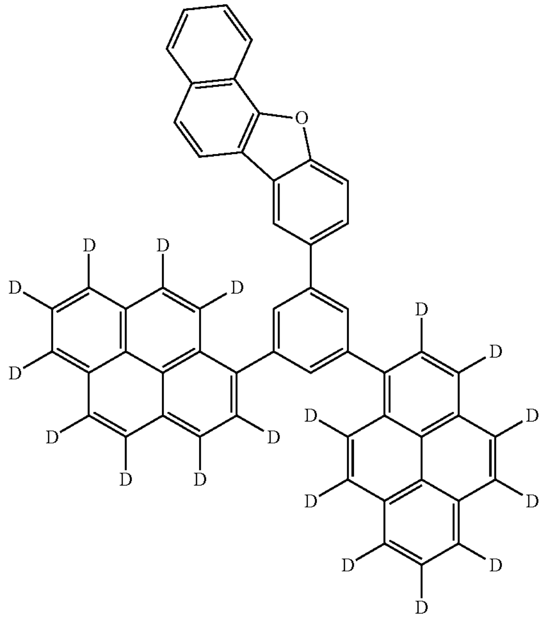

-continued
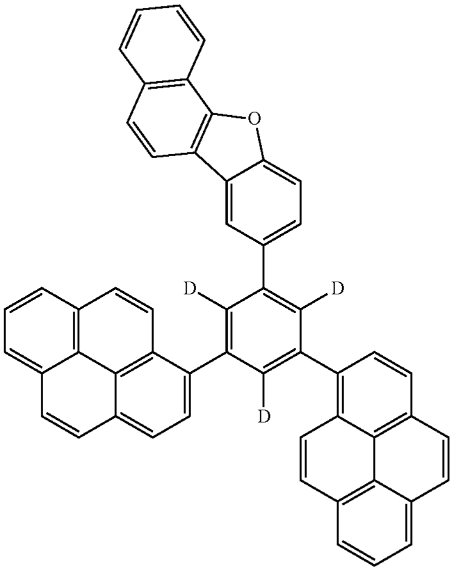
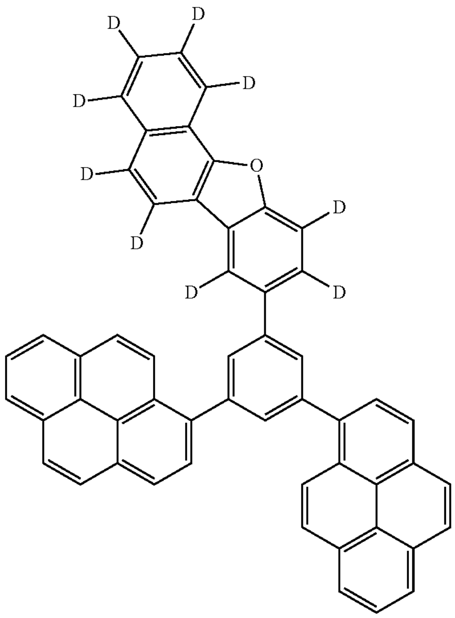
[Formula 92]
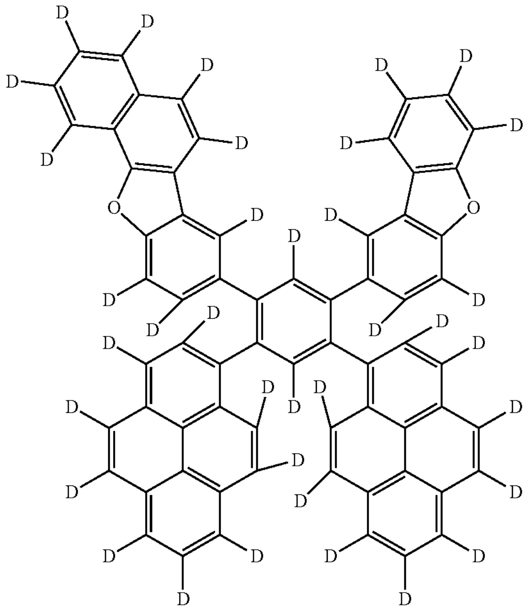
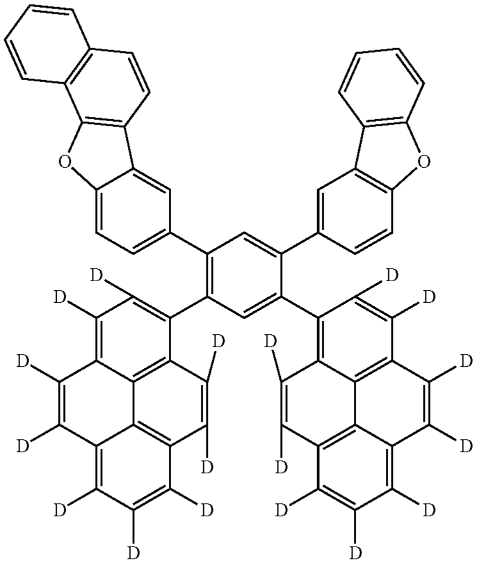

-continued
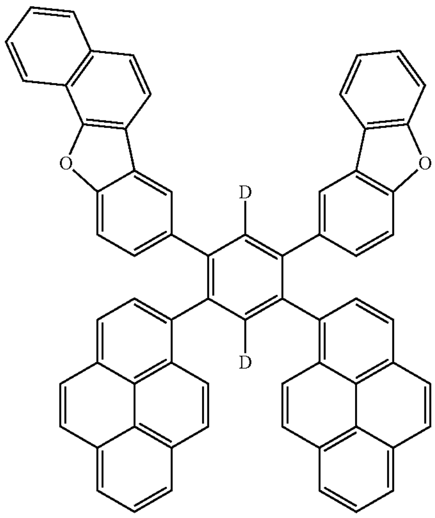
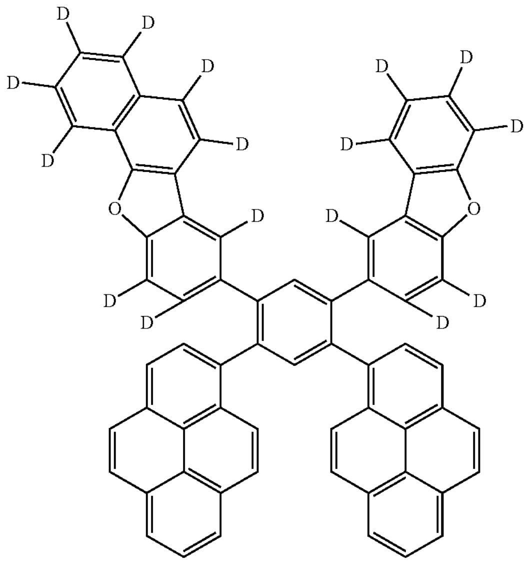
[Formula 93]
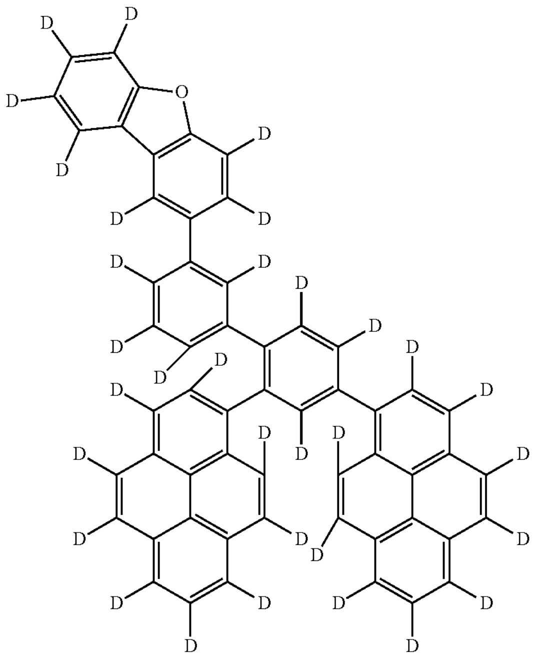
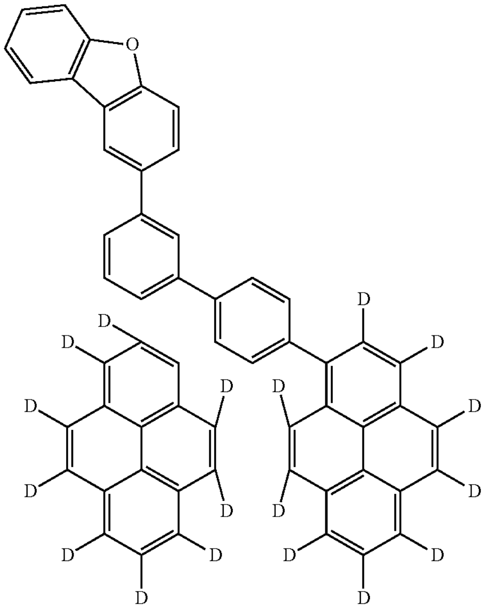

-continued
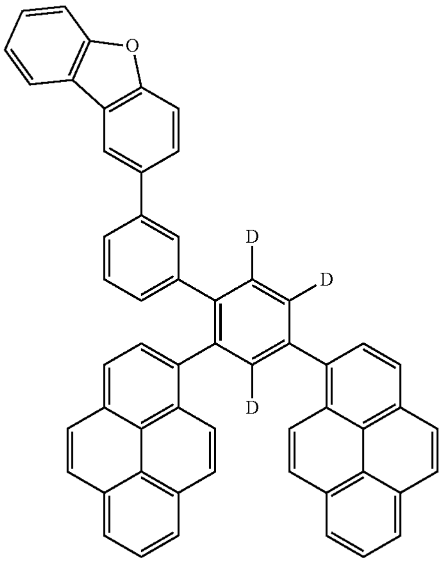
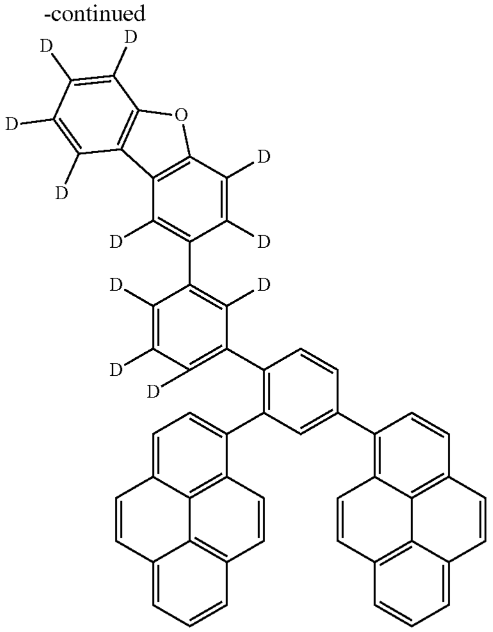
[Foromula 94]
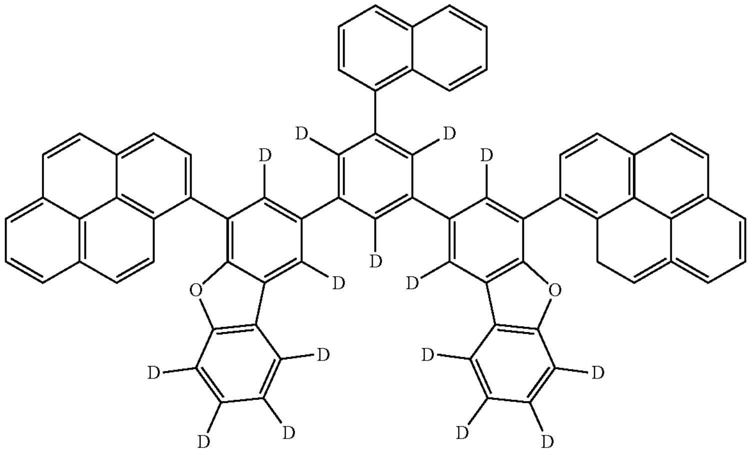
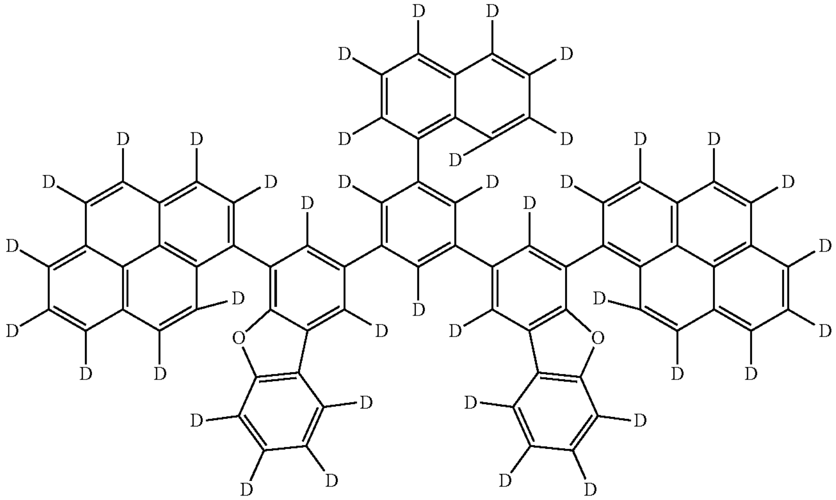

-continued
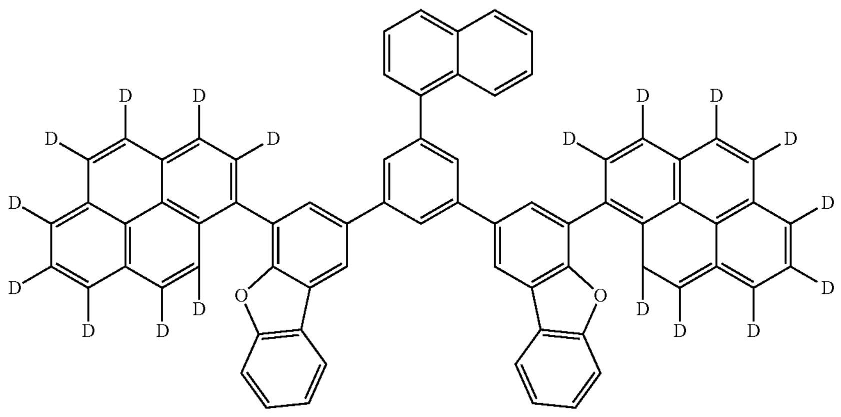
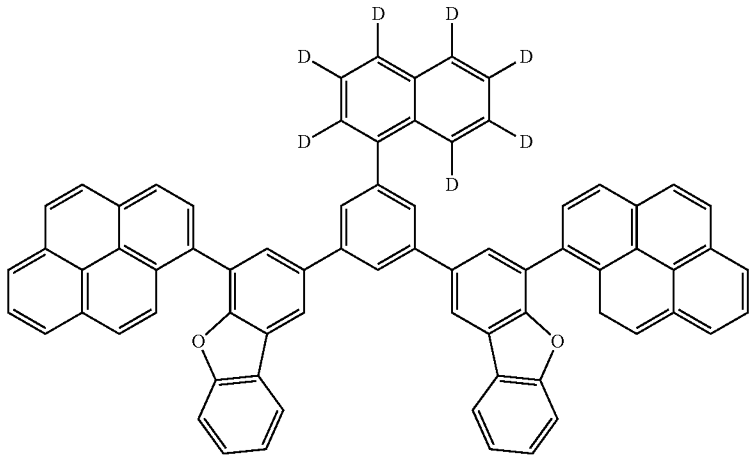
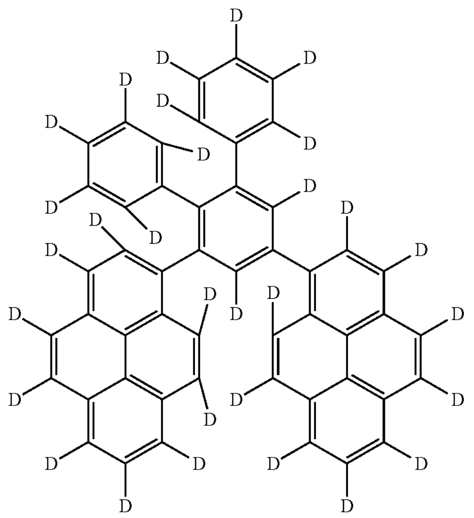
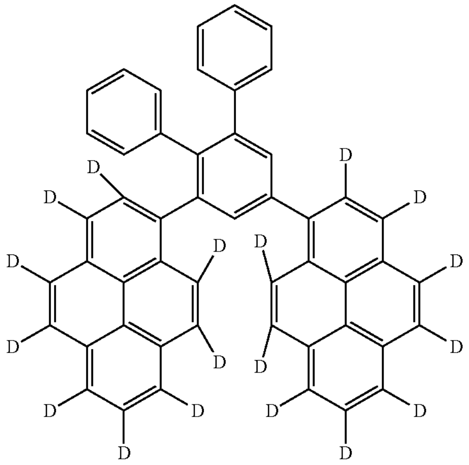

-continued
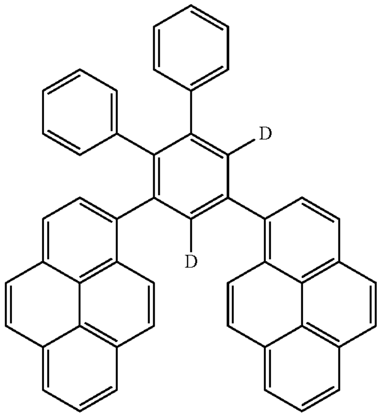
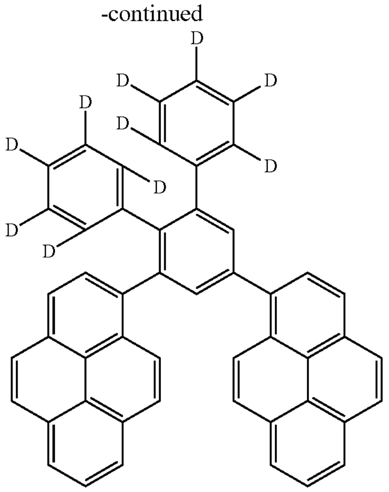
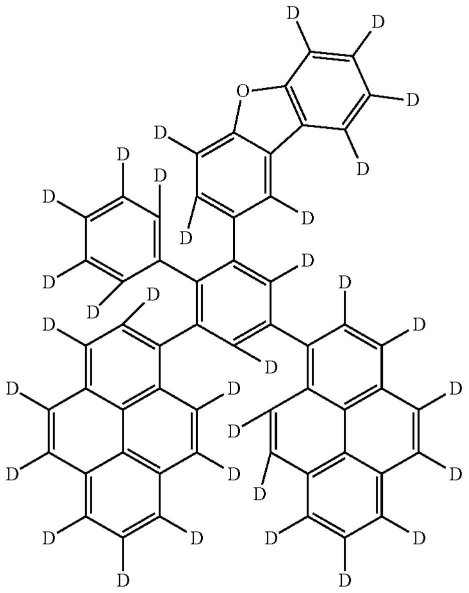
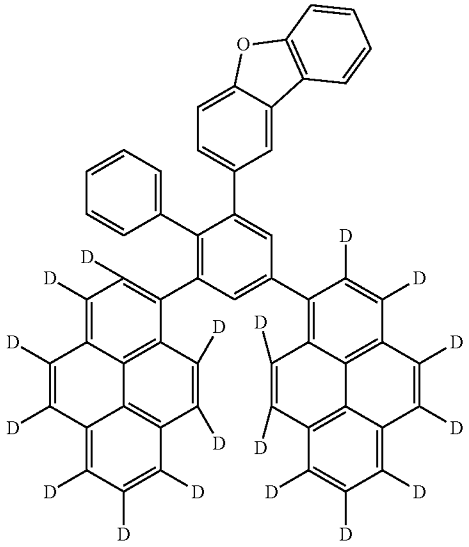
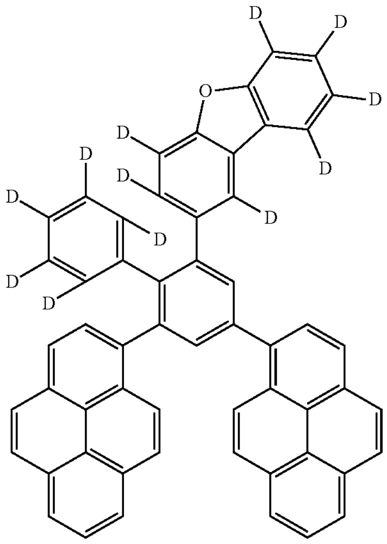

-continued
[Formula 95]
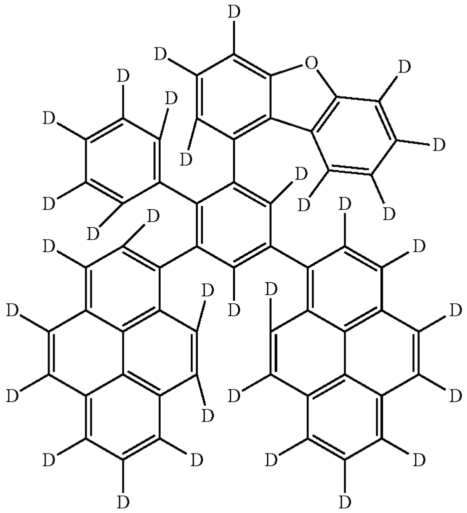
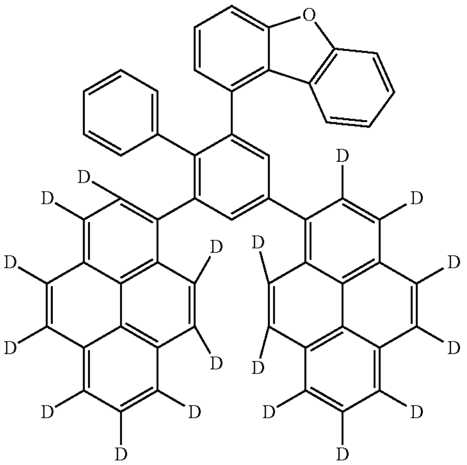
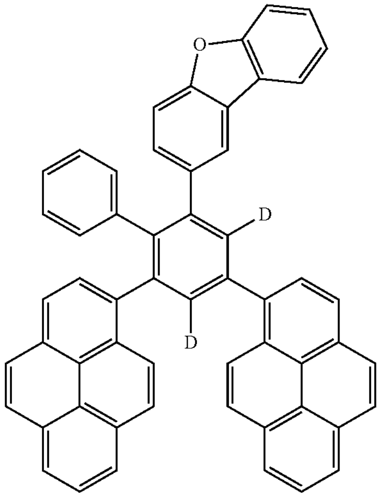
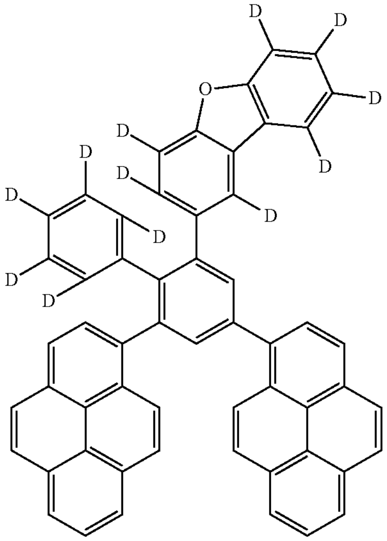
[Formula 96]
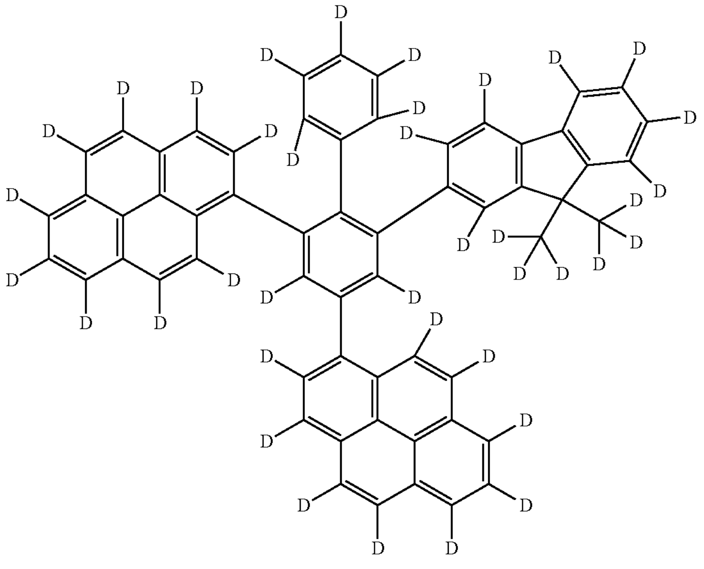

-continued
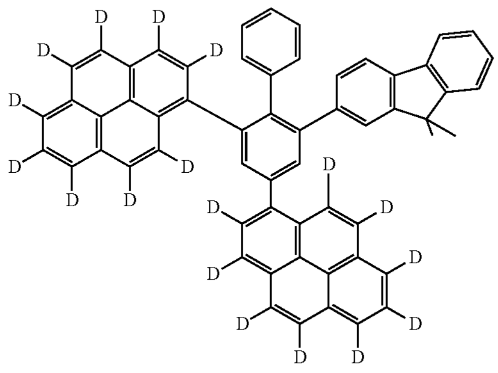
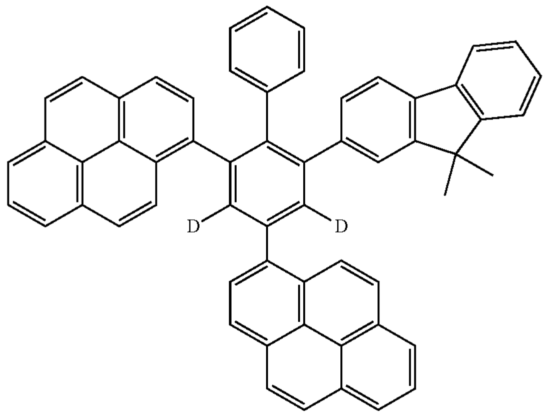
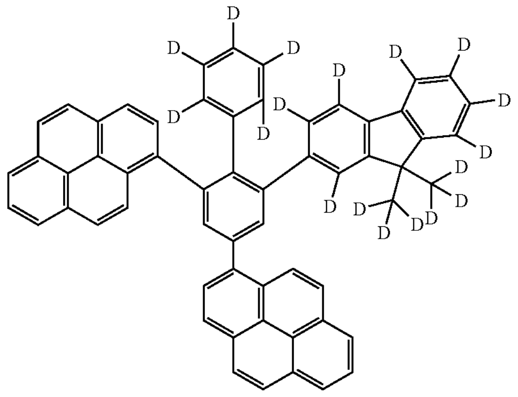
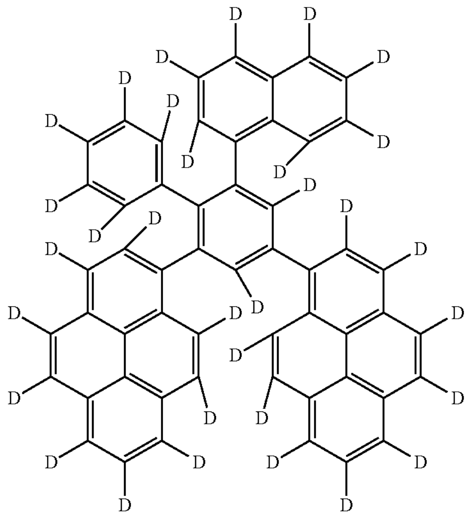
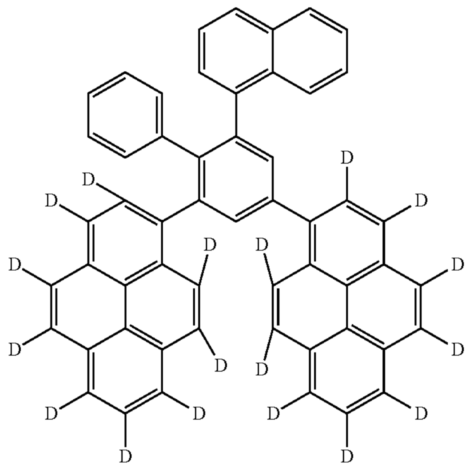
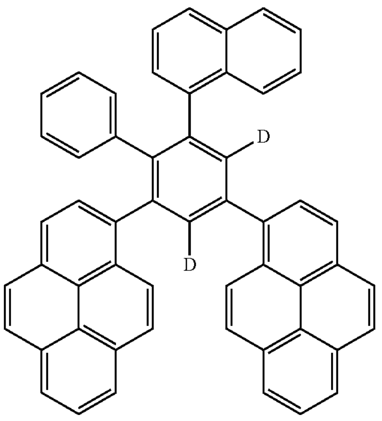

-continued
[Formula 97]
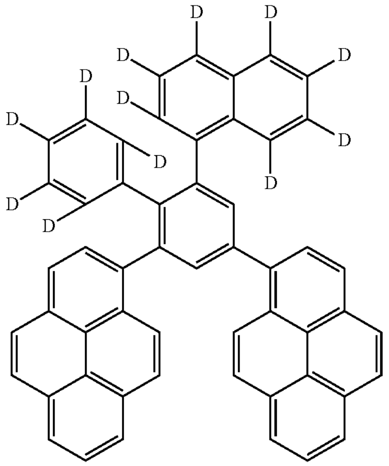
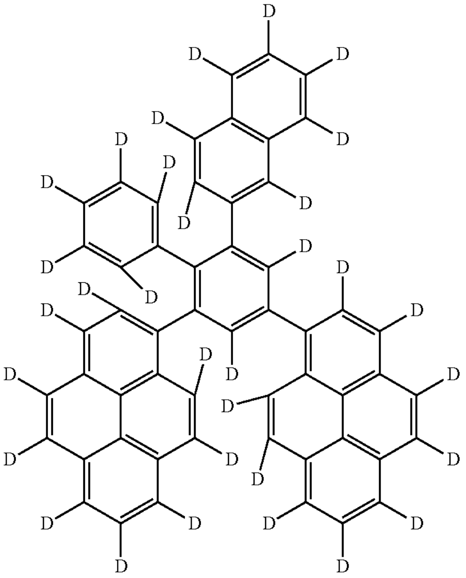
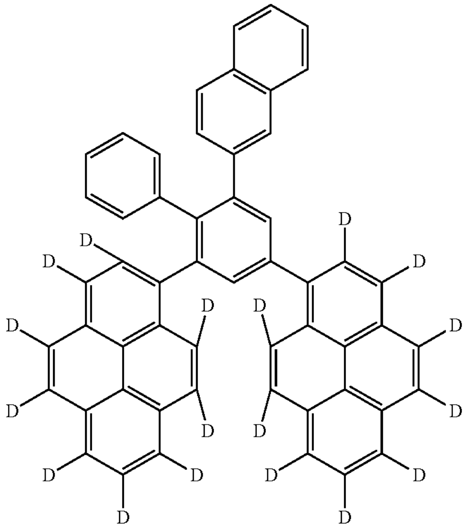
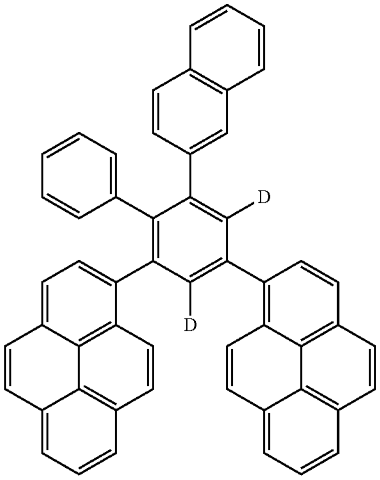
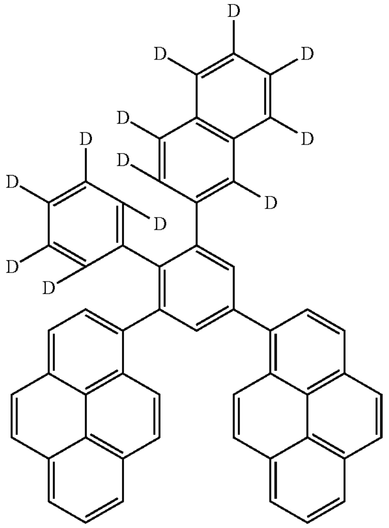

-continued
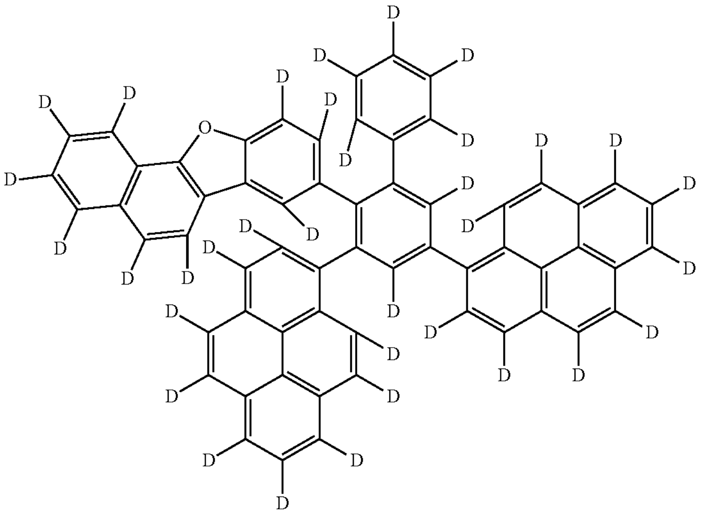
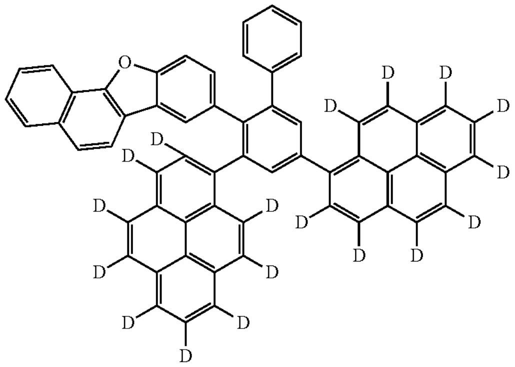
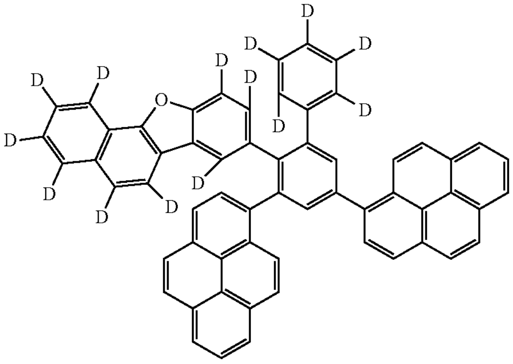
[Formula 98]
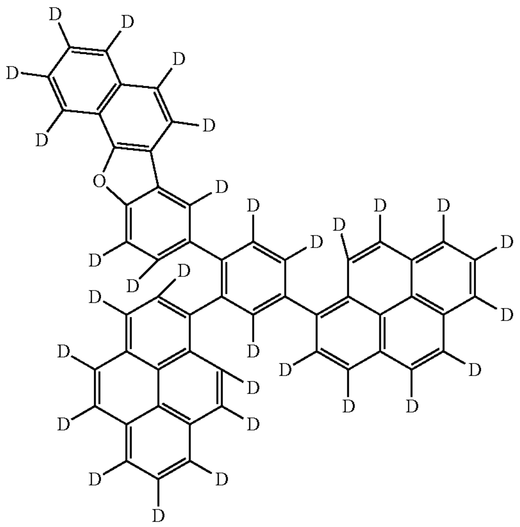
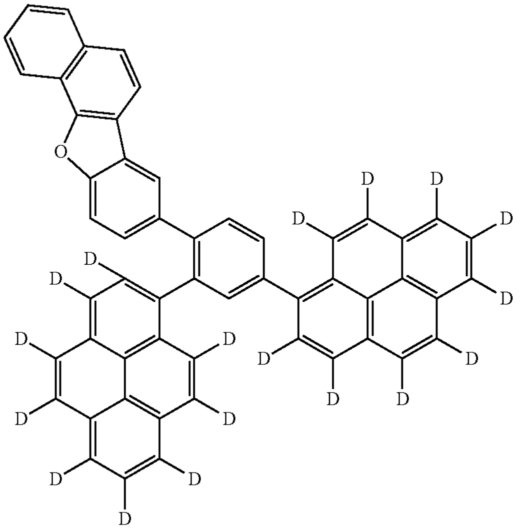

-continued
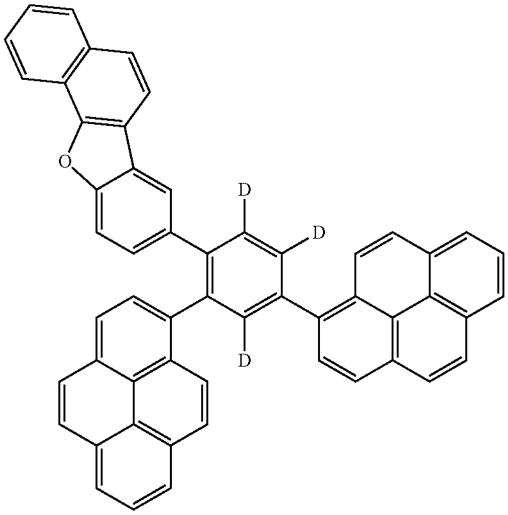
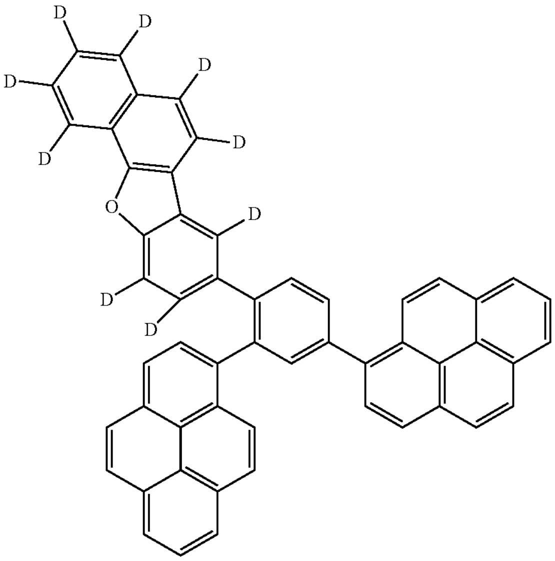
[Formula 99]
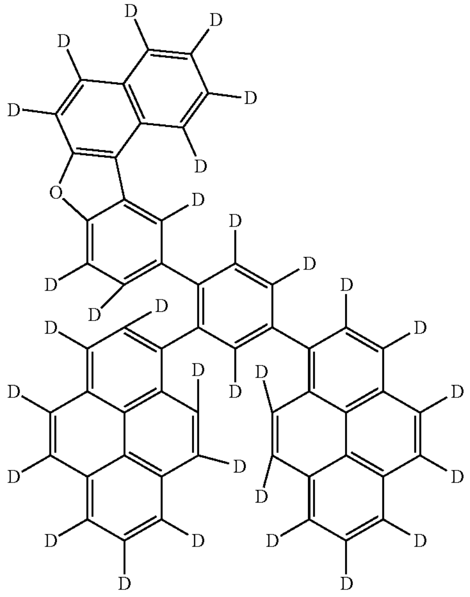
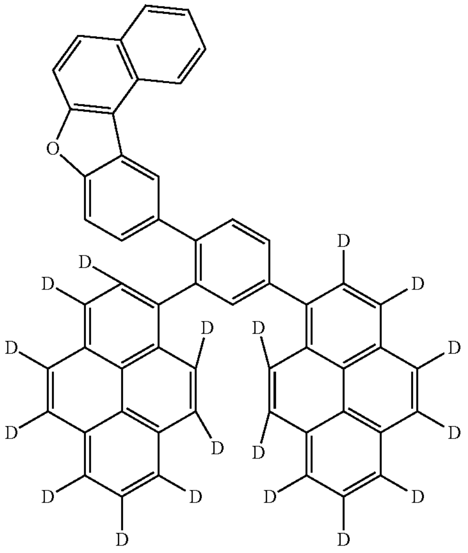

-continued
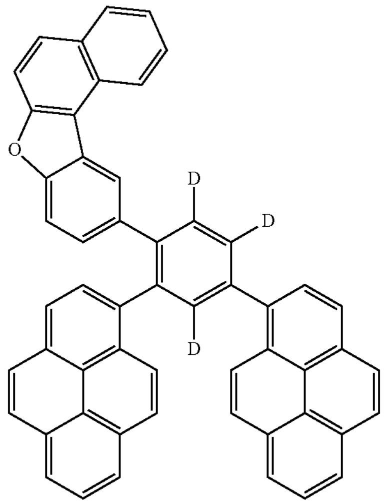
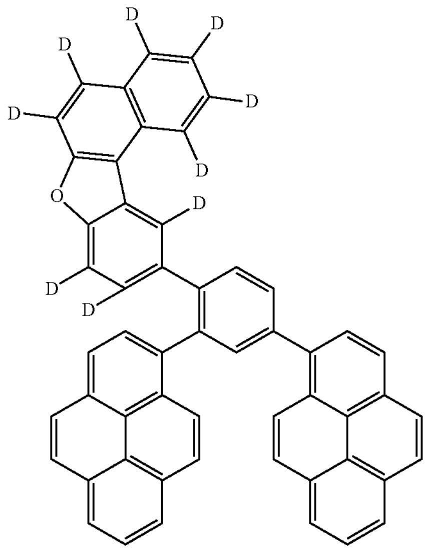
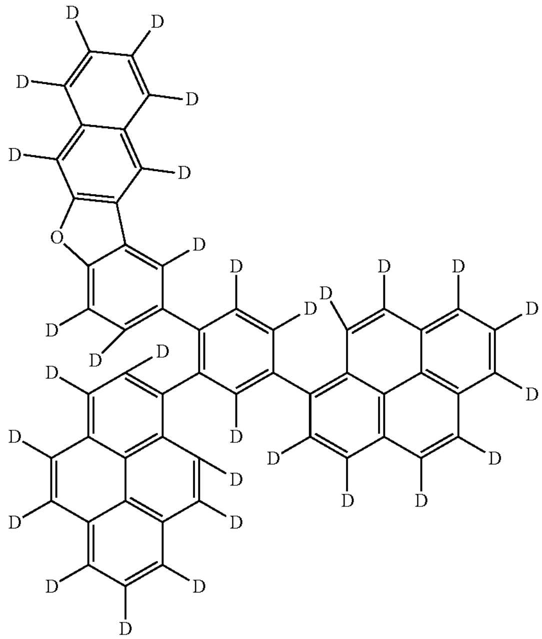
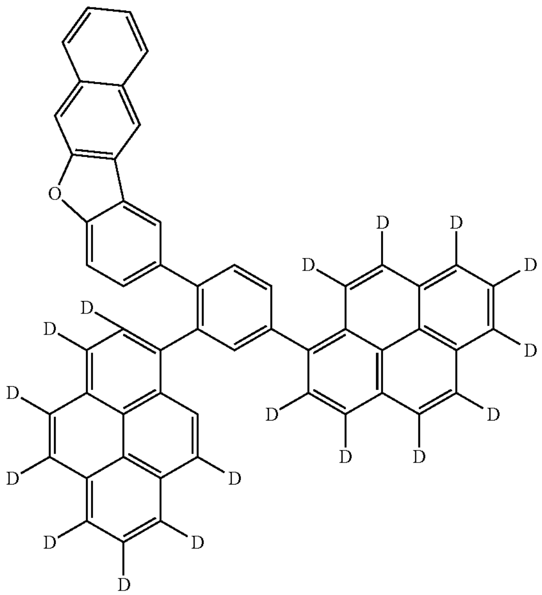

-continued
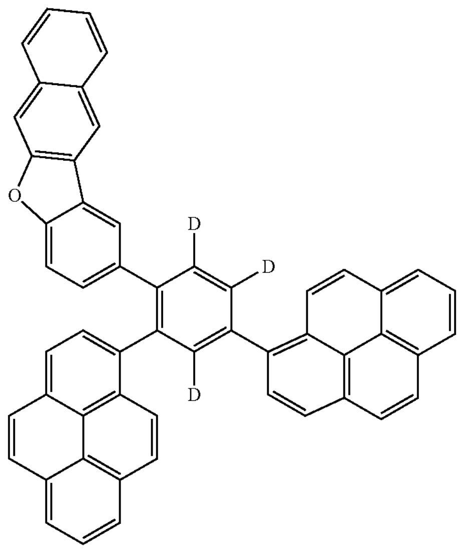
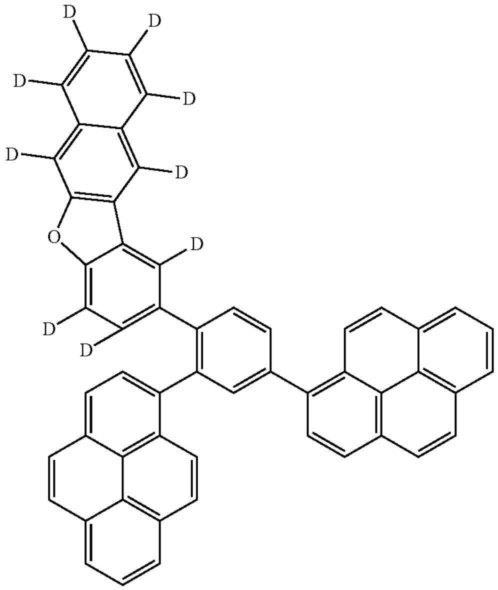
[Formula 100]
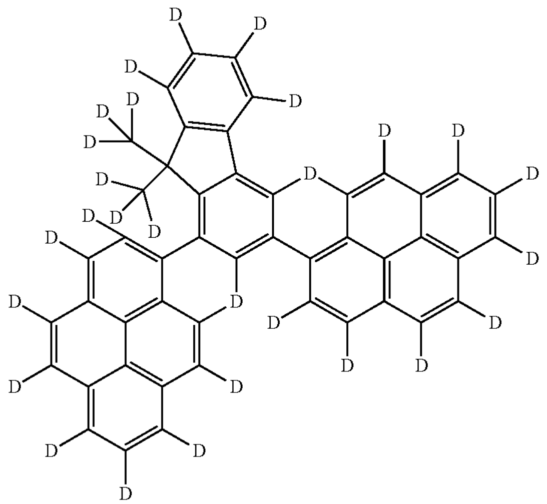
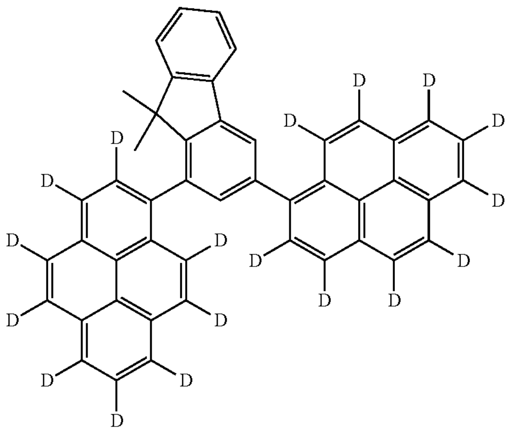
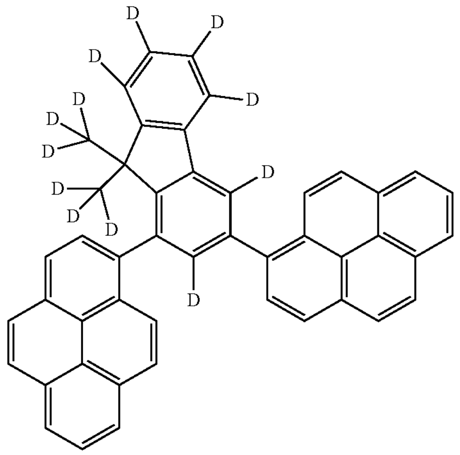
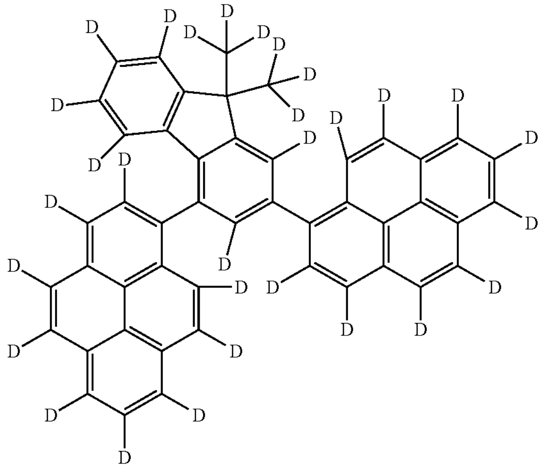

-continued
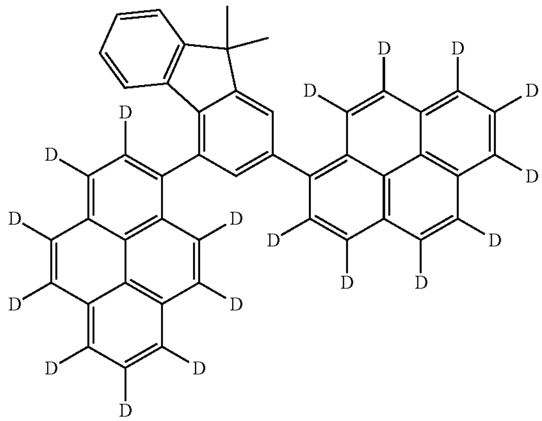
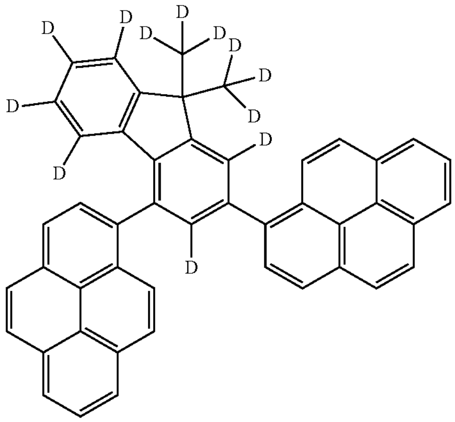
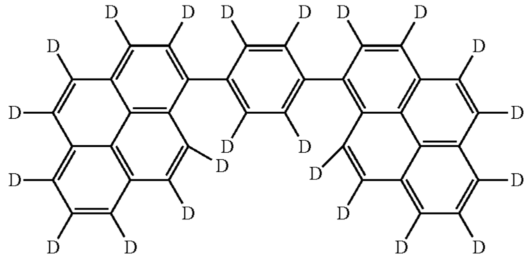
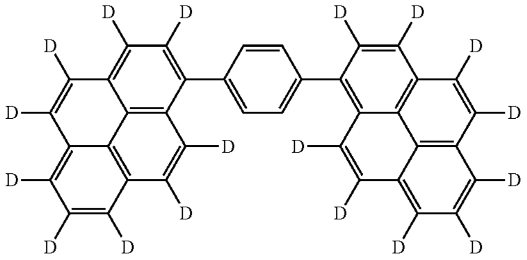
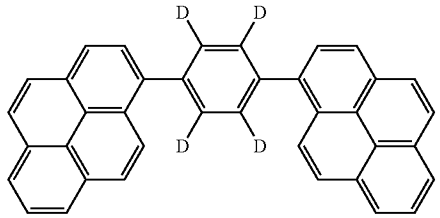
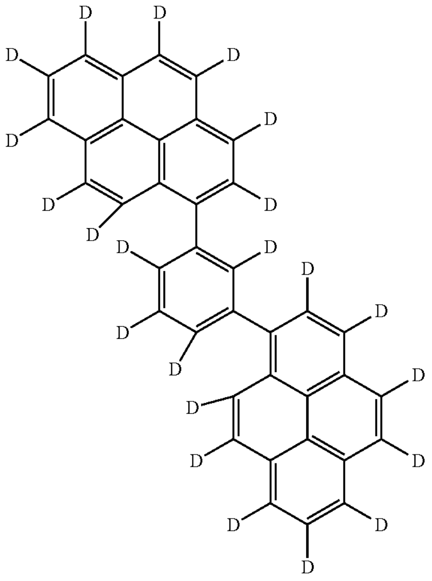

-continued
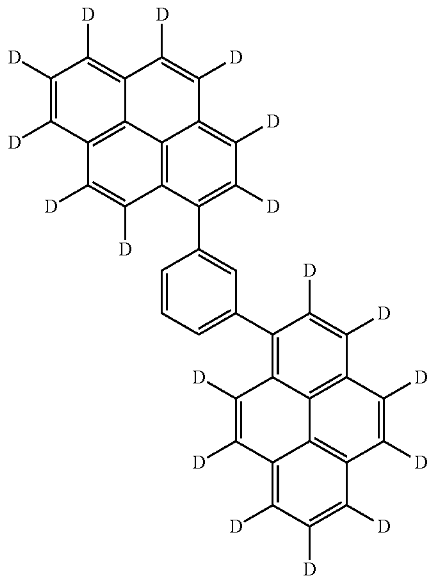
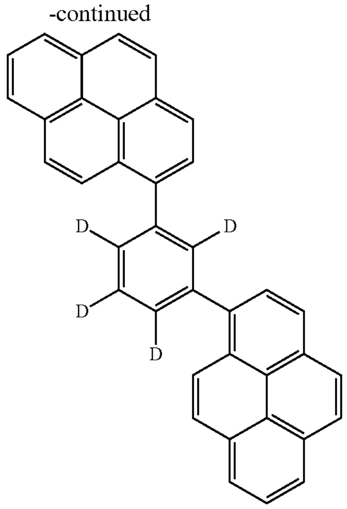
[Formula 101]
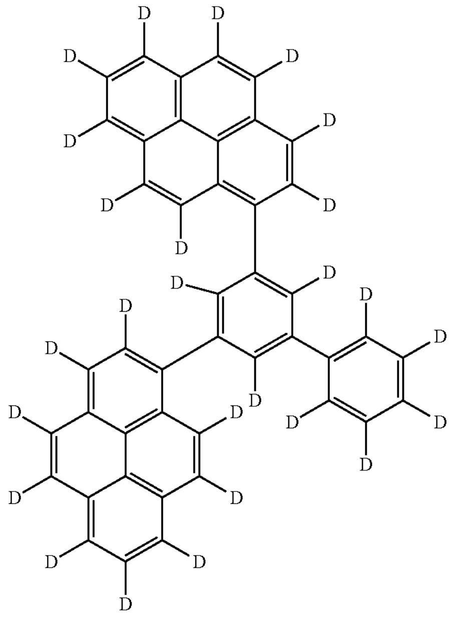
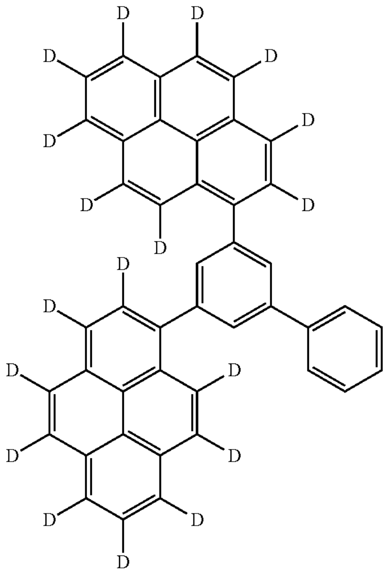

-continued
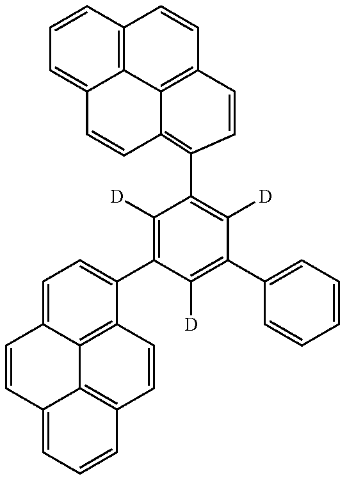
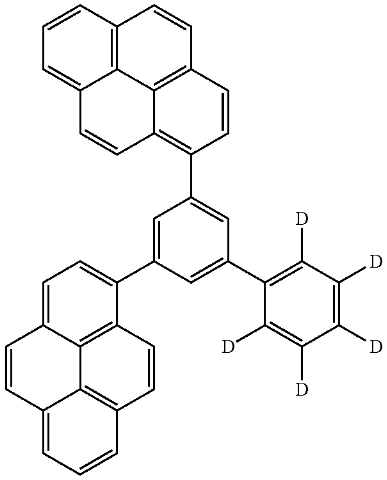
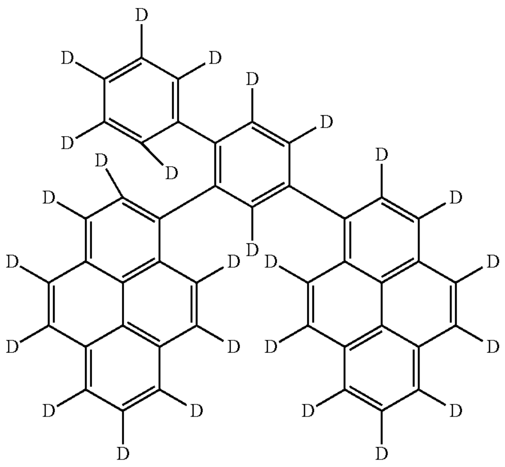
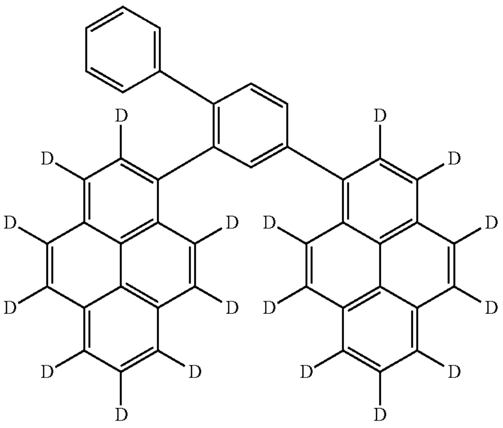
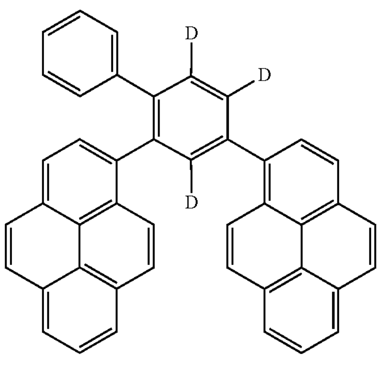
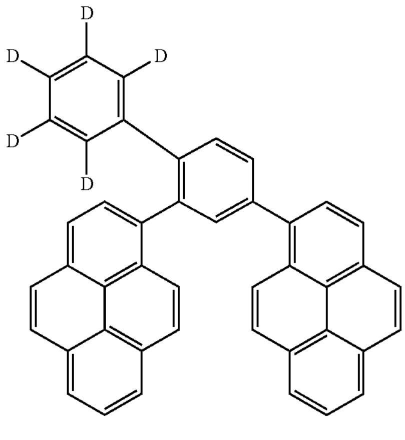

-continued
[Formula 102]
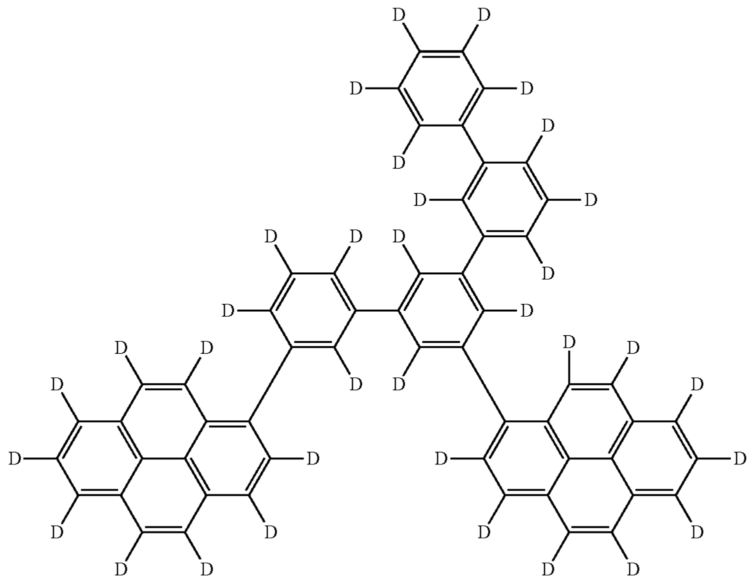
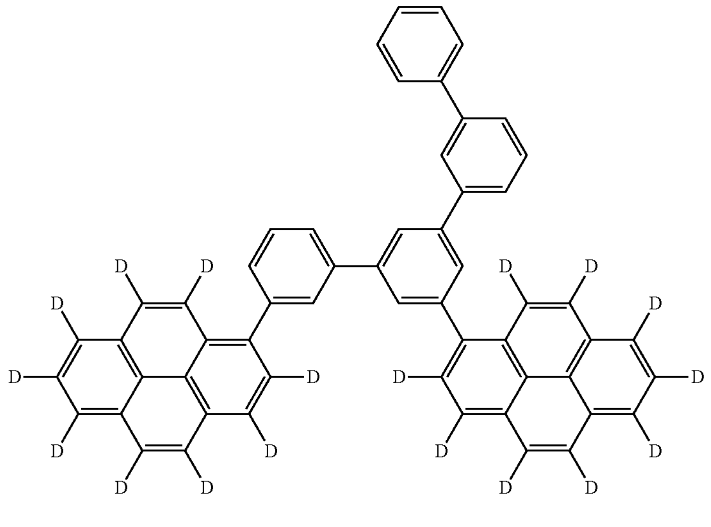
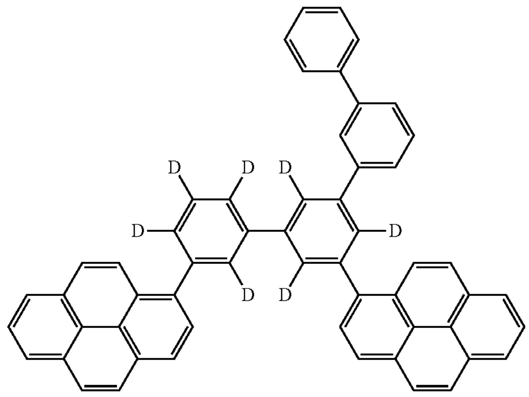
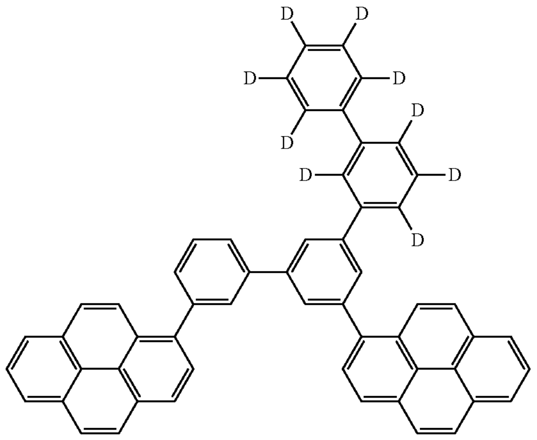

-continued
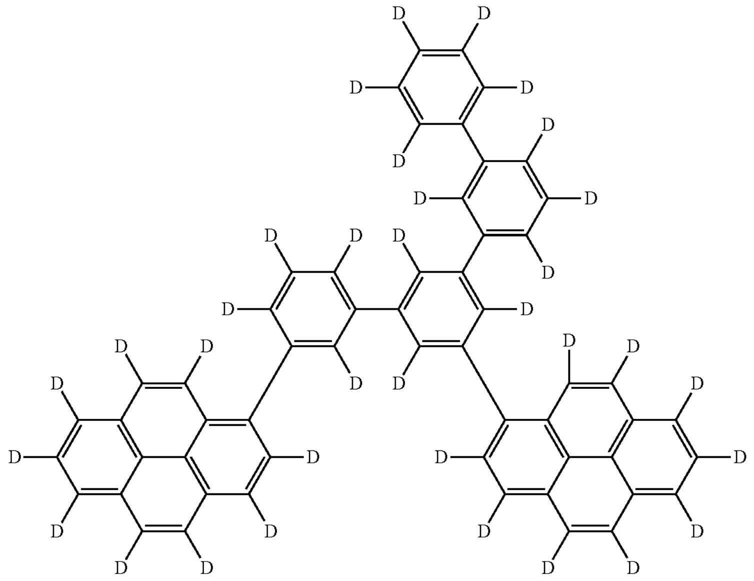
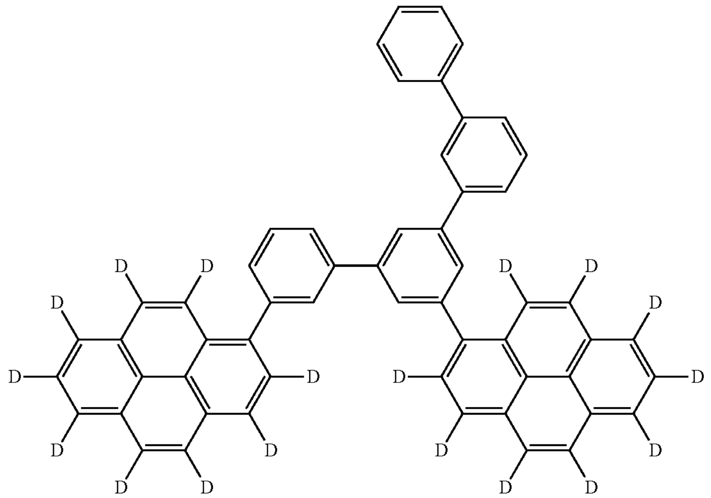
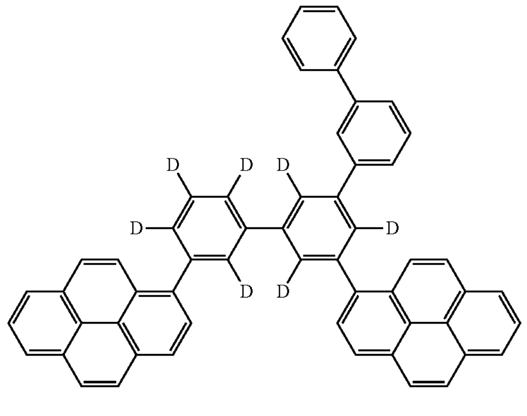
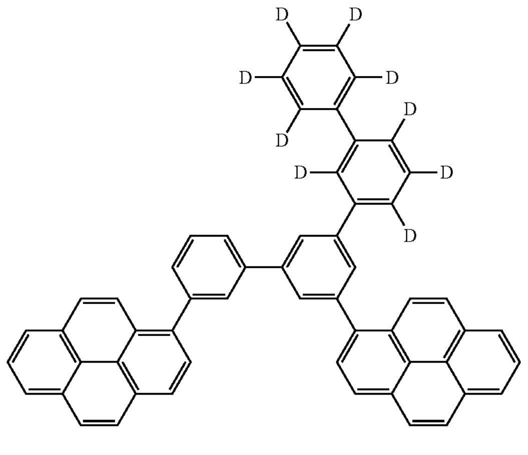

-continued
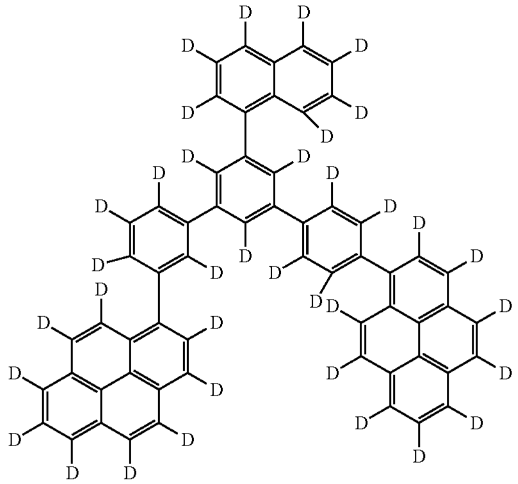
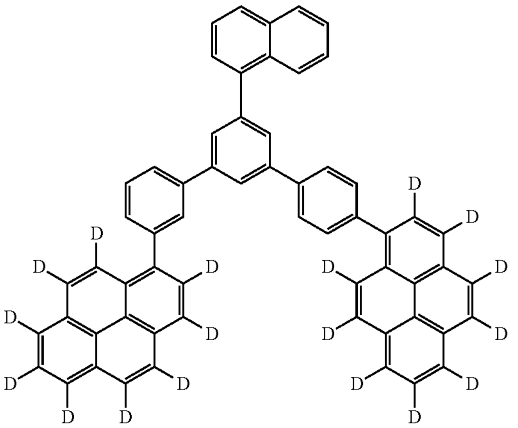
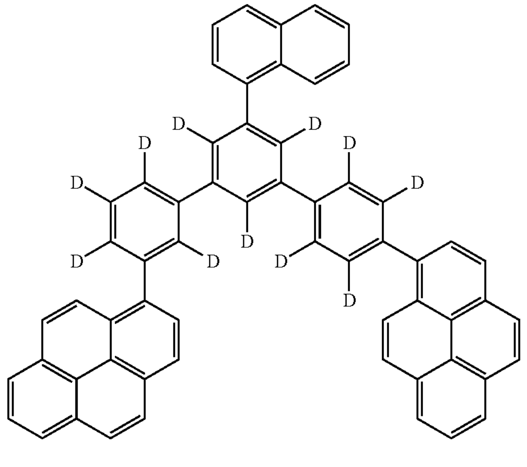
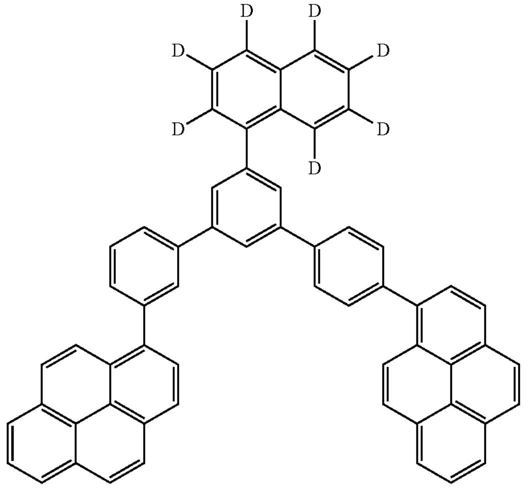
[Formula 103]
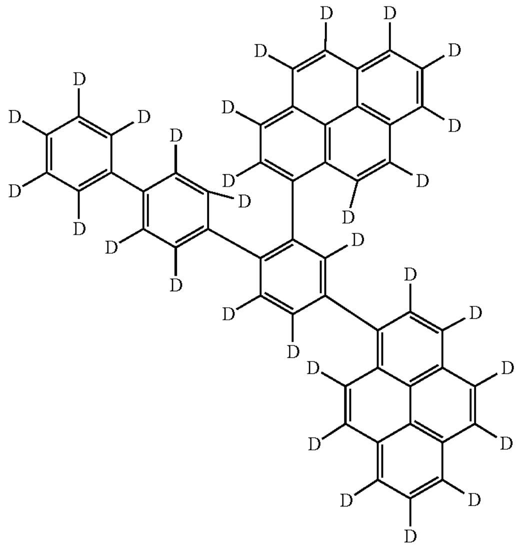
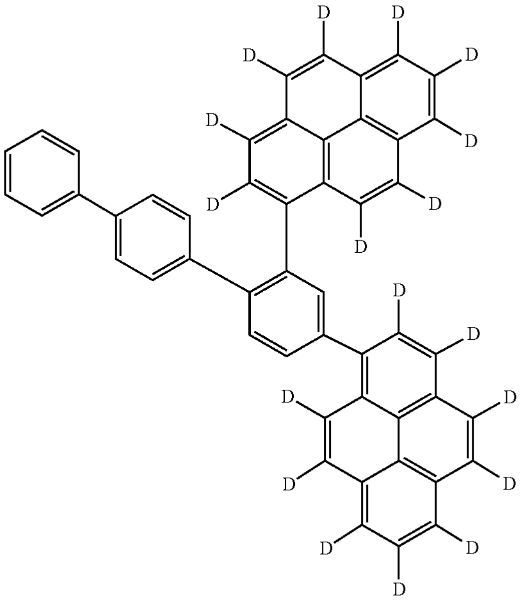

-continued
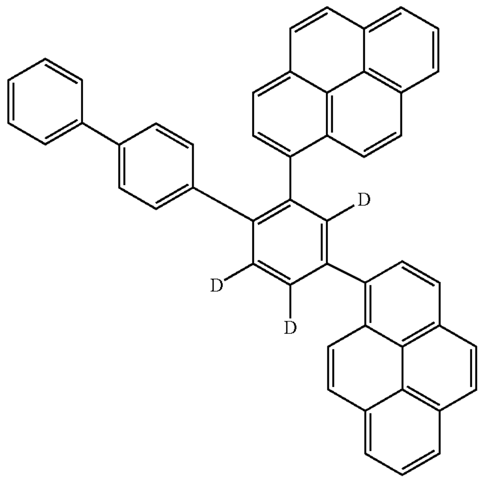
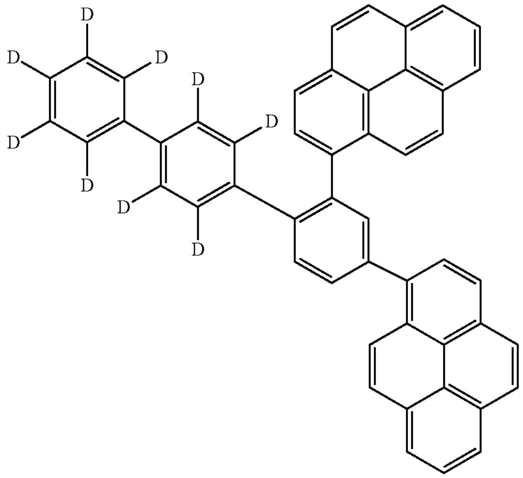
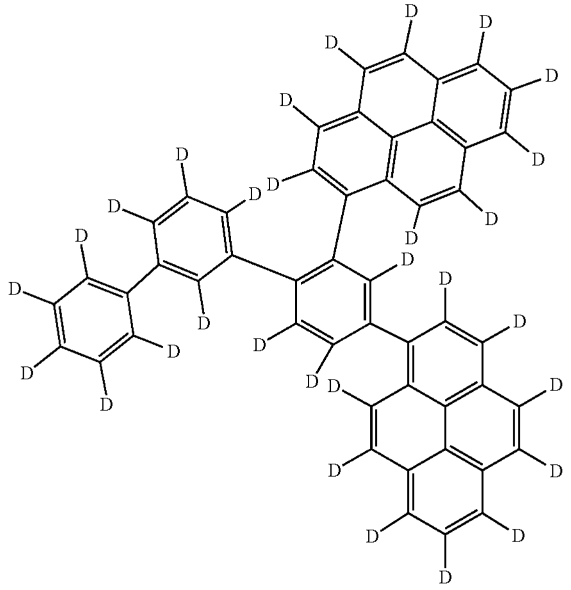
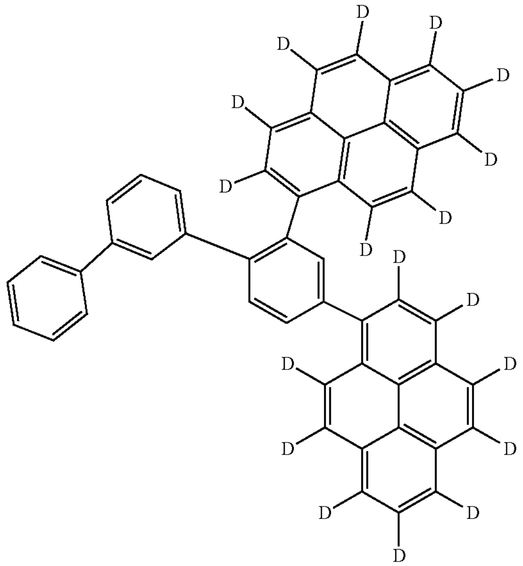
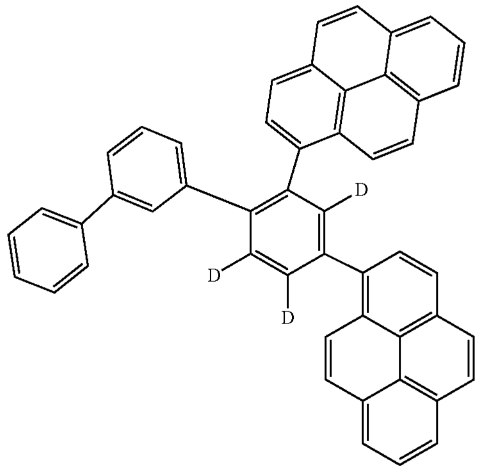
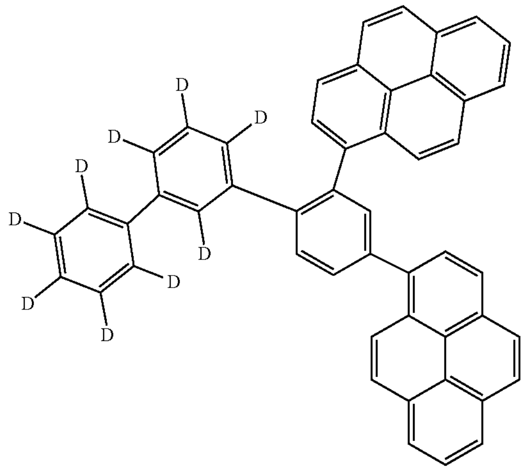

-continued
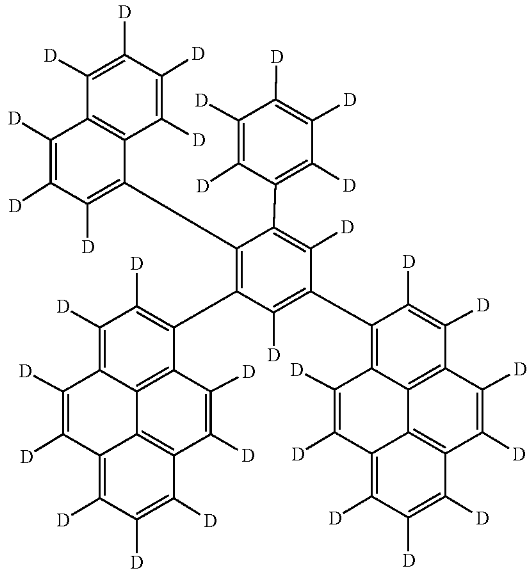
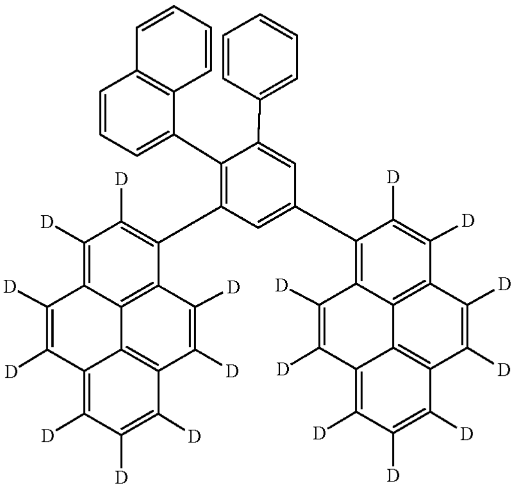
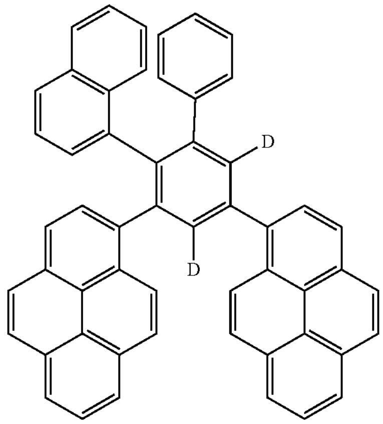
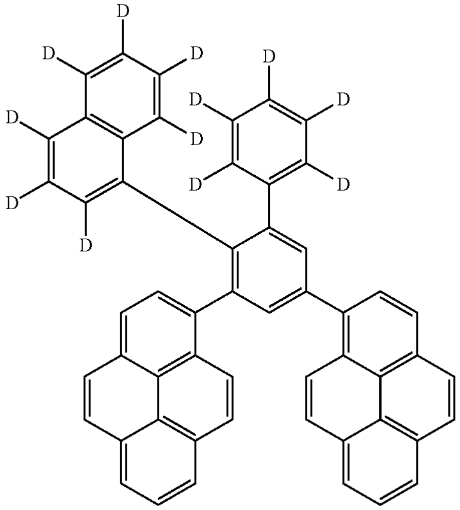
[Formula 104]
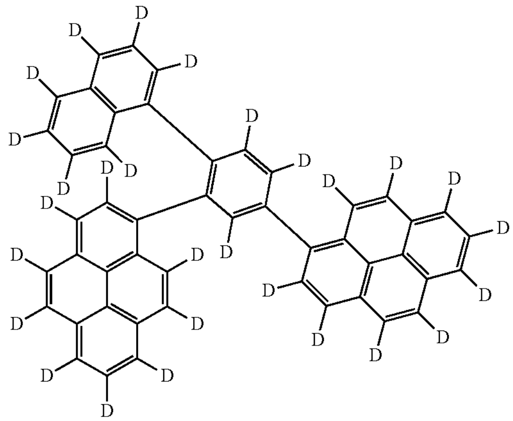
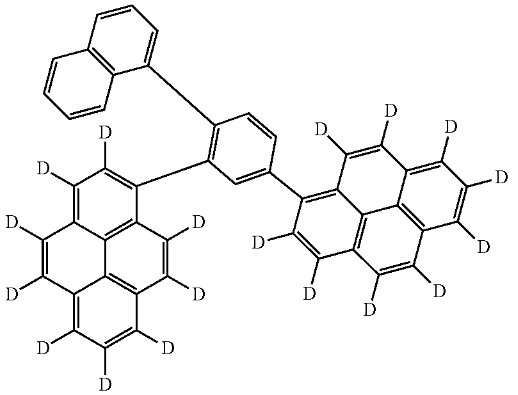

-continued
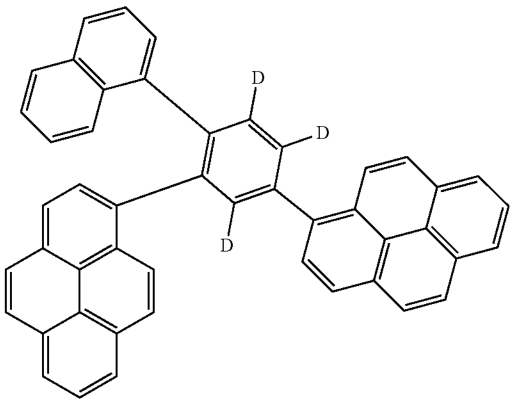
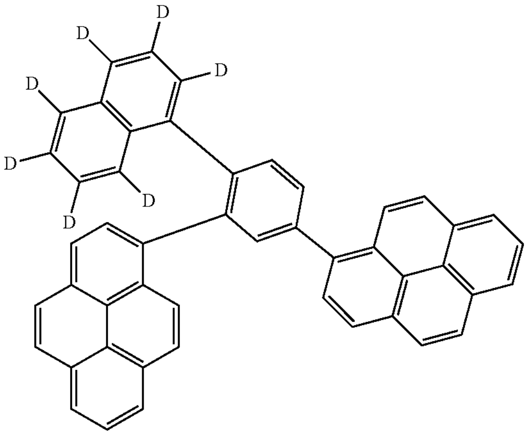
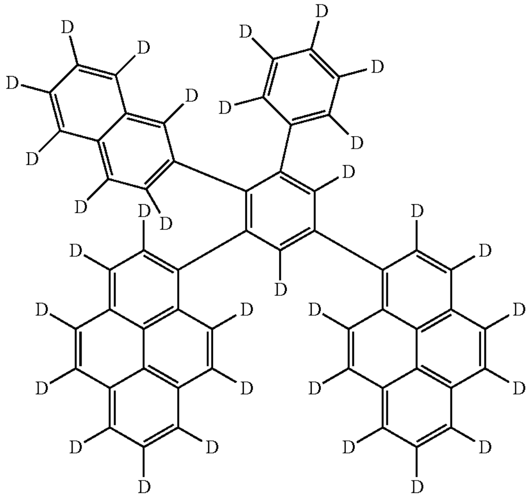
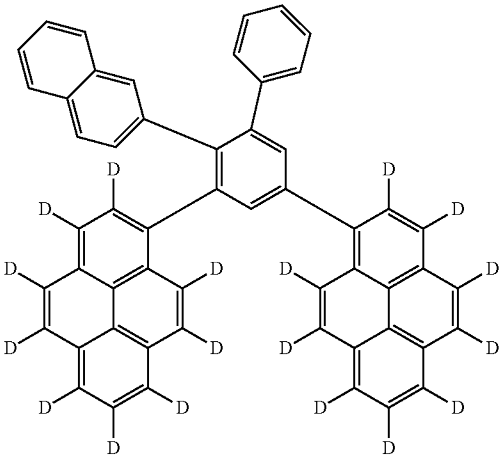
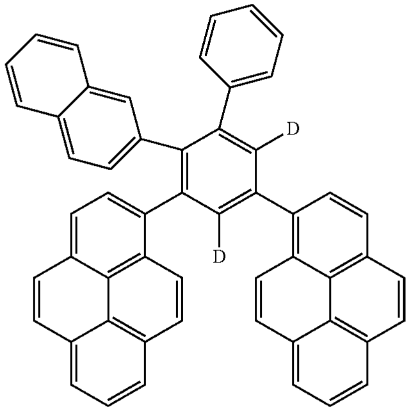
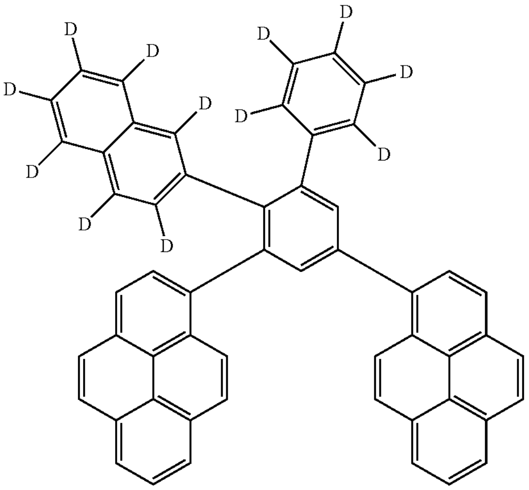

-continued
[Formula 105]
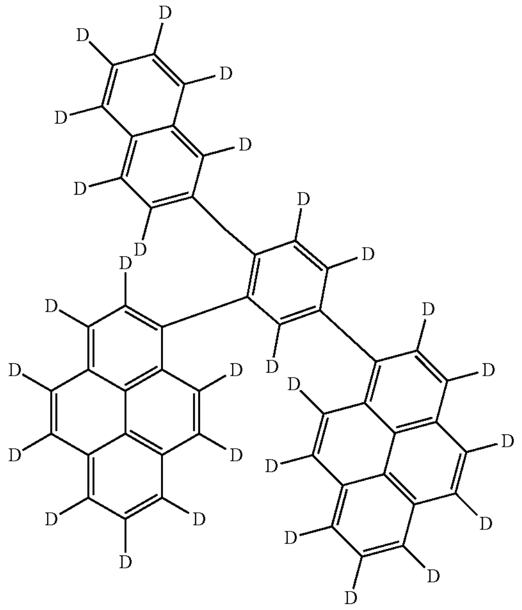
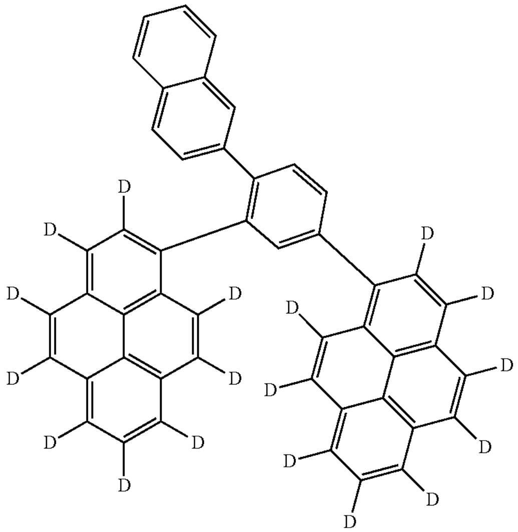
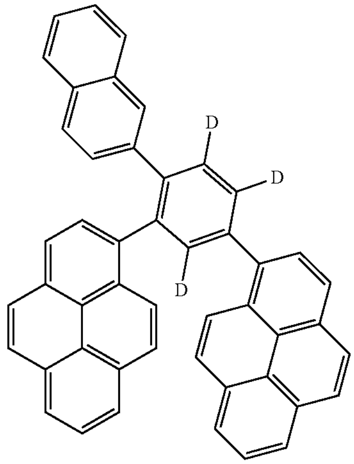
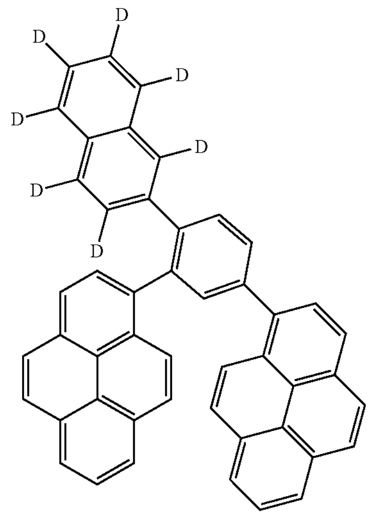
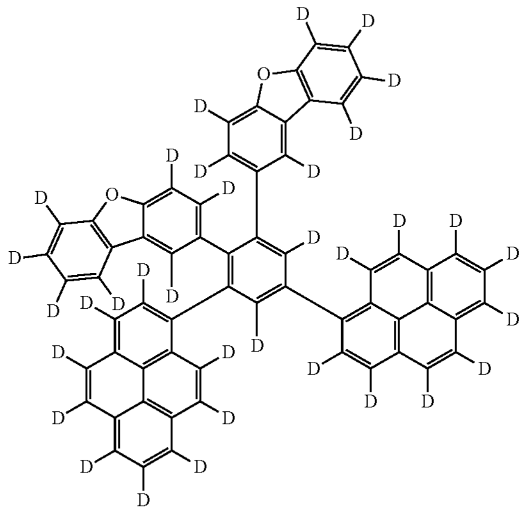
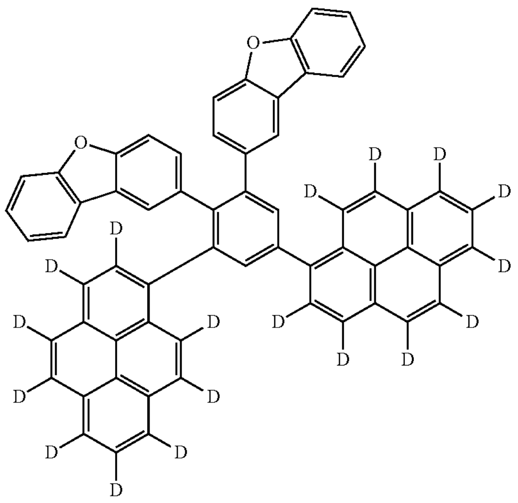

-continued
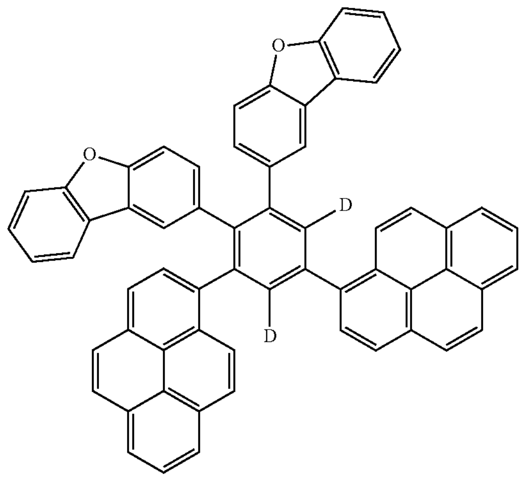
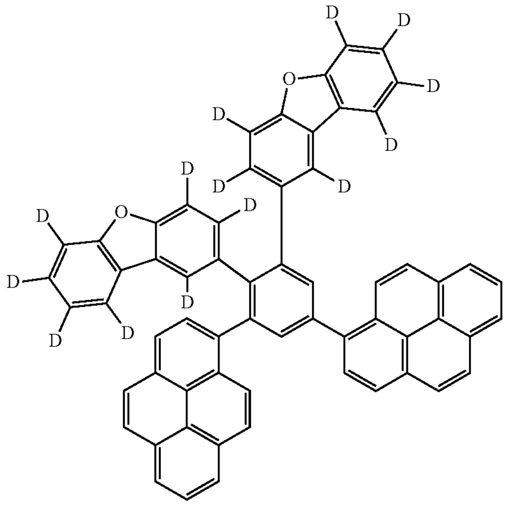
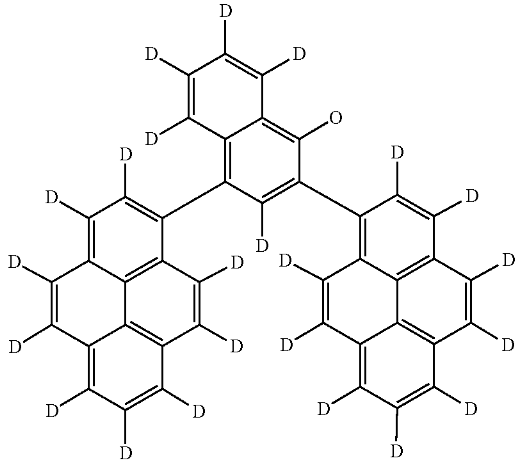
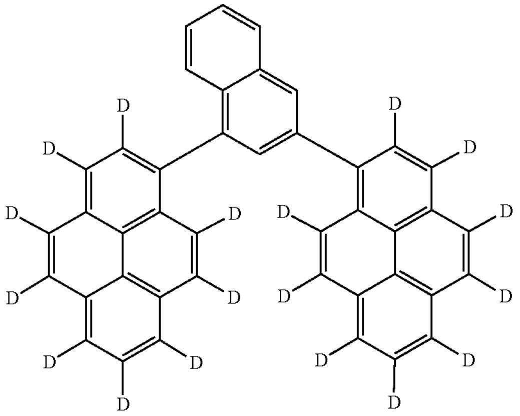
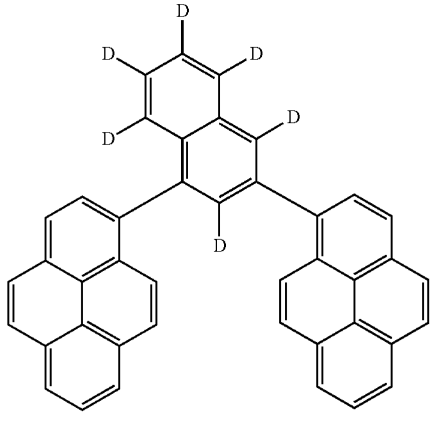
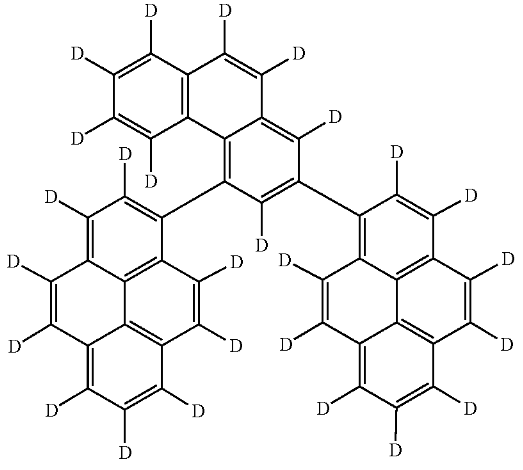

-continued
[Formula 106]
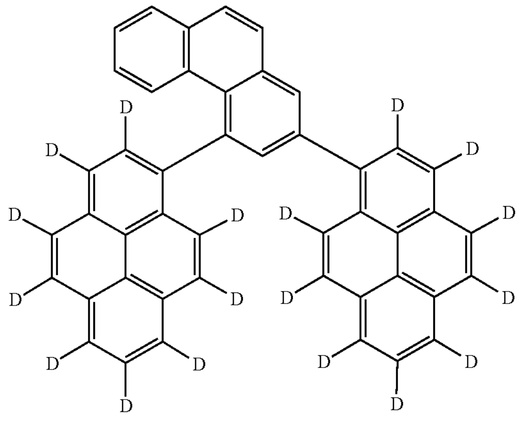
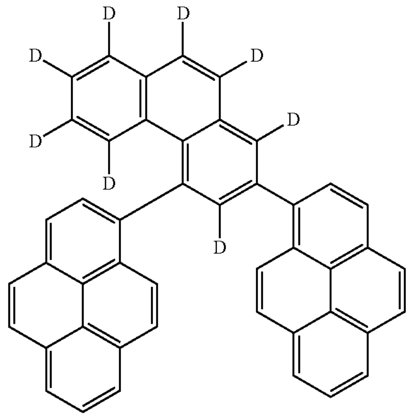
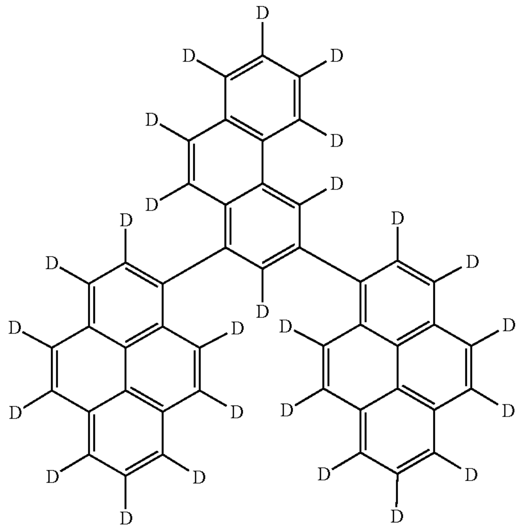
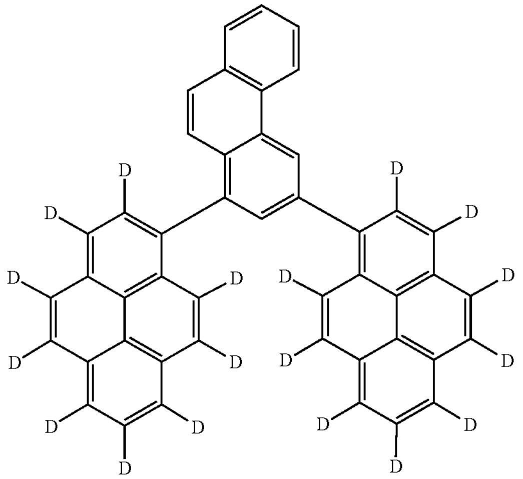
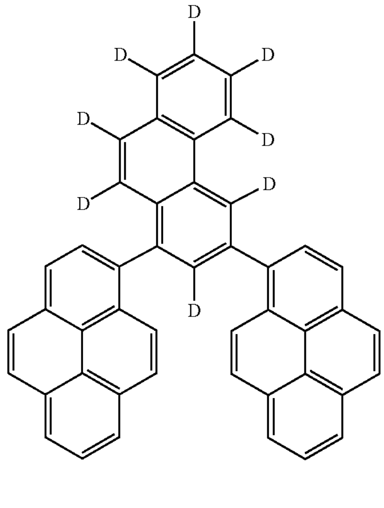
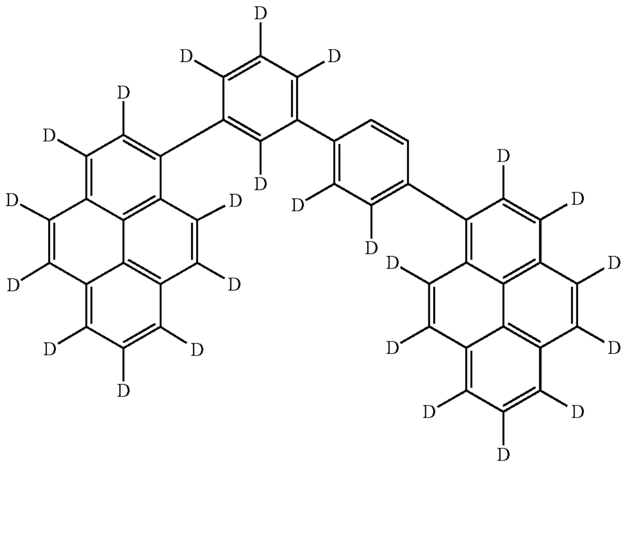

-continued
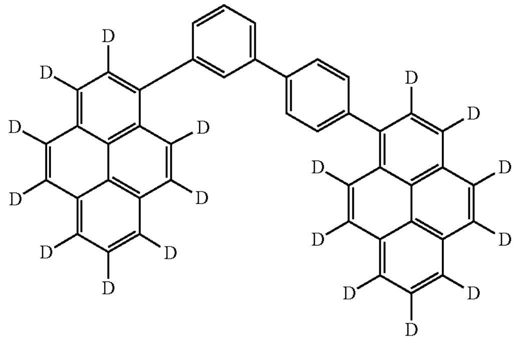
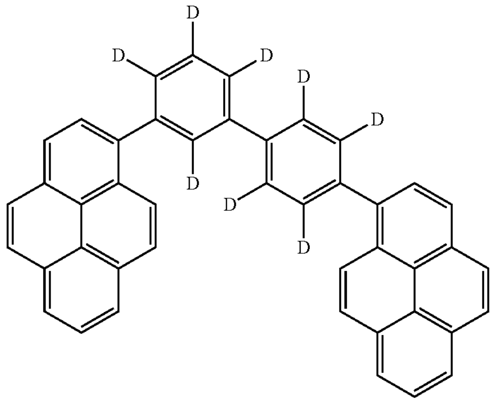
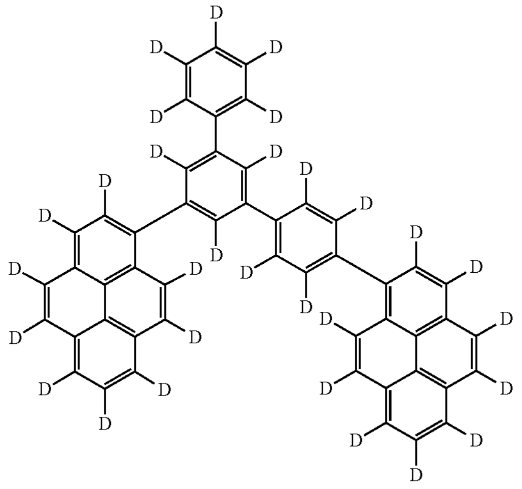
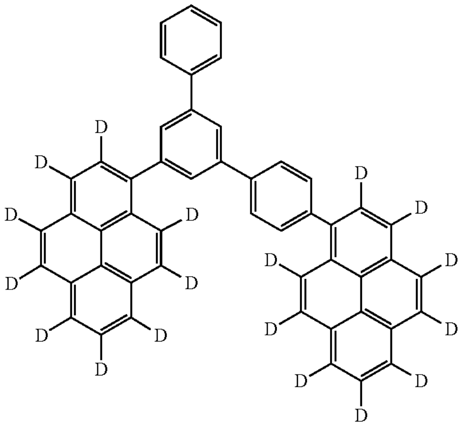
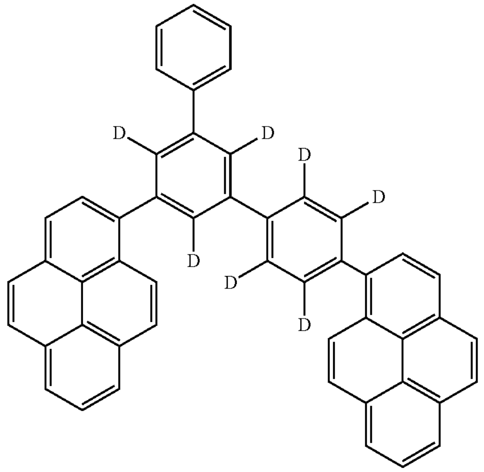
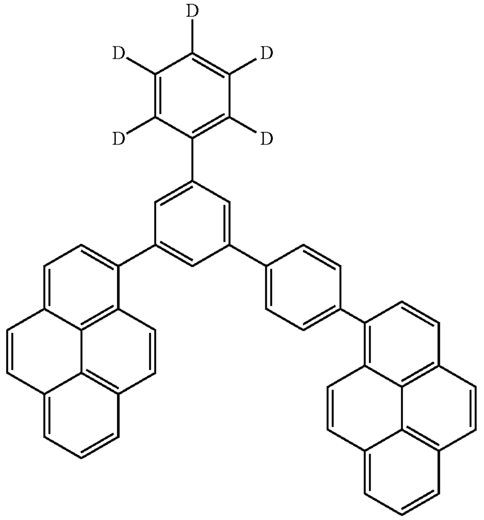

-continued
[Formula 107]
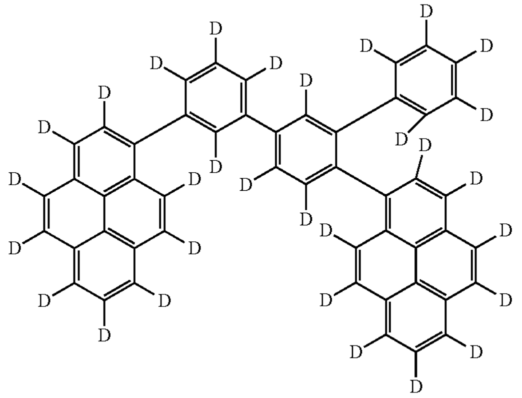
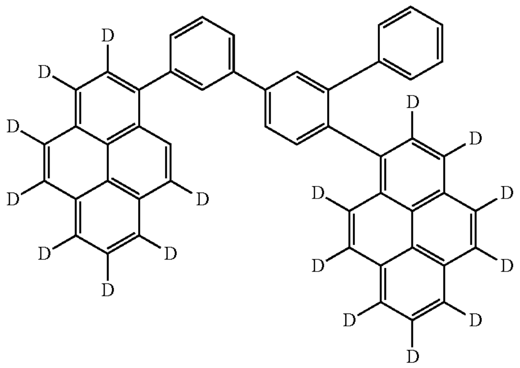
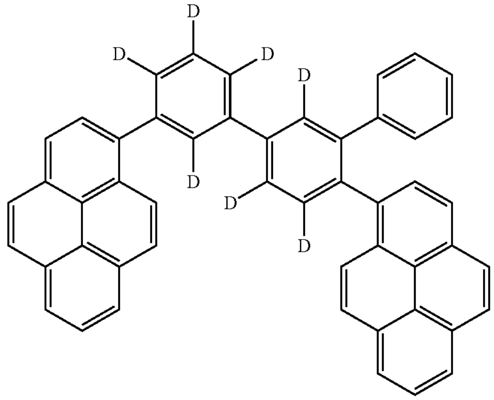
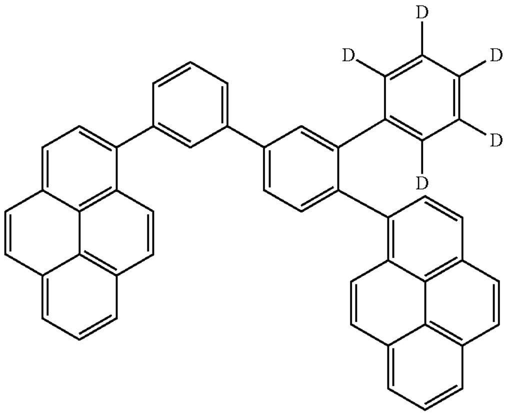
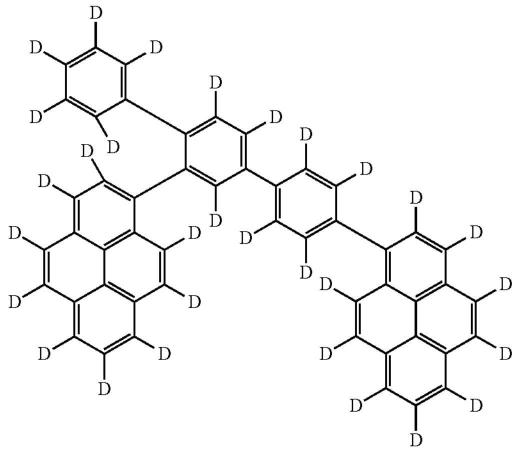
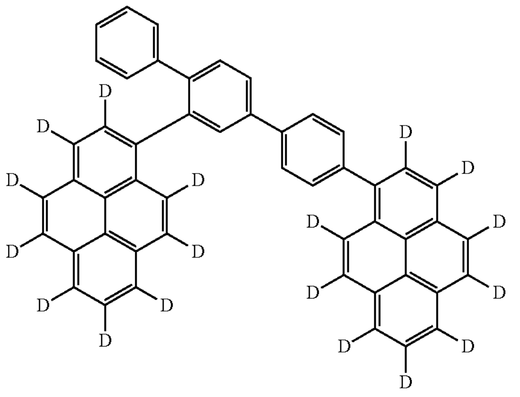

-continued
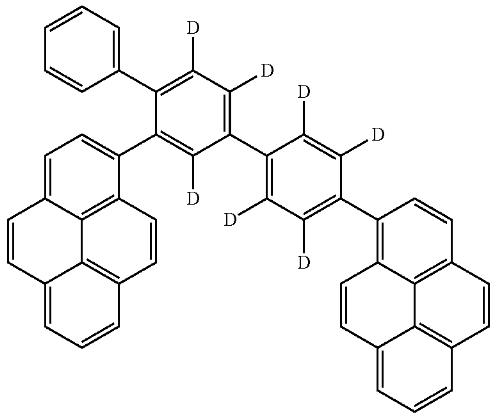
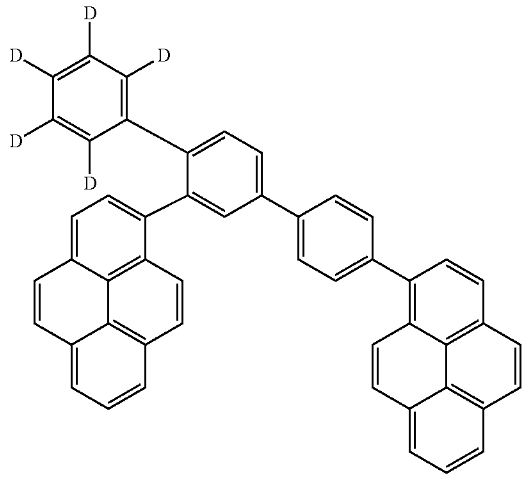
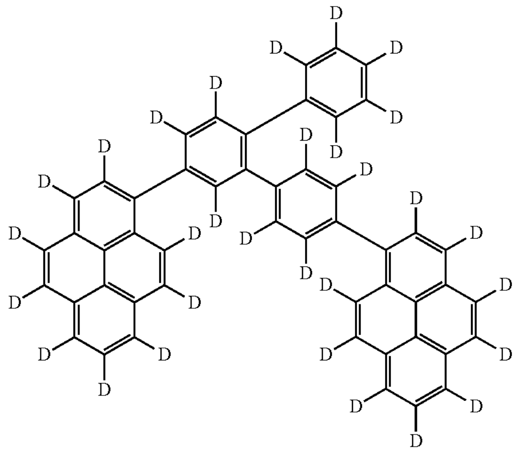
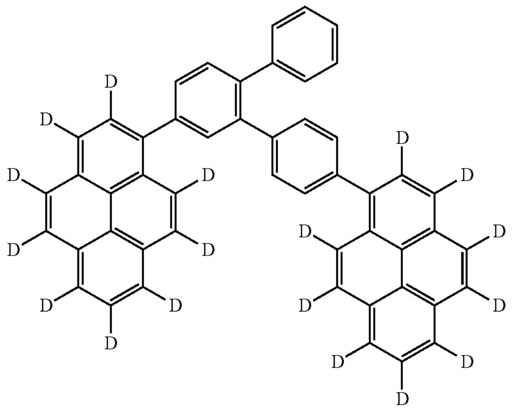
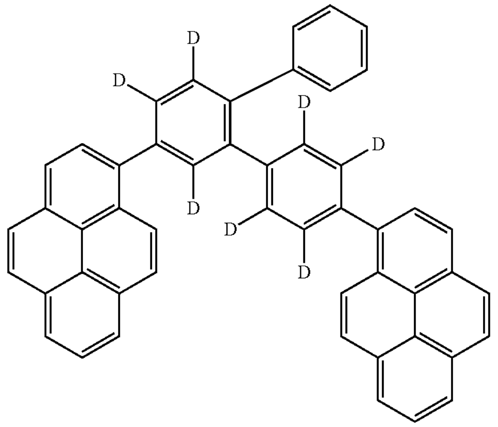
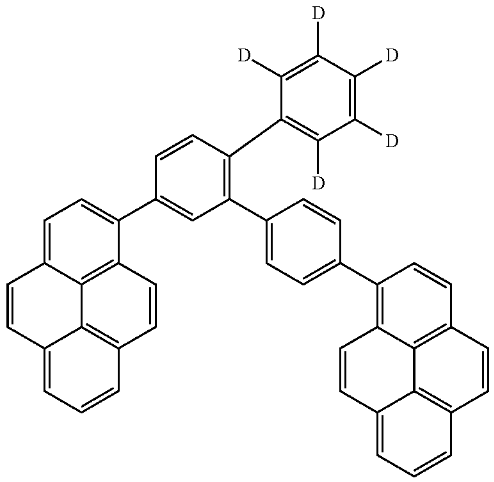

-continued
[Formula 108]
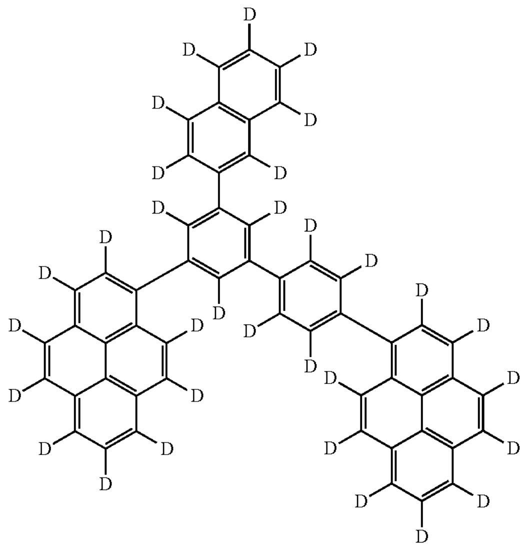
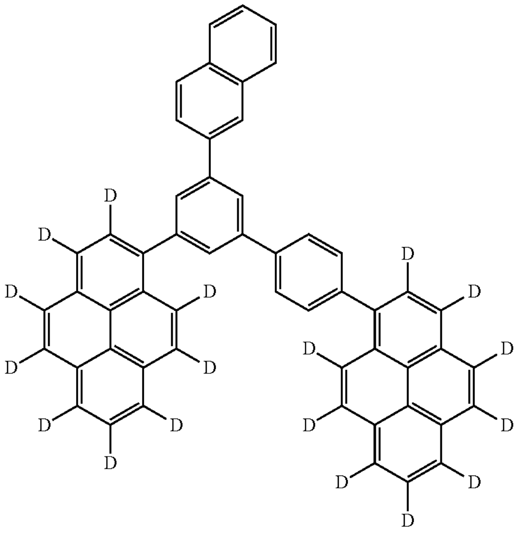
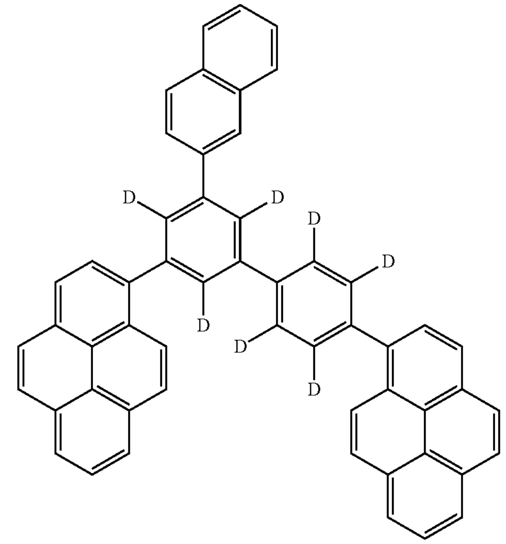
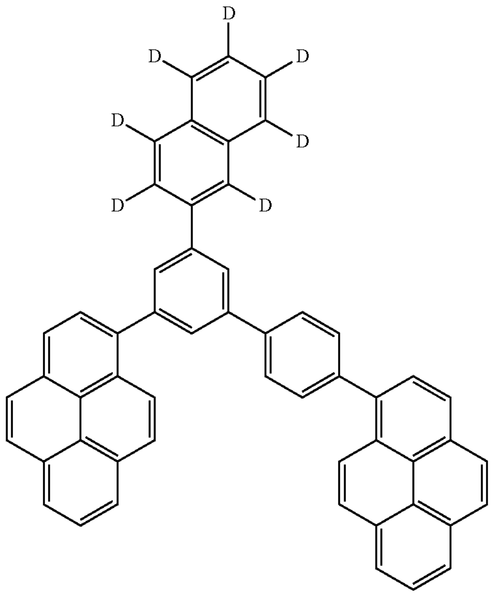
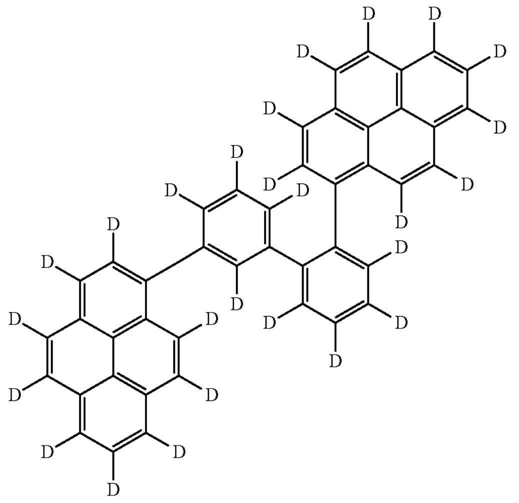
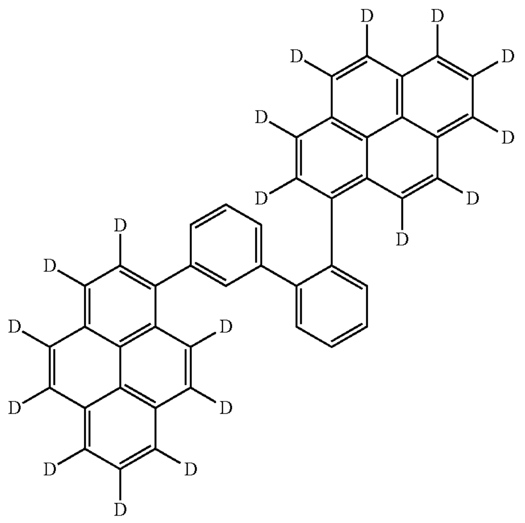

-continued
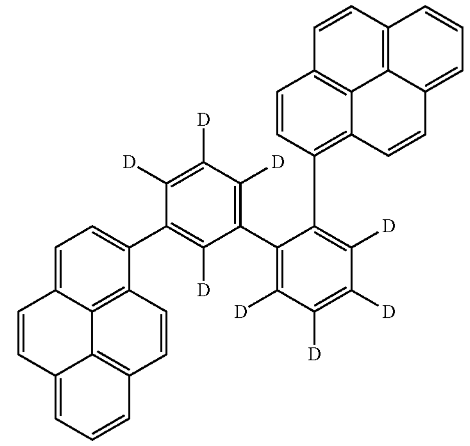
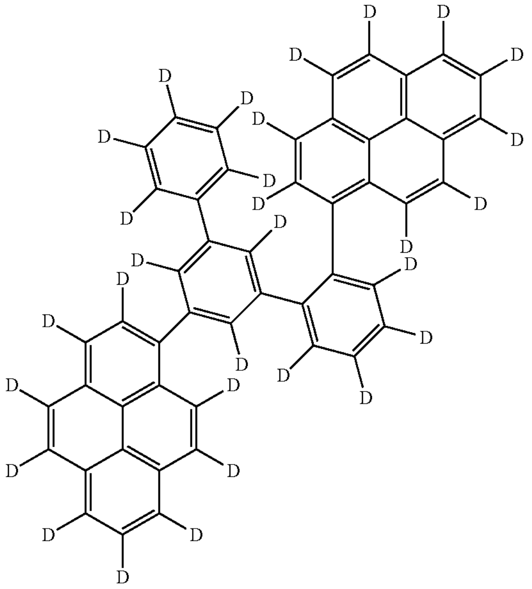
[Formula 109]
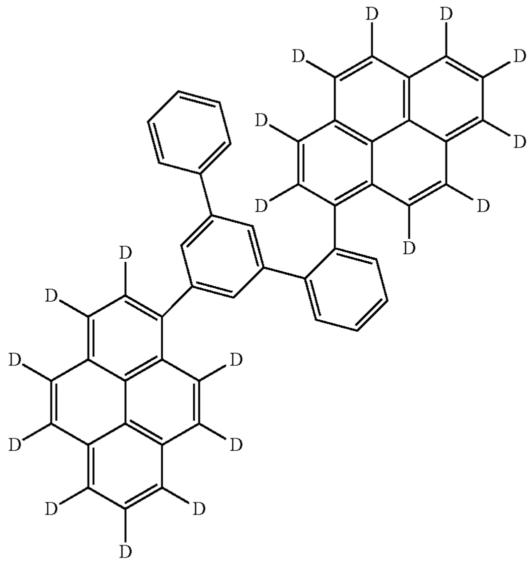
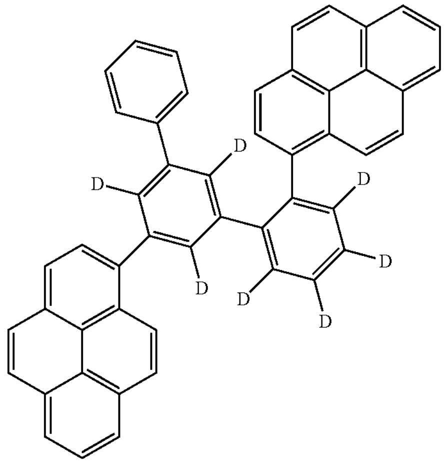
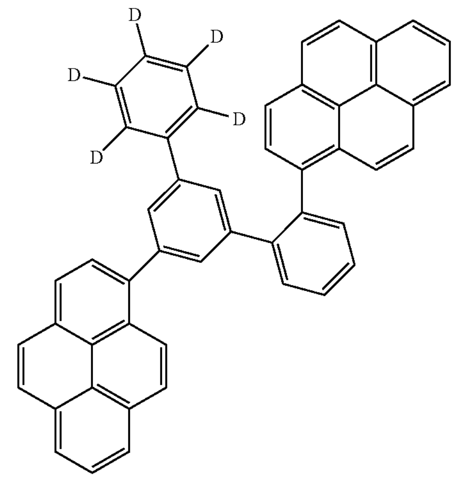
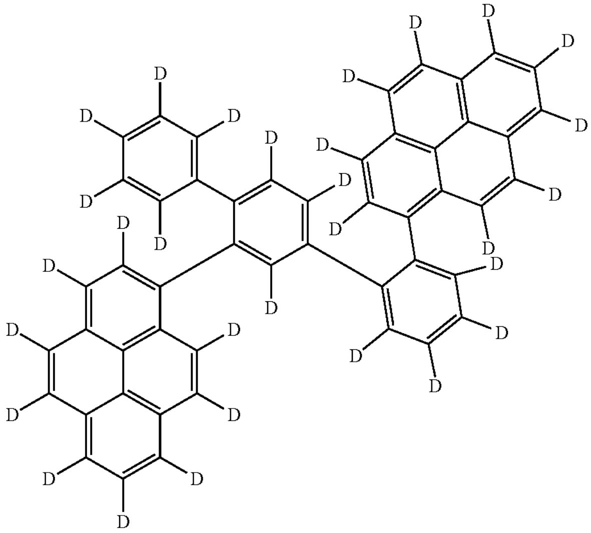

-continued
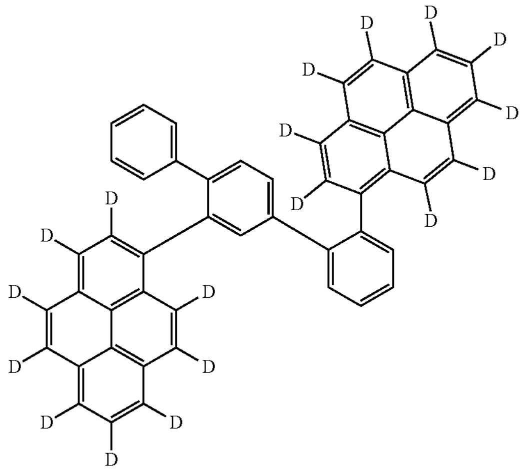
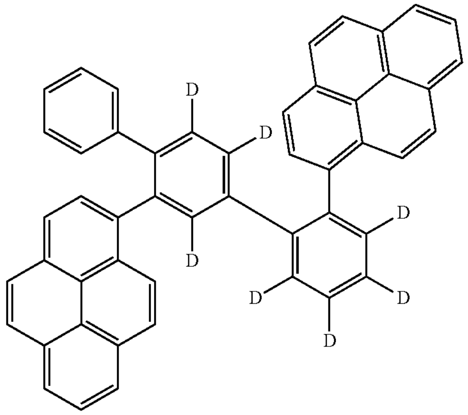
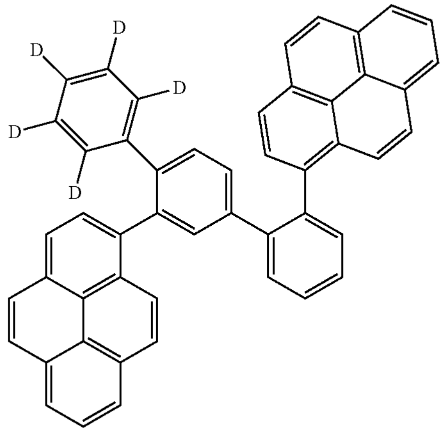
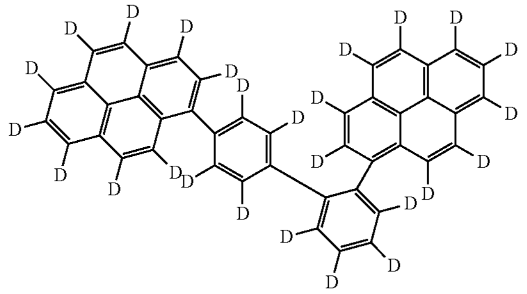
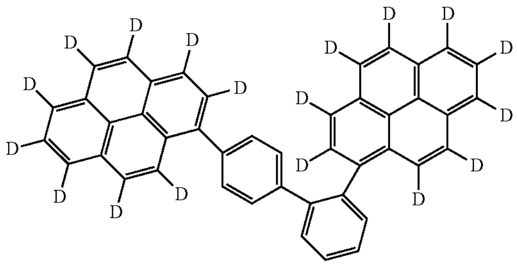
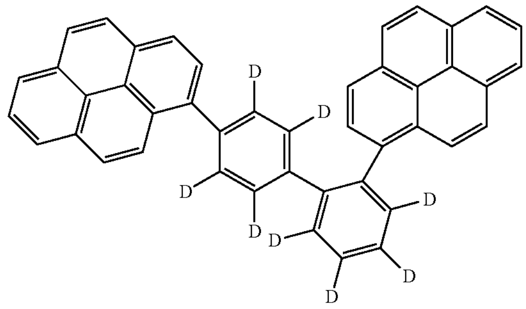
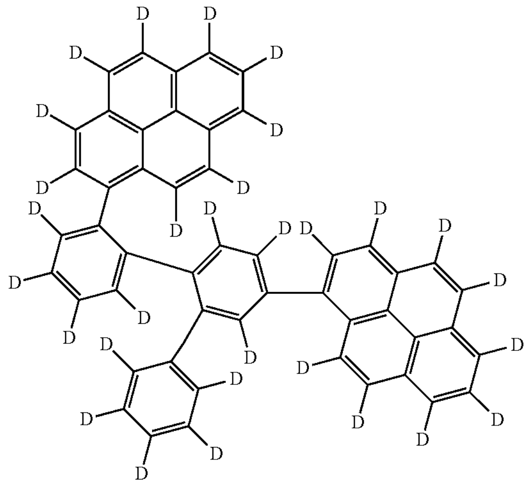
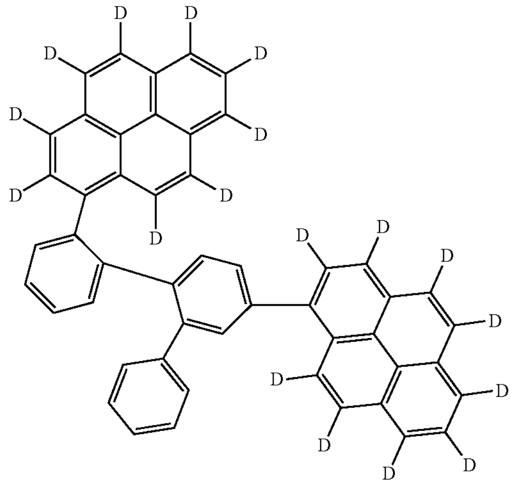

-continued
[Formula 110]
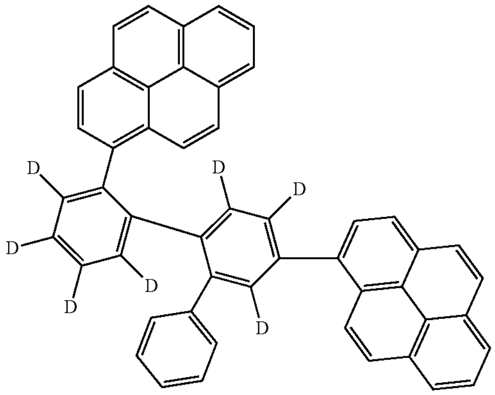
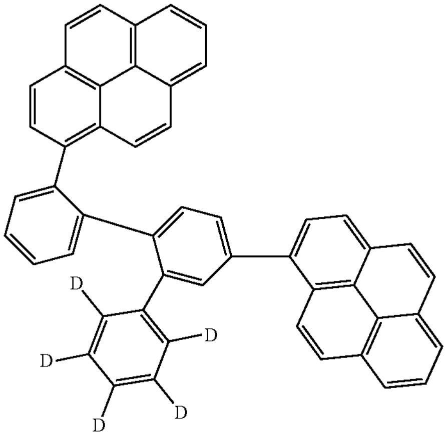
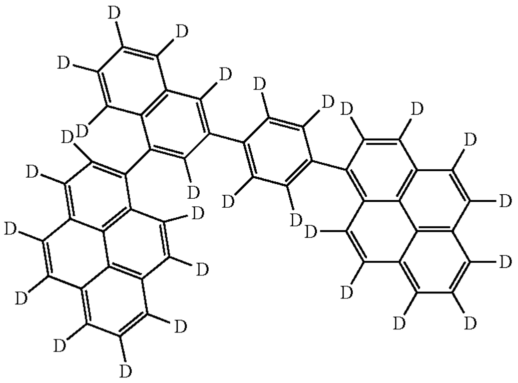
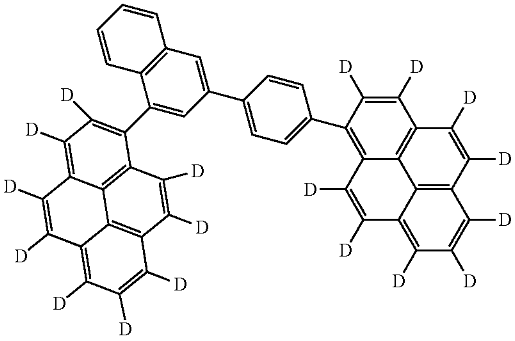
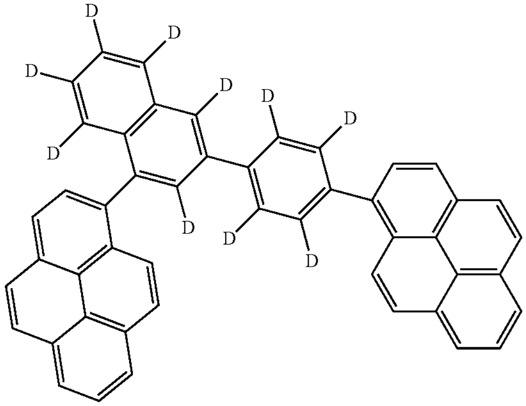
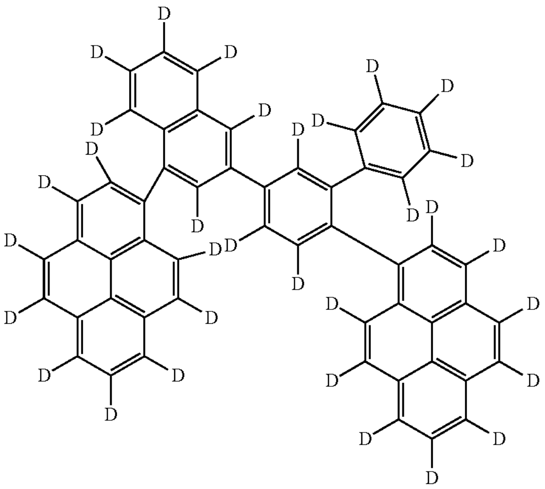

-continued
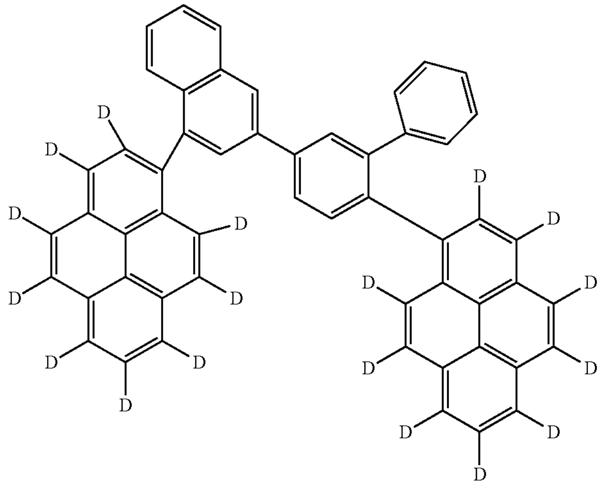
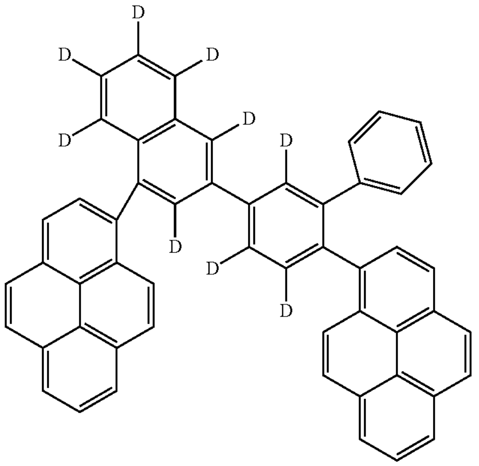
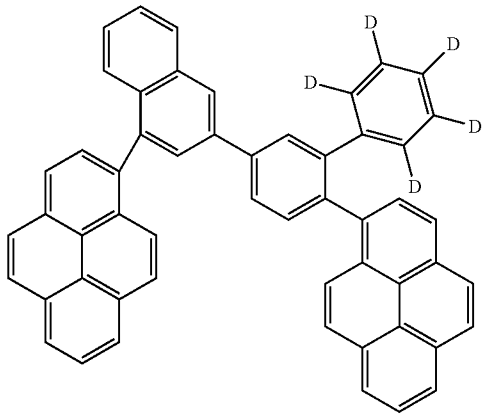
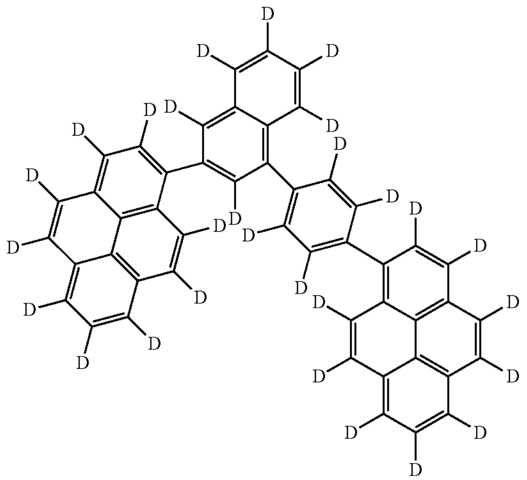
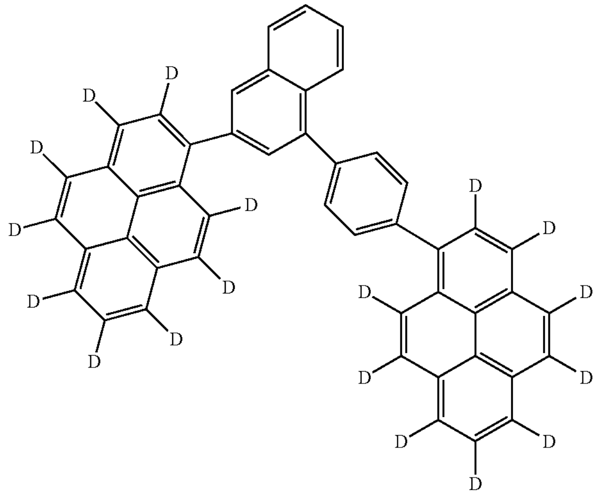
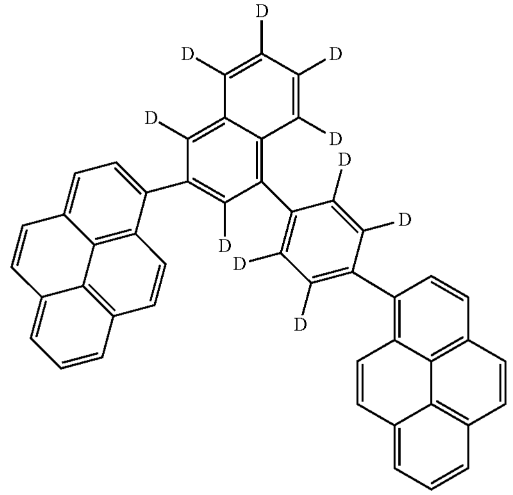

-continued
[Formula 111]
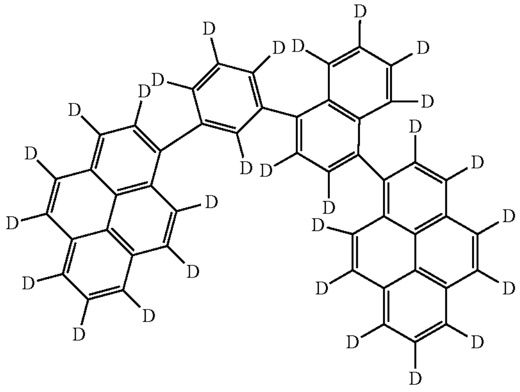
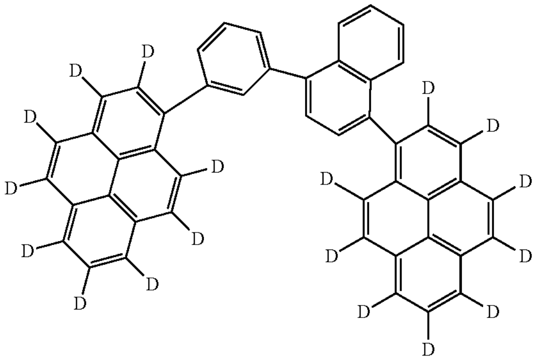
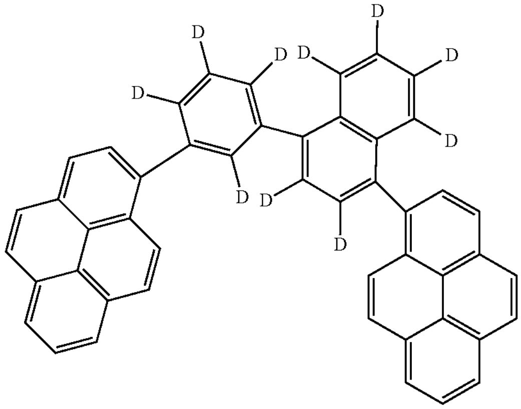
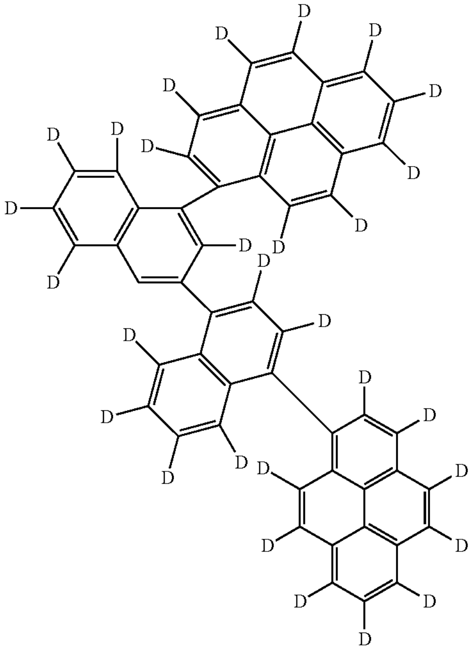

-continued
[Formula 112]
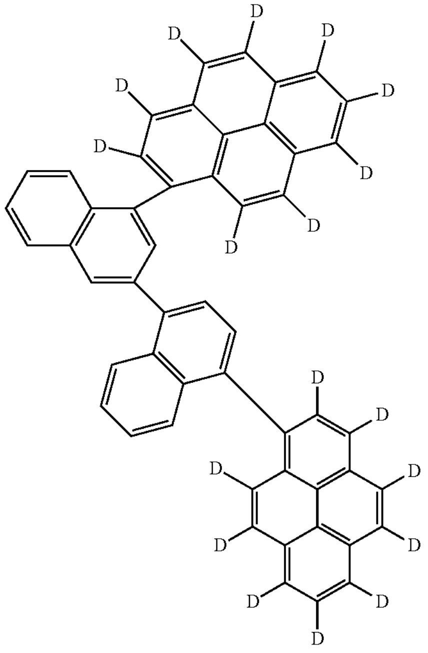
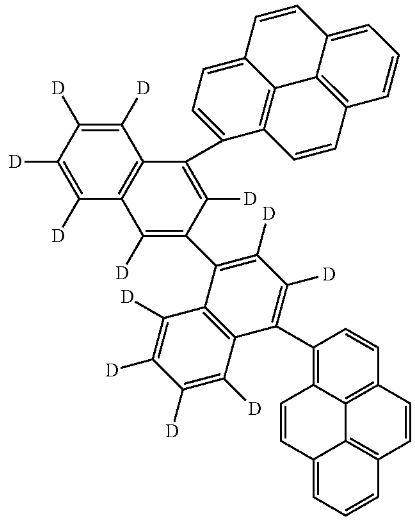
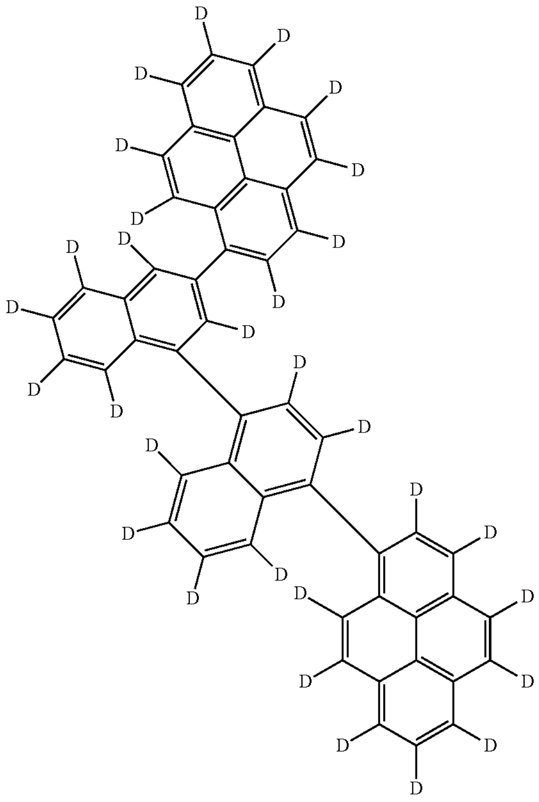
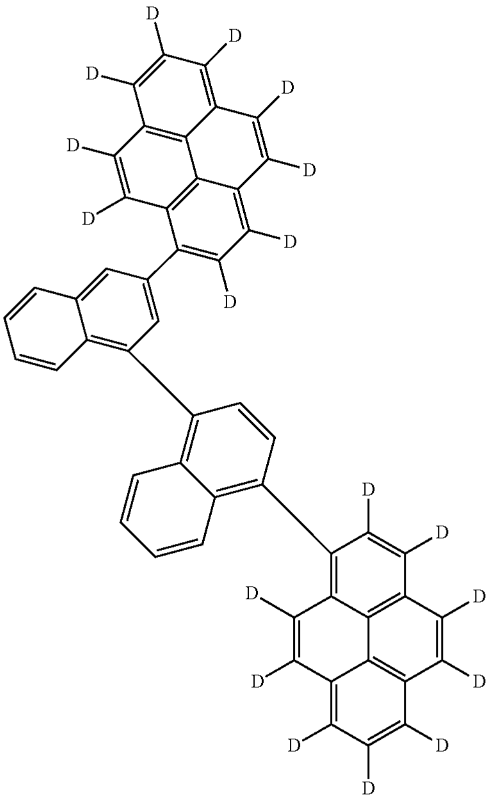

-continued
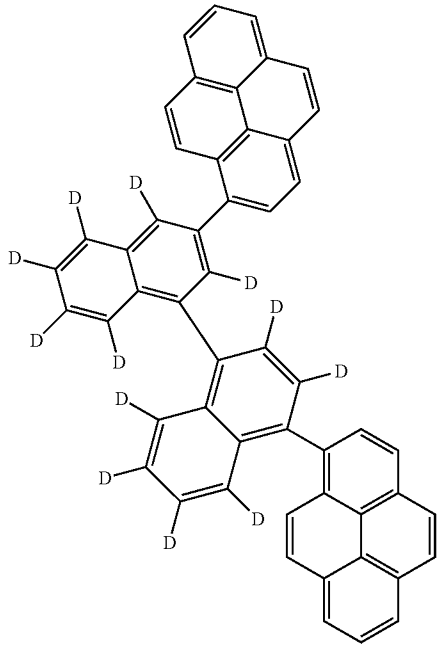
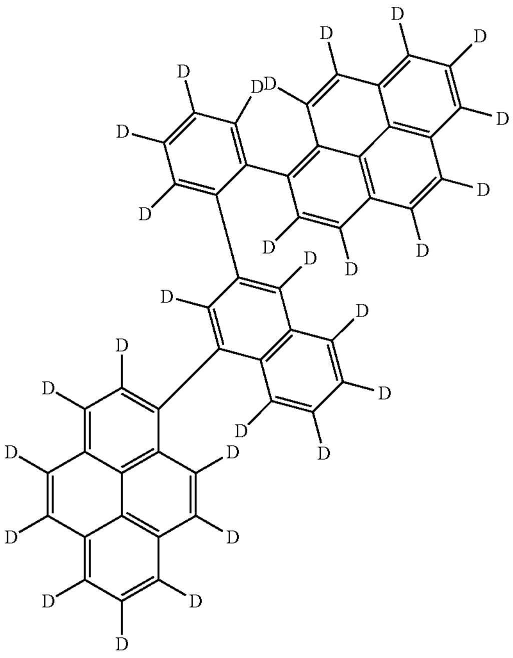
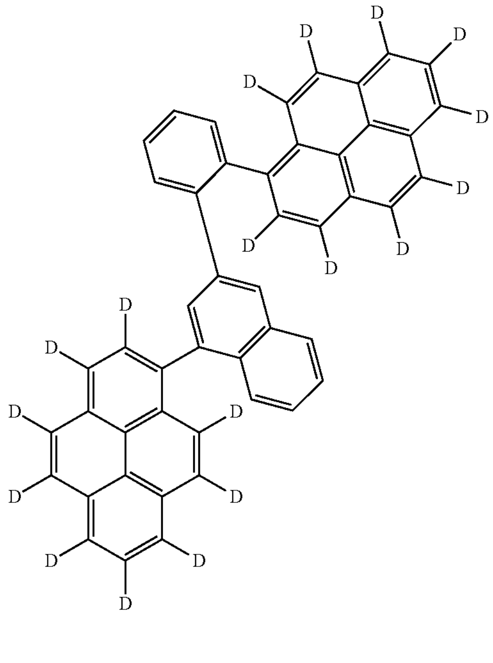
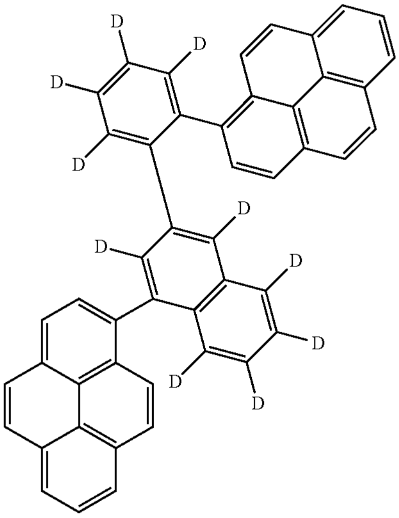

-continued
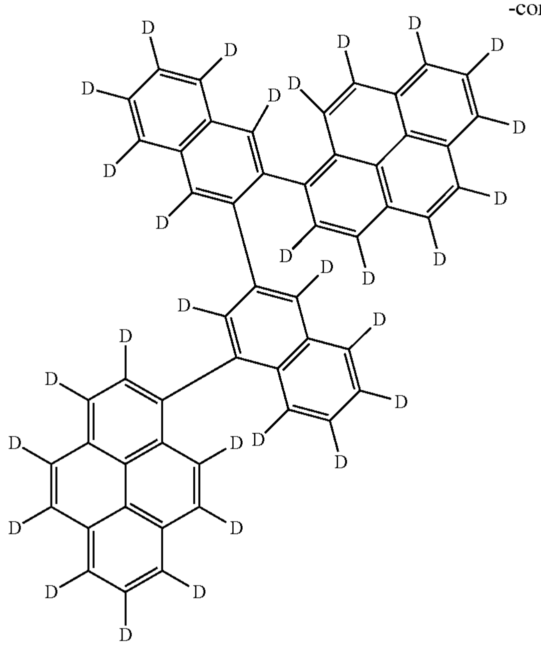
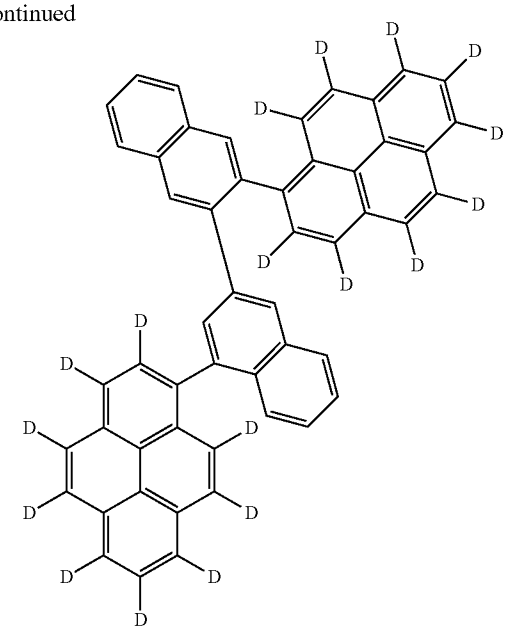
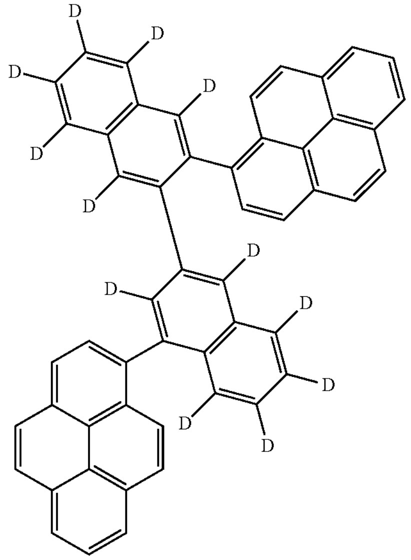
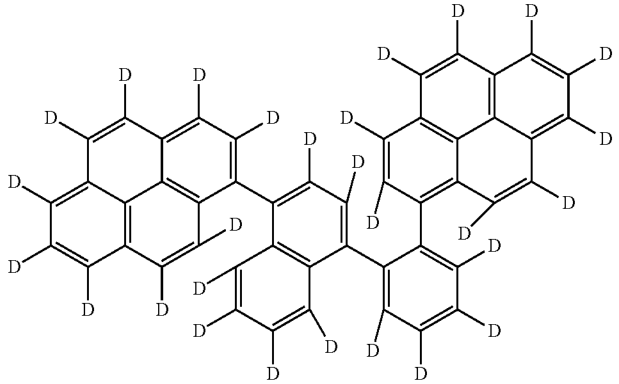
[Formula 113]
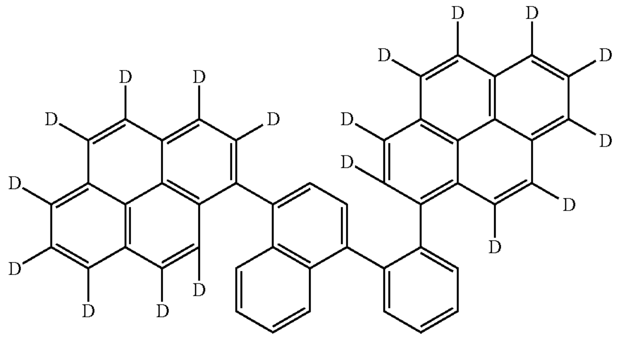

-continued
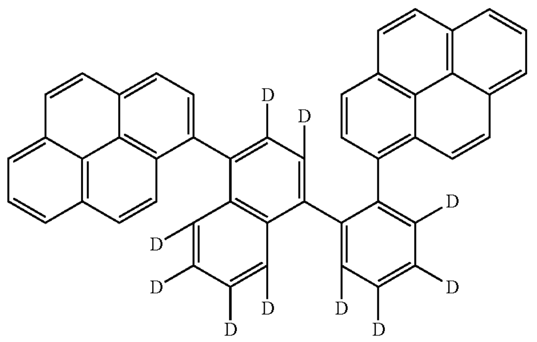
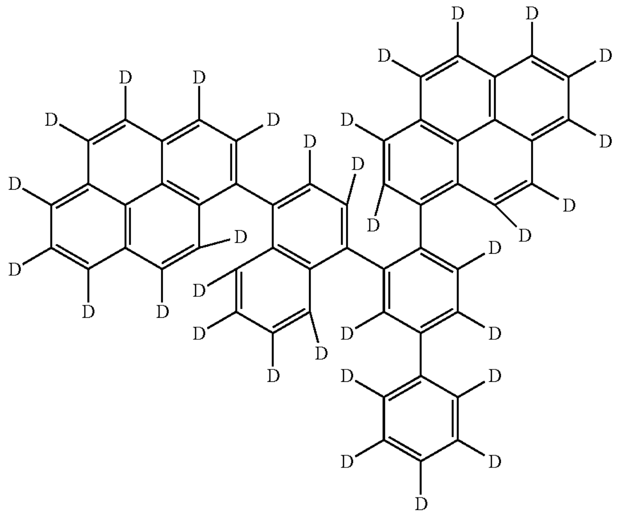
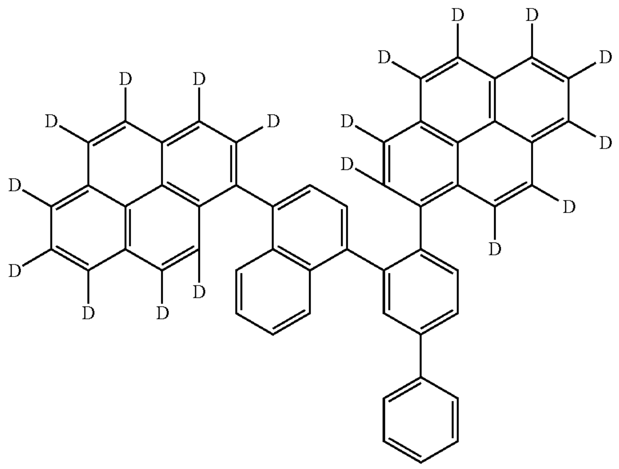

-continued
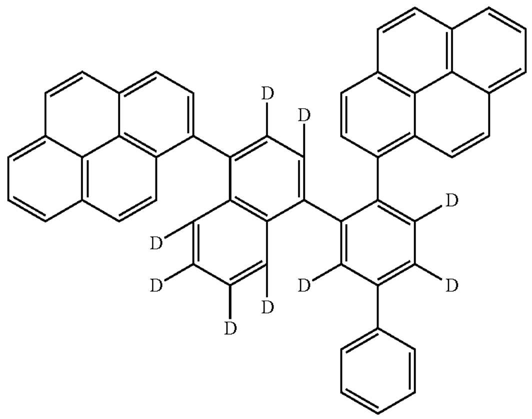
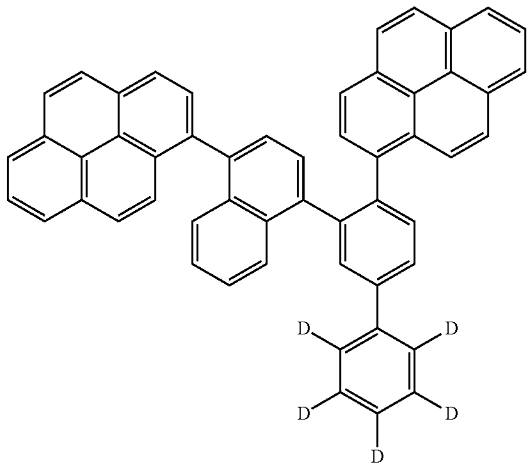
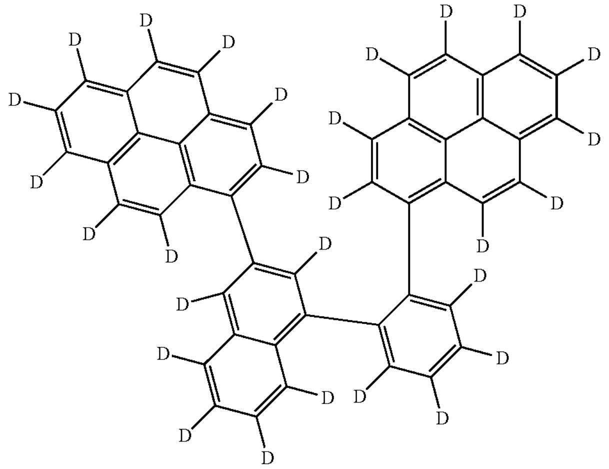
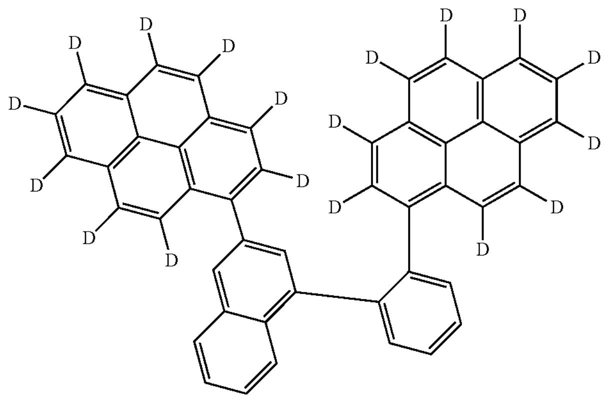
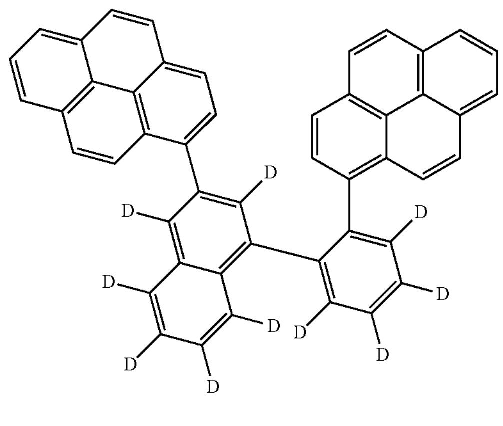

-continued
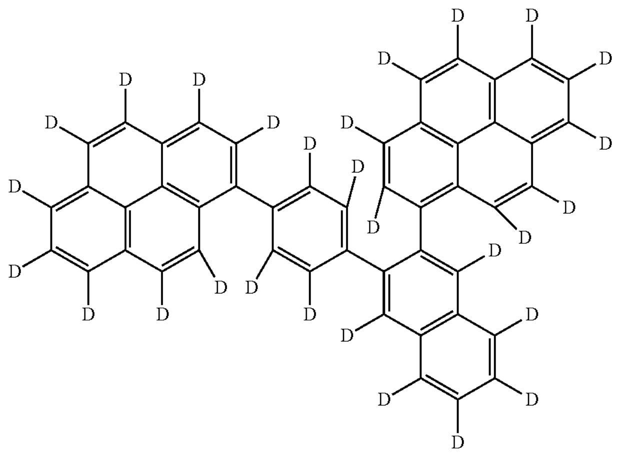
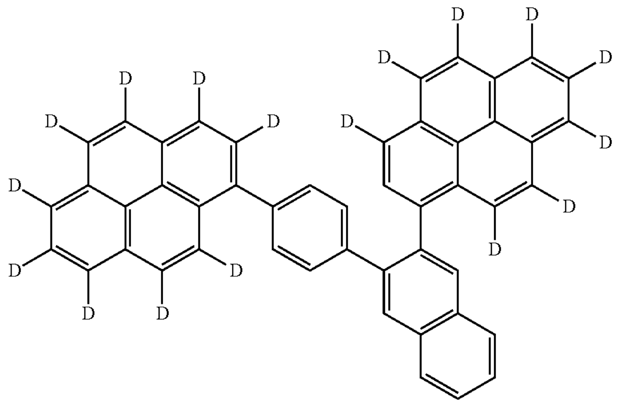
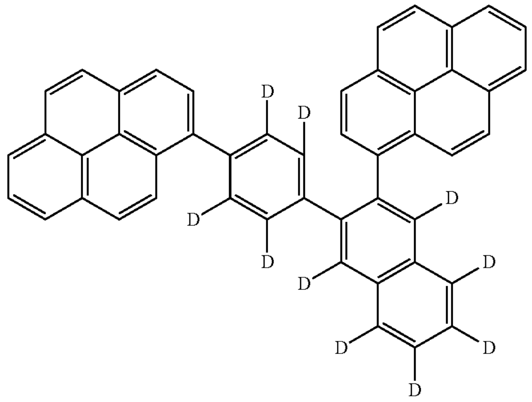

-continued
[Formula 114]
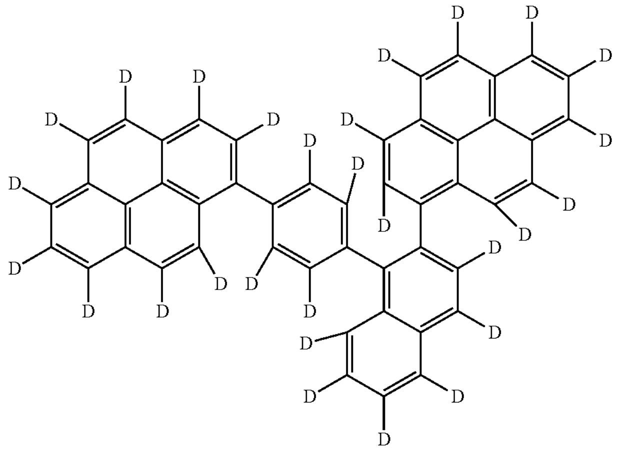
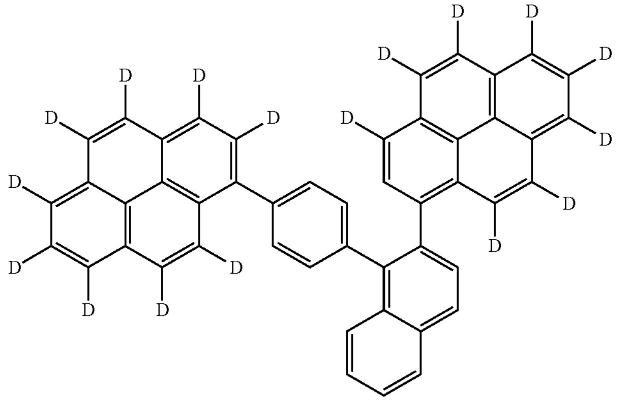
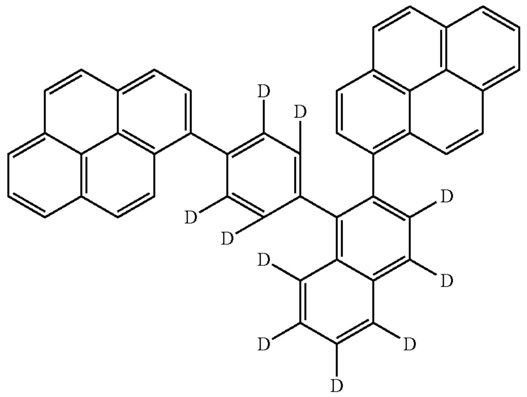
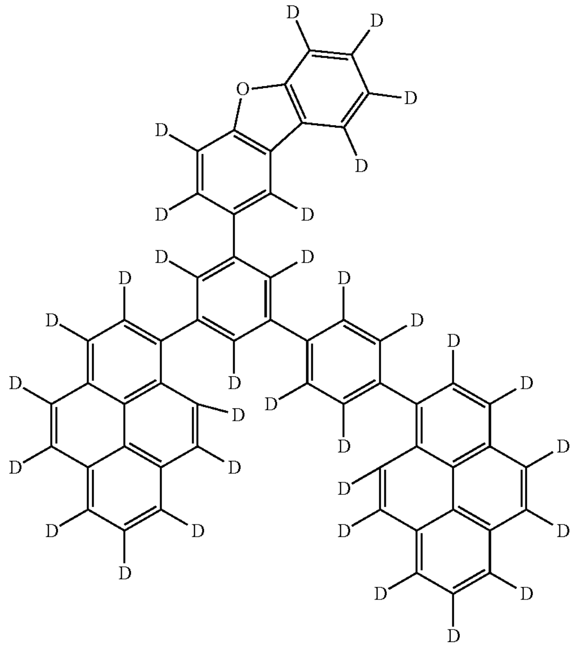

-continued
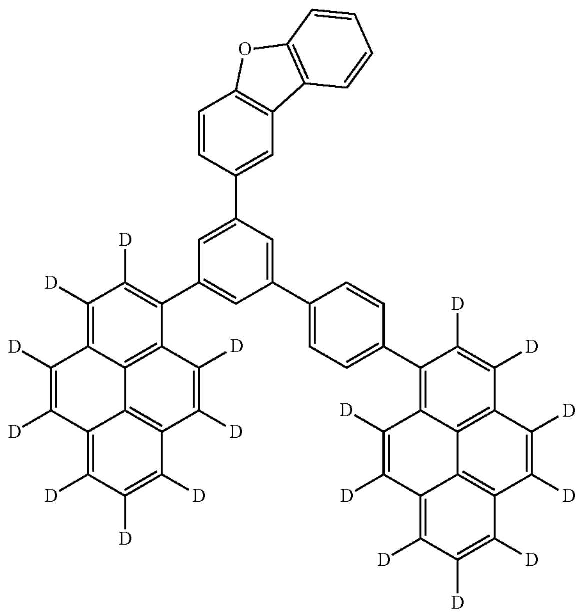
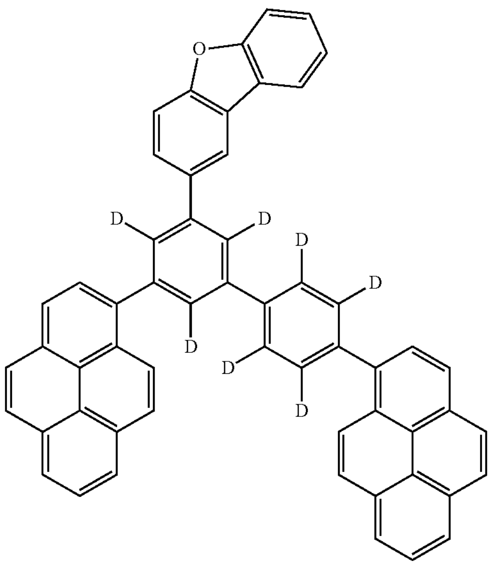
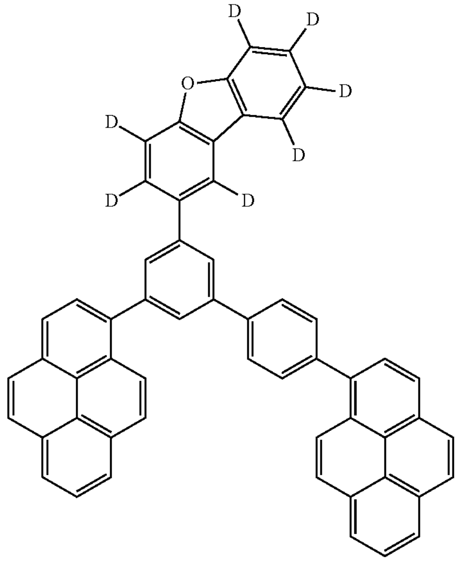
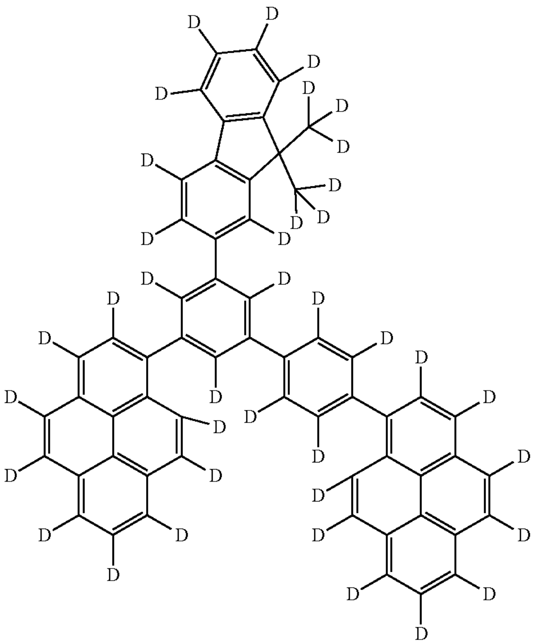

-continued
[Formula 115]
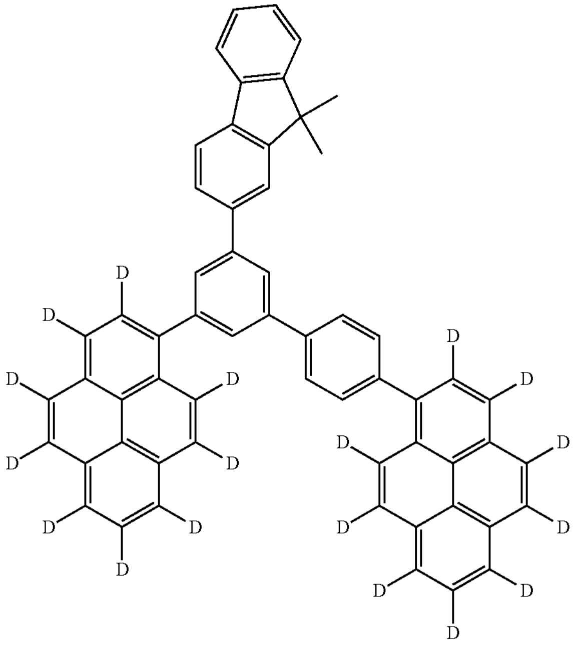
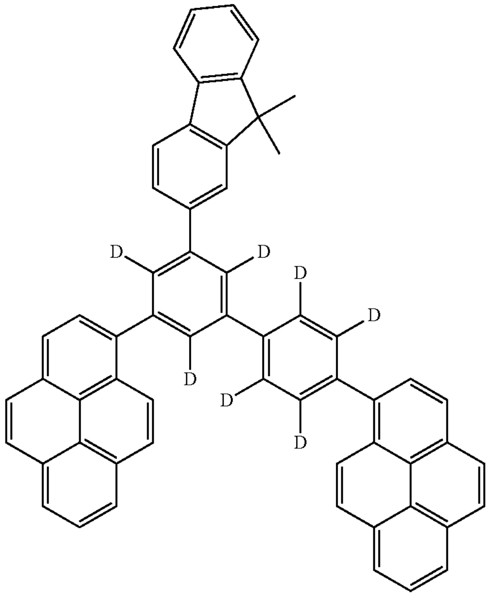
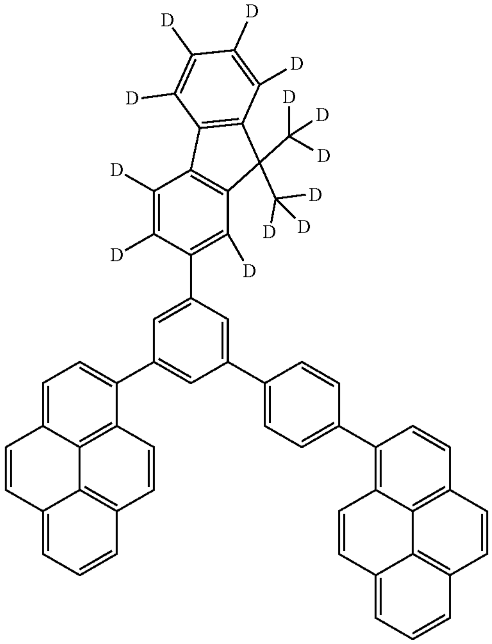
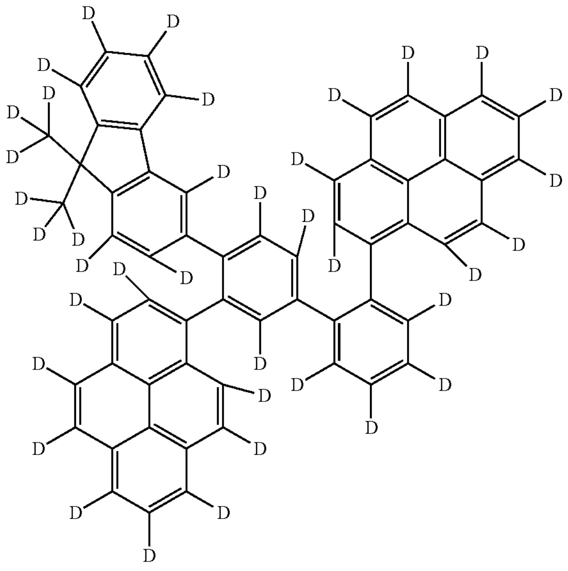

-continued
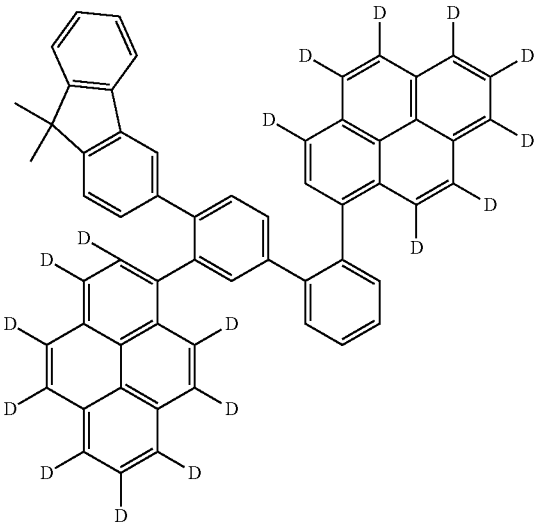
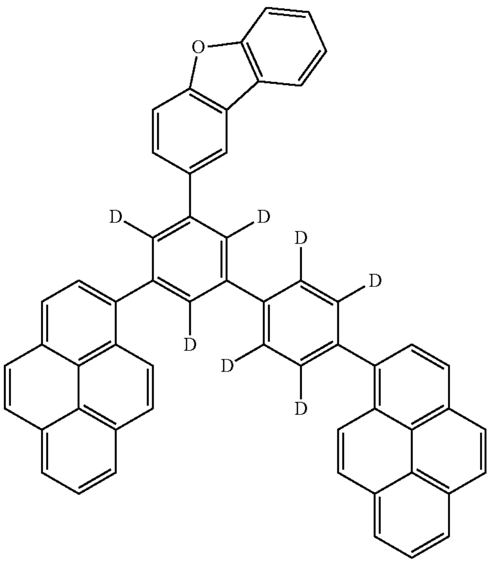
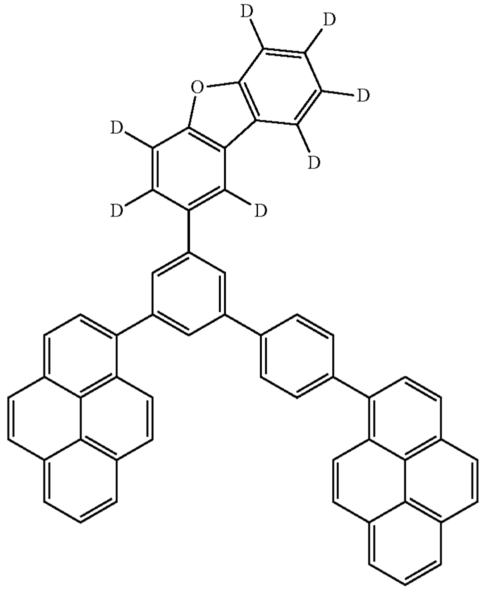
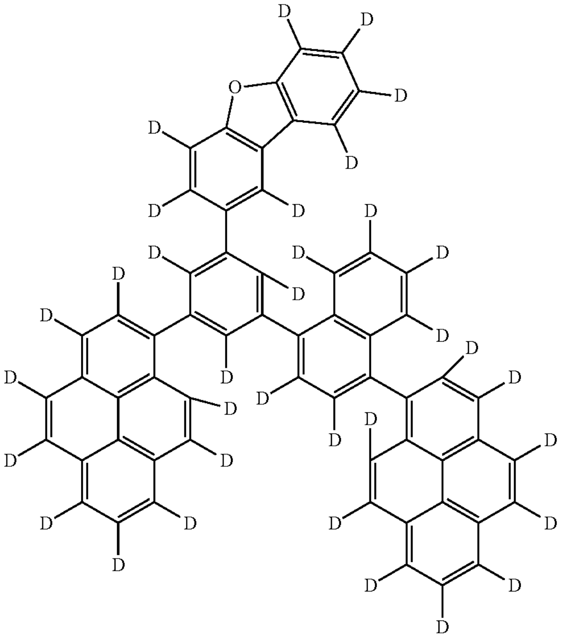

-continued
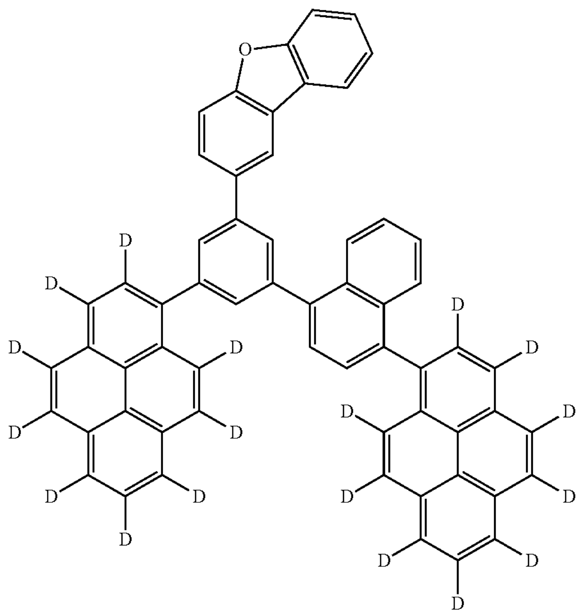
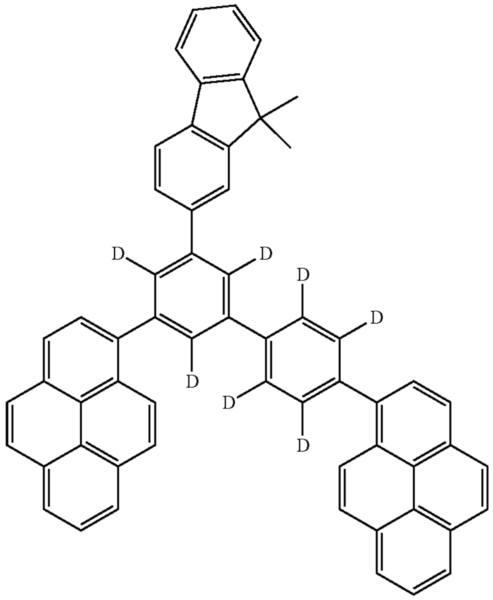
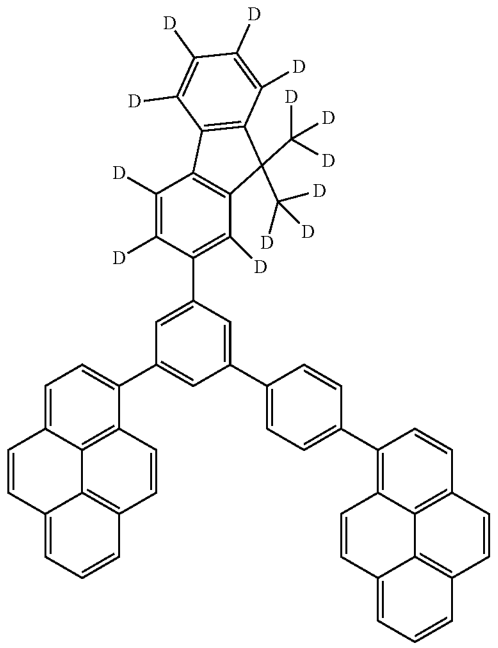

-continued
[Formula 116]
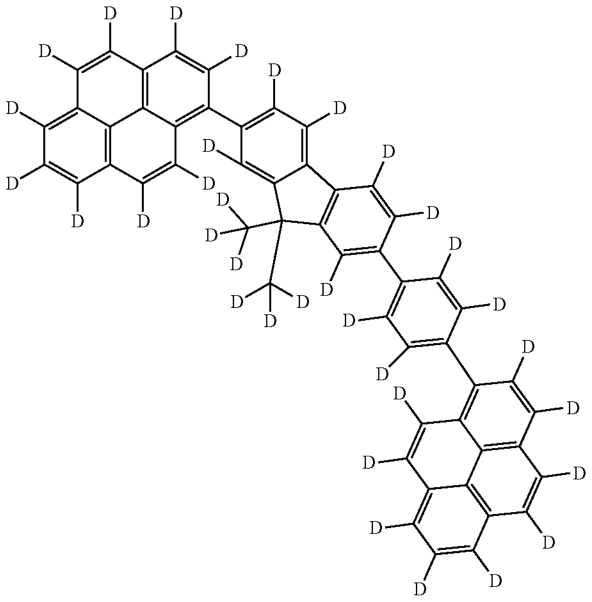
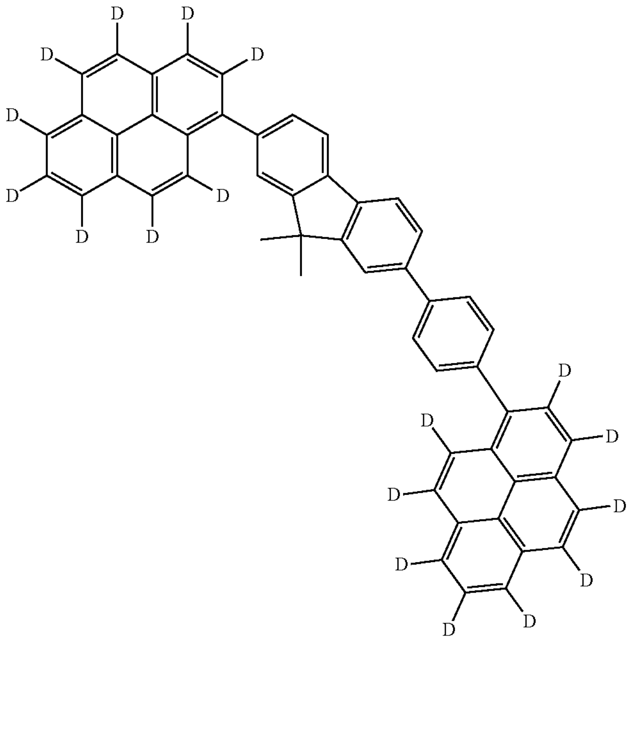

-continued
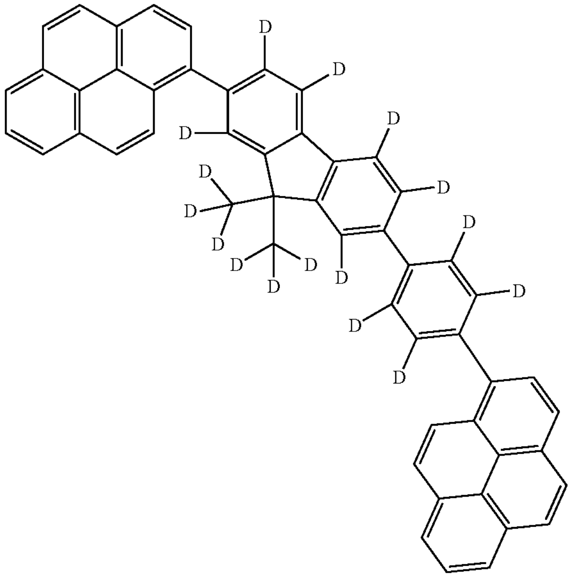
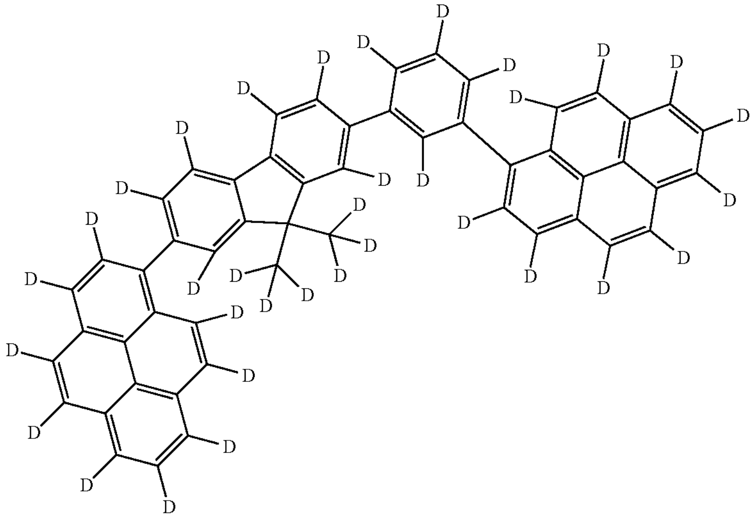
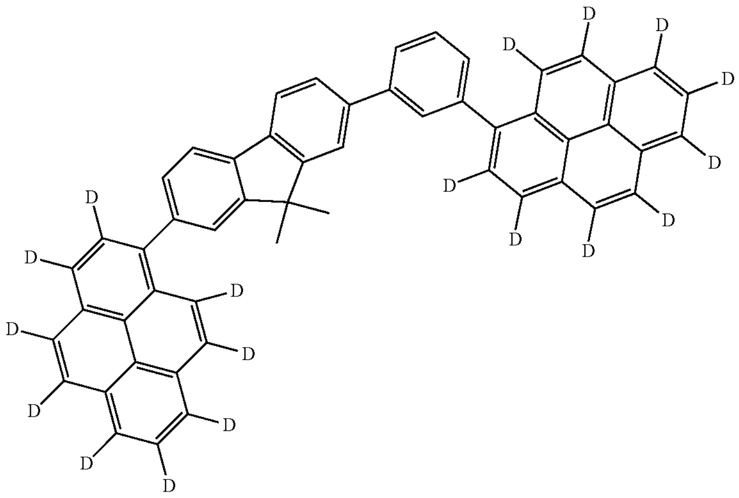

-continued
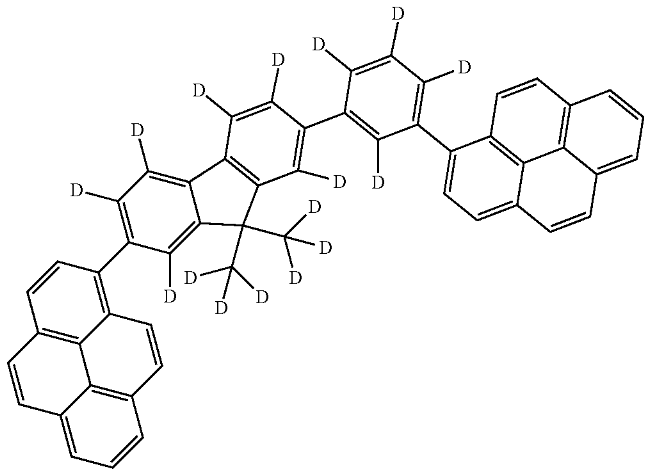
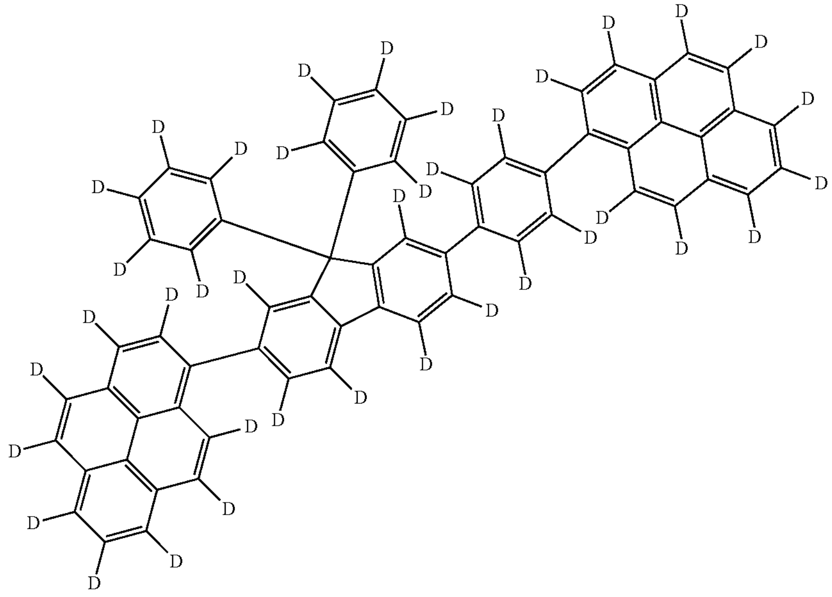
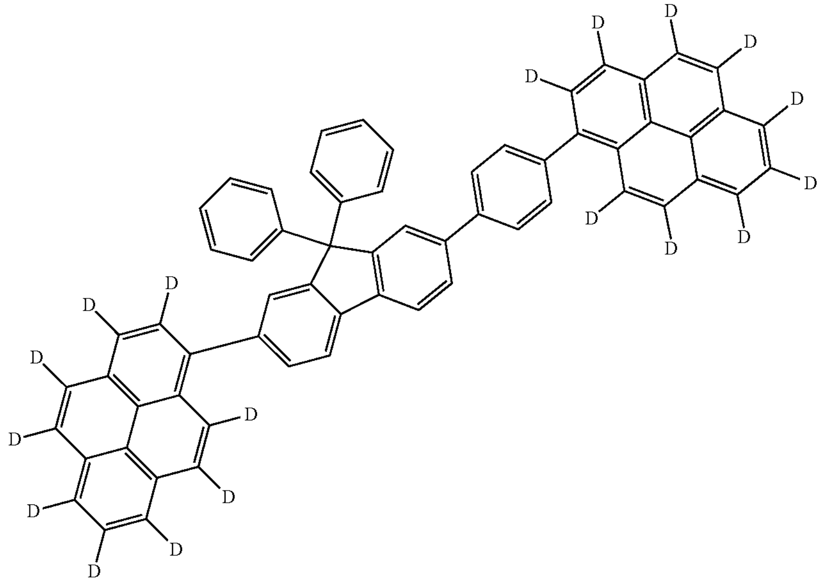

-continued
[Formula 117]
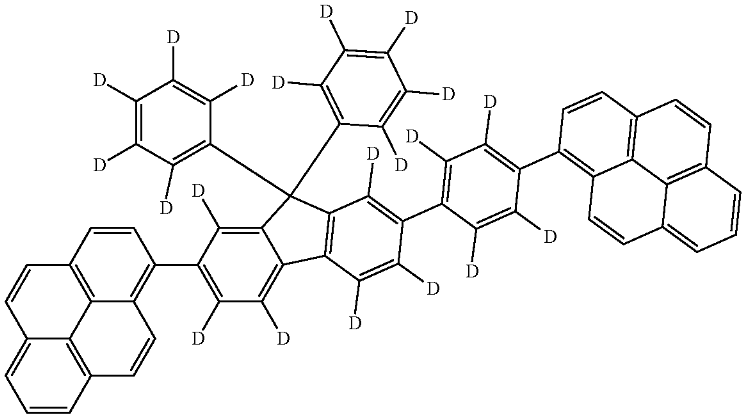
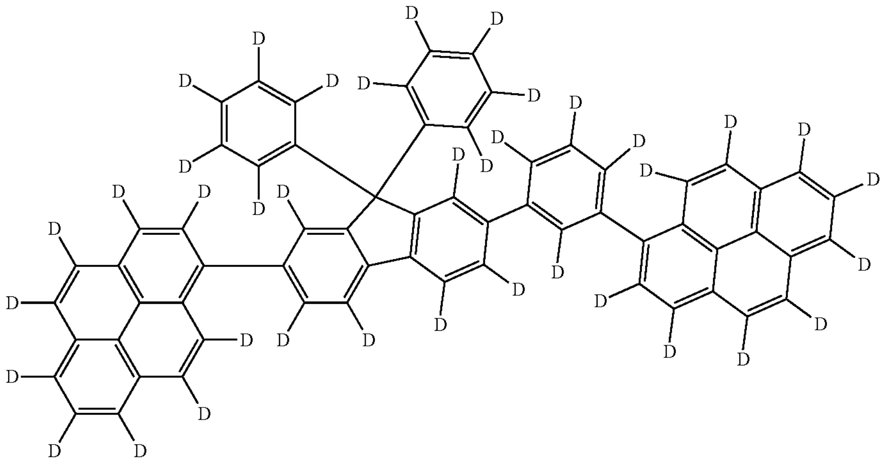
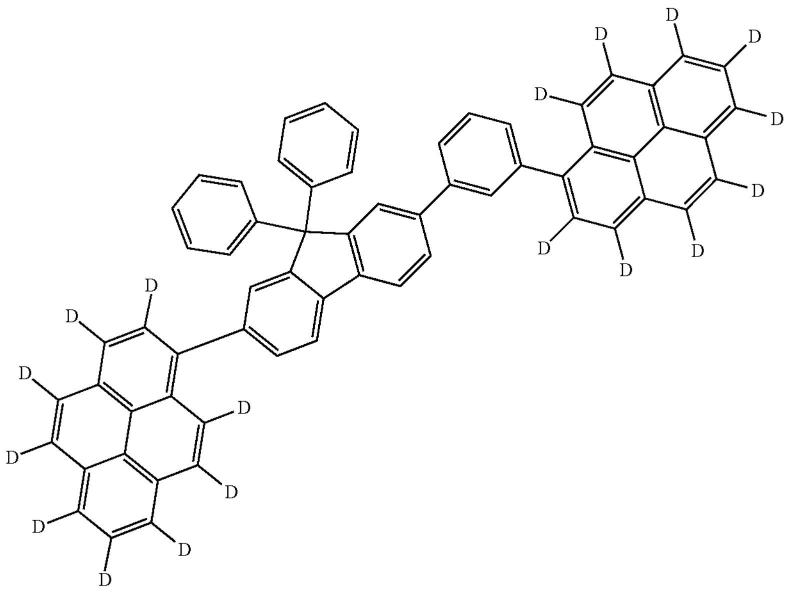

-continued
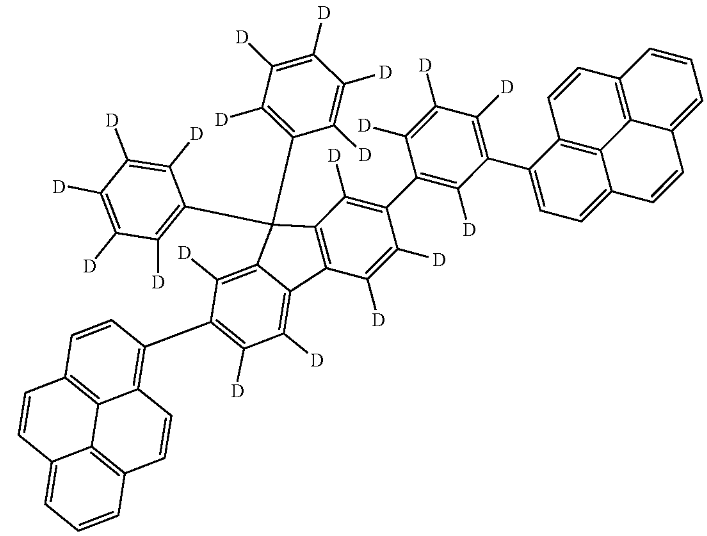
[Formula 118]
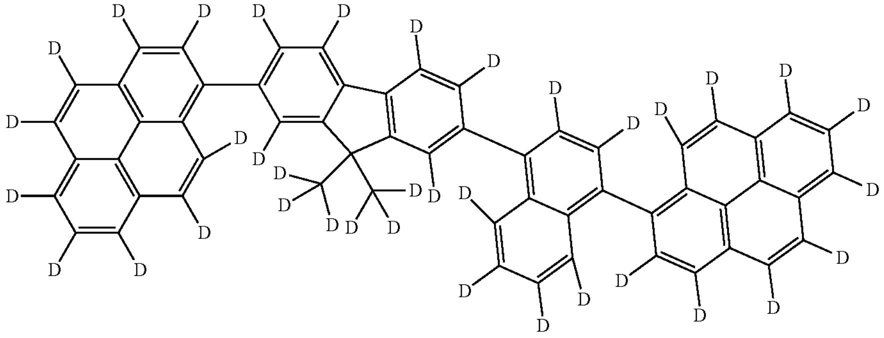
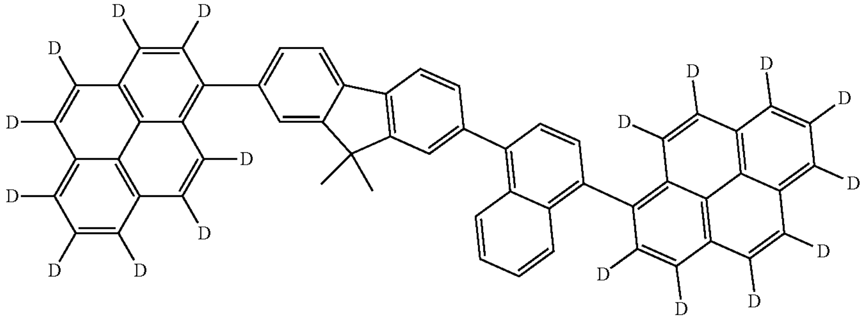
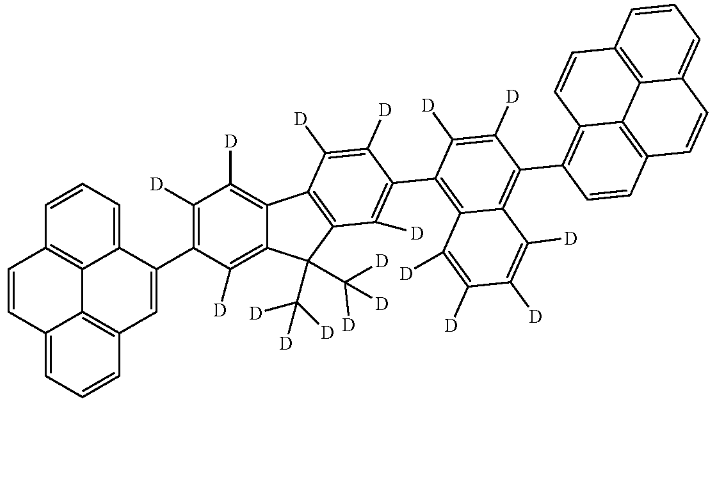

-continued
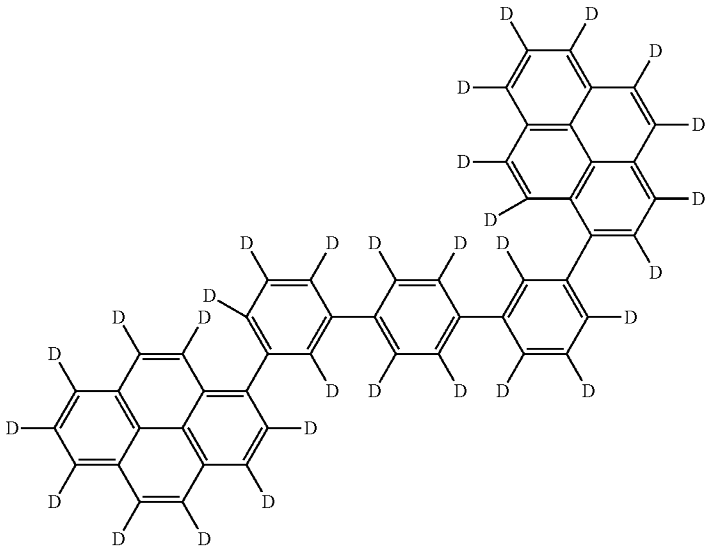
[Formula 119]
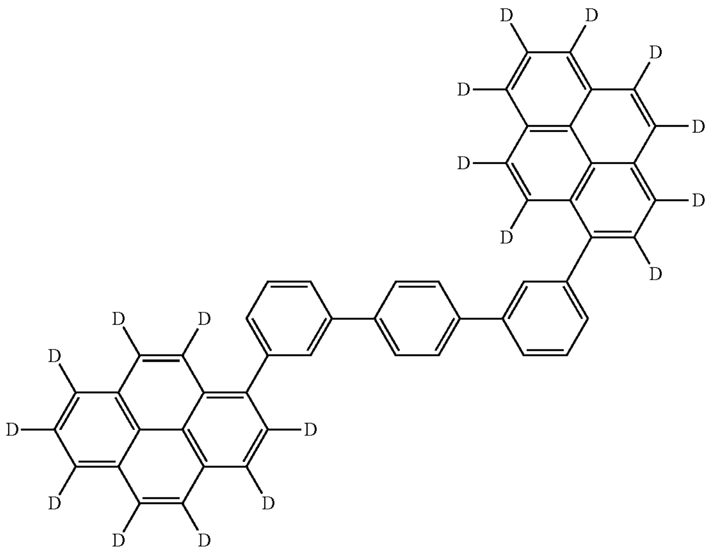
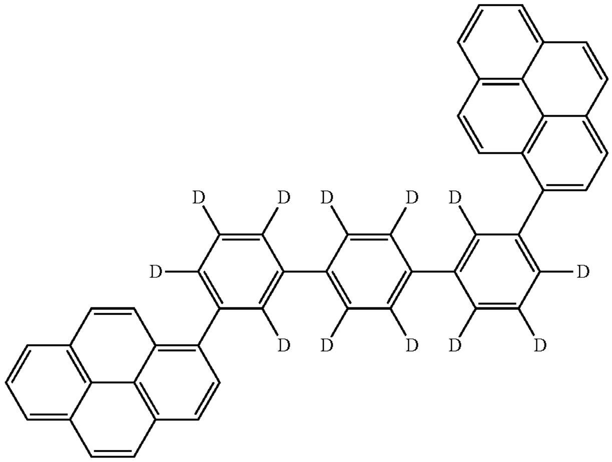

-continued
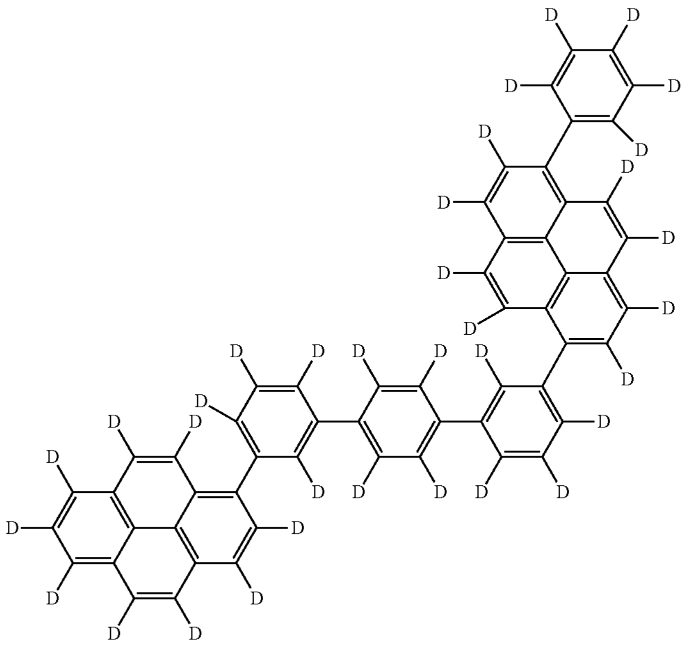
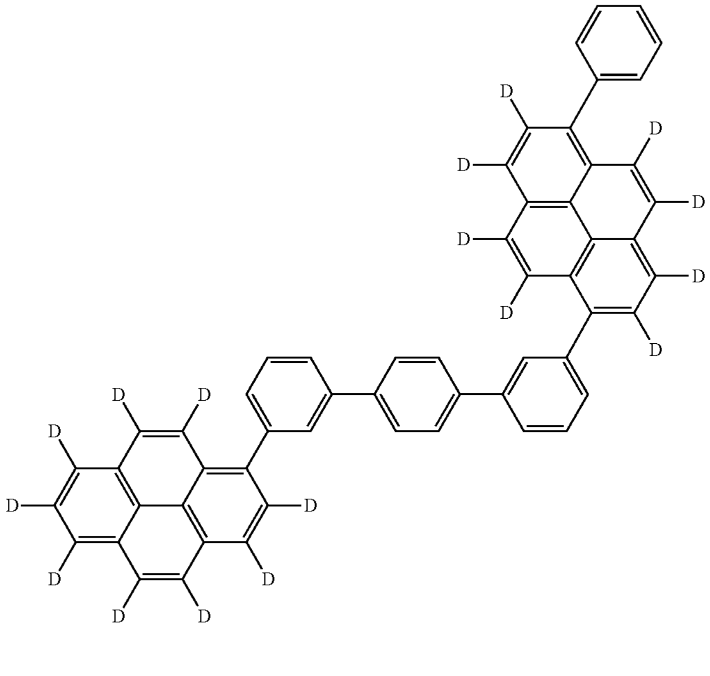

-continued
[Formula 120]
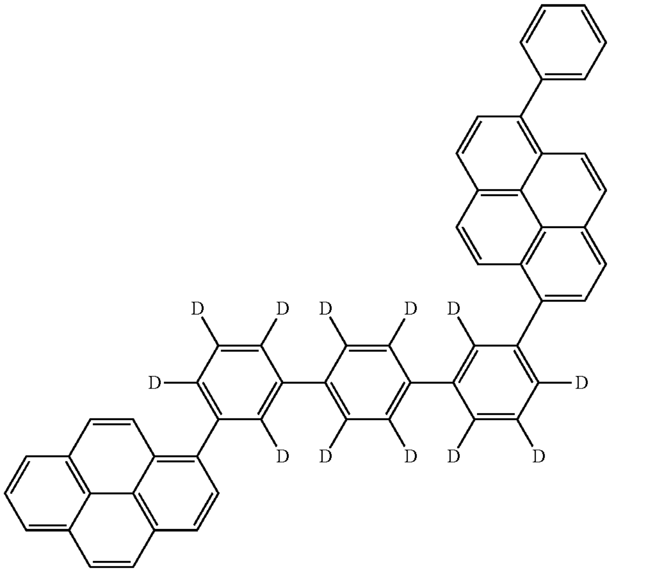
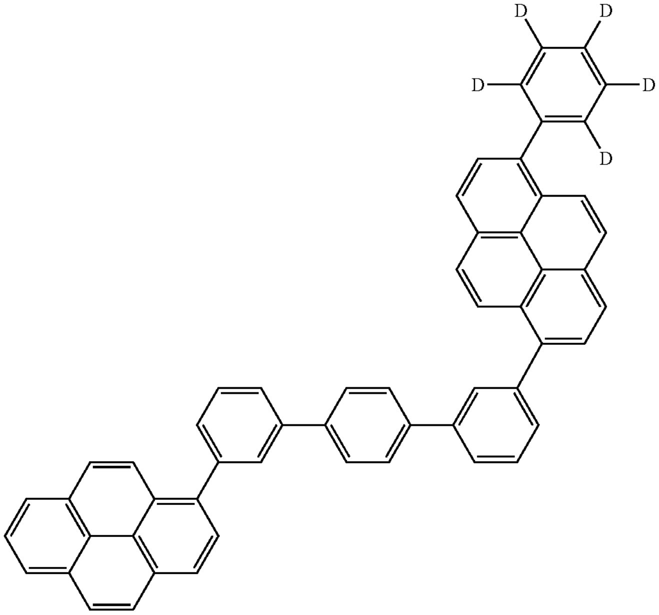
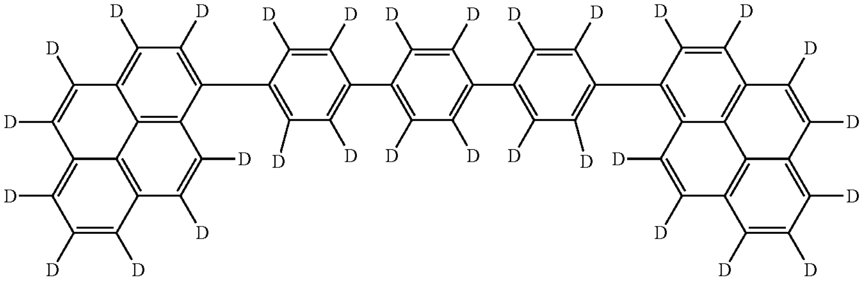

-continued
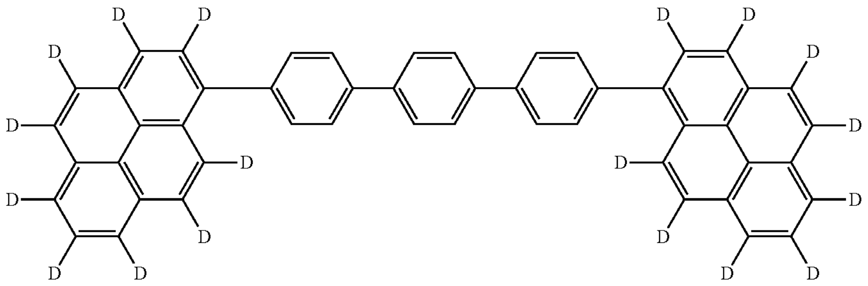
[Formula 121]
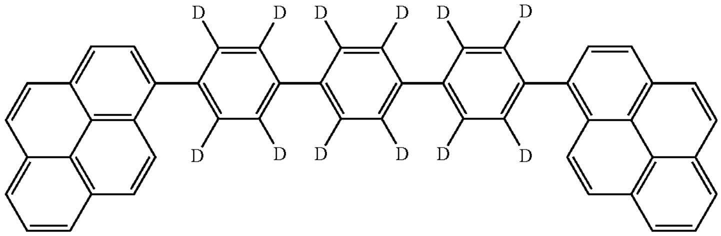
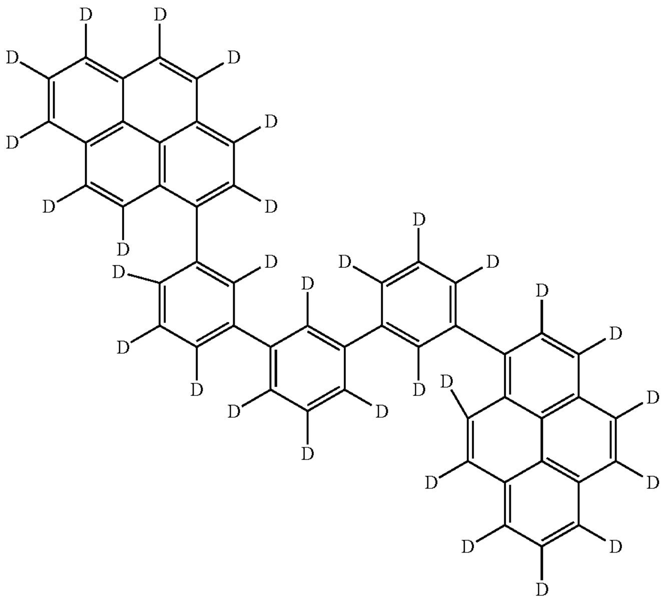

-continued
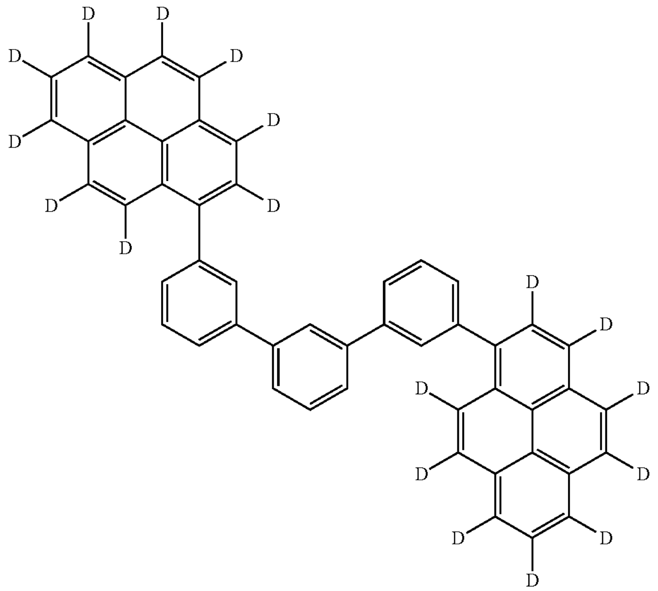
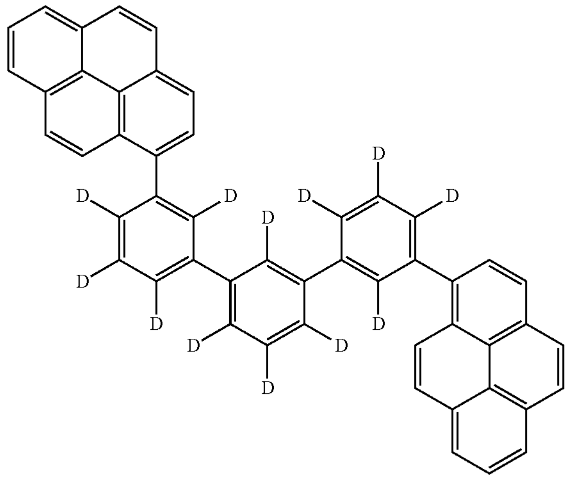
[Formula 122]
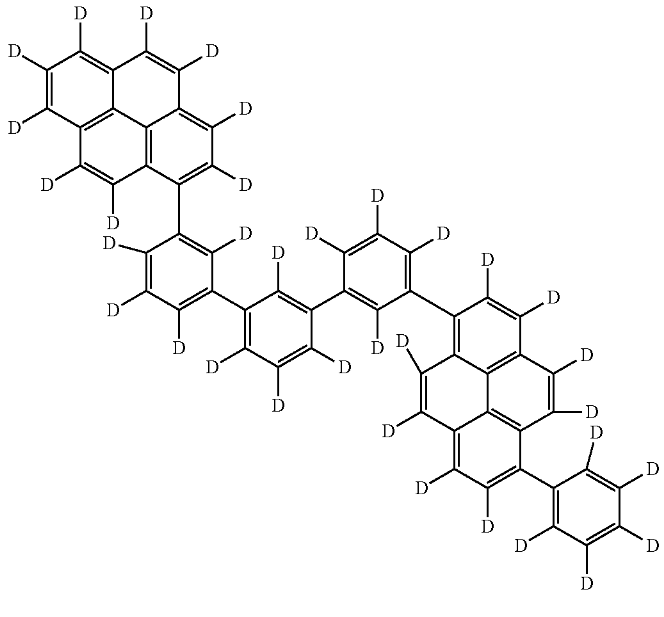

-continued
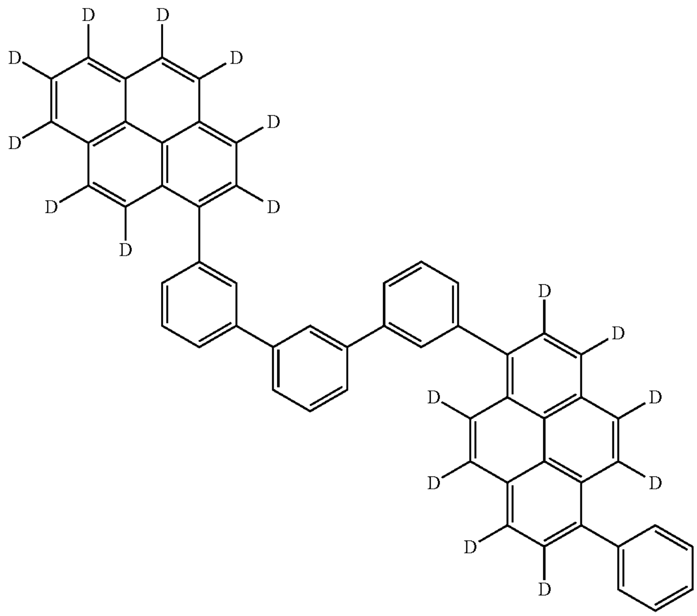
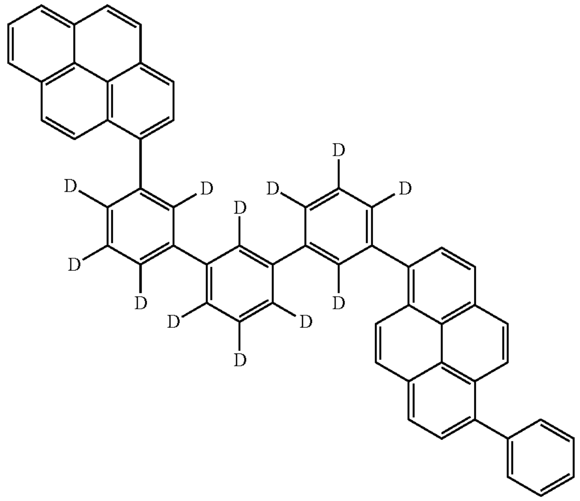
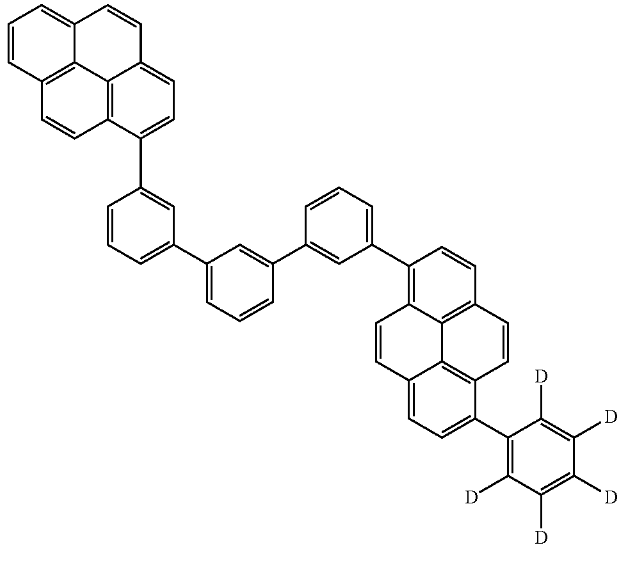

-continued
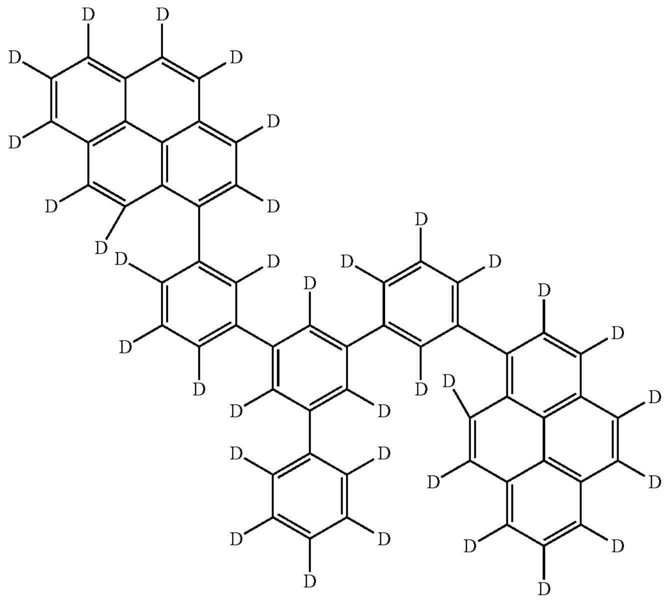
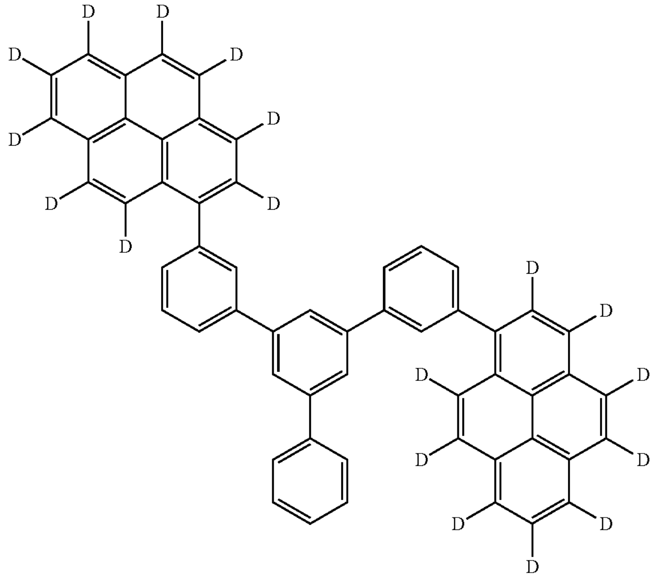
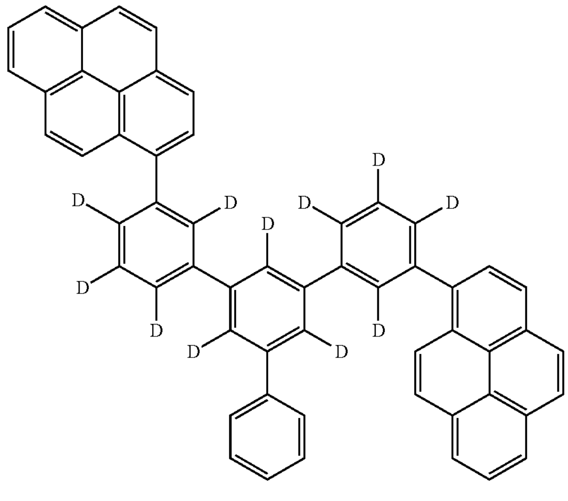
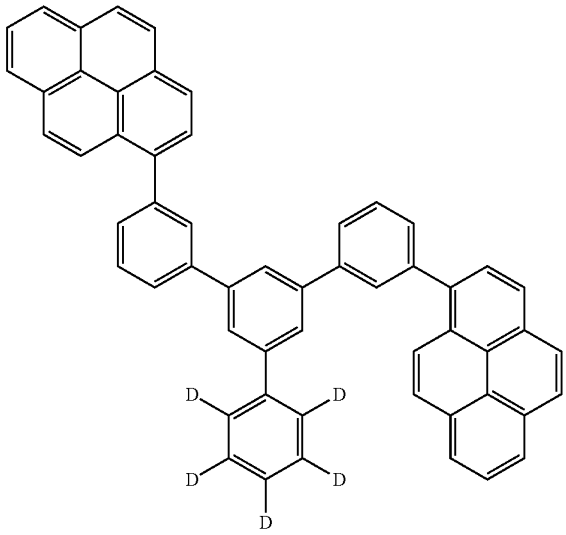

-continued
[Formula 123]
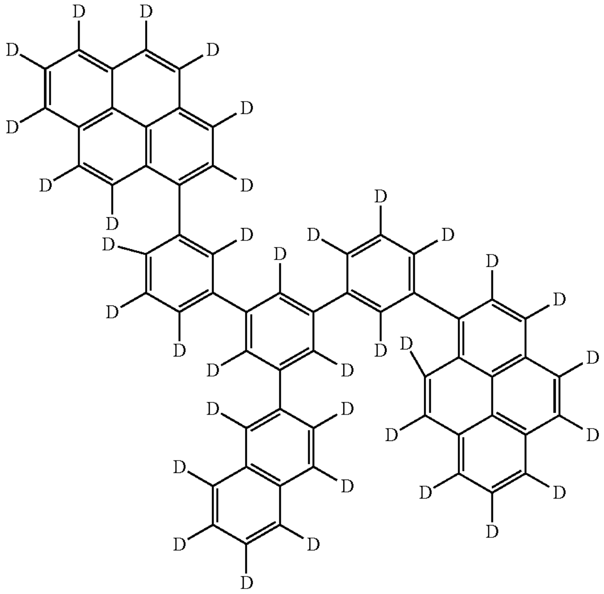
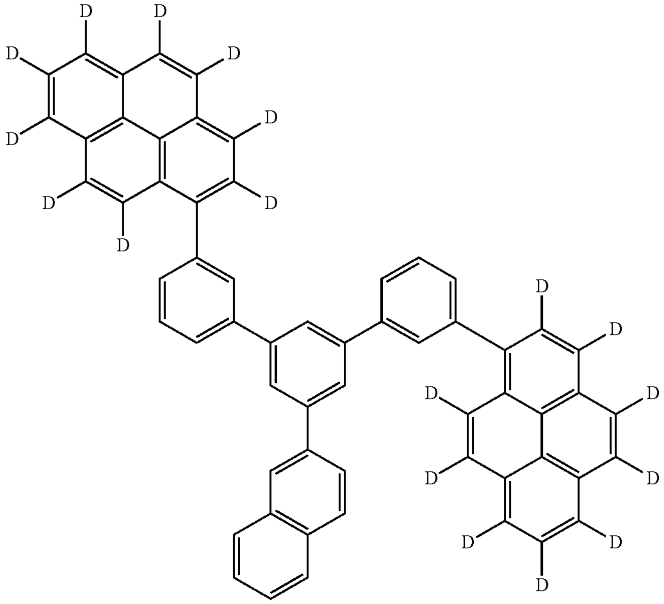

-continued
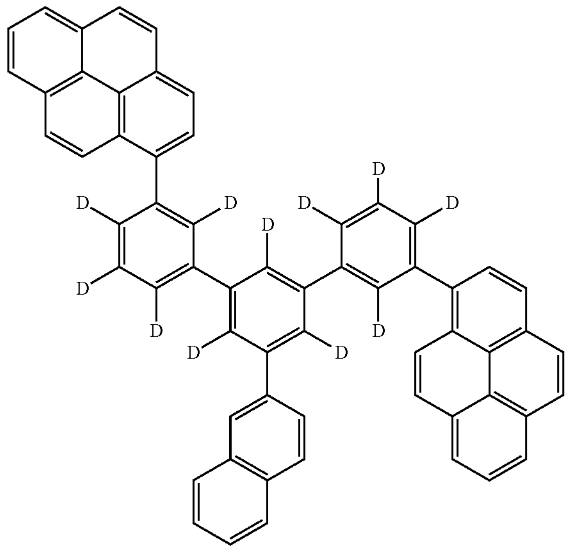
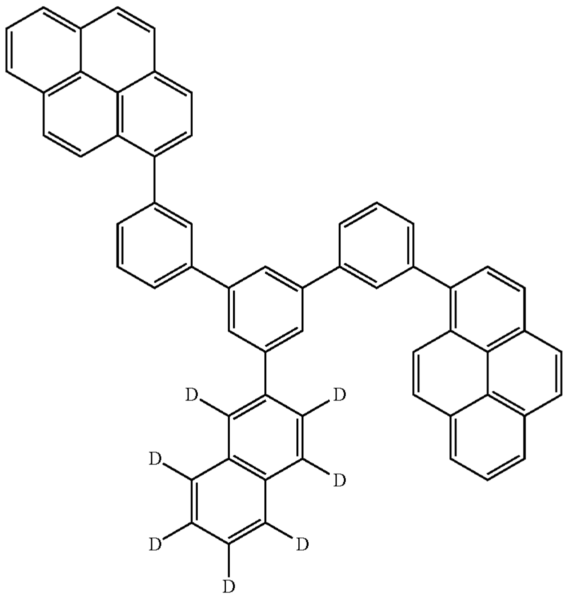
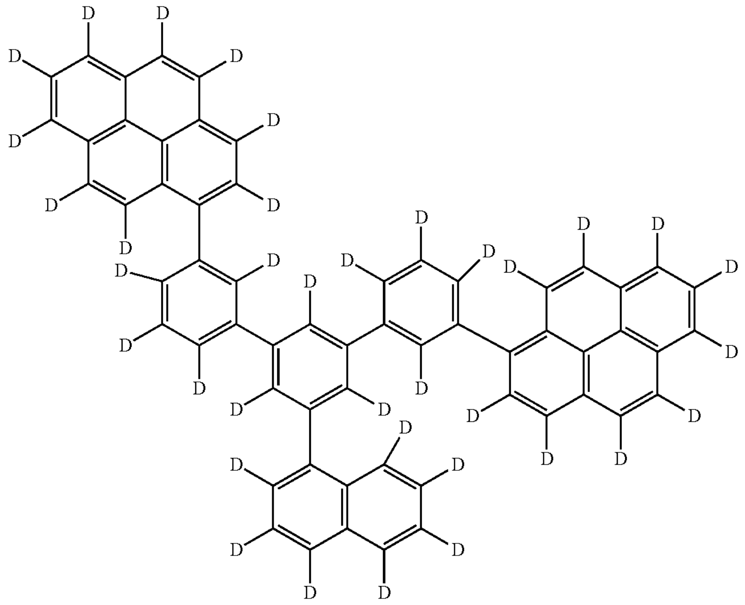

-continued
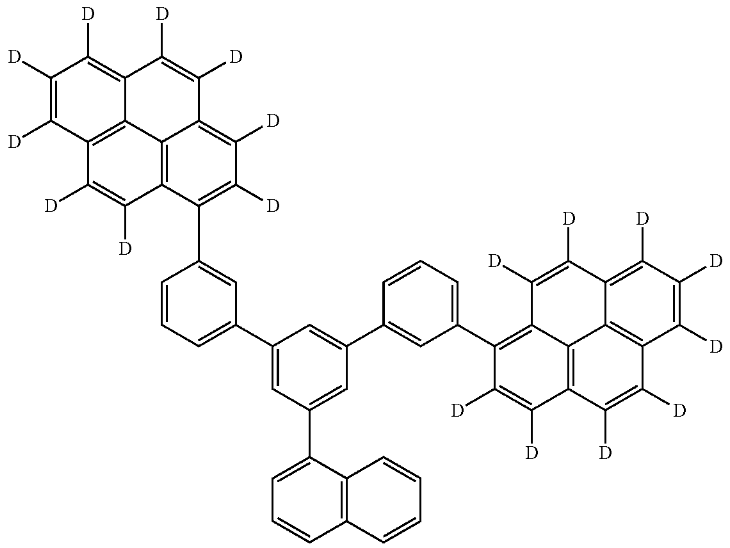
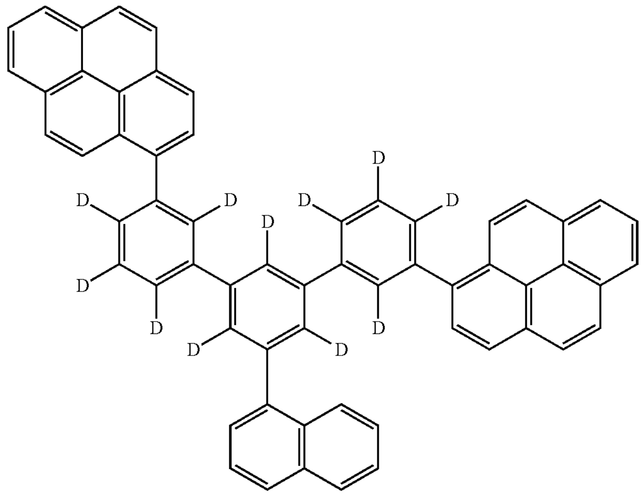
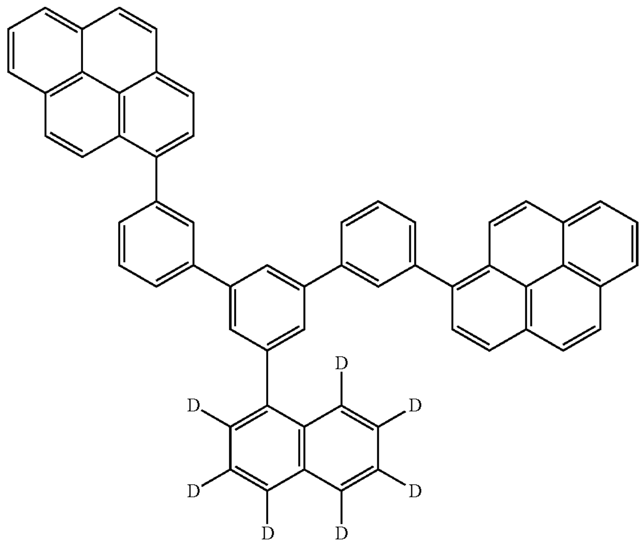

-continued
[Formula 124]
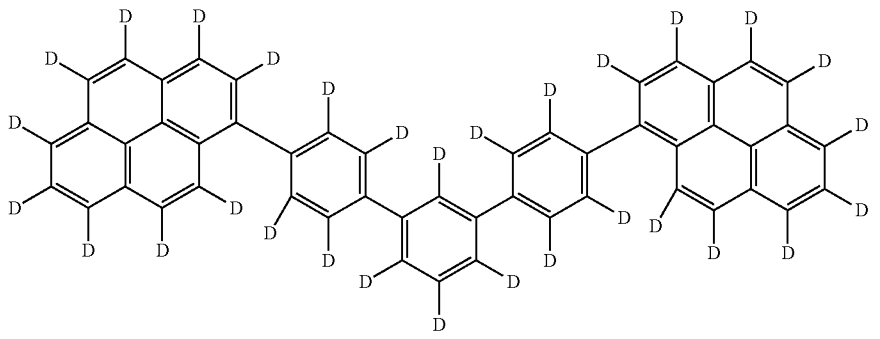
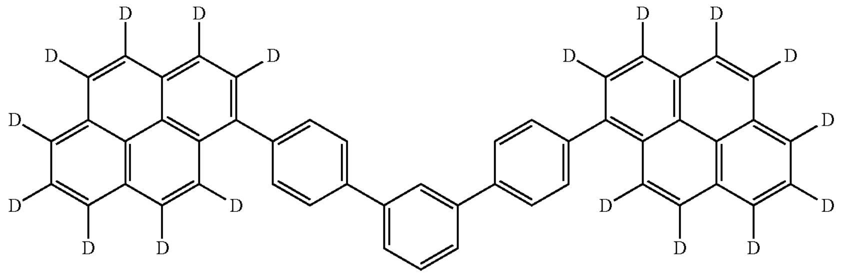
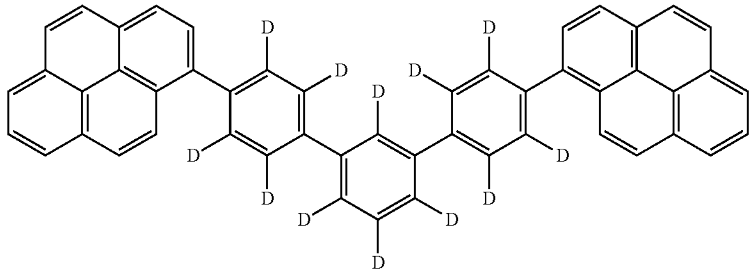
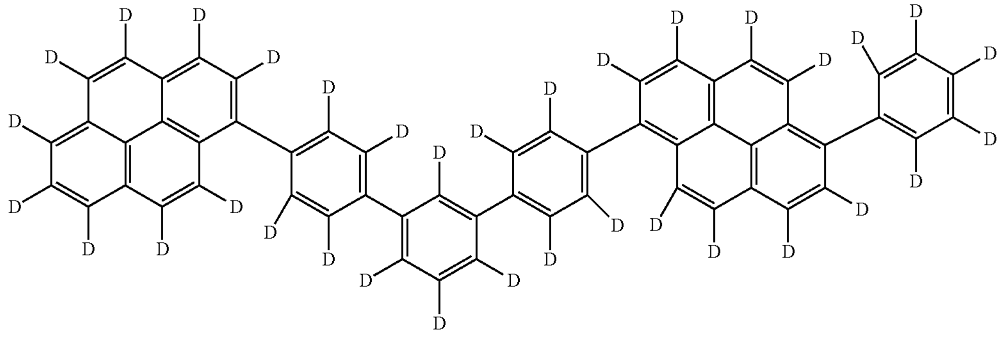
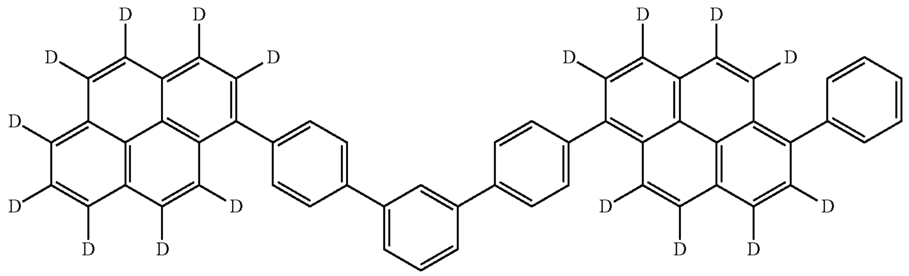

-continued
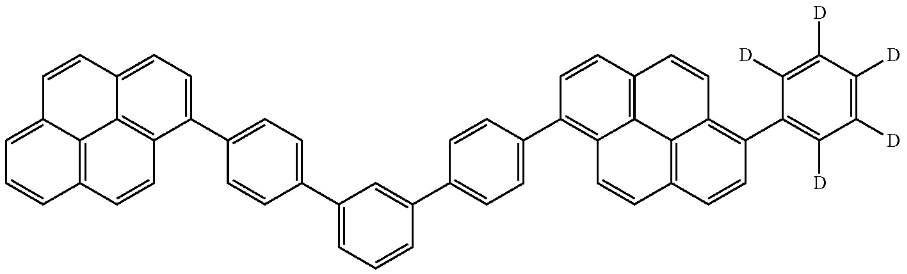
[Formula 125]
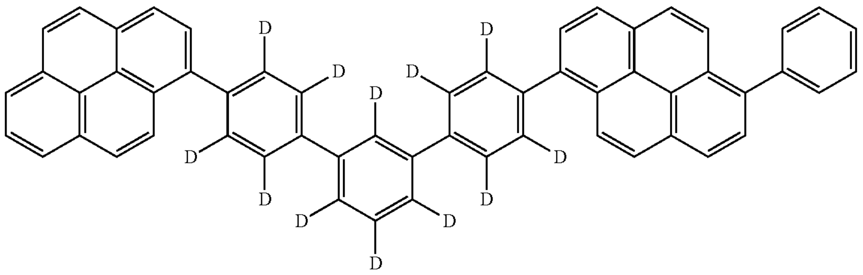
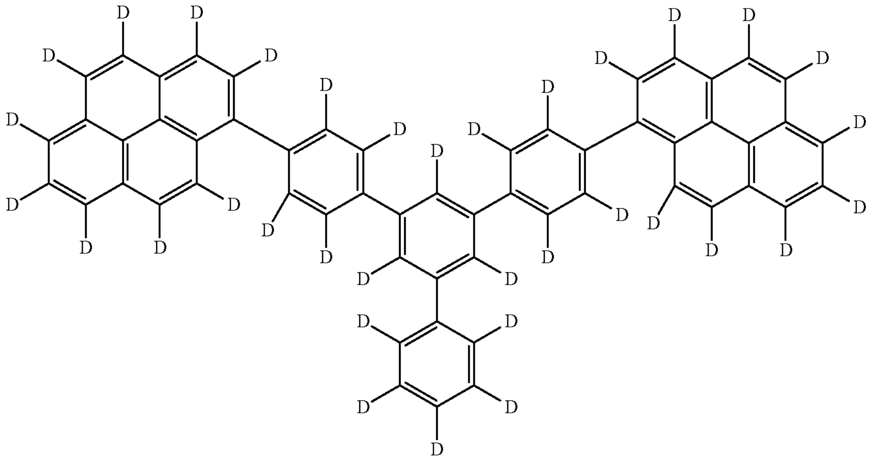
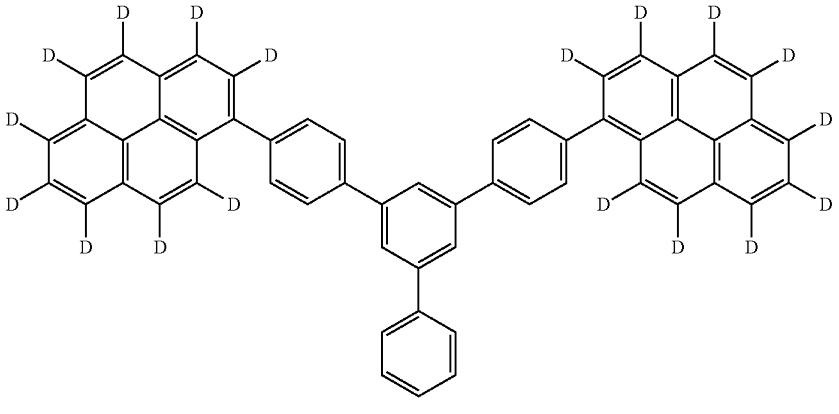

-continued
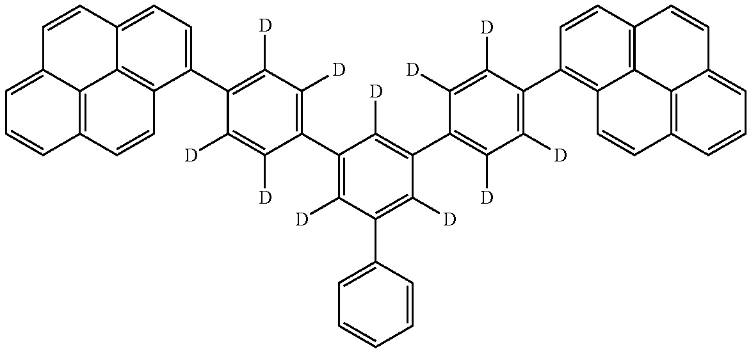
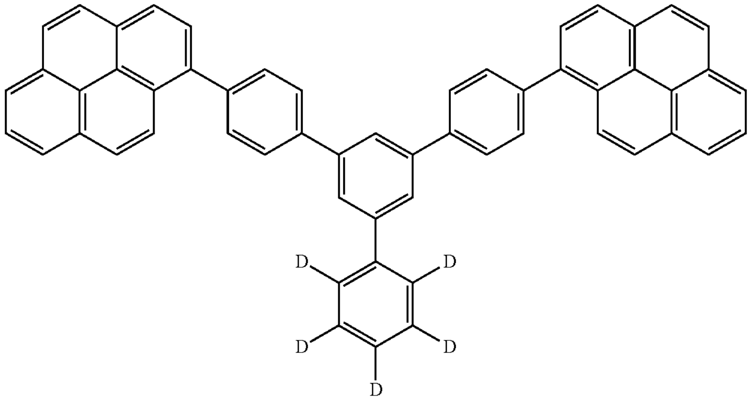
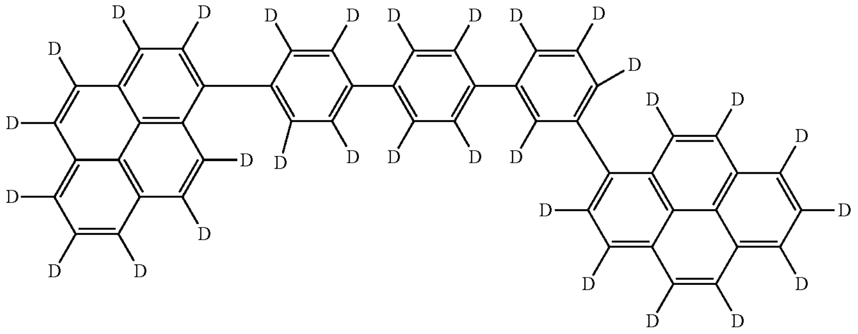
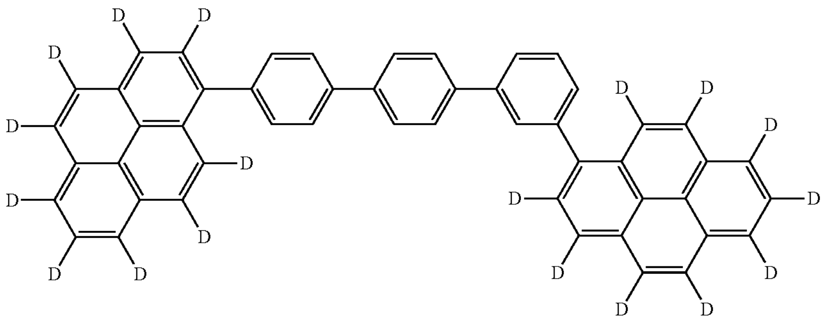
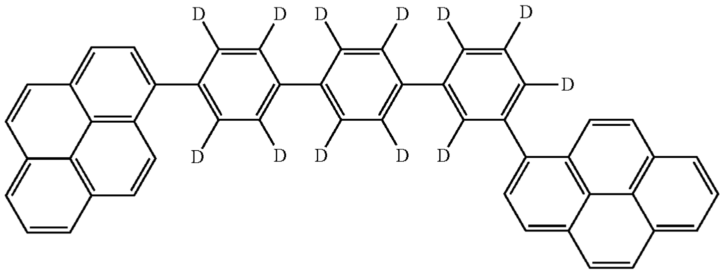

-continued
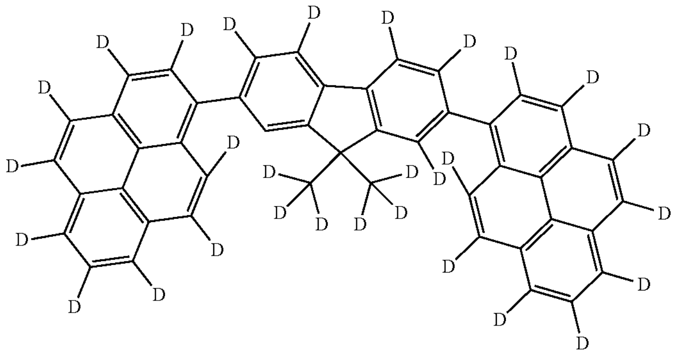
[Formula 126]
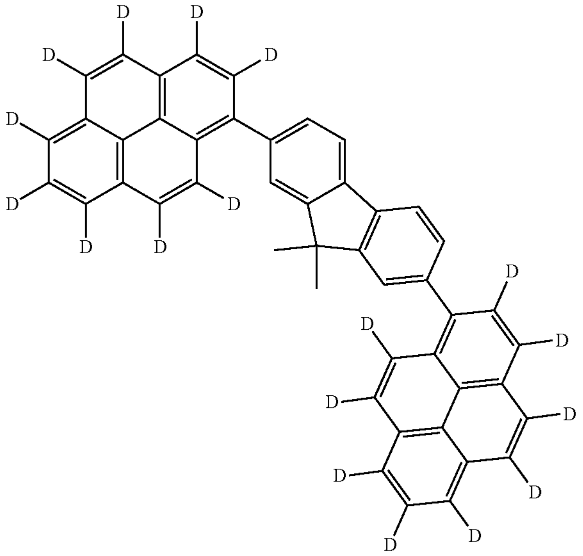
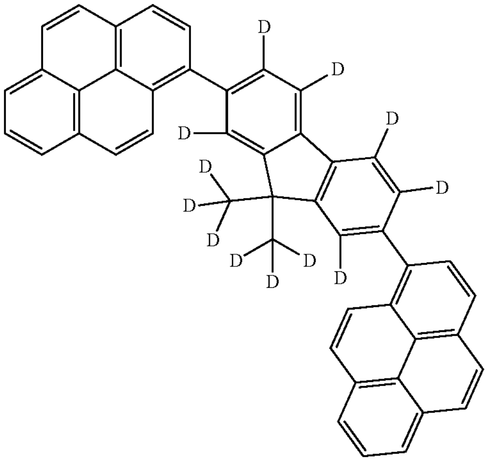
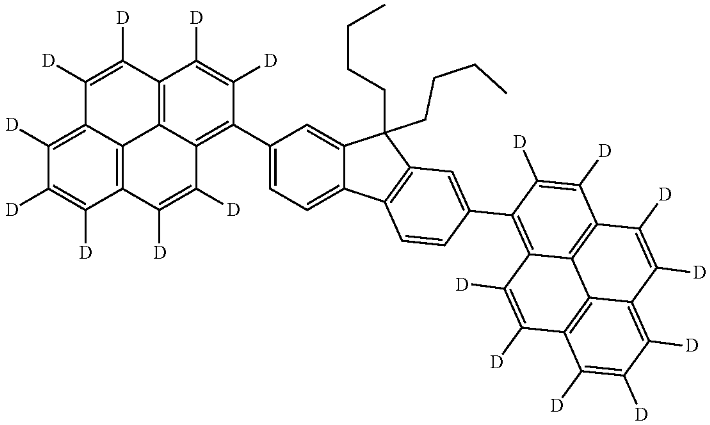

-continued
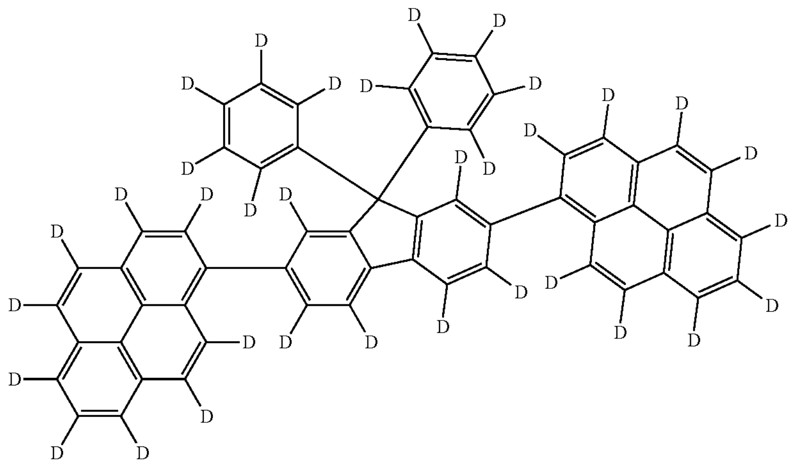
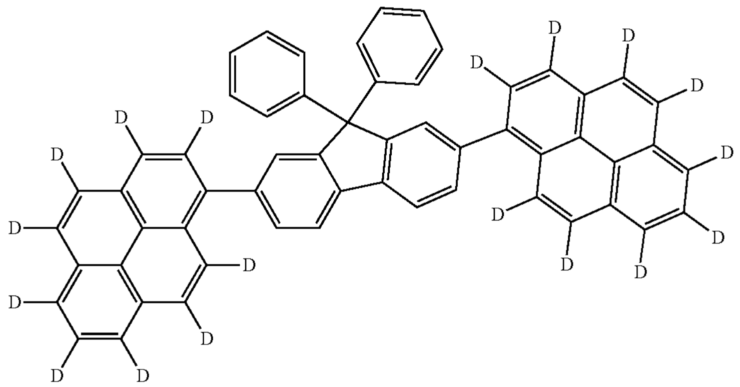
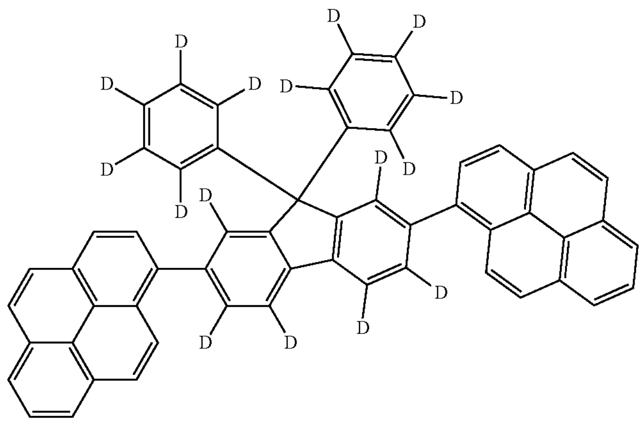

-continued
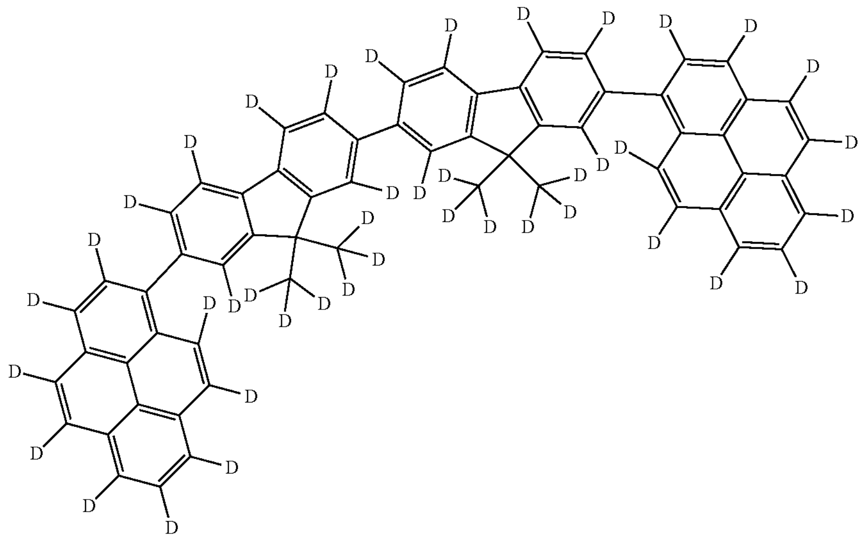
[Formula 127]
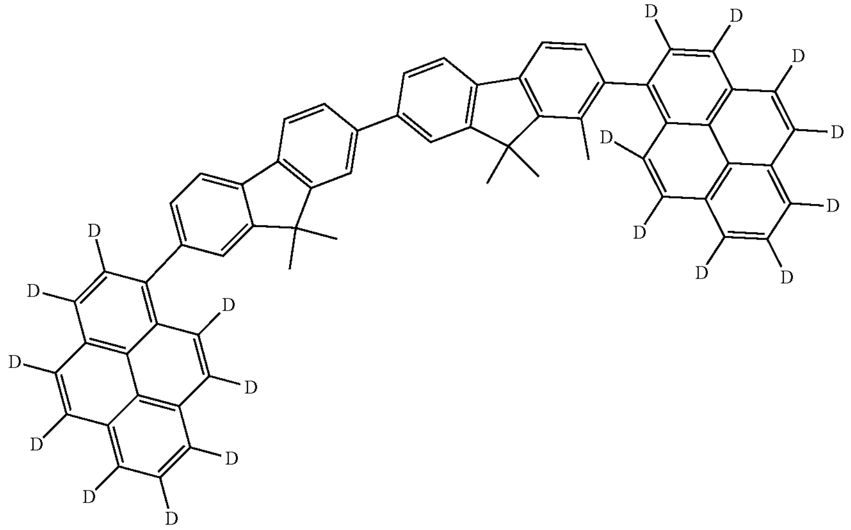
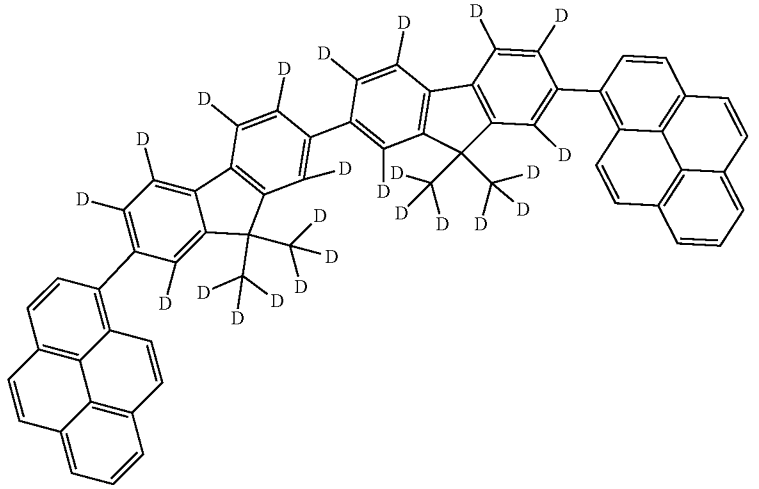

-continued
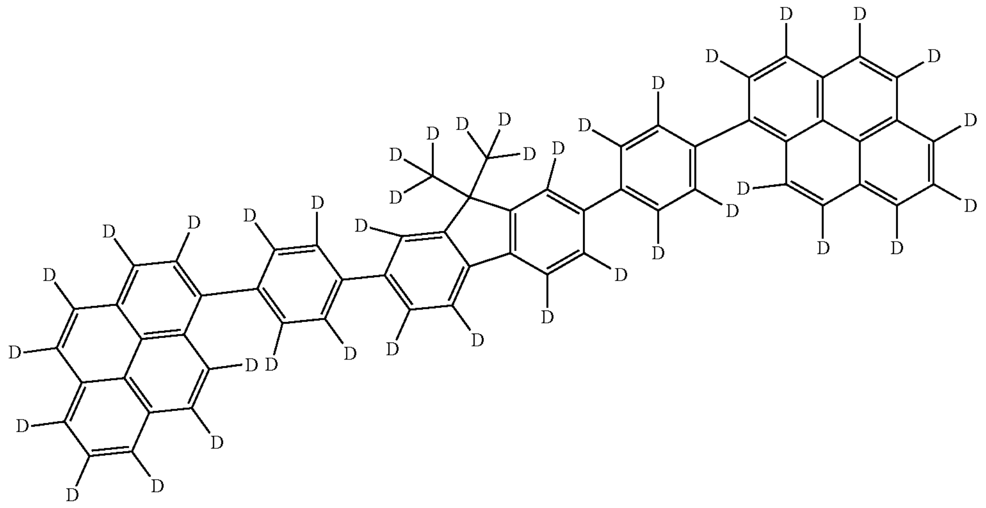
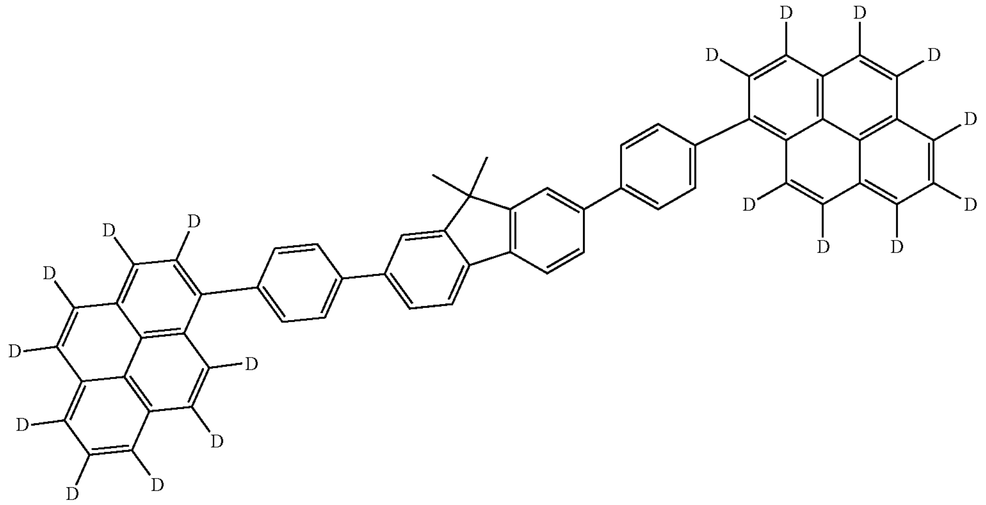
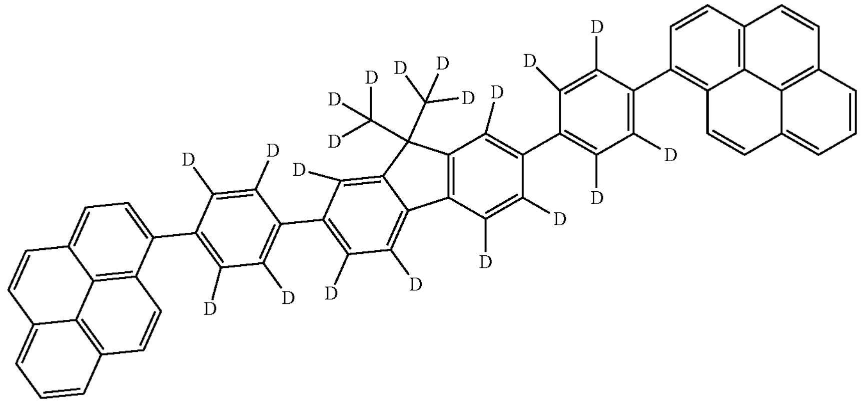

-continued
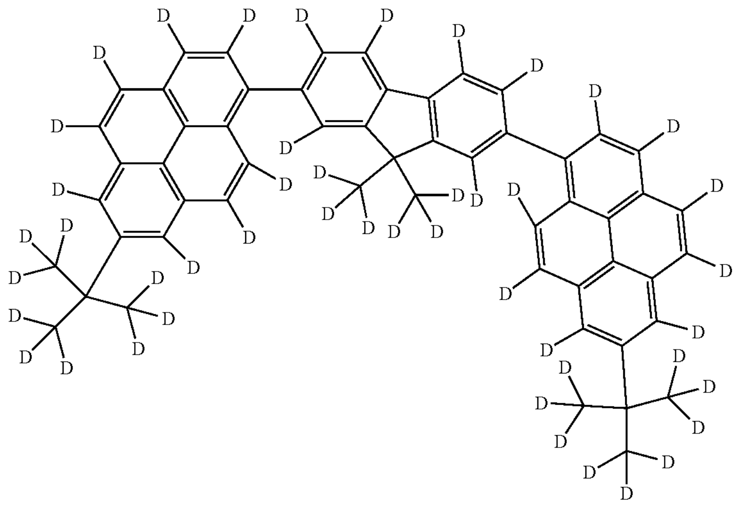
[Formula 128]
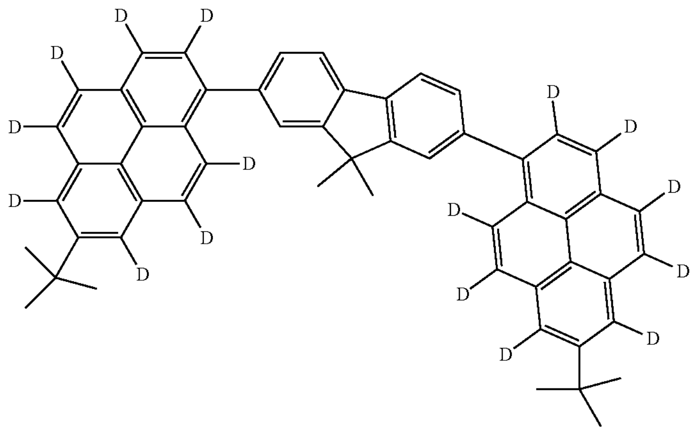
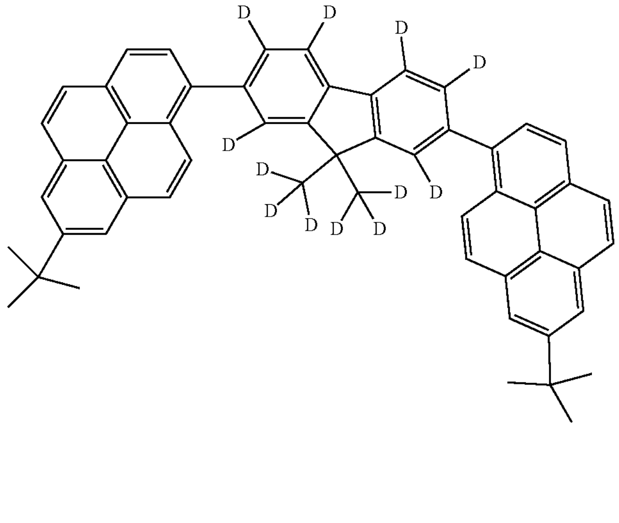

-continued
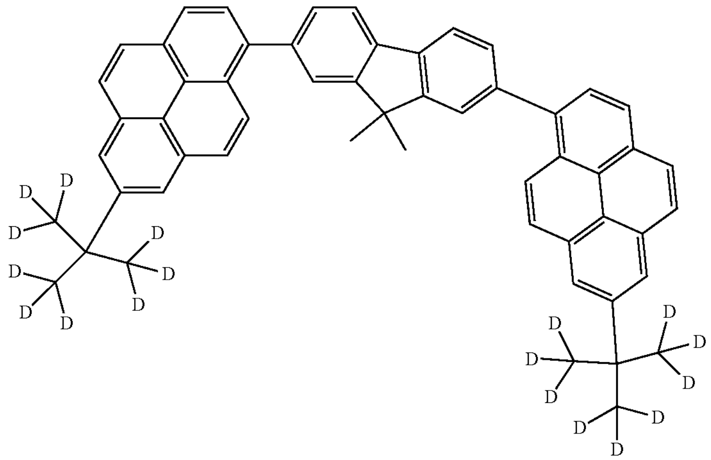
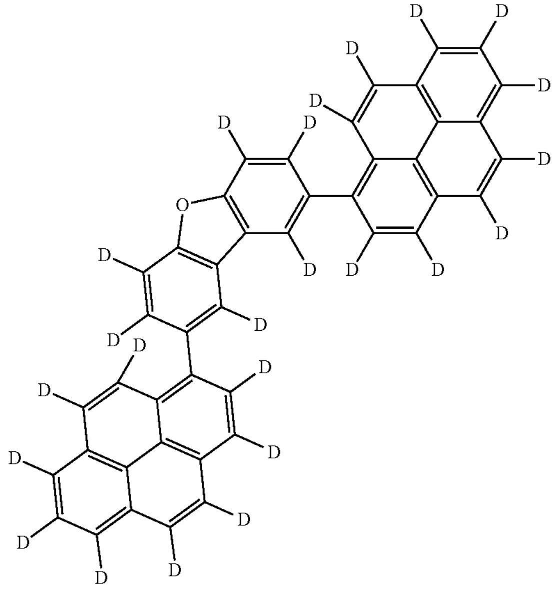
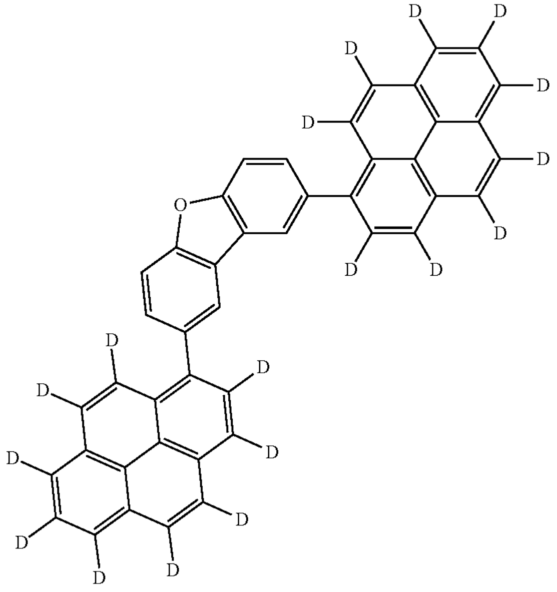
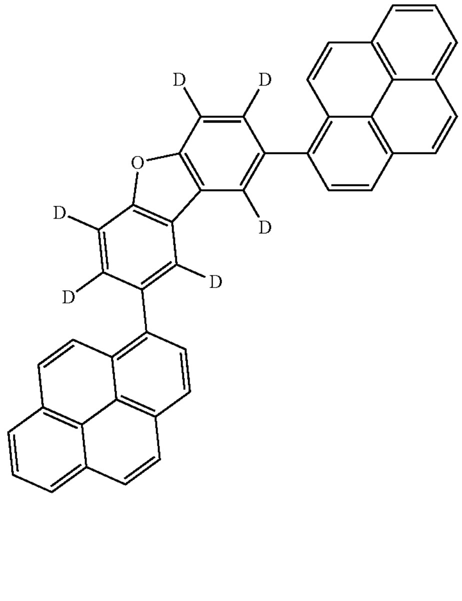
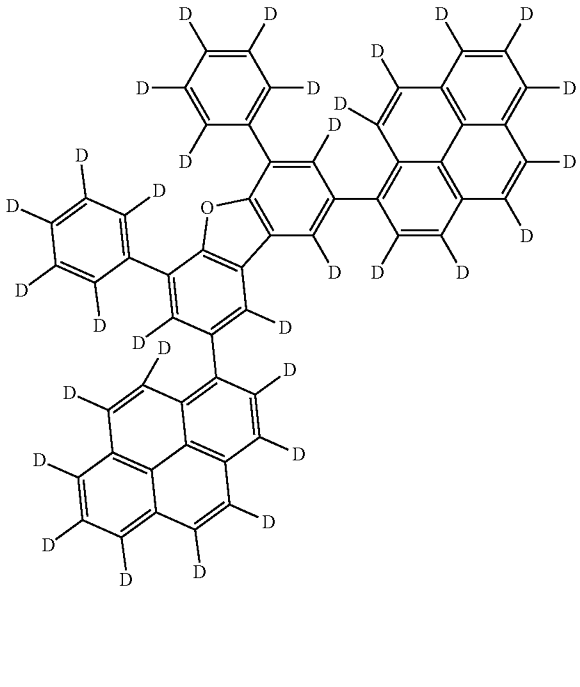

-continued
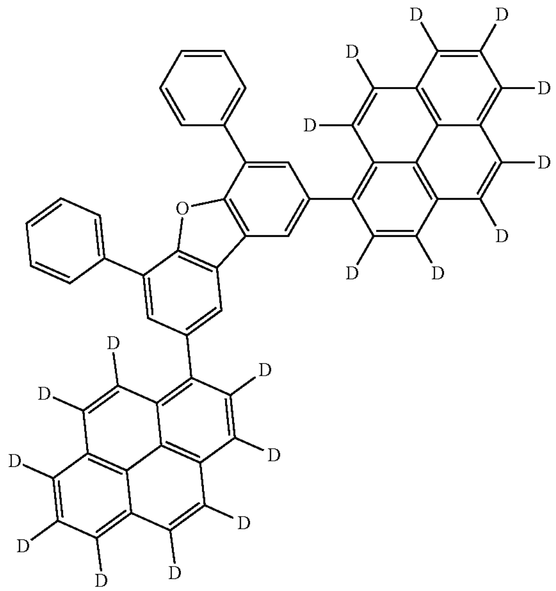
[Formula 129]
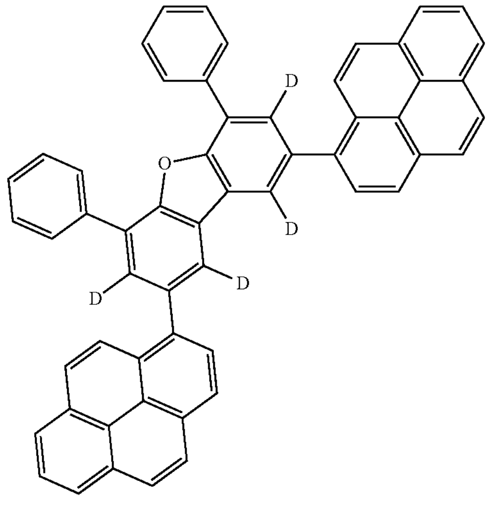
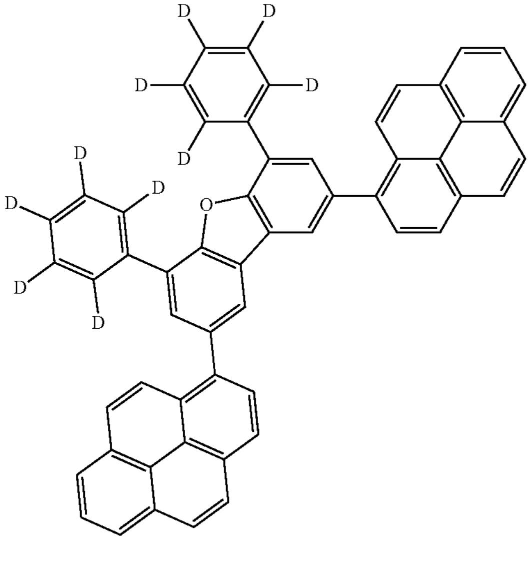
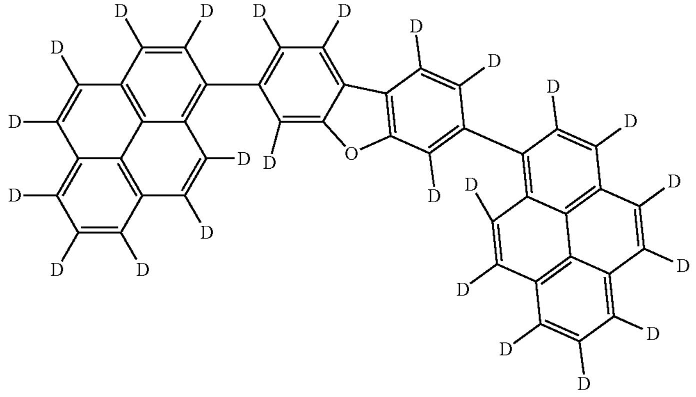

-continued
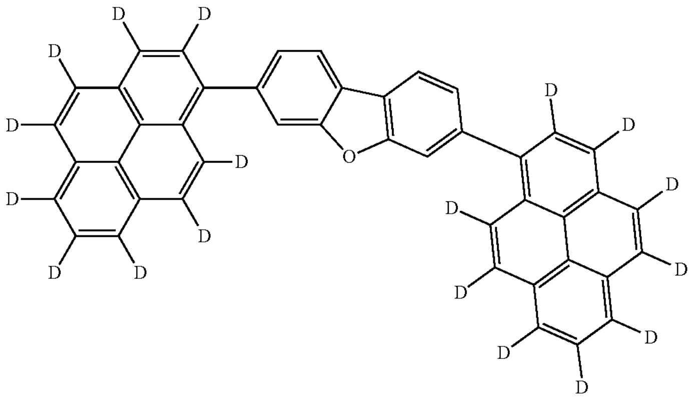
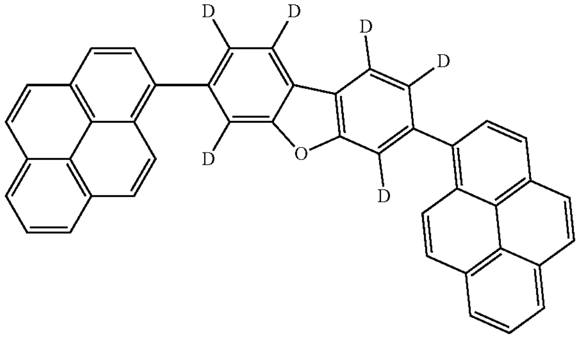
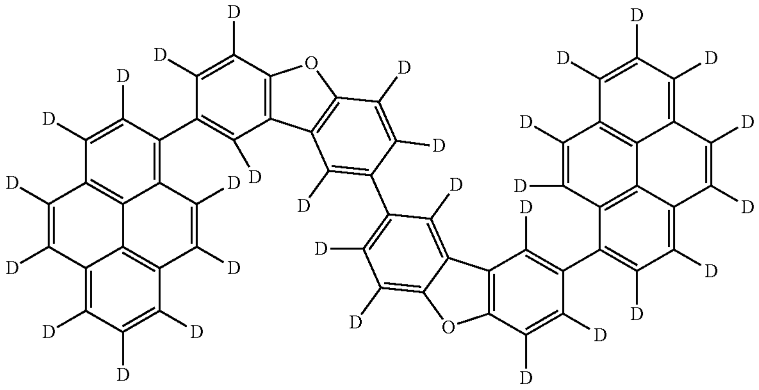
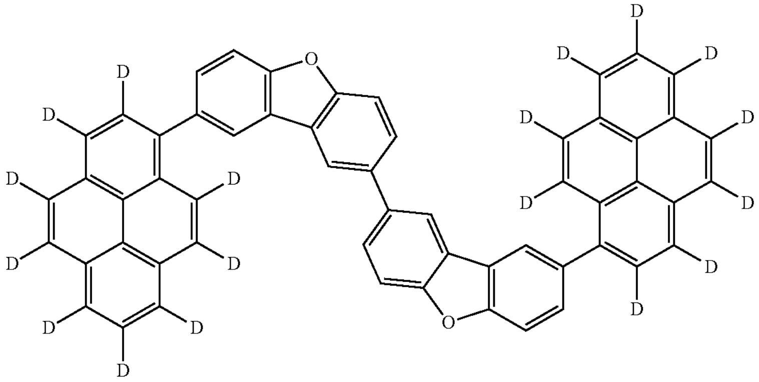

-continued
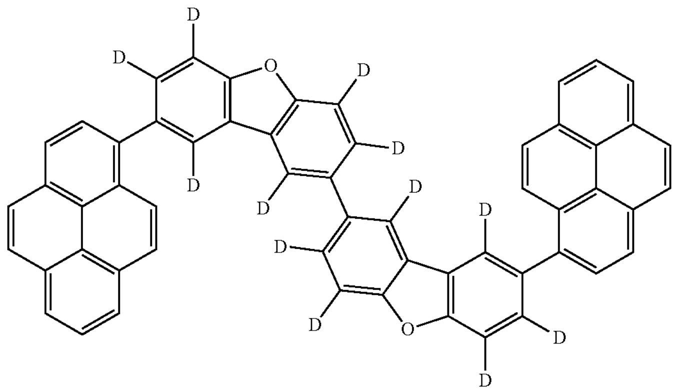
[Formula 130]
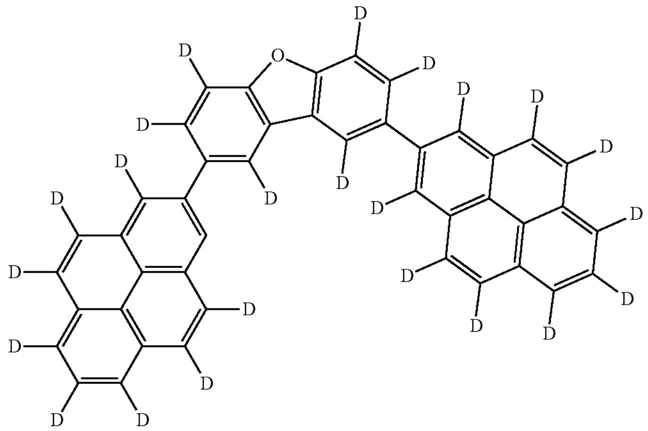
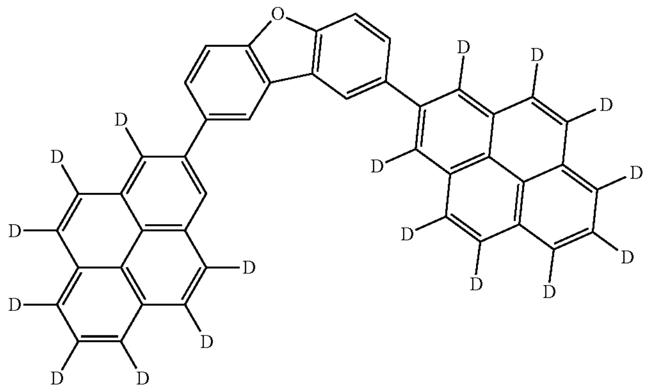
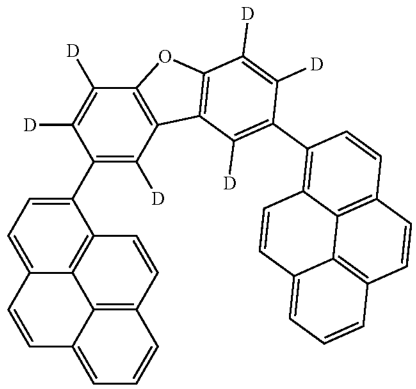

-continued
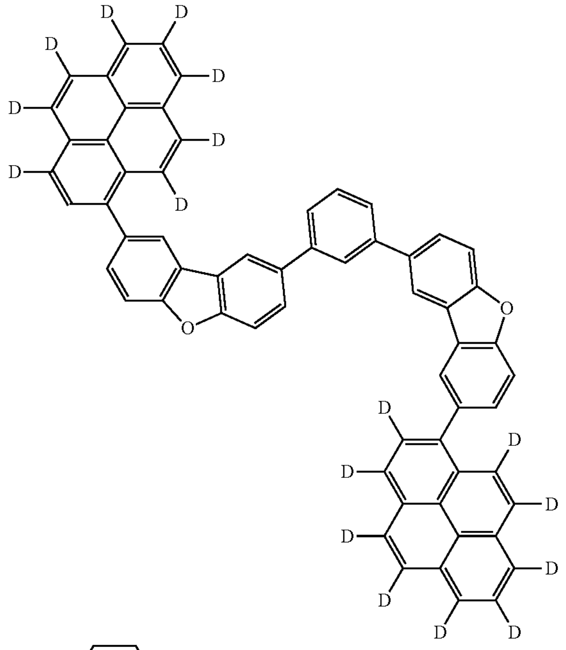
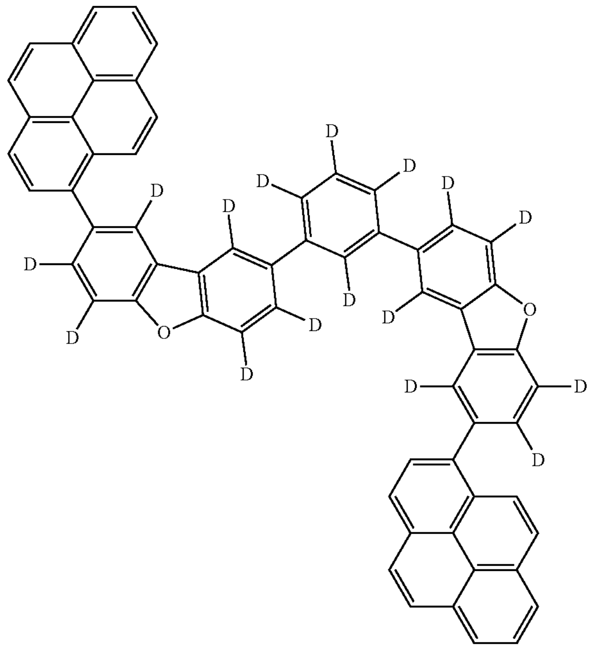
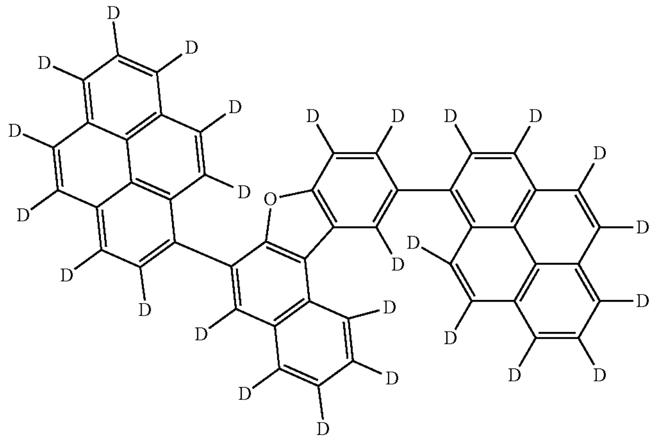

-continued
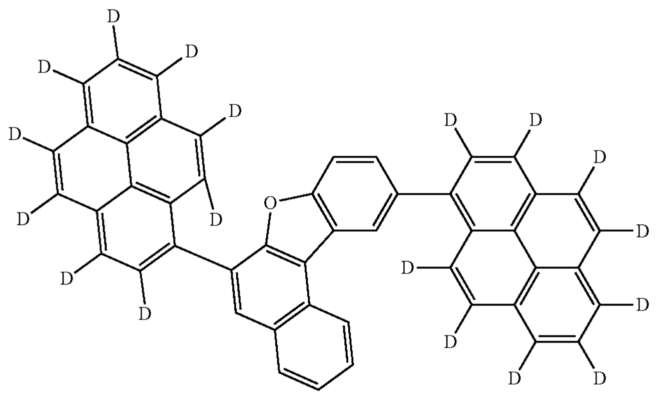
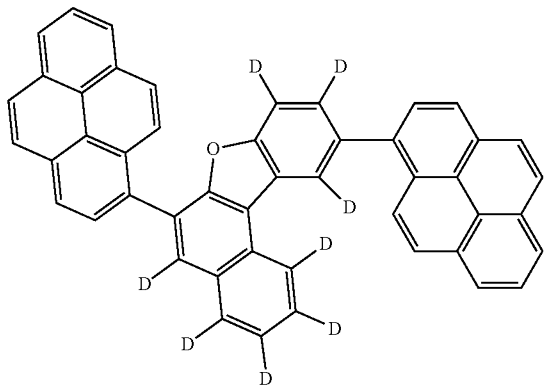
[Formula 131]
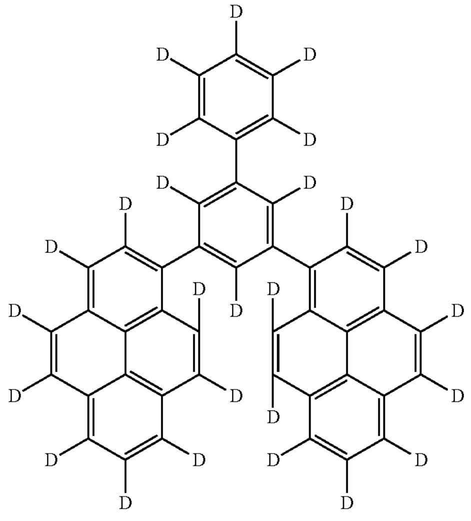
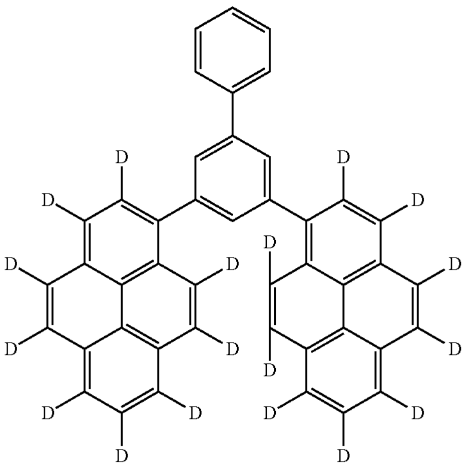

-continued
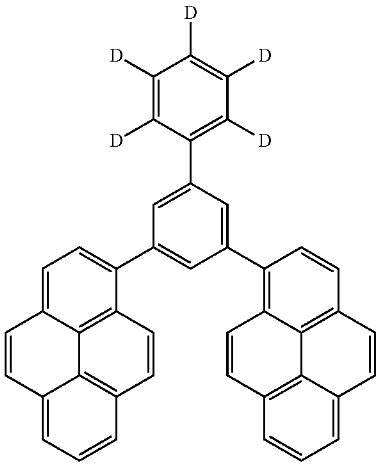 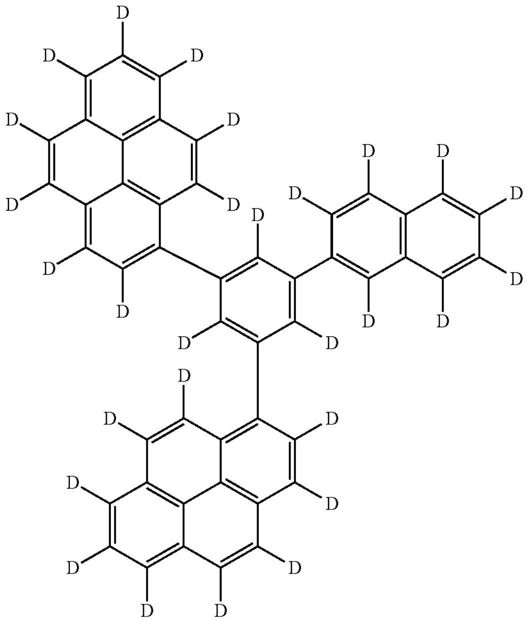
[Formula 132]
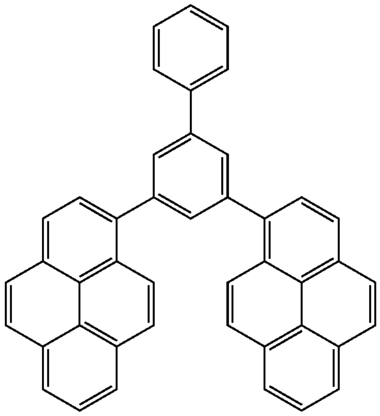 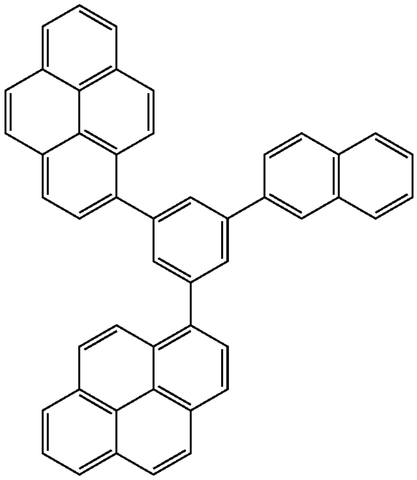
[Formula 133]
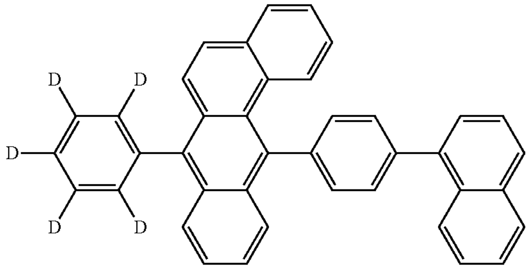 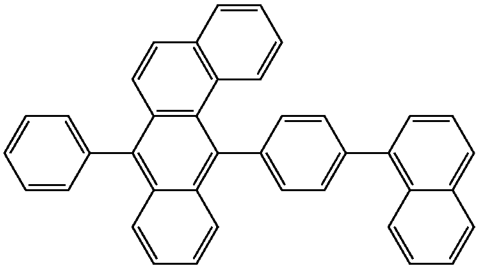

-continued

[Formula 134]

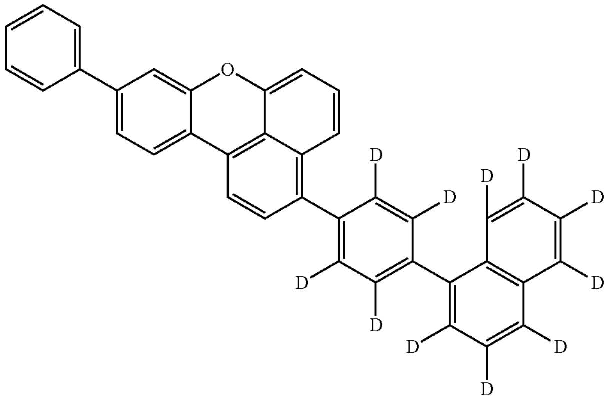

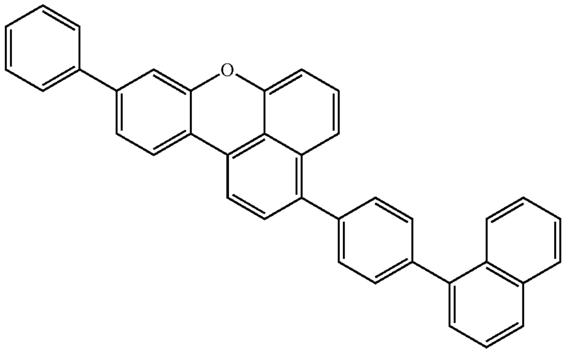

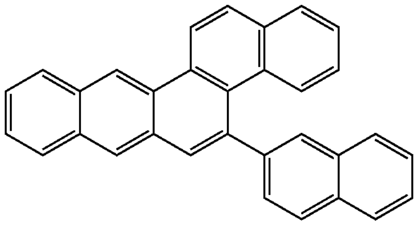

Second Compound

In the organic EL device according to the exemplary embodiment, the second compound is a compound represented by the formula (2) below.

[Formula 135]

(2)

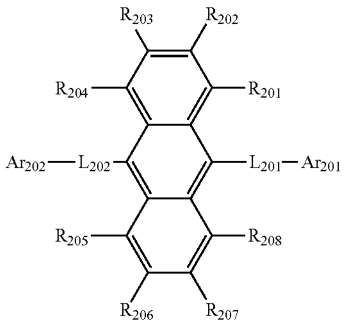

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ to $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the second compound according to the exemplary embodiment: $R_{901}$, $R_{902}$, $R_{903}$, $R_{904}$, $R_{905}$, $R_{908}$, $R_{907}$, $R_{801}$, and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, it is preferable that $R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a substituted or unsubstituted aralkyl group having 7 to 50 carbon atoms, a group represented by —C(═O)$R_{801}$, a group represented by —$COOR_{802}$, a halogen atom, a cyano group or a nitro group;

$L_{201}$ to $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that $L_{201}$ to $L_{202}$ are each independently a single bond or a substituted or unsubstituted arylene group having 6 to 50 ring carbon atoms; and $Ar_{201}$ and $Ar_{202}$ are each independently a substituted or unsubstituted aryl group having 6 to 50 ring carbon atoms.

In the organic EL device according to the exemplary embodiment, it is preferable that $Ar_{201}$ and $Ar_{202}$ are each independently a phenyl group, a naphthyl group, phenanthryl group, a biphenyl group, a terphenyl group, a diphenylfluorenyl group, a dimethylfluorenyl group, benzodiphenylfluorenyl group, a benzodimethylfluorenyl group, a dibenzofuranyl group, dibenzothienyl group, a naphthobenzofuranyl group, or a naphthobenzothienyl group.

In the organic EL device according to the exemplary embodiment, the second compound represented by the formula (2) is preferably a compound represented by a formula (201), (202), (203), (204), (205), (206), (207), (208) or (209) below.

[Formula 136]

(201)

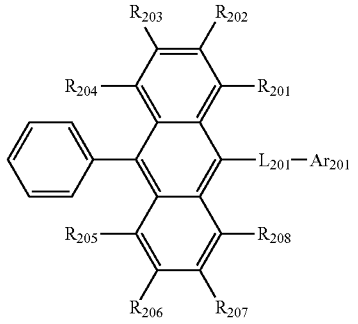

[Formula 137]

(202)

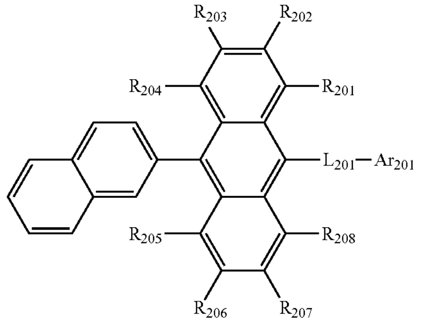

[Formula 138]

(203)

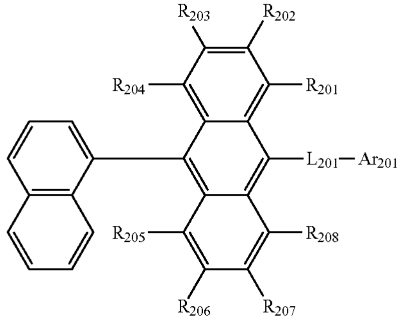

[Formula 139]

(204)

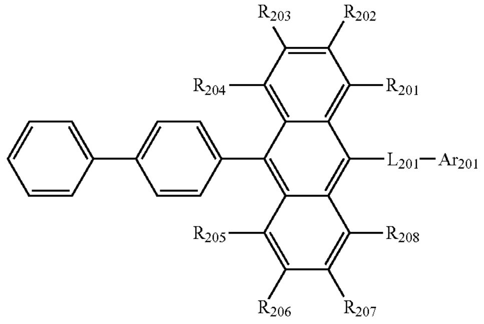

-continued

[Formula 140]

(205)

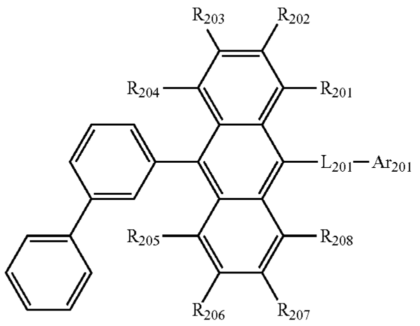

[Formula 141]

(206)

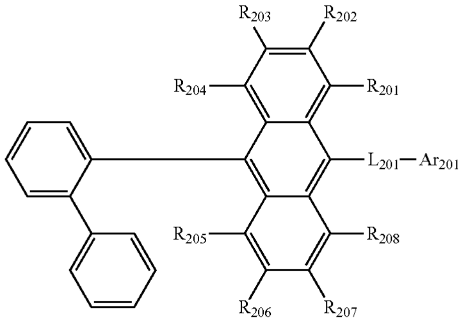

[Formula 142]

(207)

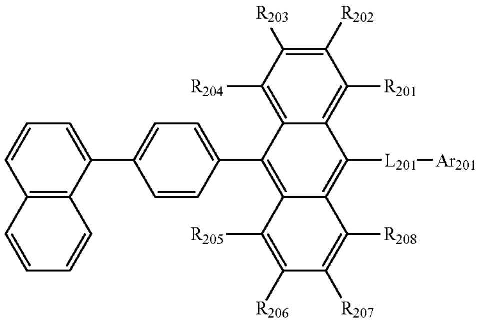

[Formula 143]

(208)

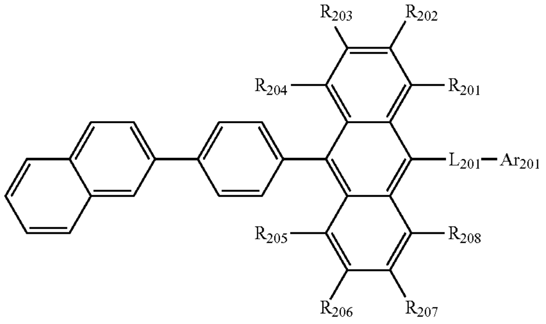

-continued

[Formula 144]

(209)

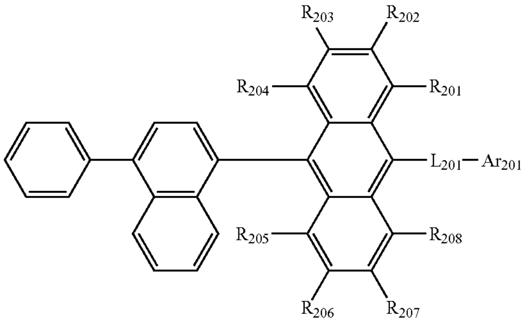

In the formulae (201) to (209):

$L_{201}$ and $Ar_{201}$ represent the same as $L_{201}$ and $Ar_{201}$ in the formula (2); and $R_{201}$ to $R_{208}$ each independently represent the same as $R_{201}$ to $R_{208}$ in the formula (2).

It is also preferable that the second compound represented by the formula (2) is a compound represented by a formula (221), a formula (222), a formula (223), a formula (224), a formula (225), a formula (226), a formula (227), a formula (228), or a formula (229) below.

[Formula 145]

(221)

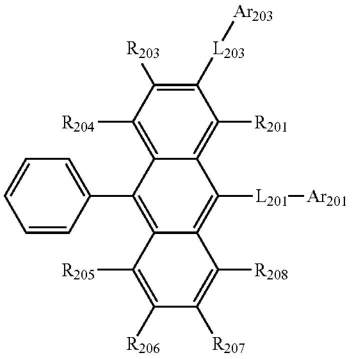

[Formula 146]

(222)

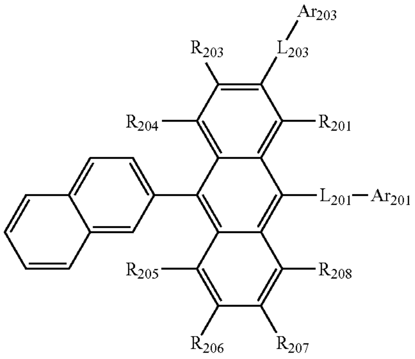

-continued

[Formula 147]

(223)

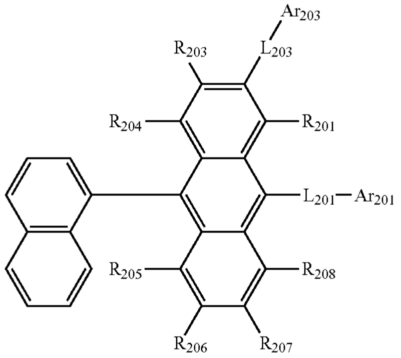

[Formula 148]

(224)

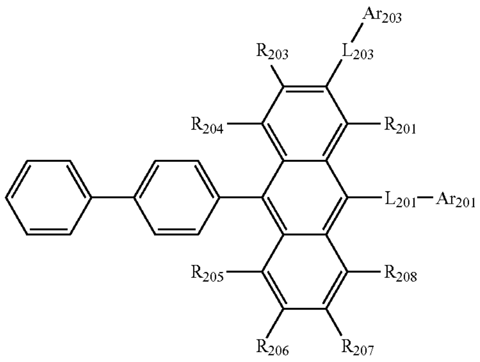

[Formula 149]

(225)

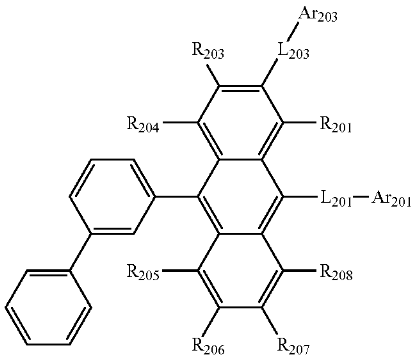

[Formula 150]

(226)

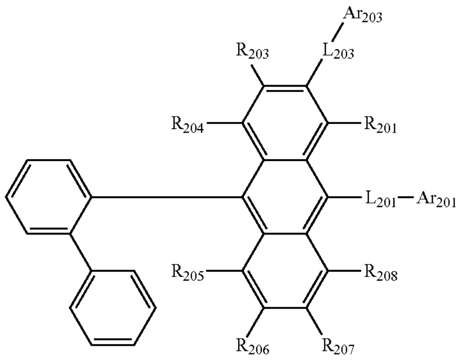

-continued

[Formula 151]

(227)

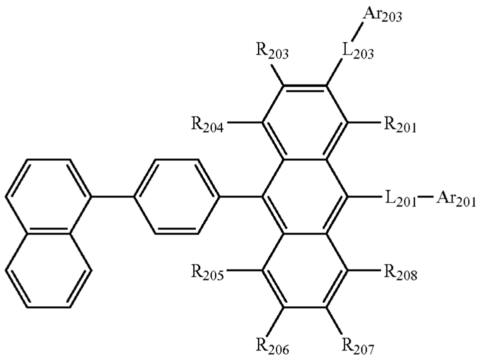

[Formula 152]

(228)

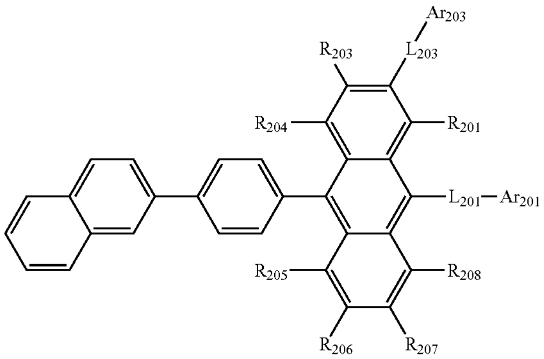

[Formula 153]

(229)

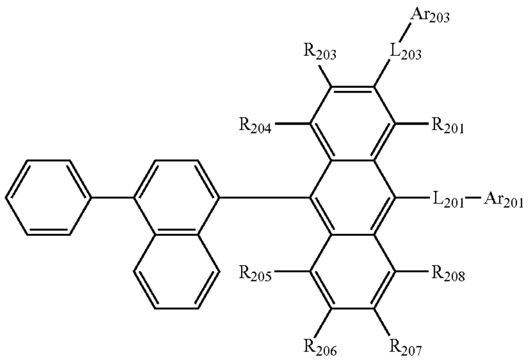

In the formulae (221), (222), (223), (224), (225), (226), (227), (228) and (229):

$R_{201}$ and $R_{203}$ to $R_{208}$ each independently represent the same as $R_{201}$ and $R_{203}$ to $R_{208}$ in the formula (2);

$L_{201}$ and $Ar_{201}$ represent the same as $L_{201}$ and $Ar_{201}$ in the formula (2); and $L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

The second compound represented by the formula (2) is also preferably a compound represented by a formula (241), (242), (243), (244), (245), (246), (247), (248) or (249).

[Formula 154]
(241)
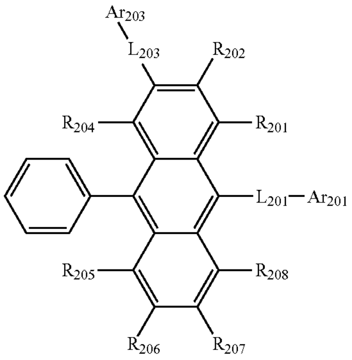
[Formula 155]
(242)
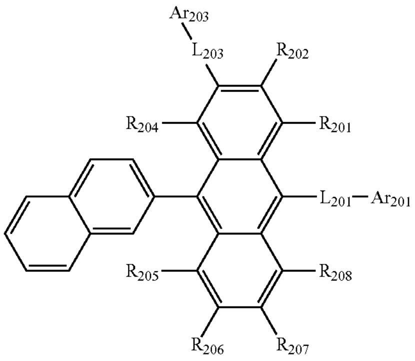
[Formula 156]
(243)
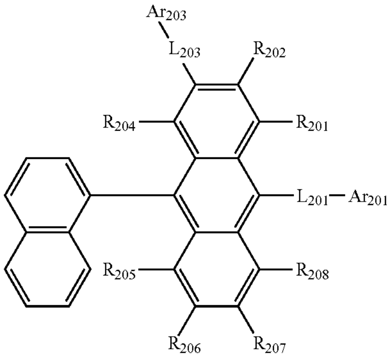
[Formula 157]
(244)
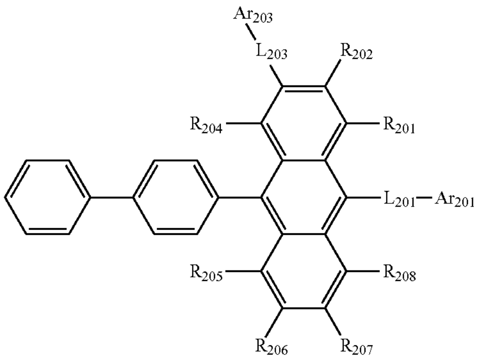
-continued
[Formula 158]
(245)
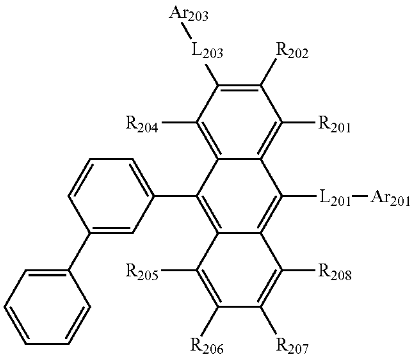
[Formula 159]
(246)
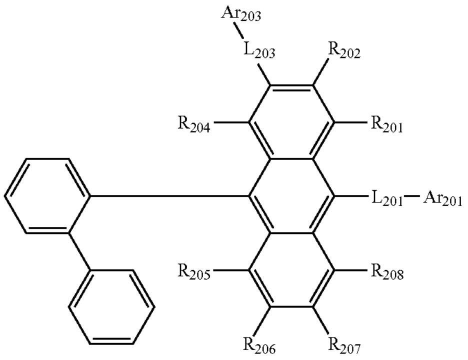
[Formula 160]
(247)
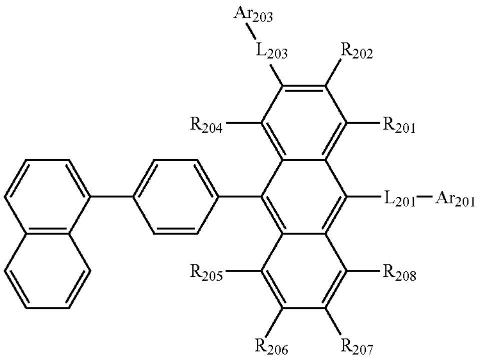
[Formula 161]
(248)
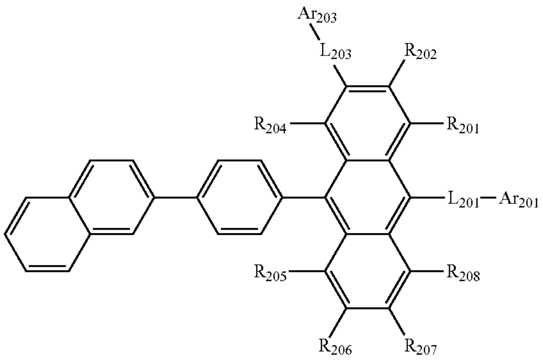

-continued

[Formula 162]

(249)

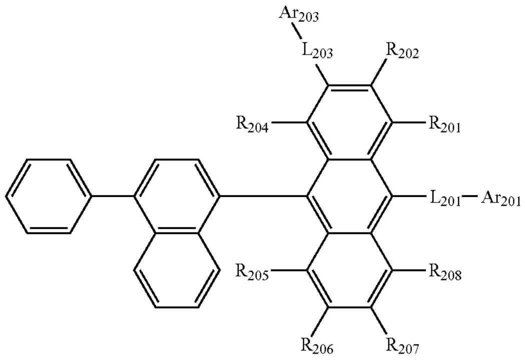

In the formulae (241), (242), (243), (244), (245), (246), (247), (248) and (249): $R_{201}$, $R_{202}$, and $R_{204}$ to $R_{208}$ each independently represent the same as $R_{201}$, $R_{202}$, and $R_{204}$ to $R_{208}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

In the second compound represented by the formula (2), $R_{201}$ to $R_{208}$ that are not represented by the formula (21) are each independently preferably a hydrogen atom, a substituted or unsubstituted alkyl group having 1 to 50 carbon atoms, a substituted or unsubstituted cycloalkyl group having 3 to 50 ring carbon atoms, or a group represented by —$Si(R_{901})(R_{902})(R_{903})$.

$L_{101}$ is preferably a single bond or an unsubstituted arylene group having 6 to 22 ring carbon atoms, and $Ar_{101}$ is preferably a substituted or unsubstituted aryl group having 6 to 22 ring carbon atoms.

In the organic EL device according to the exemplary embodiment, $R_{201}$ to $R_{208}$ that are substituents on an anthracene skeleton in the second compound represented by the formula (2) are preferably hydrogen atoms in terms of preventing inhibition of intermolecular interaction to inhibit a decrease in electron mobility. However, $R_{201}$ to $R_{208}$ may be a substituted or unsubstituted aryl group having 6 to 50 ring carbon atoms or a substituted or unsubstituted heterocyclic group having 5 to 50 ring atoms.

Assuming that $R_{201}$ to $R_{208}$ each are a bulky substituent such as an alkyl group and a cycloalkyl group, intermolecular interaction may be inhibited to decrease the electron mobility of the second compound relative to that of the first host material, so that a relationship of μH2>μH1 shown by the numerical formula (Numerical Formula 6) may not be satisfied. When the second compound is used in the second emitting layer, it can be expected that satisfying the relationship of μH2>μH1 inhibits a decrease in a recombination ability between holes and electrons in the first emitting layer and a decrease in a luminous efficiency. It should be noted that as the substituent, namely, a haloalkyl group, alkenyl group, alkynyl group, group represented by —$Si(R_{901})(R_{902})(R_{903})$, group represented by —O—$(R_{904})$, group represented by —S—$(R_{905})$, group represented by —$N(R_{906})(R_{907})$, aralkyl group, group represented by —C(=O)$R_{801}$, group represented by —$COOR_{802}$, halogen atom, cyano group, and nitro group are likely to be bulky, and an alkyl group and cycloalkyl group are likely to be further bulky.

In the second compound represented by the formula (2), $R_{201}$ to $R_{208}$, which are the substituents on the anthracene skeleton, are each preferably not a bulky substituent and preferably not an alkyl group and cycloalkyl group. More preferably, $R_{201}$ to $R_{208}$ are not an alkyl group, cycloalkyl group, haloalkyl group, alkenyl group, alkynyl group, group represented by —$Si(R_{901})(R_{902})(R_{903})$, group represented by —O—$(R_{904})$, group represented by —S—$(R_{905})$, group represented by —$N(R_{906})(R_{907})$, aralkyl group, group represented by —C(=O)$R_{801}$, group represented by —$COOR_{802}$, halogen atom, cyano group, and nitro group.

In the organic EL device according to the exemplary embodiment, it is also preferable that in the second compound represented by the formula (2), $R_{201}$ to $R_{208}$ are each independently a hydrogen atom, a substituted or unsubstituted alkyl group having 1 to 50 carbon atoms, a substituted or unsubstituted cycloalkyl group having 3 to 50 ring carbon atoms, or a group represented by —$Si(R_{901})(R_{902})(R_{903})$.

In the organic EL device according to the exemplary embodiment, $R_{201}$ to $R_{208}$ in the second compound represented by the formula (2) are each preferably a hydrogen atom.

In the second compound, examples of a substituent for a "substituted or unsubstituted" group on $R_{201}$ to $R_{208}$ also preferably do not include the above-described substituent that is likely to be bulky, especially a substituted or unsubstituted alkyl group and a substituted or unsubstituted cycloalkyl group. Since the examples of the substituent for the "substituted or unsubstituted" group on $R_{201}$ to $R_{208}$ do not include a substituted or unsubstituted alkyl group and a substituted or unsubstituted cycloalkyl group, inhibition of intermolecular interaction to be caused by presence of a bulky substituent such as an alkyl group and a cycloalkyl group can be prevented, thereby preventing a decrease in the electron mobility. Moreover, when the second compound described above is used in the second emitting layer, a decrease in a recombination ability between holes and electrons in the first emitting layer and a decrease in the luminous efficiency can be inhibited.

It is more preferably that $R_{201}$ to $R_{208}$, which are the substituents on the anthracene skeleton, are not bulky substituents, and $R_{201}$ to $R_{208}$ as substituents are unsubstituted. Assuming that $R_{201}$ to $R_{208}$, which are the substituents on the anthracene skeleton, are not bulky substituents and $R_{201}$ to $R_{208}$ that are not bulky substituents are bonded with a substituent, the substituent is preferably not a bulky substituent; the substituent bonded to $R_{201}$ to $R_{208}$ serving as substituents is preferably not an alkyl group and cycloalkyl group, more preferably not an alkyl group, cycloalkyl group, haloalkyl group, alkenyl group, alkynyl group, group represented by —$Si(R_{901})(R_{902})(R_{903})$, group represented by —O—$(R_{904})$, group represented by —S—$(R_{905})$, group represented by —$N(R_{906})(R_{907})$, aralkyl group, group represented by —C(=O)$R_{801}$, group represented by —$COOR_{802}$, halogen atom, cyano group, and nitro group.

In the second compound, the groups specified to be "substituted or unsubstituted" are each preferably an "unsubstituted" group.

Manufacturing Method of Second Compound

The second compound can be manufactured by a known method. The second compound can also be manufactured based on a known method through a known alternative reaction using a known material(s) tailored for the target compound.

Specific Examples of Second Compound
Specific examples of the second compound include the following compounds. It should however be noted that the invention is not limited by the specific examples of the second compound.
[Formula 163]
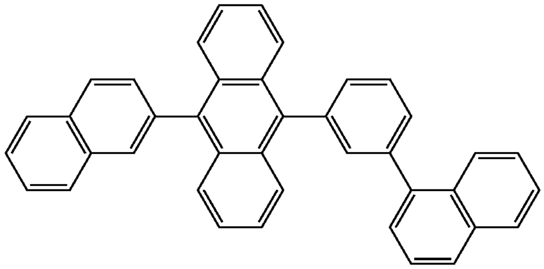
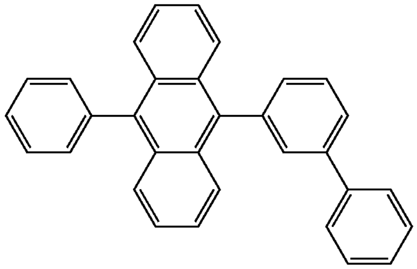
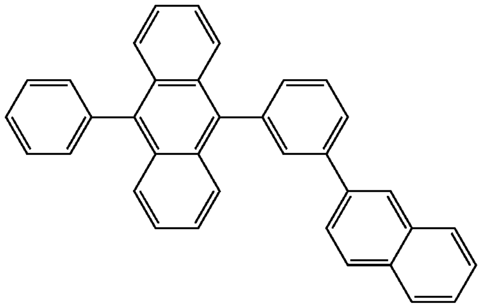
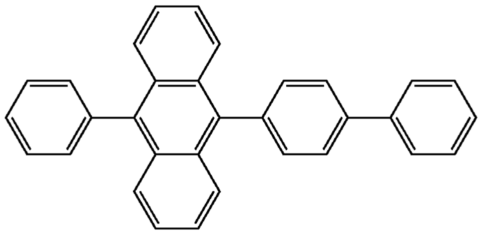
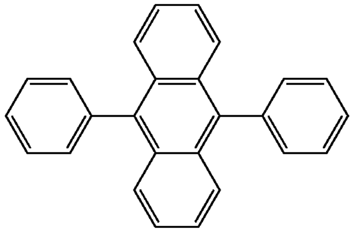
-continued
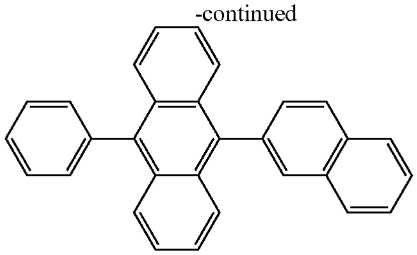
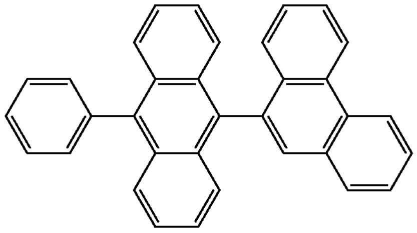
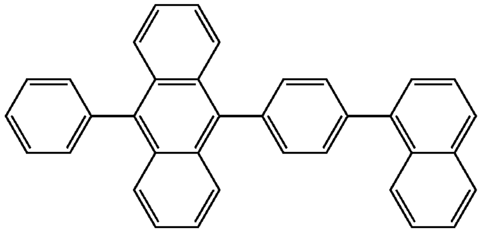
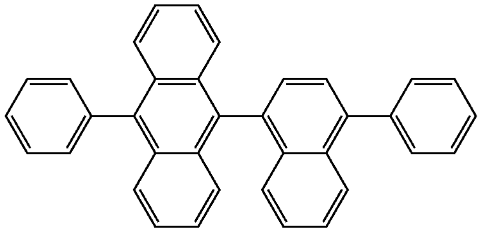
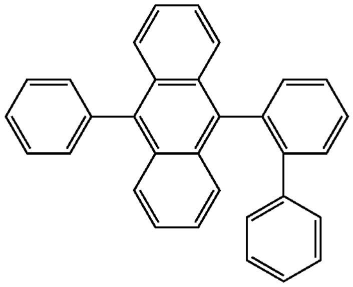
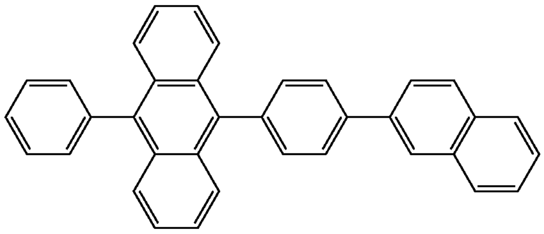
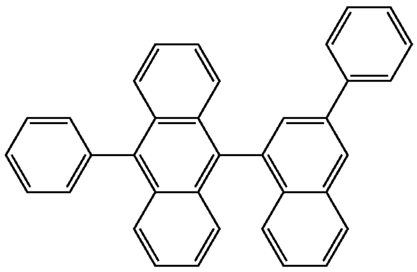

-continued
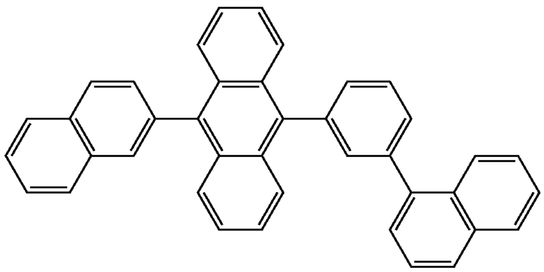
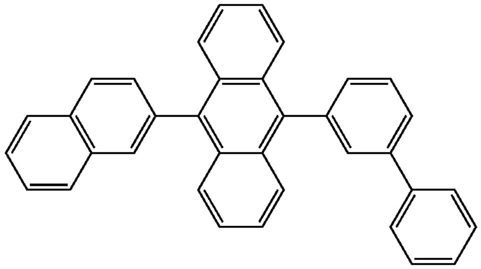
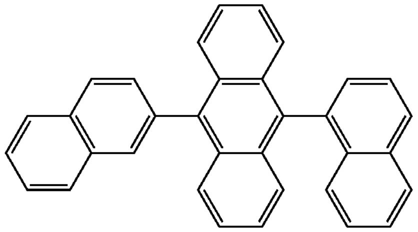
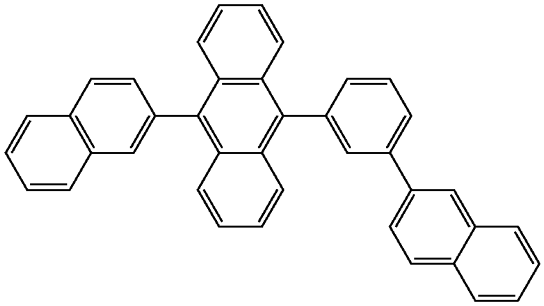
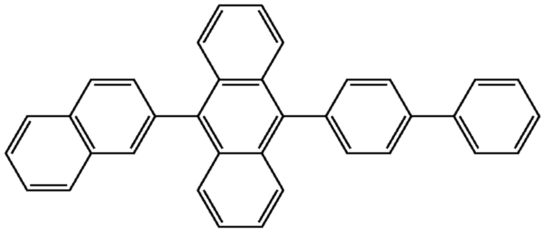
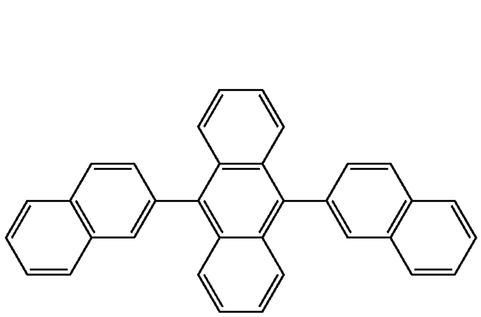
-continued
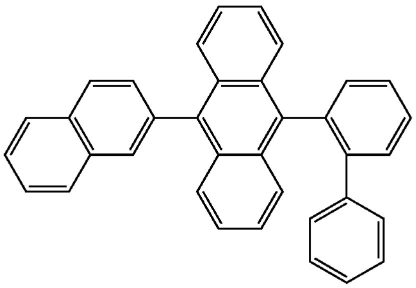
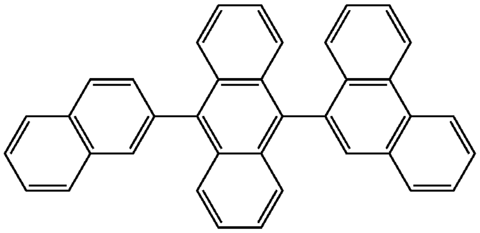
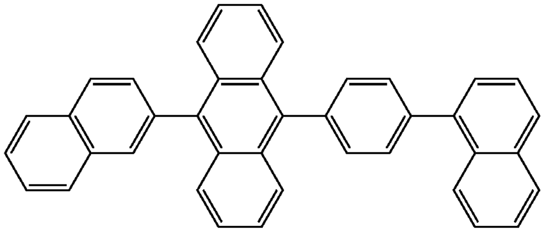
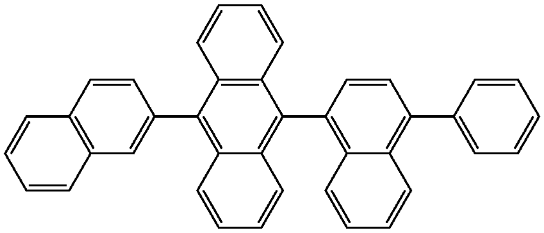
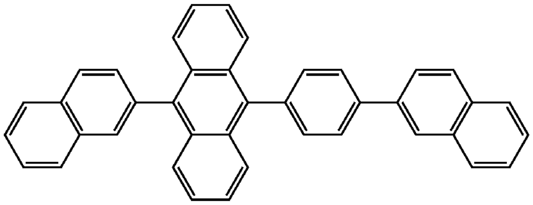
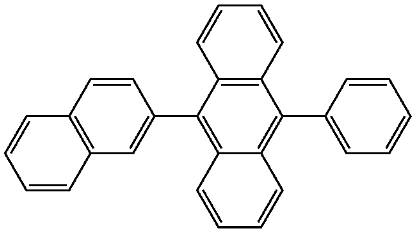
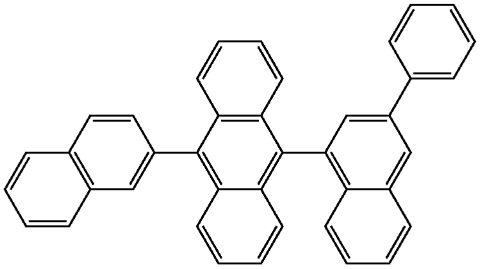

-continued
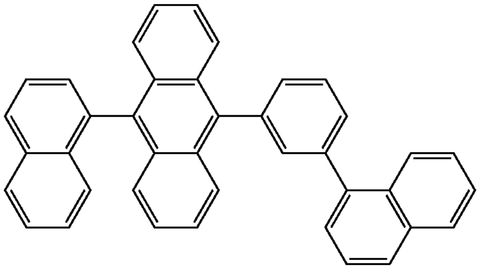
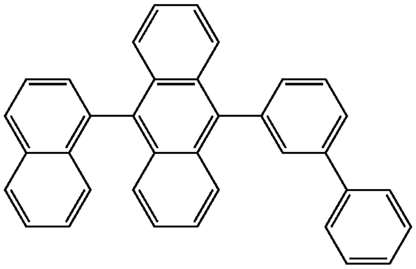
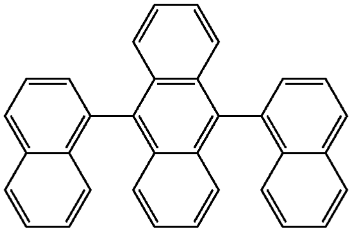
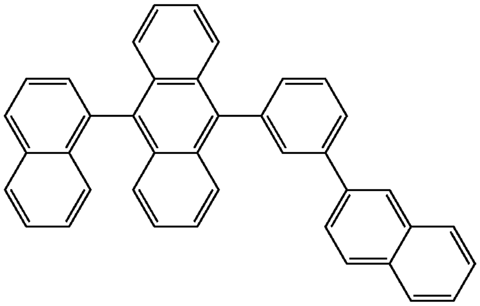
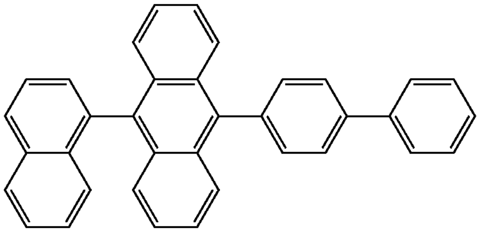
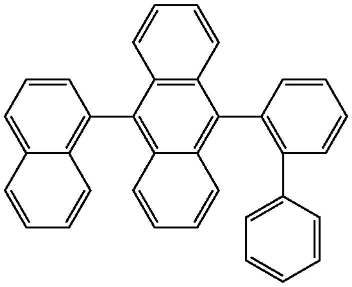
-continued
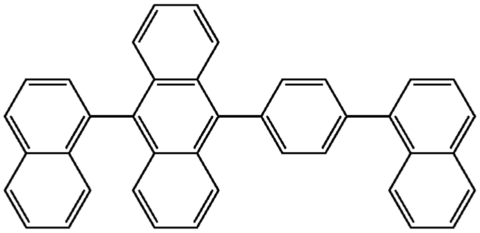
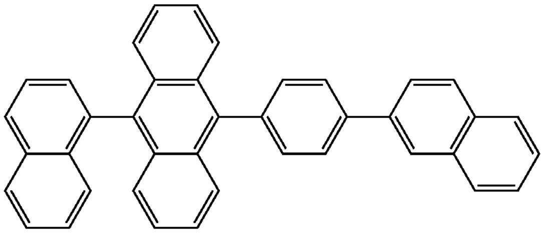
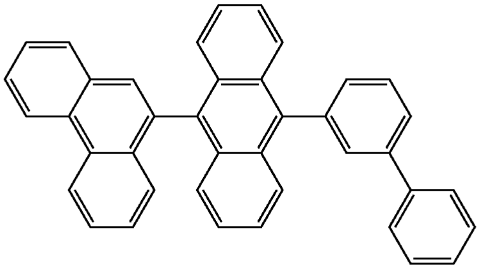
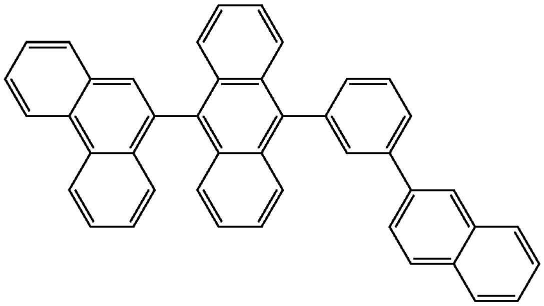
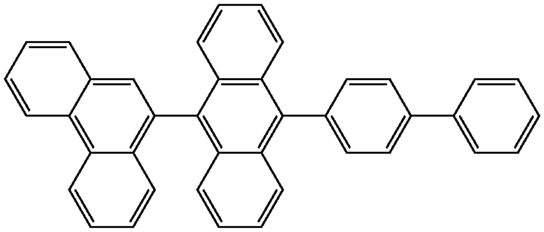
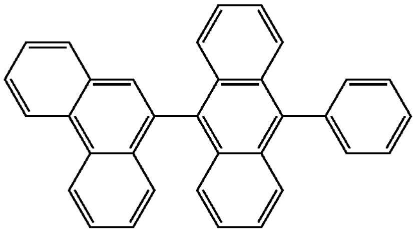
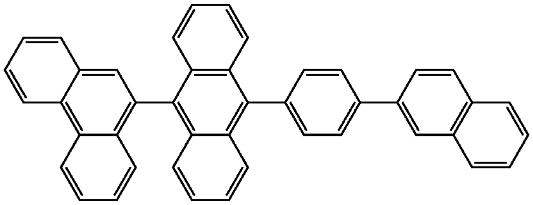

-continued
[Formula 164]
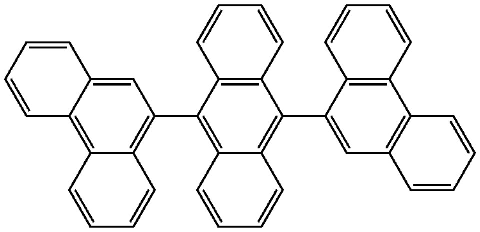
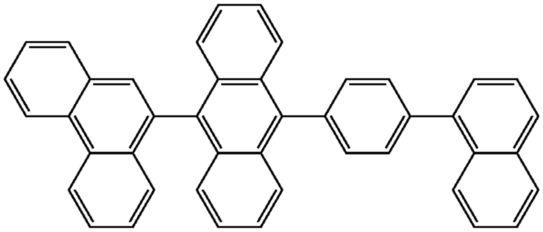
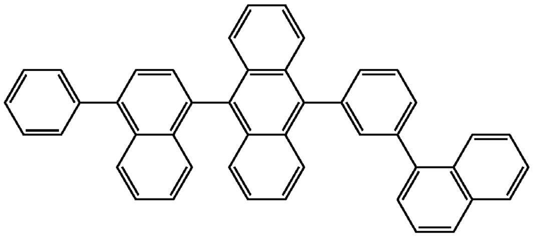
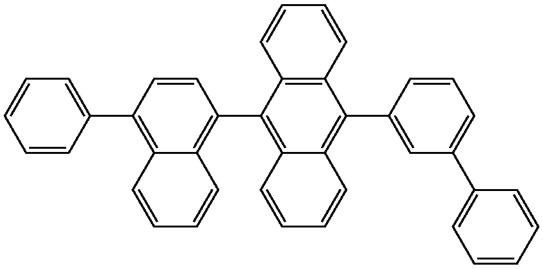
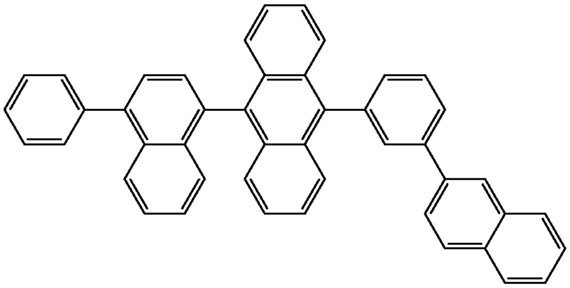
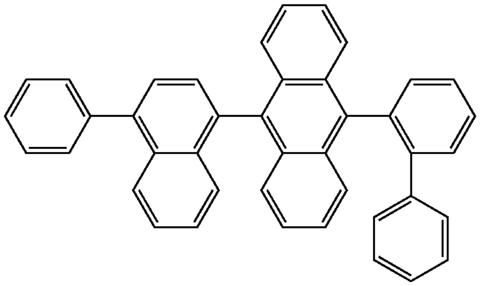
-continued
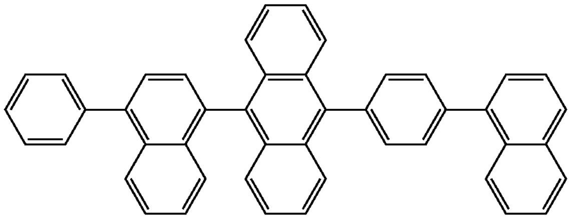
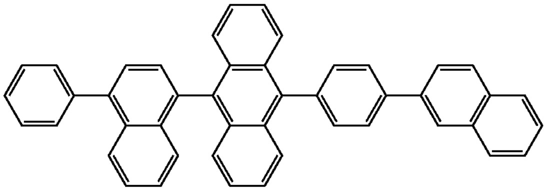
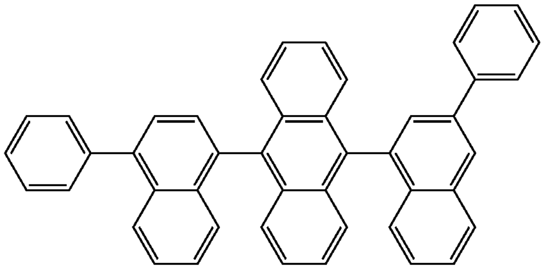
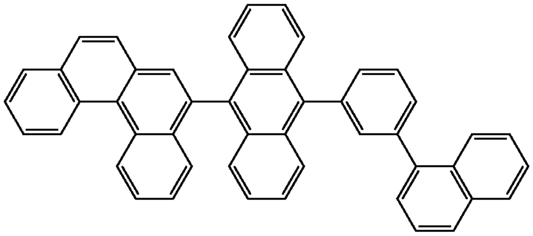
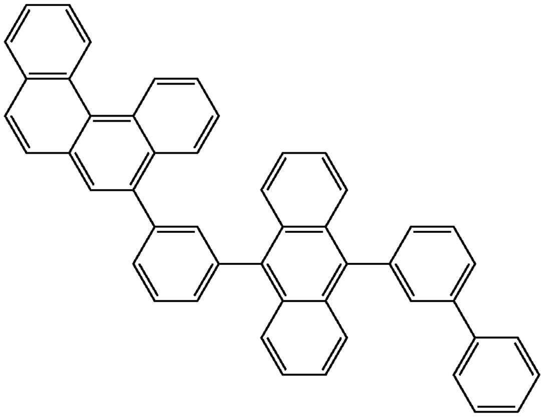
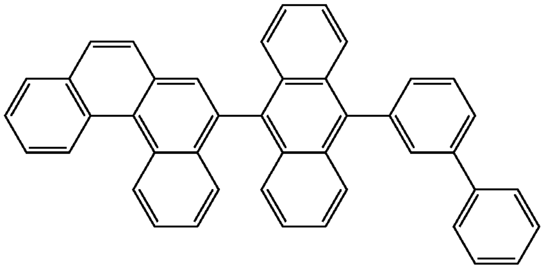

-continued
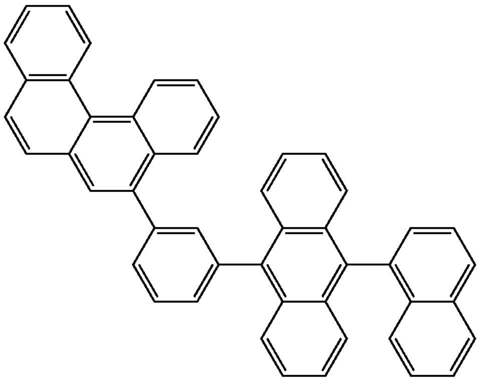
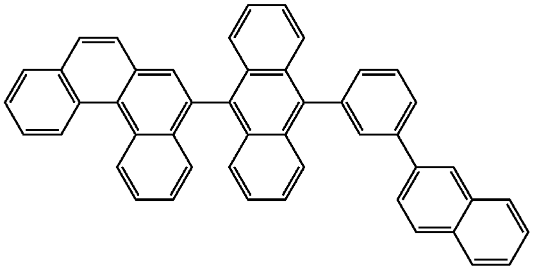
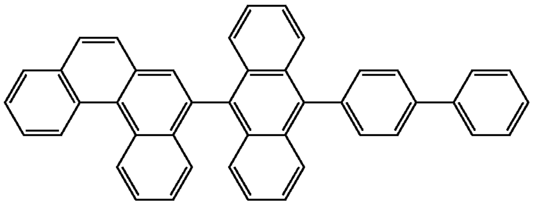
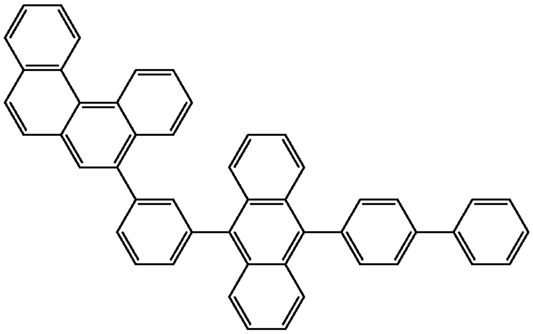
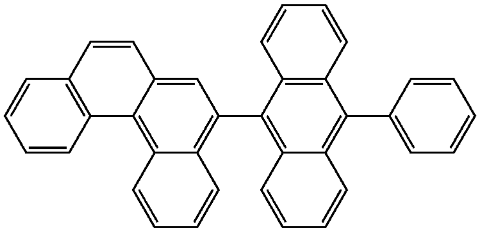
-continued
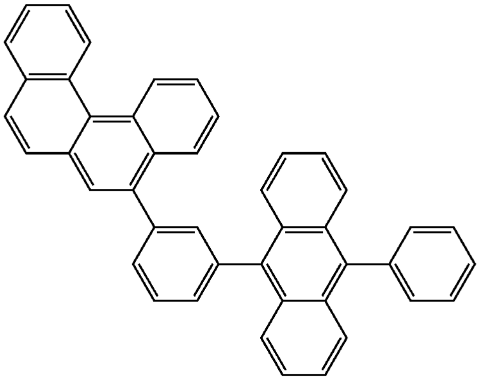
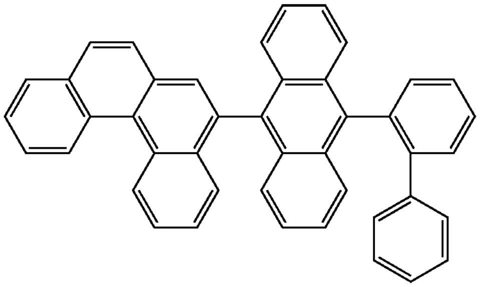
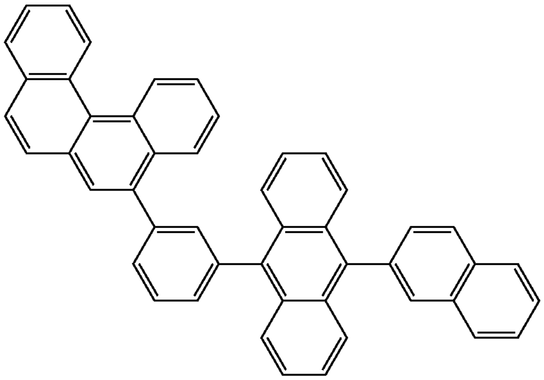
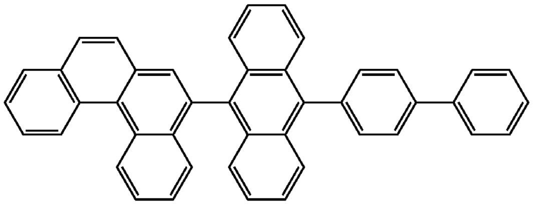
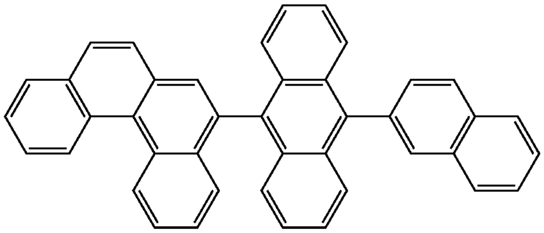

-continued
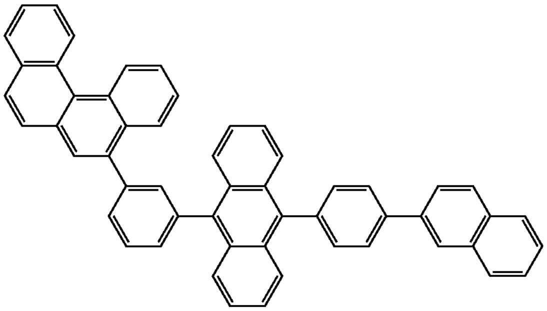
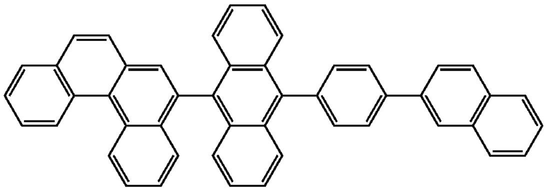
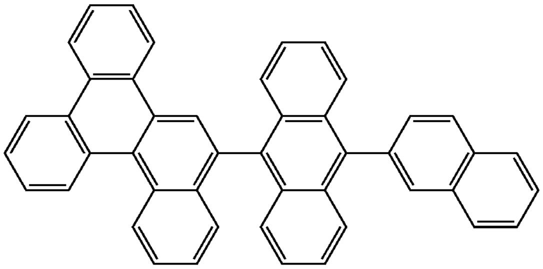
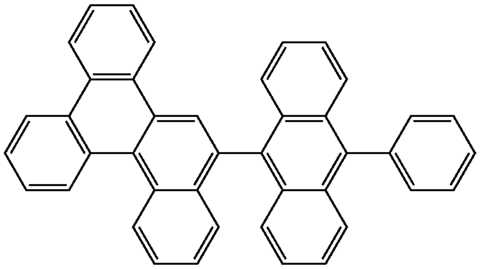
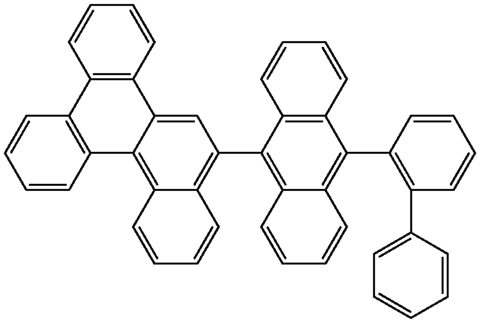
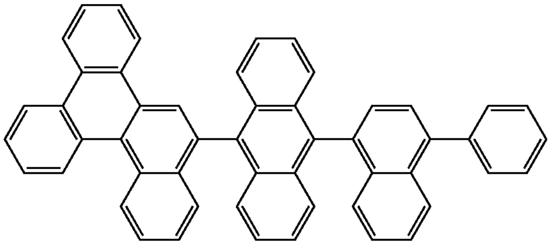
-continued
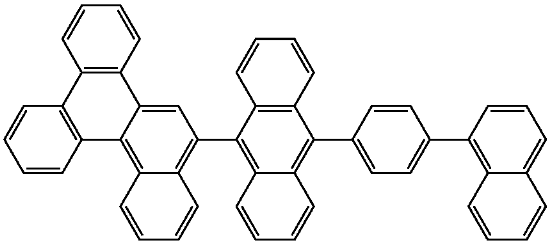
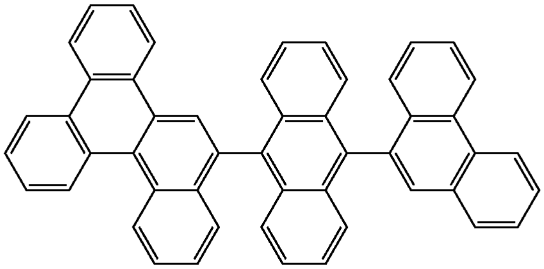
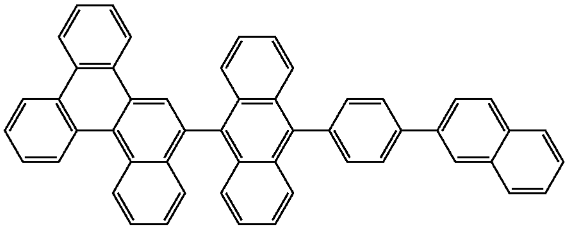
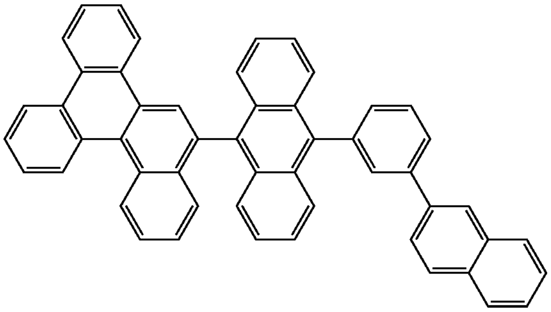
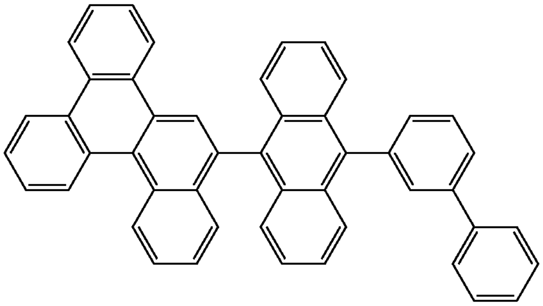
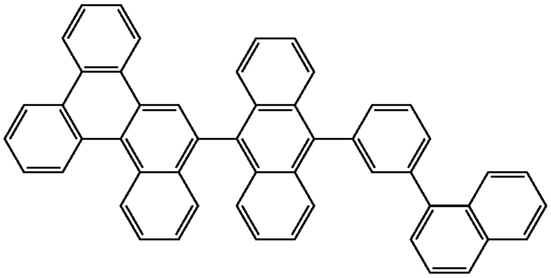

-continued
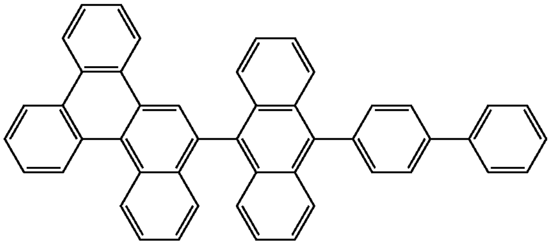
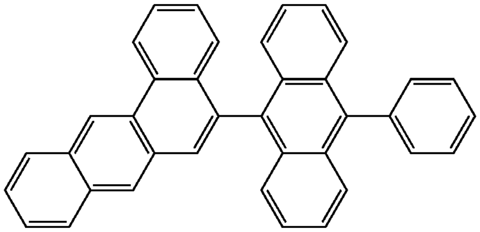
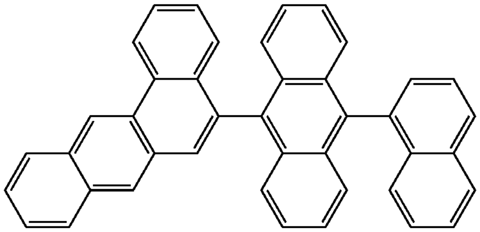
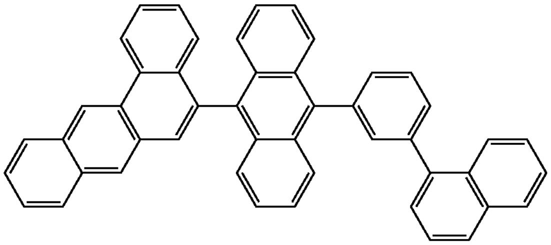
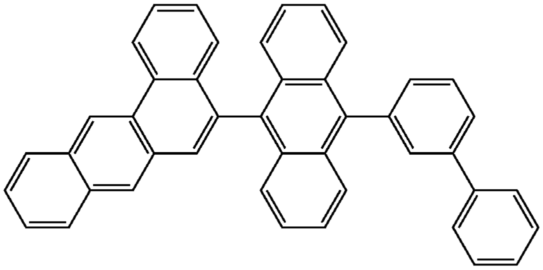
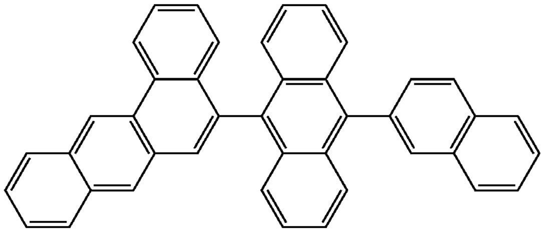
-continued
[Formula 165]
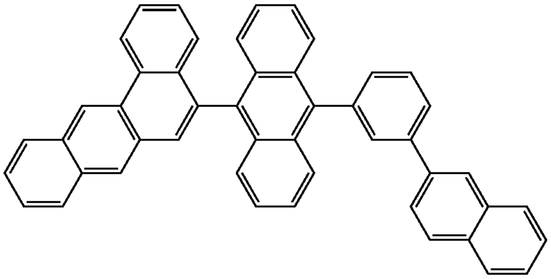
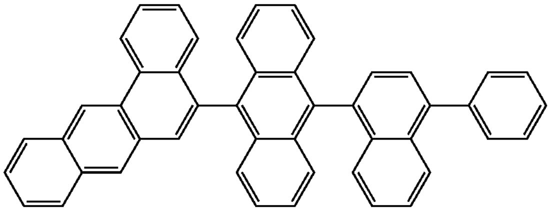
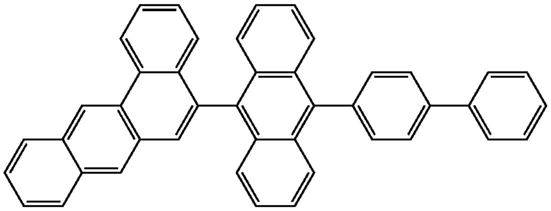
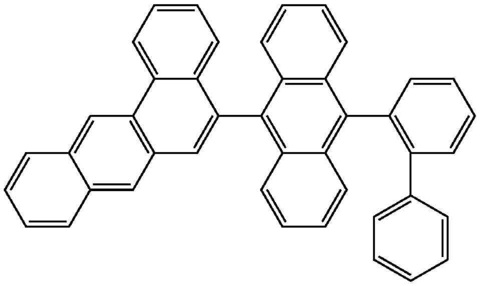
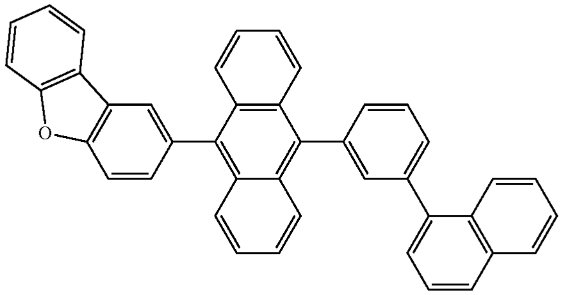
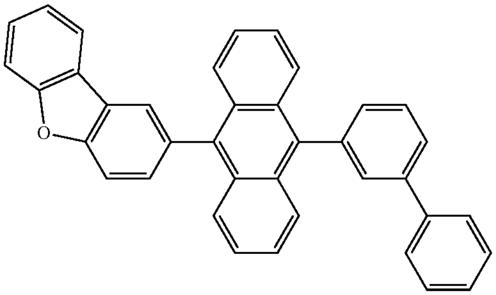

-continued
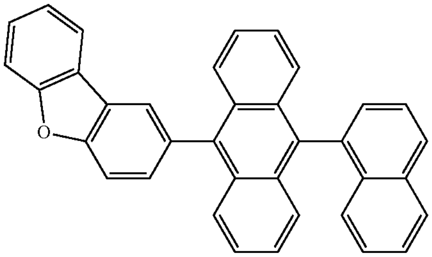
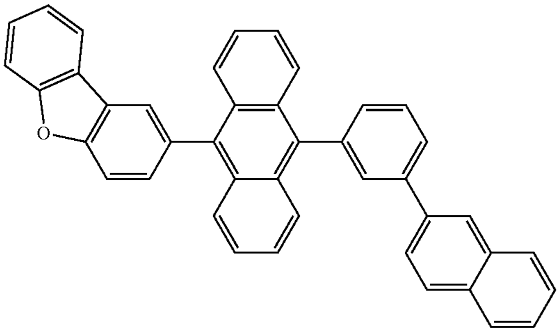
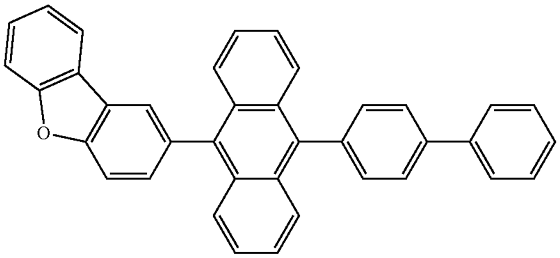
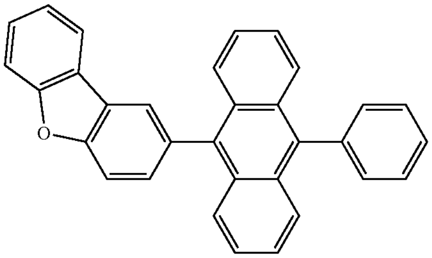
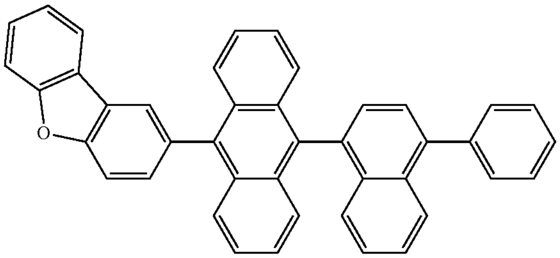
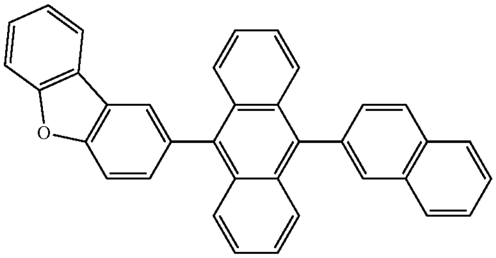
-continued
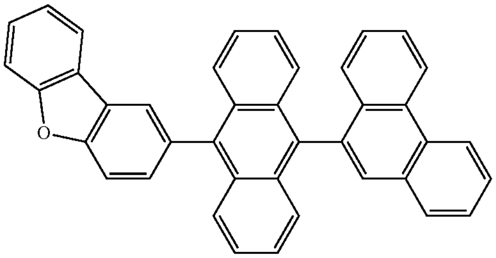
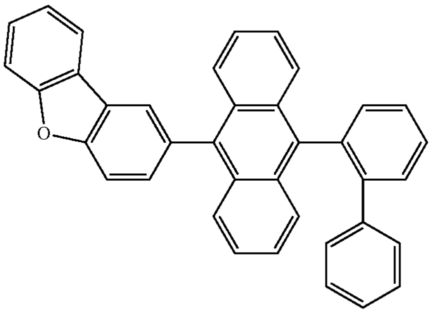
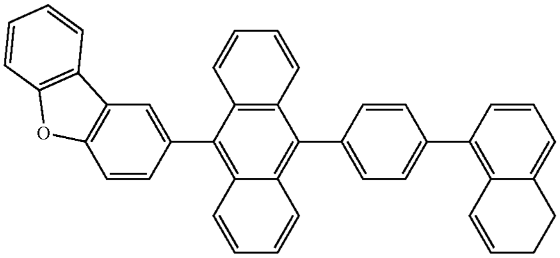
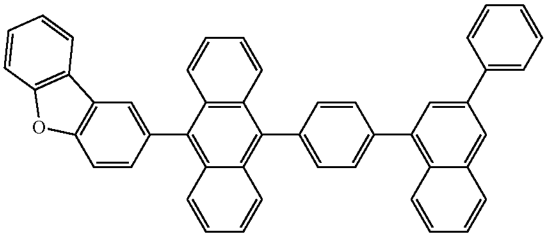
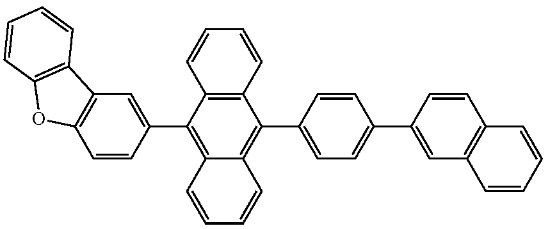
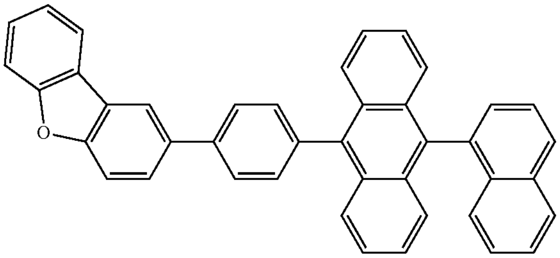

-continued
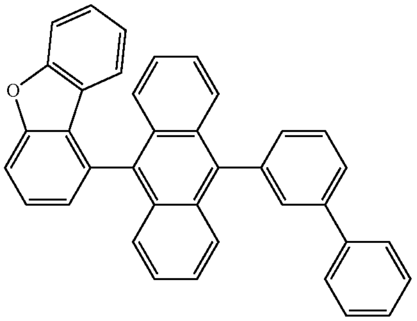
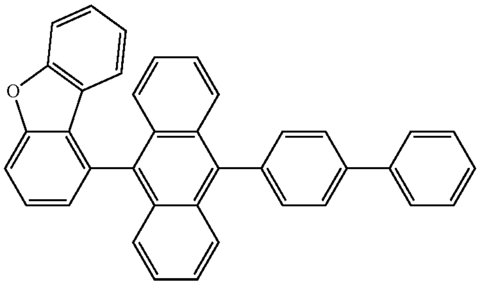
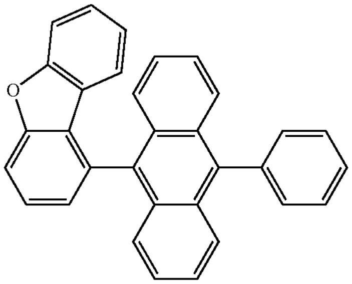
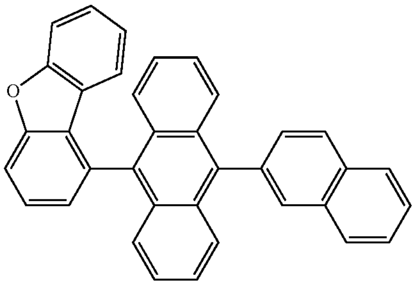
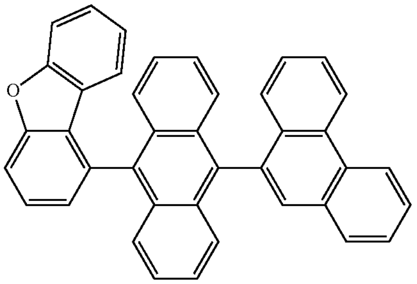
-continued
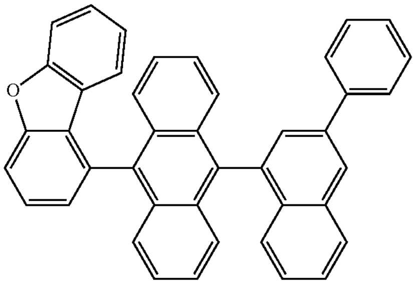
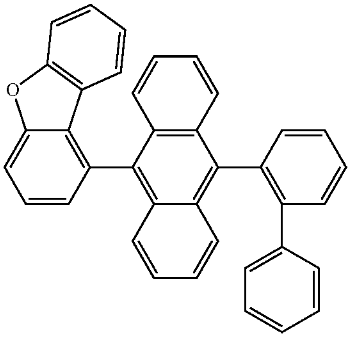
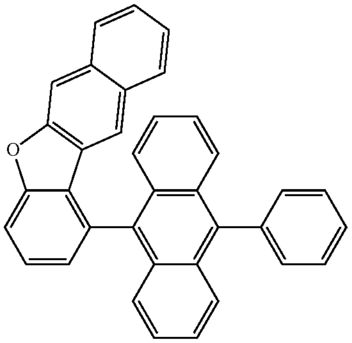
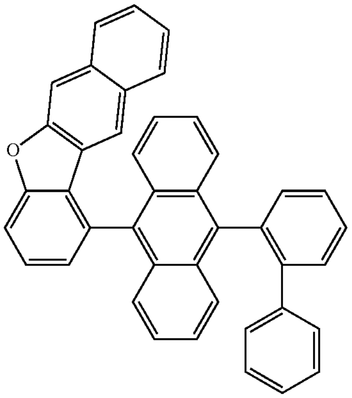
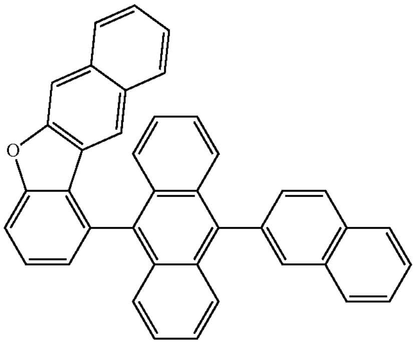

-continued
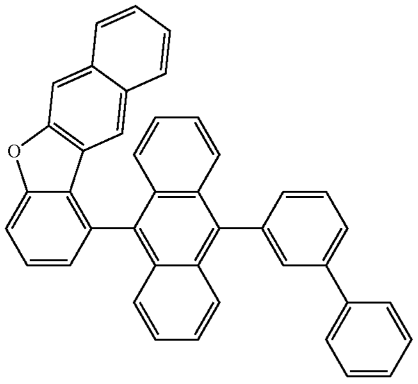
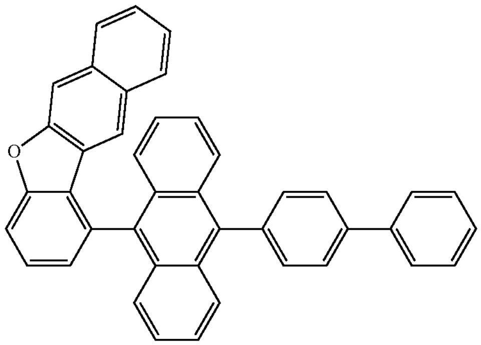
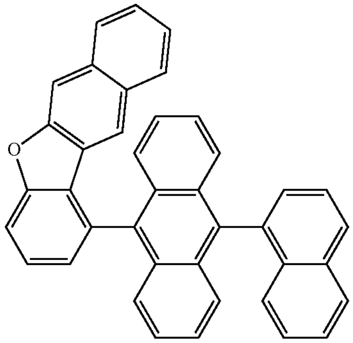
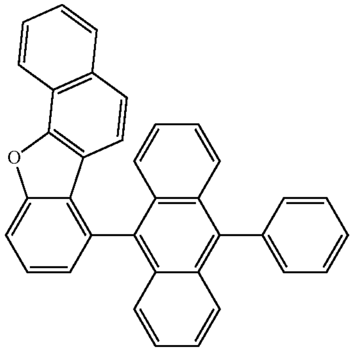
-continued
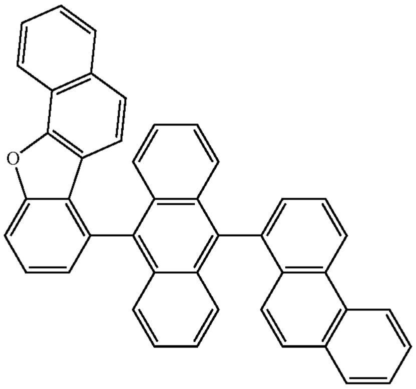
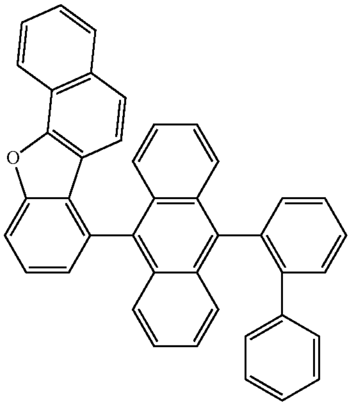
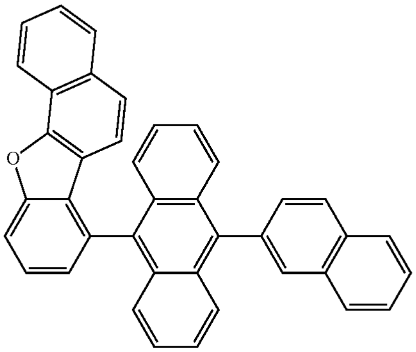
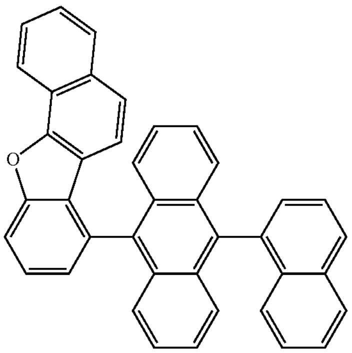

-continued
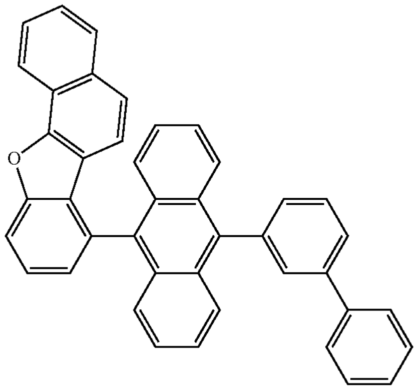
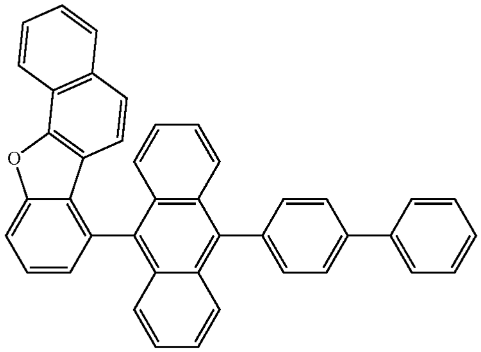
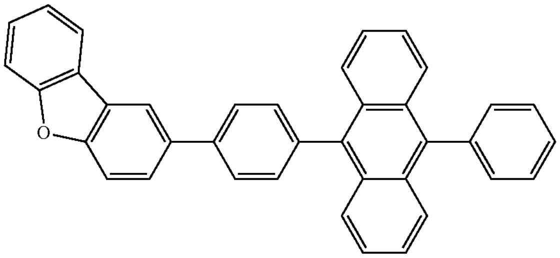
[Formula 166]
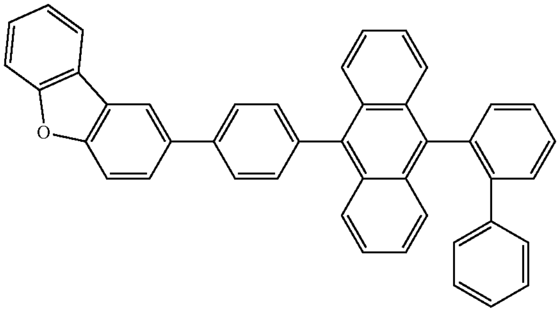
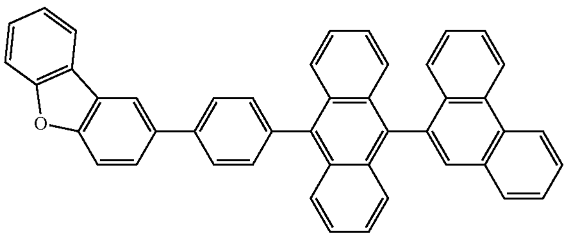
-continued
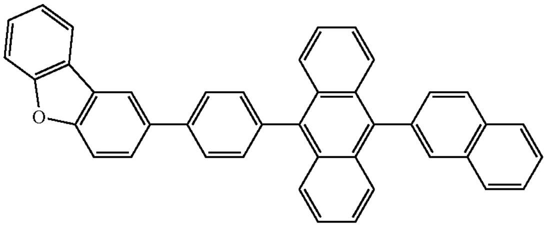
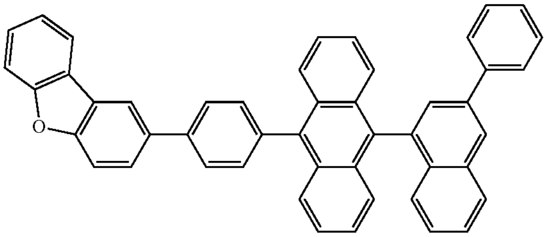
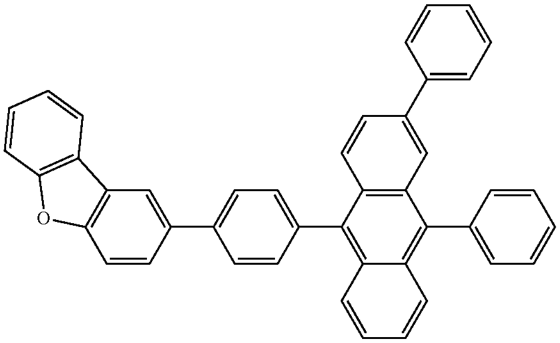
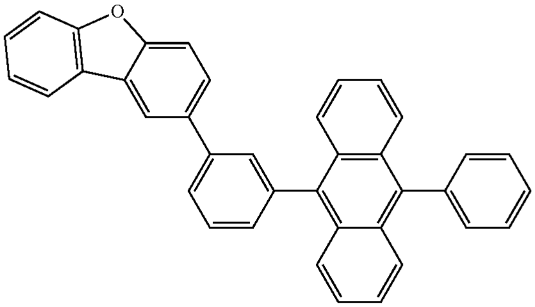
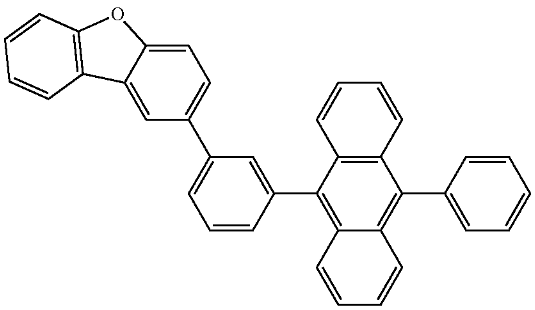

-continued
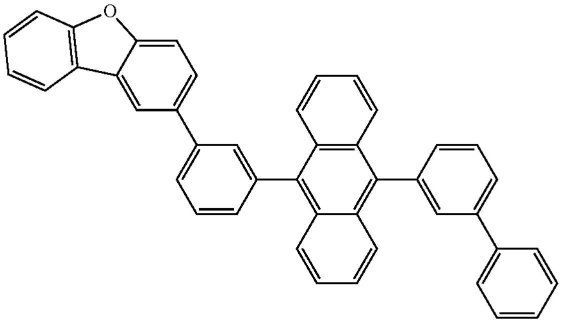
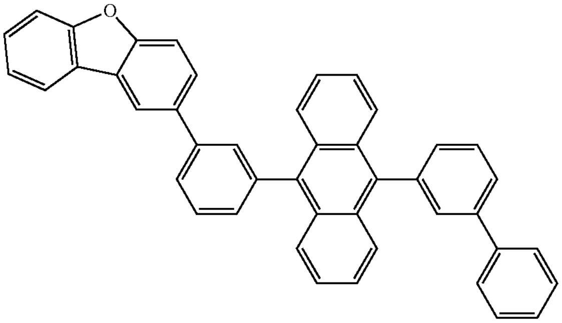
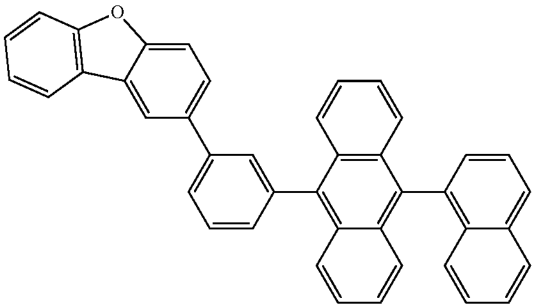
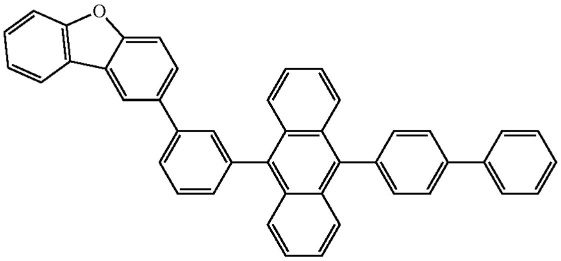
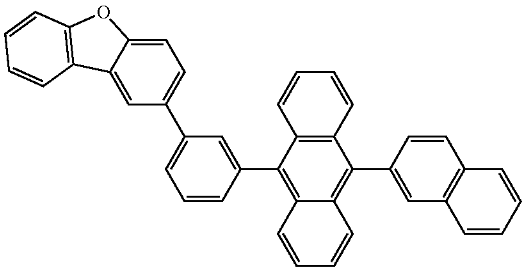
-continued
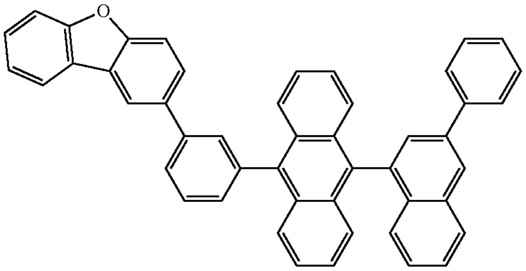
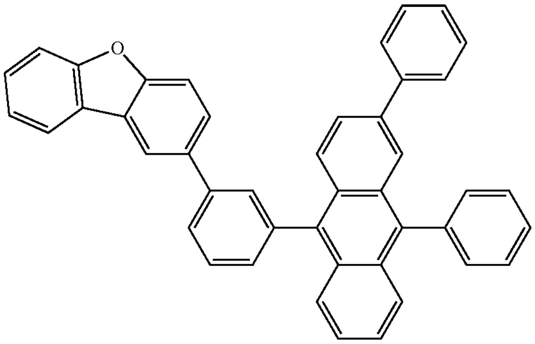
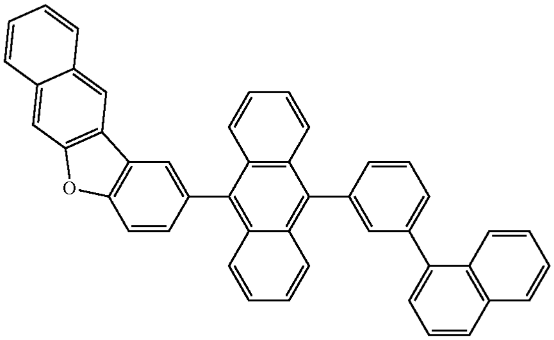
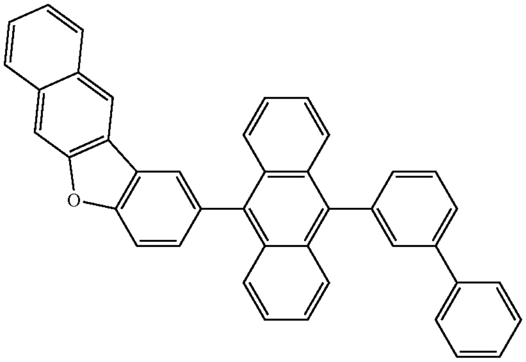
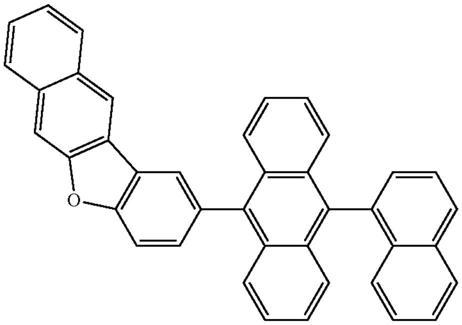

-continued
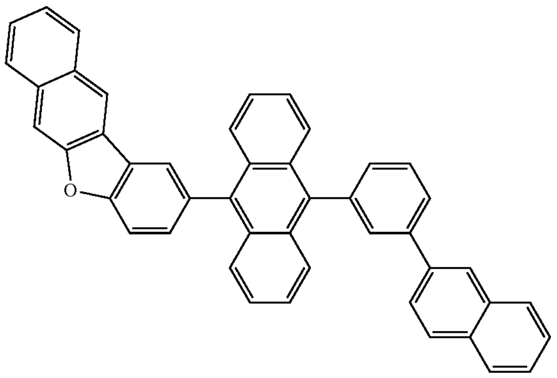
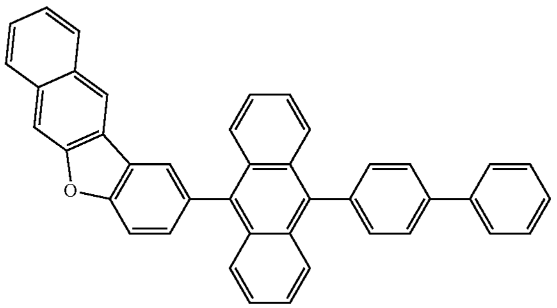
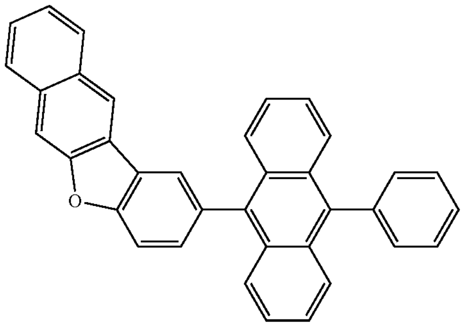
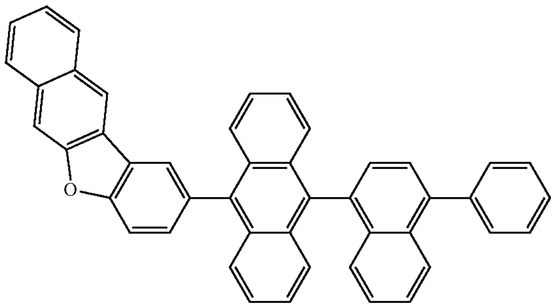
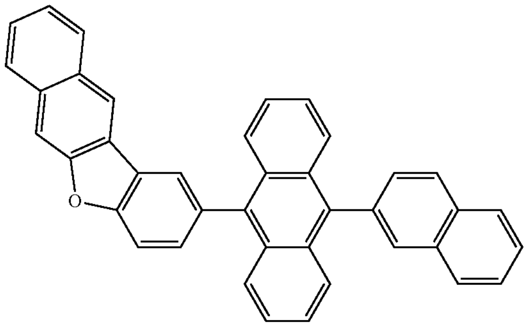
-continued
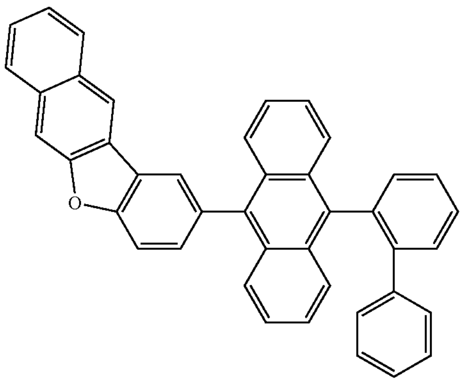
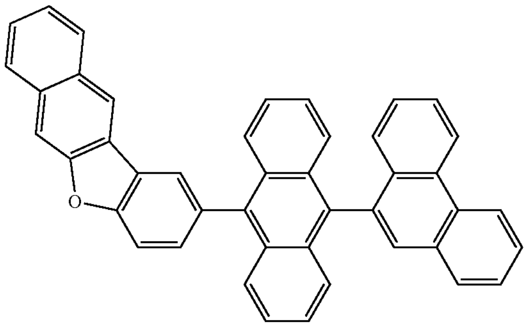
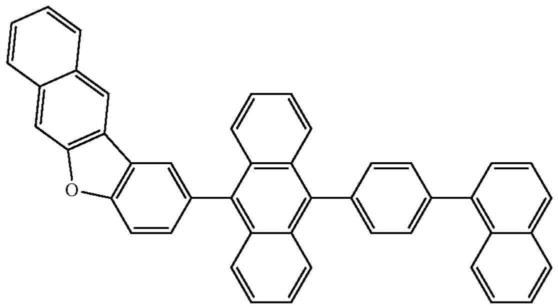
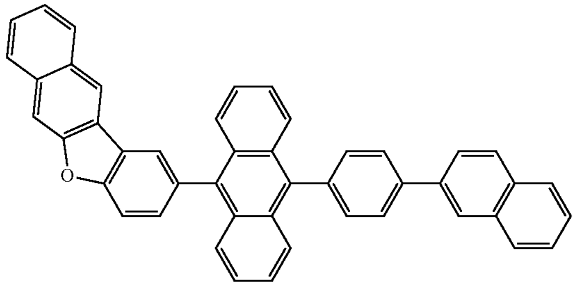
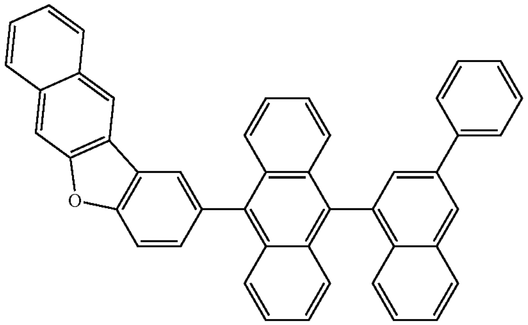

-continued
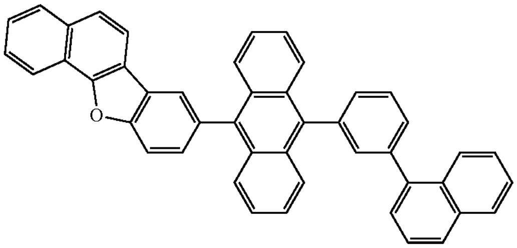
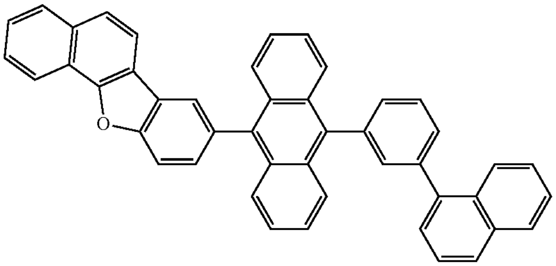
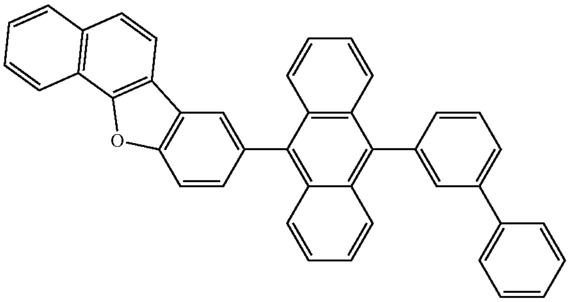
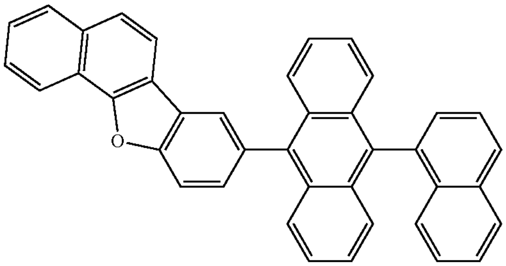
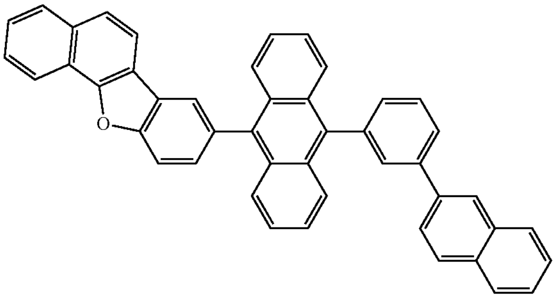
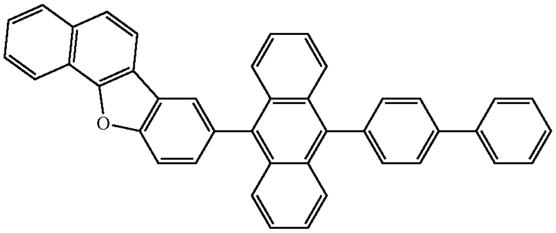
-continued
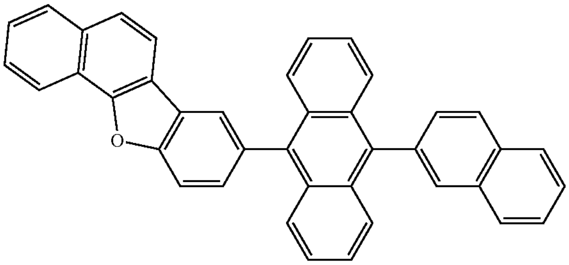
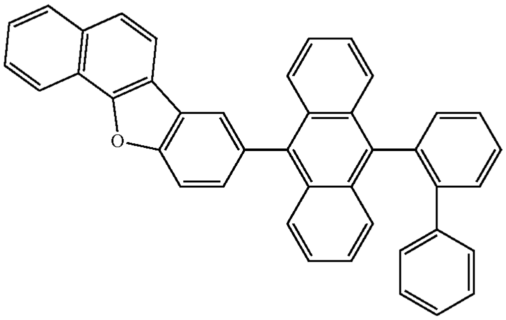
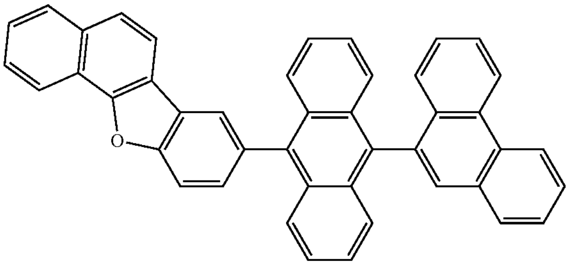
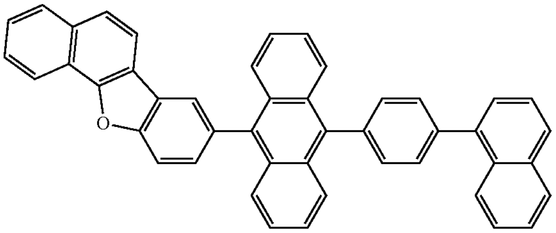
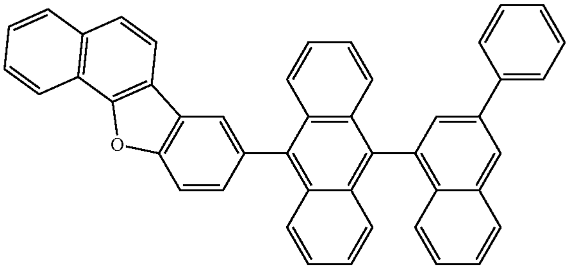
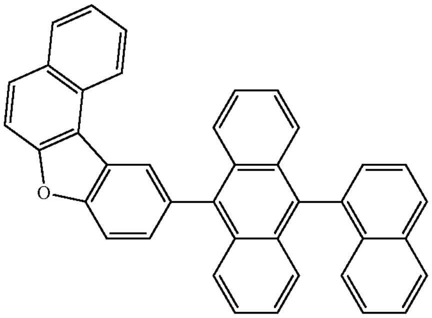

-continued
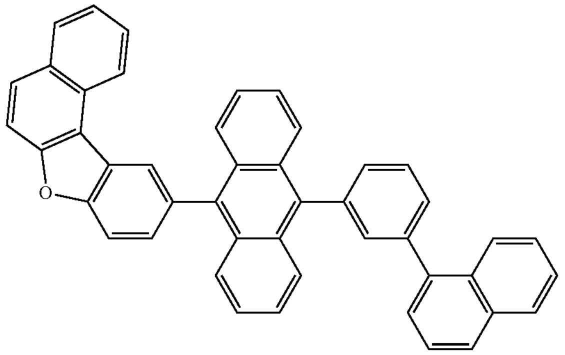
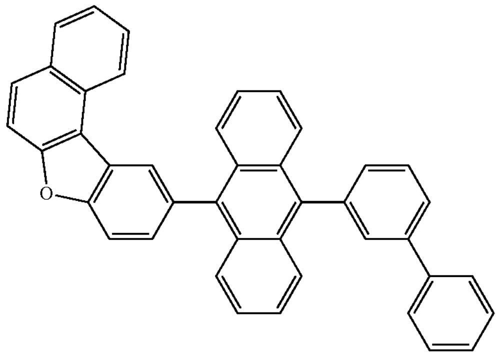
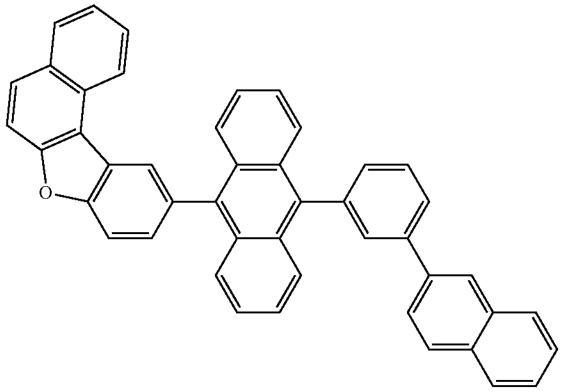
[Formula 167]
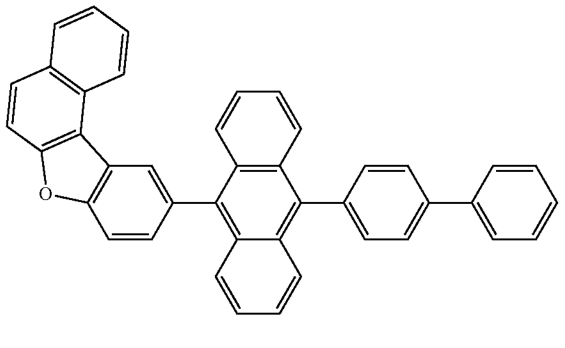
-continued
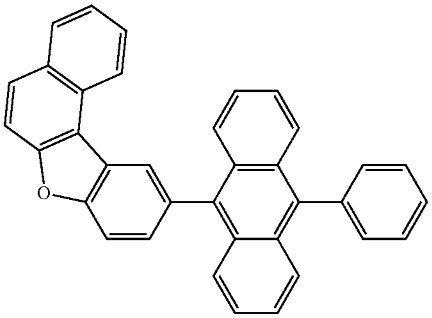
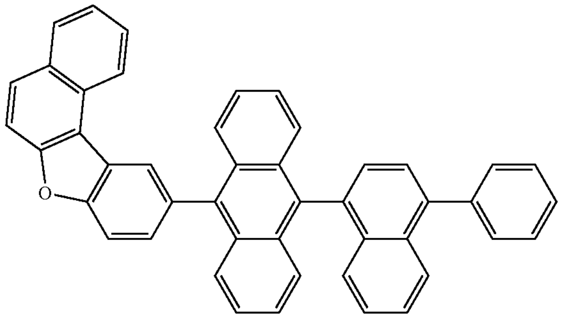
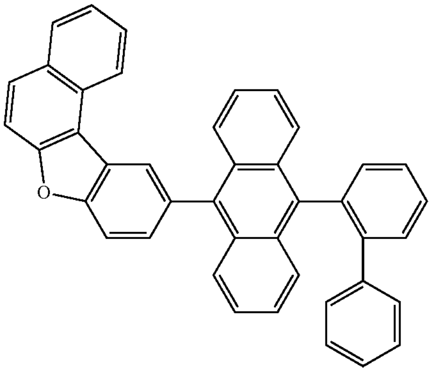
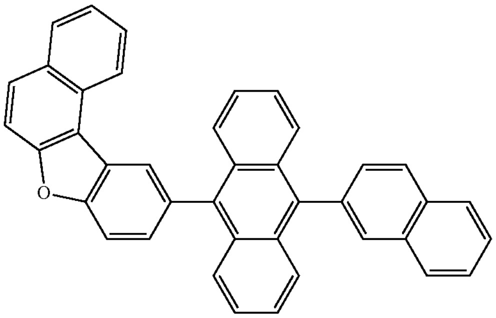
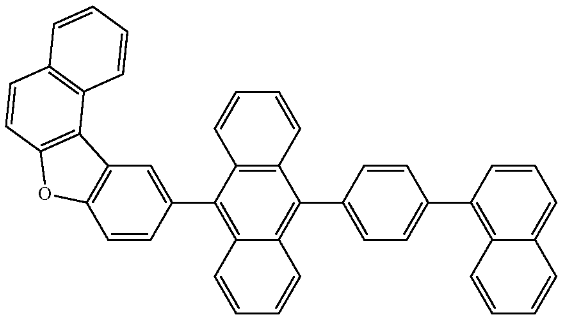

-continued
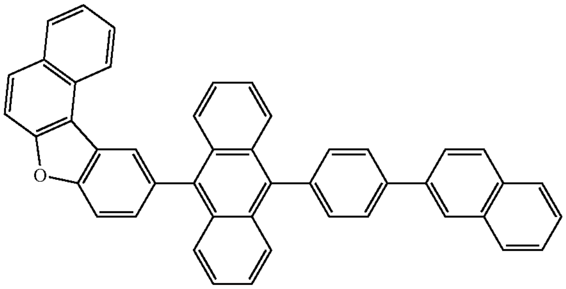
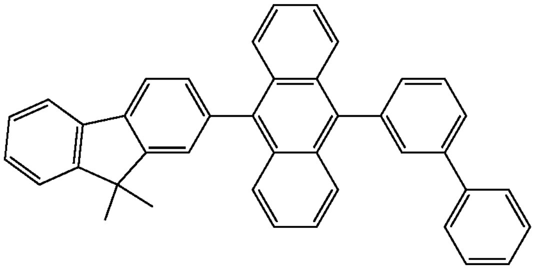
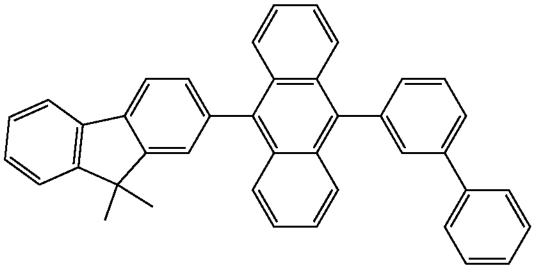
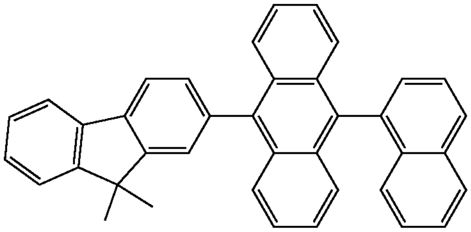
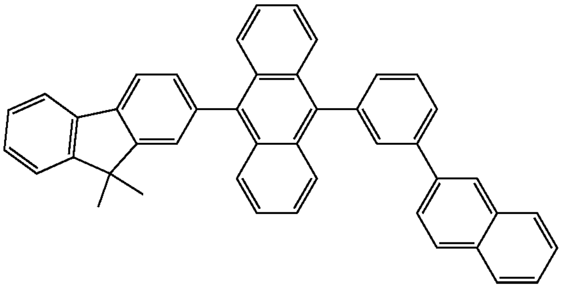
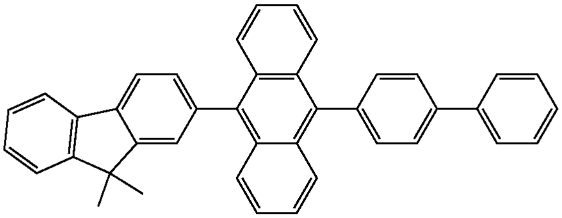
-continued
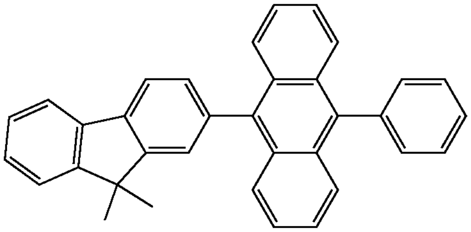
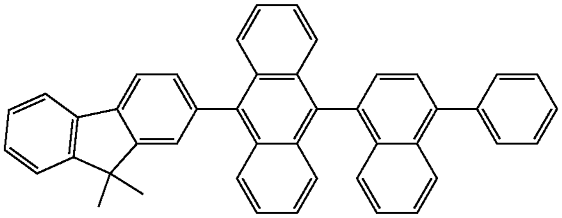
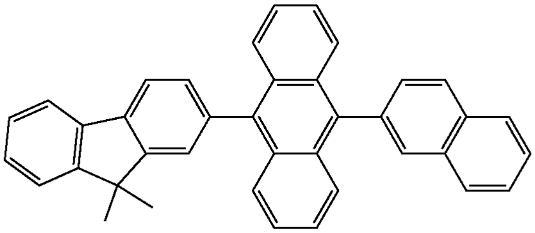
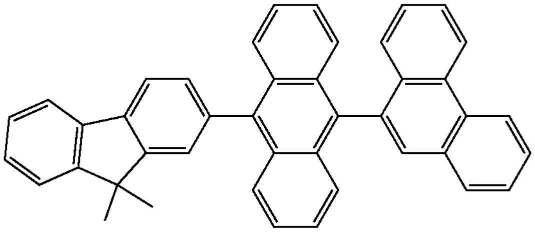
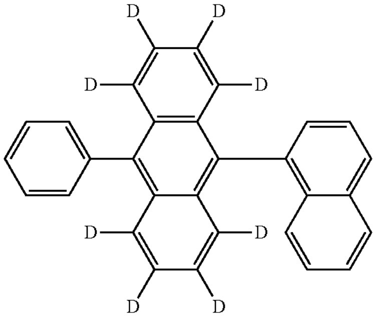
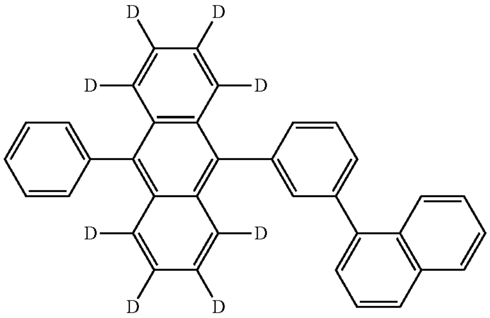

-continued
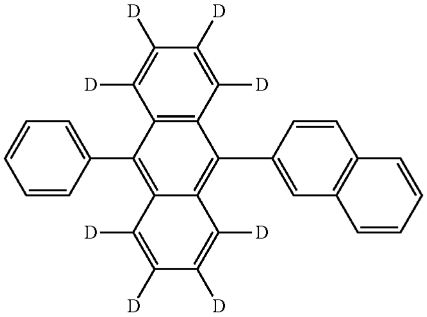
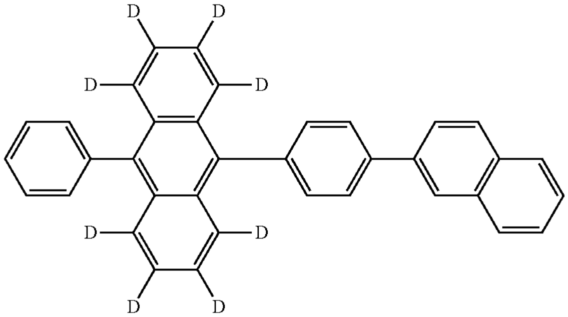
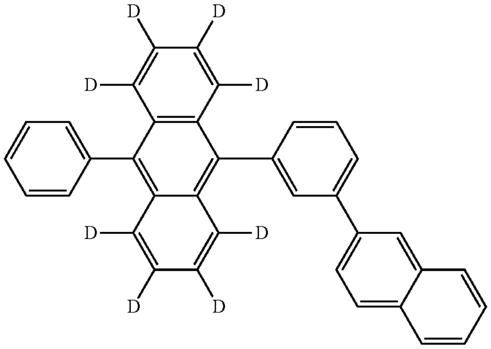
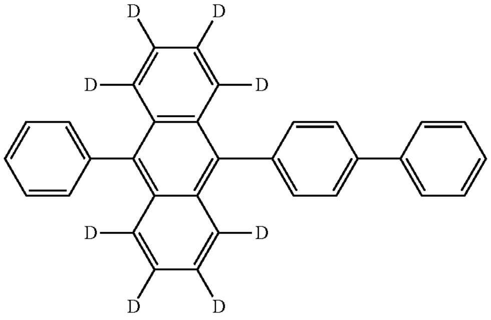
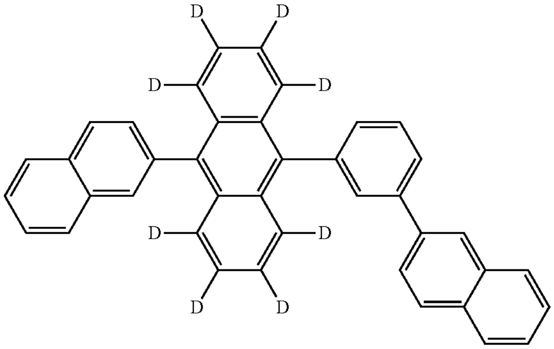
-continued
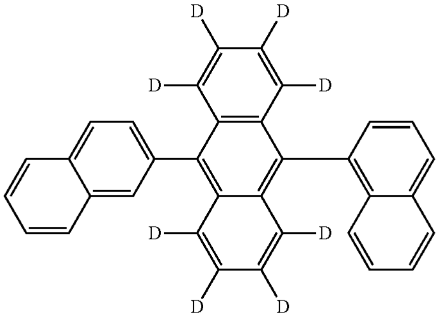
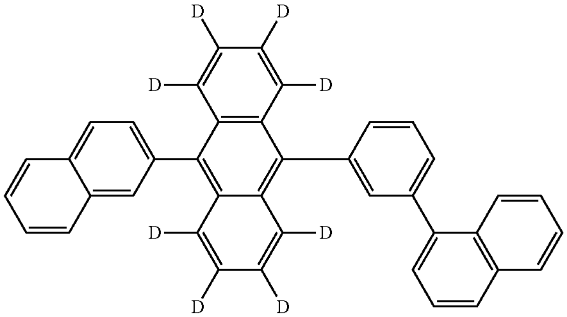
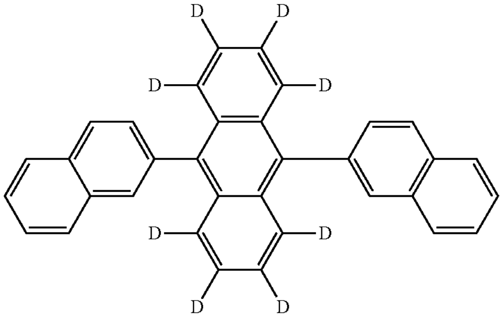
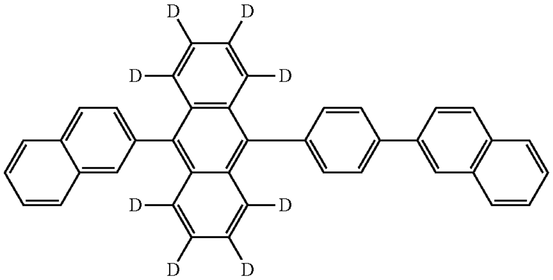
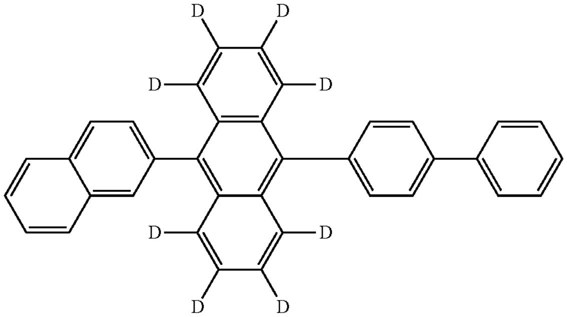

-continued
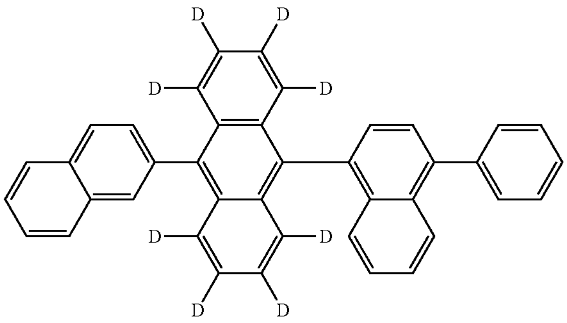
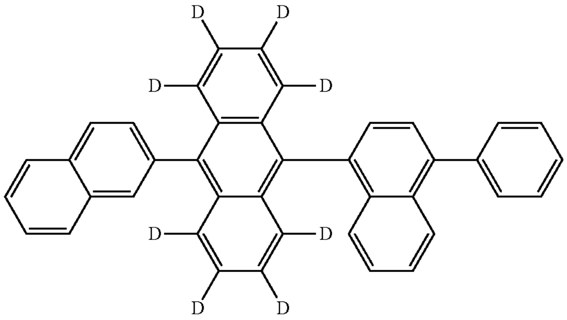
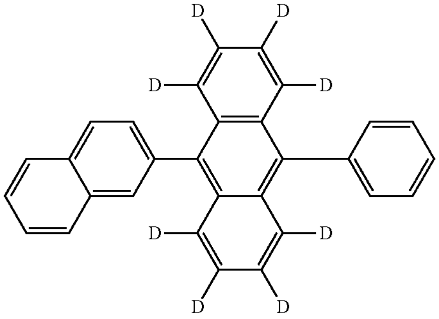
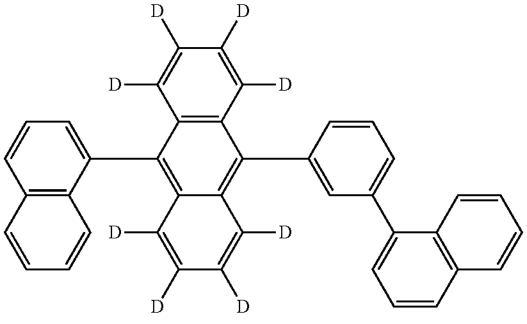
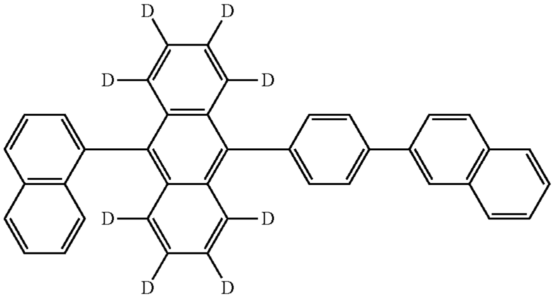
-continued
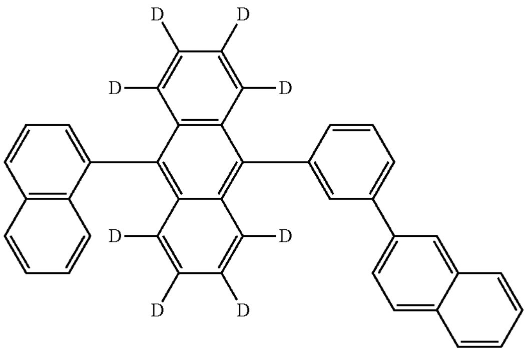
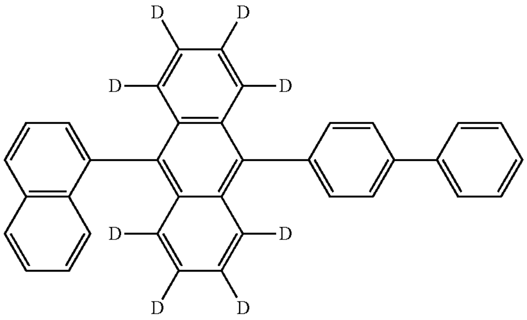
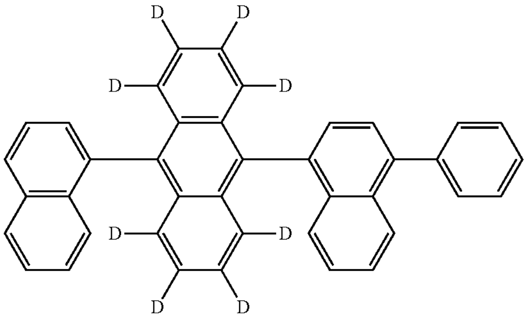
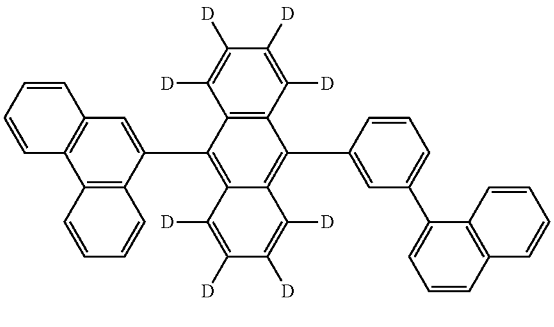
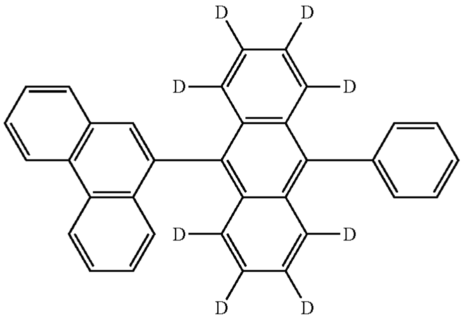

-continued
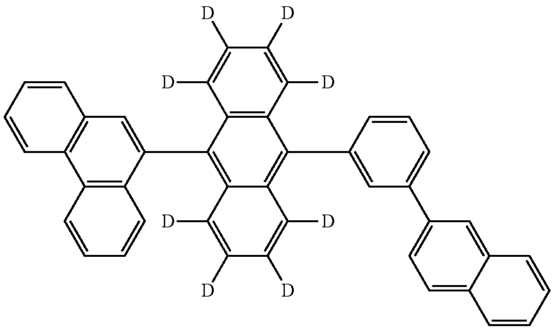
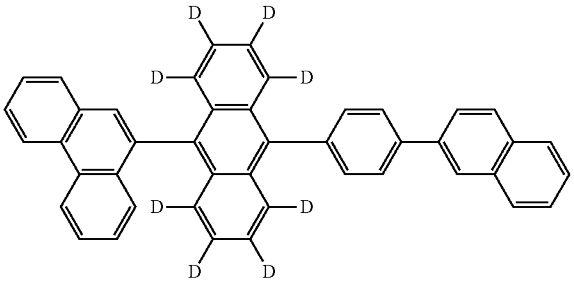 [SMILES: [2H]c1c([2H])c([2H])c2c(-c3cc4ccccc4c4ccccc34)c3c([2H])c([2H])c([2H])c([2H])c3c(-c3ccc(-c4ccc5ccccc5c4)cc3)c2c1[2H]]
[Formula 168]
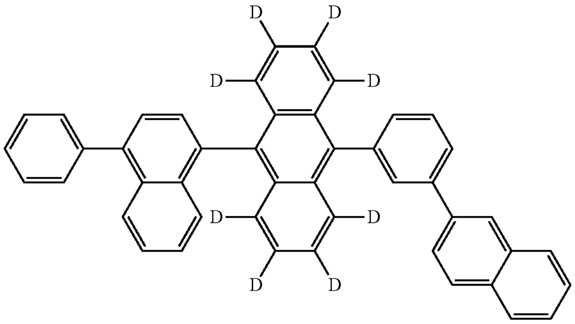
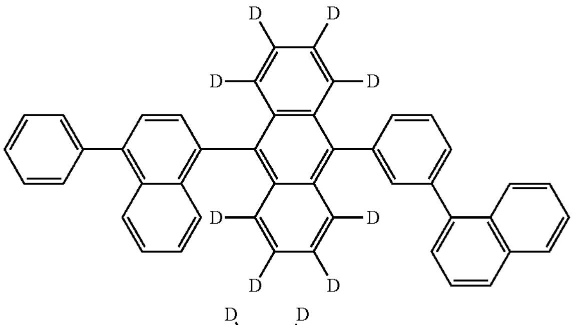
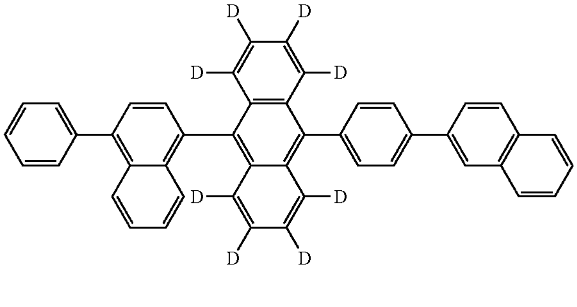
-continued
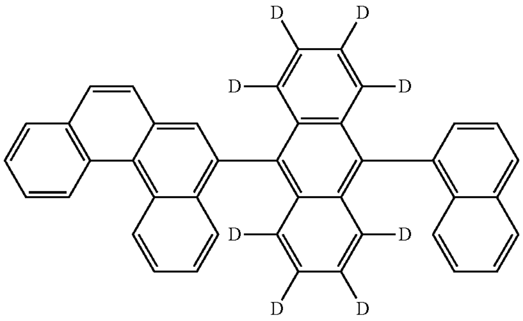
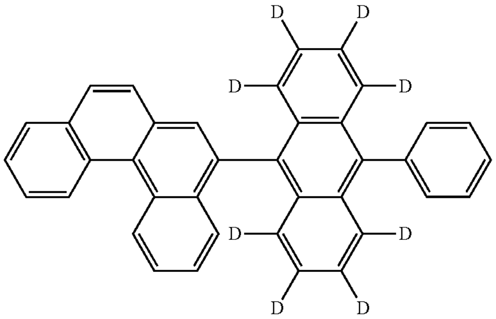
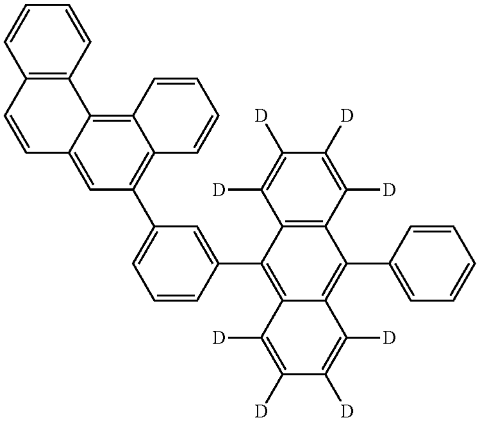
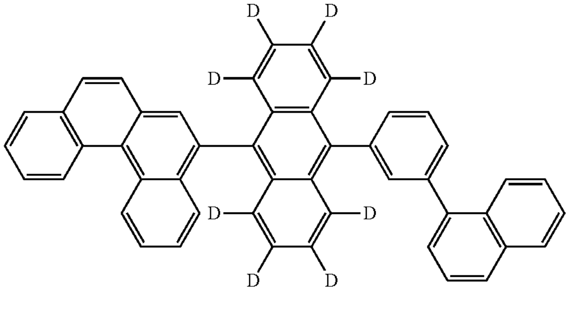

-continued
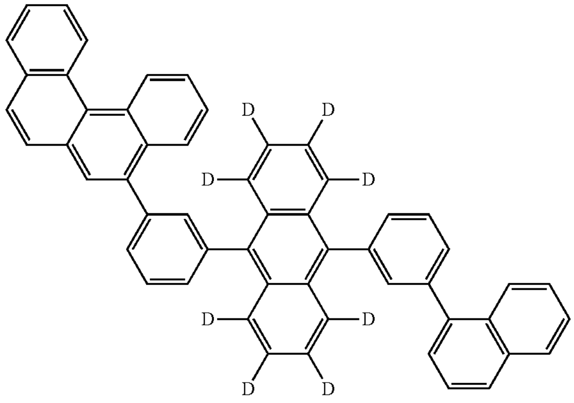
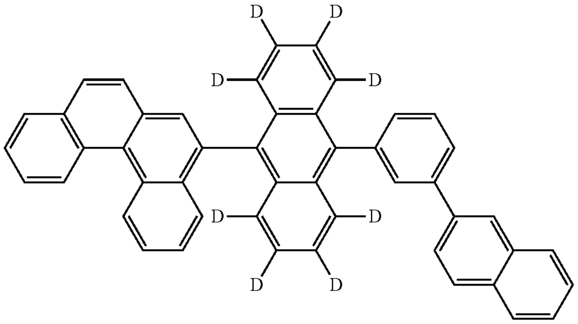
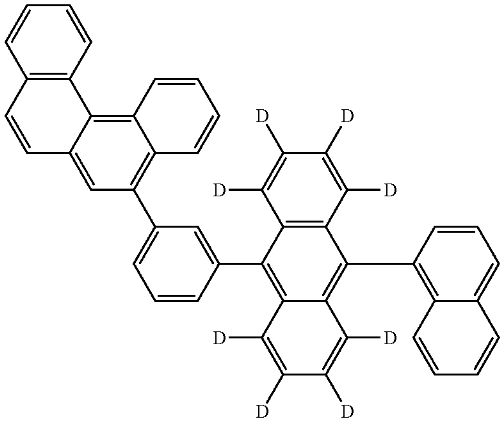
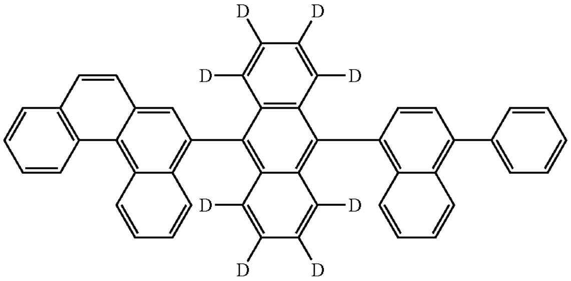
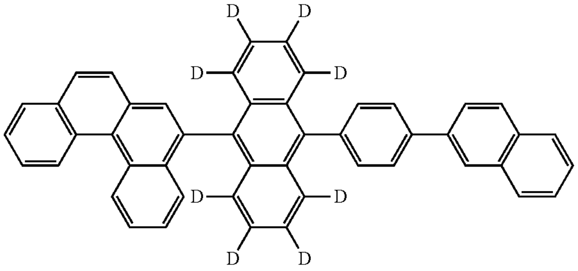
-continued
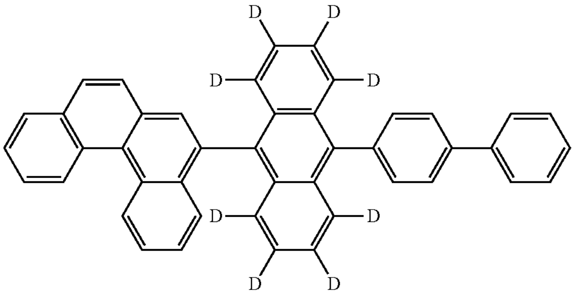
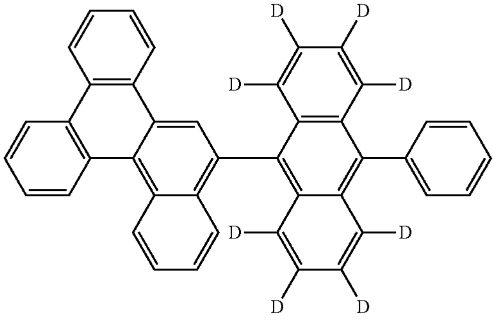
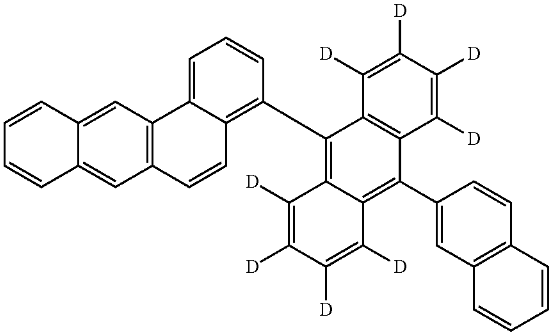
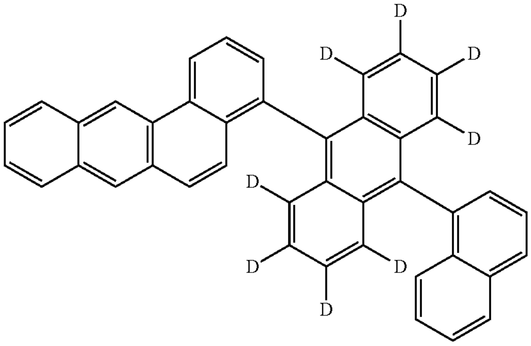
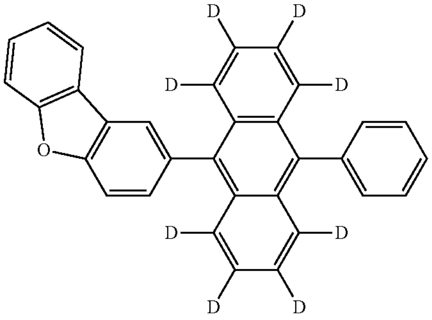

-continued
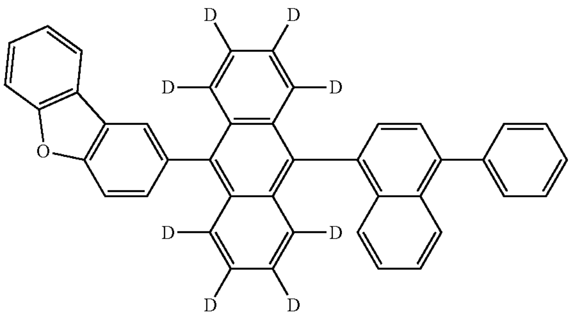
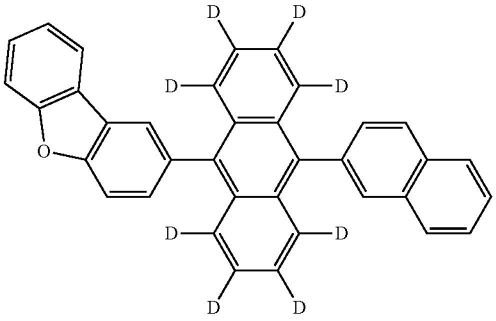
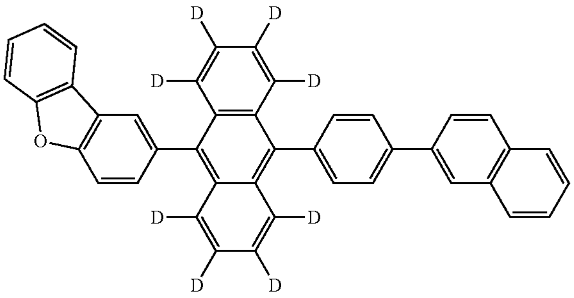
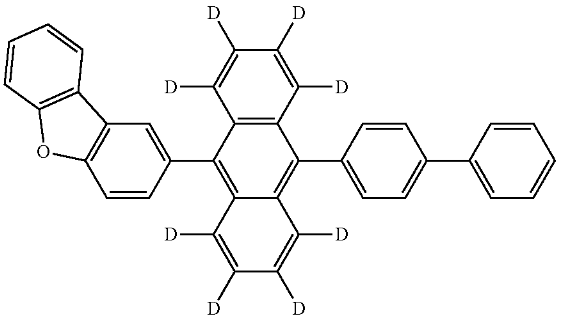
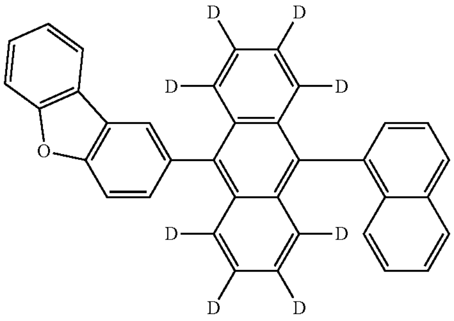
-continued
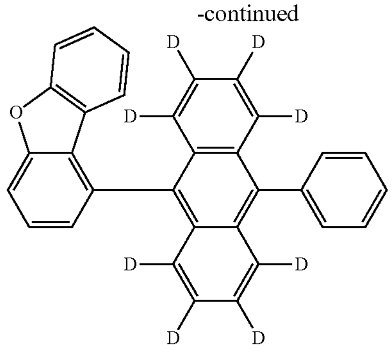
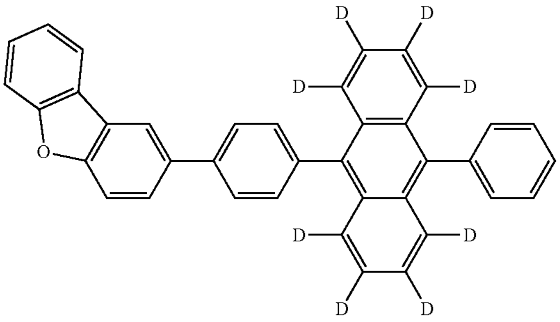
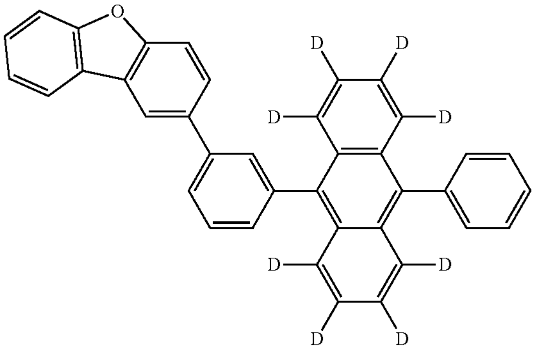
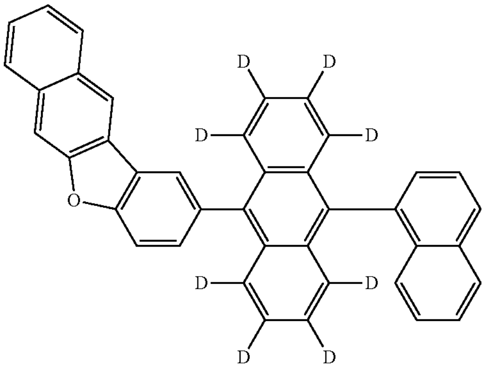
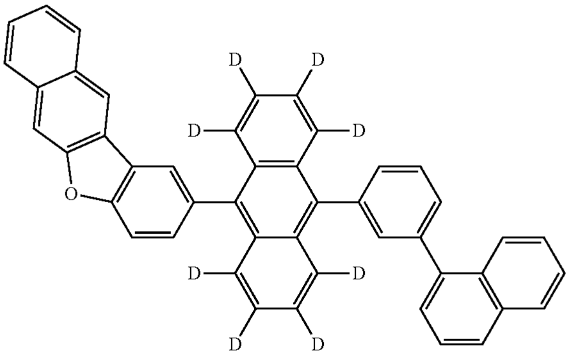

-continued
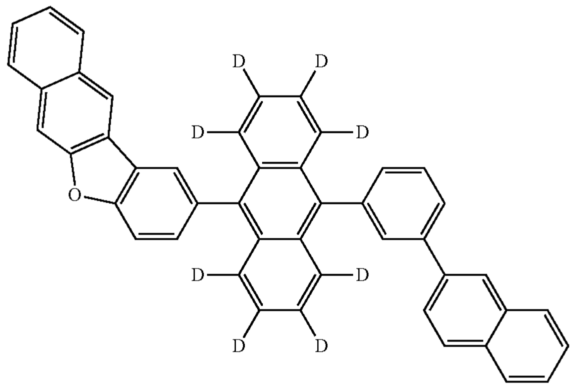
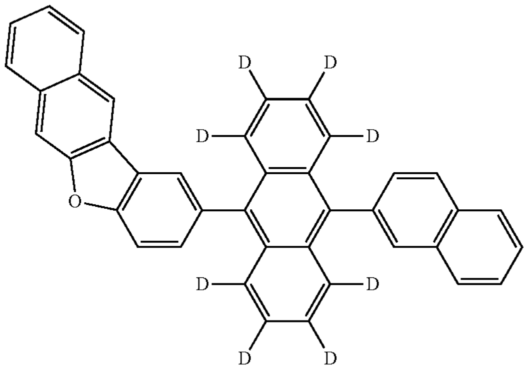
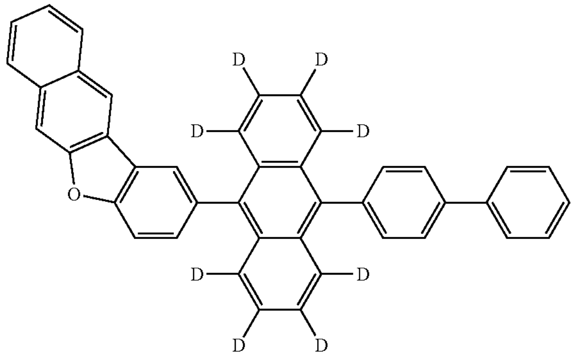
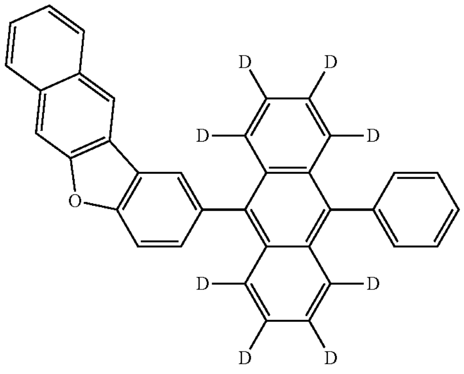
-continued
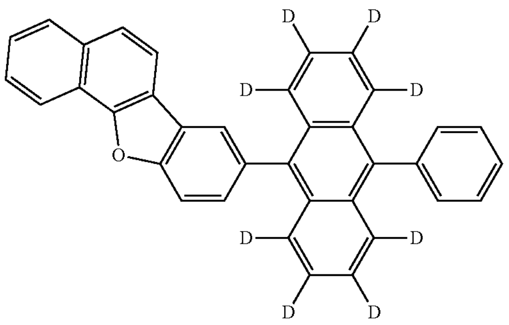
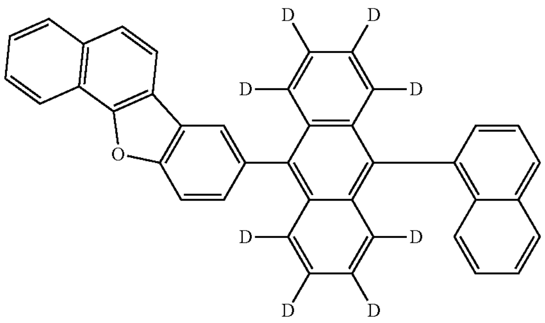
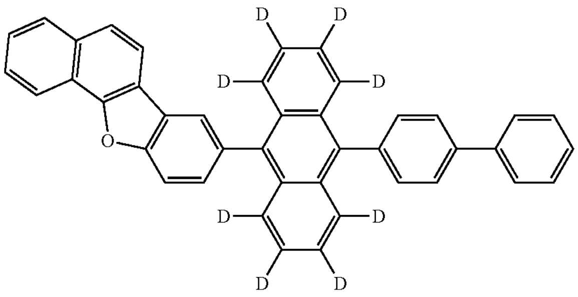
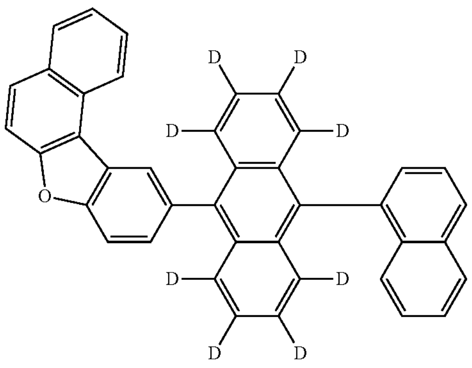
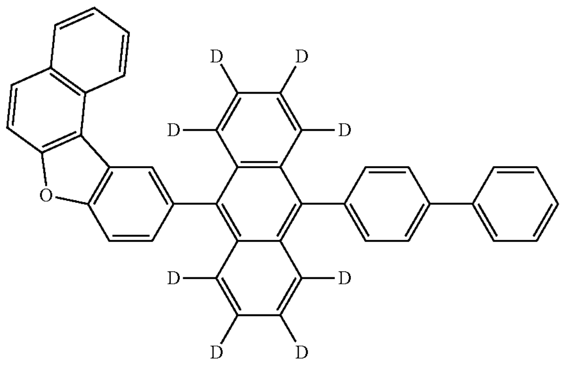

-continued
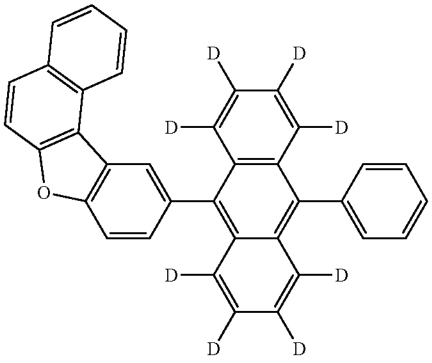
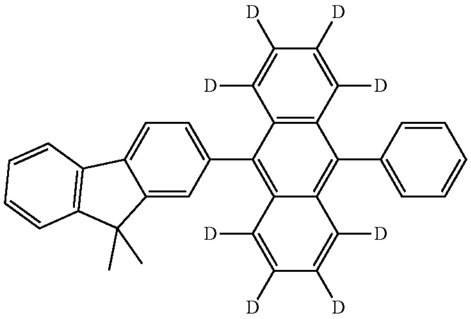
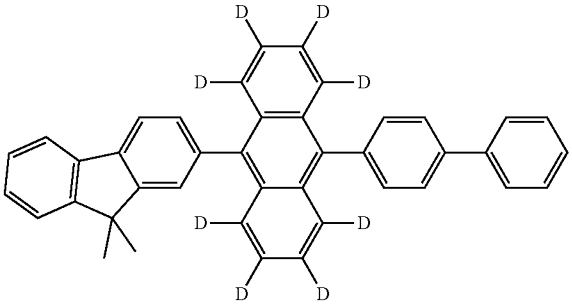
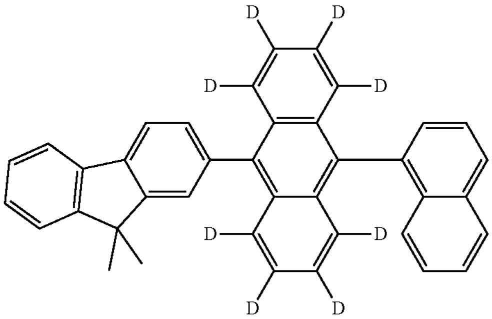
[Formula 169]
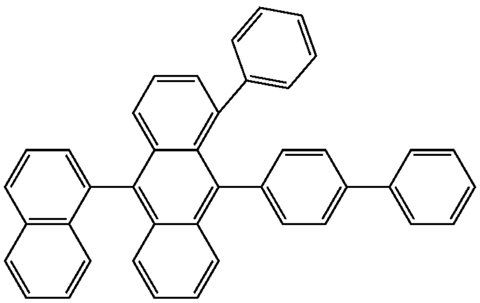
-continued
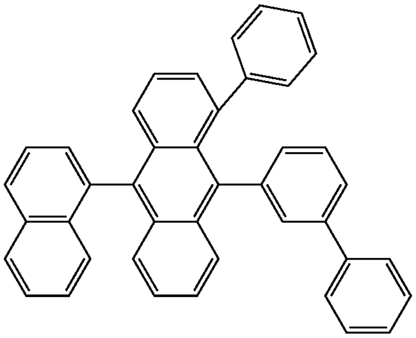
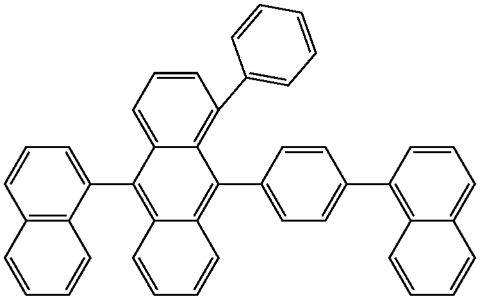
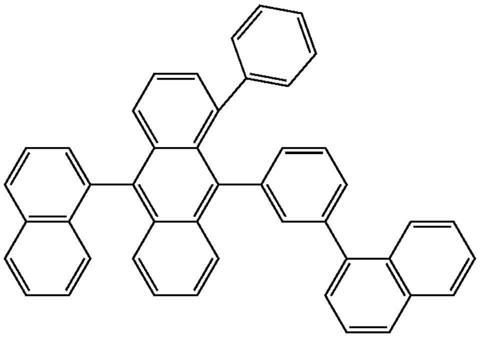
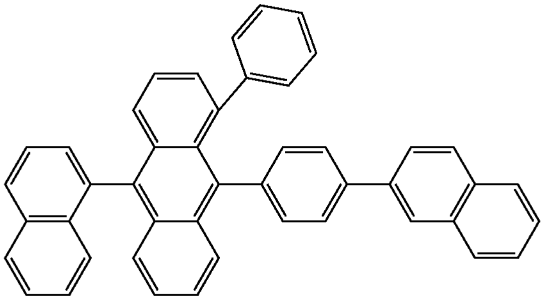
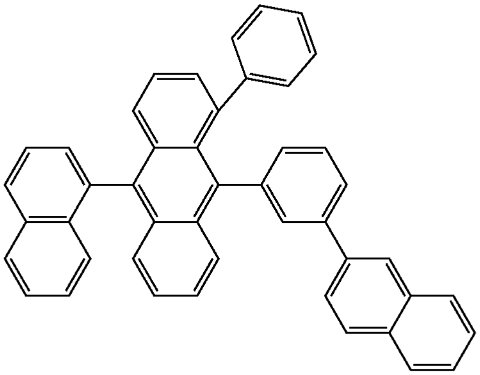

-continued
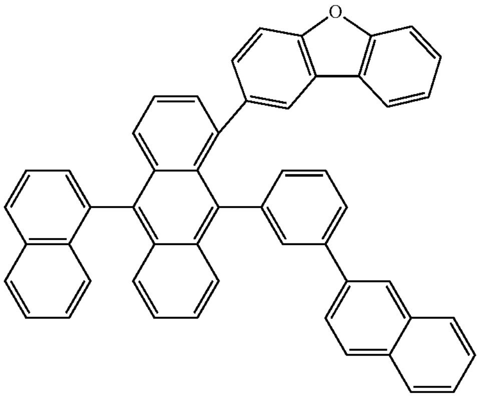
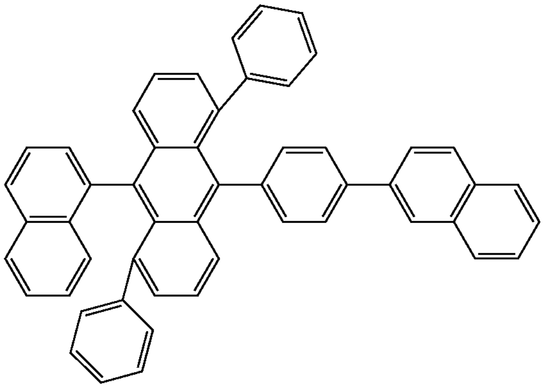
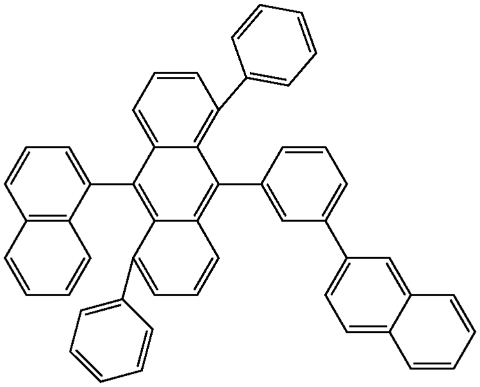
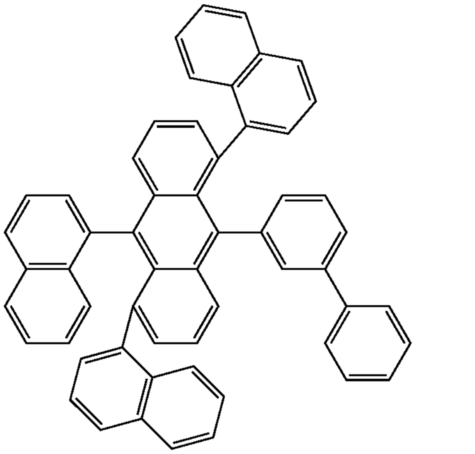
-continued
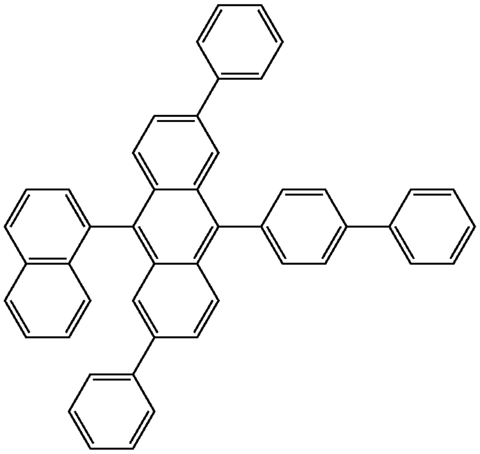
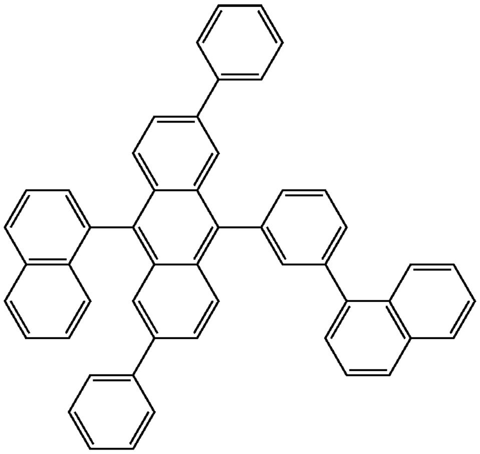
[Formula 170]
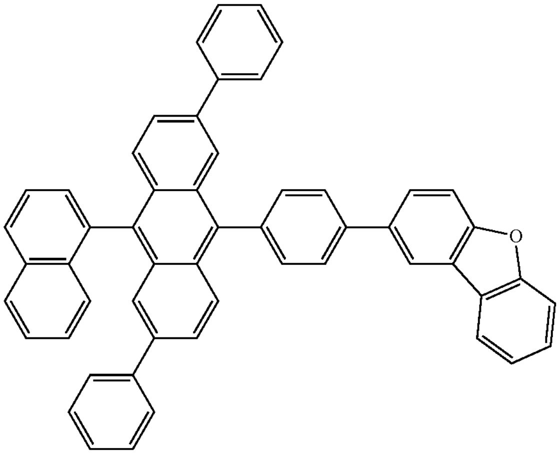

-continued
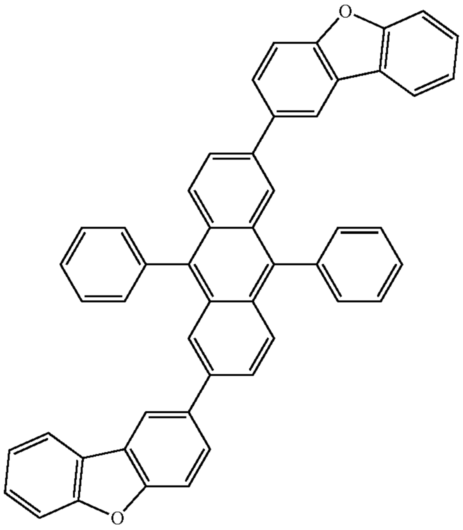
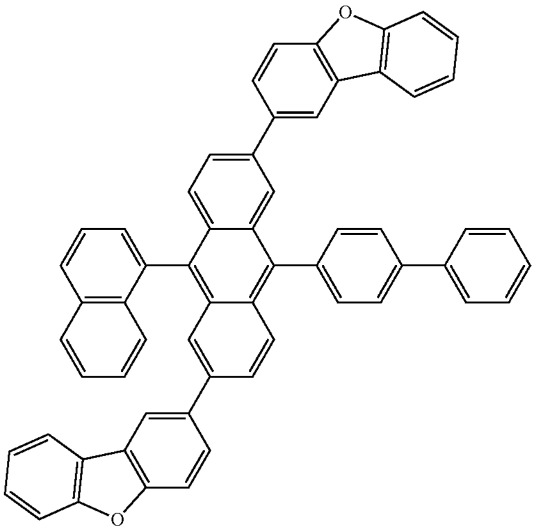
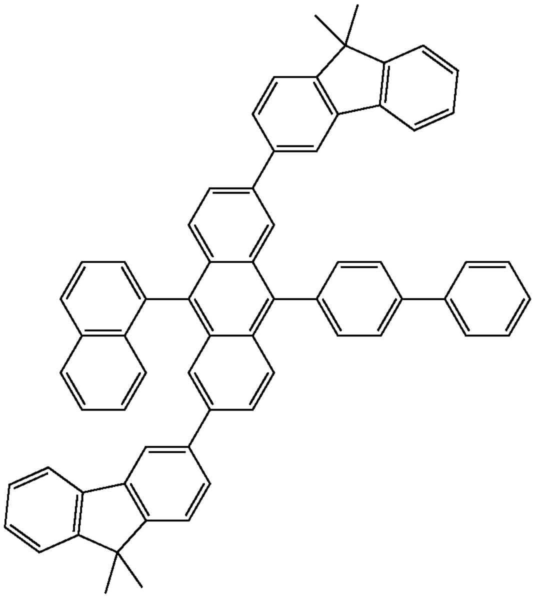
-continued
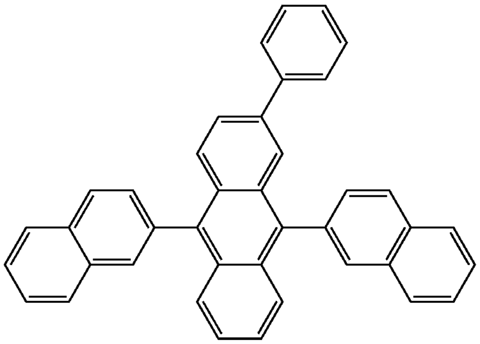
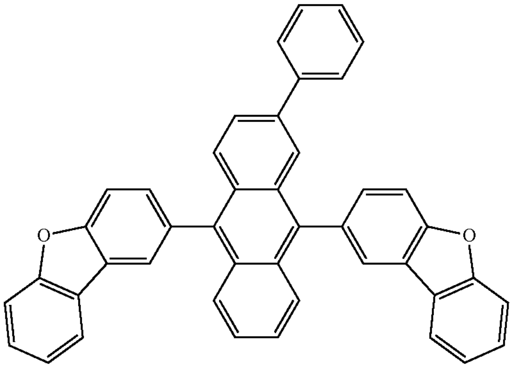
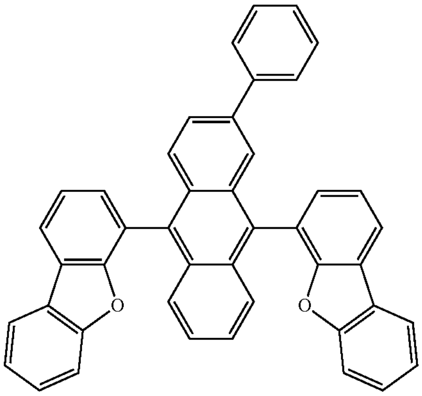
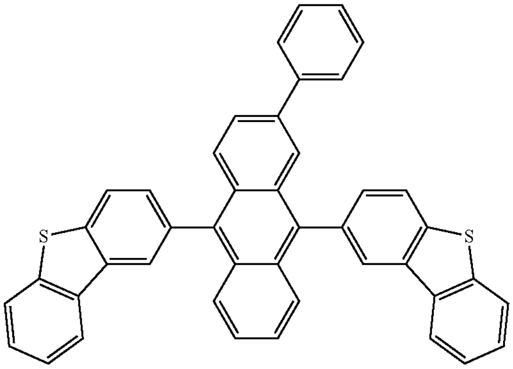

-continued
[Formula 171]
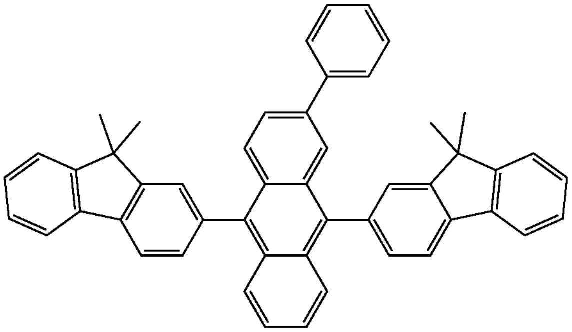
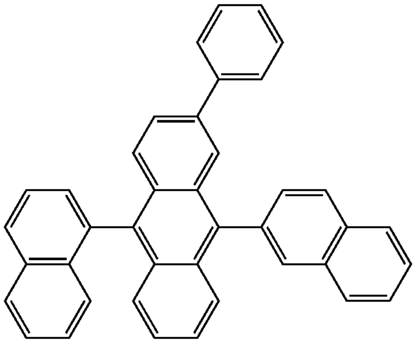
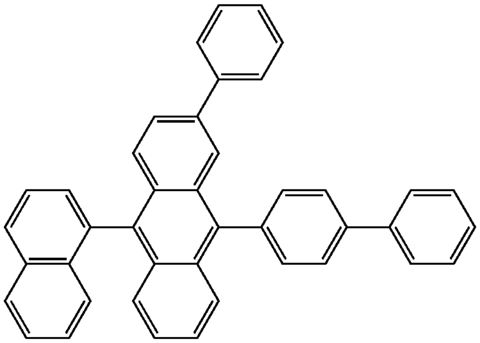
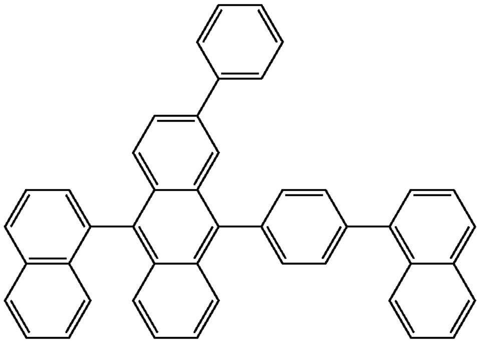
-continued
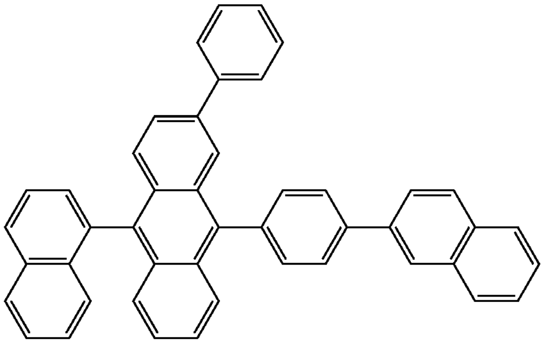
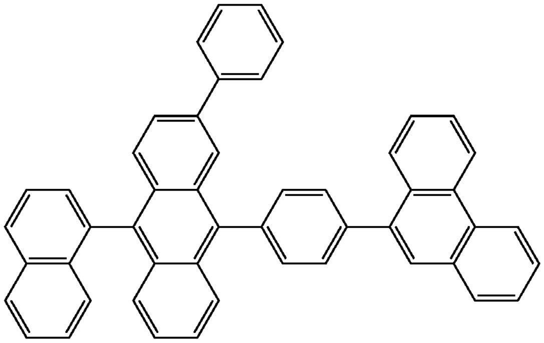
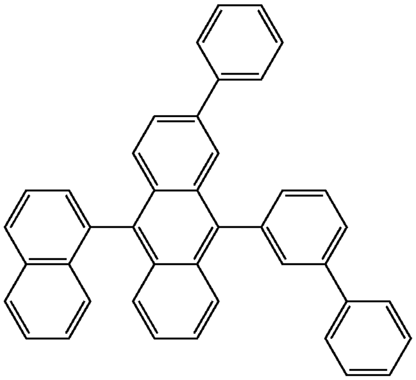
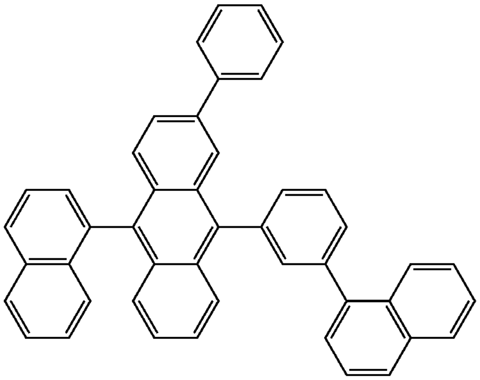

-continued
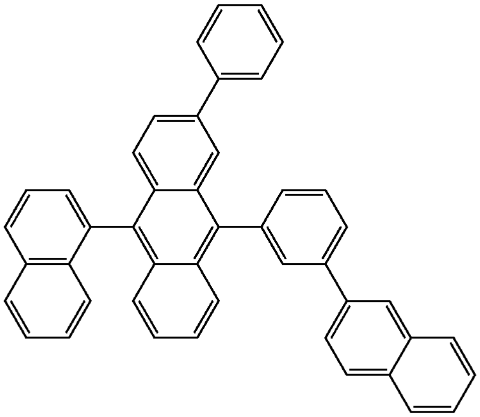
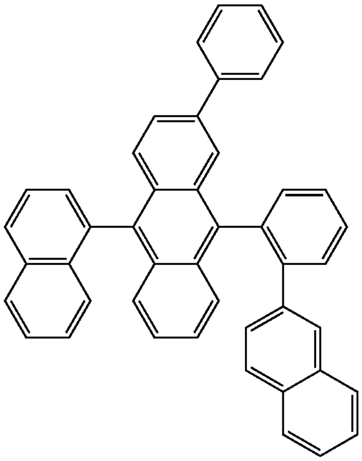
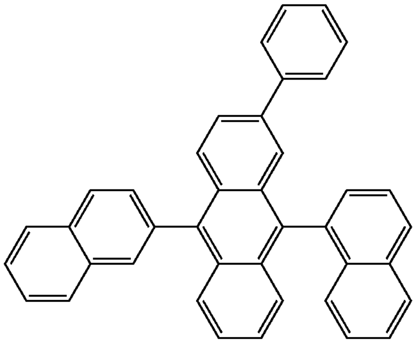
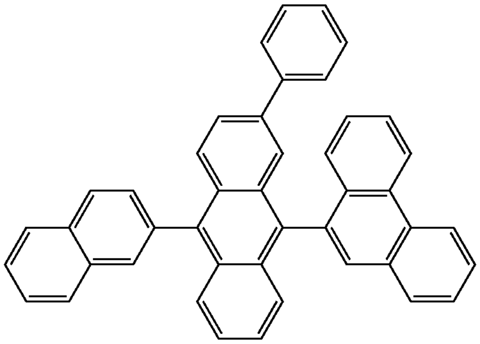
-continued
[Formula 172]
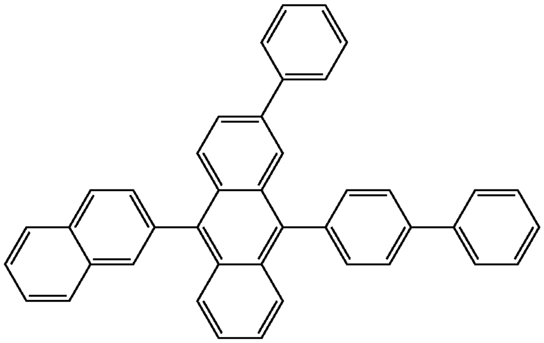
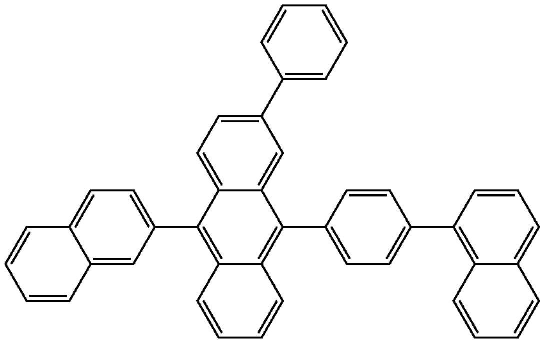
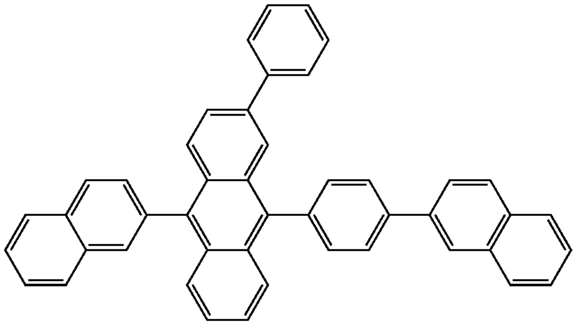
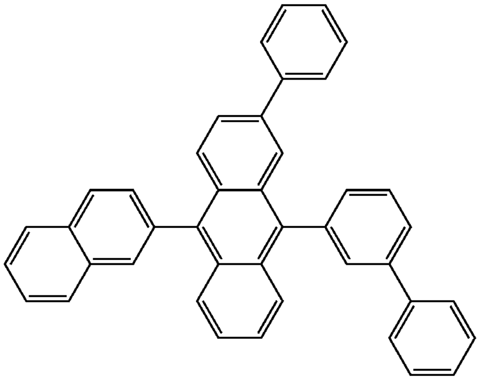

-continued
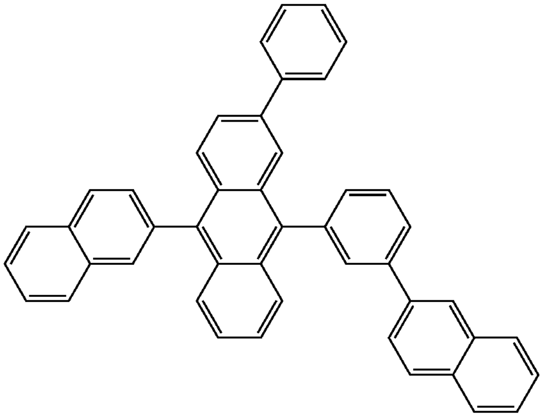
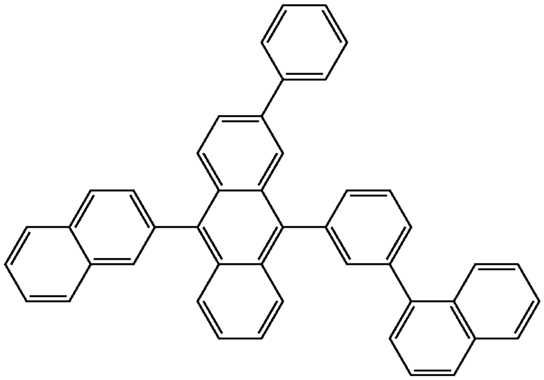
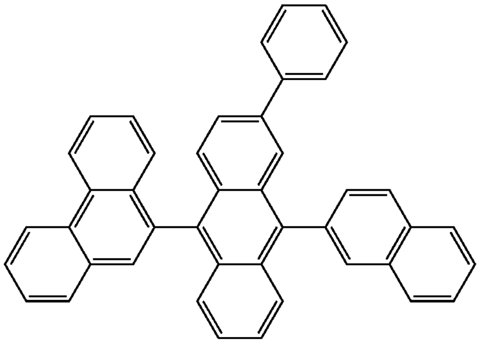
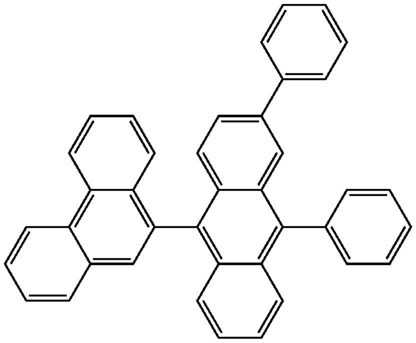
-continued
[Formula 173]
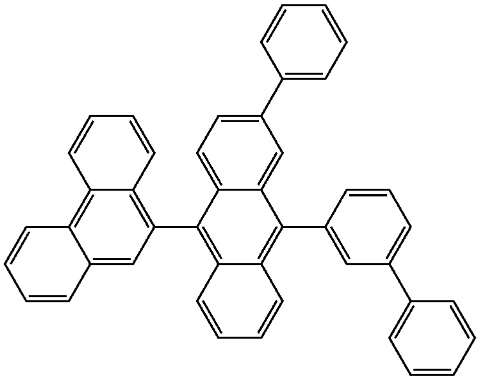
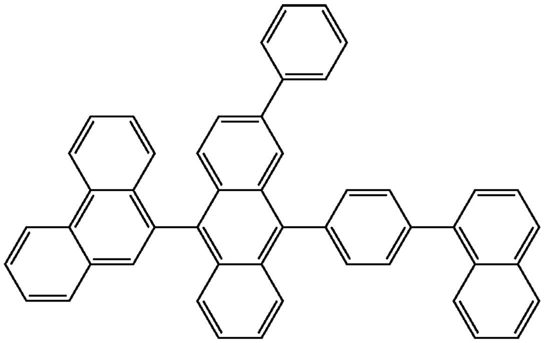
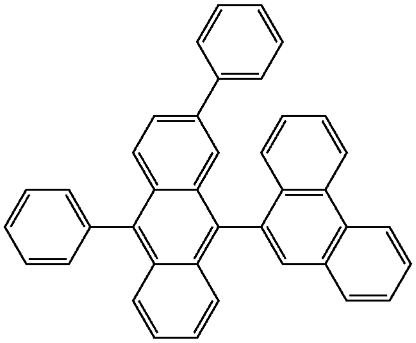
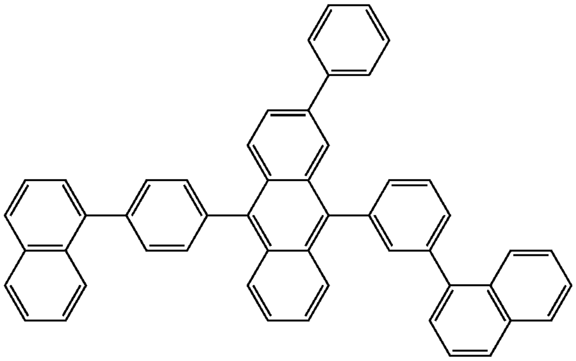

-continued
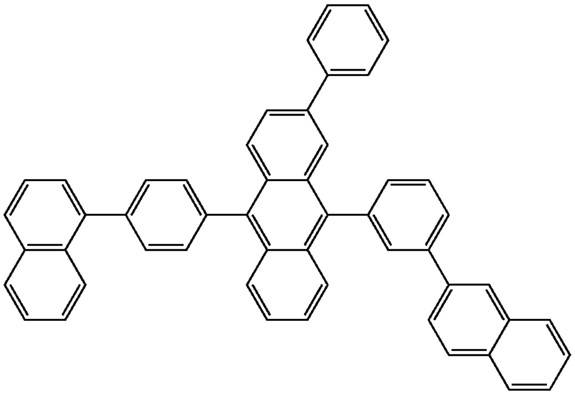
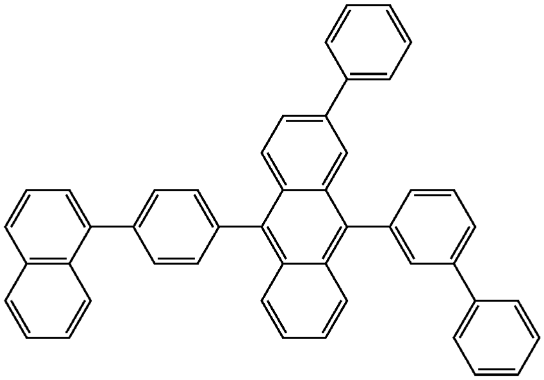
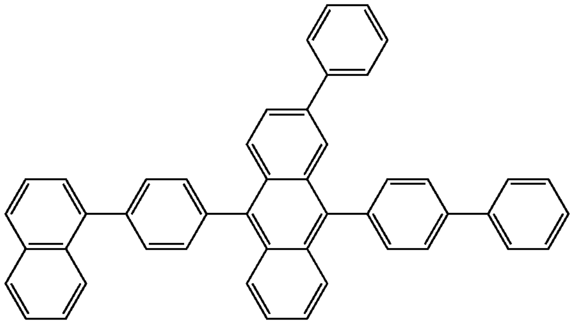
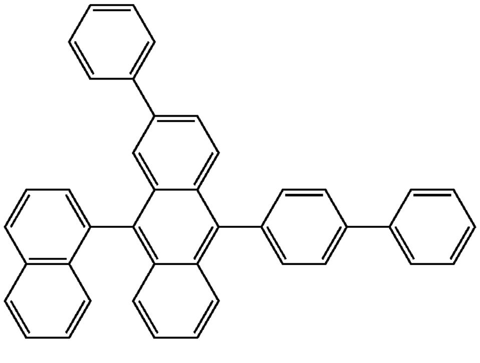
-continued
[Formula 174]
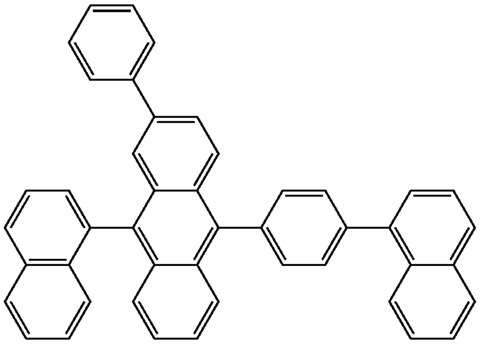
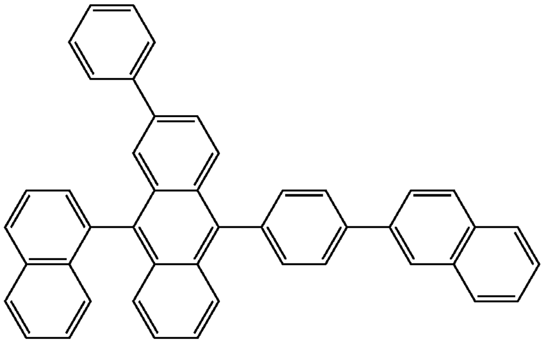
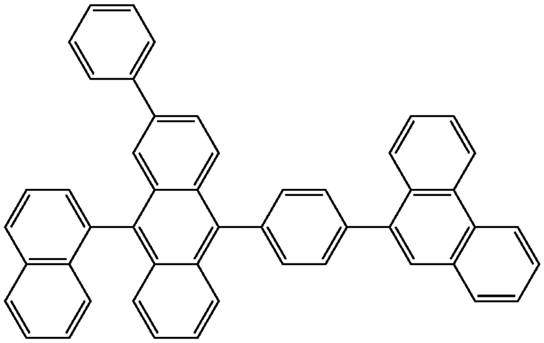
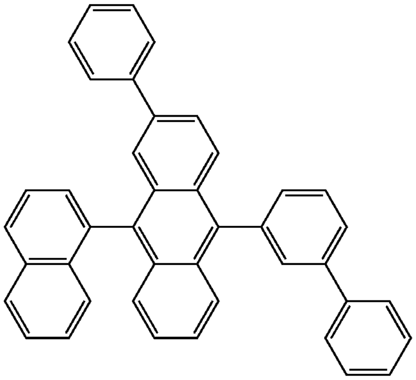

-continued
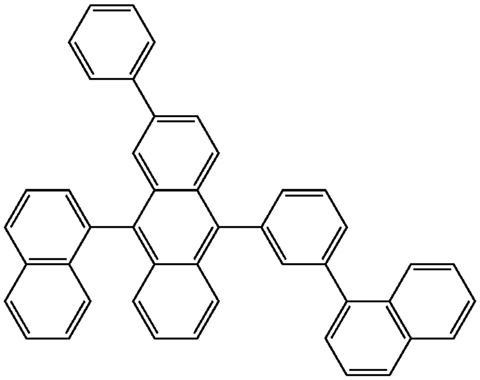
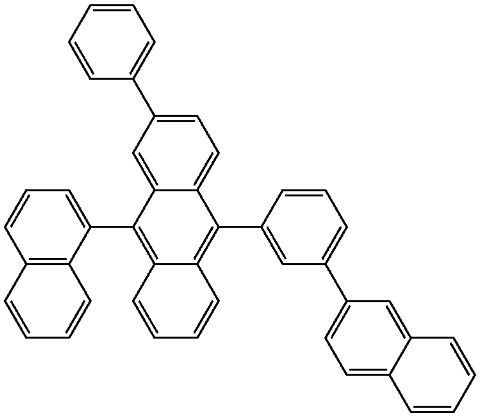
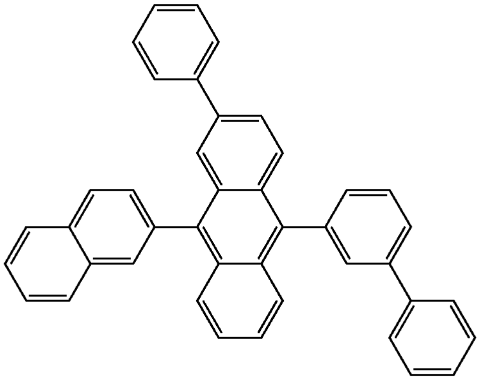
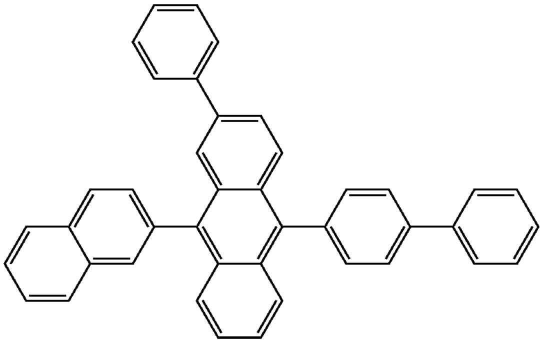
-continued
[Formula 175]
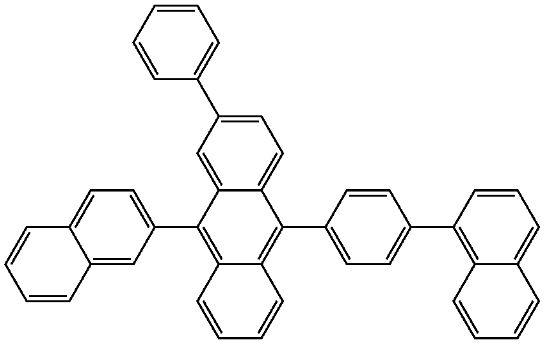
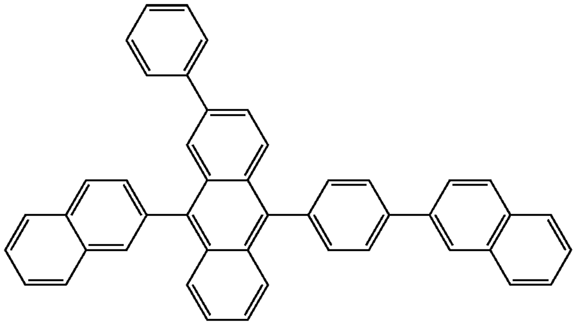
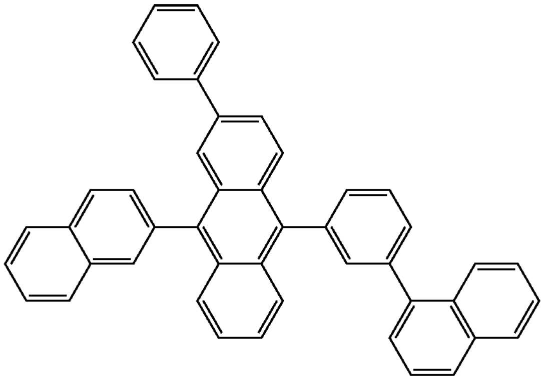
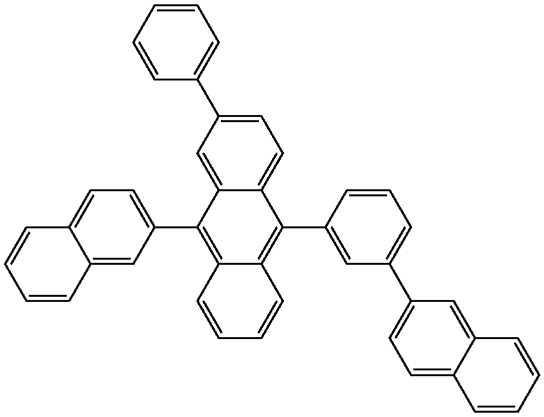

-continued
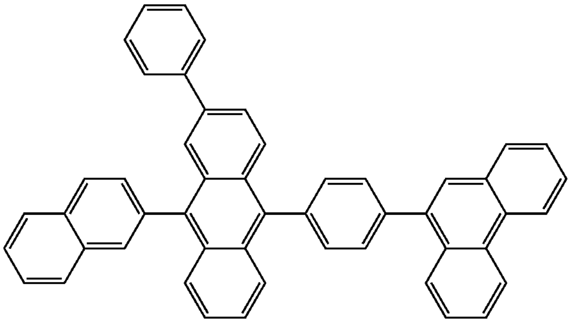
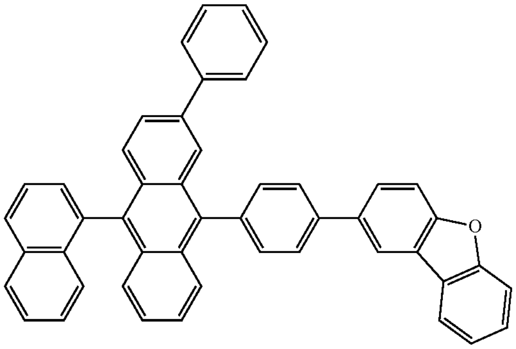
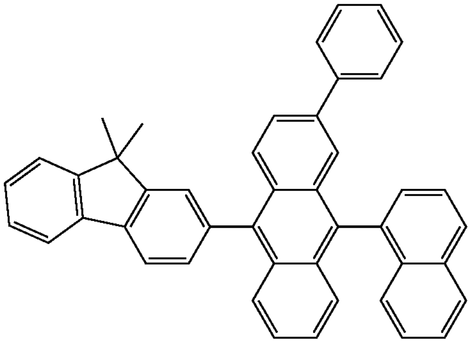
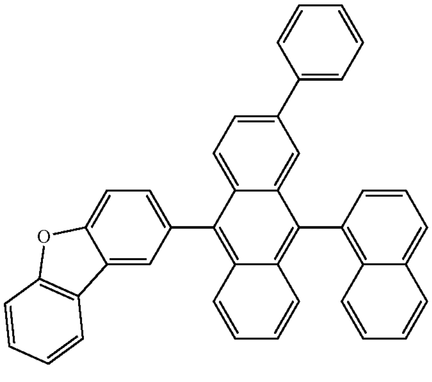
-continued
[Formula 176]
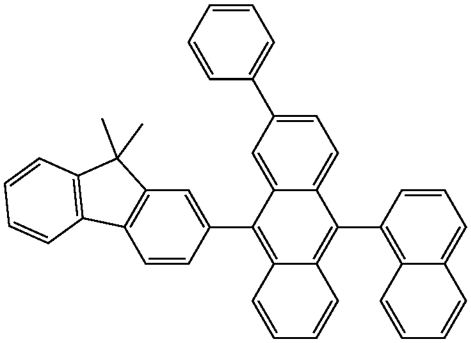
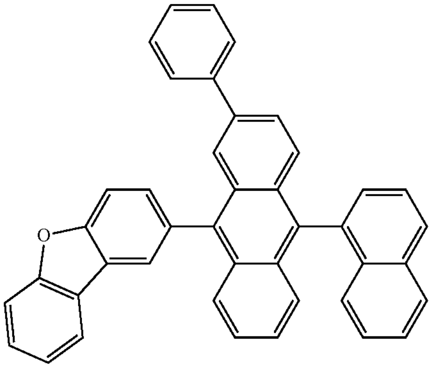
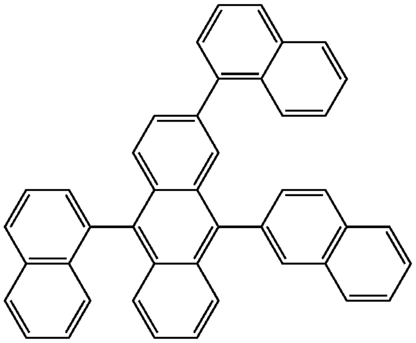
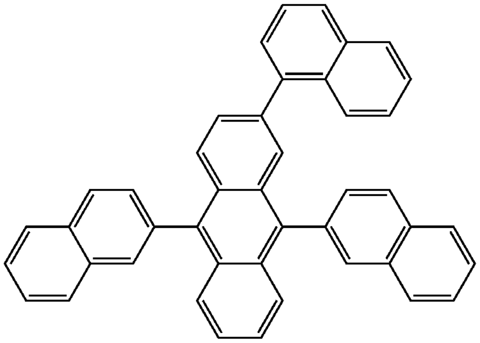

-continued
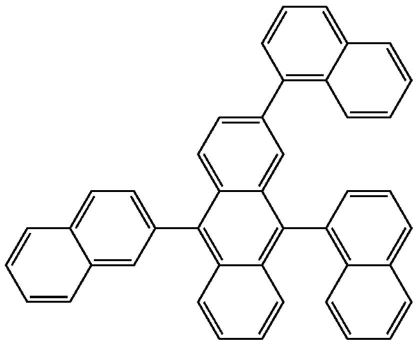
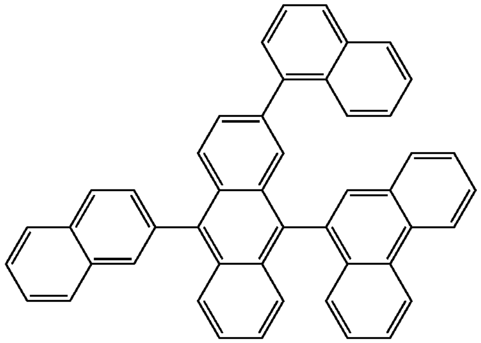
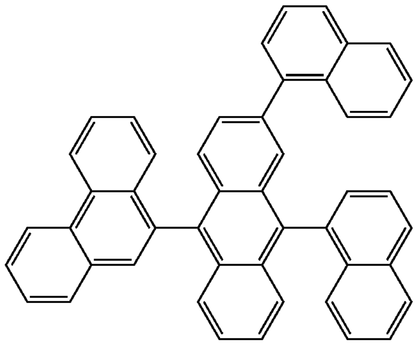
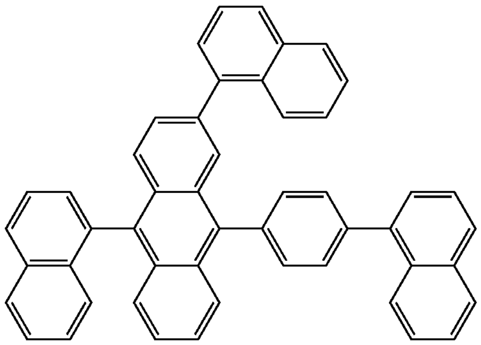
-continued
[Formula 177]
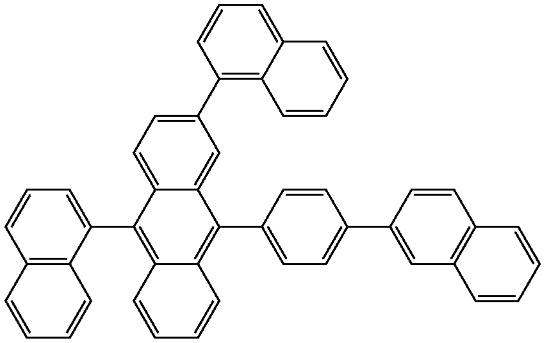
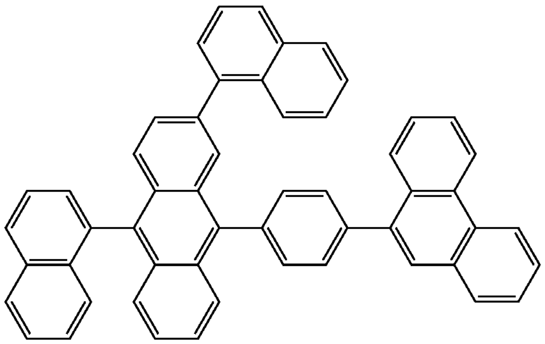
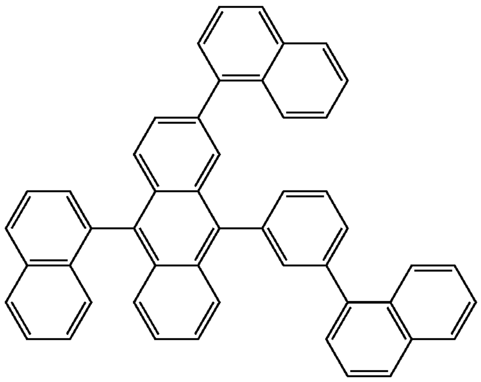
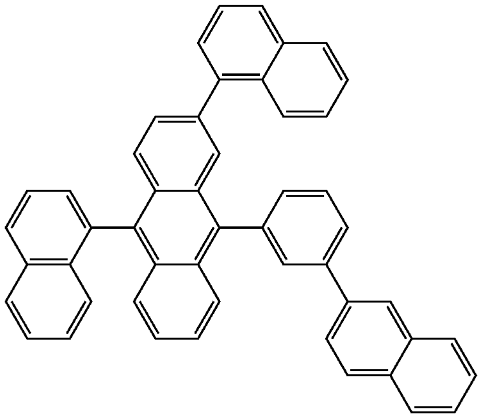

-continued
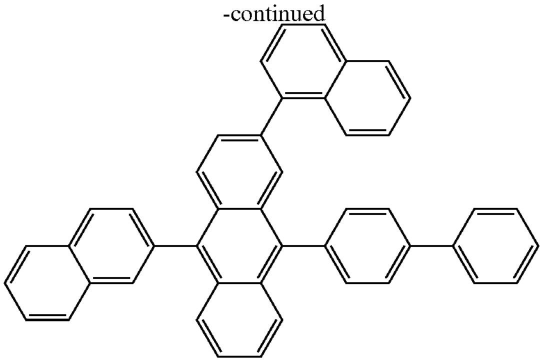
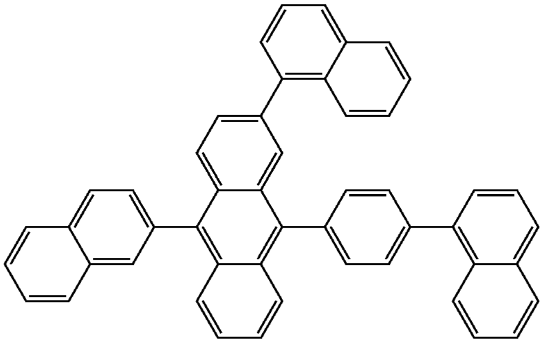
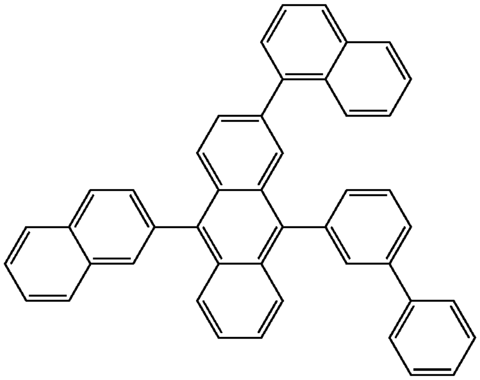
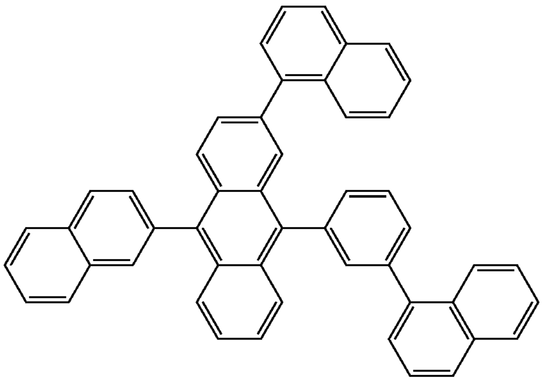
-continued
[Formula 178]
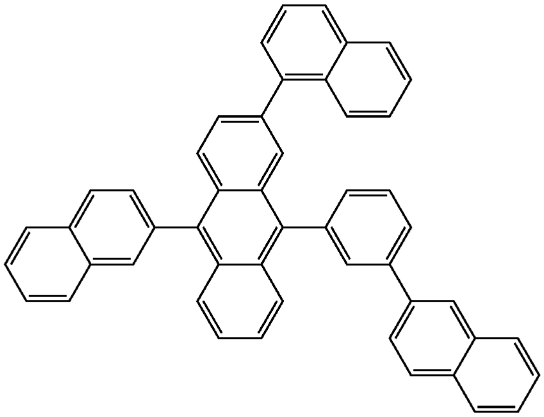
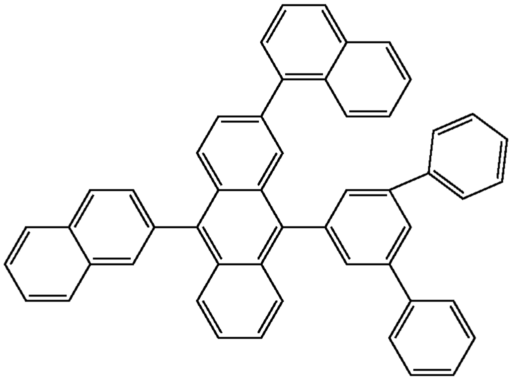
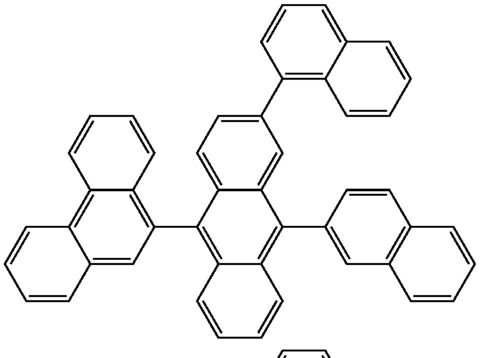
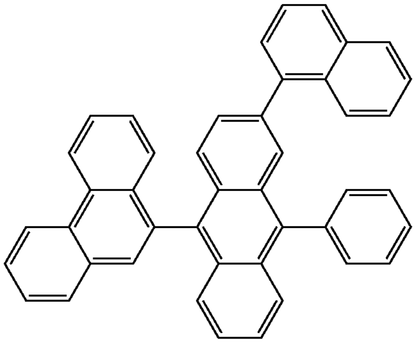

-continued
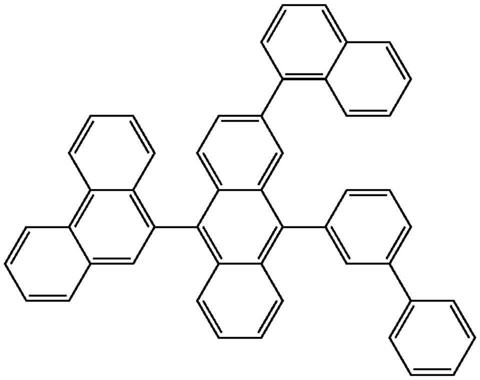
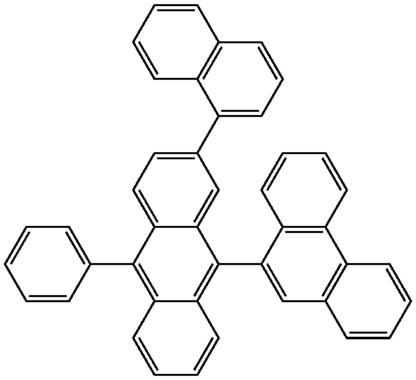
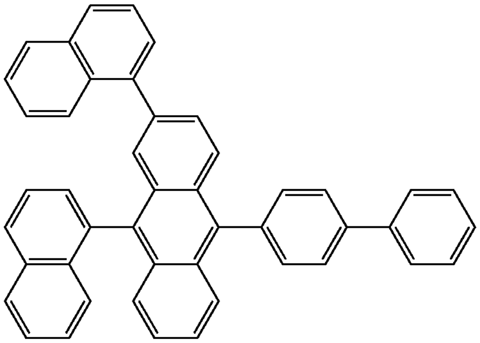
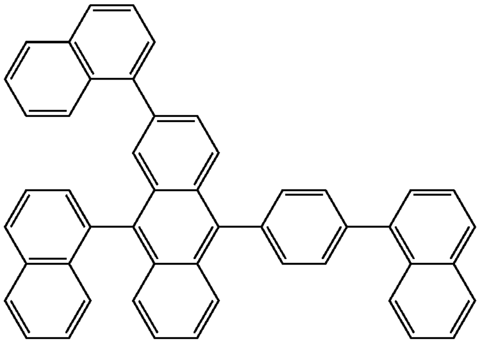
-continued
[Formula 179]
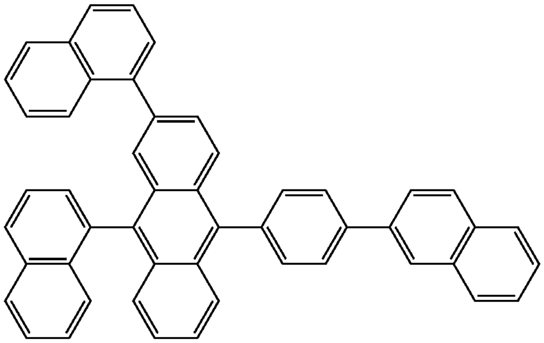
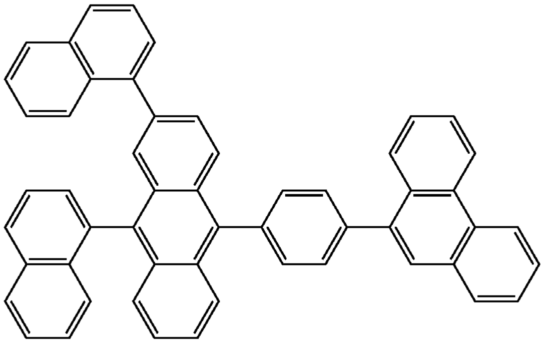
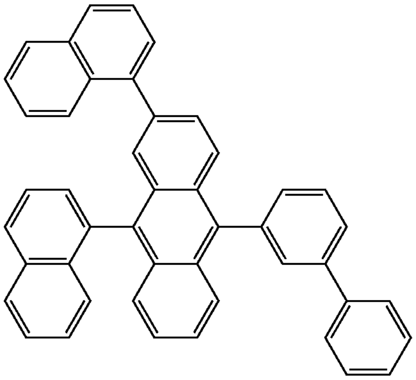
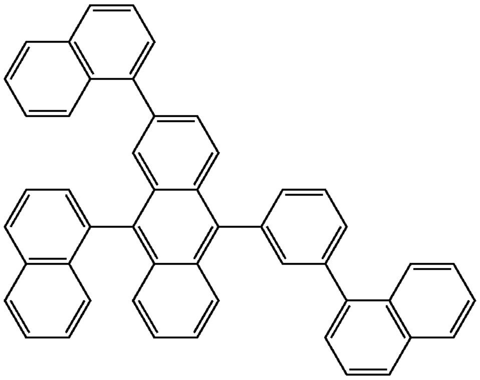

-continued
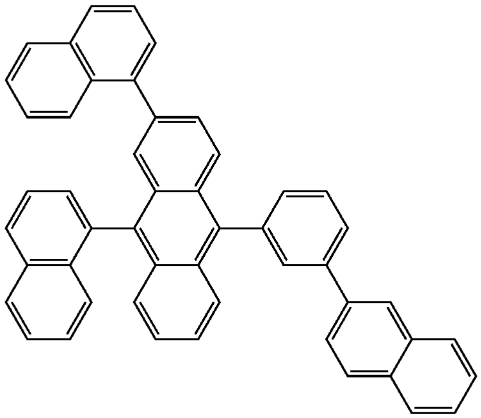
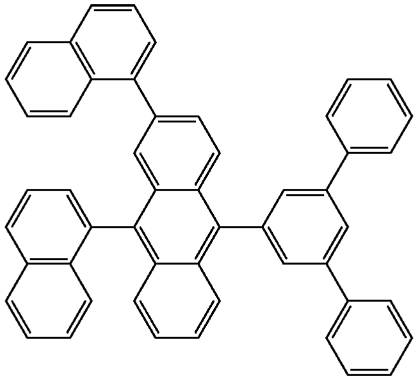
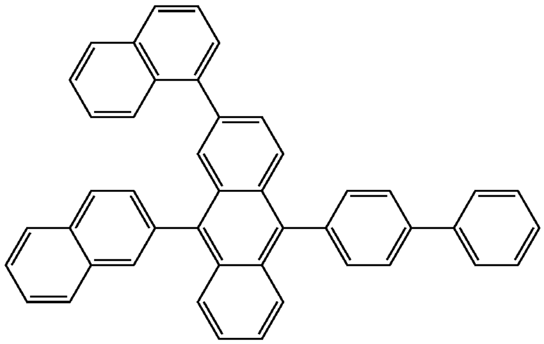
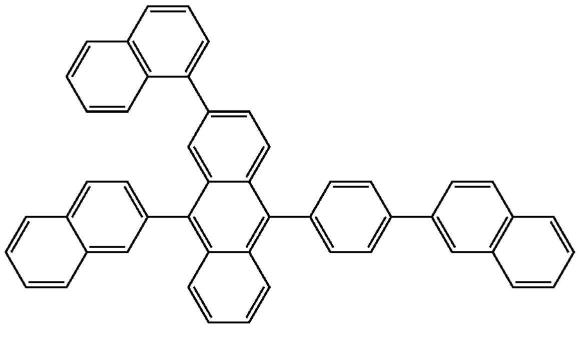
-continued
[Formula 180]
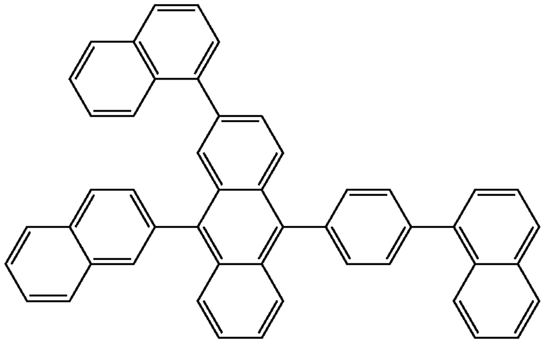
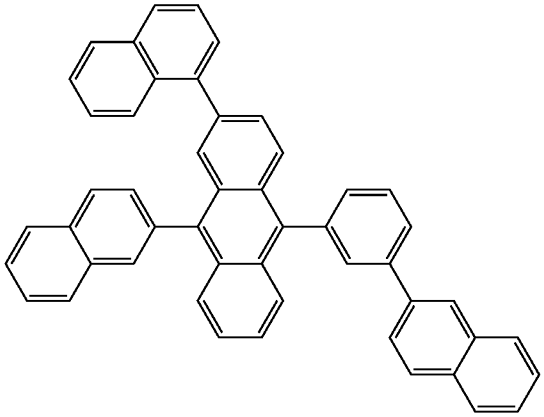
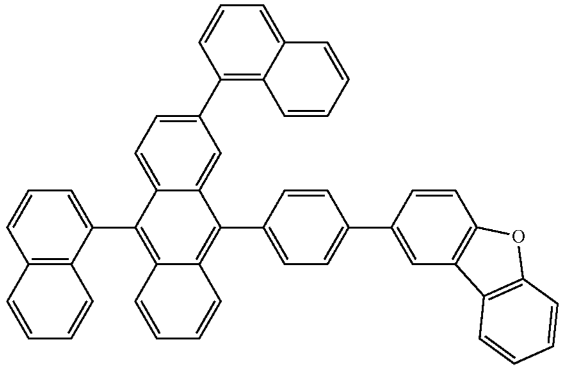
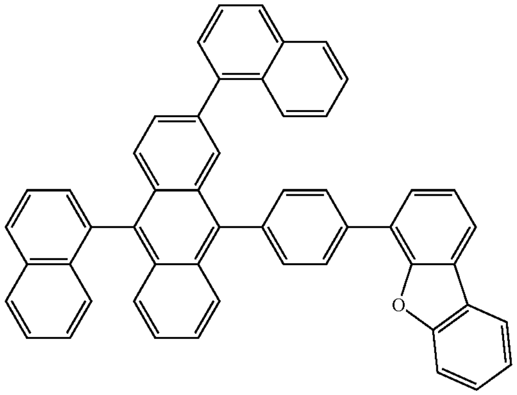

-continued
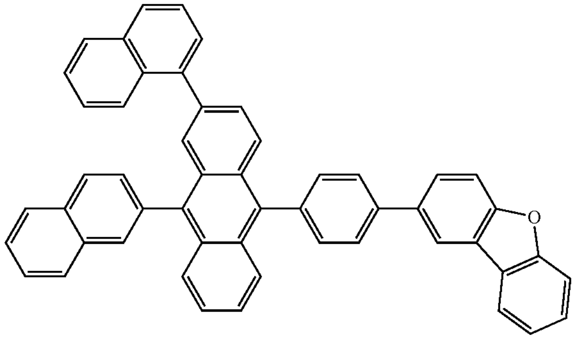
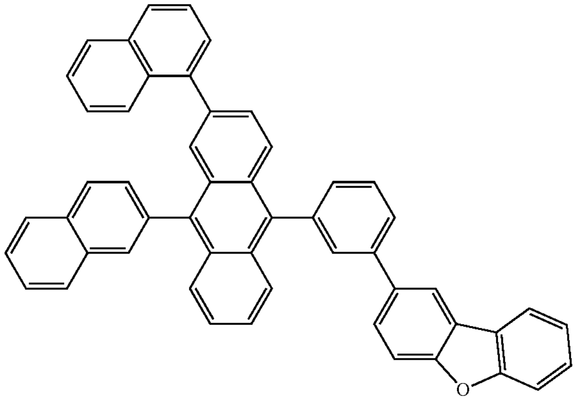
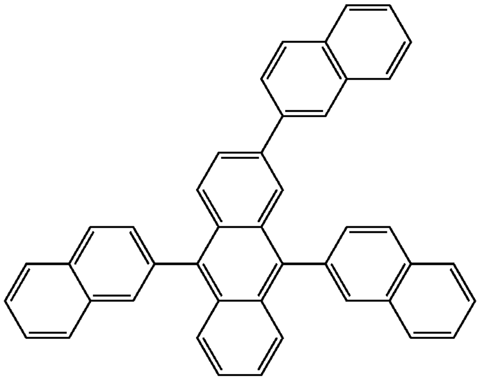
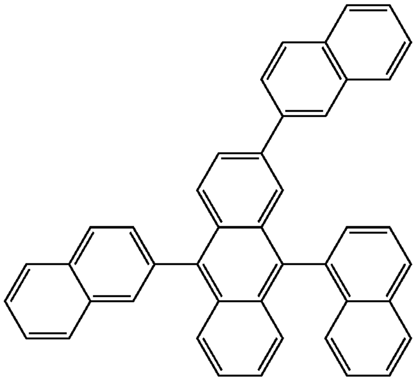
-continued
[Formula 181]
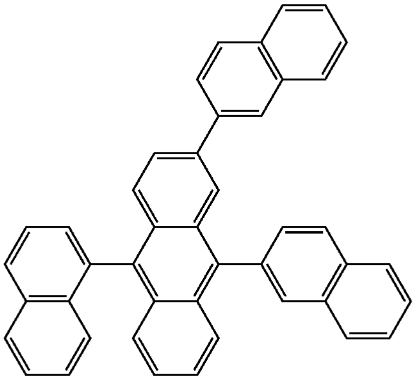
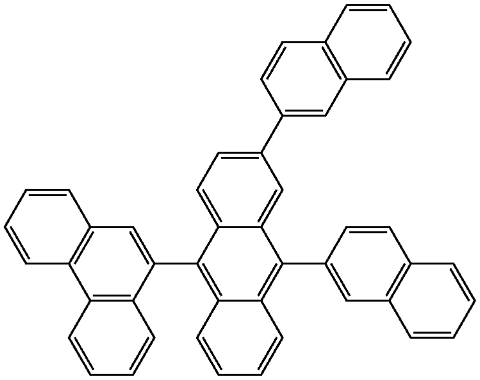
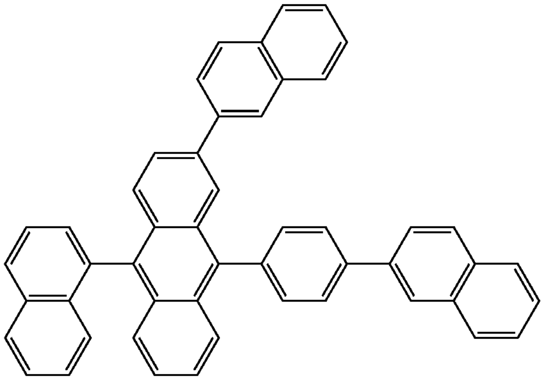
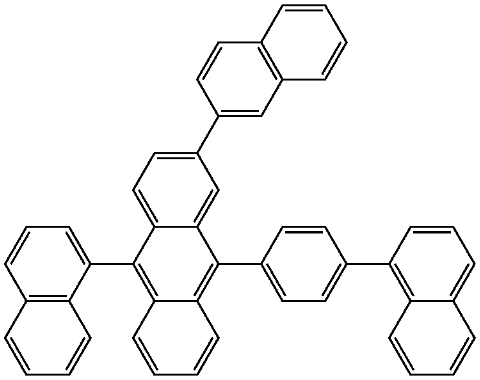

-continued
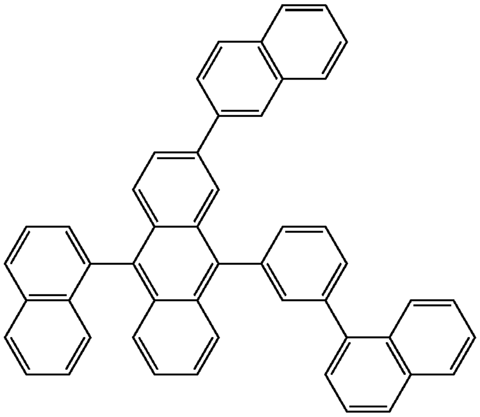
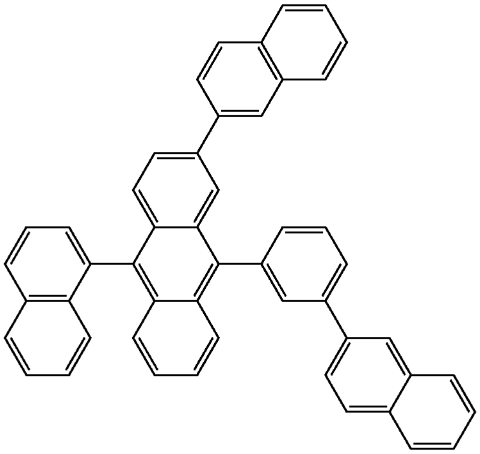
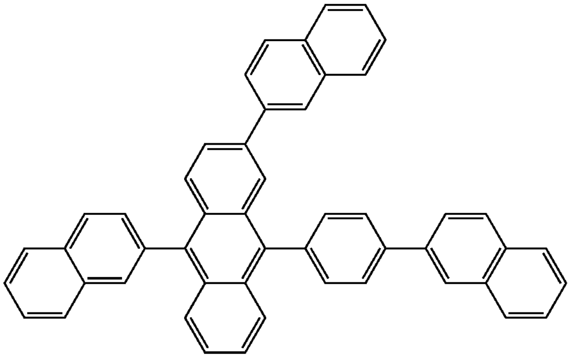
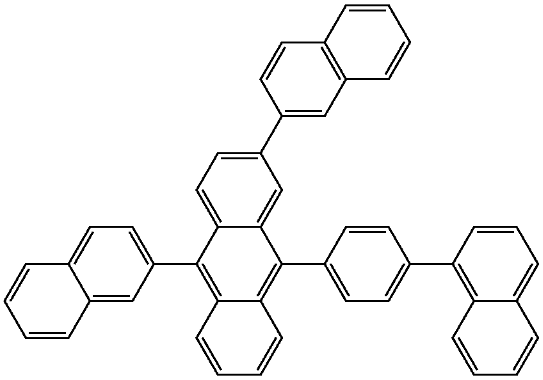
-continued
[Formula 182]
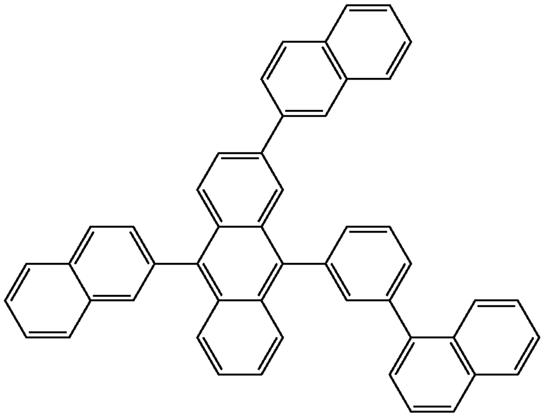
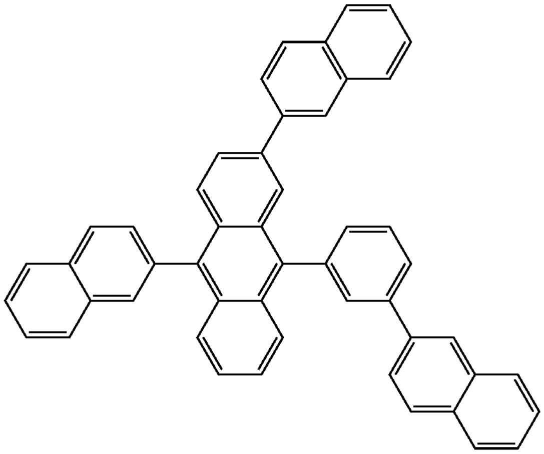
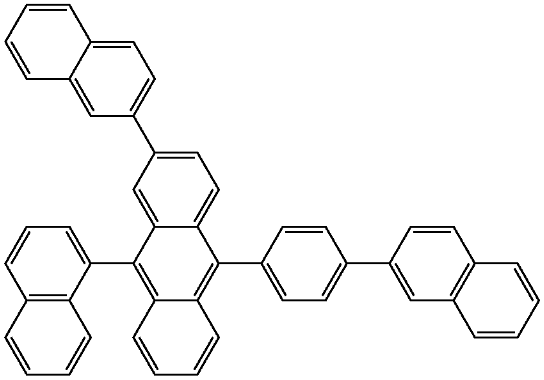
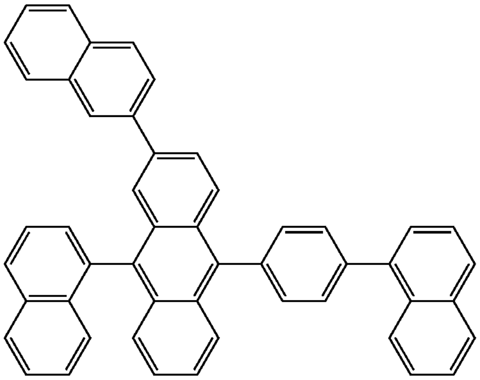

-continued
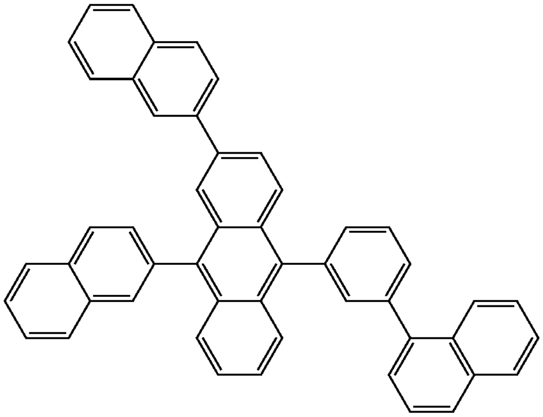
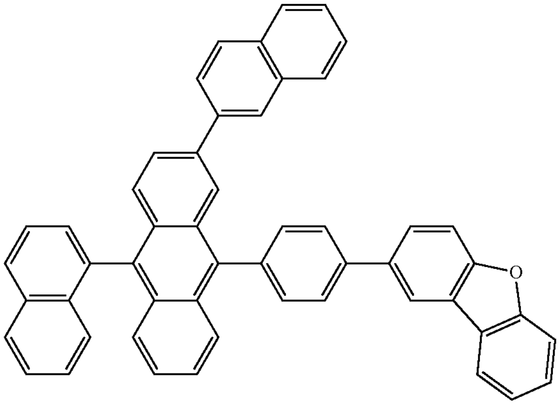
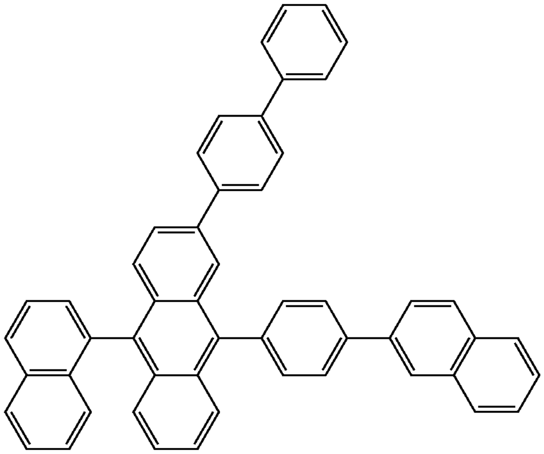
-continued
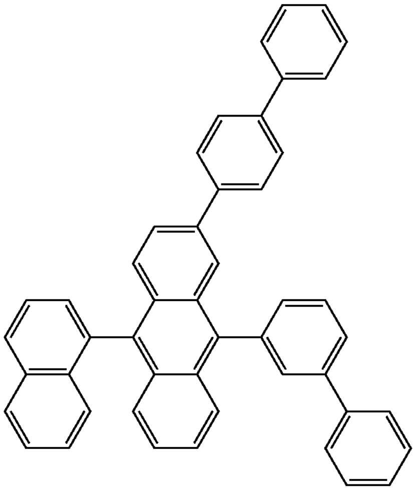
[Formula 183]
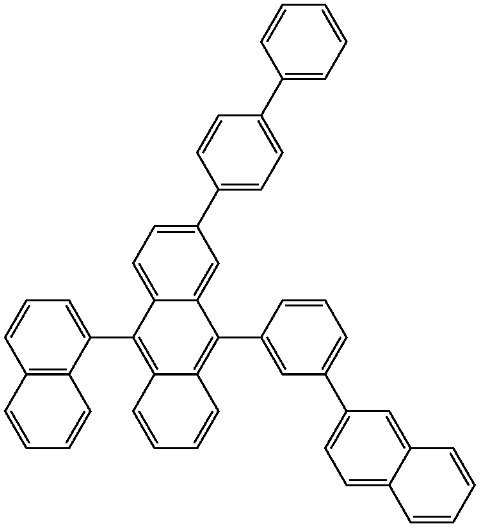
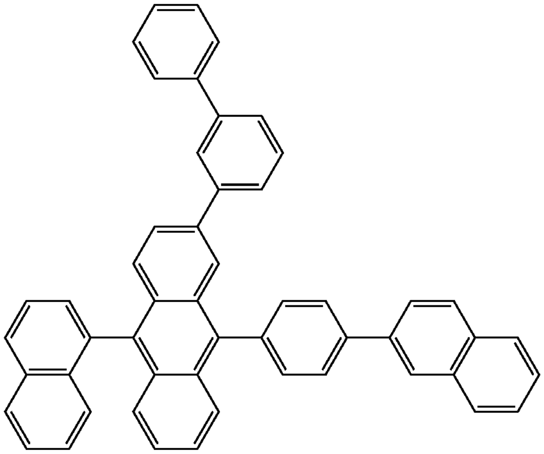

-continued
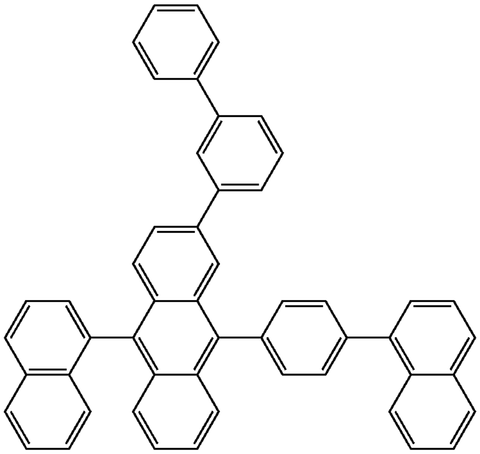
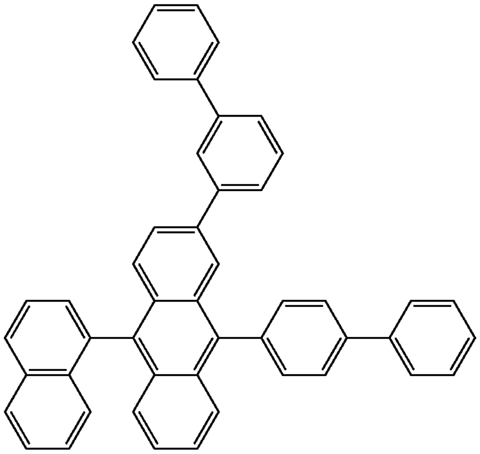
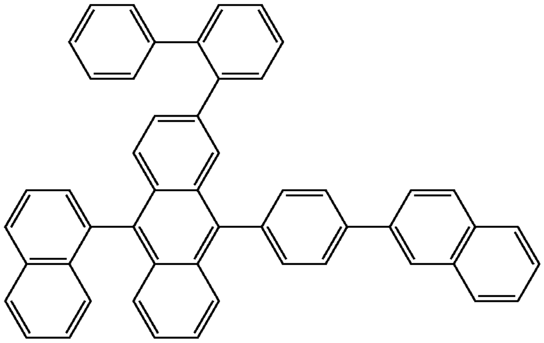
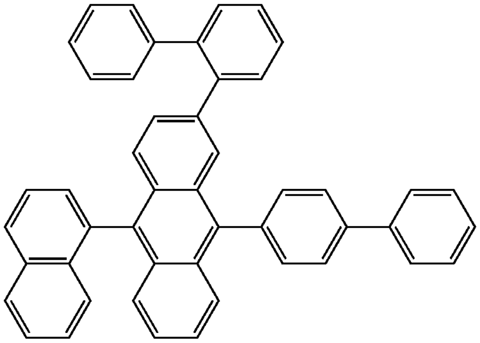
-continued
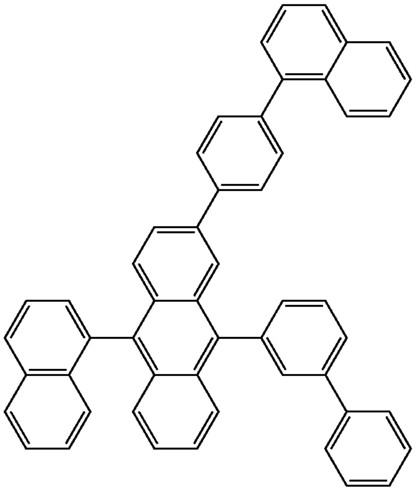
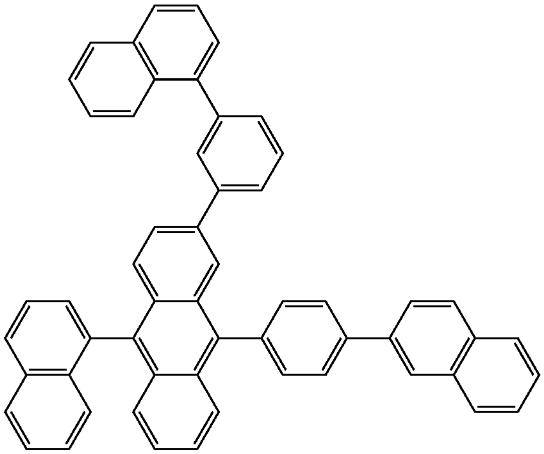
[Formula 184]
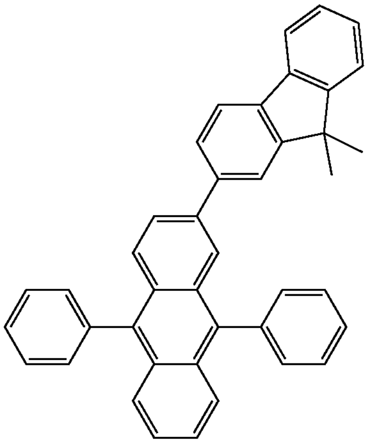

-continued
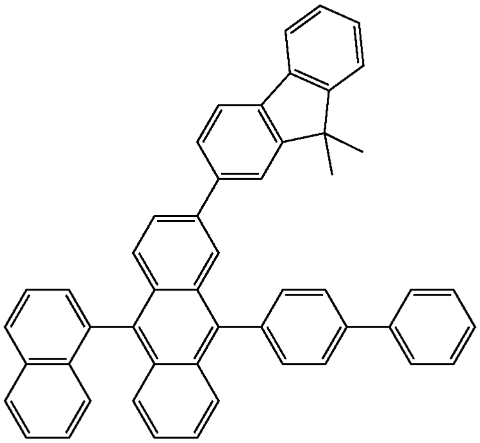
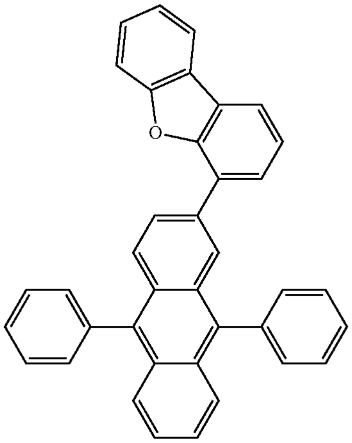
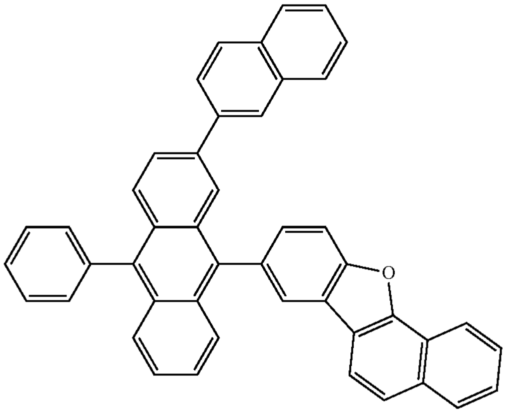
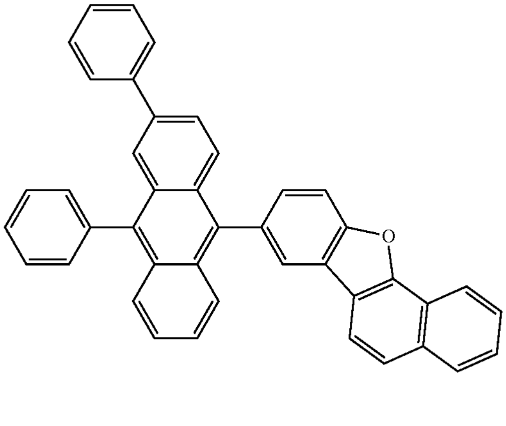
-continued
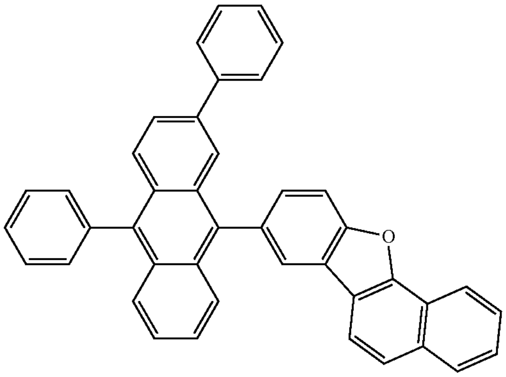
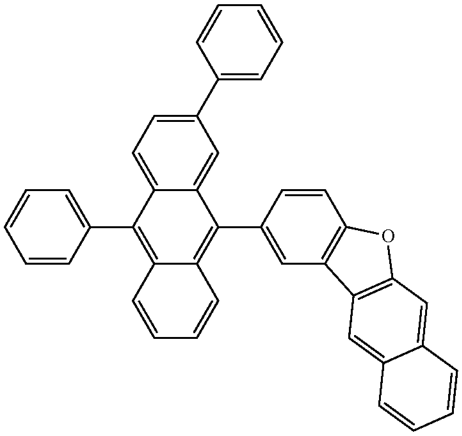
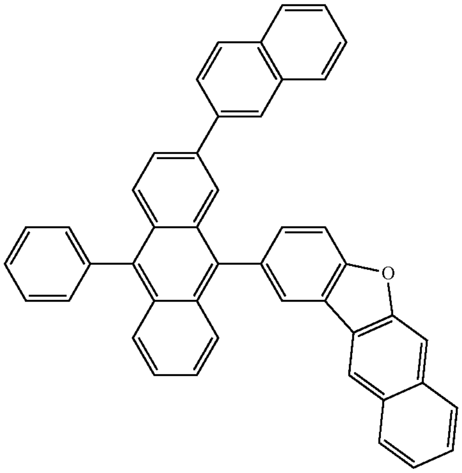

[Formula 185]
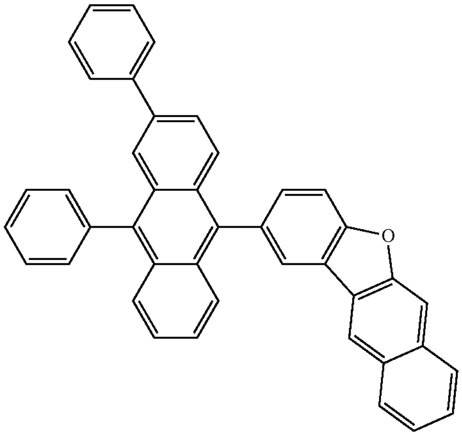
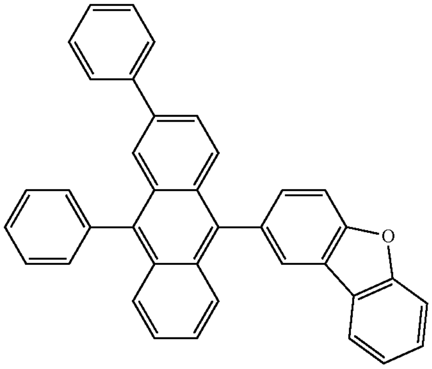
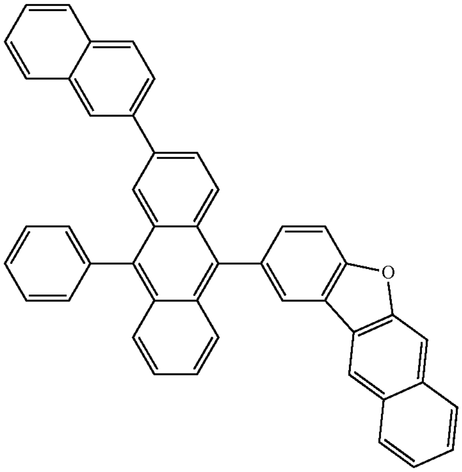
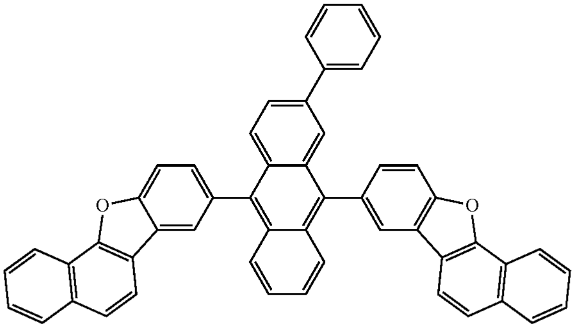
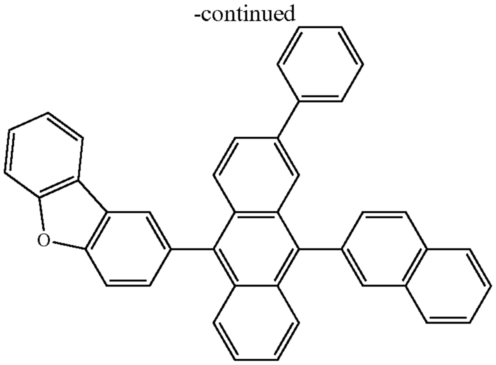
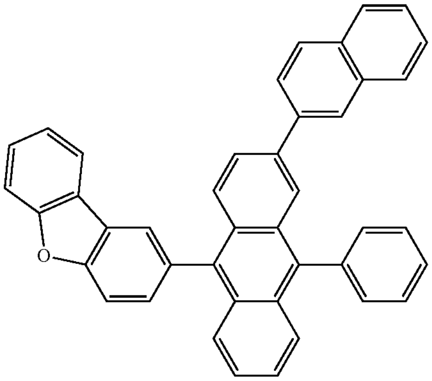
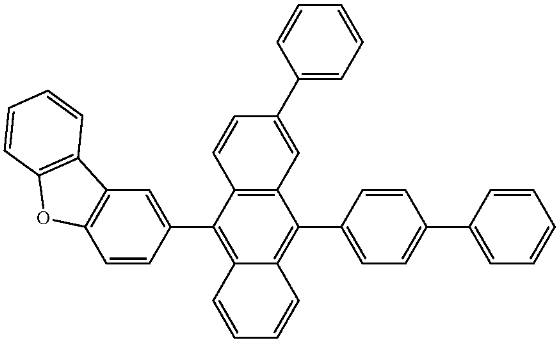
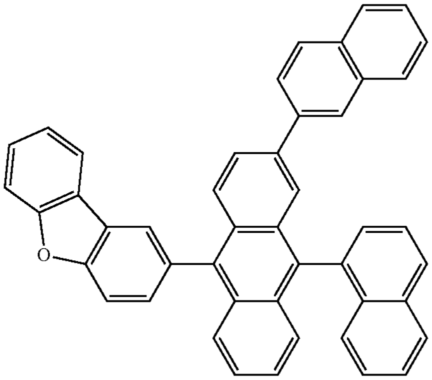

-continued
[Formula 186]
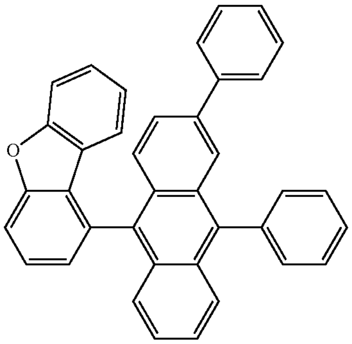
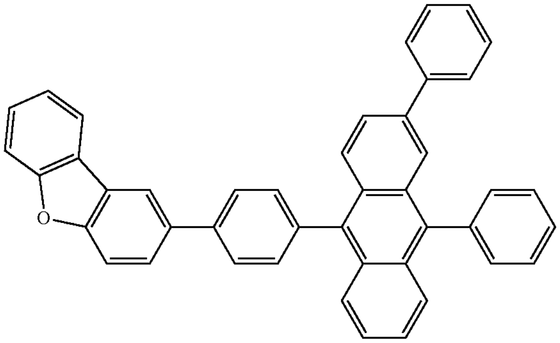
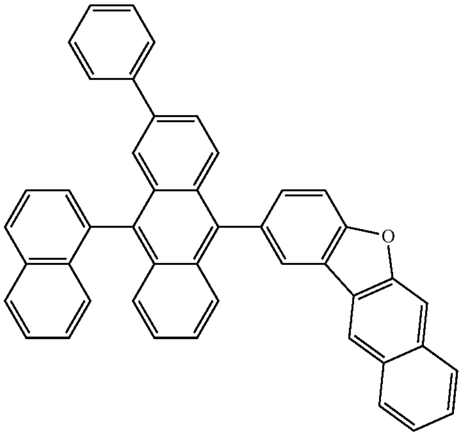
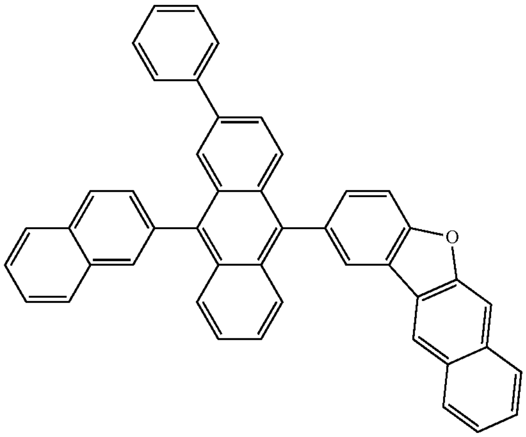
-continued
[Formula 187]
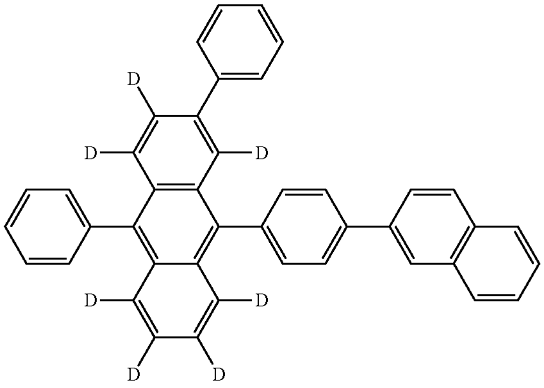
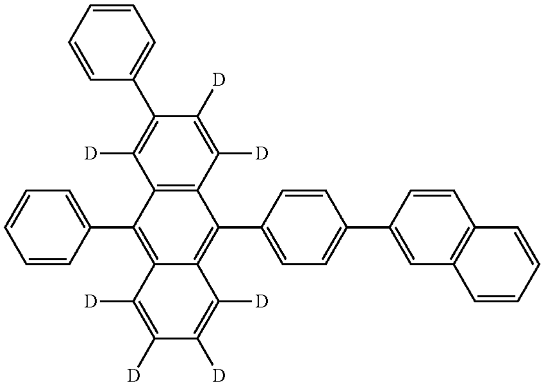
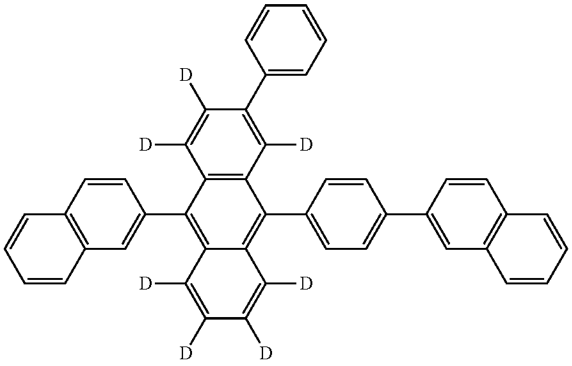
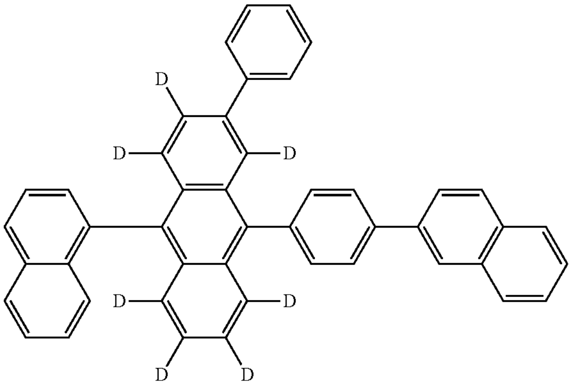

-continued

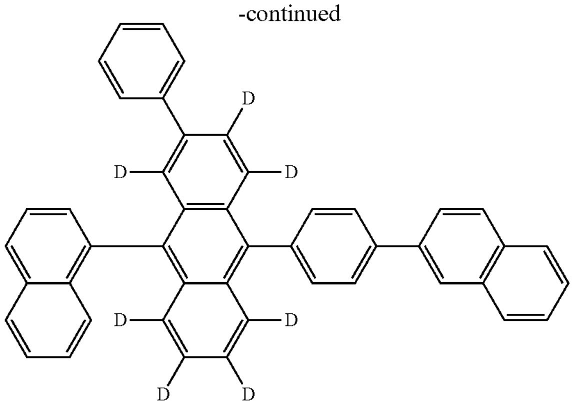

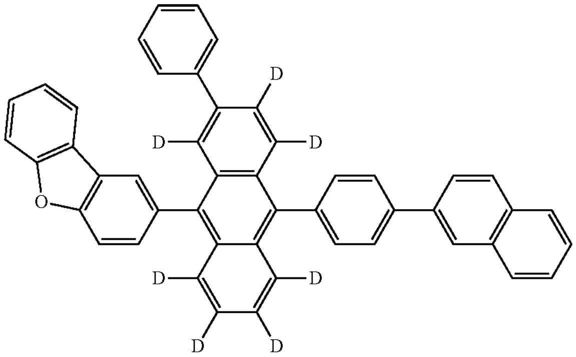

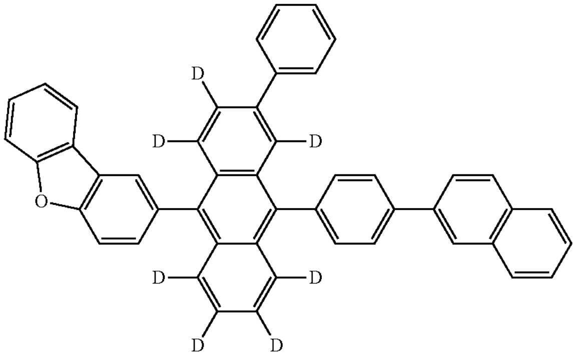

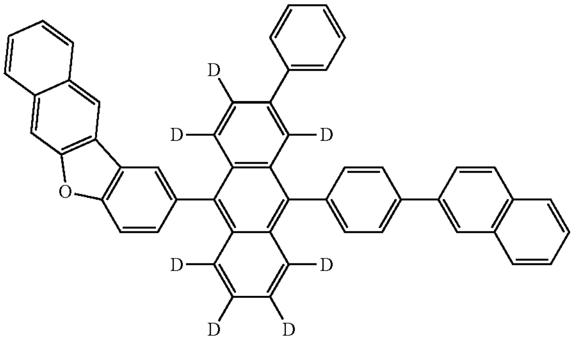

First Dopant Material, Second Dopant Material, and Third Dopant Material

In the organic EL device of the exemplary embodiment, the first dopant material, the second dopant material, and the third dopant material are exemplified by a third compound and a fourth compound.

The third compound and the fourth compound are each independently at least one compound selected from the group consisting of a compound represented by a formula (3) below, a compound represented by a formula (4) below, a compound represented by a formula (5) below, a compound represented by a formula (6) below, a compound represented by a formula (7) below, a compound represented by a formula (8) below, the compound represented by the formula (9), and a compound represented by a formula (10) below.

Compound Represented by Formula (3)

A compound represented by the formula (3) will be described.

[Formula 188]

(3)

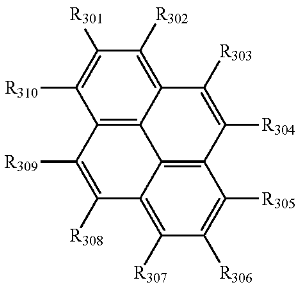

In the formula (3):

at least one combination of adjacent two or more of $R_{301}$ to $R_{310}$ are mutually bonded to form a substituted or unsubstituted monocyclic ring, mutually bonded to form a substituted or unsubstituted fused ring, or not mutually bonded;

at least one of $R_{301}$ to $R_{310}$ is a monovalent group represented by a formula (31) below; and $R_{301}$ to $R_{310}$ forming neither the monocyclic ring nor the fused ring and not being the monovalent group represented by the formula (31) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 189]

(31)

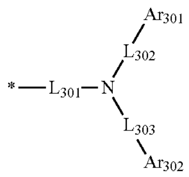

In the formula (31):

$Ar_{301}$ and $Ar_{302}$ are each independently a substituted or unsubstituted aryl group having 6 to 50 ring carbon atoms, or a substituted or unsubstituted heterocyclic group having 5 to 50 ring atoms;

$L_{301}$ to $L_{303}$ are each independently a single bond, a substituted or unsubstituted arylene group having 6 to 30 ring carbon atoms, or a substituted or unsubstituted divalent heterocyclic group having 5 to 30 ring atoms; and

* represents a bonding position with a pyrene ring in the formula (3).

In the third compound and the fourth compound, $R_{901}$, $R_{902}$, $R_{903}$, $R_{904}$, $R_{905}$, $R_{906}$, and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

Two of $R_{301}$ to $R_{310}$ in the formula (3) are preferably a group represented by the formula (31).

In an exemplary embodiment, a compound represented by the formula (3) is a compound represented by a formula (33) below.

[Formula 190]

(33)

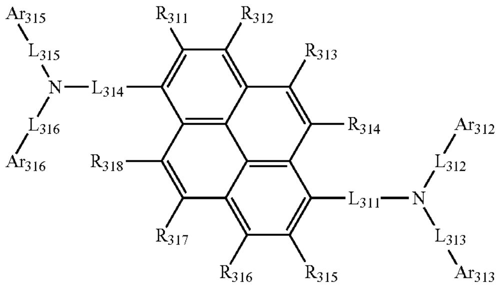

In the formula (33):

$R_{311}$ to $R_{318}$ each independently represent the same as $R_{301}$ to $R_{310}$ in the formula (3) that are not a monovalent group represented by the formula (31);

$L_{311}$ to $L_{316}$ are each independently a single bond, a substituted or unsubstituted arylene group having 6 to 30 ring carbon atoms, or a substituted or unsubstituted divalent heterocyclic group having 5 to 30 ring atoms; and $Ar_{312}$, $Ar_{313}$, $Ar_{315}$, and $Ar_{316}$ are each independently a substituted or unsubstituted aryl group having 6 to 50 ring carbon atoms, or a substituted or unsubstituted heterocyclic group having 5 to 50 ring atoms.

In the formula (31), $L_{301}$ is preferably a single bond, and $L_{302}$ and $L_{303}$ are preferably a single bond.

In an exemplary embodiment, a compound represented by the formula (3) is represented by a formula (34) or a formula (35) below.

[Formula 191]

(34)

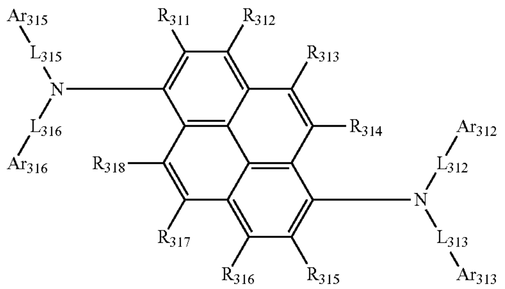

In the formula (34):

$R_{311}$ to $R_{318}$ each independently represent the same as $R_{301}$ to $R_{310}$ in the formula (3) that are not a monovalent group represented by the formula (31);

$L_{312}$, $L_{313}$, $L_{315}$, and $L_{316}$ each independently represent the same as $L_{312}$, $L_{313}$, $L_{315}$, and $L_{316}$ in the formula (33); and $Ar_{312}$, $Ar_{313}$, $Ar_{315}$, and $Ar_{316}$ each independently represent the same as $Ar_{312}$, $Ar_{313}$, $Ar_{315}$, and $Ar_{316}$ in the formula (33).

[Formula 192]

(35)

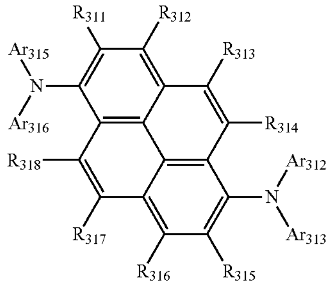

In the formula (35):

$R_{311}$ to $R_{318}$ each independently represent the same as $R_{301}$ to $R_{310}$ in the formula (3) that are not a monovalent group represented by the formula (31); and $Ar_{312}$, $Ar_{313}$, $Ar_{315}$, and $Ar_{316}$ each independently represent the same as $Ar_{312}$, $Ar_{313}$, $Ar_{315}$, and $Ar_{316}$ in the formula (33).

In the formula (31), at least one of $Ar_{301}$ or $Ar_{302}$ is preferably a group represented by a formula (36).

In the formulae (33) to (35), at least one of $Ar_{312}$ or $Ar_{313}$ is preferably a group represented by the formula (36).

In the formulae (33) to (35), at least one of $Ar_{315}$ or $Ar_{316}$ is preferably a group represented by the formula (36).

[Formula 193]

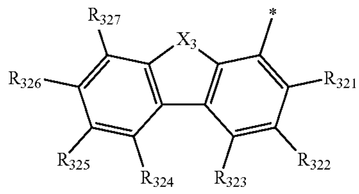

(36)

In the formula (36):

$X_3$ represents an oxygen atom or a sulfur atom;

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

$R_{321}$ to $R_{327}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and

* represents a bonding position with $L_{302}$, $L_{303}$, $L_{312}$, $L_{313}$, $L_{315}$, or $L_{316}$.

$X_3$ is preferably an oxygen atom.

At least one of $R_{321}$ to $R_{327}$ is preferably a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the formula (31), it is preferable that $Ar_{301}$ is a group represented by the formula (36) and $Ar_{302}$ is a substituted or unsubstituted aryl group having 6 to 50 ring carbon atoms.

In the formulae (33) to (35), it is preferable that $Ar_{312}$ is a group represented by the formula (36) and $Ar_{313}$ is a substituted or unsubstituted aryl group having 6 to 50 ring carbon atoms.

In the formulae (33) to (35), it is preferable that $Ar_{315}$ is a group represented by the formula (36) and $Ar_{316}$ is a substituted or unsubstituted aryl group having 6 to 50 ring carbon atoms.

In an exemplary embodiment, a compound represented by the formula (3) is represented by a formula (37) below.

[Formula 194]

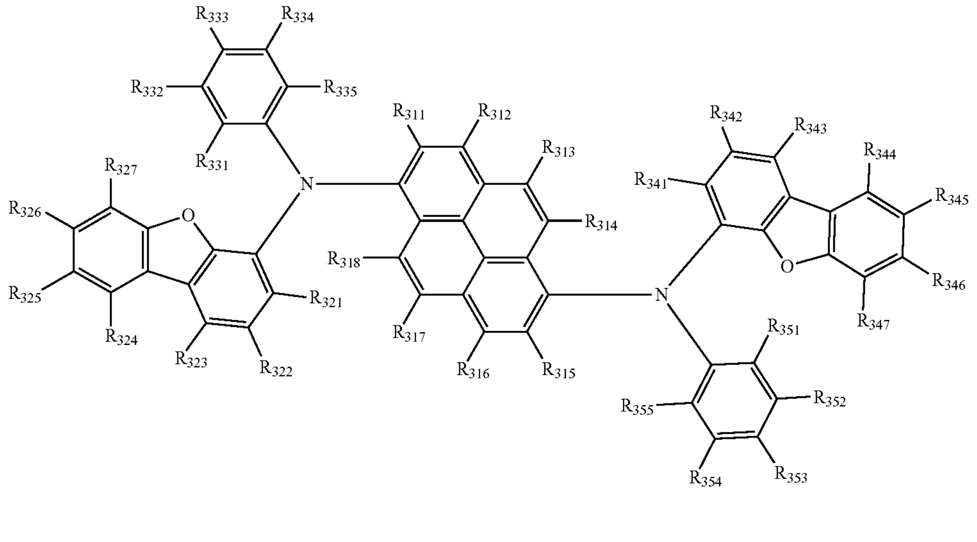

(37)

In the formula (37):

$R_{311}$ to $R_{318}$ each independently represent the same as $R_{301}$ to $R_{310}$ in the formula (3) that are not a monovalent group represented by the formula (31);

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

at least one combination of adjacent two or more of $R_{341}$ to $R_{347}$ are mutually bonded to form a substituted or unsubstituted monocyclic ring, mutually bonded to form a substituted or unsubstituted fused ring, or not mutually bonded;

$R_{321}$ to $R_{327}$ and $R_{341}$ to $R_{347}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{331}$ to $R_{335}$ and $R_{351}$ to $R_{355}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Examples of Compound Represented by Formula (3)

Specific examples of a compound represented by the formula (3) are compounds shown below.

[Formula 195]

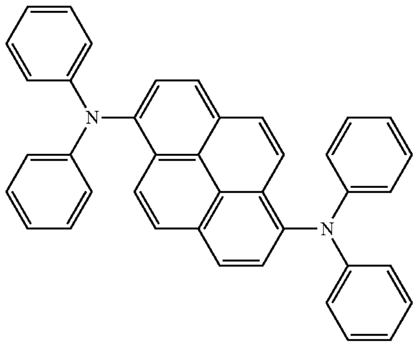

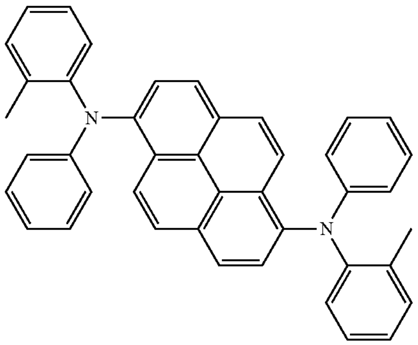

-continued

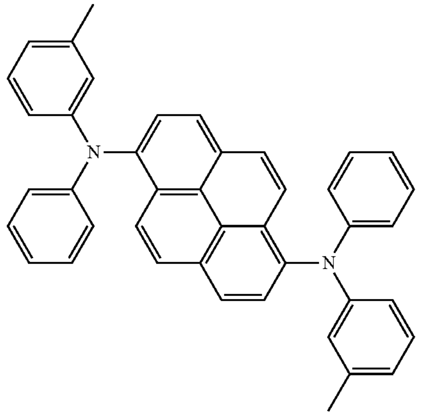

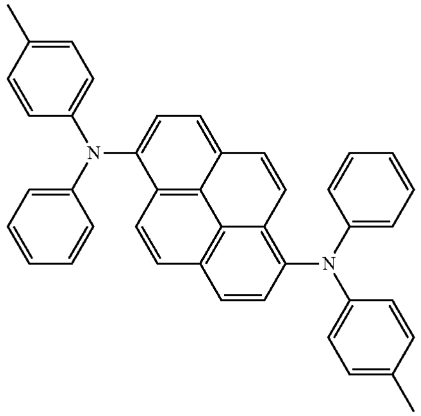

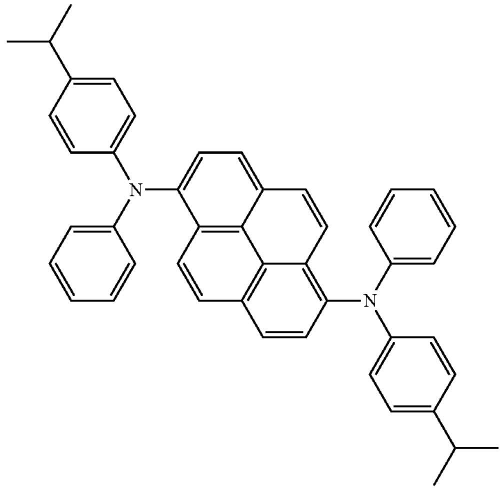

-continued
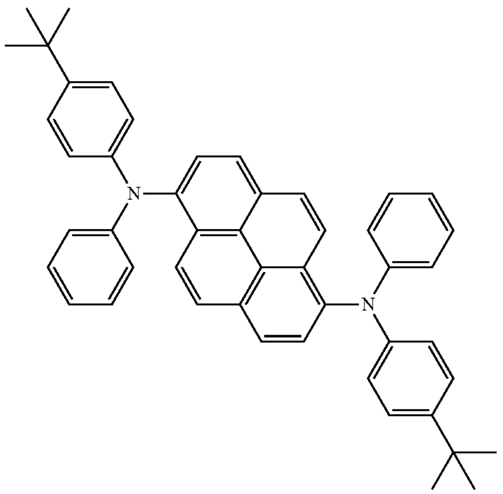
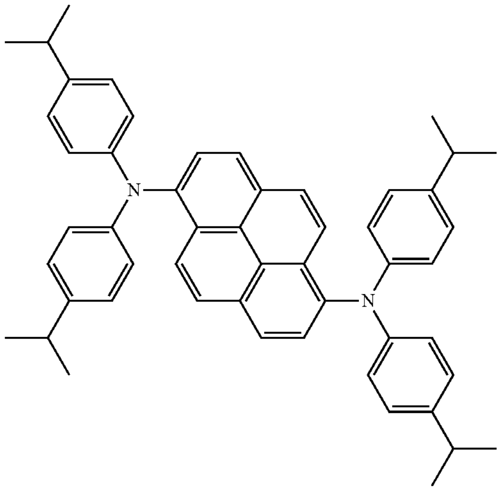
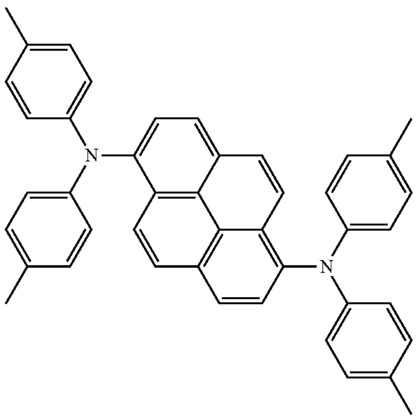
-continued
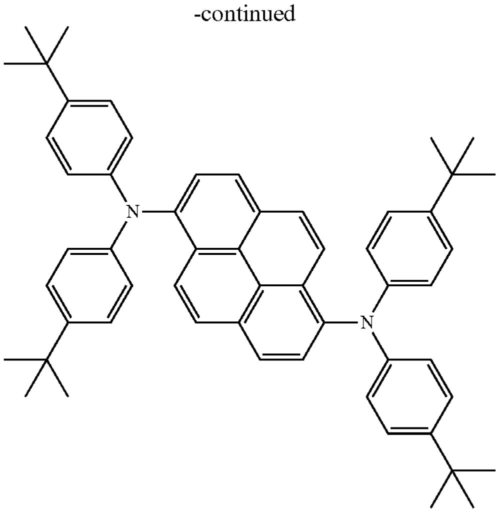
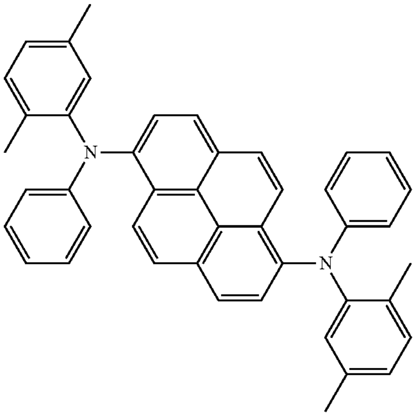
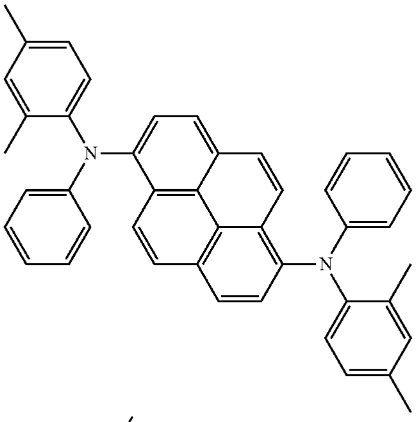
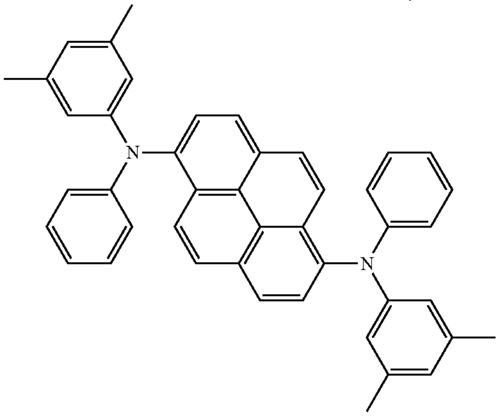

-continued
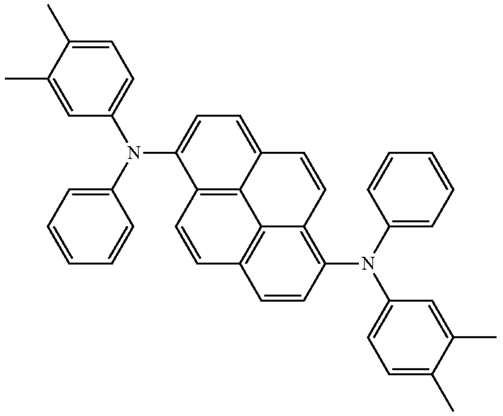
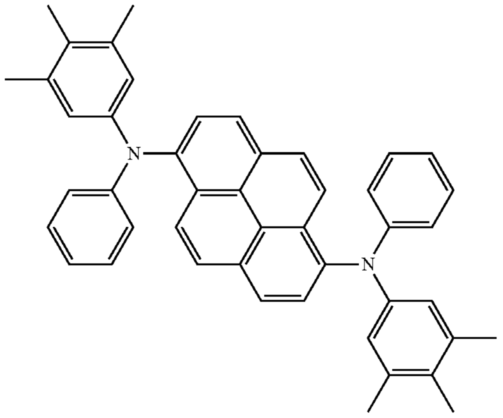
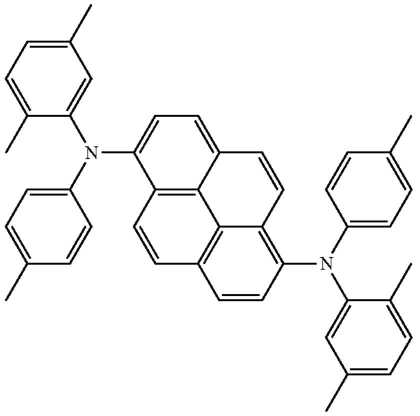
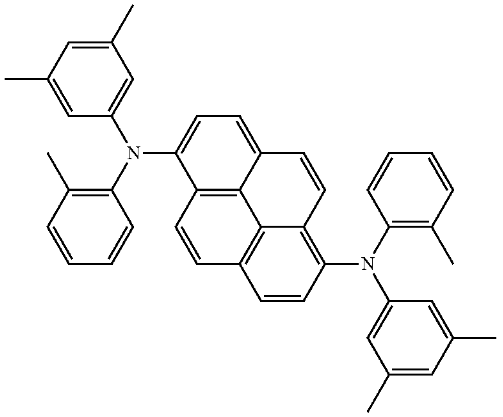
-continued
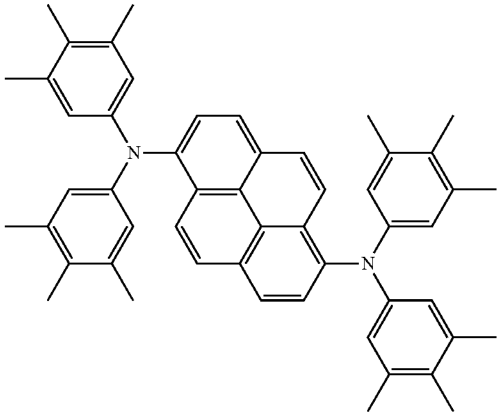
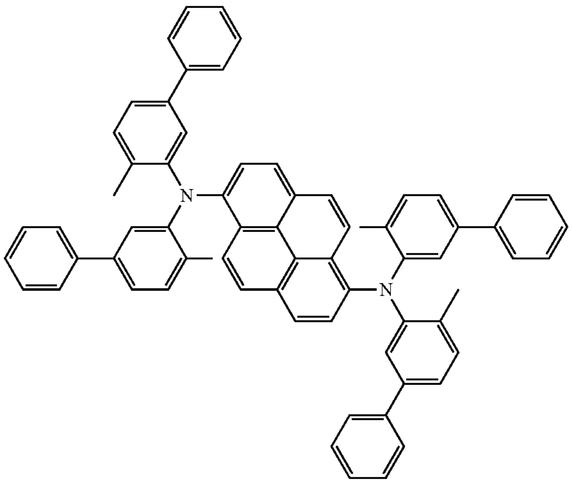
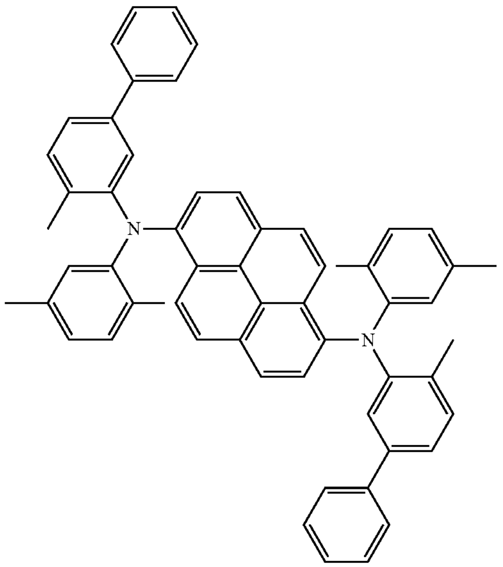

-continued
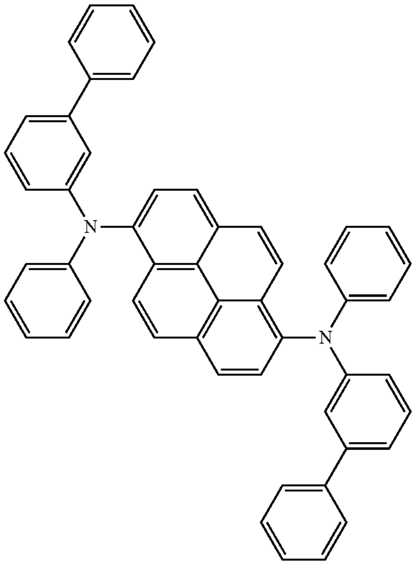
[Formula 196]
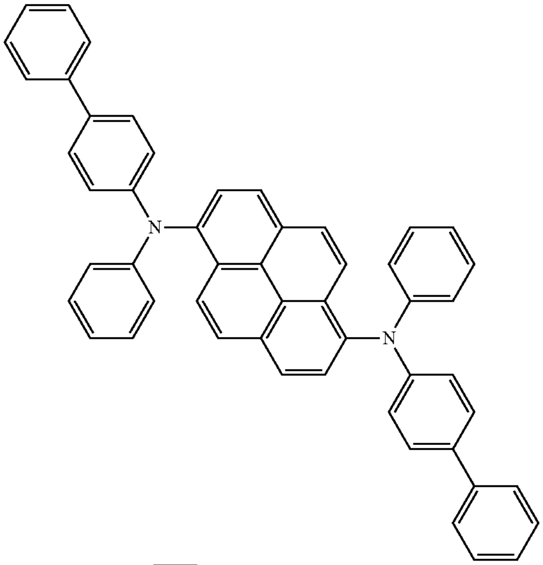
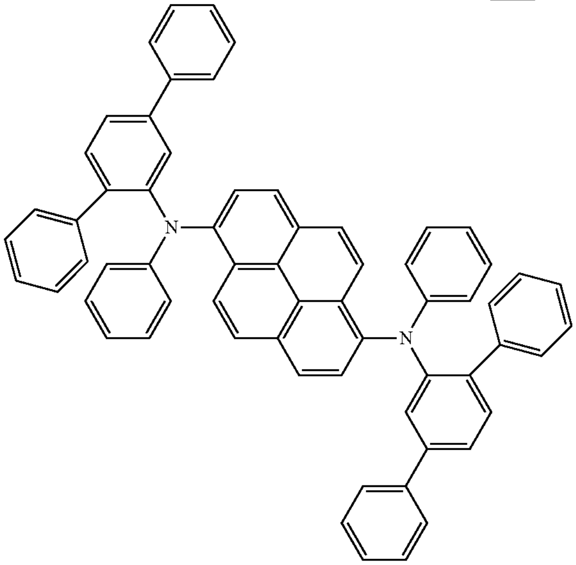
-continued
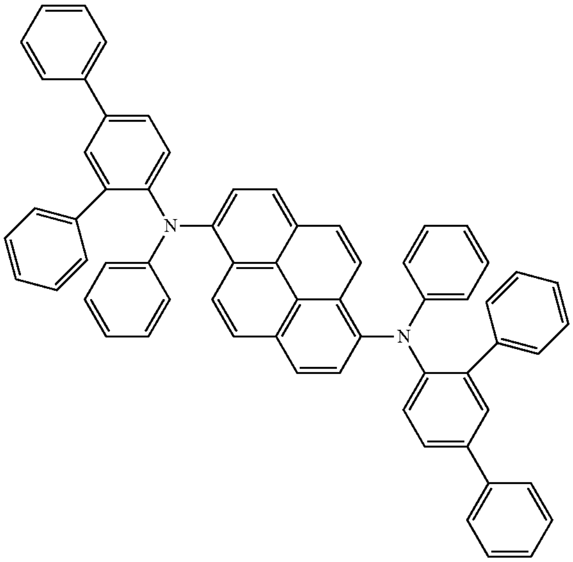
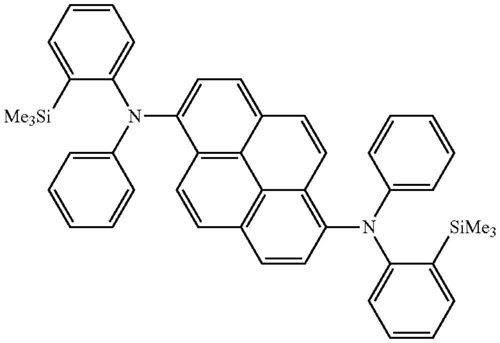
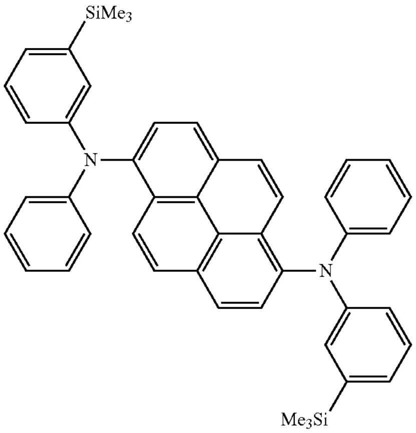

-continued
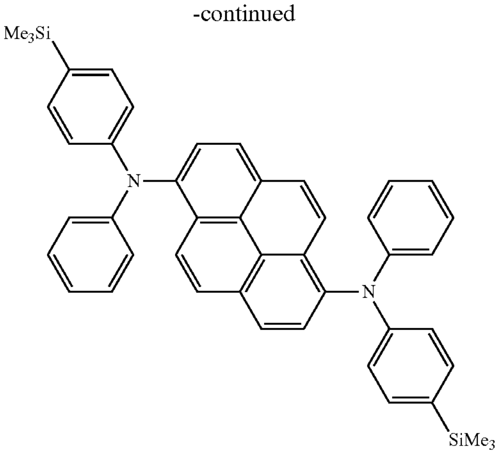
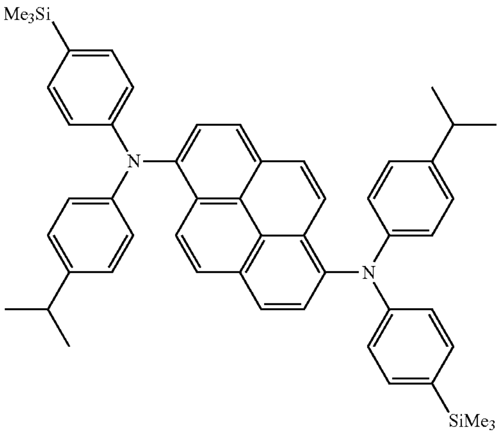
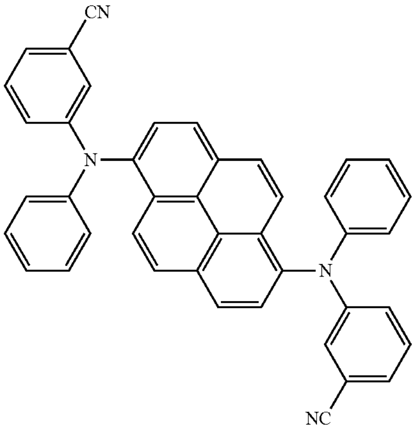
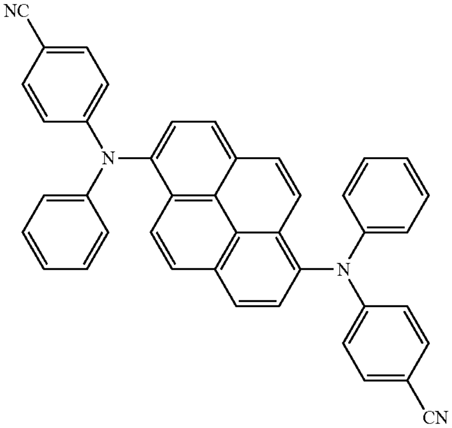
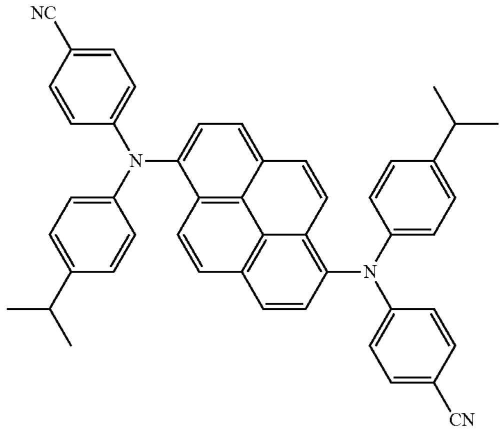
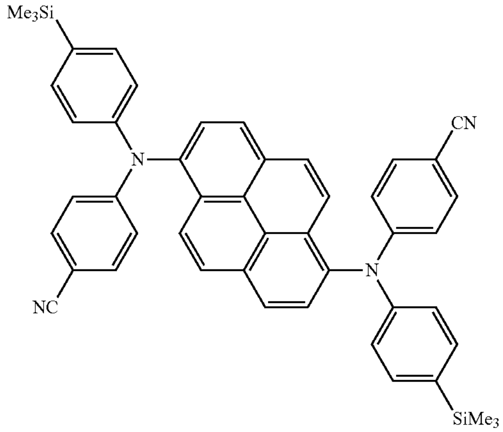
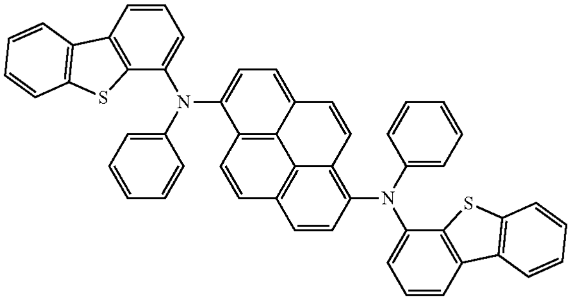
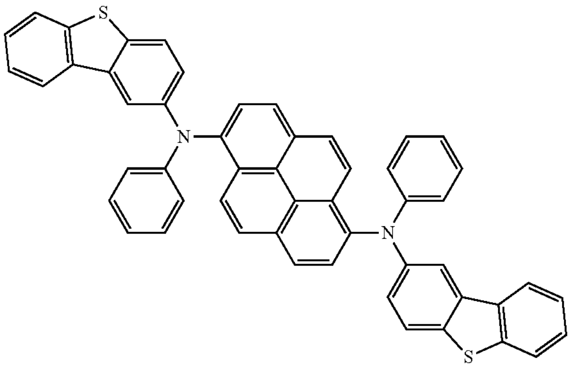

-continued
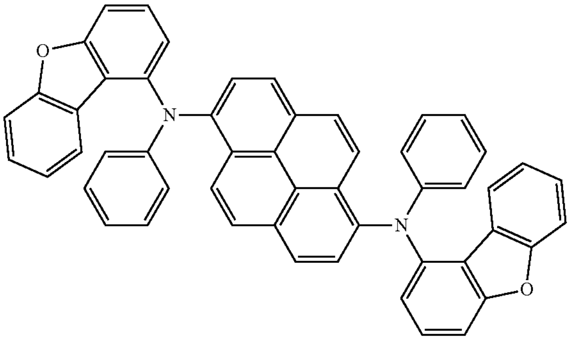
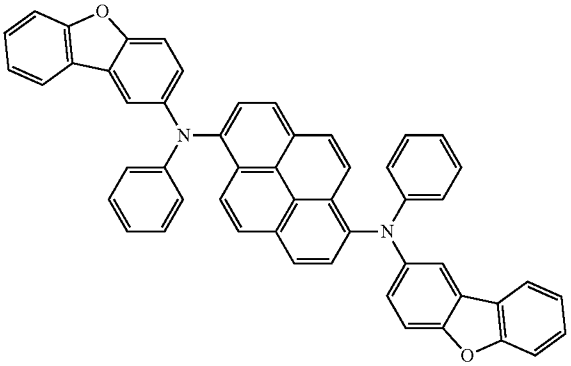
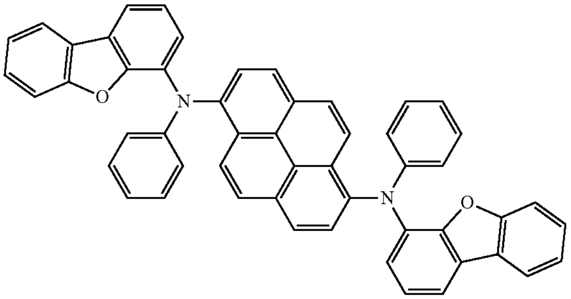
[Formula 197]
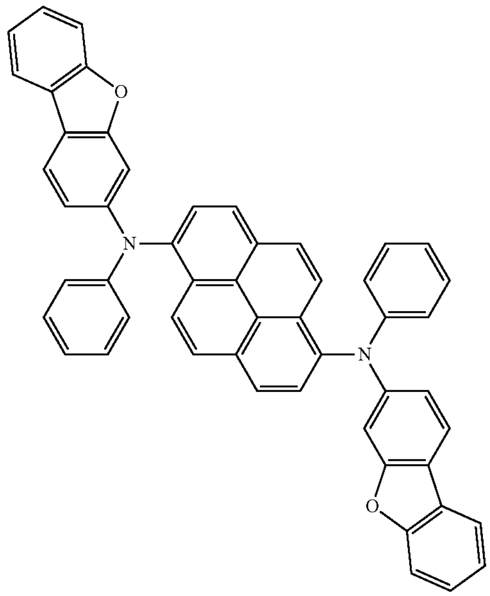
-continued
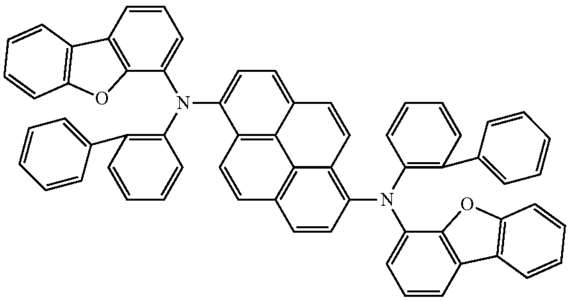
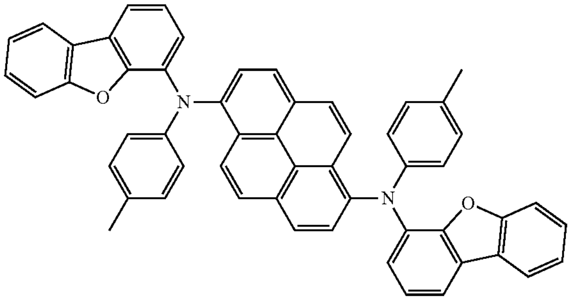
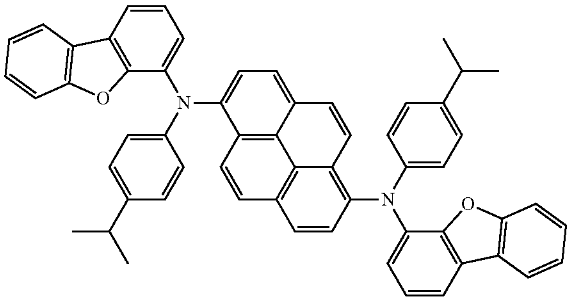
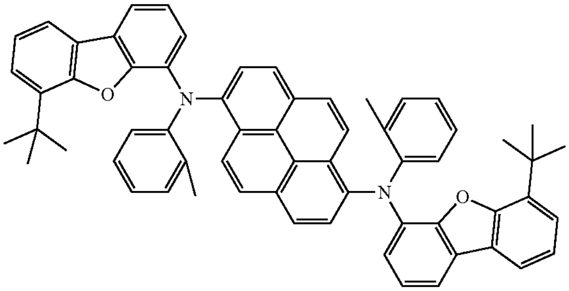
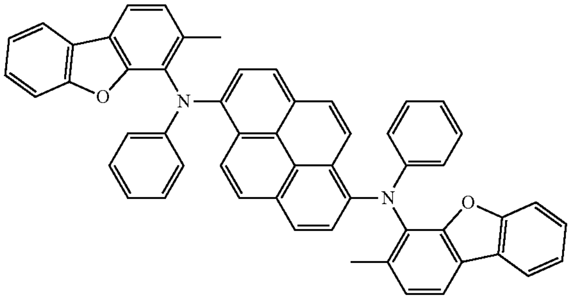

-continued
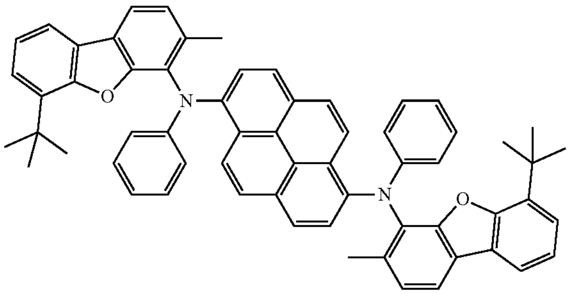
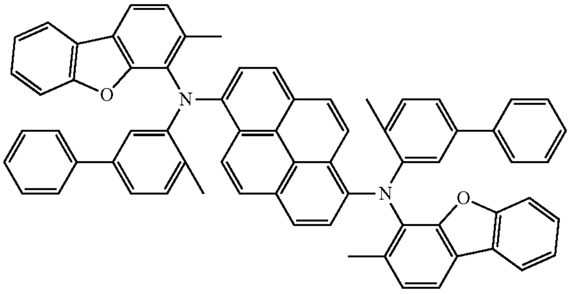
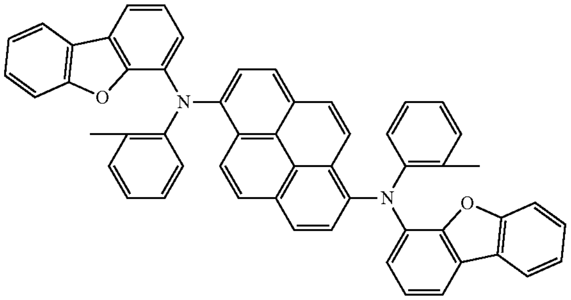
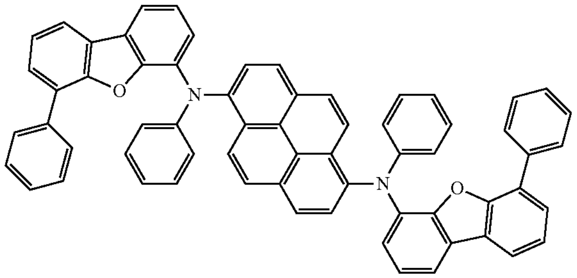
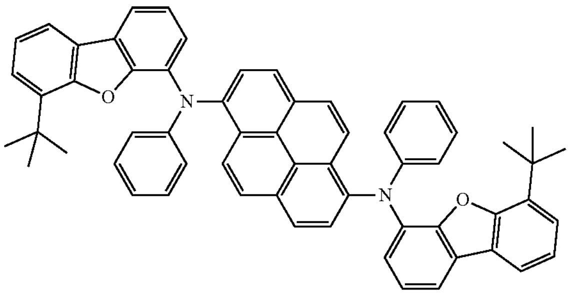
-continued
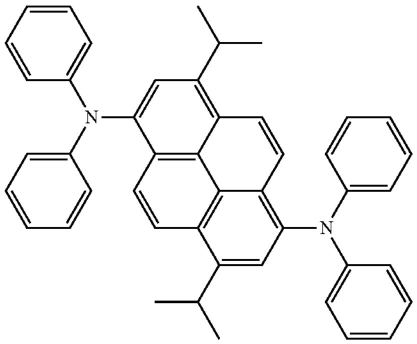
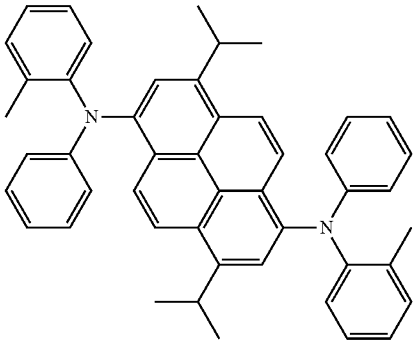
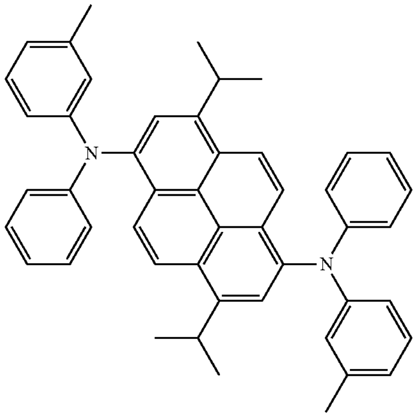
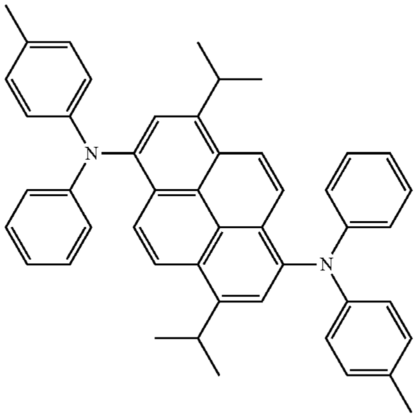

-continued
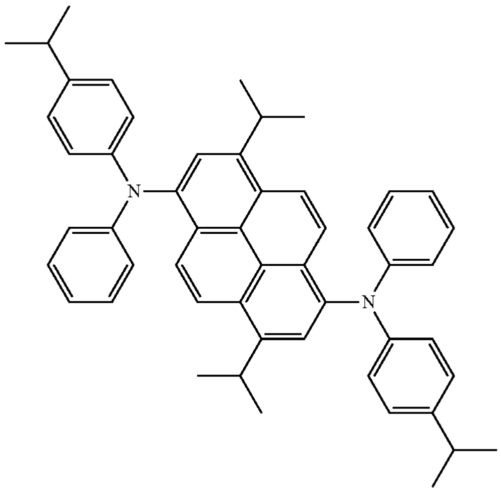
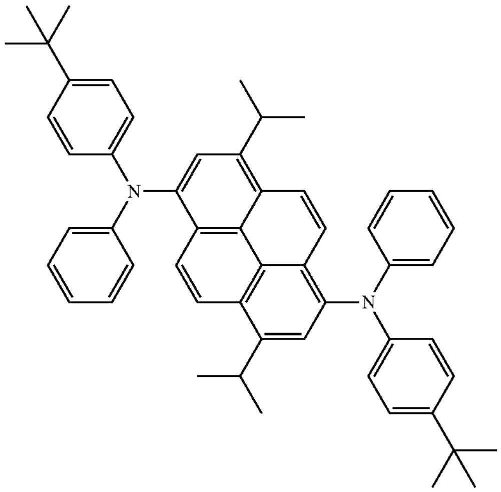
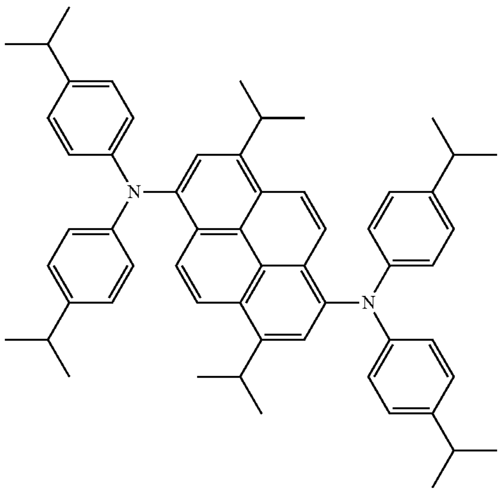
-continued
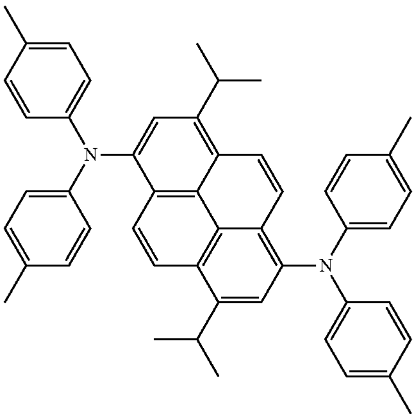
[Formula 198]
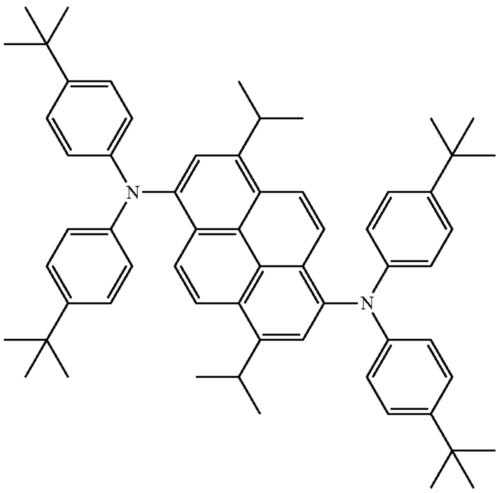
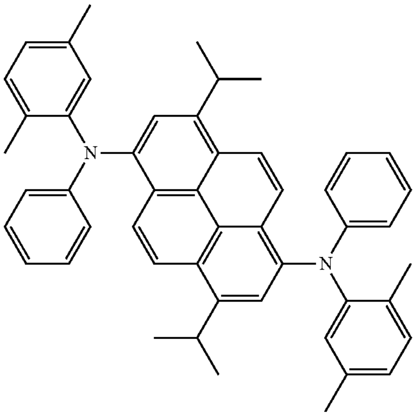

-continued
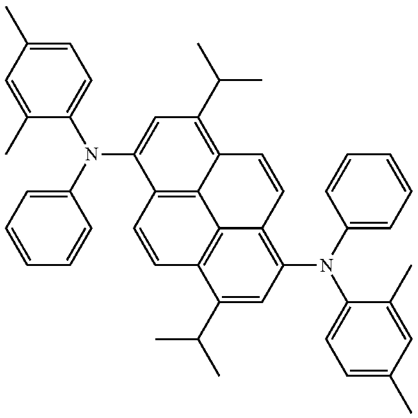
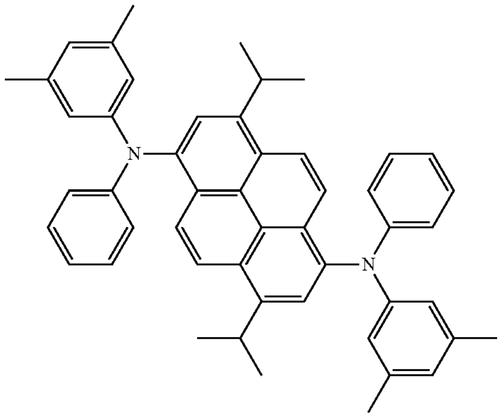
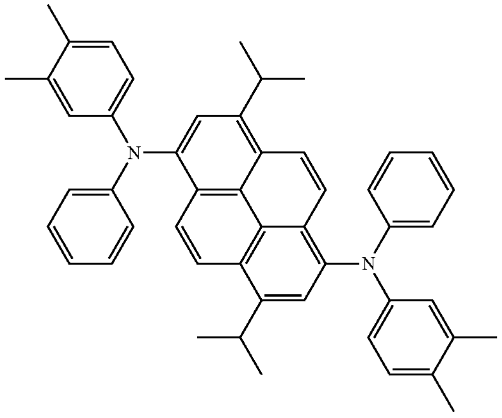
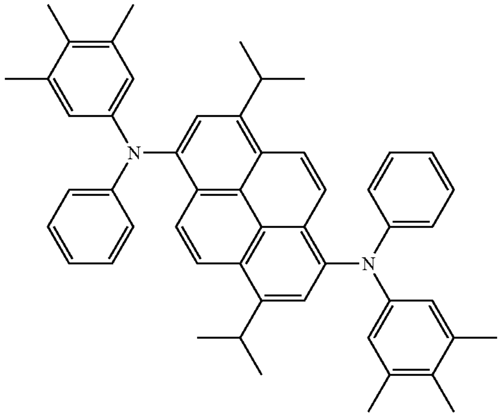
-continued
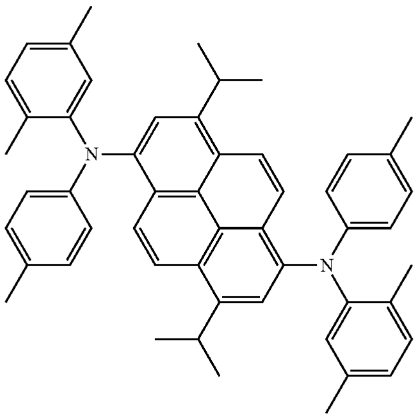
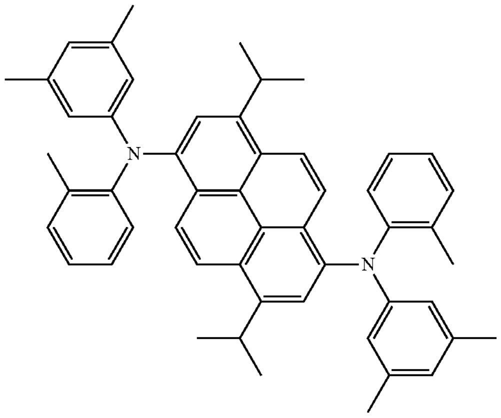
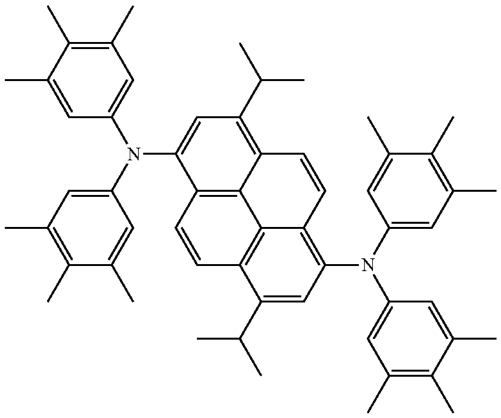
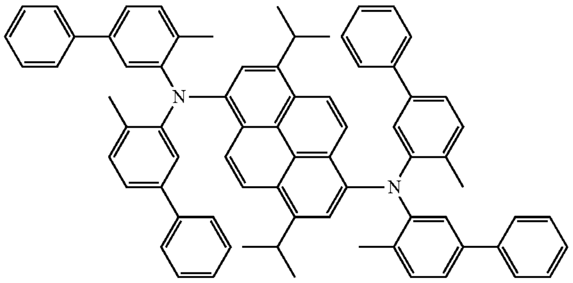

-continued
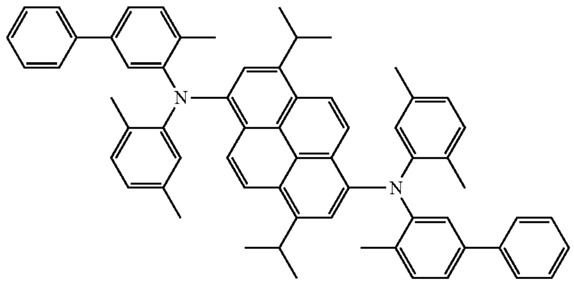
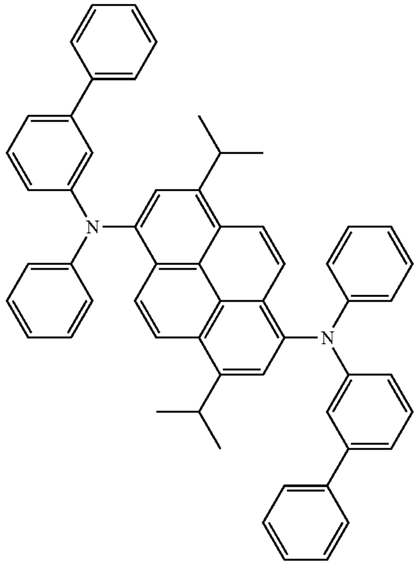
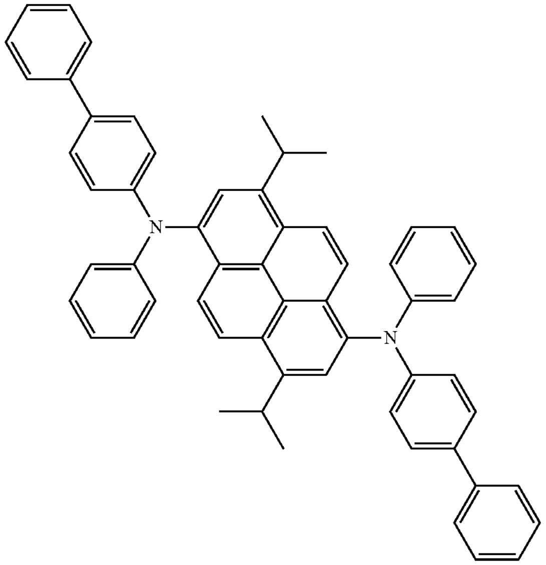
-continued
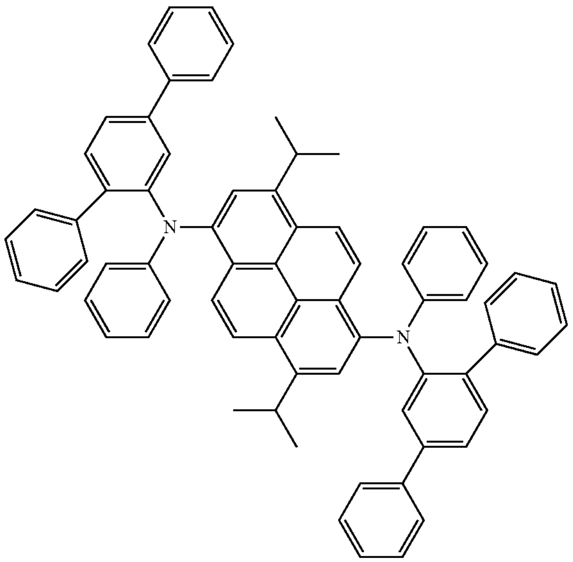
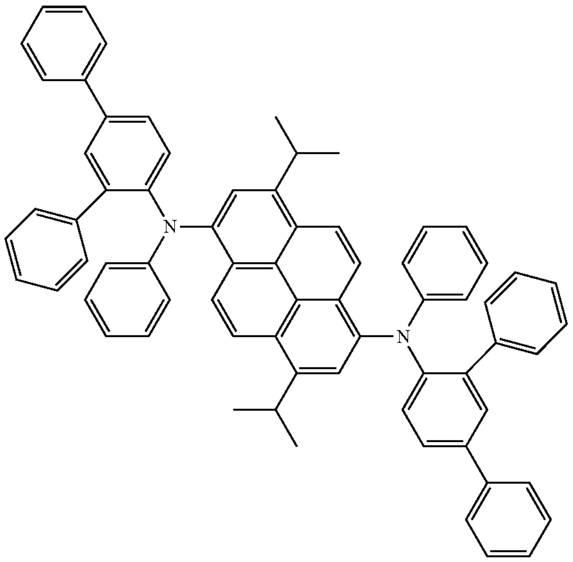
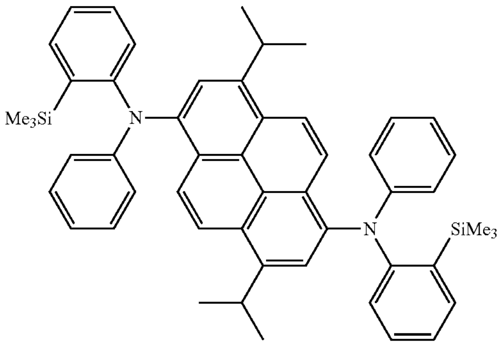

-continued
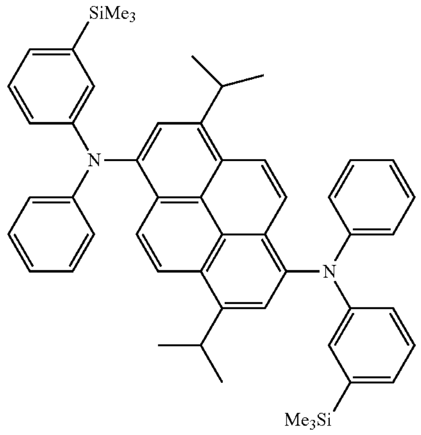
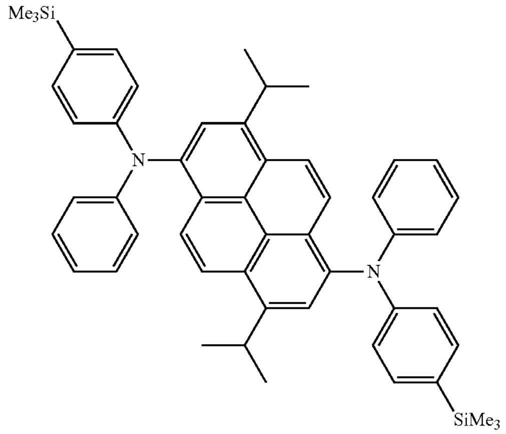
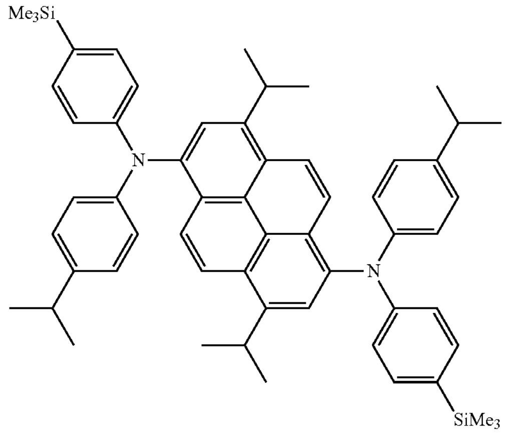
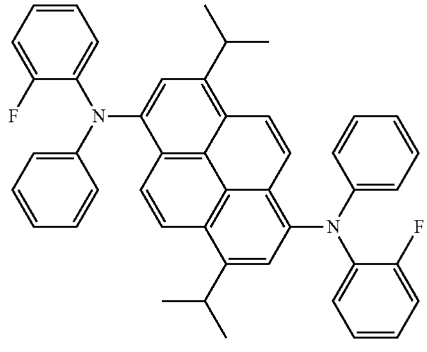
-continued
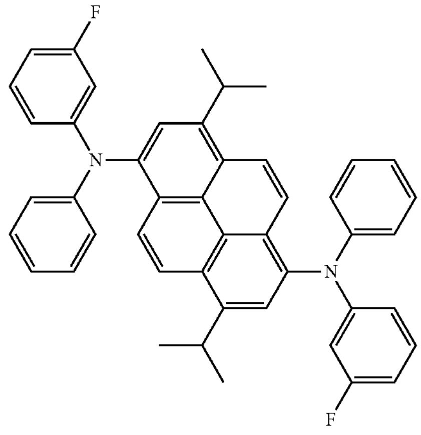
[Formula 199]
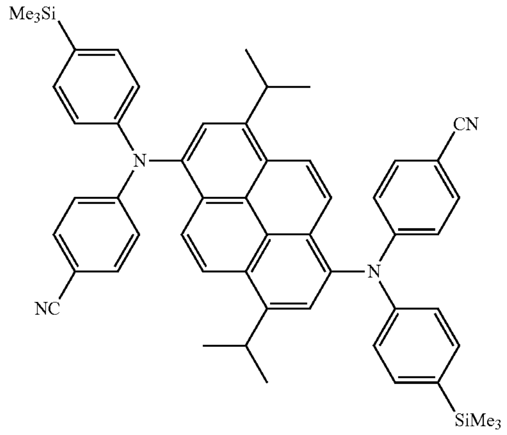
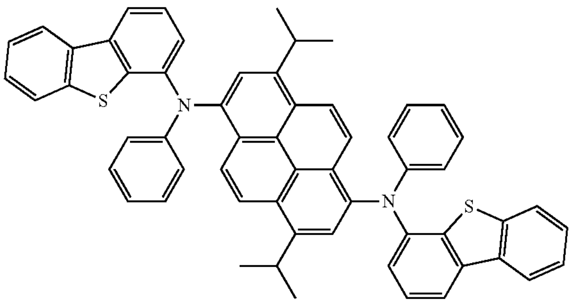
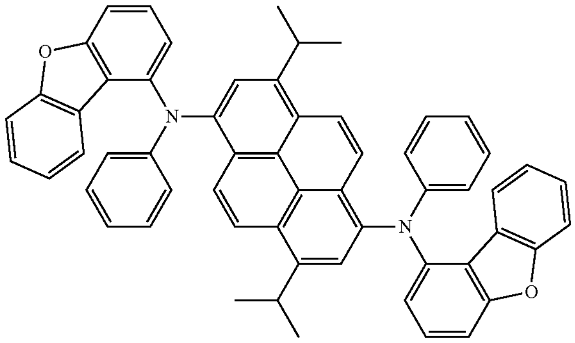

-continued
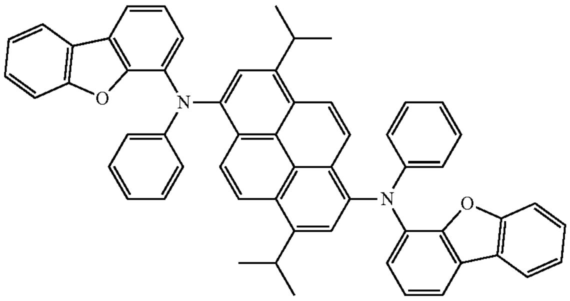
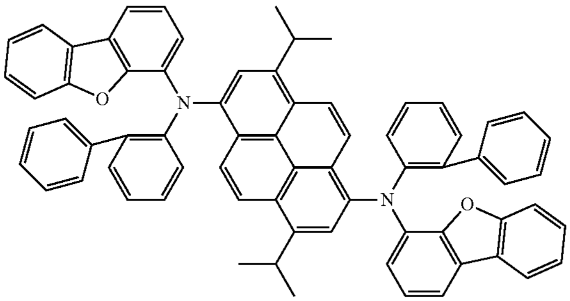
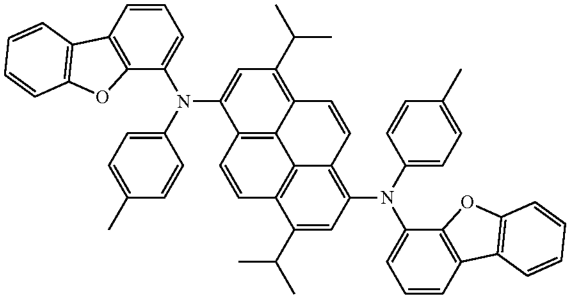
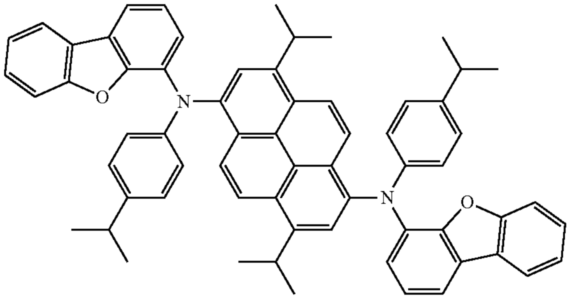
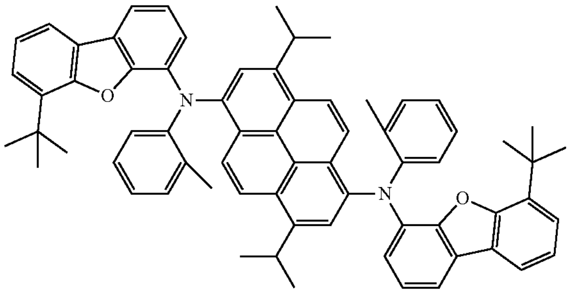
-continued
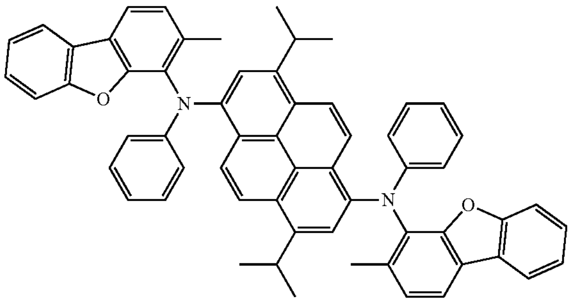
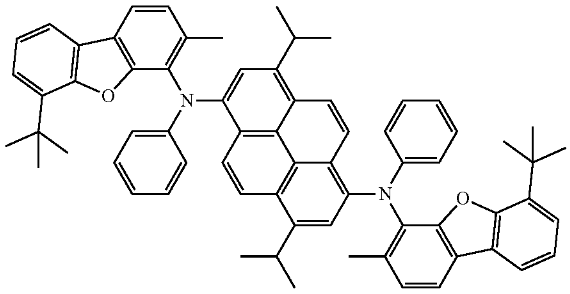
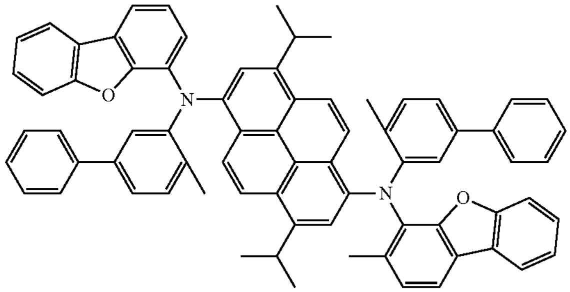
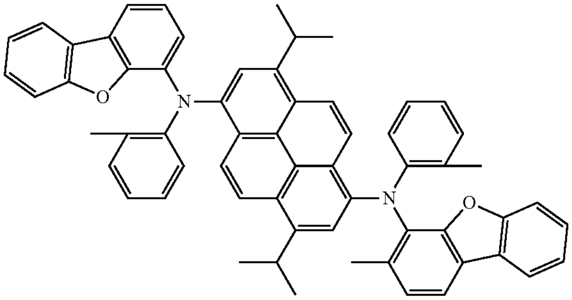
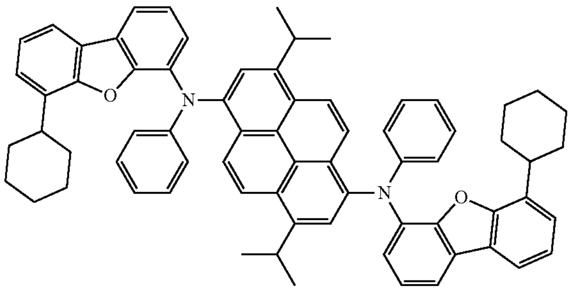

-continued

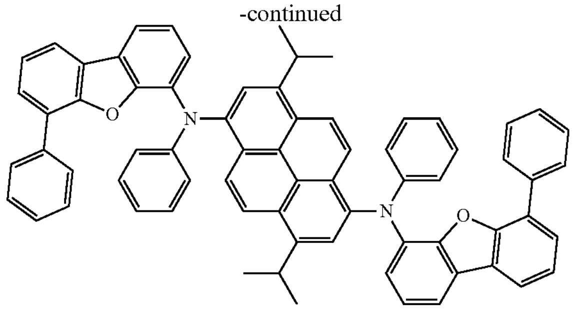

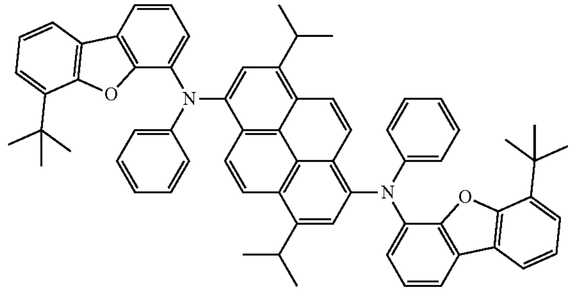

Compound Represented by Formula (4)

The compound represented by the formula (4) will be described below.

[Formula 200]

(4)

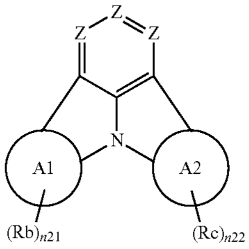

In the formula (4): Z are each independently CRa or a nitrogen atom;

A1 ring and A2 ring are each independently a substituted or unsubstituted aromatic hydrocarbon ring having 6 to 50 ring carbon atoms or a substituted or unsubstituted heterocycle having 5 to 50 ring atoms;

when a plurality of Ra are present, at least one combination of adjacent two or more of Ra are mutually bonded to form a substituted or unsubstituted monocyclic ring, mutually bonded to form a substituted or unsubstituted fused ring, or not mutually bonded;

n21 and n22 are each independently 0, 1, 2, 3 or 4;

when a plurality of Rb are present, at least one combination of adjacent two or more of Rb are mutually bonded to form a substituted or unsubstituted monocyclic ring, mutually bonded to form a substituted or unsubstituted fused ring, or not mutually bonded;

when a plurality of RC are present, at least one combination of adjacent two or more of RC are mutually bonded to form a substituted or unsubstituted monocyclic ring, mutually bonded to form a substituted or unsubstituted fused ring, or not mutually bonded; and Ra, Rb, and RC not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

The "aromatic hydrocarbon ring" for the A1 ring and A2 ring has the same structure as the compound formed by introducing a hydrogen atom to the "aryl group" described above.

Ring atoms of the "aromatic hydrocarbon ring" for the A1 ring and the A2 ring include two carbon atoms on a fused bicyclic structure at the center of the formula (4).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the A1 ring and A2 ring has the same structure as the compound formed by introducing a hydrogen atom to the "heterocyclic group" described above.

Ring atoms of the "heterocycle" for the A1 ring and the A2 ring include two carbon atoms on a fused bicyclic structure at the center of the formula (4).

Specific examples of the "substituted or unsubstituted heterocycle having 5 to 50 ring atoms" include a compound formed by introducing a hydrogen atom to the "heterocyclic group" described in the specific example group G2.

Rb is bonded to any one of carbon atoms forming the aromatic hydrocarbon ring for the A1 ring or any one of the atoms forming the heterocycle for the A1 ring.

Rc is bonded to any one of carbon atoms forming the aromatic hydrocarbon ring for the A2 ring or any one of the atoms forming the heterocycle for the A2 ring.

At least one of Ra, Rb, or Rc is preferably a group represented by the formula (4a) below. More preferably, at least two of Ra, Rb, and Rc are groups represented by the formula (4a).

[Formula 201]

$$*\text{-}L_{401}\text{-}Ar_{401} \quad (4a)$$

In the formula (4a): $L_{401}$ is preferably a single bond, a substituted or unsubstituted arylene group having 6 to 30 ring carbon atoms, or a substituted or unsubstituted divalent heterocyclic group having 5 to 30 ring atoms; and $Ar_{401}$ is a substituted or unsubstituted aryl group having 6 to 50 ring carbon atoms, a substituted or unsubstituted heterocyclic group having 5 to 50 ring atoms, or a group represented by a formula (4b) below.

[Formula 202]

(4b)

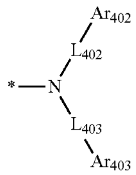

In the formula (4b): $L_{402}$ and $L_{403}$ are each independently a single bond, a substituted or unsubstituted arylene group having 6 to 30 ring carbon atoms, or a substituted or unsubstituted divalent heterocyclic group having 5 to 30 ring atoms;

a combination of $Ar_{402}$ and $Ar_{403}$ are mutually bonded to form a substituted or unsubstituted monocyclic ring, mutually bonded to form a substituted or unsubstituted fused ring, or not mutually bonded; and $Ar_{402}$ and $Ar_{403}$ not forming the monocyclic ring and not forming the fused ring are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is represented by a formula (42) below.

[Formula 203]

(42)

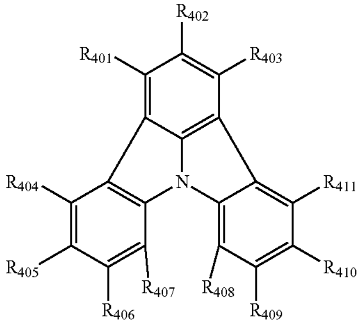

In the formula (42): at least one combination of adjacent two or more of $R_{401}$ to $R_{411}$ are mutually bonded to form a substituted or unsubstituted monocyclic ring, mutually bonded to form a substituted or unsubstituted fused ring, or not mutually bonded; and $R_{401}$ to $R_{411}$ neither forming the monocyclic ring nor forming the fused ring each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

At least one of $R_{401}$ to $R_{411}$ is preferably a group represented by the formula (4a). More preferably, at least two of $R_{401}$ to $R_{411}$ are groups represented by the formula (21a).

$R_{404}$ and $R_{411}$ are preferably groups represented by the formula (4a).

In an exemplary embodiment, the compound represented by the formula (4) is a compound formed by bonding a moiety represented by a formula (4-1) or a formula (4-2) below to the A1 ring.

Further, in an exemplary embodiment, the compound represented by the formula (42) is a compound formed by bonding the moiety represented by the formula (4-1) or the formula (4-2) to the ring bonded with $R_{404}$ to $R_{407}$.

[Formula 204]

(4-1)

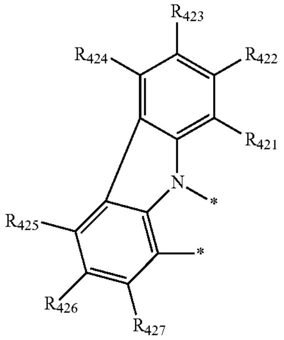

(4-2)

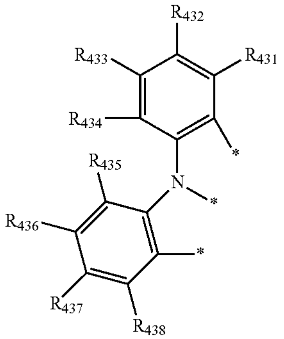

In the formula (4-1), two * are each independently bonded to the ring carbon atom of the aromatic hydrocarbon ring or the ring atom of the heterocycle for the A1 ring in the formula (4) or bonded to one of $R_{404}$ to $R_{407}$ in the formula (42).

In the formula (4-2), three * are each independently bonded to the ring carbon atom of the aromatic hydrocarbon ring or the ring atom of the heterocycle for the A1 ring in the formula (4) or bonded to one of $R_{404}$ to $R_{407}$ in the formula (42).

At least one combination of adjacent two or more of $R_{421}$ to $R_{427}$ are mutually bonded to form a substituted or unsubstituted monocyclic ring, mutually bonded to form a substituted or unsubstituted fused ring, or not mutually bonded.

At least one combination of adjacent two or more of $R_{431}$ to $R_{438}$ are mutually bonded to form a substituted or unsubstituted monocyclic ring, mutually bonded to form a substituted or unsubstituted fused ring, or not mutually bonded.

$R_{421}$ to $R_{427}$ and $R_{431}$ to $R_{438}$ neither forming the monocyclic ring nor forming the fused ring each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by a formula (41-3), a formula (41-4) or a formula (41-5) below.

[Formula 205]

(41-3)

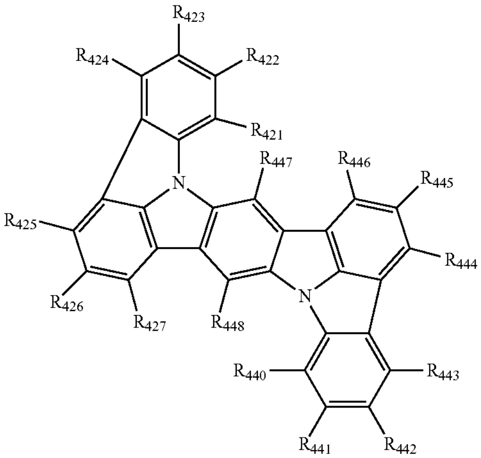

[Formula 206]

(41-4)

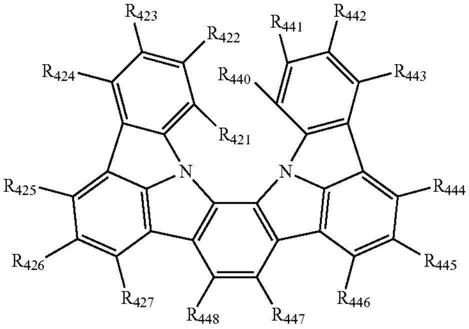

[Formula 207]

(41-5)

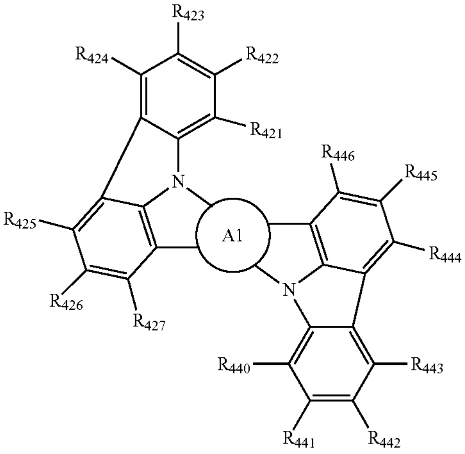

In the formulae (41-3), (41-4), and (41-5):

A1 ring is as defined for the formula (4);

$R_{421}$ to $R_{427}$ each independently represent the same as $R_{421}$ to $R_{427}$ in the formula (4-1); and $R_{440}$ to $R_{448}$ each independently represent the same as $R_{401}$ to $R_{411}$ in the formula (42).

In an exemplary embodiment, a substituted or unsubstituted aromatic hydrocarbon ring having 6 to 50 ring carbon atoms for the A1 ring in the formula (41-5) is a substituted or unsubstituted naphthalene ring, or a substituted or unsubstituted fluorene ring.

In an exemplary embodiment, a substituted or unsubstituted heterocycle having 5 to 50 ring atoms for the A1 ring in the formula (41-5) is a substituted or unsubstituted dibenzofuran ring, a substituted or unsubstituted carbazole ring, or a substituted or unsubstituted dibenzothiophene ring.

In an exemplary embodiment, the compound represented by the formula (4) or the formula (42) is a compound selected from the group consisting of compounds represented by formulae (461) to (467) below.

[Formula 208]

(461)

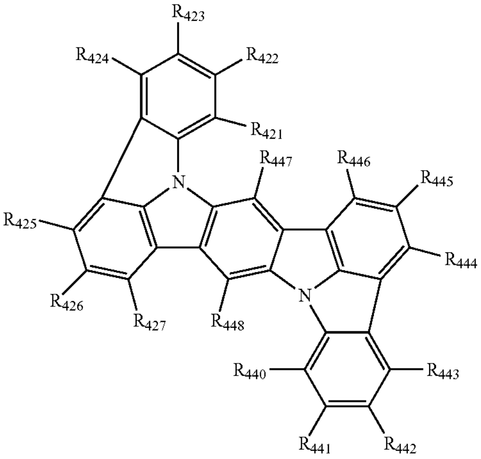

(462)

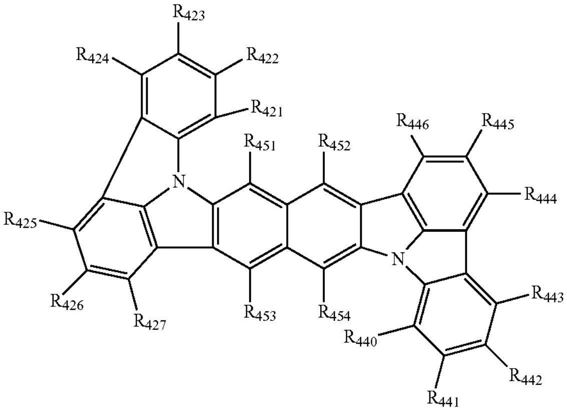

-continued

[Formula 209]

(463)

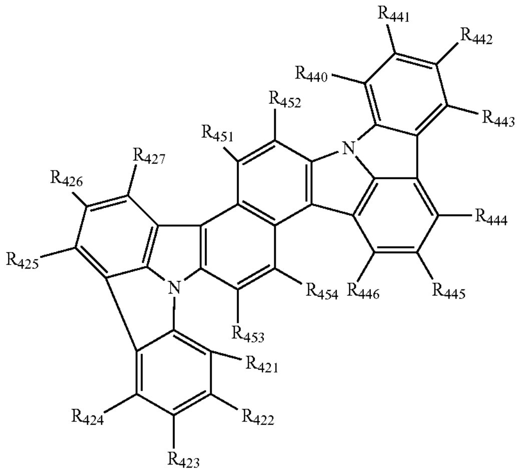

(464)

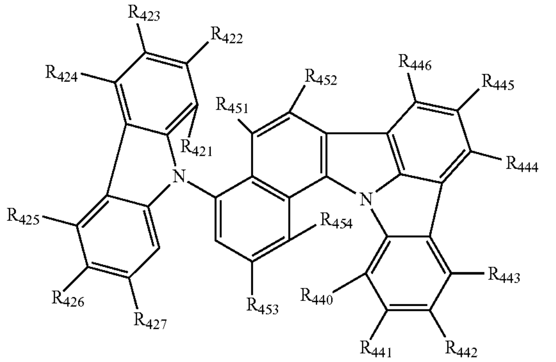

[Formula 210]

(465)

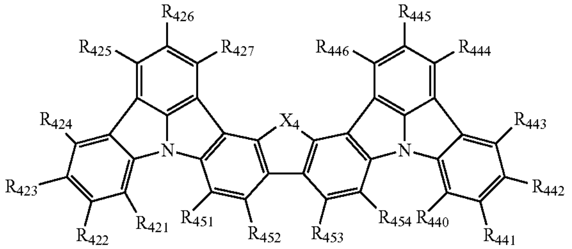

[Formula 211]

(466)

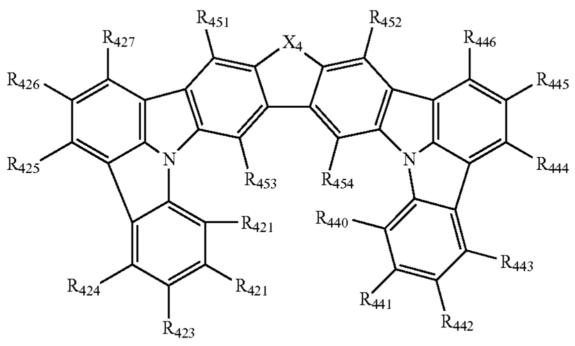

-continued

[Formula 212]

(467)

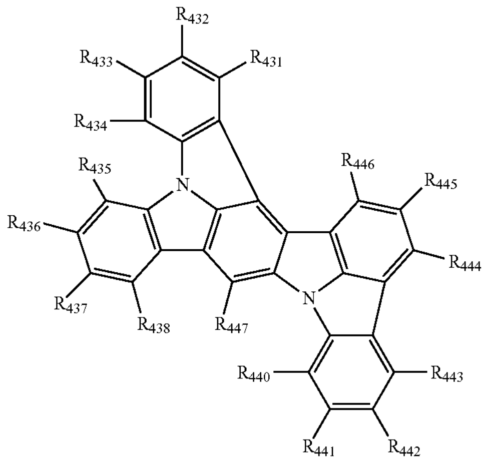

In the formulae (461), (462), (463), (464), (465), (466), and (467):

$R_{421}$ to $R_{427}$ each independently represent the same as $R_{421}$ to $R_{427}$ in the formula (4-1);

$R_{431}$ to $R_{43}$ each independently represent the same as $R_{431}$ to $R_{438}$ in the formula (4-2);

$R_{440}$ to $R_{448}$ and $R_{41}$ to $R_{454}$ each independently represent the same as $R_{401}$ to $R_{411}$ in the formula (42);

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, in the compound represented by the formula (42), at least one combination of adjacent two or more of $R_{401}$ to $R_{411}$ are mutually bonded to form a substituted or unsubstituted monocyclic ring or a substituted or unsubstituted fused ring. The compound represented by the formula (42) in the exemplary embodiment is described in detail as a compound represented by a formula (45).

Compound Represented by Formula (45)

The compound represented by the formula (45) will be described.

[Formula 213]

(45)

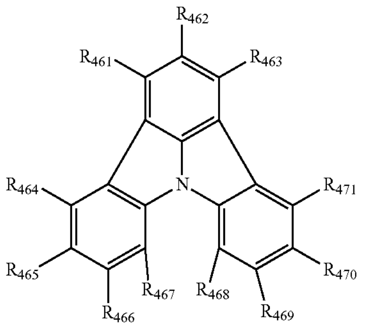

In the formula (45), two or more of combinations selected from the group consisting of a combination of $R_{461}$ and $R_{462}$, a combination of $R_{462}$ and $R_{463}$, a combination of $R_{464}$ and $R_{465}$, a combination of $R_{465}$ and $R_{466}$, a combination of $R_{466}$ and $R_{467}$, a combination of $R_{468}$ and $R_{469}$, a combination of $R_{469}$ and $R_{470}$, and a combination of $R_{470}$ and $R_{471}$ are mutually bonded to form a substituted or unsubstituted monocyclic ring or a substituted or unsubstituted fused ring.

However, the combination of $R_{461}$ and $R_{462}$ and the combination of $R_{462}$ and $R_{463}$, the combination of $R_{464}$ and $R_{465}$ and the combination of $R_{465}$ and $R_{466}$, the combination of $R_{465}$ and $R_{466}$ and the combination of $R_{466}$ and $R_{467}$, the combination of $R_{468}$ and $R_{469}$ and the combination of $R_{469}$ and $R_{470}$, and the combination of $R_{469}$ and $R_{470}$ and the combination of $R_{470}$ and $R_{471}$ do not form a ring at the same time.

At least two rings formed by $R_{461}$ to $R_{471}$ are mutually the same or different.

$R_{461}$ to $R_{471}$ neither forming the monocyclic ring nor forming the fused ring each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

In the formula (45), $R_n$ and $R_{n+1}$ (n being an integer selected from 461, 462, 464 to 466, and 468 to 470) are mutually bonded to form a substituted or unsubstituted monocyclic ring or fused ring together with two ring carbon atoms bonded with $R_n$ and $R_{n+1}$. The ring is preferably formed of atoms selected from the group consisting of a carbon atom, an oxygen atom, a sulfur atom, and a nitrogen atom, and is made of 3 to 7, more preferably 5 or 6 atoms.

The number of the above cyclic structures in the compound represented by the formula (45) is, for instance, 2, 3, or 4. The two or more of the cyclic structures may be present on the same benzene ring on the basic skeleton represented by the formula (45) or may be present on different benzene rings. For instance, when three cyclic structures are present, each of the cyclic structures may be present on corresponding one of the three benzene rings of the formula (45).

Examples of the above cyclic structures in the compound represented by the formula (45) include structures represented by formulae (451) to (460) below.

[Formula 214]

(451)

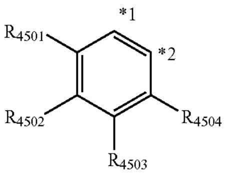

(452)

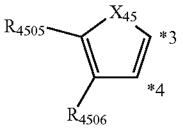

(453)

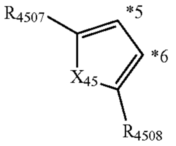

(454)

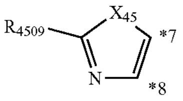

(455)

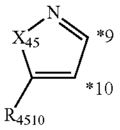

(456)

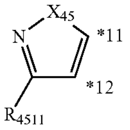

(457)

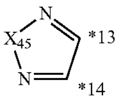

In the formulae (451) to (457):

each combination of *1 and *2, *3 and *4, *5 and *6, *7 and *8, *9 and *10, *11 and *12, and *13 and *14 represent the two ring carbon atoms respectively bonded with $R_n$ and $R_{n+1}$;

the ring carbon atom bonded with $R_n$ may be any one of the two ring carbon atoms represented by *1 and *2, *3 and *4, *5 and *6, *7 and *8, *9 and *10, *11 and *12, and *13 and *14;

$X_{45}$ is $C(R_{4512})(R_{4513})$, $NR_{4514}$, an oxygen atom, or a sulfur atom;

at least one combination of adjacent two or more of $R_{4501}$ to $R_{4506}$ and $R_{4512}$ to $R_{4513}$ are mutually bonded to form a substituted or unsubstituted monocyclic ring, mutually bonded to form a substituted or unsubstituted fused ring, or not mutually bonded; and $R_{4501}$ to $R_{4514}$ not forming the monocyclic ring and not forming the fused ring represent the same as $R_{461}$ to $R_{471}$ in the formula (45).

[Formula 215]

(458)

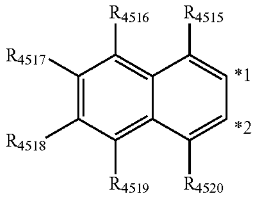

(459)

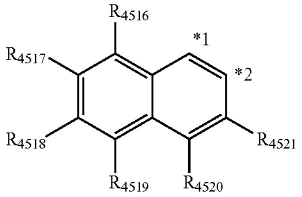

(460)

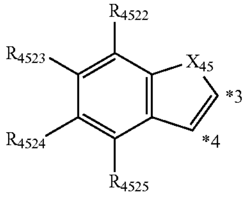

In the formulae (458) to (460):

each combination of *1 and *2, and *3 and *4 represent the two ring carbon atoms each bonded with $R_n$ and $R_{n+1}$;

the ring carbon atom bonded with $R_n$ may be any one of the two ring carbon atoms represented by *1 and *2, or *3 and *4;

$X_{45}$ is $C(R_{4512})(R_{4513})$, $NR_{4514}$, an oxygen atom, or a sulfur atom; at least one combination of adjacent two or more of $R_{4512}$, $R_{4513}$ and $R_{4515}$ to $R_{4525}$ are mutually bonded to form a substituted or unsubstituted monocyclic ring, mutually bonded to form a substituted or unsubstituted fused ring, or not mutually bonded; and $R_{4512}$, $R_{4513}$, $R_{4515}$ to $R_{4521}$ and $R_{4522}$ to $R_{4525}$ not forming the monocyclic ring and not forming the fused ring, and $R_{4514}$ represent the same as $R_{461}$ to $R_{471}$ in the formula (45).

In the formula (45), it is preferable that at least one of $R_{462}$, $R_{464}$, $R_{465}$, $R_{470}$ or $R_{471}$ (preferably, at least one of $R_{462}$, $R_{465}$ or $R_{470}$, more preferably $R_{462}$) is a group not forming the cyclic structure.

(i) A substituent, if present, of the cyclic structure formed by $R_n$ and $R_{n+1}$ of the formula (45), (ii) $R_{461}$ to $R_{471}$ not forming the cyclic structure in the formula (45), and (iii) $R_{4501}$ to $R_{4514}$ and $R_{4515}$ to $R_{4525}$ in the formulae (451) to (460) are each independently preferably selected from the group consisting of a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, a substituted or unsubstituted aryl group having 6 to 50 ring carbon atoms, a substituted or unsubstituted heterocyclic group having 5 to 50 ring atoms, or groups represented by formulae (461) to (464).

[Formula 216]

(461)

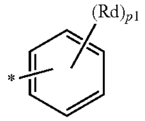

(462)

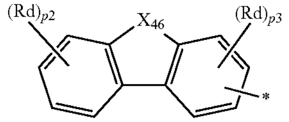

(463)

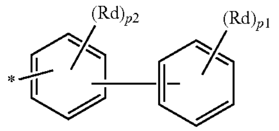

(464)

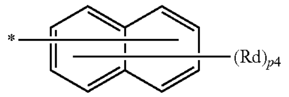

In the formulae (461) to (464): $R_d$ each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

$X_{46}$ represents $C(R_{801})(R_{802})$, $NR_{803}$, an oxygen atom or a sulfur atom;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different; and when a plurality of $R_{802}$ are present, the plurality of $R_{802}$ are mutually the same or different;

when a plurality of $R_{803}$ are present, the plurality of $R_{803}$ are mutually the same or different;

p1 is 5;

p2 is 4;

p3 is 3;

p4 is 7; and

* in the formulae (461) to (464) each independently represents a bonding position with a ring structure.

In the third and fourth compounds, $R_{901}$ to $R_{907}$ represent the same as those as described above.

In an exemplary embodiment, the compound represented by the formula (45) is represented by one of formulae (45-1) to (45-6) below.

[Formula 217]

(45-1)

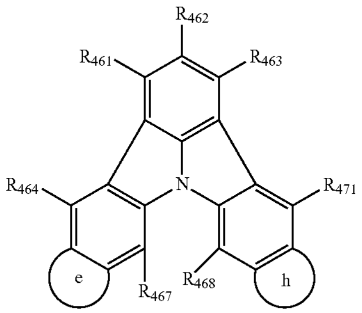

(45-2)

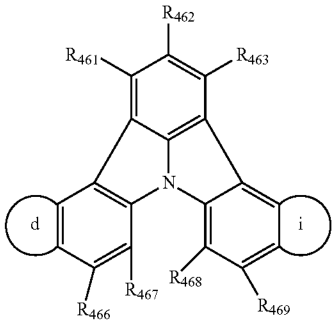

(45-3)

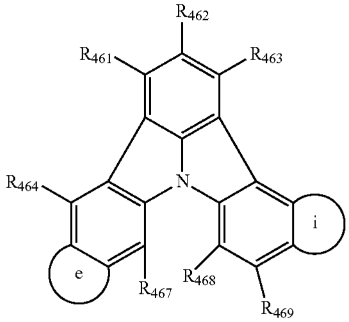

[Formula 218]

(45-4)

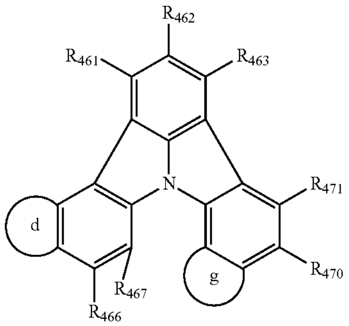

-continued (45-5)

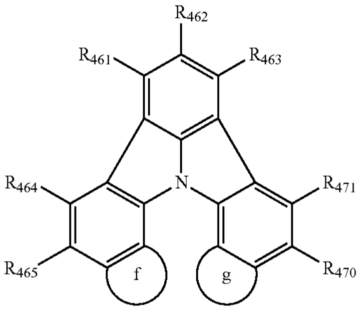

(45-6)

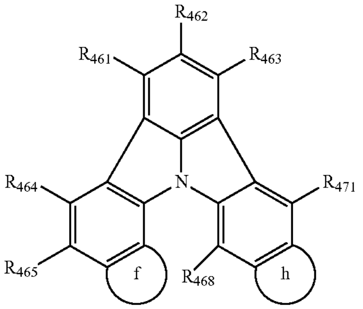

In the formulae (45-1) to (45-6):

rings d to i are each dependently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-7) to (45-12) below.

[Formula 219]

(45-7)

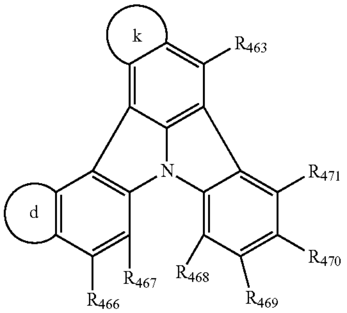

(45-8)

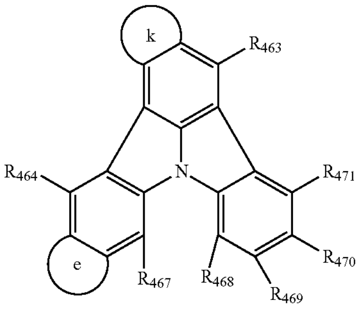

-continued (45-9)

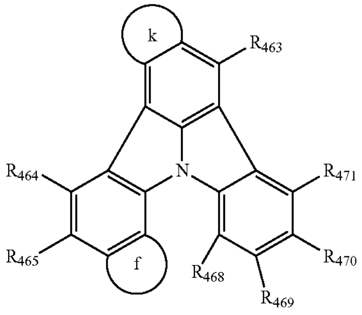

[Formula 220]

(45-10)

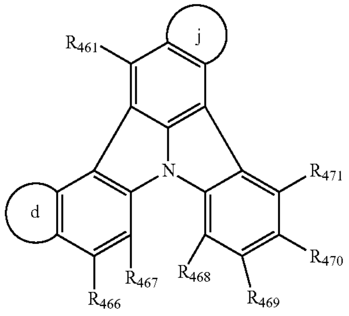

(45-11)

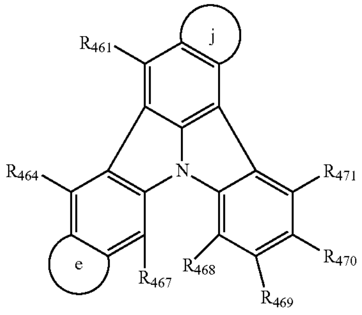

(45-12)

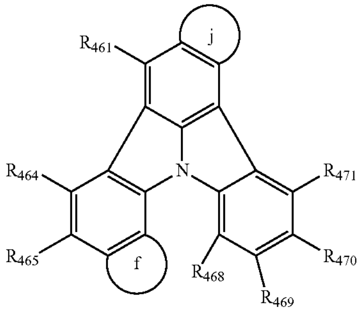

In the formulae (45-7) to (45-12):

rings d to f, k and j are each dependently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-13) to (45-21) below.

[Formula 221]

(45-13)

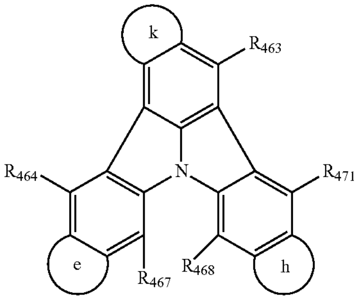

(45-14)

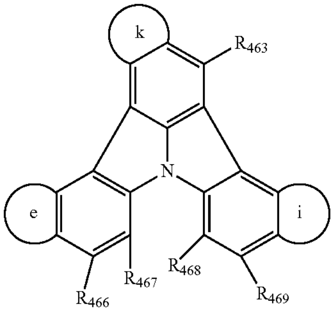

(45-15)

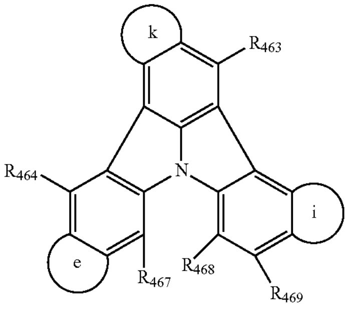

[Formula 222]

(45-16)

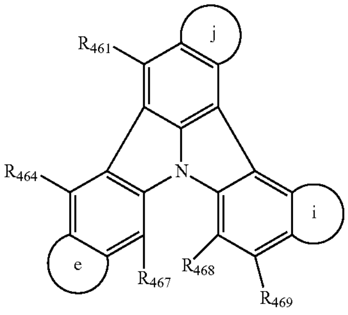

-continued (45-17)

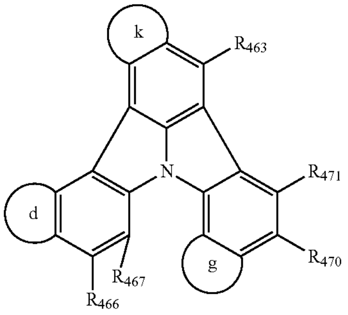

(45-18)

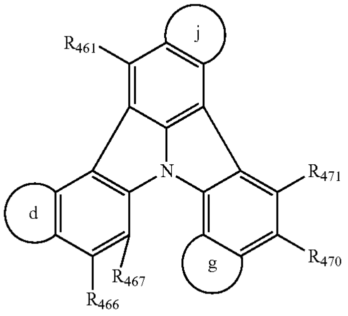

[Formula 223]

(45-19)

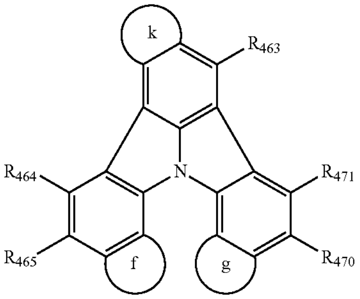

(45-20)

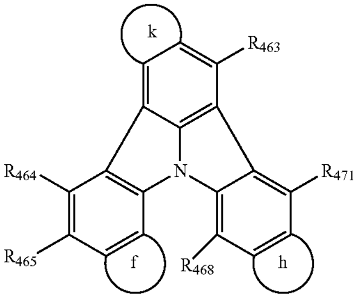

(45-21)

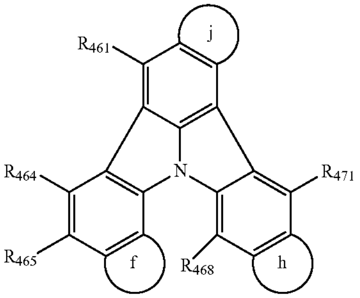

In the formulae (45-13) to (45-21):

rings d to k are each dependently a substituted or unsubstituted monocyclic ring or a substituted or unsubstituted fused ring, and $R_{461}$ to $R_{471}$ each independently represent the same as $R_{461}$ to $R_{471}$ in the formula (45).

When the ring g or the ring h further has a substituent, examples of the substituent include a substituted or unsubstituted alkyl group having 1 to 50 carbon atoms, a substituted or unsubstituted aryl group having 6 to 50 ring carbon atoms, a group represented by the formula (461), a group represented by the formula (463), and a group represented by the formula (464).

In an exemplary embodiment, the compound represented by the formula (45) is represented by one of formulae (45-22) to (45-25) below.

[Formula 224]

(45-22)

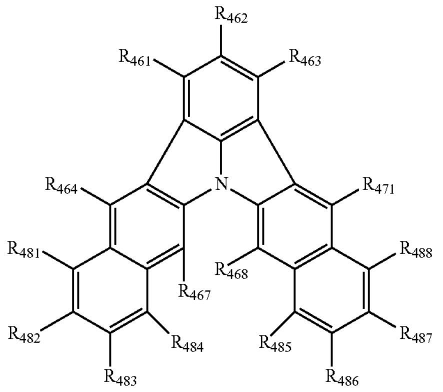

(45-23)

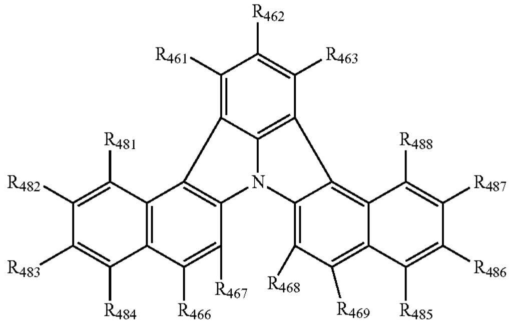

(45-24)

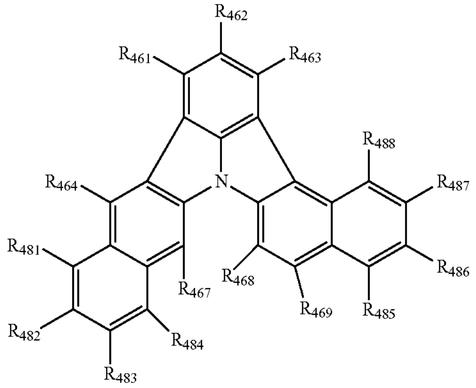

-continued (45-25)

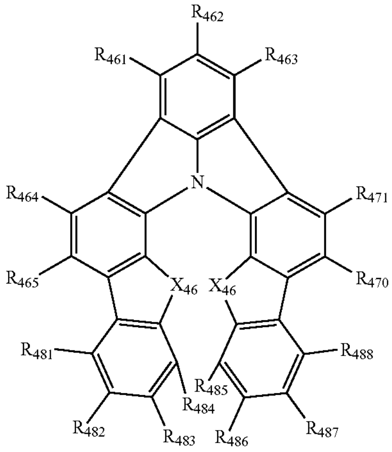

In the formulae (45-22) to (45-25):

$X_{46}$ and $X_{47}$ are each independently $C(R_{801})(R_{802})$, $NR_{803}$, an oxygen atom or a sulfur atom;

$R_{461}$ to $R_{471}$ and $R_{481}$ to $R_{488}$ respectively represent the same as $R_{461}$ to $R_{471}$ of the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, a substituted or unsubstituted heterocyclic group having 5 to 50 ring atoms;

a substituted or unsubstituted alkyl group having 1 to 50 carbon atoms, a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, the compound represented by the formula (45) is represented by a formula (45-26) below.

[Formula 225]

(45-26)

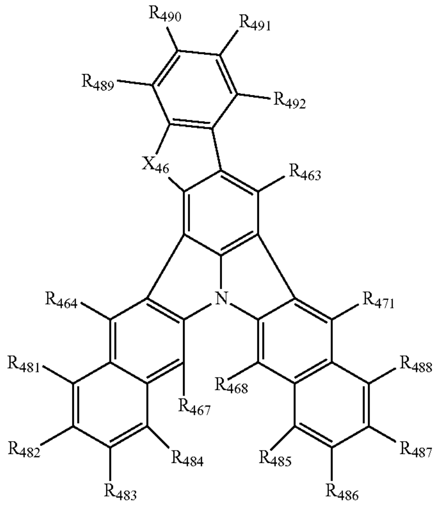

In the formula (45-26): $X_{46}$ represents $C(R_{801})(R_{802})$, $NR_{803}$, an oxygen atom or a sulfur atom;

$R_{463}$, $R_{464}$, $R_{467}$, $R_{468}$, $R_{471}$, and $R_{481}$ to $R_{492}$ each independently represent the same as $R_{461}$ to $R_{471}$ in the formula (45);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

Specific Examples of Compound Represented by Formula (4)

Specific examples of the compound represented by the formula (4) include compounds shown below. In the specific examples below, Ph represents a phenyl group, and D represents a deuterium atom.

[Formula 226]

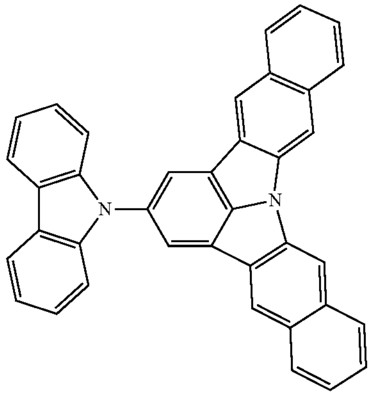

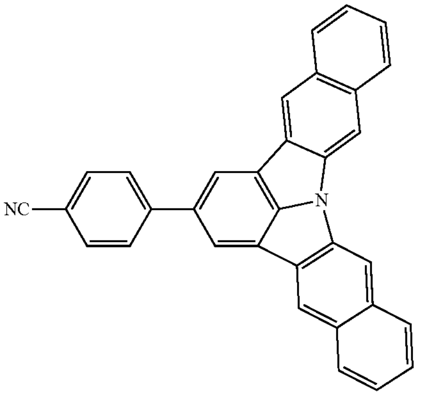

-continued
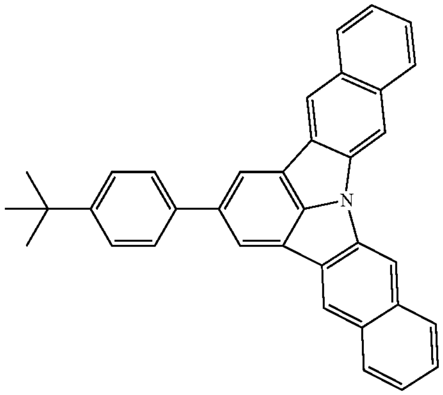
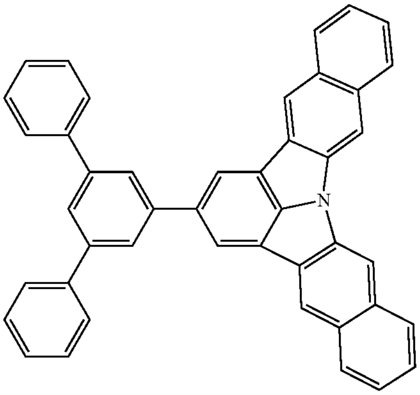
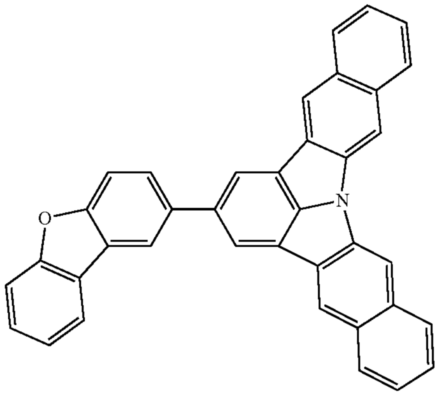
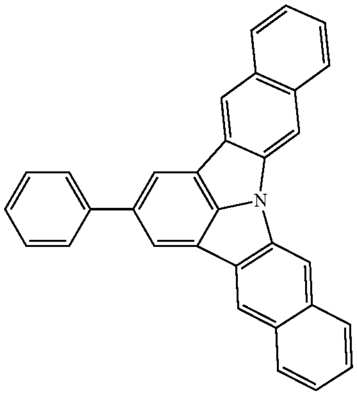
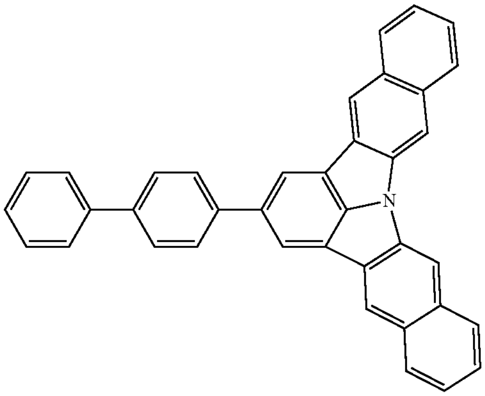
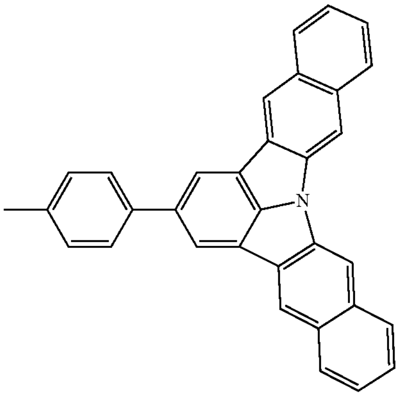
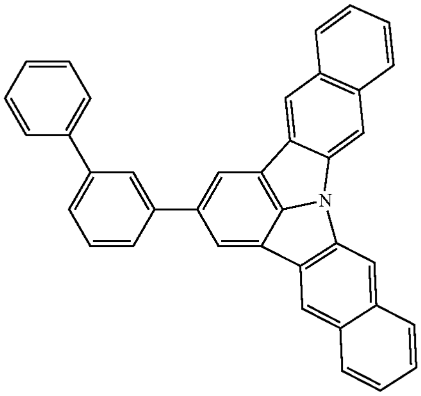
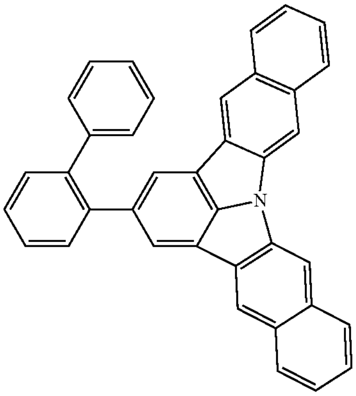

-continued
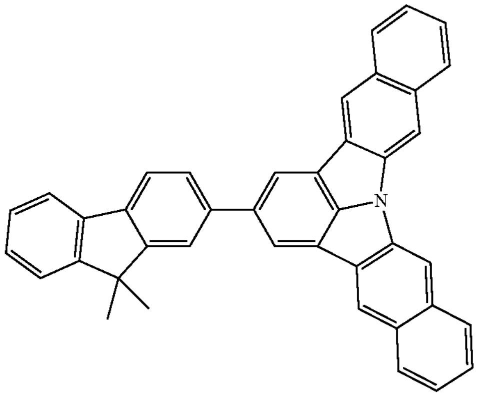
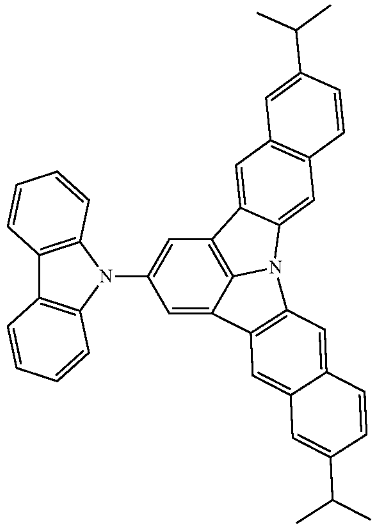
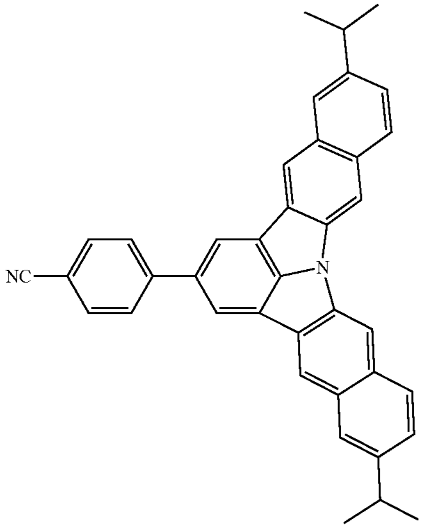
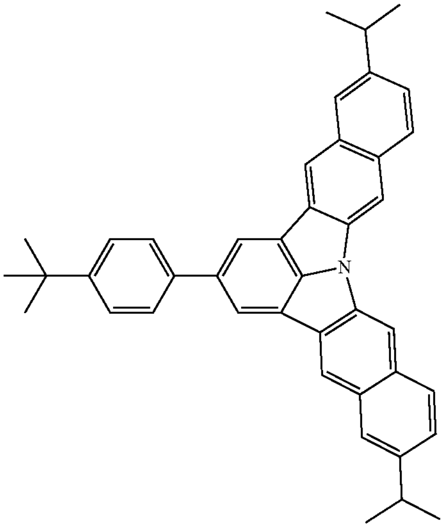
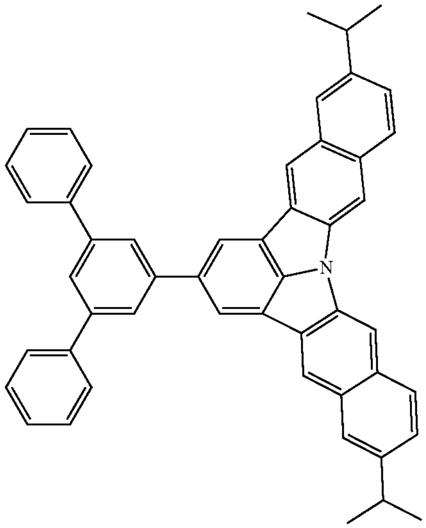
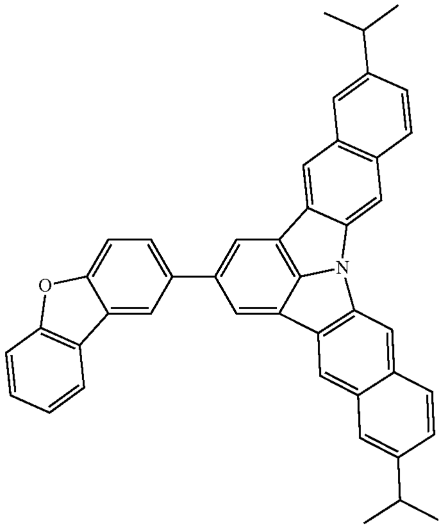

-continued
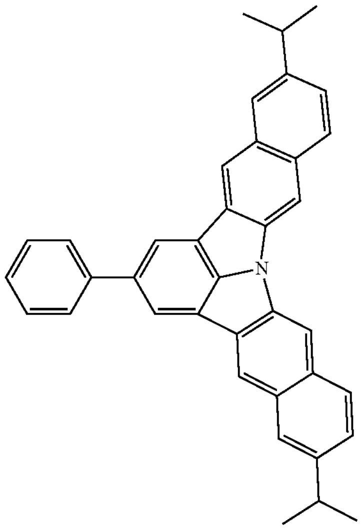
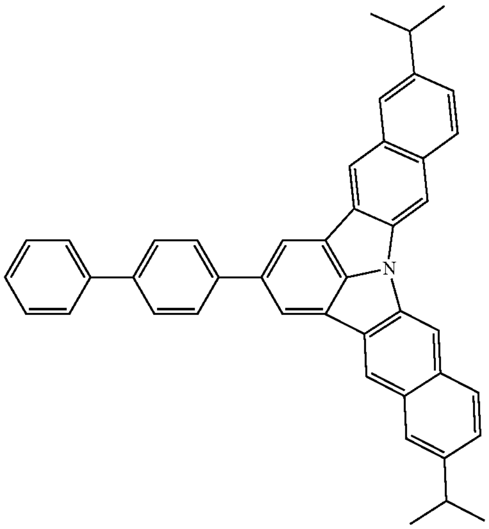
[Formula 227]
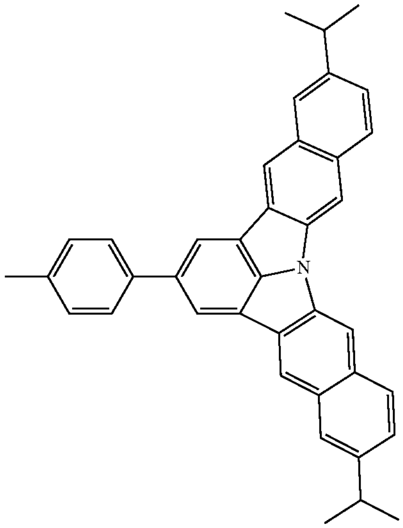
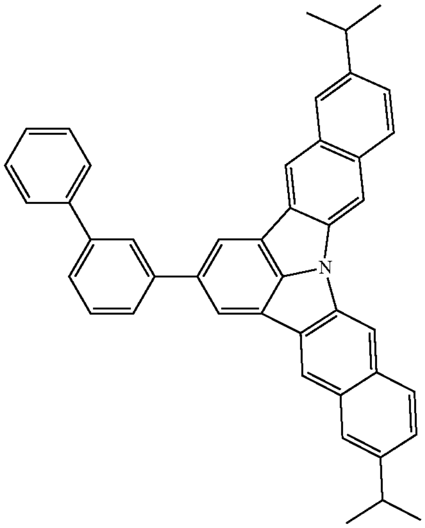
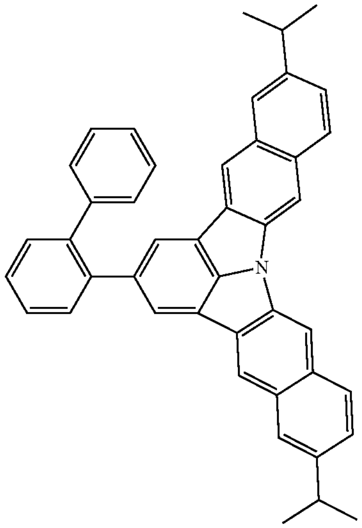
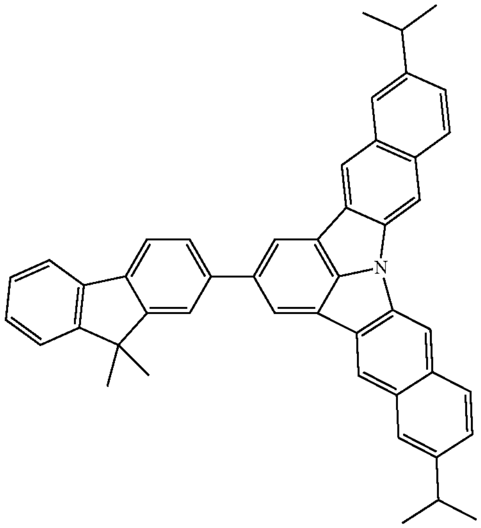

-continued
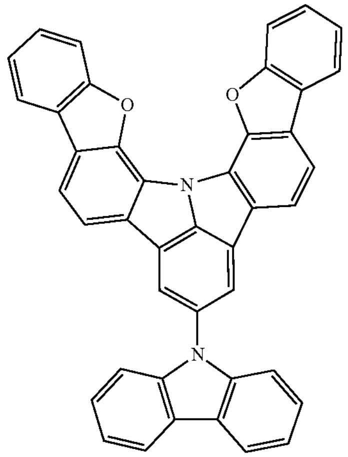
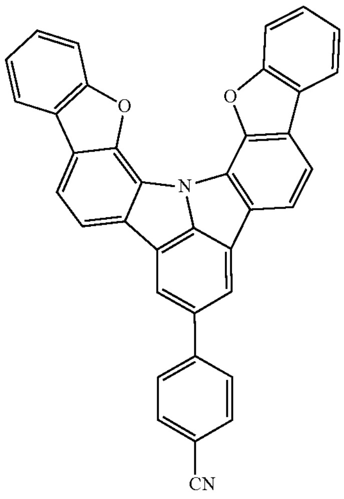
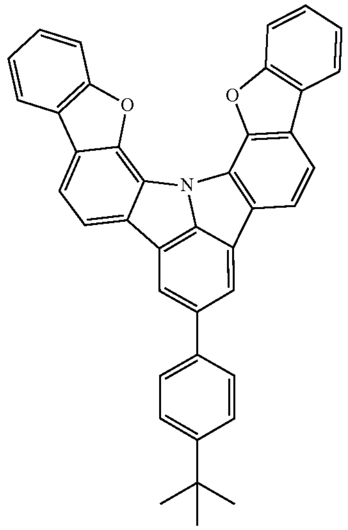
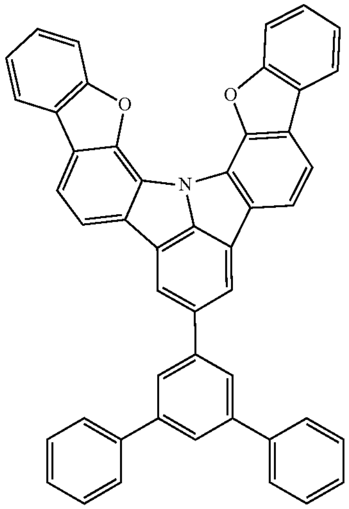
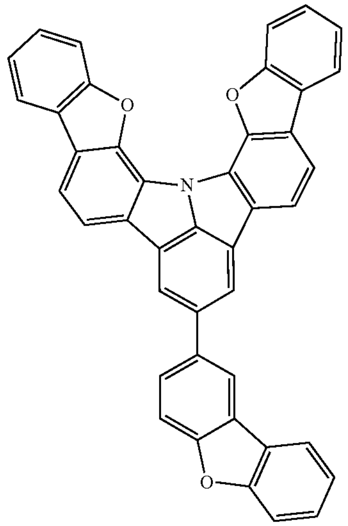
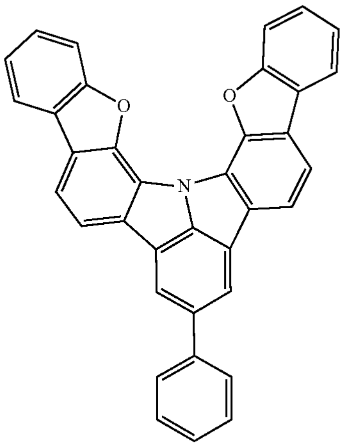

-continued
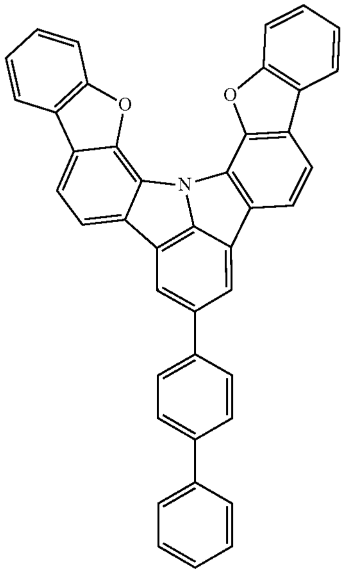
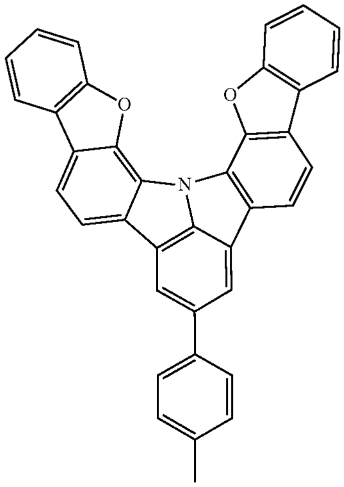
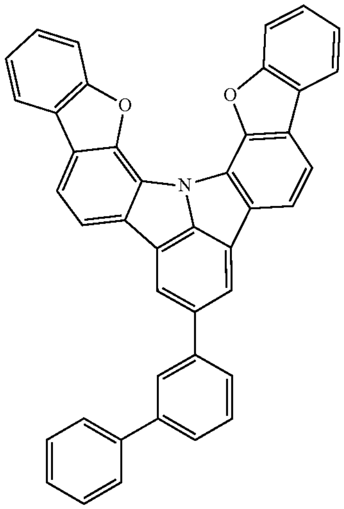
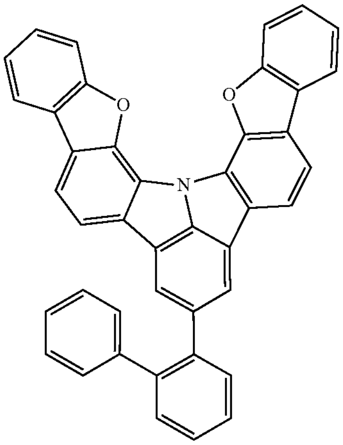
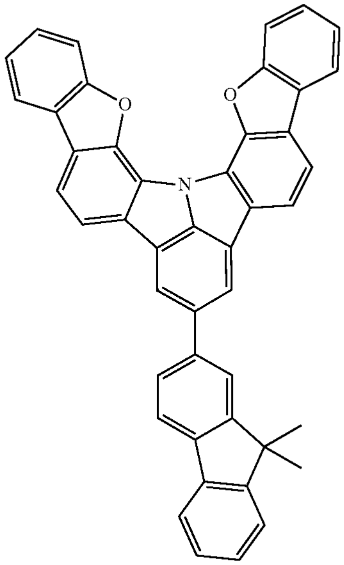
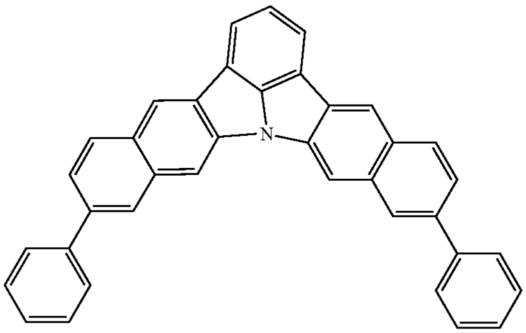

-continued
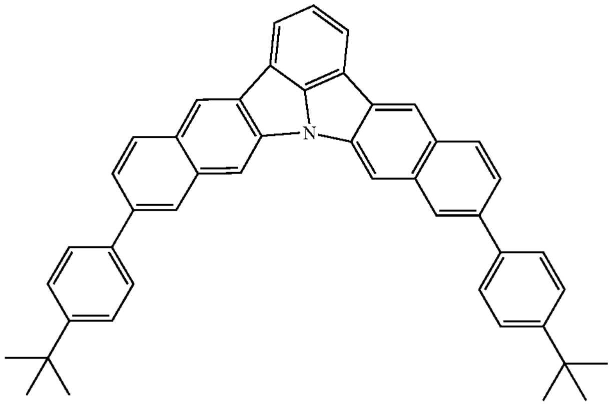
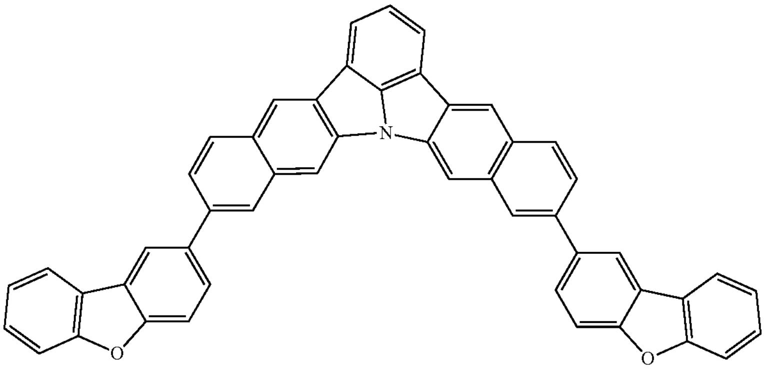 [SMILES: c1ccc2c(c1)oc1ccc(-c3ccc4cc5c6cccc7c8cc9ccc(-c%10ccc%11oc%12ccccc%12c%11c%10)cc9cc8n(c5cc4c3)c67)cc12]
[Formula 228]
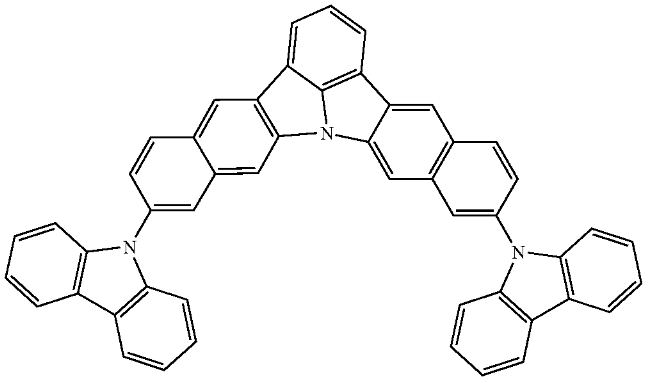
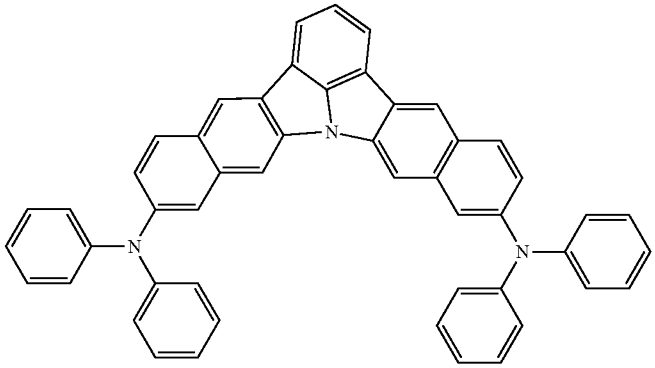

-continued
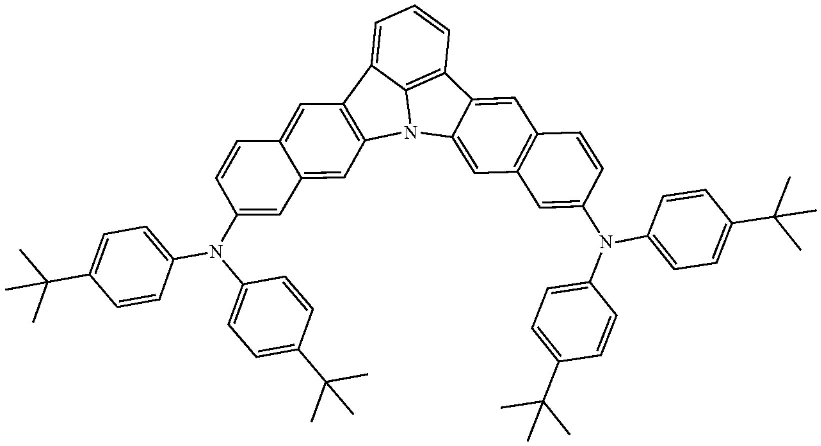
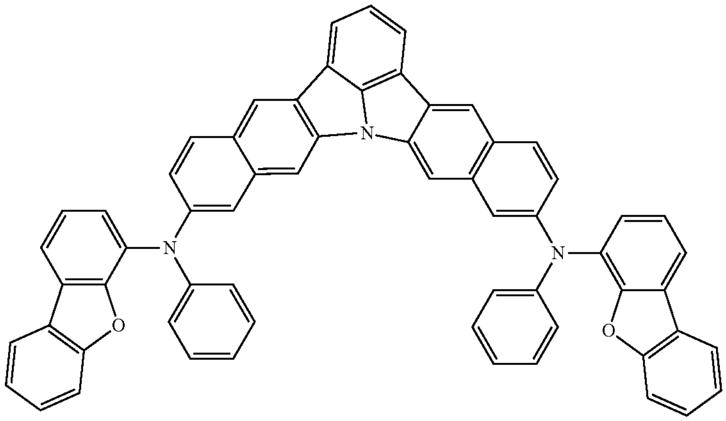
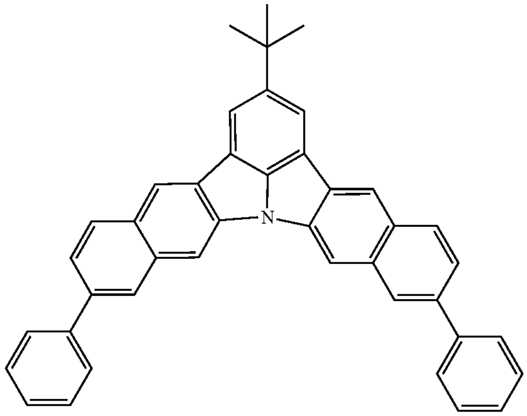
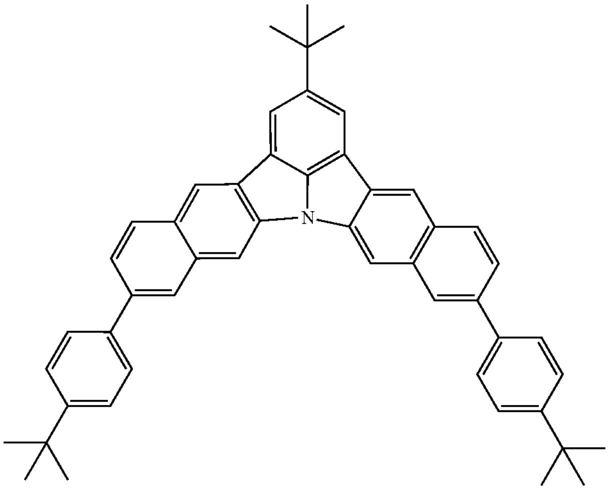

-continued
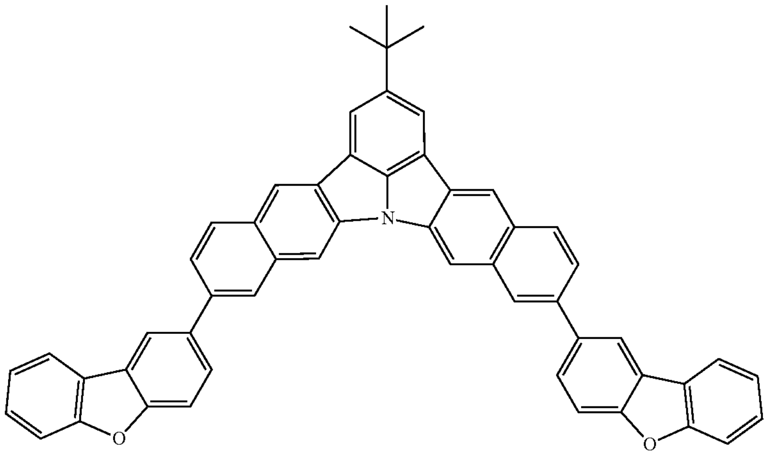
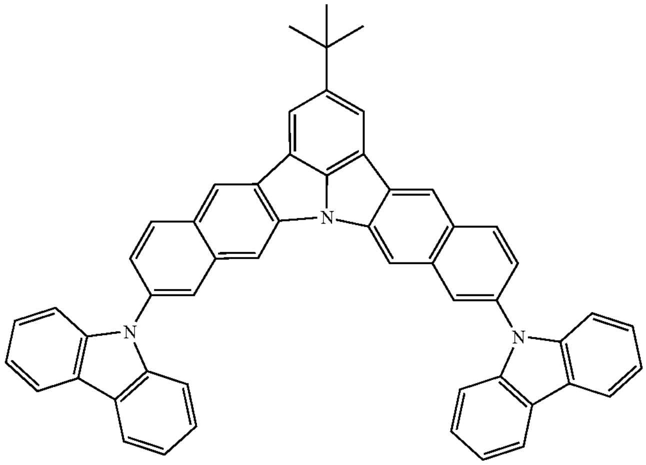
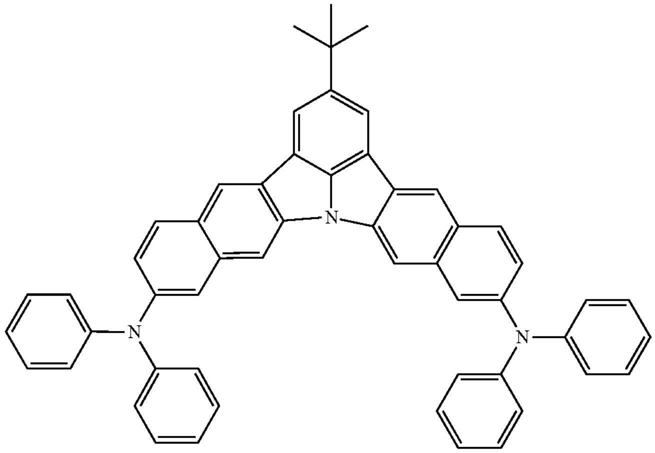

-continued
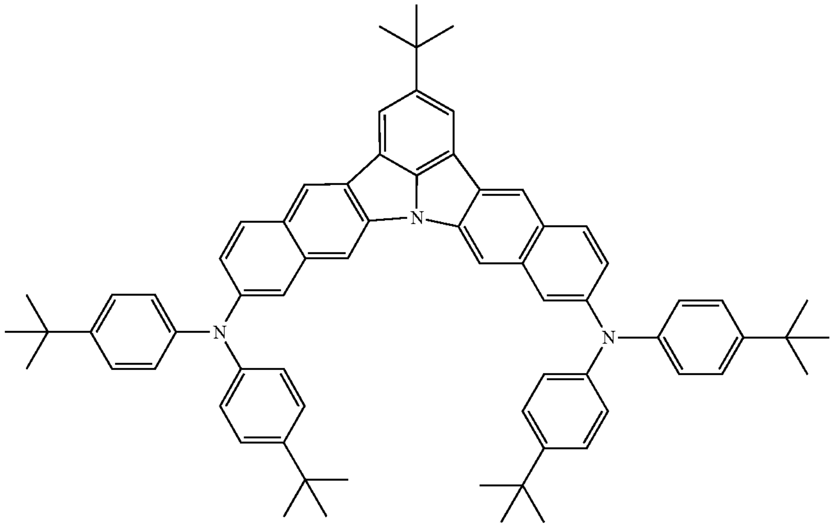
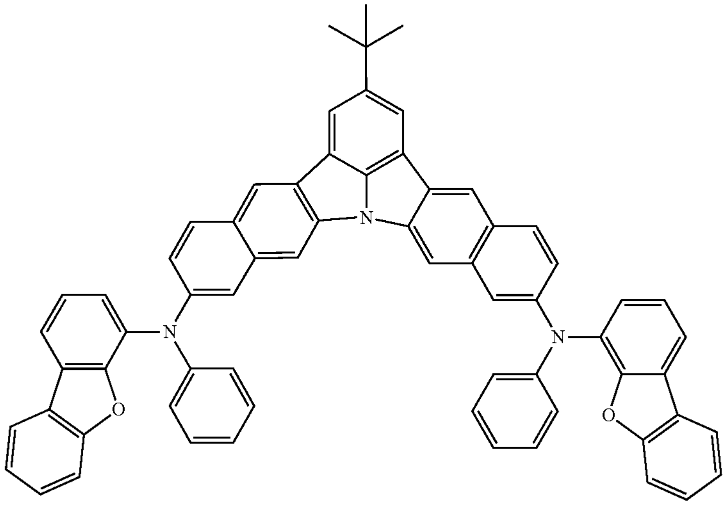
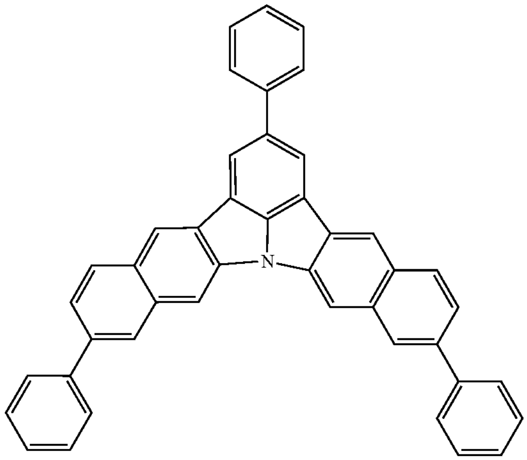

-continued
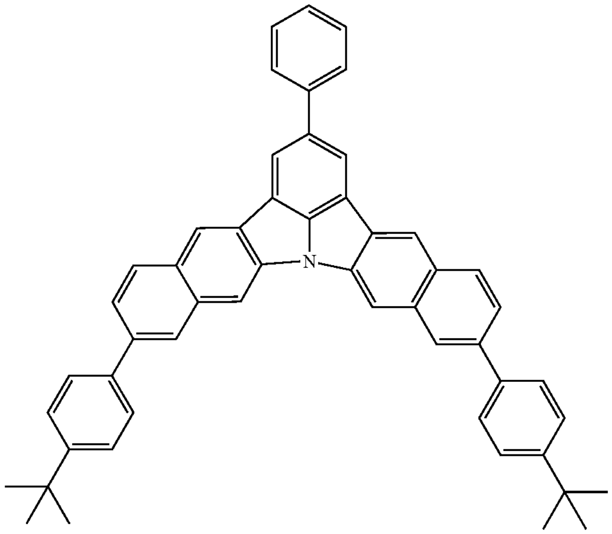
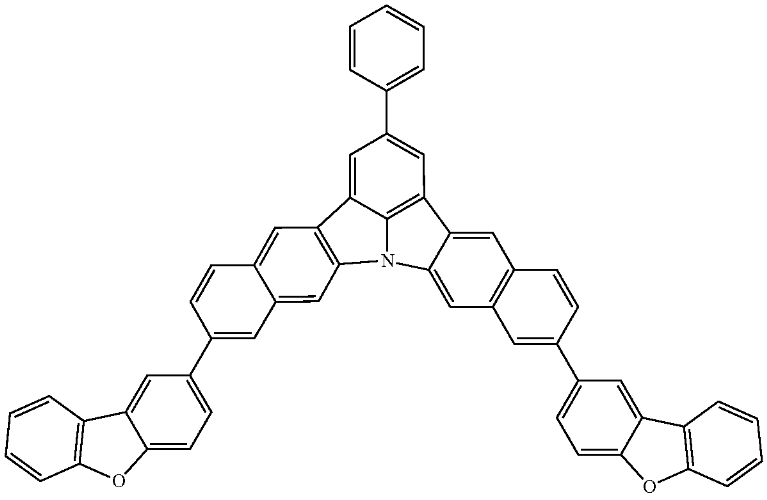
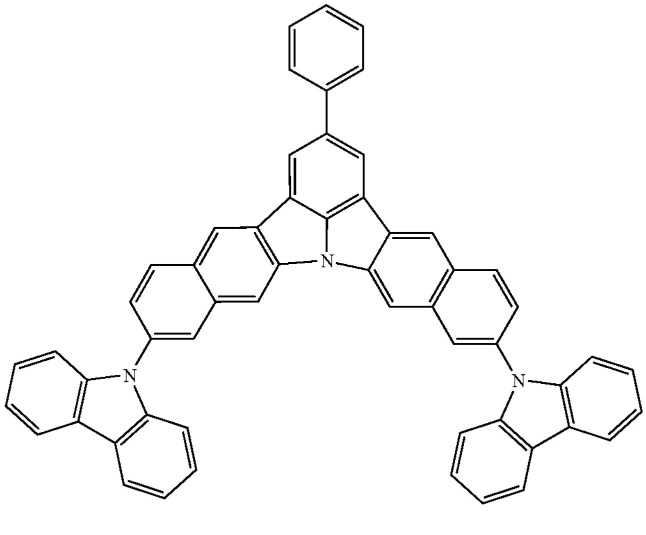

-continued
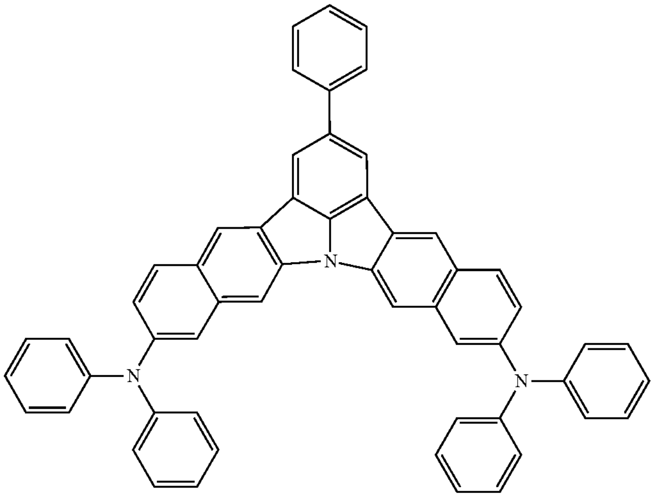
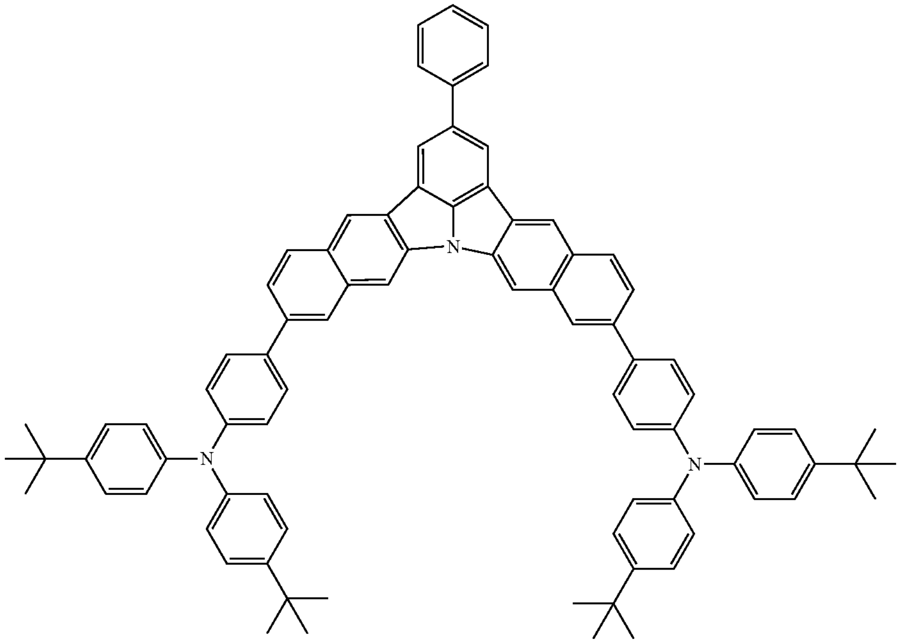
[Formula 229]
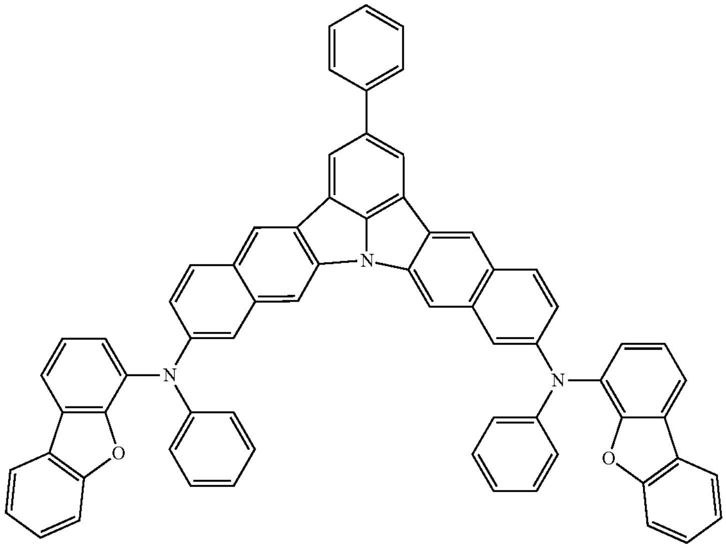

-continued
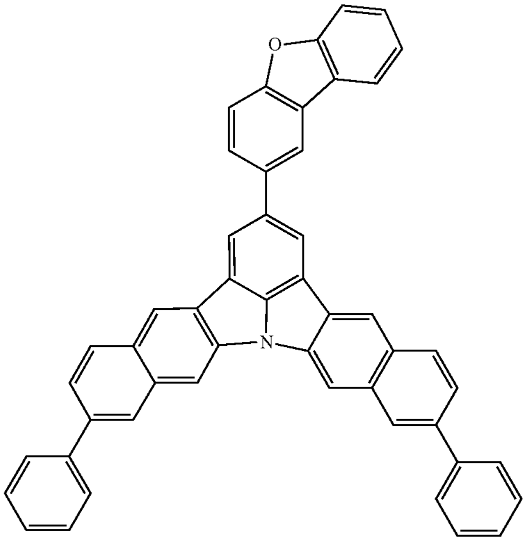
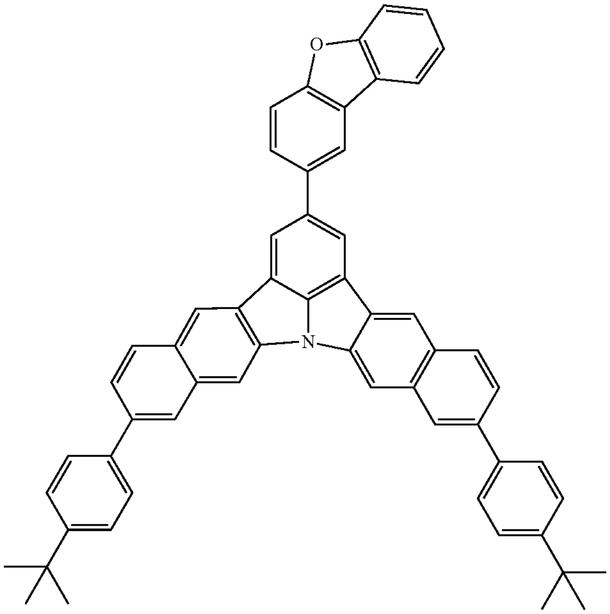

-continued
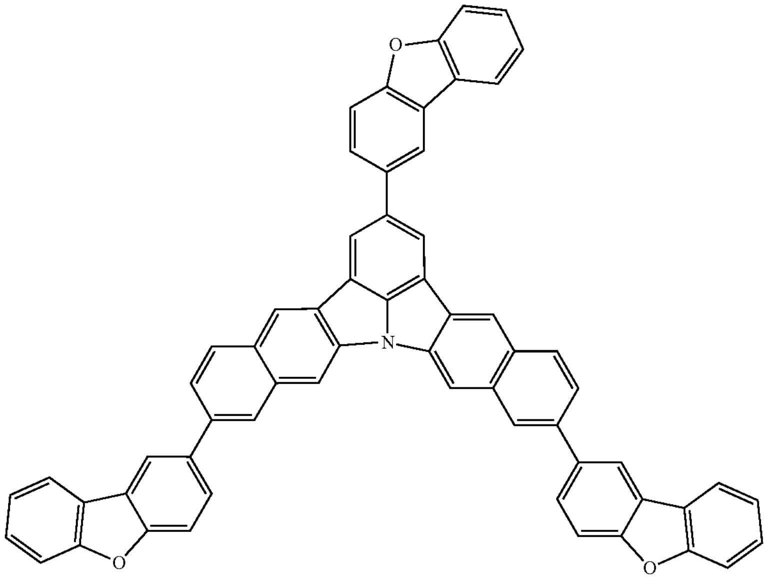
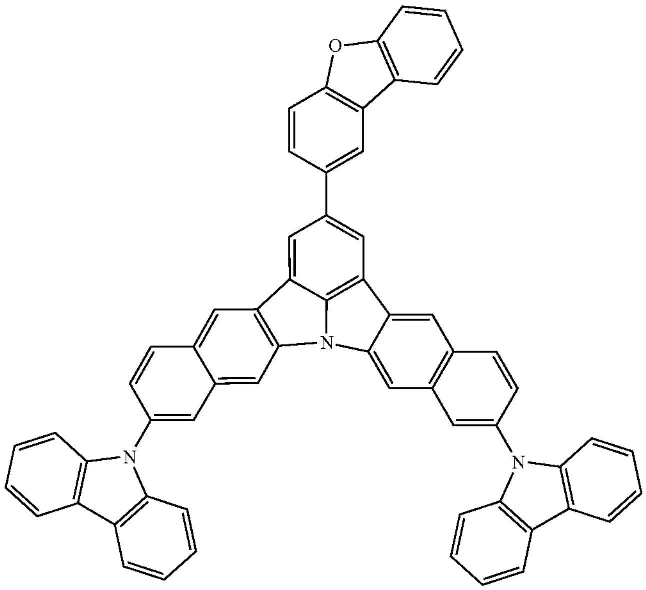

-continued
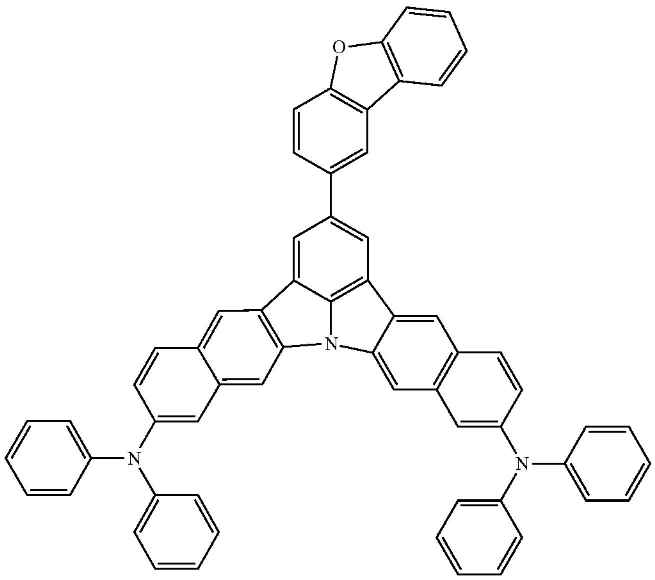
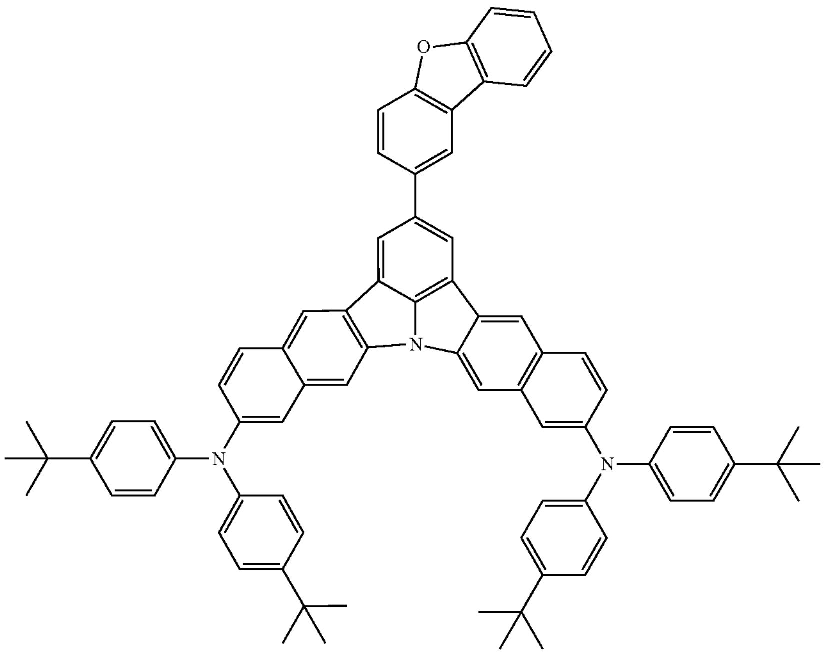

-continued
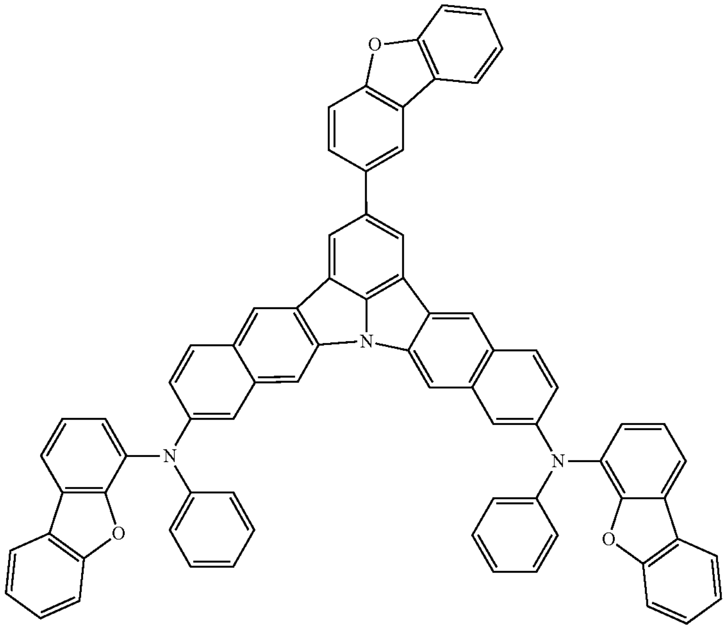
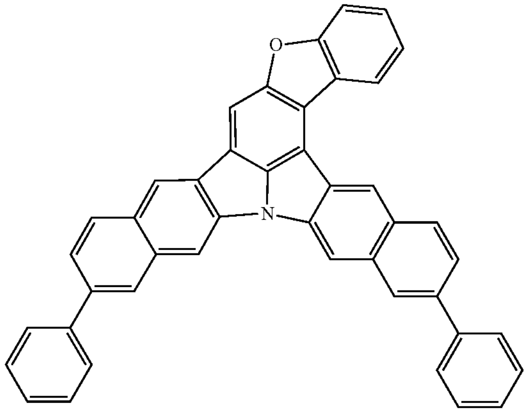
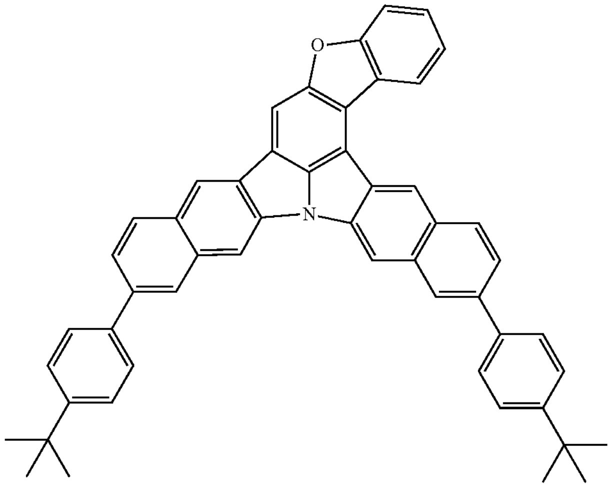

-continued
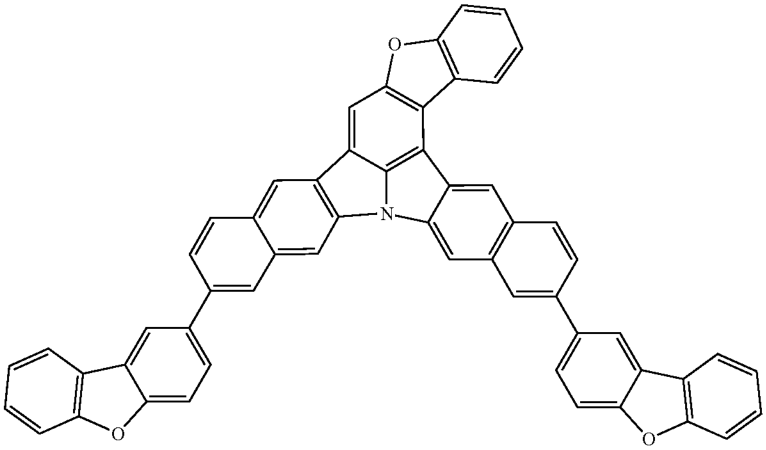
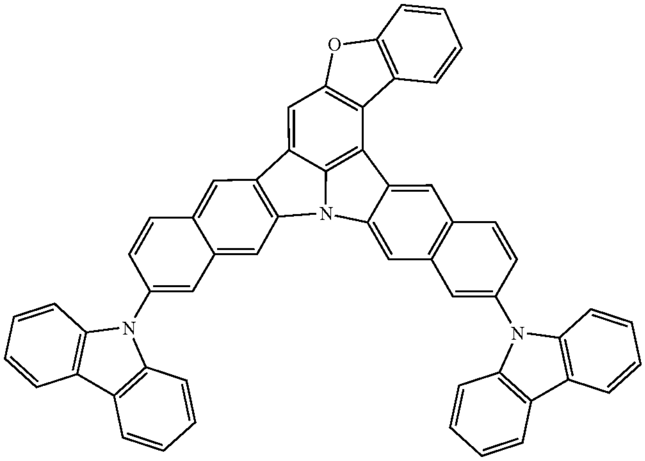
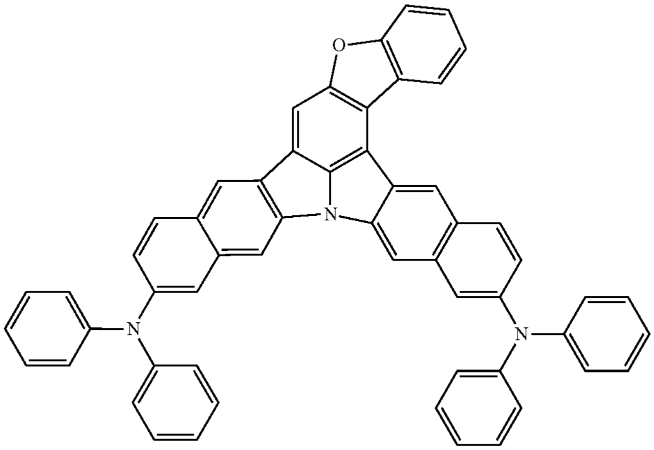

-continued
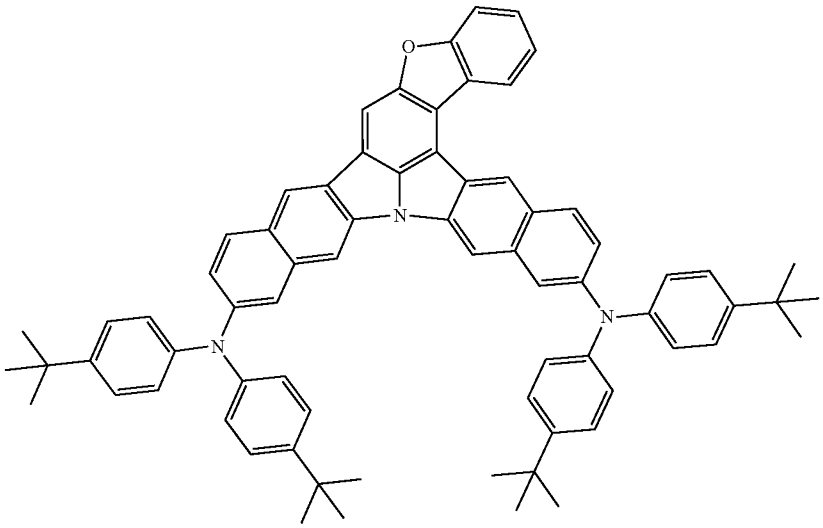
[Formula 230]
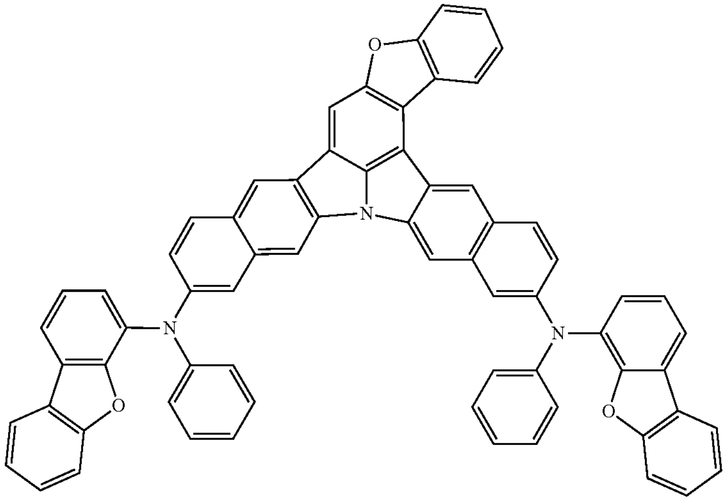
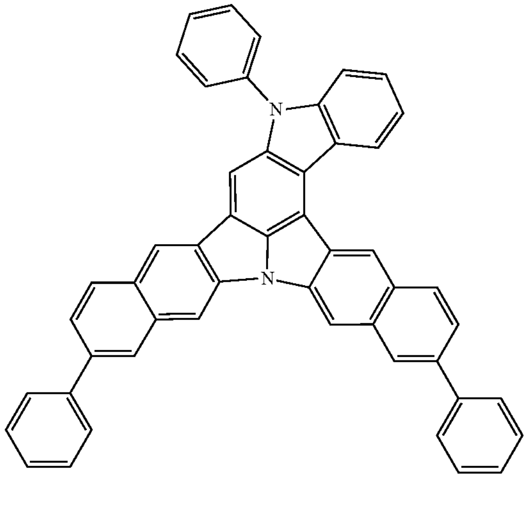

-continued
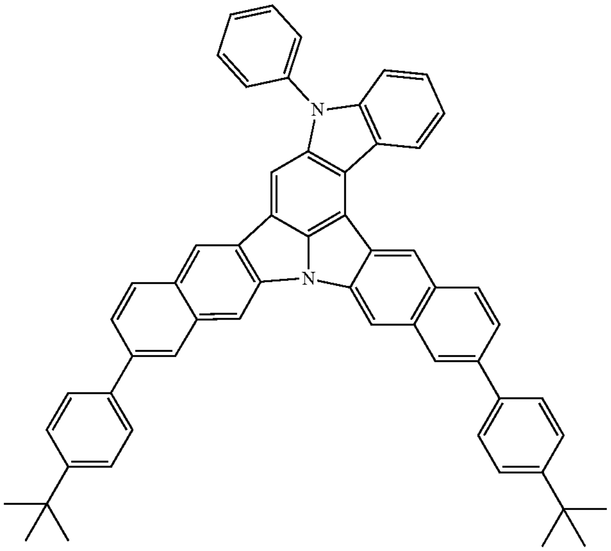
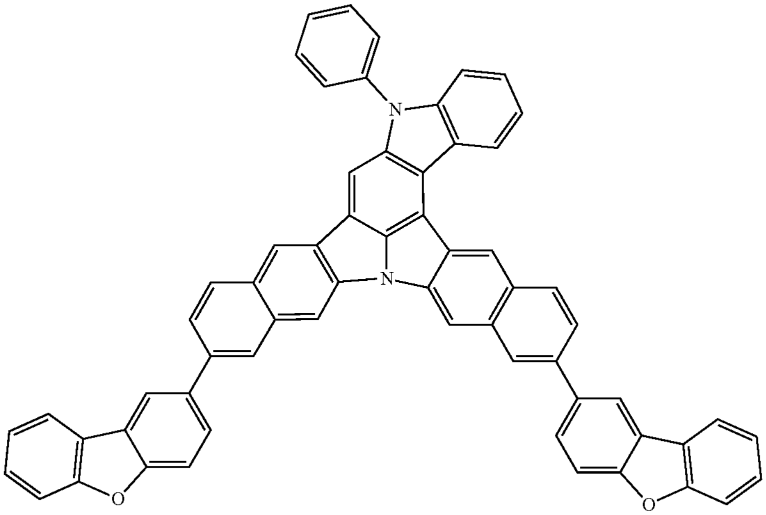
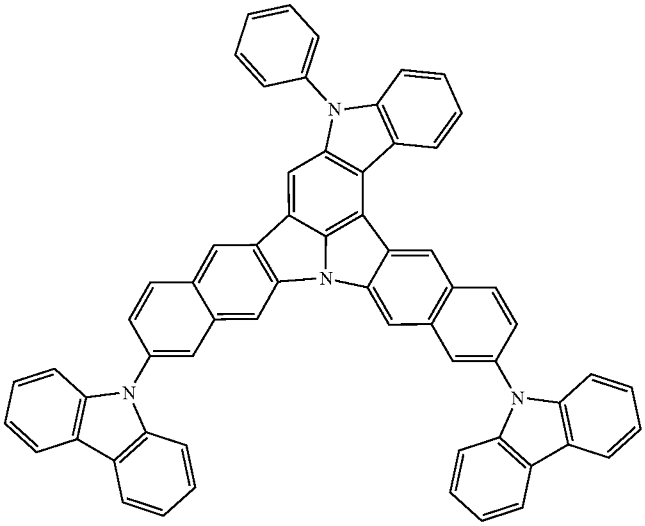

-continued
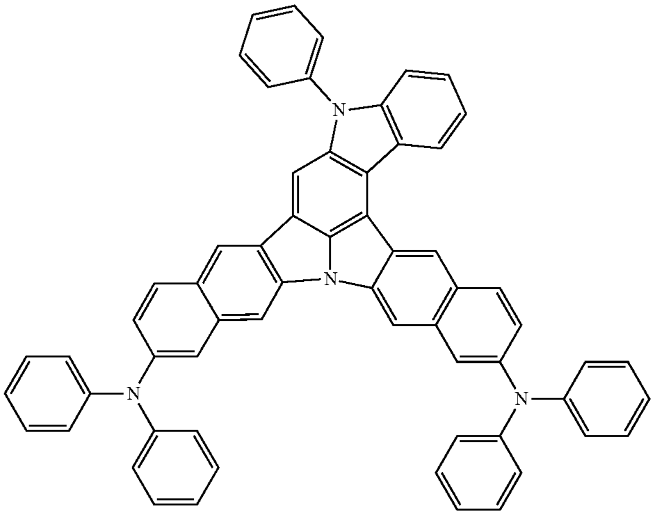
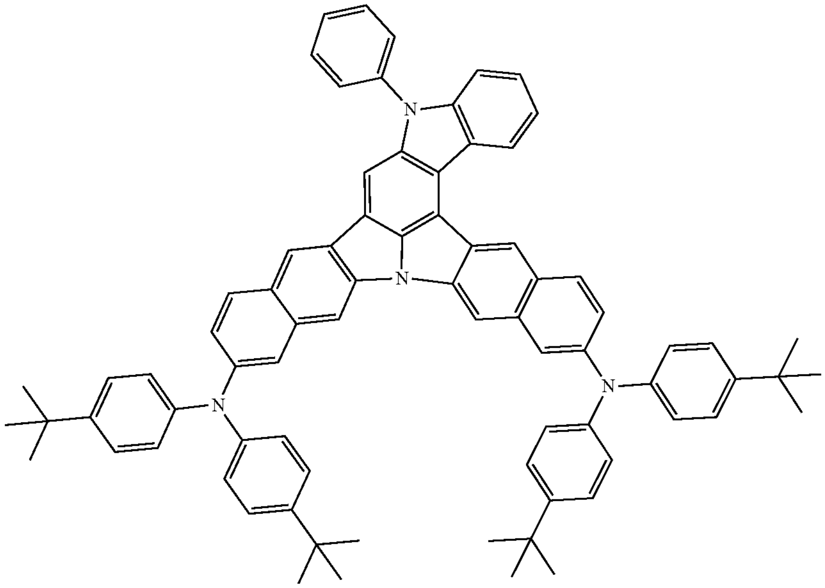
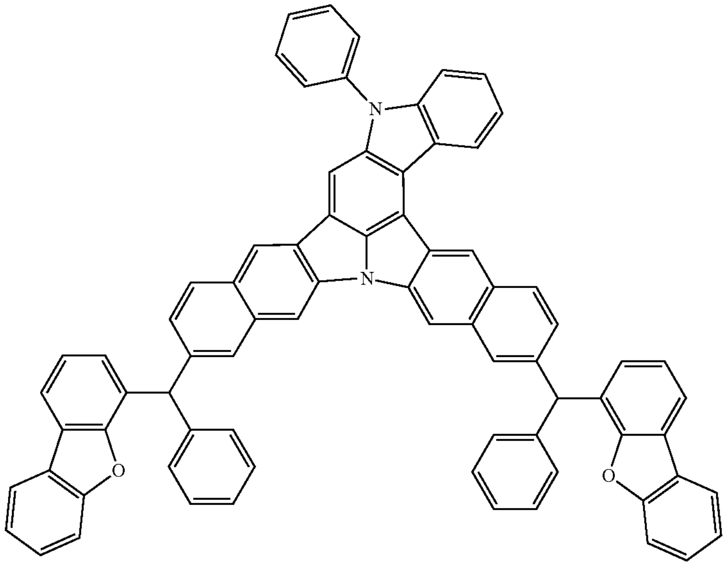

-continued
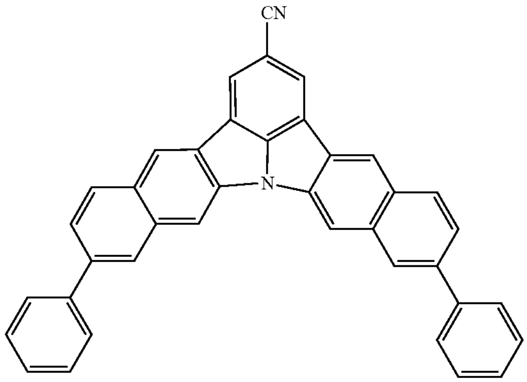
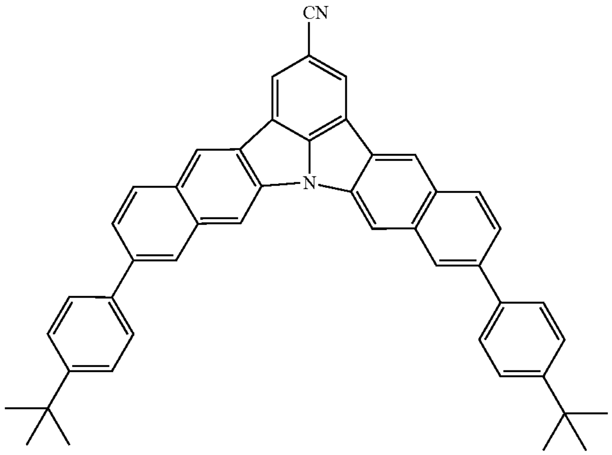
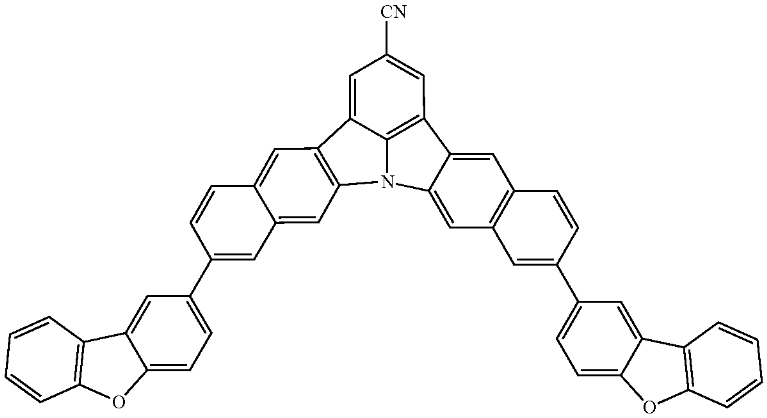
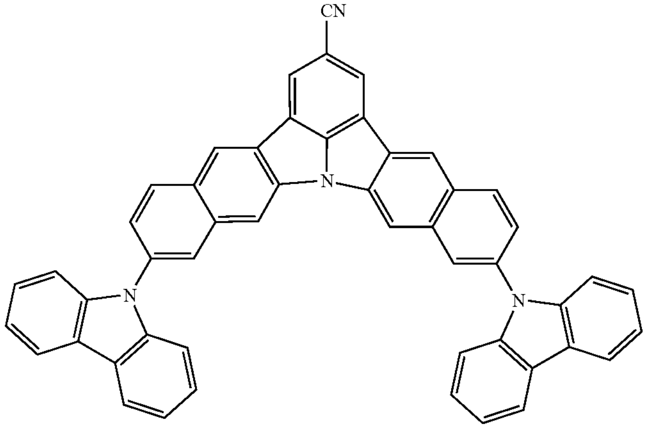

-continued
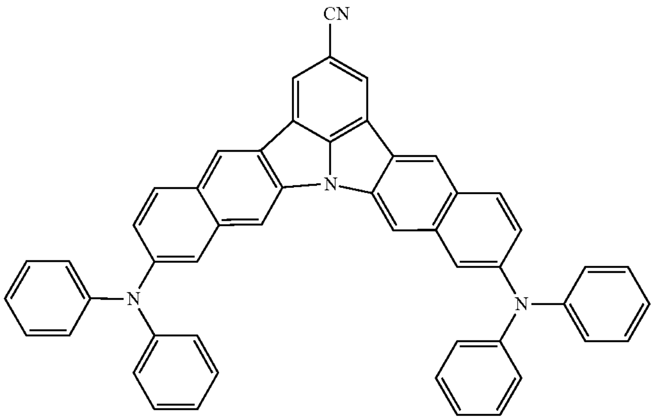
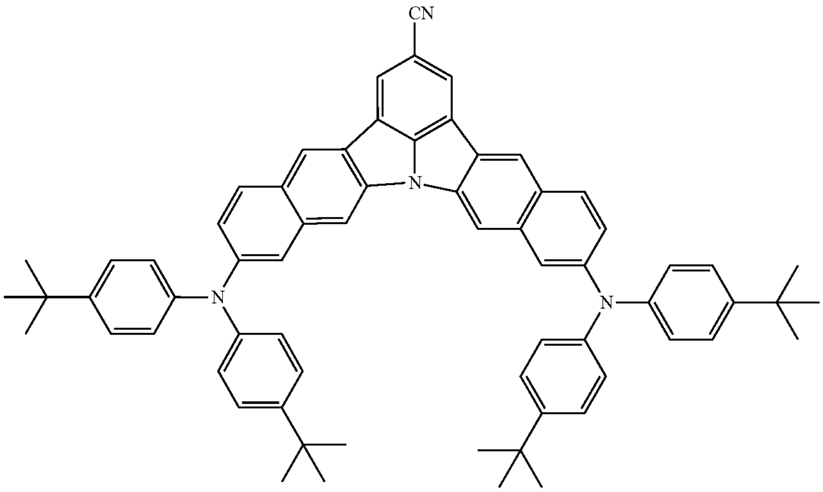
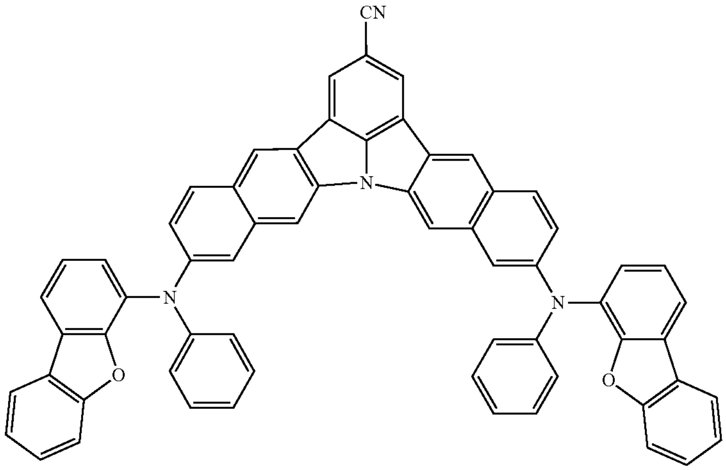
[Formula 231]
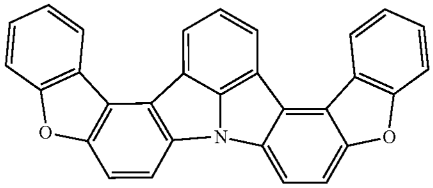
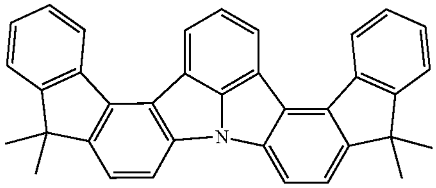

-continued
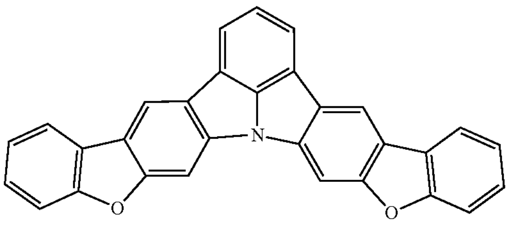
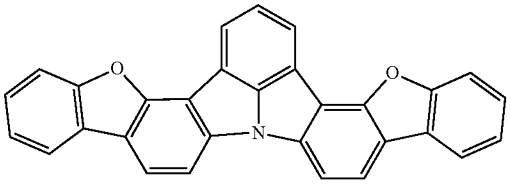
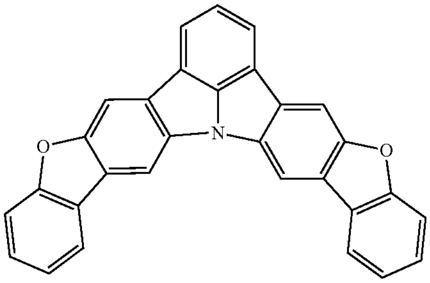
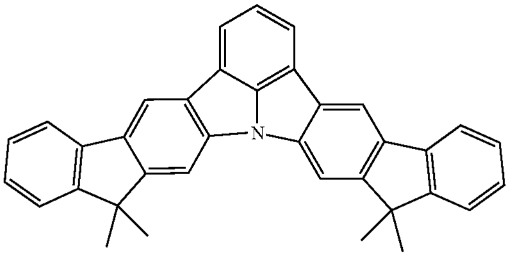
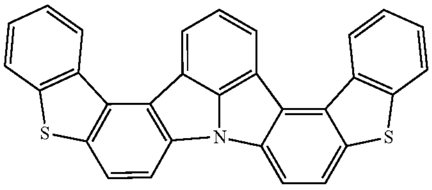
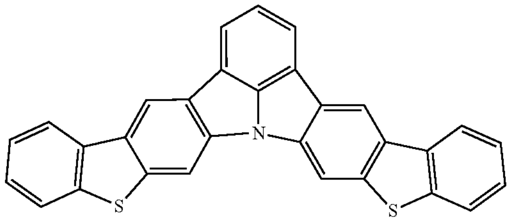
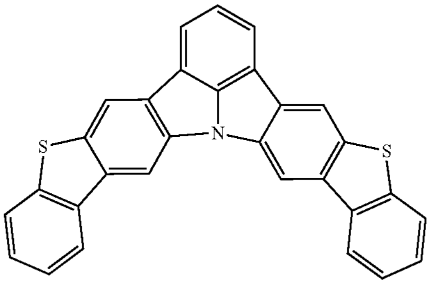
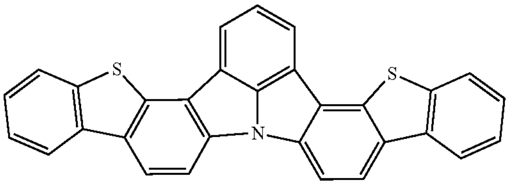
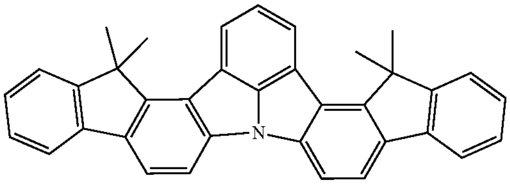
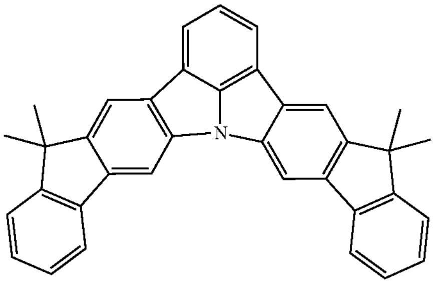
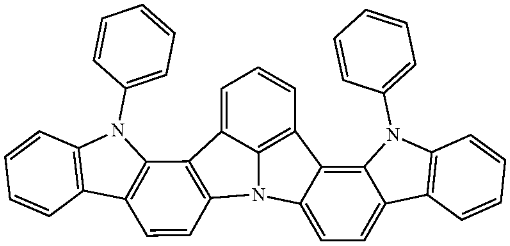
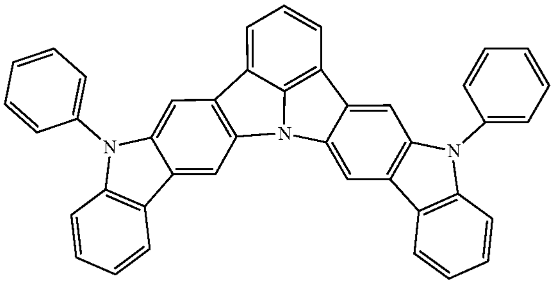

-continued
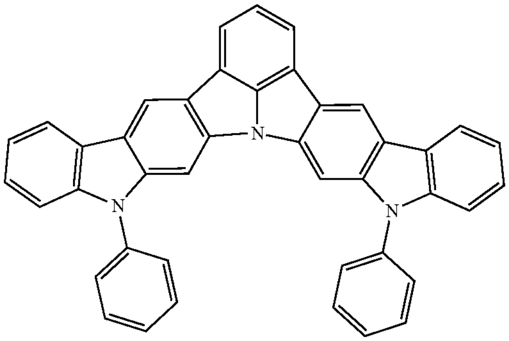
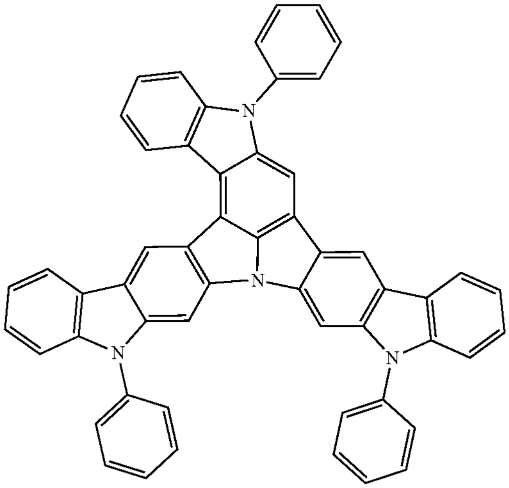
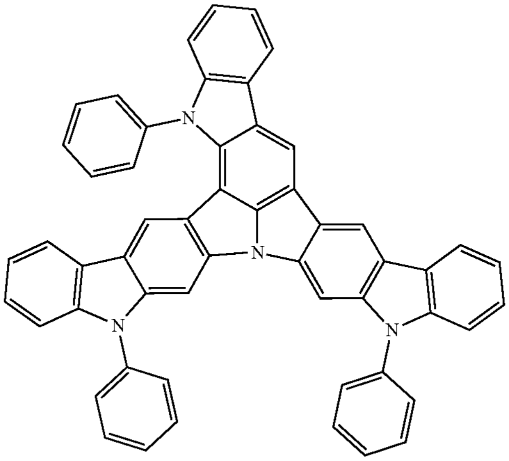
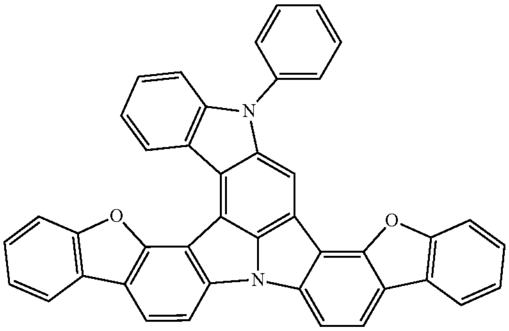
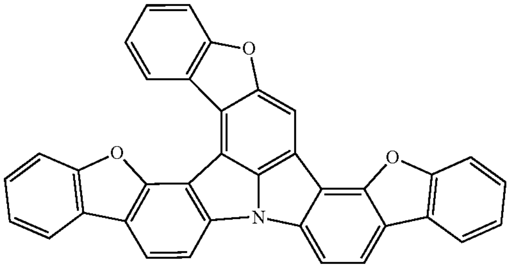
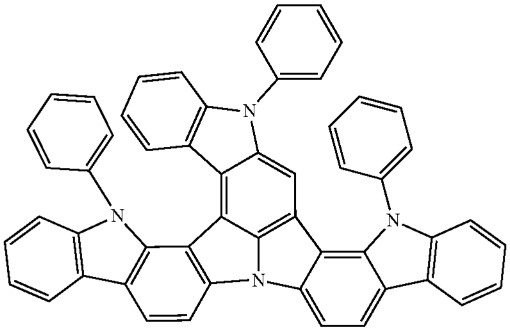
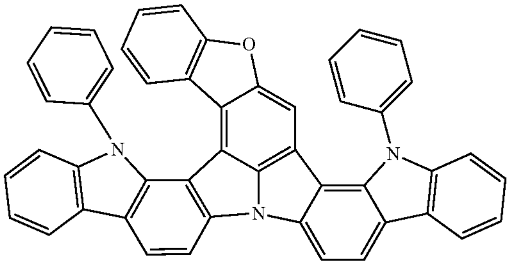
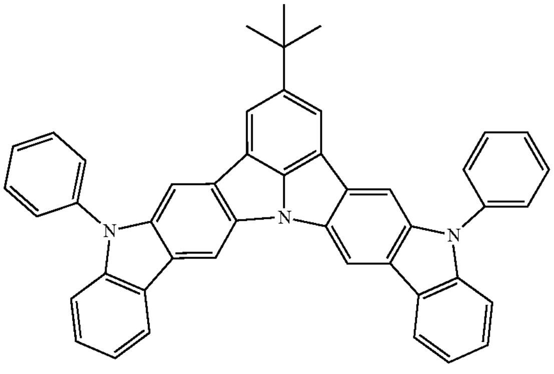

-continued
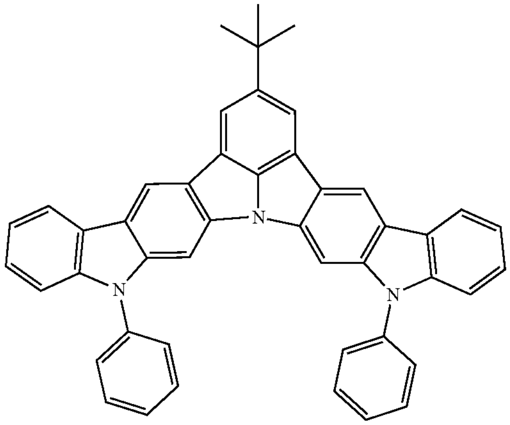
[Formula 232]
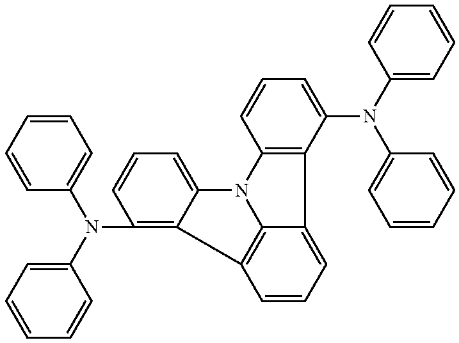
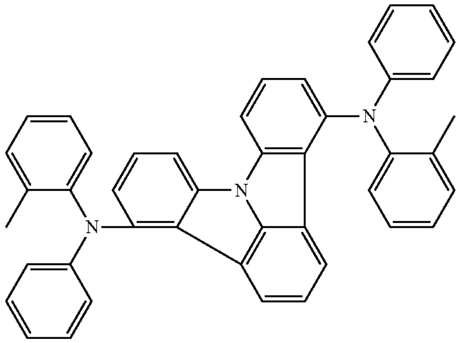
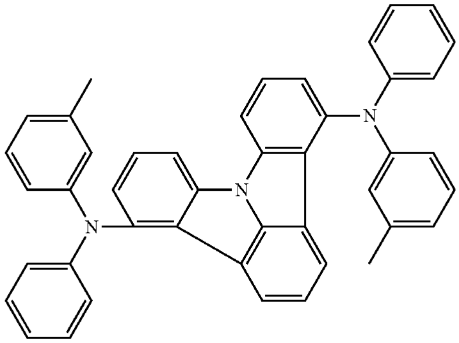
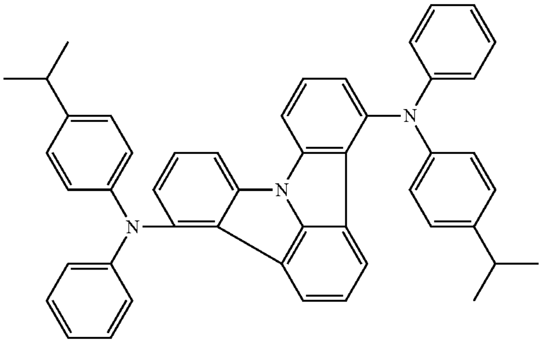
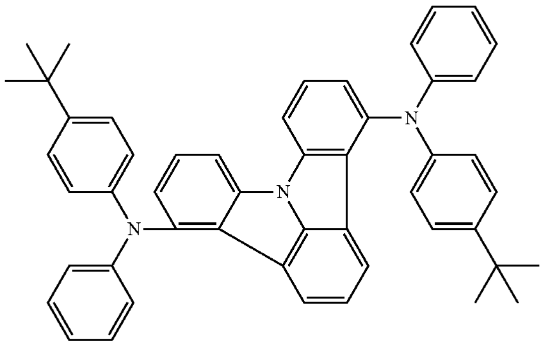
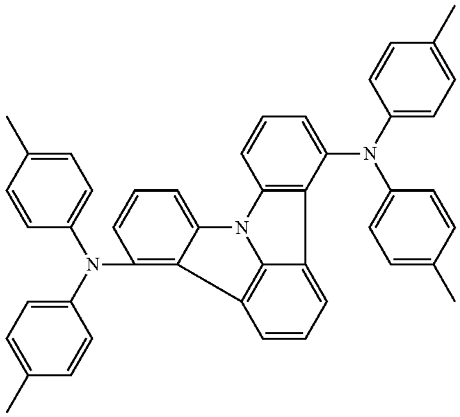

-continued
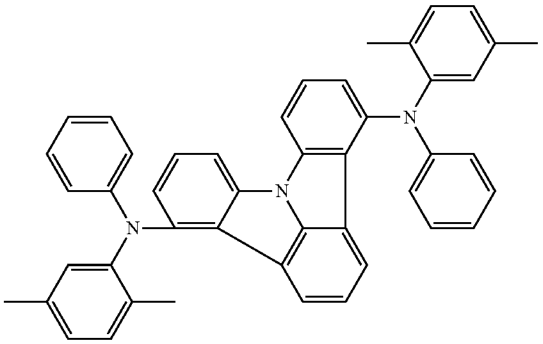
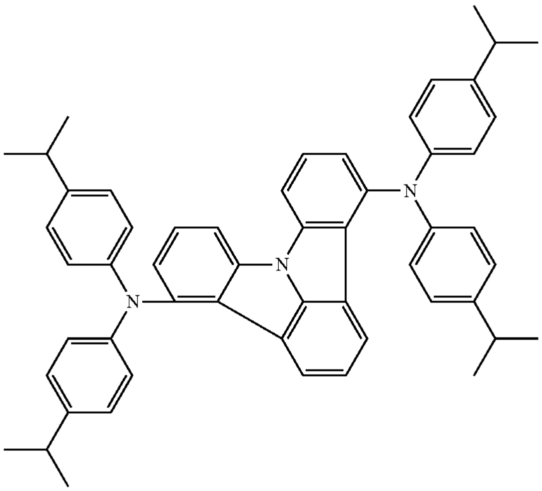
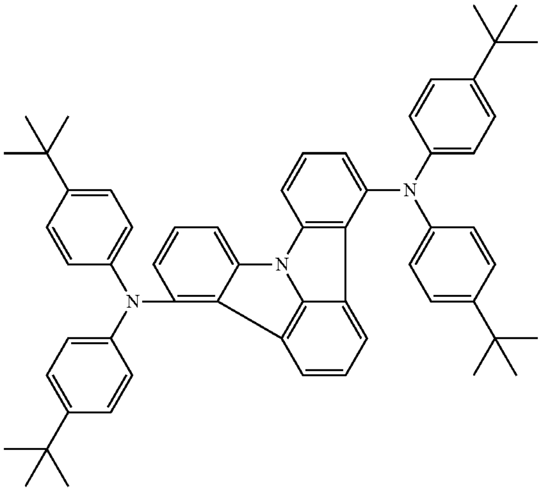
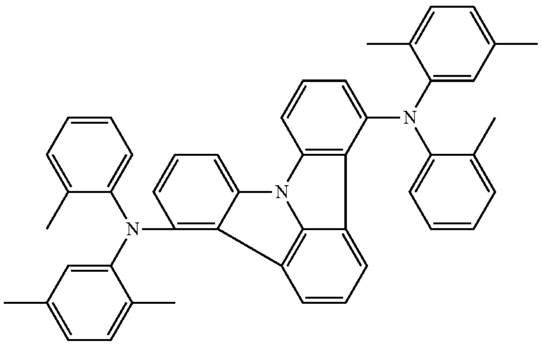
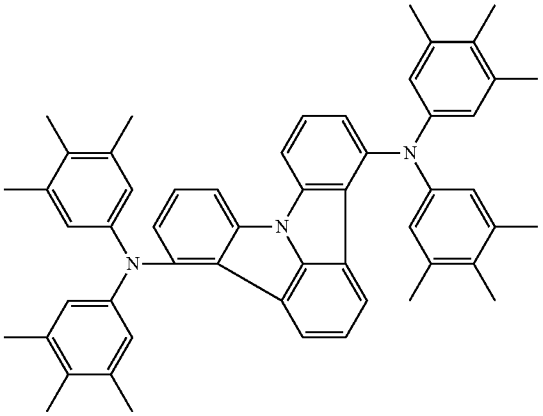

-continued
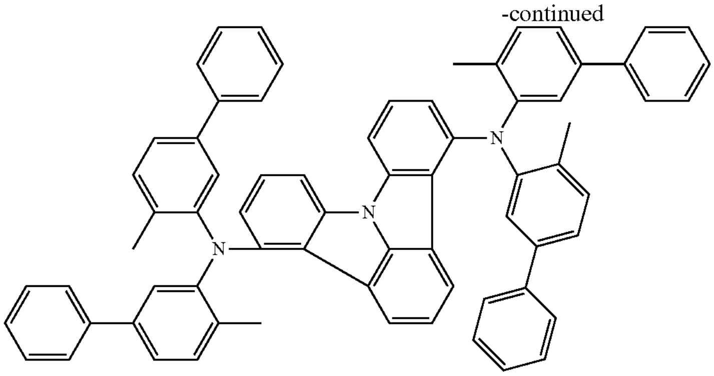
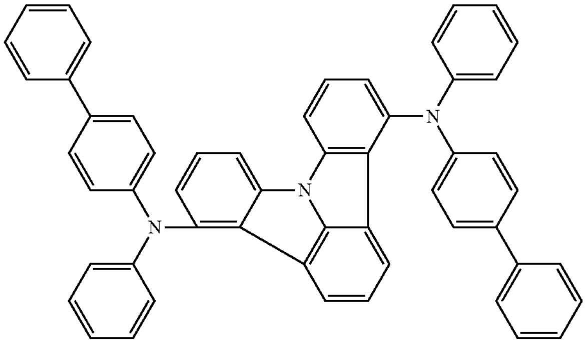
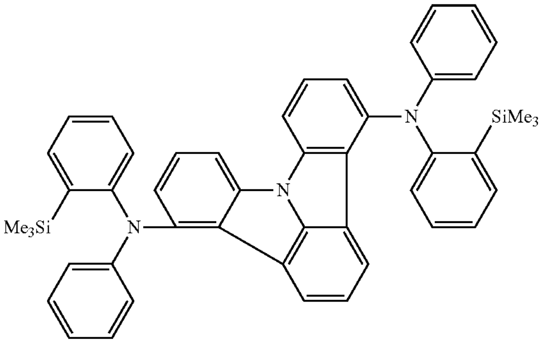
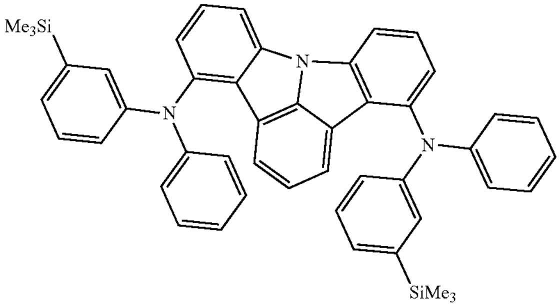
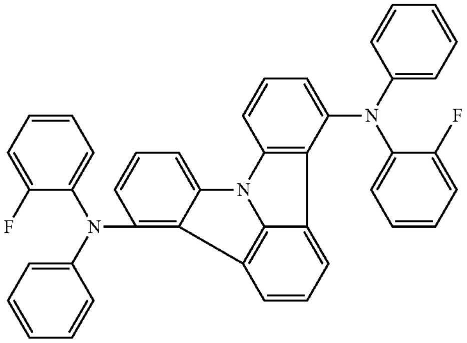
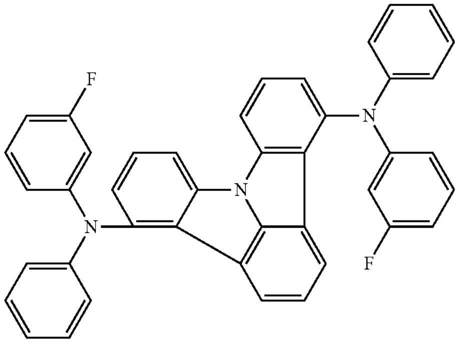
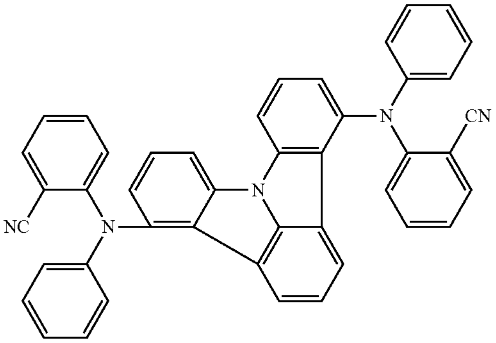
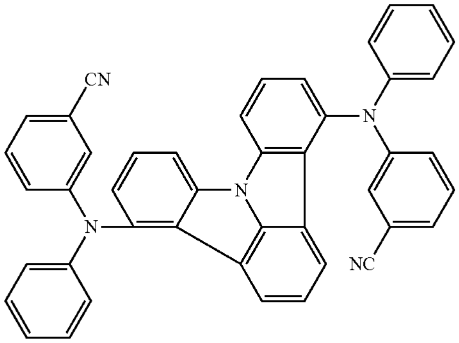

-continued
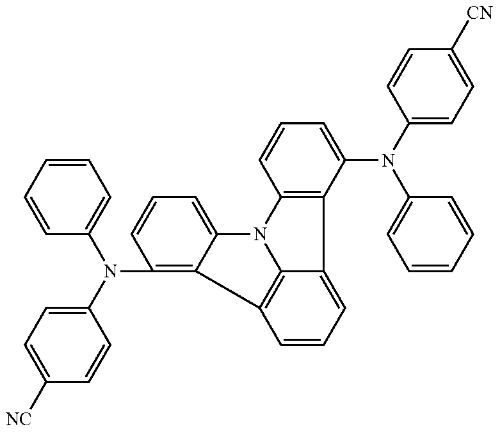
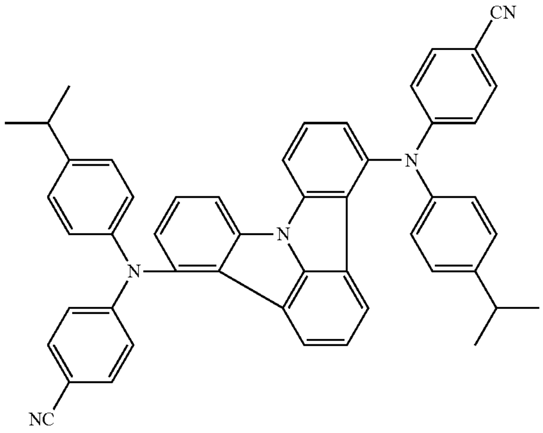
[Formula 233]
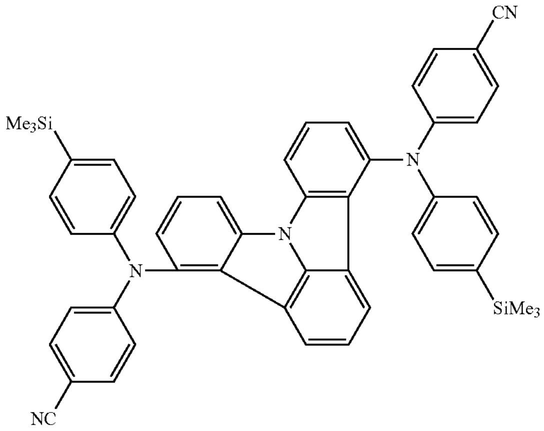
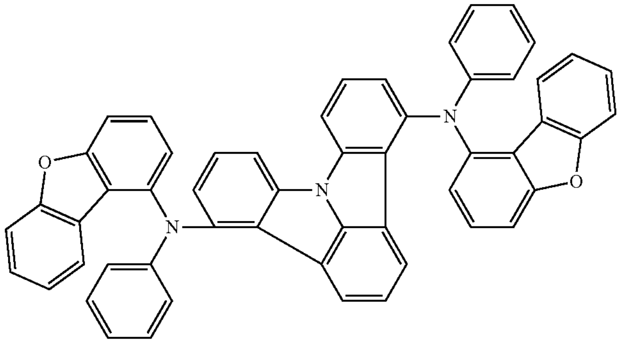
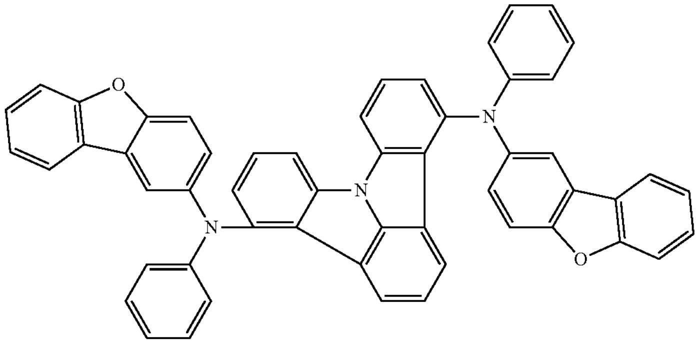

-continued
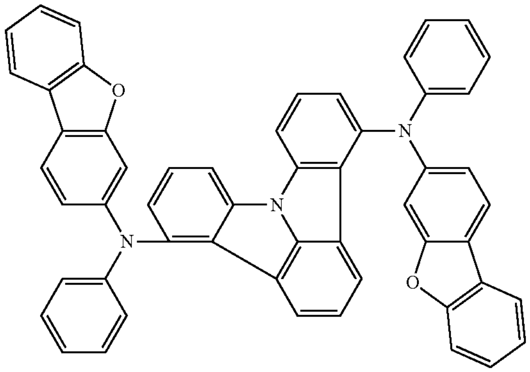
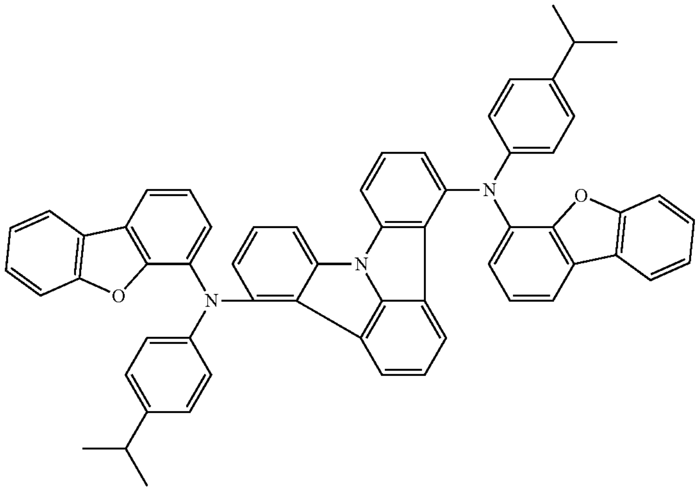
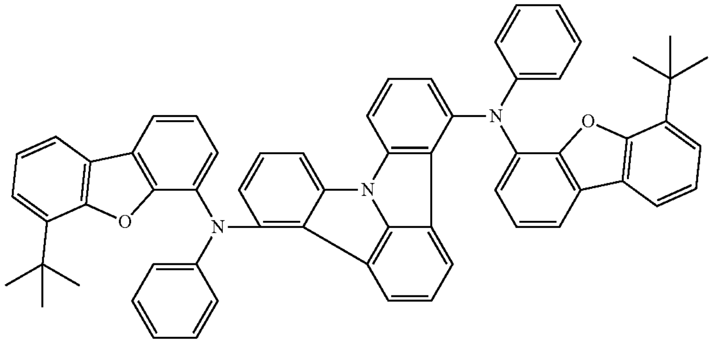
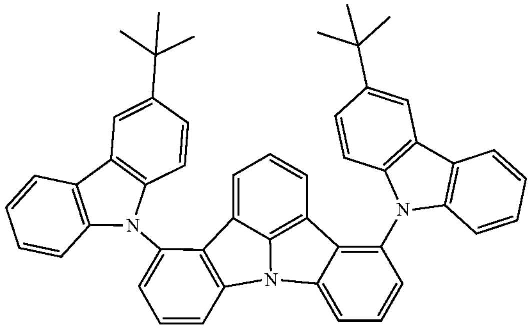

-continued
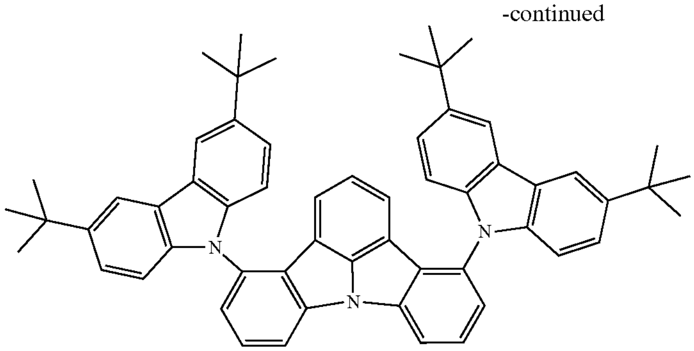
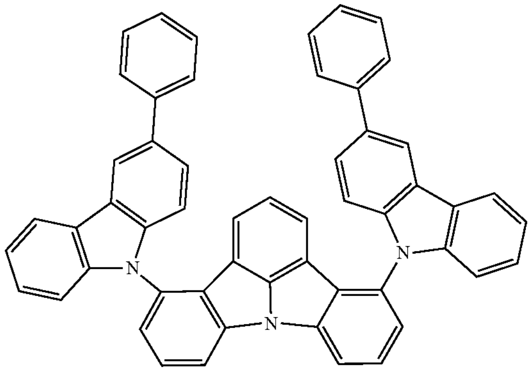
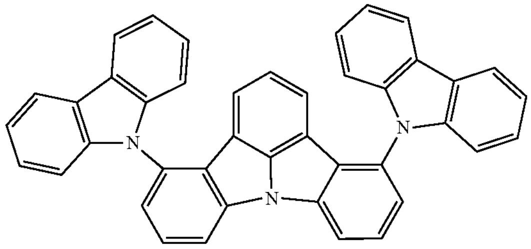
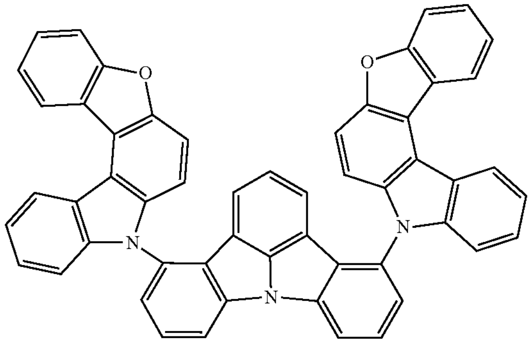
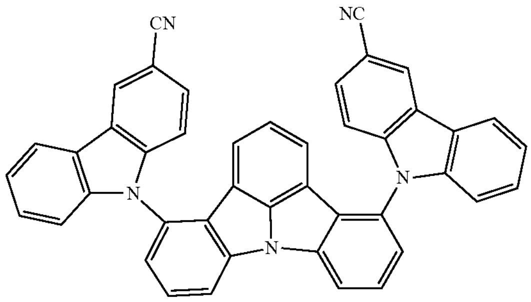
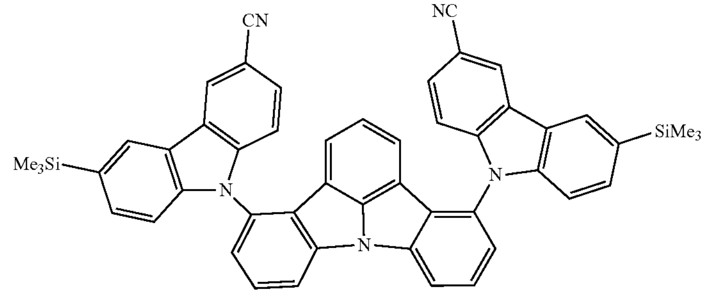
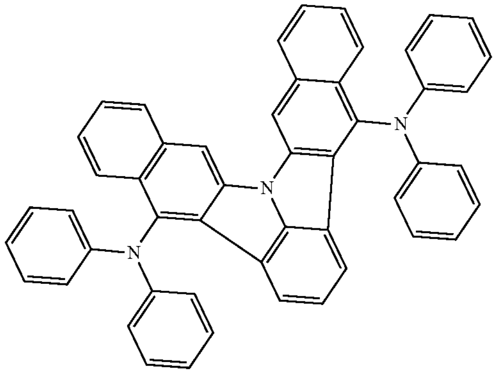
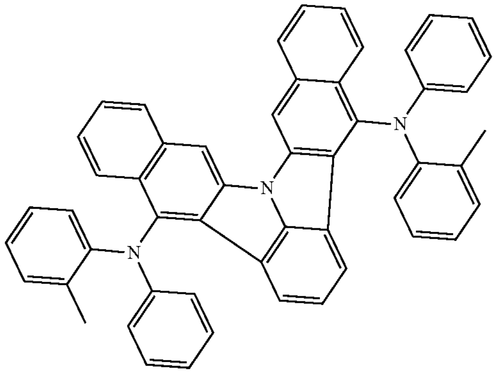

-continued
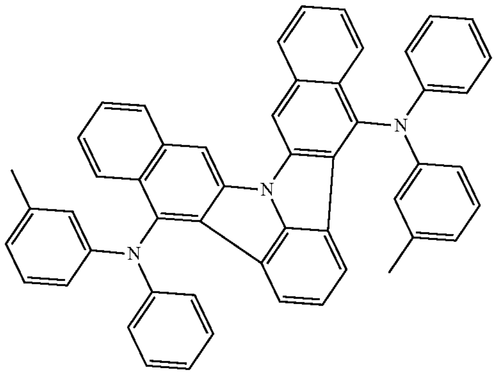
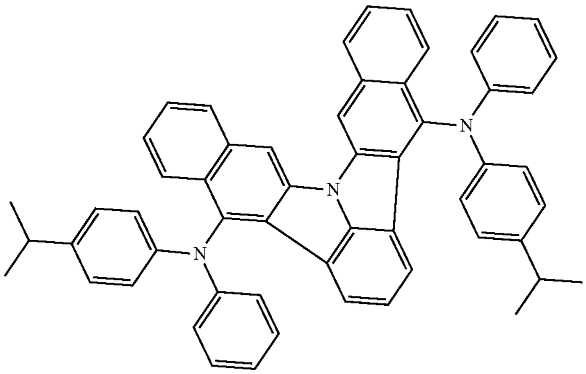
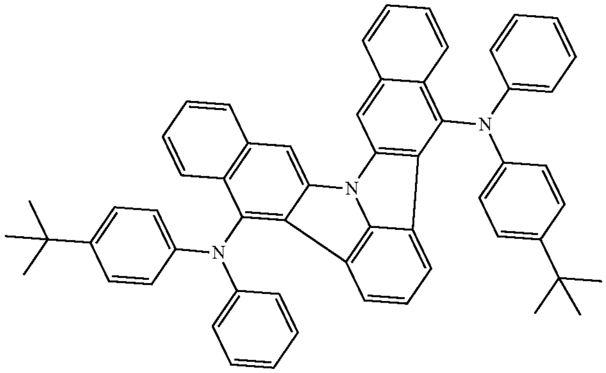
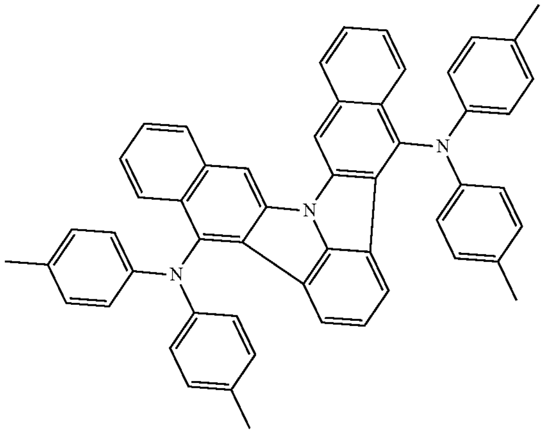
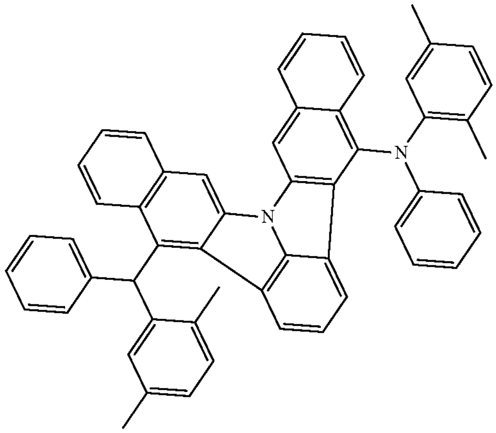
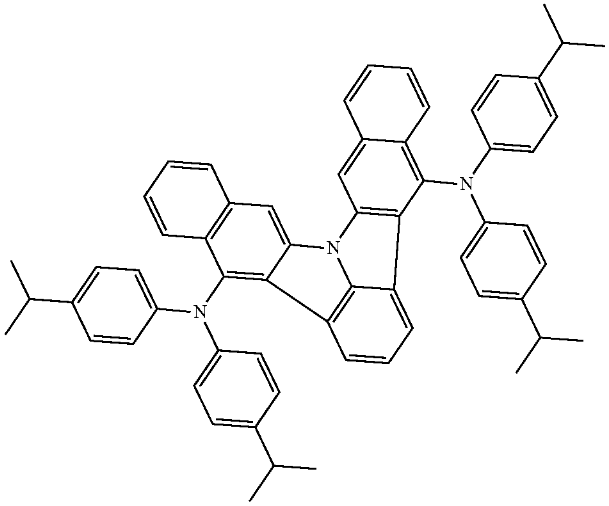

-continued
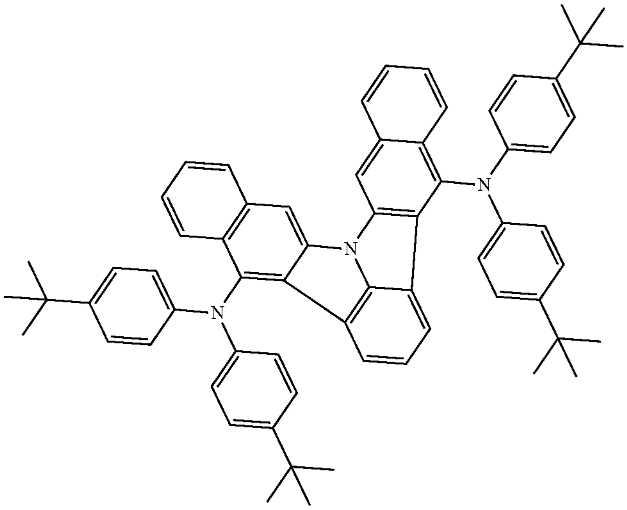
[Formula 234]
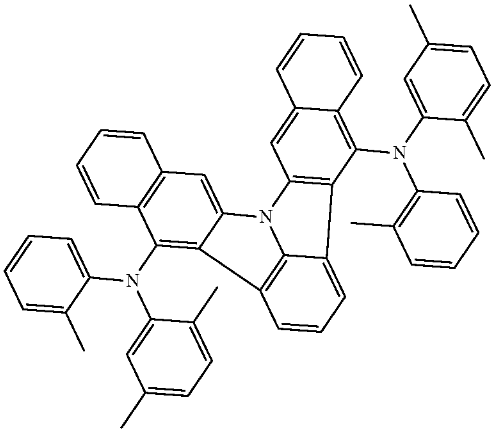
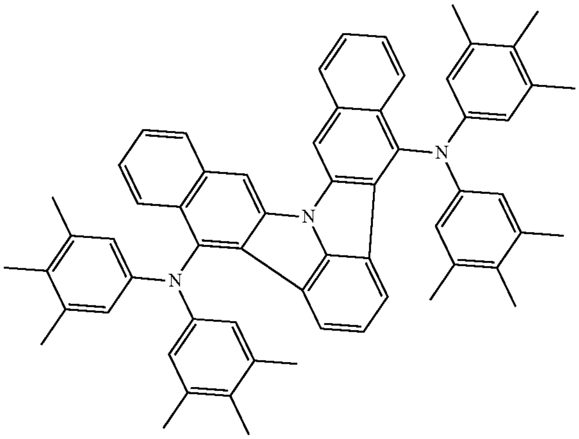
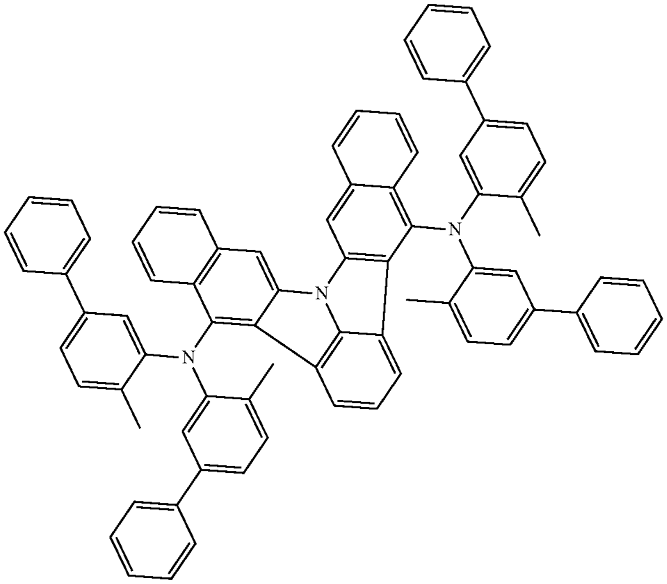

-continued
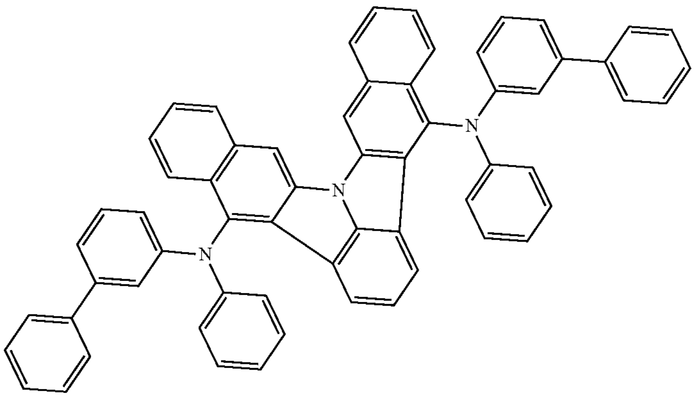
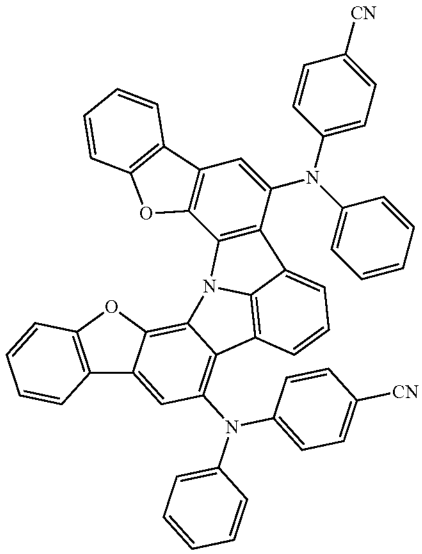
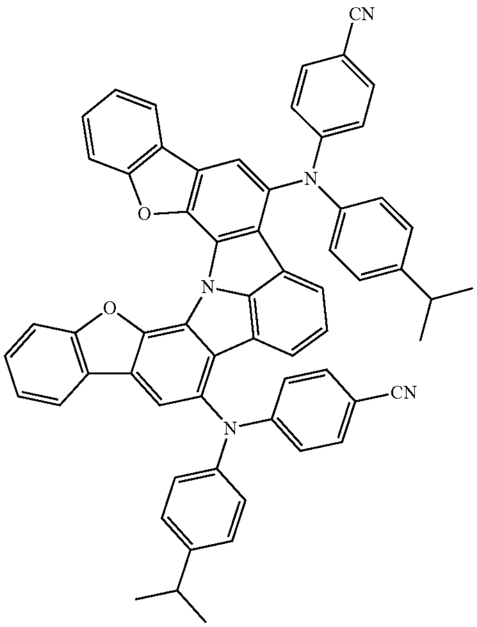
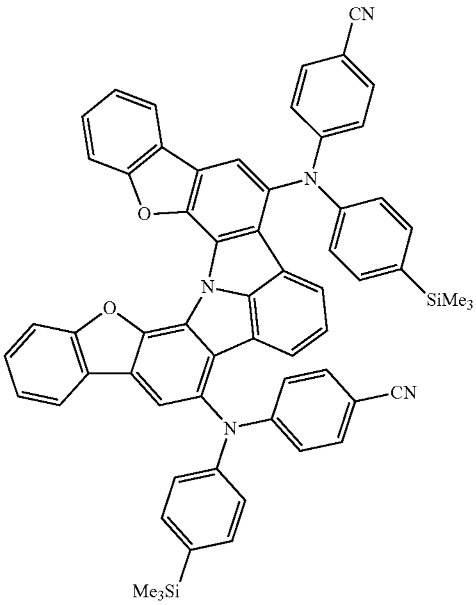

-continued
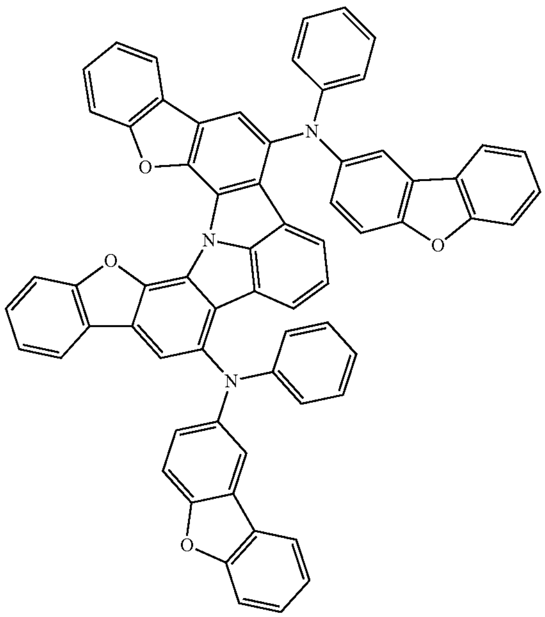
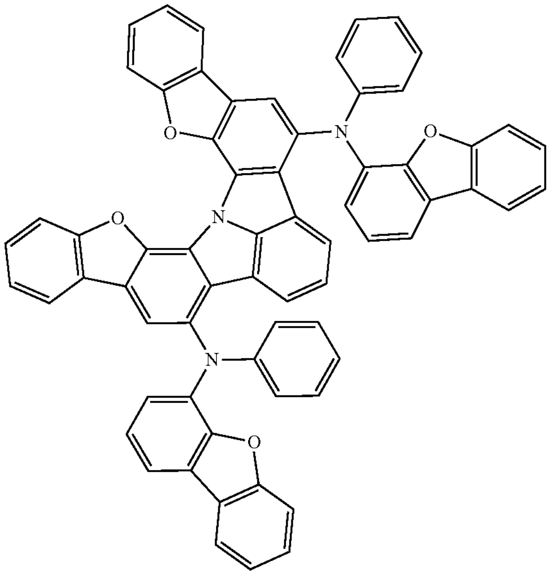
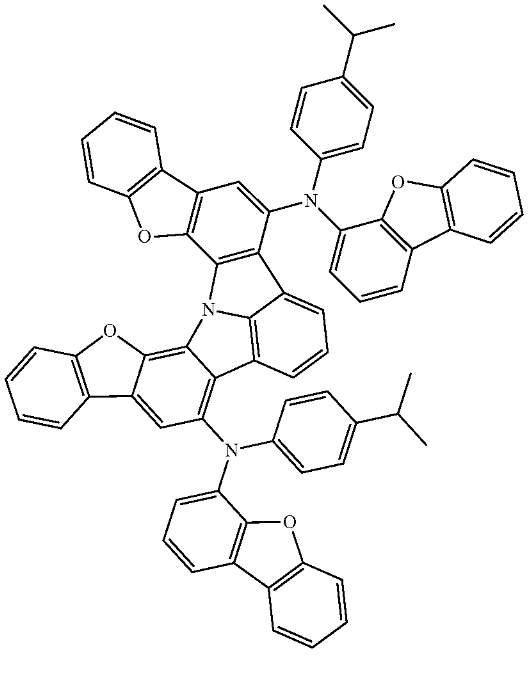
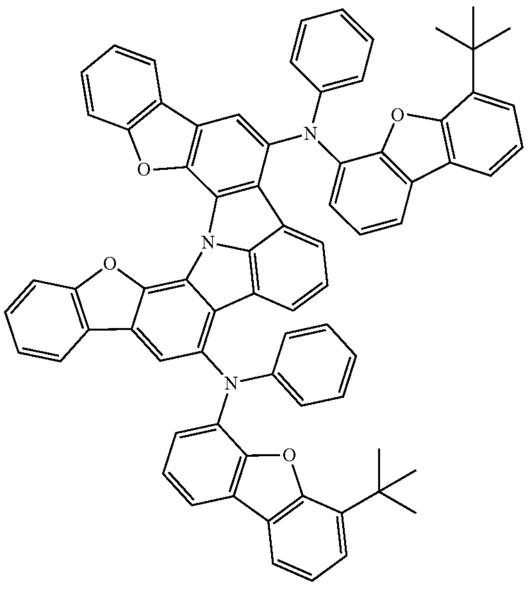

-continued
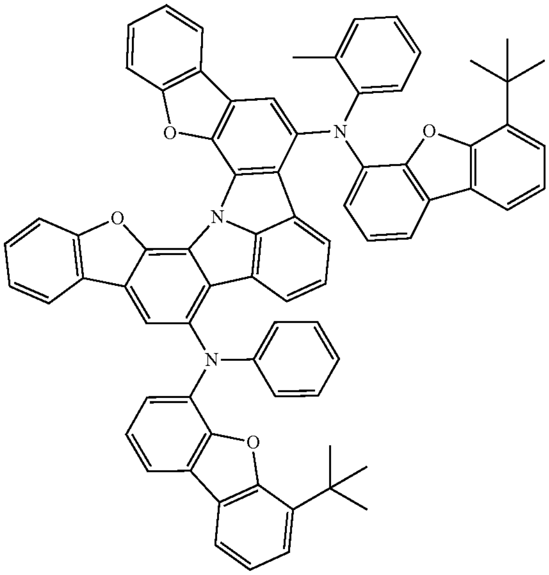
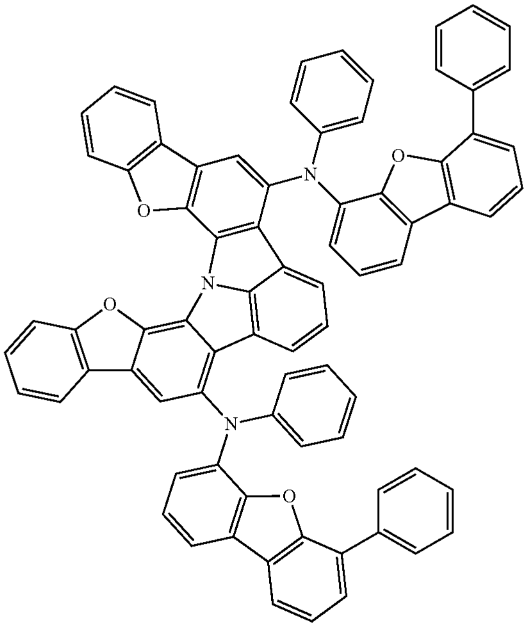
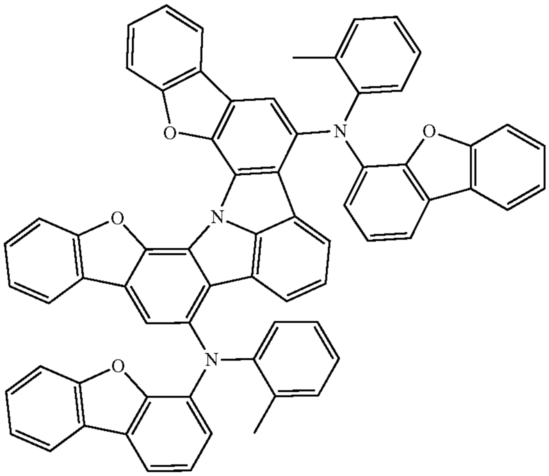
[Formula 235]
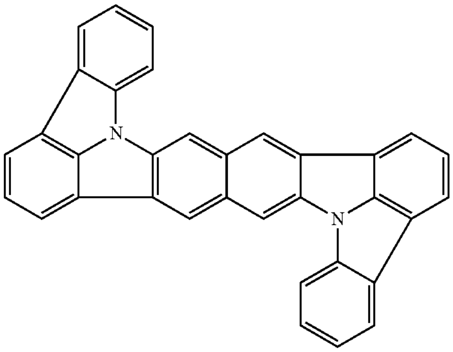
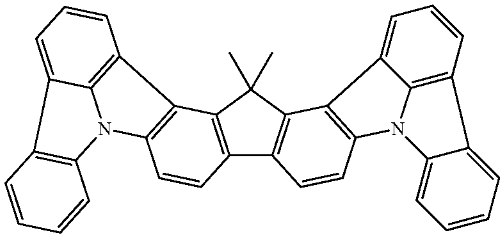

-continued
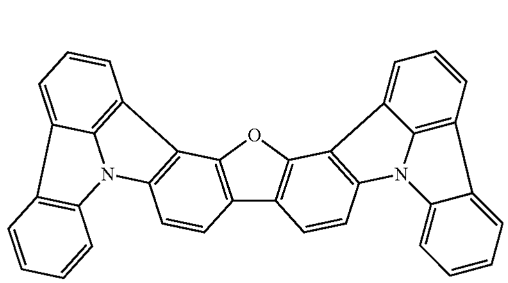
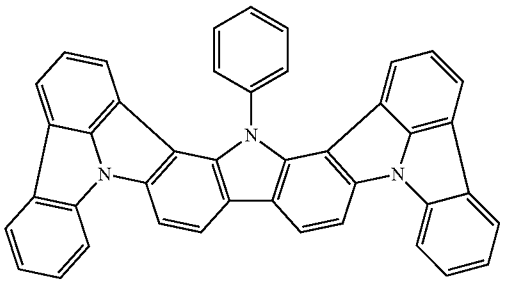
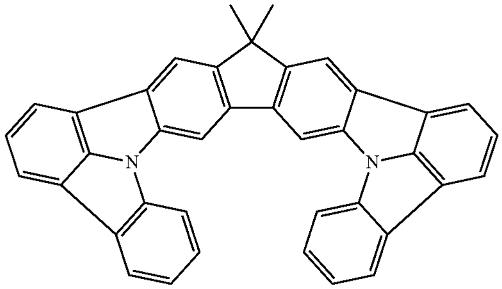
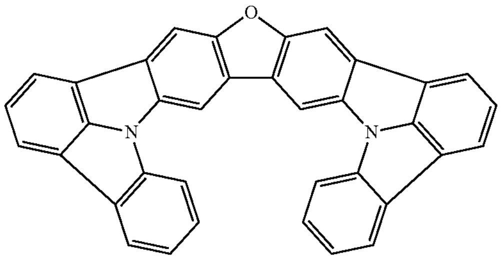
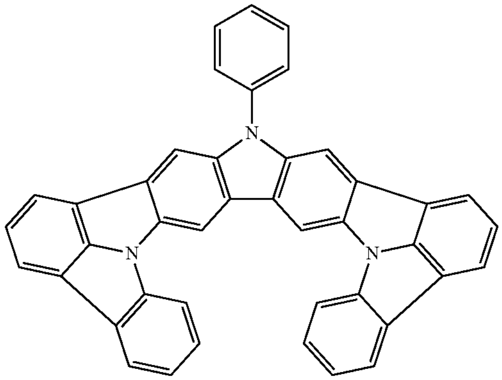
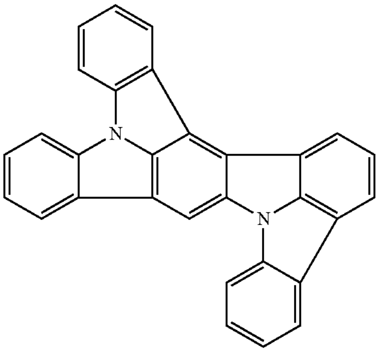
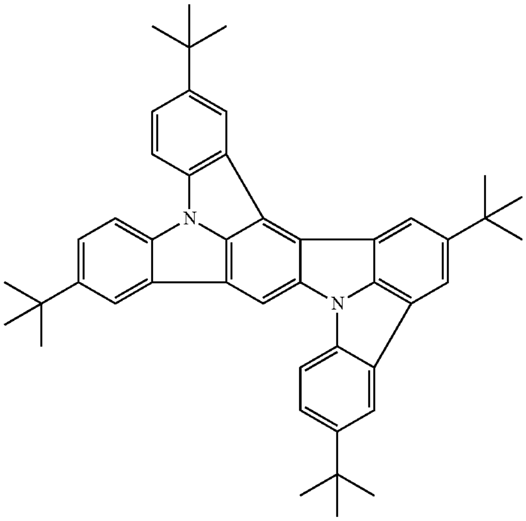

-continued

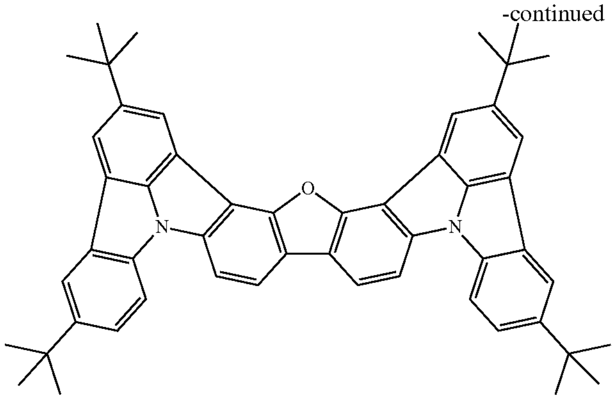

Compound Represented by Formula (5)

The compound represented by the formula (5) will be described below. The compound represented by the formula (5) corresponds to the compound represented by the above-described formula (41-3).

[Formula 236]

(5)

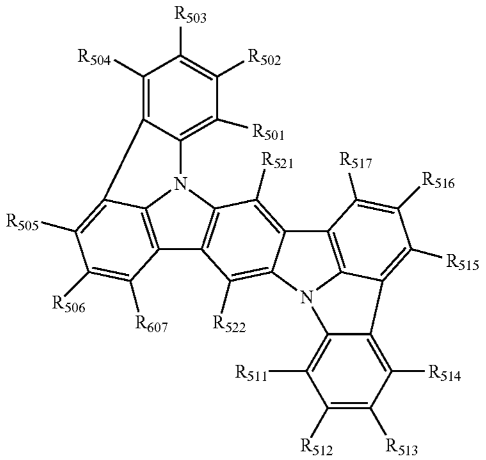

In the formula (5): at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ neither forming the monocyclic ring nor forming the fused ring each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{521}$ and $R_{522}$ each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

"A combination of adjacent two or more of $R_{501}$ to $R_{507}$ and $R_{511}$ to $R_{517}$" refers to, for instance, a combination of $R_{501}$ and $R_{502}$, a combination of $R_{502}$ and $R_{503}$, a combination of $R_{503}$ and $R_{504}$, a combination of $R_{505}$ and $R_{506}$, a combination of $R_{506}$ and $R_{507}$, and a combination of $R_{501}$, $R_{502}$, and $R_{503}$.

In an exemplary embodiment, at least one, preferably two of $R_{501}$ to $R_{507}$ and $R_{511}$ to $R_{517}$ are groups represented by —N($R_{906}$)($R_{907}$).

In an exemplary embodiment, $R_{501}$ to $R_{507}$ and $R_{511}$ to $R_{517}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (52).

[Formula 237]

(52)

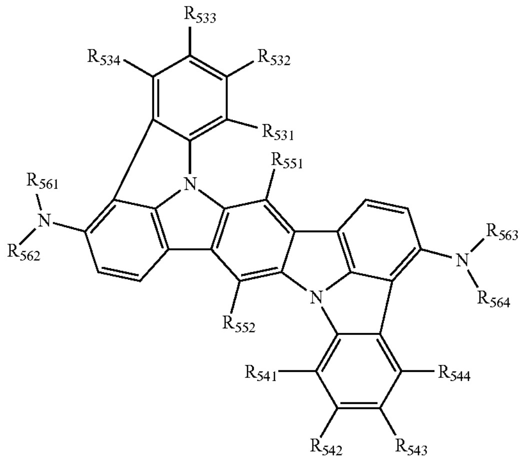

In the formula (52): at least one combination of adjacent two or more of $R_{531}$ to $R_{534}$ and $R_{541}$ to $R_{544}$ are mutually bonded to form a substituted or unsubstituted monocyclic ring, mutually bonded to form a substituted or unsubstituted fused ring, or not mutually bonded;

$R_{531}$ to $R_{534}$ and $R_{541}$ to $R_{544}$ neither forming the monocyclic ring nor forming the fused ring and $R_{551}$ and $R_{552}$ each independently represent a hydrogen atom, a substituted or unsubstituted aryl group having 6 to 50 ring carbon atoms, or a substituted or unsubstituted heterocyclic group having 5 to 50 ring atoms; and $R_{561}$ to $R_{564}$ are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (53).

[Formula 238]

(53)

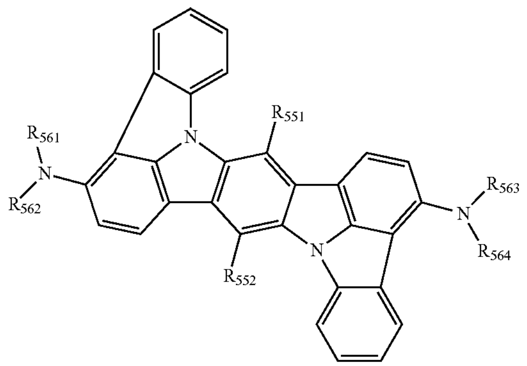

In the formula (53), $R_{551}$, $R_{552}$ and $R_{561}$ to $R_{564}$ each independently represent the same as $R_{551}$, $R_{552}$ and $R_{561}$ to $R_{564}$ in the formula (52).

In an exemplary embodiment, $R_{561}$ to $R_{564}$ in the formulae (52) and (53) are each independently a substituted or unsubstituted aryl group having 6 to 50 ring carbon atoms (preferably a phenyl group).

In an exemplary embodiment, $R_{521}$ and $R_{522}$ in the formula (5) and $R_{551}$ and $R_{552}$ in the formulae (52) and (53) are hydrogen atoms.

In an exemplary embodiment, the substituent for "substituted or unsubstituted" in the formulae (5), (52) and (53) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

Specific Examples of Compound Represented by Formula (5)

Specific examples of the compound represented by the formula (5) include compounds shown below.

[Formula 239]

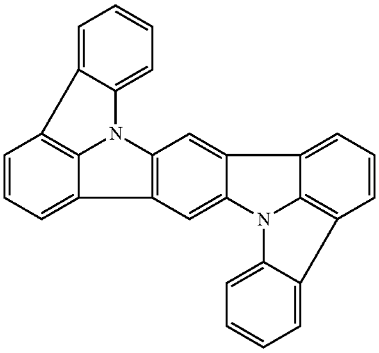

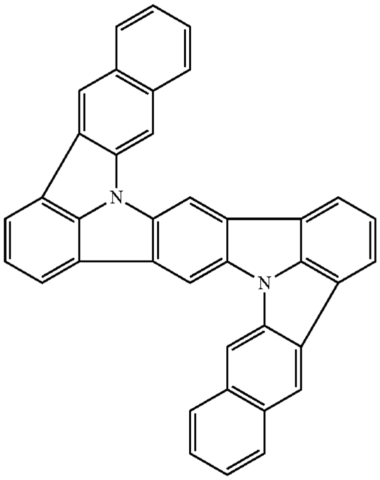

-continued
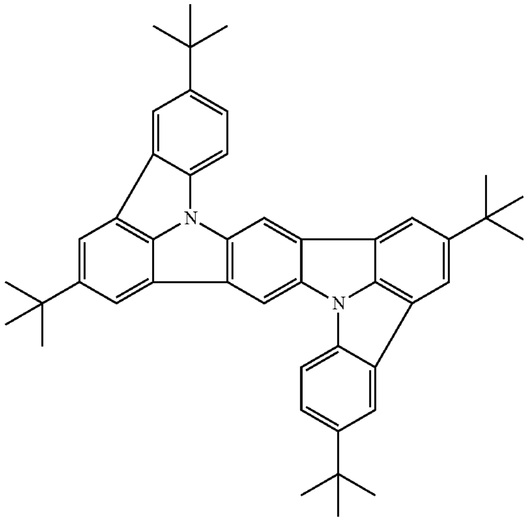
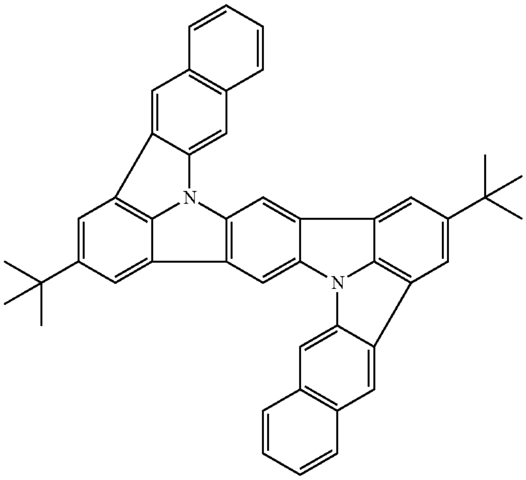
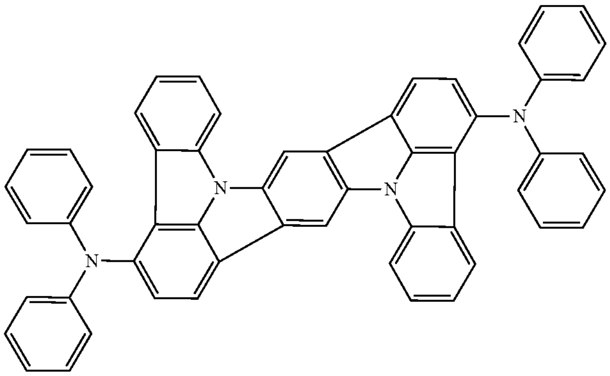
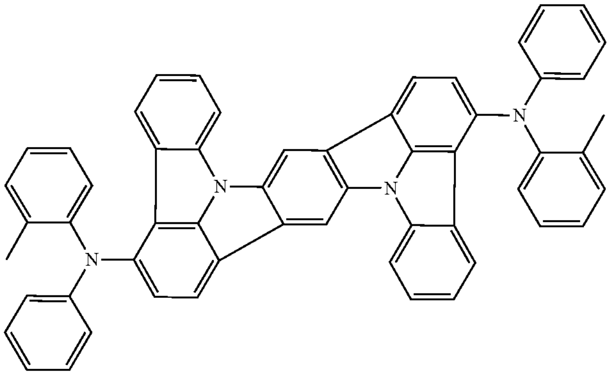
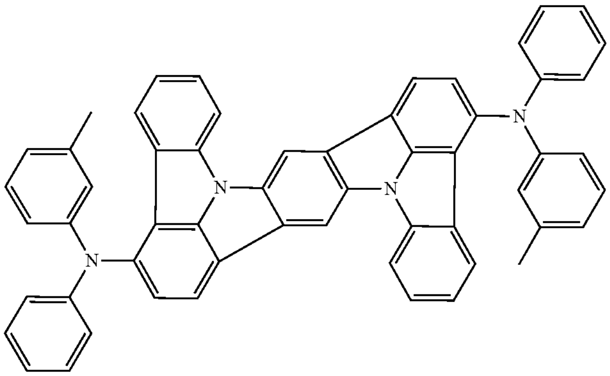

-continued
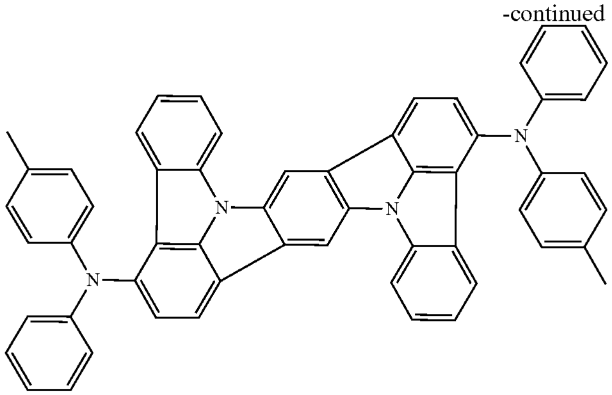
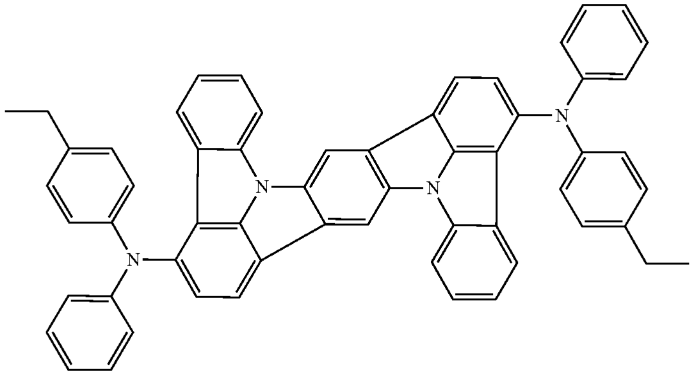
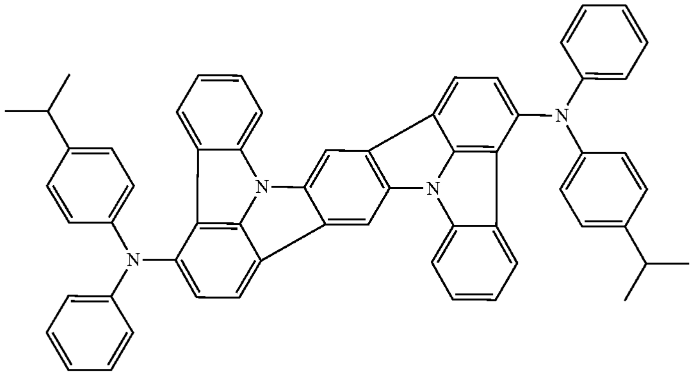
[Formula 240]
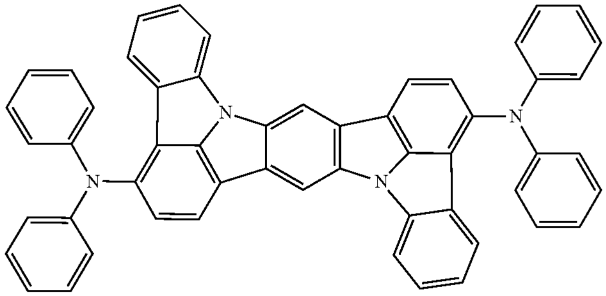
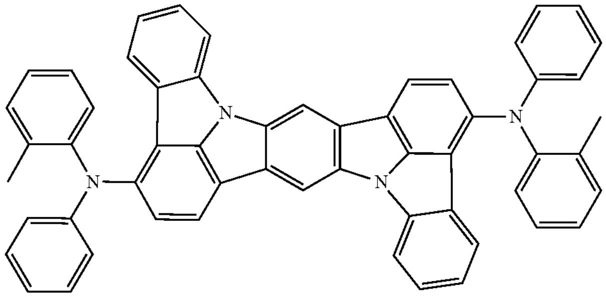

-continued
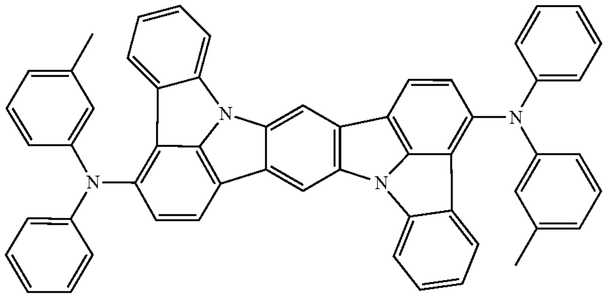
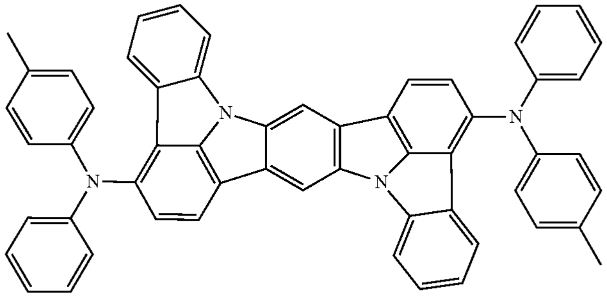
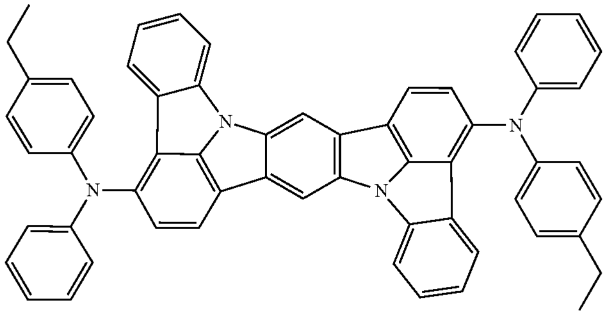
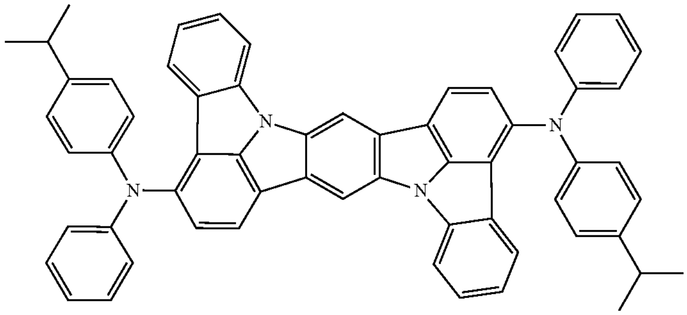
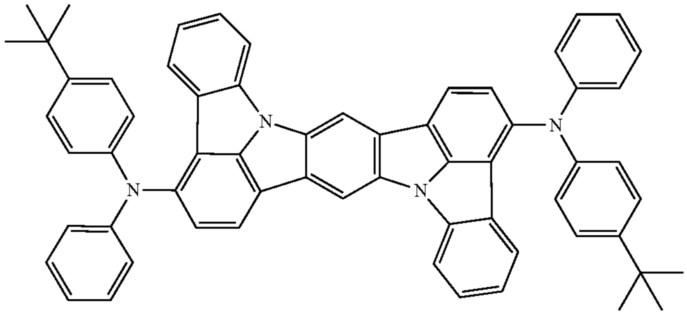

-continued
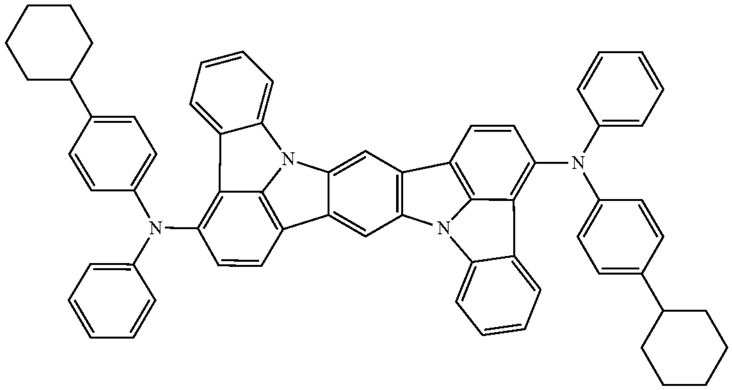
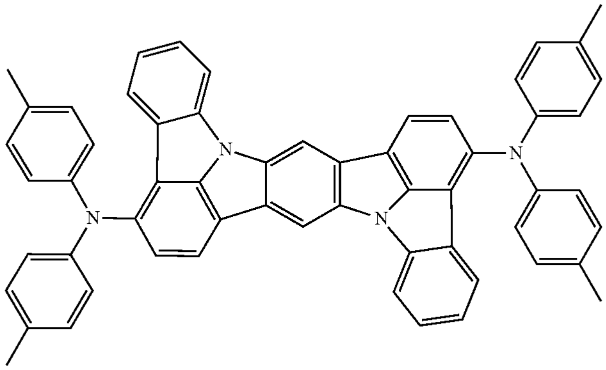
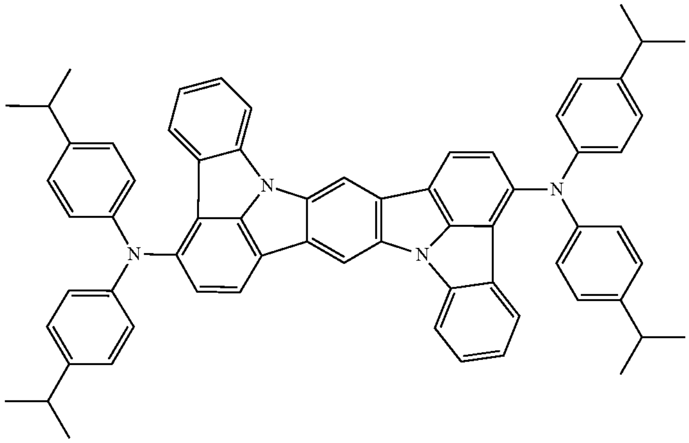
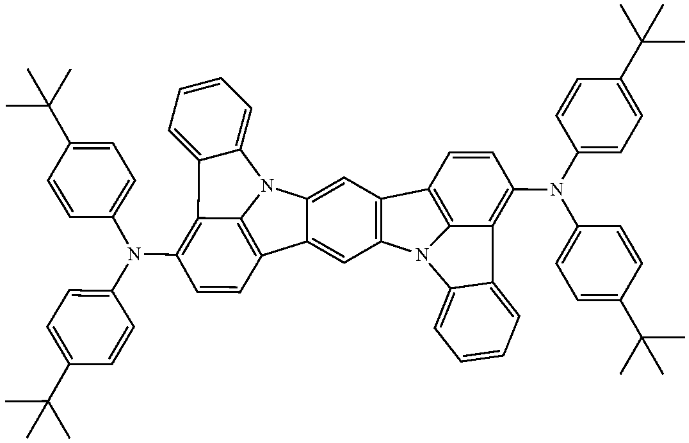

-continued
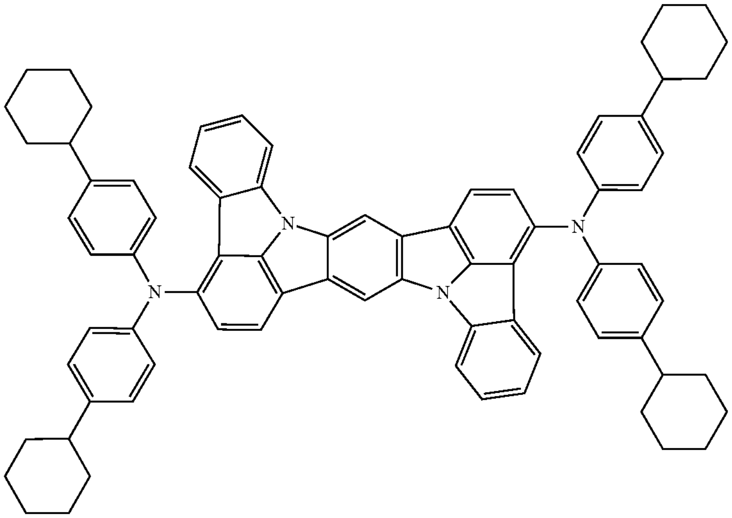
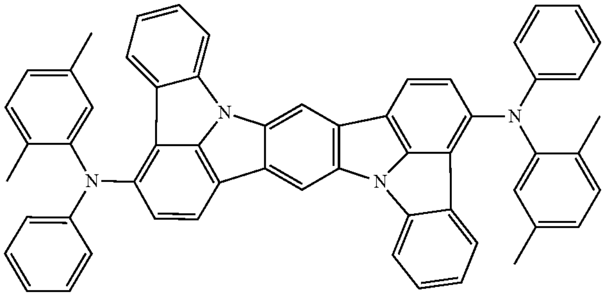
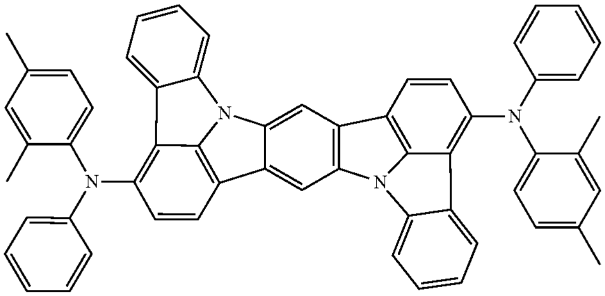
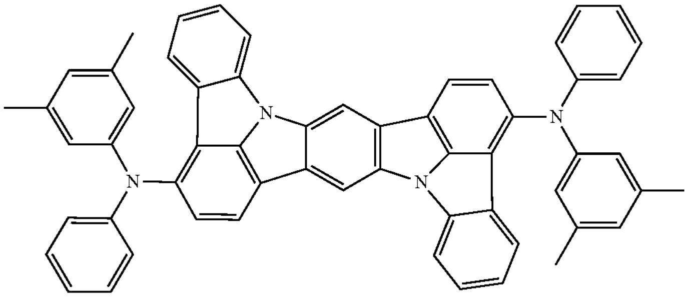
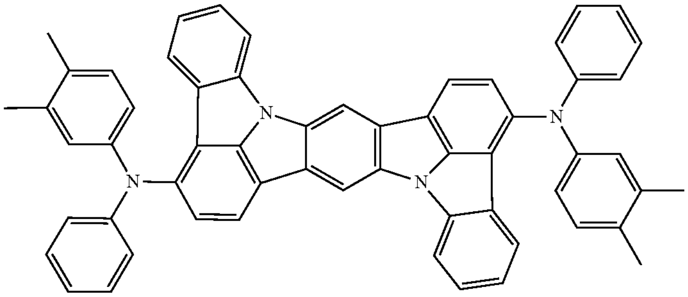

-continued
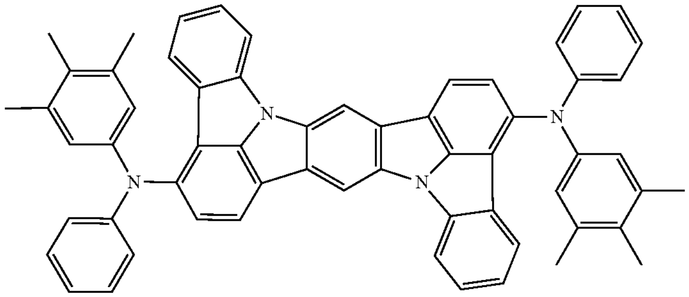
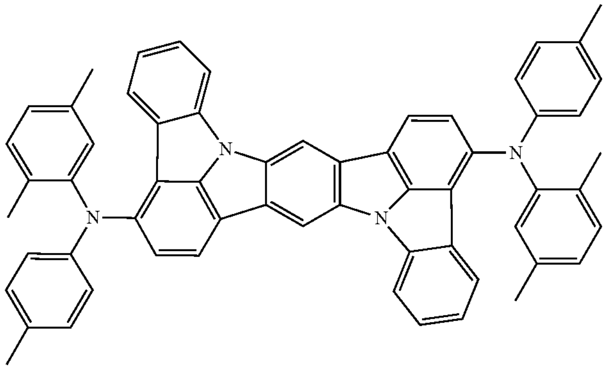
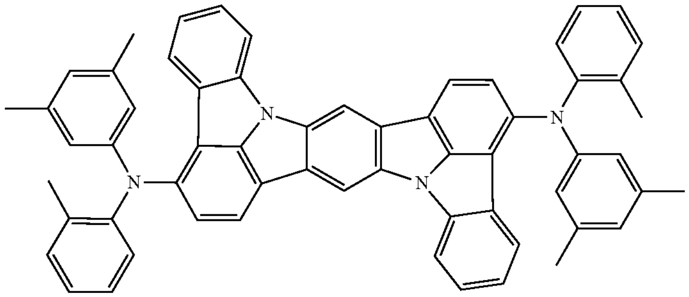
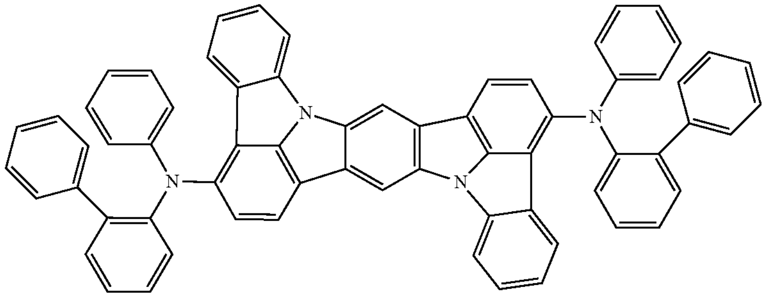
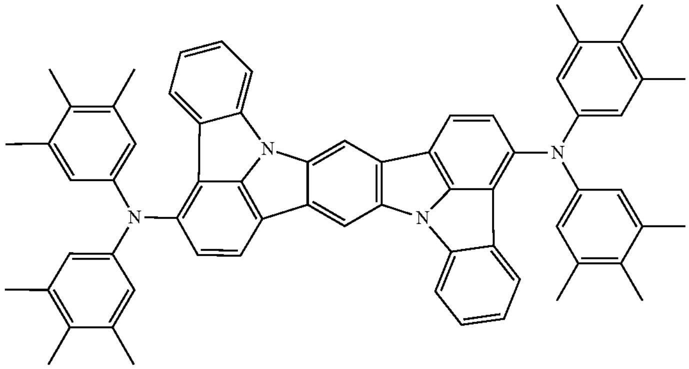

-continued
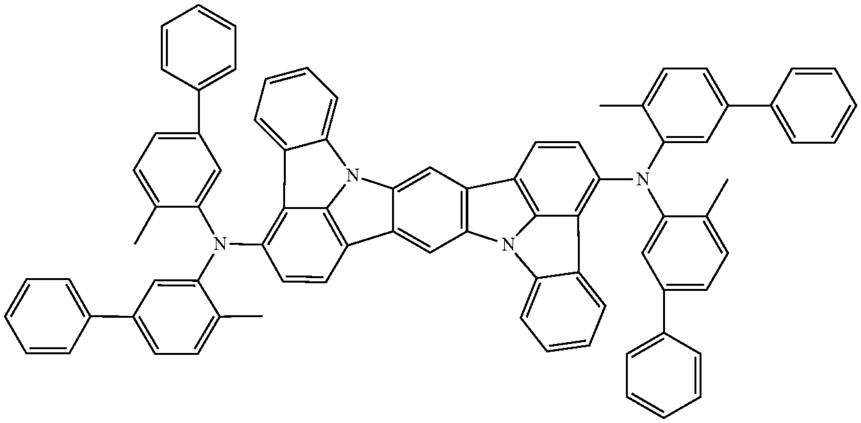
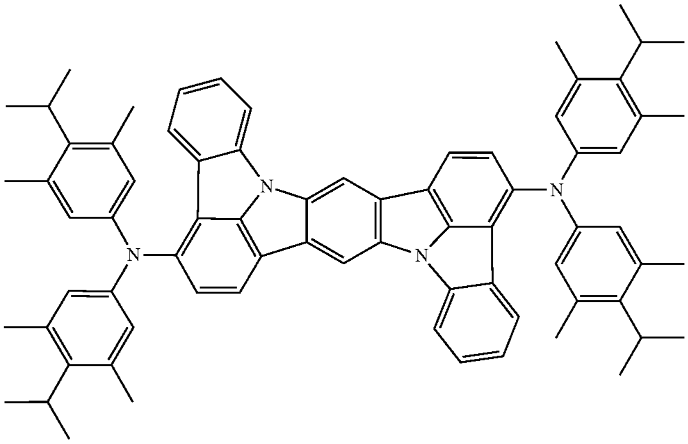
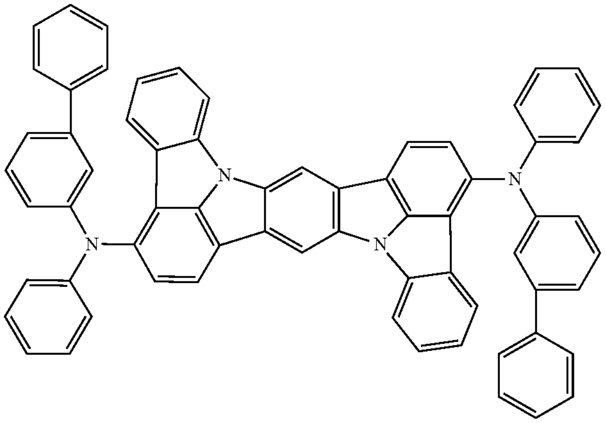
[Formula 241]
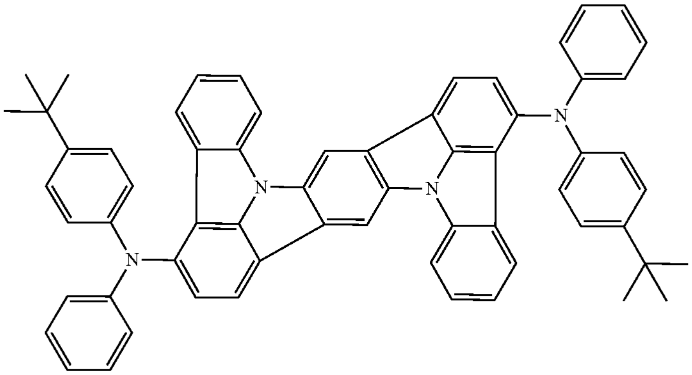

-continued
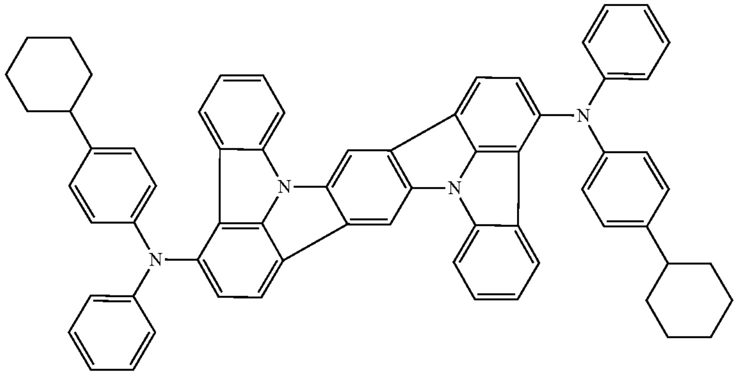
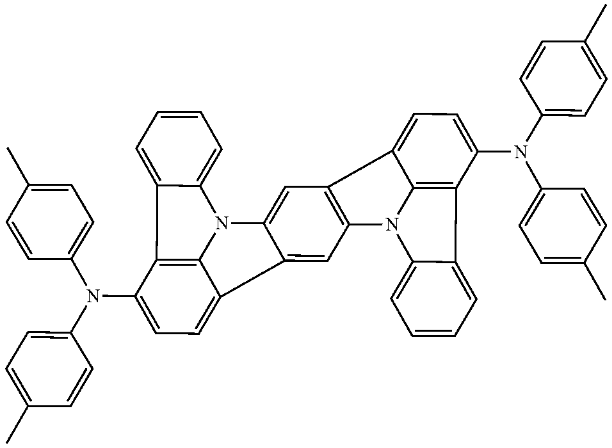
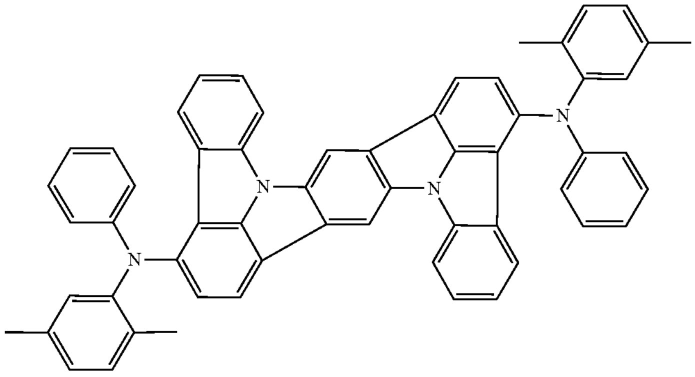
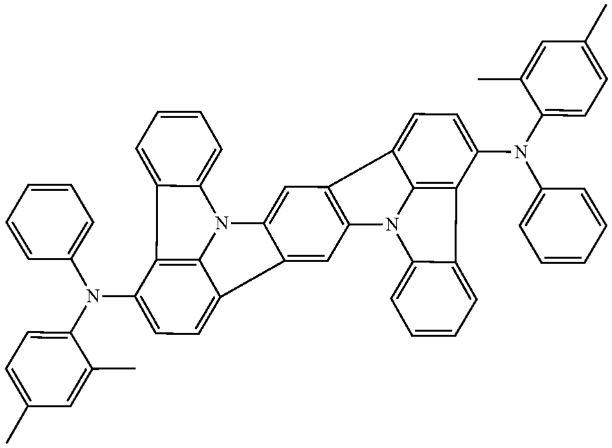

-continued
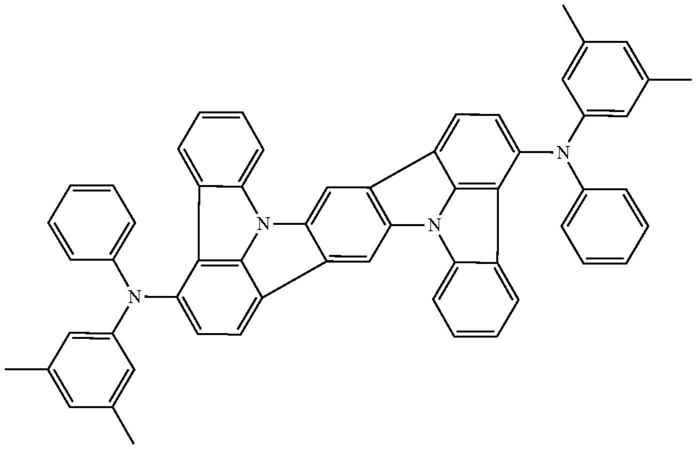
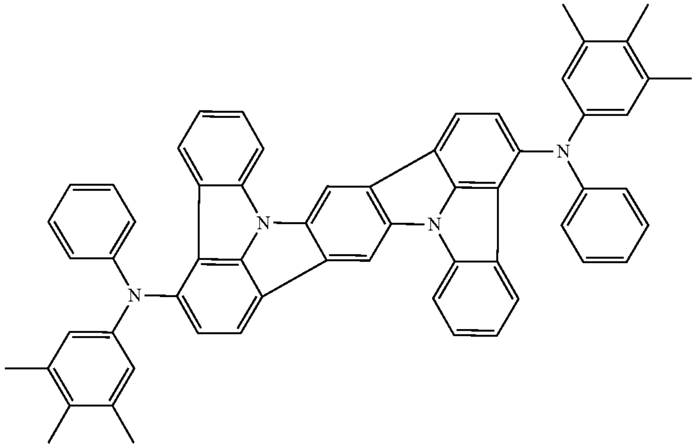
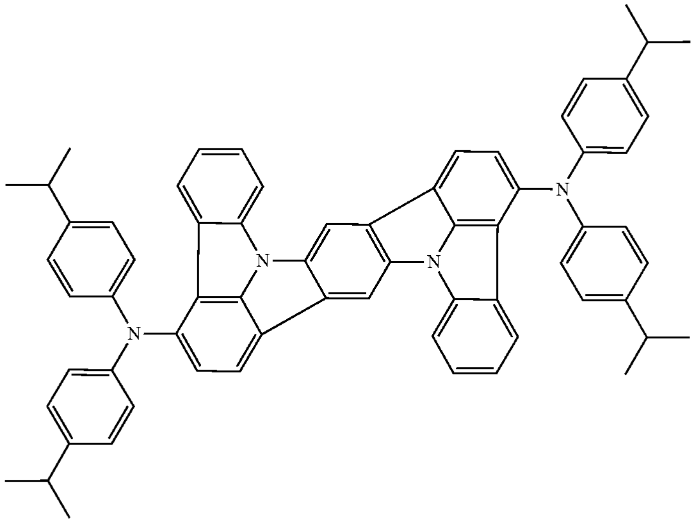

-continued
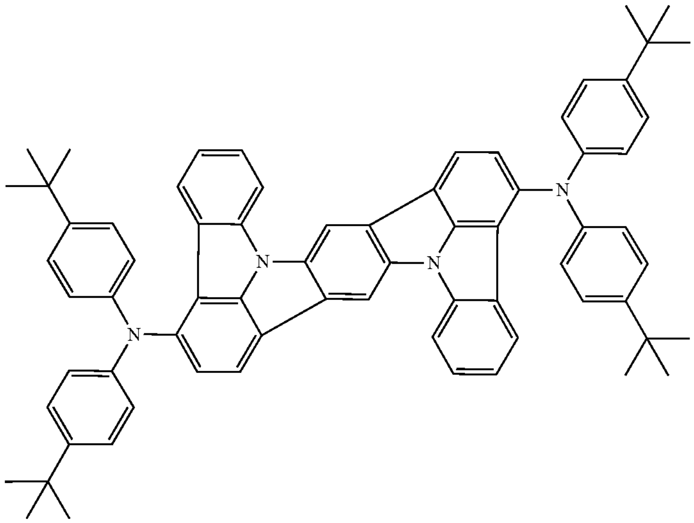
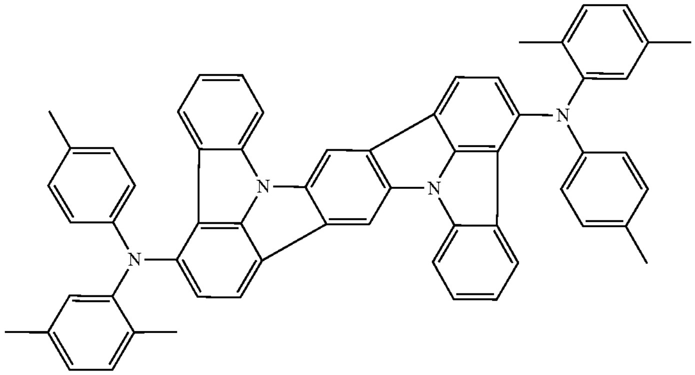
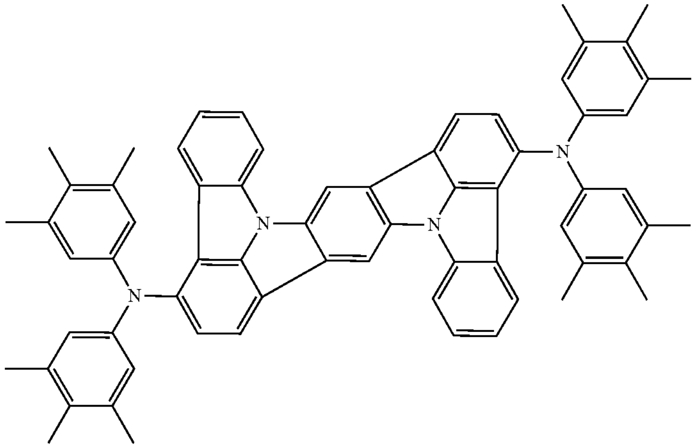
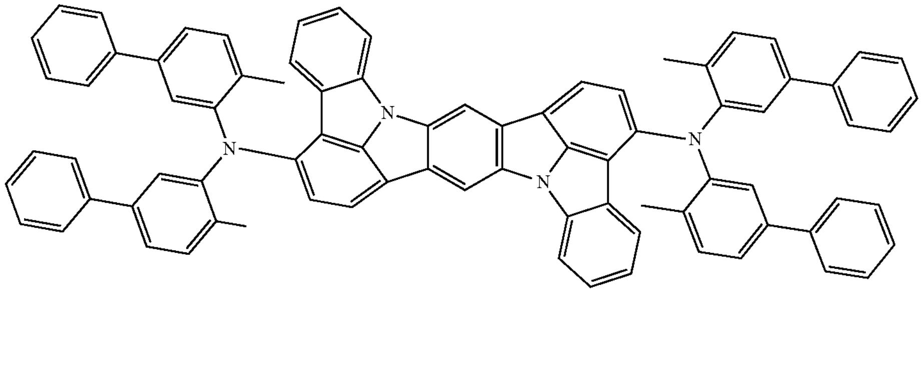

-continued
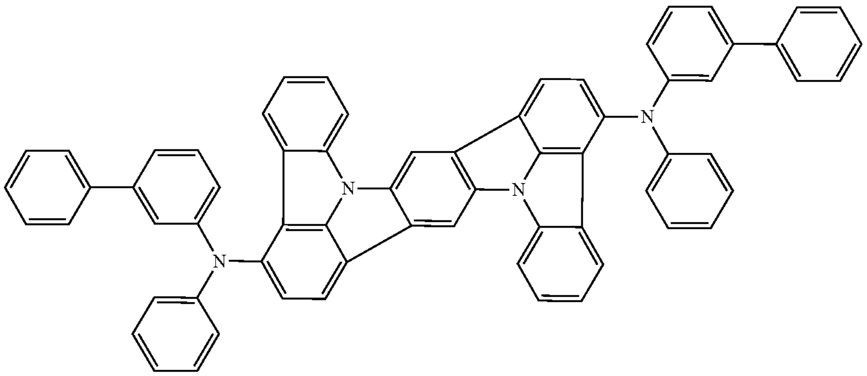
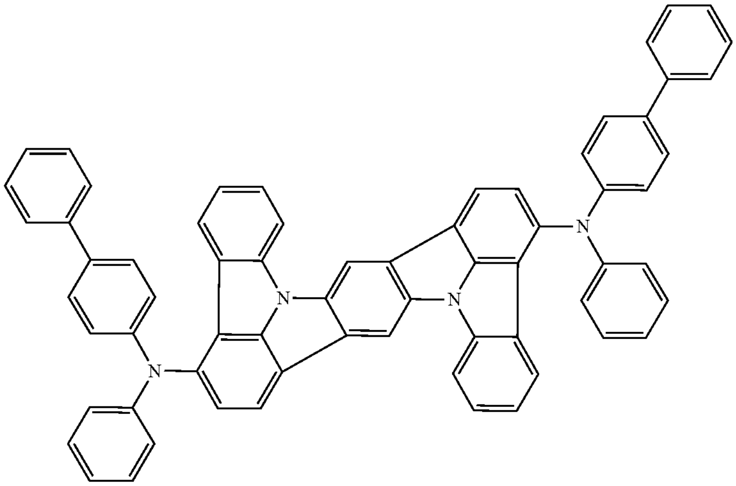
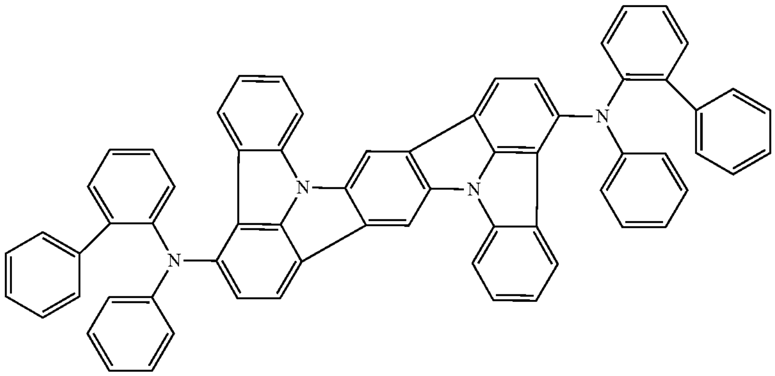
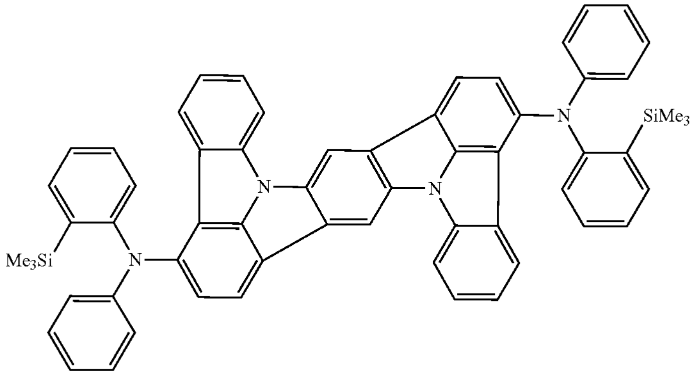

-continued
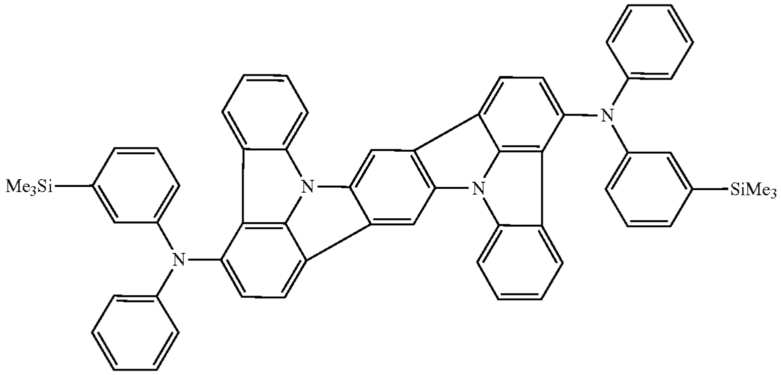
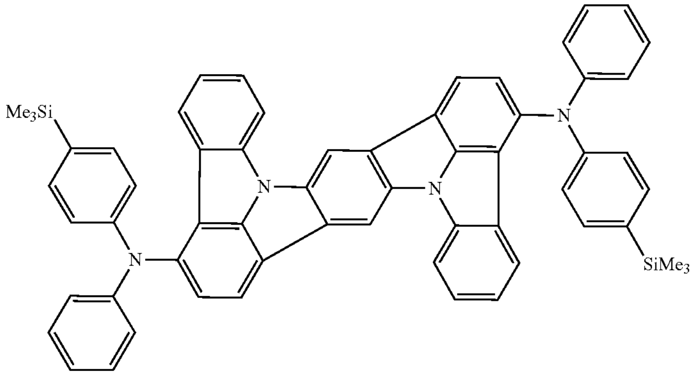
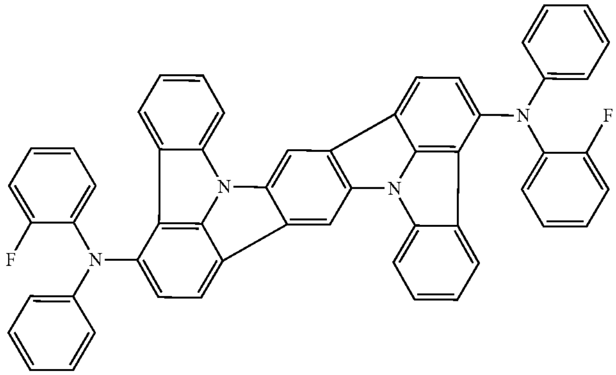
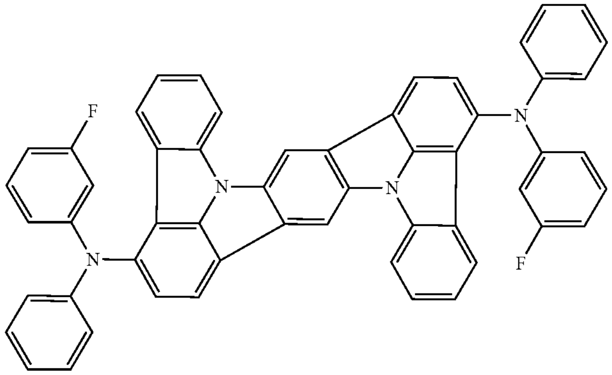

-continued
[Formula 242]
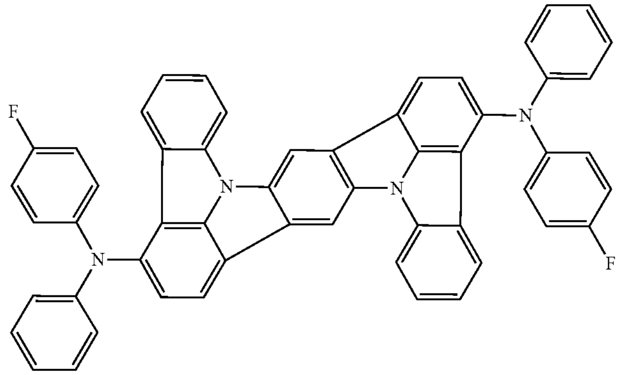
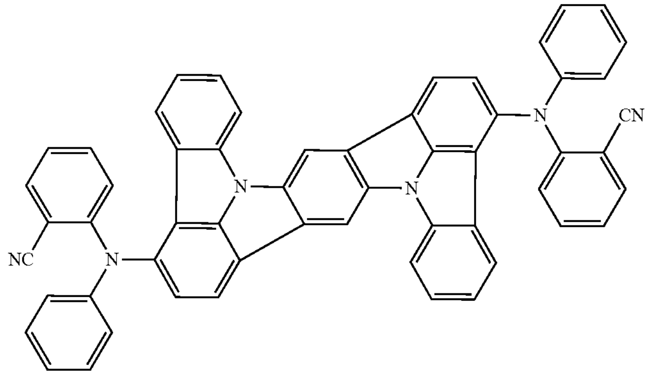
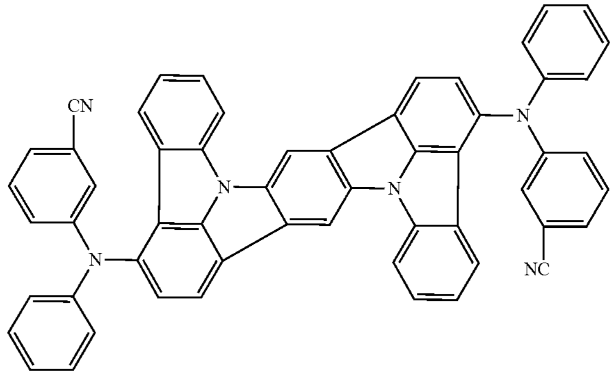
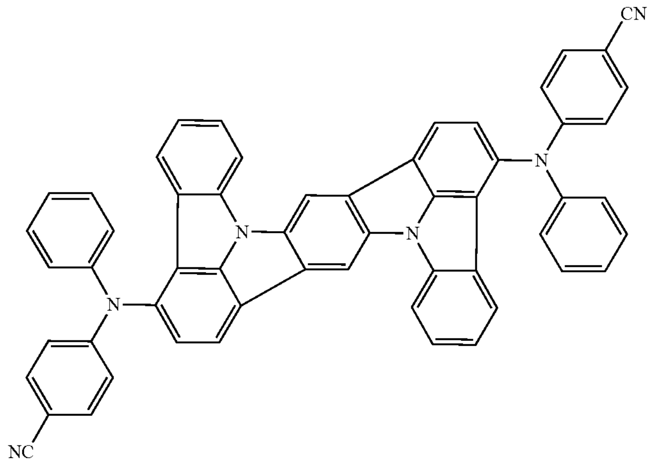

-continued
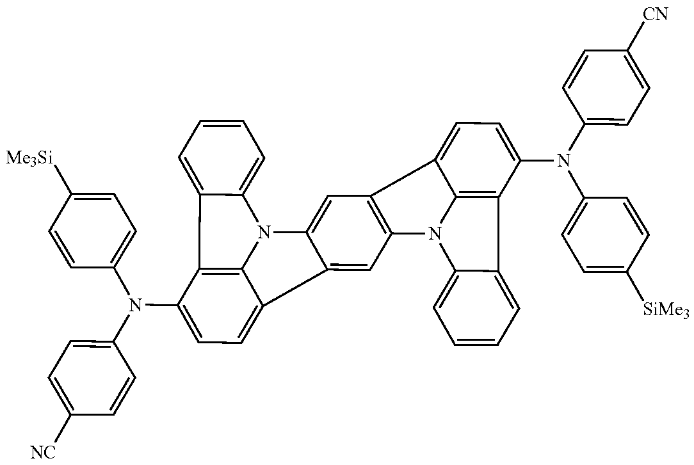
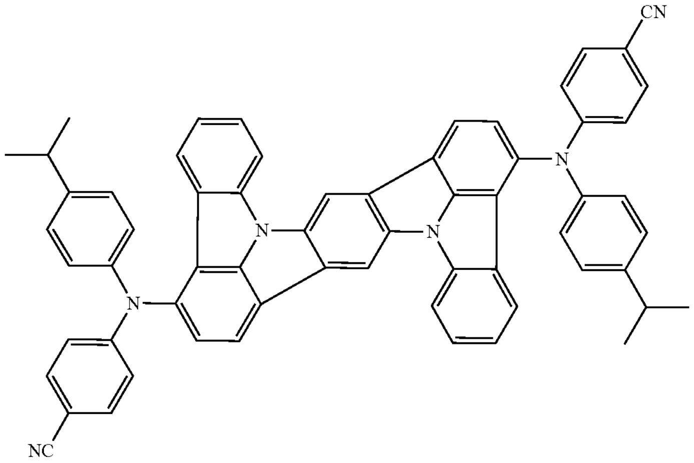
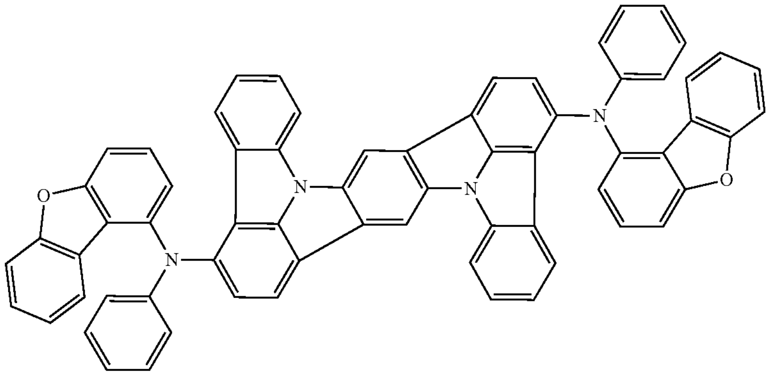
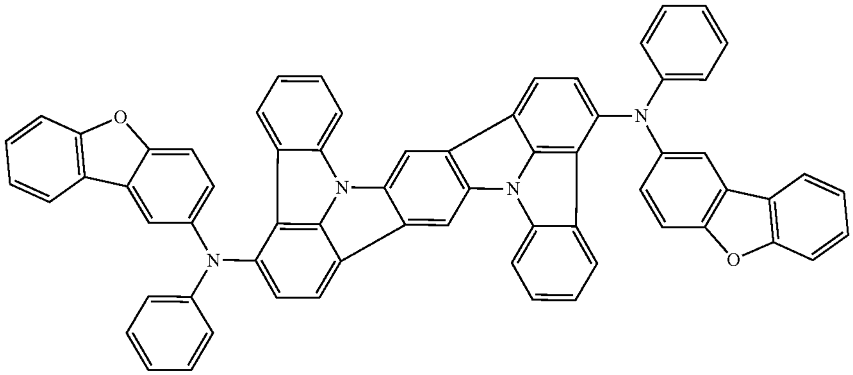

-continued
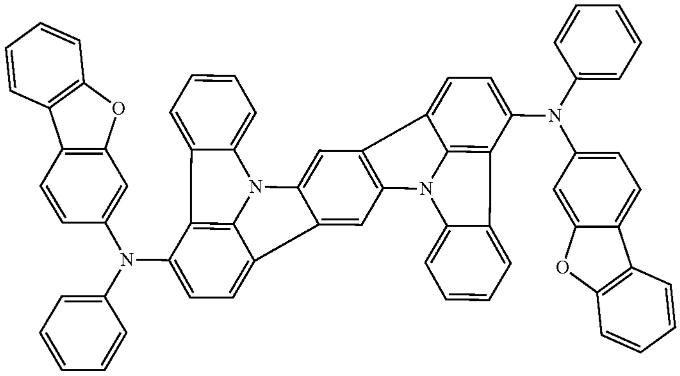
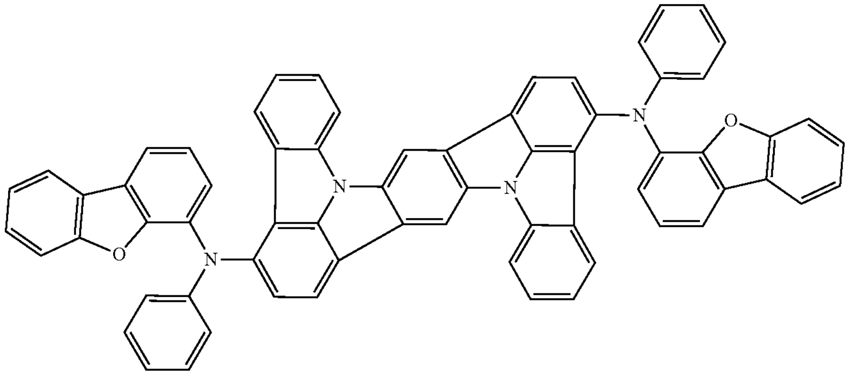
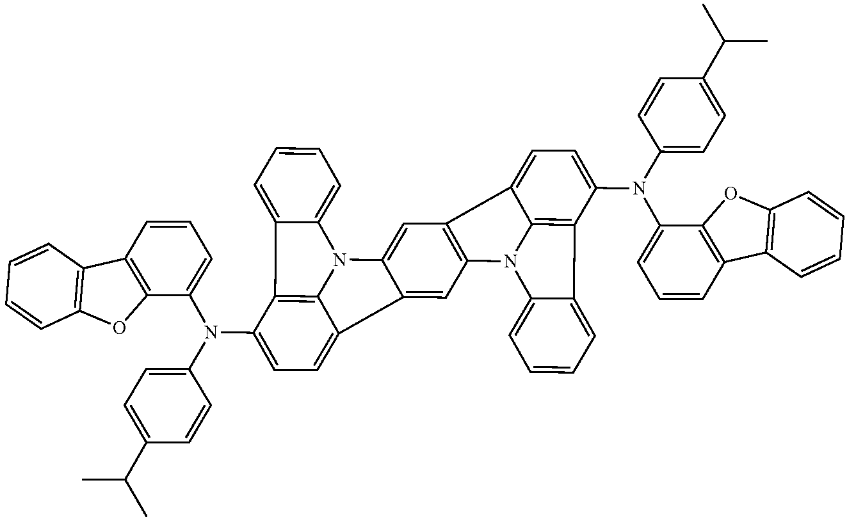
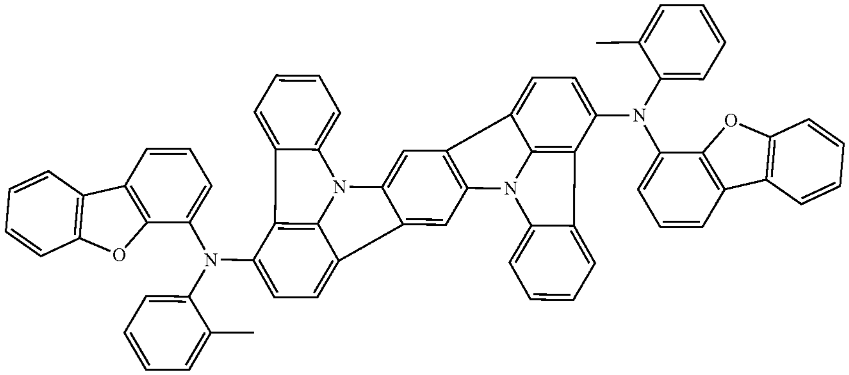

-continued
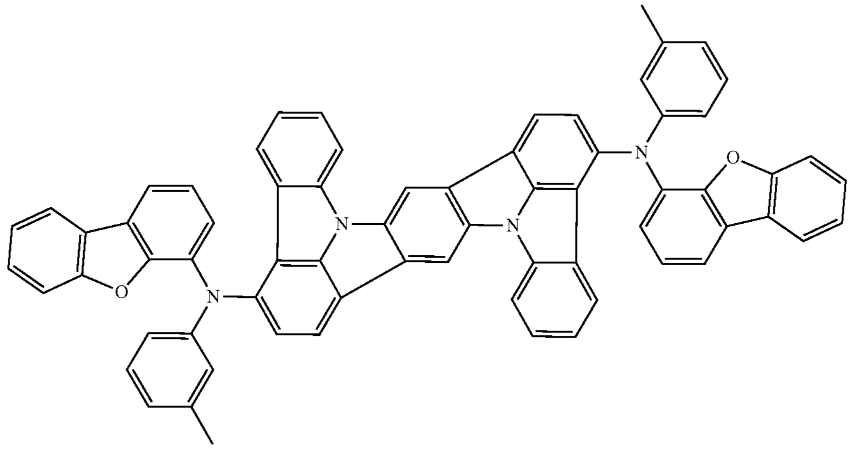
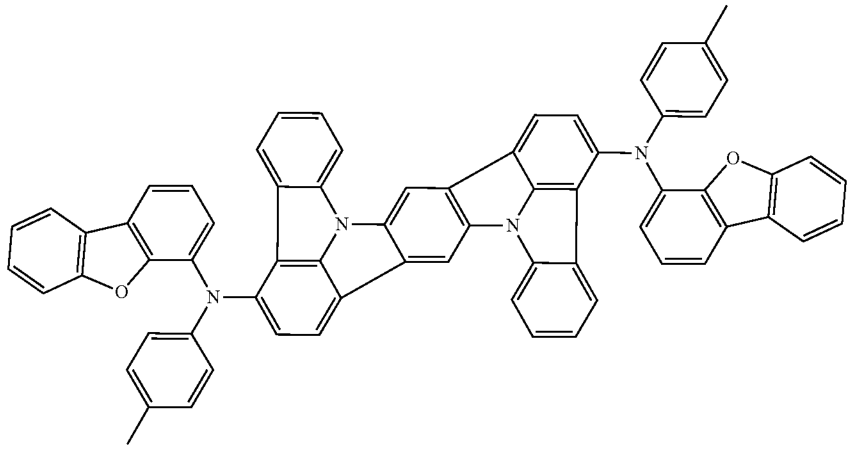
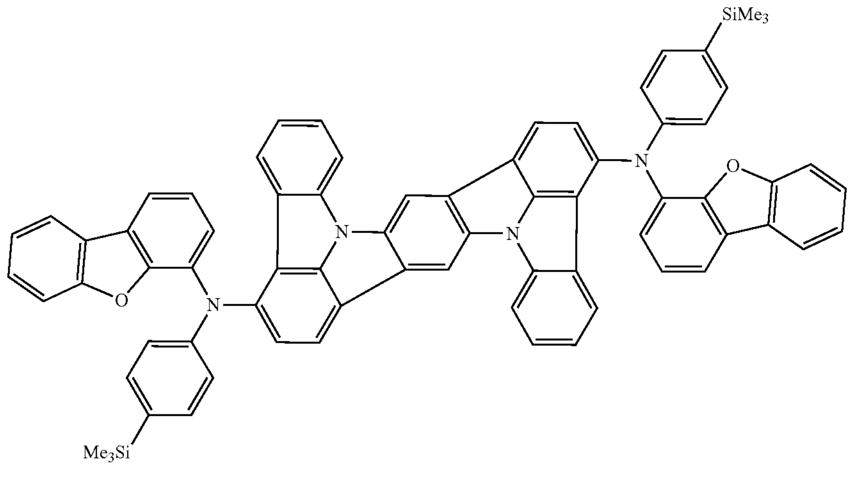

-continued
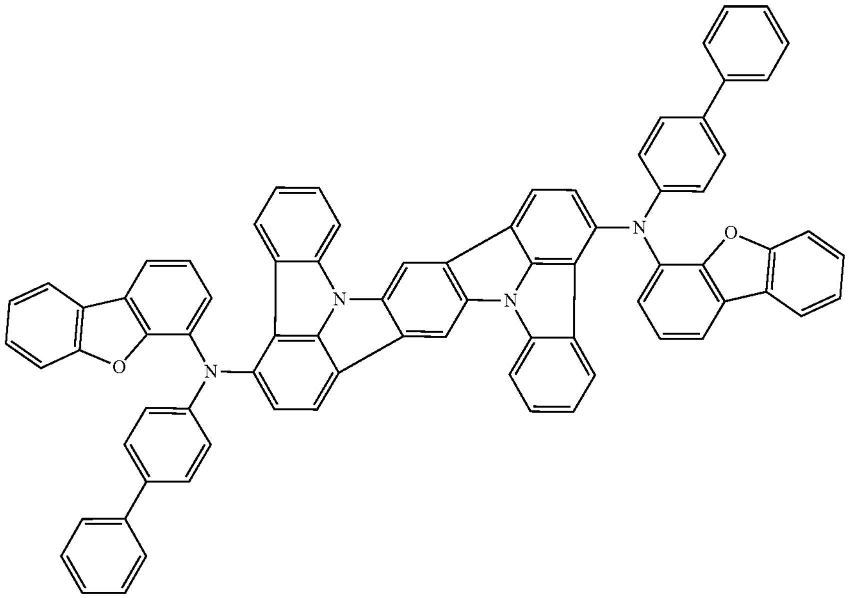
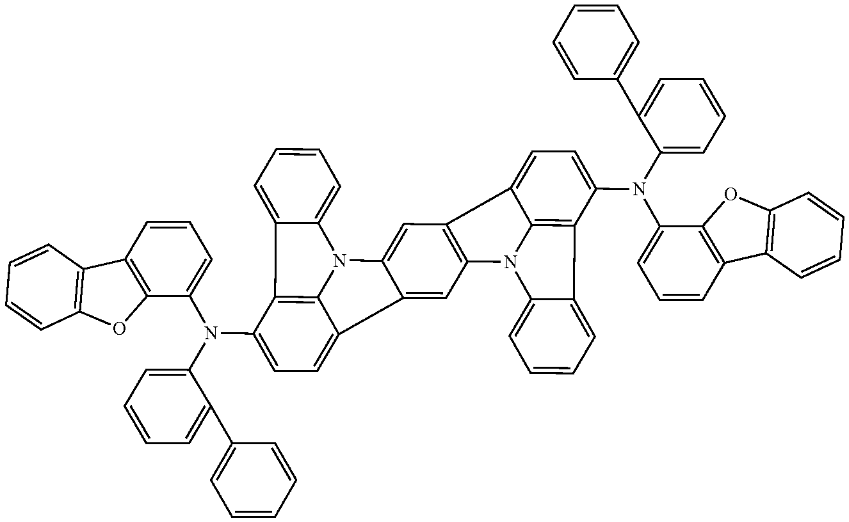
[Formula 243]
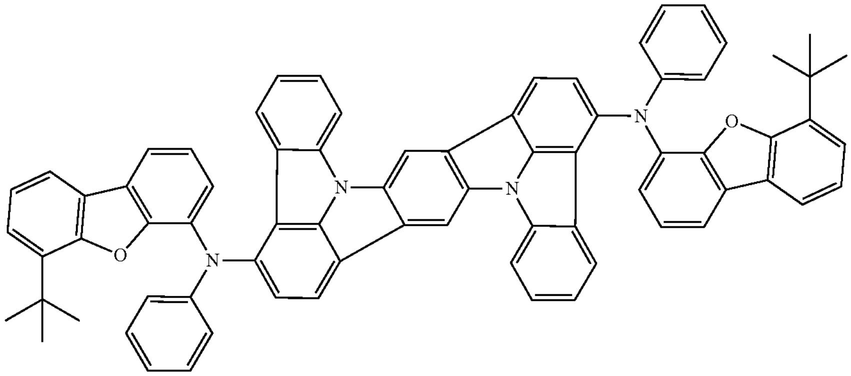

-continued
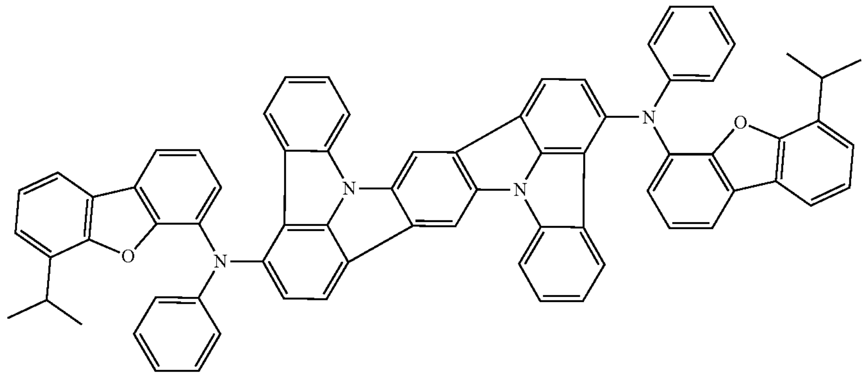
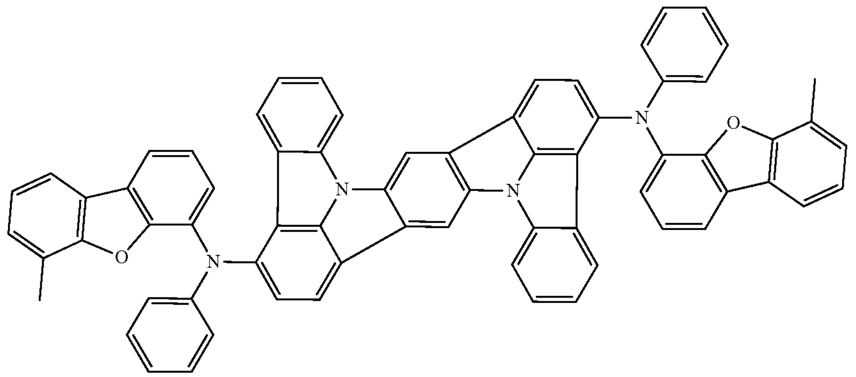
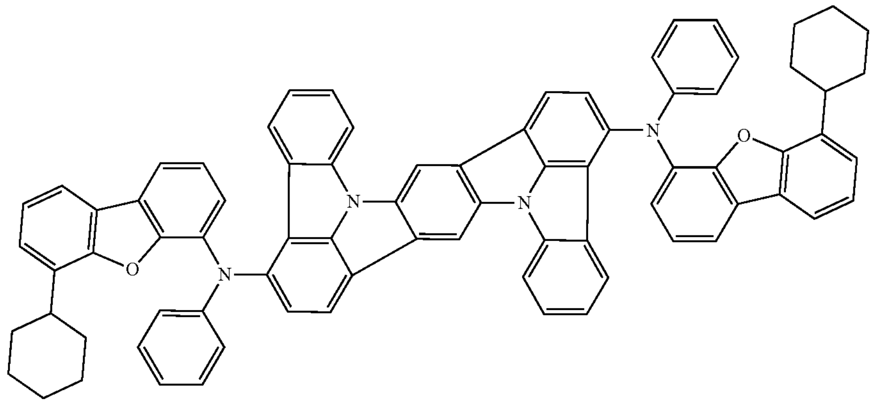
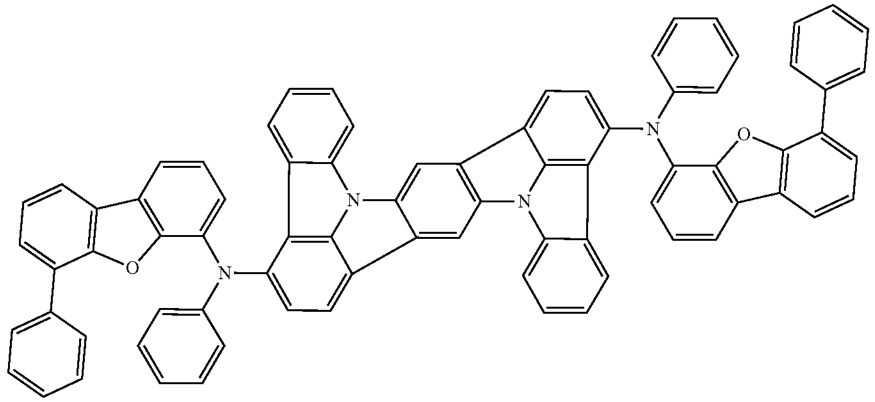

-continued
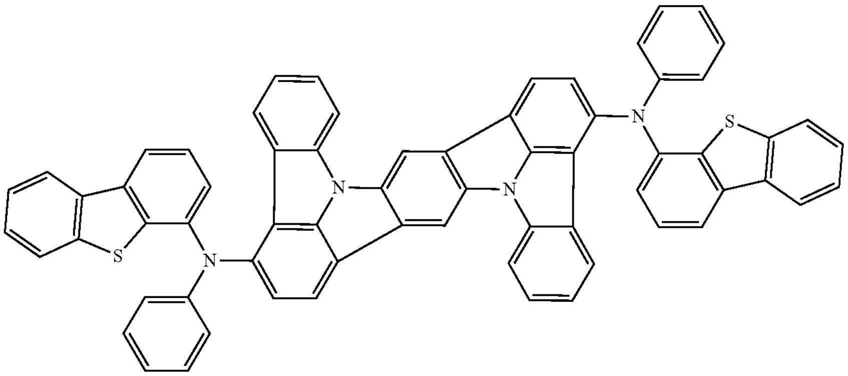
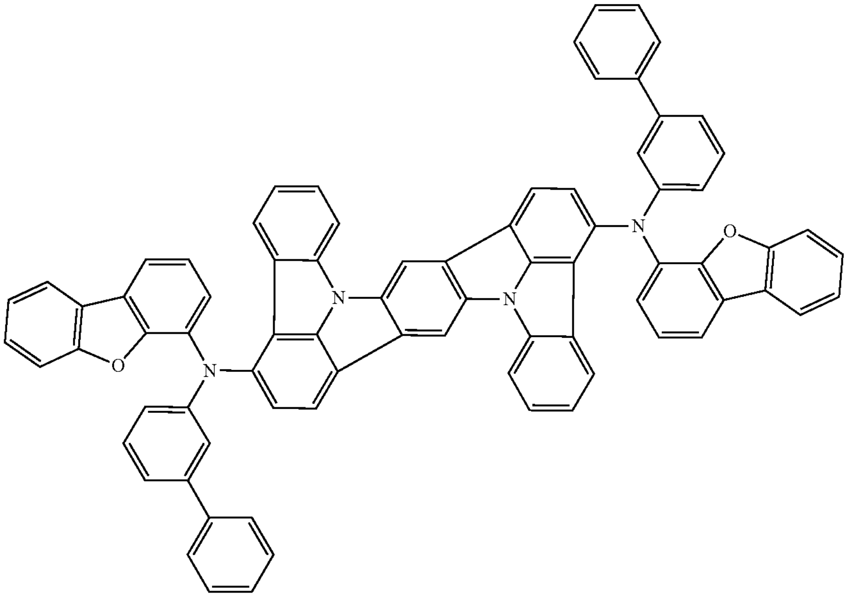
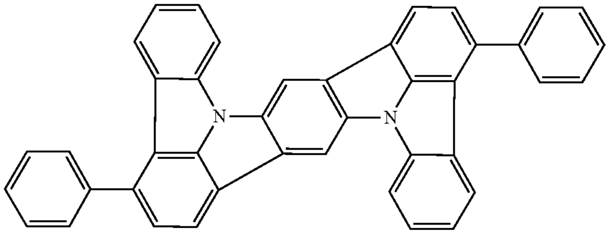
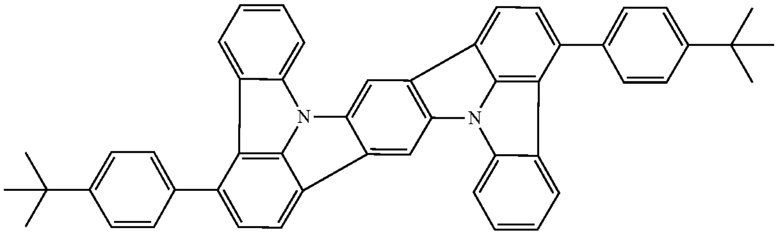
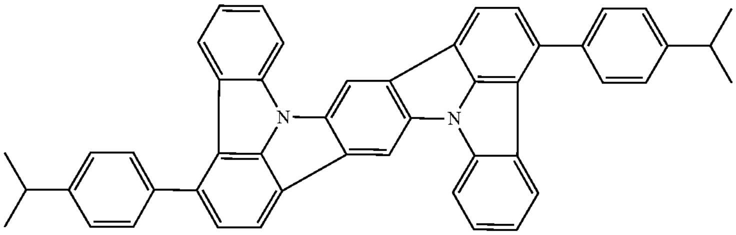

-continued
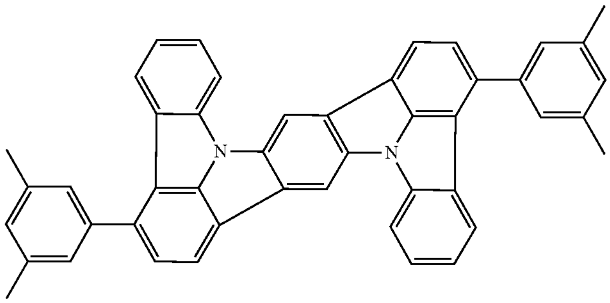
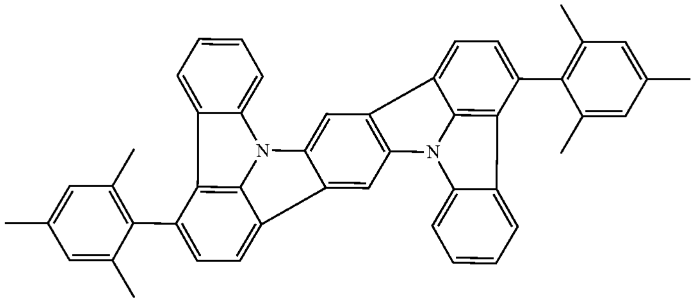
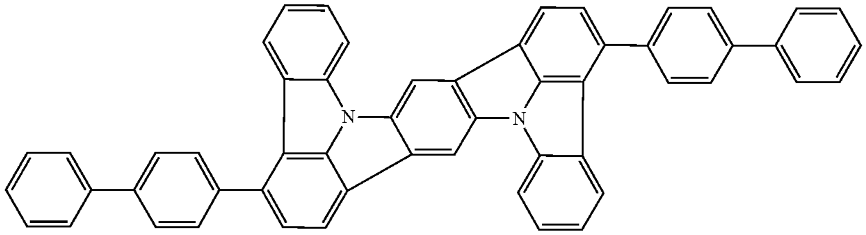
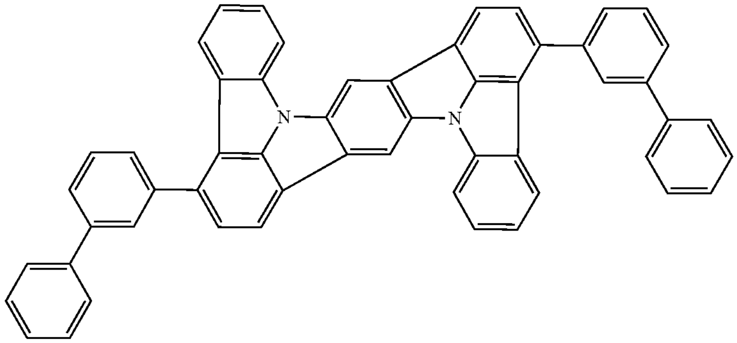
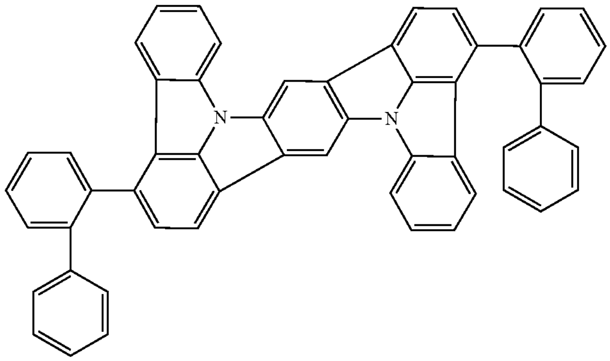

-continued
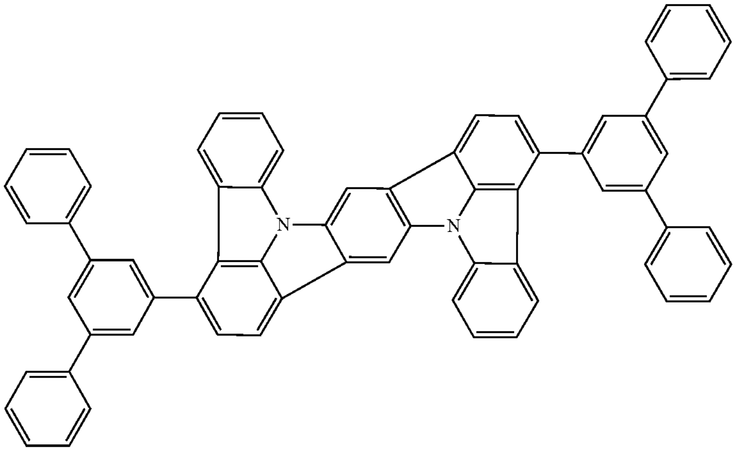
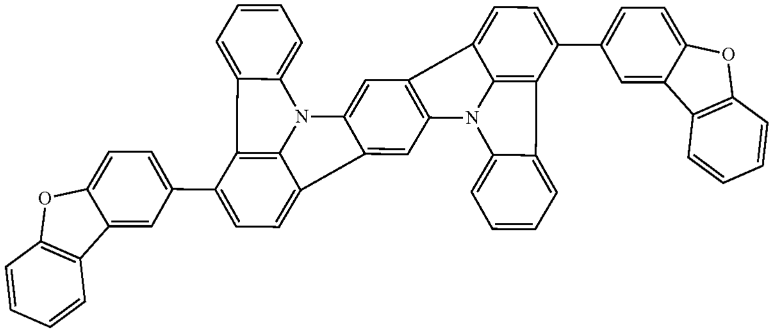
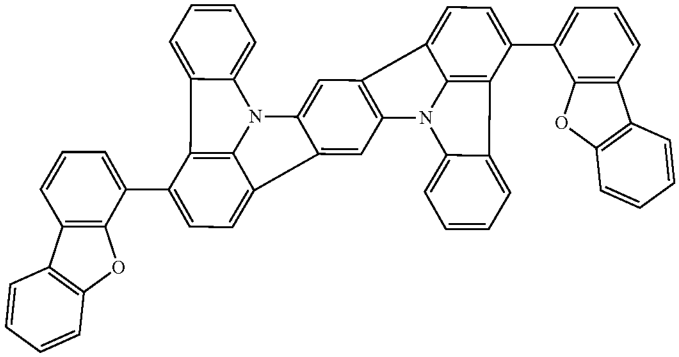
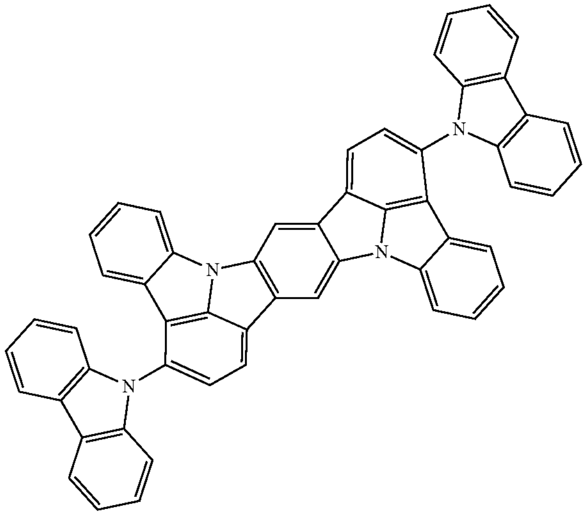

-continued
[Formula 244]
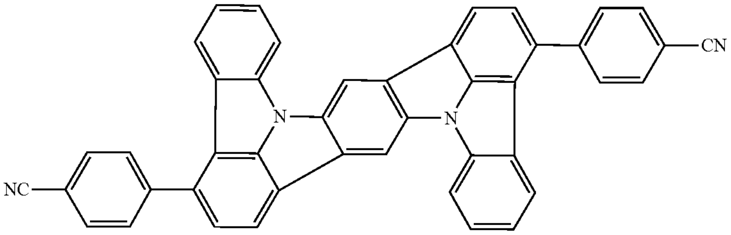
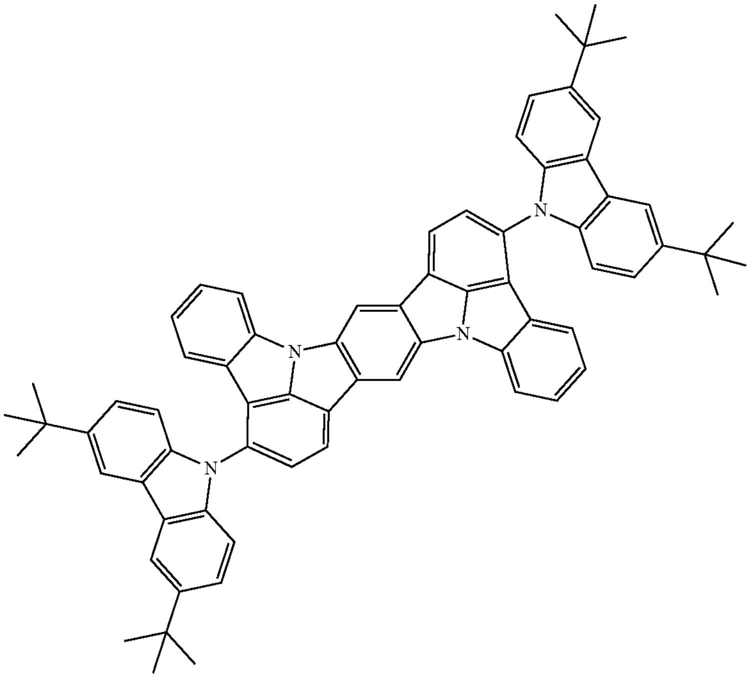
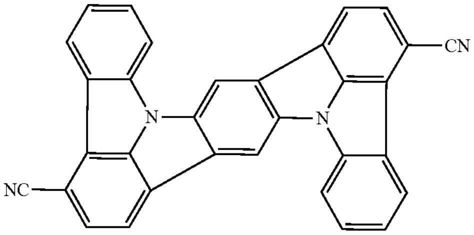
[Formula 245]
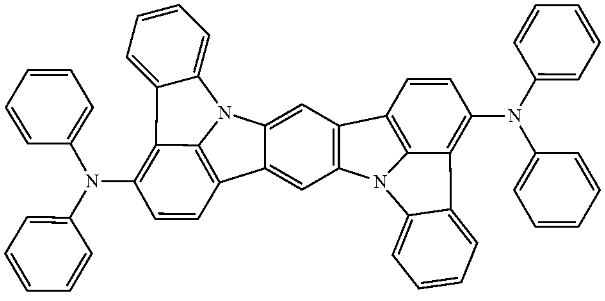

-continued
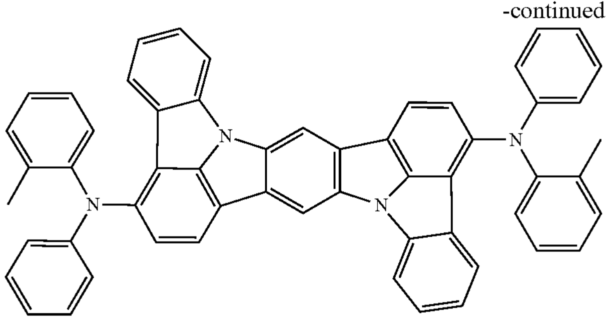
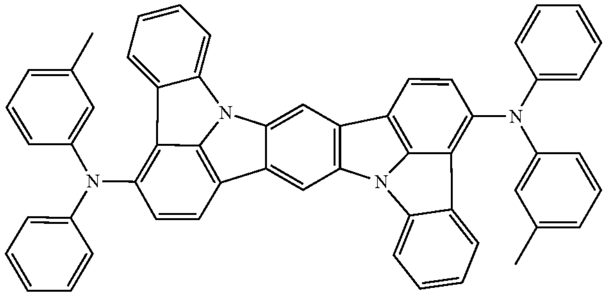
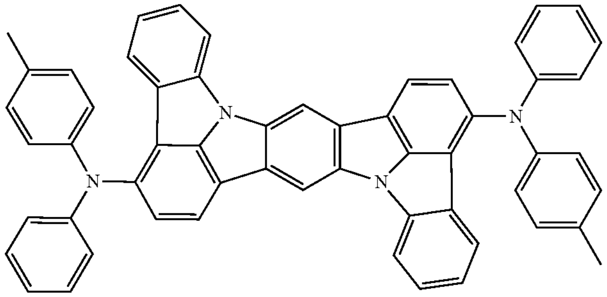
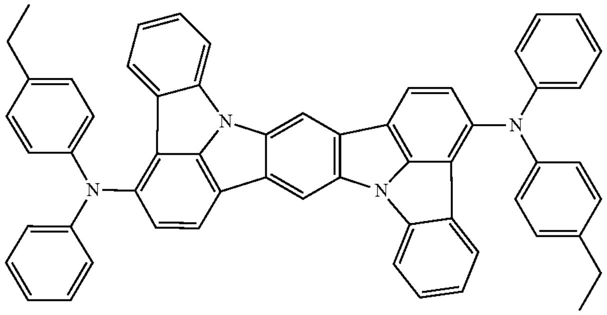
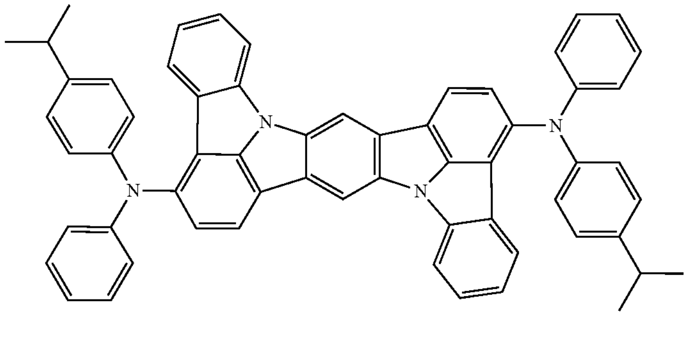

-continued
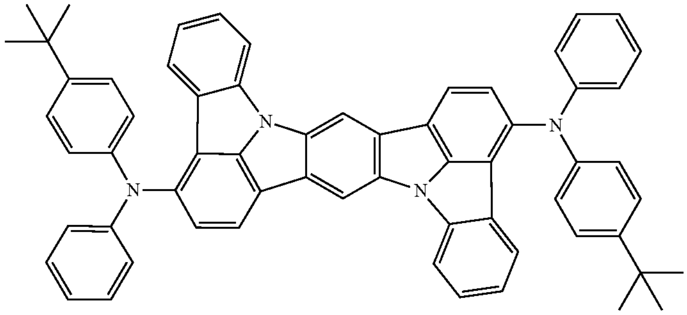
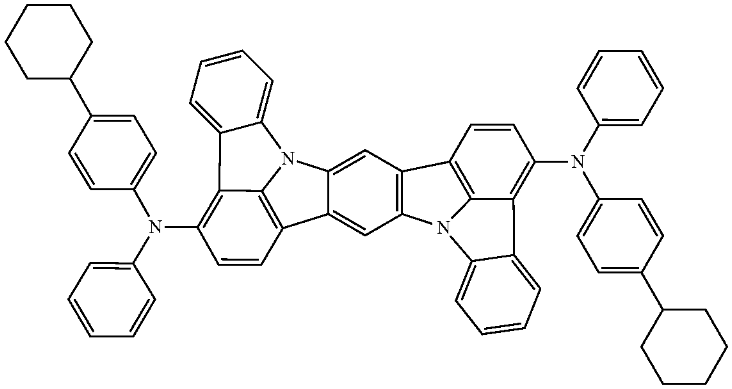
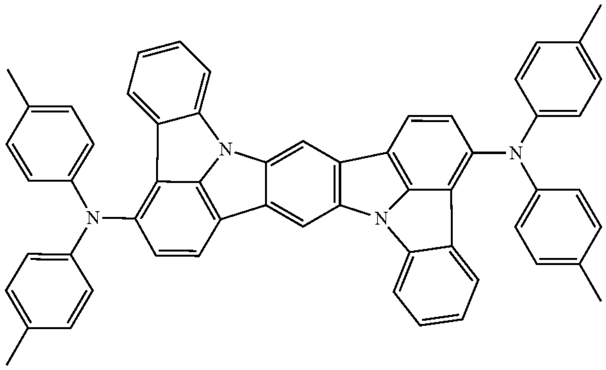
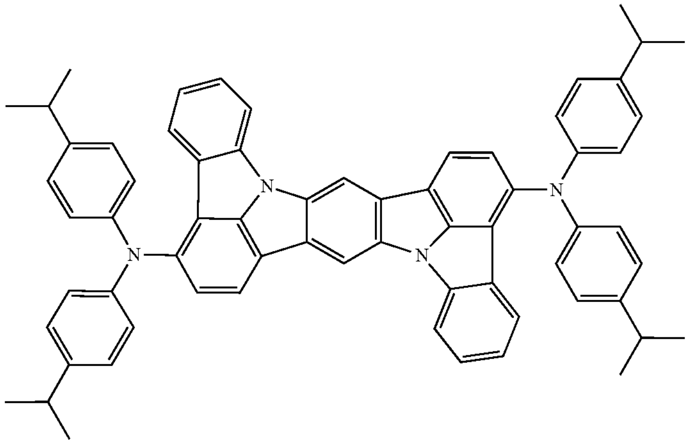

-continued
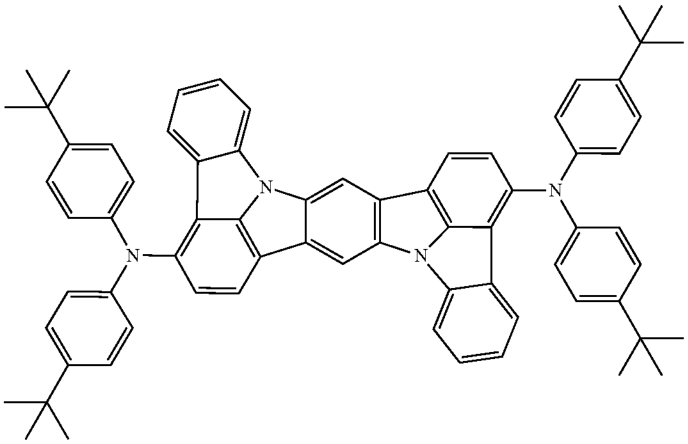
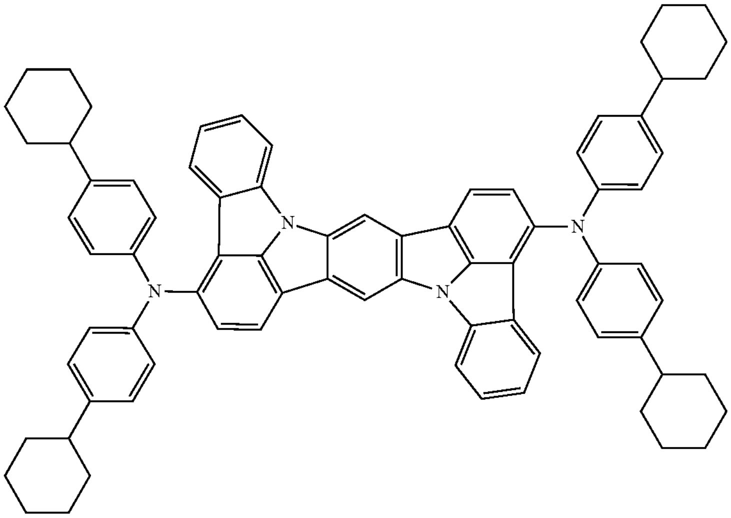
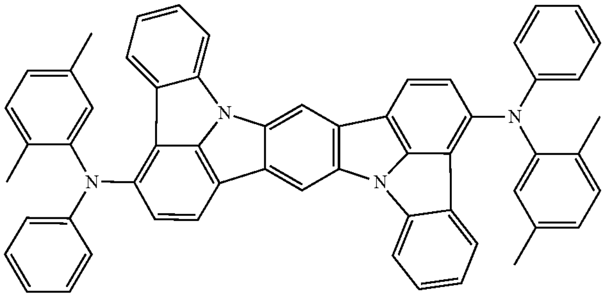
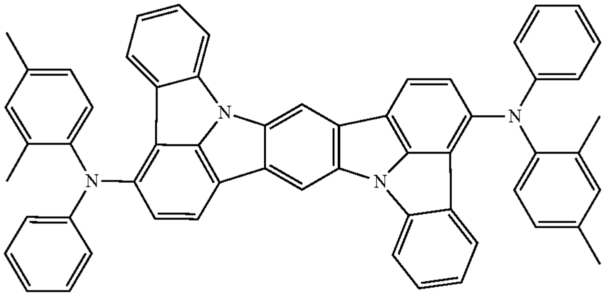

-continued
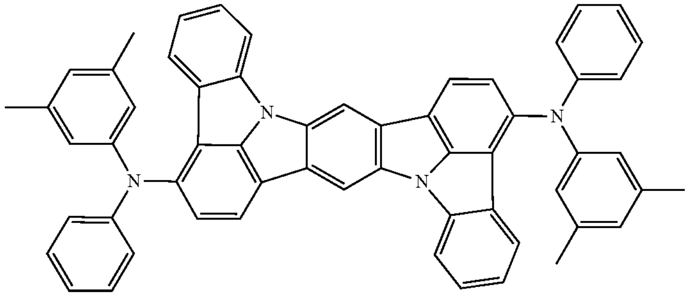
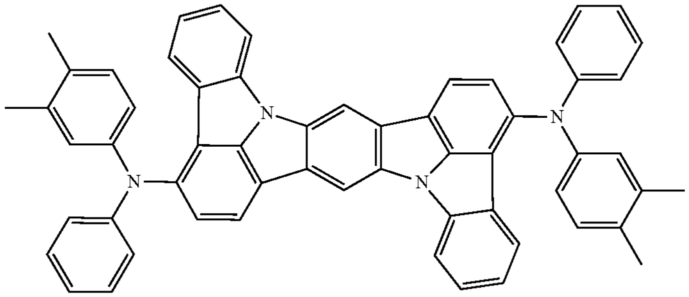
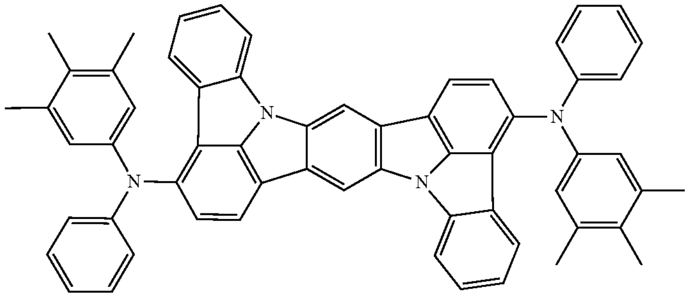
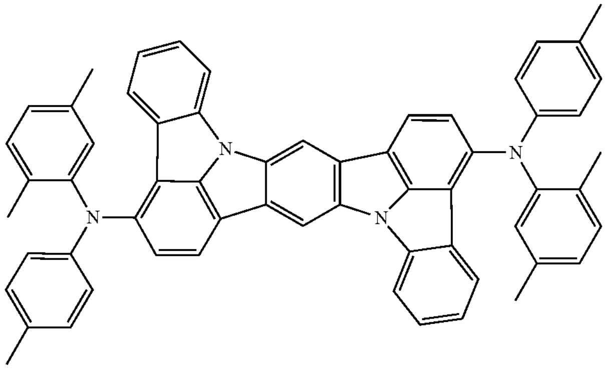
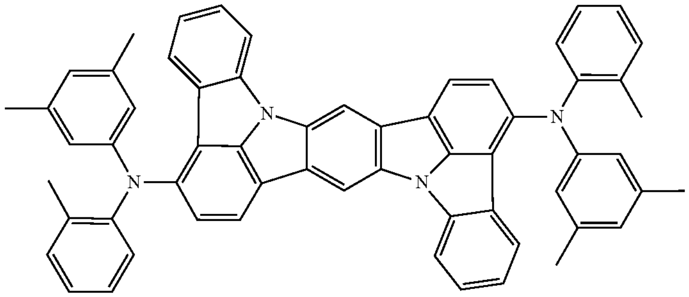

-continued
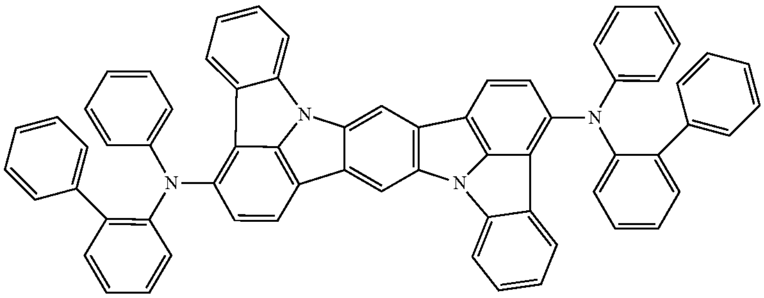
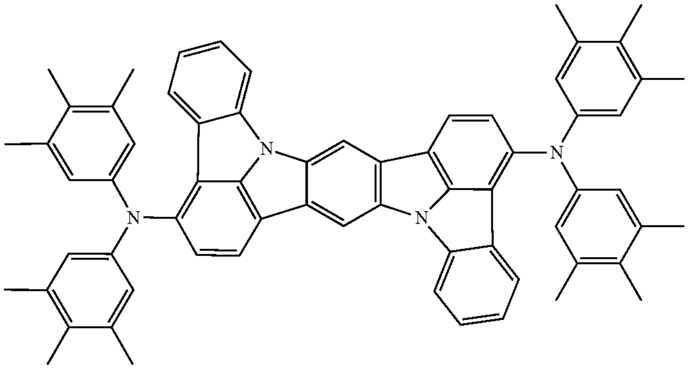
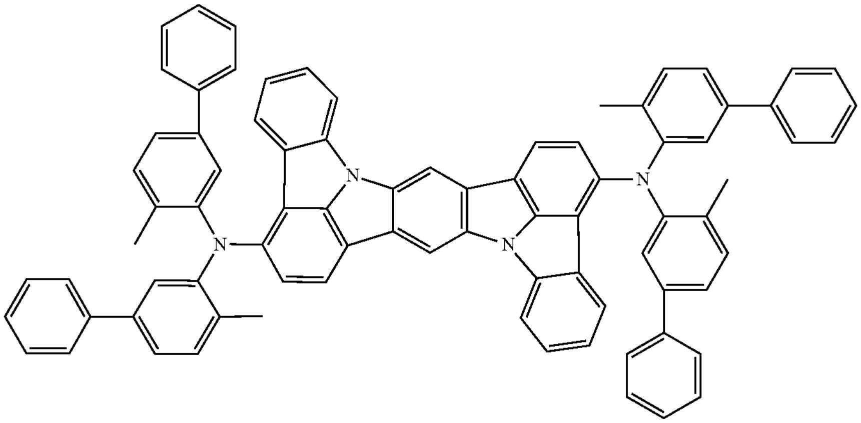
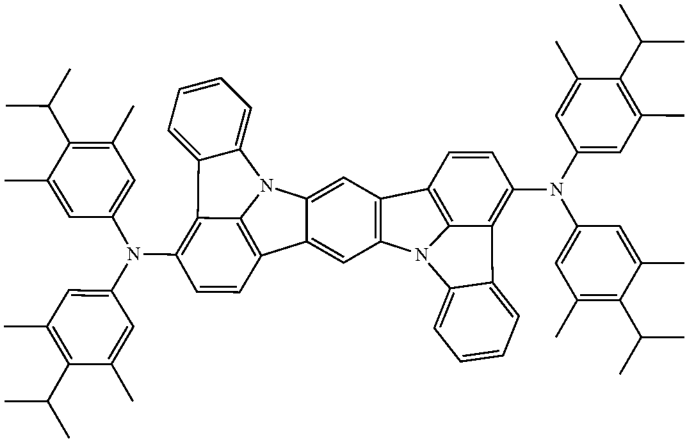

-continued
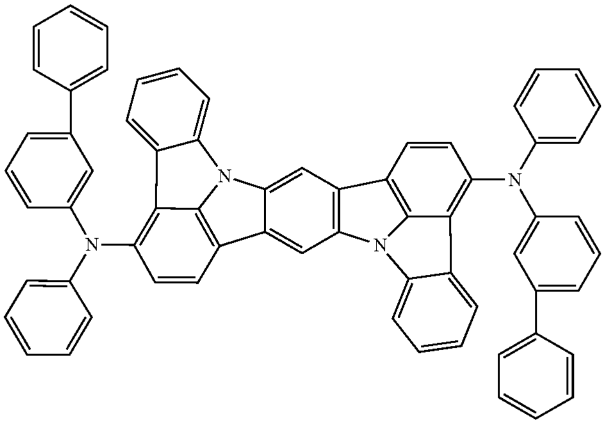
[Formula 246]
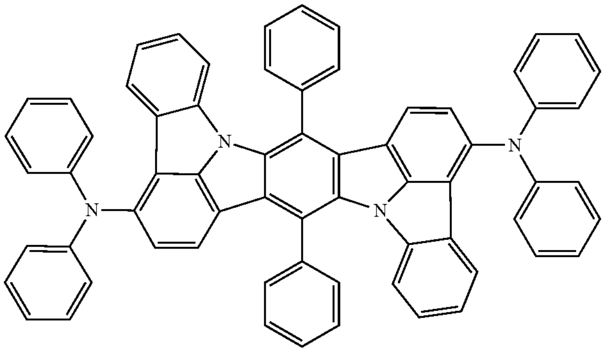
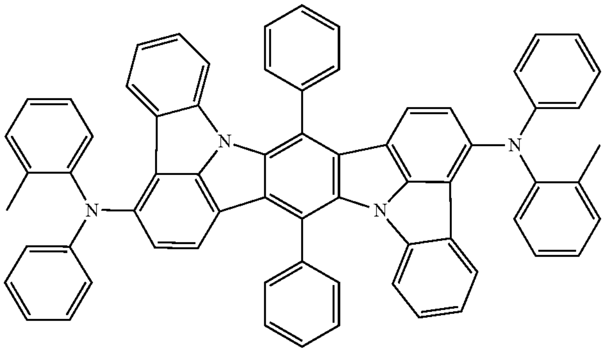
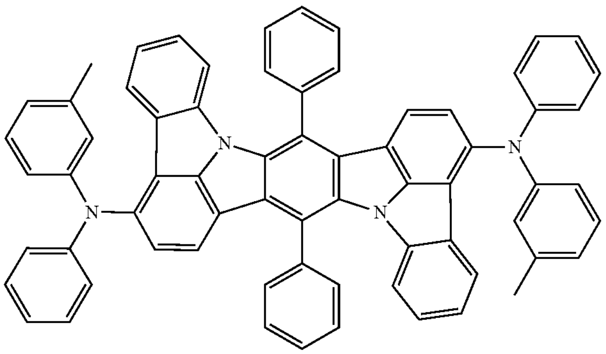

-continued
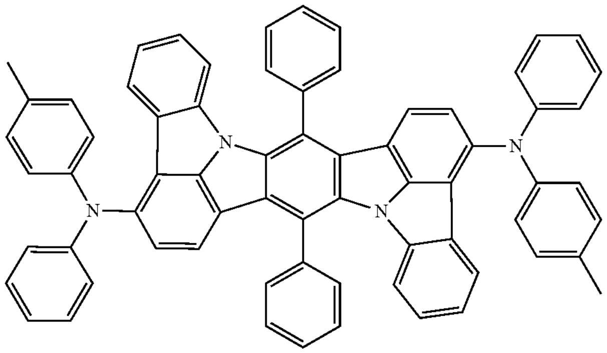
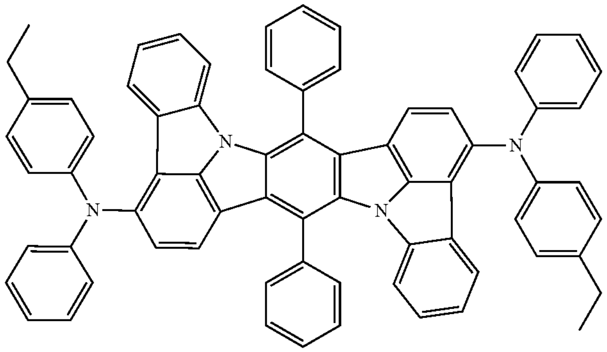
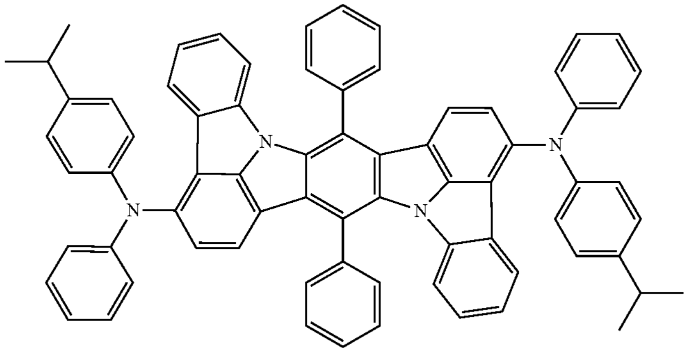
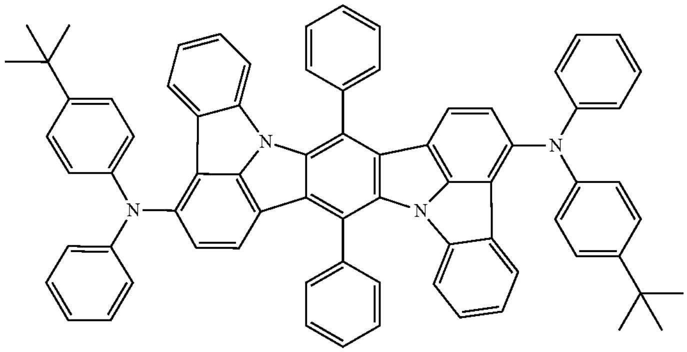

-continued
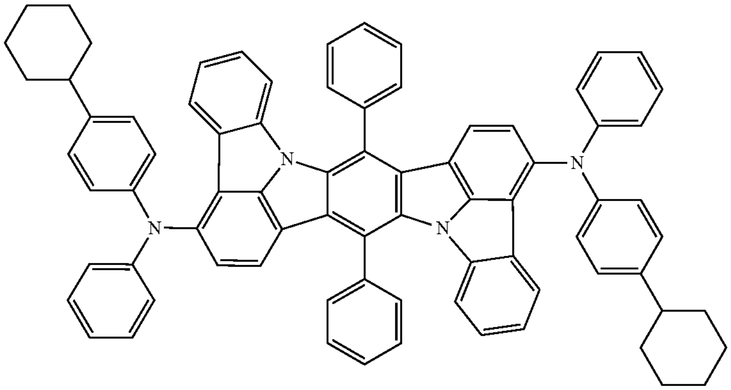
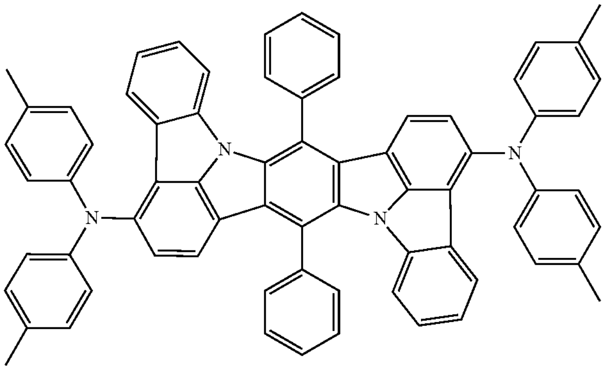
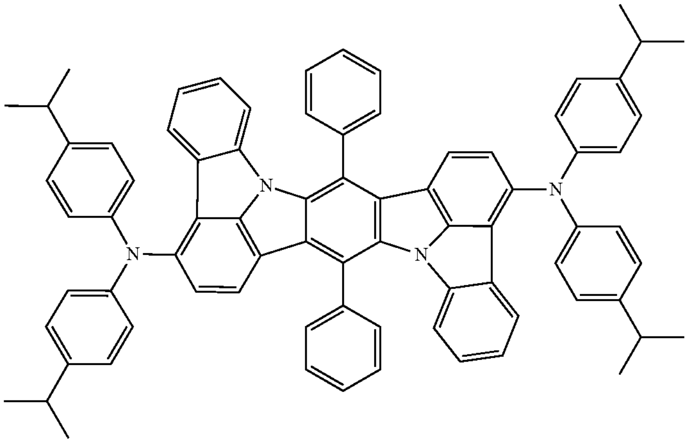
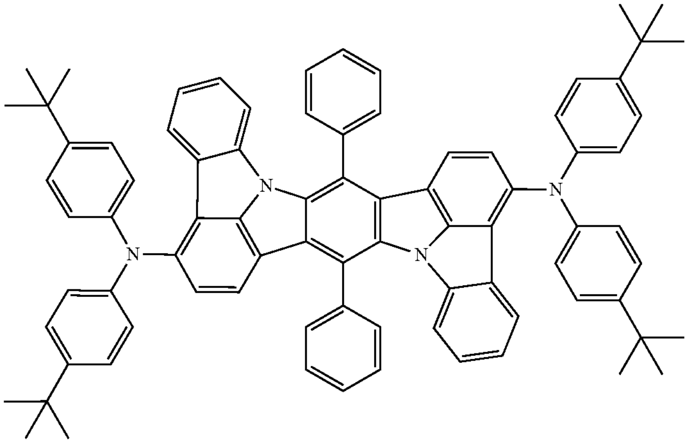

-continued
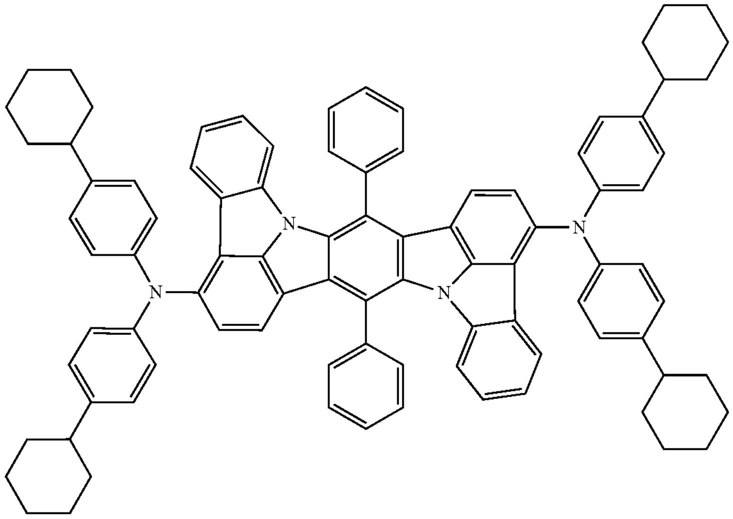
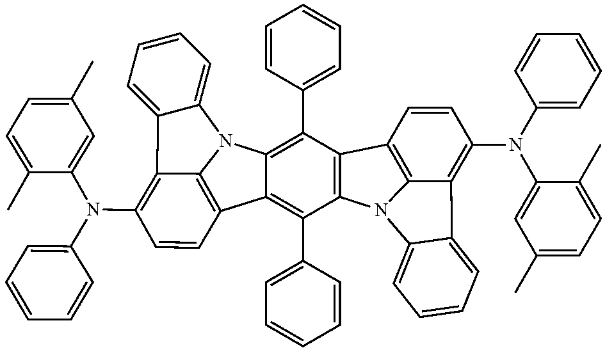
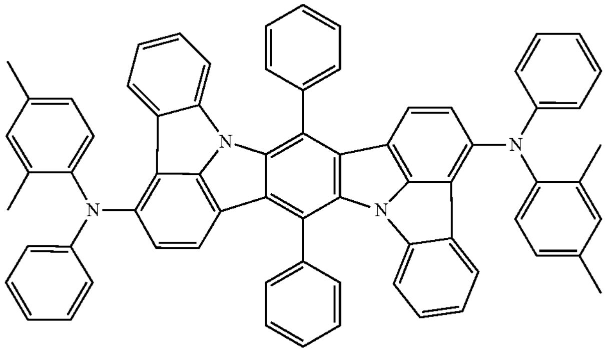
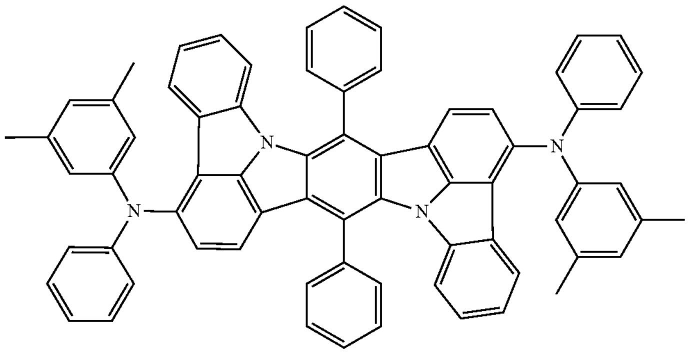

-continued
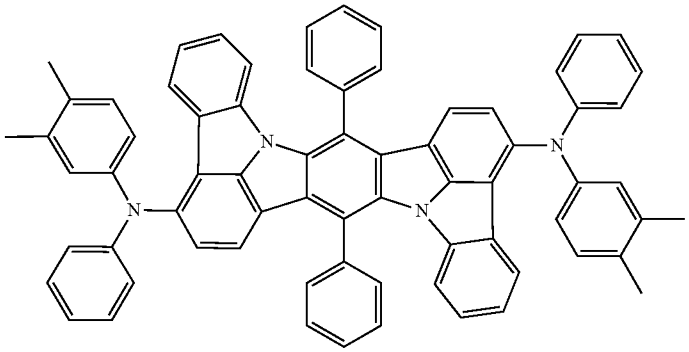
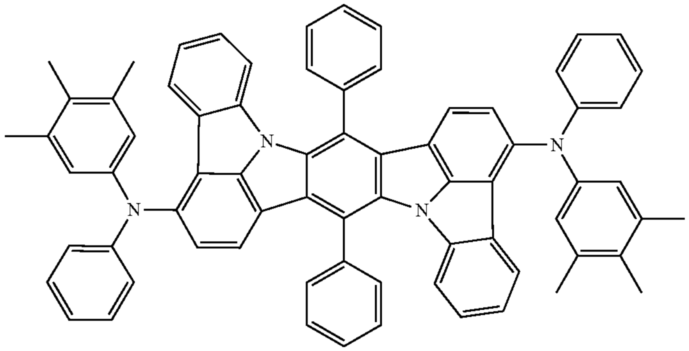
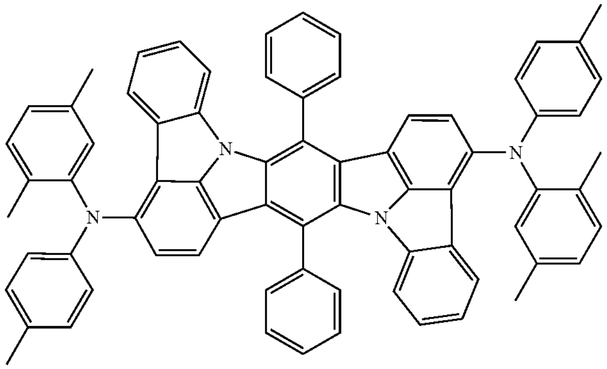
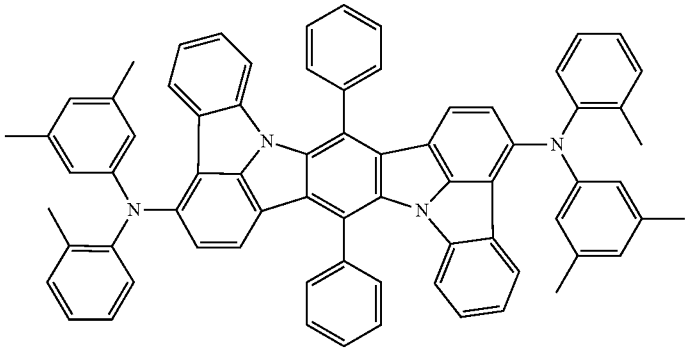

-continued
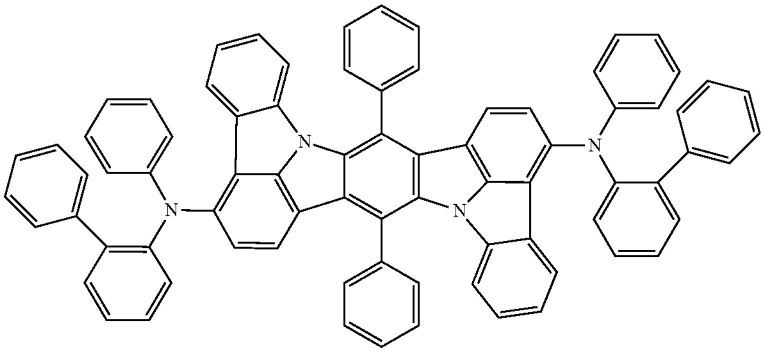
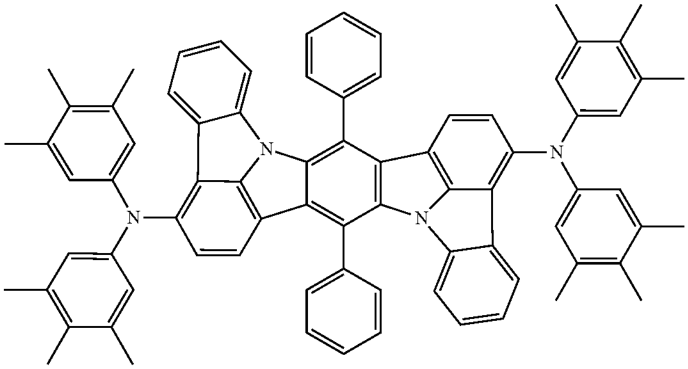
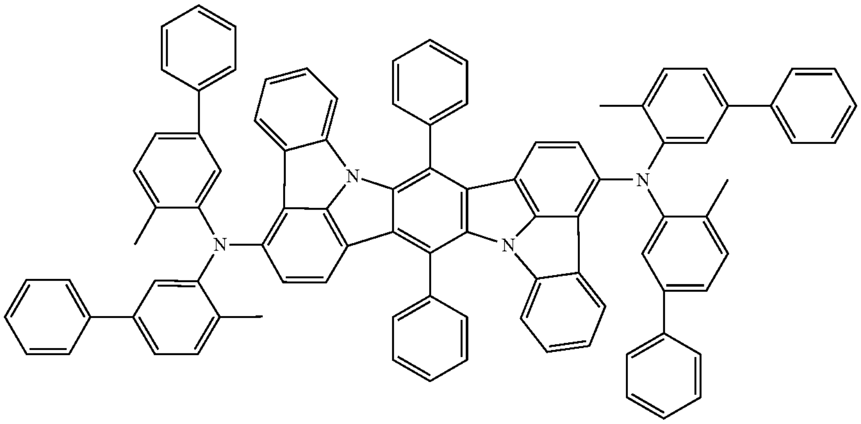
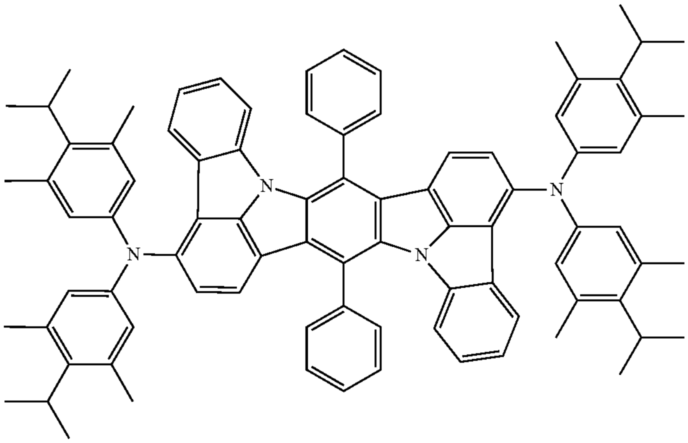

-continued
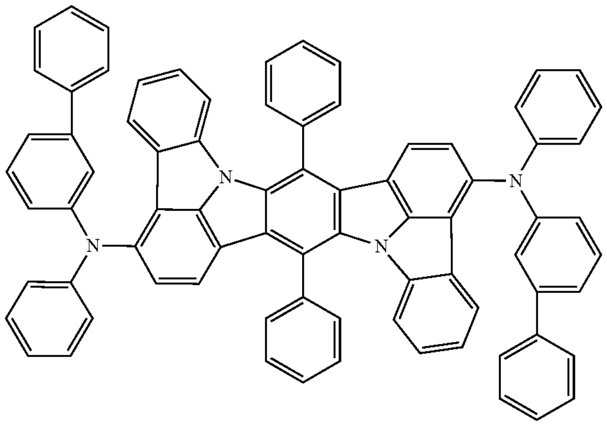
[Formula 247]
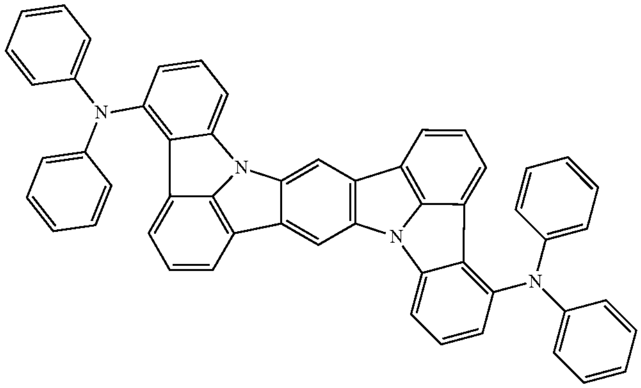
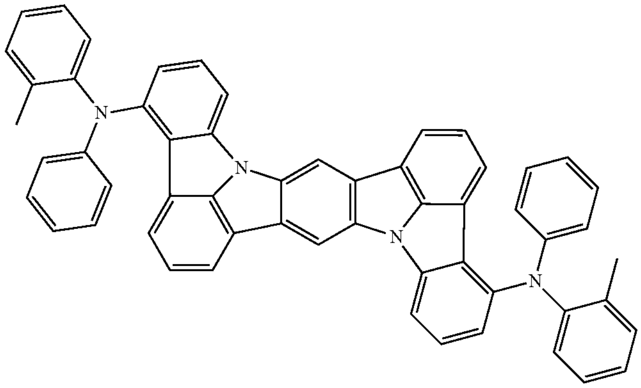
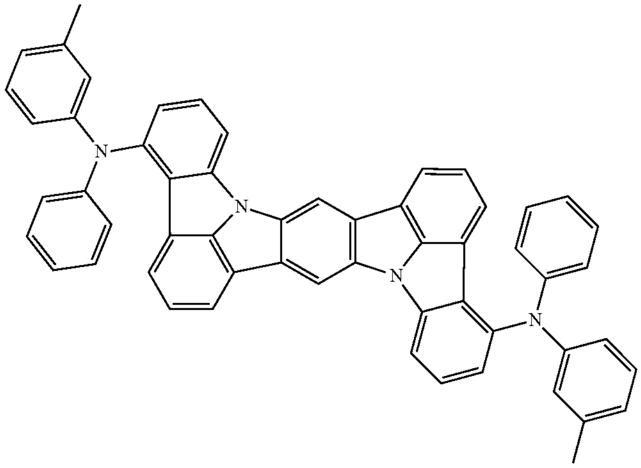

-continued
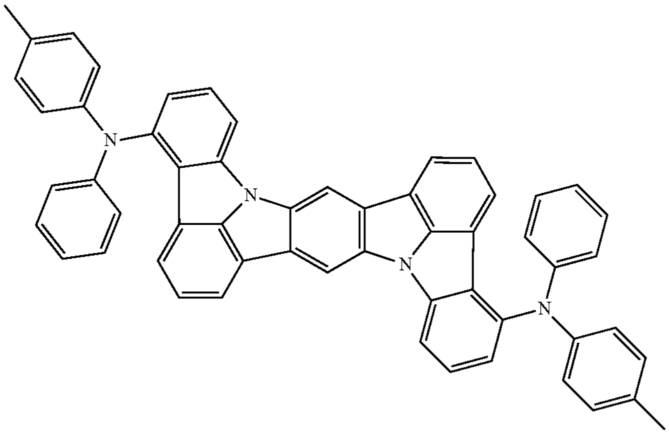
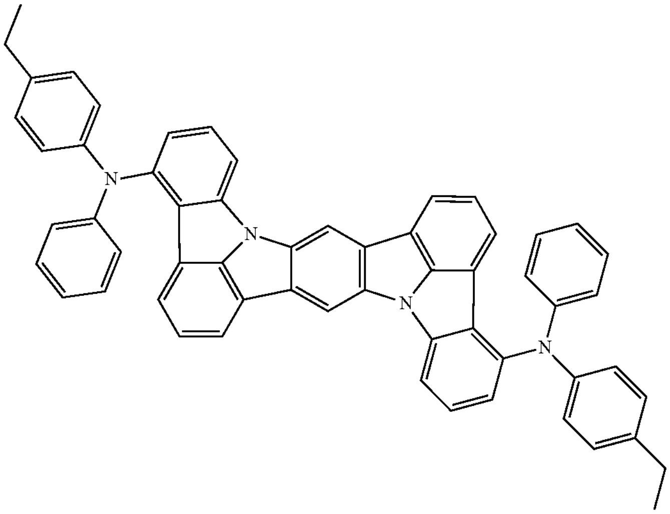
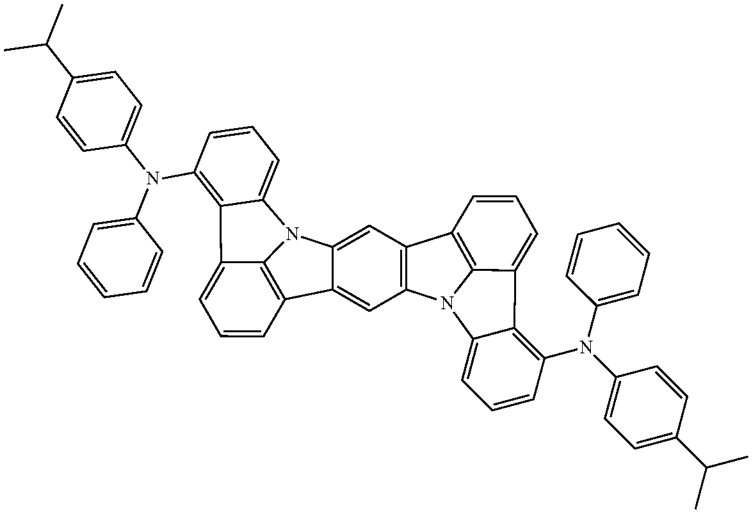

-continued
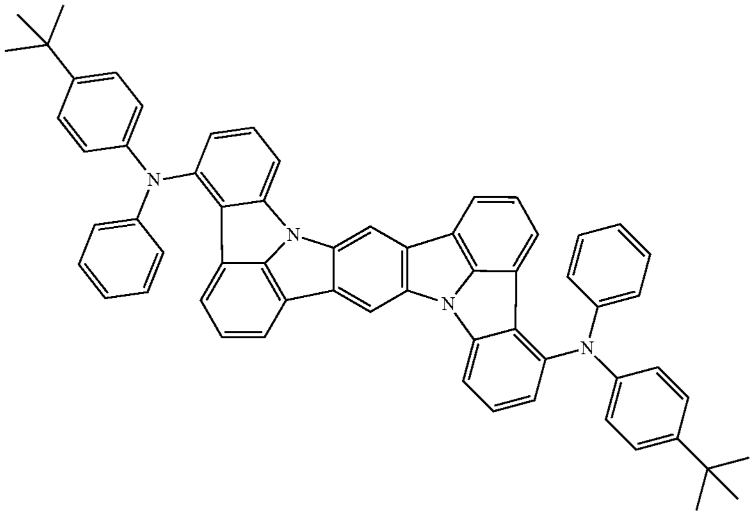
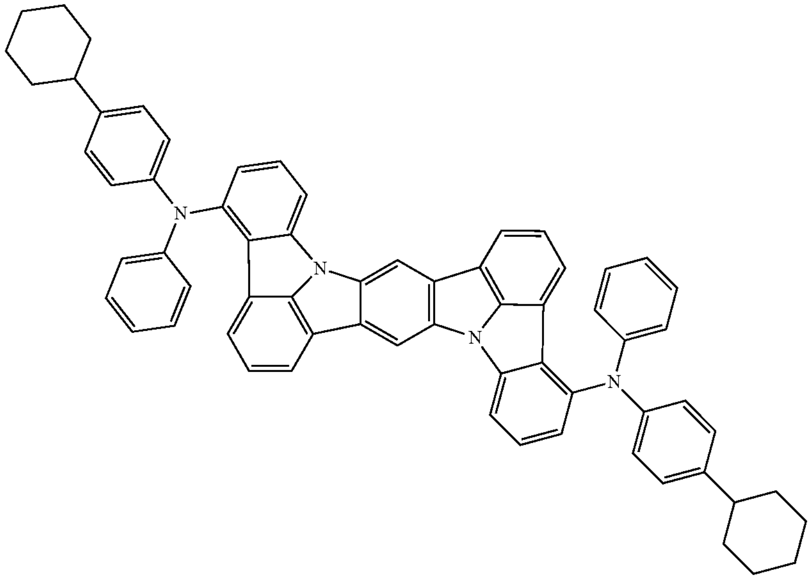
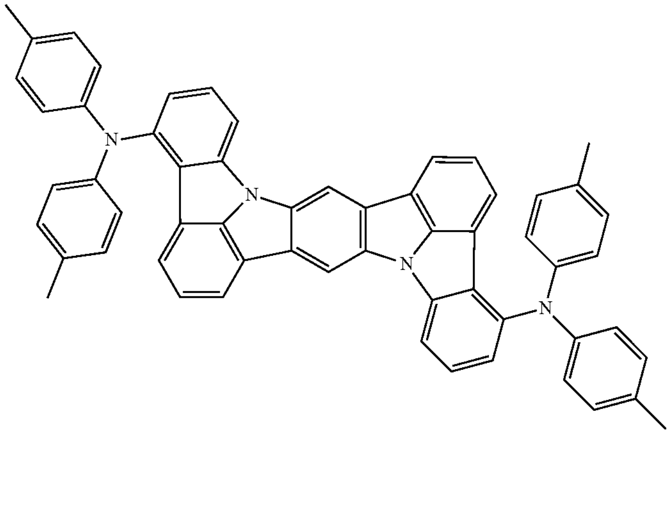

-continued
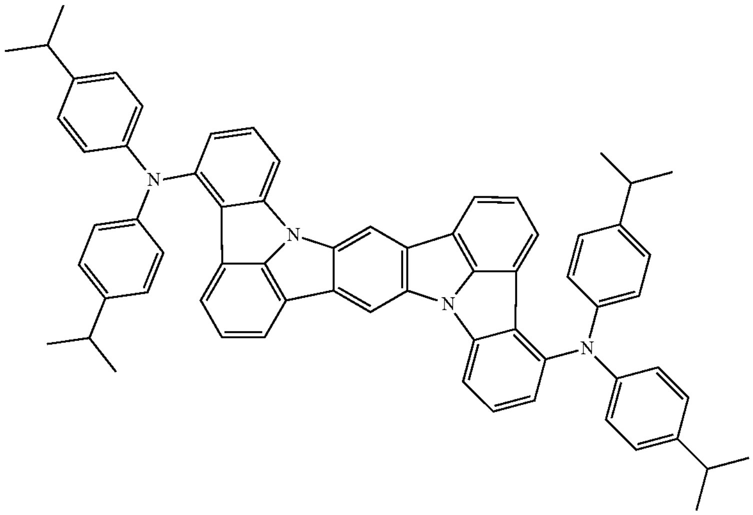
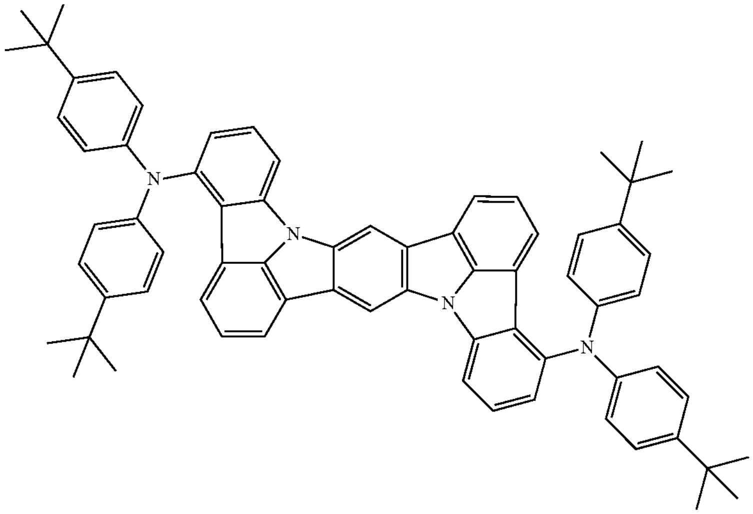
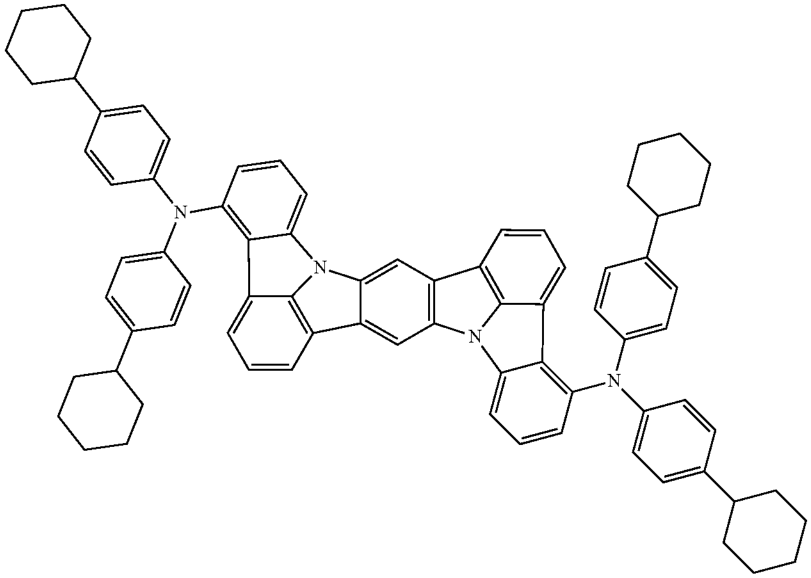

-continued
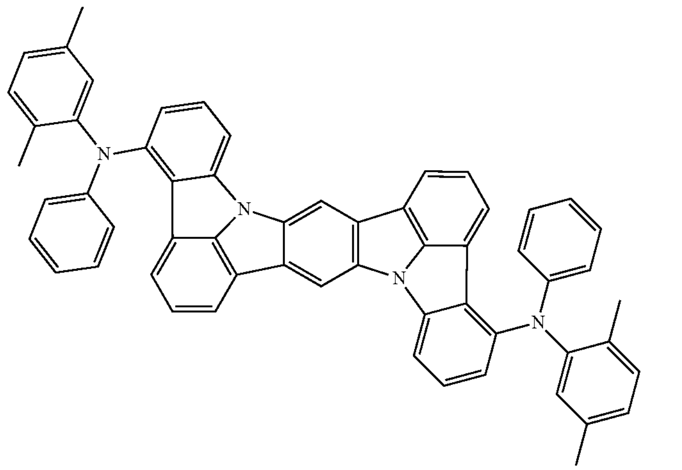
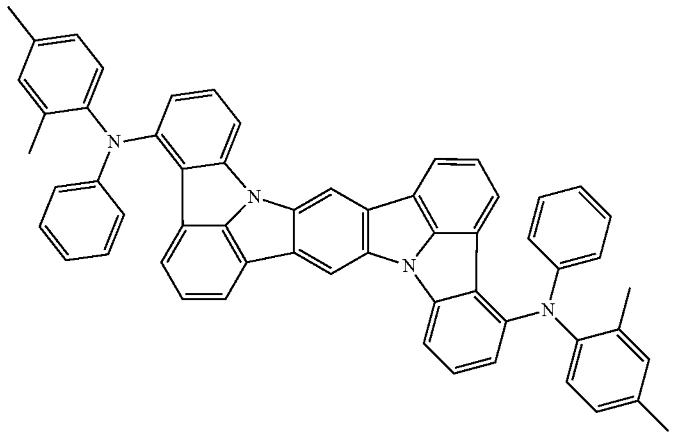
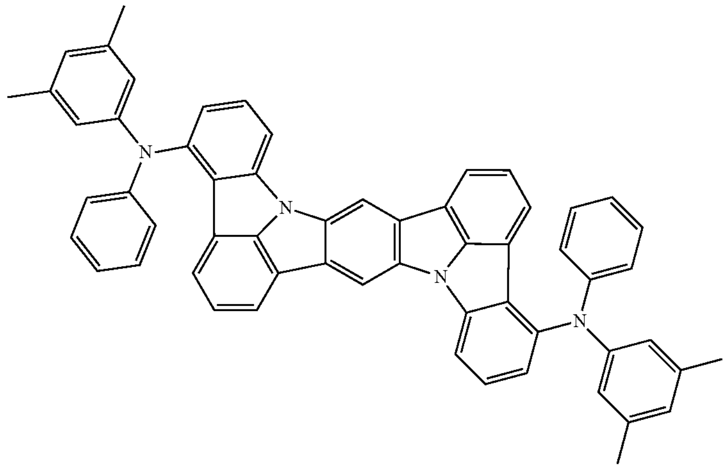

-continued
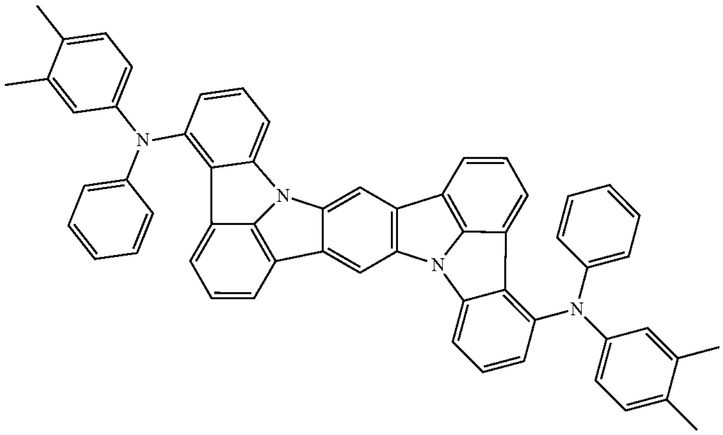
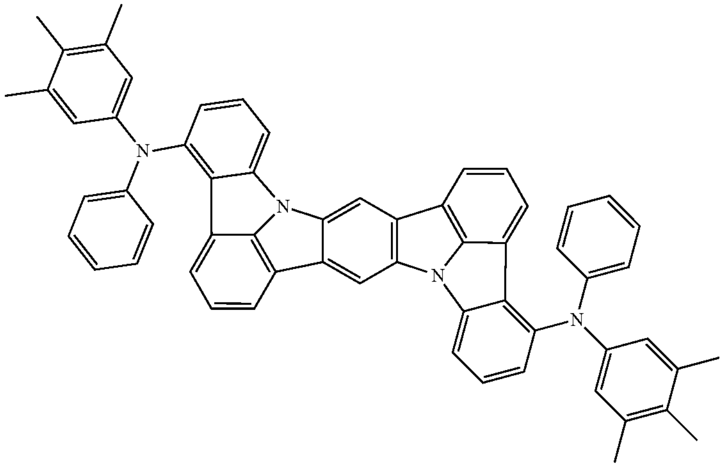
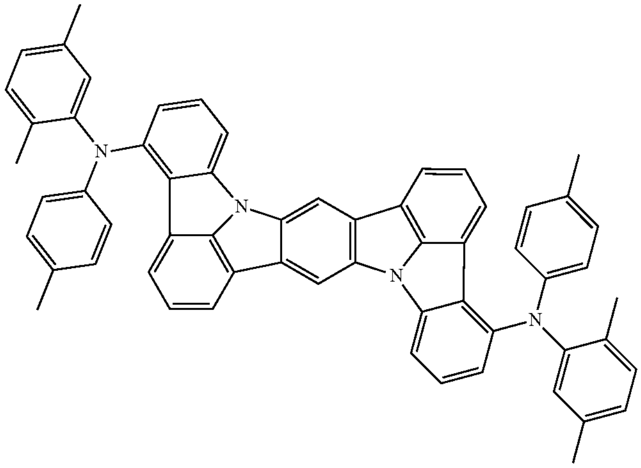

-continued
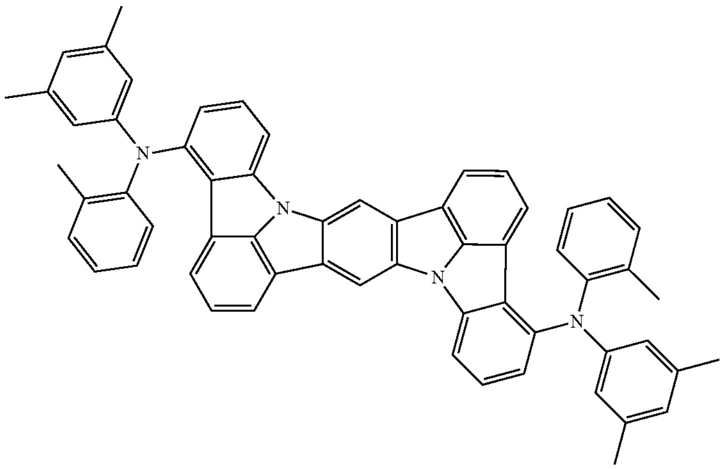
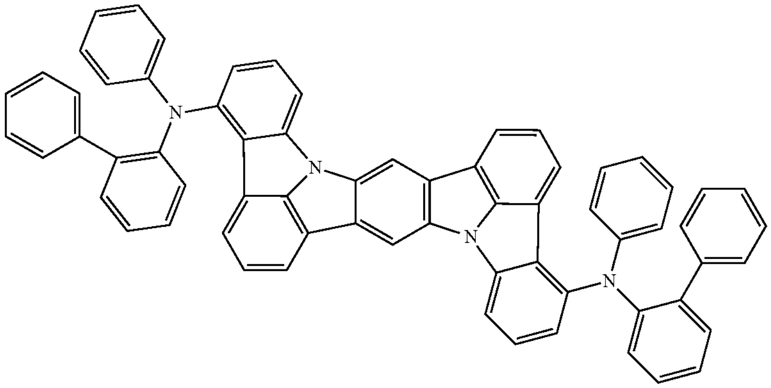
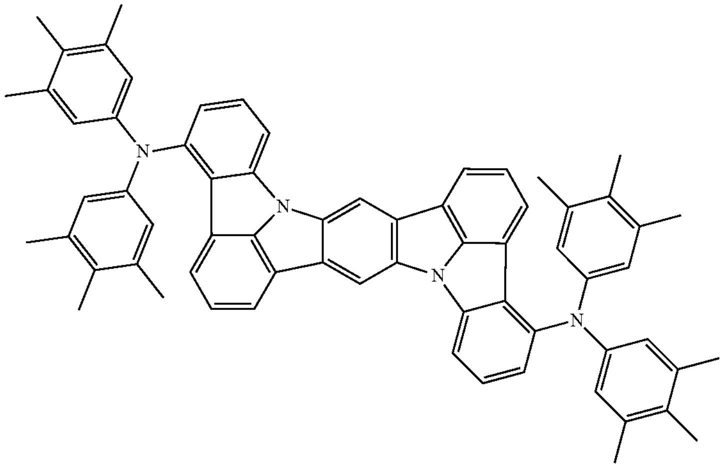

-continued
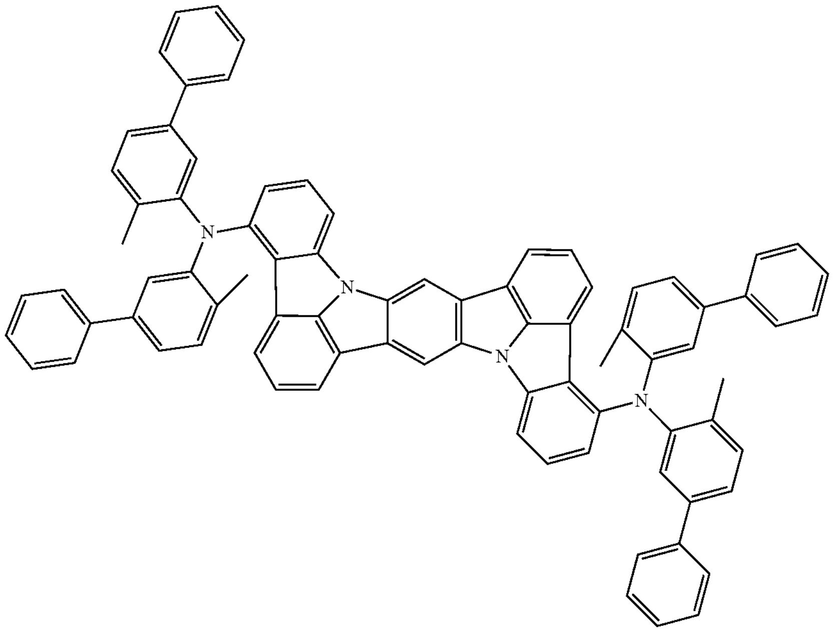
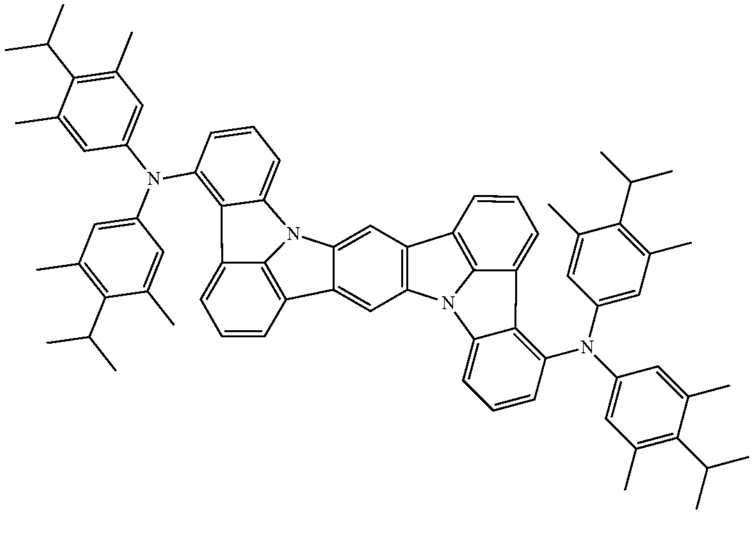

-continued
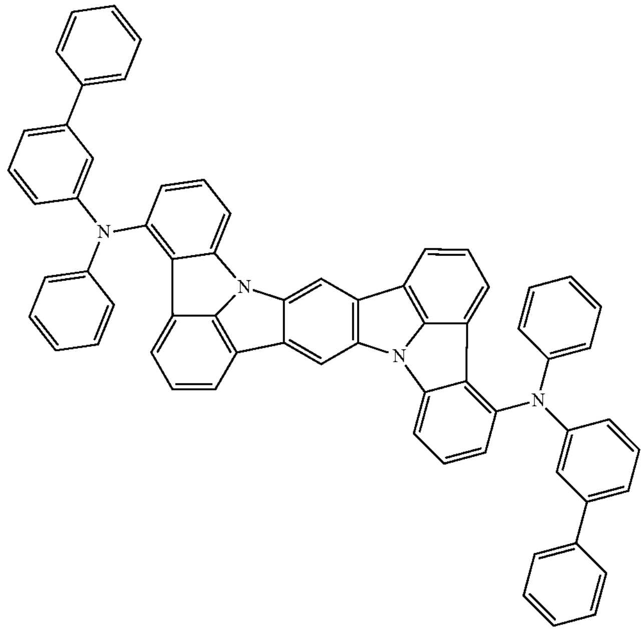 [SMILES: c1ccc(-c2cccc(N(c3ccccc3)c3cccc4c3c3cccc5c6cc7c(cc6n4c53)c3cccc4c5c(N(c6ccccc6)c6cccc(-c8ccccc8)c6)cccc5n7c34)c2)cc1]
[Formula 248]
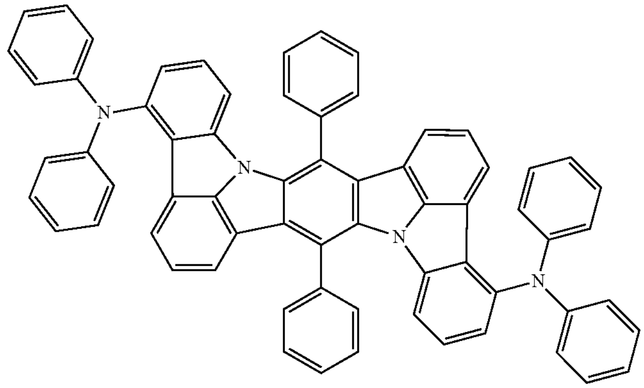
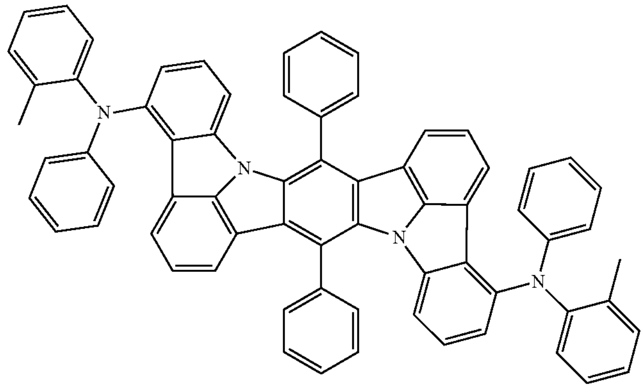

-continued
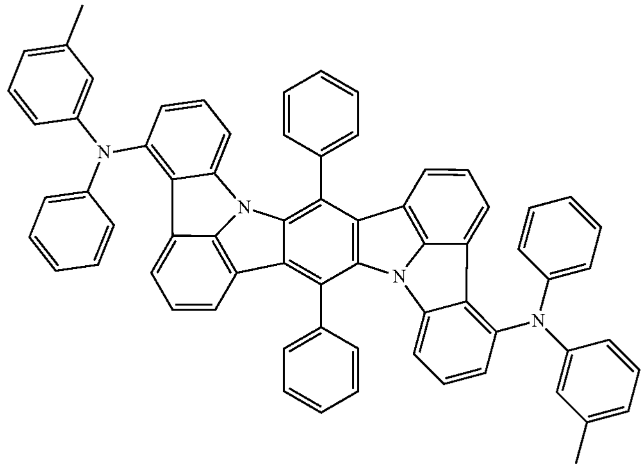
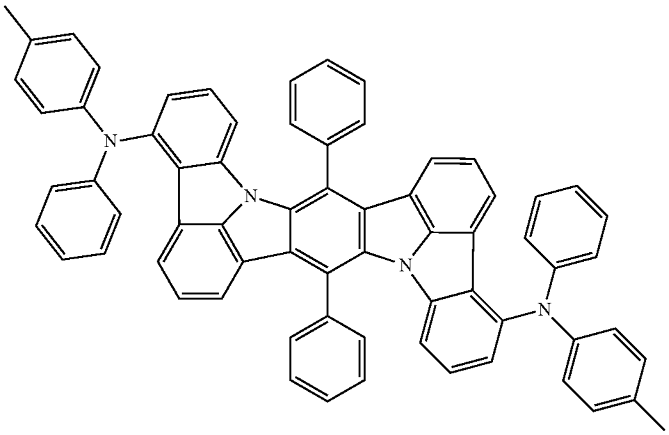
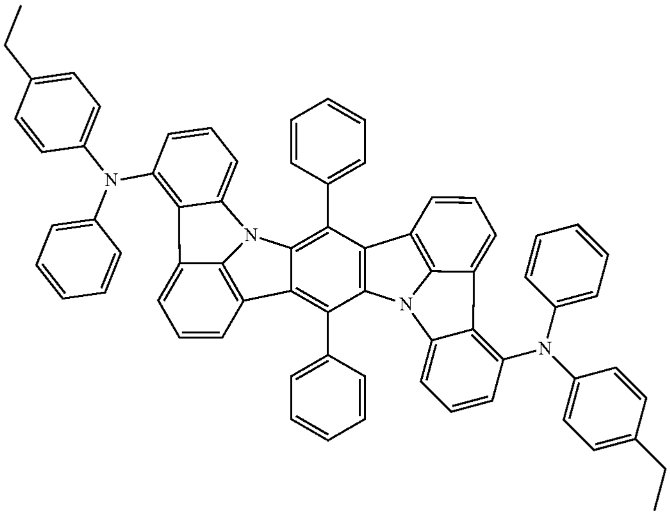

-continued
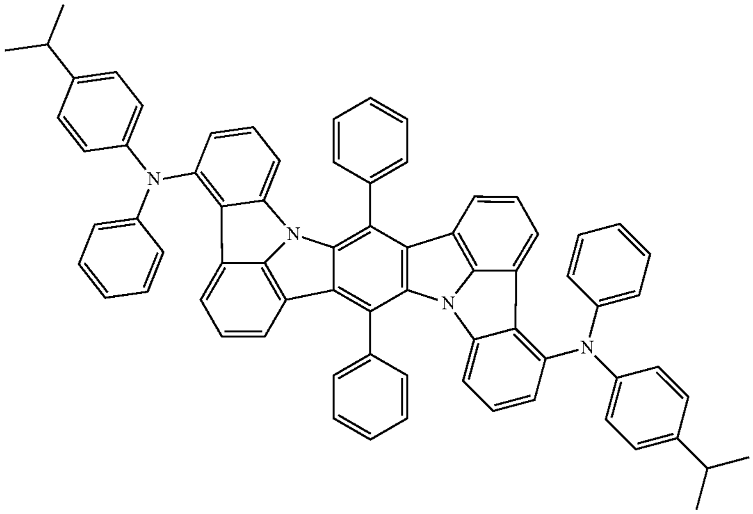
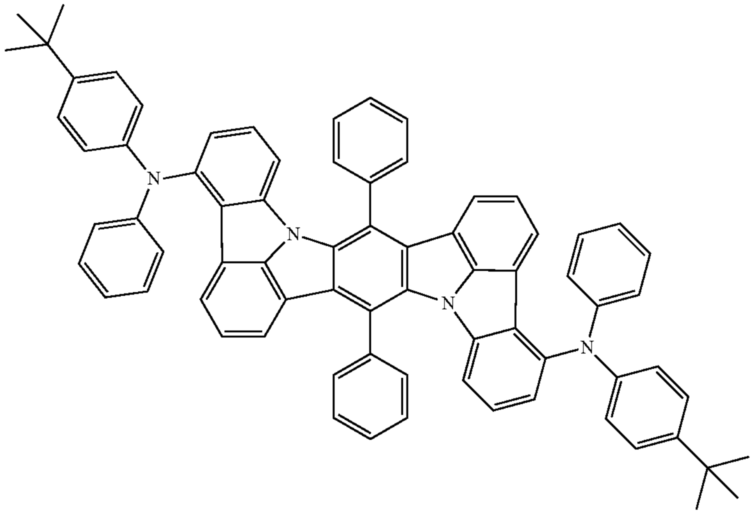
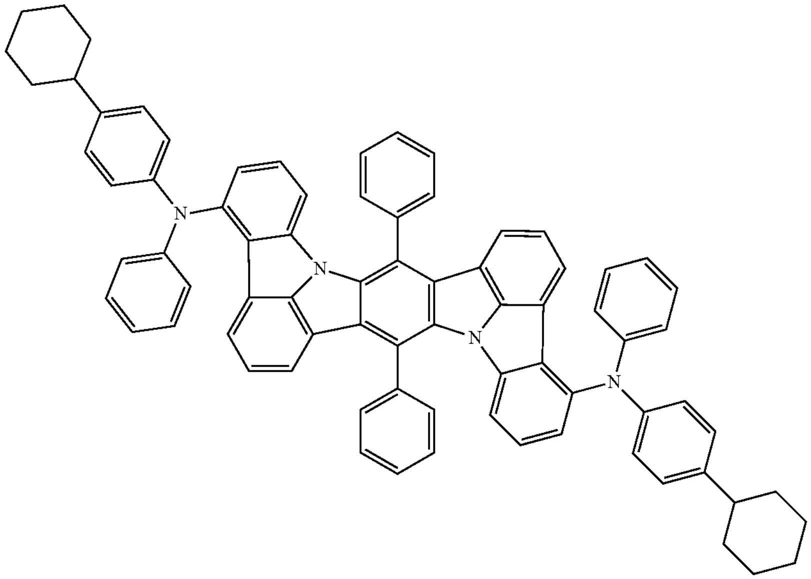

-continued
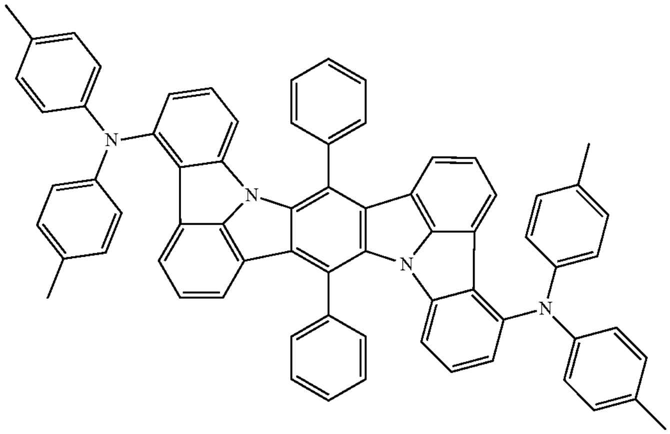
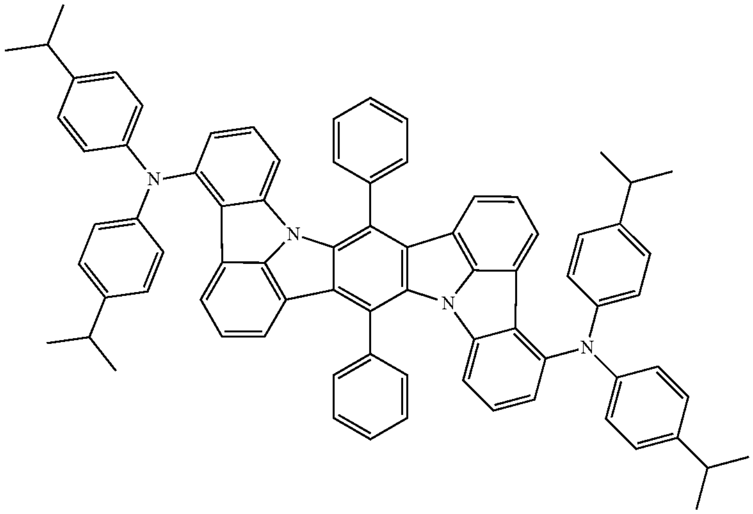
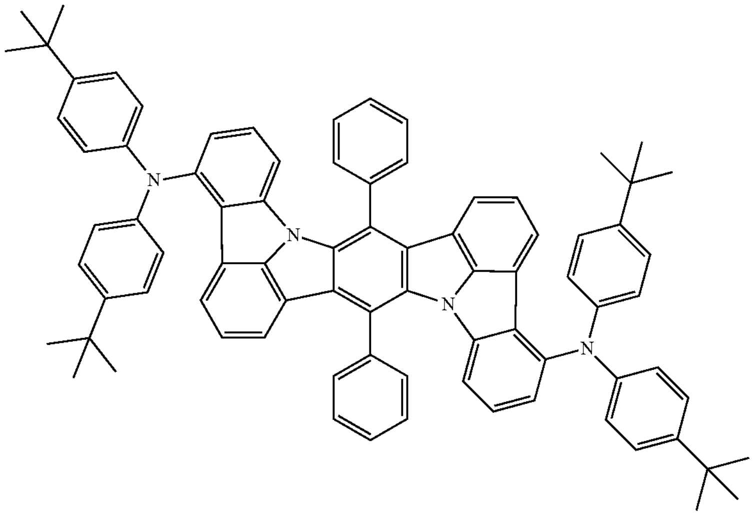

-continued
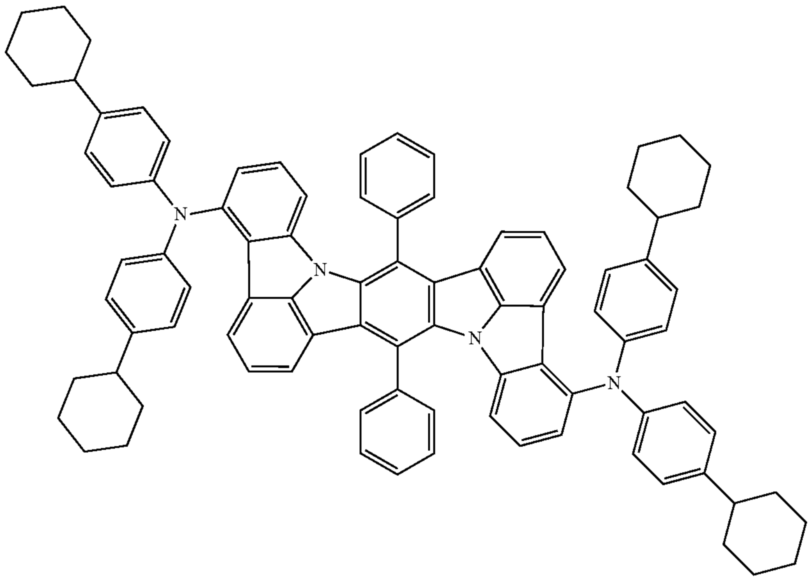
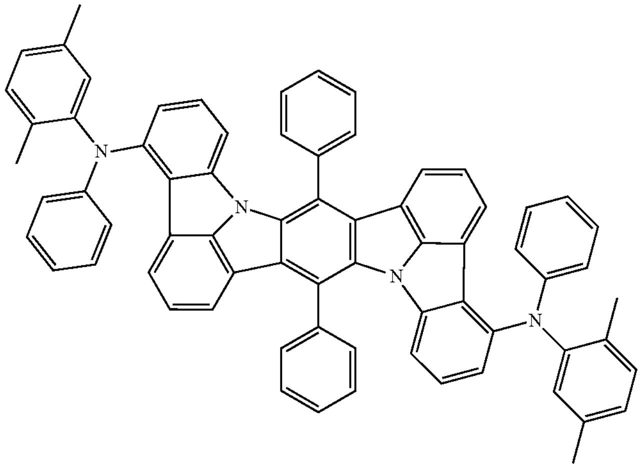
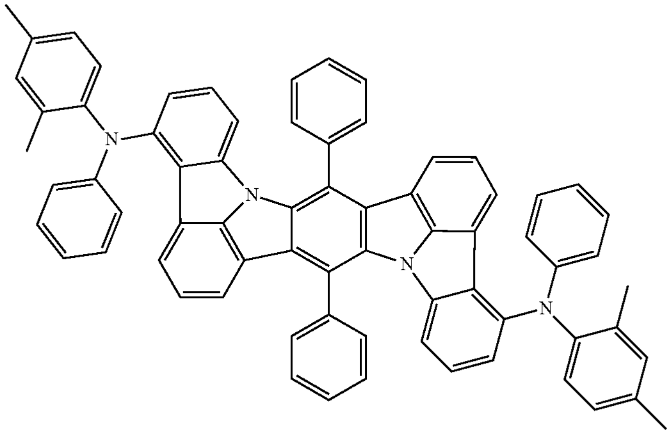

-continued
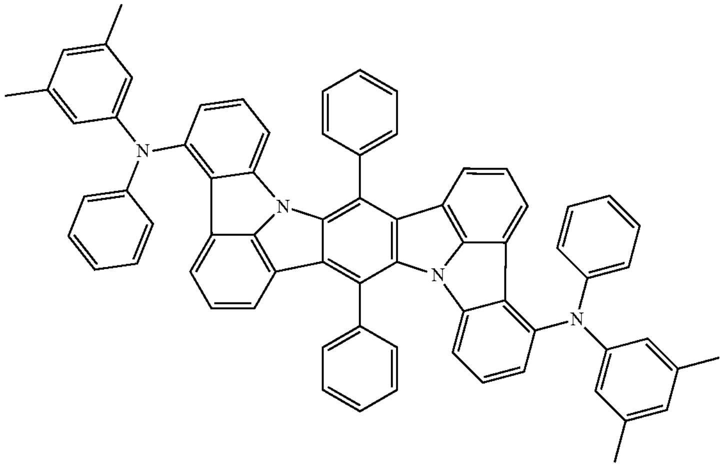
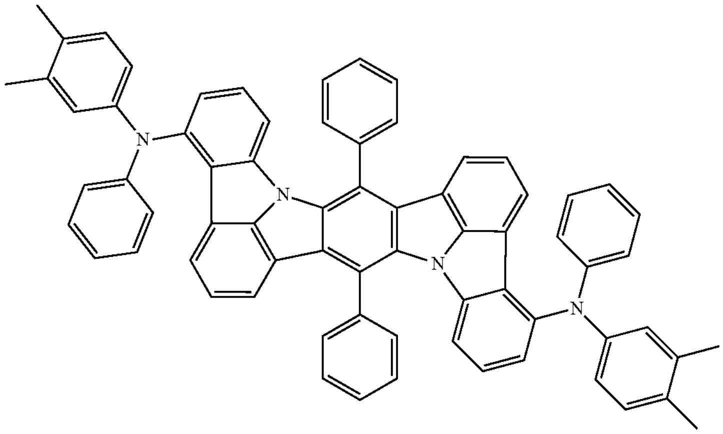
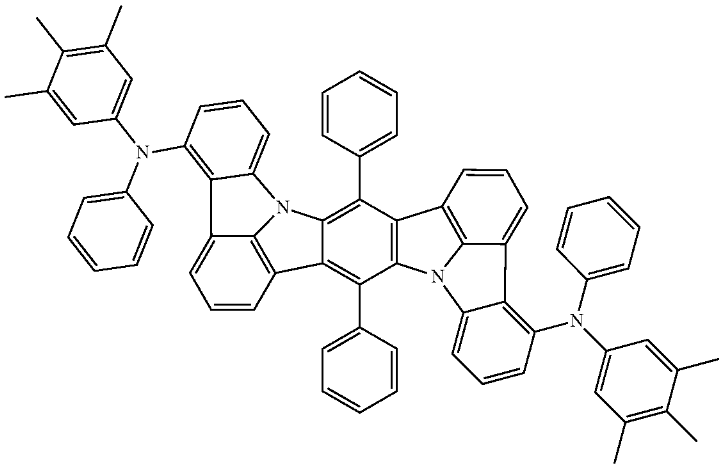

-continued
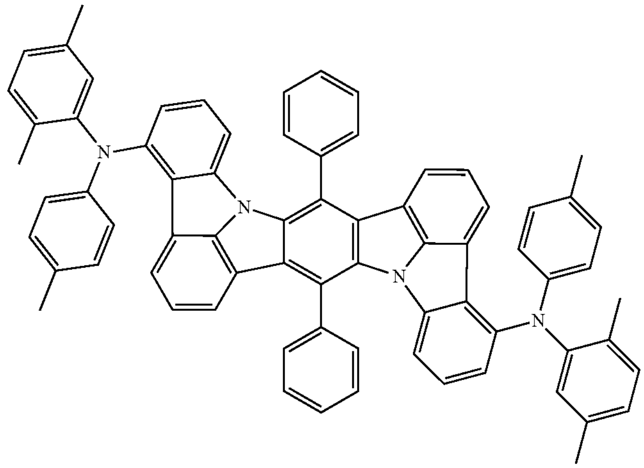
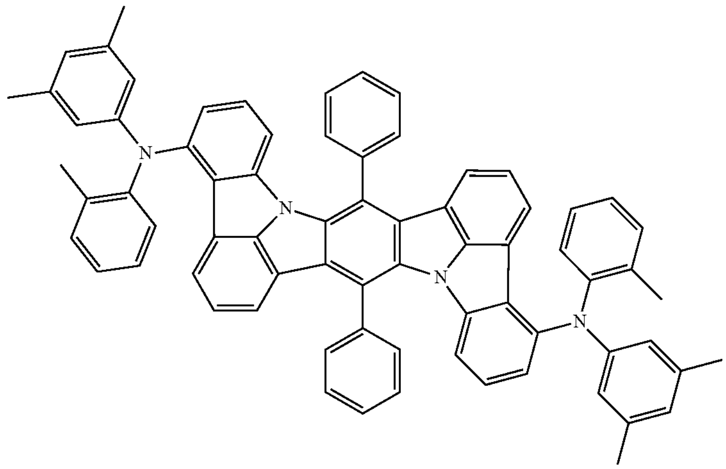
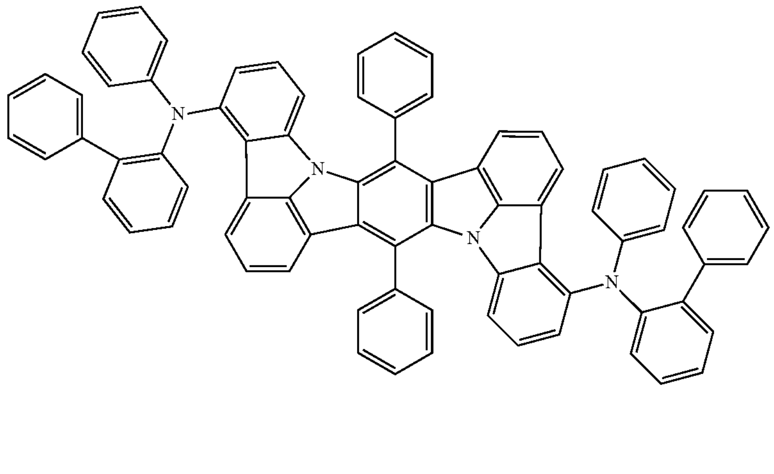

-continued
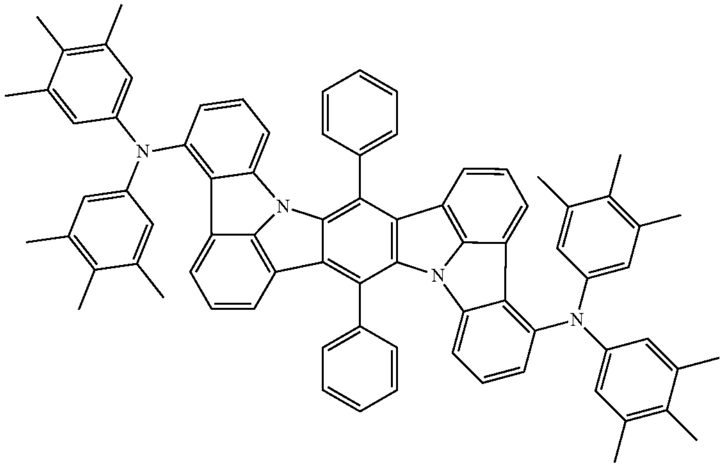
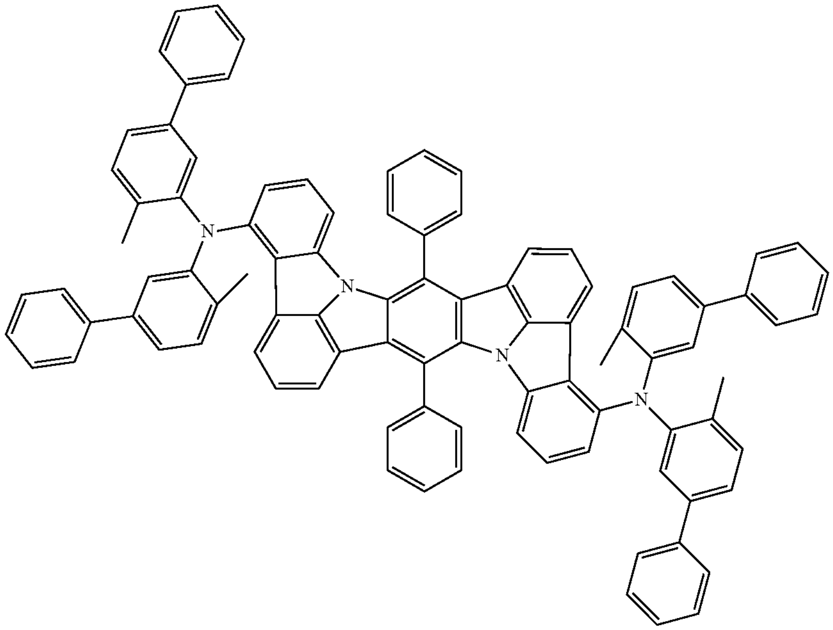
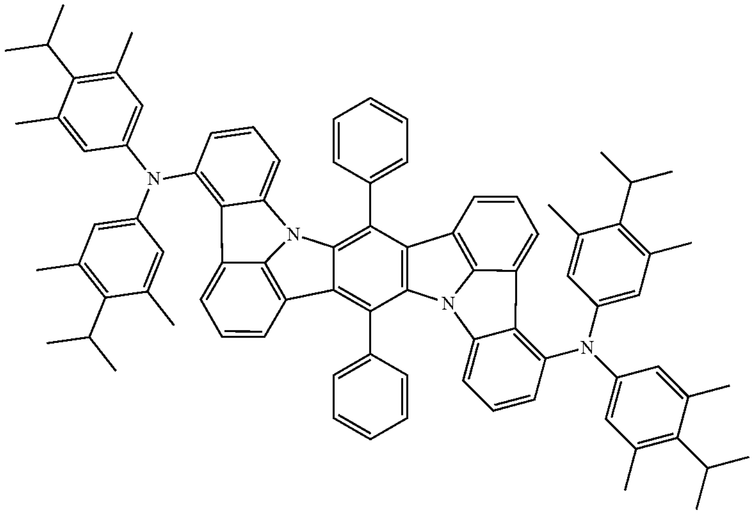

-continued
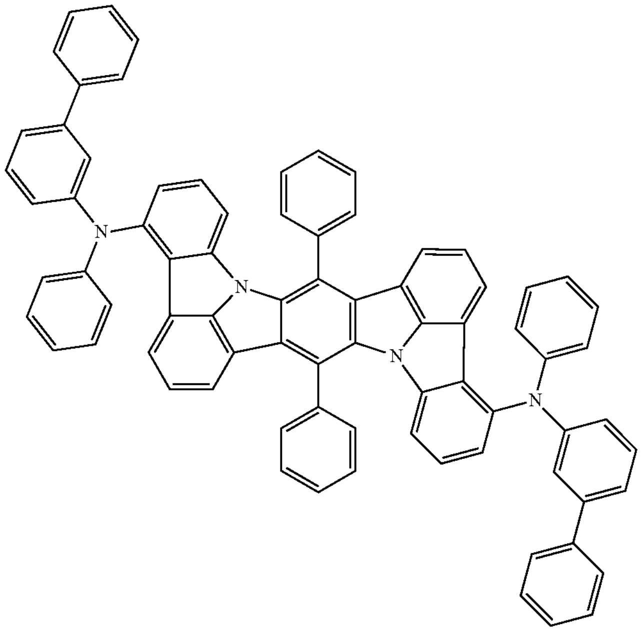 [SMILES: c1ccc(-c2cccc(N(c3ccccc3)c3cccc4c3c3cccc5c6c(-c7ccccc7)c7c(c(-c8ccccc8)c6n4c35)c3cccc4c5c(N(c6ccccc6)c6cccc(-c8ccccc8)c6)cccc5n7c43)c2)cc1]
[Formula 249]
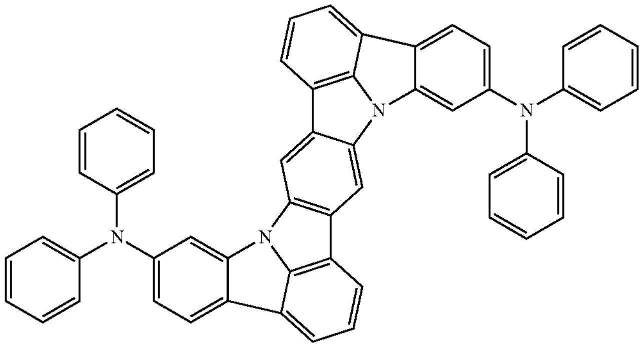
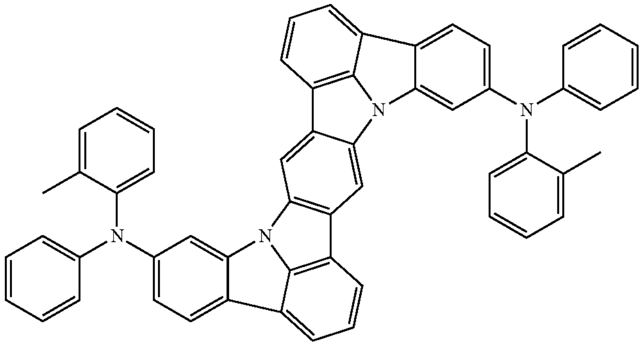
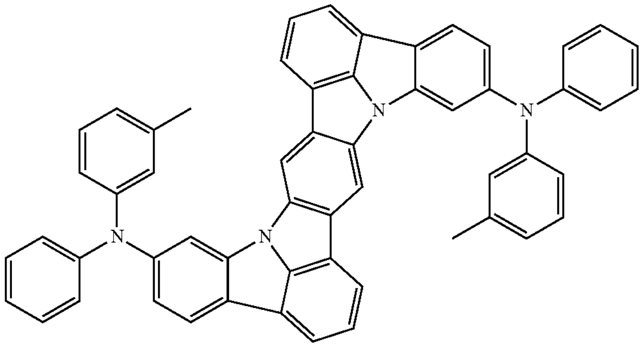

-continued
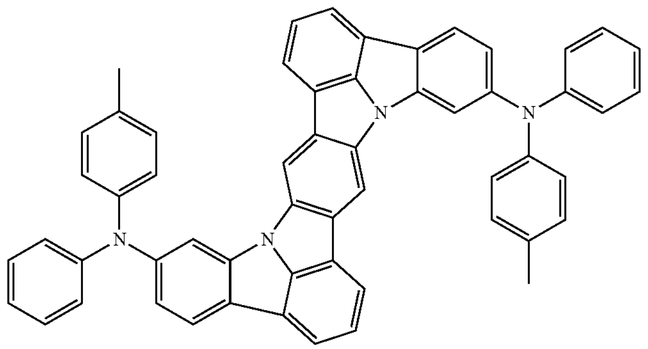
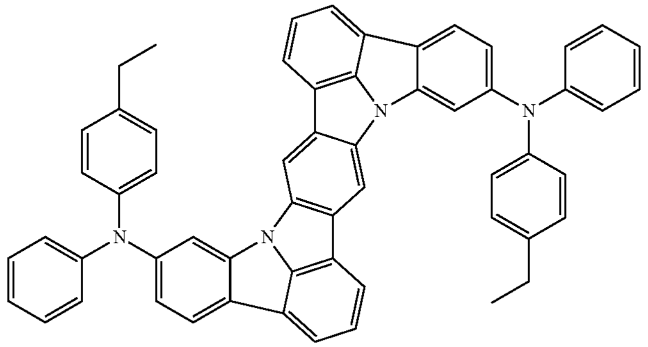
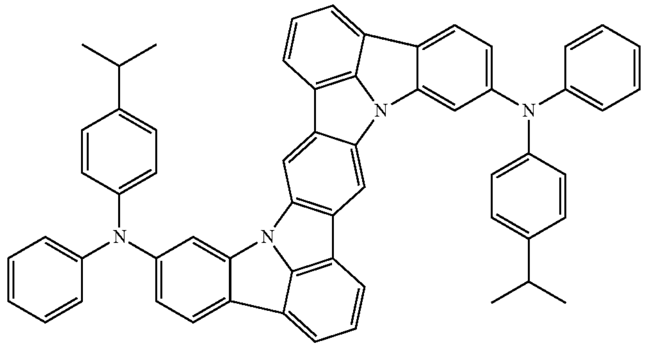
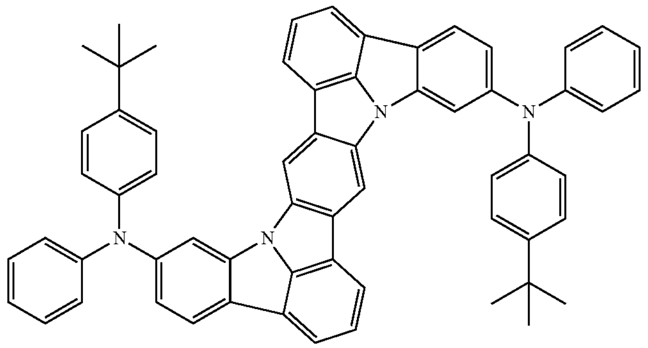

-continued
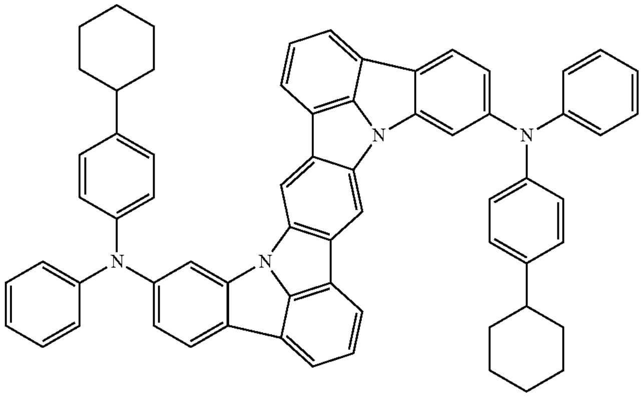
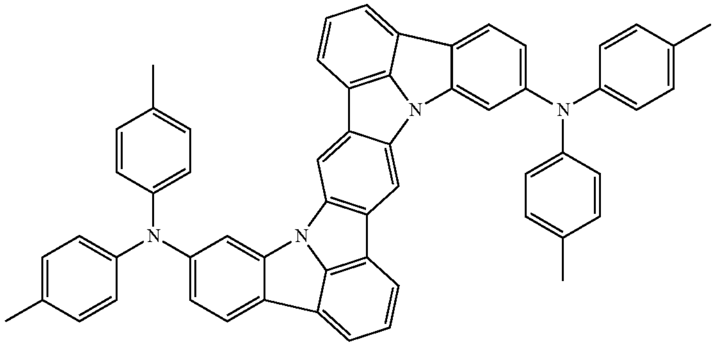
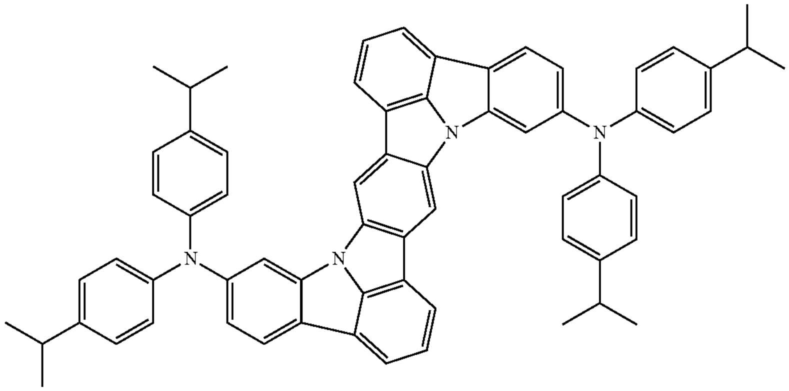
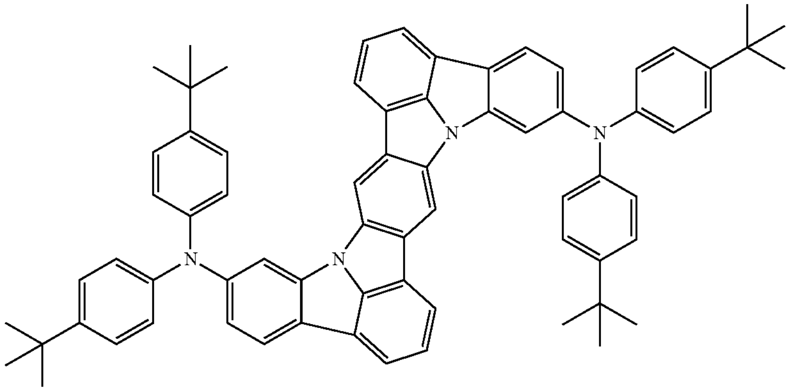

-continued
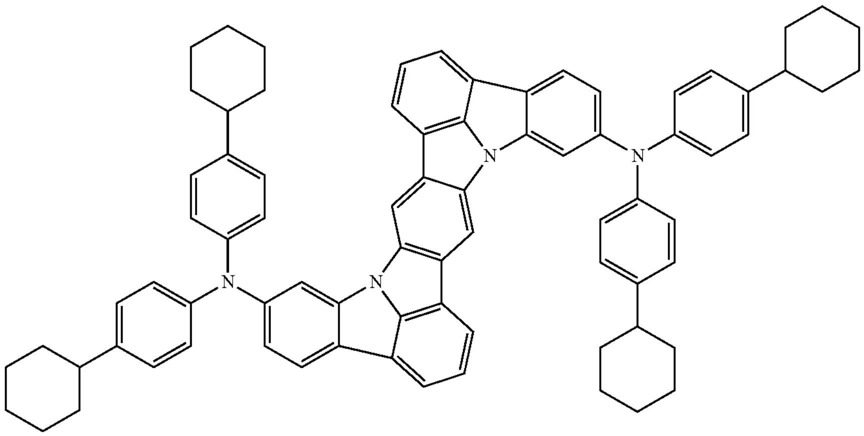
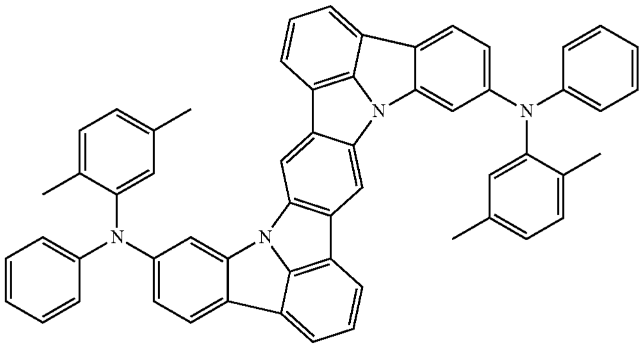
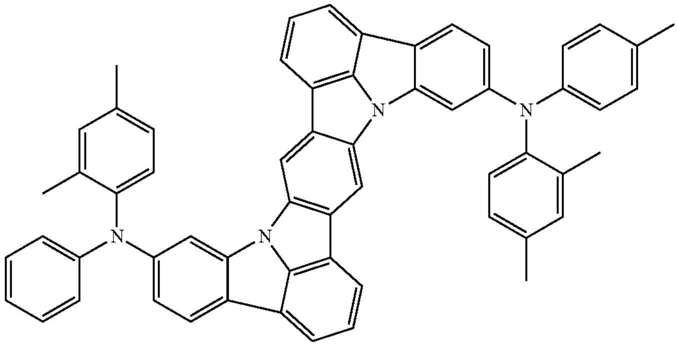
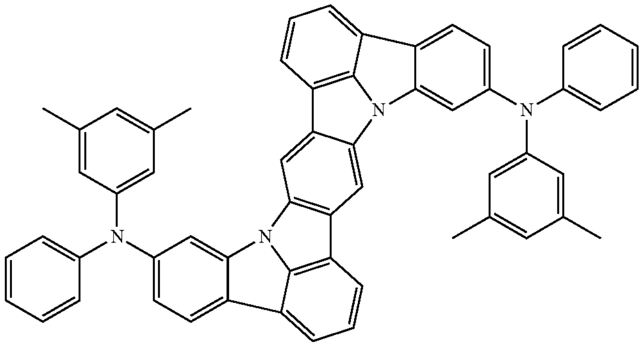

-continued
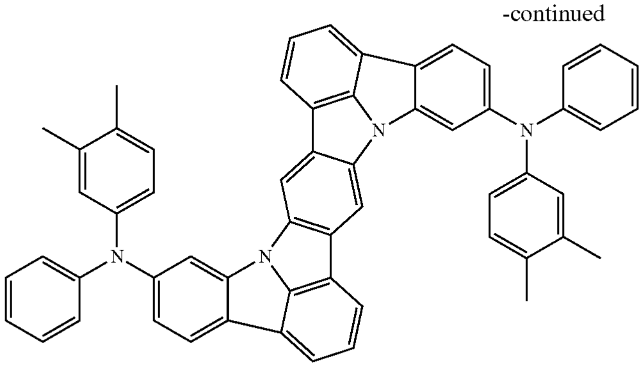
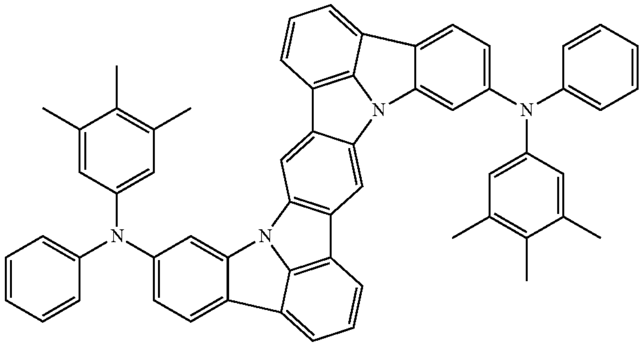
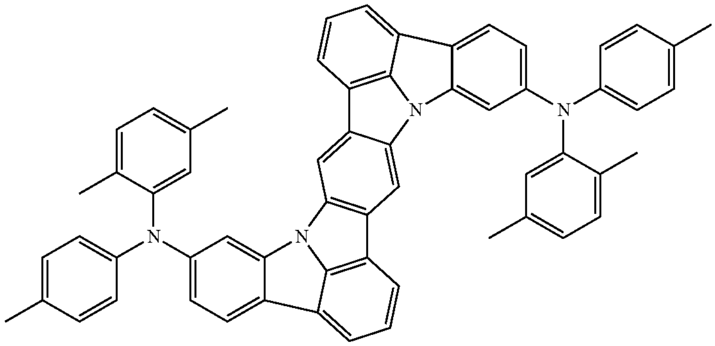
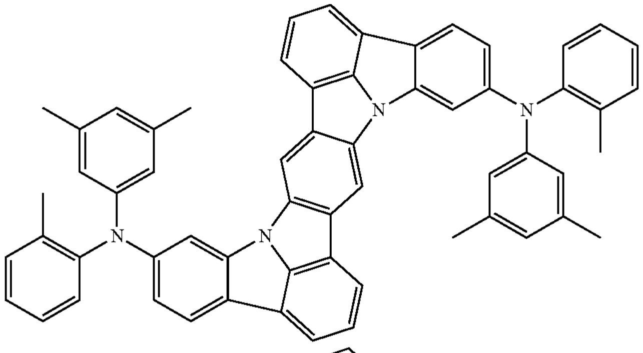
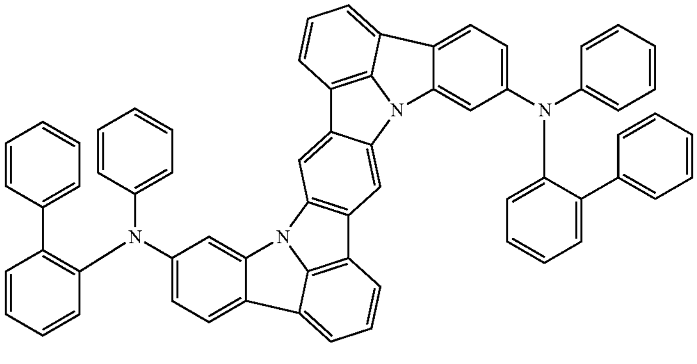

-continued
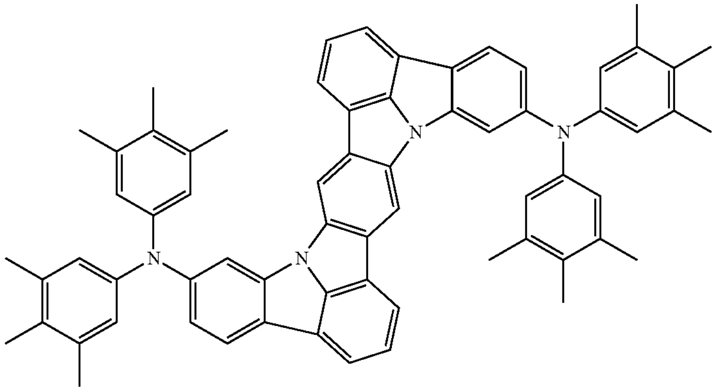
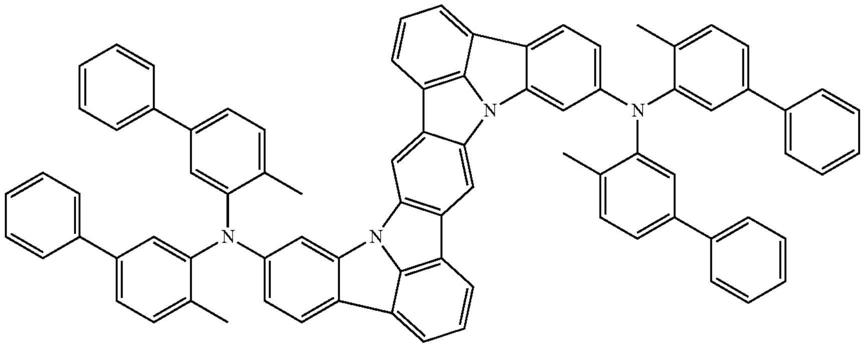
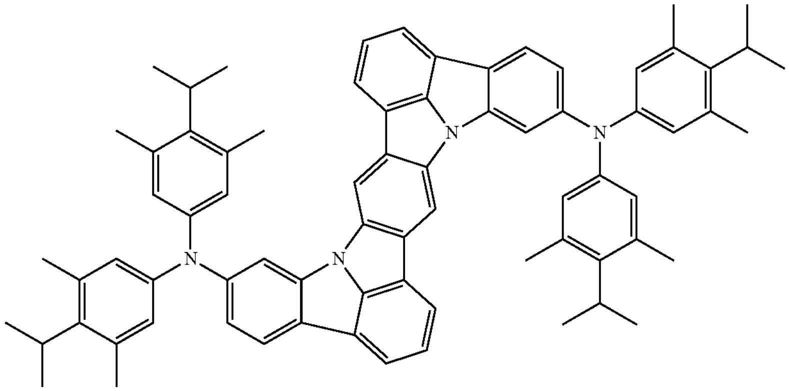
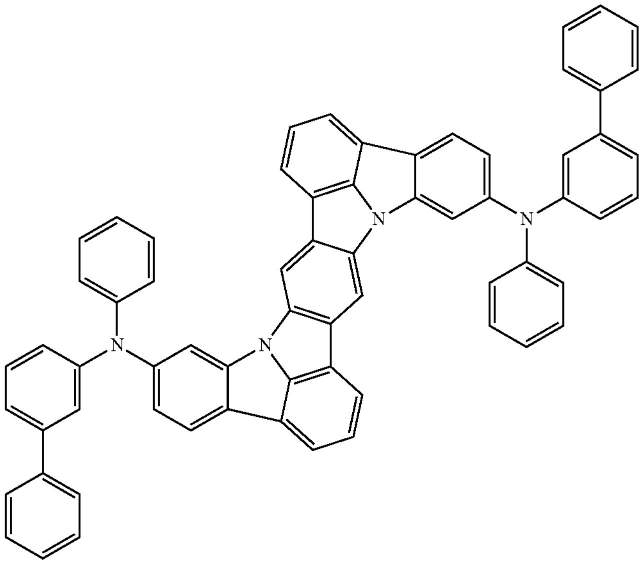

-continued
[Formula 250]
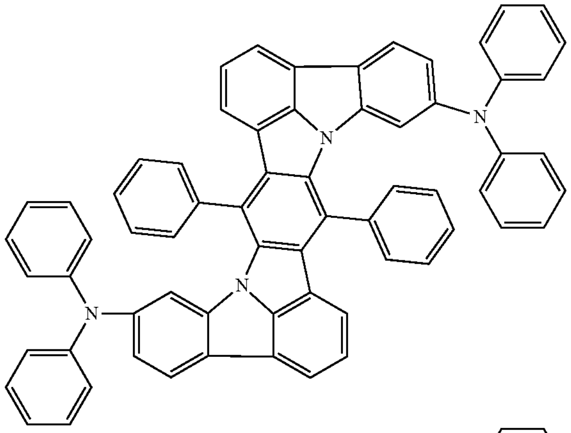
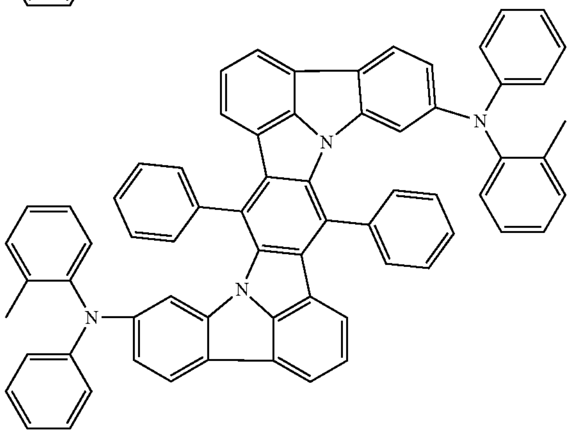
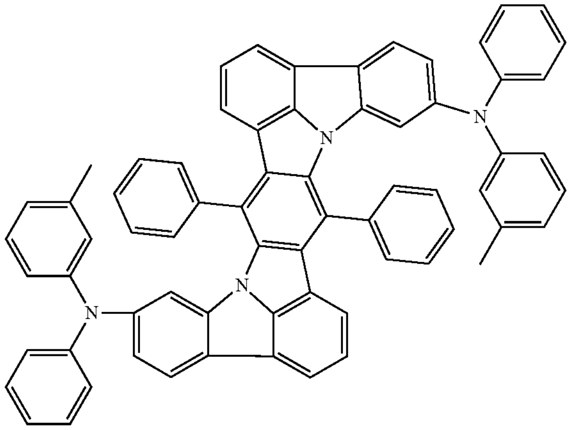
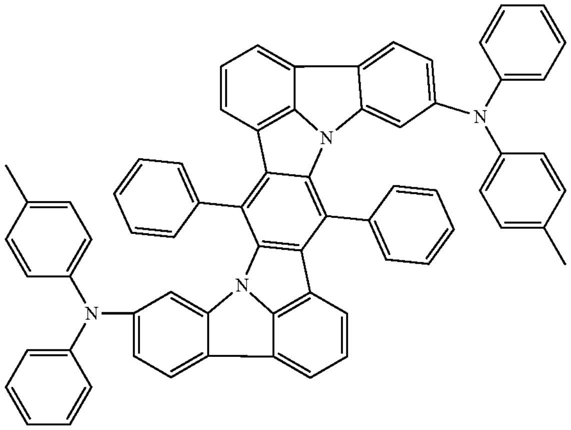

-continued
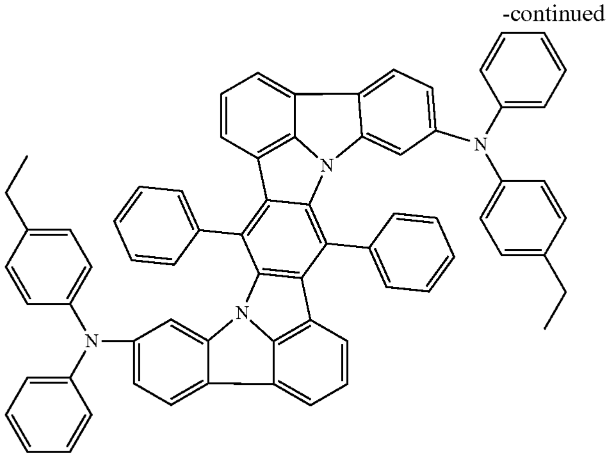
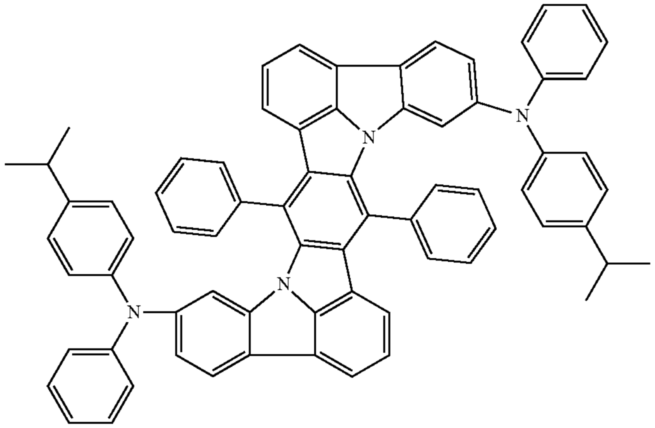
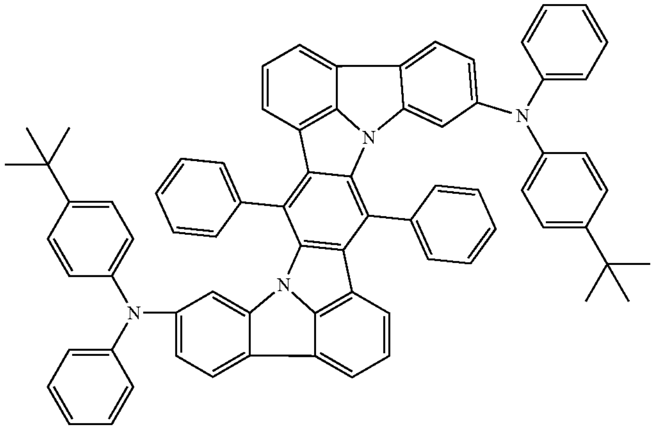
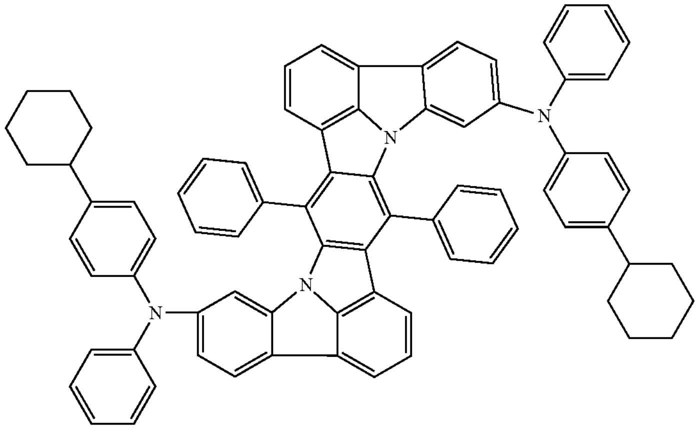

-continued
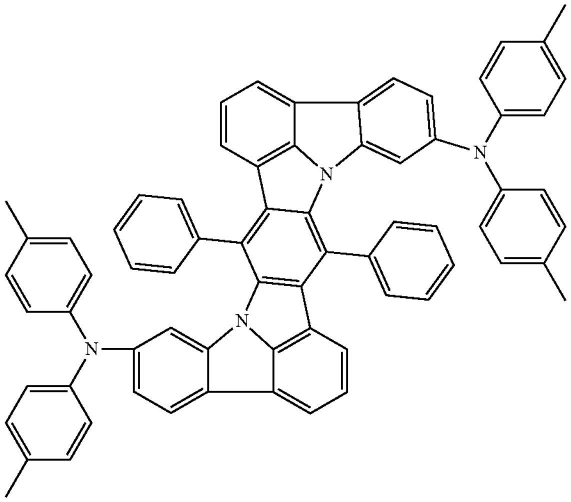
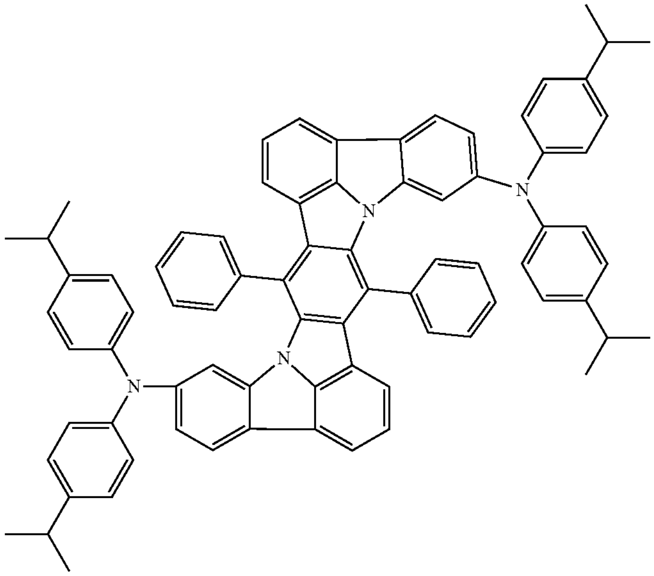
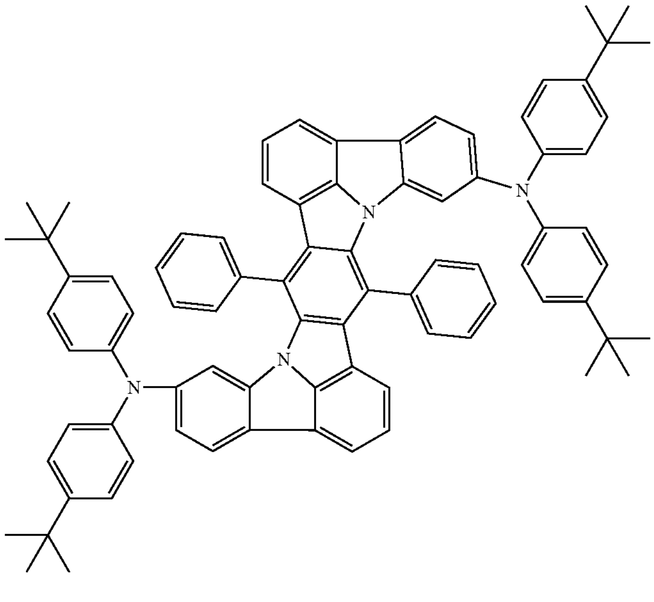

-continued
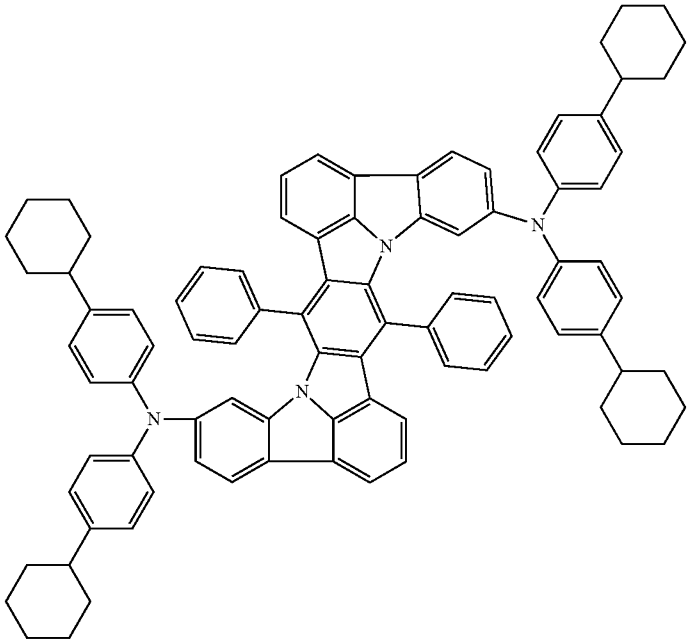
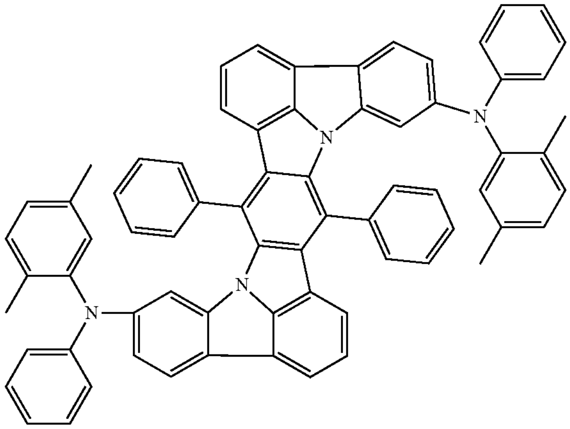
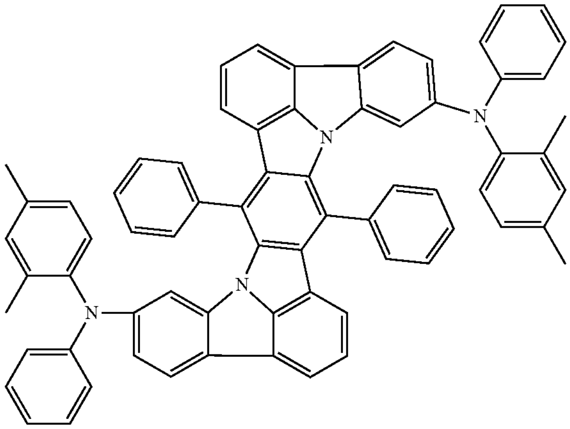

-continued
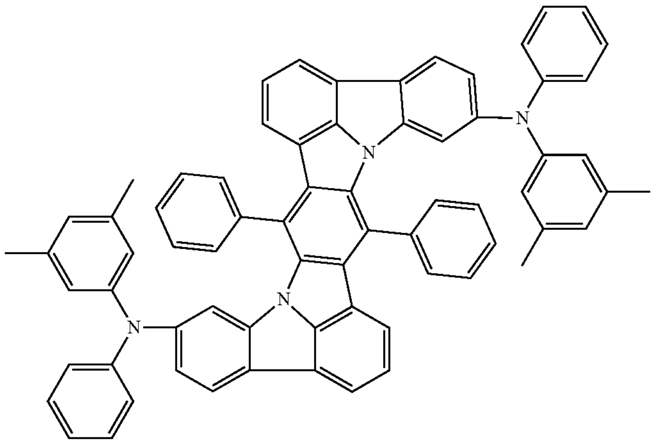
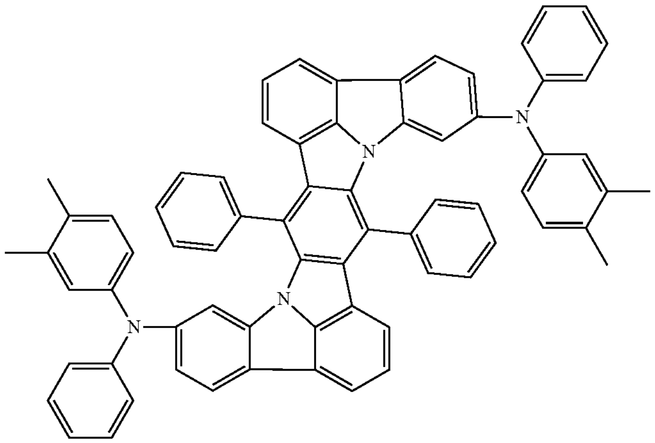
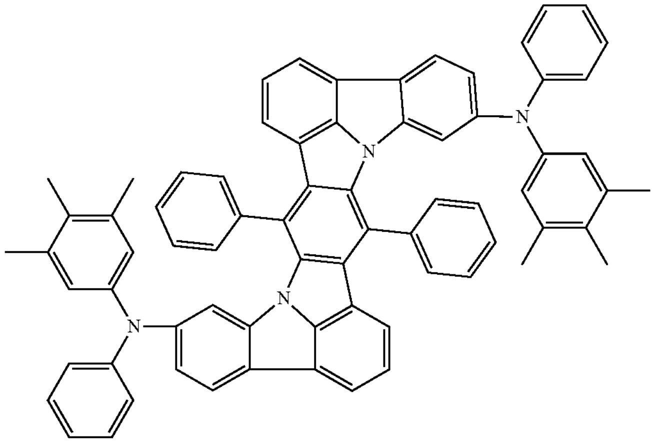

-continued
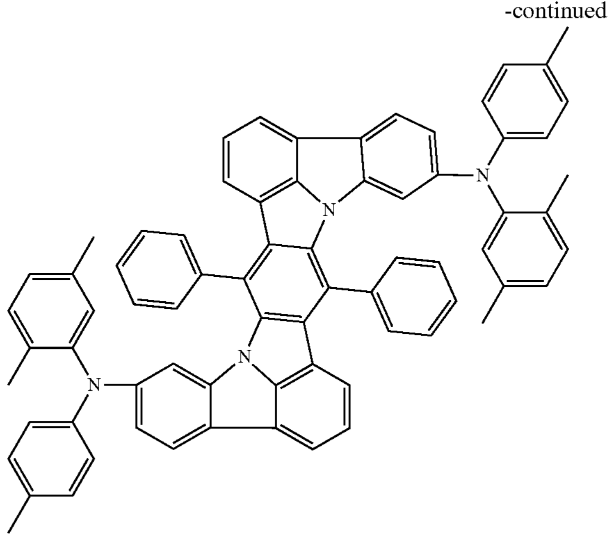
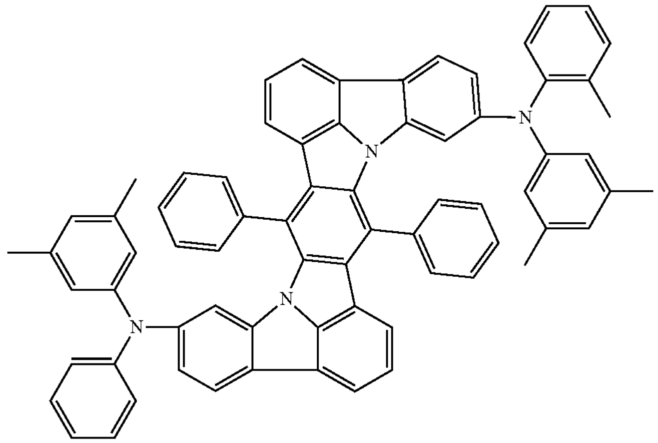
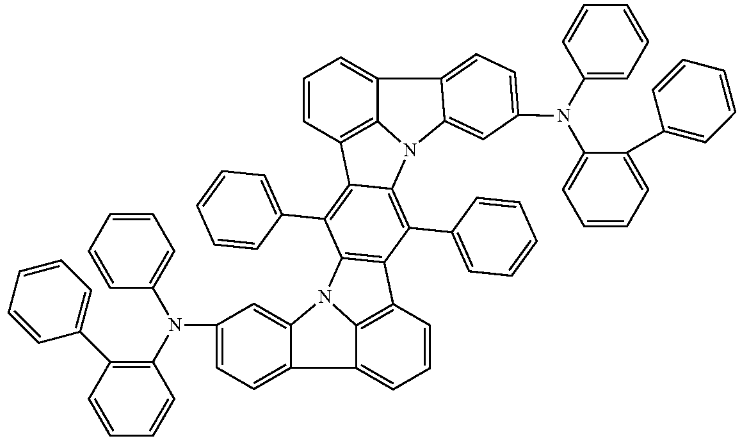

-continued
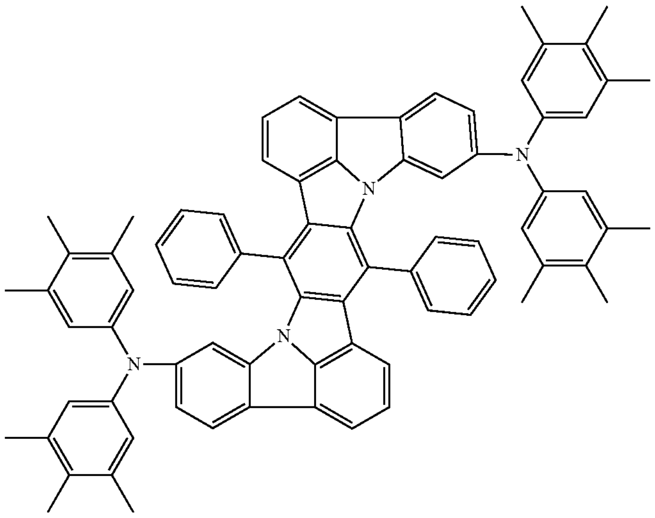
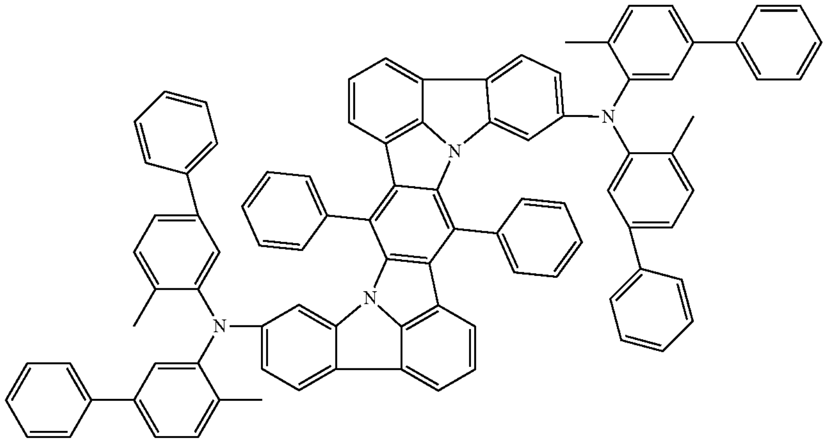
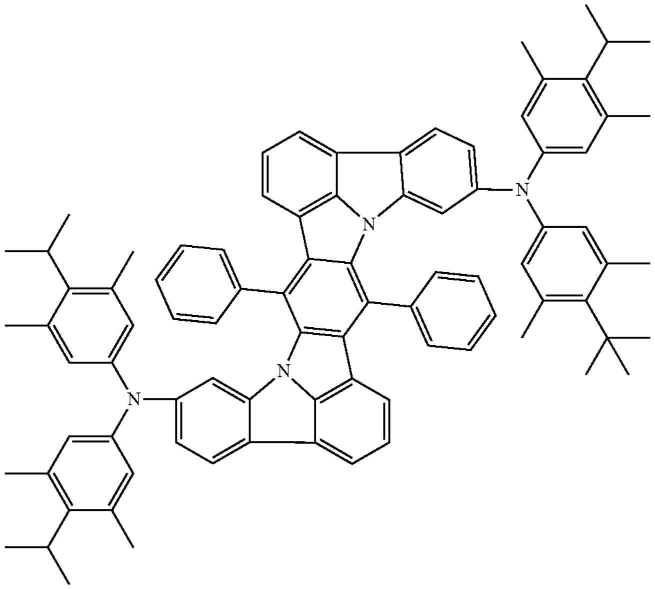

-continued
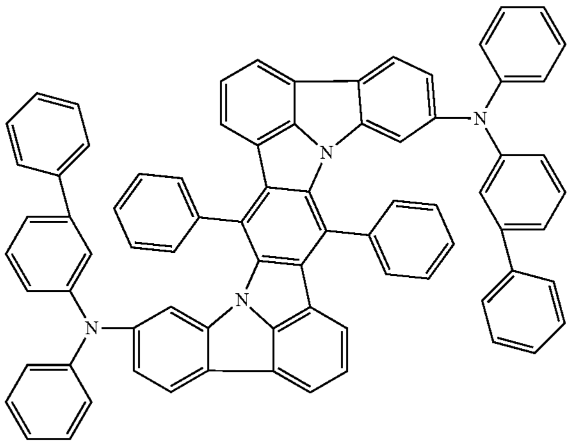
[Formula 251]
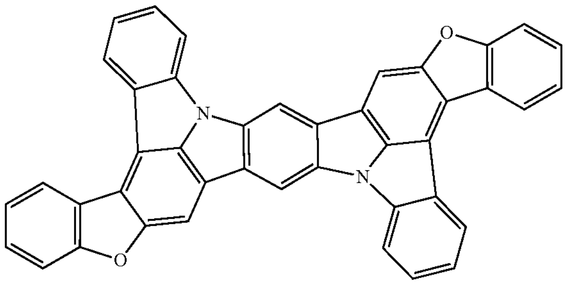
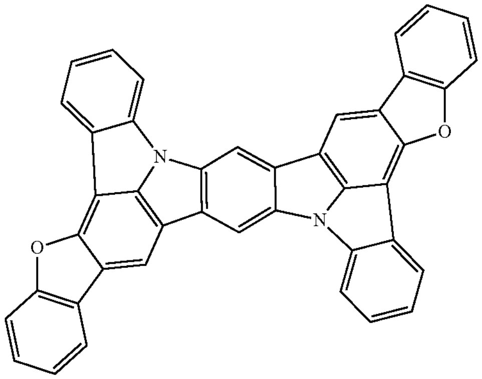
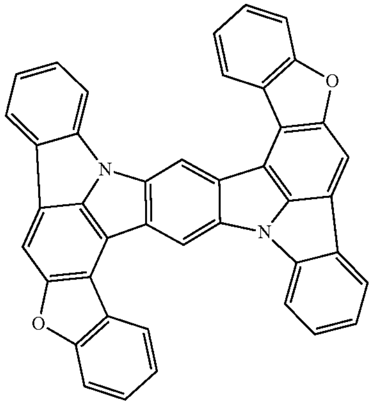
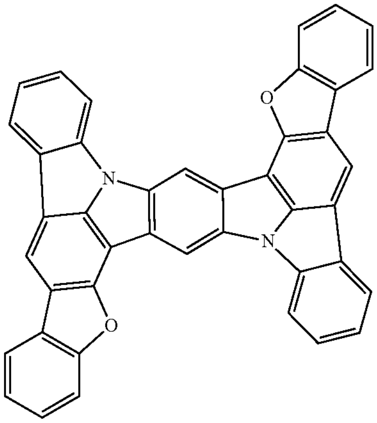
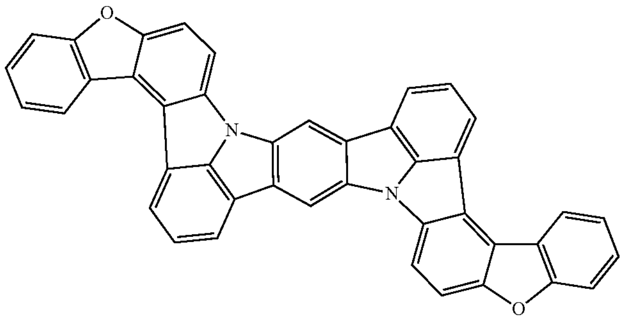

-continued
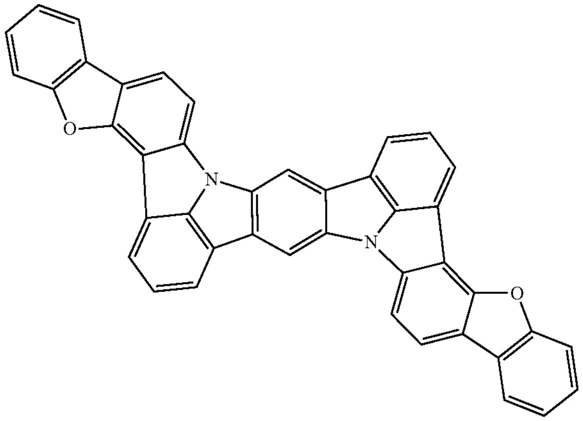
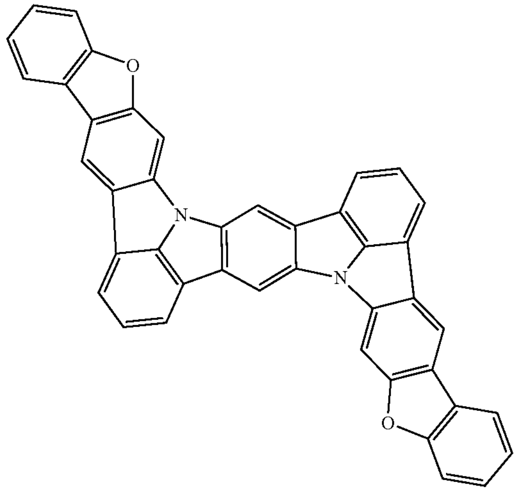
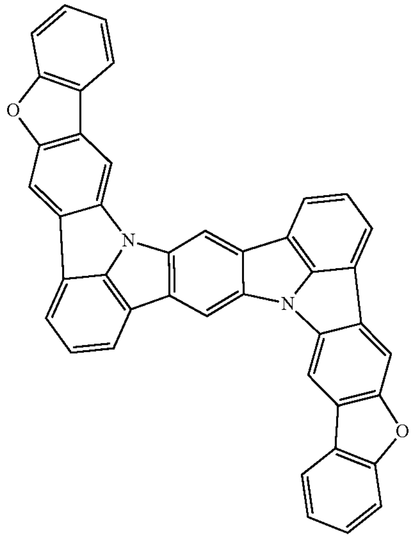
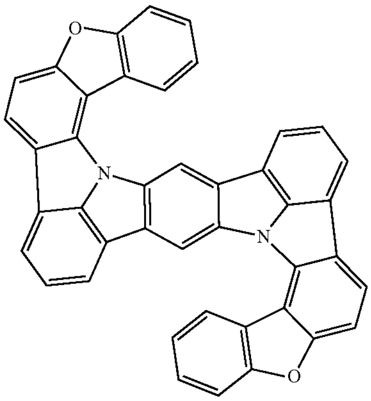
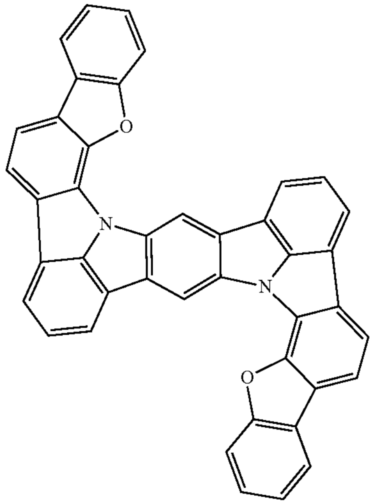

-continued
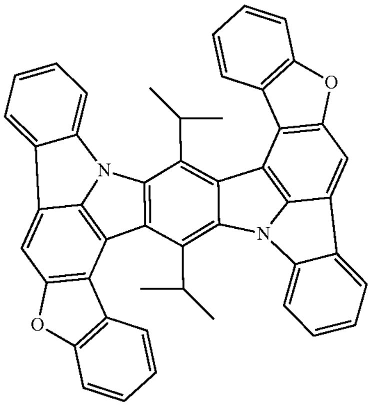
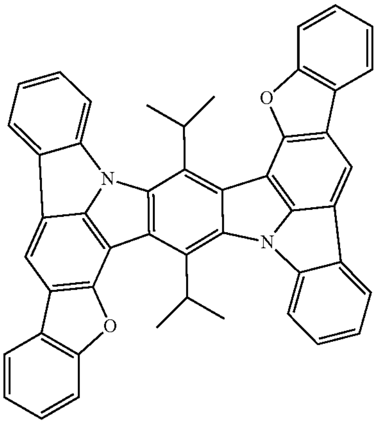
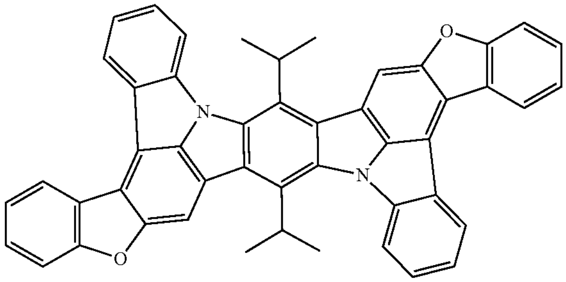
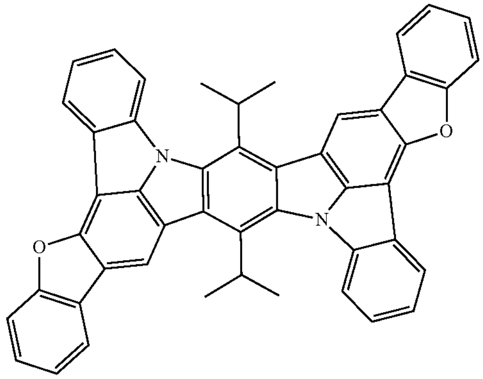
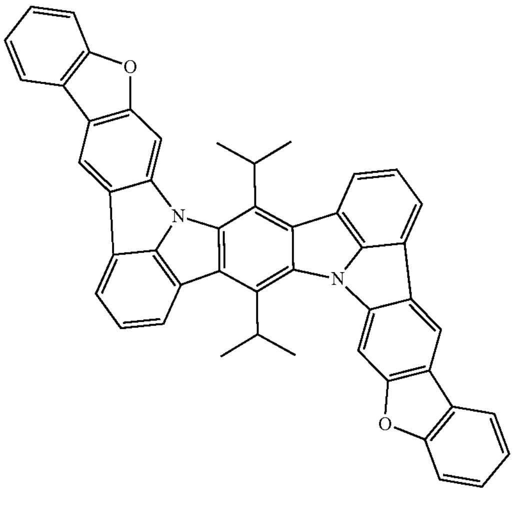
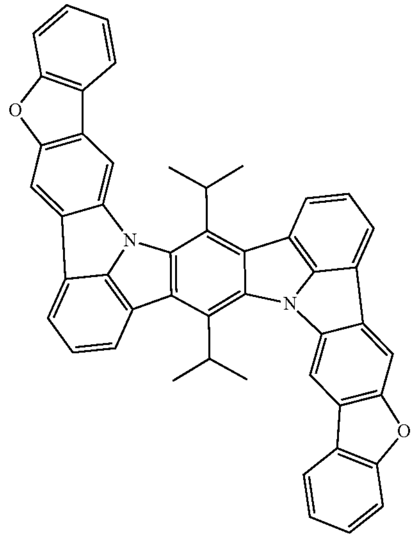
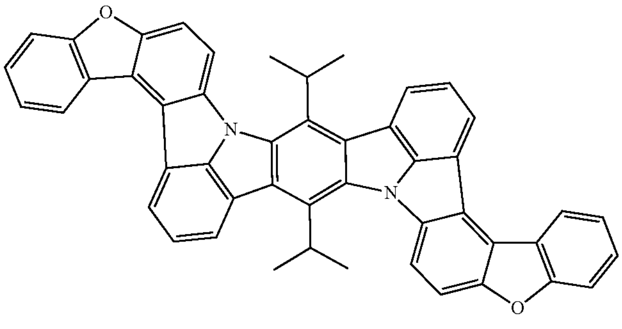

-continued
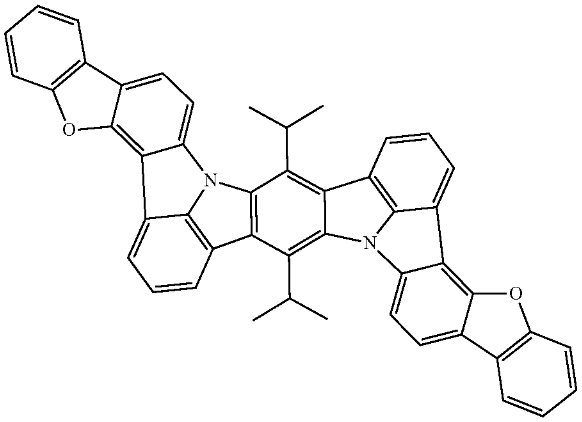
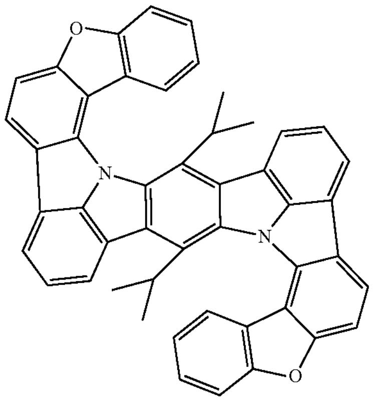
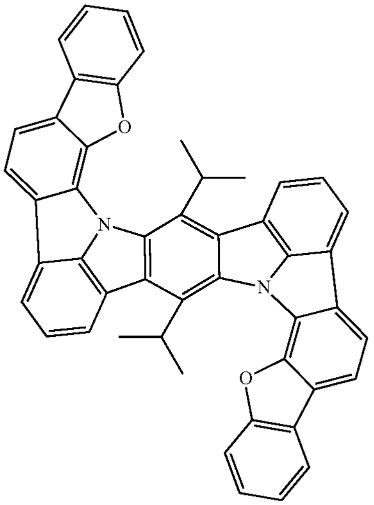
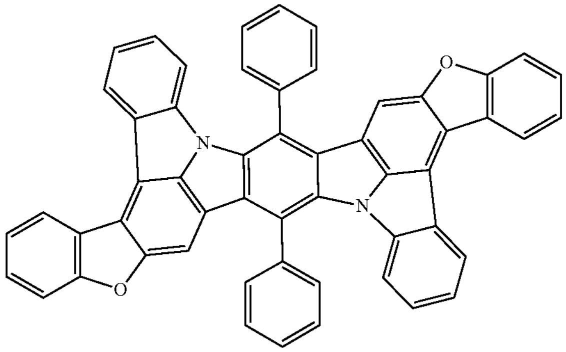
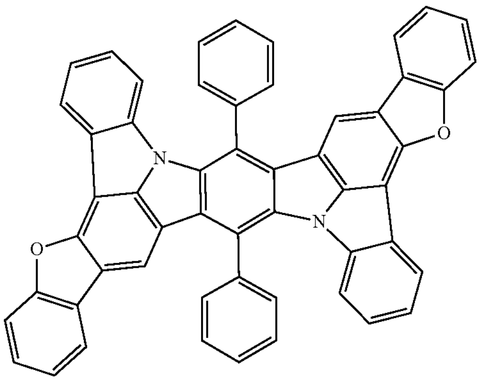
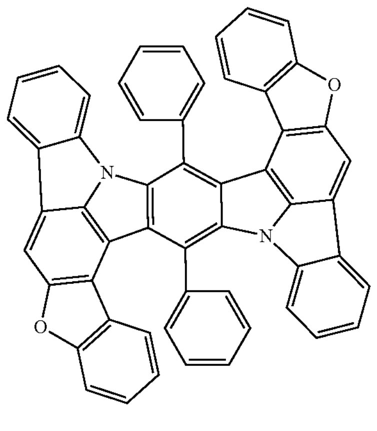

-continued
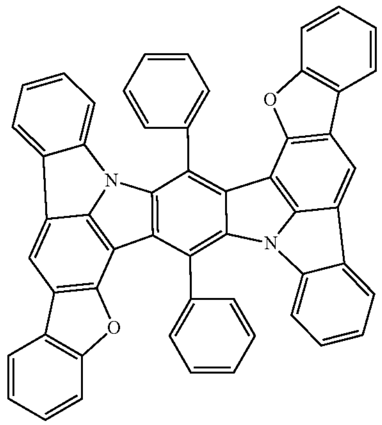
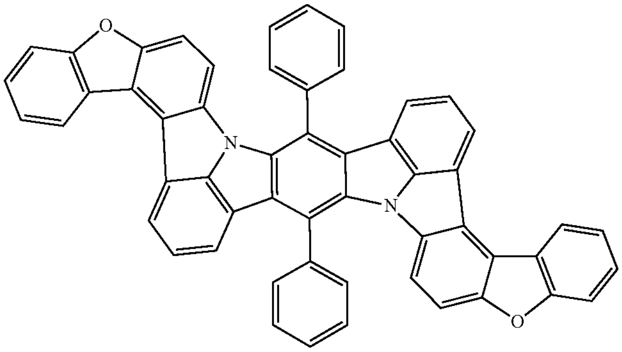
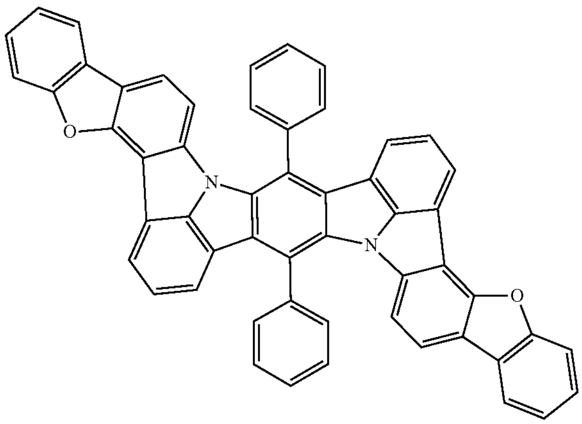
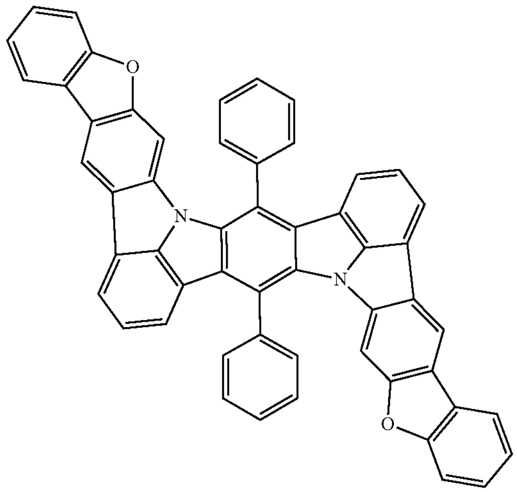
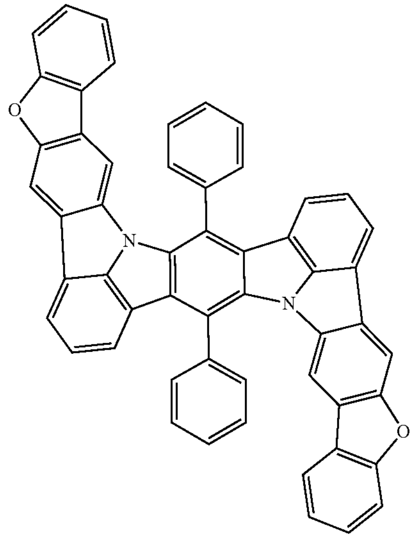

-continued
[Formula 252]
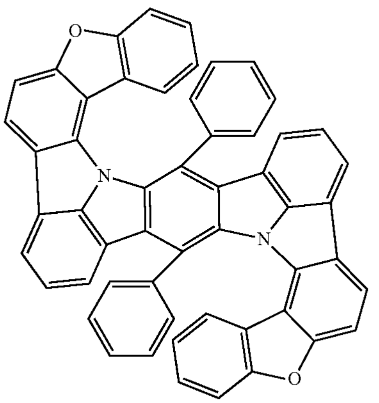
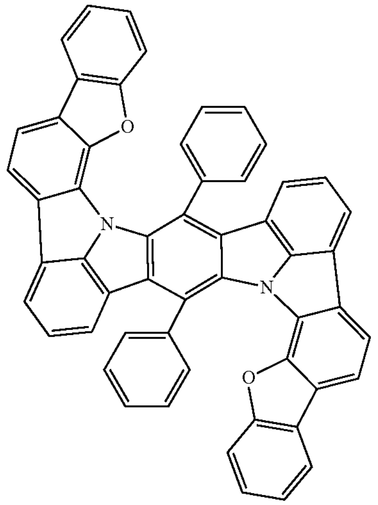
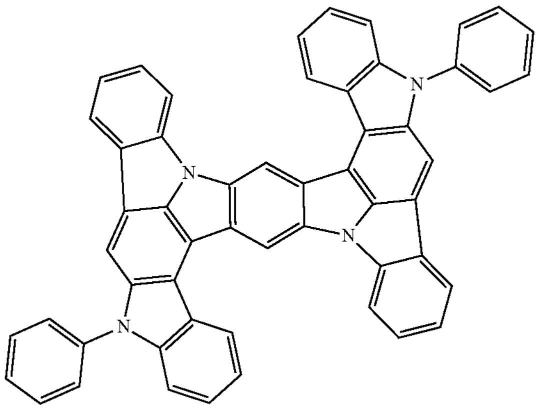
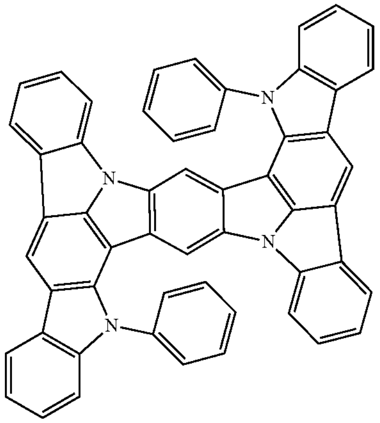
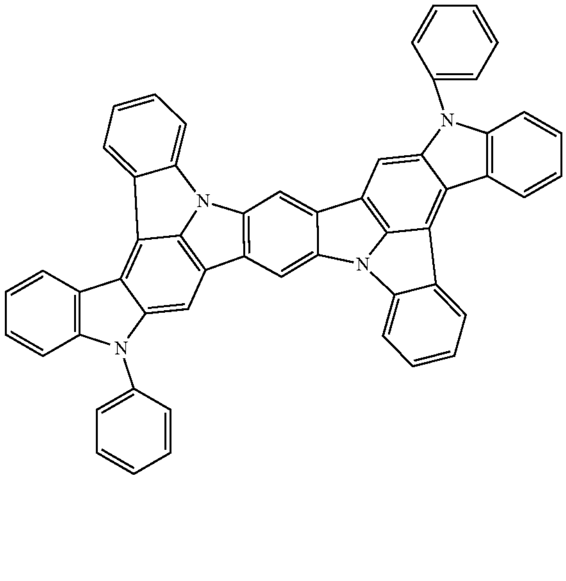

-continued
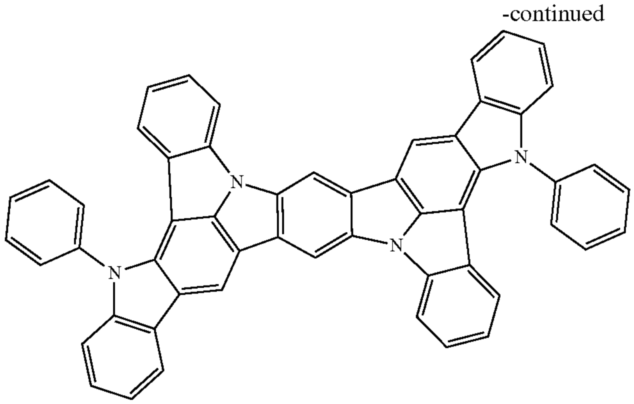
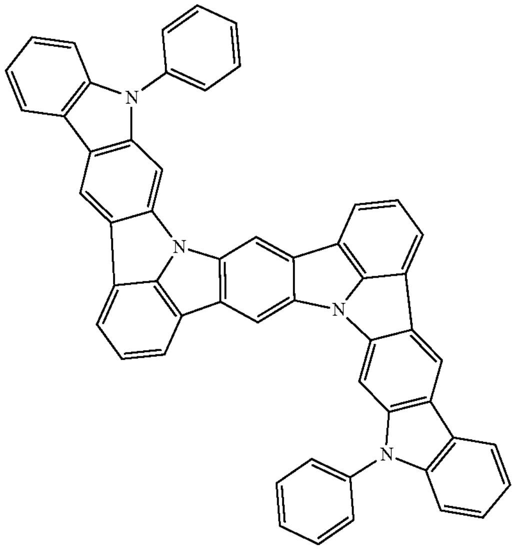
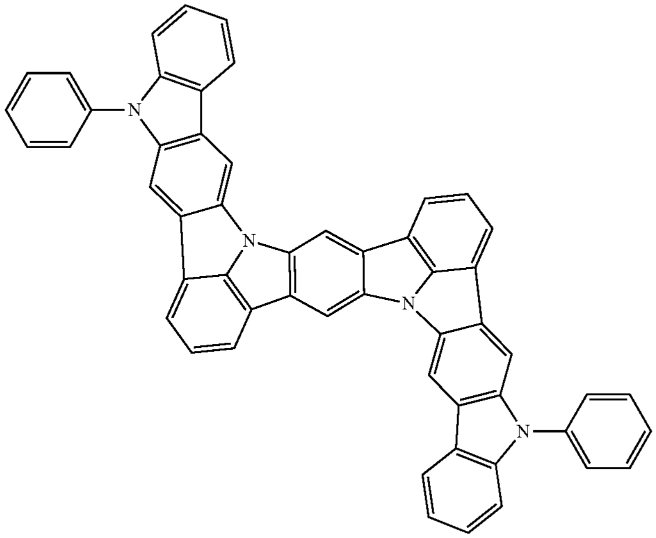

-continued
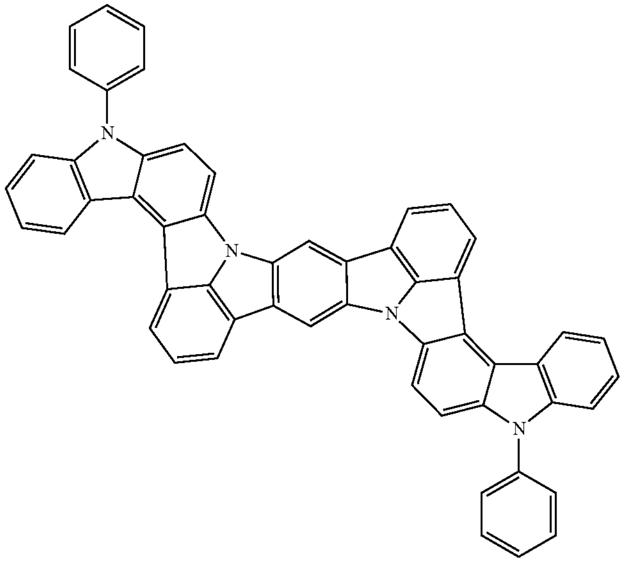
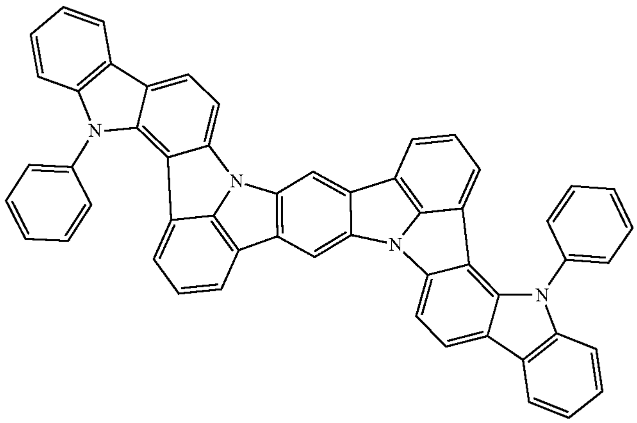
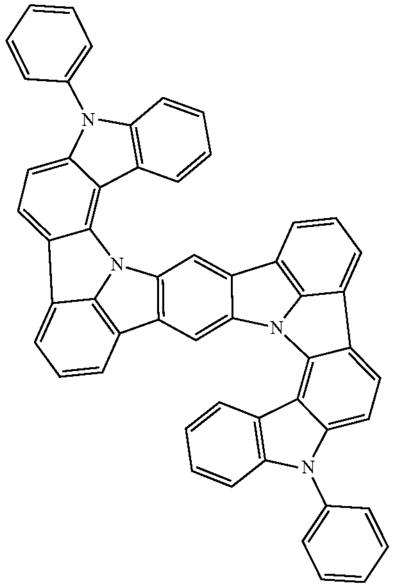
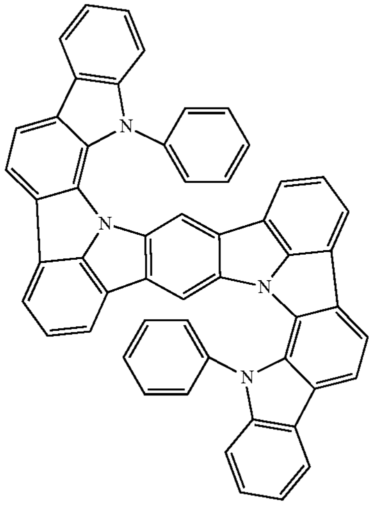

-continued
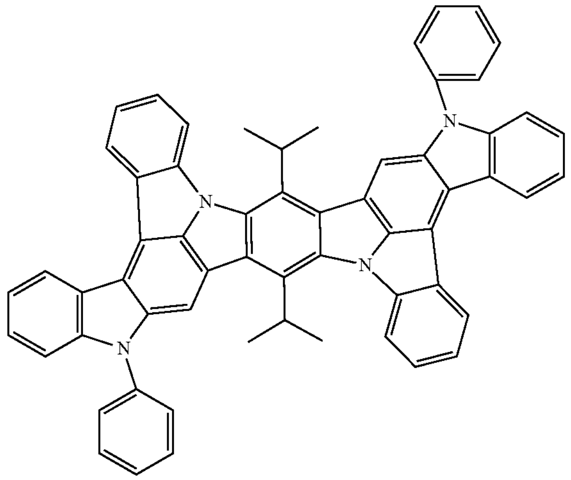
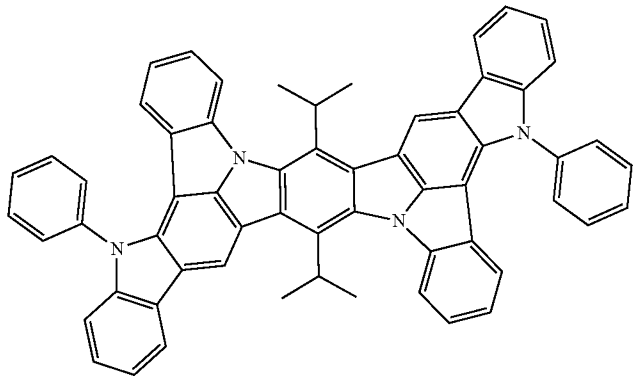
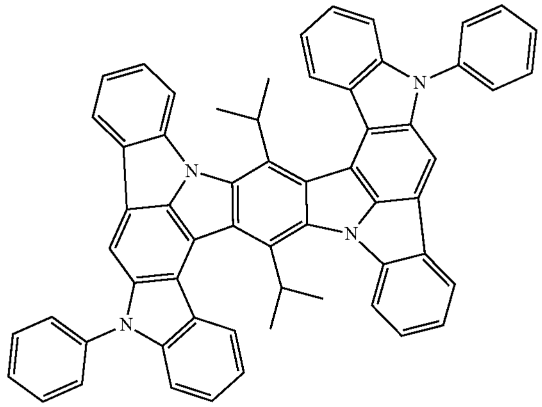
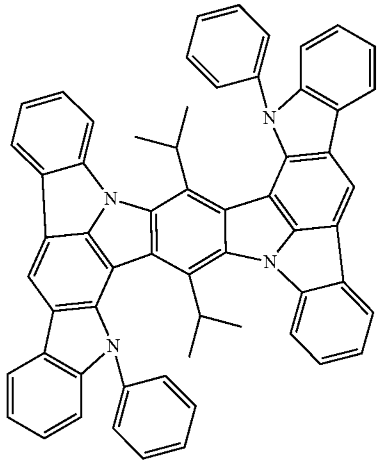

-continued
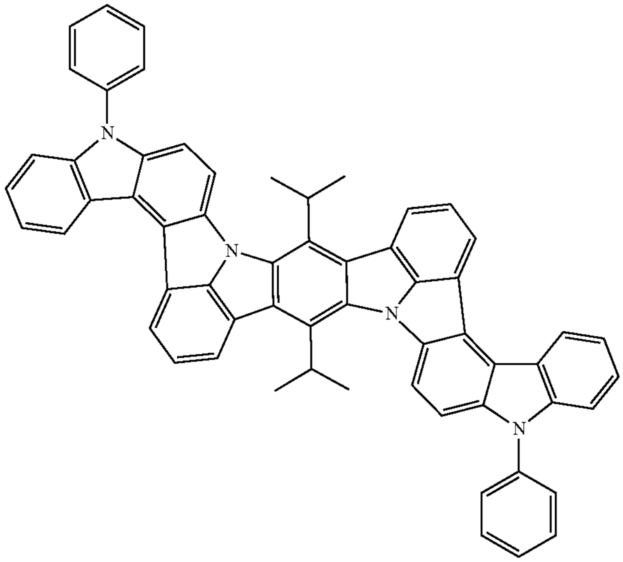
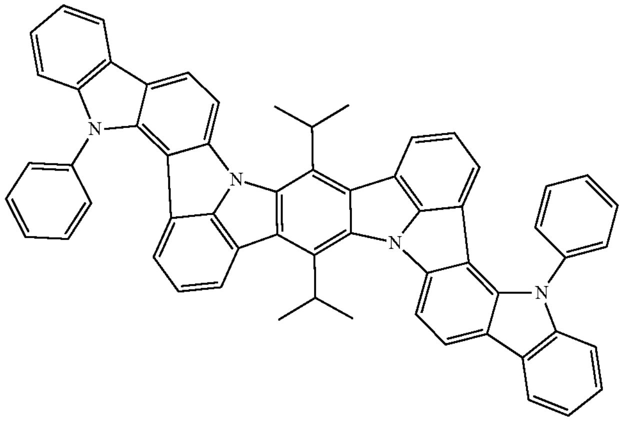
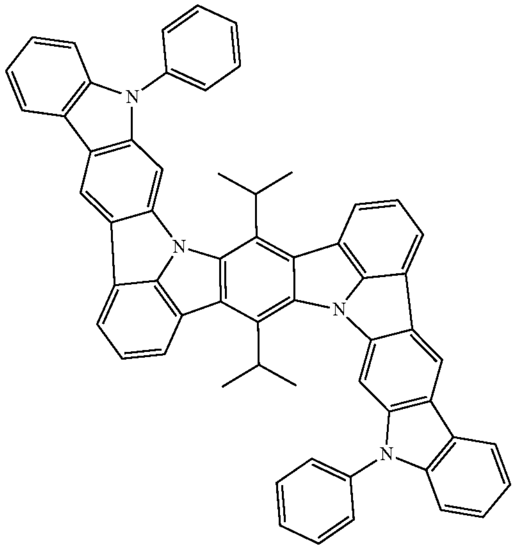
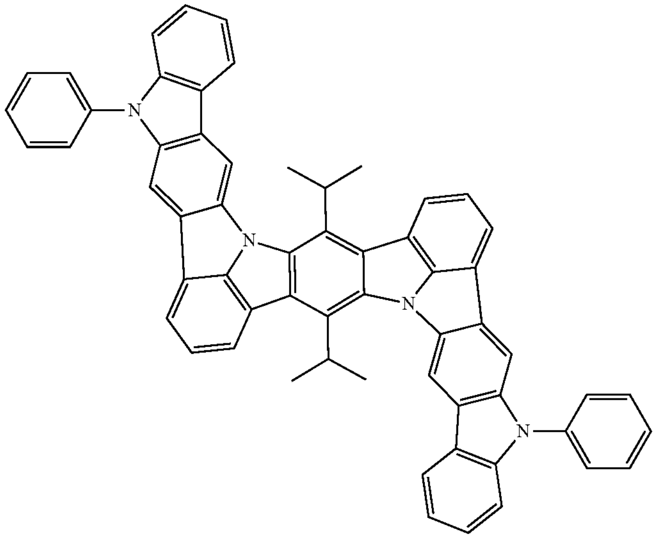

-continued
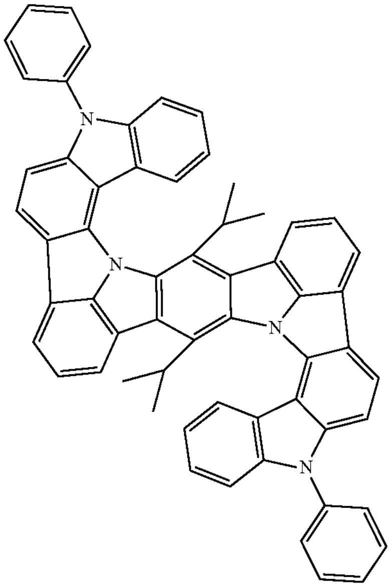
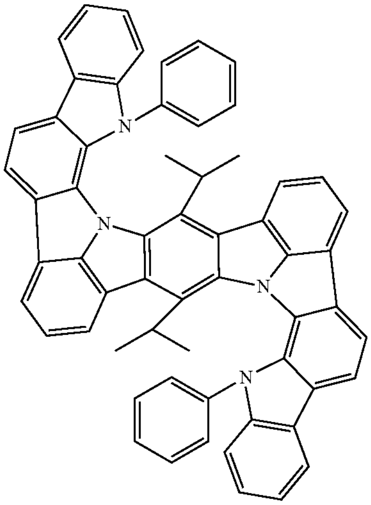
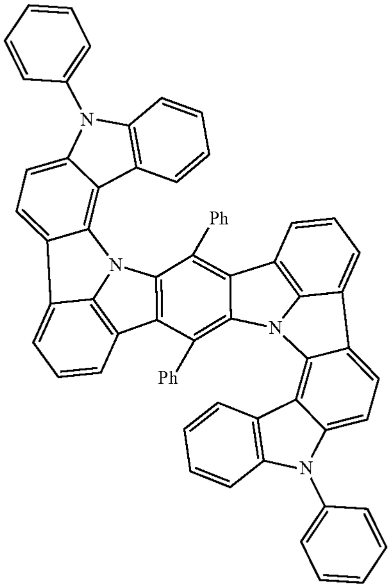
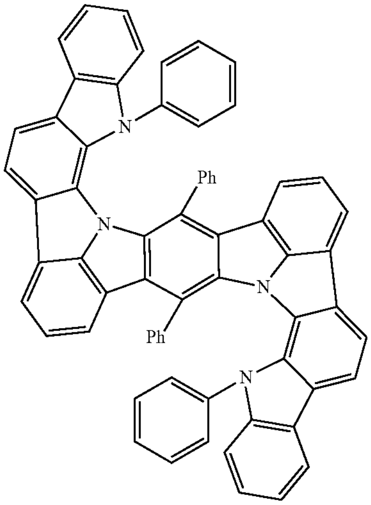
In formulae, Ph is a phenyl group.
[Formula 253]
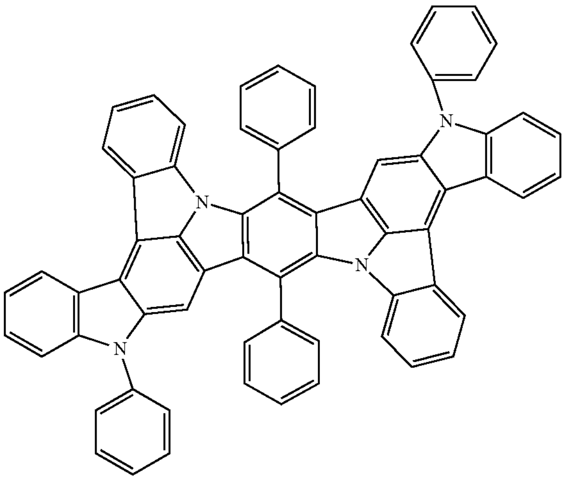

-continued
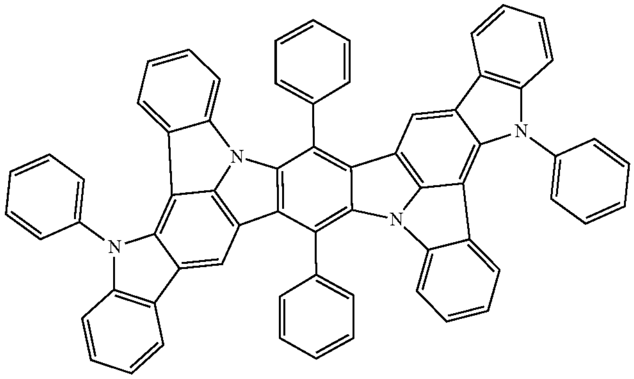
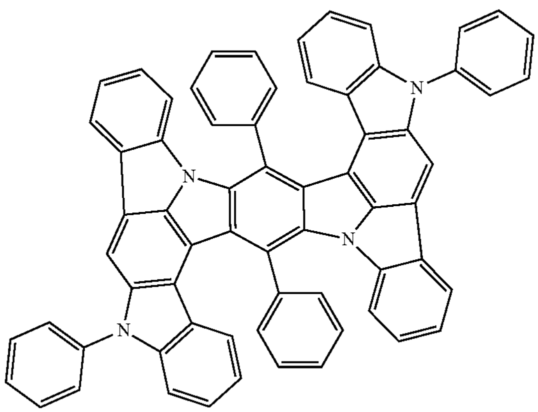
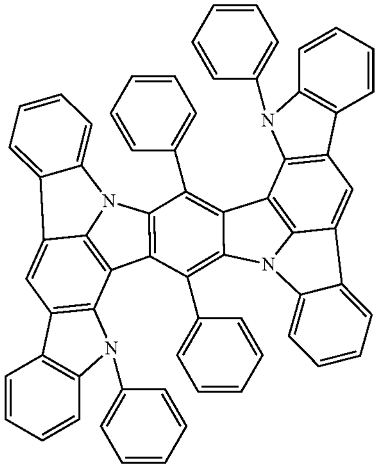
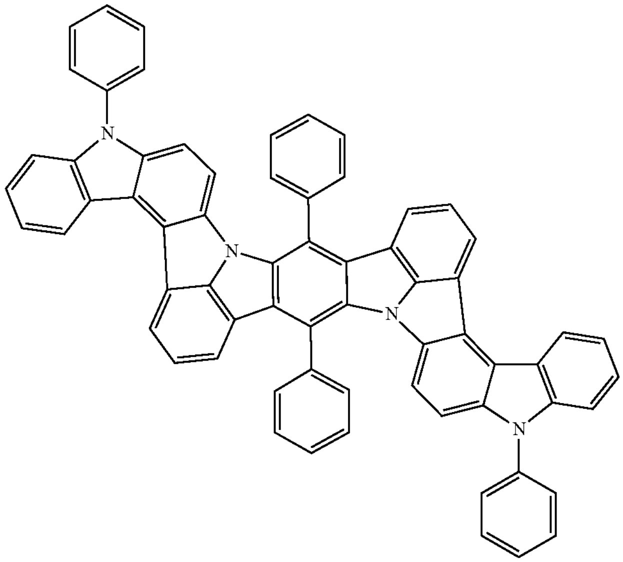

-continued
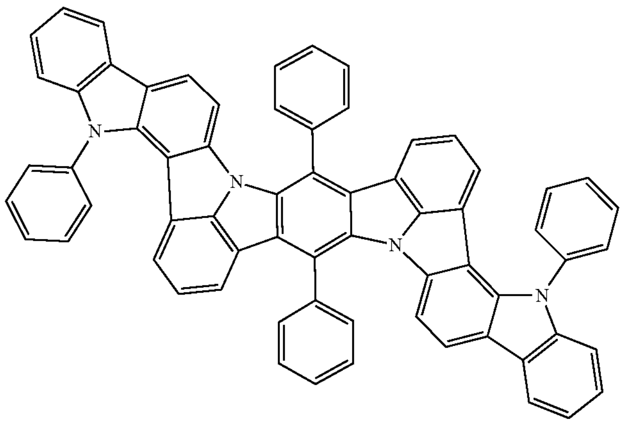
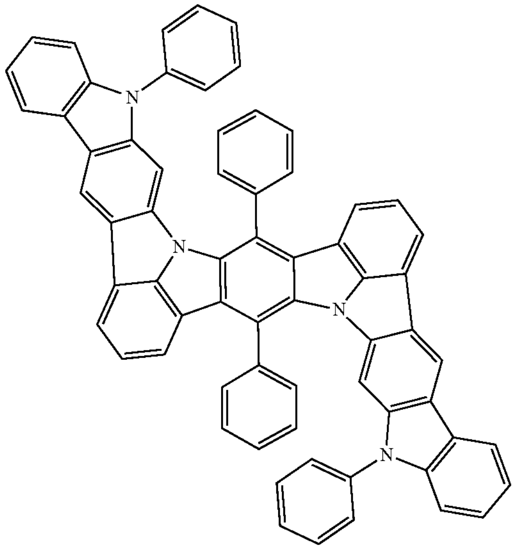
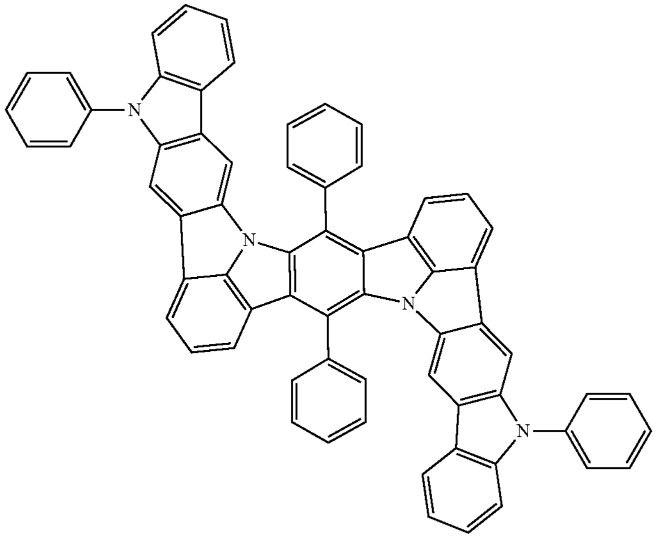
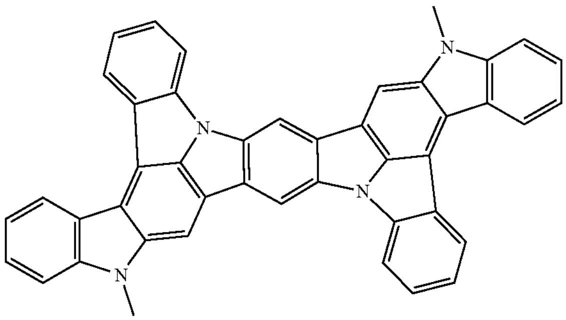
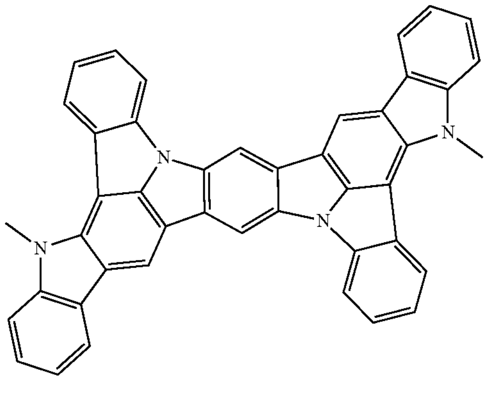

-continued
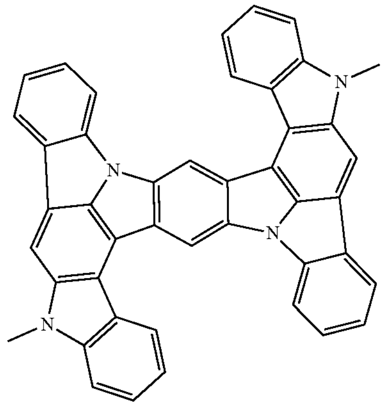
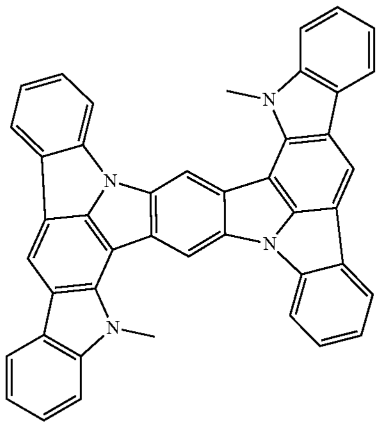
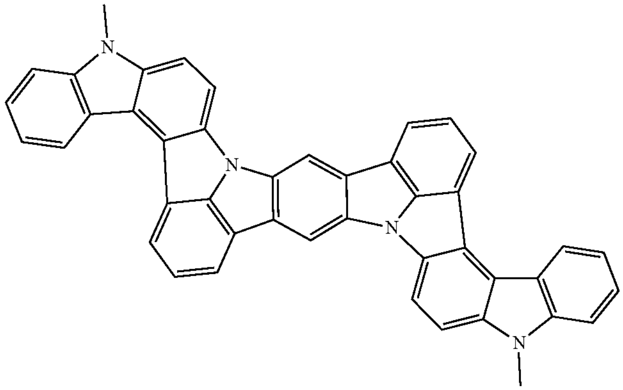
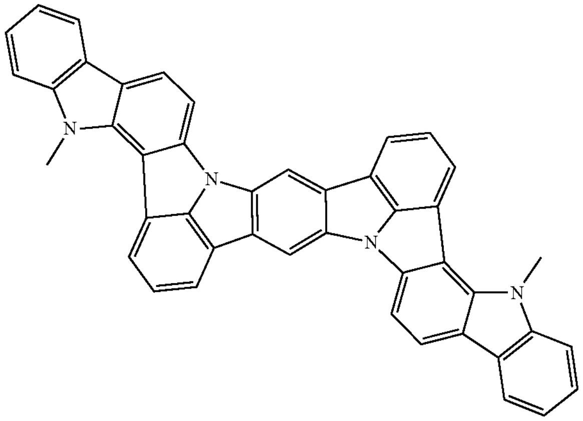

-continued
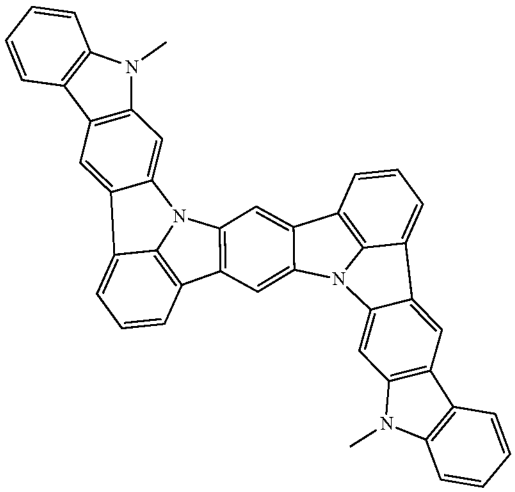
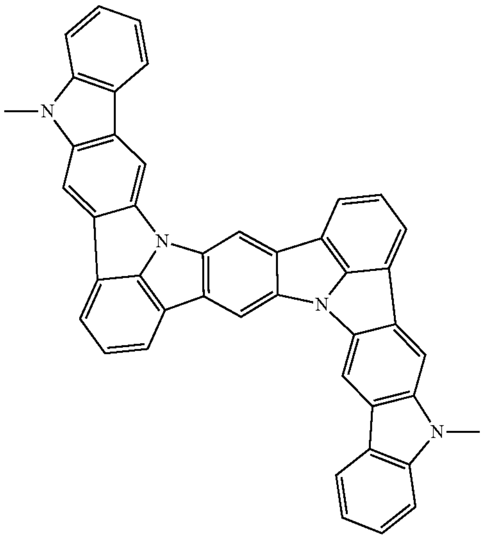
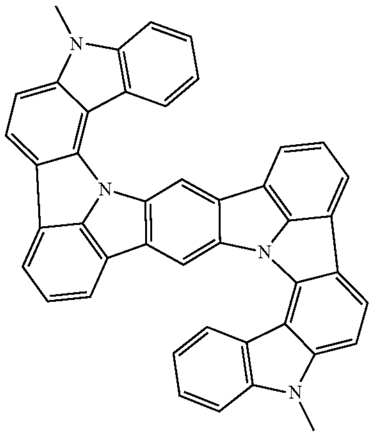
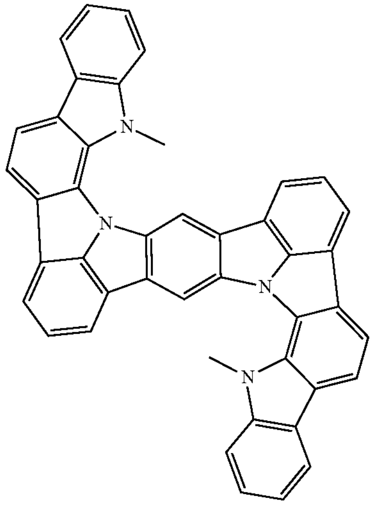
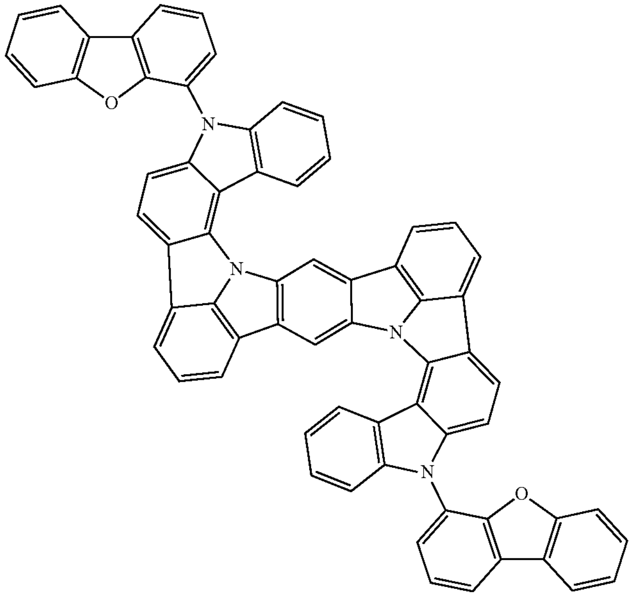
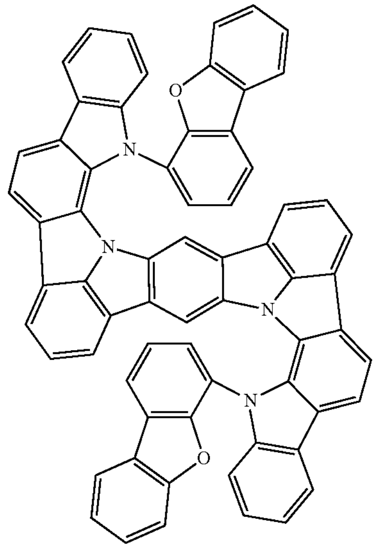

-continued
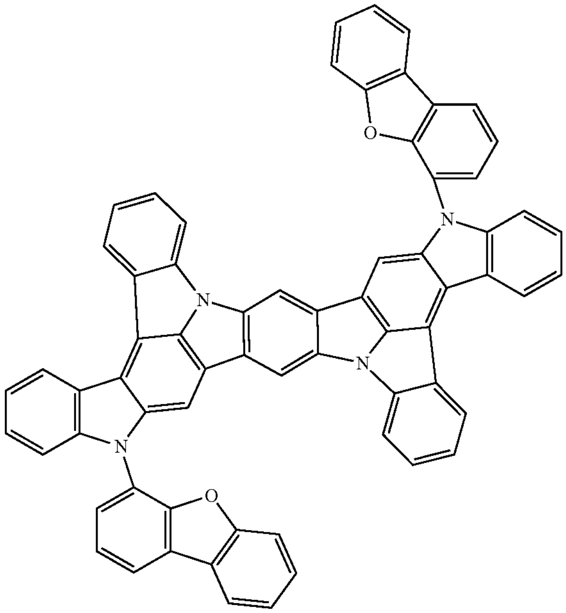
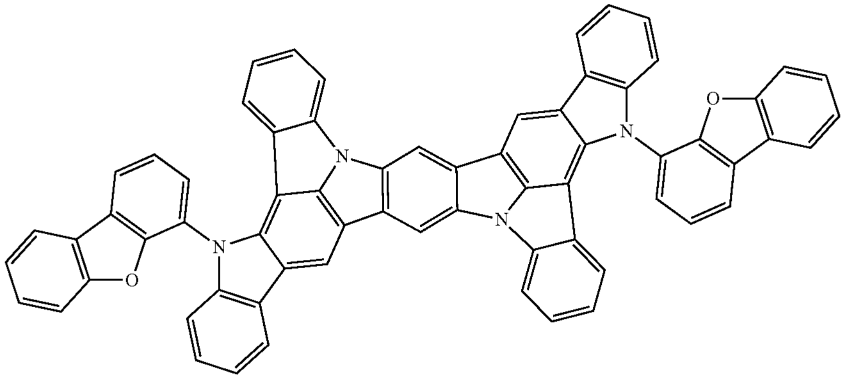
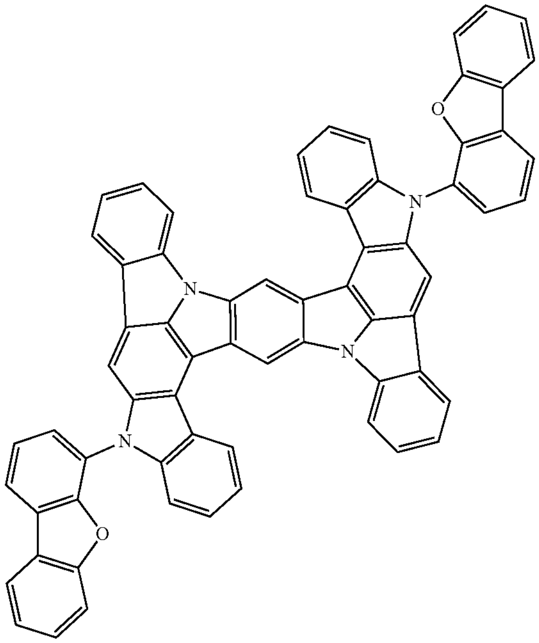
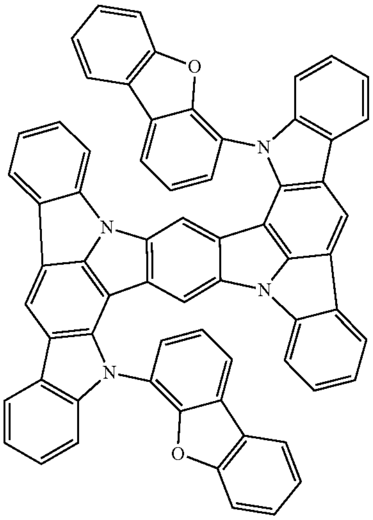

-continued
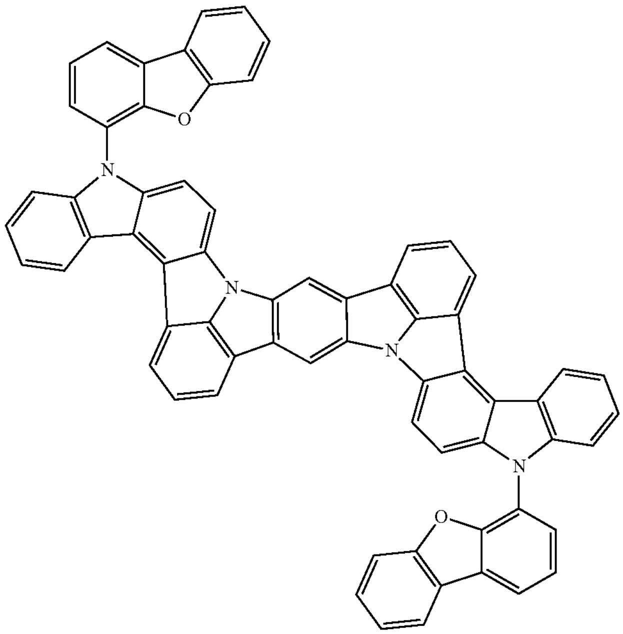
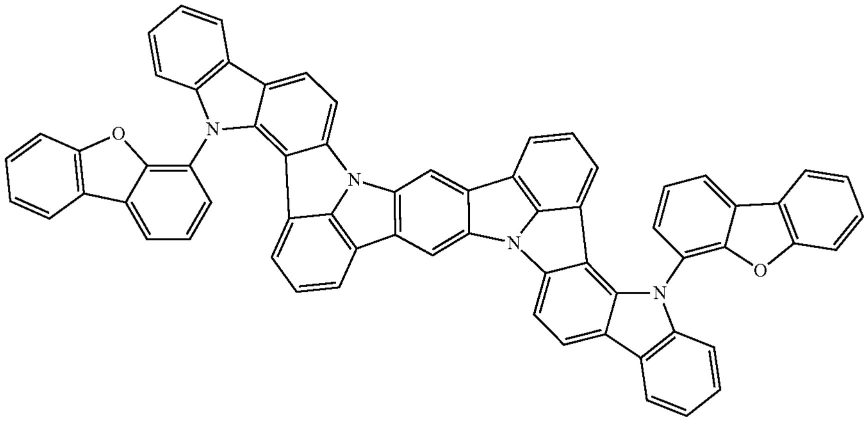
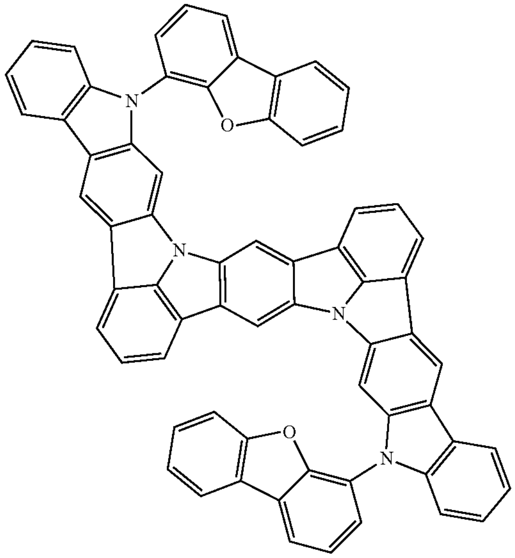

-continued
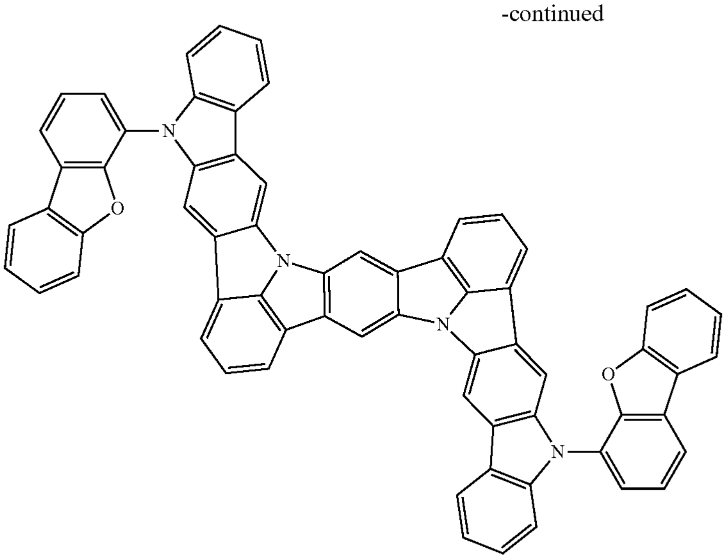
[Formula 254]
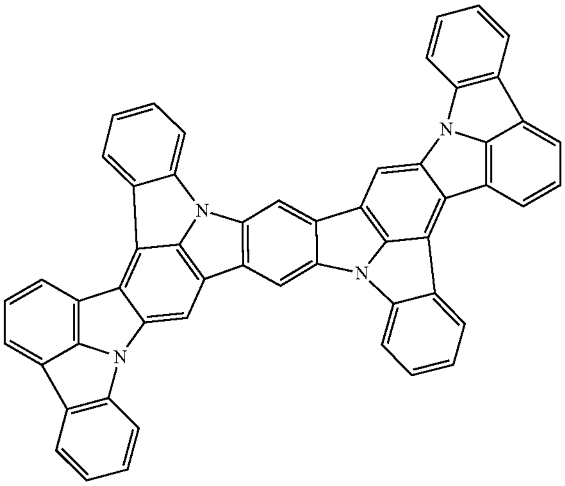
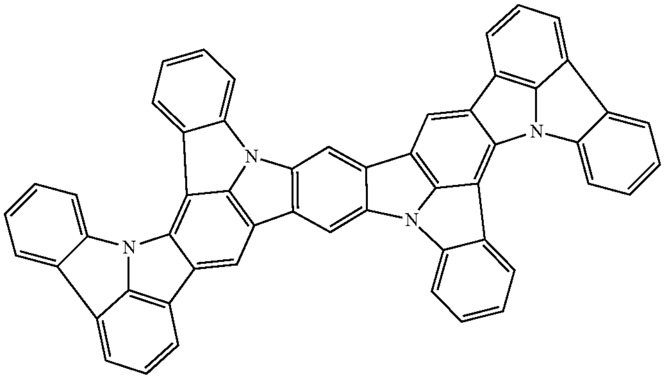

-continued
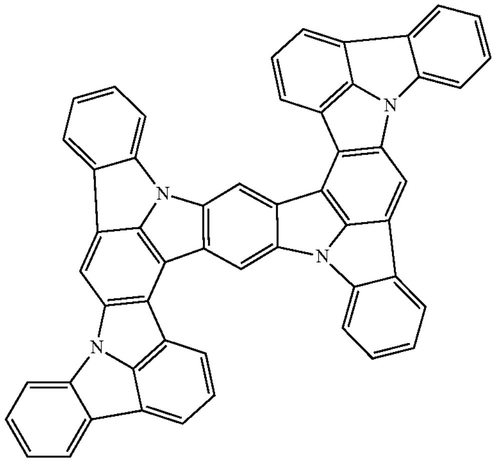
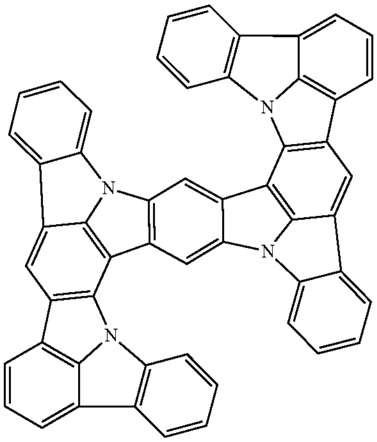
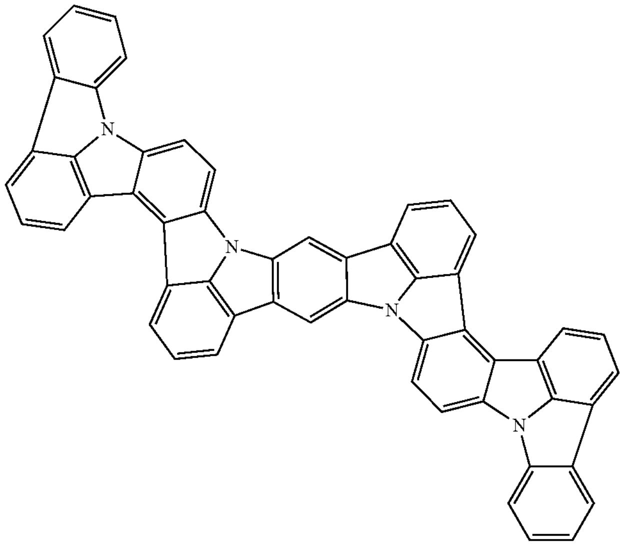
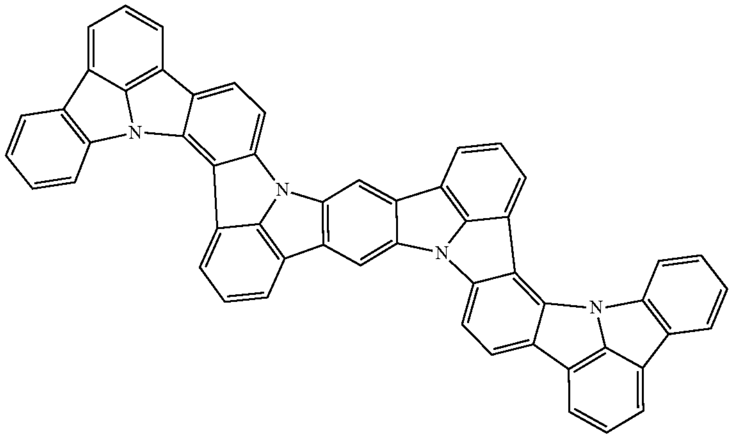

-continued
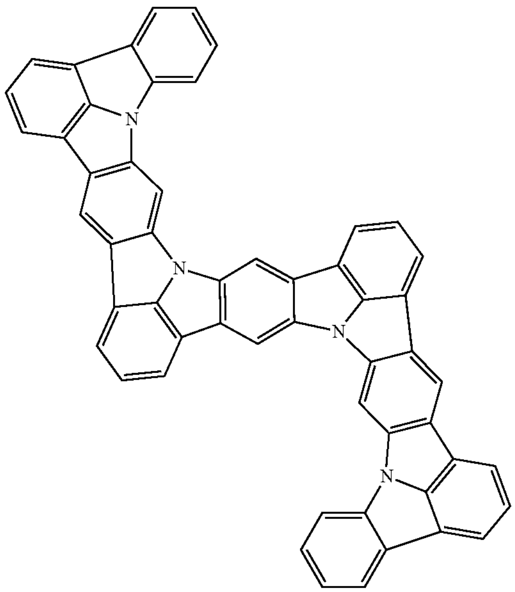
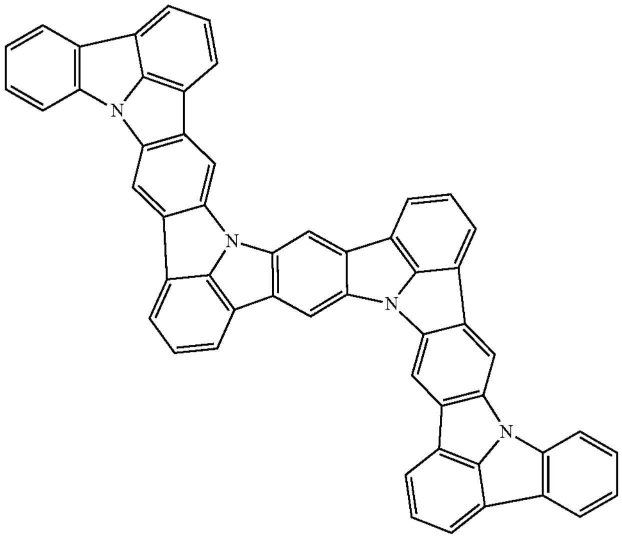
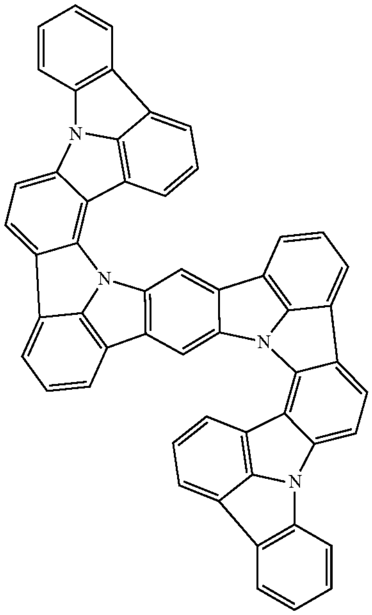
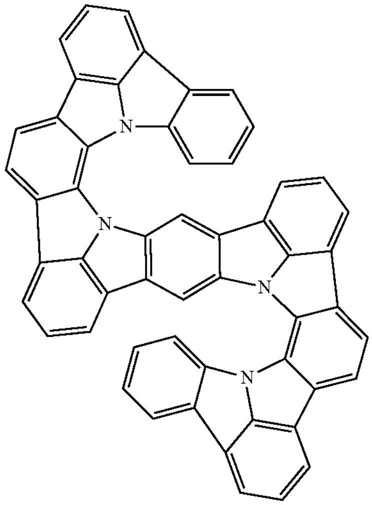
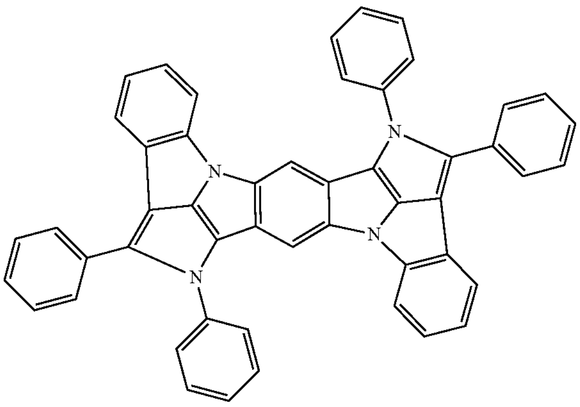

-continued
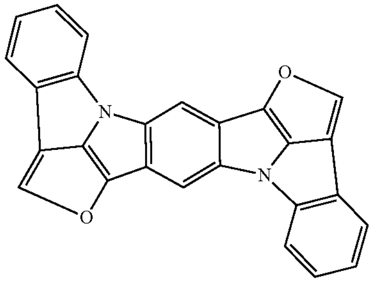
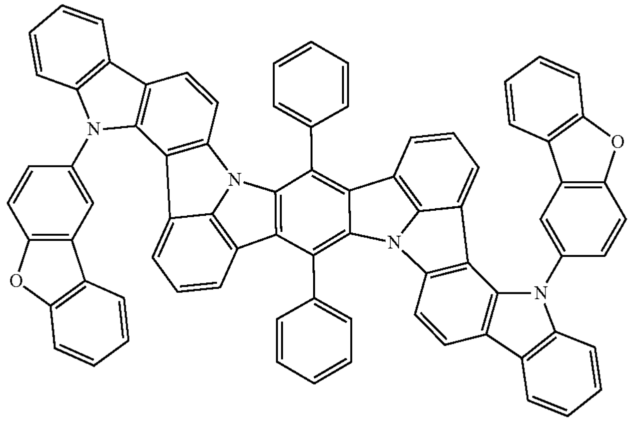
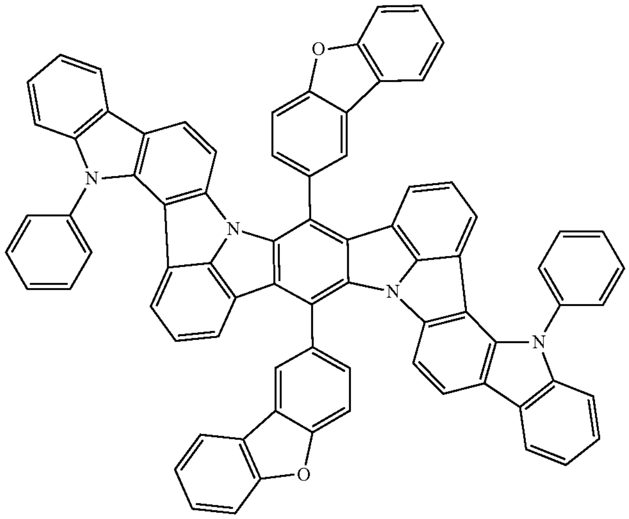
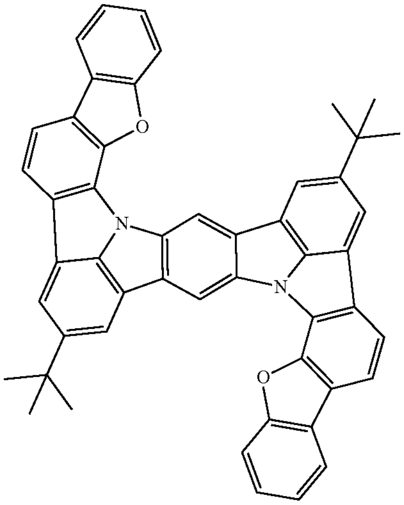
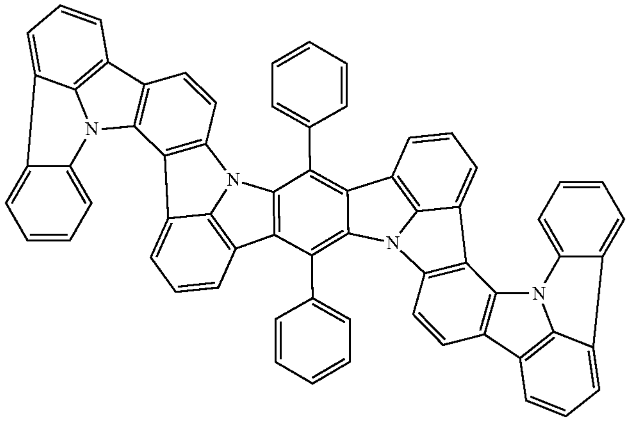

-continued
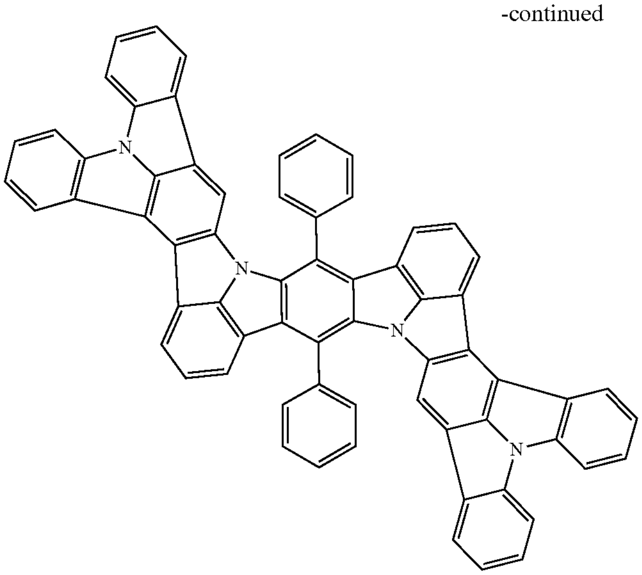
[Formula 247]
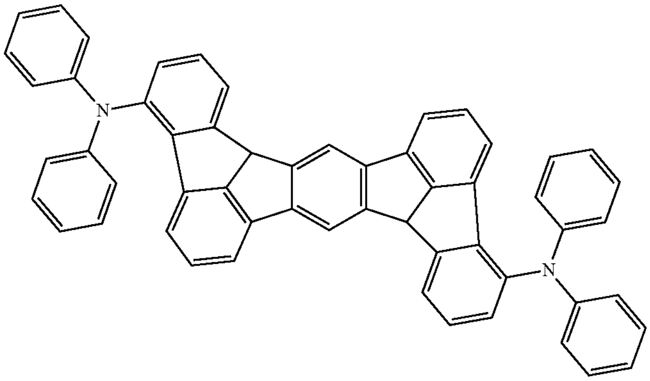
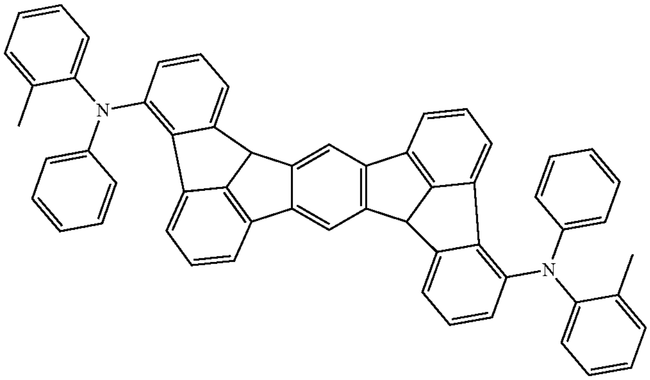

-continued
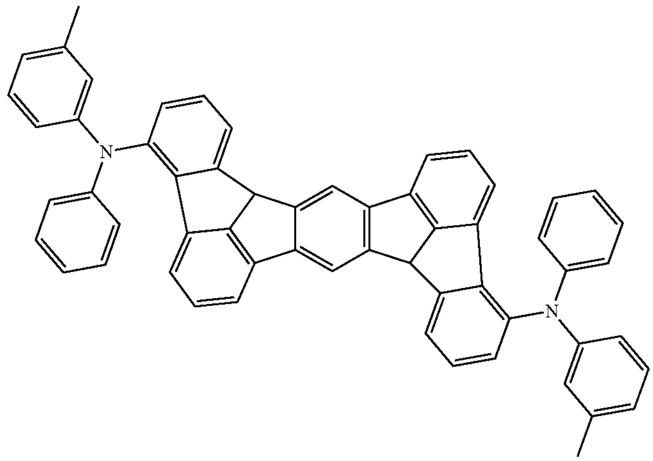
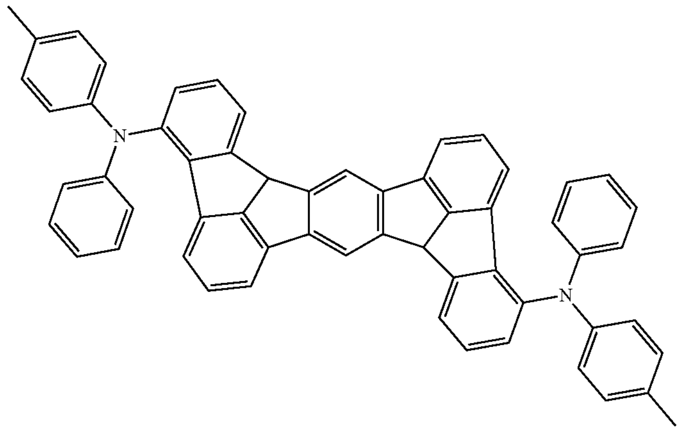
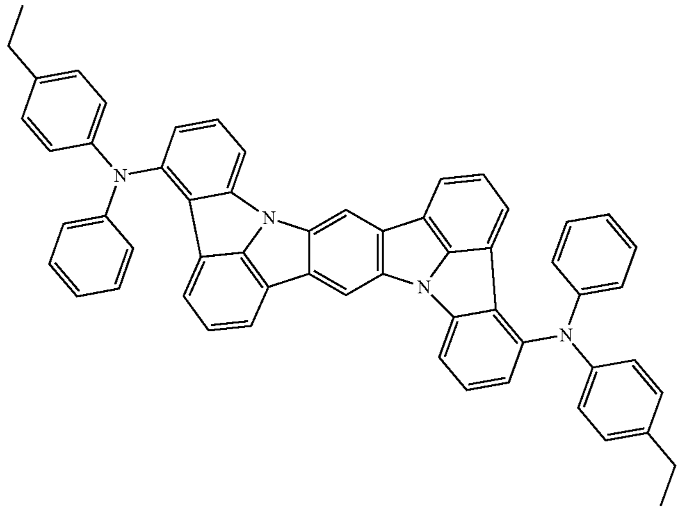

-continued
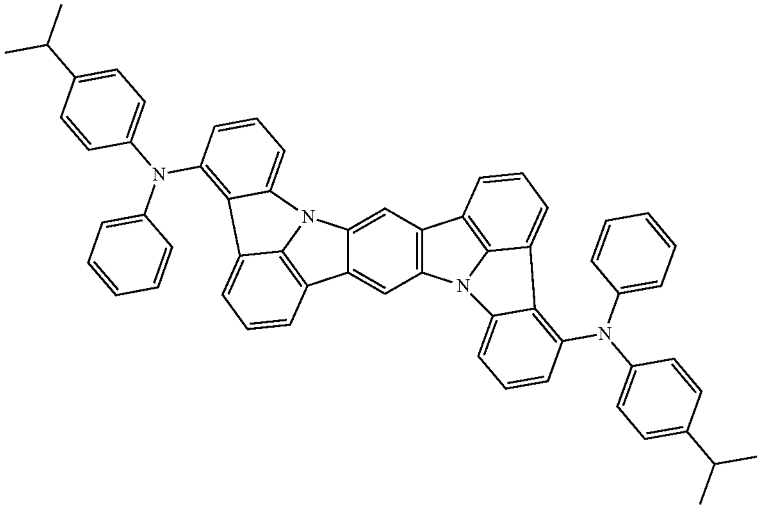
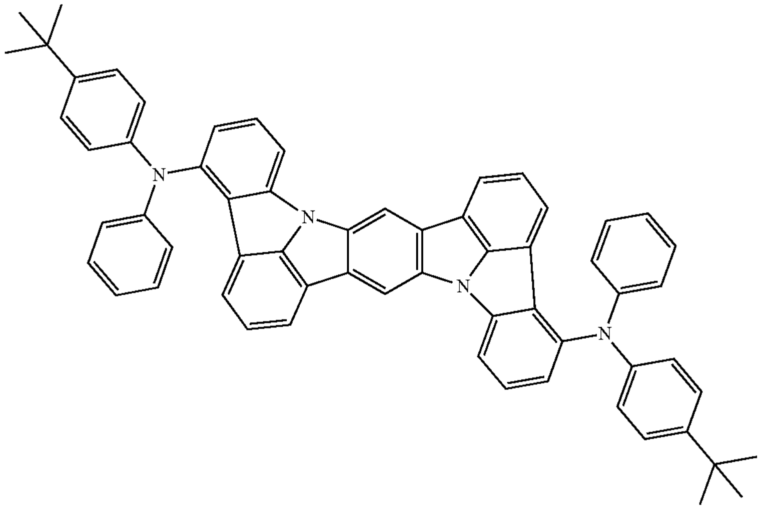
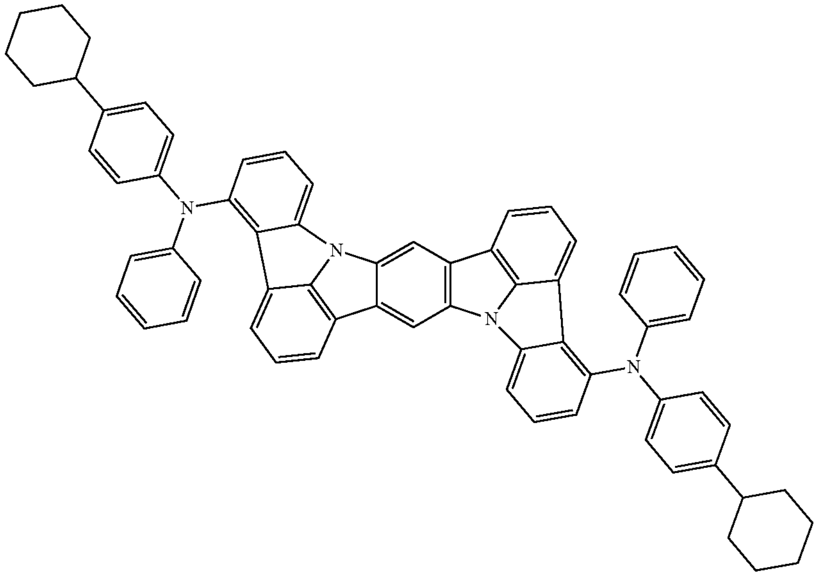

-continued
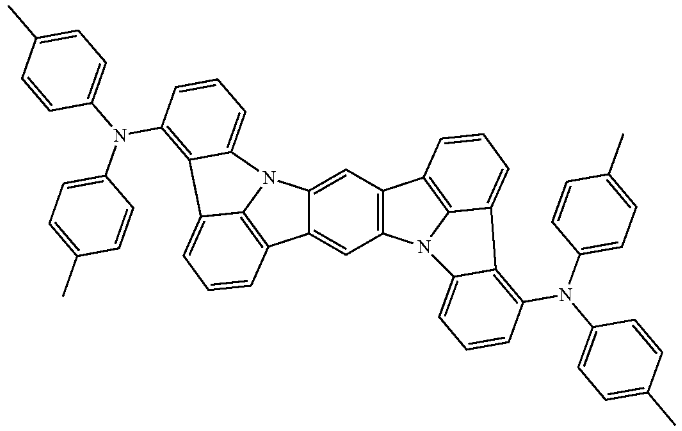
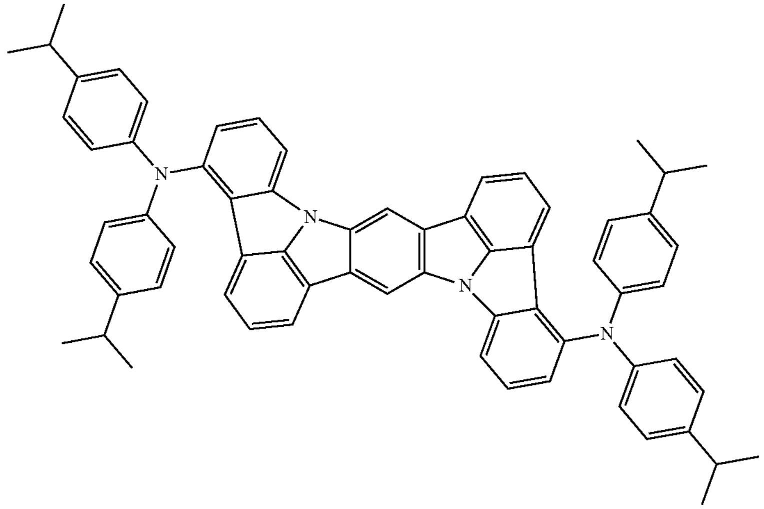
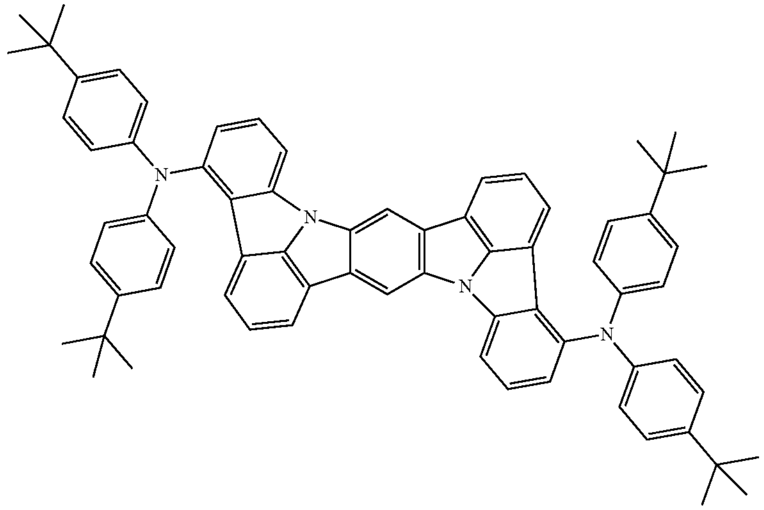

-continued
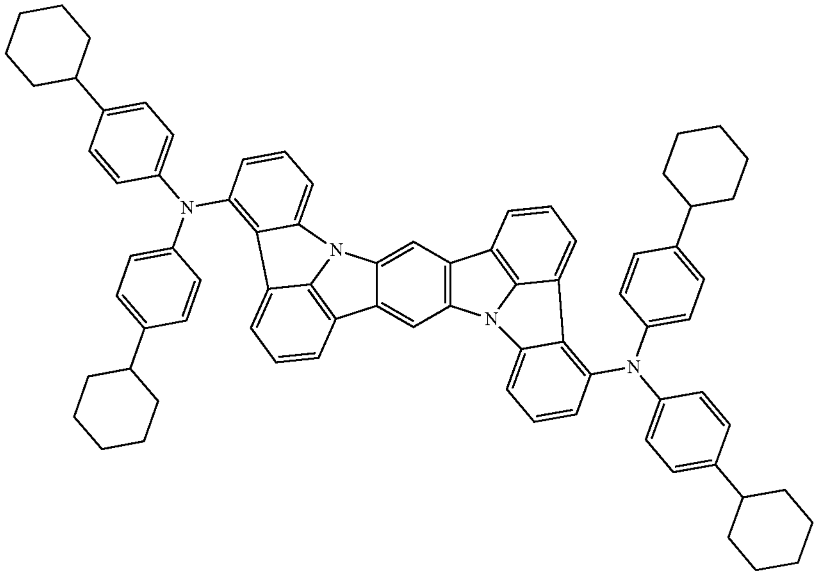
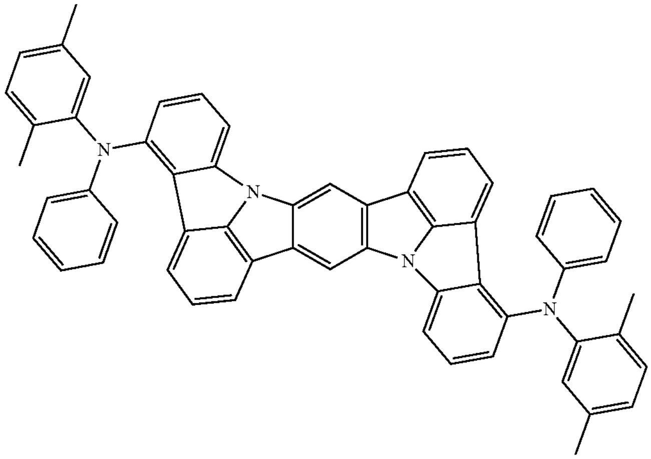
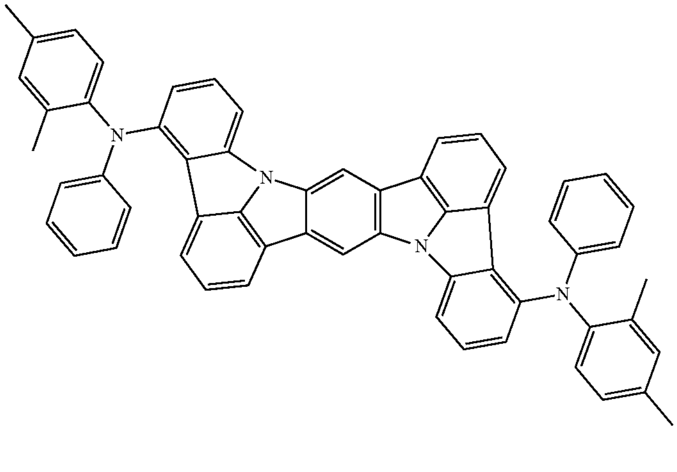

-continued
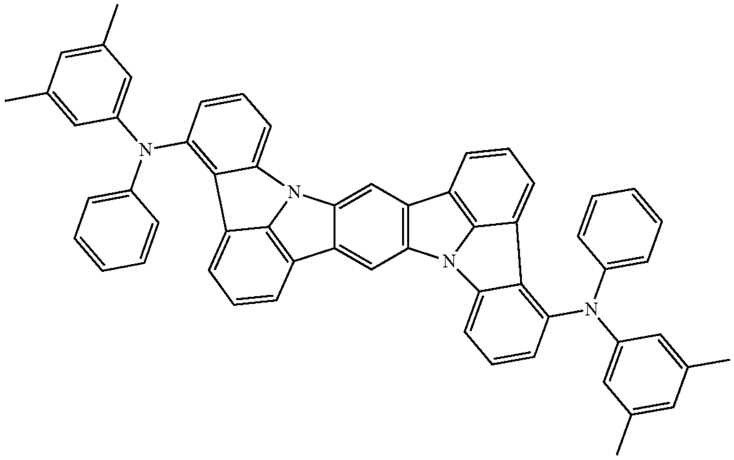
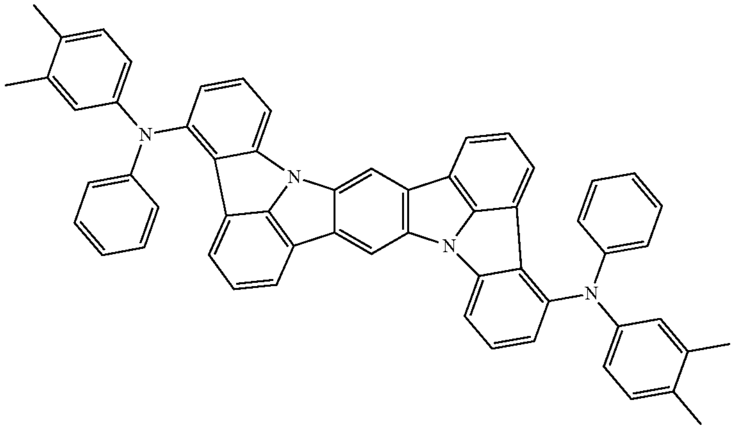
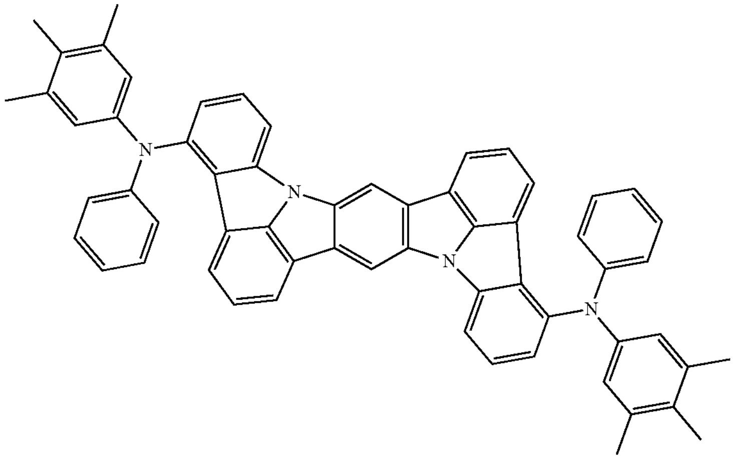

-continued
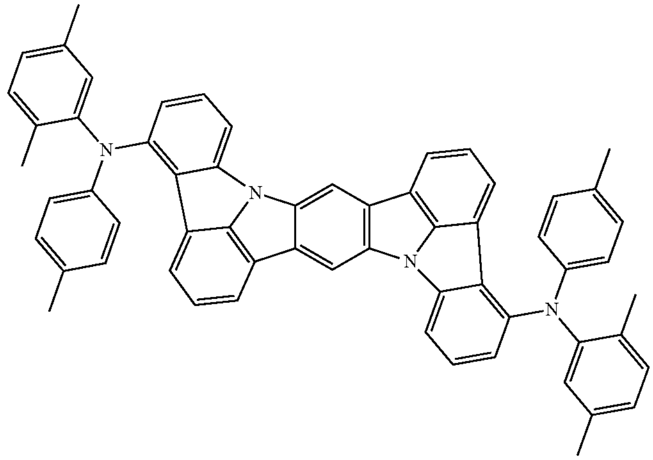
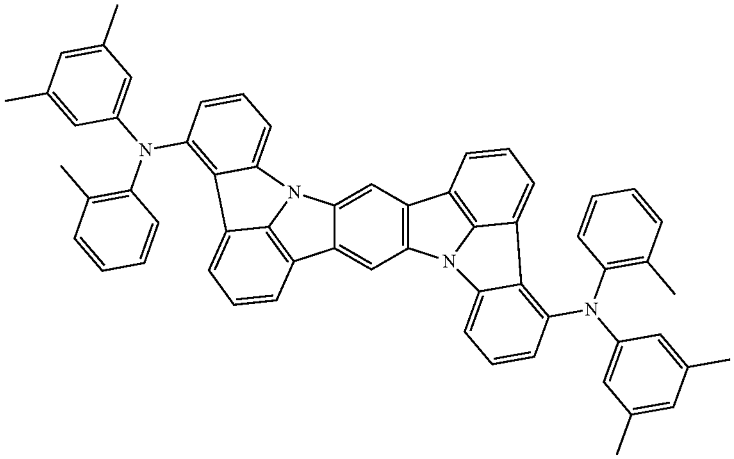
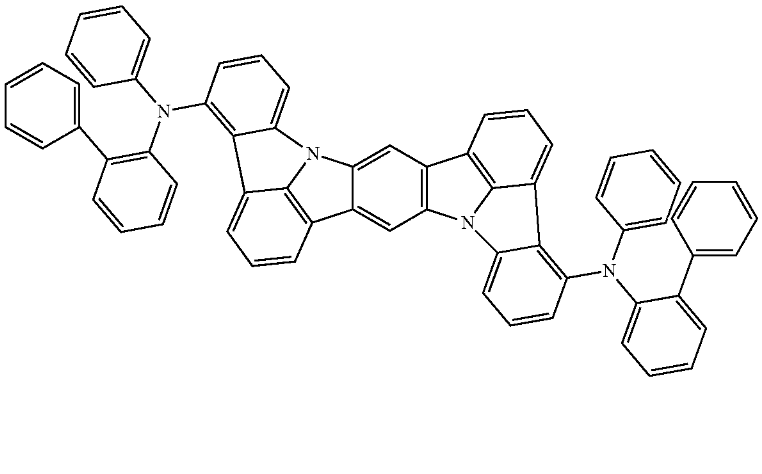

-continued
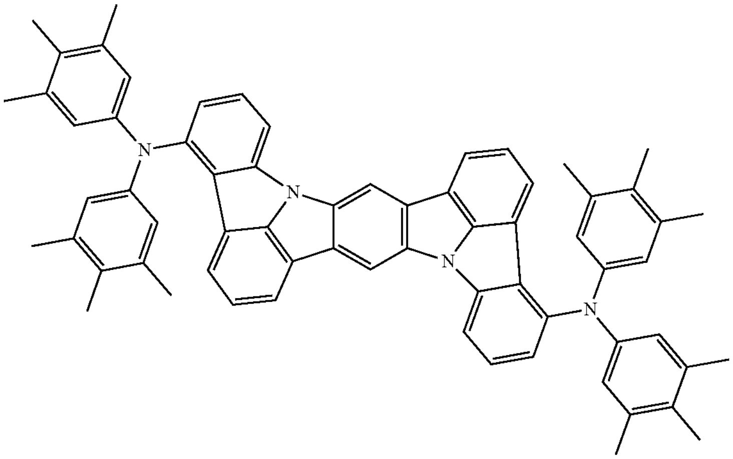
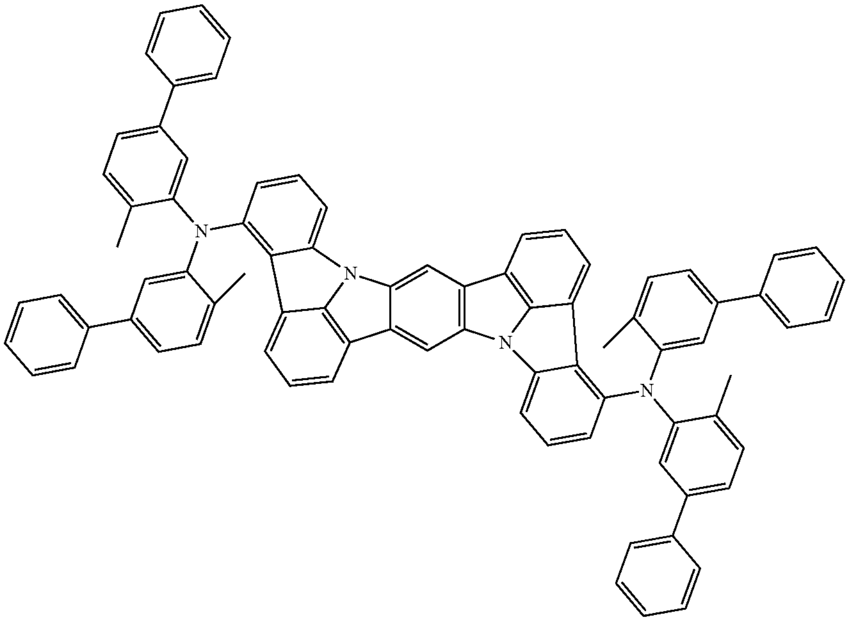
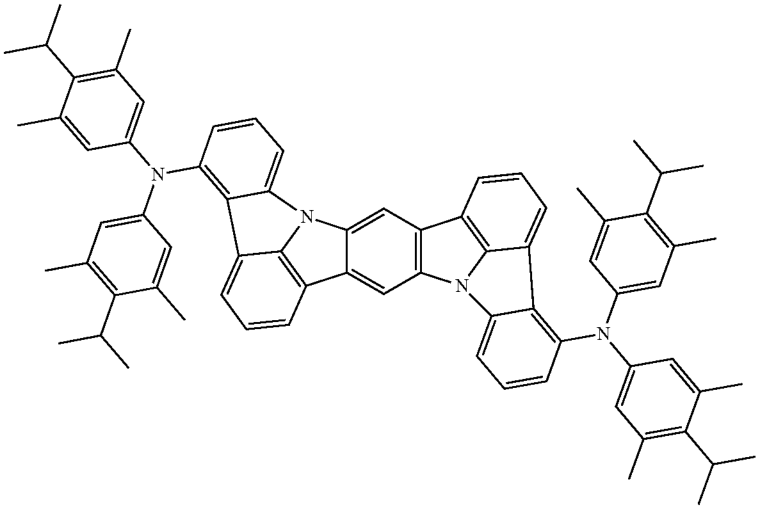

-continued
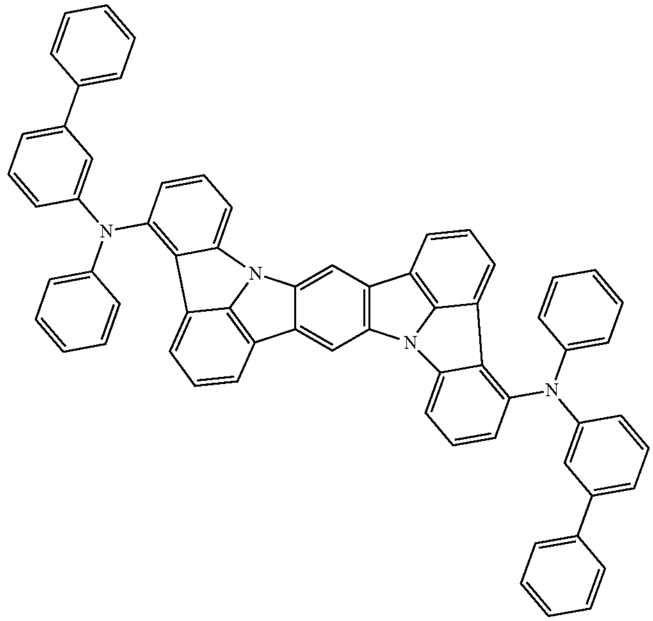
[Formula 248]
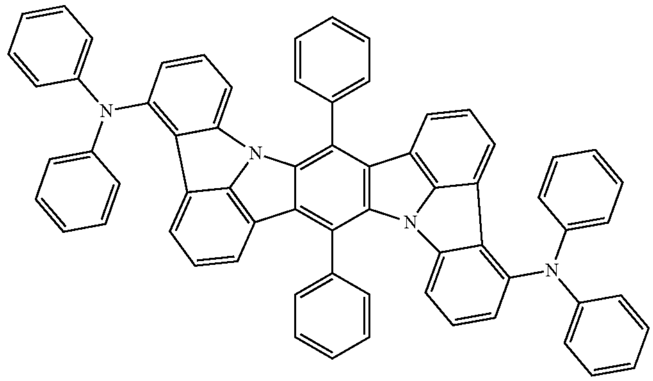
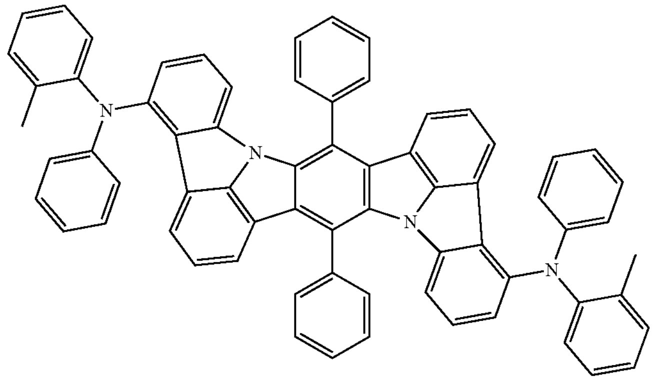

-continued
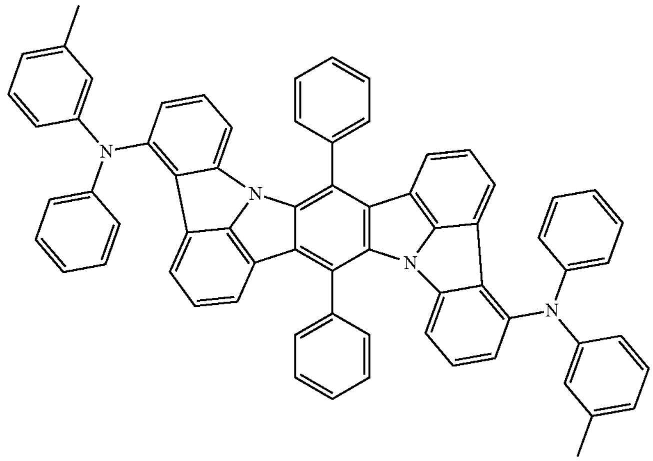
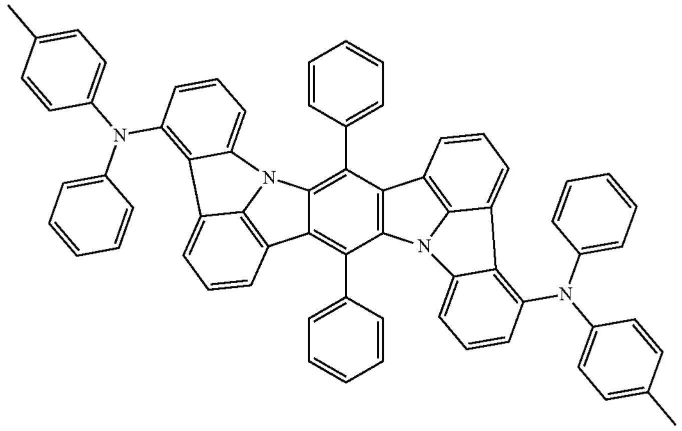
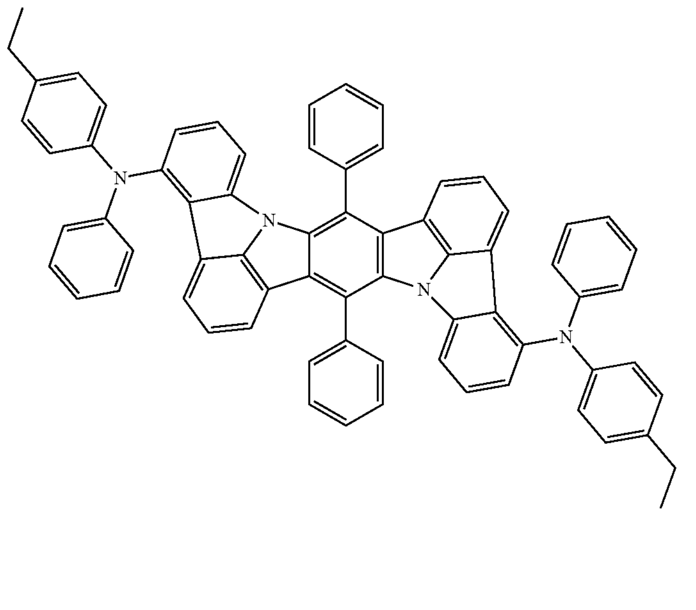

-continued
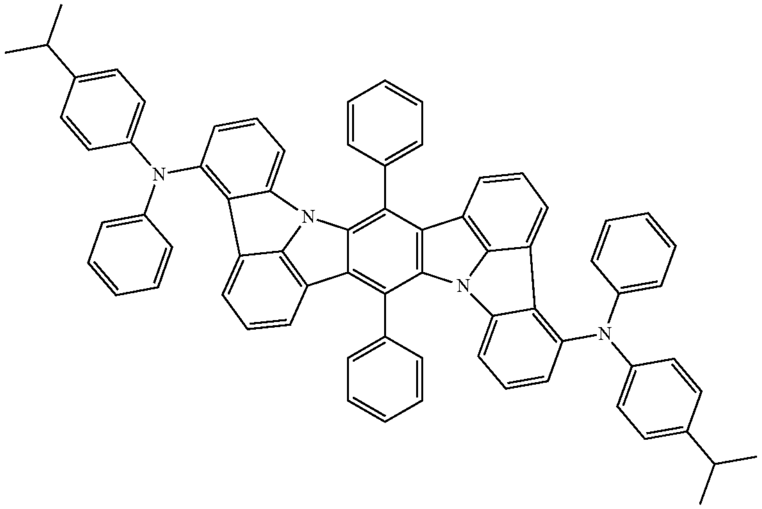
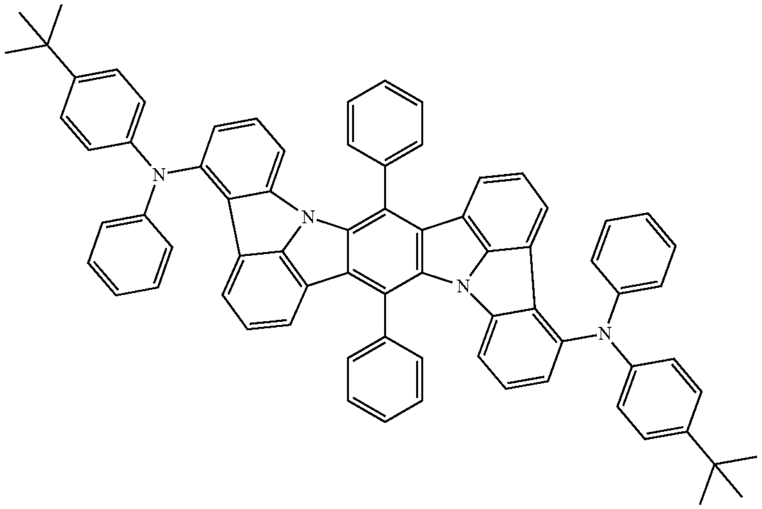
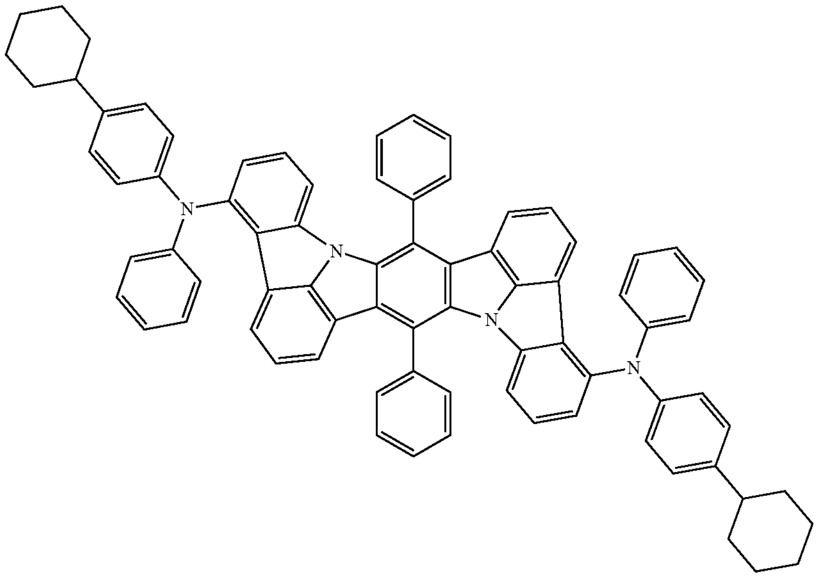

-continued
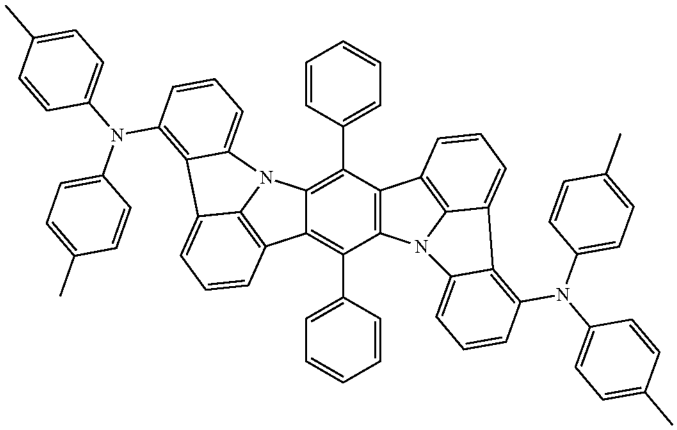
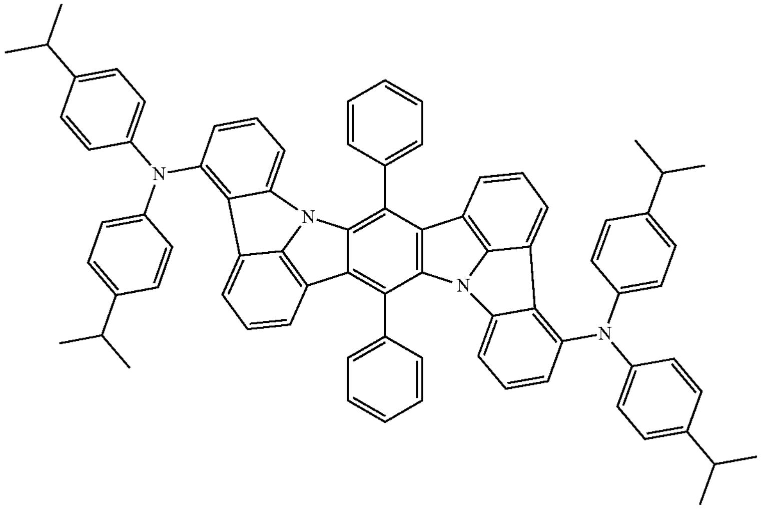
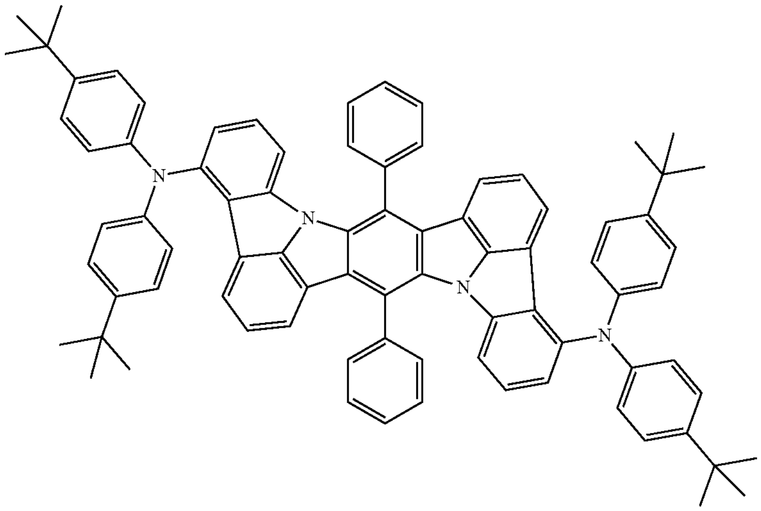

-continued
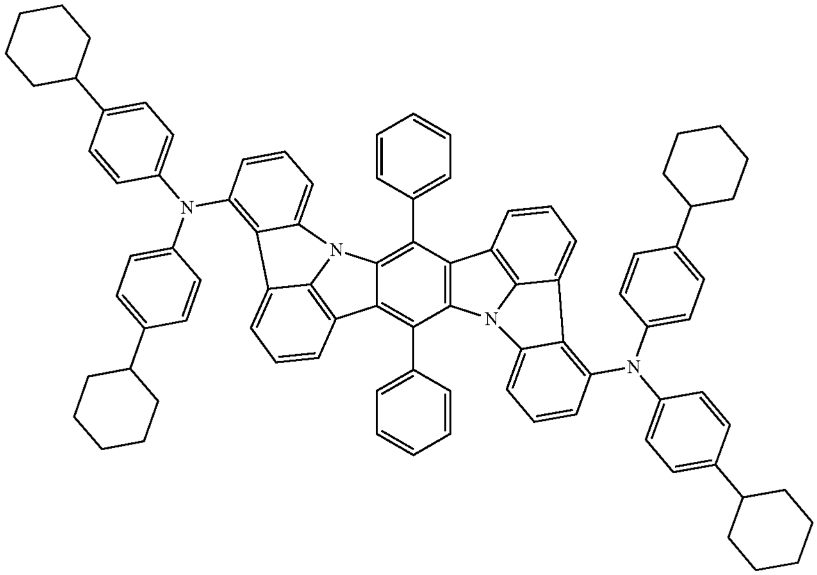
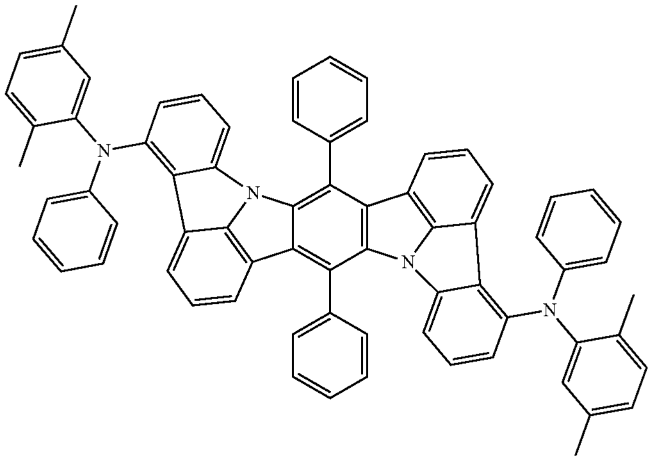
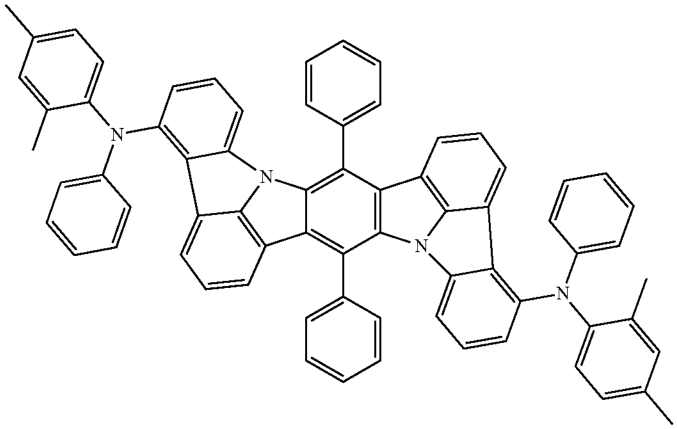

-continued
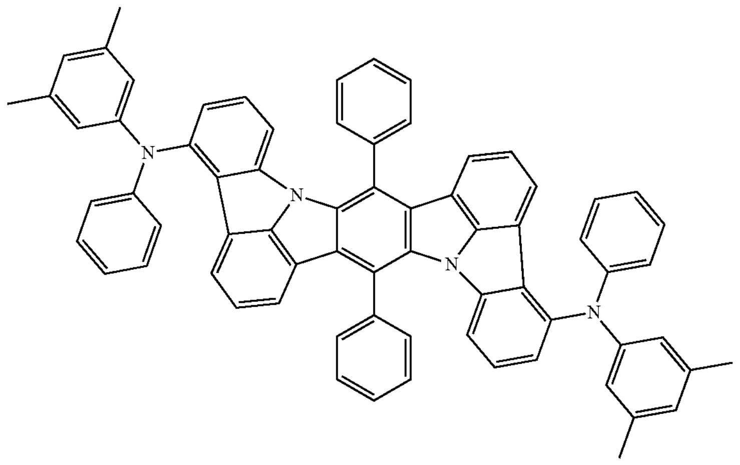
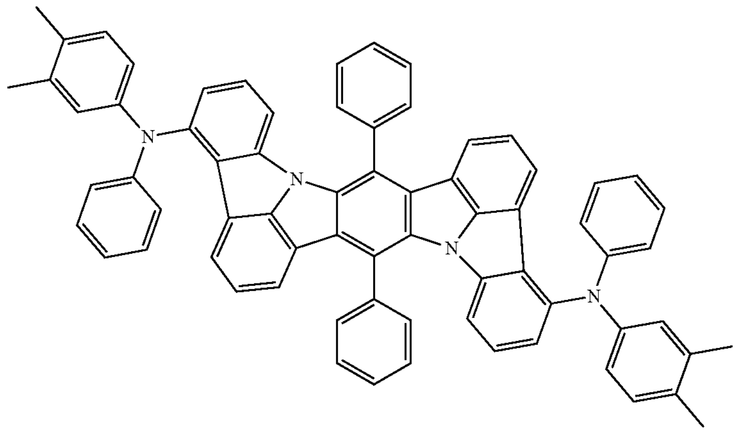
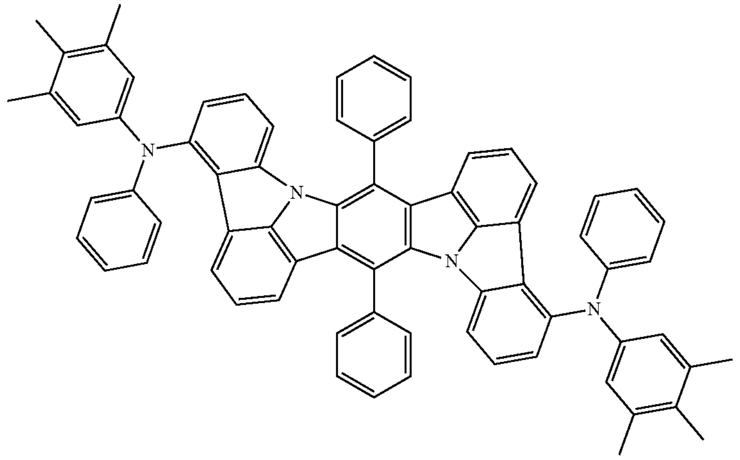

-continued
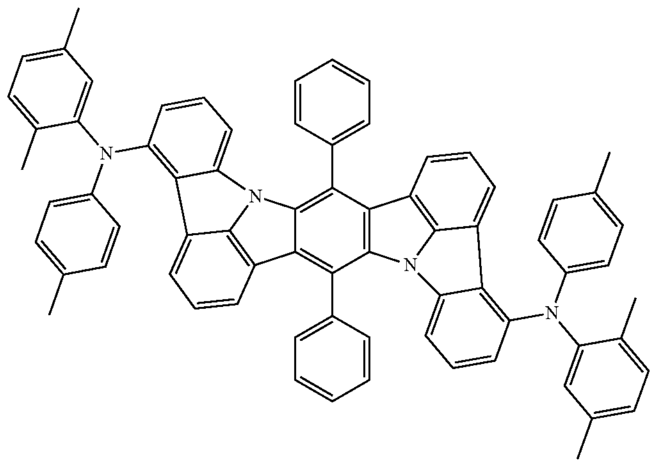
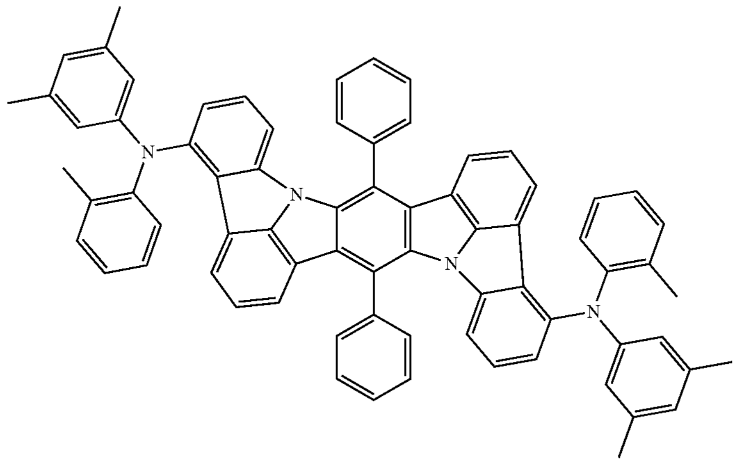
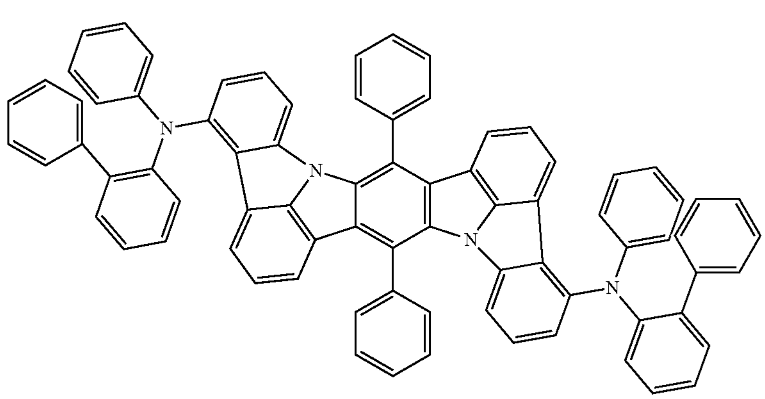

-continued
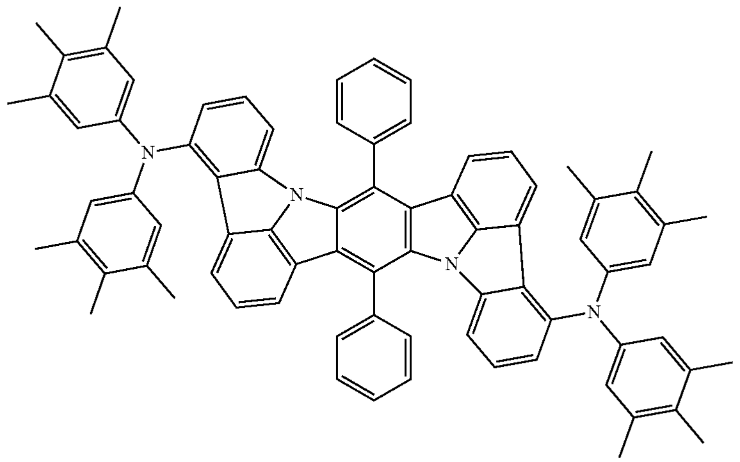
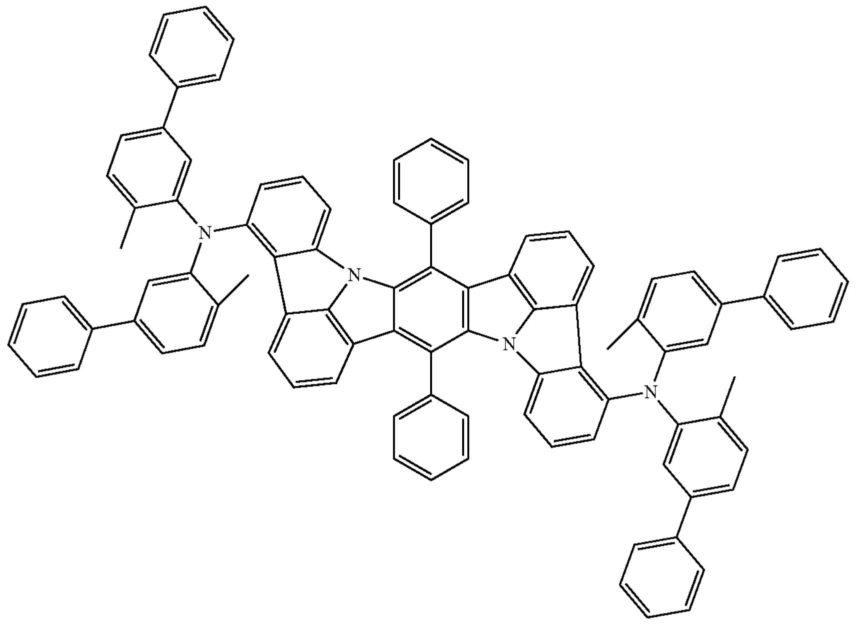
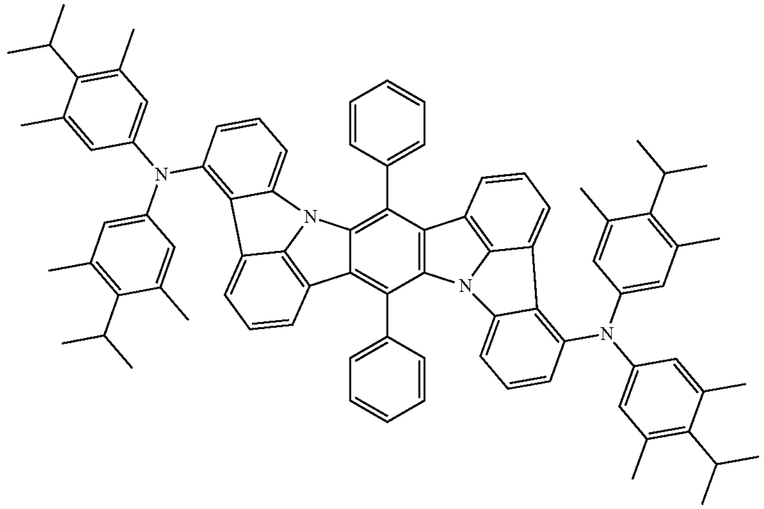

-continued
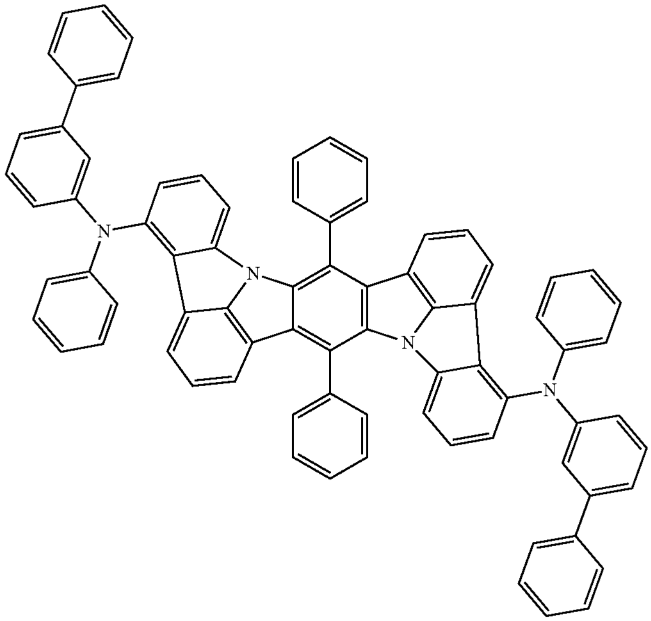
[Formula 249]
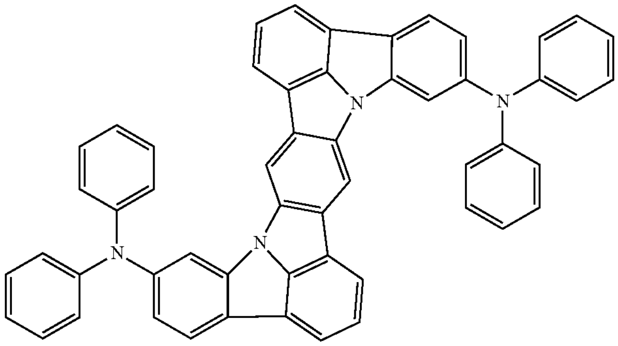
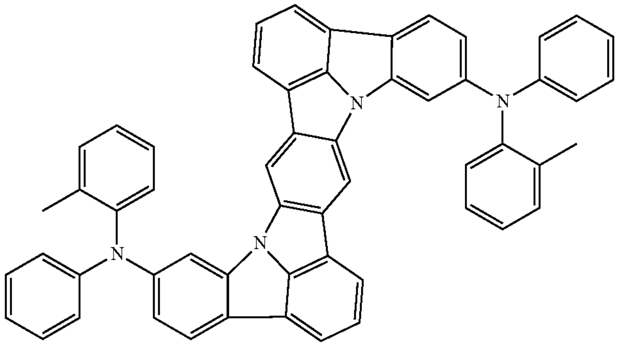
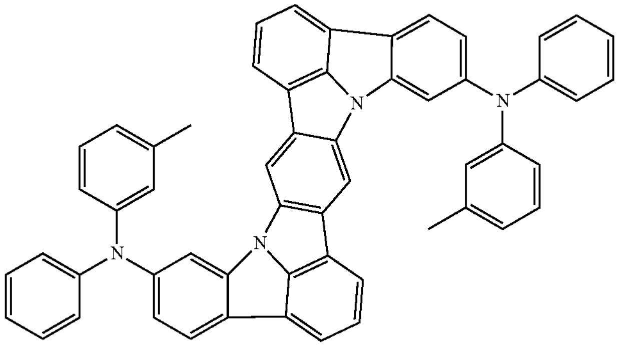

-continued
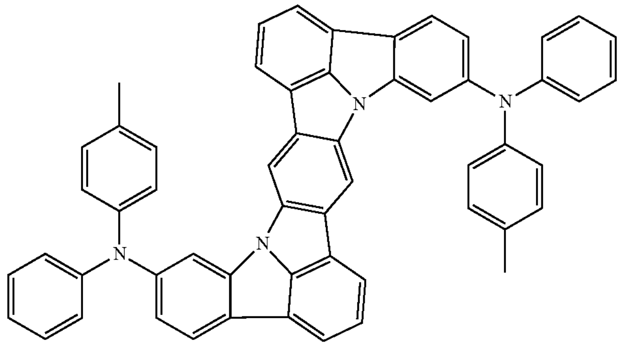
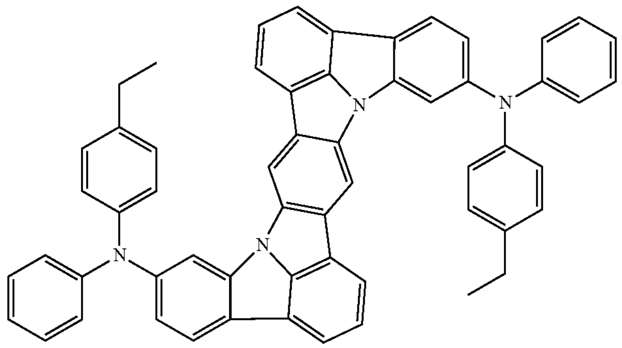
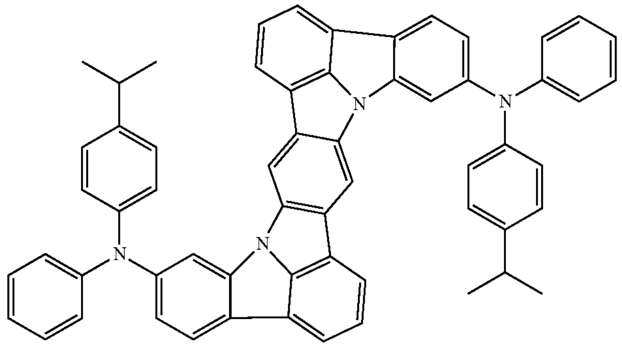
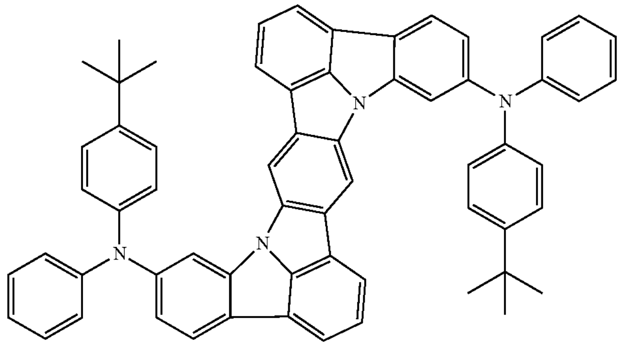

-continued
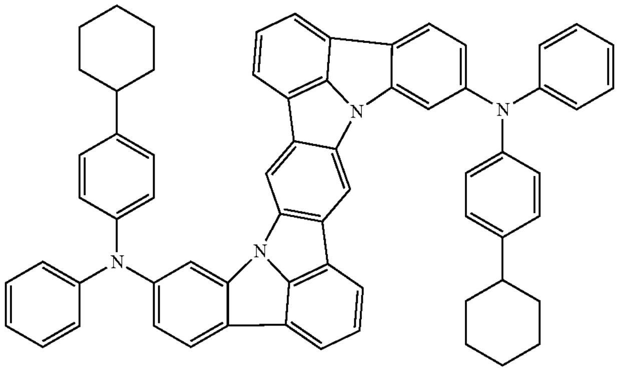
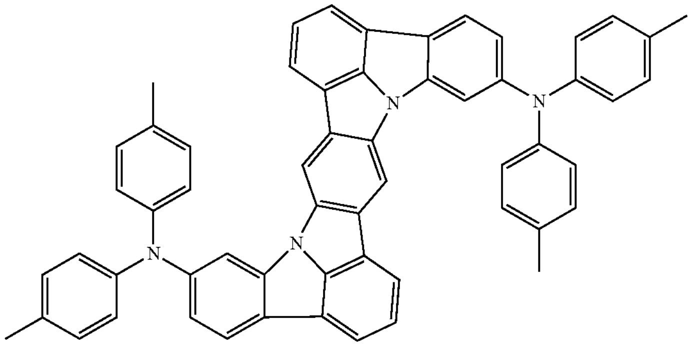
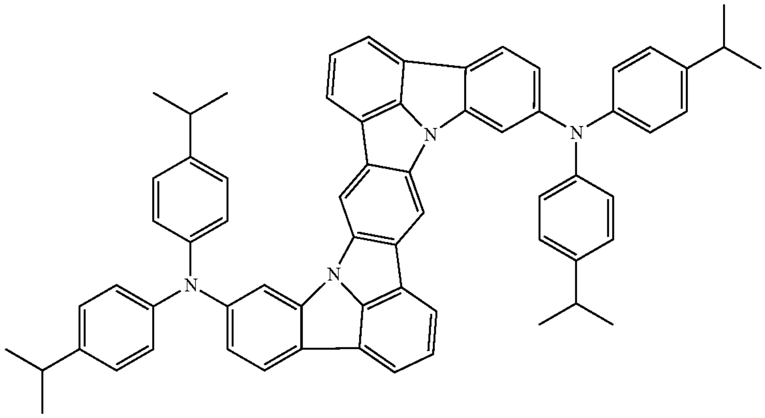
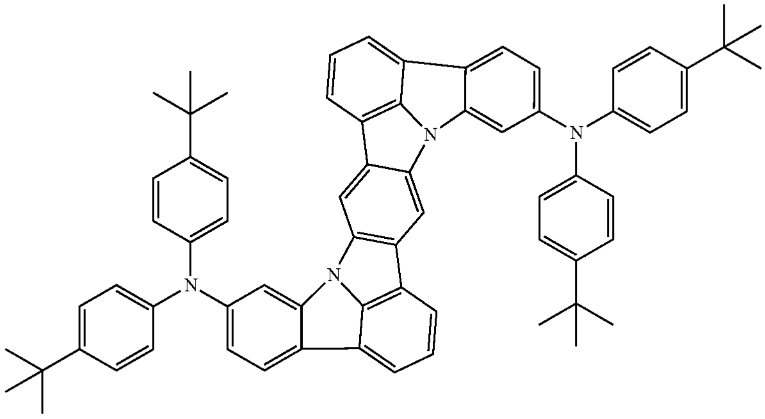

-continued
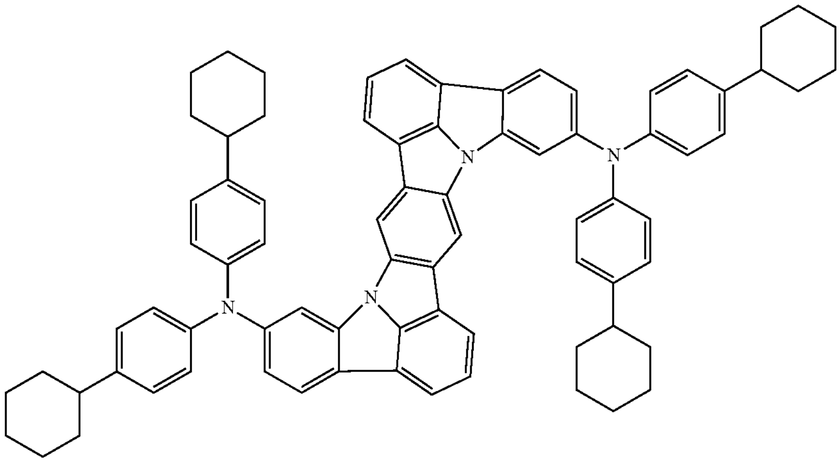
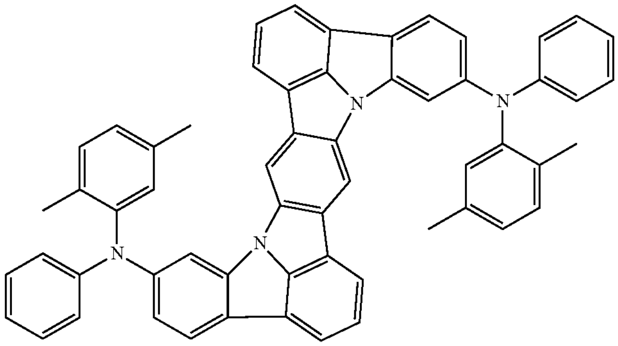
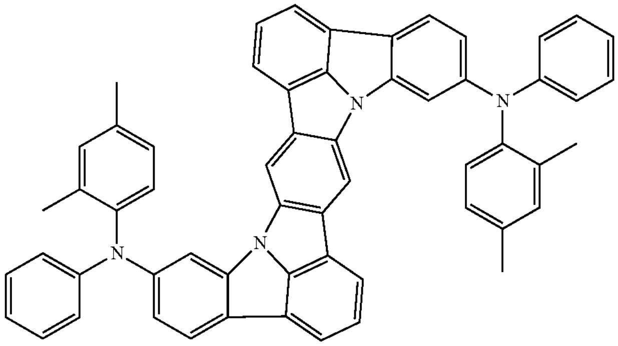
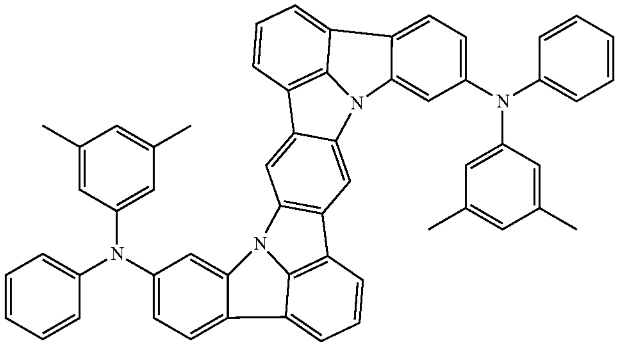

-continued
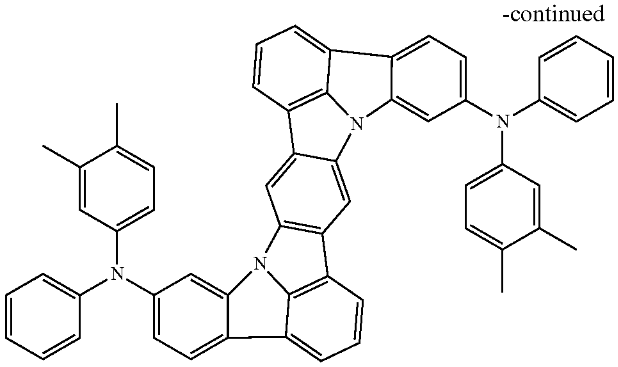
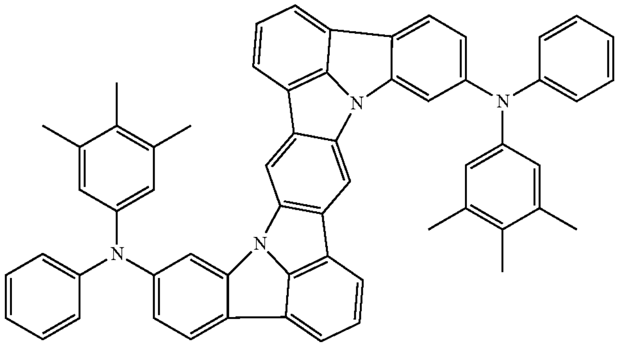
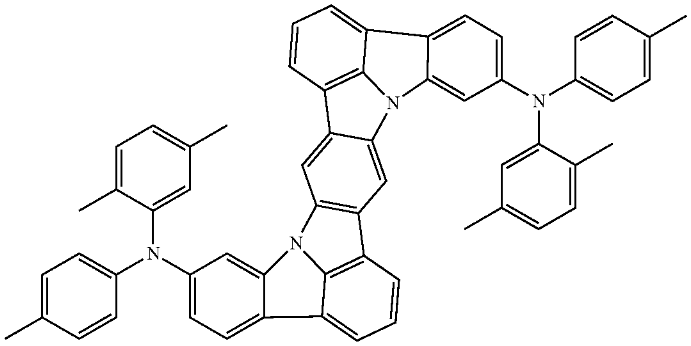
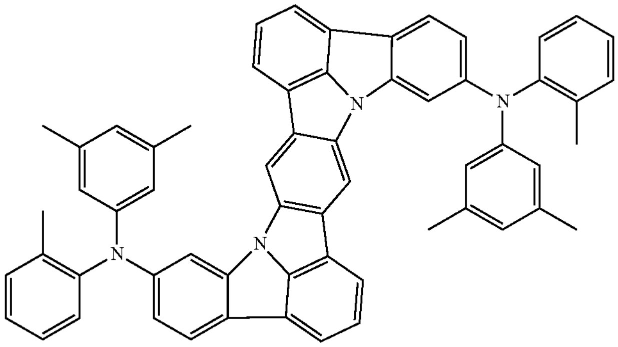
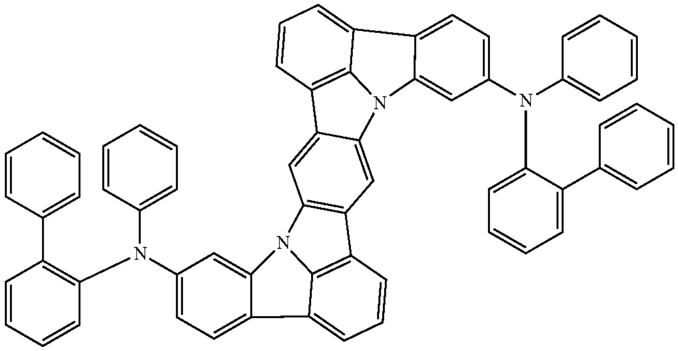

-continued
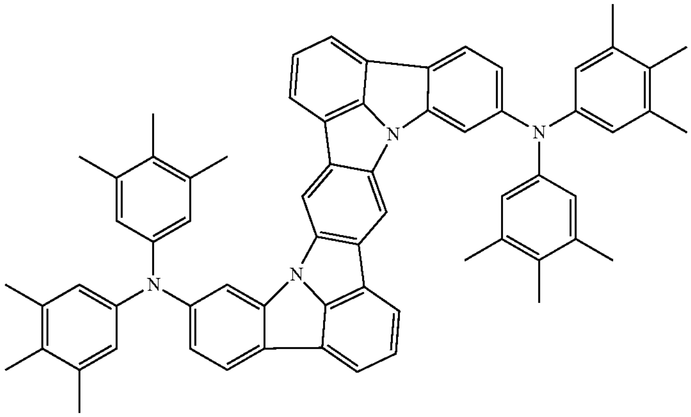
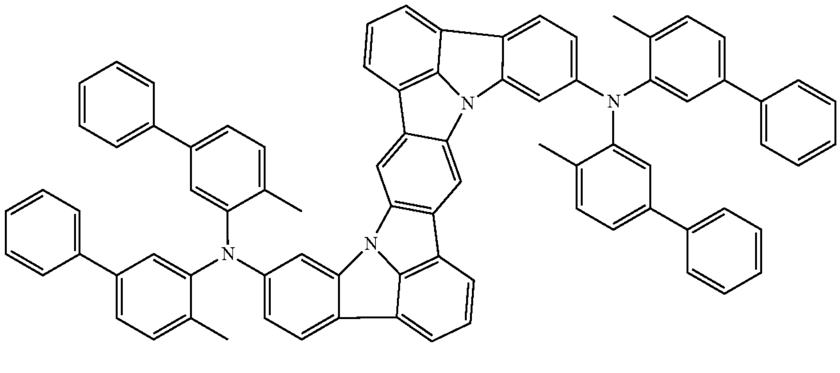
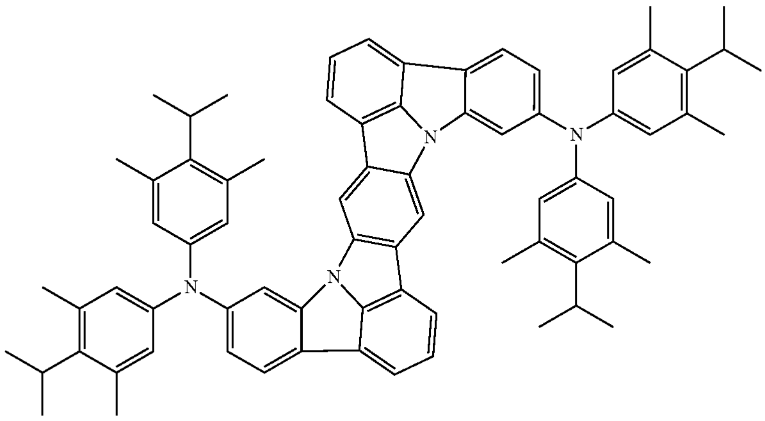

-continued
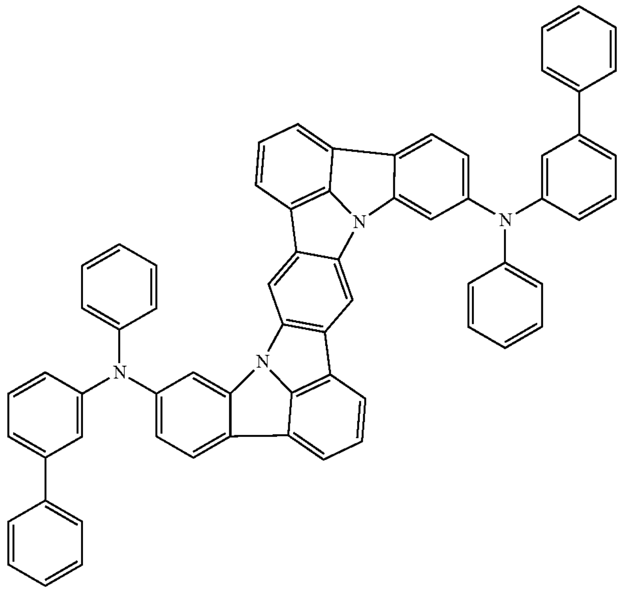
[Formula 250]
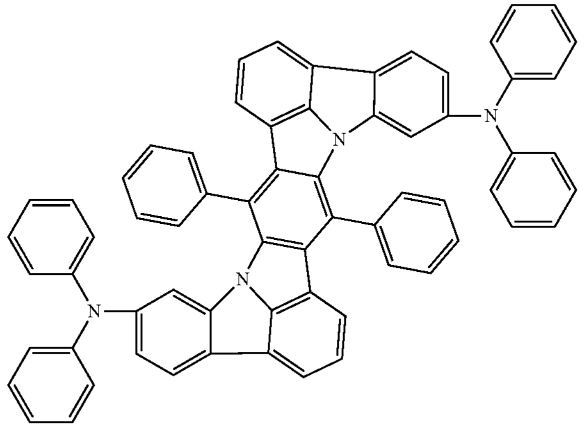
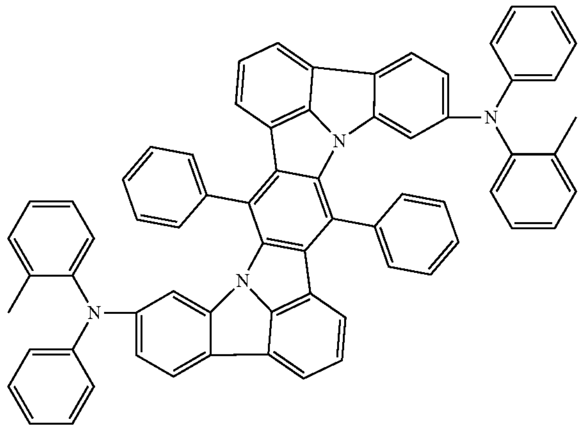

-continued
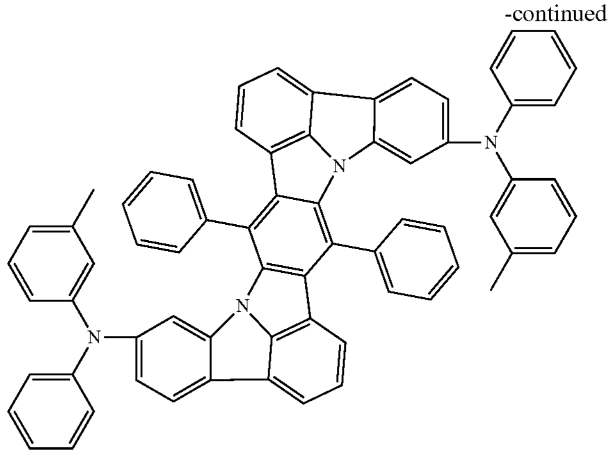
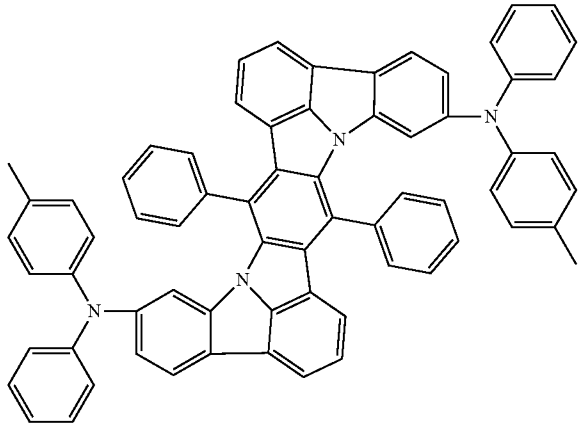
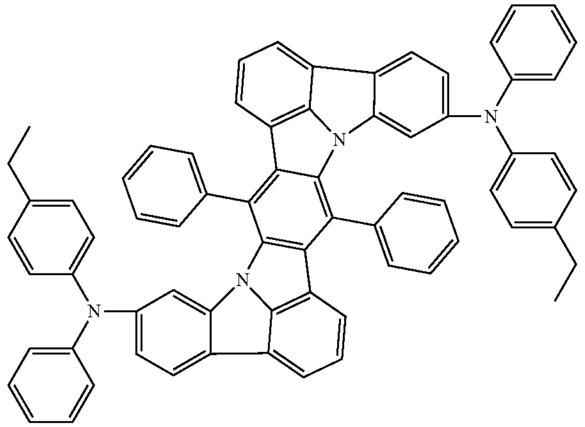
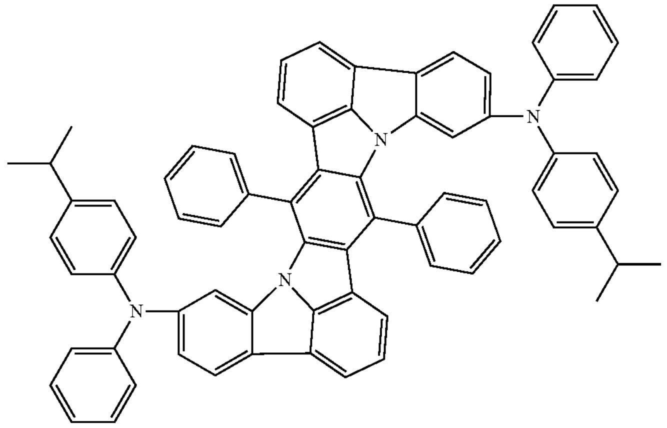

-continued
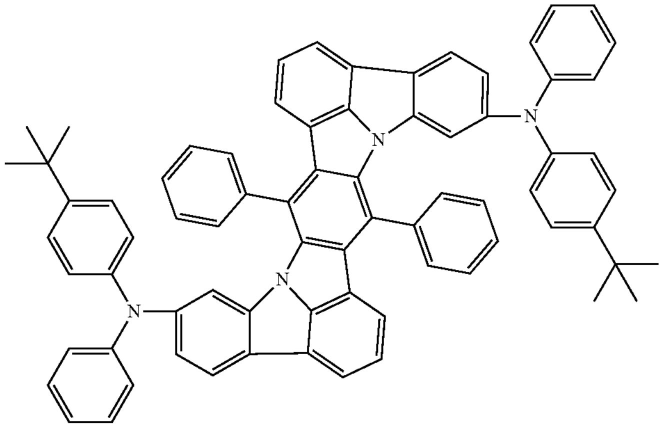
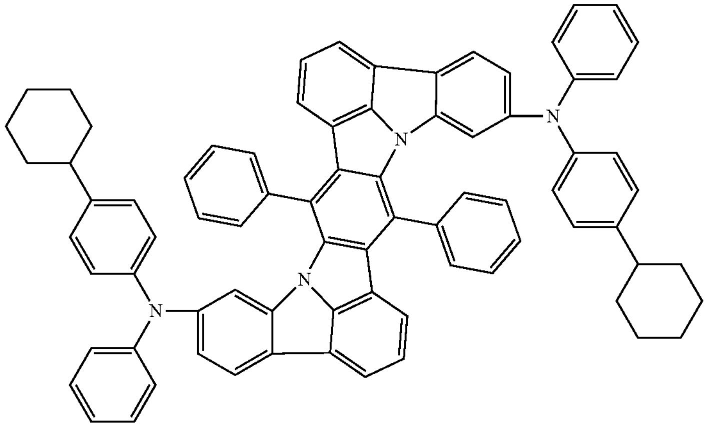
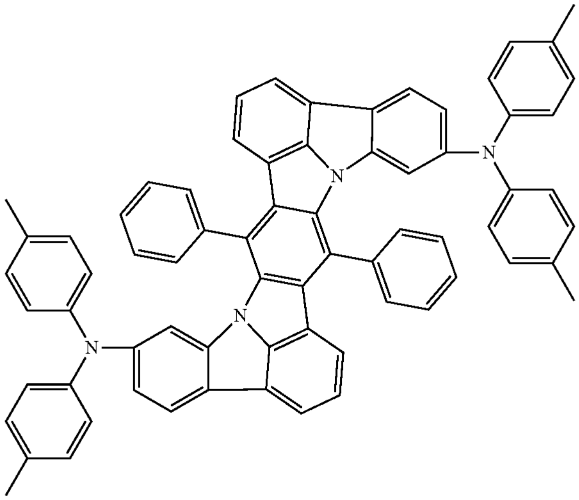

-continued
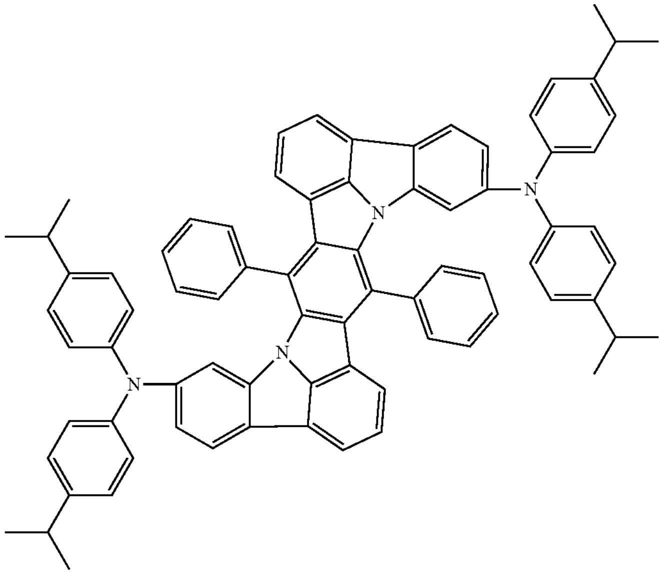
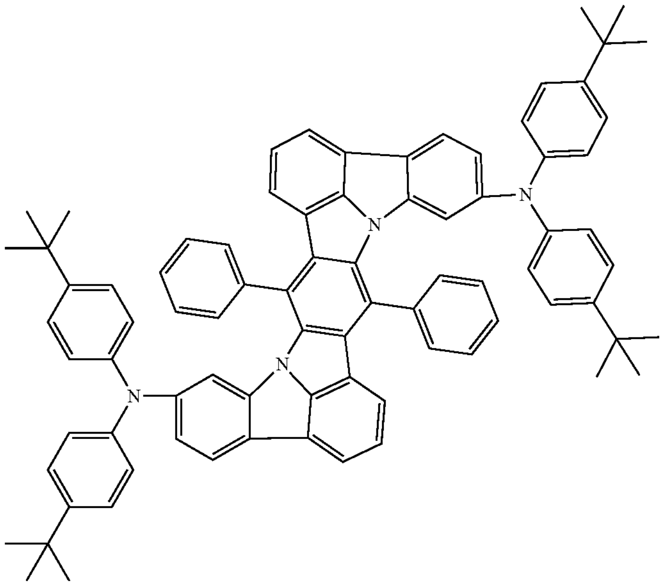

-continued
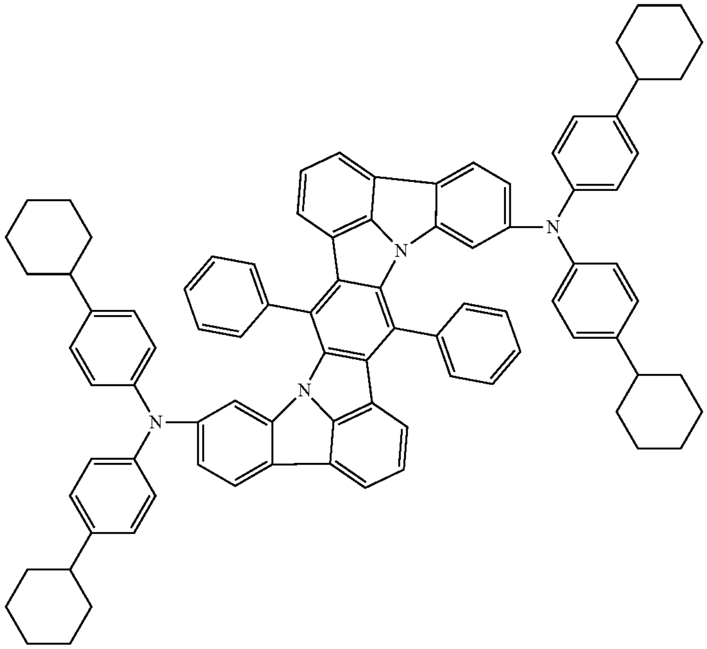
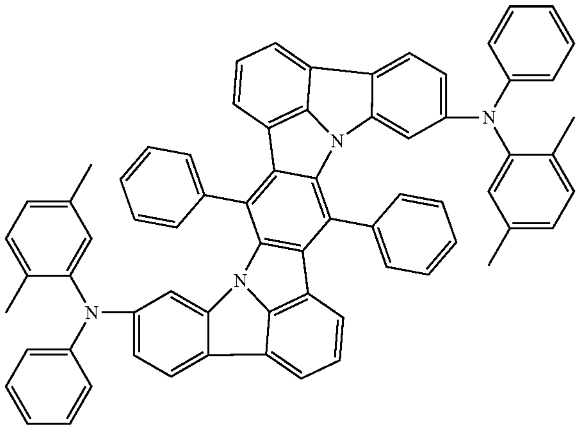
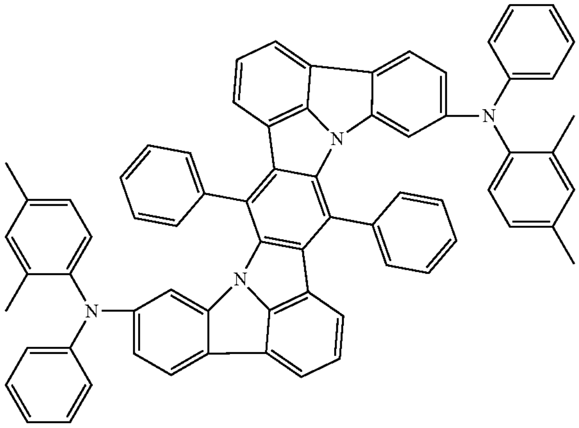

-continued
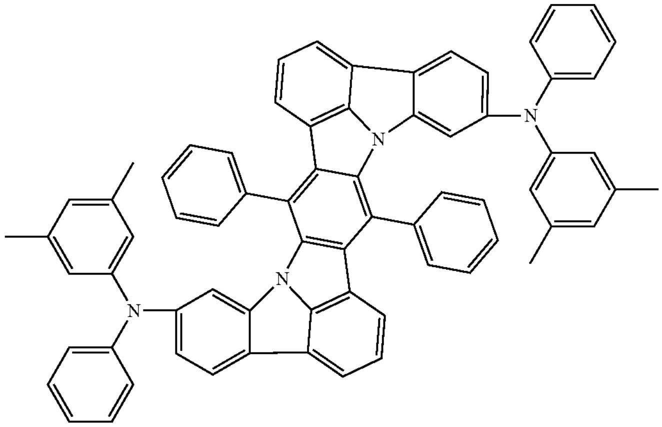
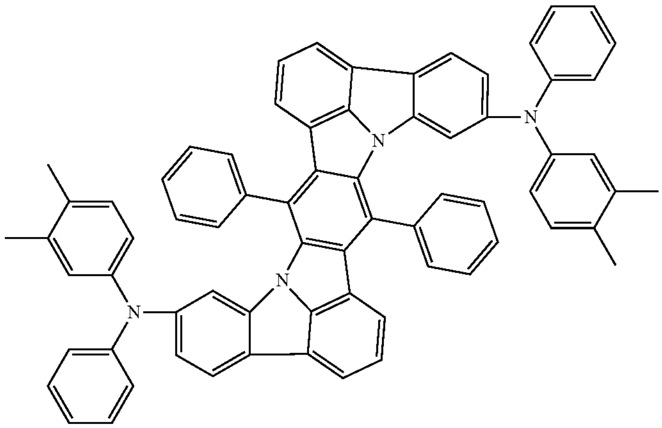
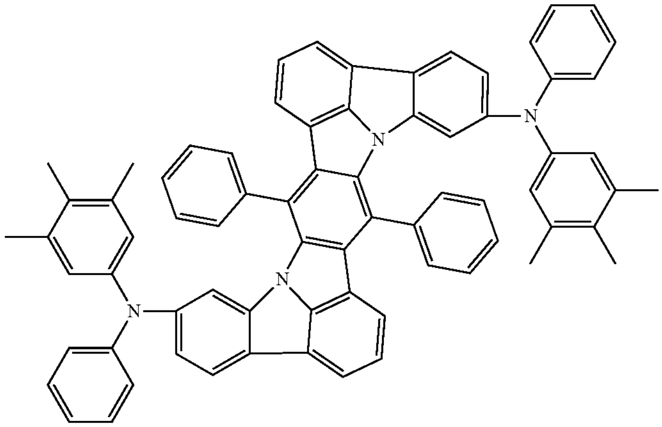

-continued
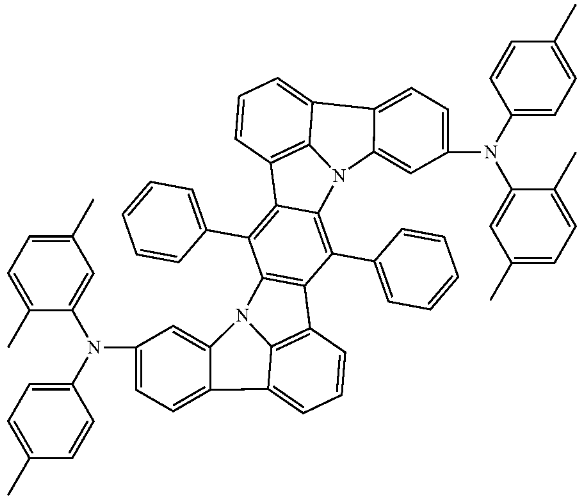
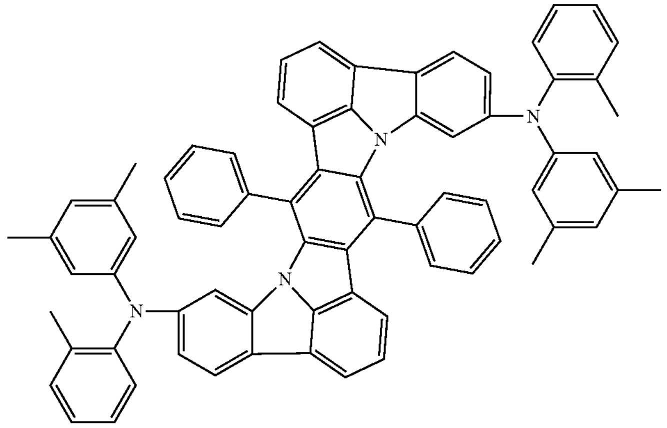
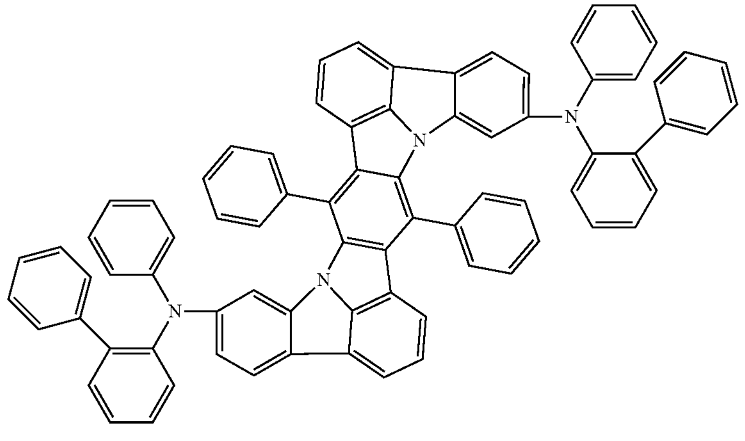

-continued
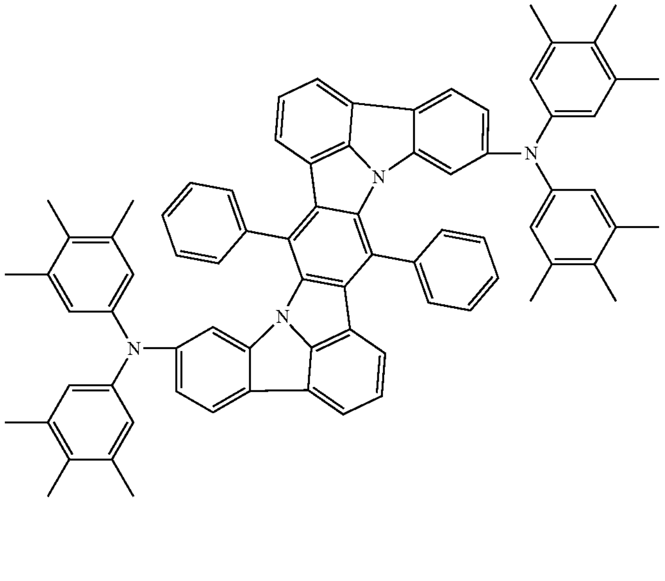
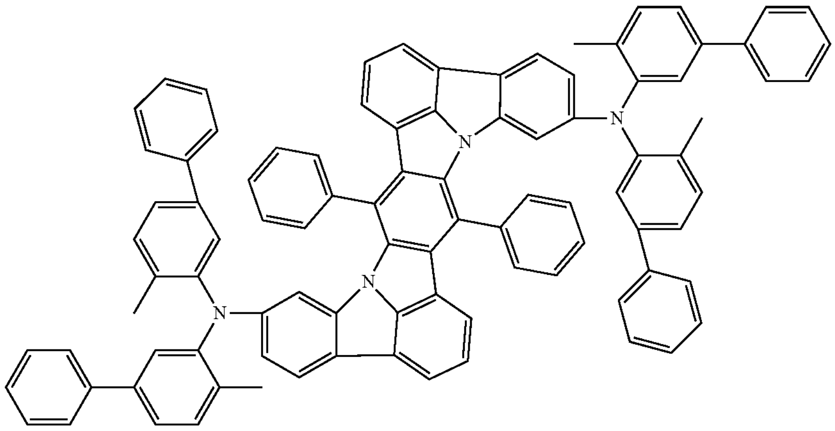
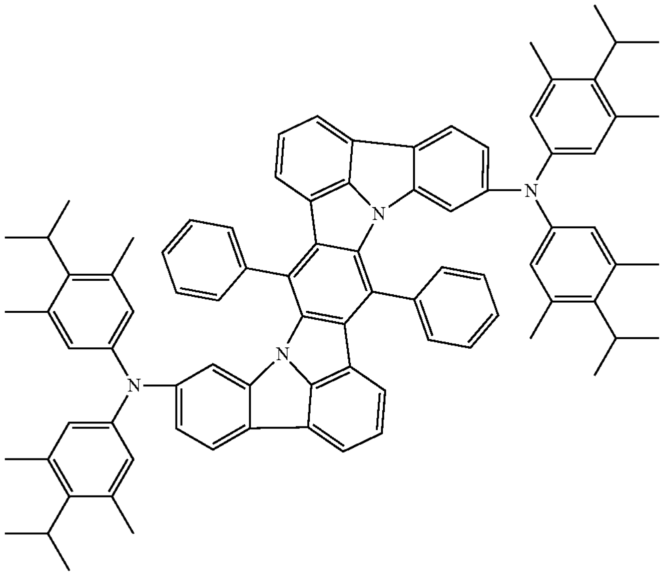

-continued
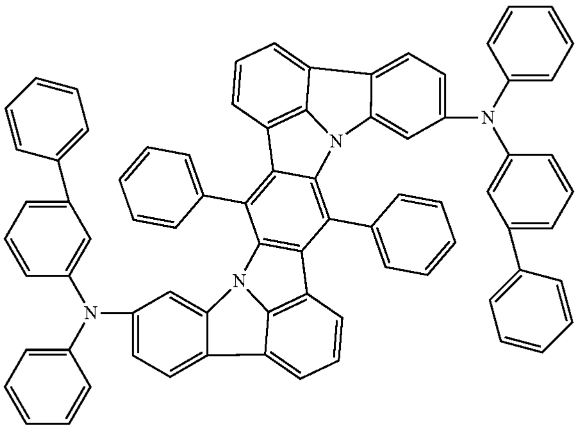
[Formula 251]
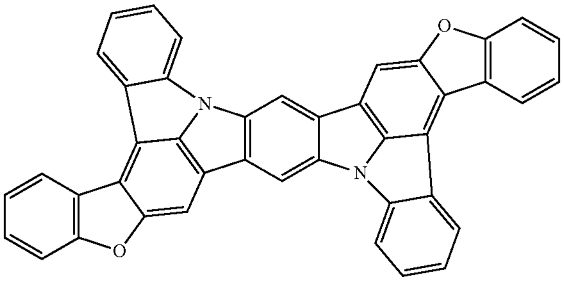
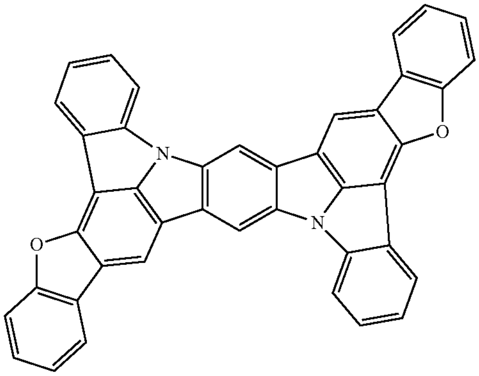
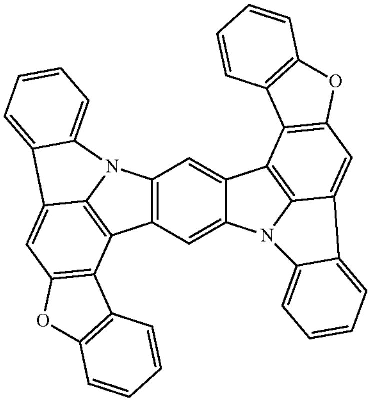
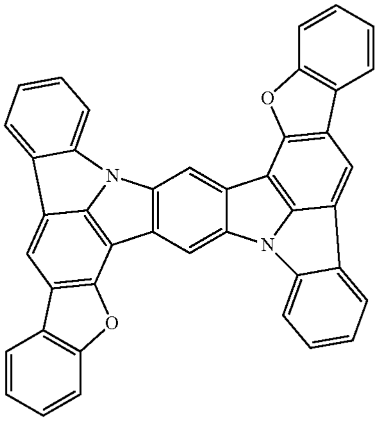
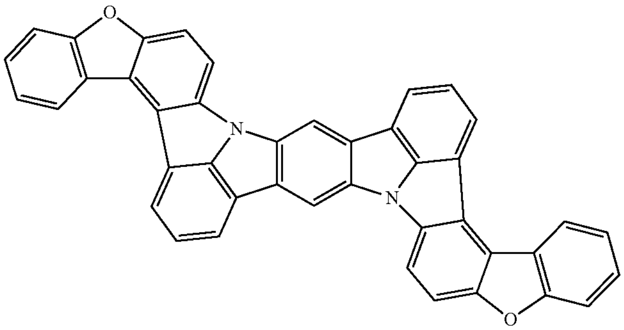

-continued
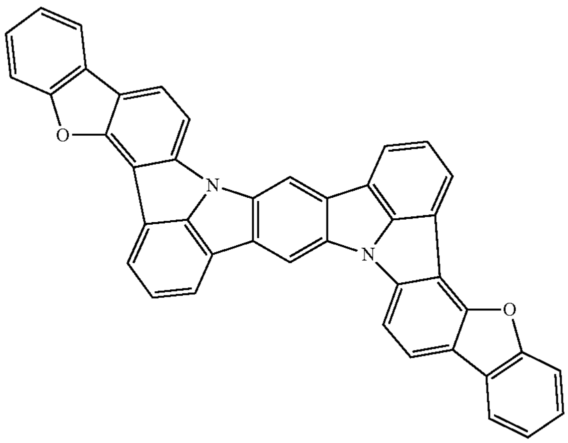
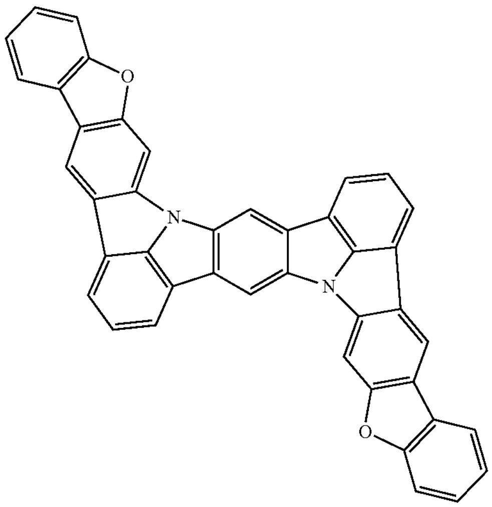
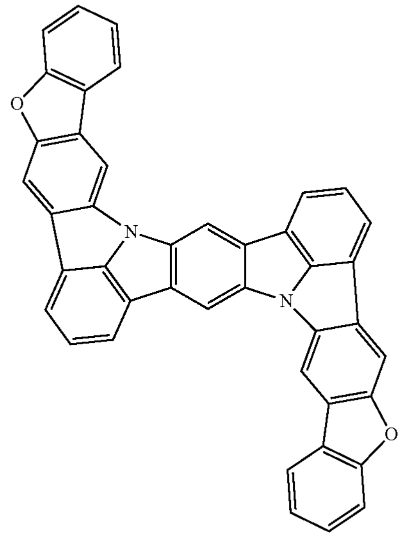
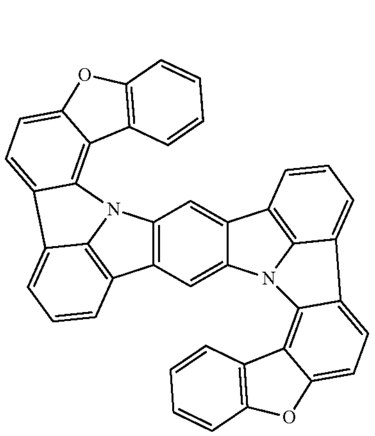
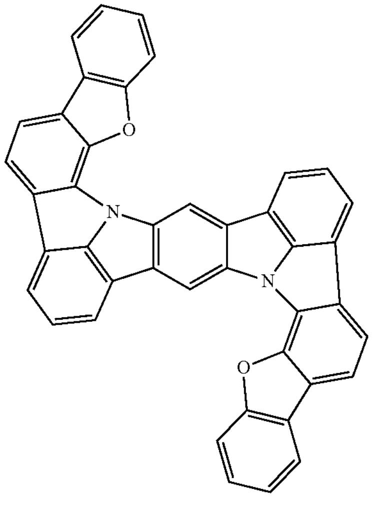

-continued
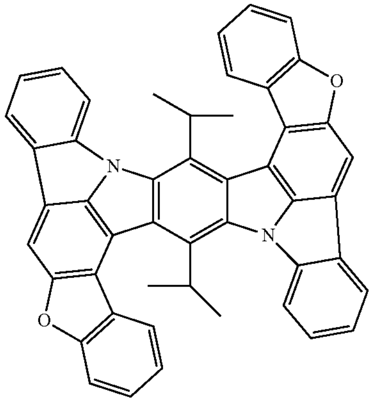
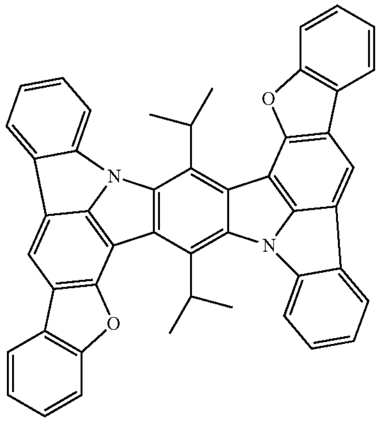
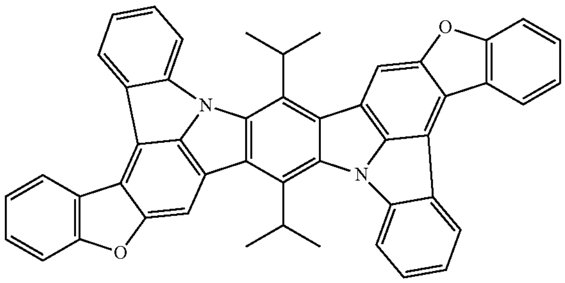
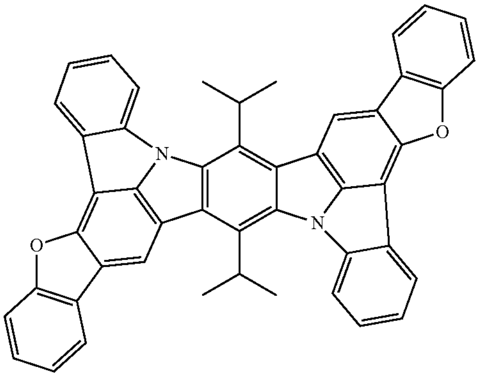
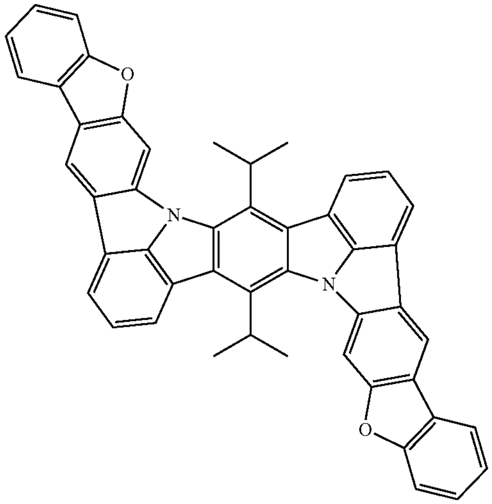
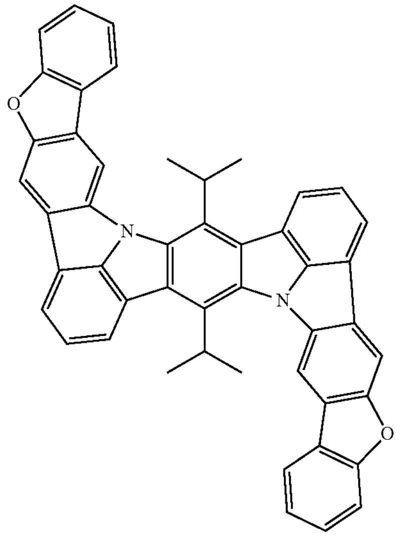
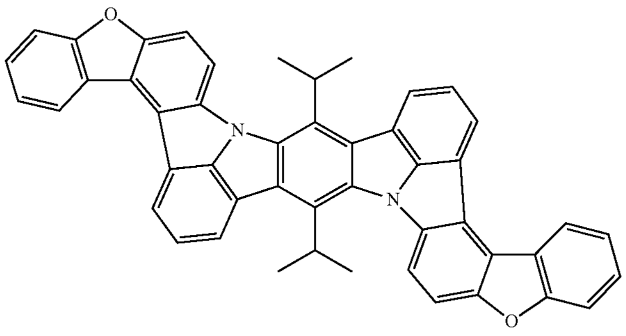

-continued
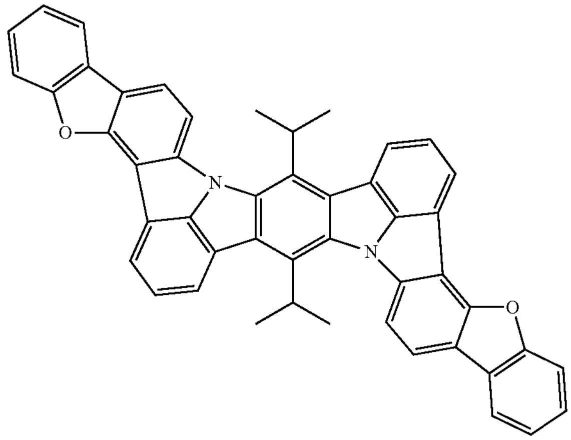
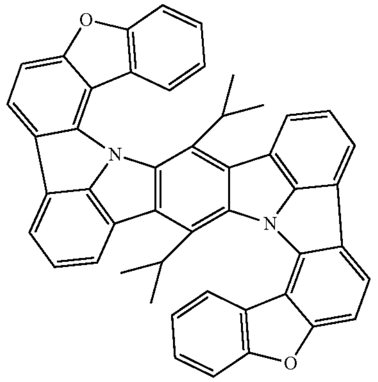
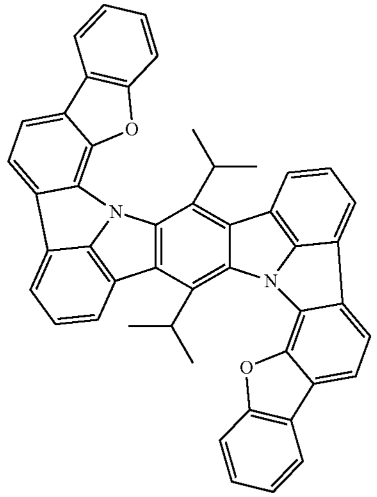
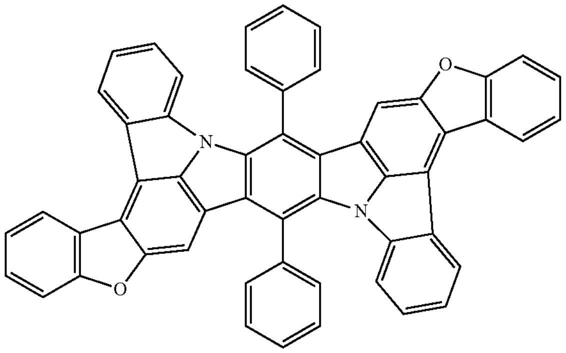
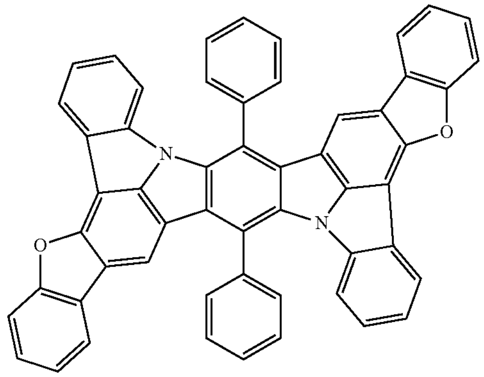
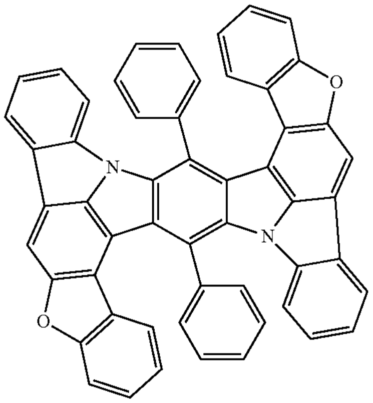

-continued
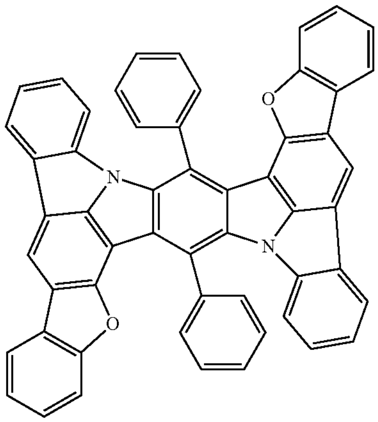
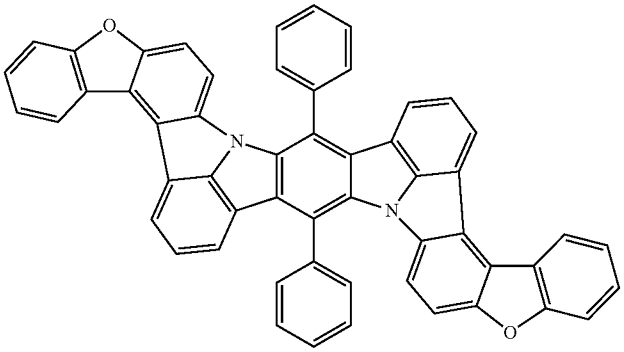
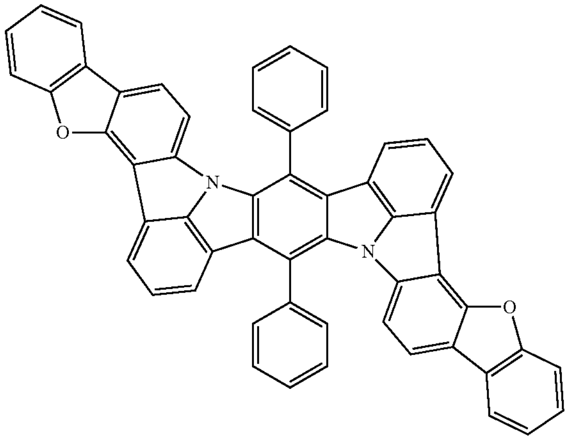
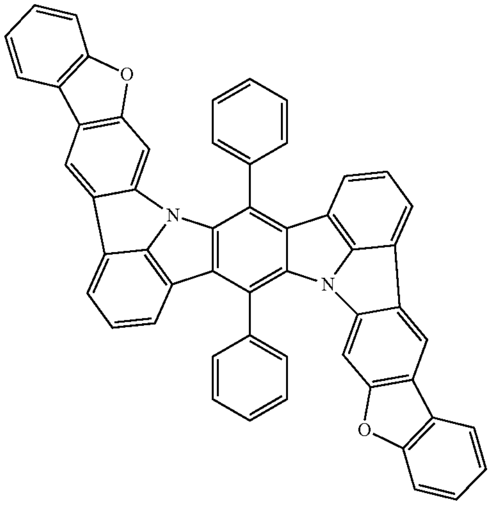
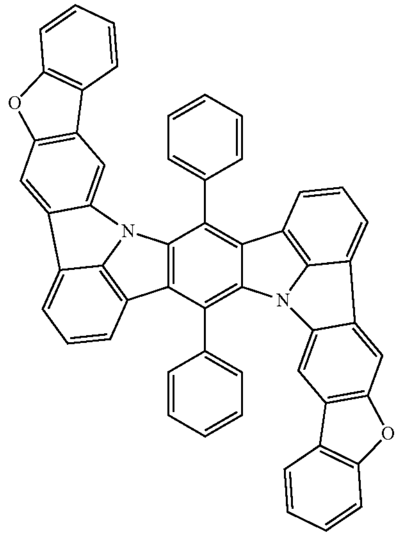 [SMILES: c1ccc(-c2c3c4cccc5c6cc7oc8ccccc8c7cc6n(c3c(-c3ccccc3)c3c6cccc7c8cc9oc%10ccccc%10c9cc8n(c23)c76)c54)cc1]

-continued
[Formula 252]
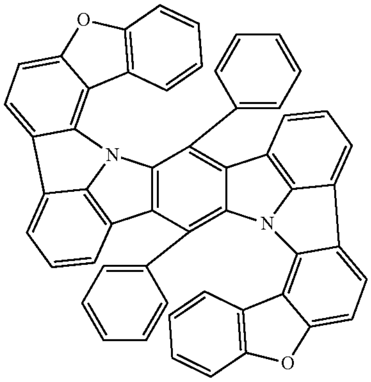
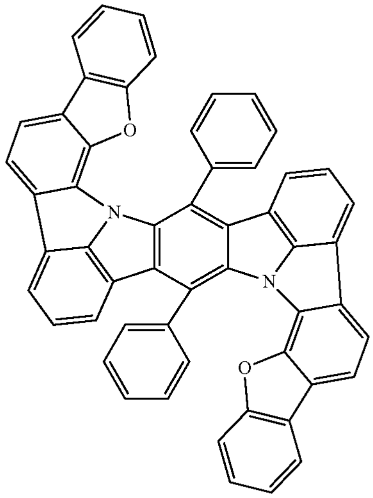
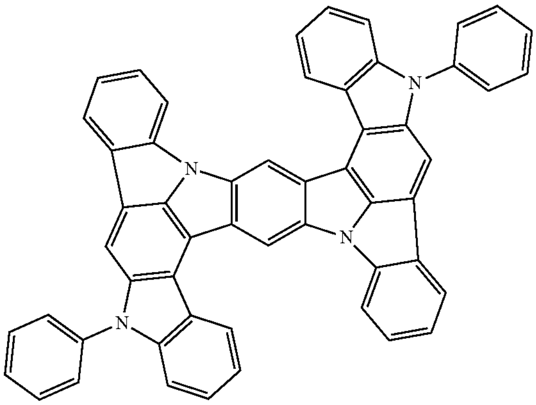
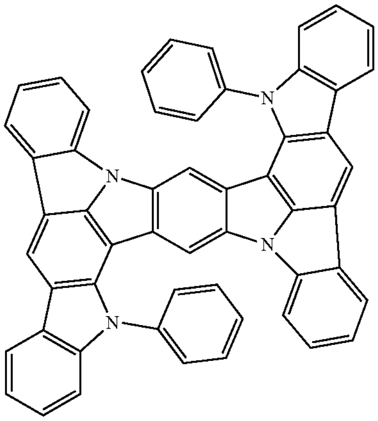
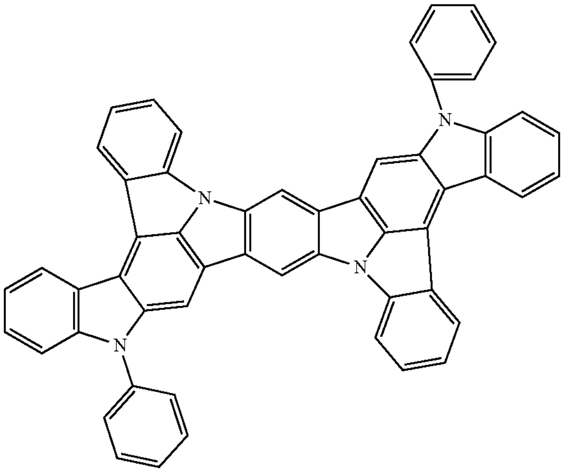

-continued
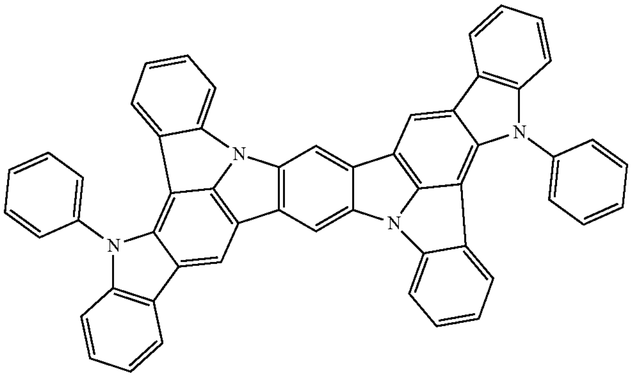
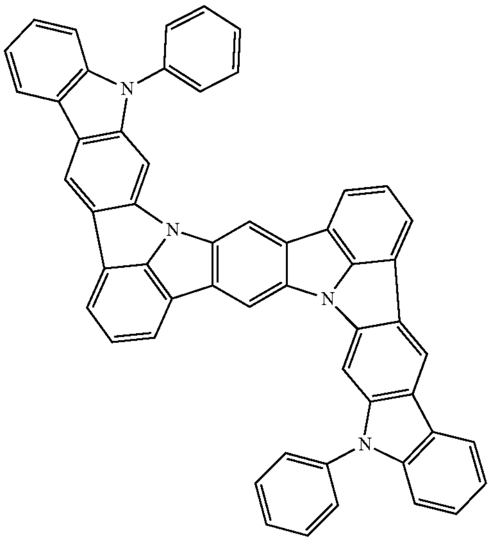
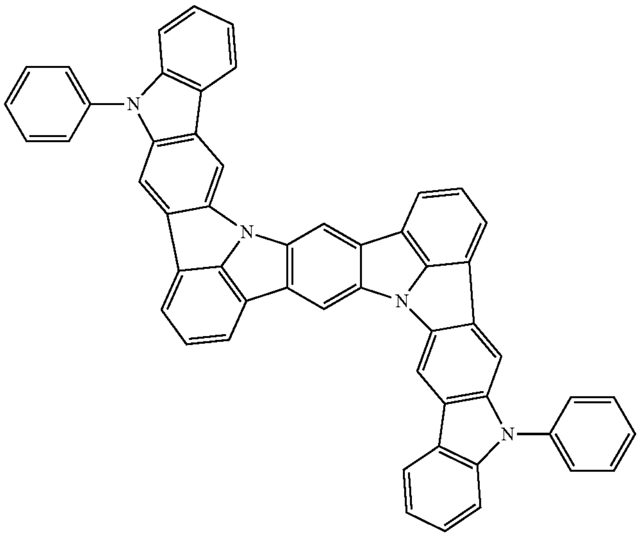
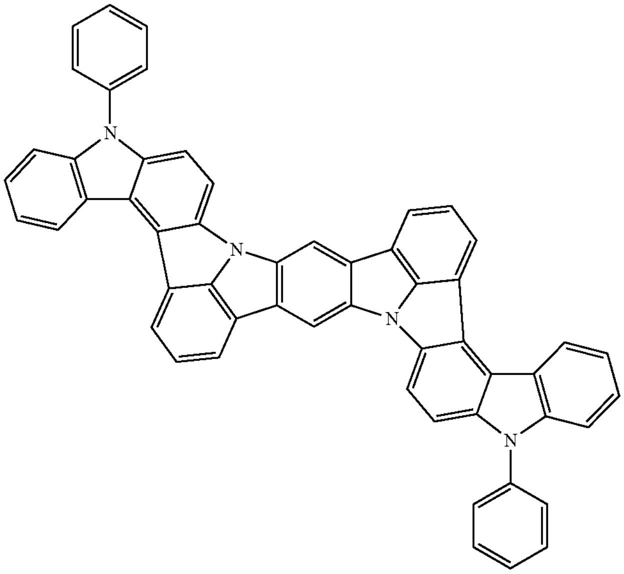

-continued
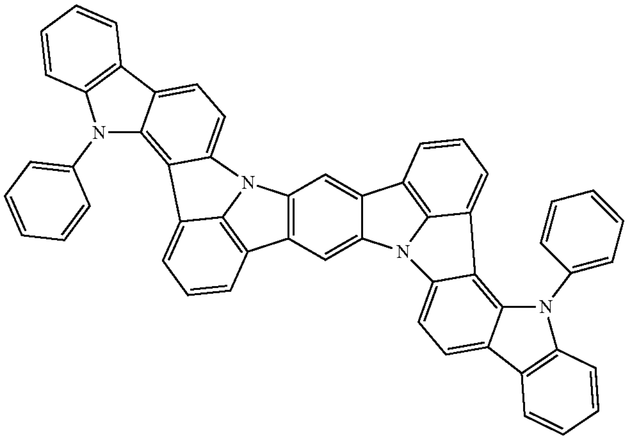
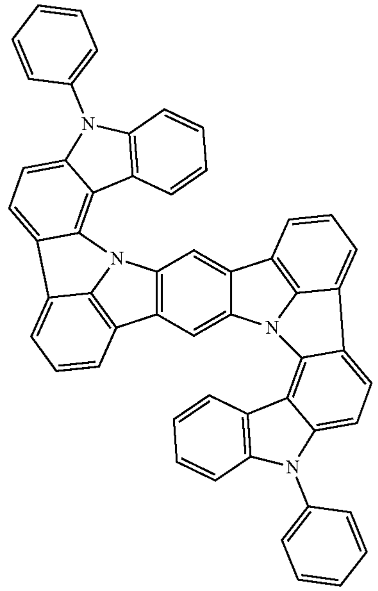
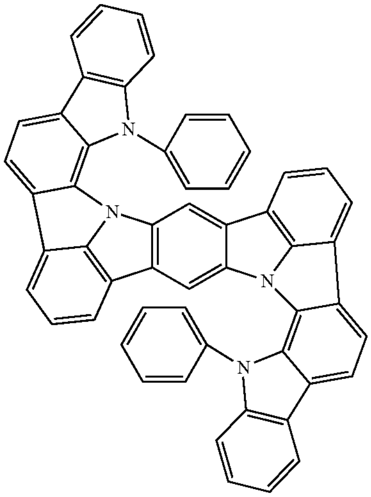
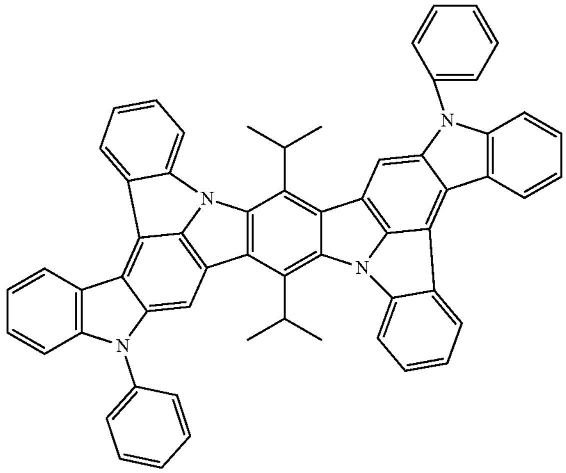
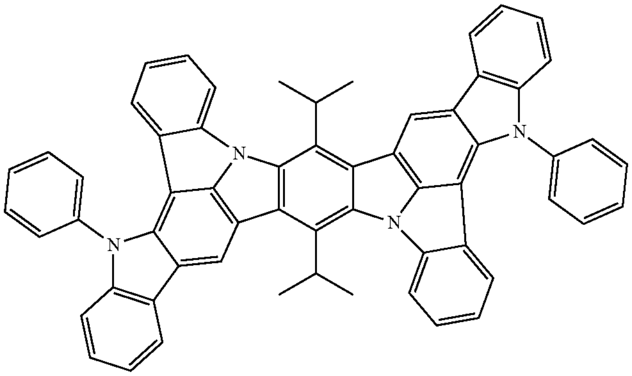

-continued
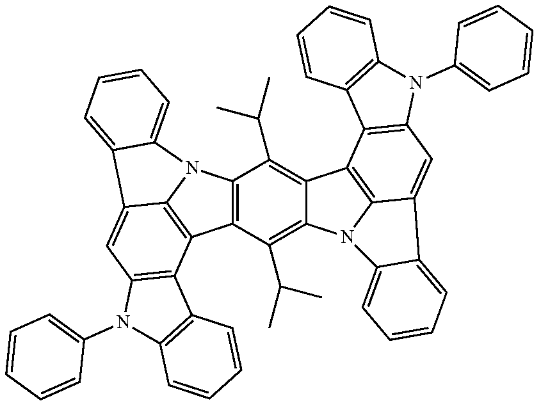
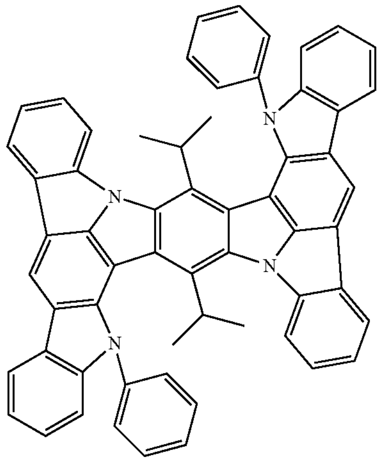
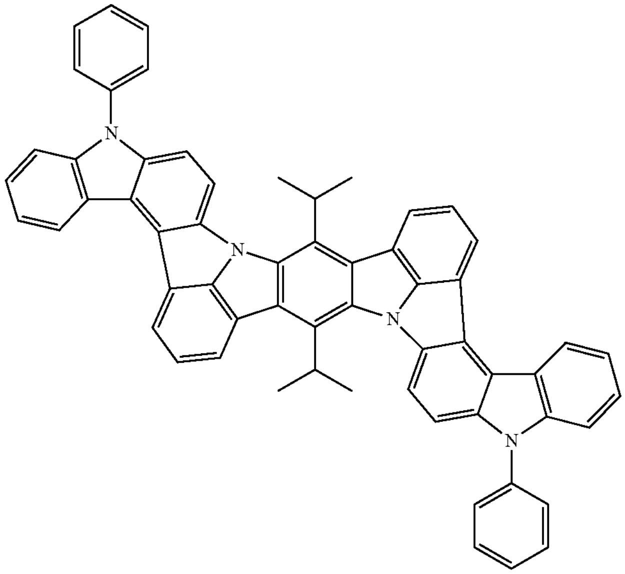
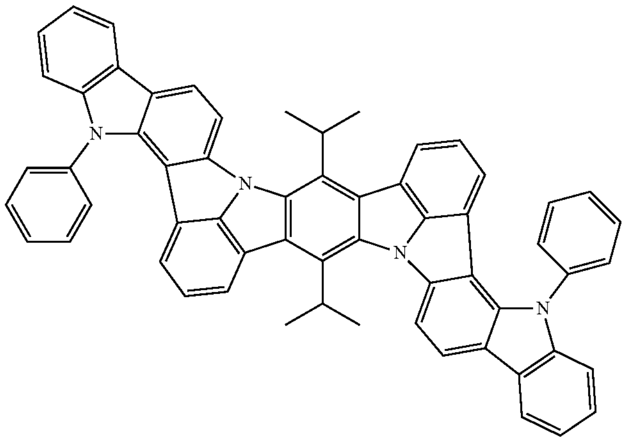
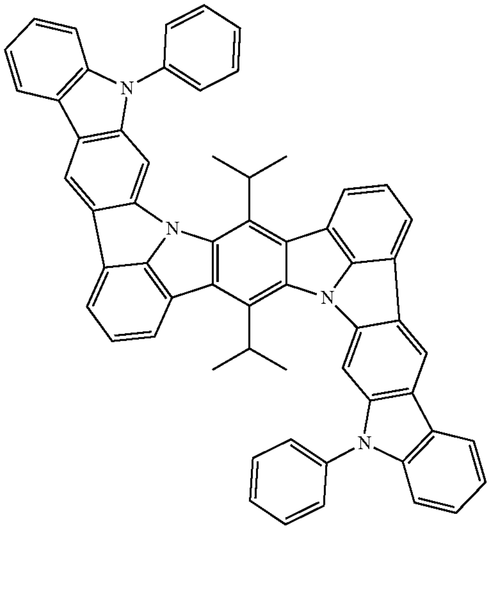

-continued
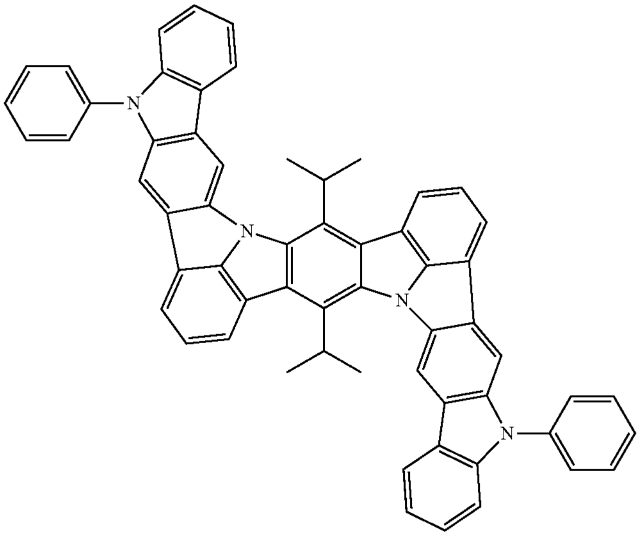
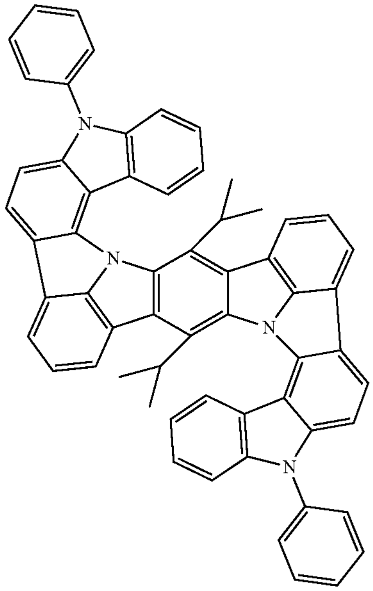
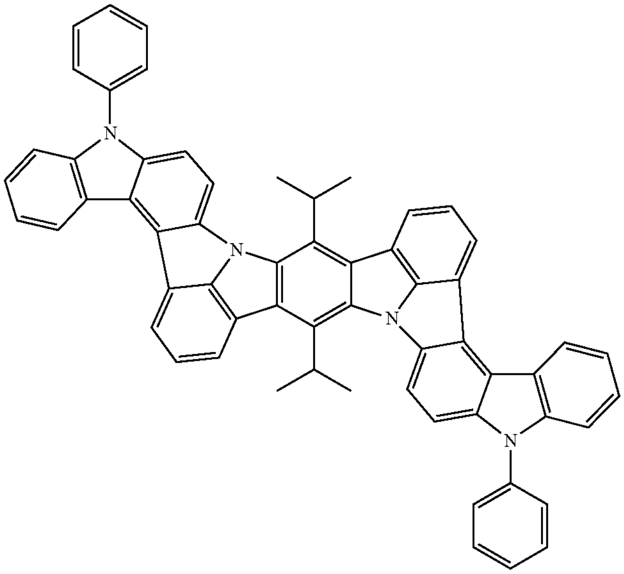
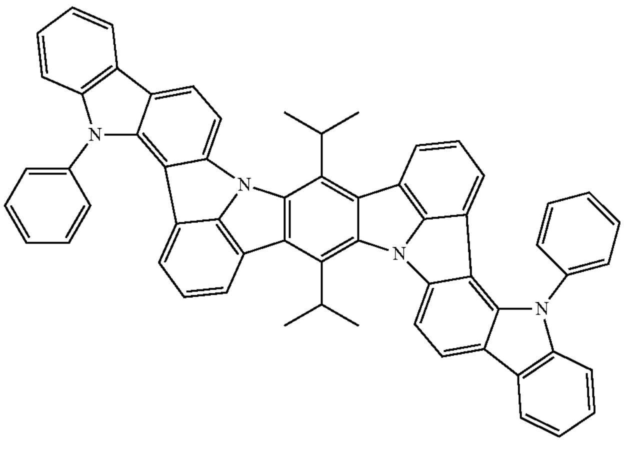
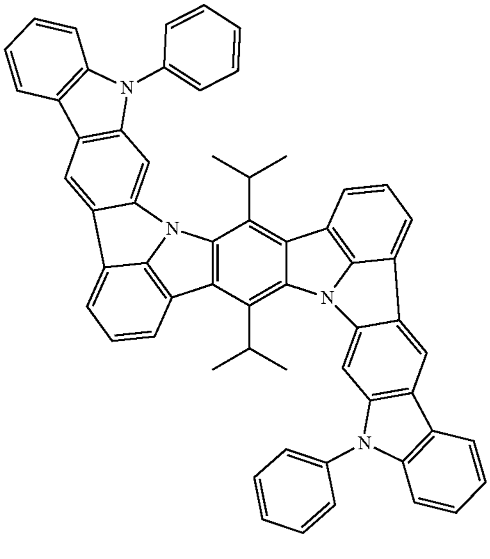

-continued
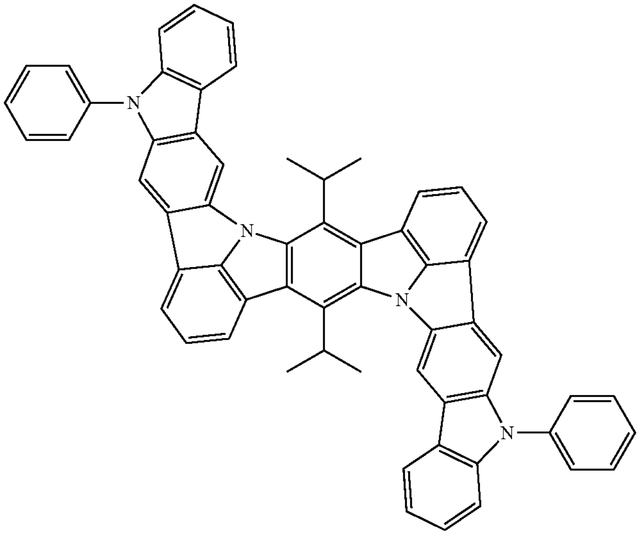
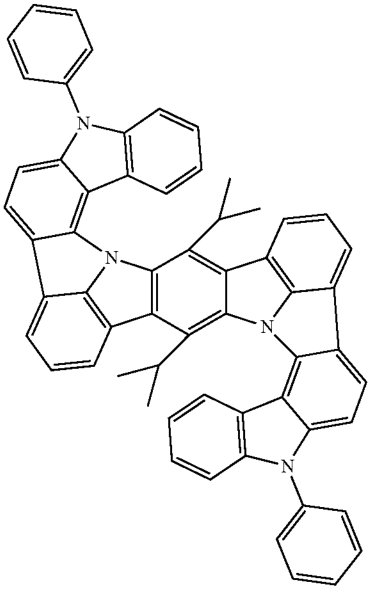
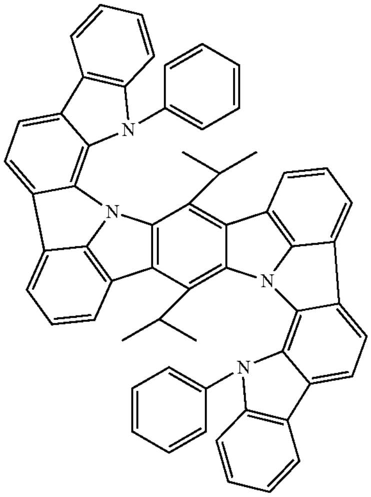
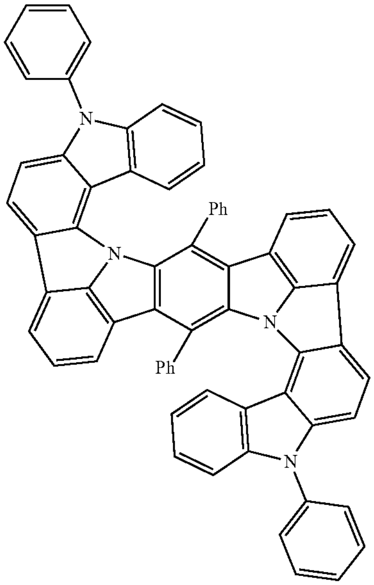
In formulae, Ph is a phenyl group
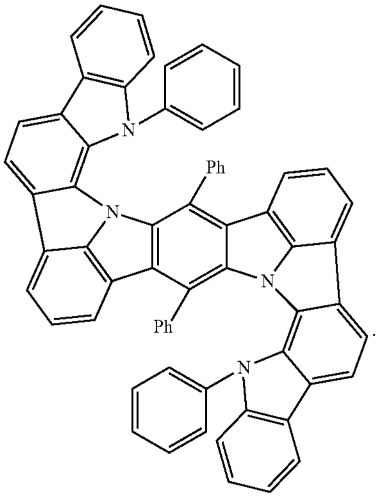

-continued
[Formula 253]
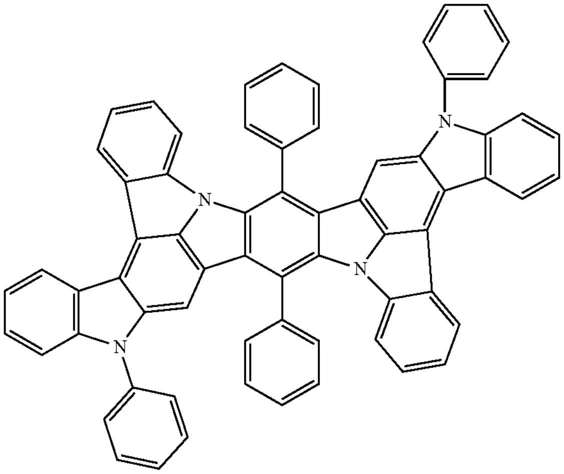
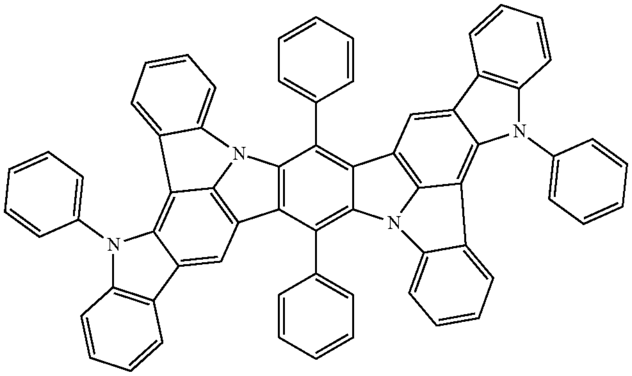
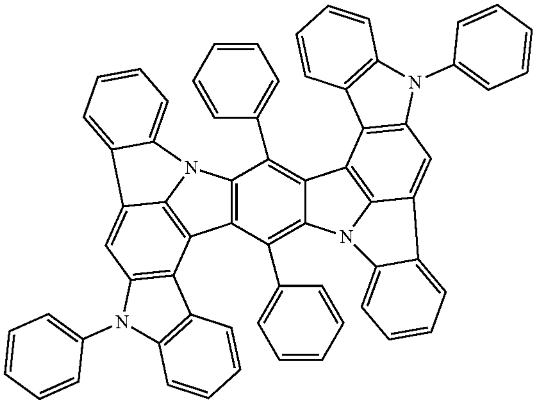
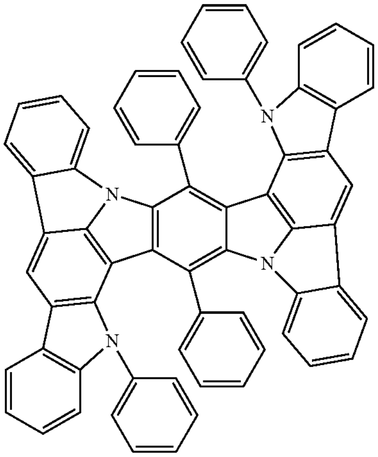

-continued
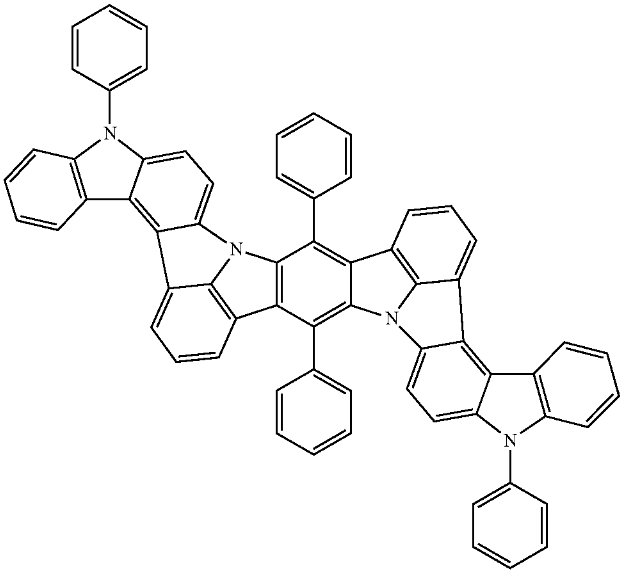
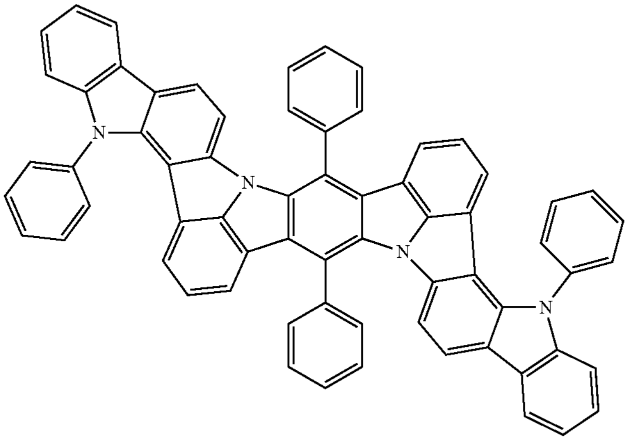
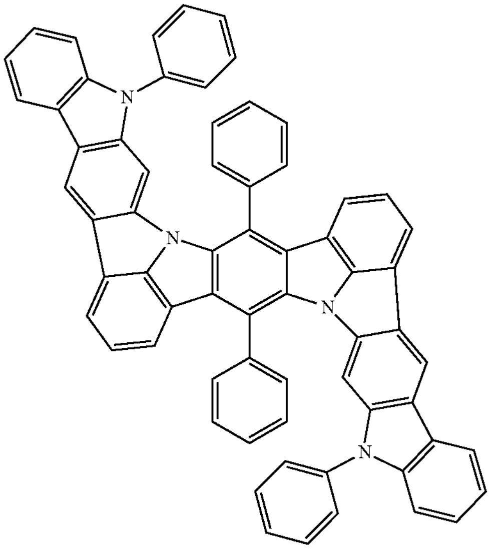
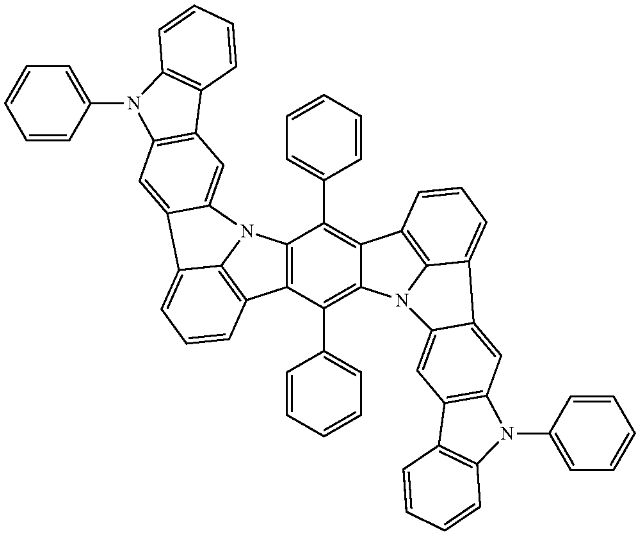

-continued
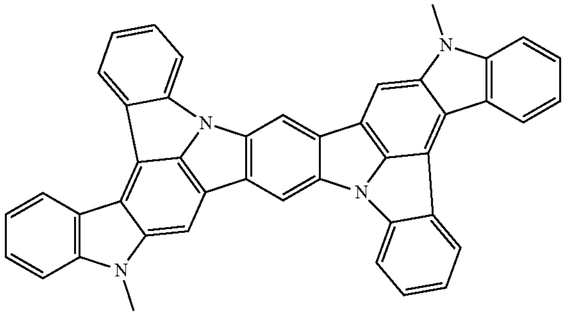
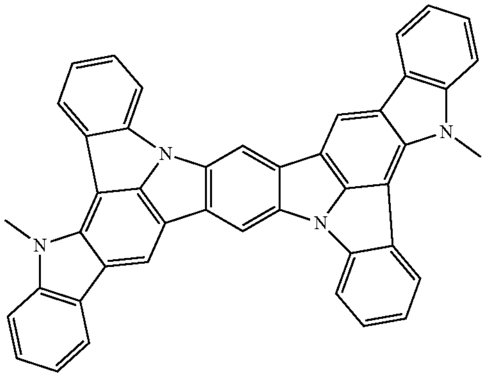
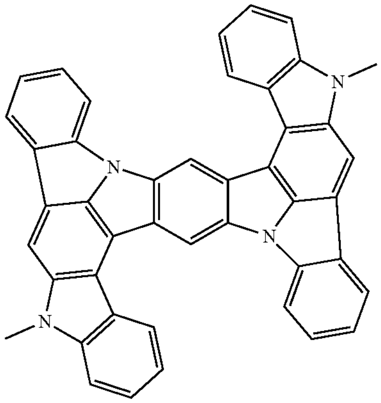
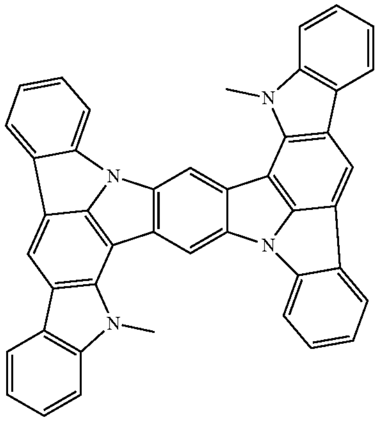
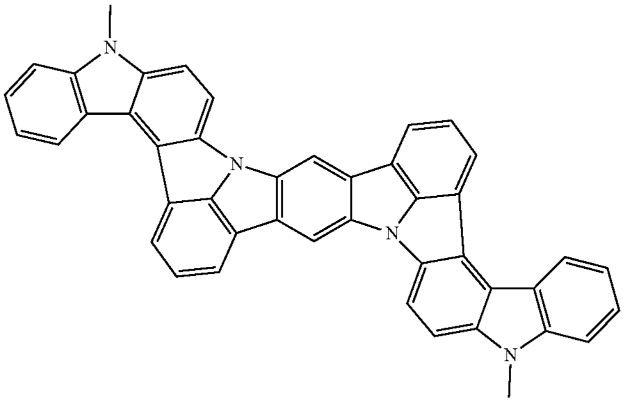
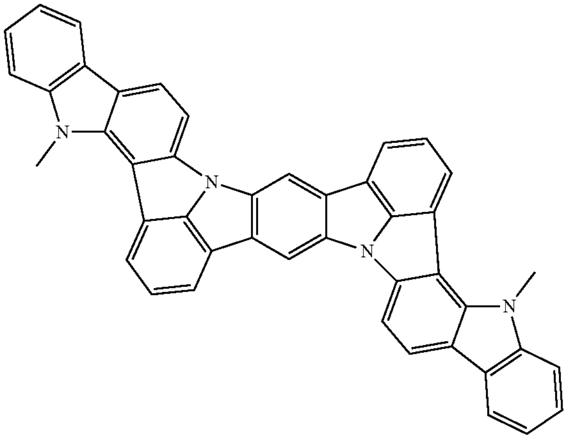

-continued
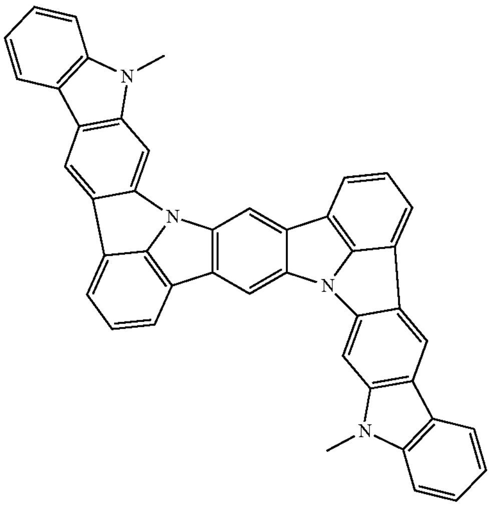
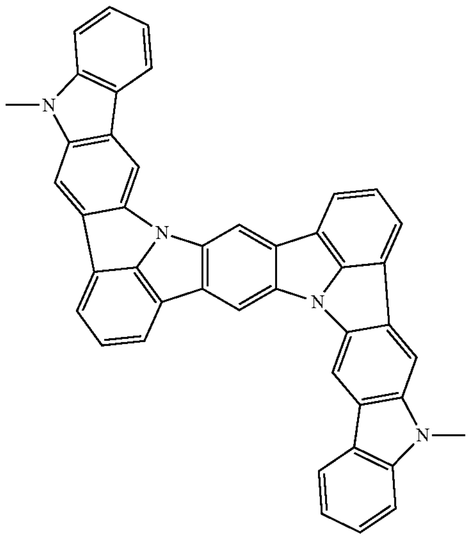
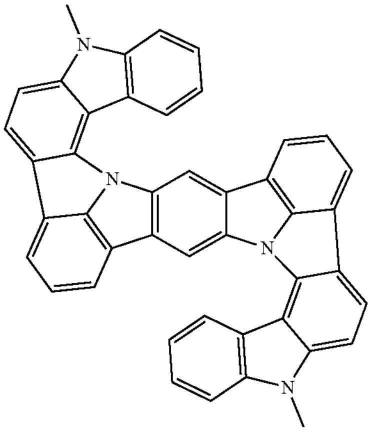
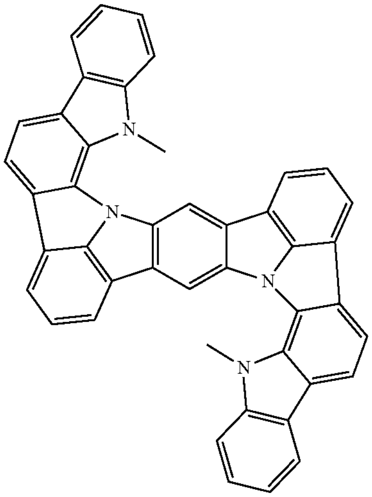
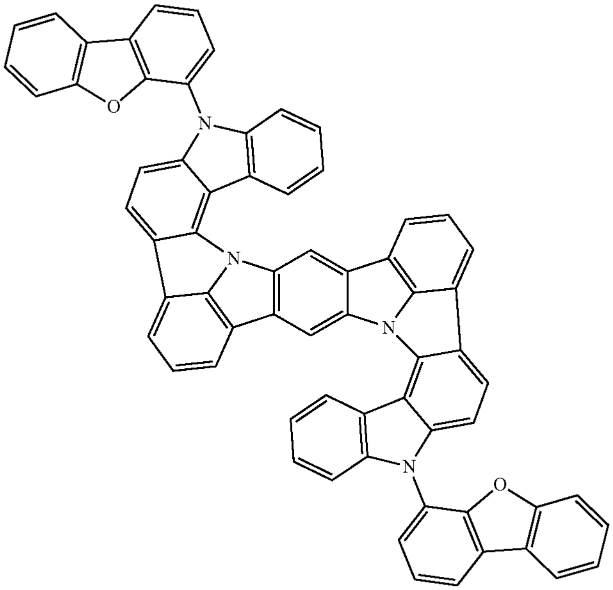
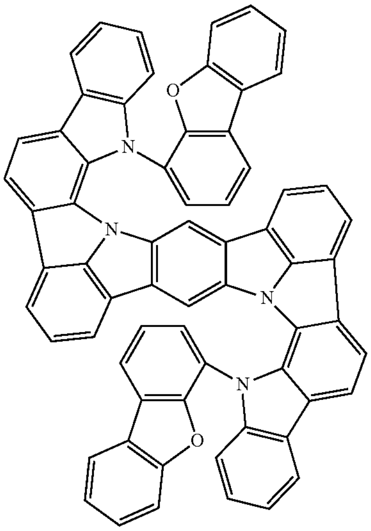

-continued
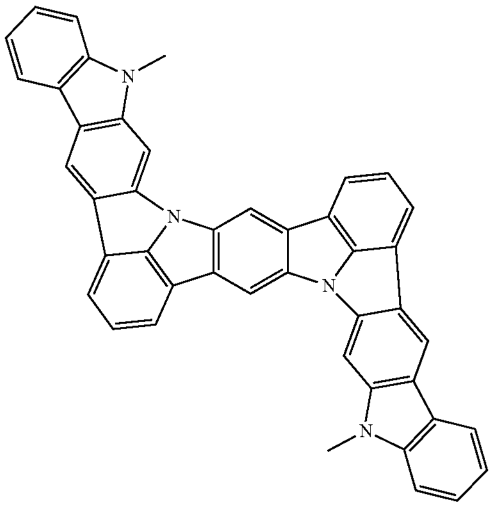
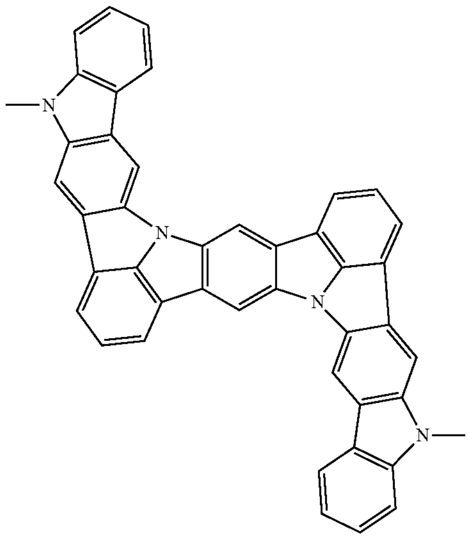
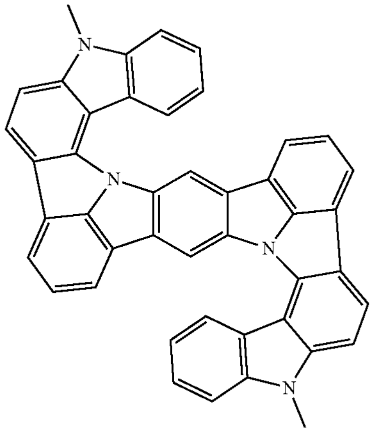
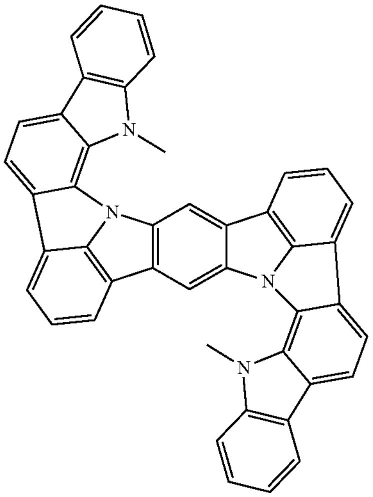
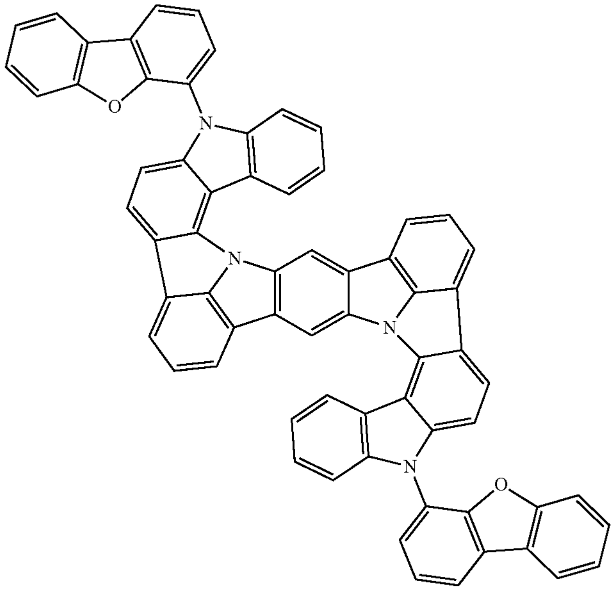
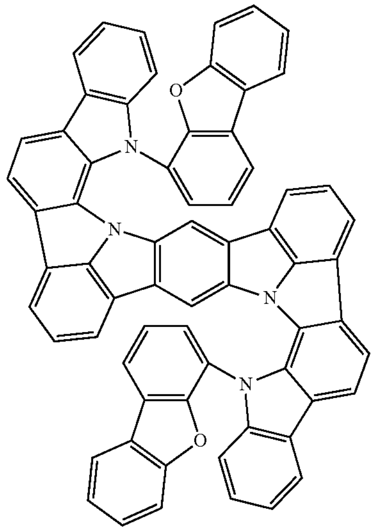

-continued
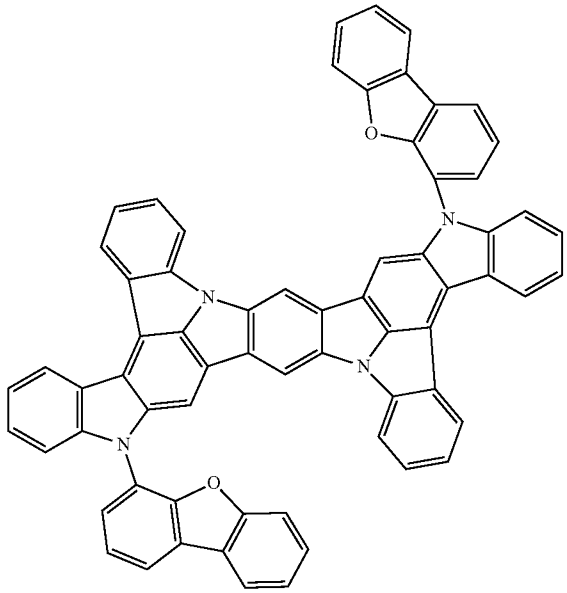
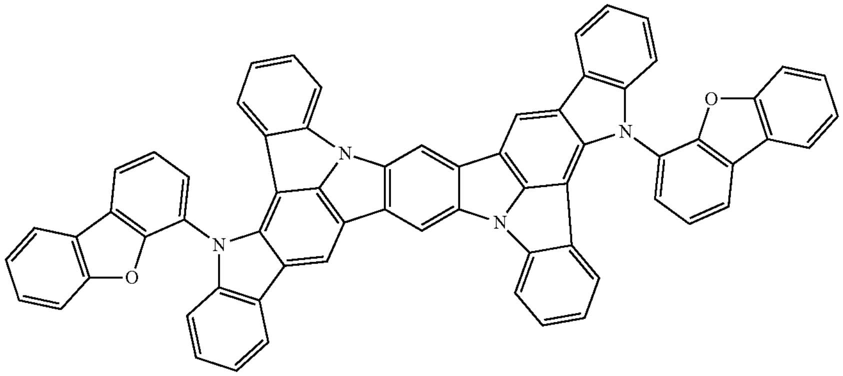
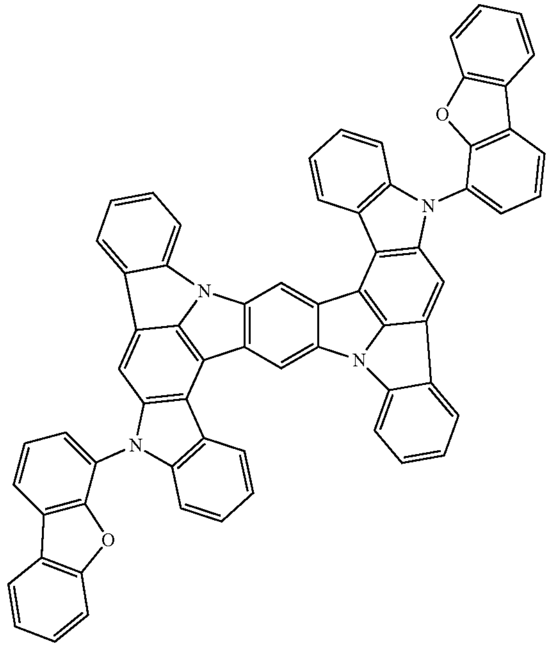
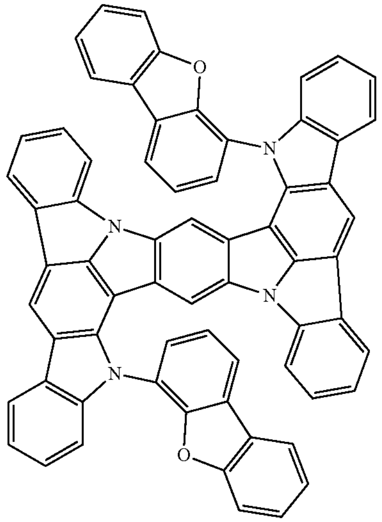

-continued
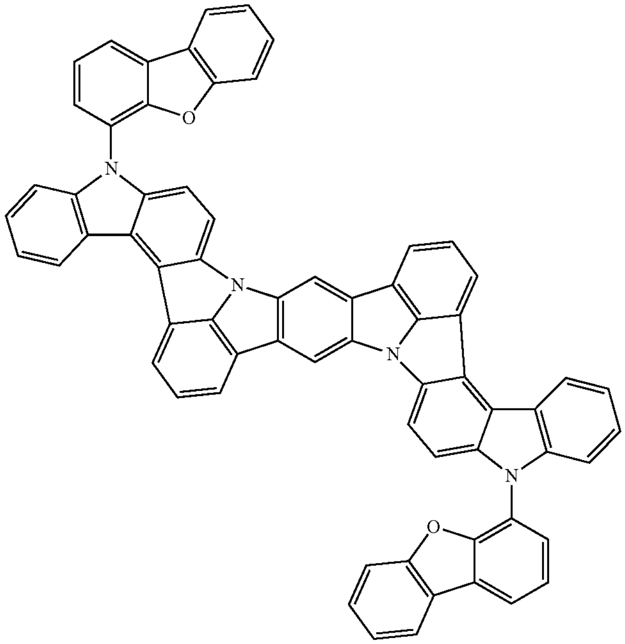
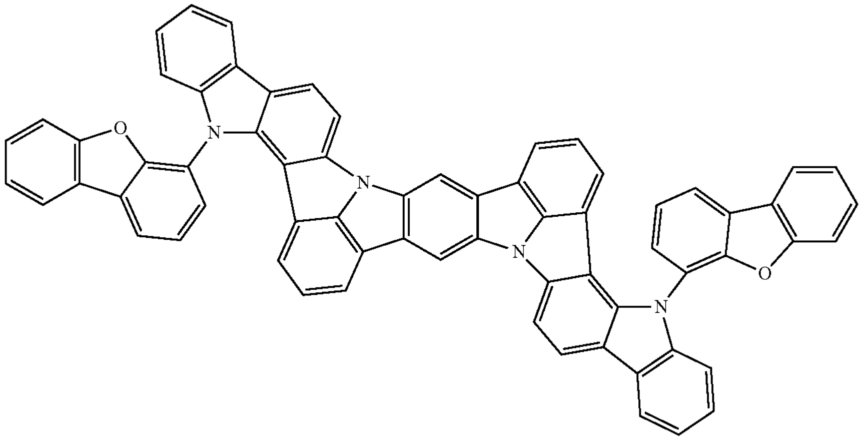
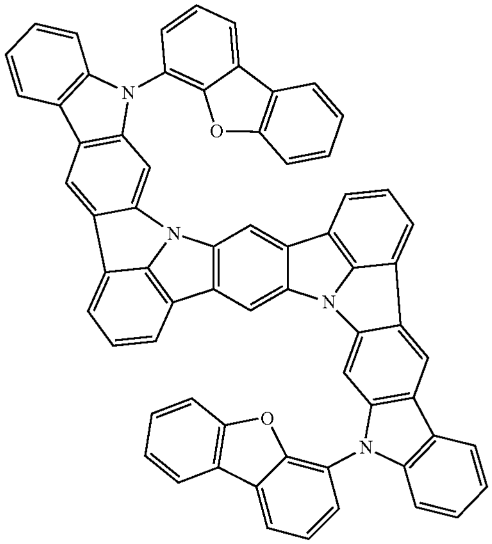

-continued
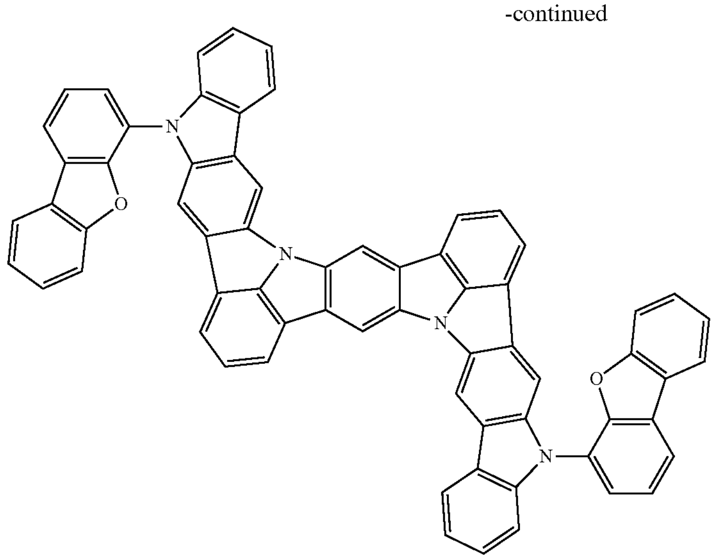
[Formula 254]
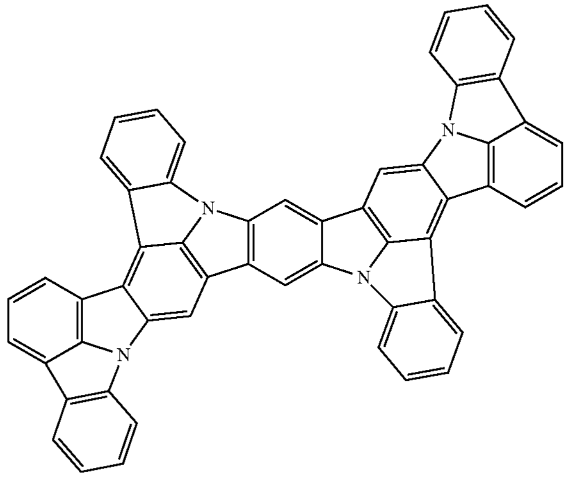
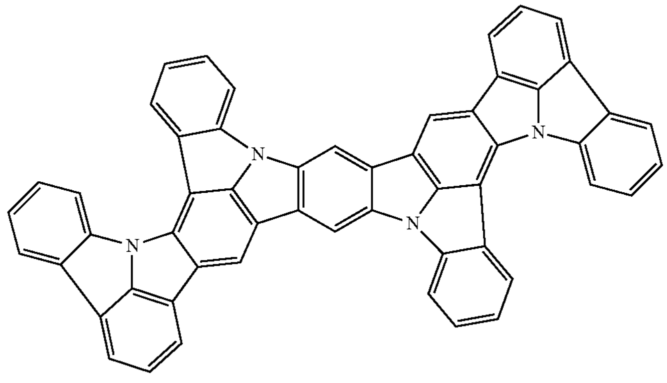

-continued
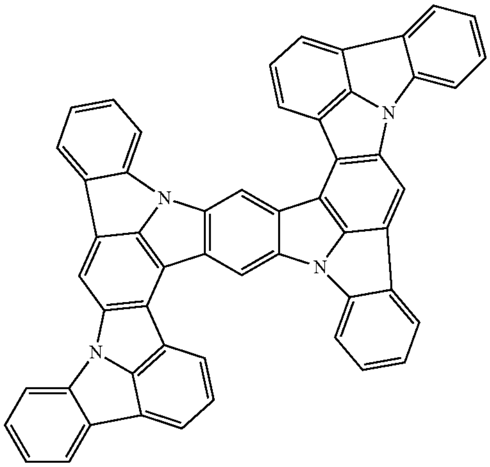
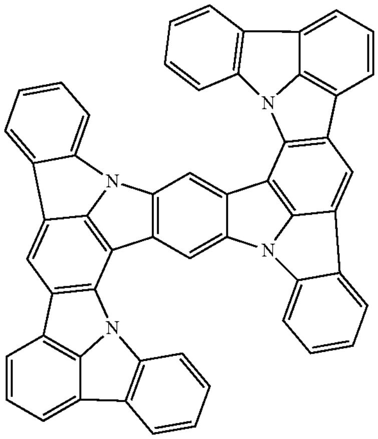
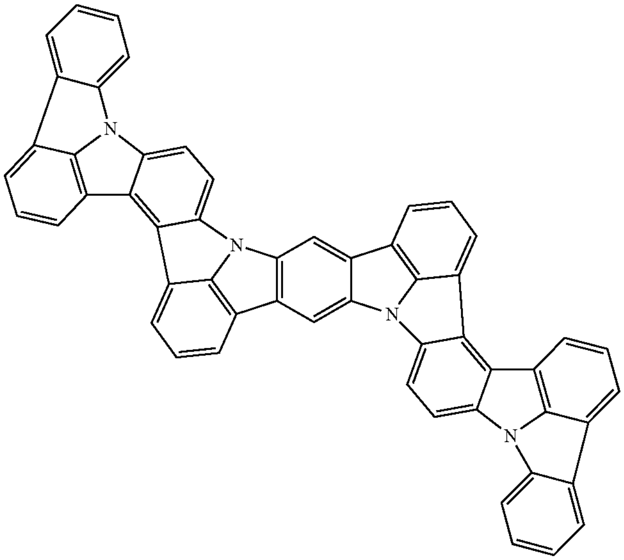
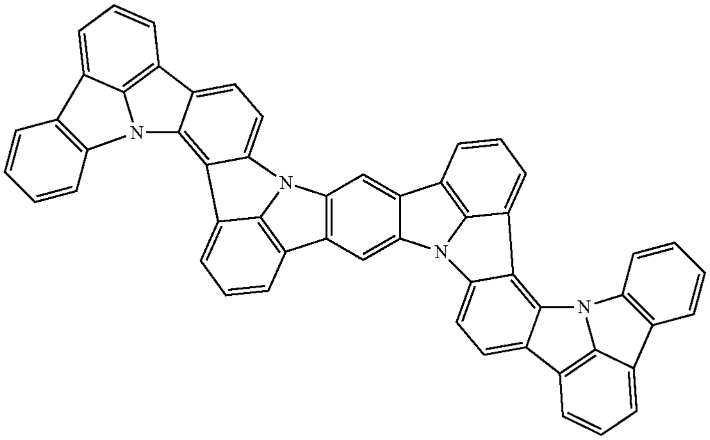

-continued
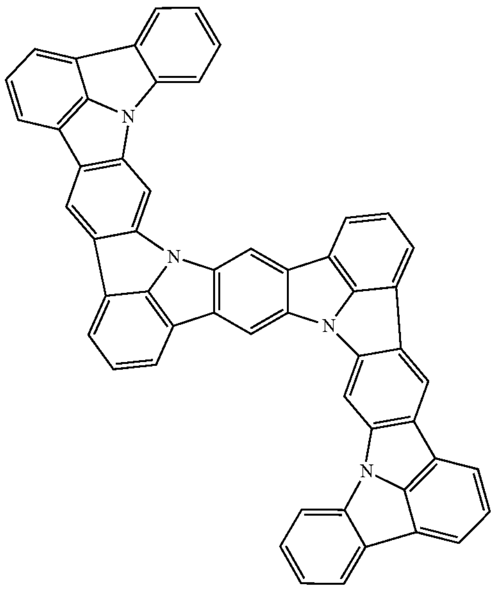
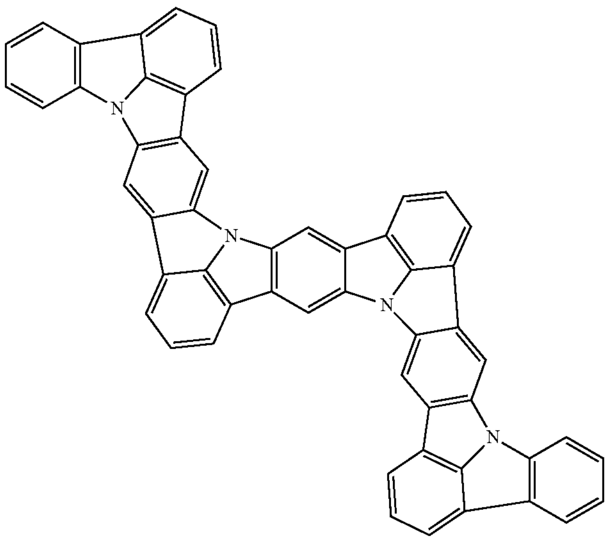
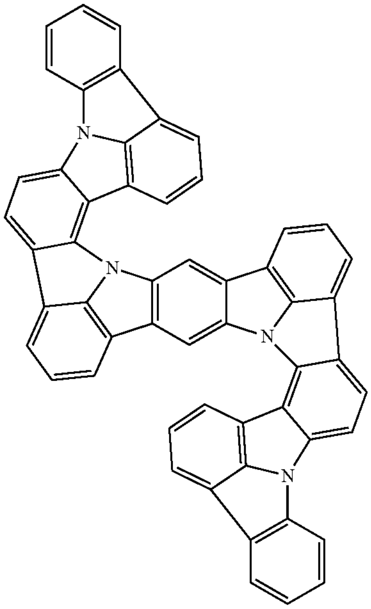
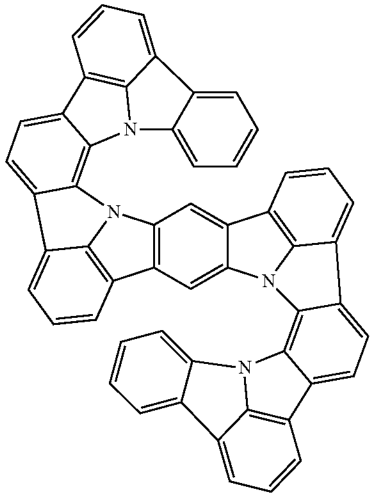
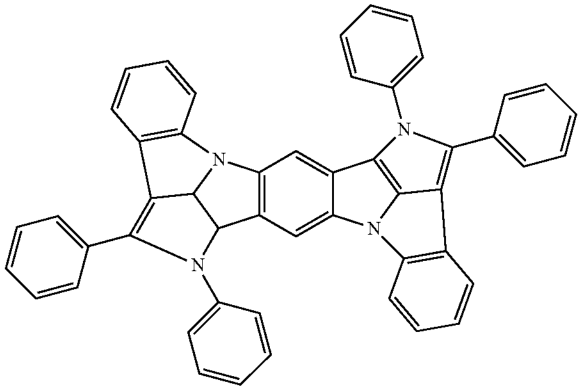
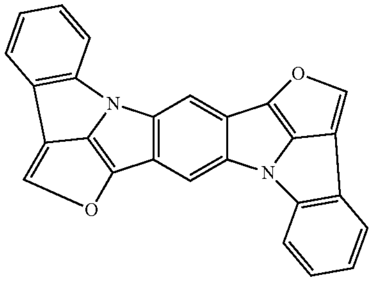

-continued
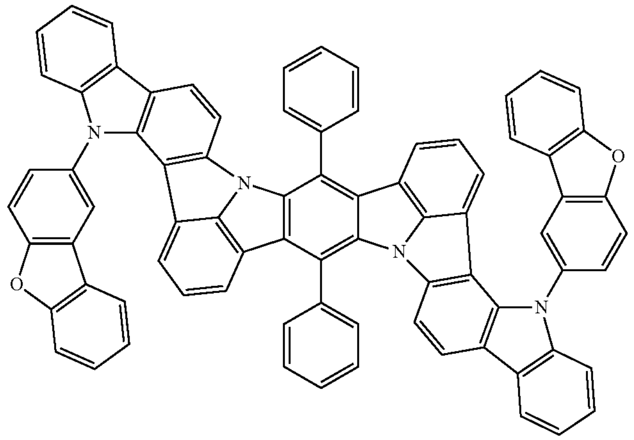
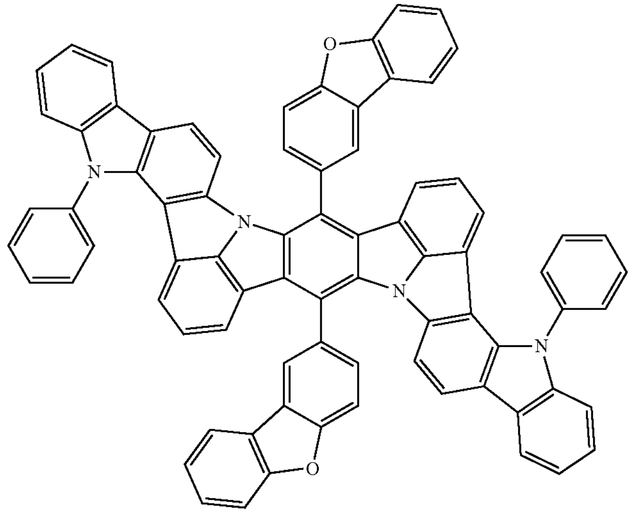
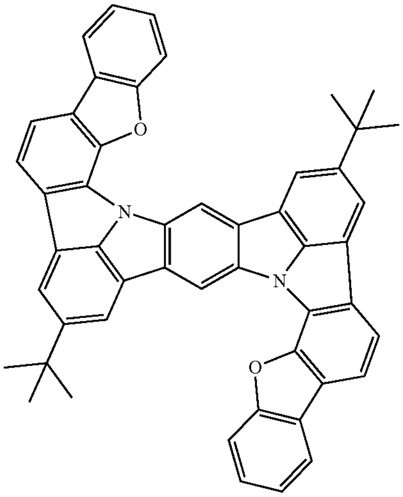
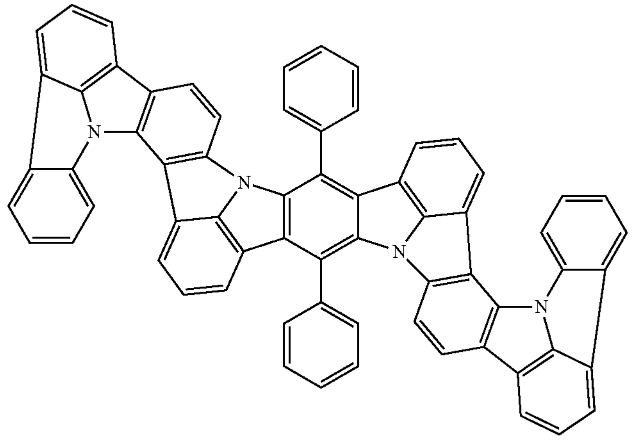

-continued

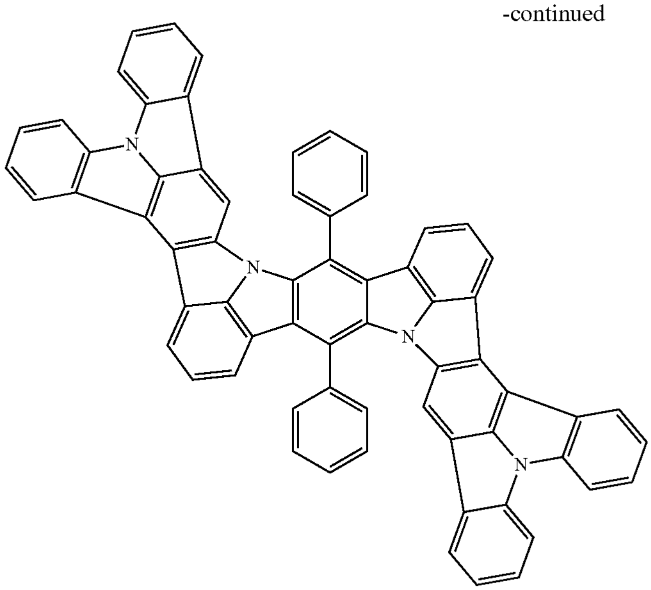

Compound Represented by Formula (6)

The compound represented by the formula (6) will be described below.

[Formula 255]

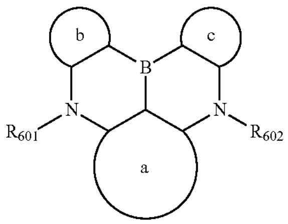

(6)

In the formula (6): a ring, b ring and c ring are each independently a substituted or unsubstituted aromatic hydrocarbon ring having 6 to 50 ring carbon atoms or a substituted or unsubstituted heterocycle having 5 to 50 ring atoms;

$R_{601}$ and $R_{602}$ are each independently bonded with the a ring, b ring, or a c ring to form a substituted or unsubstituted heterocycle or does not form a substituted or unsubstituted heterocycle; and $R_{601}$ and $R_{602}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with the fused bicyclic moiety formed of a boron atom and two nitrogen atoms at the center of the formula (6).

The "aromatic hydrocarbon ring" for the a, b, and c rings has the same structure as the compound formed by introducing a hydrogen atom to the "aryl group" described above.

Ring atoms of the "aromatic hydrocarbon ring" for the a ring include three carbon atoms on the fused bicyclic structure at the center of the formula (6).

Ring atoms of the "aromatic hydrocarbon ring" for the b ring and the c ring include two carbon atoms on a fused bicyclic structure at the center of the formula (6).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as the compound formed by introducing a hydrogen atom to the "heterocyclic group" described above.

Ring atoms of the "heterocycle" for the a ring include three carbon atoms on the fused bicyclic structure at the center of the formula (6). Ring atoms of the "heterocycle" for the b ring and the c ring include two carbon atoms on a fused bicyclic structure at the center of the formula (6). Specific examples of the "substituted or unsubstituted heterocycle having 5 to 50 ring atoms" include a compound formed by introducing a hydrogen atom to the "heterocyclic group" described in the specific example group G2.

$R_{601}$ and $R_{602}$ are optionally each independently bonded with the a ring, b ring, or c ring to form a substituted or unsubstituted heterocycle. The "heterocycle" in this arrangement includes the nitrogen atom on the fused bicyclic structure at the center of the formula (6). The heterocycle in the above arrangement optionally include a hetero atom other than the nitrogen atom. $R_{601}$ and $R_{602}$ bonded with the a ring, b ring, or c ring specifically means that atoms forming $R_{601}$ and $R_{602}$ are bonded with atoms forming the a ring, b ring, or c ring. For instance, $R_{601}$ may be optionally bonded to the a ring to form a bicyclic (or tri-or-more cyclic) fused nitrogen-containing heterocycle, in which the ring including $R_{601}$ and the a ring are fused. Specific examples of the nitrogen-containing heterocycle include a compound corresponding to the nitrogen-containing bi(or-more)cyclic heterocyclic group in the specific example group G2.

The same applies to $R_{601}$ bonded with the b ring, $R_{602}$ bonded with the a ring, and $R_{602}$ bonded with the c ring.

In an exemplary embodiment, the a ring, b ring and c ring in the formula (6) are each independently a substituted or unsubstituted aromatic hydrocarbon ring having 6 to 50 ring carbon atoms.

In an exemplary embodiment, the a ring, b ring and c ring in the formula (6) are each independently a substituted or unsubstituted benzene ring or a substituted or unsubstituted naphthalene ring.

In an exemplary embodiment, $R_{601}$ and $R_{602}$ in the formula (6) are each independently a substituted or unsubstituted aryl group having 6 to 50 ring carbon atoms, or a substituted or unsubstituted heterocyclic group having 5 to 50 ring atoms, preferably a substituted or unsubstituted aryl group having 6 to 50 ring carbon atoms.

In an exemplary embodiment, the compound represented by the formula (6) is represented by a formula (62) below.

[Formula 256]

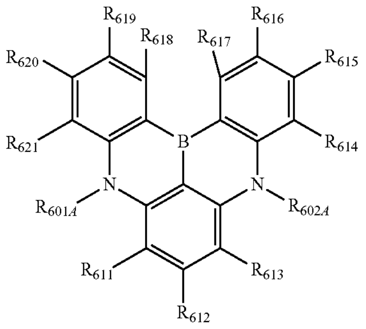

(62)

In the formula (62): $R_{601A}$ is bonded with at least one of $R_{611}$ or $R_{621}$ to form a substituted or unsubstituted heterocycle or does not form a substituted or unsubstituted heterocycle;

$R_{602A}$ is bonded with at least one of $R_{613}$ or $R_{614A}$ to form a substituted or unsubstituted heterocycle or does not form a substituted or unsubstituted heterocycle;

$R_{601A}$ and $R_{602A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

at least one combination of adjacent two or more of $R_{611}$ to $R_{621}$ may be mutually bonded to form a substituted or unsubstituted monocyclic ring, mutually bonded to form a substituted or unsubstituted fused ring, or not mutually bonded; and $R_{611}$ to $R_{621}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{601A}$ and $R_{602A}$ in the formula (62) are groups corresponding to $R_{601}$ and $R_{602}$ in the formula (6), respectively.

For instance, $R_{601A}$ and $R_{611}$ are optionally bonded with each other to form a bicyclic (or tri-or-more cyclic) nitrogen-containing heterocycle, in which the ring including $R_{601A}$ and $R_{611}$ and a benzene ring corresponding to the a ring are fused. Specific examples of the nitrogen-containing heterocycle include a compound corresponding to the nitrogen-containing bi(or-more)cyclic heterocyclic group in the specific example group G2. The same applies to $R_{601A}$ bonded with $R_{621}$, $R_{602A}$ bonded with $R_{613}$, and $R_{602A}$ bonded with $R_{614}$.

At least one combination of adjacent two or more of $R_{611}$ to $R_{621}$ may be mutually bonded to form a substituted or unsubstituted monocyclic ring, or mutually bonded to form a substituted or unsubstituted monocyclic ring.

For instance, $R_{611}$ and $R_{612}$ are mutually bonded to form a structure in which a benzene ring, indole ring, pyrrole ring, benzofuran ring, benzothiophene ring or the like is bonded to the six-membered ring bonded with $R_{611}$ and $R_{612}$, the resultant fused ring forming a naphthalene ring, carbazole ring, indole ring, dibenzofuran ring, or dibenzothiophene ring, respectively.

In an exemplary embodiment, $R_{611}$ to $R_{621}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, or a substituted or unsubstituted alkyl group having 1 to 50 carbon atoms.

In an exemplary embodiment, $R_{611}$ to $R_{621}$ not contributing to ring formation are each independently a hydrogen atom, or a substituted or unsubstituted alkyl group having 1 to 50 carbon atoms, and at least one of $R_{611}$ to $R_{621}$ is a substituted or unsubstituted alkyl group having 1 to 50 carbon atoms.

In an exemplary embodiment, the compound represented by the formula (62) is represented by a formula (63) below.

[Formula 256]

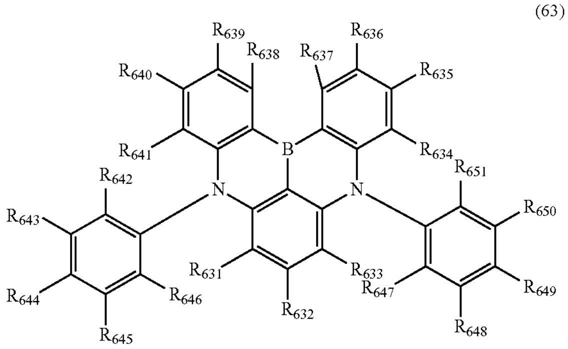

(63)

In the formula (63): $R_{631}$ is bonded with $R_{646}$ to form a substituted or unsubstituted heterocycle or does not form a substituted or unsubstituted heterocycle;

$R_{633}$ is bonded with $R_{647}$ to form a substituted or unsubstituted heterocycle or does not form a substituted or unsubstituted heterocycle;

$R_{634}$ is bonded with $R_{651}$ to form a substituted or unsubstituted heterocycle or does not form a substituted or unsubstituted heterocycle;

$R_{641}$ is bonded with $R_{642}$ to form a substituted or unsubstituted heterocycle or does not form a substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded; and $R_{631}$ to $R_{651}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{631}$ are optionally mutually bonded with $R_{646}$ to form a substituted or unsubstituted heterocycle. For instance, $R_{631}$ and $R_{646}$ are optionally bonded with each other to form a tri-or-more cyclic nitrogen-containing heterocycle, in which a benzene ring bonded with $R_{646}$, a ring including a nitrogen atom, and a benzene ring corresponding to the a ring are fused. Specific examples of the nitrogen-containing heterocycle include a compound corresponding to the nitrogen-containing tri(-or-more)cyclic heterocyclic group in the specific example group G2. The same applies to $R_{633}$ bonded with $R_{647}$, $R_{634}$ bonded with $R_{651}$, and $R_{641}$ bonded with $R_{642}$.

In an exemplary embodiment, $R_{631}$ to $R_{651}$, which do not contribute to ring formation, are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$, which do not contribute to ring formation, are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$, which do not contribute to ring formation, are each independently a hydrogen atom, or a substituted or unsubstituted alkyl group having 1 to 50 carbon atoms.

In an exemplary embodiment, $R_{631}$ to $R_{651}$, which do not contribute to ring formation, are each independently a hydrogen atom, or a substituted or unsubstituted alkyl group having 1 to 50 carbon atoms, and at least one of $R_{631}$ to $R_{651}$ is a substituted or unsubstituted alkyl group having 1 to 50 carbon atoms.

In an exemplary embodiment, the compound represented by the formula (63) is represented by a formula (63A) below.

[Formula 258]

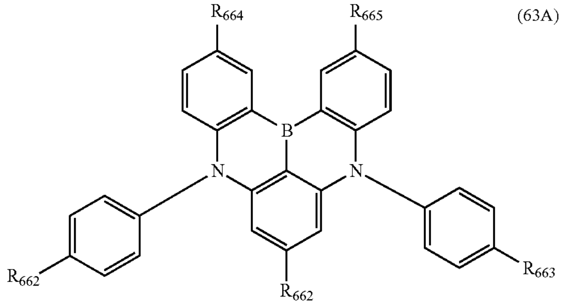

(63A)

In the formula (63A): $R_{661}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{662}$ to $R_{665}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{661}$ to $R_{665}$, which do not contribute to ring formation, are each independently a substituted or unsubstituted alkyl group having 1 to 50 carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms.

In an exemplary embodiment, the compound represented by the formula (63) is represented by a formula (63B) below.

[Formula 259]

(63B)

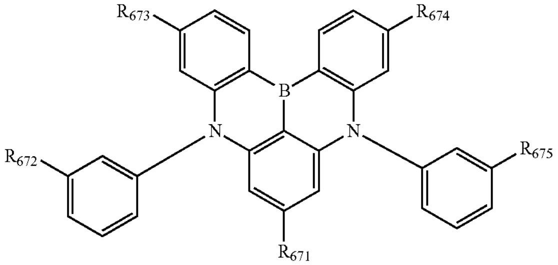

In the formula (63B): $R_{671}$ and $R_{672}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, or a substituted or unsubstituted aryl group having 6 to 50 ring carbon atoms; and $R_{673}$ to $R_{675}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, or a substituted or unsubstituted aryl group having 6 to 50 ring carbon atoms.

In an exemplary embodiment, the compound represented by the formula (63) is represented by a formula (63B') below.

[Formula 260]

(63B')

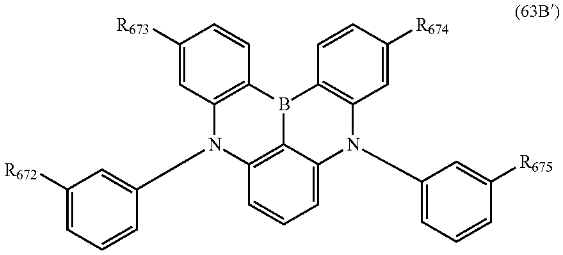

In the formula (63B'), $R_{672}$ to $R_{675}$ each independently represent the same as $R_{672}$ to $R_{675}$ in the formula (63B).

In an exemplary embodiment, at least one of $R_{671}$ to $R_{675}$ is: a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, or a substituted or unsubstituted aryl group having 6 to 50 ring carbon atoms; and In an exemplary embodiment: $R_{672}$ is a hydrogen atom, a substituted or unsubstituted alkyl group having 1 to 50 carbon atoms, a group represented by —$N(R_{906})(R_{907})$, or a substituted or unsubstituted aryl group having 6 to 50 ring carbon atoms; and $R_{671}$, and $R_{673}$ to $R_{675}$ are each independently a substituted or unsubstituted alkyl group having 1 to 50 carbon atoms, a group represented by —$N(R_{906})(R_{907})$, or a substituted or unsubstituted aryl group having 6 to 50 ring carbon atoms.

In an exemplary embodiment, the compound represented by the formula (63) is represented by a formula (63C) below.

[Formula 261]

(63C)

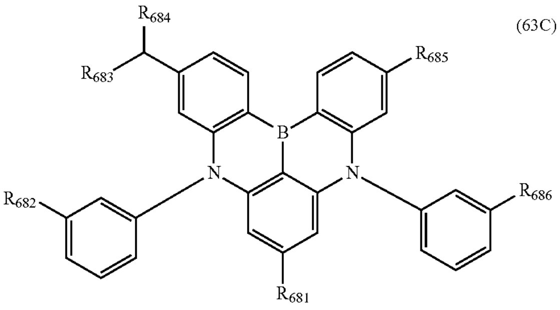

In the formula (63C): $R_{681}$ and $R_{682}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{683}$ to $R_{686}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (63) is represented by a formula (63C') below.

[Formula 262]

(63C')

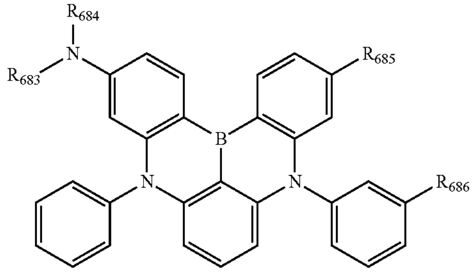

In the formula (63C'), $R_{683}$ to $R_{686}$ each independently represent the same as $R_{683}$ to $R_{686}$ in the formula (63C).

In an exemplary embodiment, $R_{681}$ to $R_{686}$, which do not contribute to ring formation, are each independently a substituted or unsubstituted alkyl group having 1 to 50 carbon atoms, or a substituted or unsubstituted aryl group having 6 to 50 ring carbon atoms.

In an exemplary embodiment, $R_{681}$ to $R_{686}$ are each independently a substituted or unsubstituted aryl group having 6 to 50 ring carbon atoms.

The compound represented by the formula (6) is producible by initially bonding the a ring, b ring and c ring with linking groups (a group including N—$R_{601}$ and a group including N—$R_{602}$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel-Crafts Reactions or the like is applicable.

Specific Examples of Compound Represented by Formula (6)

Specific examples of the compound represented by the formula (6) are shown below. It should however be noted that these specific examples are merely exemplary and do not limit the compound represented by the formula (6).

[Formula 263]

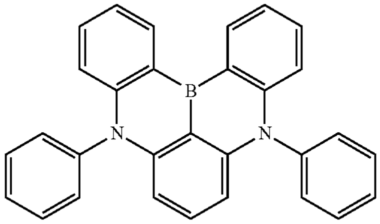

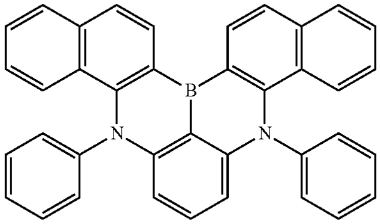

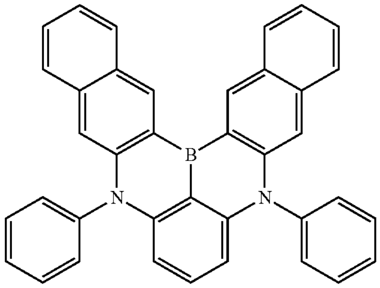

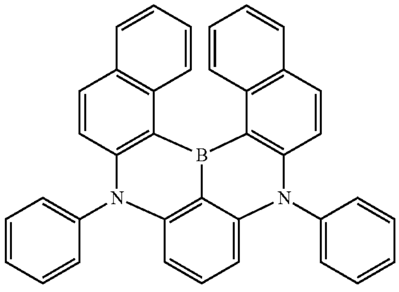

-continued

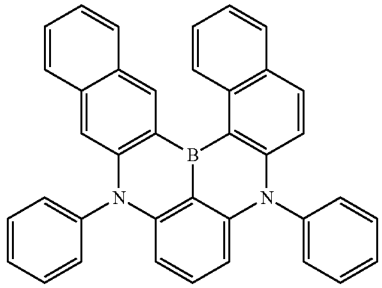

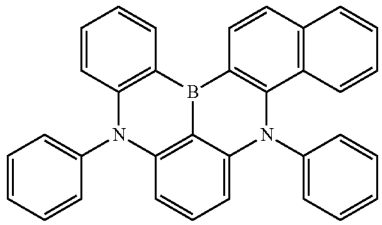

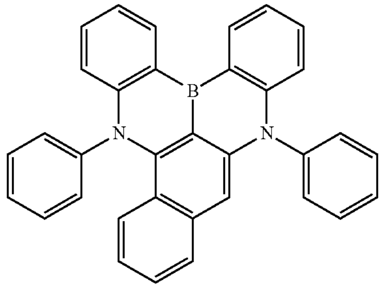

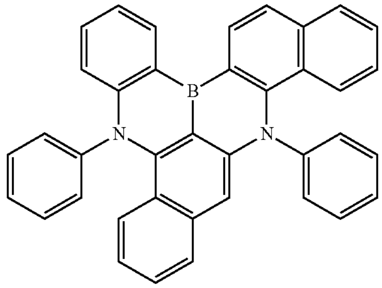

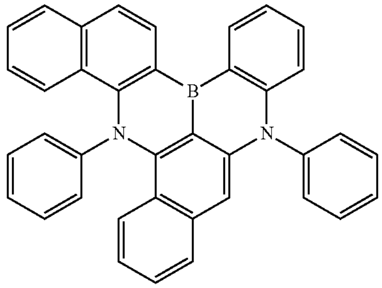

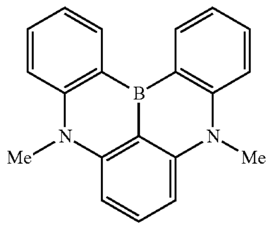

-continued
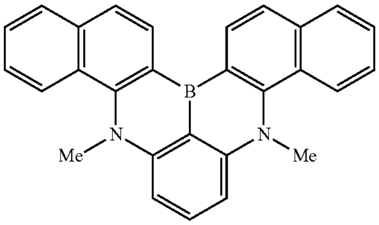
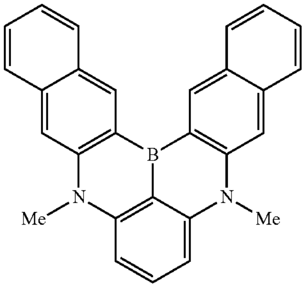
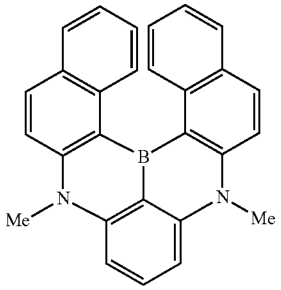
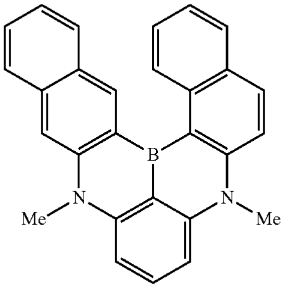
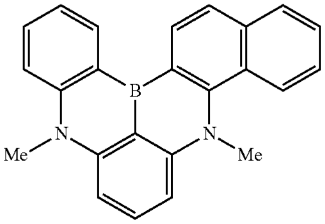
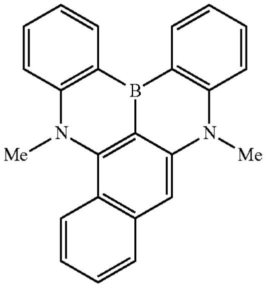
-continued
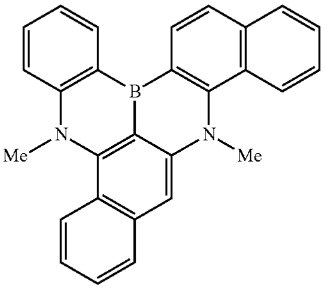
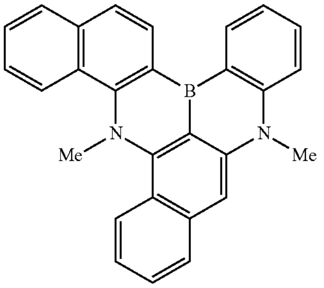
[Formula 264]
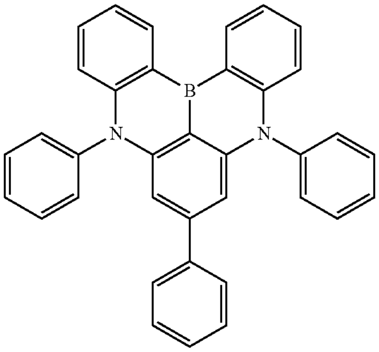
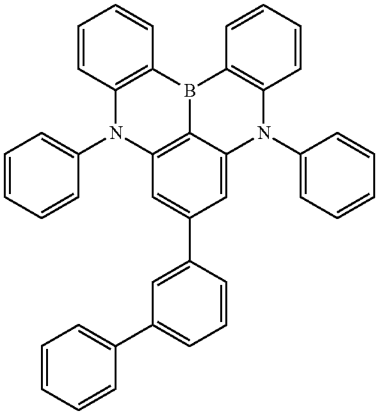

-continued
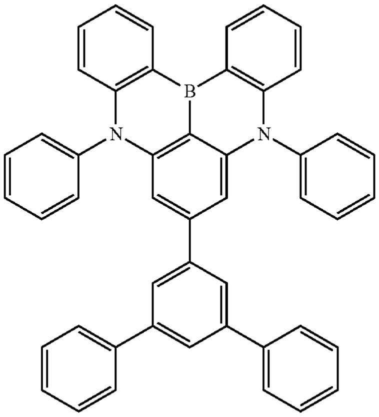
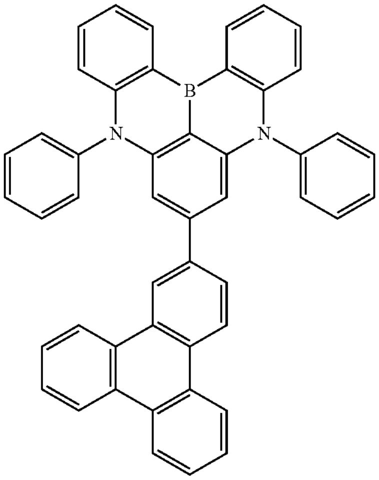
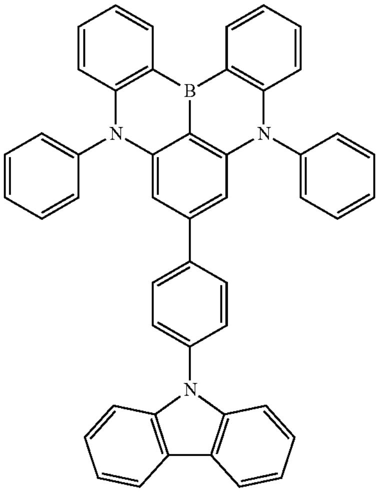
-continued
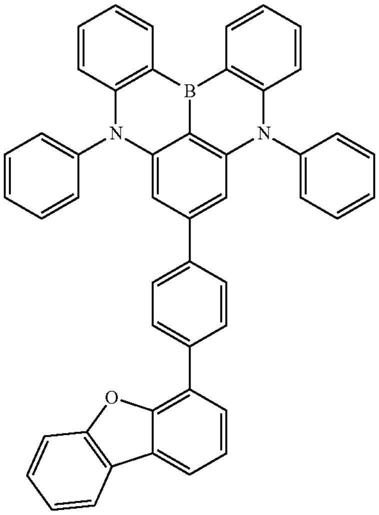
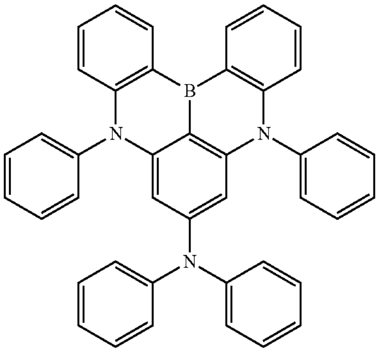
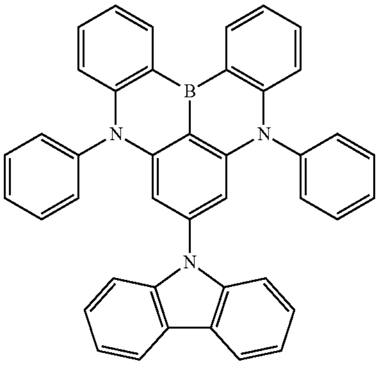
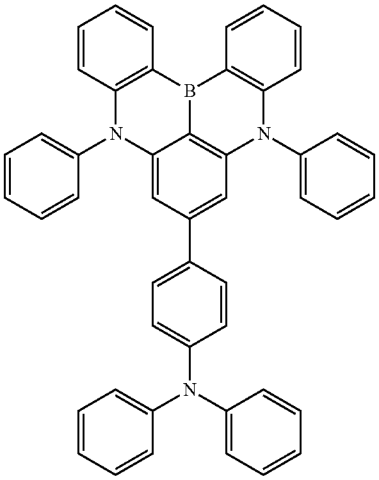

-continued
[Formula 265]
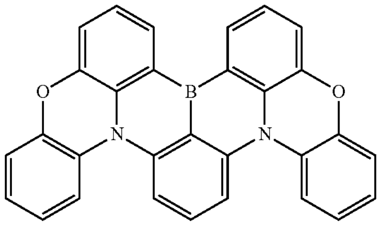
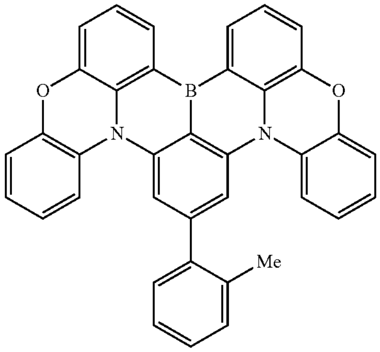
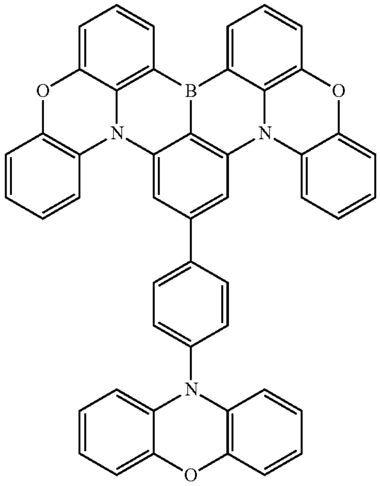
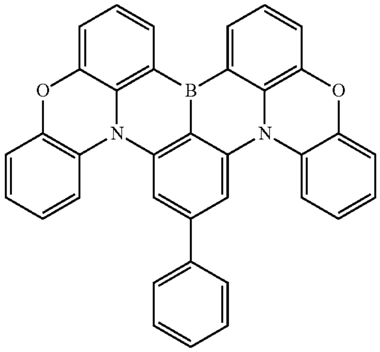
-continued
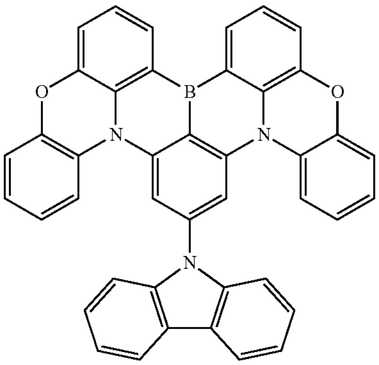
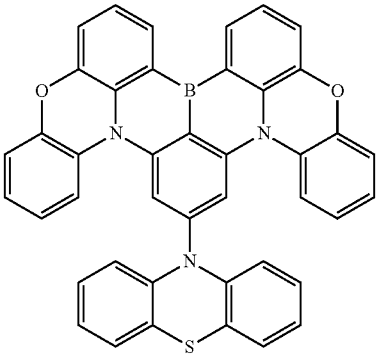
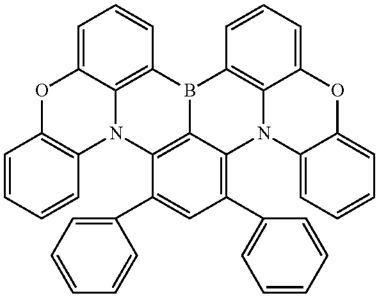
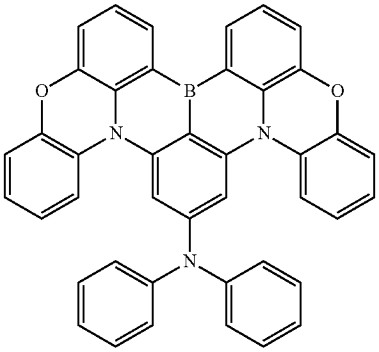

-continued
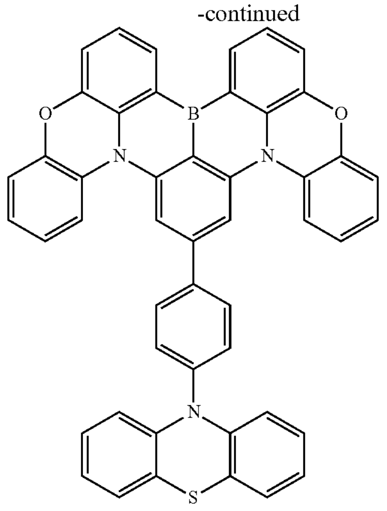
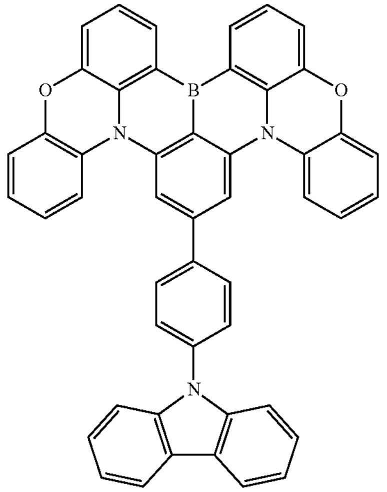
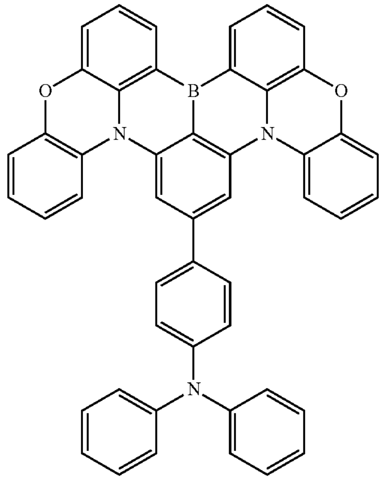
-continued
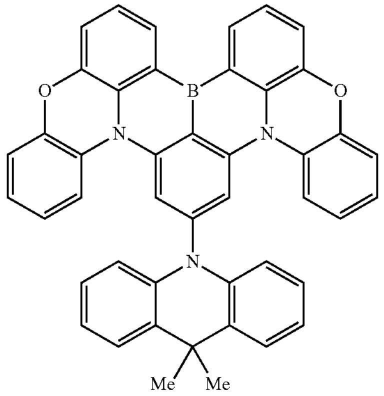
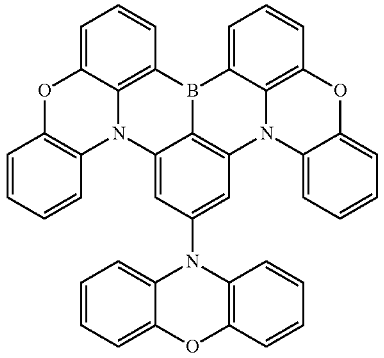
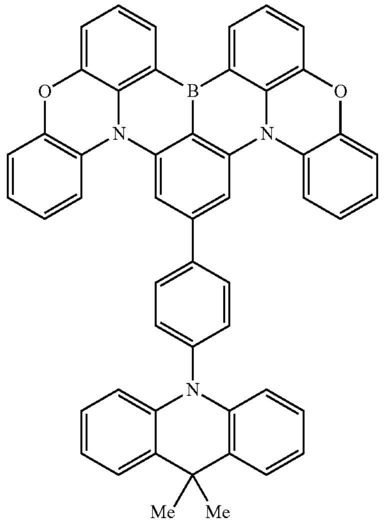
[Formula 266]
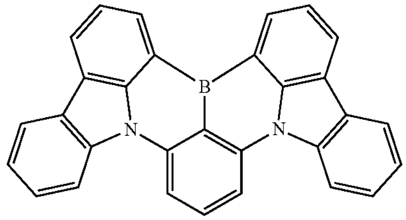

-continued
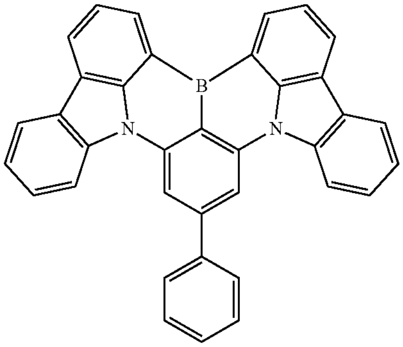
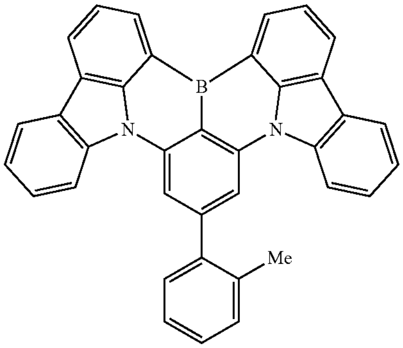
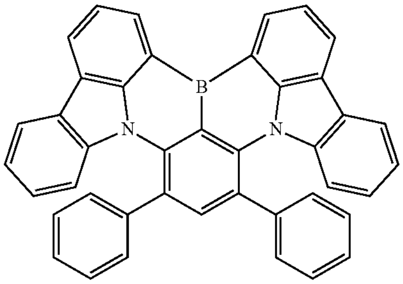
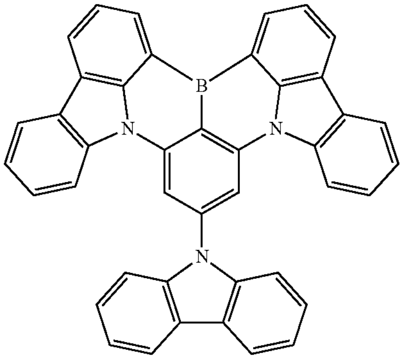
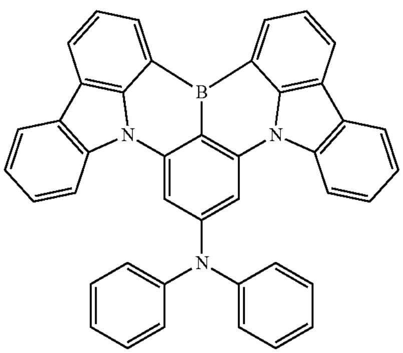
-continued
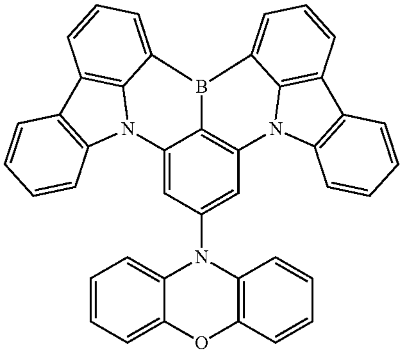
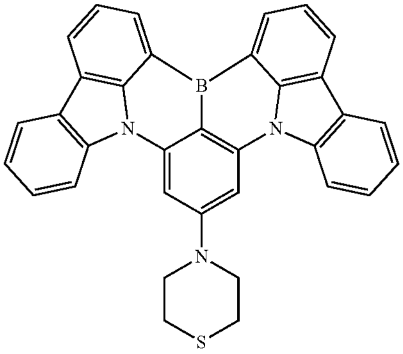
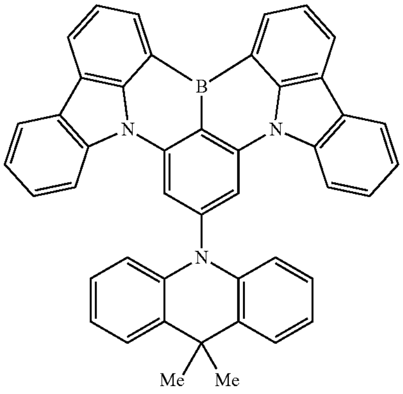
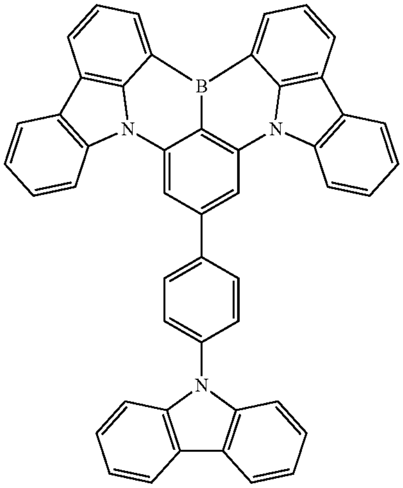

-continued
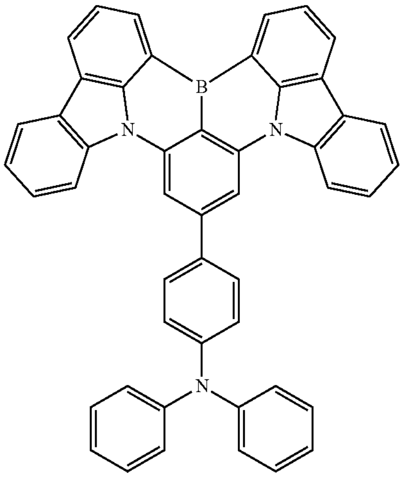
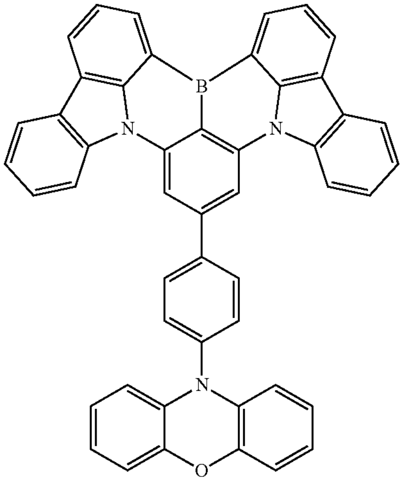
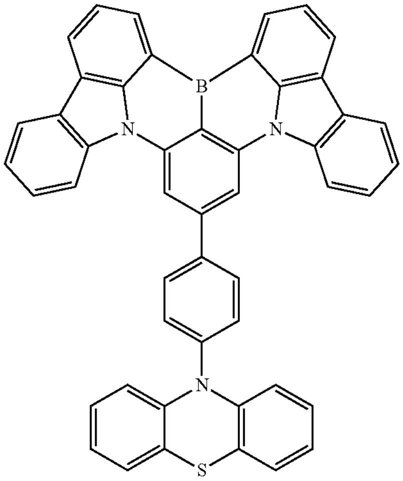
-continued
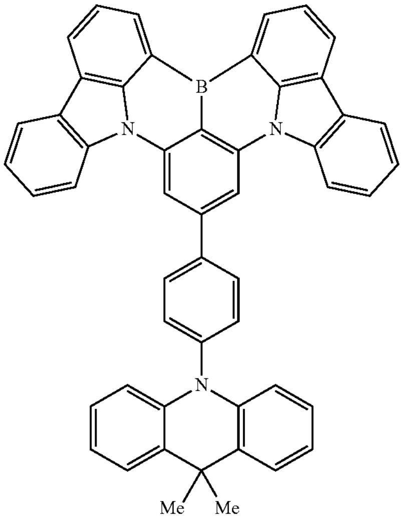
[Formula 267]
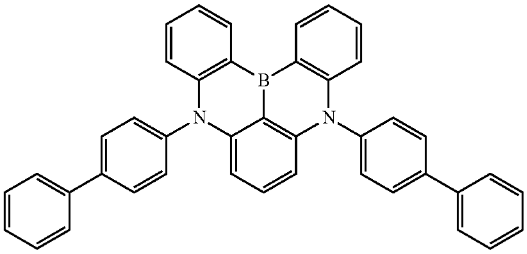
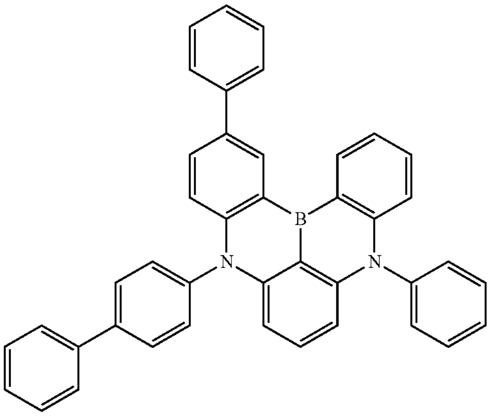
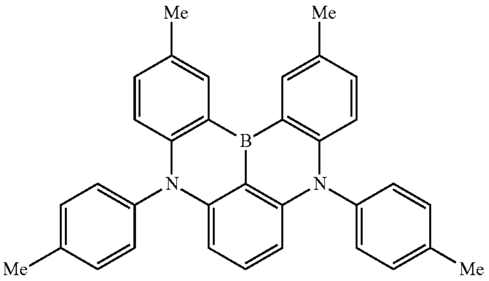

-continued
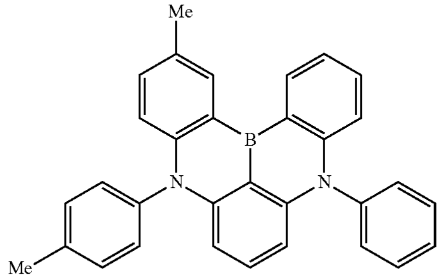
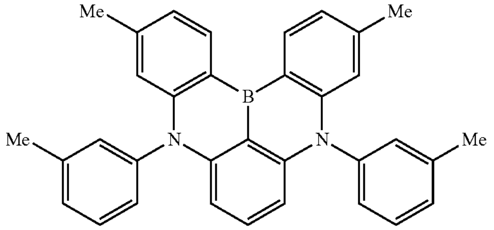
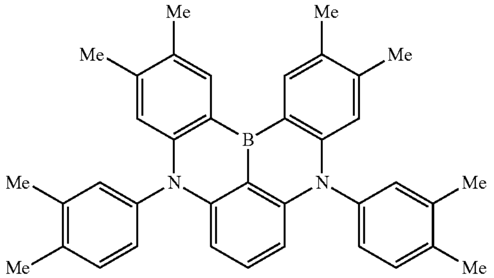
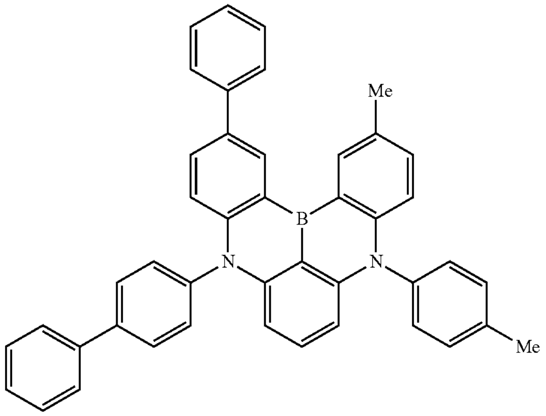
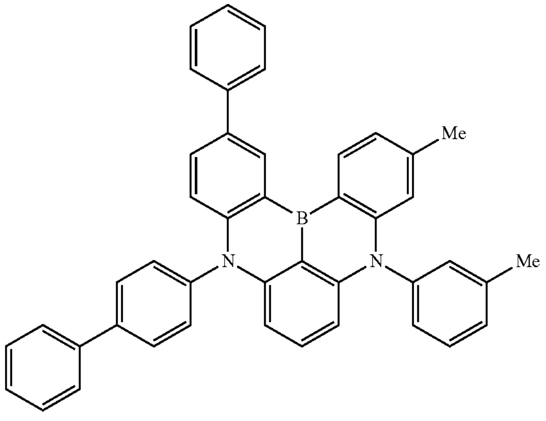
-continued
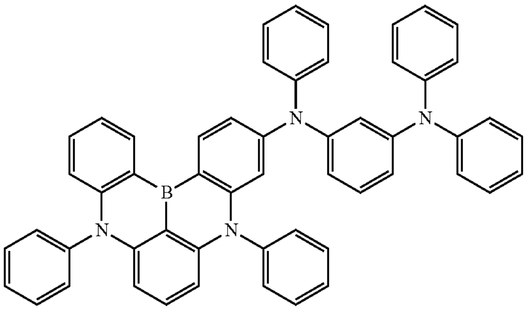
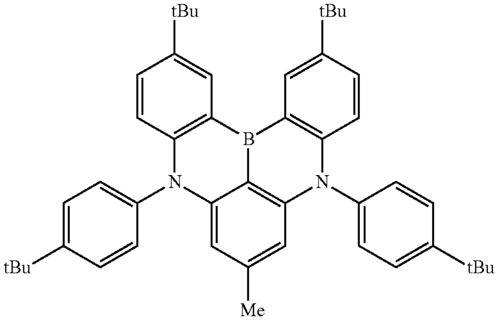
[Formula 268]
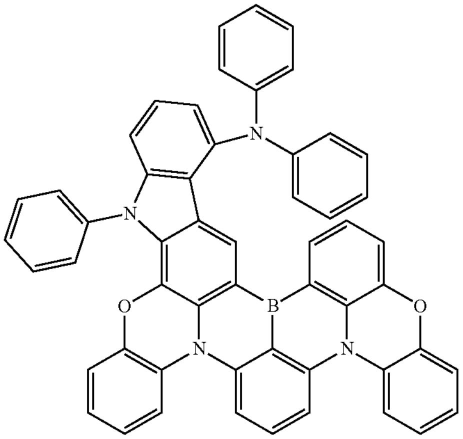
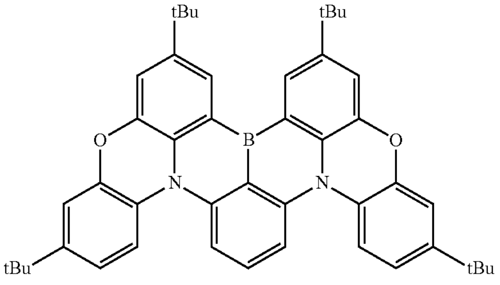
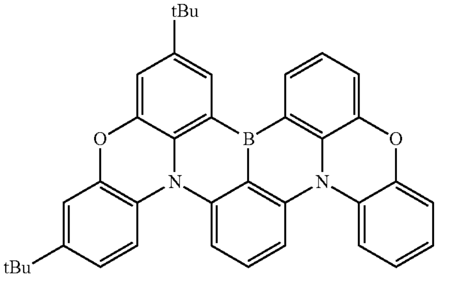

-continued
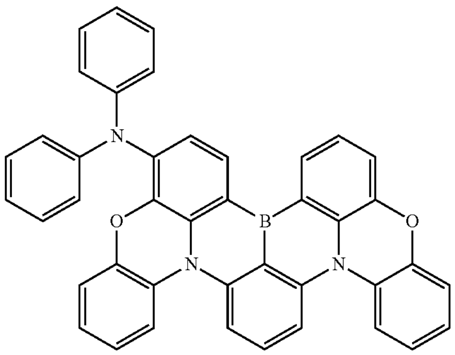
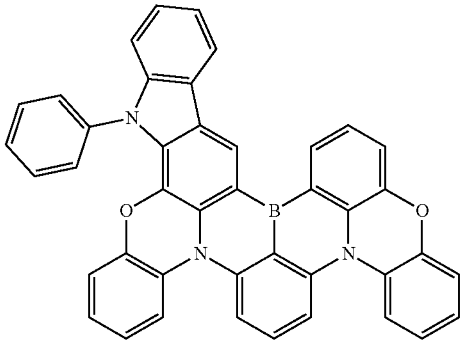
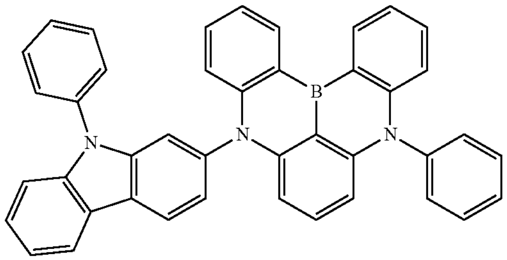
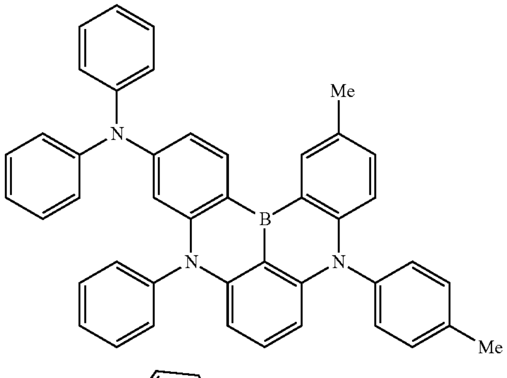
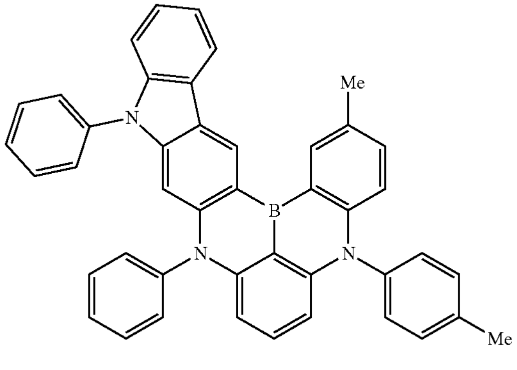
-continued
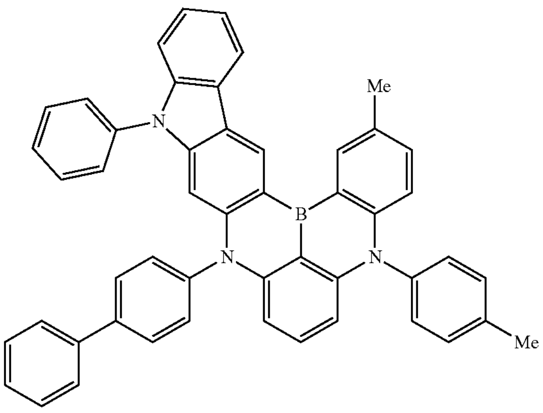
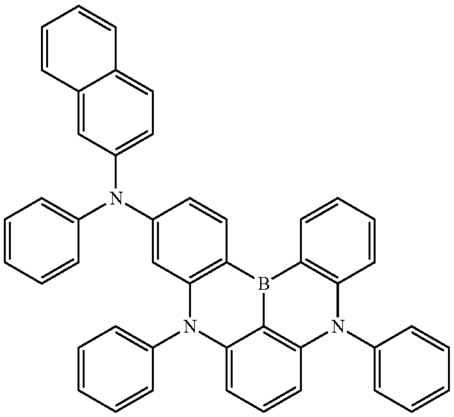
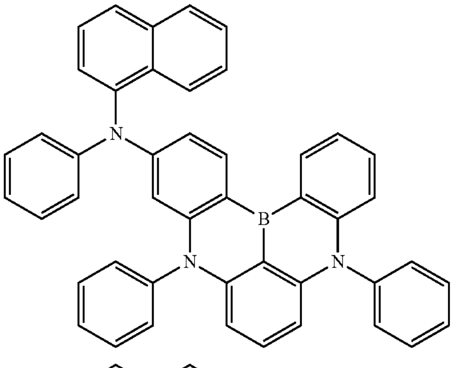
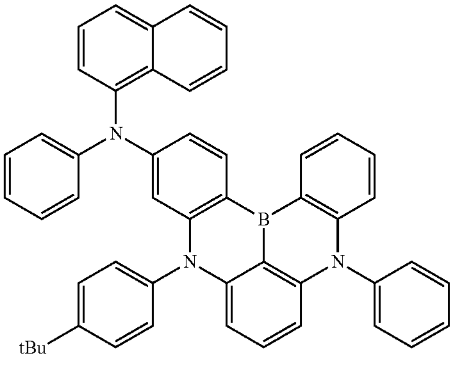

-continued
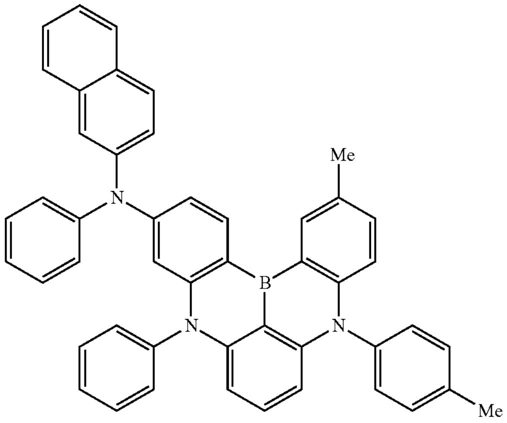
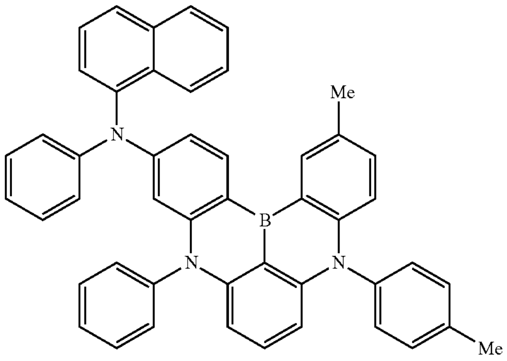
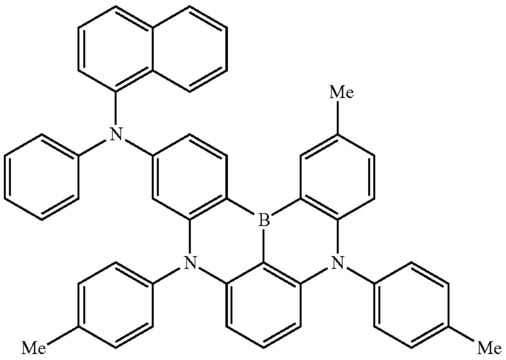
[Formula 269]
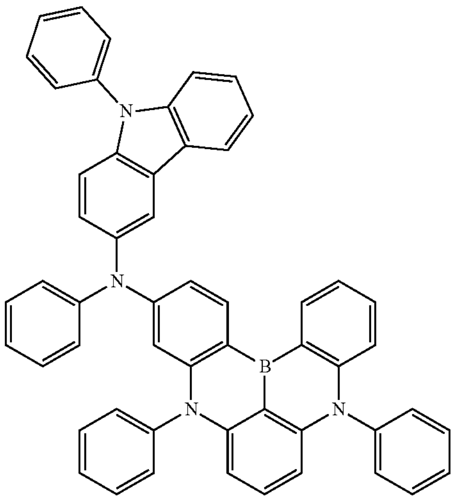
-continued
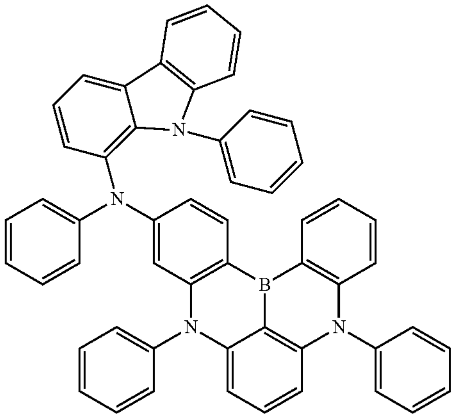
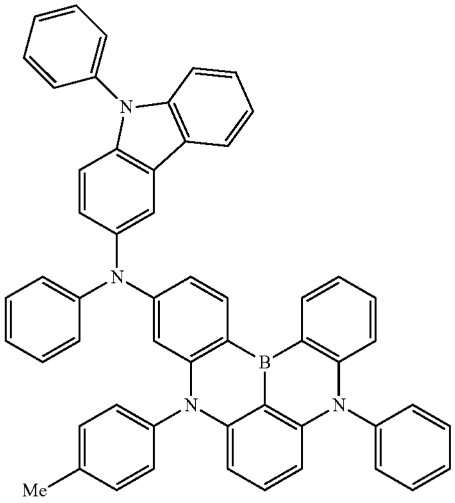
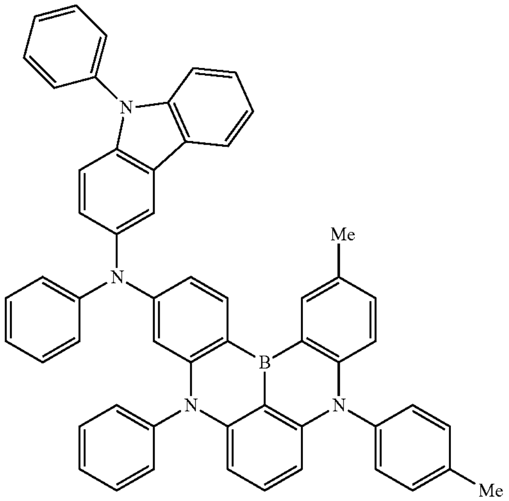

-continued
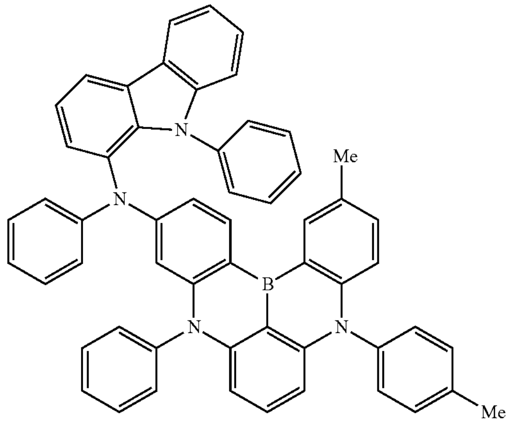
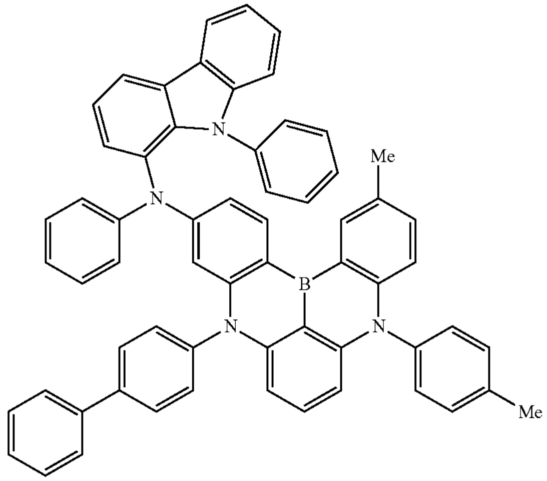
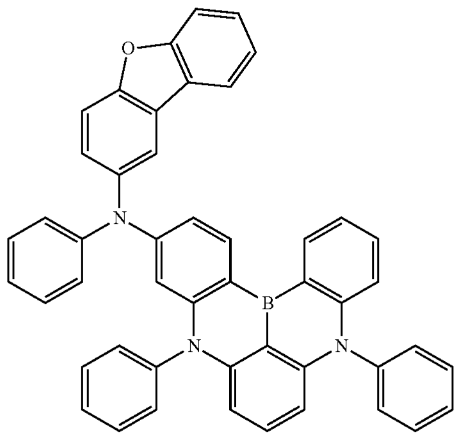
-continued
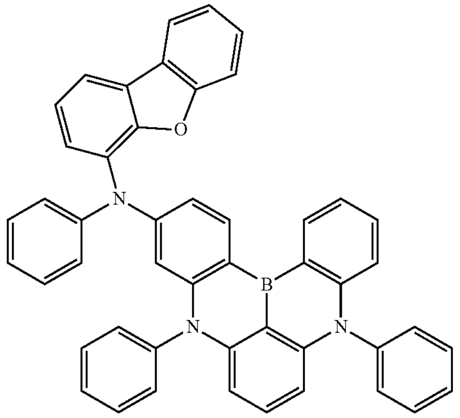
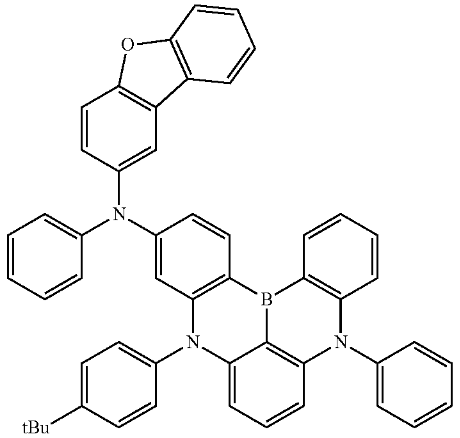
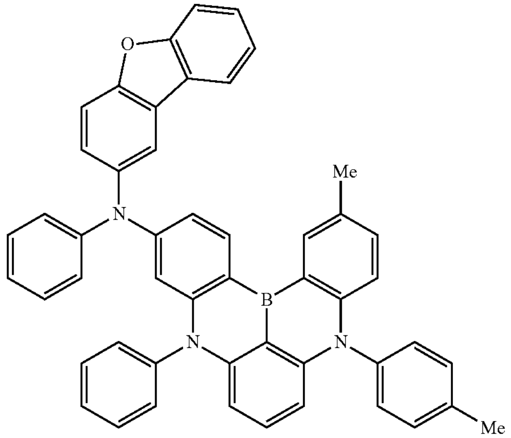
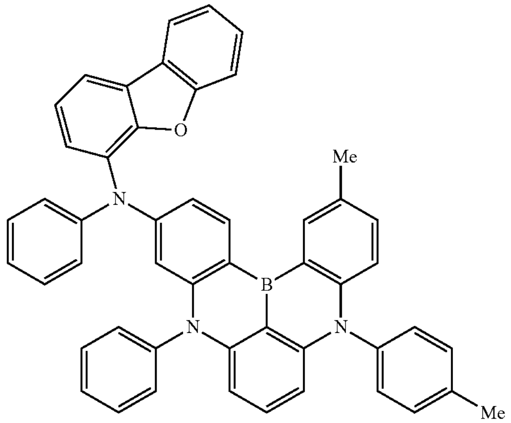

-continued
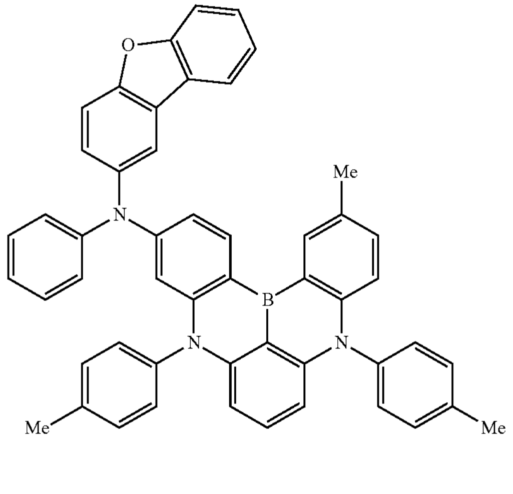
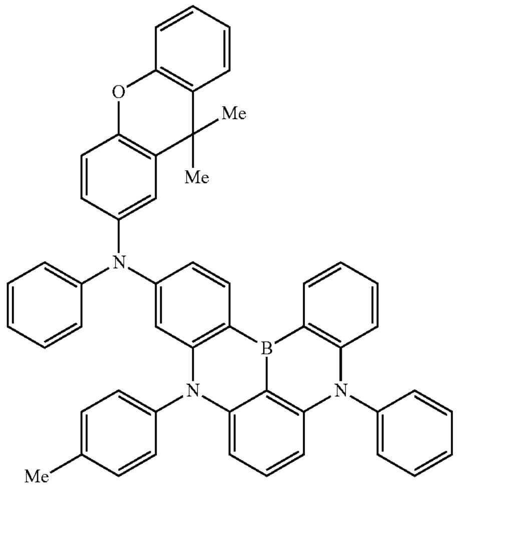
[Formula 270]
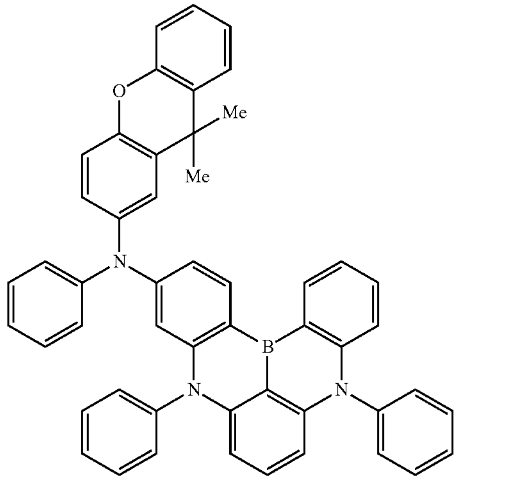
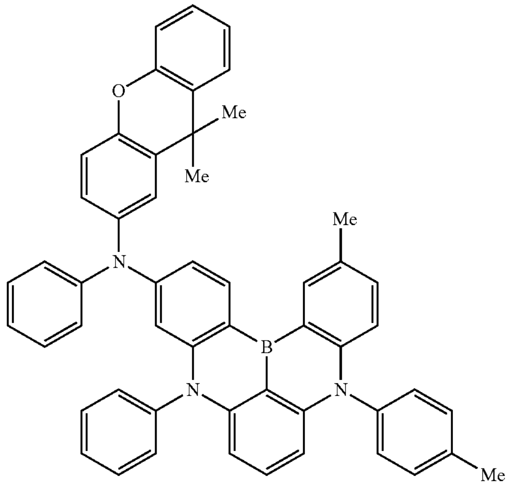
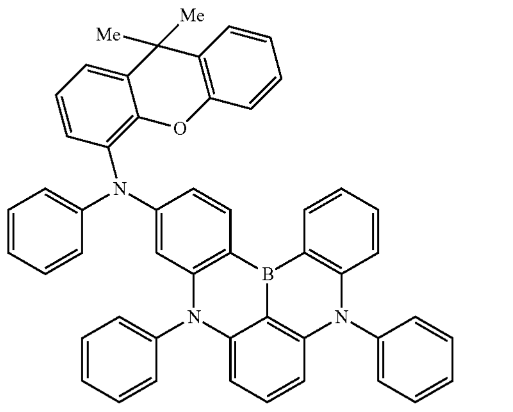
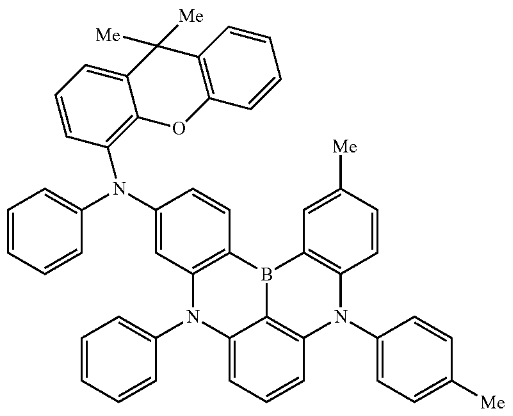

-continued
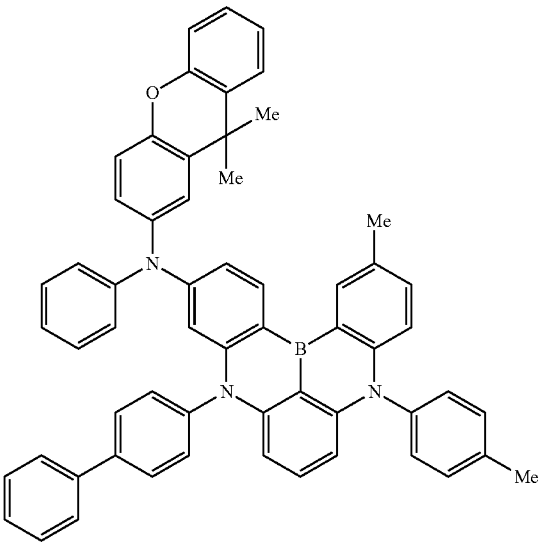
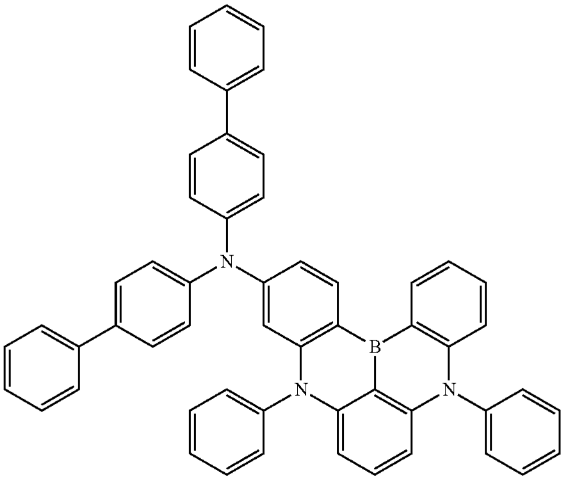
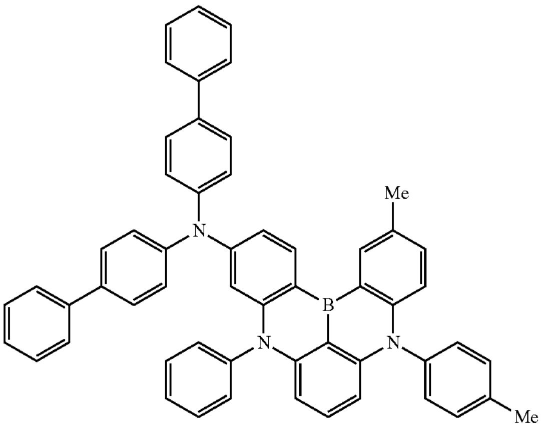
-continued
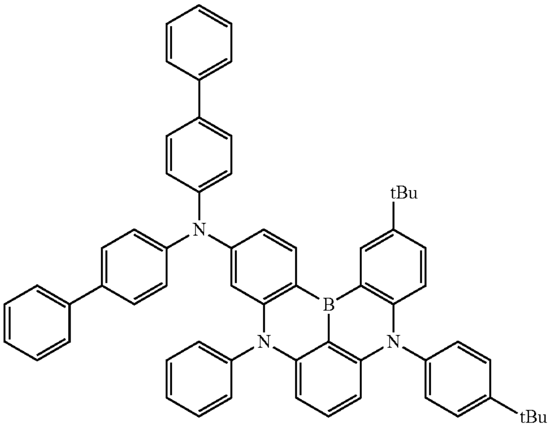
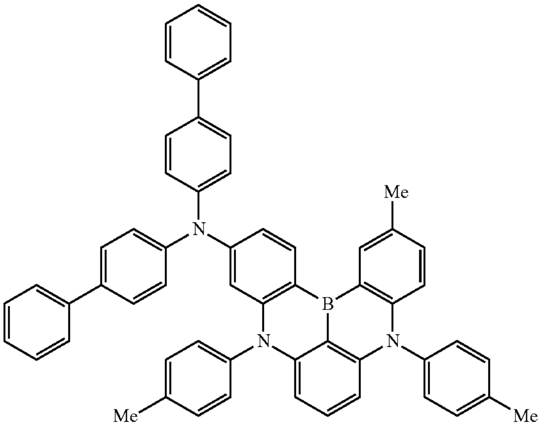
[Formula 271]
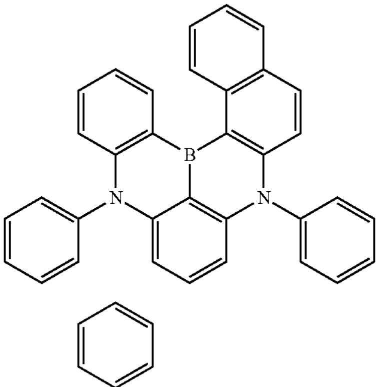
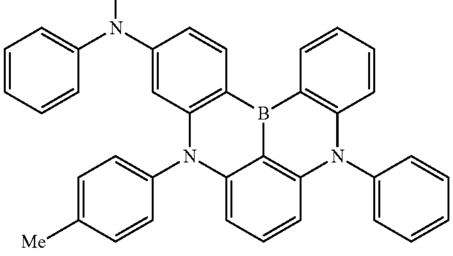

-continued
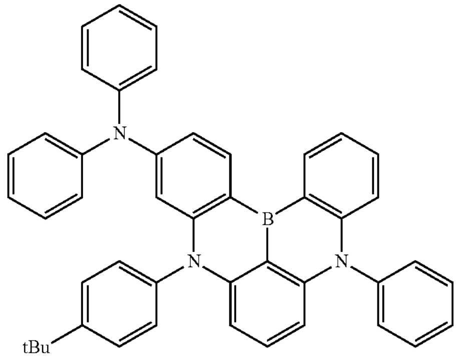
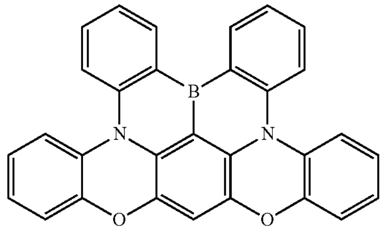
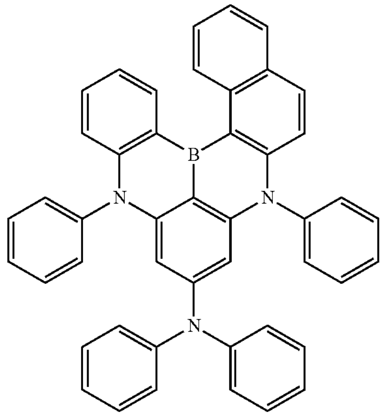
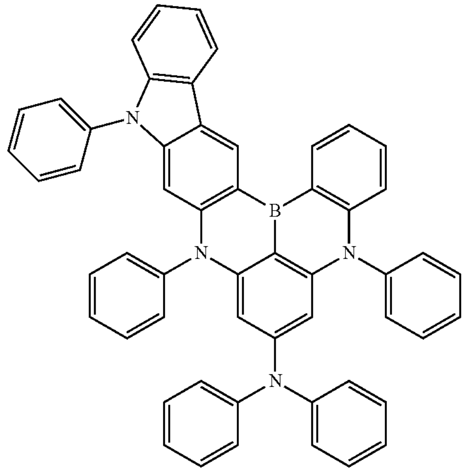
-continued
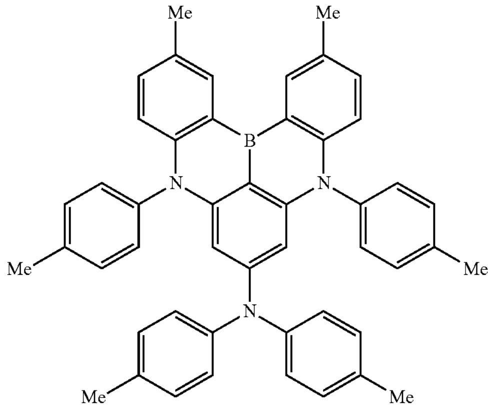
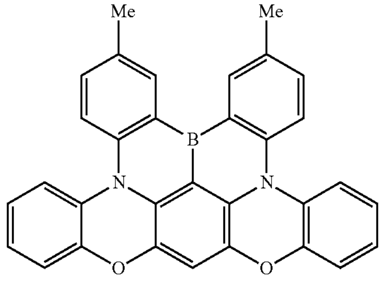
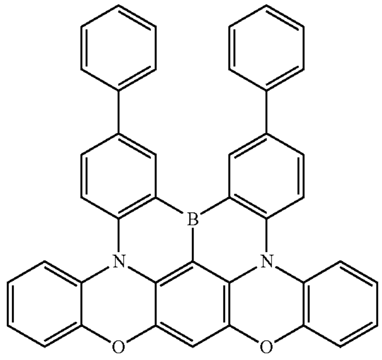
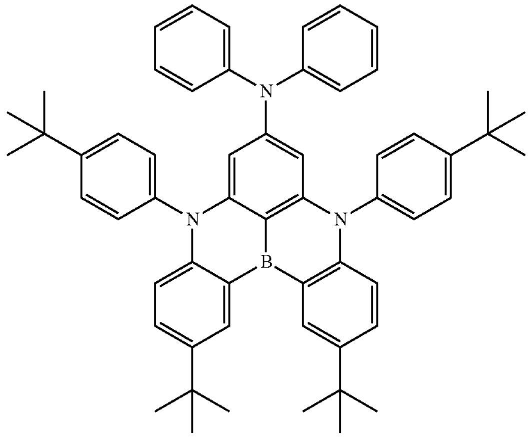

[Formula 272]
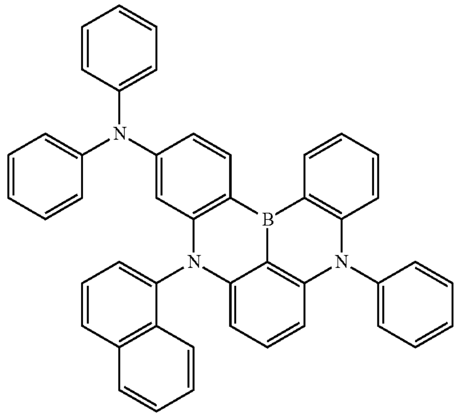
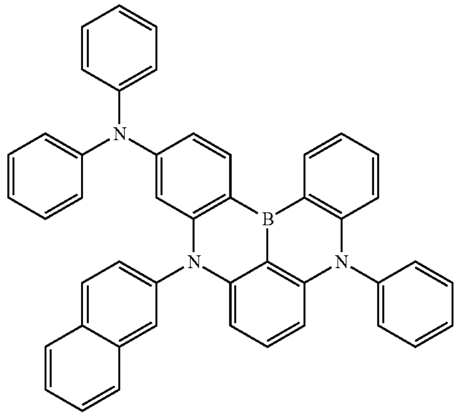
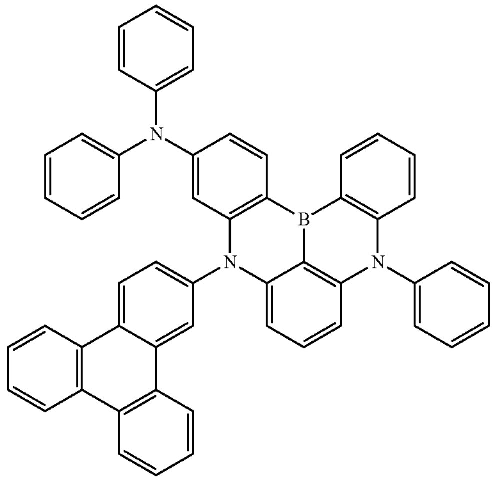
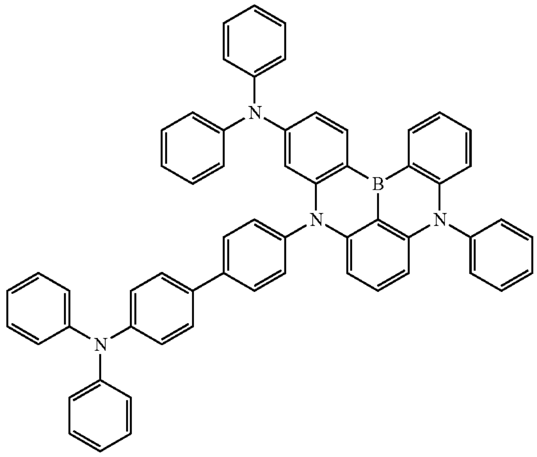
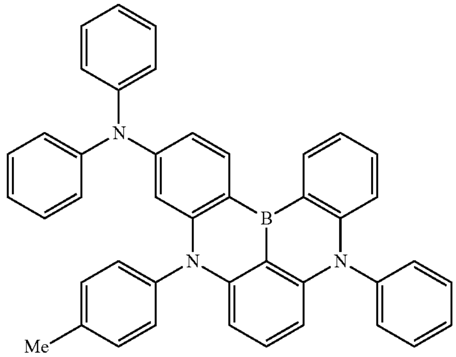
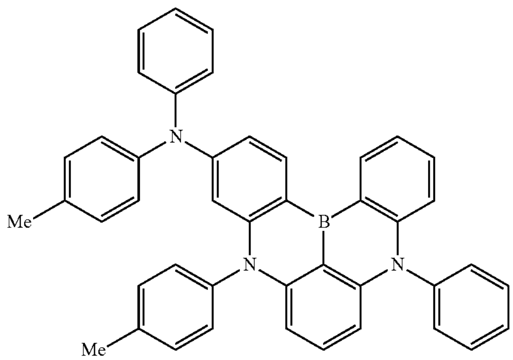
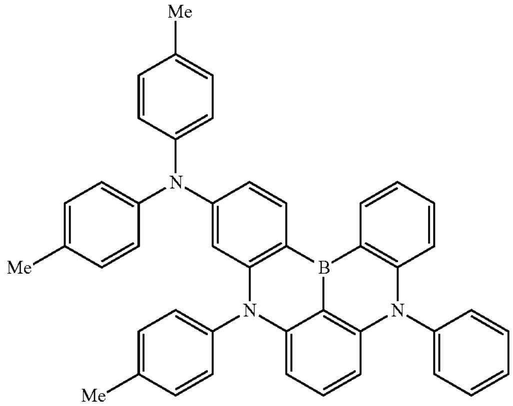

-continued
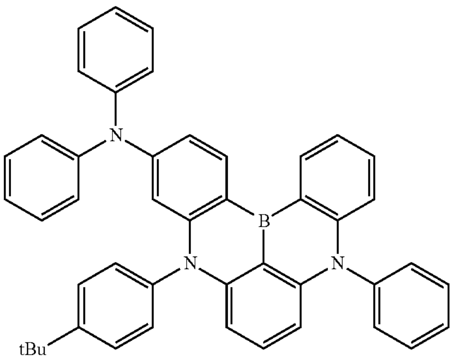
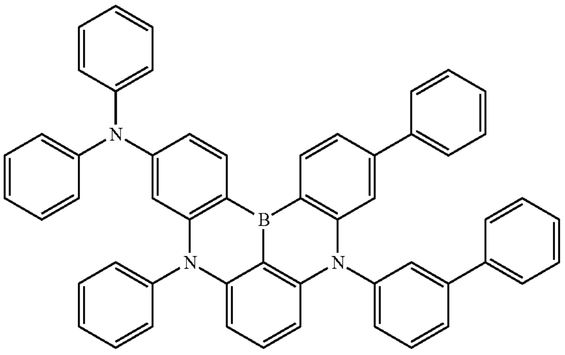
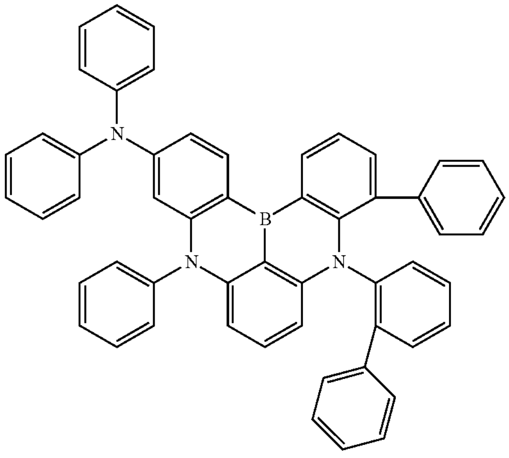
[Formula 273]
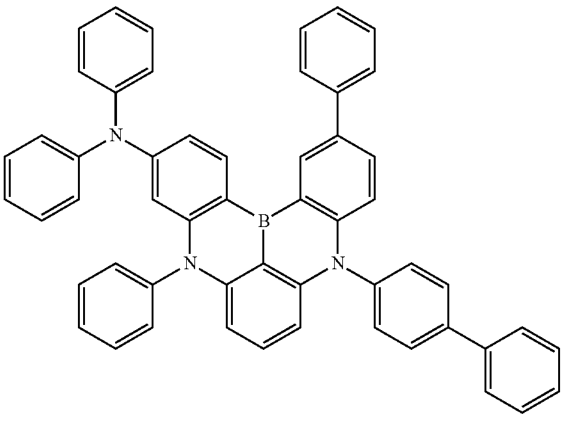
-continued
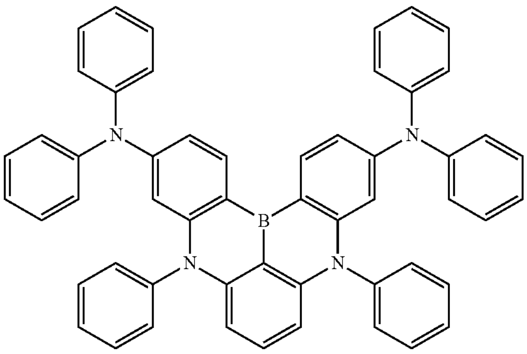
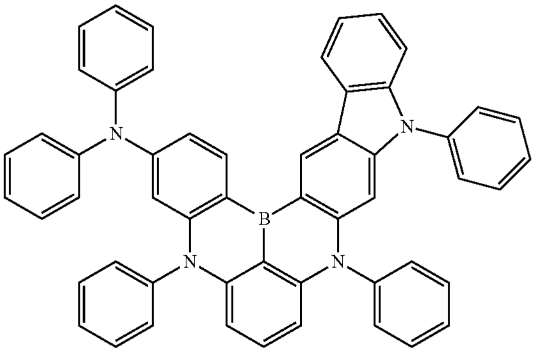
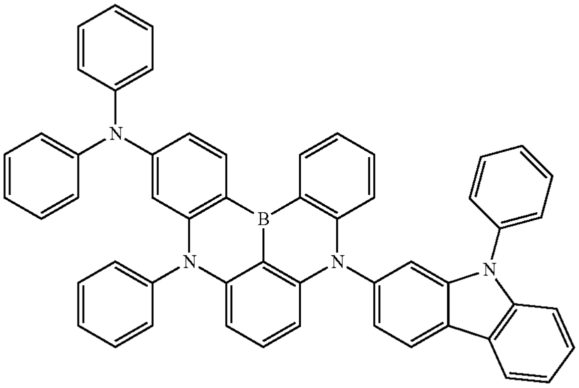
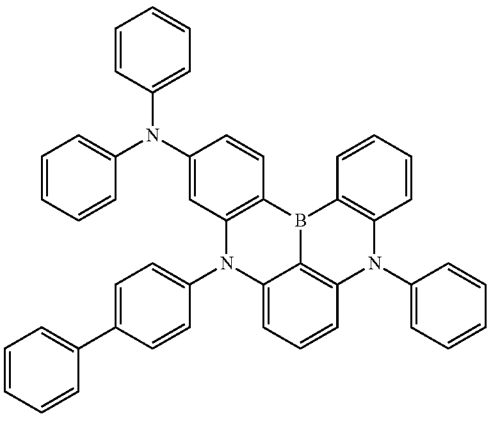

-continued
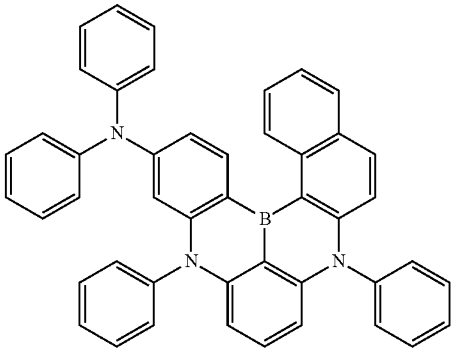
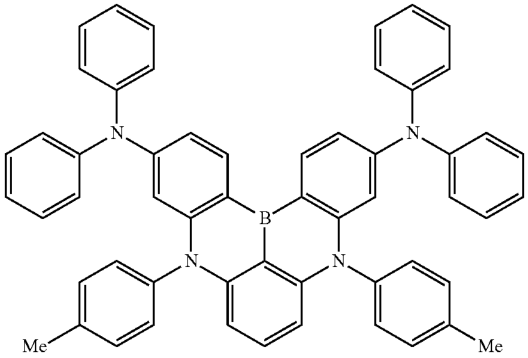
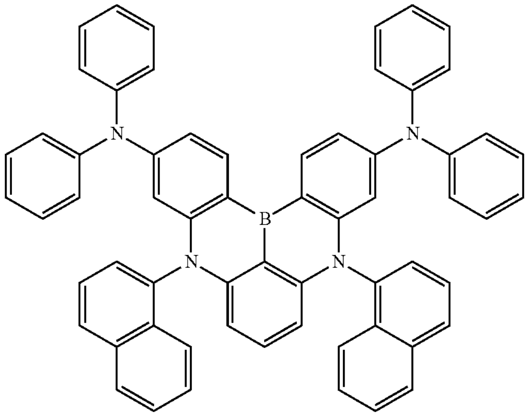
[Formula 274]
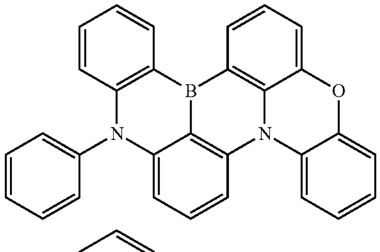
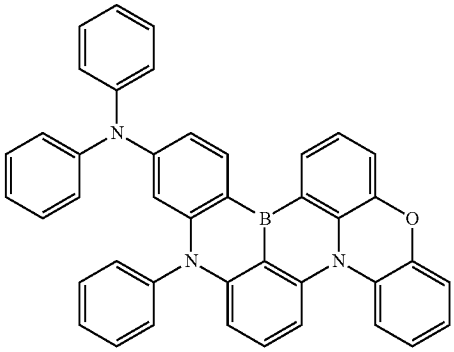
-continued
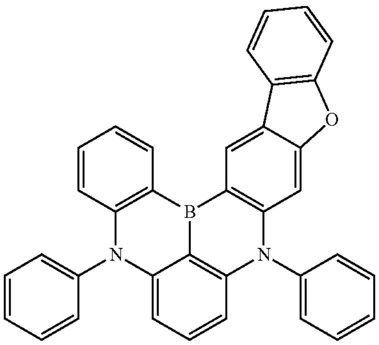
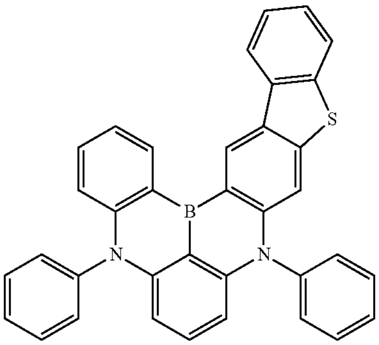
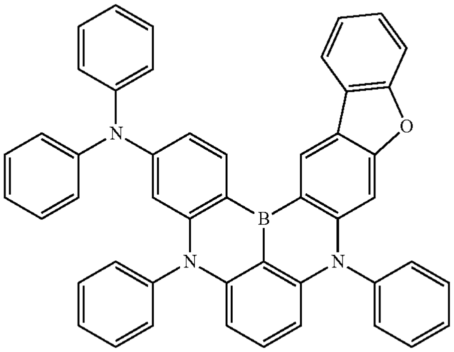
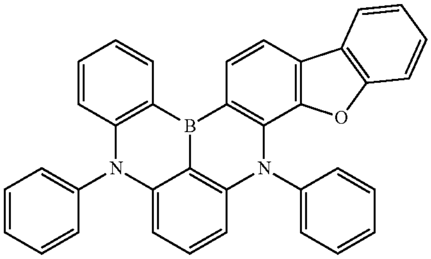
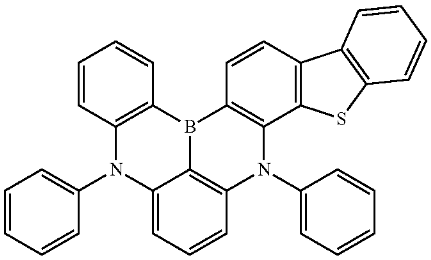

-continued

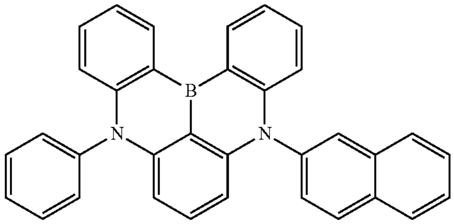

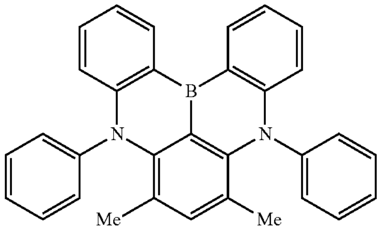

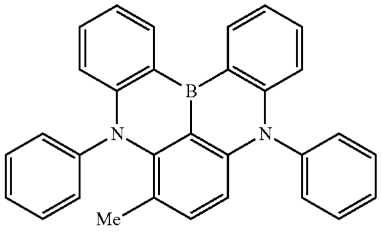

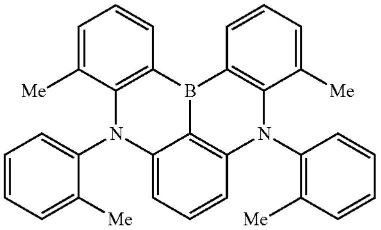

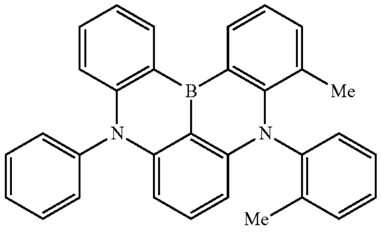

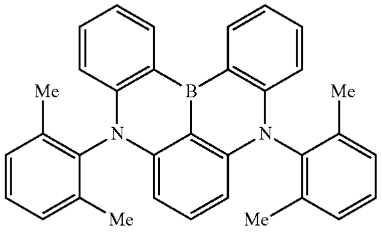

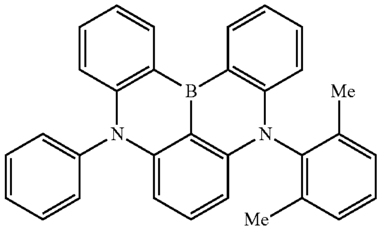

Compound Represented by Formula (7)

The compound represented by the formula (7) will be described below.

[Formula 275]

p—q—r—s—t (7)

[Formula 276]

(72)

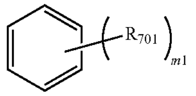

(73)

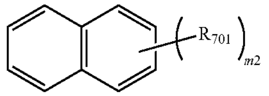

(74)

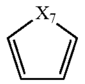

(75)

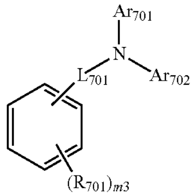

(76)

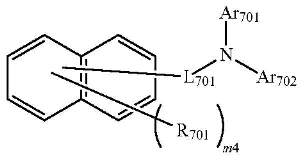

In the formula (7): r ring is a ring represented by the formula (72) or the formula (73), the r ring being fused with at any position(s) of respective adjacent rings;

q ring and s ring are each independently a ring represented by the formula (74) and fused with any position(s) of respective adjacent rings;

p ring and t ring are each independently a moiety represented by the formula (75) or the formula (76) and fused with any position(s) of respective adjacent rings;

$X_7$ is an oxygen atom, a sulfur atom, or $NR_{702}$;

when a plurality of $R_{701}$ are present, adjacent ones of the plurality of $R_{701}$ are mutually bonded to form a substituted or unsubstituted monocyclic ring, mutually bonded to form a substituted or unsubstituted fused ring, or not mutually bonded;

$R_{701}$ and $R_{702}$ not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

$Ar_{701}$ and $Ar_{702}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{701}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is 0, 1, or 2;

m2 is 0, 1, 2, 3, or 4;

m3 is each independently 0, 1, 2, 3 or 3;

m4 is each independently 0, 1, 2, 3, 4, or 5;

when a plurality of $R_{701}$ are present, the plurality of $R_{701}$ are mutually the same or different;

when a plurality of $X_7$ are present, the plurality of $X_7$ are mutually the same or different;

when a plurality of $R_{702}$ are present, the plurality of $R_{702}$ are mutually the same or different;

when a plurality of $Ar_{701}$ are present, the plurality of $Ar_{701}$ are mutually the same or different;

when a plurality of $Ar_{702}$ are present, the plurality of $Ar_{702}$ are mutually the same or different; and when a plurality of $L_{701}$ are present, the plurality of $L_{701}$ are mutually the same or different.

In the formula (7), each of the p ring, q ring, r ring, s ring, and t ring is fused with an adjacent ring(s) sharing two carbon atoms. The fused position and orientation are not limited but may be defined as required.

In an exemplary embodiment, in the formula (72) or the formula (73) representing the r ring, m1 is 0 or m2 is 0.

In an exemplary embodiment, the compound represented by the formula (7) is represented by any one of formulae (71-1) to (71-6) below.

[Formula 277]

(71-1)

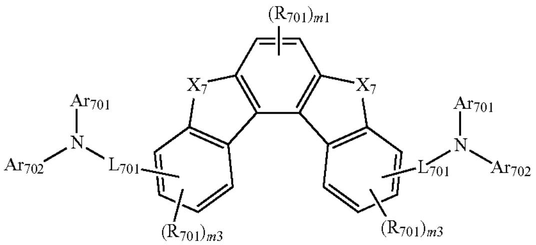

[Formula 278]

(71-2)

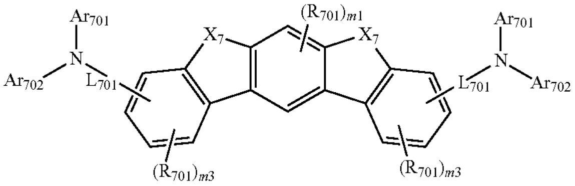

-continued

[Formula 279]

(71-3)

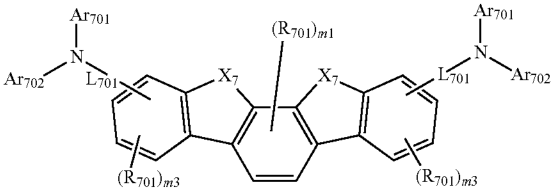

[Formula 280]

(71-4)

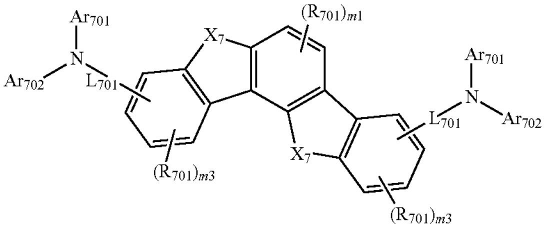

[Formula 281]

(71-5)

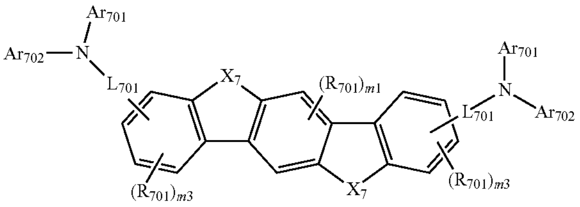

[Formula 282]

(71-6)

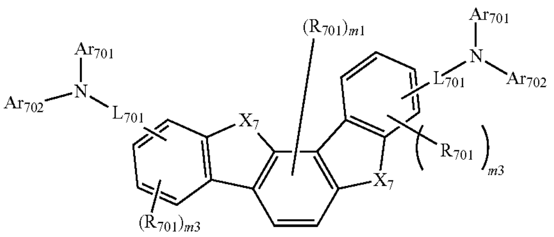

In the formulae (71-1) to (71-6), $R_{701}$, $X_7$, $Ar_{701}$, $Ar_{702}$, $L_{701}$, m1, and m3 respectively represent the same as $R_{701}$, $X_7$, $Ar_{701}$, $Ar_{702}$, $L_{701}$, m1, and m3 in the formula (7).

In an exemplary embodiment, the compound represented by the formula (7) is represented by any one of formulae (71-11) to (71-13) below.

[Formula 283]

(71-11)

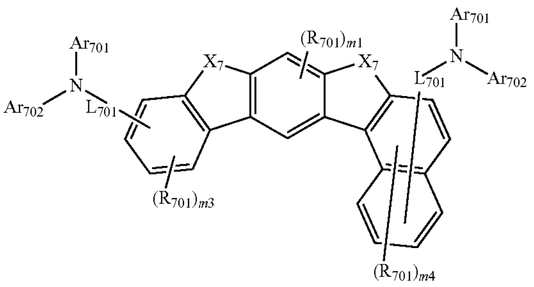

[Formula 284]

(71-12)

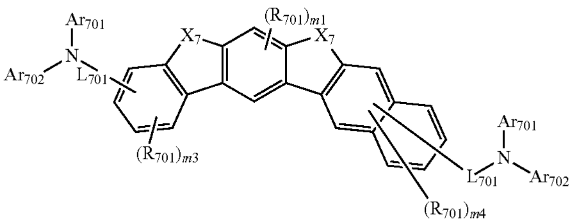

[Formula 285]

(71-13)

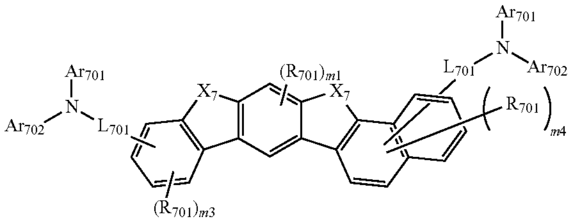

In the formulae (71-11) to (71-13), $R_{701}$, $X_7$, $Ar_{701}$, $Ar_{702}$, $L_{701}$, m1, m3 and m4 respectively represent the same as $R_{701}$, $X_7$, $Ar_{701}$, $Ar_{702}$, $L_{701}$, m1, m3 and m4 in the formula (7).

In an exemplary embodiment, the compound represented by the formula (7) is represented by any one of formulae (71-21) to (71-25) below.

[Formula 286]

(71-21)

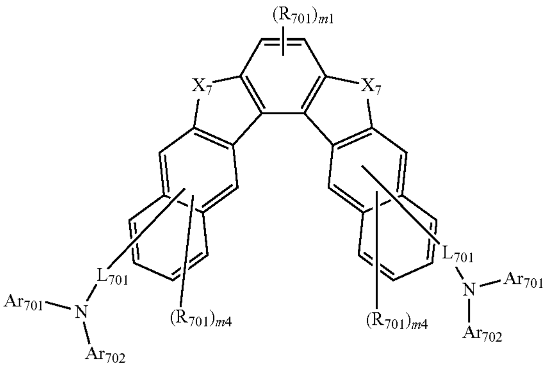

[Formula 287]

-continued (71-22)

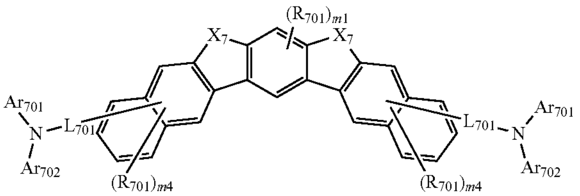

[Formula 288]

(71-23)

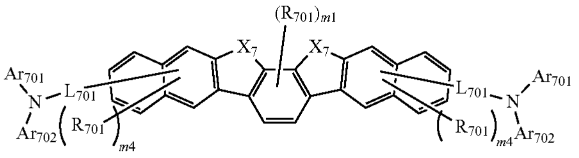

[Formula 289]

(71-24)

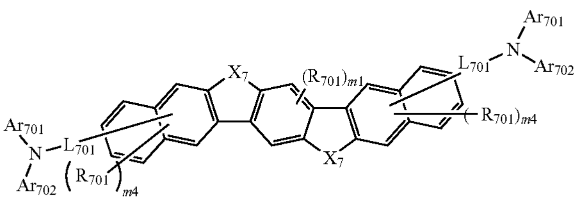

[Formula 290]

(71-25)

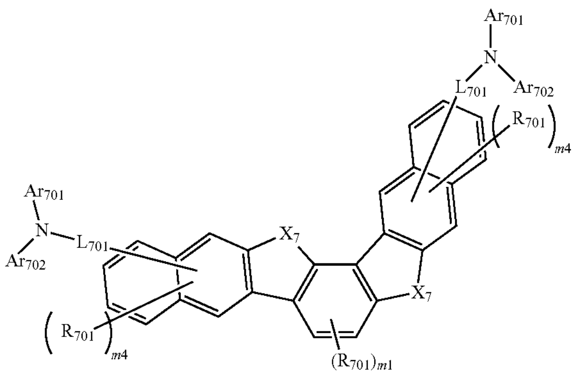

In the formulae (71-21) to (71-25), $R_{701}$, $X_7$, $Ar_{701}$, $Ar_{702}$, $L_{701}$, m1, and m4 respectively represent the same as $R_{701}$, $X_7$, $Ar_{701}$, $Ar_{702}$, $L_{701}$, m1, and m4 in the formula (7).

In an exemplary embodiment, the compound represented by the formula (7) is represented by any one of formulae (71-31) to (71-33) below.

[Formula 291]

(71-31)

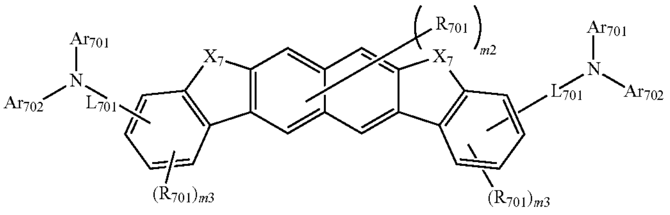

[Formula 292]

(71-32)

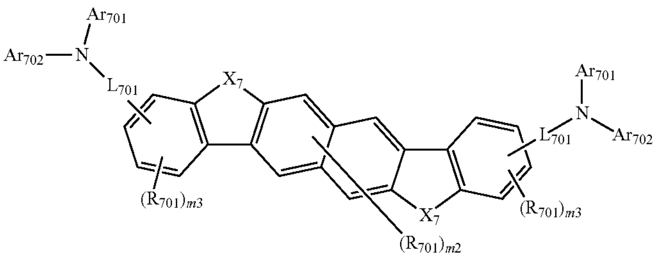

[Formula 293]

(71-33)

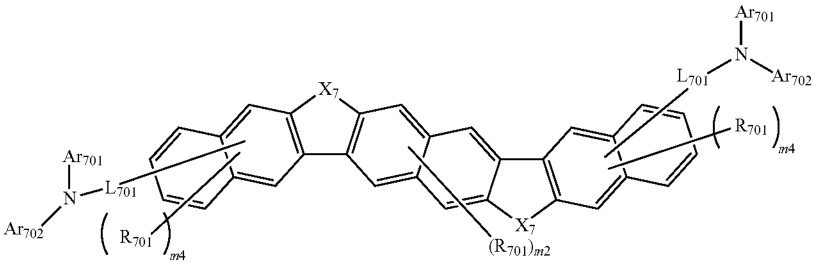

In the formulae (71-31) to (71-33), $R_{701}$, $X_7$, $Ar_{701}$, $Ar_{702}$, $L_{701}$, and m2 to m4 respectively represent the same as $R_{701}$, $X_7$, $Ar_{701}$, $Ar_{702}$, $L_{701}$, and m2 to m4 in the formula (7).

In an exemplary embodiment, $Ar_{701}$ and $Ar_{702}$ are each independently a substituted or unsubstituted aryl group having 6 to 50 ring carbon atoms.

In an exemplary embodiment, one of $Ar_{701}$ and $Ar_{702}$ is a substituted or unsubstituted aryl group having 6 to 50 ring carbon atoms, and the other of $Ar_{701}$ and $Ar_{702}$ is a substituted or unsubstituted heterocyclic group having 5 to 50 ring atoms.

Specific Examples of Compound Represented by Formula (7)

Specific examples of the compound represented by the formula (7) include compounds shown below.

[Formula 294]

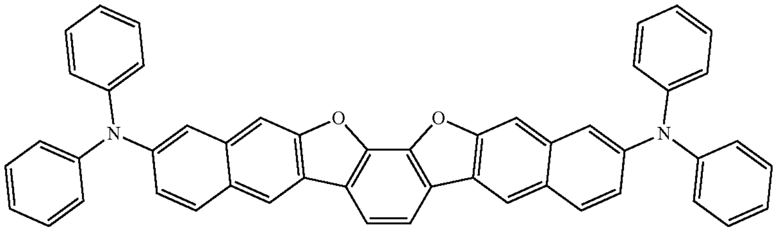

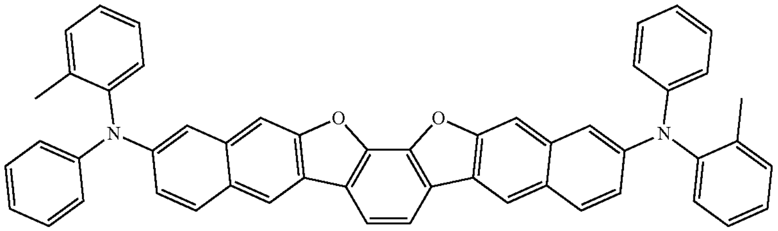

-continued
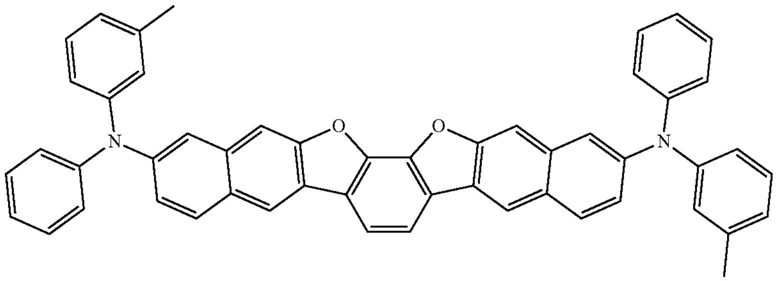
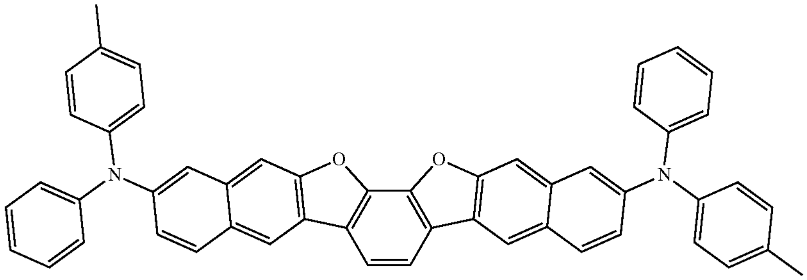
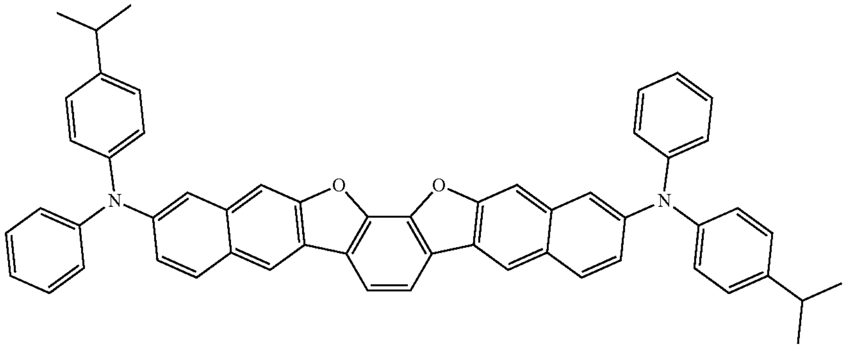
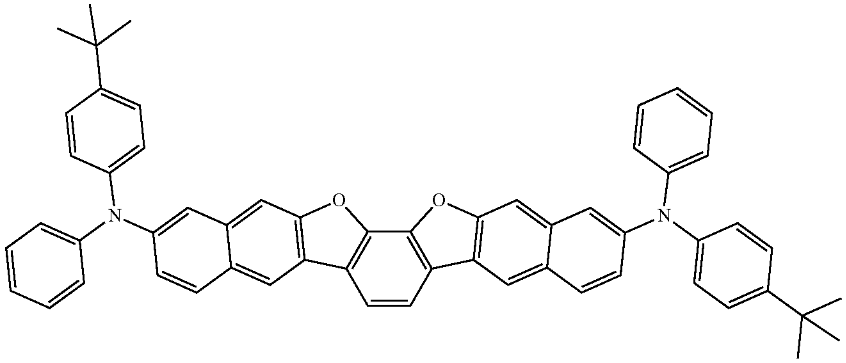
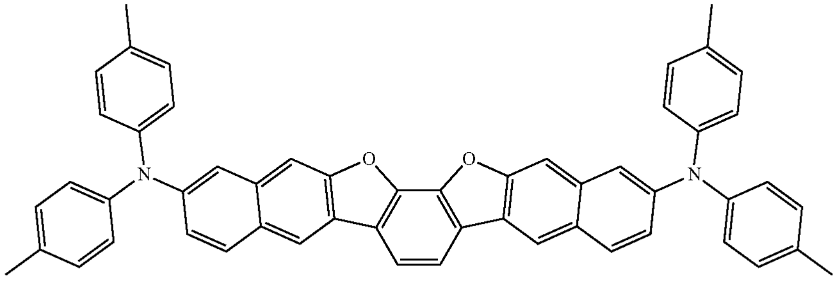

-continued
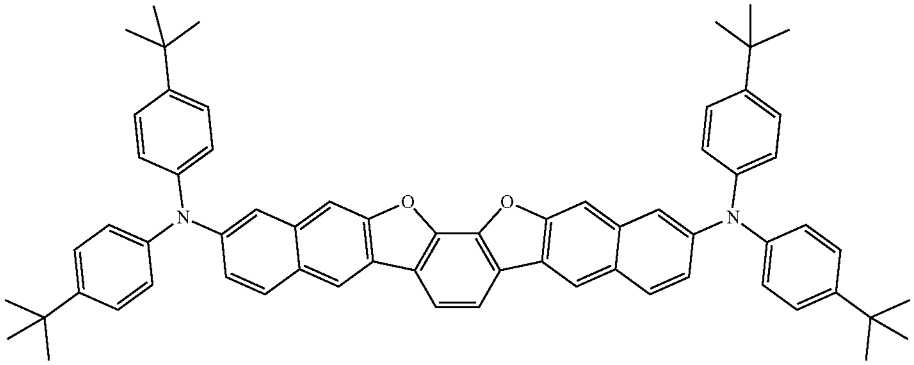
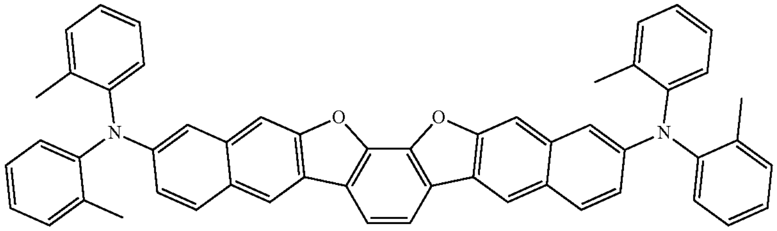
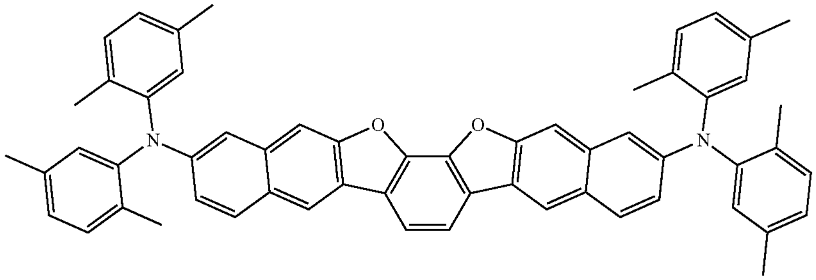
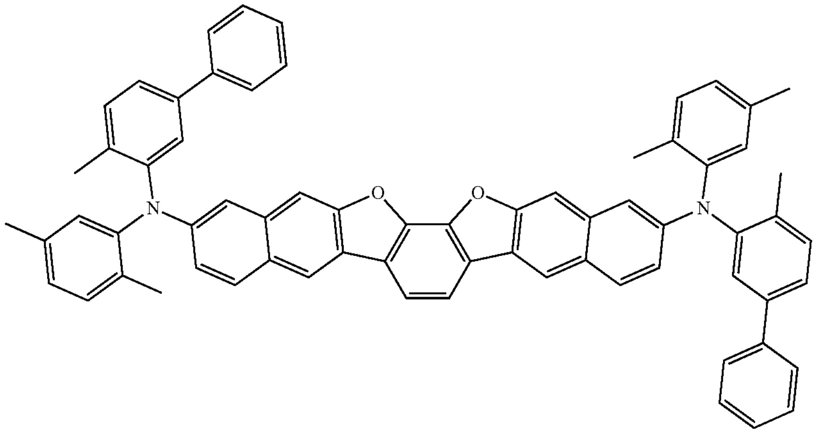

-continued
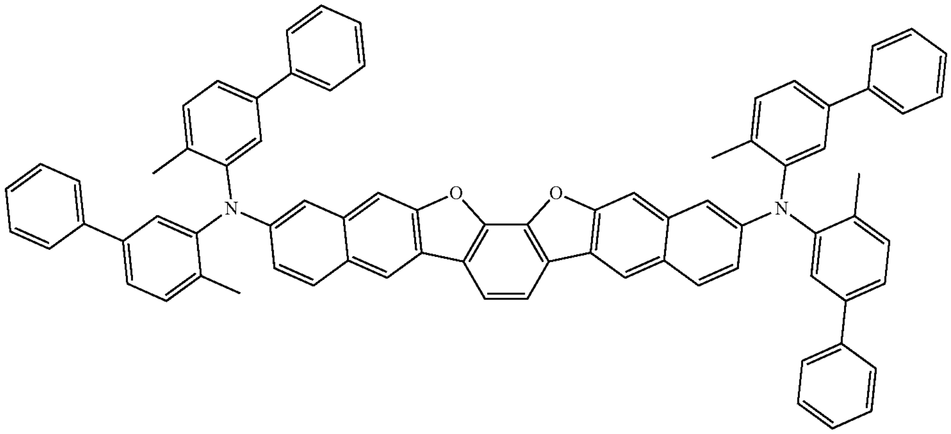
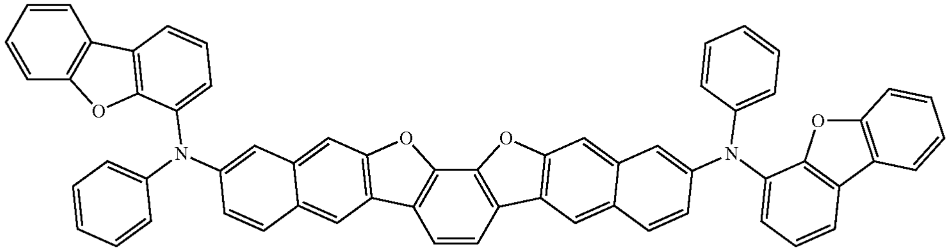
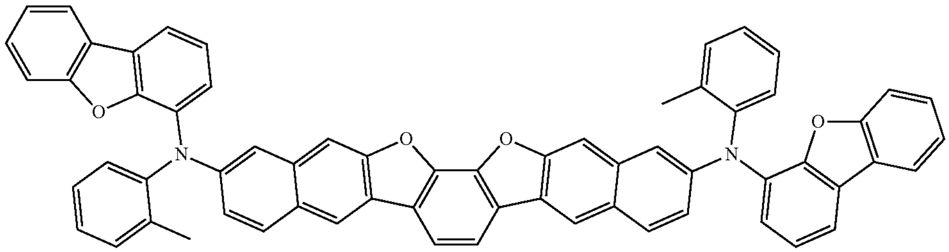
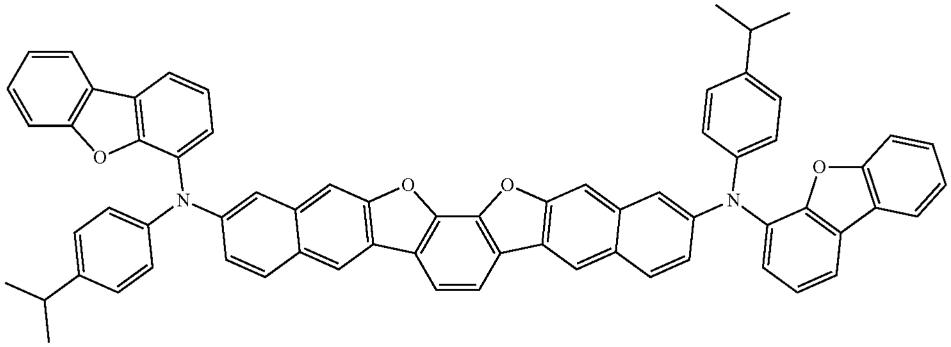
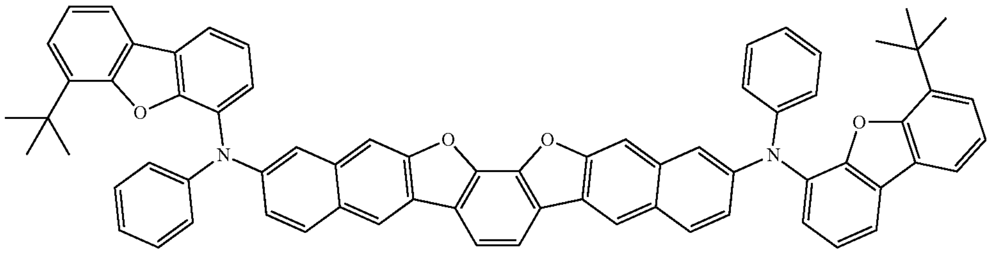

-continued
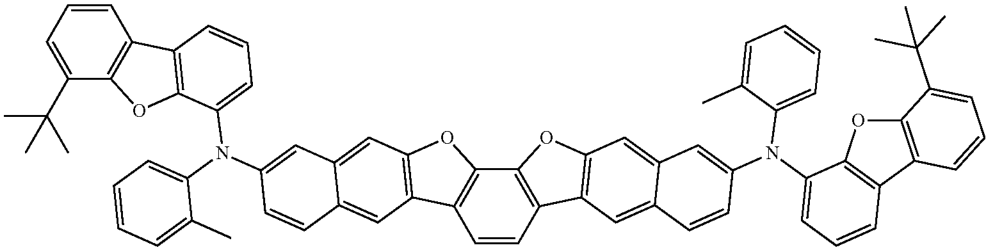
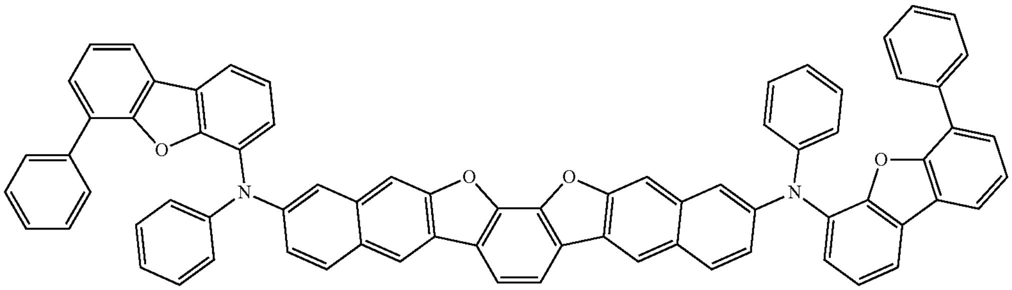
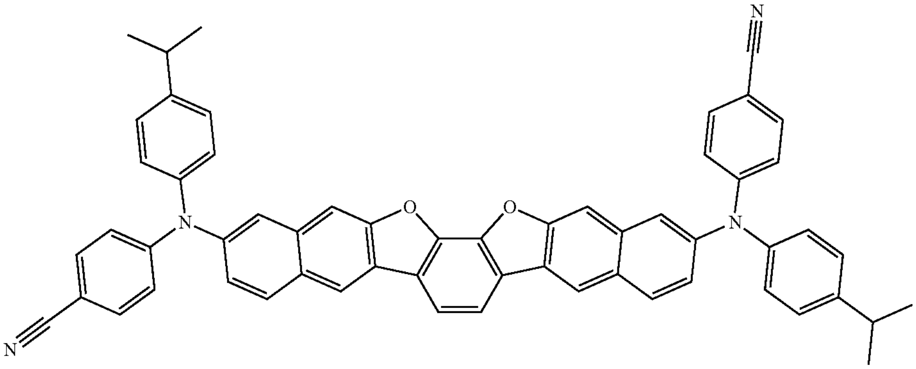
[Formula 295]
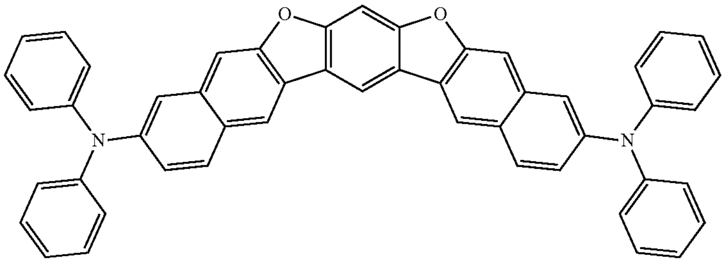
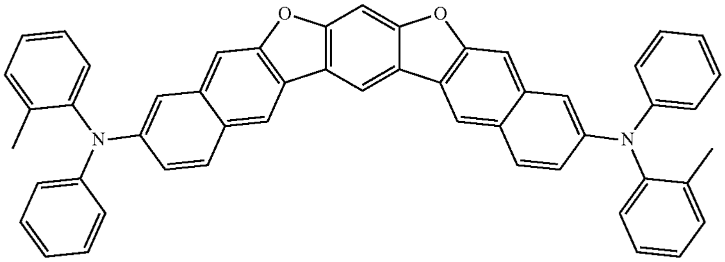

-continued
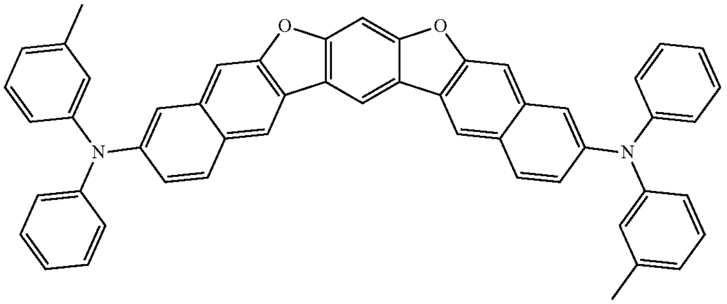
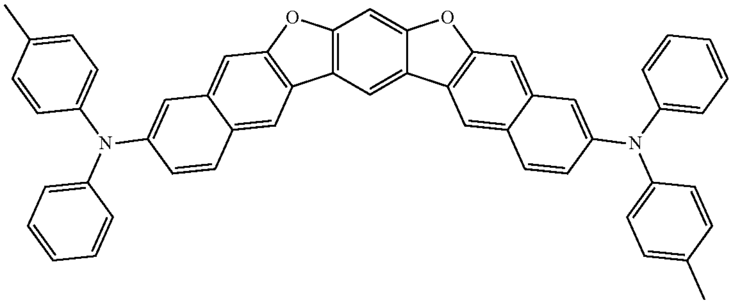
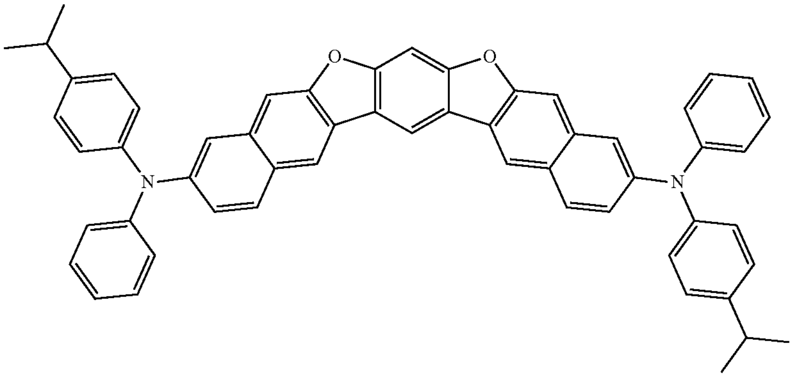
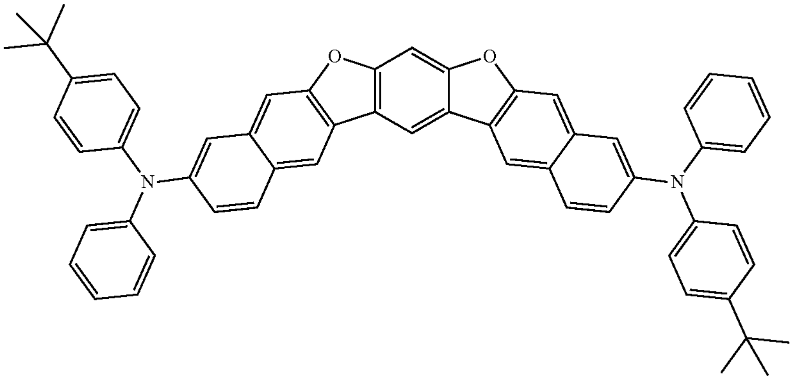
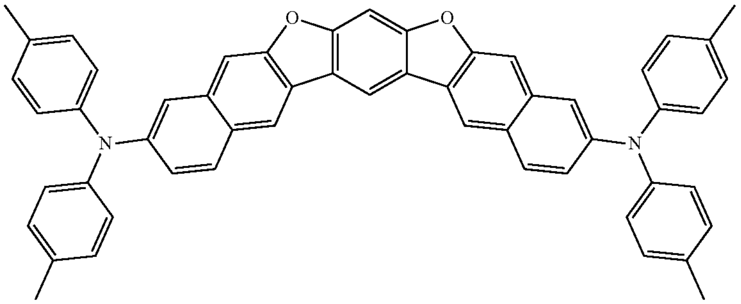

-continued
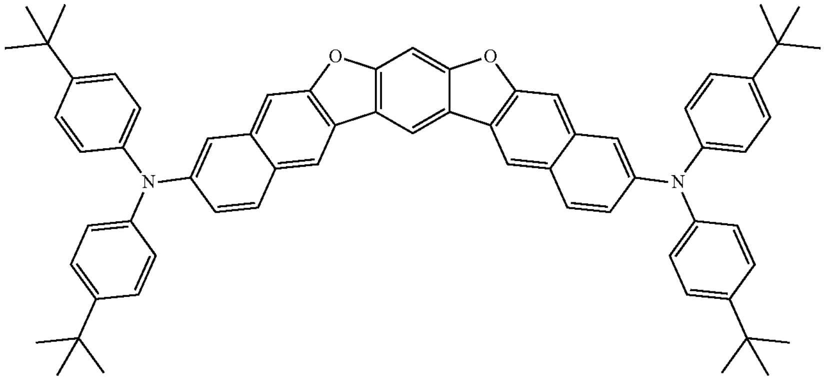
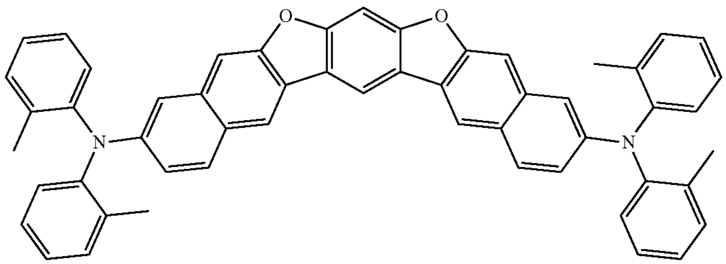
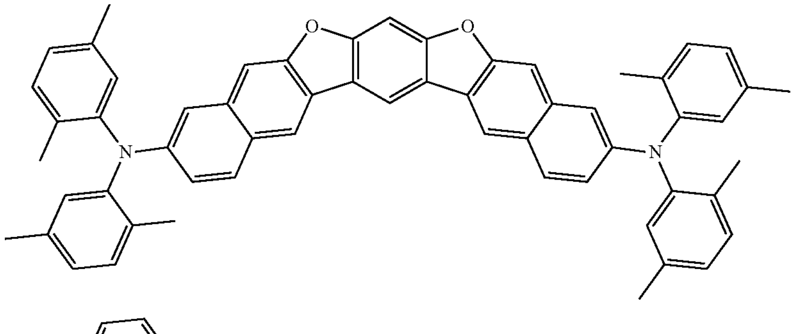
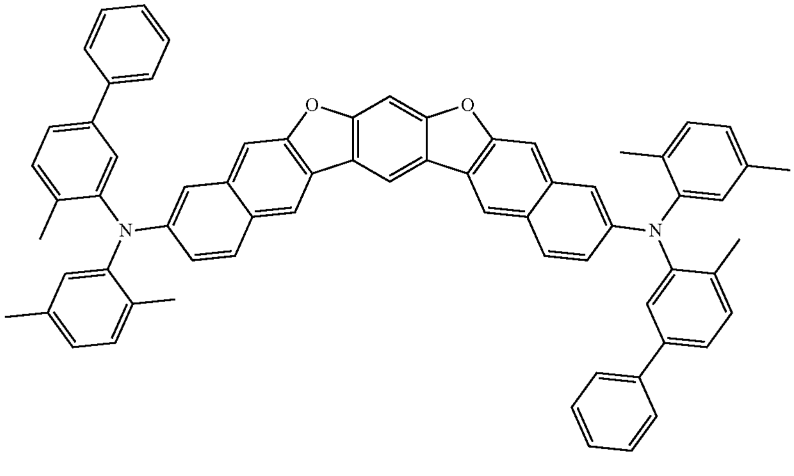

-continued
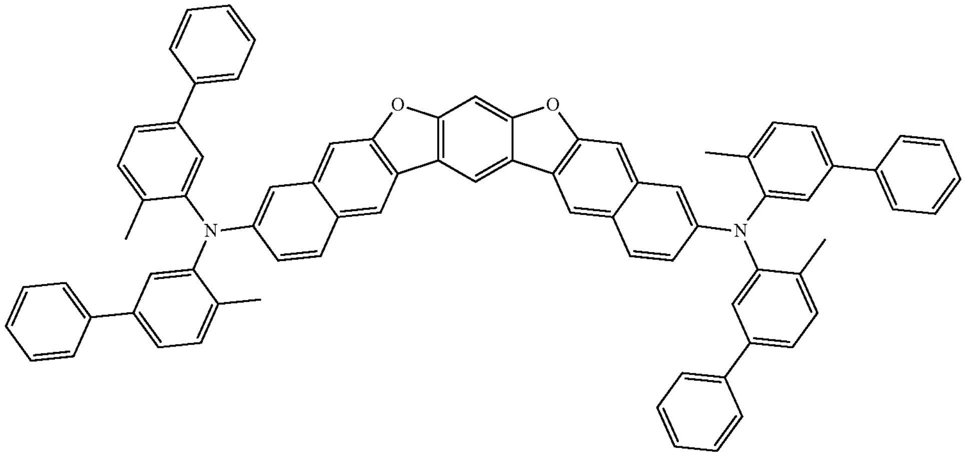
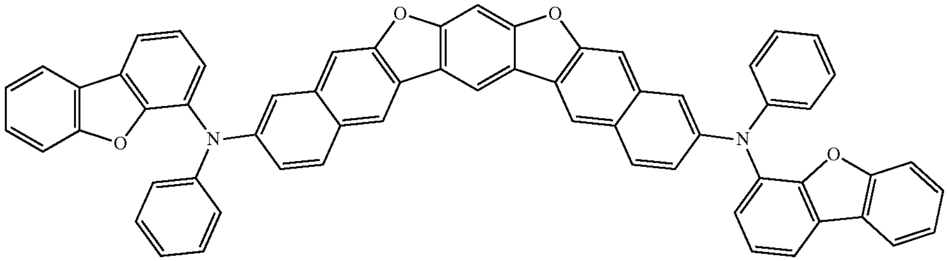
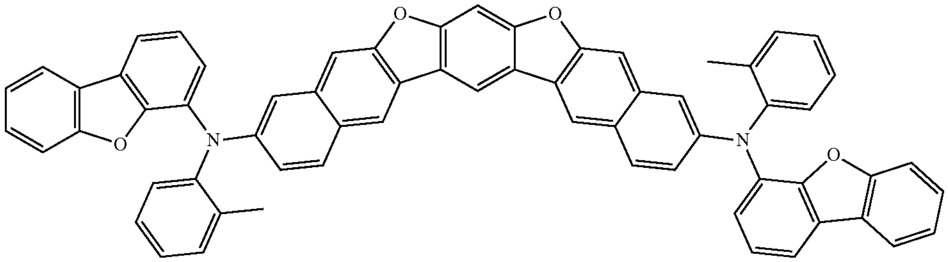
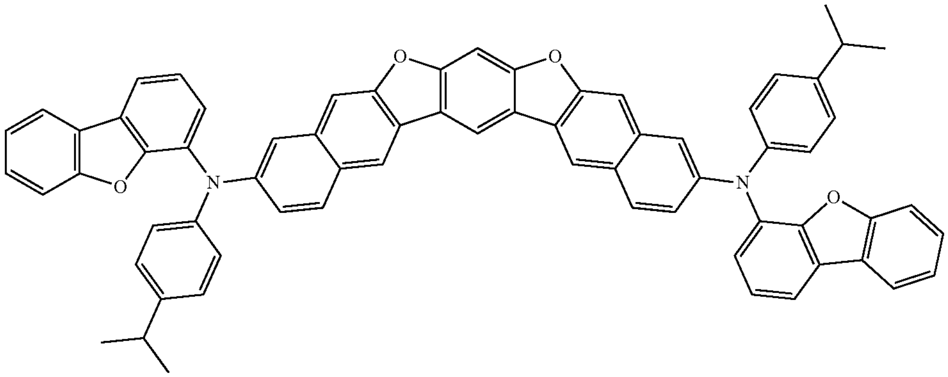
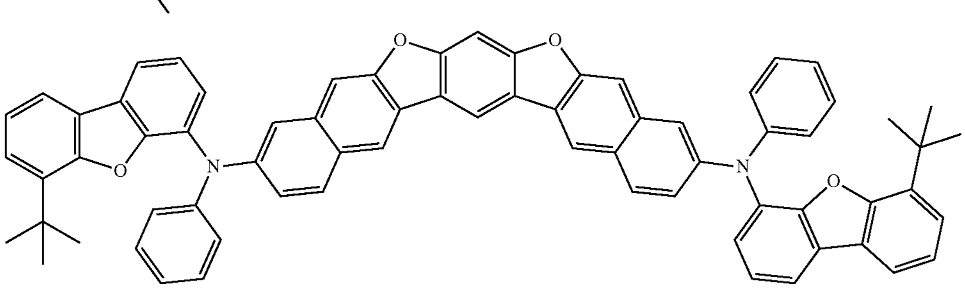

-continued
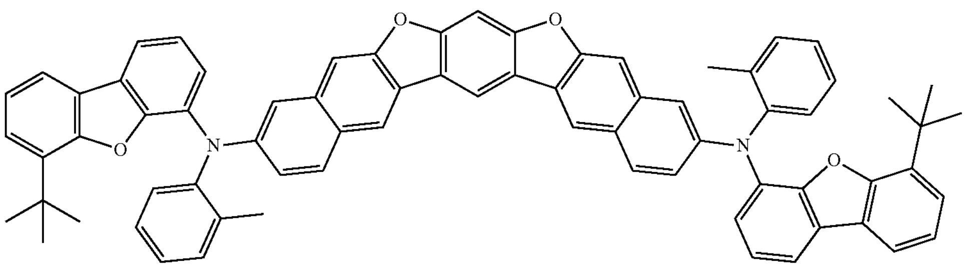
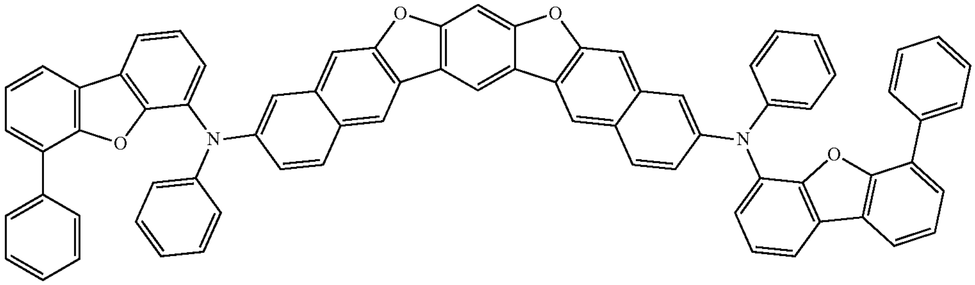
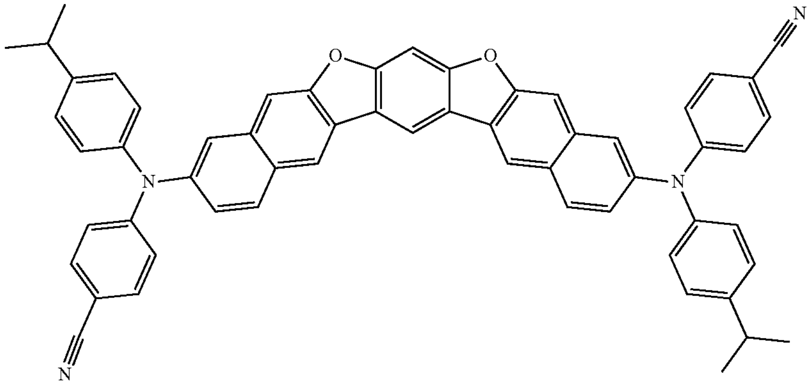
[Formula 296]
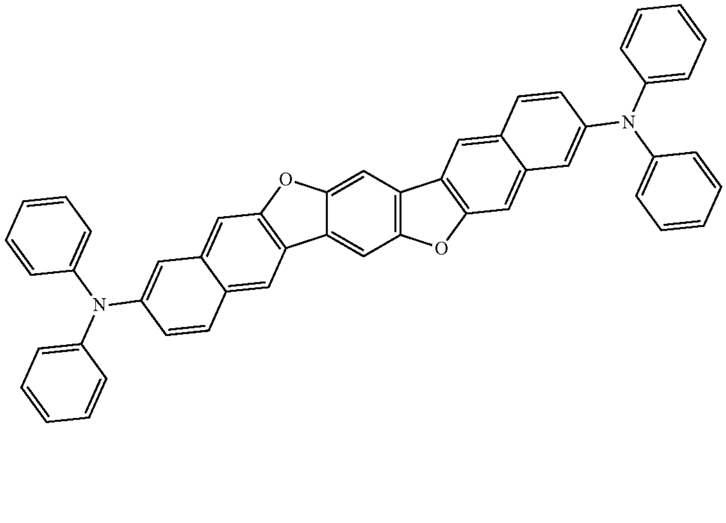

-continued
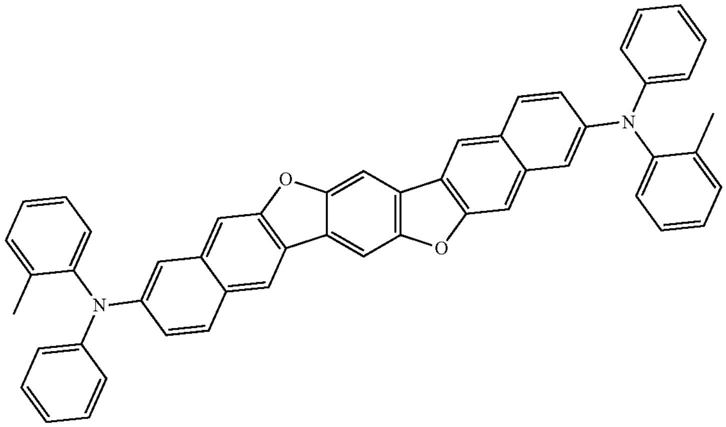
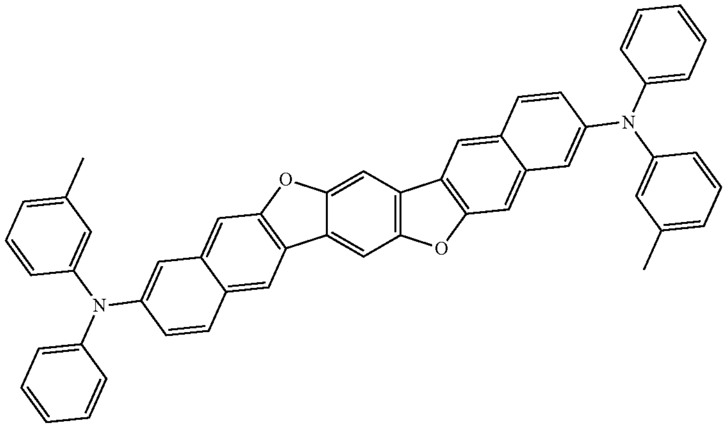
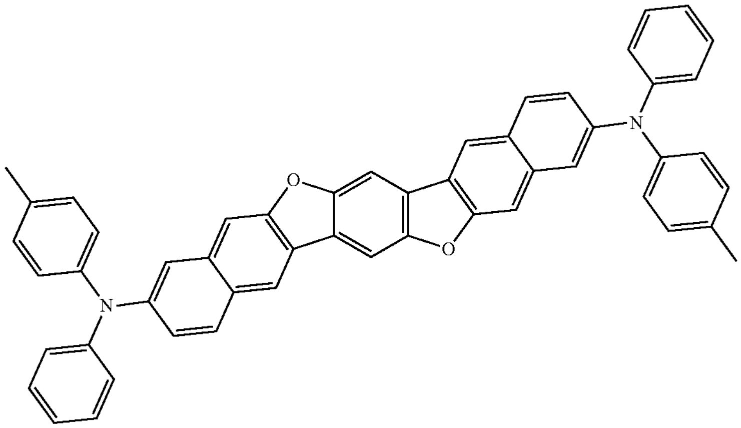
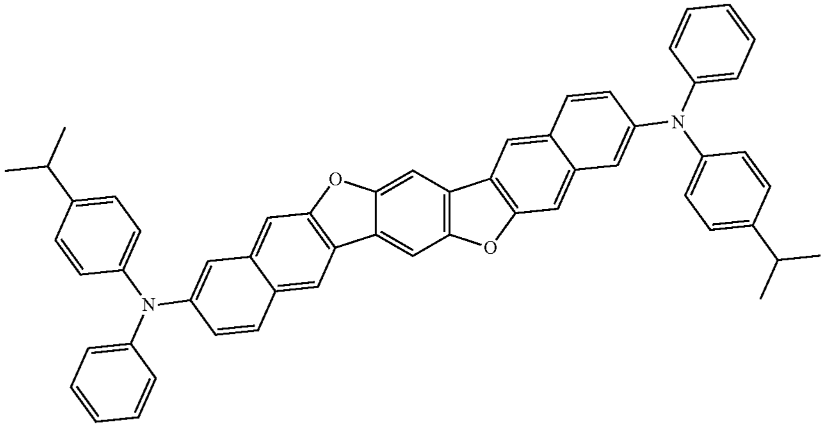

-continued
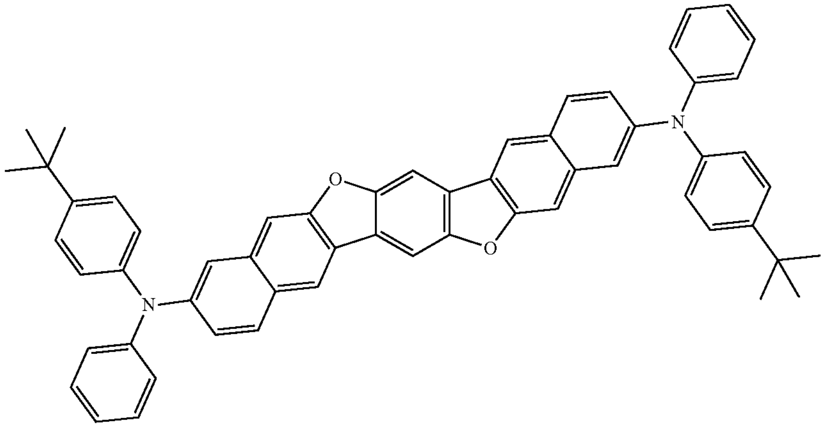
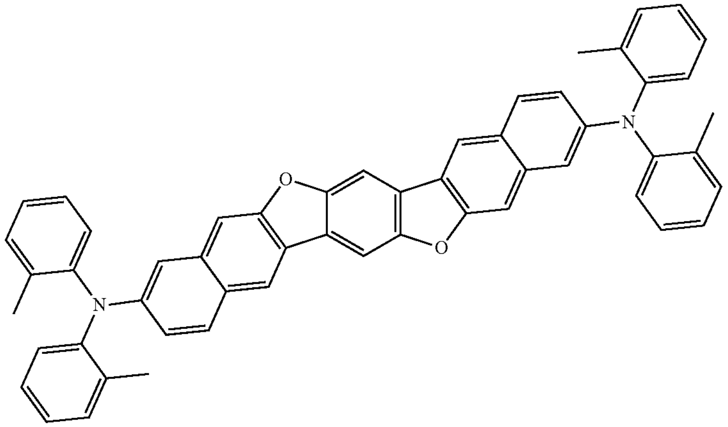
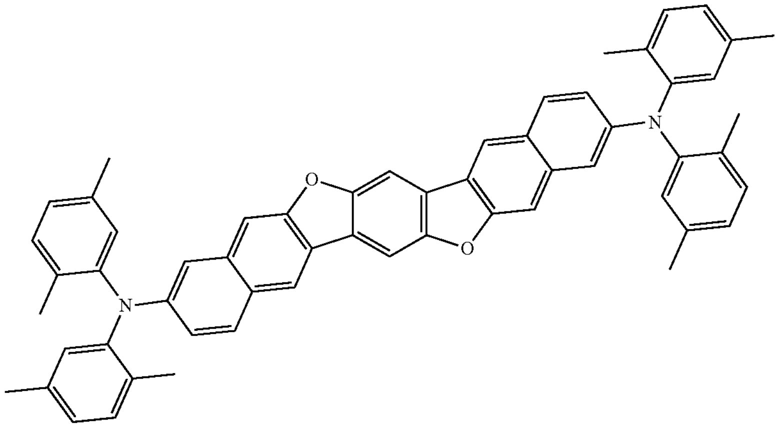
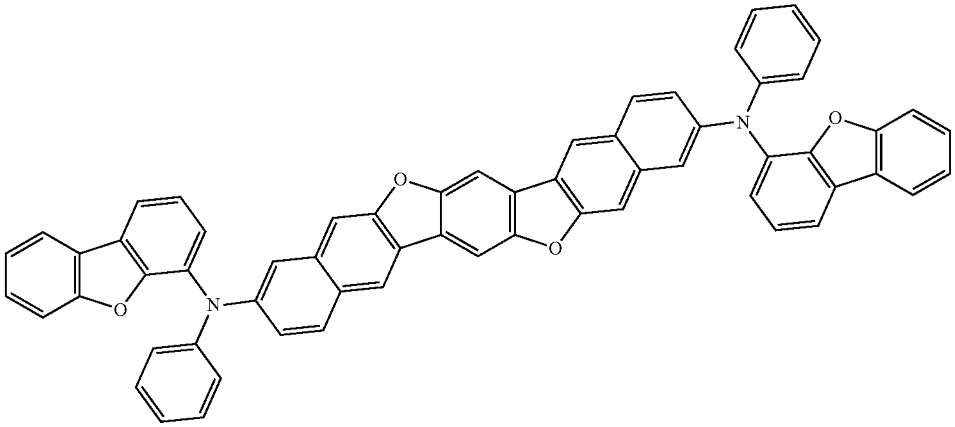

-continued
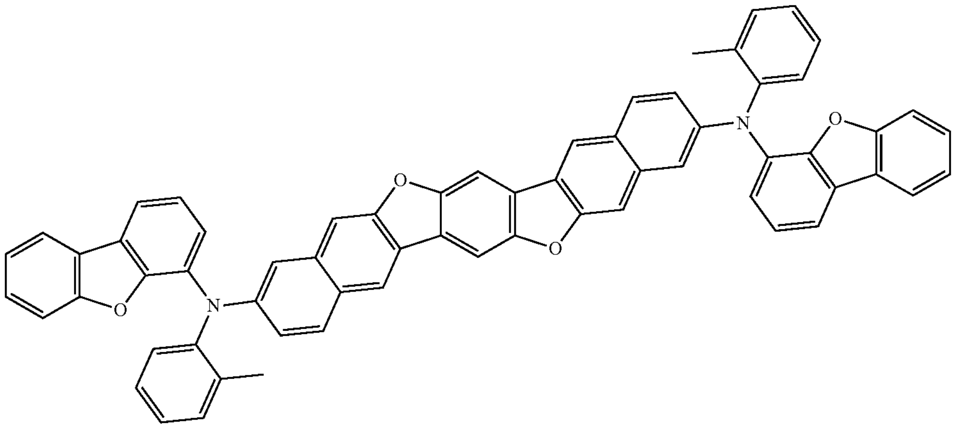
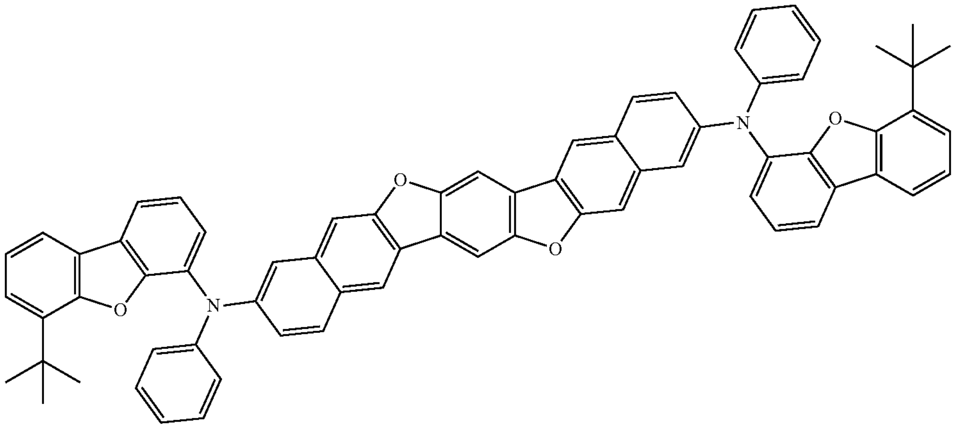
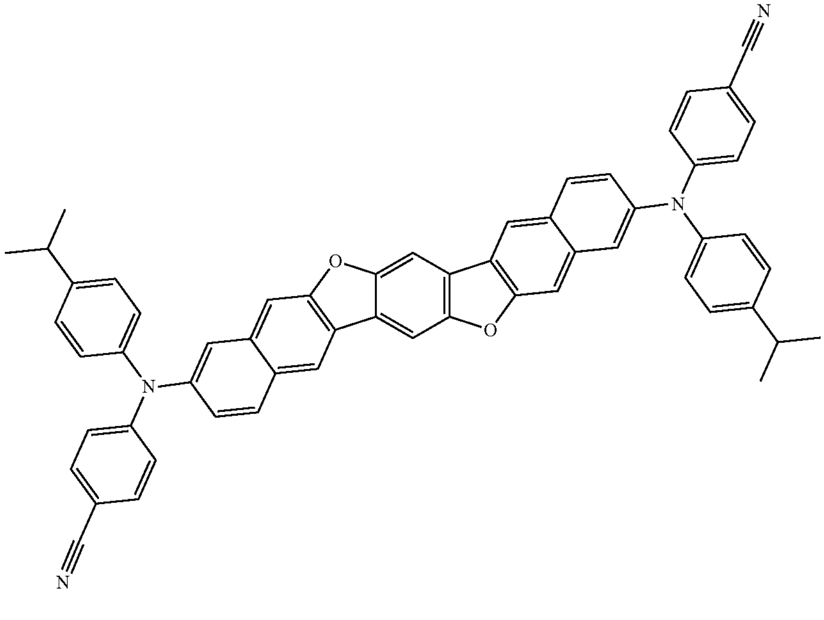

-continued
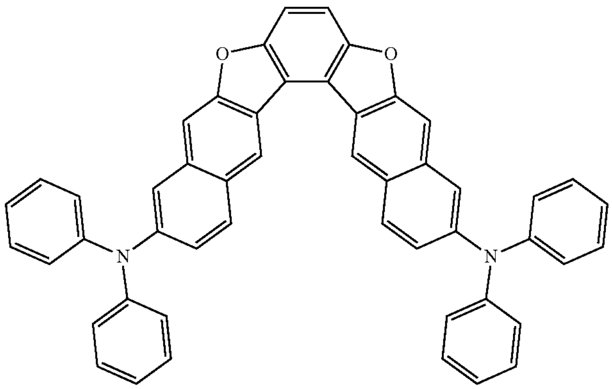
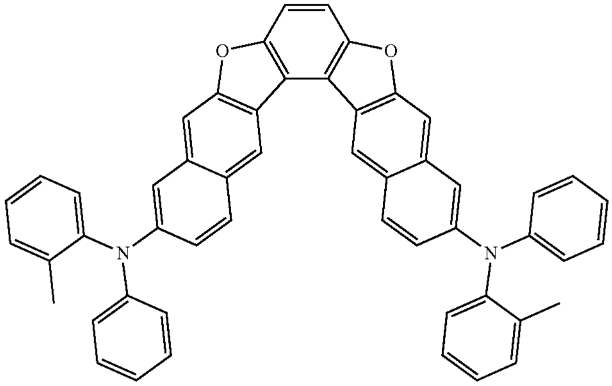
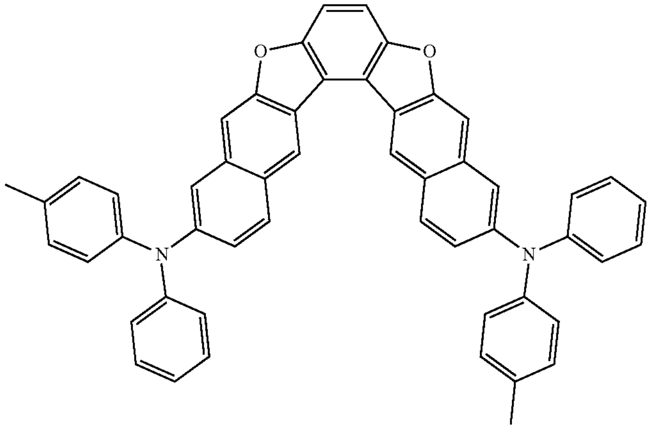
[Formula 297]
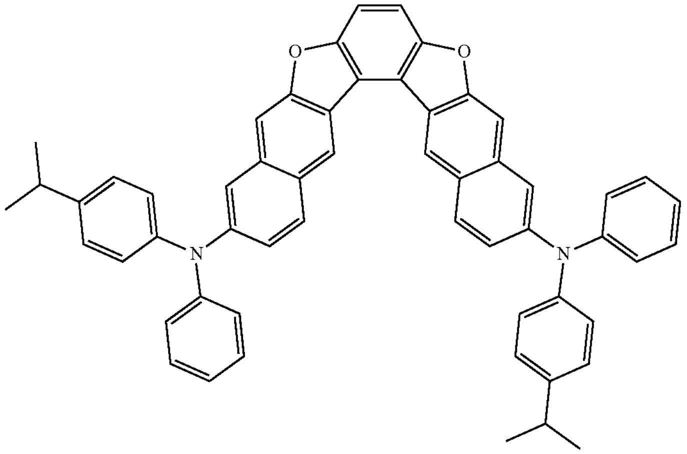

-continued
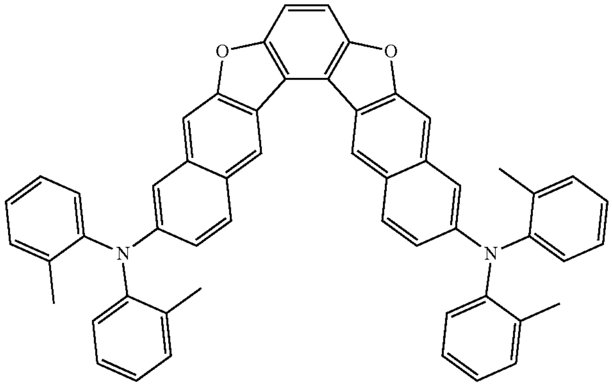
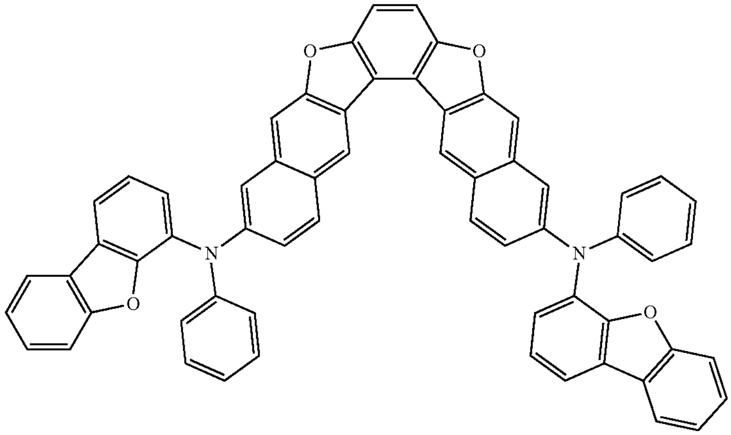
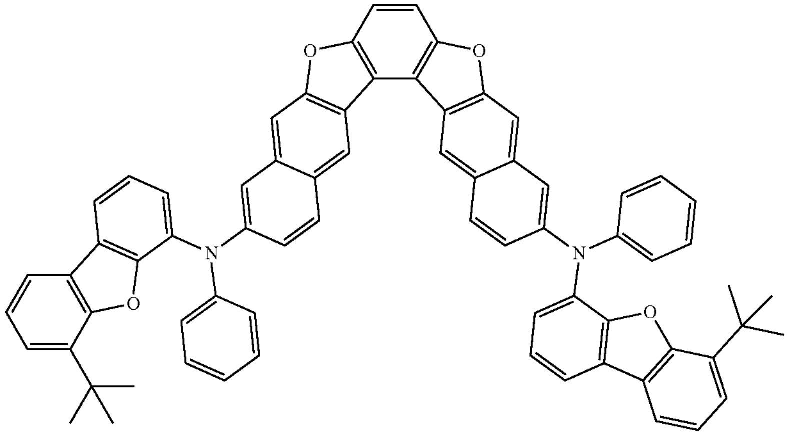
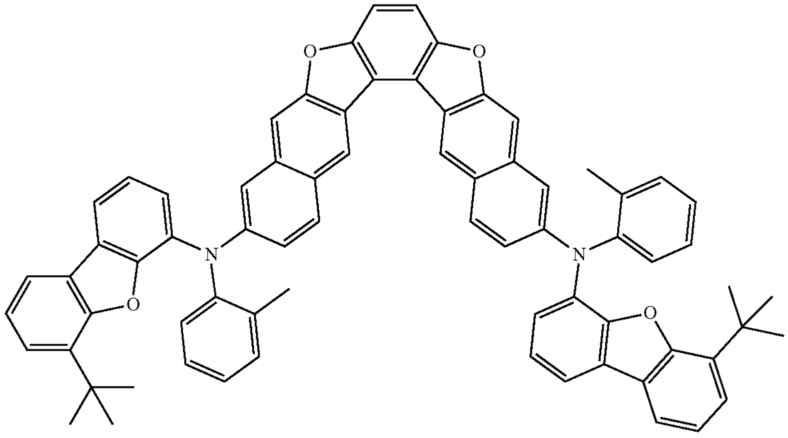

-continued
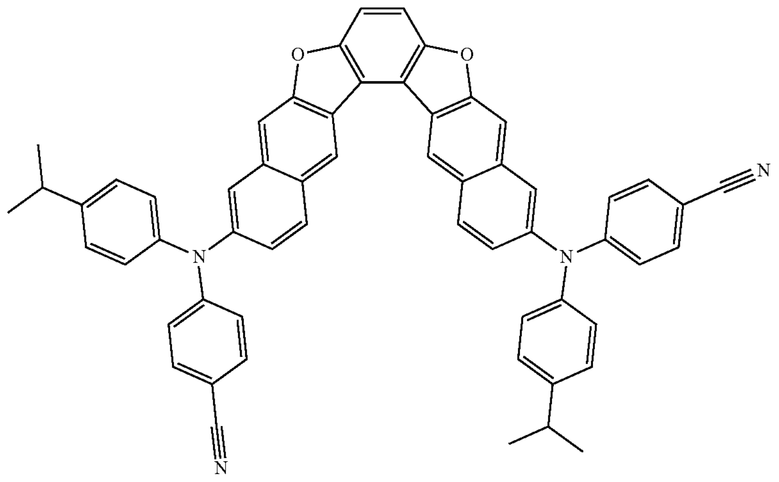
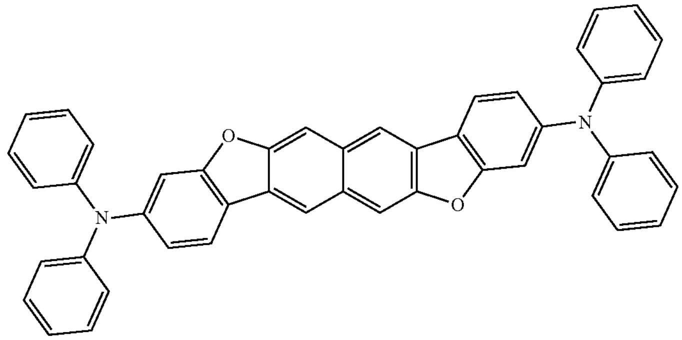
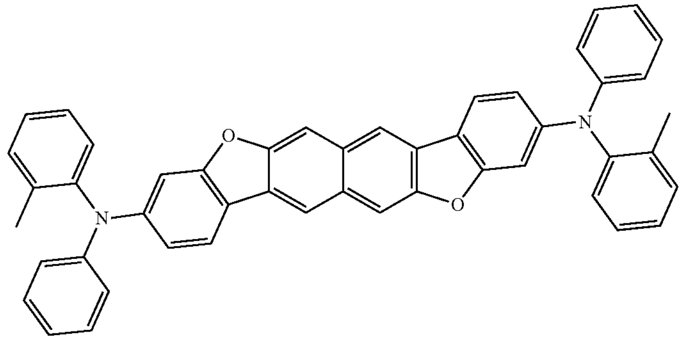
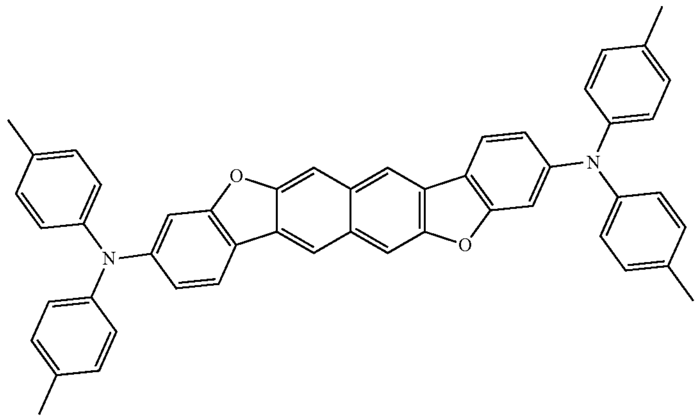

-continued
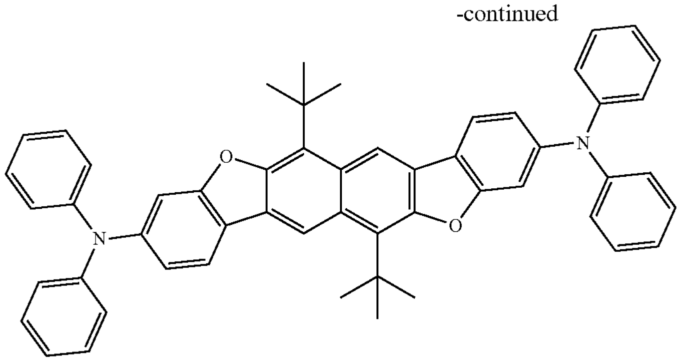
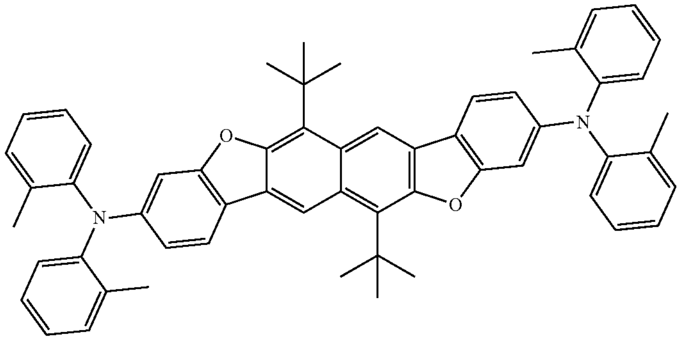
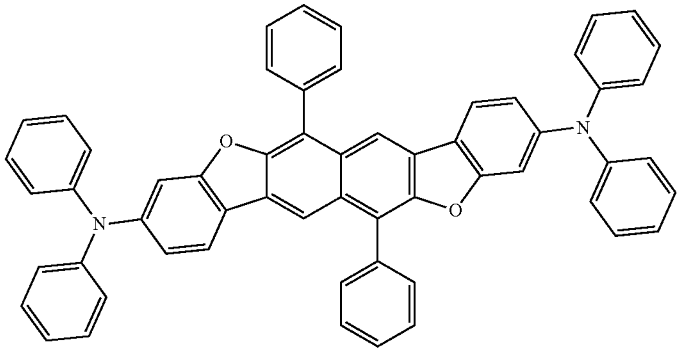
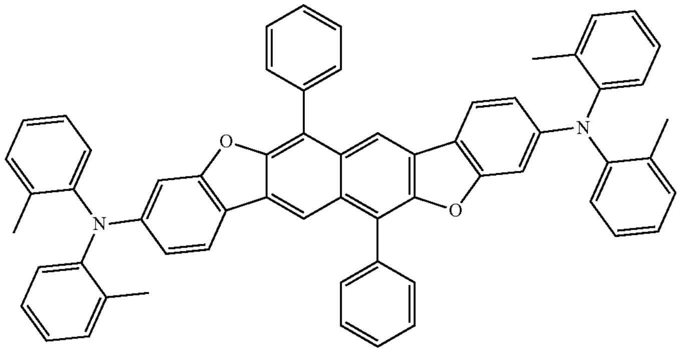
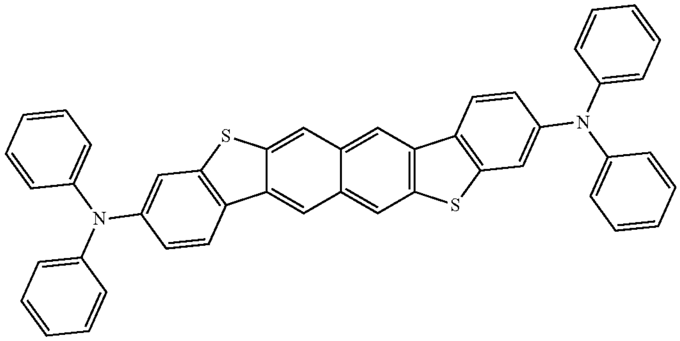

-continued
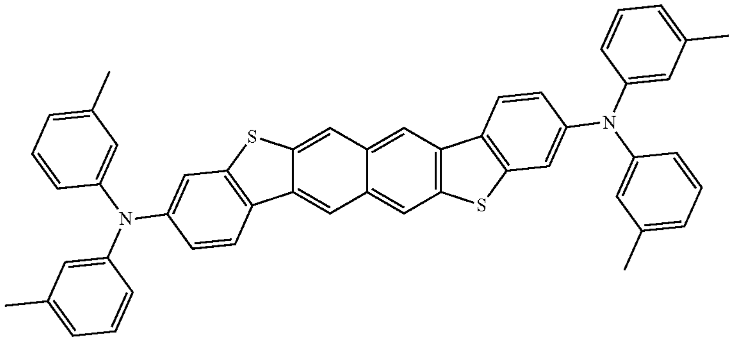
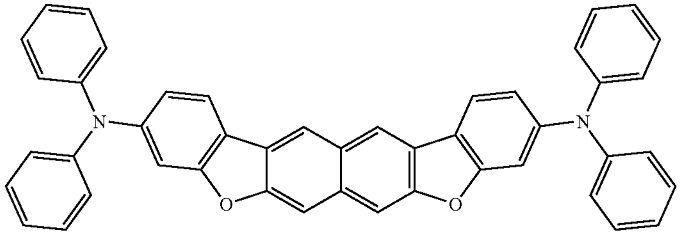
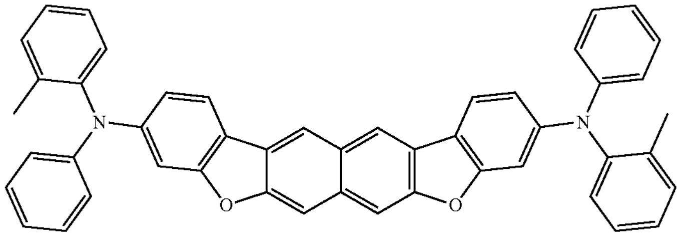
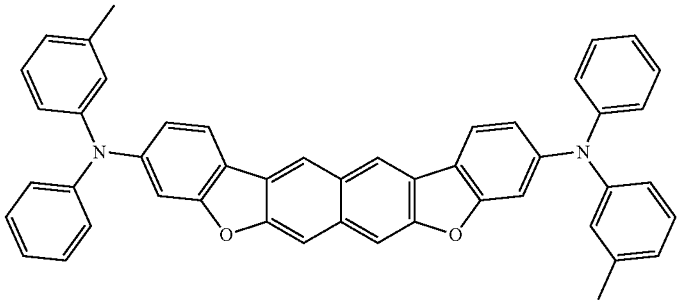
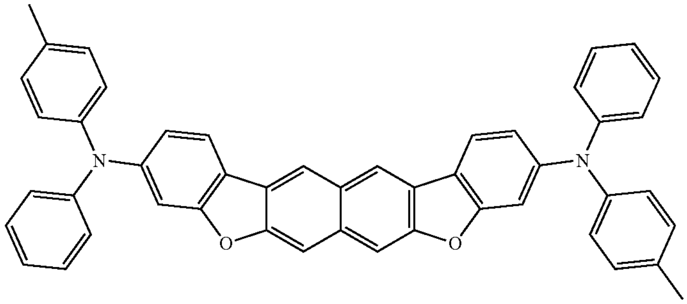

-continued
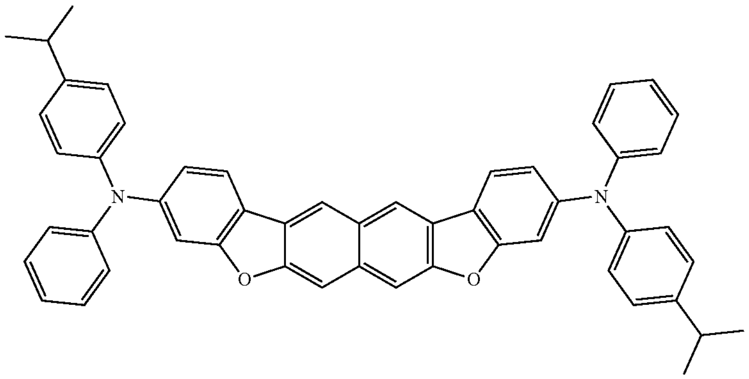
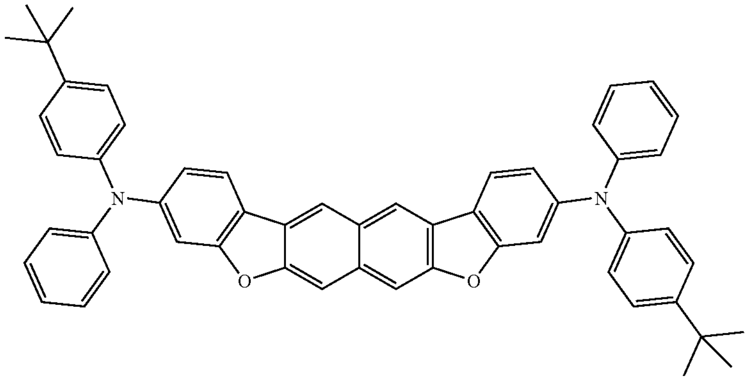
[Formula 298]
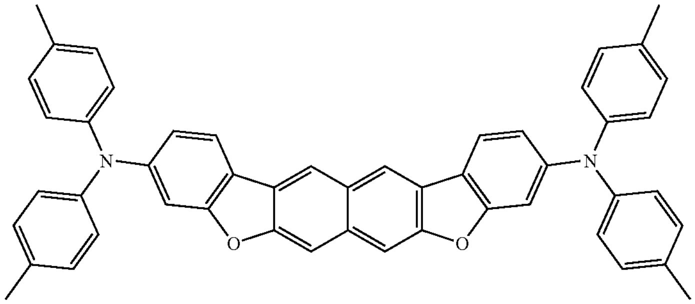
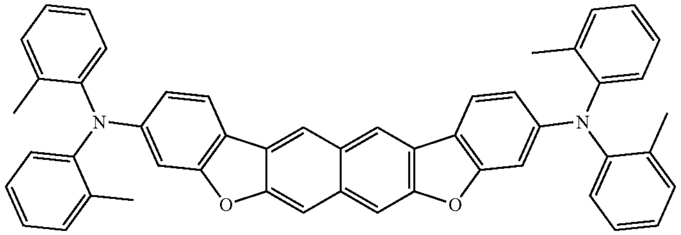
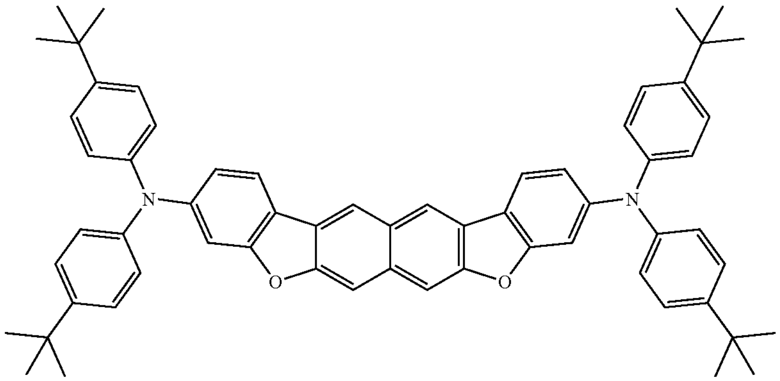

-continued
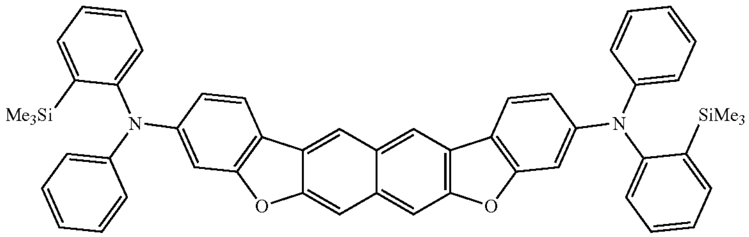
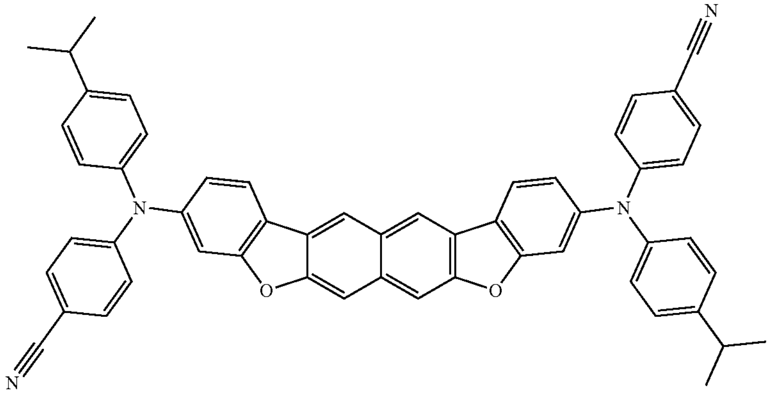
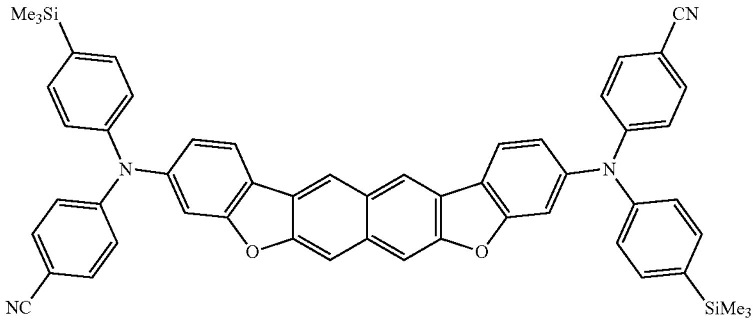
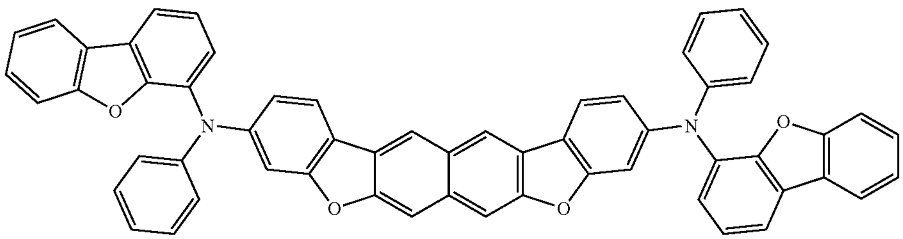
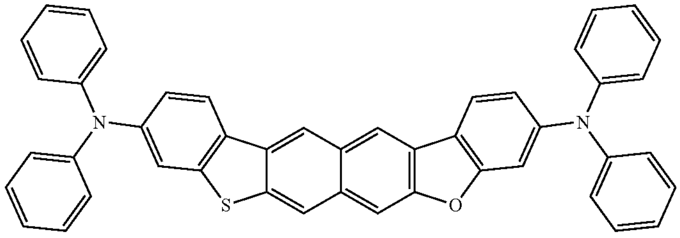

-continued
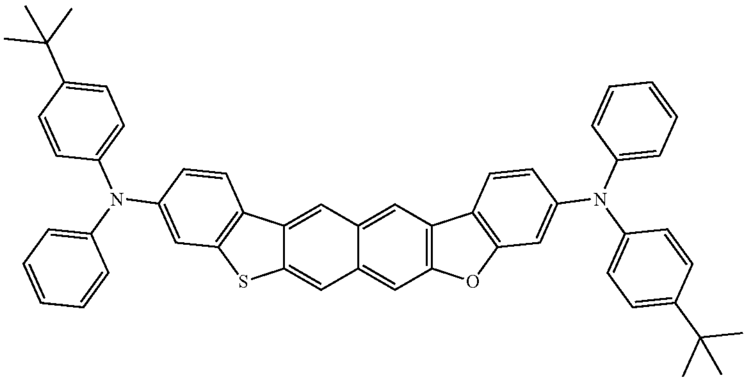
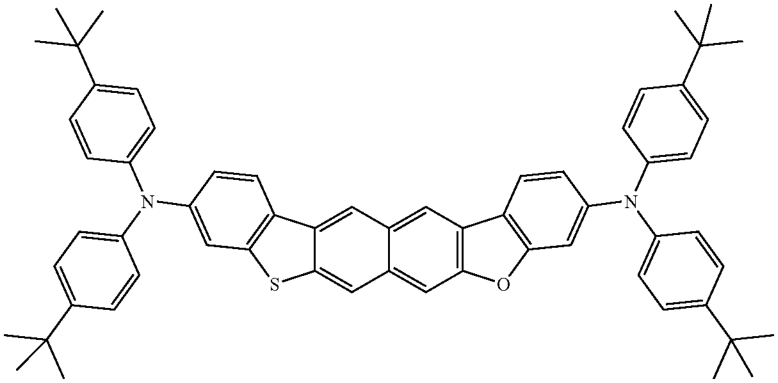
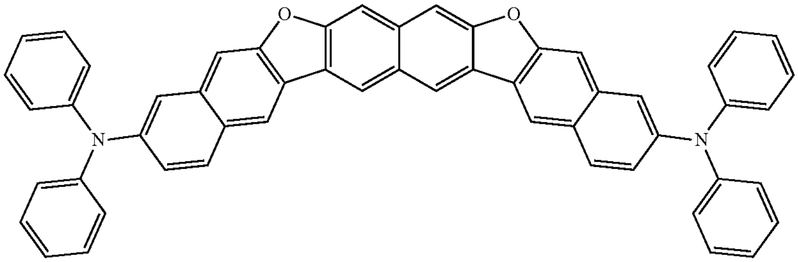
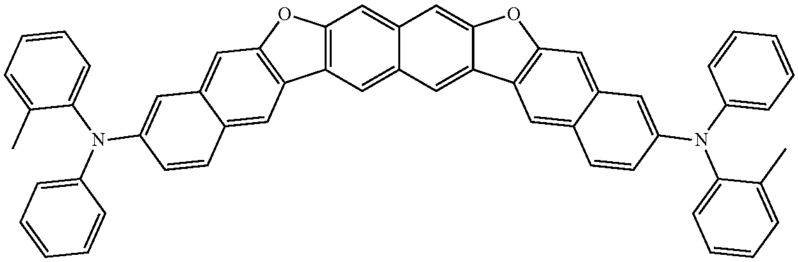
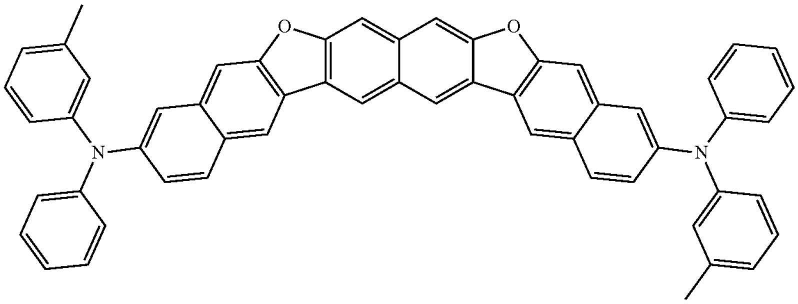

-continued
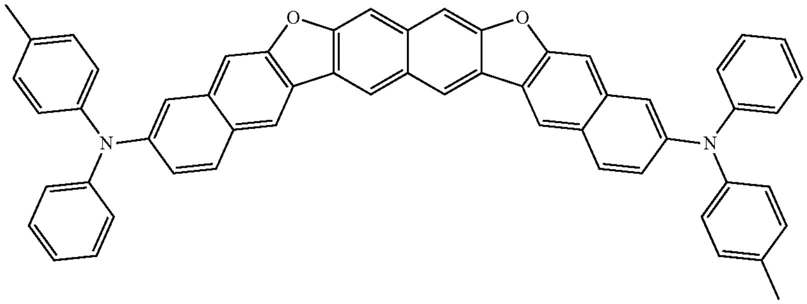
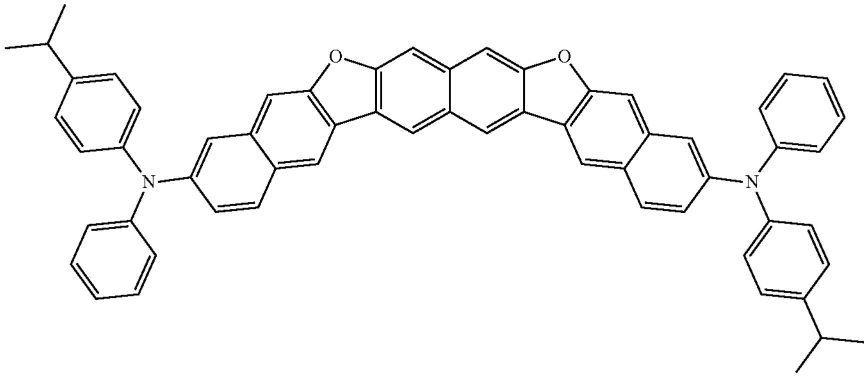
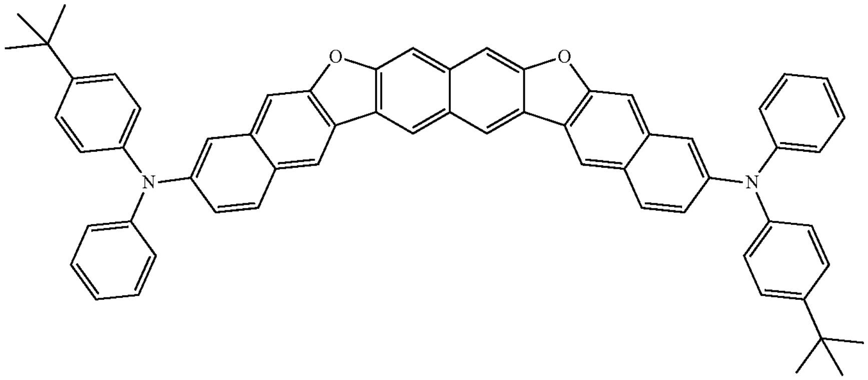
[Formula 299]
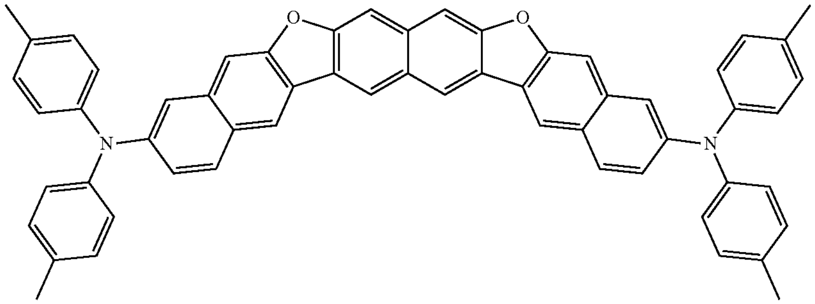
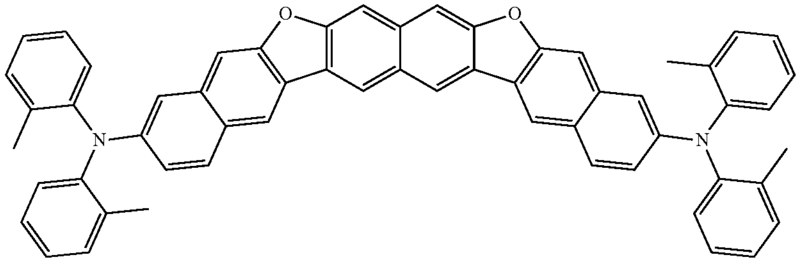

-continued

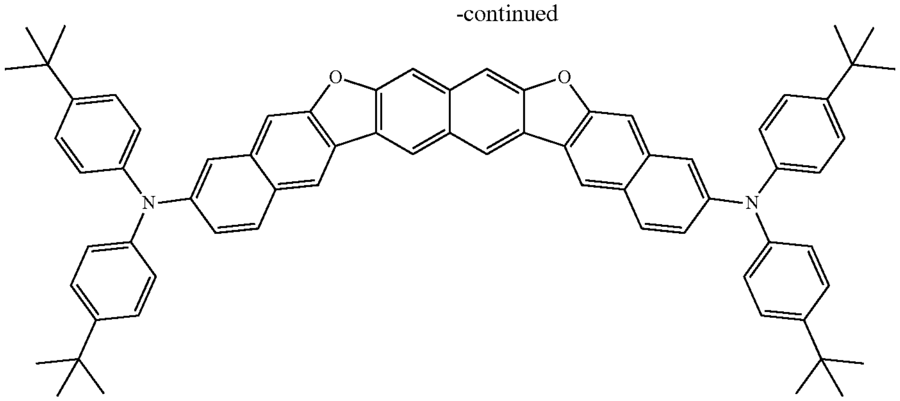

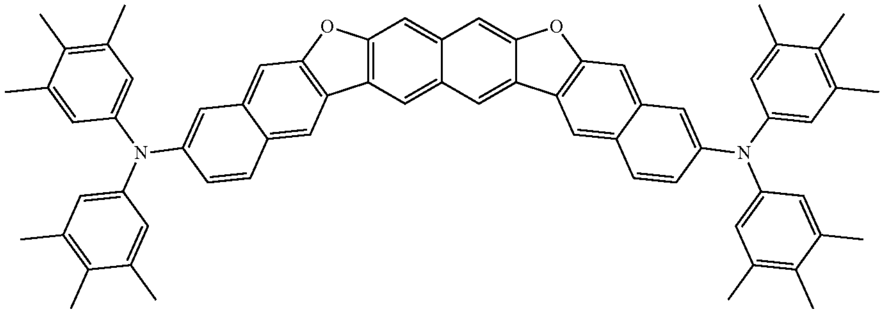

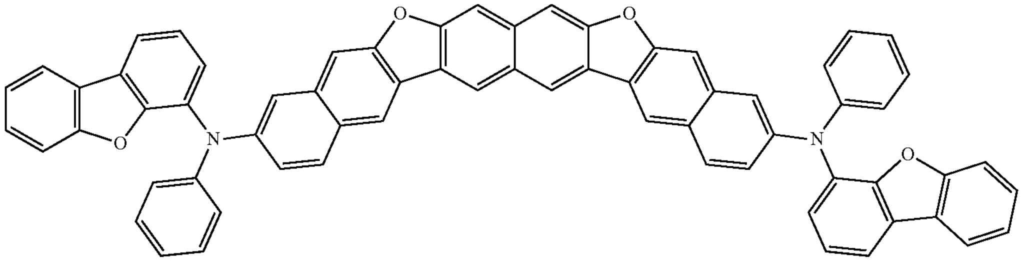

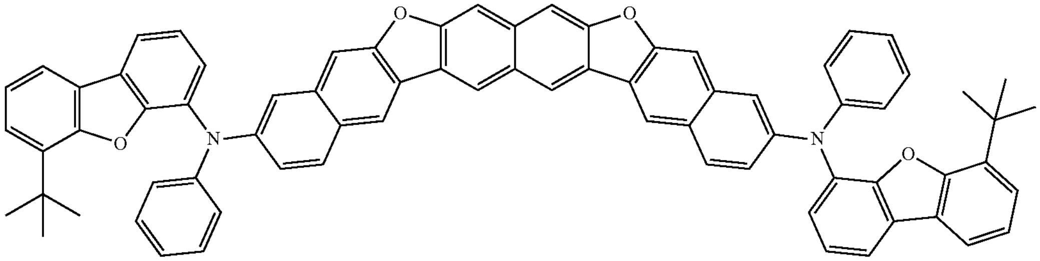

Compound Represented by Formula (8)

The compound represented by the formula (8) will be described below.

[Formula 300]

(8)

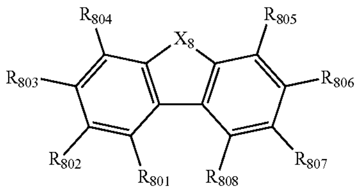

In the formula (8): at least one combination of $R_{801}$ and $R_{802}$, $R_{802}$ and $R_{803}$, or $R_{803}$ and $R_{804}$ are mutually bonded to form a divalent group represented by a formula (82) below; and at least one combination of $R_{805}$ and $R_{806}$, $R_{806}$ and $R_{807}$, or $R_{807}$ and $R_{808}$ are mutually bonded to form a divalent group represented by a formula (83) below.

[Formula 301]

(82)

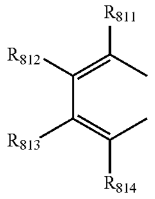

-continued (83)

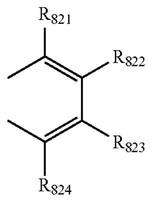

At least one of $R_{801}$ to $R_{804}$ not forming the divalent group represented by the formula (82) or $R_{811}$ to $R_{814}$ is a monovalent group represented by a formula (84) below.

At least one of $R_{805}$ to $R_{808}$ not forming the divalent group represented by the formula (83) or $R_{821}$ to $R_{824}$ is a monovalent group represented by a formula (84) below.

$X_8$ is an oxygen atom, a sulfur atom, or $NR_{809}$.

$R_{801}$ to $R_{808}$ not forming the divalent group represented by the formula (82) or (83) and not being the monovalent group represented by the formula (84), $R_{811}$ to $R_{814}$ and $R_{821}$ to $R_{824}$ not being the monovalent group represented by the formula (84), and $R_{809}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 302]

(84)

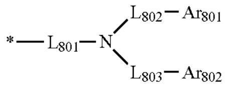

In the formula (84): $Ar_{801}$ and $Ar_{802}$ each independently represent a substituted or unsubstituted aryl group having 6 to 50 ring carbon atoms, or a substituted or unsubstituted heterocyclic group having 5 to 50 ring atoms;

$L_{801}$ to $L_{803}$ each independently represent a single bond, a substituted or unsubstituted arylene group having 6 to 30 ring carbon atoms, a substituted or unsubstituted heterocyclic group having 5 to 30 ring atoms, or a divalent linking group formed by bonding two, three or four groups selected from the group consisting of the substituted or unsubstituted arylene group having 6 to 30 ring carbon atoms and a substituted or unsubstituted divalent heterocyclic group having 5 to 30 ring atoms; and

* in the formula (84) represents a bonding position with the cyclic structure represented by the formula (8) or a bonding position to the group represented by the formula (82) or (83).

In the formula (8), the positions for the divalent group represented by the formula (82) and the divalent group represented by the formula (83) to be formed are not specifically limited but the divalent groups may be formed at any possible positions on $R_{801}$ to $R_{808}$.

In an exemplary embodiment, the compound represented by the formula (8) is represented by any one of formulae (81-1) to (81-6) below.

[Formula 303]

(81-1)

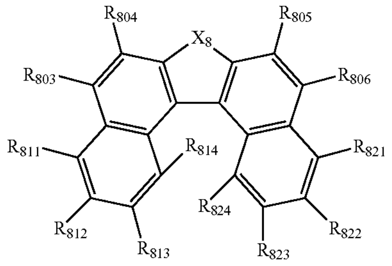

(81-2)

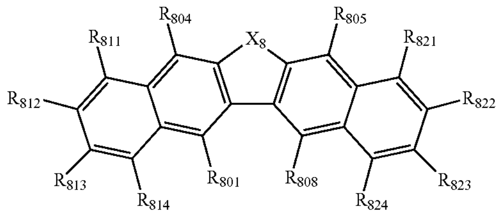

[Formula 304]

(81-3)

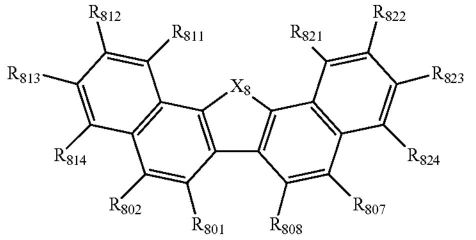

(81-4)

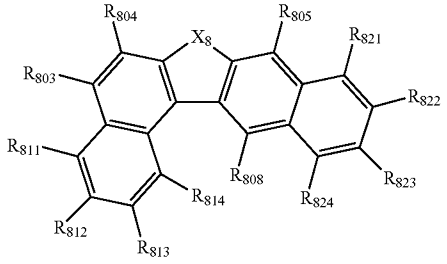

[Formula 305]

(81-5)

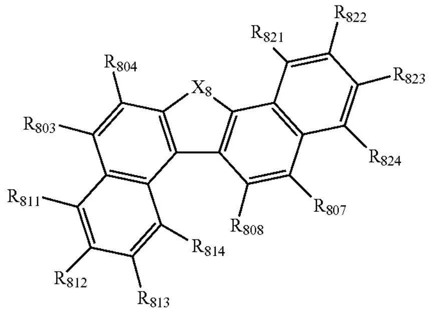

-continued (81-6)

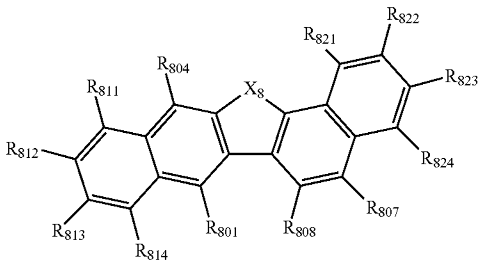

In the formulae (81-1) to (81-6):

$X_8$ represents the same as $X_8$ in the formula (8);

at least two of $R_{801}$ to $R_{824}$ are each a monovalent group represented by the formula (84); and $R_{801}$ to $R_{824}$ that are not the monovalent group represented by the formula (84) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (8) is represented by any one of formulae (81-7) to (81-18) below.

[Formula 306]

(81-7)

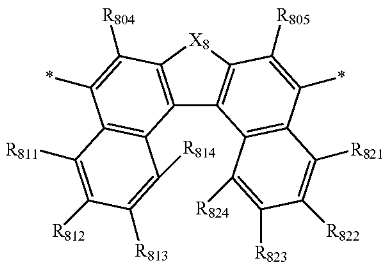

(81-8)

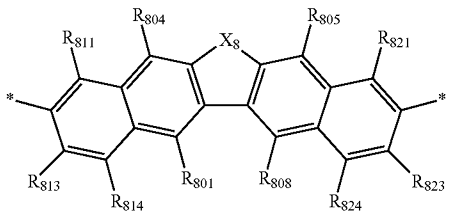

-continued

[Formula 307]

(81-9)

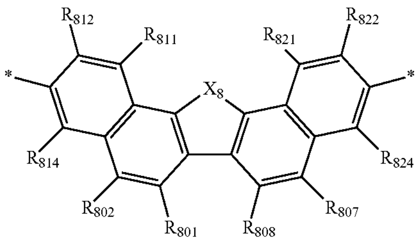

(81-10)

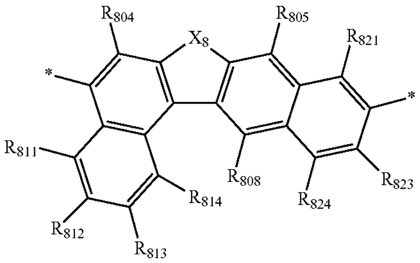

[Formula 308]

(81-11)

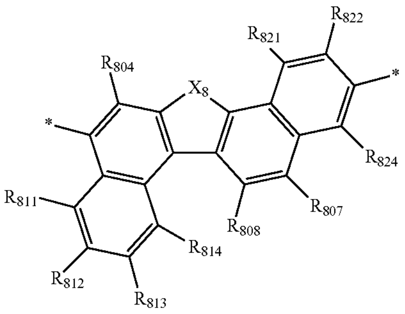

(81-12)

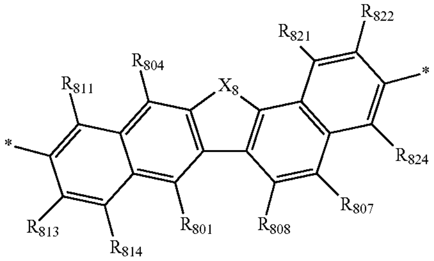

[Formula 309]

(81-13)

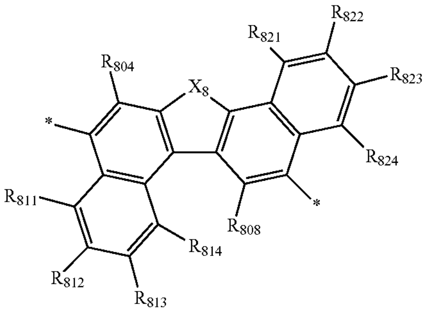

-continued (81-14)

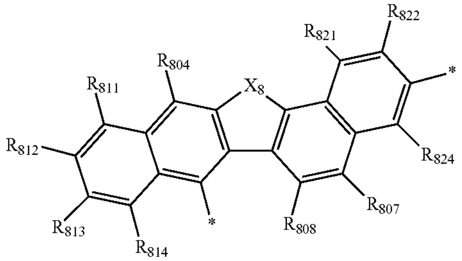

[Formula 310]

(81-15)

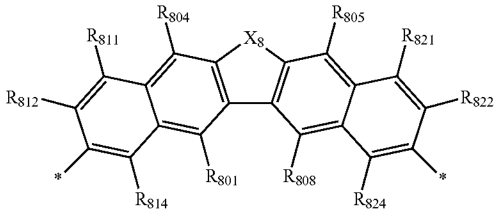

(81-16)

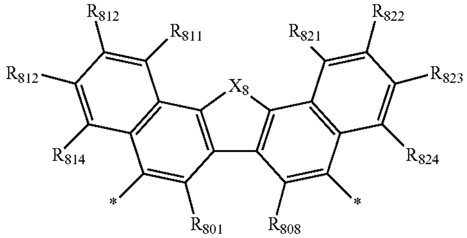

[Formula 311]

(81-17)

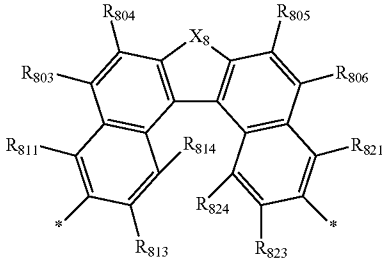

(81-18)

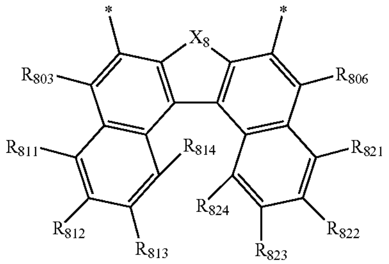

In the formulae (81-7) to (81-18):

$X_8$ represents the same as $X_8$ in the formula (8);

* is a single bond to be bonded with the monovalent group represented by the formula (84);

$R_{801}$ to $R_{824}$ each independently represent the same as $R_{801}$ to $R_{824}$ in the formulae (81-1) to (81-6) that are not the monovalent group represented by the formula (84).

$R_{801}$ to $R_{808}$ not forming the divalent group represented by the formula (82) or (83) and not being the monovalent group represented by the formula (84), and $R_{811}$ to $R_{814}$ and $R_{821}$ to $R_{824}$ not being the monovalent group represented by the formula (84) are each independently preferably a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The monovalent group represented by the formula (84) is preferably represented by a formula (85) or (86) below.

[Formula 312]

(85)

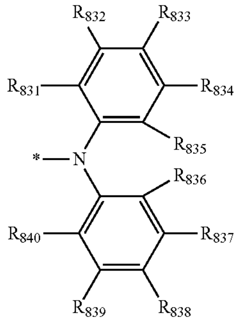

In the formula (85): $R_{831}$ to $R_{840}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formula (85) represents the same as * in the formula (84).

[Formula 313]

(86)

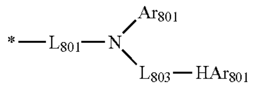

In the formula (86): $Ar_{801}$, $L_{801}$, and $L_{803}$ represent the same as $Ar_{801}$, $L_{801}$, and $L_{803}$ in the formula (84); and $HAr_{801}$ is a moiety represented by a formula (87) below.

[Formula 314]

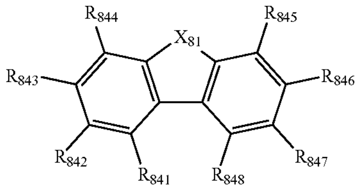

(87)

In the formula (87):

$X_{81}$ represents an oxygen atom or a sulfur atom;

one of $R_{841}$ to $R_{848}$ is a single bond with $L_{803}$; and $R_{841}$ to $R_{848}$ not being the single bond are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Specific Examples of Compound Represented by Formula (8)

Specific examples of the compound represented by the formula (8) include compounds shown below as well as the compounds disclosed in International Publication No. WO 2014/104144.

[Formula 315]

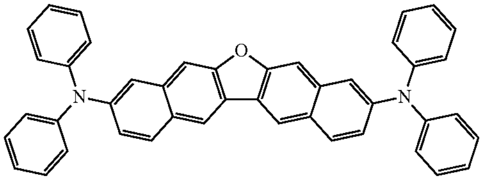

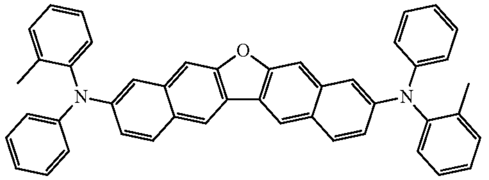

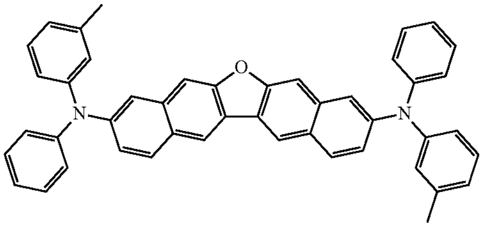

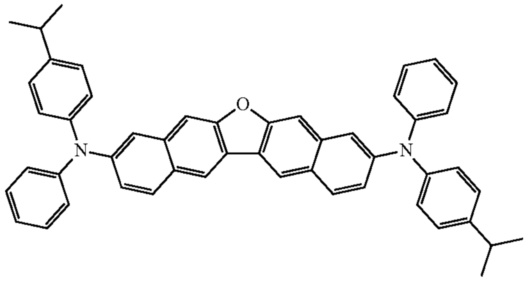

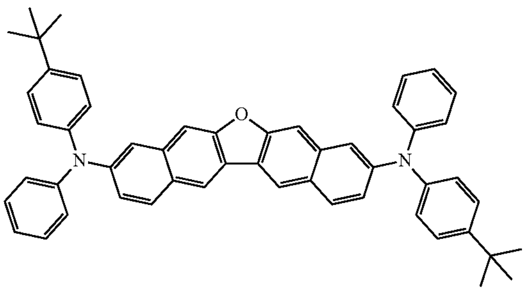

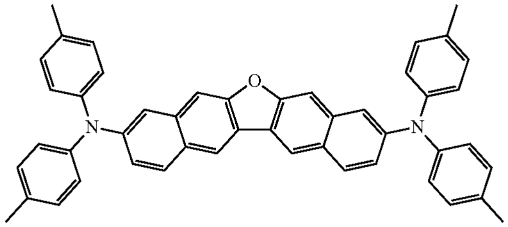

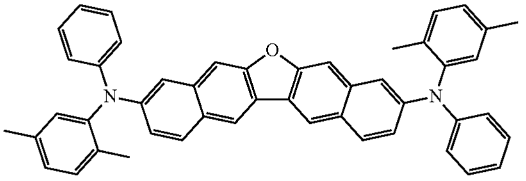

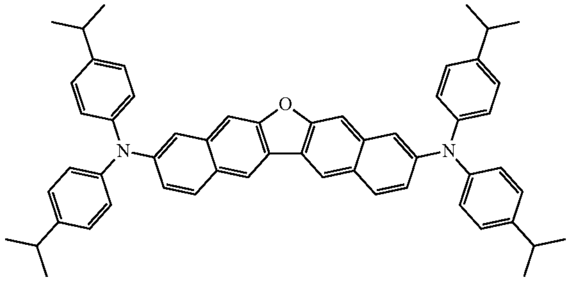

-continued
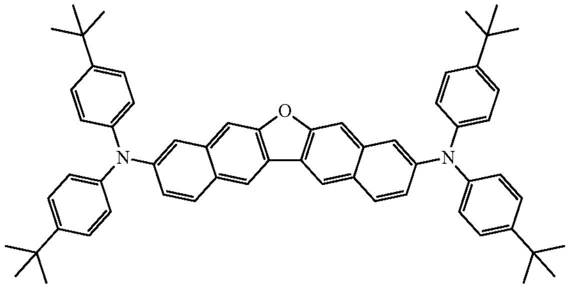
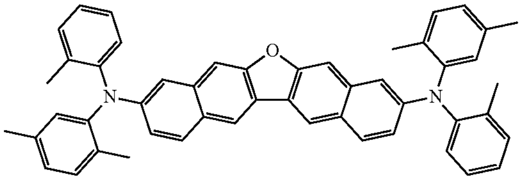
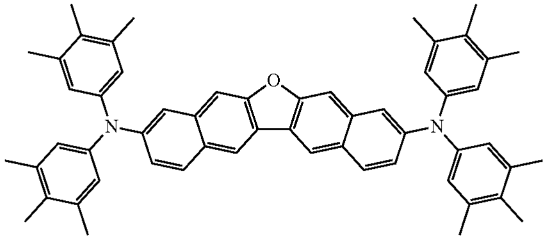
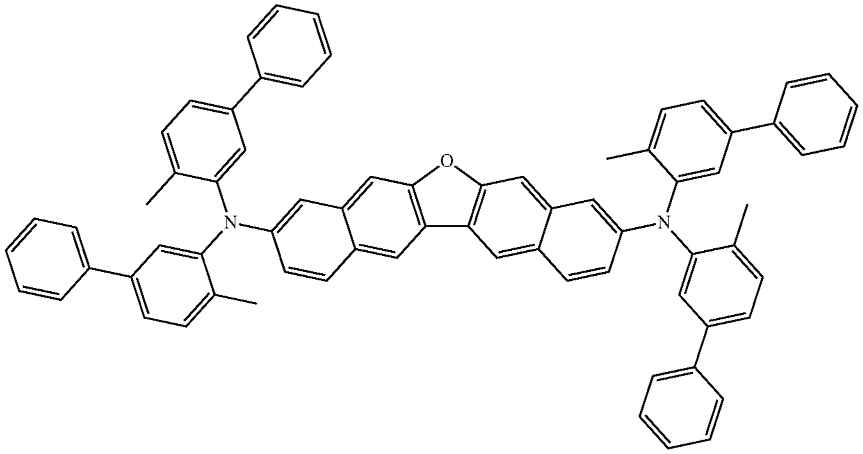
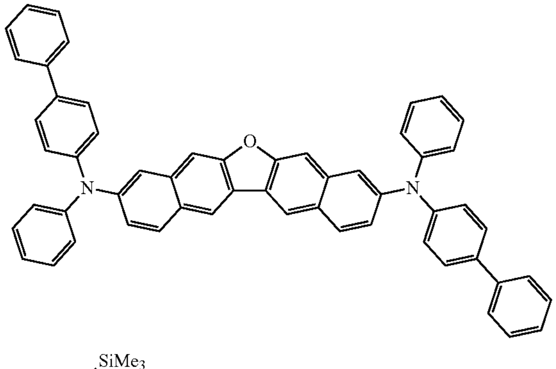
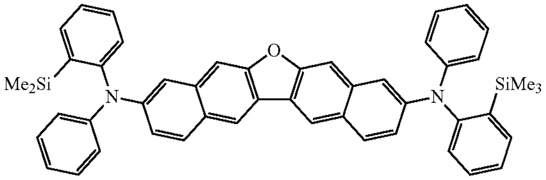
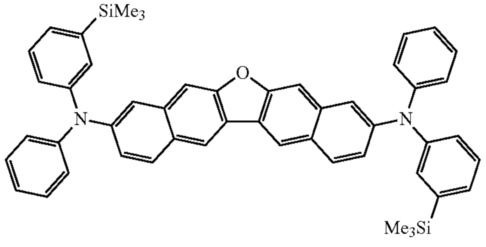
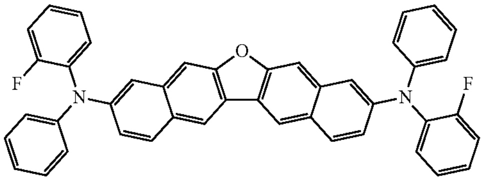

-continued
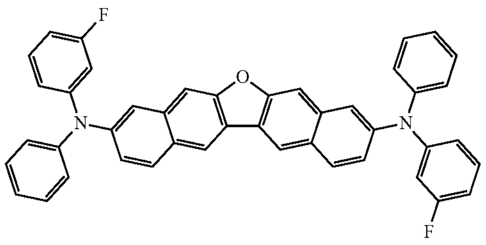
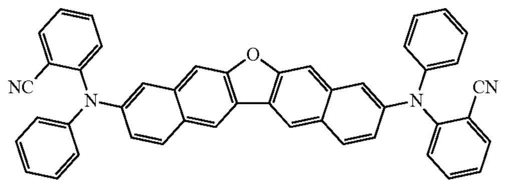
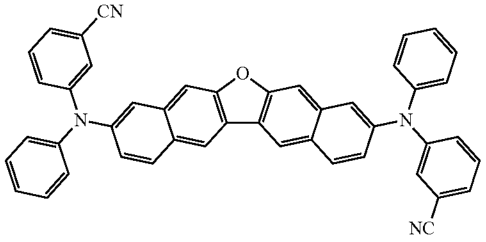
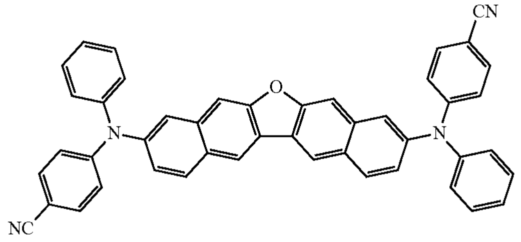
[Formula 316]
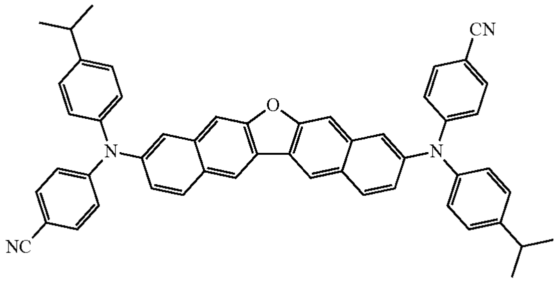
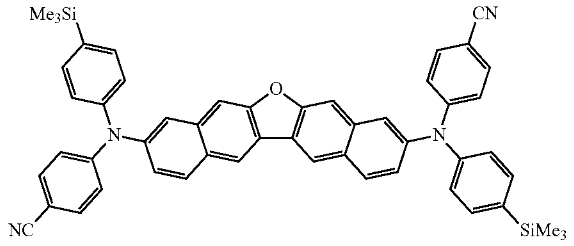
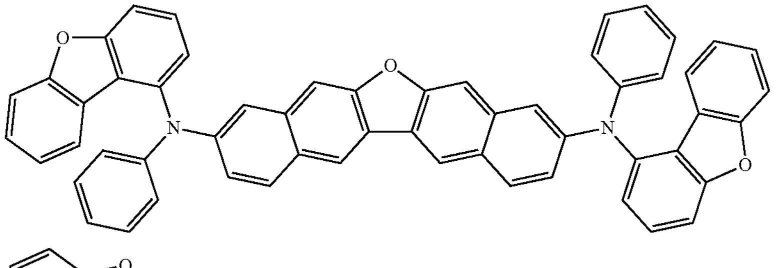
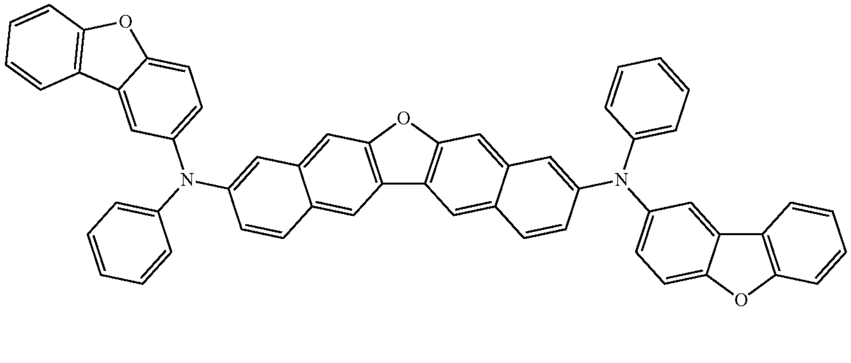

-continued
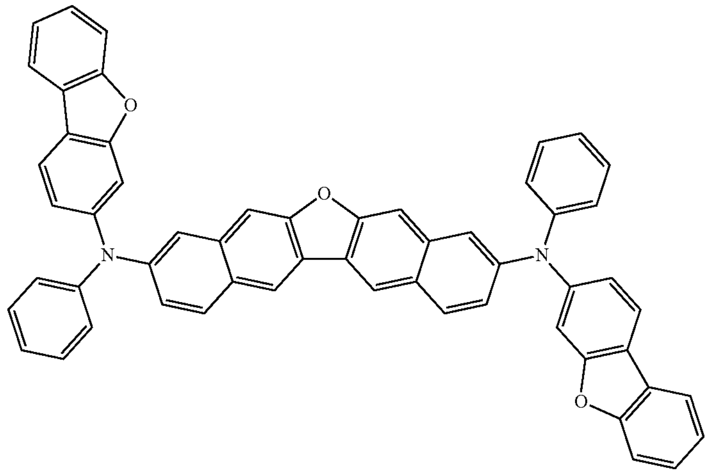
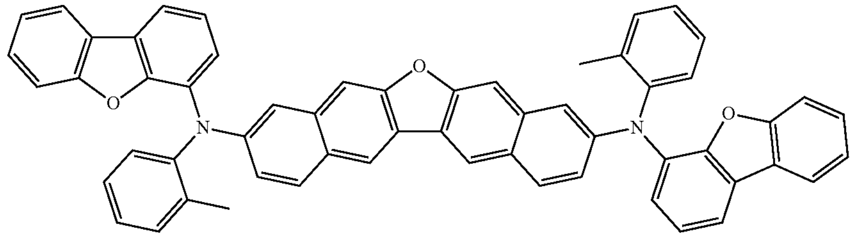
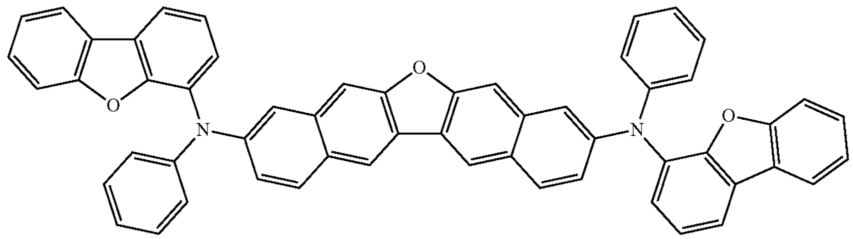
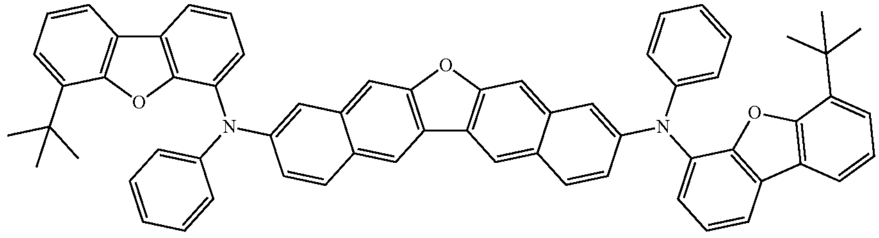
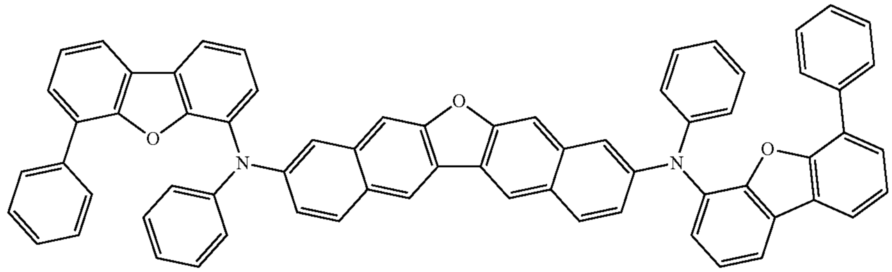

-continued
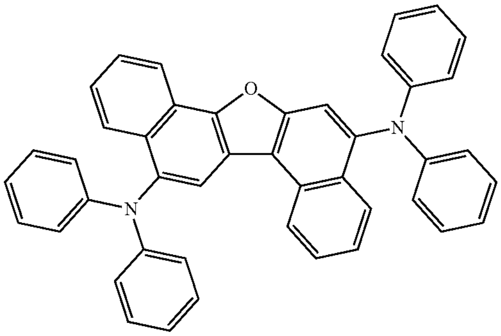
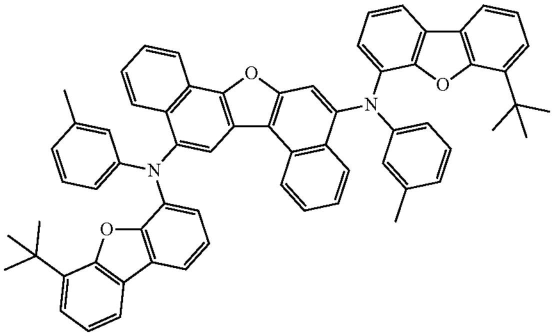
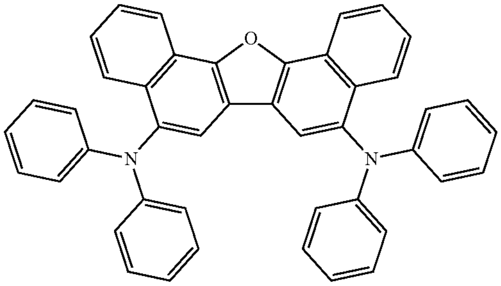
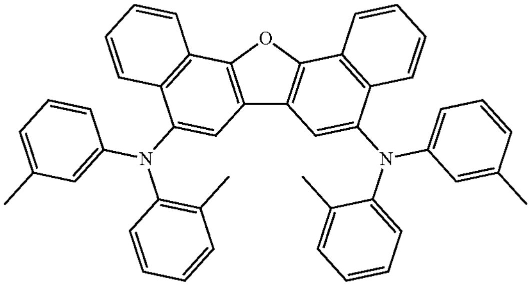
[Formula 317]
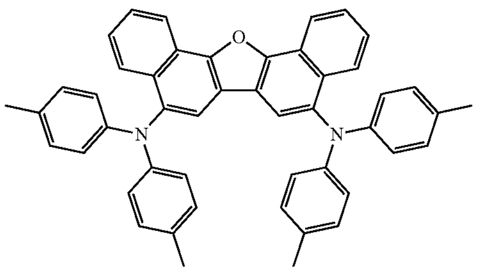
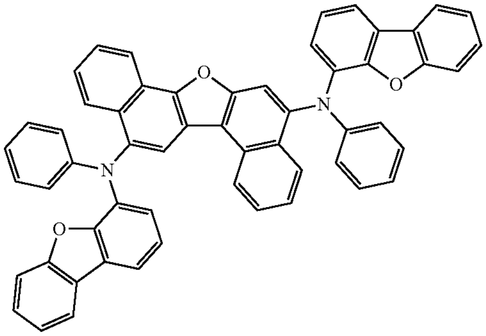
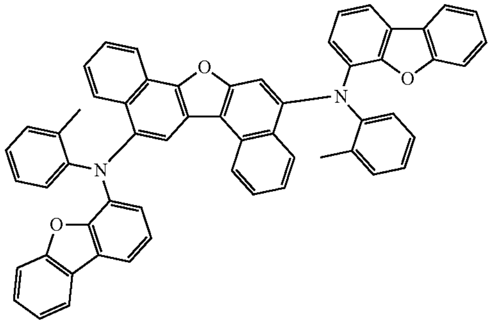
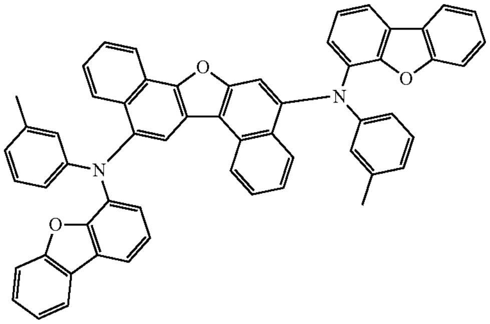
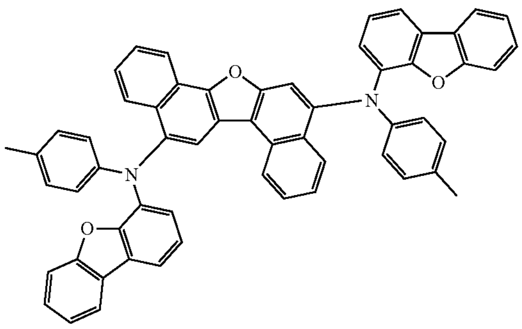
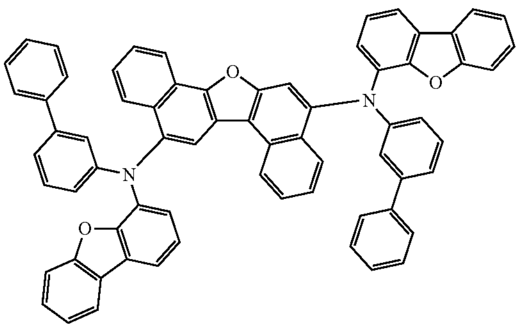

-continued
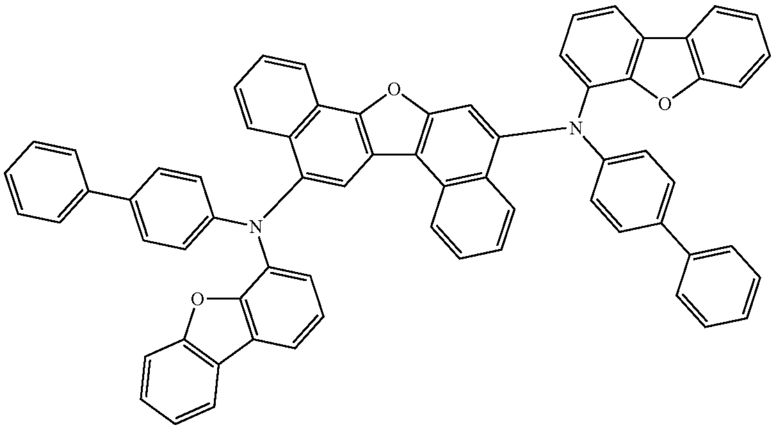
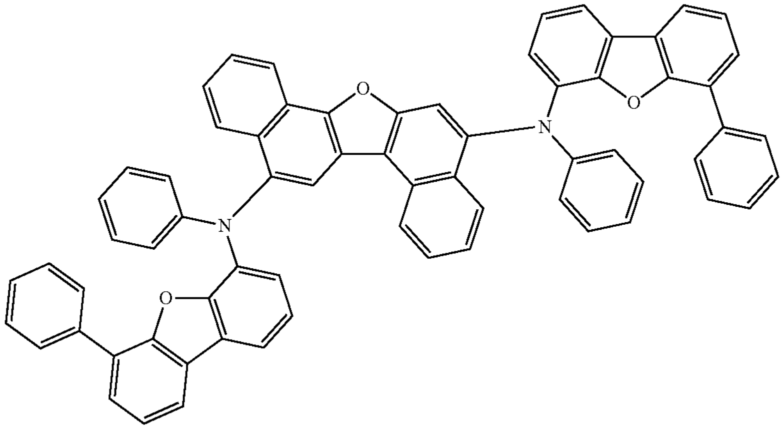
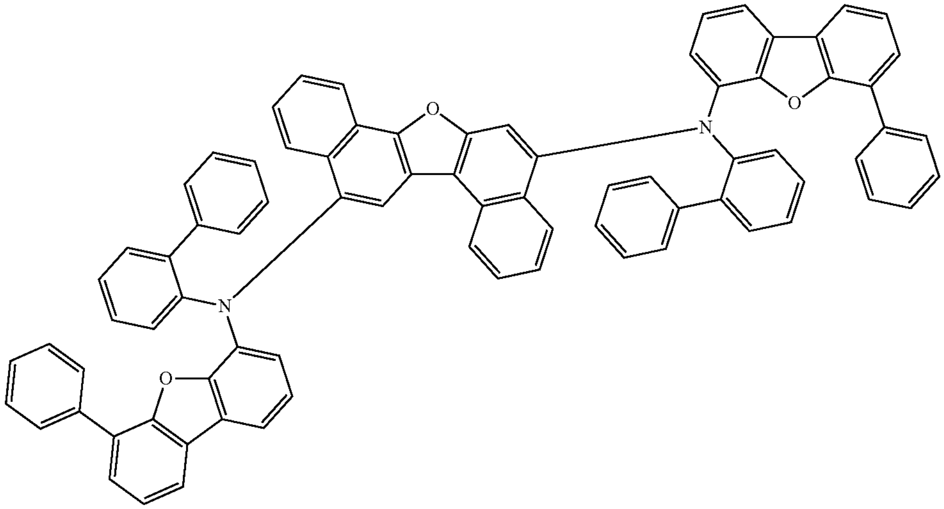

-continued
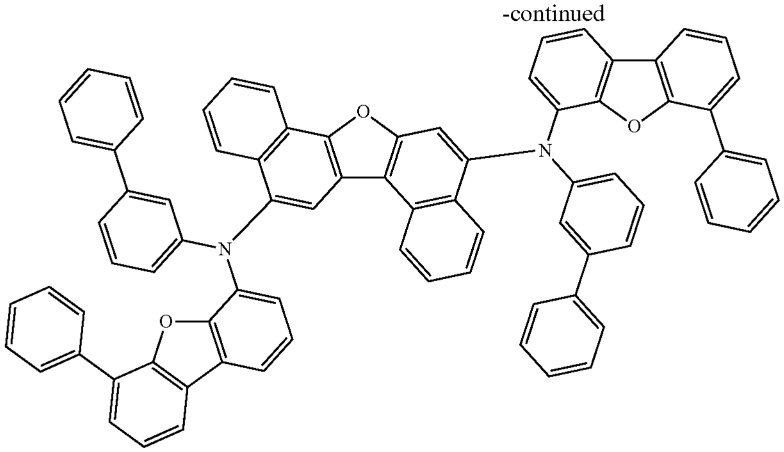
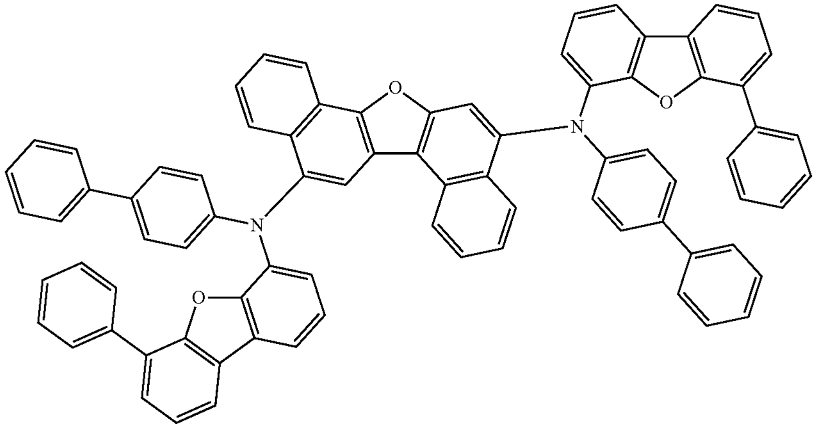
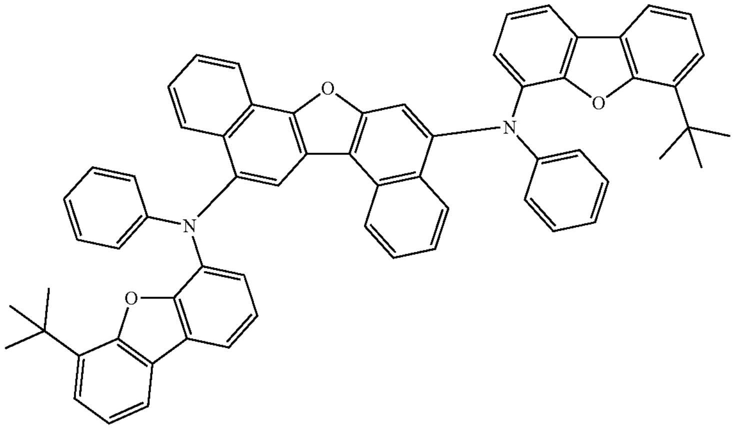
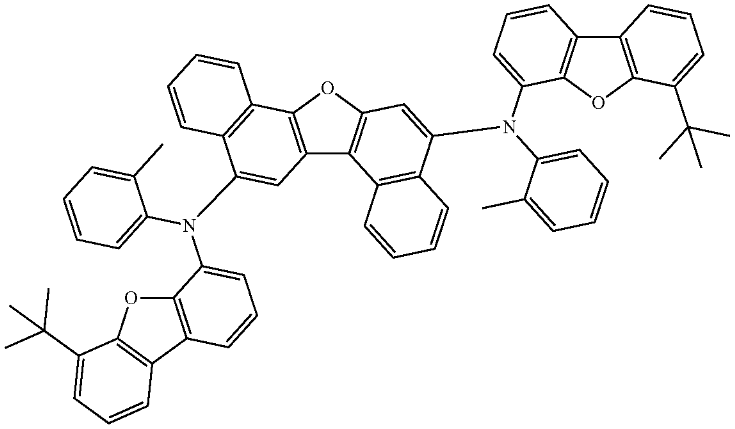

-continued
[Formula 318]
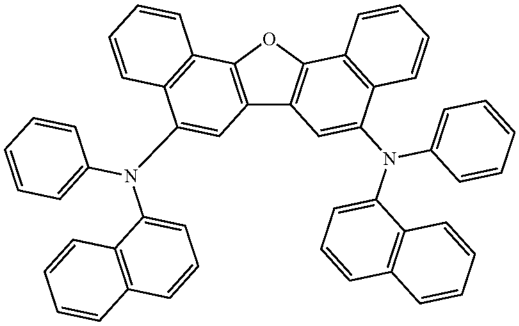
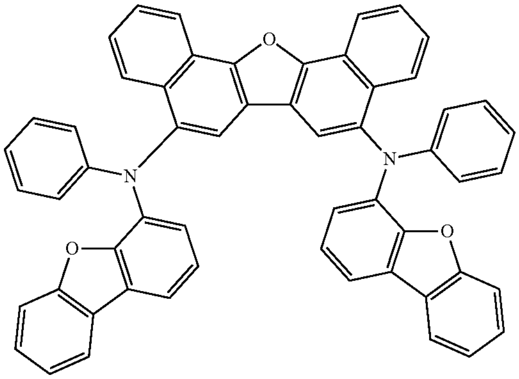
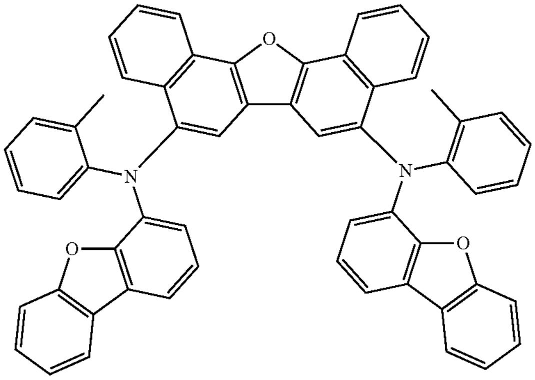
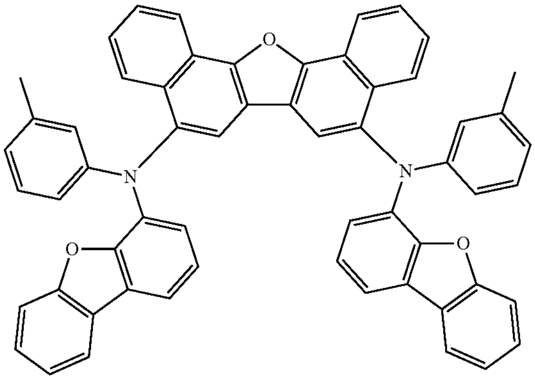
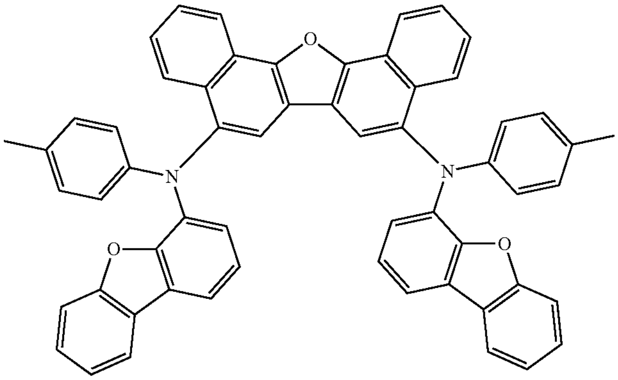
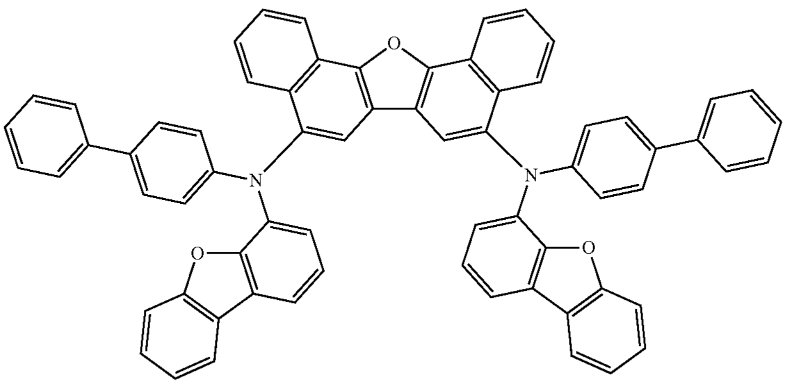

-continued
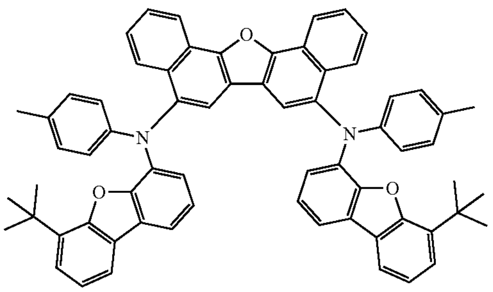
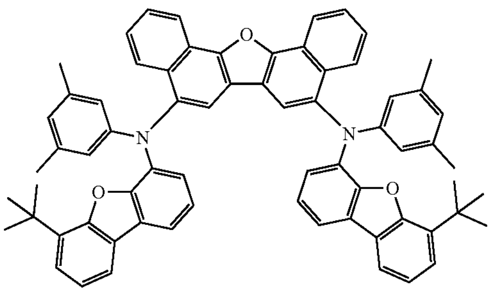
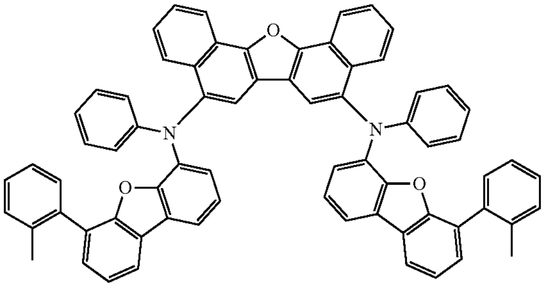
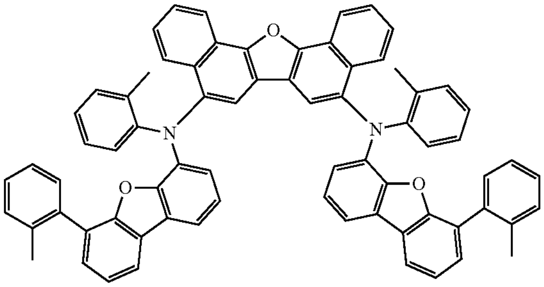
[Formula 319]
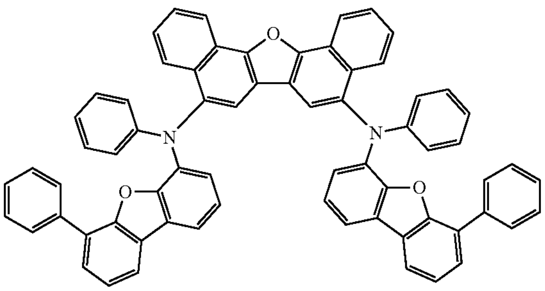
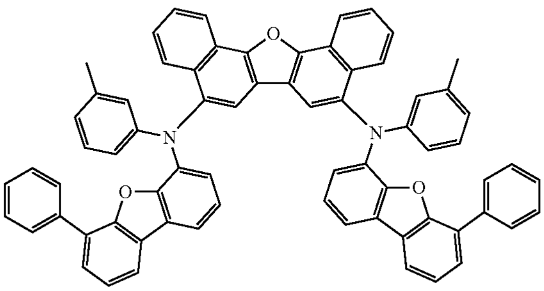
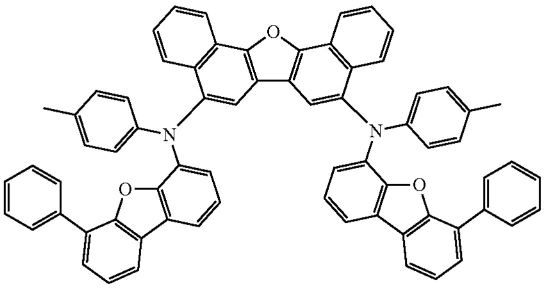
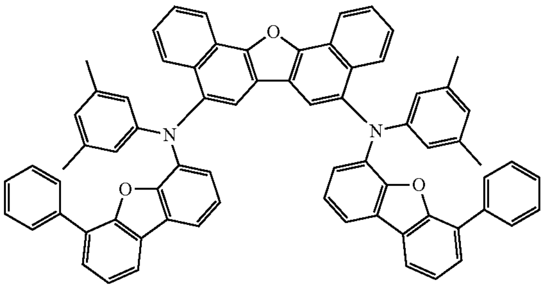
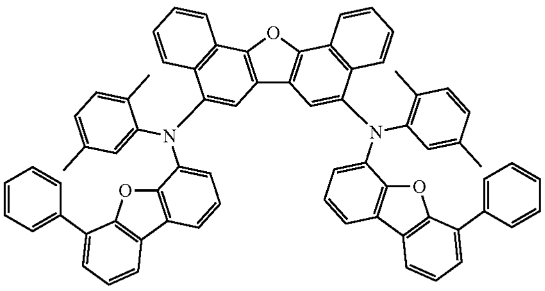
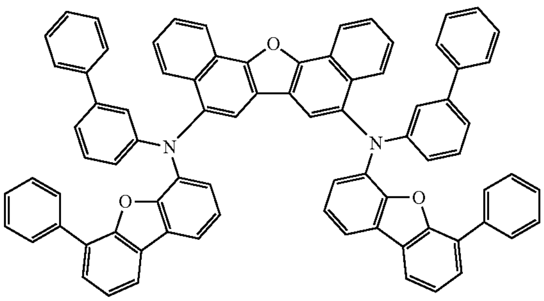

-continued
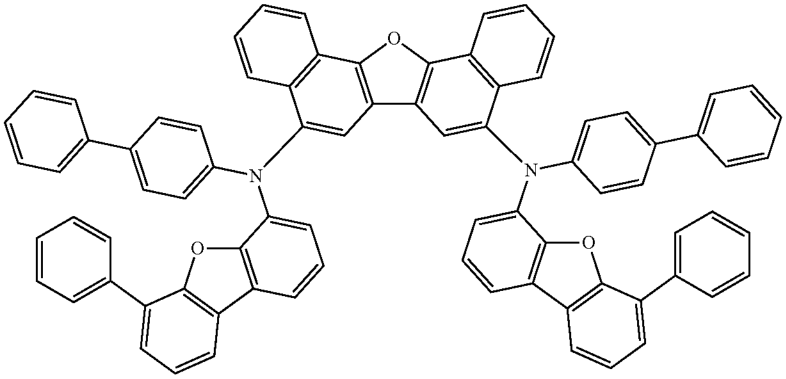
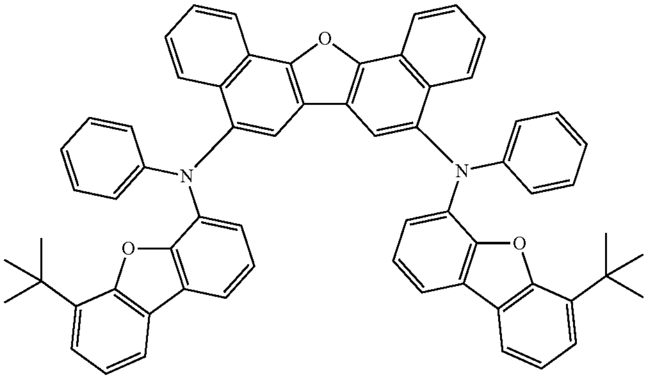
[Formula 320]
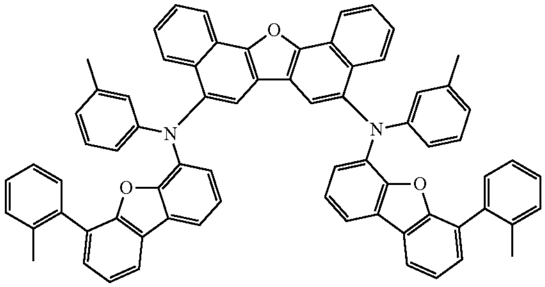
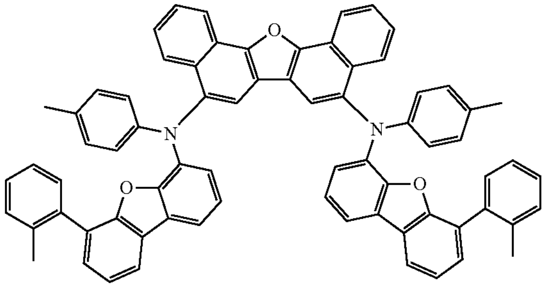
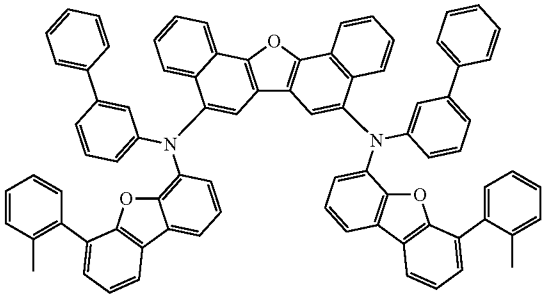
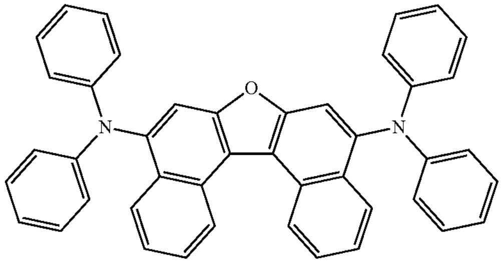
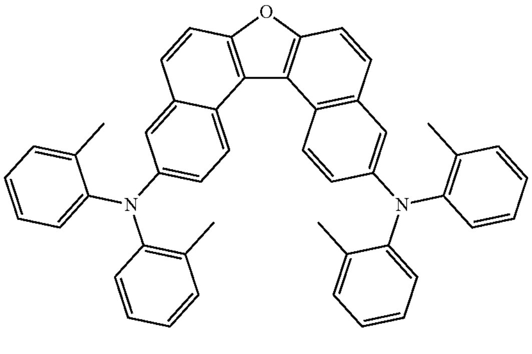
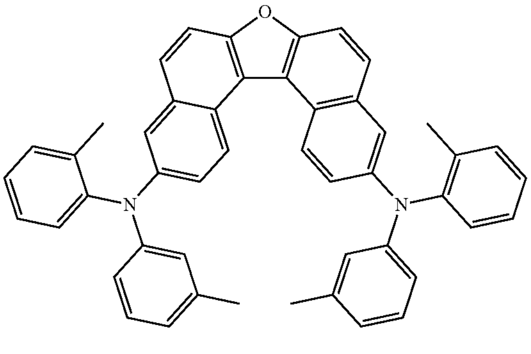

-continued
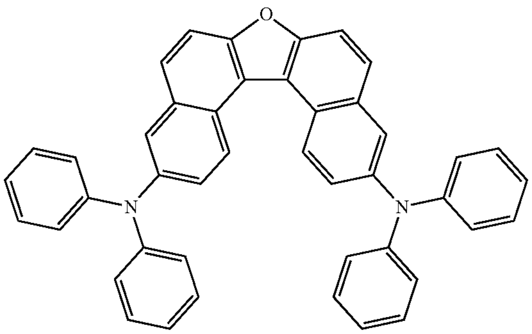
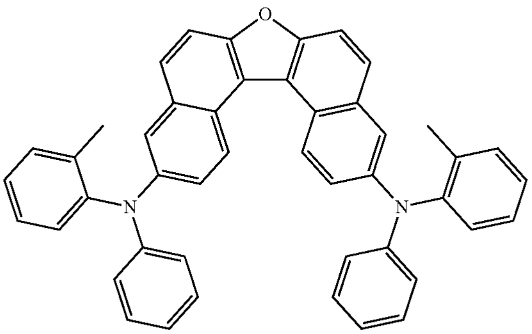
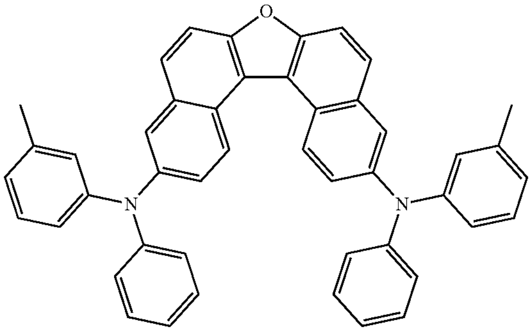
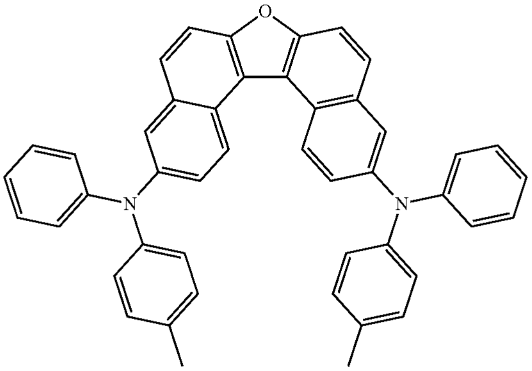
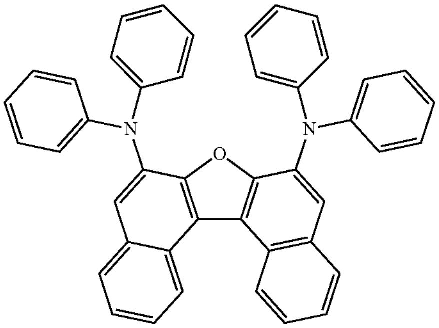
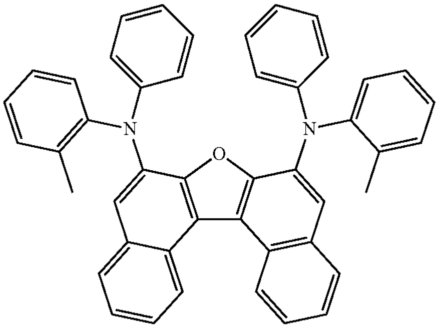
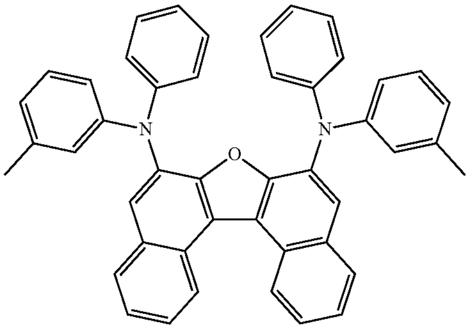
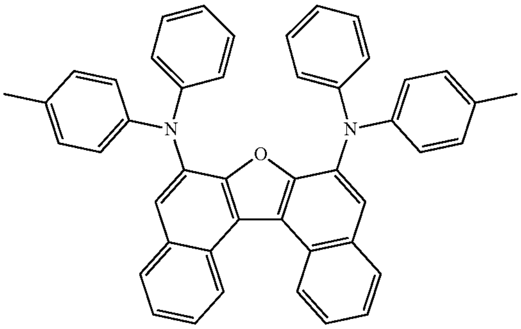

-continued

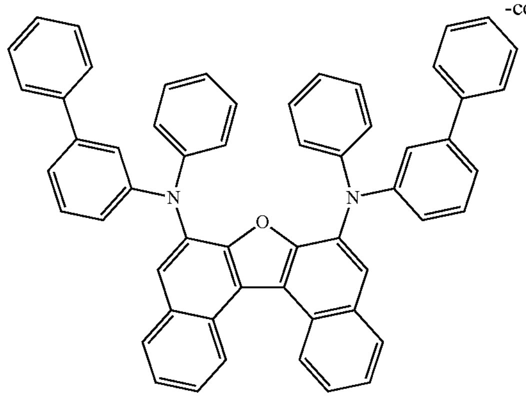

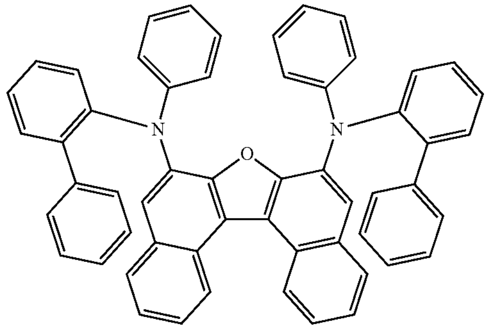

Compound Represented by Formula (9)

The compound represented by the formula (9) will be described below.

[Formula 321]

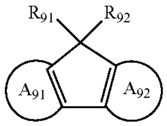

(9)

In the formula (9): $A_{91}$ ring and $A_{92}$ ring are each independently a substituted or unsubstituted aromatic hydrocarbon ring having 6 to 50 ring carbon atoms or a substituted or unsubstituted heterocycle having 5 to 50 ring atoms; and at least one of the $A_{91}$ ring or the $A_{92}$ ring is bonded with * in a moiety represented by a formula (92) below.

[Formula 322]

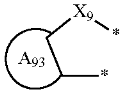

(92)

In the formula (92): $A_{93}$ ring is a substituted or unsubstituted aromatic hydrocarbon ring having 6 to 50 ring carbon atoms or a substituted or unsubstituted heterocycle having 5 to 50 ring atoms;

$X_9$ is $NR_{93}$, $C(R_{94})(R_{95})$, $Si(R_{96})(R_{97})$, $Ge(R_{98})(R_{99})$, an oxygen atom, a sulfur atom, or a selenium atom;

$R_{91}$ and $R_{92}$ are mutually bonded to form a substituted or unsubstituted monocyclic ring, mutually bonded to form a substituted or unsubstituted fused ring, or not mutually bonded; and $R_{91}$ and $R_{92}$ not forming the monocyclic ring and not forming the fused ring, and $R_{93}$ to $R_{99}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

At least one ring selected from the group consisting of the $A_{91}$ ring and the $A_{92}$ ring is bonded to a bond * of the moiety represented by the formula (92). In other words, the ring carbon atoms of the aromatic hydrocarbon ring or the ring atoms of the heterocycle of the $A_{91}$ ring in an exemplary embodiment are bonded to the bonds * in the moiety represented by the formula (92). Further, the ring carbon atoms of the aromatic hydrocarbon ring or the ring atoms of the heterocycle of the $A_{92}$ ring in an exemplary embodiment are bonded to the bonds * in the moiety represented by the formula (92).

In an exemplary embodiment, the group represented by a formula (93) below is bonded to one or both of the $A_{91}$ ring and $A_{92}$ ring.

[Formula 323]

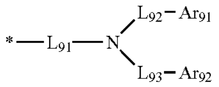

(93)

In the formula (93): $Ar_{91}$ and $Ar_{92}$ are each independently a substituted or unsubstituted aryl group having 6 to 50 ring carbon atoms, or a substituted or unsubstituted heterocyclic group having 5 to 50 ring atoms;

$L_{91}$ to $L_{93}$ each independently represent a single bond, a substituted or unsubstituted arylene group having 6 to 30 ring carbon atoms, a substituted or unsubstituted heterocyclic group having 5 to 30 ring atoms, or a divalent linking group formed by bonding two, three or four groups selected from the group consisting of the substituted or unsubstituted arylene group having 6 to 30 ring carbon atoms and a substituted or unsubstituted divalent heterocyclic group having 5 to 30 ring atoms; and

* in the formula (93) represents a bonding position with one of the $A_{91}$ ring and the $A_{92}$ ring.

In an exemplary embodiment, in addition to the $A_{91}$ ring, the ring carbon atoms of the aromatic hydrocarbon ring or the ring atoms of the heterocycle of the $A_{92}$ ring are bonded to * in the moiety represented by the formula (92). In this case, the moieties represented by the formula (92) are mutually the same or different.

In an exemplary embodiment, $R_{91}$ and $R_{92}$ are each independently a substituted or unsubstituted aryl group having 6 to 50 ring carbon atoms.

In an exemplary embodiment, $R_{91}$ and $R_{92}$ are mutually bonded to form a fluorene structure.

In an exemplary embodiment, the rings $A_{91}$ and $A_{92}$ are each independently a substituted or unsubstituted aromatic hydrocarbon ring having 6 to 50 ring carbon atoms, example of which is a substituted or unsubstituted benzene ring.

In an exemplary embodiment, the ring $A_{93}$ is a substituted or unsubstituted aromatic hydrocarbon ring having 6 to 50 ring carbon atoms, example of which is a substituted or unsubstituted benzene ring.

In an exemplary embodiment, $X_9$ is an oxygen atom or a sulfur atom.

Specific Examples of Compound Represented by Formula (9)

Specific examples of the compound represented by the formula (9) include compounds shown below.

[Formula 324]

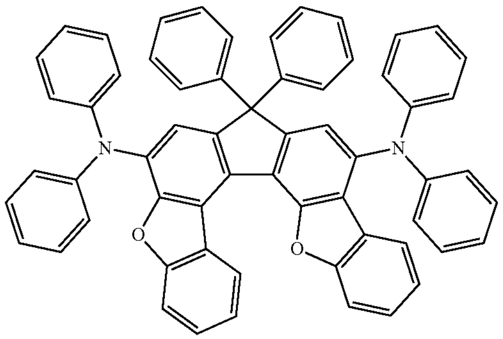

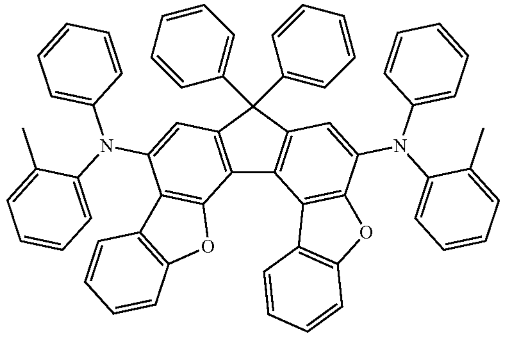

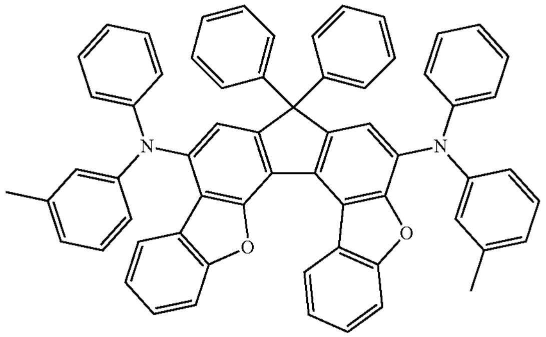

-continued

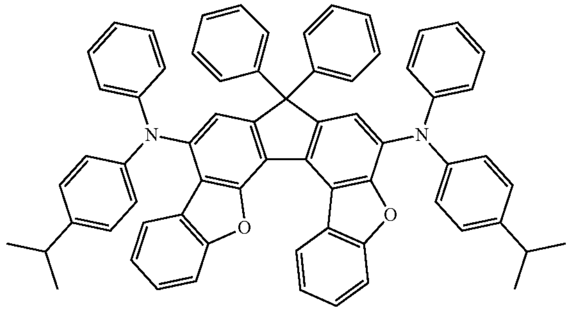

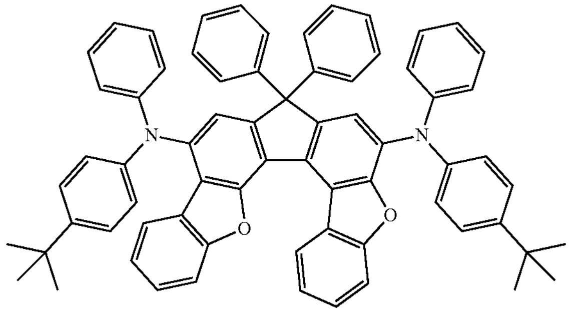

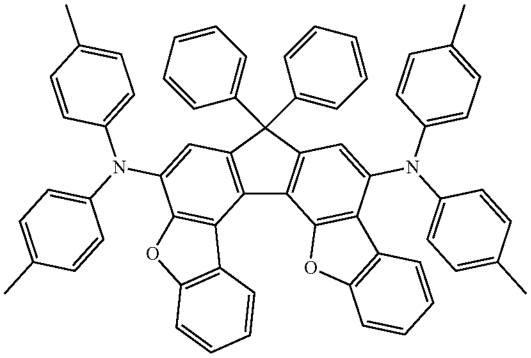

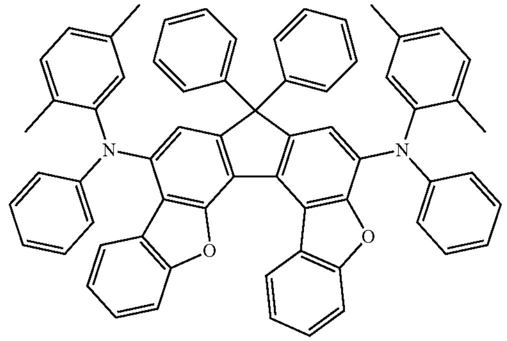

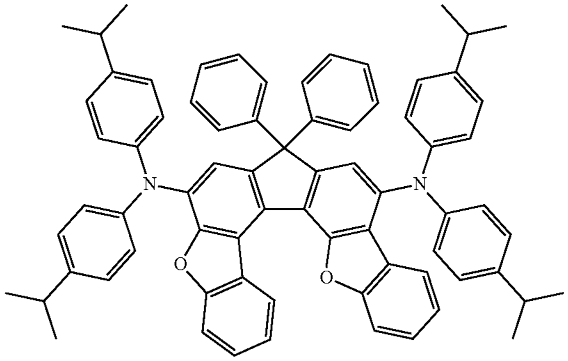

-continued
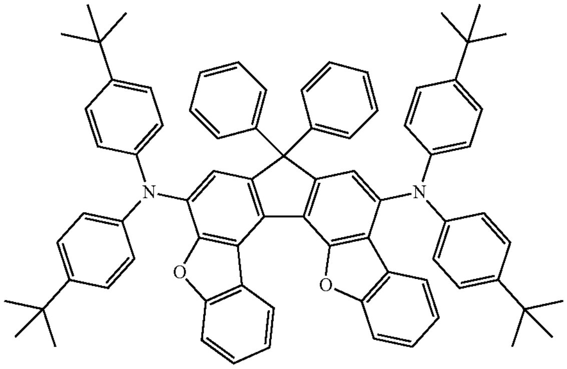
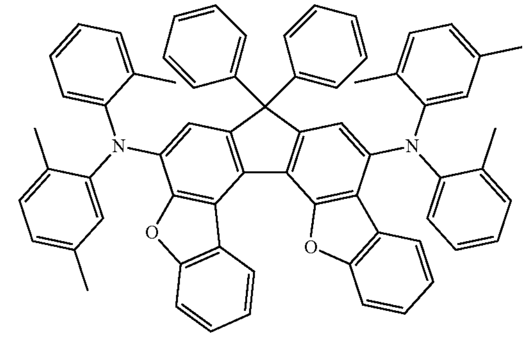
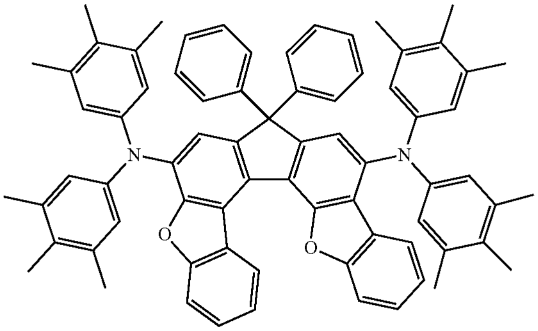
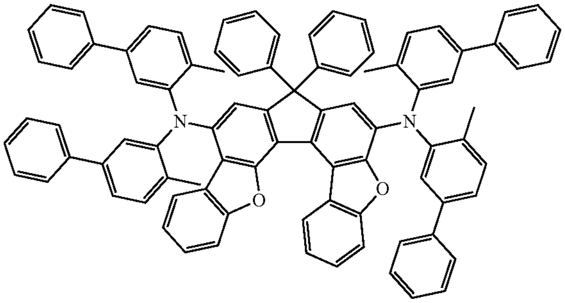
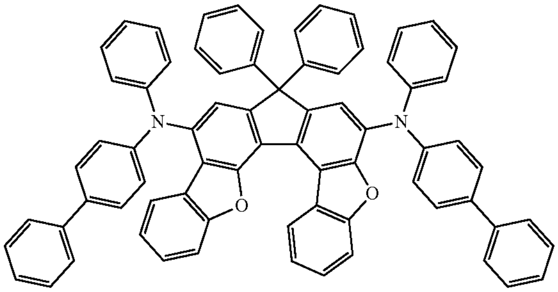
-continued
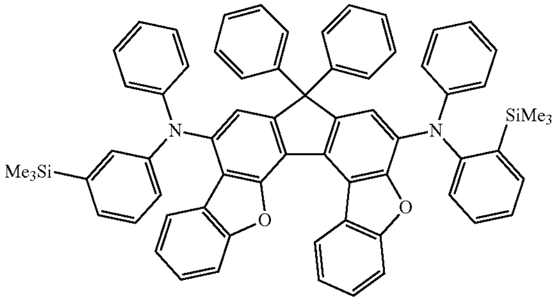
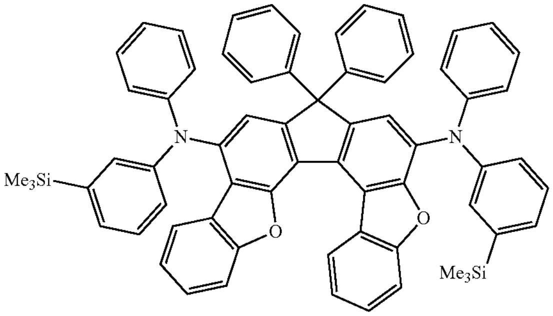
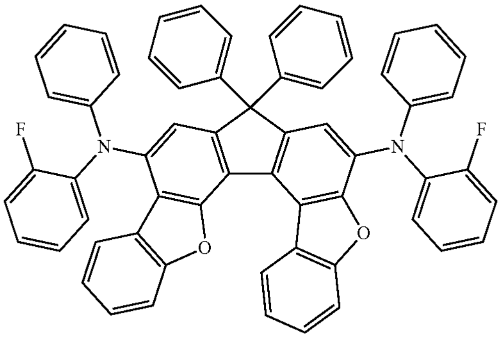
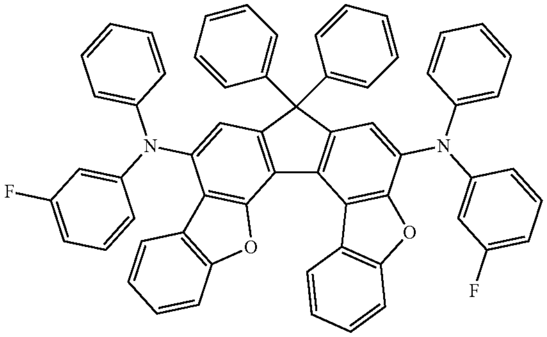
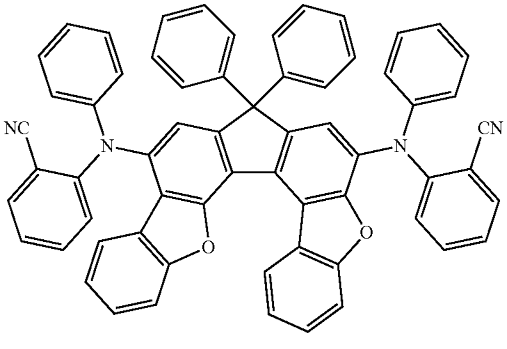

-continued
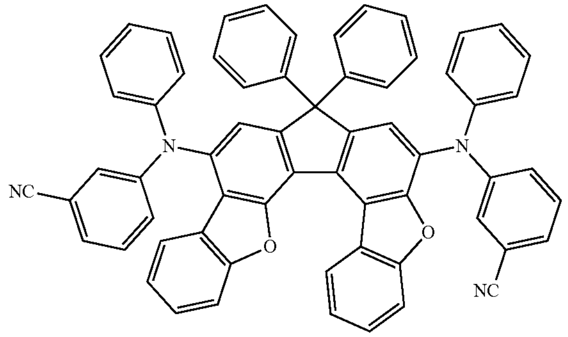
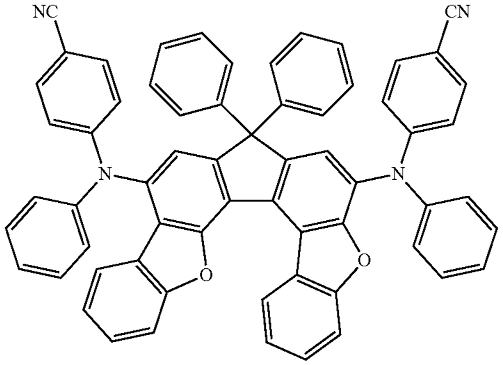
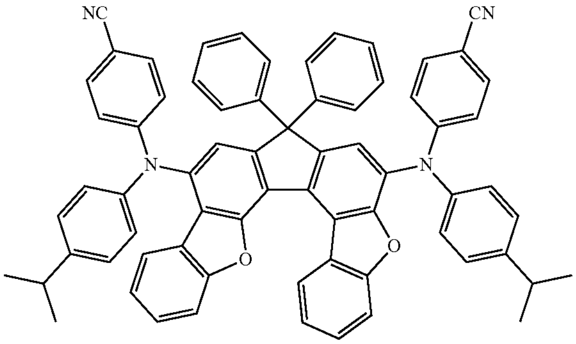
[Formula 325]
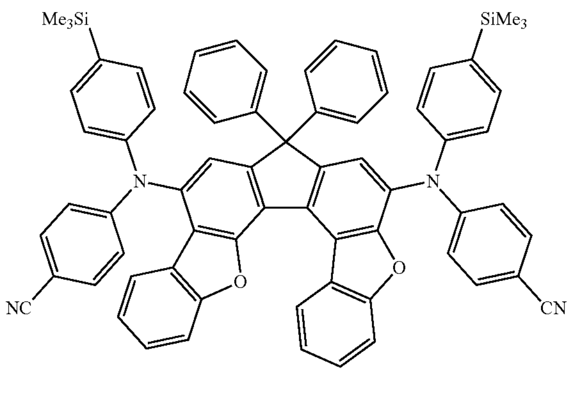
-continued
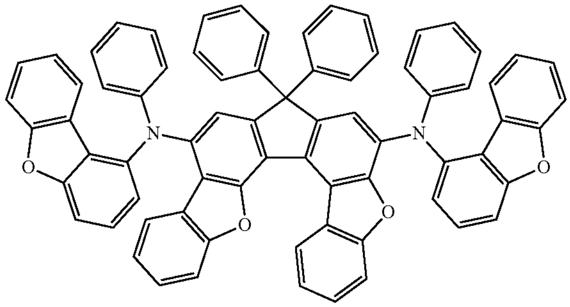
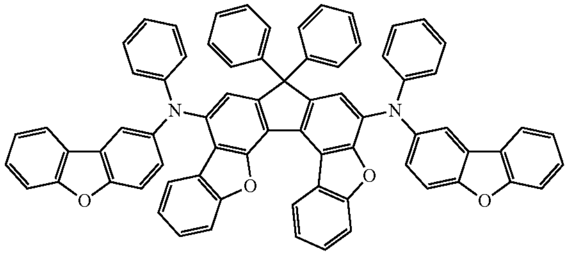
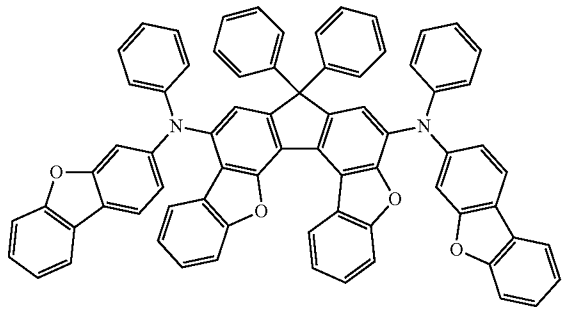
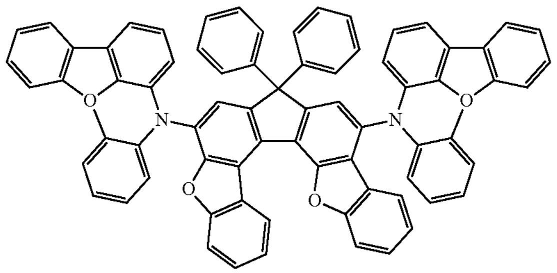
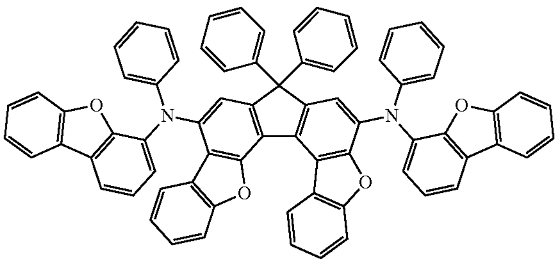
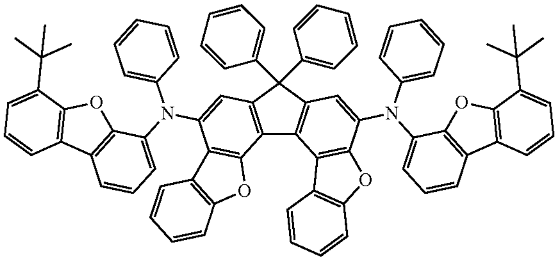

-continued
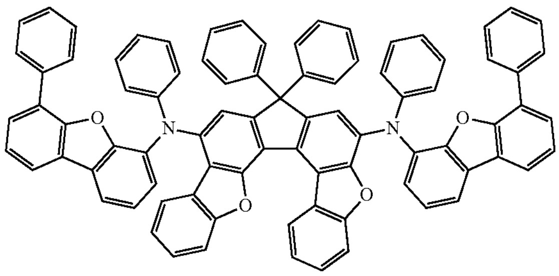
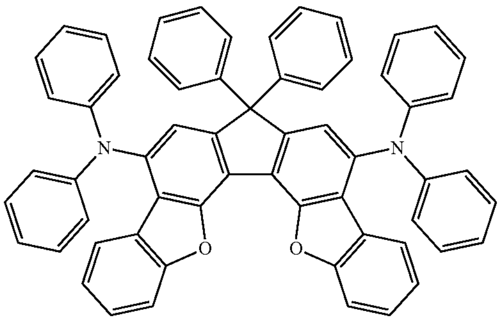
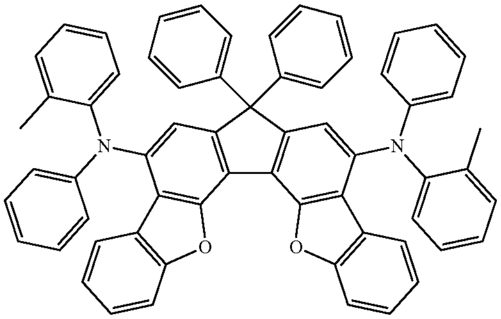
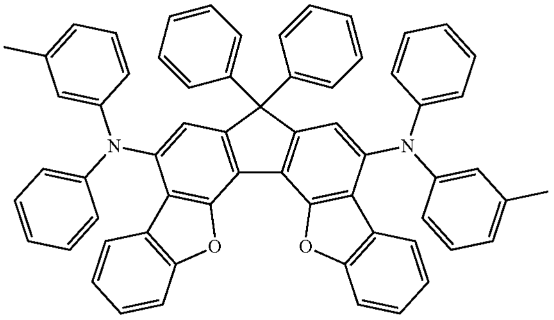
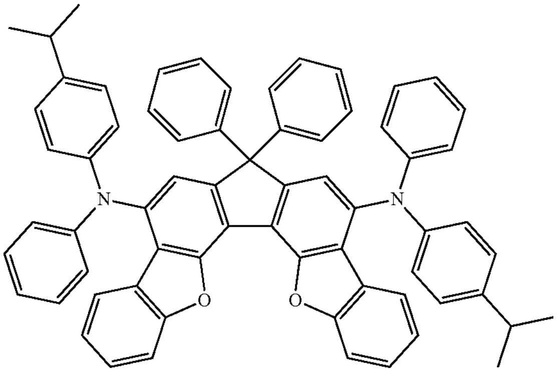
-continued
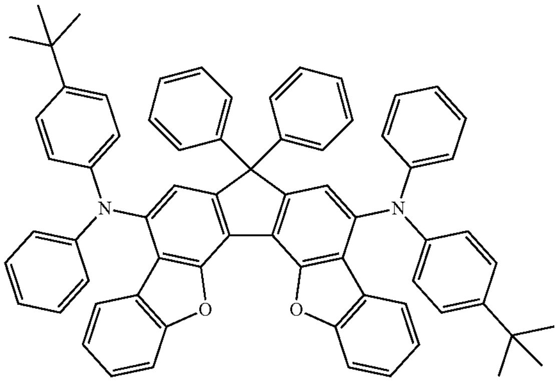
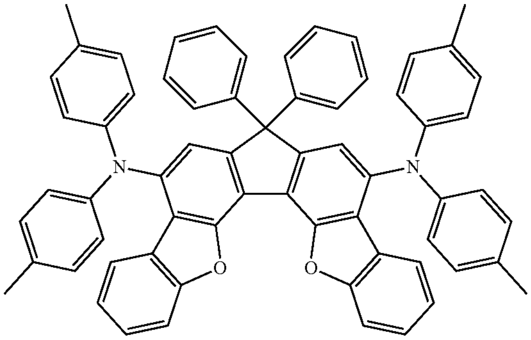
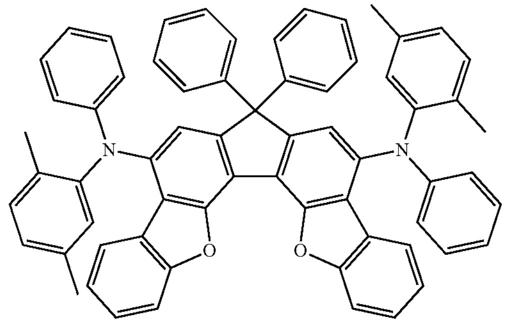
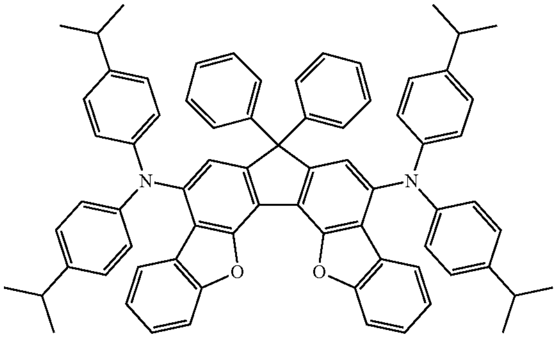
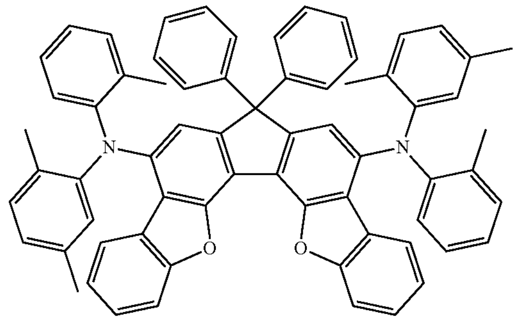

-continued
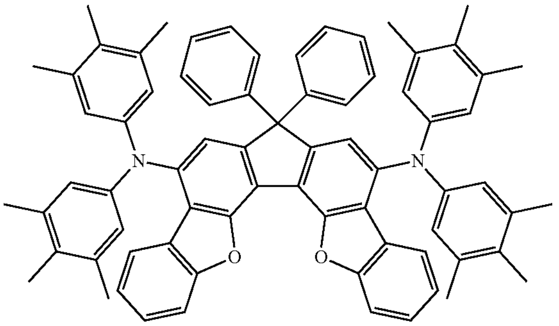
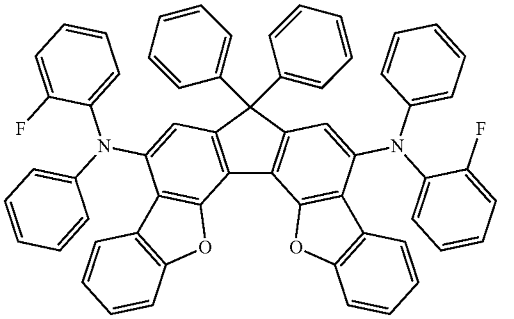
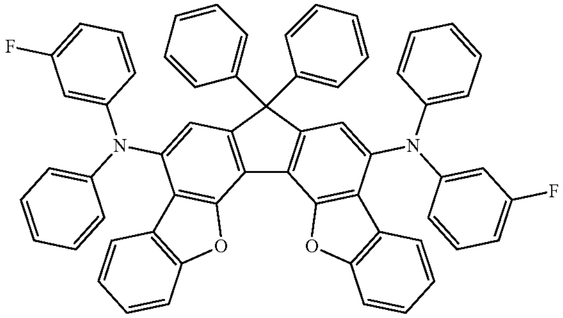
[Formula 326]
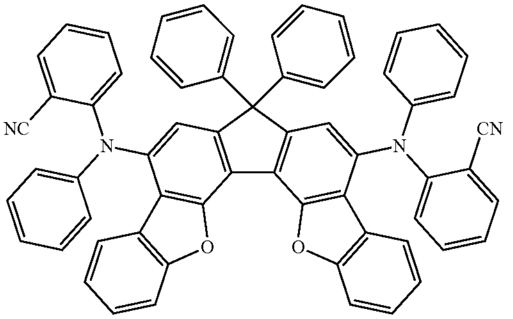
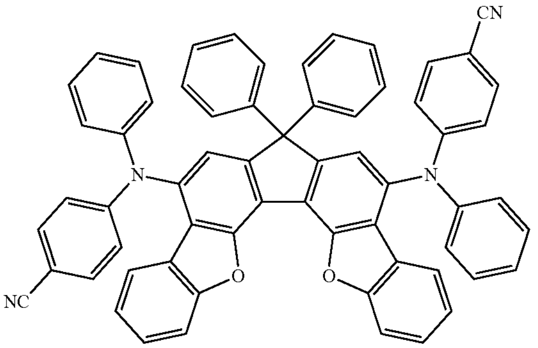
-continued
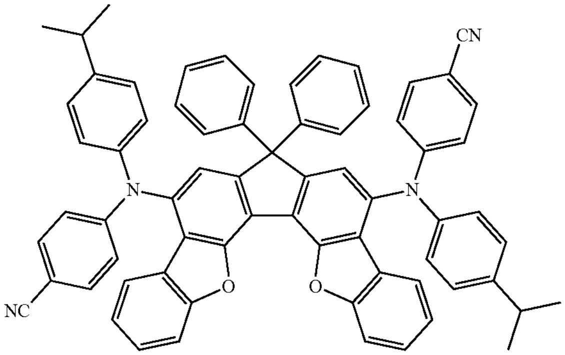
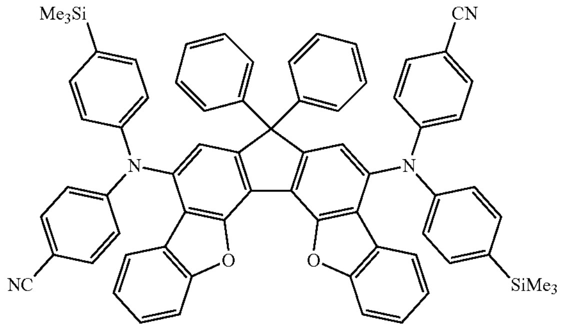
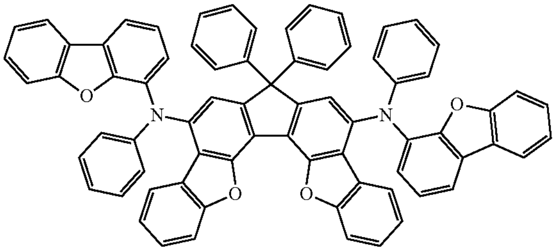
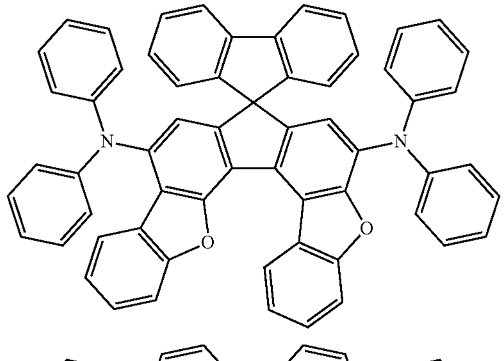
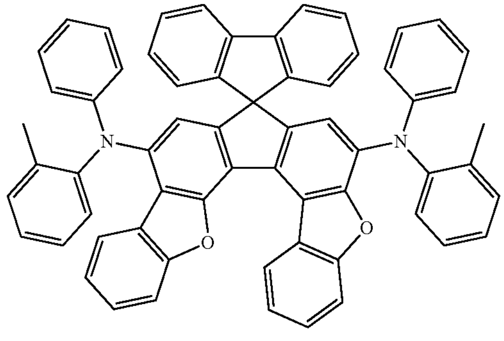

-continued
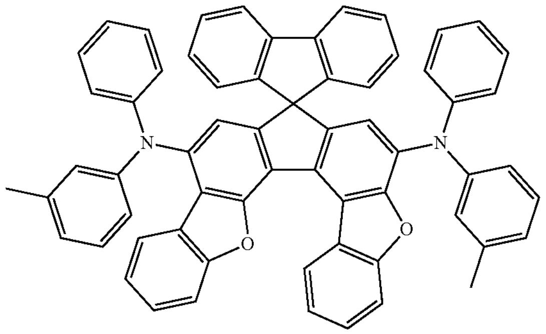
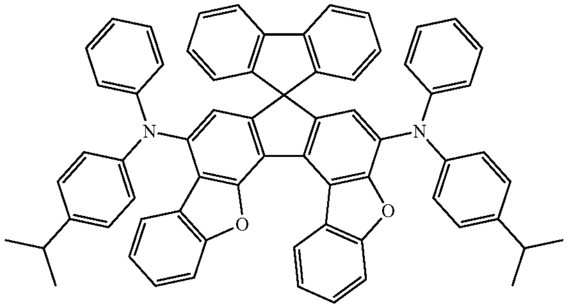
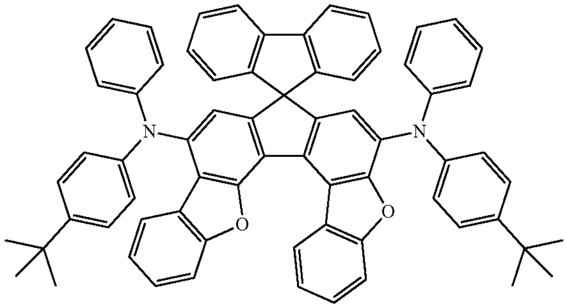
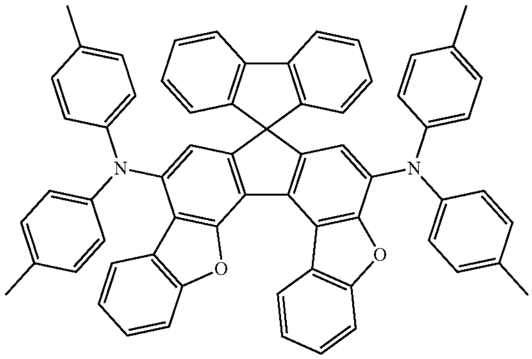
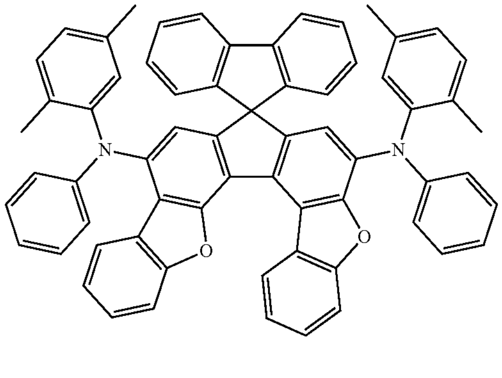
-continued
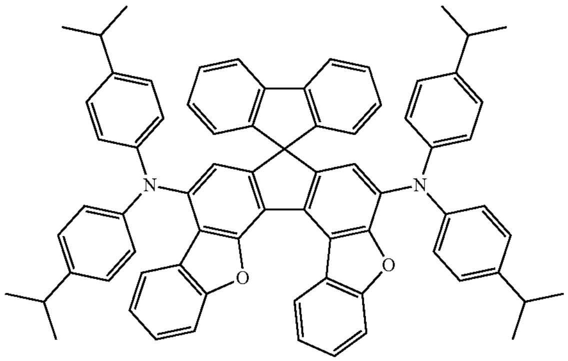
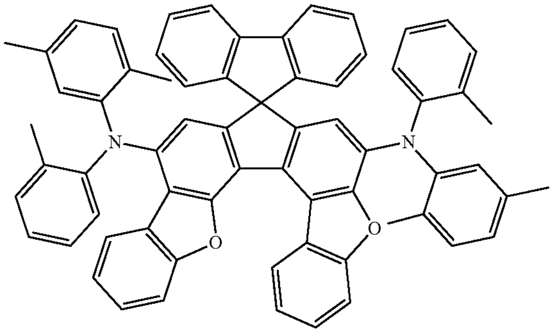
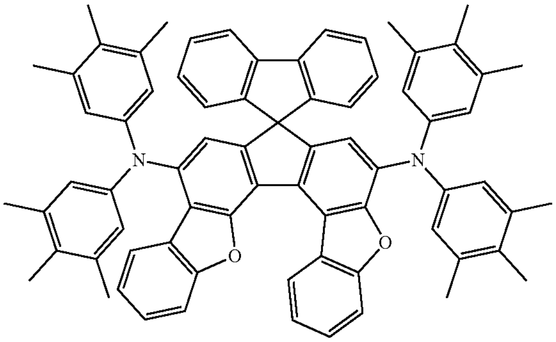
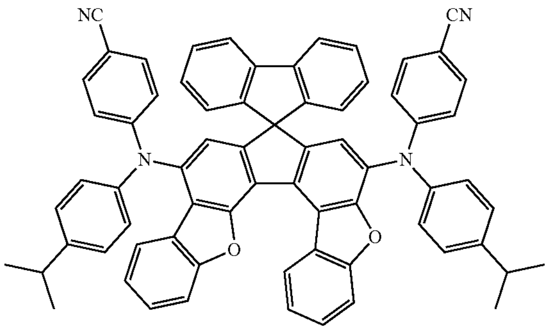
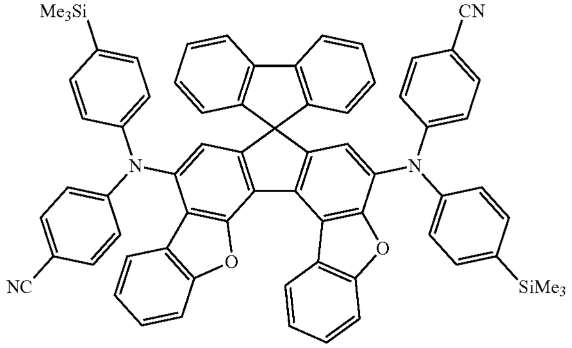

-continued
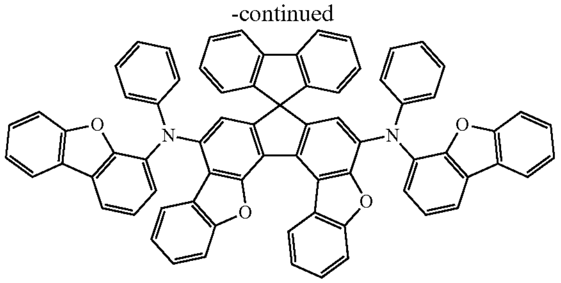
[Formula 327]
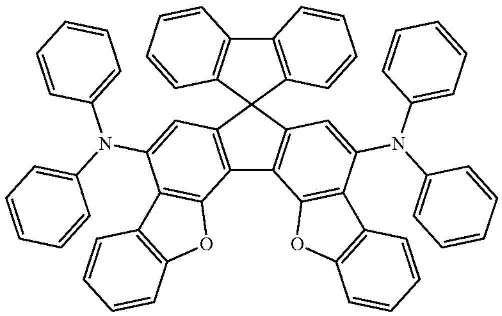
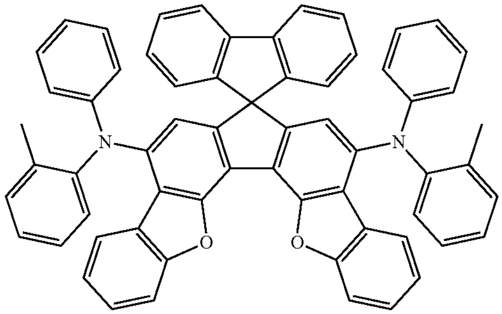
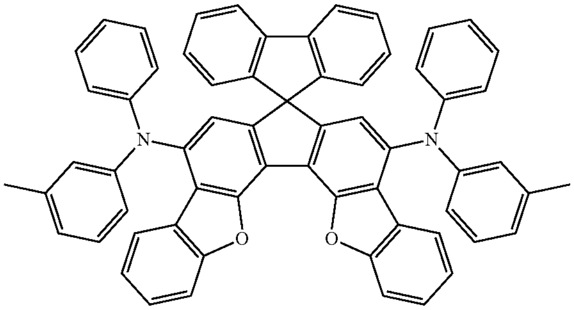
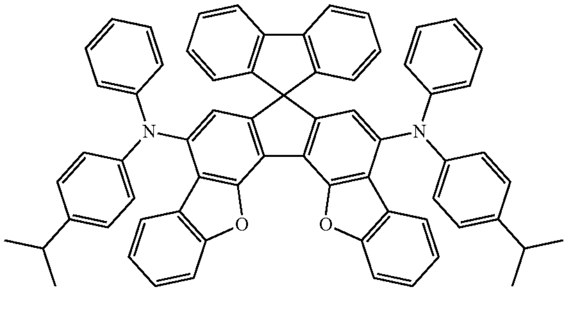
-continued
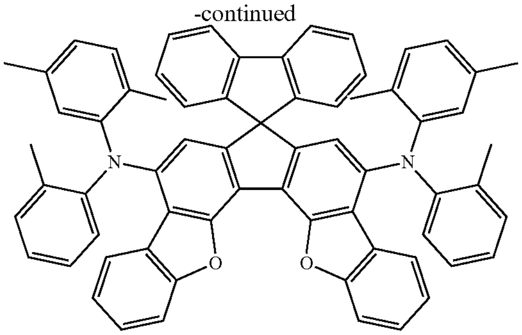
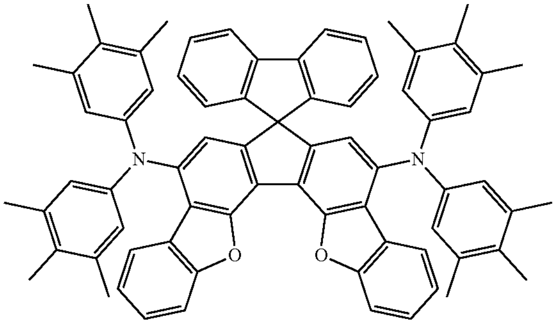
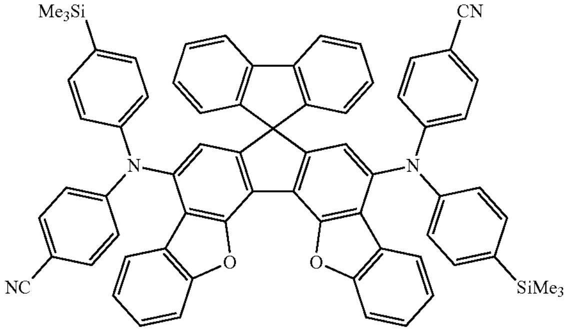
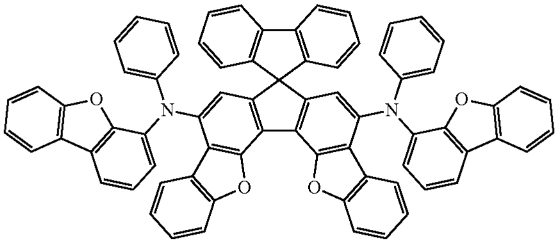
Compound Represented by Formula (10)
The compound represented by the formula (10) will be described below.
[Formula 328]
(10)
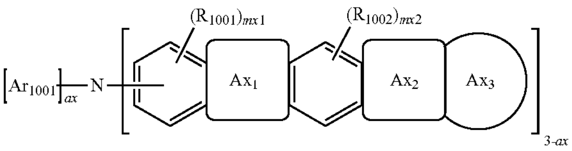
[Formula 329]
(10a)
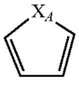

-continued (10b)

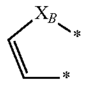

In the formula (10):

$Ax_1$ ring is a ring represented by the formula (10a) and fused with any positions of adjacent rings;

$Ax_2$ ring is a ring represented by the formula (10b) and fused with any positions of adjacent rings;

two * in the formula (10b) are bonded to any position of $Ax_3$ ring;

$X_A$ and $X_B$ are each independently $C(R_{1003})(R_{1004})$, $Si(R_{1005})(R_{1006})$, an oxygen atom or a sulfur atom;

$Ax_3$ ring is a substituted or unsubstituted aromatic hydrocarbon ring having 6 to 50 ring carbon atoms or a substituted or unsubstituted heterocycle having 5 to 50 ring atoms;

$Ar_{1001}$ is a substituted or unsubstituted aryl group having 6 to 50 ring carbon atoms, or a substituted or unsubstituted heterocyclic group having 5 to 50 ring atoms;

$R_{1001}$ to $R_{1006}$ each independently represent a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

mx1 is 3, mx2 is 2;

a plurality of $R_{1001}$ are mutually the same or different;

a plurality of $R_{1002}$ are mutually the same or different;

ax is 0, 1, or 2;

when ax is 0 or 1, the structures enclosed by brackets indicated by "3-ax" are mutually the same or different; and when ax is 2, a plurality of $Ar_{1001}$ are mutually the same or different.

In an exemplary embodiment, $Ar_{1001}$ is a substituted or unsubstituted aryl group having 6 to 50 ring carbon atoms.

In an exemplary embodiment, $Ax_3$ ring is a substituted or unsubstituted aromatic hydrocarbon ring having 6 to 50 ring carbon atoms, example of which is a substituted or unsubstituted benzene ring, a substituted or unsubstituted naphthalene ring, or a substituted or unsubstituted anthracene ring.

In an exemplary embodiment, $R_{1003}$ and $R_{1004}$ are each independently a substituted or unsubstituted alkyl group having 1 to 50 carbon atoms.

In an exemplary embodiment, ax is 1.

Specific Examples of Compound Represented by Formula (10)

Specific examples of the compound represented by the formula (10) include compounds shown below.

[Formula 330]

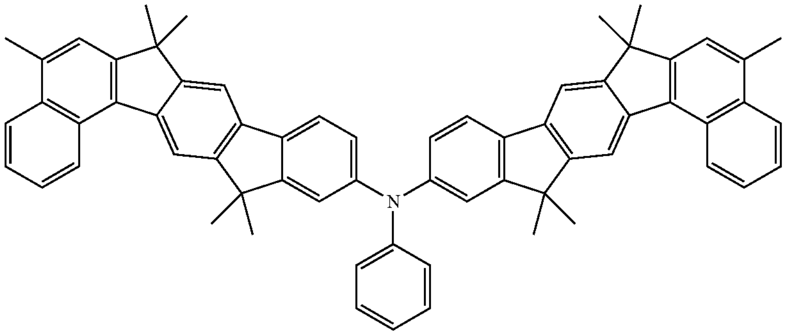

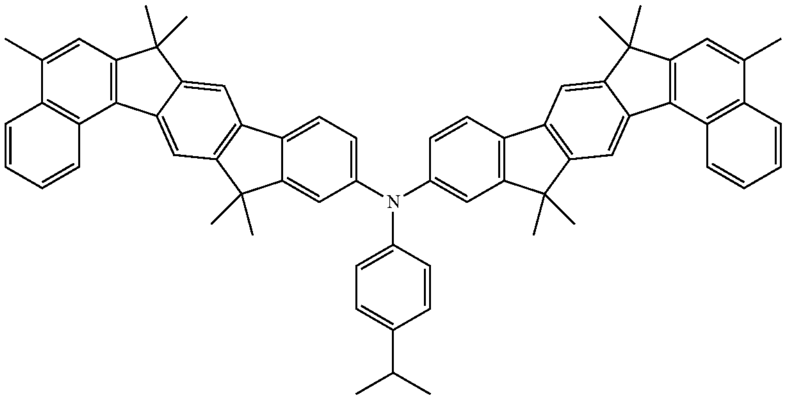

-continued
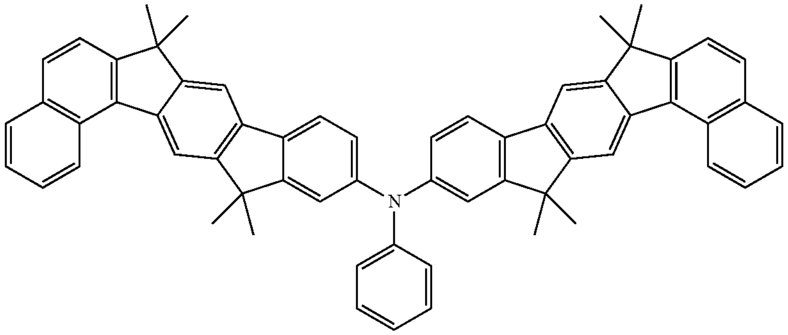
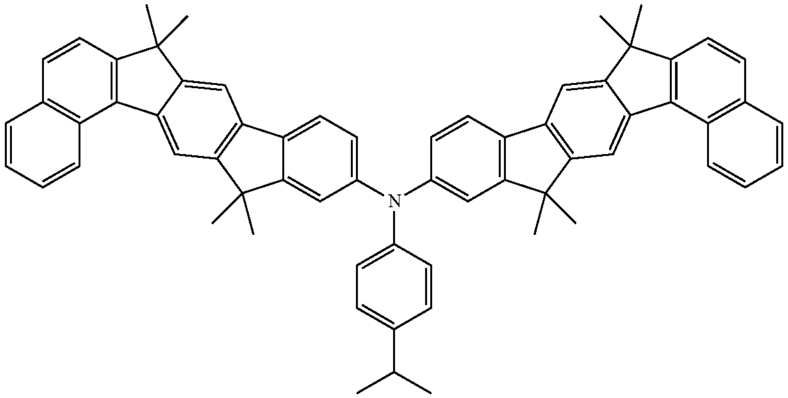
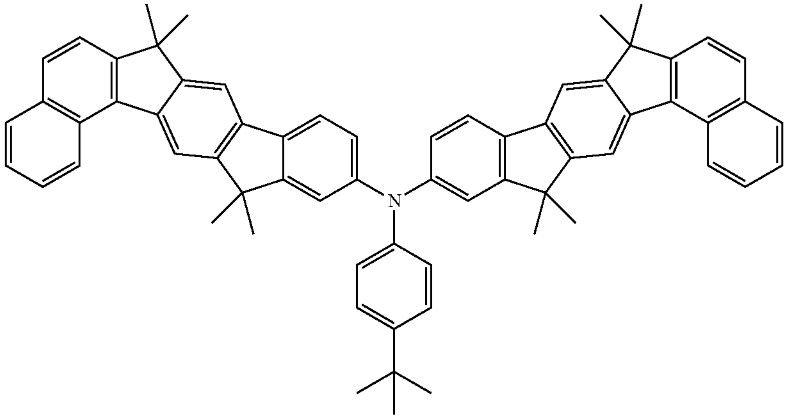
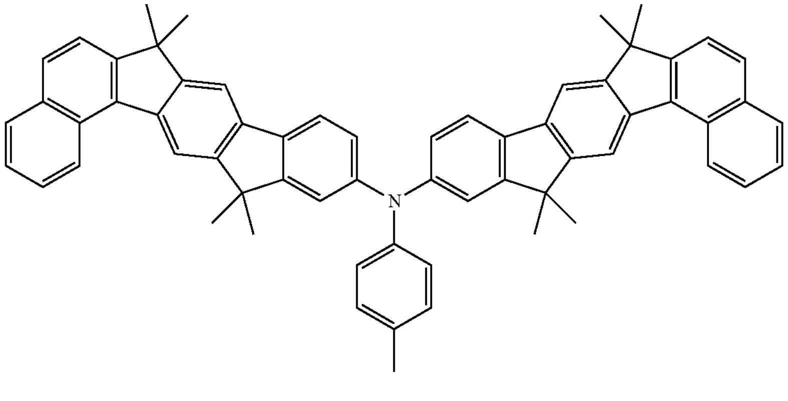

-continued
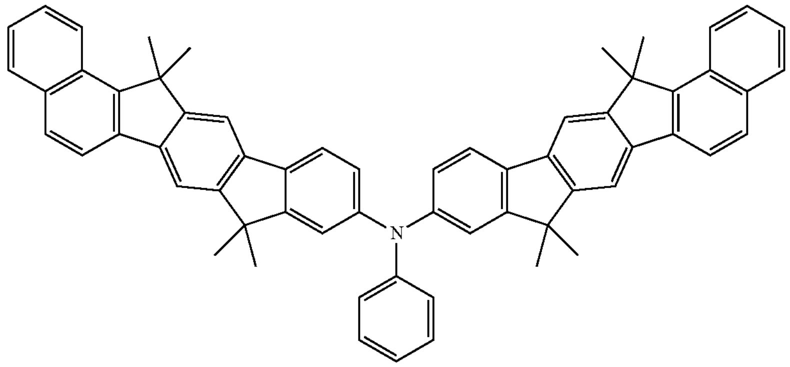
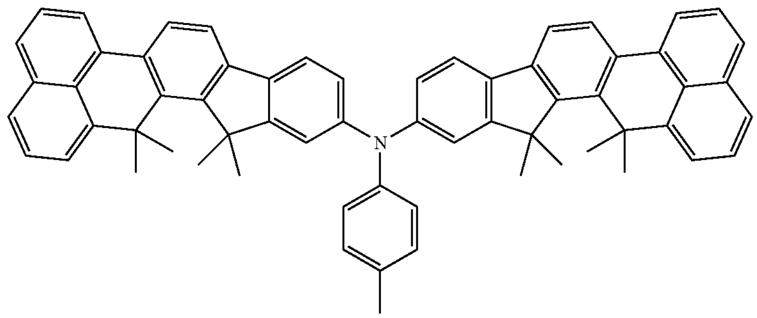
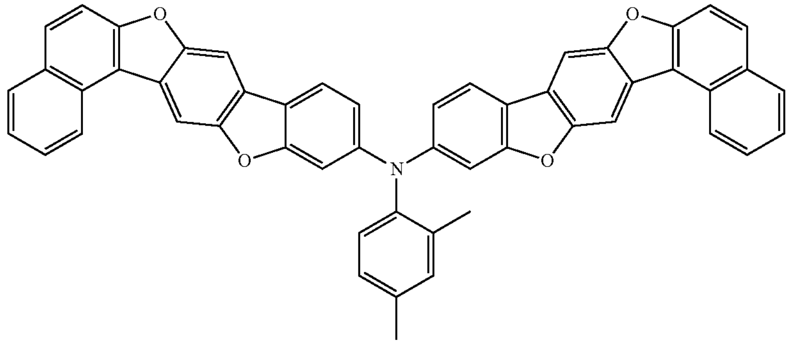
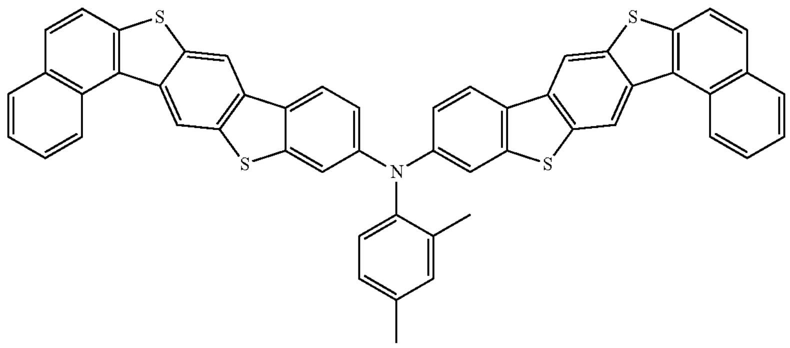

-continued

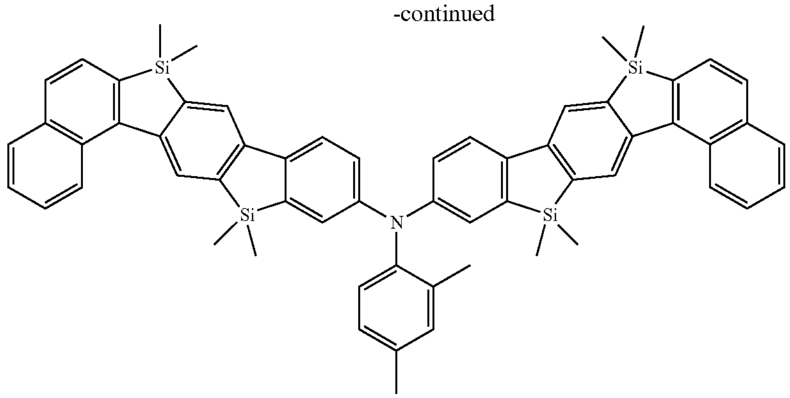

In an exemplary embodiment, the emitting layer contains, as at least one of the third compound or the fourth compound, at least one compound selected from the group consisting of the compound represented by the formula (4), the compound represented by the formula (5), the compound represented by the formula (7), the compound represented by the formula (8), the compound represented by the formula (9), and a compound represented by a formula (63a) below.

[Formula 331]

(63a)

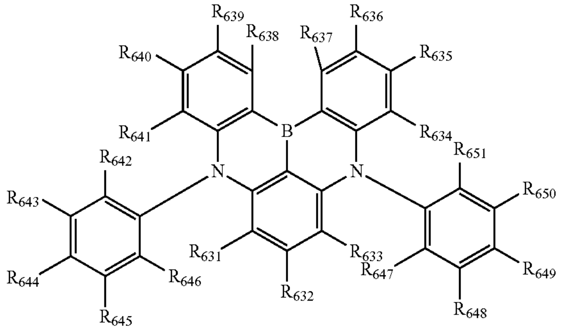

In the formula (63a): $R_{631}$ is bonded with $R_{646}$ to form a substituted or unsubstituted heterocycle or does not form a substituted or unsubstituted heterocycle;

$R_{633}$ is bonded with $R_{647}$ to form a substituted or unsubstituted heterocycle or does not form a substituted or unsubstituted heterocycle;

$R_{634}$ is bonded with $R_{651}$ to form a substituted or unsubstituted heterocycle or does not form a substituted or unsubstituted heterocycle;

$R_{641}$ is bonded with $R_{642}$ to form a substituted or unsubstituted heterocycle or does not form a substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded;

$R_{631}$ to $R_{651}$ not forming the substituted or unsubstituted heterocycle, not forming the monocyclic ring, and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aryl group having 6 to 50 ring carbon atoms, or a substituted or unsubstituted heterocyclic group having 5 to 50 ring atoms; and at least one of $R_{631}$ to $R_{651}$ not forming the substituted or unsubstituted heterocycle, not forming the monocyclic ring, and not forming the fused ring are a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is the compound represented by the formula (41-3), the formula (41-4) or the formula (41-5), the A1 ring in the formula (41-5) being a substituted or unsubstituted fused aromatic hydrocarbon ring having 10 to 50 ring carbon atoms, or a substituted or unsubstituted fused heterocycle having 8 to 50 ring atoms.

In an exemplary embodiment, the substituted or unsubstituted fused aromatic hydrocarbon ring having 10 to 50 ring carbon atoms in the formulae (41-3), (41-4) and (41-5) is a substituted or unsubstituted naphthalene ring, a substituted or unsubstituted anthracene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the substituted or unsubstituted fused aromatic hydrocarbon ring having 10 to 50 ring carbon atoms in the formula (41-3), (41-4) or (41-5) is a substituted or unsubstituted naphthalene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the compound represented by the formula (4) is selected from the group consisting of a compound represented by a formula (461) below, a compound represented by a formula (462) below, a compound represented by a formula (463) below, a compound represented by a formula (464) below, a compound represented by a formula (465) below, a compound represented by a formula (466) below, and a compound represented by a formula (467) below.

[Formula 332]

(461)

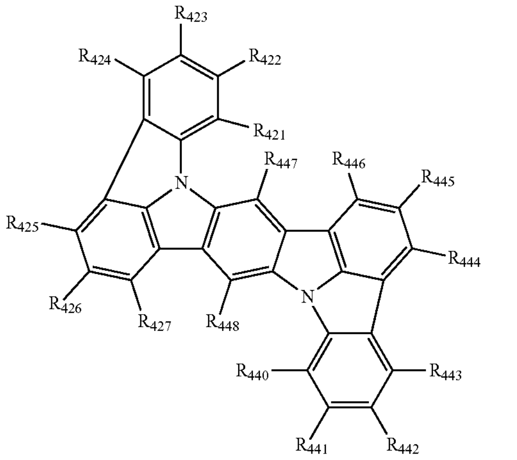

(462)

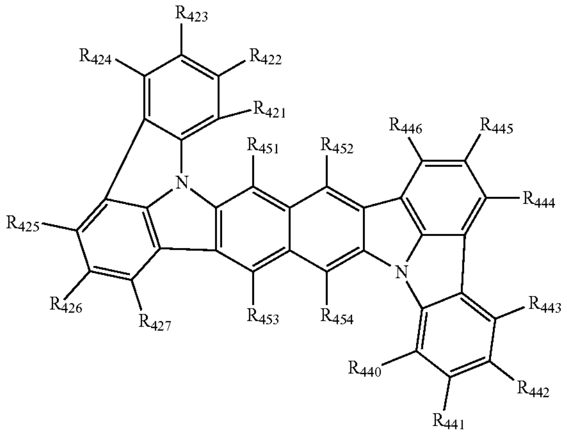

-continued

[Formula 333]

(463)

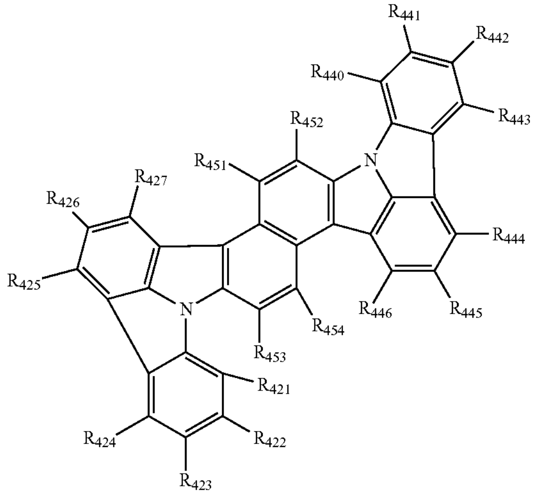

(464)

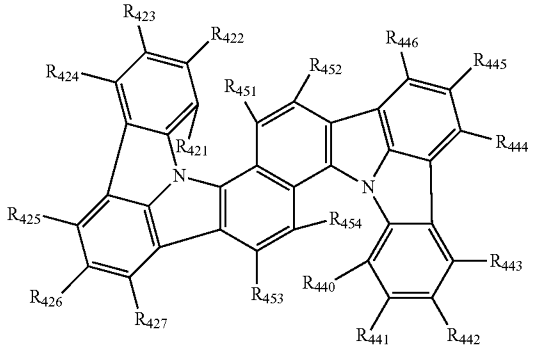

[Formula 334]

(465)

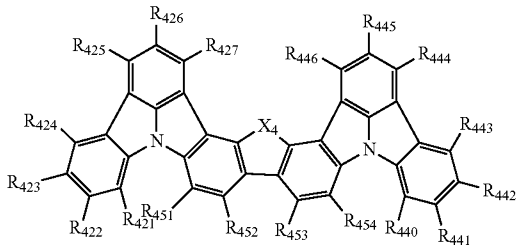

[Formula 335]

(466)

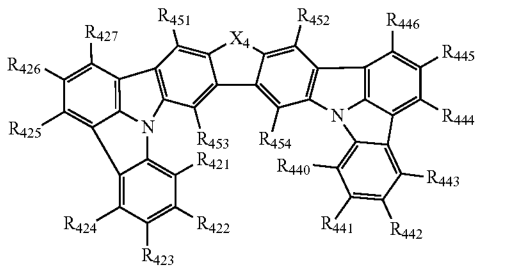

-continued

[Formula 336]

(467)

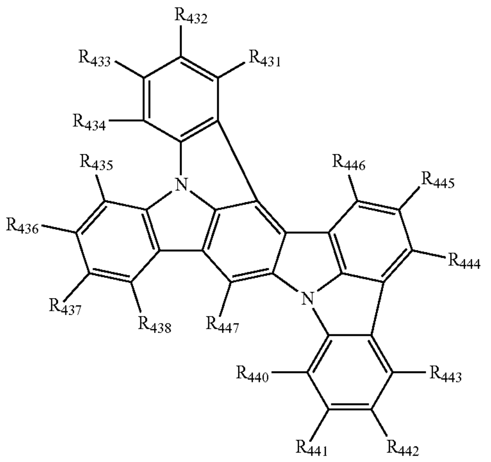

In the formulae (461) to (467): at least one combination of adjacent two or more of moieties selected from $R_{421}$ to $R_{427}$, $R_{431}$ to $R_{436}$, $R_{440}$ to $R_{448}$, and $R_{451}$ to $R_{454}$ are mutually bonded to form a substituted or unsubstituted monocyclic ring, mutually bonded to form a substituted or unsubstituted fused ring, or not mutually bonded;

$R_{437}$, $R_{438}$, and $R_{421}$ to $R_{427}$, $R_{431}$ to $R_{436}$, $R_{440}$ to $R_{448}$, and $R_{451}$ to $R_{454}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_4$ is an oxygen atom, $NR_{801}$, or C($R_{802}$)($R_{803}$);

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, $R_{421}$ to $R_{427}$ and $R_{440}$ to $R_{448}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{421}$ to $R_{427}$ and $R_{440}$ to $R_{447}$ are each independently selected from the group consisting of a hydrogen atom, a substituted or unsubstituted aryl group having 6 to 18 ring carbon atoms, and a substituted or unsubstituted heterocyclic group having 5 to 18 ring atoms.

In an exemplary embodiment, the compound represented by the formula (41-3) is represented by a formula (41-3-1) below.

[Formula 337]

(41-3-1)

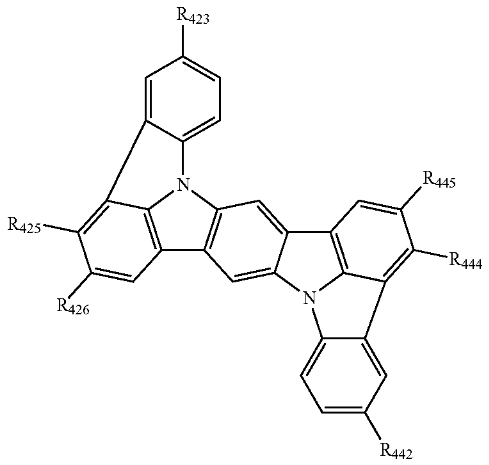

In the formula (41-3-1), $R_{423}$, $R_{425}$, $R_{426}$, $R_{442}$, $R_{444}$ and $R_{445}$ each independently represent the same as $R_{423}$, $R_{425}$, $R_{426}$, $R_{442}$, $R_{444}$ and $R_{445}$ in the formula (41-3).

In an exemplary embodiment, the compound represented by the formula (41-3) is represented by a formula (41-3-2) below.

[Formula 338]

(41-3-2)

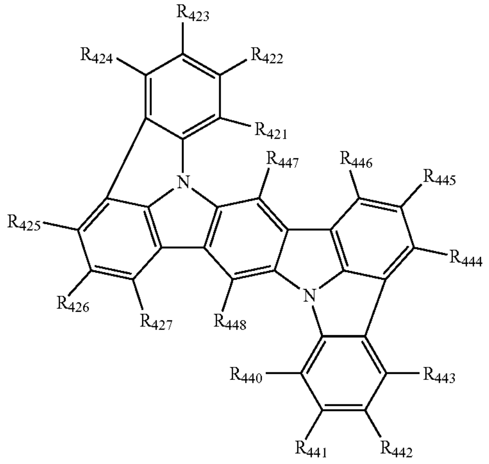

In the formula (41-3-2), $R_{421}$ to $R_{427}$ and $R_{440}$ to $R_{448}$ each independently represent the same as $R_{421}$ to $R_{427}$ and $R_{440}$ to $R_{448}$ in the formula (41-3); and at least one of $R_{421}$ to $R_{427}$ or $R_{440}$ to $R_{446}$ is a group represented by —N($R_{906}$)($R_{907}$).

In an exemplary embodiment, two of $R_{421}$ to $R_{427}$ and $R_{440}$ to $R_{446}$ in the formula (41-3-2) are groups represented by —$N(R_{906})(R_{907})$.

In an exemplary embodiment, the compound represented by the formula (41-3-2) is represented by a formula (41-3-3) below.

[Formula 339]

(41-3-3)

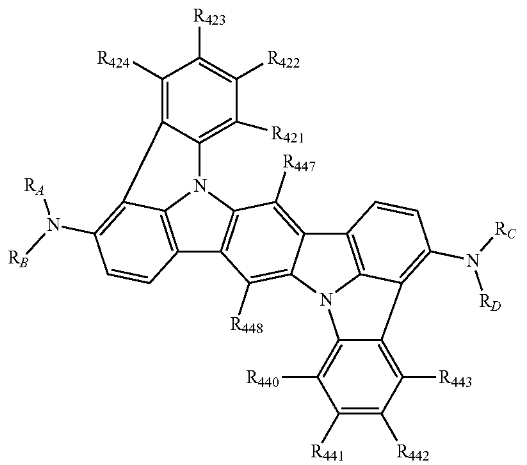

In the formula (41-3-3), $R_{421}$ to $R_{424}$, $R_{440}$ to $R_{443}$, $R_{447}$, and $R_{448}$ each independently represent the same as $R_{421}$ to $R_{424}$, $R_{440}$ to $R_{443}$, $R_{447}$, and $R_{448}$ in the formula (41-3); and $R_A$, $R_B$, $R_C$, and $R_D$ are each independently a substituted or unsubstituted aryl group having 6 to 18 ring carbon atoms, or a substituted or unsubstituted heterocyclic group having 5 to 18 ring atoms.

In an exemplary embodiment, the compound represented by the formula (41-3-3) is represented by a formula (41-3-4) below.

[Formula 340]

(41-3-4)

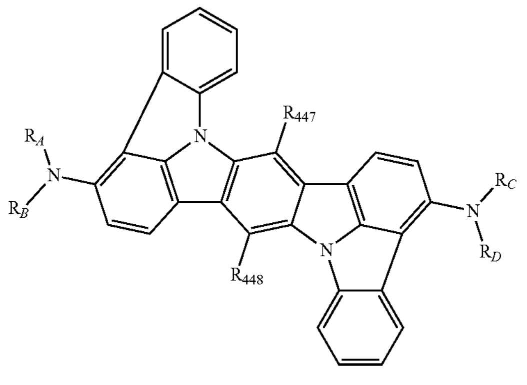

In the formula (41-3-4), $R_{447}$, $R_{448}$, $R_A$, $R_B$, $R_C$ and $R_D$ each independently represent the same as $R_{447}$, $R_{448}$, $R_A$, $R_B$, $R_C$ and $R_D$ in the formula (41-3-3).

In an exemplary embodiment, $R_A$, $R_B$, $R_C$, and $R_D$ are each independently a substituted or unsubstituted aryl group having 6 to 18 ring carbon atoms.

In an exemplary embodiment, $R_A$, $R_B$, $R_C$, and $R_D$ are each independently a substituted or unsubstituted phenyl group.

In an exemplary embodiment, $R_{447}$ and $R_{448}$ are each a hydrogen atom.

In an exemplary embodiment, the substituent for "substituted or unsubstituted" is an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —$Si(R_{901a})(R_{902a})(R_{903a})$, —O—$(R_{904a})$, —S—$(R_{905a})$, —$N(R_{906a})(R_{907a})$, a halogen atom, a cyano group, a nitro group, an unsubstituted aryl group having 6 to 50 ring carbon atoms, or an unsubstituted heterocyclic group having 5 to 50 ring atoms;

$R_{901a}$ to $R_{907a}$ are each independently a hydrogen atom, an unsubstituted alkyl group having 1 to 50 carbon atoms, an unsubstituted aryl group having 6 to 50 ring carbon atoms, or an unsubstituted heterocyclic group having 5 to 50 ring atoms;

when two or more $R_{901a}$ are present, the two or more $R_{901a}$ are mutually the same or different;

when two or more $R_{902a}$ are present, the two or more $R_{902a}$ are mutually the same or different;

when two or more $R_{903a}$ are present, the two or more $R_{903a}$ are mutually the same or different;

when two or more $R_{904a}$ are present, the two or more $R_{904a}$ are mutually the same or different;

when two or more $R_{905a}$ are present, the two or more $R_{905a}$ are mutually the same or different;

when two or more $R_{906a}$ are present, the two or more $R_{906a}$ are mutually the same or different; and when two or more $R_{907a}$ are present, the two or more $R_{907a}$ are mutually the same or different.

In an exemplary embodiment, the substituent for "substituted or unsubstituted" is an unsubstituted alkyl group having 1 to 50 carbon atoms, an unsubstituted aryl group having 6 to 50 ring carbon atoms, or an unsubstituted heterocyclic group having 5 to 50 ring atoms.

In an exemplary embodiment, the substituent for "substituted or unsubstituted" is an unsubstituted alkyl group having 1 to 18 carbon atoms, an unsubstituted aryl group having 6 to 18 ring carbon atoms, or an unsubstituted heterocyclic group having 5 to 18 ring atoms.

Second Exemplary Embodiment

Electronic Device

An electronic device according to a second exemplary embodiment is installed with any one of the organic EL devices according to the above exemplary embodiments. Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

Modification of Embodiment(s)

The scope of the invention is not limited by the above-described exemplary embodiments but includes any modification and improvement as long as such modification and improvement are compatible with the invention.

For instance, the number of emitting layers is not limited to two, and more than two emitting layers may be provided and laminated with each other. When the organic EL device includes more than two emitting layers, it is only necessary that at least two of the emitting layers should satisfy the requirements mentioned in the above exemplary embodiment. For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are laminated via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, and excitons.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

The invention will be described in further detail with reference to Examples. It should be noted that the scope of the invention is by no means limited by Examples.

Compounds

Structures of compounds used as the first host material or the second host material for manufacturing organic EL devices in Examples 1 to 174, A2 to A4, and Reference Example 1 are shown below.

[Formula 341]

BH1-1

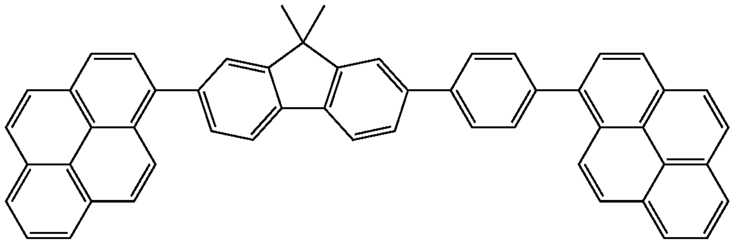

[Formula 342]

BH1-2

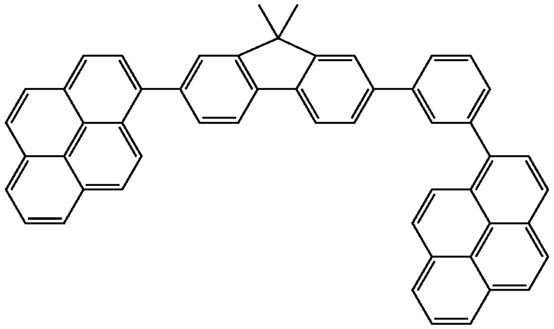

BH1-3

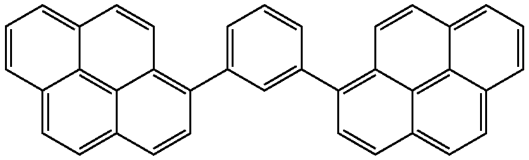

-continued
[Formula 343]
BH1-4
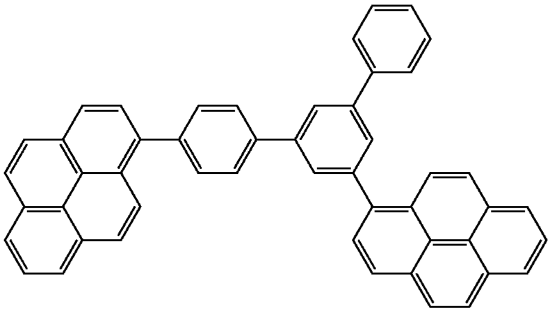
BH1-5
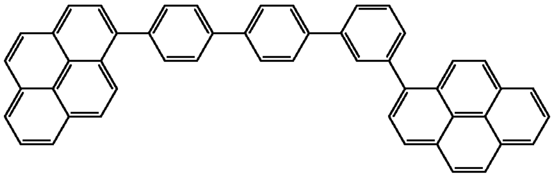
[Formula 344]
BH1-6
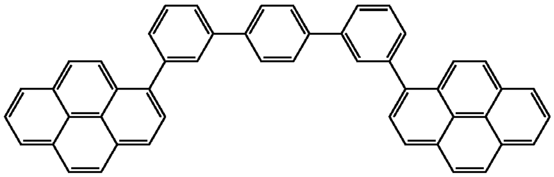
BH1-7
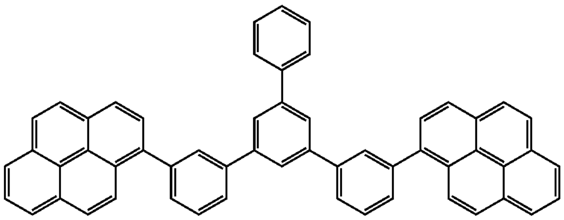
[Formula 345]
BH1-8
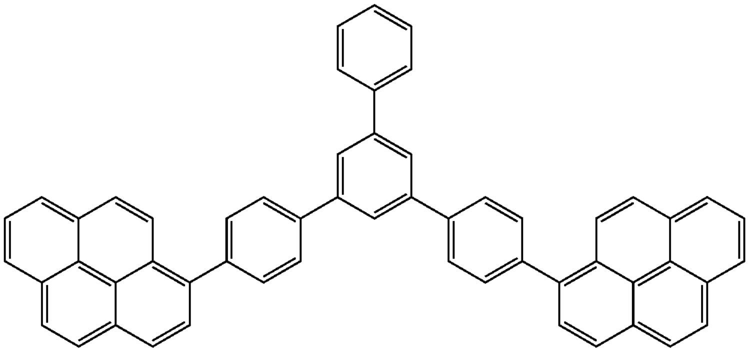
BH1-9
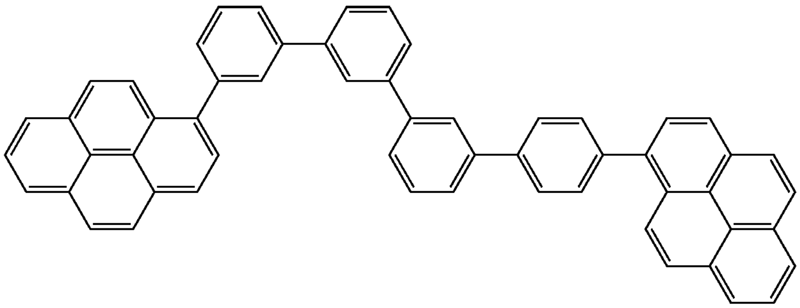

-continued
[Formula 346]
BH1-10
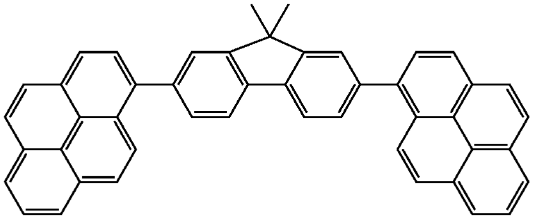
BH1-11
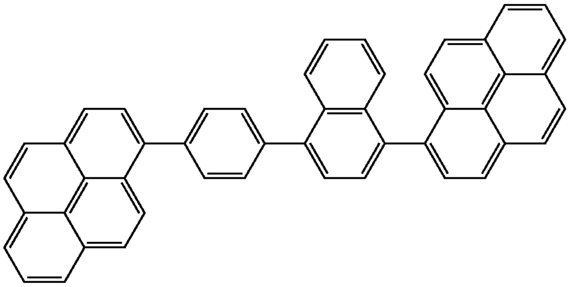
[Formula 347]
BH1-12
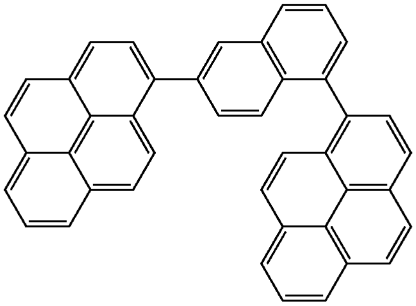
BH1-13
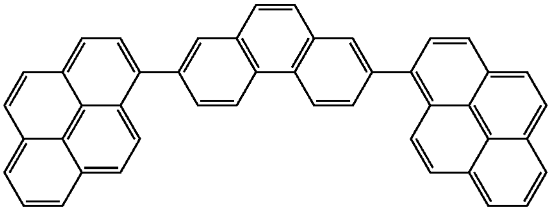
[Formula 348]
BH-14
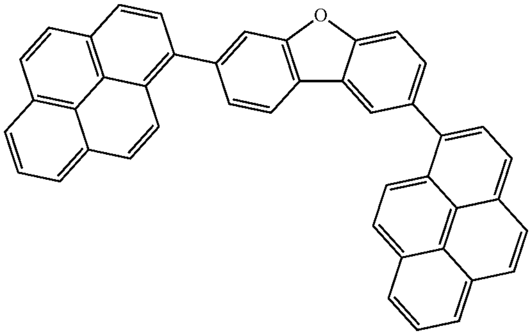
BH-15
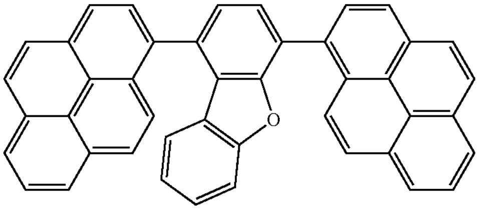
[Formula 349]
BH-16
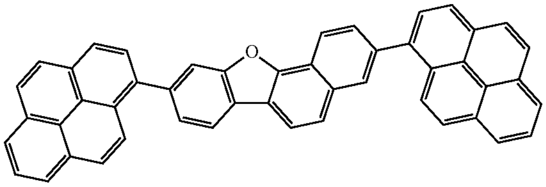
BH-17
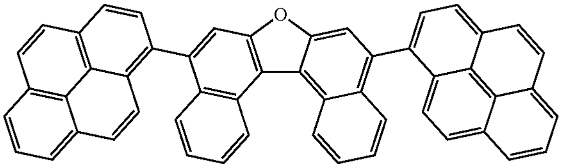

-continued
[Formula 350]
BH1-18
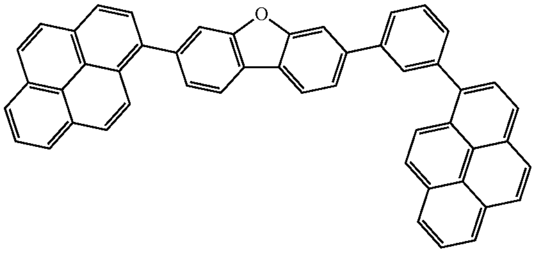
BH1-19
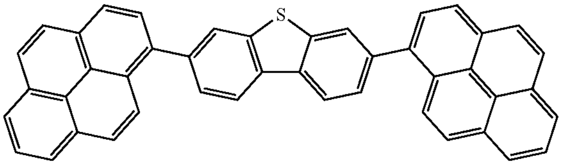
[Formula 351]
BH1-20
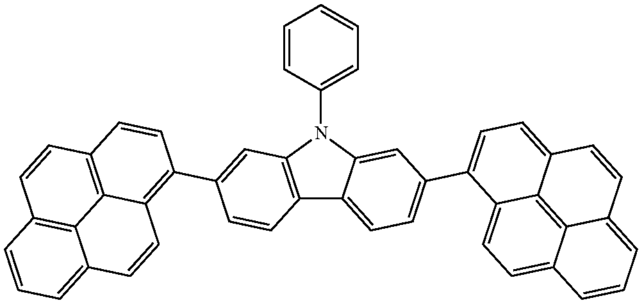
[Formula 352]
BH1-21
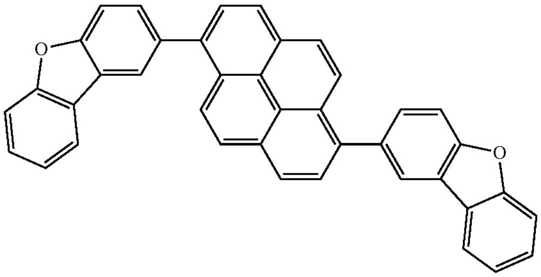
BH1-22
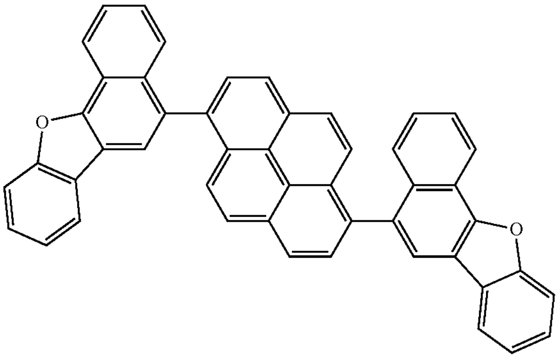

-continued
[Formula 353]
BH1-23
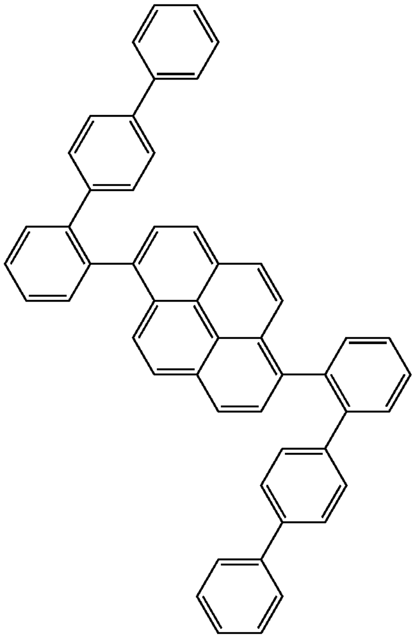
BH1-24
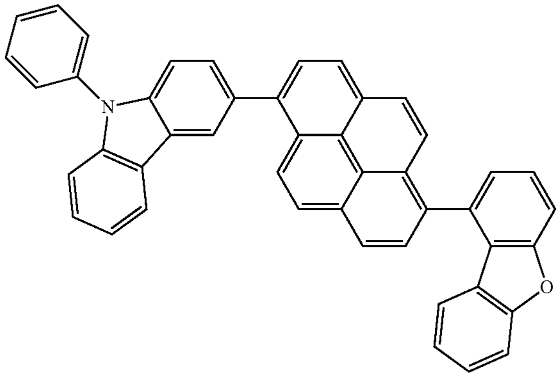
BH1-25
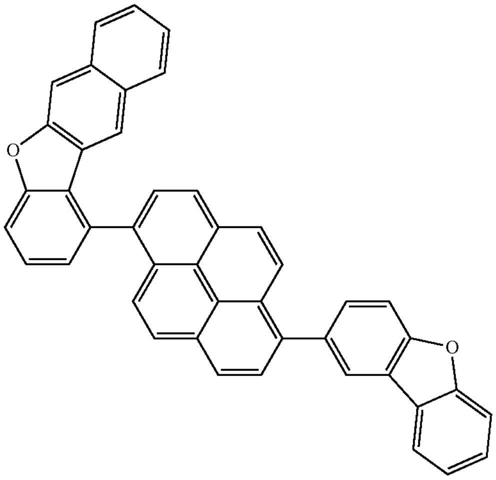
[Formula 354]
BH1-26
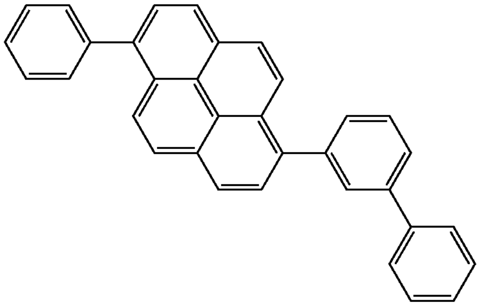
BH1-27
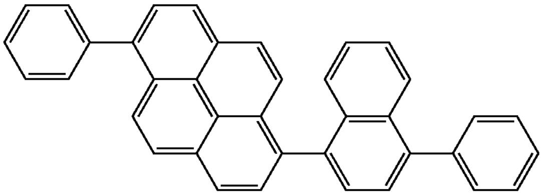

-continued
[Formula 355]
BH1-28
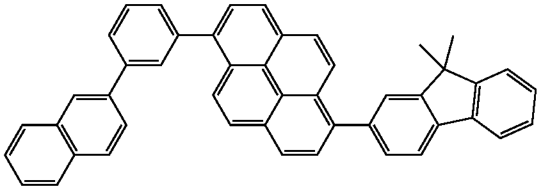
BH1-29
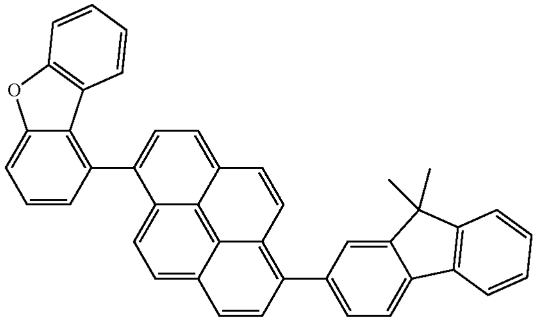
[Formula 356]
BH1-30
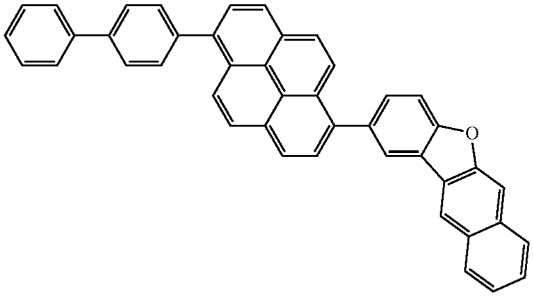
BH1-31
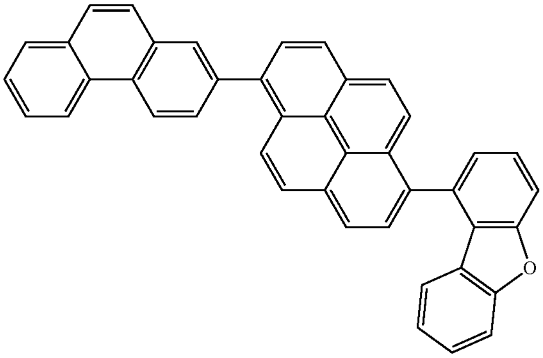
[Formula 357]
BH1-32
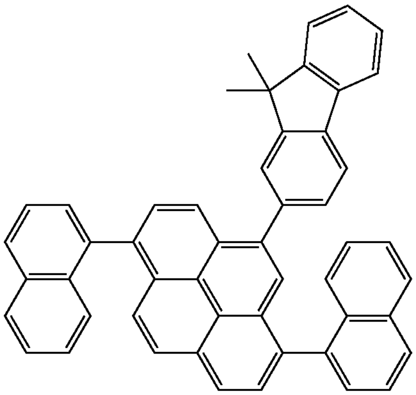
BH1-33
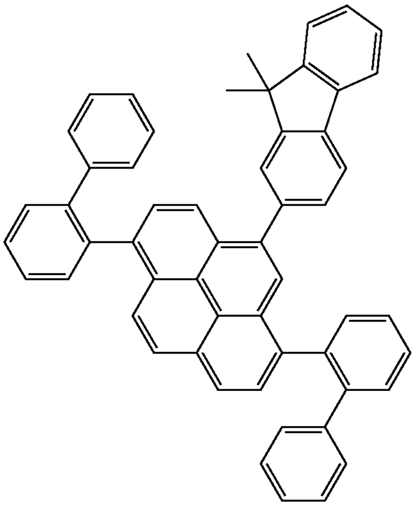

-continued
BH1-34
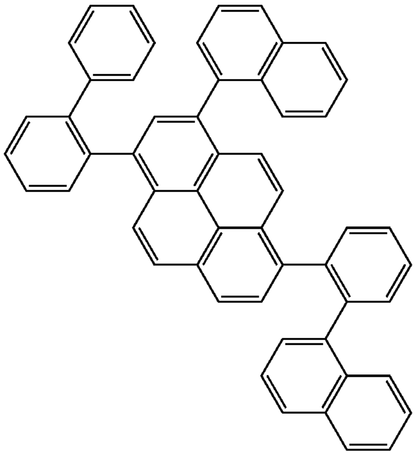
[Formula 358]
BH1-35
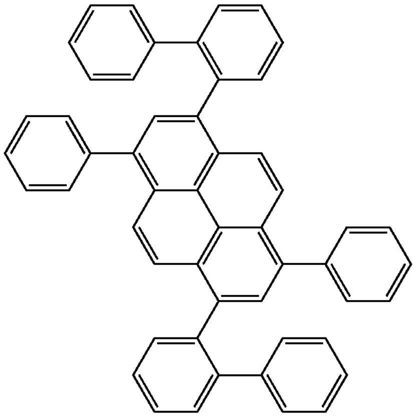
BH1-36
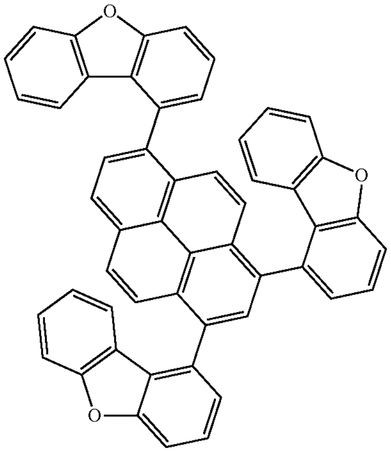
BH1-37
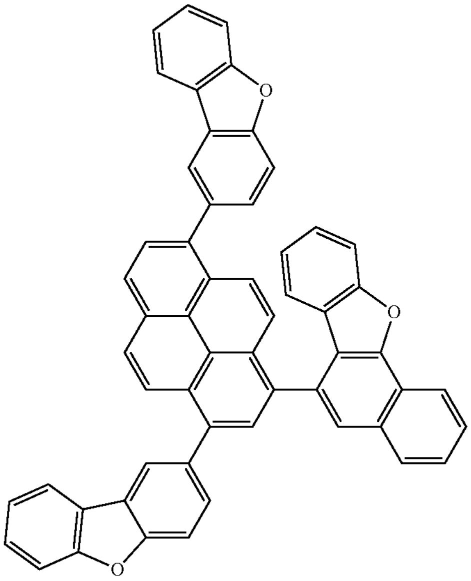

-continued
[Formula 359]
BH1-38
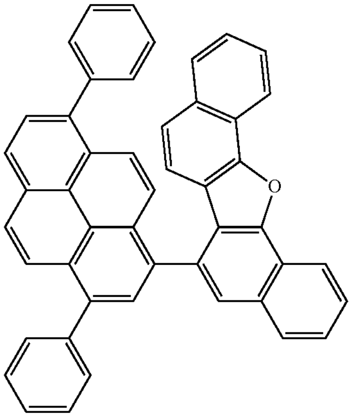
BH1-39
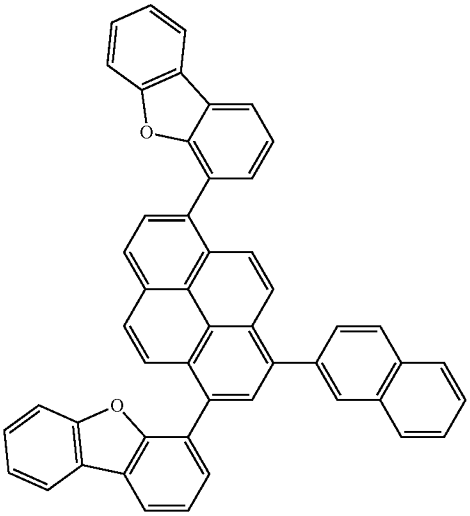
BH1-40
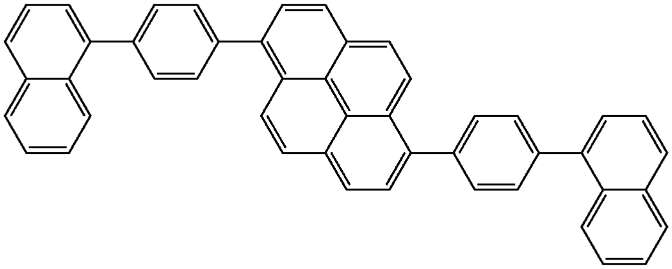
[Formula 360]
BH1-41
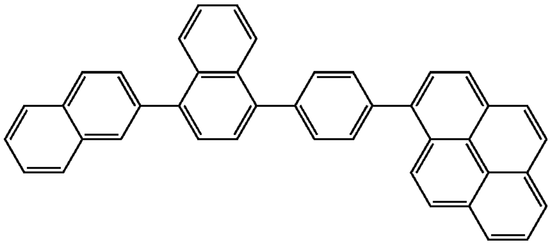
BH1-42
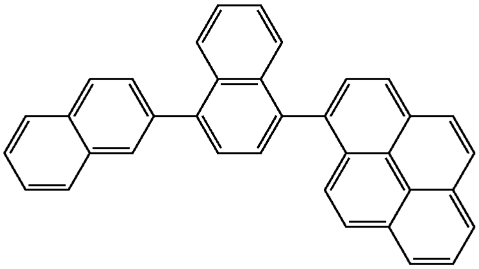
[Formula 361]
BH1-43
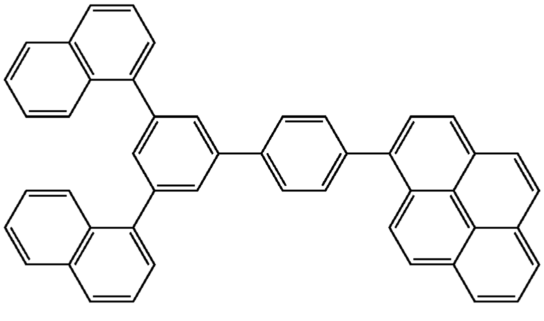
BH1-44
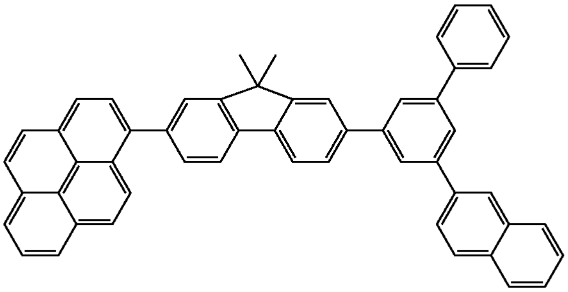

-continued
[Formula 362]
BH1-45
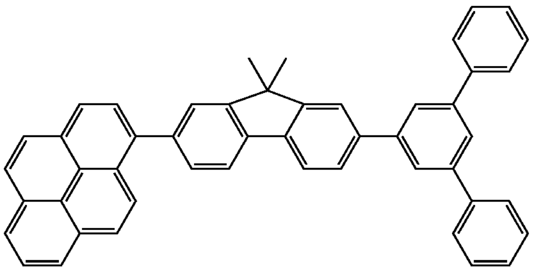
BH1-46
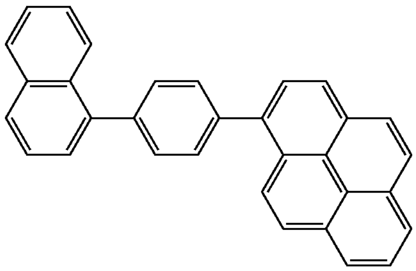
[Formula 363]
BH1-47
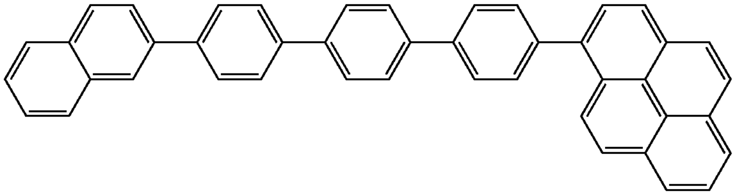
BH1-48
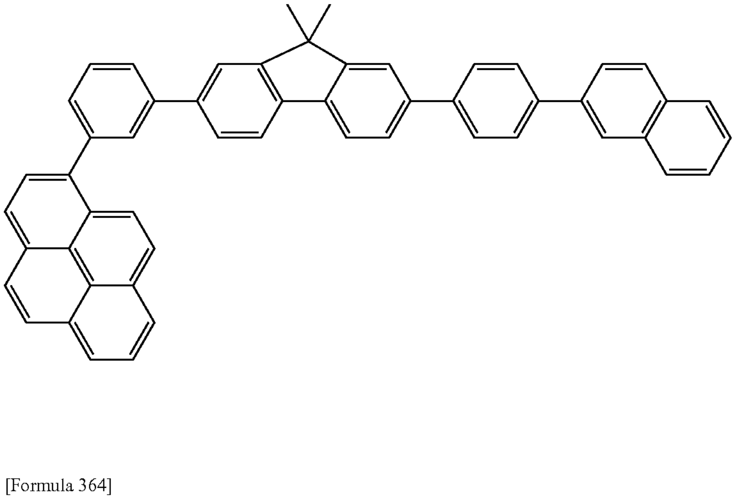
[Formula 364]
BH1-49
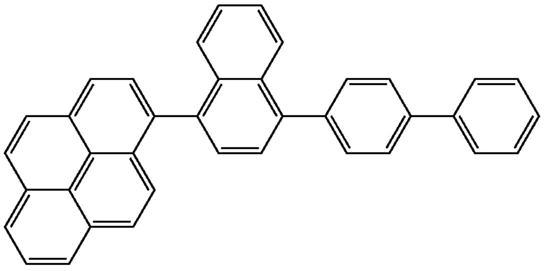
BH1-50
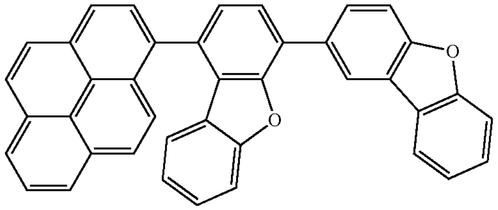

-continued
[Formula 365]
BH1-51
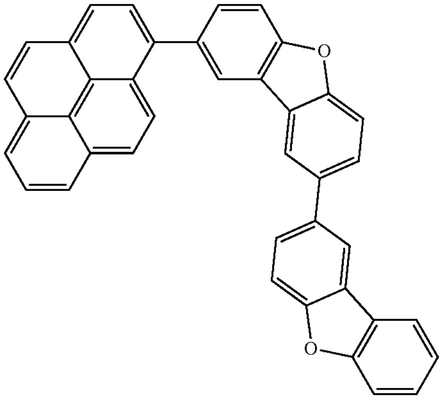
BH1-52
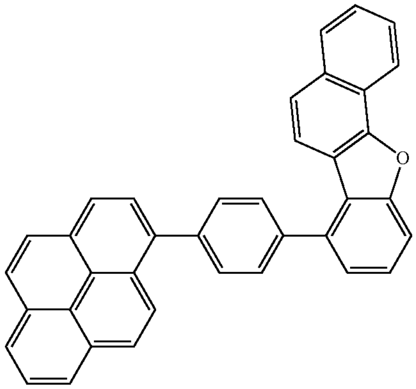
[Formula 366]
BH1-53
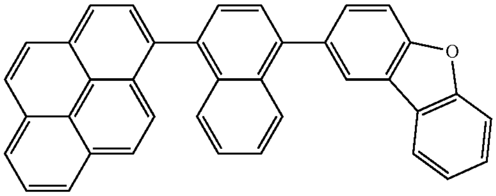
BH1-54
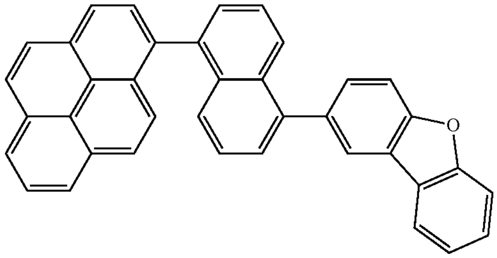
[Formula 367]
BH1-55
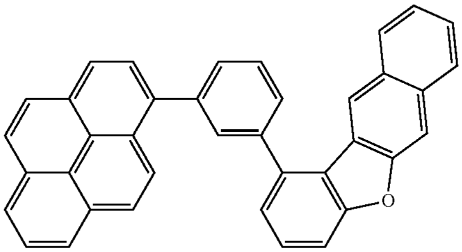
BH1-56
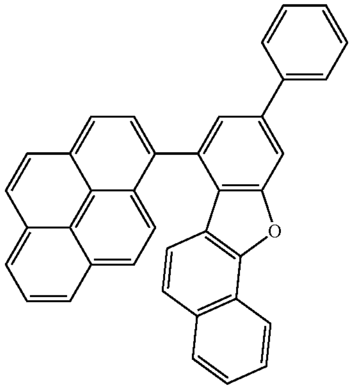
BH1-57
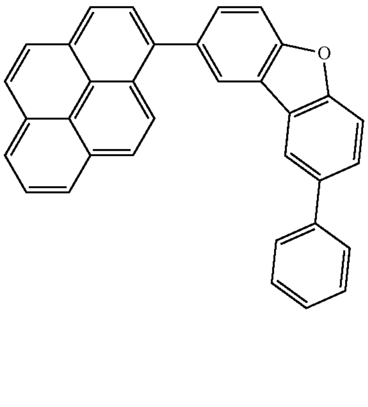

-continued
[Formula 368]
R-BH1
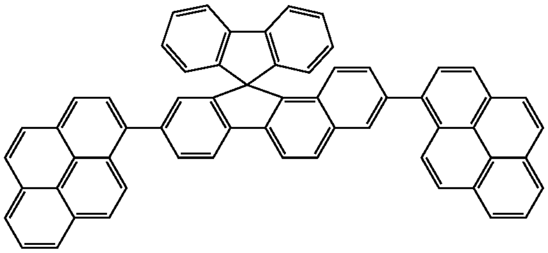
R-BH2
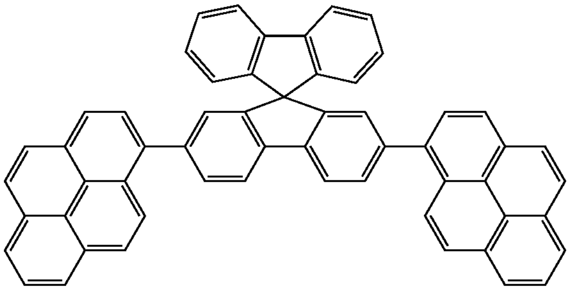
[Formula 369]
R-BH3
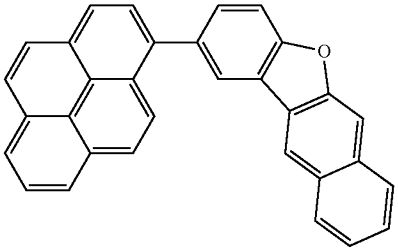
[Formula 370]
BH1-61
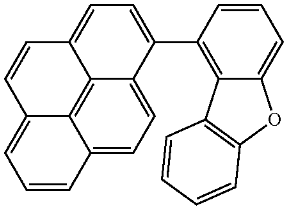
BH1-62
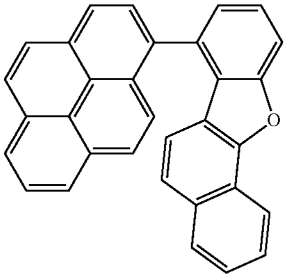
BH1-63
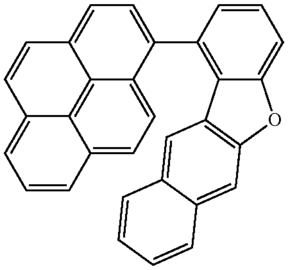
[Formula 371]
BH1-64
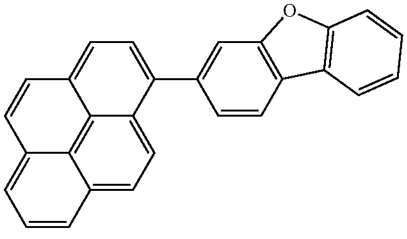
BH1-65
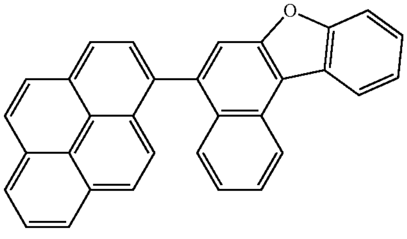

-continued
BH1-66
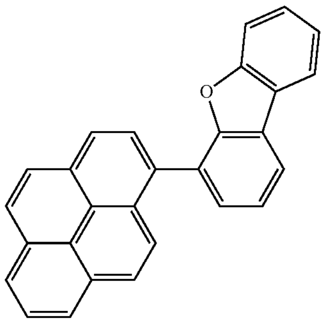
[Formula 372]
BH1-67
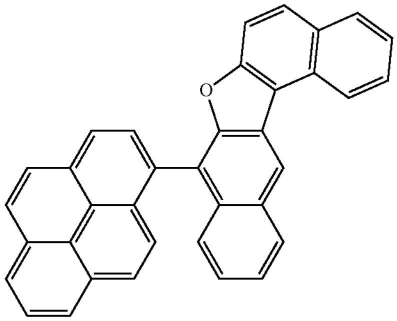
BH1-68
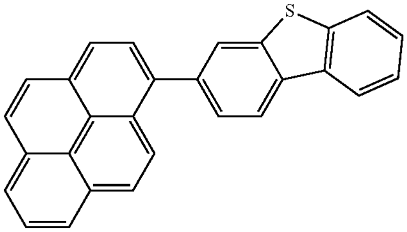
BH1-69
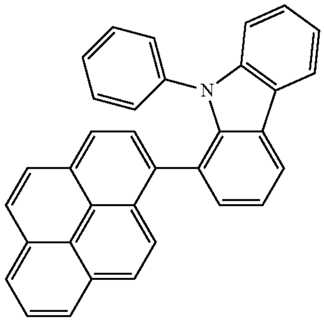
[Formula 373]
BH1-70
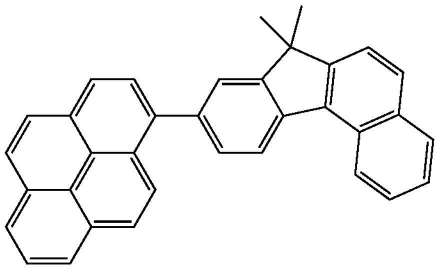
BH1-71
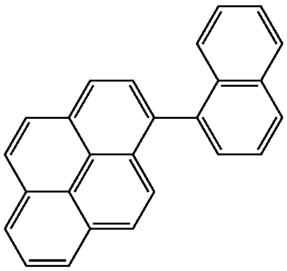
BH1-72
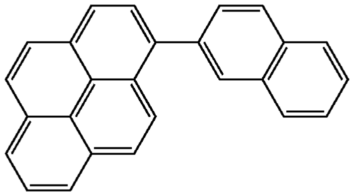

-continued
[Formula 374]
BH1-73
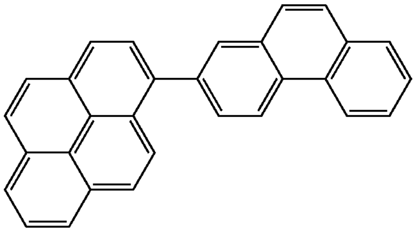
BH1-74
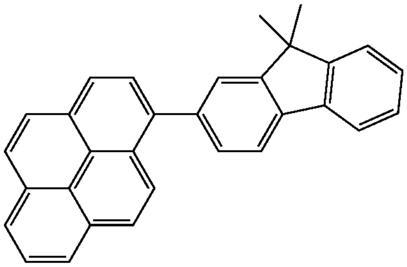
BH1-75
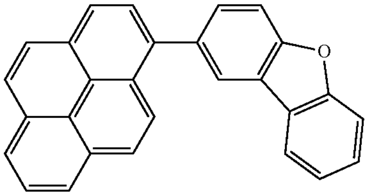
[Formula 375]
BH1-81
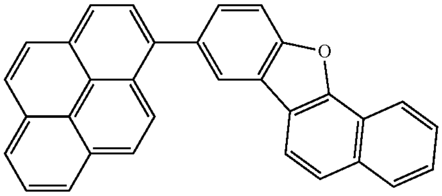
BH1-82
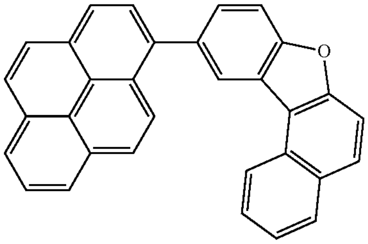
BH1-83
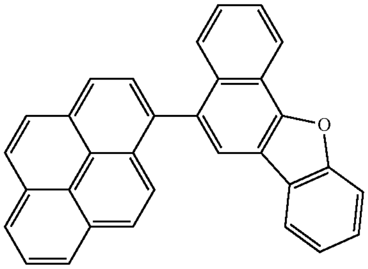
[Formula 376]
1BH-1
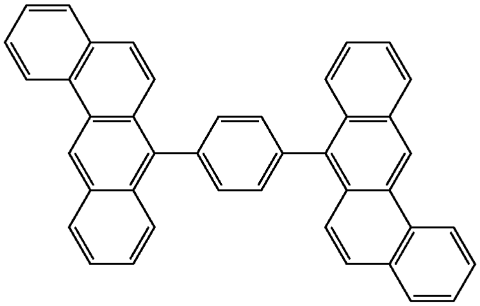

-continued
[Formula 377]
BH2
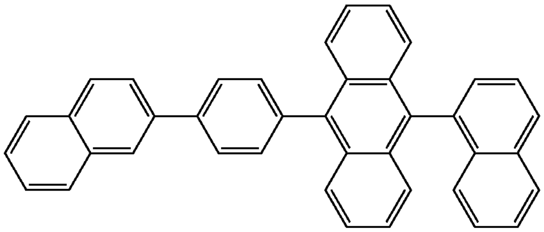
BH4
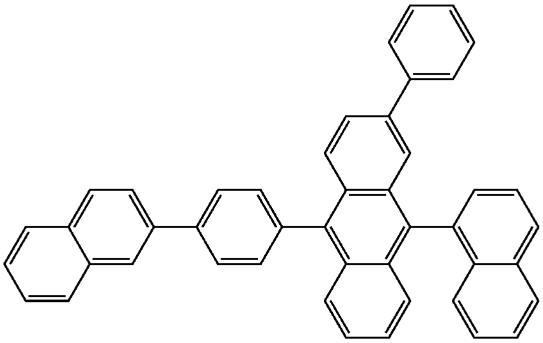
[Formula 378]
BH2-2
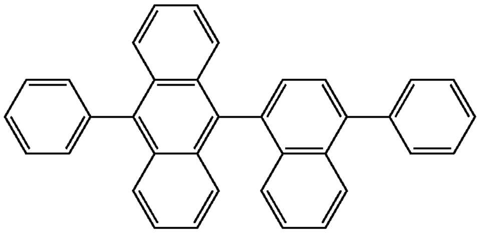
BH2-3
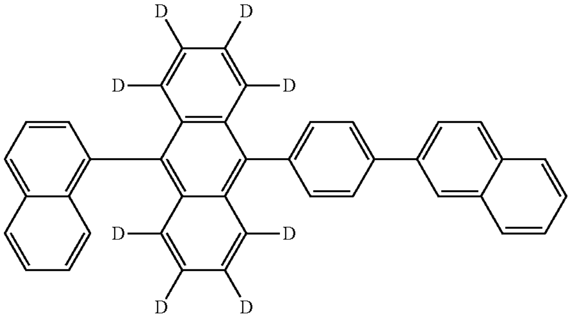
[Formula 379]
BH2-4
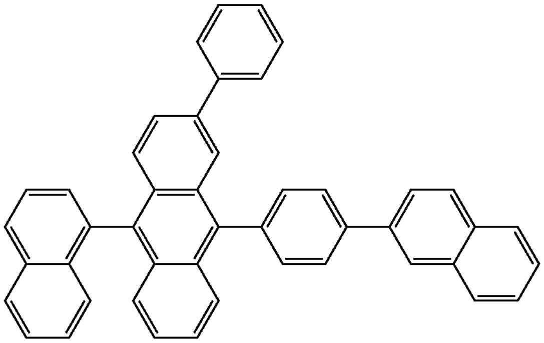
BH2-5
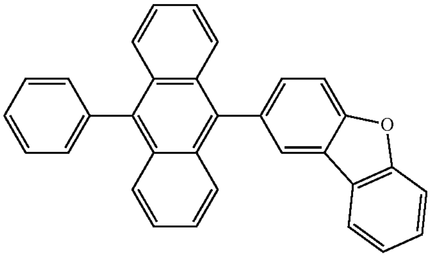
BH2-6
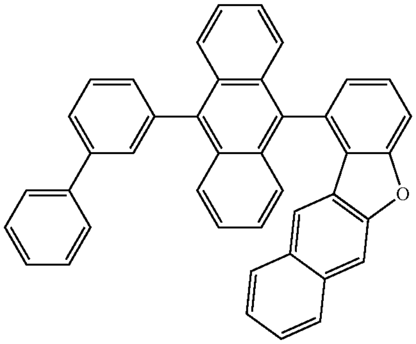

-continued
[Formula 380]
BH2-7
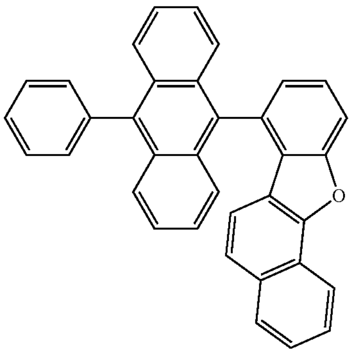
BH2-8
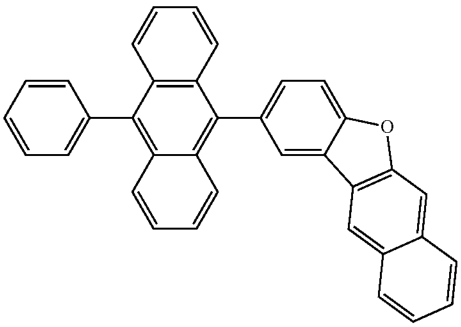
[Formula 381]
BH2-9
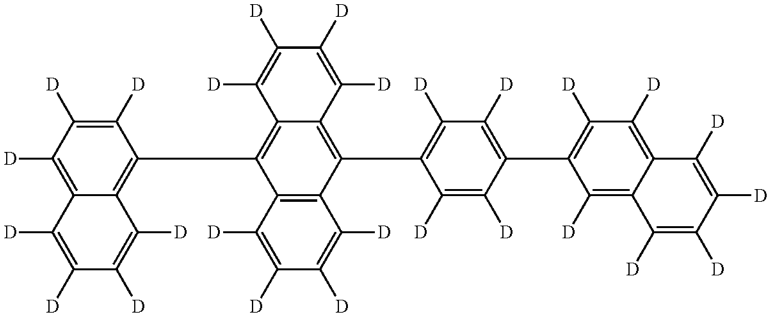
BH2-10
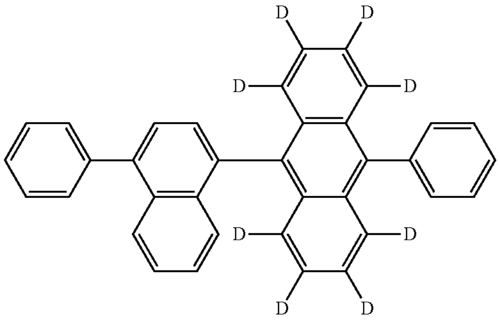
[Formula 382]
BH2-11
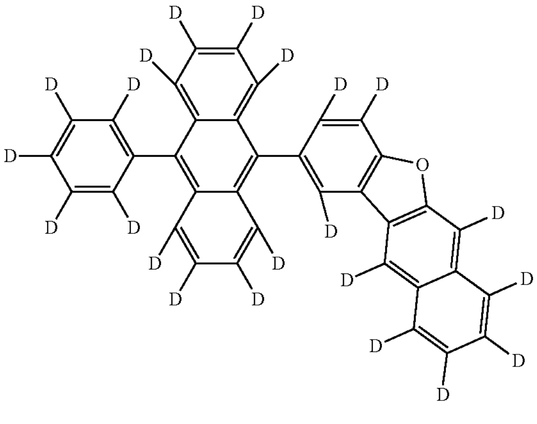
BH2-12
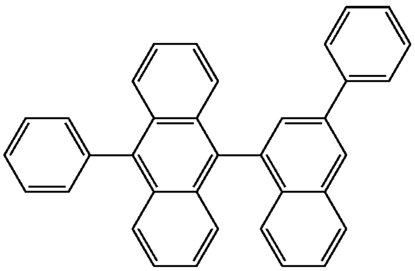

-continued
[Formula 383]
BH2-13
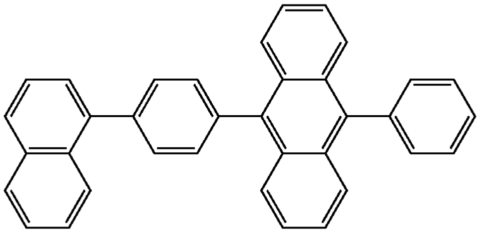
BH2-14
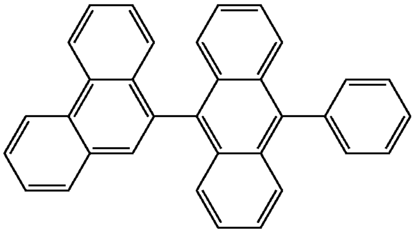
[Formula 384]
BH2-15
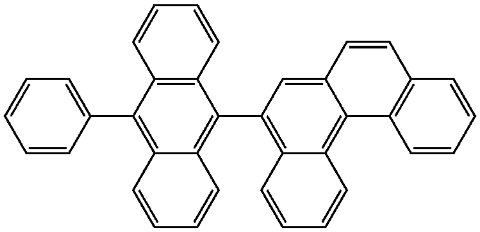
BH2-16
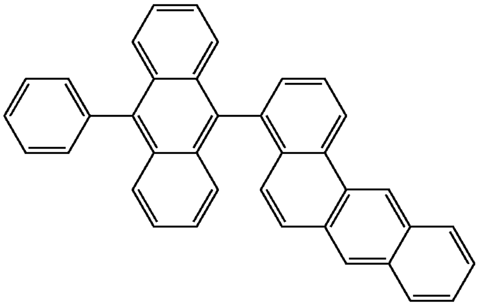
[Formula 385]
BH2-17
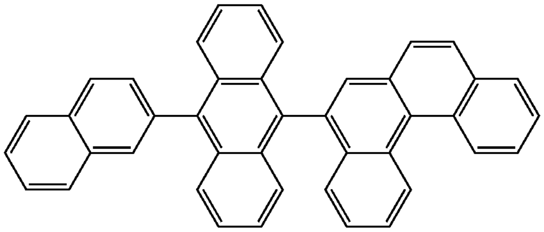
BH2-18
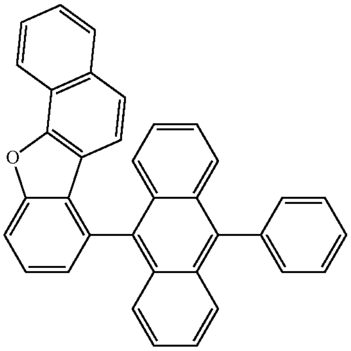
[Formula 386]
BH2-19
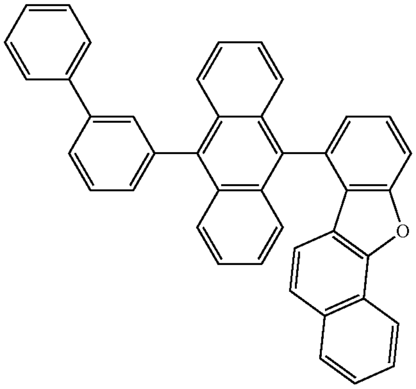
BH2-20
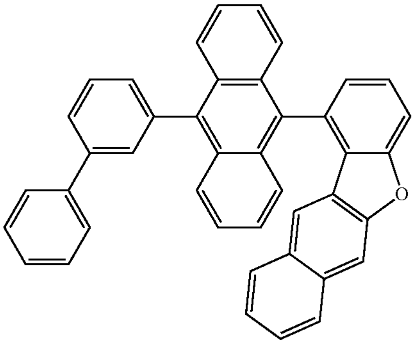

-continued
[Formula 387]
BH2-21
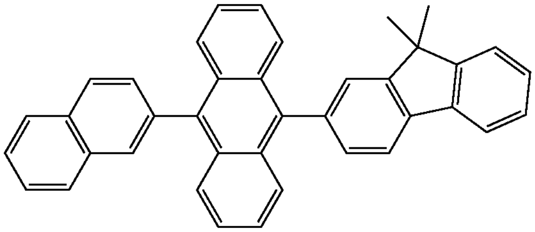
BH2-22
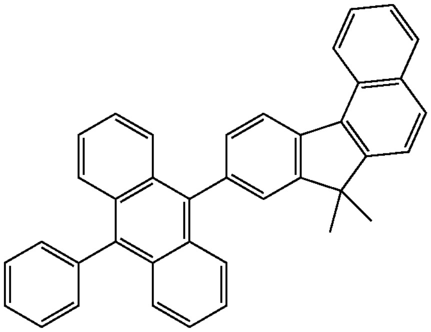
[Formula 388]
BH2-23
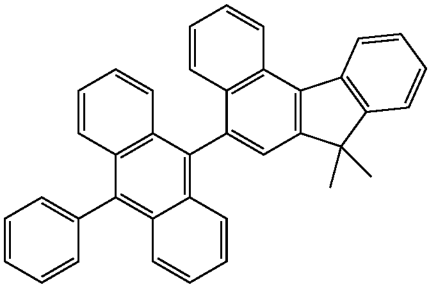
BH2-24
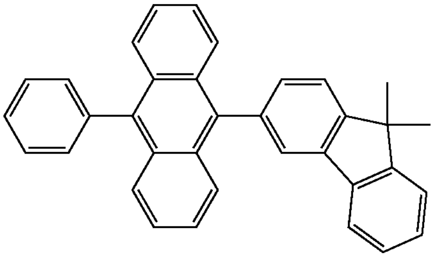
[Formula 389]
BH2-25
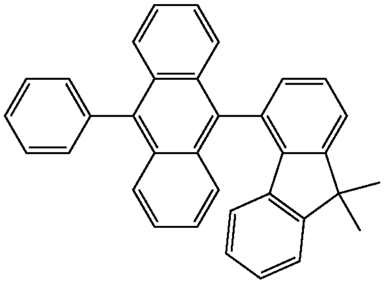
BH2-26
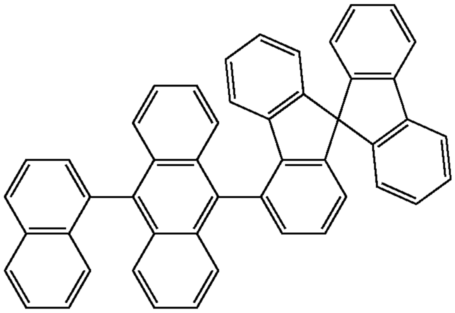
BH2-27
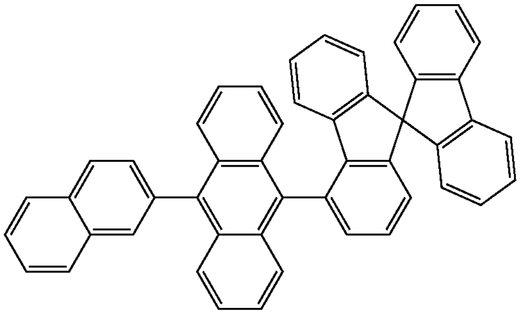

-continued
[Formula 390]
BH2-28
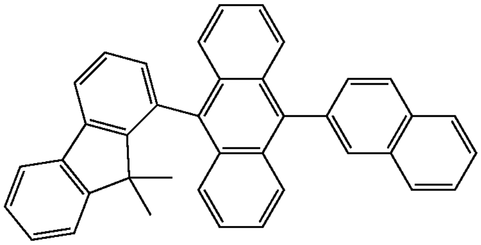
BH2-29
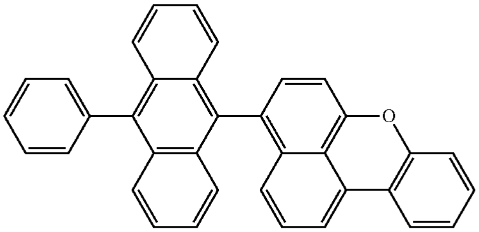
[Formula 391]
BH3-1
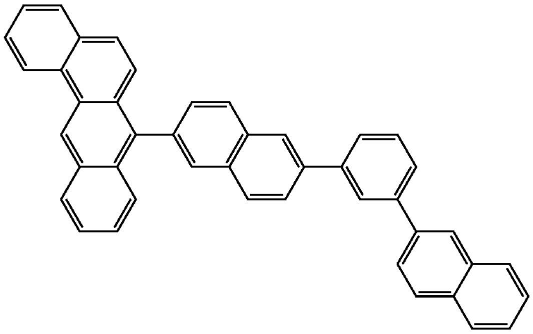
BH3-2
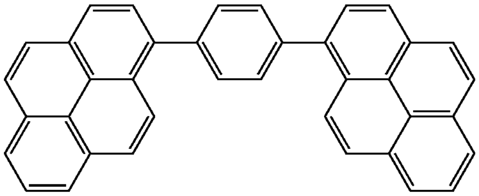
[Formula 392]
BH3-3
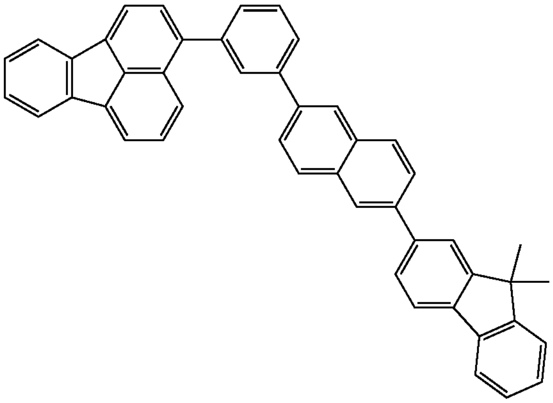
BH3-4
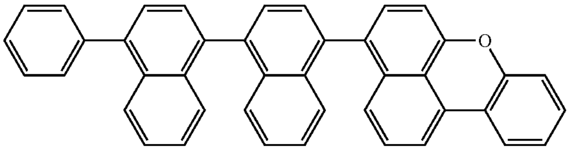
[Formula 393]
BH3-5
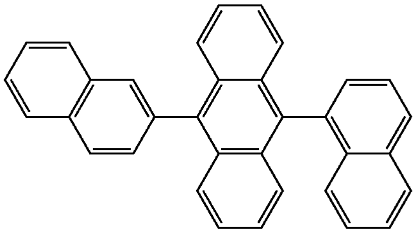
BH3-6
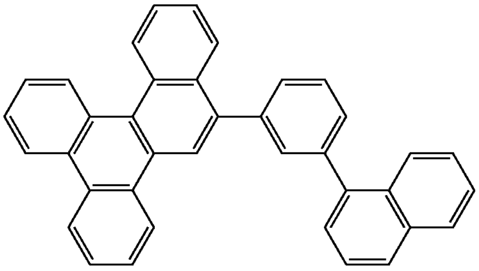

-continued
[Formula 394]
BH3-7
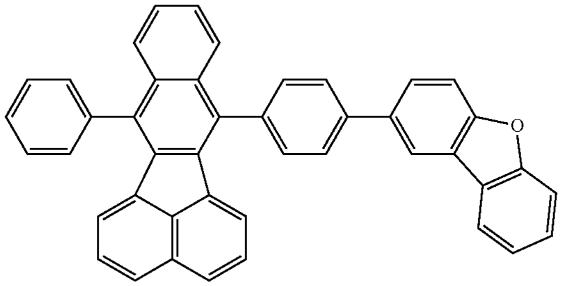
[Formula 395]
BH1-84
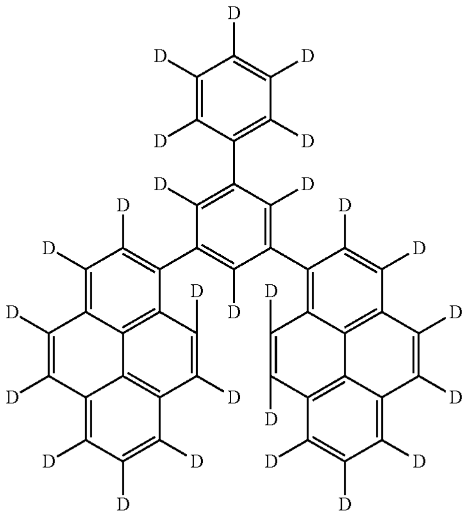
BH1-85
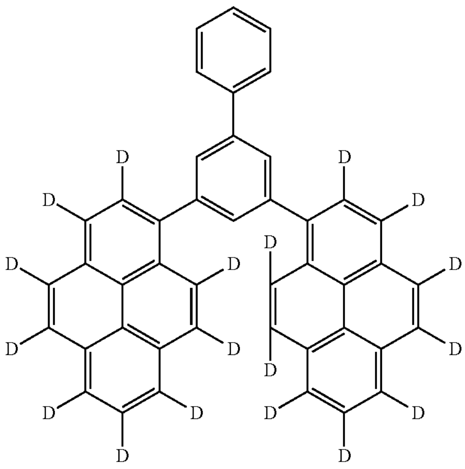
BH1-86
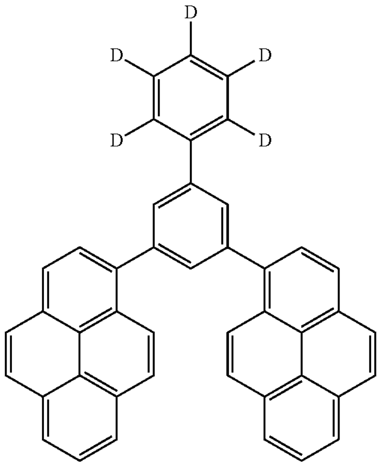

-continued
[Formula 396]
BH1-87
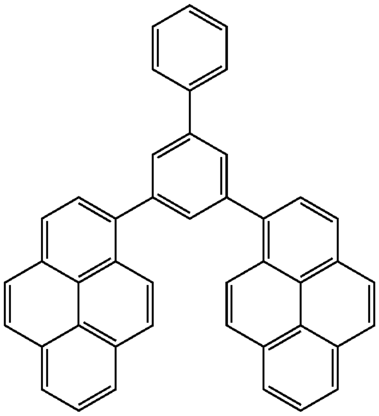
[Formula 397]
BH4-1
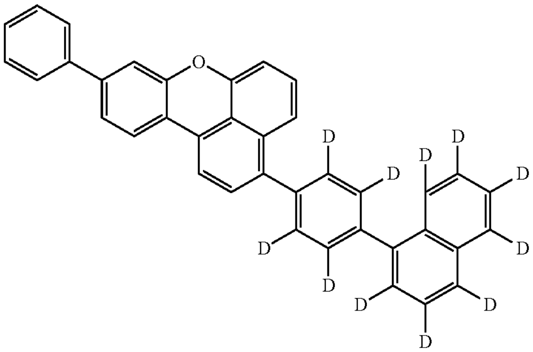
BH4-2
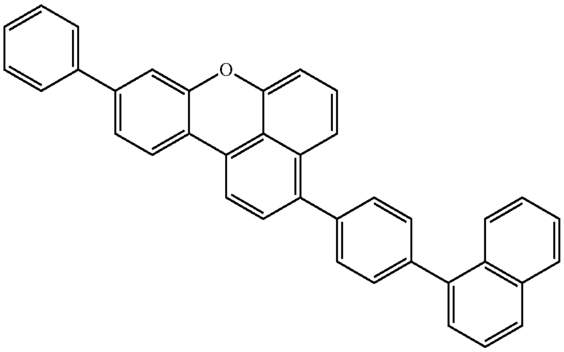
[Formula 398]
BH4-3
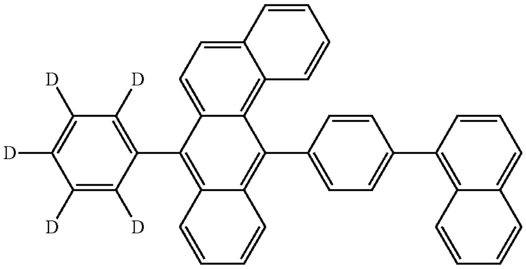
BH4-4
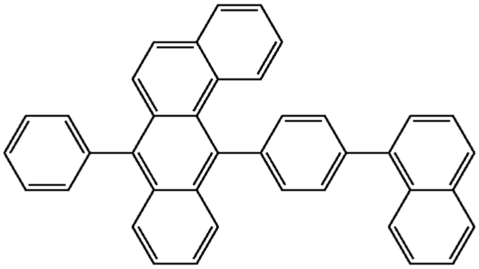
[Formula 399]
BH4-5
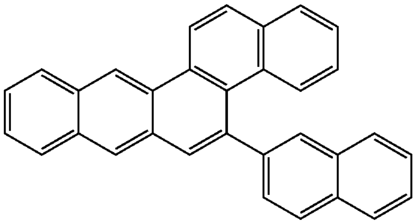
Structures of other compounds used for manufacturing the organic EL devices in Examples 1, A2 to A4, 2 to 174, Reference Example 1, and Comparative Examples 1, 2, A3 to A5, and 3 to 135 are shown below.

[Formula 400]
HA1
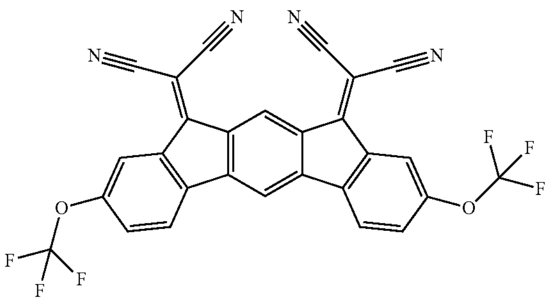
HT1
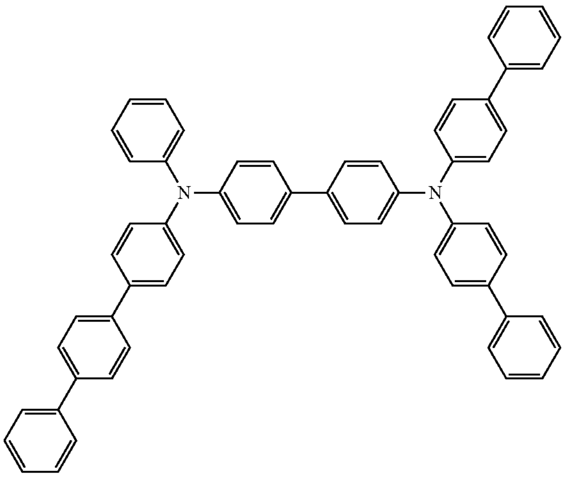
[Formula 401]
HT2
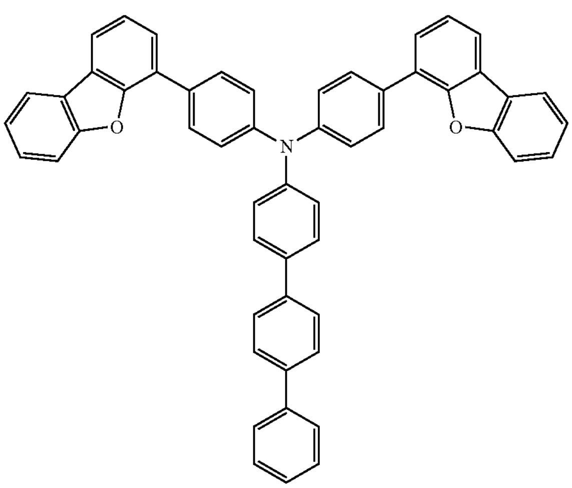
-continued
BD1
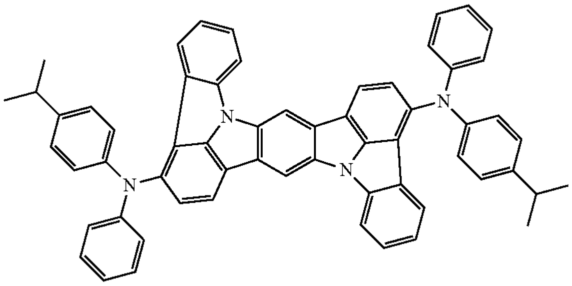
[Formula 402]
ET1
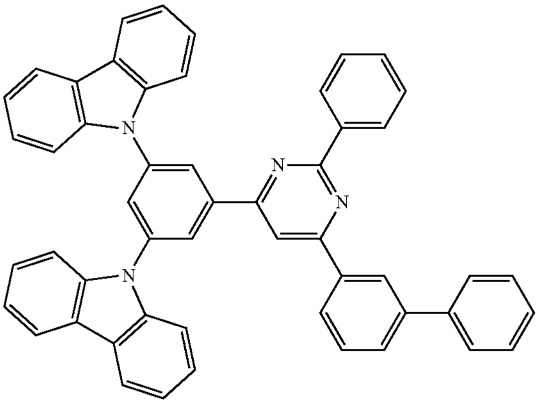
ET2
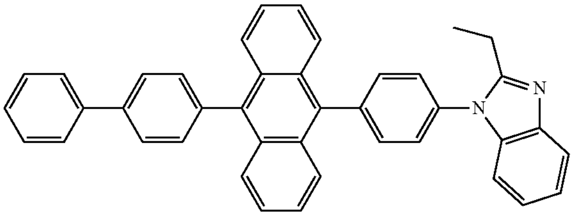
[Formula 403]
HA2-2
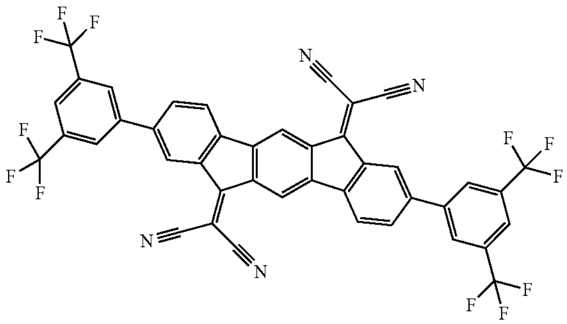

-continued
HT3-2
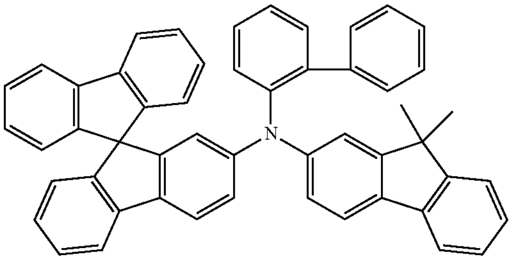
[Formula 404]
HT4-2
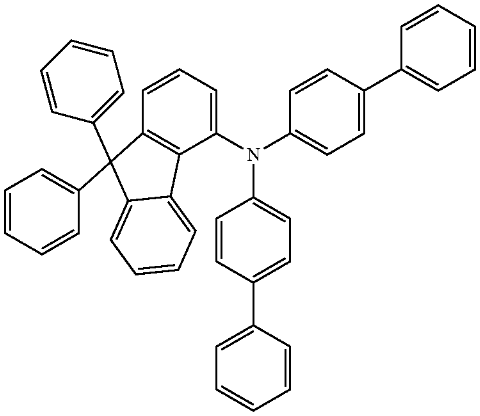
[Formula 405]
HT3
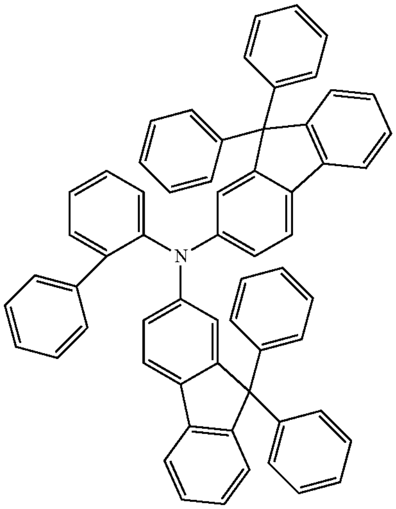
-continued
HT4
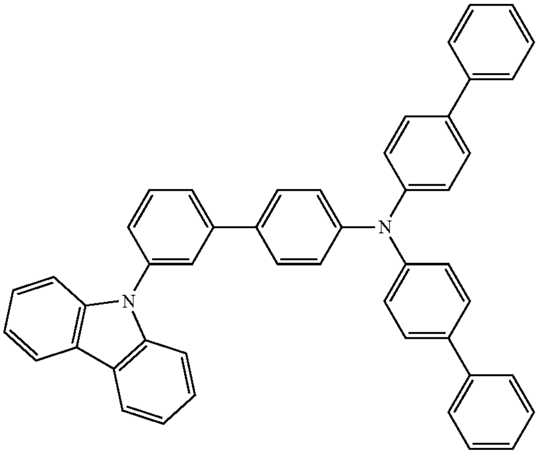
[Formula 406]
HT5
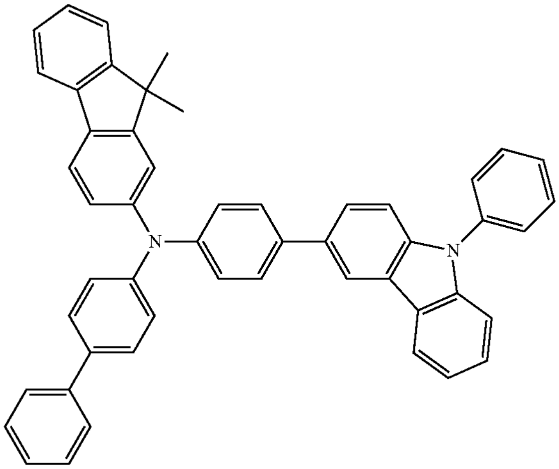
HA2
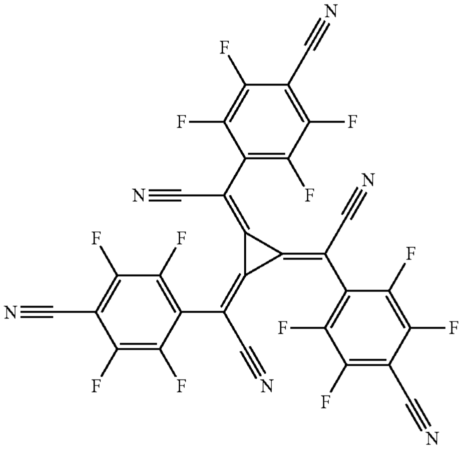

-continued
[Formula 407]
HT6
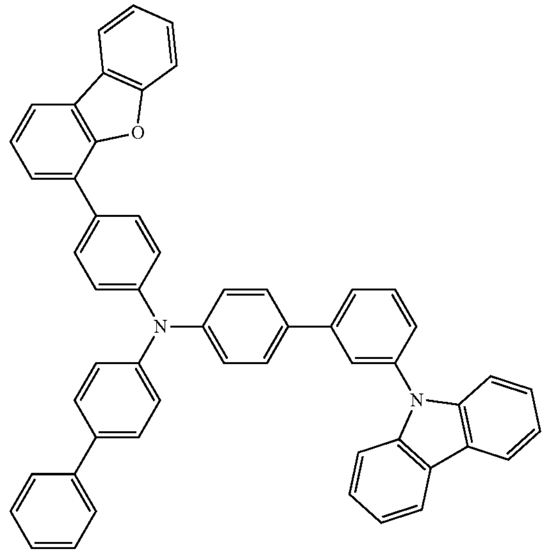
HT7
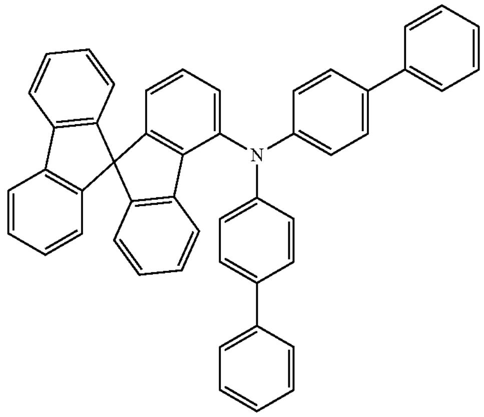
[Formula 408]
HT8
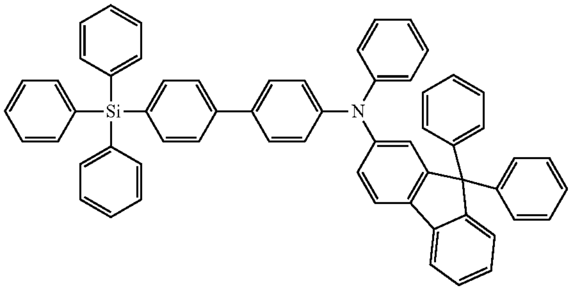
-continued
HT9
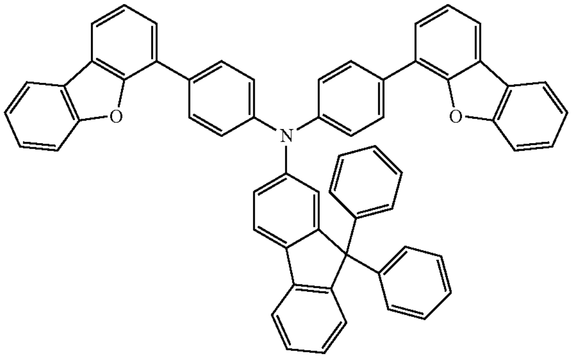
[Formula 409]
HT10
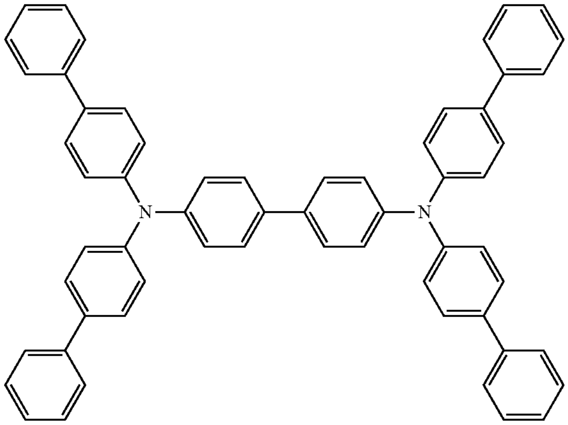
HT11
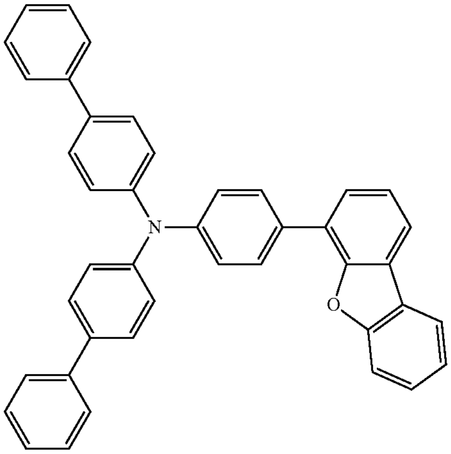
[Formula 410]
HA3
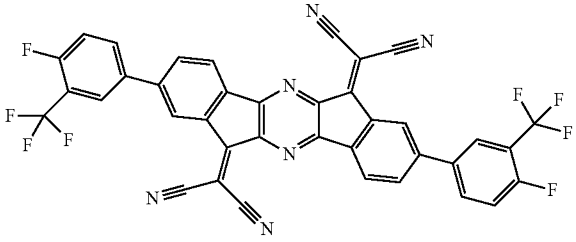

-continued
[Formula 411]
BD2
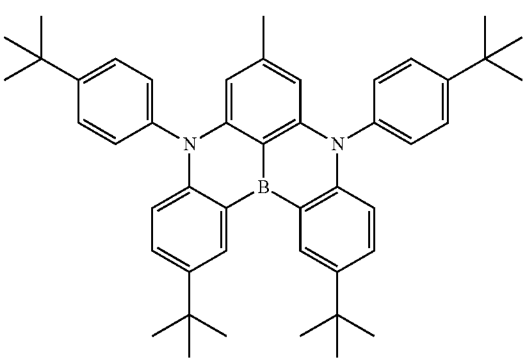
BD3
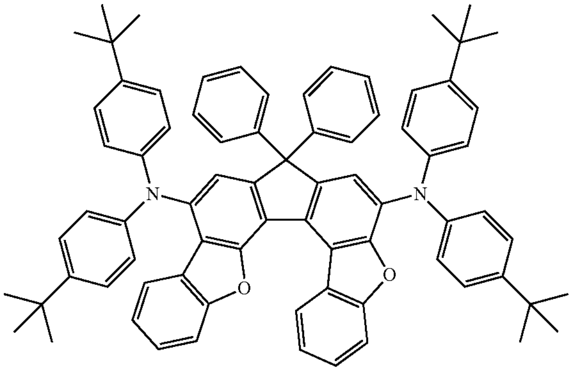
[Formula 412]
BD4
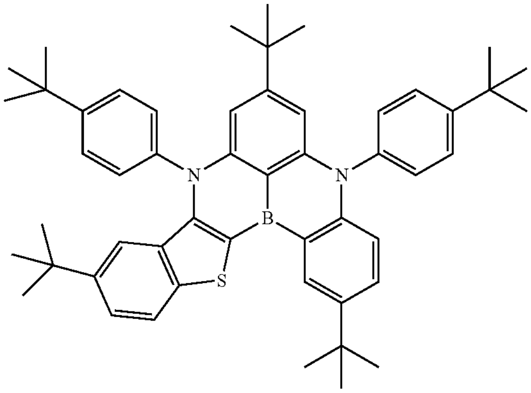
[Formula 413]
ET3
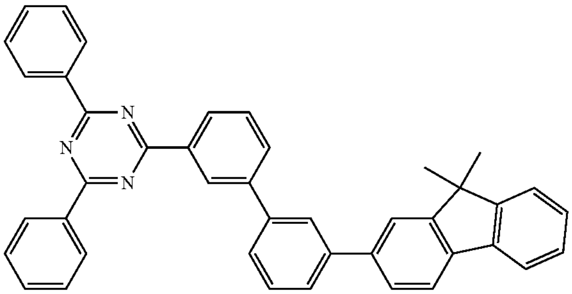
-continued
ET4
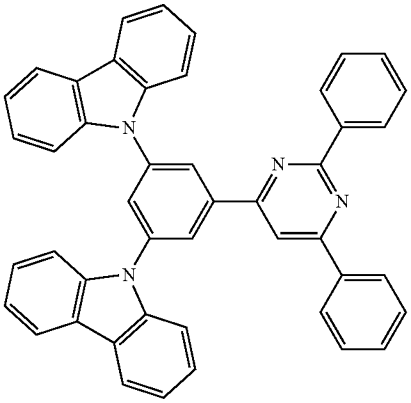
[Formula 414]
ET5
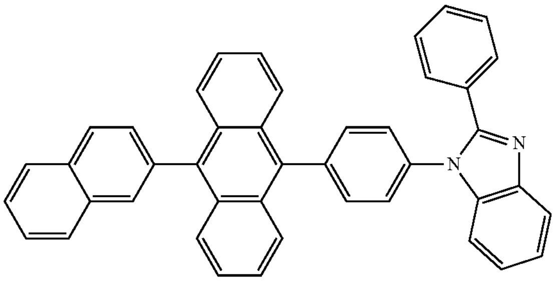
ET6
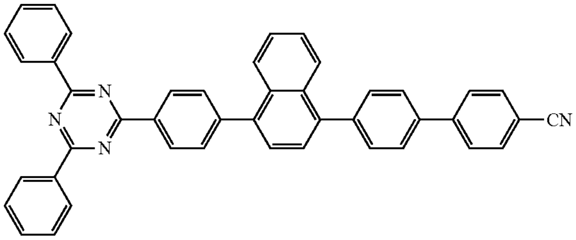
[Formula 415]
ET7
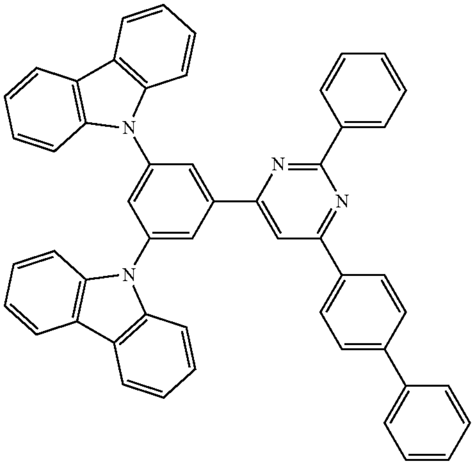

-continued nCGL

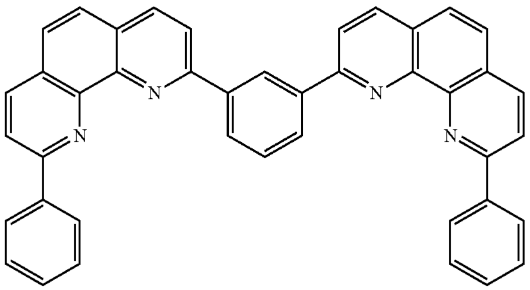

[Formula 416]

ET8

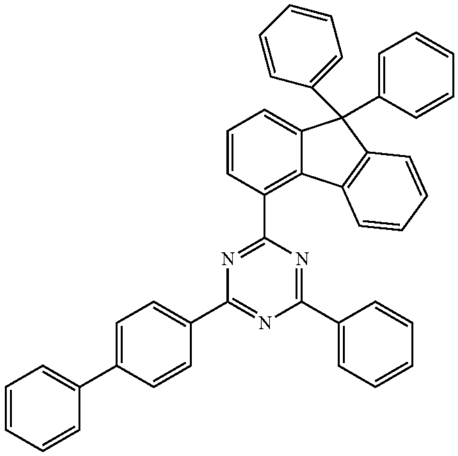

Liq

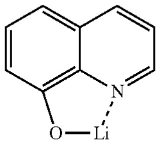

[Formula 417]

ET9

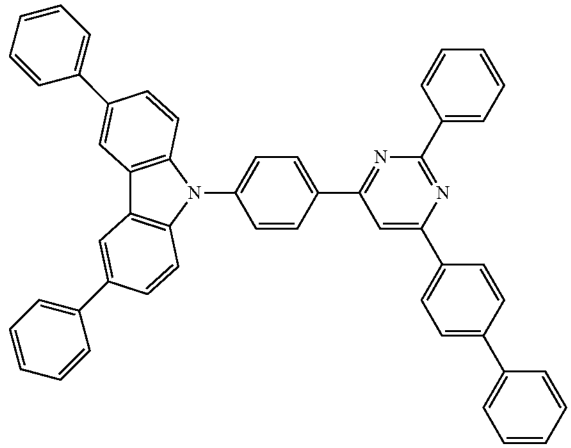

Manufacture 1 of Organic EL Device

Organic EL devices were manufactured and evaluated as follows.

Example 1

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. A film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound BH1 (first host material (BH)) and a compound BD1 (first dopant material (BD)) were co-deposited on the second hole transporting layer so that a ratio of the compound BD1 accounted for 2 mass %, thereby forming a 5-nm-thick first emitting layer.

A compound BH2 (second host material (BH)) and the compound BD1 (second dopant material (BD)) were co-deposited on the first emitting layer so that a ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 1 is roughly shown as follows.

ITO(130)/HA1(5)/HT1(80)/HT2(10)/BH1:BD1(5.98%:2%)/BH2:BD1(20.98%:2%)/ET1(10)/ET2(15)/LiF(1)/Al (80)

The numerals in parentheses represent a film thickness (unit: nm).

The numerals (98%:2%) represented by percentage in the same parentheses indicate a ratio (mass %) between the first host material or the second host material (compound BH1 or compound BH2) and the compound BD1 in each of the first emitting layer and the second emitting layer. Similar notations apply to the description below.

Comparative Example 1

The organic EL device of Comparative Example 1 was manufactured in the same manner as that of Example 1 except that only the first emitting layer was formed as the emitting layer as shown in Table 1.

Comparative Example 2

The organic EL device of Comparative Example 2 was manufactured in the same manner as that of Example 1 except that only the second emitting layer was formed as the emitting layer as shown in Table 1.

Example A2

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HA2-2 was vapor-deposited on a surface provided with the transparent electrode line to cover the transparent electrode, thereby forming a 5-nm-thick hole injecting layer (HI).

After the formation of the hole injecting layer, a compound HT3-2 was vapor-deposited to form an 80-nm-thick first hole transporting layer (HT).

After the formation of the first hole transporting layer, a compound HT4-2 was vapor-deposited to form a 10-nm-thick second hole transporting layer (also referred to as an electron blocking layer (EBL)).

The compound BH2 (first host material (BH)) and the compound BD1 (first dopant material (BD)) were co-deposited on the second hole transporting layer so that a ratio of the compound BD1 accounted for 2 mass %, thereby forming a 10-nm-thick first emitting layer.

A compound BH4 (second host material (BH)) and the compound BD1 (second dopant material (BD)) were co-deposited on the first emitting layer so that a ratio of the compound BD1 accounted for 2 mass %, thereby forming a 15-nm-thick second emitting layer.

A compound ET7 was deposited on the second emitting layer to form a 10-nm-thick electron transporting layer.

A compound nCGL and metal Li were co-deposited on the electron transporting layer so that a ratio of metal Li accounted for 4 mass %, thereby forming a 30-nm-thick electron injecting layer.

Metal (Al) was vapor-deposited on the electron injecting layer to form a 50-nm-thick cathode.

A device arrangement of the organic EL device in Example A2 is roughly shown as follows.

ITO(130)/HA2-2(5)/HT3-2(80)/HT4-2(10)/BH2:BD1 (10.98%:2%)/BH4:BD1 (15.98%:2%)/ET7(10)/nCGL:Li (30.96%:4%)/Al(50))

The numerals in parentheses represent a film thickness (unit: nm).

The numerals (98%:2%) represented by percentage in the same parentheses indicate a ratio (mass %) between the first host material or the second host material (compound BH2 or compound BH4) and the compound BD1 in each of the first emitting layer and the second emitting layer. The numerals (96%:4%) represented by percentage in the same parentheses indicate a ratio (mass %) between the compound nCGL ad metal Li in the electron injecting layer. Similar notations apply to the description below.

Example A3

The organic EL device according to Example A3 was manufactured in the same manner as that of Example A2 except that the compounds and the film thicknesses in the first and second emitting layers of Example A2 were changed to those shown in Table 2.

Example A4

The organic EL device of Example A4 was manufactured in the same manner as that of Example A3 except that the compounds and the film thicknesses in the first and second emitting layers of Example A3 were changed to those shown in Table 2.

Comparative Example A3

The organic EL device of Comparative Example A3 was manufactured in the same manner as that of Example A2 except that only the first emitting layer was formed as the emitting layer as shown in Table 2.

Comparative Example A4

The organic EL device of Comparative Example A4 was manufactured in the same manner as that of Example A2 except that only the second emitting layer was formed as the emitting layer as shown in Table 2.

Comparative Example A5

The organic EL device of Comparative Example A5 was manufactured in the same manner as that of Example A3 except that only the first emitting layer was formed as the emitting layer as shown in Table 2.

Evaluation of Organic EL Device

The organic EL devices in Examples 1, A2 to A4, 2 to 174, Reference Example 1, and Comparative Examples 1 to 2, A3 to A5, and 3 to 135 were evaluated as follows. Tables 1 to 61 show the evaluation results.

Drive Voltage

The voltage (unit: V) when electric current was applied between the anode and the cathode so that the current density was 10 $mA/cm^2$ was measured.

External Quantum Efficiency EQE

Voltage was applied on the organic EL devices so that a current density was 10 $mA/cm^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

Lifetime LT90

Voltage was applied on the resultant organic EL devices so that a current density was 50 $mA/cm^2$, where a time (LT90 (unit: hr)) elapsed before a luminance intensity was reduced to 90% of the initial luminance intensity was measured.

Lifetime LT95

Voltage was applied on the resultant organic EL devices so that a current density was 50 $mA/cm^2$, where a time (LT95 (unit: hr)) elapsed before a luminance intensity was reduced to 95% of the initial luminance intensity was measured.

Maximum Peak Wavelength λp of Light Emitted from Device when Device is Driven

Voltage was applied on the organic EL devices so that a current density of the organic EL device was 10 $mA/cm^2$, where spectral radiance spectrum was measured by a spectroradiometer CS-2000 (manufactured by Konica Minolta, Inc.). The main peak wavelength λp (unit: nm) was calculated based on the obtained spectral radiance spectrum.

Maximum Peak Wavelength λp of Light Emitted from Emitting Layer when Device is Driven For a main peak wavelength $\lambda p_1$ of light emitted from the first emitting layer when the organic EL device is driven, the organic EL device was manufactured by using the same material as the first emitting layer for the second emitting layer, and voltage is applied on the organic EL device so that a current density became 10 mA/cm$^2$, where spectral radiance spectrum was measured by a spectroradiometer CS-2000 (manufactured by Konica Minolta, Inc.). The main peak wavelength $\lambda p_1$ (unit: nm) was calculated based on the obtained spectral radiance spectrum.

For a main peak wavelength $\lambda p_2$ of light emitted from the second emitting layer when the organic EL device was driven, the organic EL device was manufactured by using the same material as the second emitting layer for the first emitting layer, and voltage was applied on the organic EL device so that a current density became 10 mA/cm$^2$, where spectral radiance spectrum was measured by a spectroradiometer CS-2000 (manufactured by Konica Minolta, Inc.). The main peak wavelength $\lambda p_2$ (unit: nm) was calculated based on the obtained spectral radiance spectrum.

CIE1931 Chromaticity

Voltage was applied on the organic EL devices so that a current density was 10 mA/cm$^2$, where spectral radiance spectrum was measured by a spectroradiometer (CS-2000 manufactured by Konica Minolta, Inc.).

CIEx and CIEy were calculated based on the obtained spectral radiance spectrum.

TABLE 1

| | First Emitting Layer | | | | | Second Emitting Layer | | | | | | | |
|---|---|---|---|---|---|---|---|---|---|---|---|---|---|
| | First Host Material | | | First Dopant Material | Film | Second Host Material | | | Second Dopant Material | Film | | | |
| | Compound Name | $S_1$[ev] | $T_1$[ev] | Compound Name | Thick-ness | Compound Name | $S_1$[ev] | $T_1$[ev] | Compound Name | Thick-ness | EQE [%] | LT90 [hr] | λp [nm] |
| Example 1 | BH1 | 3.12 | 2.10 | BD1 | 5 | BH2 | 3.01 | 1.87 | BD1 | 20 | 10.6 | 600 | 461 |
| Comparative Ex. 1 | BH1 | 3.12 | 2.10 | BD1 | 25 | — | — | — | — | — | 7.6 | 360 | 462 |
| Comparative Ex. 2 | — | — | — | — | — | BH2 | 3.01 | 1.87 | BD1 | 25 | 9.9 | 363 | 460 |

TABLE 2

| | First Emitting Layer | | | | | Second Emitting Layer | | | | | | | |
|---|---|---|---|---|---|---|---|---|---|---|---|---|---|
| | First Host Material | | | First Dopant Material | Film | Second Host Material | | | Second Dopant Material | Film | Drive Voltage V | | |
| | Compound Name | $S_1$ [ev] | $T_1$ [ev] | Compound Name | Thickness [nm] | Compound Name | $S_1$ [ev] | $T_1$ [ev] | Compound Name | Thickness [nm] | @10 mA [V] | λp [nm] | EQE [%] |
| Example A2 | BH2 | 3.01 | 1.87 | BD1 | 10 | BH4 | 2.93 | 1.82 | BD1 | 15 | 3.72 | 460 | 10.7 |
| Example A3 | BH2-3 | 3.01 | 1.87 | BD1 | 5 | BH4 | 2.93 | 1.82 | BD1 | 20 | 3.77 | 460 | 10.8 |
| Example A4 | BH2-3 | 3.01 | 1.87 | BD1 | 10 | BH4 | 2.93 | 1.82 | BD1 | 15 | 3.75 | 460 | 10.7 |
| Comparative Ex. A3 | BH2 | 3.01 | 1.87 | BD1 | 25 | — | — | — | — | — | 4.03 | 460 | 9.6 |
| Comparative Ex. A4 | — | — | — | — | — | BH4 | 2.93 | 1.82 | BD1 | 25 | 3.72 | 460 | 9.9 |
| Comparative Ex. A5 | BH2-3 | 3.01 | 1.87 | BD1 | 25 | — | — | — | — | — | 4.11 | 460 | 9.5 |

Since the organic EL devices in Examples 1 and A2 to A4 include the first emitting layer and the second emitting layer including the respective host materials satisfying the relationship of the numerical formula (Numerical Formula 1), the organic EL devices in Examples 1 and A2 to A4 improved EQE more than the organic EL devices in Comparatives Examples 1, 2, and A3 to A5.

Examples 2 to 20

The organic EL devices of Examples 2 and 20 were manufactured in the same manner as that of Example 1 except that the compound BH1 (first host material) in the first emitting layer was replaced with the compounds shown in Table 3.

Comparative Examples 3 to 21

The organic EL devices of Comparative Examples 3 and 21 were manufactured in the same manner as that of Comparative Example 1 except that the compound BH1 (first host material) in the first emitting layer was replaced with the first compounds shown in Table 4.

TABLE 3

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 1 | BH1 | BD1 | 5 | BH2 | BD1 | 20 | 3.47 | 10.6 | 255 |
| Example 2 | BH1-2 | BD1 | 5 | BH2 | BD1 | 20 | 3.47 | 10.2 | 205 |
| Example 3 | BH1-3 | BD1 | 5 | BH2 | BD1 | 20 | 3.56 | 10.5 | 268 |
| Example 4 | BH1-4 | BD1 | 5 | BH2 | BD1 | 20 | 3.56 | 10.7 | 222 |
| Example 5 | BH1-5 | BD1 | 5 | BH2 | BD1 | 20 | 3.64 | 10.7 | 251 |
| Example 6 | BH1-6 | BD1 | 5 | BH2 | BD1 | 20 | 3.65 | 10.6 | 224 |
| Example 7 | BH1-7 | BD1 | 5 | BH2 | BD1 | 20 | 3.63 | 10.4 | 239 |
| Example 8 | BH1-8 | BD1 | 5 | BH2 | BD1 | 20 | 3.62 | 10.4 | 224 |
| Example 9 | BH1-9 | BD1 | 5 | BH2 | BD1 | 20 | 3.70 | 10.8 | 249 |
| Example 10 | BH1-10 | BD1 | 5 | BH2 | BD1 | 20 | 3.34 | 10.4 | 216 |
| Example 11 | BH1-11 | BD1 | 5 | BH2 | BD1 | 20 | 3.48 | 10.8 | 275 |
| Example 12 | BH1-12 | BD1 | 5 | BH2 | BD1 | 20 | 3.39 | 10.6 | 212 |
| Example 13 | BH1-13 | BD1 | 5 | BH2 | BD1 | 20 | 3.51 | 10.6 | 231 |
| Example 14 | BH1-14 | BD1 | 5 | BH2 | BD1 | 20 | 3.36 | 10.4 | 198 |
| Example 15 | BH1-15 | BD1 | 5 | BH2 | BD1 | 20 | 3.43 | 10.5 | 190 |
| Example 16 | BH1-16 | BD1 | 5 | BH2 | BD1 | 20 | 3.30 | 10.5 | 192 |
| Example 17 | BH1-17 | BD1 | 5 | BH2 | BD1 | 20 | 3.38 | 10.2 | 185 |
| Example 18 | BH1-18 | BD1 | 5 | BH2 | BD1 | 20 | 3.41 | 10.6 | 204 |
| Example 19 | BH1-19 | BD1 | 5 | BH2 | BD1 | 20 | 3.39 | 10.3 | 191 |
| Example 20 | R-BH1 | BD1 | 5 | BH2 | BD1 | 20 | 3.91 | 10.1 | — |

TABLE 4

| | First Emitting Layer | | | Second Emitting Layer | | | | | |
|---|---|---|---|---|---|---|---|---|---|
| | First Compound | Third Compound | Film Thickness [nml | Second Compound | Fourth Compound | Film Thickness [nm] | Voltage [V] | EQE [%] | LT95 [hr] |
| Comparative Ex. 1 | BH1 | BD1 | 25 | — | — | — | — | 7.6 | 65 |
| Comparative Ex. 2 | — | — | — | BH2 | BD1 | 25 | — | 9.9 | 167 |
| Comparative Ex. 3 | BH1-2 | BD1 | 25 | — | — | — | — | 7.2 | 59 |
| Comparative Ex. 4 | BH1-3 | BD1 | 25 | — | — | — | — | 7.4 | 71 |
| Comparative Ex. 5 | BH1-4 | BD1 | 25 | — | — | — | — | 7.8 | 70 |
| Comparative Ex. 6 | BH1-5 | BD1 | 25 | — | — | — | — | 7.5 | 62 |
| Comparative Ex. 7 | BH1-6 | BD1 | 25 | — | — | — | — | 7.4 | 60 |
| Comparative Ex. 8 | BH1-7 | BD1 | 25 | — | — | — | — | 7.3 | 53 |
| Comparative Ex. 9 | BH1-8 | BD1 | 25 | — | — | — | — | 7.4 | 55 |
| Comparative Ex. 10 | BH1-9 | BD1 | 25 | — | — | — | — | 7.5 | 67 |
| Comparative Ex. 11 | BH1-10 | BD1 | 25 | — | — | — | — | 7.1 | 51 |
| Comparative Ex. 12 | BH1-11 | BD1 | 25 | — | — | — | — | 7.8 | 81 |
| Comparative Ex. 13 | BH1-12 | BD1 | 25 | — | — | — | — | 7.0 | 48 |
| Comparative Ex. 14 | BH1-13 | BD1 | 25 | — | — | — | — | 7.1 | 53 |
| Comparative Ex. 15 | BH1-14 | BD1 | 25 | — | — | — | — | 6.9 | 56 |
| Comparative Ex. 16 | BH1-15 | BD1 | 25 | — | — | — | — | 7.1 | 59 |

TABLE 4-continued

| | First Emitting Layer | | | Second Emitting Layer | | | | | |
|---|---|---|---|---|---|---|---|---|---|
| | First Compound | Third Compound | Film Thickness [nml | Second Compound | Fourth Compound | Film Thickness [nm] | Voltage [V] | EQE [%] | LT95 [hr] |
| Comparative Ex. 17 | BH1-16 | BD1 | 25 | — | — | — | — | 7.0 | 62 |
| Comparative Ex. 18 | BH1-17 | BD1 | 25 | — | — | — | — | 6.7 | 53 |
| Comparative Ex. 19 | BH1-18 | BD1 | 25 | — | — | — | — | 7.1 | 62 |
| Comparative Ex. 20 | BH1-19 | BD1 | 25 | — | — | — | — | 6.9 | 43 |
| Comparative Ex. 21 | BH1-20 | BD1 | 25 | — | — | — | — | 6.5 | 21 |

Example 21

The organic EL devices of Example 21 was manufactured in the same manner as that of Reference Example 1 except that the compound BH2 (second host material) in the second emitting layer was replaced with the compound shown in Table 5.

Examples 22 and 23

The organic EL devices of Examples 22 and 23 were manufactured in the same manner as that of Example 1 except that the compound BH1 (first host material) in the first emitting layer and the compound BH2 (second host material) in the second emitting layer were replaced with the compounds shown in Table 5.

Comparative Example 22

The organic EL device of Comparative Example 22 was manufactured in the same manner as that of Comparative Example 2 except that the compound BH2 (second host material) in the second emitting layer was replaced with the compound shown in Table 5.

TABLE 5

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 21 | BH1 | BD1 | 5 | BH2-2 | BD1 | 20 | 3.96 | 9.8 | 192 |
| Example 22 | R-BH1 | BD1 | 5 | BH2-2 | BD1 | 20 | 4.40 | 9.4 | — |
| Example 23 | R-BH2 | BD1 | 5 | BH2-2 | BD1 | 20 | 4.68 | 9.5 | — |
| Comparative Ex. 1 | BH1 | BD1 | 25 | — | — | — | — | 7.6 | 65 |
| Comparative Ex. 22 | — | — | — | BH2-2 | BD1 | 25 | — | 9.2 | 115 |

Example 24

The organic EL device of Example 24 was manufactured in the same manner as that of Example 1 except that the compound BH2 (second host material) in the second emitting layer was replaced with the compound shown in Table 6.

Examples 25 and 26

The organic EL devices of Examples 25 and 26 were manufactured in the same manner as that of Example 1 except that the compound BH1 (first host material) in the first emitting layer and the compound BH2 (second host material) in the second emitting layer were replaced with the compounds shown in Table 6.

Comparative Example 23

The organic EL device of Comparative Example 23 was manufactured in the same manner as that of Comparative Example 2 except that the compound BH2 (second host material) in the second emitting layer was replaced with the compound shown in Table 6.

TABLE 6

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 24 | BH1 | BD1 | 5 | BH2-3 | BD1 | 20 | 3.54 | 10.6 | 278 |
| Example 25 | R-BH1 | BD1 | 5 | BH2-3 | BD1 | 20 | 3.98 | 10.1 | — |
| Example 26 | R-BH2 | BD1 | 5 | BH2-3 | BD1 | 20 | 4.26 | 10.2 | — |
| Comparative Ex. 1 | BH1 | BD1 | 25 | — | — | — | — | 7.6 | 65 |
| Comparative Ex. 23 | — | — | — | BH2-3 | BD1 | 25 | — | 9.9 | 182 |

Example 27

The organic EL device of Example 27 was manufactured in the same manner as that of Example 1 except that the compound BH2 (second host material) in the second emitting layer were replaced with the compound shown in Table 7.

Examples 28 and 29

The organic EL devices of Examples 28 and 29 were manufactured in the same manner as that of Example 1 except that the compound BH1 (first host material) in the first emitting layer and the compound BH2 (second host material) in the second emitting layer were replaced with the compounds shown in Table 7.

Comparative Example 24

The organic EL device of Comparative Example 24 was manufactured in the same manner as that of Comparative Example 2 except that the compound BH2 (second host material) in the second emitting layer was replaced with the compound shown in Table 7.

TABLE 7

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 27 | BH1 | BD1 | 5 | BH2-4 | BD1 | 20 | 3.26 | 8.1 | 272 |
| Example 28 | R-BH1 | BD1 | 5 | BH2-4 | BD1 | 20 | 3.70 | 7.9 | — |
| Example 29 | R-BH2 | BD1 | 5 | BH2-4 | BD1 | 20 | 3.98 | 7.9 | — |
| Comparative Ex. 1 | BH1 | BD1 | 25 | — | — | — | — | 7.6 | 65 |
| Comparative Ex. 24 | — | — | — | BH2-4 | BD1 | 25 | — | 7.7 | 114 |

Example 30

The organic EL device of Example 30 was manufactured in the same manner as that of Example 1 except that the compound BH2 (second host material) in the second emitting layer was replaced with the compound shown in Table 8.

Examples 31 and 32

The organic EL devices of Examples 31 and 32 were manufactured in the same manner as that of Example 1 except that the compound BH1 (first host material) in the first emitting layer and the compound BH2 (second host material) in the second emitting layer were replaced with the compounds shown in Table 8.

Comparative Example 25

The organic EL device of Comparative Example 25 was manufactured in the same manner as that of Comparative Example 2 except that the compound BH2 (second host material) in the second emitting layer was replaced with the compound shown in Table 8.

TABLE 8

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 30 | BH1 | BD1 | 5 | BH2-5 | BD1 | 20 | 3.76 | 8.0 | 196 |
| Example 31 | R-BH1 | BD1 | 5 | BH2-5 | BD1 | 20 | 4.20 | 7.8 | — |
| Example 32 | R-BH2 | BD1 | 5 | BH2-5 | BD1 | 20 | 4.48 | 7.8 | — |
| Comparative Ex. 1 | BH1 | BD1 | 25 | — | — | — | — | 7.6 | 65 |
| Comparative Ex. 25 | — | — | — | BH2-5 | BD1 | 25 | — | 7.6 | 92 |

Example 33

The organic EL device of Example 33 was manufactured in the same manner as that of Example 1 except that the compound BH2 (second host material) in the second emitting layer was replaced with the compound shown in Table 9.

Examples 34 and 35

The organic EL devices of Examples 34 and 35 were manufactured in the same manner as that of Example 1 except that the compound BH1 (first host material) in the first emitting layer and the compound BH2 (second host material) in the second emitting layer were replaced with the compounds shown in Table 9.

Comparative Example 26

The organic EL device according to Comparative Example 26 was manufactured in the same manner as that of Reference Example 2 except that the compound BH2 (second host material) in the second emitting layer was replaced with the compound listed in Table 9.

TABLE 9

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 33 | BH1 | BD1 | 5 | BH2-6 | BD1 | 20 | 3.14 | 10.5 | 198 |
| Example 34 | R-BH1 | BD1 | 5 | BH2-6 | BD1 | 20 | 3.58 | 8.2 | — |
| Example 35 | R-BH2 | BD1 | 5 | BH2-6 | BD1 | 20 | 3.86 | 8.2 | — |
| Comparative Ex. 1 | BH1 | BD1 | 25 | — | — | — | — | 7.6 | 65 |
| Comparative Ex. 26 | — | — | — | BH2-6 | BD1 | 25 | — | 8.0 | 71 |

Example 36

The organic EL devices of Example 36 was manufactured in the same manner as that of Example 1 except that the compound BH2 (second host material) in the second emitting layer were replaced with the compound shown in Table 6.

Examples 37 and 38

The organic EL devices of Examples 37 and 38 were manufactured in the same manner as that of Example 1 except that the compound BH1 (first host material) in the first emitting layer and the compound BH2 (second host material) in the second emitting layer were replaced with the compounds shown in Table 10.

Comparative Example 27

The organic EL devices according to Comparative Example 27 was manufactured in the same manner as that of Comparative Example 2 except that the compound BH2 (second host material) in the second emitting layer was replaced with the compound shown in Table 10.

TABLE 10

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 36 | BH1 | BD1 | 5 | BH2-7 | BD1 | 20 | 3.21 | 10.7 | 217 |
| Example 37 | R-BH1 | BD1 | 5 | BH2-7 | BD1 | 20 | 3.65 | 8.0 | — |
| Example 38 | R-BH2 | BD1 | 5 | BH2-7 | BD1 | 20 | 3.93 | 8.0 | — |
| Comparative Ex. 1 | BH1 | BD1 | 25 | — | — | — | — | 7.6 | 65 |
| Comparative Ex. 27 | — | — | — | BH2-7 | BD1 | 25 | — | 7.8 | 106 |

Example 39

The organic EL device of Example 39 was manufactured in the same manner as that of Example 1 except the compound BH2 (second host material) in the second emitting layer were replaced with the compound shown in Table 11.

Examples 40 and 41

The organic EL devices of Examples 40 and 41 were manufactured in the same manner as that of Example 1 except that the compound BH1 (first host material) in the first emitting layer and the compound BH2 (second host material) in the second emitting layer were replaced with the compounds shown in Table 11.

Comparative Example 28

The organic EL device of Comparative Example 28 was manufactured in the same manner as that of Comparative Example 2 except that the compound BH2 (second host material) in the second emitting layer was replaced with the compound shown in Table 11.

TABLE 11

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 39 | BH1 | BD1 | 5 | BH2-8 | BD1 | 20 | 3.39 | 9.2 | 192 |
| Example 40 | R-BH1 | BD1 | 5 | BH2-8 | BD1 | 20 | 3.83 | 8.0 | — |
| Example 41 | R-BH2 | BD1 | 5 | BH2-8 | BD1 | 20 | 4.11 | 8.0 | — |
| Comparative Ex. 1 | BH1 | BD1 | 25 | — | — | — | — | 7.6 | 65 |
| Comparative Ex. 28 | — | — | — | BH2-8 | BD1 | 25 | — | 7.8 | 74 |

Example 42

The organic EL device of Example 42 was manufactured in the same manner as that of Example 1 except that the compound BH2 (second host material) in the second emitting layer were replaced with the compound shown in Table 12.

Examples 43 and 44

The organic EL devices of Examples 43 and 44 were manufactured in the same manner as that of Example 1 except that the compound BH1 (first host material) in the first emitting layer and the compound BH2 (second host material) in the second emitting layer were replaced with the compounds shown in Table 12.

Comparative Example 29

The organic EL device of Comparative Example 29 was manufactured in the same manner as that of Comparative Example 2 except that the compound BH2 (second host material) in the second emitting layer was replaced with the compound shown in Table 12.

TABLE 12

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 42 | BH1 | BD1 | 5 | BH2-9 | BD1 | 20 | 3.56 | 10.5 | 300 |
| Example 43 | R-BH1 | BD1 | 5 | BH2-9 | BD1 | 20 | 4.00 | 10.0 | — |
| Example 44 | R-BH2 | BD1 | 5 | BH2-9 | BD1 | 20 | 4.28 | 10.1 | — |
| Comparative Ex. 1 | BH1 | BD1 | 25 | — | — | — | — | 7.6 | 65 |
| Comparative Ex. 29 | — | — | — | BH2-9 | BD1 | 25 | — | 9.8 | 195 |

Example 45

The organic EL device of Example 45 was manufactured in the same manner as that of Example 1 except that the compound BD1 in the first emitting layer and the compound BD1 in the second emitting layer were replaced with the compound shown in Table 13

Examples 46 and 47

The organic EL devices of Examples 46 and 47 were manufactured in the same manner as that of Example 1 except that the compound BH1 (first host material) and the compound BD1 in the first emitting layer and the compound BD1 in the second emitting layer were replaced with the compounds shown in Table 13.

Comparative Example 30

The organic EL device of Comparative Example 30 was manufactured in the same manner as that of Comparative Example 1 except that the compound BD1 in the first emitting layer was replaced with the compound shown in Table 13.

Comparative Example 31

The organic EL device of Comparative Example 31 was manufactured in the same manner as that of Comparative Example 2 except that the compound BD1 in the second emitting layer was replaced with the compound shown in Table 13

TABLE 13

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 45 | BH1 | BD2 | 5 | BH2 | BD2 | 20 | 3.57 | 9.7 | 203 |
| Example 46 | R-BH1 | BD2 | 5 | BH2 | BD2 | 20 | 4.01 | 9.3 | — |
| Example 47 | R-BH2 | BD2 | 5 | BH2 | BD2 | 20 | 4.29 | 9.4 | — |
| Comparative Ex. 30 | BH1 | BD2 | 25 | — | — | — | — | 7.0 | 51 |
| Comparative Ex. 31 | — | — | — | BH2 | BD2 | 25 | — | 9.1 | 120 |

Example 48

The organic EL device of Example 48 was manufactured in the same manner as that of Example 1 except that the compound BD1 in the first emitting layer and the compound BD1 in the second emitting layer were replaced with the compounds shown in Table 14.

Examples 49 and 50

The organic EL devices of Examples 49 and 50 were manufactured in the same manner as that of Example 1 except that the compound BH1 (first host material) and the compound BD1 in the first emitting layer and the compound BD1 in the second emitting layer were replaced with the compounds shown in Table 14.

Comparative Example 32

The organic EL device of Comparative Example 32 was manufactured in the same manner as that of Example 1 except that the compound BD1 in the first emitting layer was replaced with the compound shown in Table 14.

Comparative Example 33

The organic EL device of Comparative Example 33 was manufactured in the same manner as that of Comparative Example 2 except that the compound BD1 in the second emitting layer was replaced with the compound shown in Table 14.

TABLE 14

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 48 | BH1 | BD3 | 5 | BH2 | BD3 | 20 | 3.51 | 10.2 | 167 |
| Example 49 | R-BH1 | BD3 | 5 | BH2 | BD3 | 20 | 3.95 | 9.7 | — |
| Example 50 | R-BH2 | BD3 | 5 | BH2 | BD3 | 20 | 4.23 | 9.8 | — |
| Comparative Ex. 32 | BH1 | BD3 | 25 | — | — | — | — | 7.4 | 46 |
| Comparative Ex. 33 | — | — | — | BH2 | BD3 | 25 | — | 9.5 | 103 |

Examples 51 to 69

The organic EL devices of Examples 51 to 69 were manufactured in the same manner as that of Example 1 except that the compound BH1 (first host material) in the first emitting layer was replaced with the compound shown in Table 15.

TABLE 15

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 51 | BH1-23 | BD1 | 5 | BH2 | BD1 | 20 | 10.2 | 198 |
| Example 52 | BH1-26 | BD1 | 5 | BH2 | BD1 | 20 | 10.3 | 214 |
| Example 53 | BH1-27 | BD1 | 5 | BH2 | BD1 | 20 | 10.6 | 239 |
| Example 54 | BH1-28 | BD1 | 5 | BH2 | BD1 | 20 | 10.5 | 222 |
| Example 55 | BH1-32 | BD1 | 5 | BH2 | BD1 | 20 | 10.4 | 207 |
| Example 56 | BH1-33 | BD1 | 5 | BH2 | BD1 | 20 | 10.3 | 205 |
| Example 57 | BH1-34 | BD1 | 5 | BH2 | BD1 | 20 | 10.5 | 213 |
| Example 58 | BH1-35 | BD1 | 5 | BH2 | BD1 | 20 | 10.4 | 198 |
| Example 59 | BH1-40 | BD1 | 5 | BH2 | BD1 | 20 | 10.4 | 221 |
| Example 60 | BH1-41 | BD1 | 5 | BH2 | BD1 | 20 | 10.7 | 248 |
| Example 61 | BH1-42 | BD1 | 5 | BH2 | BD1 | 20 | 10.5 | 232 |
| Example 62 | BH1-43 | BD1 | 5 | BH2 | BD1 | 20 | 10.6 | 211 |
| Example 63 | BH1-44 | BD1 | 5 | BH2 | BD1 | 20 | 10.5 | 205 |
| Example 64 | BH1-45 | BD1 | 5 | BH2 | BD1 | 20 | 10.4 | 230 |
| Example 65 | BH1-46 | BD1 | 5 | BH2 | BD1 | 20 | 10.8 | 249 |
| Example 66 | BH1-47 | BD1 | 5 | BH2 | BD1 | 20 | 10.6 | 217 |
| Example 67 | BH1-48 | BD1 | 5 | BH2 | BD1 | 20 | 10.6 | 243 |
| Example 68 | BH1-49 | BD1 | 5 | BH2 | BD1 | 20 | 10.7 | 268 |
| Example 69 | R-BH3 | BD1 | 5 | BH2 | BD1 | 20 | 10.1 | 183 |

Comparative Examples 34 to 51

The organic EL devices of Comparative Examples 34 to 51 were manufactured in the same manner as that of Comparative Example 1 except that the compound BH1 (first host material) in the first emitting layer was replaced with the compound shown in Table 16.

TABLE 16

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comparative Ex. 34 | BH1-23 | BD1 | 25 | — | — | — | 6.3 | 50 |
| Comparative Ex. 35 | BH1-26 | BD1 | 25 | — | — | — | 6.6 | 78 |
| Comparative Ex. 36 | BH1-27 | BD1 | 25 | — | — | — | 6.7 | 81 |
| Comparative Ex. 37 | BH1-28 | BD1 | 25 | — | — | — | 6.5 | 72 |
| Comparative Ex. 38 | BH1-32 | BD1 | 25 | — | — | — | 6.1 | 49 |
| Comparative Ex. 39 | BH1-33 | BD1 | 25 | — | — | — | 6.2 | 55 |
| Comparative Ex. 40 | BH1-34 | BD1 | 25 | — | — | — | 6.2 | 57 |
| Comparative Ex. 41 | BH1-35 | BD1 | 25 | — | — | — | 6.0 | 49 |
| Comparative Ex. 42 | BH1-40 | BD1 | 25 | — | — | — | 6.2 | 68 |
| Comparative Ex. 43 | BH1-41 | BD1 | 25 | — | — | — | 6.6 | 91 |
| Comparative Ex. 44 | BH1-42 | BD1 | 25 | — | — | — | 6.4 | 85 |
| Comparative Ex. 45 | BH1-43 | BD1 | 25 | — | — | — | 6.4 | 72 |
| Comparative Ex. 46 | BH1-44 | BD1 | 25 | — | — | — | 6.4 | 77 |
| Comparative Ex. 47 | BH1-45 | BD1 | 25 | — | — | — | 6.2 | 81 |
| Comparative Ex. 48 | BH1-46 | BD1 | 25 | — | — | — | 6.3 | 94 |
| Comparative Ex. 49 | BH1-47 | BD1 | 25 | — | — | — | 6.2 | 67 |
| Comparative Ex. 50 | BH1-48 | BD1 | 25 | — | — | — | 6.1 | 64 |
| Comparative Ex. 51 | BH1-49 | BD1 | 25 | — | — | — | 6.8 | 97 |
| Comparative Ex. 2 | — | — | — | BH2 | BD1 | 25 | 9.9 | 167 |

Manufacture 2 of Organic EL Device

Organic EL devices were manufactured and evaluated as follows.

Example 70

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

A compound BH1-21 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET4 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 70 is roughly shown as follows.

ITO(130)/HA1(5)/HT3(80)/HT4(10)/BH1-21:BD1(5.98%: 2%)/BH2:BD1(20.98%:2%)/ET4(10)/ET2(15)/LiF(1)/Al (80)

The numerals in parentheses represent a film thickness (unit: nm).

The numerals (98%:2%) represented by percentage in the same parentheses indicate a ratio (mass %) between the host material (compound BH1-21 or BH2) and the compound BD1 in the first emitting layer or the second emitting layer. Similar notations apply to the description below.

Examples 71 to 78

The organic EL devices of Examples 71 to 78 were manufactured in the same manner as that of Example 70 except that the compound BH1-21 (first host material) in the first emitting layer was replaced with the compounds shown in Table 17.

Comparative Examples 52 to 59

The organic EL devices of Comparative Examples 52 to 59 were manufactured in the same manner as that of Example 70 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 17.

Comparative Example 60

The organic EL device according to Comparative Example 60 was manufactured in the same manner as that of Example 70 except that a 25-nm-thick second emitting layer was formed on the second hole transporting layer without forming the first emitting layer as shown in Table 17.

UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

A compound BH1-29 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

TABLE 17

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Example 70 | BH1-21 | BD1 | 5 | BH2 | BD1 | 20 | 3.40 | 8.7 | 160 |
| Example 71 | BH1-22 | BD1 | 5 | BH2 | BD1 | 20 | 3.46 | 9.0 | 225 |
| Example 72 | BH1-24 | BD1 | 5 | BH2 | BD1 | 20 | 3.27 | 8.4 | 79 |
| Example 73 | BH1-25 | BD1 | 5 | BH2 | BD1 | 20 | 3.35 | 8.7 | 174 |
| Example 74 | BH1-36 | BD1 | 5 | BH2 | BD1 | 20 | 3.39 | 8.5 | 125 |
| Example 75 | BH1-37 | BD1 | 5 | BH2 | BD1 | 20 | 3.44 | 8.8 | 135 |
| Example 76 | BH1-50 | BD1 | 5 | BH2 | BD1 | 20 | 3.42 | 8.5 | 111 |
| Example 77 | BH1-51 | BD1 | 5 | BH2 | BD1 | 20 | 3.31 | 8.4 | 105 |
| Example 78 | R-BH3 | BD1 | 5 | BH2 | BD1 | 20 | 3.53 | 7.9 | 36 |
| Comparative Ex. 52 | BH1-21 | BD1 | 25 | — | — | — | — | 6.2 | 32 |
| Comparative Ex. 53 | BH1-22 | BD1 | 25 | — | — | — | — | 6.4 | 45 |
| Comparative Ex. 54 | BH1-24 | BD1 | 25 | — | — | — | — | 6.0 | 13 |
| Comparative Ex. 55 | BH1-25 | BD1 | 25 | — | — | — | — | 6.2 | 25 |
| Comparative Ex. 56 | BH1-36 | BD1 | 25 | — | — | — | — | 6.1 | 25 |
| Comparative Ex. 57 | BH1-37 | BD1 | 25 | — | — | — | — | 6.3 | 27 |
| Comparative Ex. 58 | BH1-50 | BD1 | 25 | — | — | — | — | 6.1 | 21 |
| Comparative Ex. 59 | BH1-51 | BD1 | 25 | — | — | — | — | 6.0 | 19 |
| Comparative Ex. 60 | — | — | — | BH2 | BD1 | 25 | — | 7.7 | 56 |

Manufacture 3 of Organic EL Device

Organic EL devices were manufactured and evaluated as follows.

Example 79

A glass substrate (size: 25 mm×75 mm×1.1 mm thick, manufactured by Geomatec Go., Ltd.) having an ITO (Indium Tin Oxide) transparent electrode (anode) was ultrasonic-cleaned in isopropyl alcohol for five minutes, and then A compound ET3 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 79 is roughly shown as follows.

ITO(130)/HA1(5)/HT3(80)/HT4(10)/BH1-29:BD1(5.98%:2%)/BH2:BD1(20.98%:2%)/ET3(10)/ET2(15)/LiF(1)/Al (80)

The numerals in parentheses represent a film thickness (unit: nm).

The numerals (98%:2%) represented by percentage in the same parentheses indicate a ratio (mass %) between the host material (compound BH1-29 or BH2) and the compound BD1 in the first emitting layer or the second emitting layer. Similar notations apply to the description below.

second emitting layer, and the first compound (first host material) in the first emitting layer was replaced by the first compound shown in Table 18.

Comparative Example 72

The organic EL device of Comparative Example 72 was manufactured in the same manner as that of Example 79 except that a 25-nm-thick second emitting layer was formed on the second hole transporting layer without forming the first emitting layer as shown in Table 18.

TABLE 18

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 79 | BH1-29 | BD1 | 5 | BH2 | BD1 | 20 | 9.3 | 125 |
| Example 80 | BH1-30 | BD1 | 5 | BH2 | BD1 | 20 | 9.3 | 103 |
| Example 81 | BH1-31 | BD1 | 5 | BH2 | BD1 | 20 | 9.6 | 119 |
| Example 82 | BH1-38 | BD1 | 5 | BH2 | BD1 | 20 | 9.8 | 138 |
| Example 83 | BH1-39 | BD1 | 5 | BH2 | BD1 | 20 | 9.7 | 122 |
| Example 84 | BH1-52 | BD1 | 5 | BH2 | BD1 | 20 | 9.5 | 151 |
| Example 85 | BH1-53 | BD1 | 5 | BH2 | BD1 | 20 | 9.3 | 132 |
| Example 86 | BH1-54 | BD1 | 5 | BH2 | BD1 | 20 | 9.1 | 110 |
| Example 87 | BH1-55 | BD1 | 5 | BH2 | BD1 | 20 | 9.4 | 109 |
| Example 88 | BH1-56 | BD1 | 5 | BH2 | BD1 | 20 | 9.2 | 111 |
| Example 89 | BH1-57 | BD1 | 5 | BH2 | BD1 | 20 | 9.2 | 121 |
| Example 90 | R-BH3 | BD1 | 5 | BH2 | BD1 | 20 | 8.3 | 97 |
| Comparative Ex. 61 | BH1-29 | BD1 | 25 | — | — | — | 6.7 | 61 |
| Comparative Ex. 62 | BH1-30 | BD1 | 25 | — | — | — | 6.9 | 53 |
| Comparative Ex. 63 | BH1-31 | BD1 | 25 | — | — | — | 6.4 | 51 |
| Comparative Ex. 64 | BH1-38 | BD1 | 25 | — | — | — | 6.1 | 48 |
| Comparative Ex. 65 | BH1-39 | BD1 | 25 | — | — | — | 6.1 | 45 |
| Comparative Ex. 66 | BH1-52 | BD1 | 25 | — | — | — | 6.8 | 62 |
| Comparative Ex. 67 | BH1-53 | BD1 | 25 | — | — | — | 6.8 | 54 |
| Comparative Ex. 68 | BH1-54 | BD1 | 25 | — | — | — | 6.7 | 42 |
| Comparative Ex. 69 | BH1-55 | BD1 | 25 | — | — | — | 6.7 | 59 |
| Comparative Ex. 70 | BH1-56 | BD1 | 25 | — | — | — | 6.5 | 40 |
| Comparative Ex. 71 | BH1-57 | BD1 | 25 | — | — | — | 6.2 | 34 |
| Comparative Ex. 72 | — | — | — | BH2 | BD1 | 25 | 8.1 | 89 |

Examples 80 to 90

The organic EL devices of Comparative Examples 80 to 90 were manufactured in the same manner as that of Example 79 except that the compound BH1-2 (first host material) in the first emitting layer was replaced with the first compounds shown in Table 18.

Comparative Examples 61 to 71

Organic EL devices of Comparative Examples 61 to 71 were manufactured in the same manner as that of Example 79 except that a 25-nm thick first emitting layer was formed as the emitting layer, the first electron transporting layer was formed on the first emitting layer without forming the Manufacture 4 of Organic EL Device Organic EL devices were manufactured and evaluated as follows.

Example 91

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratios of the compound HT5 and the compound HA2 in the hole injecting layer were 97 mass % and 3 mass %, respectively.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-61 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

The compound ET6 and the compound Liq were co-deposited on the first electron transporting layer (HBL) to form a 25-nm-thick electron transporting layer (ET). The ratios of the compound ET6 and the compound Liq in the electron transporting layer (ET) were 50 mass % and 50 mass %, respectively. Liq is an abbreviation of (8-quinolinolato)lithium.

Liq was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 91 is roughly shown as follows.

ITO(130)/HT5:HA2(10.97%:3%)/HT5(85)/HT4(5)/BH1-61:BD1(5.98%:2%)/BH2:BD1(20.98%:2%)/ET3(5)/ET6:Liq(25, 50%:50%)/Liq(1)/Al(80)

The numerals in parentheses represent a film thickness (unit: nm).

The numerals (97%:3%) represented by percentage in the same parentheses indicate a ratio (mass %) between the compound HT5 and the compound HA2 in the hole injecting layer, the numerals (98%:2%) represented by percentage in the same parentheses indicate a ratio (mass %) between the host material (compound BH1-61 or BH2) and the dopant material (compound BD1) in the first emitting layer or the second emitting layer, and the numerals (50%:50%) represented by percentage in the same parentheses indicate a ratio (mass %) between the compound ET6 and the compound Liq in the electron transporting layer (ET). Similar notations apply to the description below.

Examples 92 to 95

The organic EL device of Examples 92 to 95 were manufactured in the same manner as that of Example 91 except that the compound BH1-61 (first host material) in the first emitting layer was replaced with the first compounds shown in Table 19.

Comparative Examples 73 to 76

The organic EL devices of Comparative Examples 73 to 76 were manufactured in the same manner as that of Example 91 except that a 25-nm-thick first emitting layer was formed as the emitting layer, the first electron transporting layer was formed on the first emitting layer without forming the second emitting layer, and the first compound (first host material) in the first emitting layer was replaced with the first compounds shown in Table 19.

Comparative Example 77

The organic EL device of Comparative Example 77 was manufactured in the same manner as that of Example 91 except that a 25-nm-thick second emitting layer was formed on the second hole transporting layer without forming the first emitting layer as shown in Table 19.

TABLE 19

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 91 | BH1-61 | BD1 | 5 | BH2 | BD1 | 20 | 9.2 | 128 |
| Example 92 | BH1-62 | BD1 | 5 | BH2 | BD1 | 20 | 9.7 | 153 |
| Example 93 | BH1-63 | BD1 | 5 | BH2 | BD1 | 20 | 9.5 | 144 |
| Example 94 | BH1-69 | BD1 | 5 | BH2 | BD1 | 20 | 9.0 | 110 |
| Example 95 | R-BH3 | BD1 | 5 | BH2 | BD1 | 20 | 8.8 | 101 |
| Comparative Ex. 73 | BH1-61 | BD1 | 25 | — | — | — | 6.1 | 47 |
| Comparative Ex. 74 | BH1-62 | BD1 | 25 | — | — | — | 6.4 | 64 |
| Comparative Ex. 75 | BH1-63 | BD1 | 25 | — | — | — | 6.3 | 60 |
| Comparative Ex. 76 | BH1-69 | BD1 | 25 | — | — | — | 5.9 | 19 |
| Comparative Ex. 77 | — | — | — | BH2 | BD1 | 25 | 8.4 | 72 |

Manufacture 5 of Organic EL Device

Organic EL devices were manufactured and evaluated as follows.

Example 96

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT3 and the compound HA2 were co-deposited on a surface provided with the transparent electrode line to cover the transparent electrode, thereby forming a 10-nm-thick hole injecting layer (HI). The ratios of the compound HT3 and the compound HA2 in the hole injecting layer were 97 mass % and 3 mass %, respectively.

After the formation of the hole injecting layer, the compound HT3 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-75 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

The compound ET8 and the compound Liq were co-deposited on the first electron transporting layer (HBL) to form a 25-nm-thick electron transporting layer (ET). The ratios of the compound ET5 and the compound Liq in the electron transporting layer (ET) were 50 mass % and 50 mass %, respectively. Liq is an abbreviation of (8-quinolinolato)lithium.

Liq was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 96 is roughly shown as follows.

ITO(130)/HT3:HA2(10.97%:3%)/HT3(85)/HT4(5)/BH1-75:BD1(5.98%:2%)/BH2:BD1(20.98%:2%)/ET3(5)/ET8:Liq(25, 50%:50%)/Liq(1)/Al(80)

The numerals in parentheses represent a film thickness (unit: nm).

The numerals (97%:3%) represented by percentage in the same parentheses indicate a ratio (mass %) between the compound HT3 and the compound HA2 in the hole injecting layer, the numerals (98%:2%) represented by percentage in the same parentheses indicate a ratio (mass %) between the host material (compound BH1-75 or BH2) and the dopant material (compound BD1) in the first emitting layer or the second emitting layer, and the numerals (50%:50%) represented by percentage in the same parentheses indicate a ratio (mass %) between the compound ET8 and the compound Liq in the electron transporting layer (ET). Similar notations apply to the description below.

Example 97

The organic EL device of Example 97 was manufactured in the same manner as that of Example 96 except that the compound BH1-75 (first host material) in the first emitting layer was replaced with the first compound shown in Table 20.

Comparative Example 78

The organic EL device of Comparative Example 78 was manufactured in the same manner as that of Example 96 except that a 25-nm-thick first emitting layer was formed as the emitting layer, the first electron transporting layer was formed on the first emitting layer without forming the second emitting layer, and the first compound (first host material) in the first emitting layer was replaced with the first compound shown in Table 20.

Comparative Example 79

The organic EL device of Comparative Example 79 was manufactured in the same manner as that of Example 96 except that a 25-nm-thick second emitting layer was formed on the second hole transporting layer without forming the first emitting layer as shown in Table 20.

TABLE 20

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 96 | BH1-75 | BD1 | 5 | BH2 | BD1 | 20 | 9.2 | 169 |
| Example 97 | R-BH3 | BD1 | 5 | BH2 | BD1 | 20 | — | 118 |
| Comparative Ex. 78 | BH1-75 | BD1 | 25 | — | — | — | 6.0 | 63 |
| Comparative Ex. 79 | — | — | — | BH2 | BD1 | 25 | 8.1 | 91 |

Manufacture 6 of Organic EL Device

Organic EL devices were manufactured and evaluated as follows.

Example 98

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratios of the compound HT5 and the compound HA2 in the hole injecting layer were 97 mass % and 3 mass %, respectively.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-64 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

The compound ET8 and the compound Liq were co-deposited on the first electron transporting layer (HBL) to form a 25-nm-thick electron transporting layer (ET). The ratios of the compound ET8 and the compound Liq in the electron transporting layer (ET) were 50 mass % and 50 mass %, respectively.

Liq was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 98 is roughly shown as follows.

ITO(130)/HT5:HA2(10.97%:3%)/HT5(85)/HT4(5)/BH1-64:BD1(5.98%:2%)/BH2:BD1(20.98%:2%)/ET3(5)/ET8:Liq(25, 50%:50%)/Liq(1)/Al(80)

The numerals in parentheses represent a film thickness (unit: nm).

The numerals (97%:3%) represented by percentage in the same parentheses indicate a ratio (mass %) between the compound HT5 and the compound HA2 in the hole injecting layer, the numerals (98%:2%) represented by percentage in the same parentheses indicate a ratio (mass %) between the host material (compound BH1-64 or BH2) and the dopant material (compound BD1) in the first emitting layer or the second emitting layer, and the numerals (50%:50%) represented by percentage in the same parentheses indicate a ratio (mass %) between the compound ET8 and the compound Liq in the electron transporting layer (ET). Similar notations apply to the description below.

Examples 99 to 103

The organic EL devices of Examples 99 to 103 were manufactured in the same manner as that of Example 98 except that the compound BH1-6 (first host material) in the first emitting layer was replaced with the first compounds shown in Table 21.

Comparative Examples 80 to 84

The organic EL devices of Comparative Examples 80 to 84 were manufactured in the same manner as that of Example 98 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 21.

Comparative Example 85

The organic EL device according to Comparative Example 85 was manufactured in the same manner as that of Example 98 except that a 25-nm-thick second emitting layer was formed on the second hole transporting layer without forming the first emitting layer as shown in Table 21.

TABLE 21

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 98 | BH1-64 | BD1 | 5 | BH2 | BD1 | 20 | 9.6 | 106 |
| Example 99 | BH1-65 | BD1 | 5 | BH2 | BD1 | 20 | 9.7 | 112 |
| Example 100 | BH1-66 | BD1 | 5 | BH2 | BD1 | 20 | 9.5 | 83 |
| Example 101 | BH1-67 | BD1 | 5 | BH2 | BD1 | 20 | 9.4 | 93 |
| Example 102 | BH1-68 | BD1 | 5 | BH2 | BD1 | 20 | 9.5 | 101 |
| Example 103 | R-BH3 | BD1 | 5 | BH2 | BD1 | 20 | 9.1 | — |
| Comparative Ex. 80 | BH1-64 | BD1 | 25 | — | — | — | 6.1 | 31 |
| Comparative Ex. 81 | BH1-65 | BD1 | 25 | — | — | — | 6.3 | 48 |
| Comparative Ex. 82 | BH1-66 | BD1 | 25 | — | — | — | 6.1 | 31 |

TABLE 21-continued

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comparative Ex. 83 | BH1-67 | BD1 | 25 | — | — | — | 6.3 | 55 |
| Comparative Ex. 84 | BH1-68 | BD1 | 25 | — | — | — | 6.0 | 28 |
| Comparative Ex. 85 | — | — | — | BH2 | BD1 | 25 | 8.6 | 61 |

Manufacture 7 of Organic EL Device

Organic EL devices were manufactured and evaluated as follows.

Example 104

A glass substrate (size: 25 mm×75 mm×1.1 mm thick, manufactured by Geomatec Go., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratios of the compound HT5 and the compound HA2 in the hole injecting layer were 97 mass % and 3 mass %, respectively.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-70 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 5-nm-thick first electron transporting layer (also referred to as a hole blocking layer (HBL)).

The compound ET6 and the compound Liq were co-deposited on the first electron transporting layer (HBL) to form a 25-nm-thick electron transporting layer (ET). The ratios of the compound ET6 and the compound Liq in the electron transporting layer (ET) were 50 mass % and 50 mass %, respectively.

Liq was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 104 is roughly shown as follows.

ITO(130)/HT5:HA2(10.97%:3%)/HT5(85)/HT4(5)/BH1-70:BD1(5.98%:2%)/BH2:BD1(20.98%:2%)/ET1(5)/ET6:Liq(25, 50%:50%)/Liq(1)/Al(80)

The numerals in parentheses represent a film thickness (unit: nm).

The numerals (97%:3%) represented by percentage in the same parentheses indicate a ratio (mass %) between the compound HT5 and the compound HA2 in the hole injecting layer, the numerals (98%:2%) represented by percentage in the same parentheses indicate a ratio (mass %) between the host material (compound BH1-70 or BH2) and the dopant material (compound BD1) in the first emitting layer or the second emitting layer, and the numerals (50%:50%) represented by percentage in the same parentheses indicate a ratio (mass %) between the compound ET6 and the compound Liq in the electron transporting layer (ET). Similar notations apply to the description below.

Examples 105 to 109

The organic EL devices of Examples 105 to 109 were manufactured in the same manner as that of Example 104 except that the compound BH1-70 (first host material) in the first emitting layer was replaced with the first compounds shown in in Table 70.

Comparative Examples 86 to 90

The organic EL devices of Comparative Examples 86 to 90 were manufactured in the same manner as that of Example 104 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 22.

Comparative Example 91

The organic EL device of Comparative Example 91 was manufactured in the same manner as that of Example 104 except that a 25-nm-thick second emitting layer was formed on the second hole transporting layer without forming the first emitting layer shown in Table 104.

TABLE 22

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 104 | BH1-70 | BD1 | 5 | BH2 | BD1 | 20 | 10.2 | 185 |
| Example 105 | BH1-71 | BD1 | 5 | BH2 | BD1 | 20 | 10.7 | 223 |
| Example 106 | BH1-72 | BD1 | 5 | BH2 | BD1 | 20 | 10.4 | 212 |
| Example 107 | BH1-73 | BD1 | 5 | BH2 | BD1 | 20 | 10.6 | 220 |
| Example 108 | BH1-74 | BD1 | 5 | BH2 | BD1 | 20 | 10.3 | 218 |
| Example 109 | R-BH3 | BD1 | 5 | BH2 | BD1 | 20 | 8.7 | 101 |
| Comparative Ex. 86 | BH1-70 | BD1 | 25 | — | — | — | 6.2 | 59 |
| Comparative Ex. 87 | BH1-71 | BD1 | 25 | — | — | — | 6.6 | 63 |
| Comparative Ex. 88 | BH1-72 | BD1 | 25 | — | — | — | 6.5 | 51 |
| Comparative Ex. 89 | BH1-73 | BD1 | 25 | — | — | — | 6.5 | 62 |
| Comparative Ex. 90 | BH1-74 | BD1 | 25 | — | — | — | 6.4 | 60 |
| Comparative Ex. 91 | — | — | — | BH2 | BD1 | 25 | 8.3 | 76 |

Manufacture 8 of Organic EL Device

Example 110

A glass substrate (size: 25 mm×75 mm×1.1 mm thick, manufactured by Geomatec Go., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, a compound HT8 was vapor-deposited to form a 10-nm-thick second hole transporting layer (also referred to as an electron blocking layer (EBL)).

A compound BH1-81 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 110 is roughly shown as follows.

ITO(130)/HA1(5)/HT1(80)/HT8(10)/BH1-81:BD1(5.98%:2%)/BH2:BD1(20.98%:2%)/ET1(10)/ET2(15)/LiF(1)/Al(80)

The numerals in parentheses represent a film thickness (unit: nm).

The numerals (98%:2%) represented by percentage in the same parentheses indicate a ratio (mass %) between the host material (compound BH1-81 or BH2) and the compound BD1 in the first emitting layer or the second emitting layer. Similar notations apply to the description below.

Example 111

The organic EL device of Example 111 was manufactured in the same manner as that of Example 110 except that the compound BH1-81 (first host material) in the first emitting layer was replaced with the first compound shown in Table 23.

Comparative Example 92

The organic EL device of Comparative Example 92 was manufactured in the same manner as that of Example 110 except that a 25-nm-thick first emitting layer was formed as the emitting layer and the first electron transporting layer was formed on the first emitting layer without forming the second emitting layer.

Comparative Example 93

The organic EL device of Comparative Example 93 was manufactured in the same manner as that of Example 110 except that a 25-nm-thick second emitting layer was formed on the second hole transporting layer without forming the first emitting layer as shown in Table 23.

TABLE 23

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 110 | BH1-81 | BD1 | 5 | BH2 | BD1 | 20 | 10.7 | 134 |
| Example 111 | R-BH3 | BD1 | 5 | BH2 | BD1 | 20 | 10.4 | — |
| Comparative Ex. 92 | BH1-81 | BD1 | 25 | — | — | — | 6.4 | 35 |
| Comparative Ex. 93 | — | — | — | BH2 | BD1 | 25 | 10.2 | 102 |

Manufacture 9 of Organic EL Device

Examples 112 and 113

The organic EL devices of Examples 112 and 113 were manufactured in the same manner as that of Example 1 except that the compound BH1 (first host material) in the first emitting layer was replaced with the compounds shown in Table 24.

Comparative Example 94

The organic EL device of Comparative Example 94 was manufactured in the same manner as that of Comparative Example 1 except that the compound BH1 (first host material) in the first emitting layer was replaced with the compound shown in Table 24.

TABLE 24

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 112 | BH1-82 | BD1 | 5 | BH2 | BD1 | 20 | 10.4 | 219 |
| Example 113 | R-BH3 | BD1 | 5 | BH2 | BD1 | 20 | 10.1 | 183 |
| Comparative Ex. 94 | BH1-82 | BD1 | 25 | — | — | — | 6.2 | 71 |
| Comparative Ex. 2 | — | — | — | BH2 | BD1 | 25 | 9.9 | 167 |

Manufacture 10 of Organic EL Device

Example 114

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound BH1-83 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 114 is roughly shown as follows.

ITO(130)/HA1(5)/HT1(80)/HT2(10)/BH1-83:BD1(5.98%:2%)/BH2:BD1(20.98%:2%)/ET7(10)/ET2(15)/LiF(1)/Al (80)

The numerals in parentheses represent a film thickness (unit: nm).

The numerals (98%:2%) represented by percentage in the same parentheses indicate a ratio (mass %) between the host material (compound BH1-83 or BH2) and the compound BD1 in the first emitting layer or the second emitting layer. Similar notations apply to the description below.

Example 115

The organic EL device of Example 115 was manufactured in the same manner as that of Example 114 except that the compound BH1-83 (first host material) in the first emitting layer was replaced with the first compound shown in Table 25.

Comparative Example 95

The organic EL device of Comparative Example 95 was manufactured in the same manner as that of Example 114 except that a 25-nm-thick first emitting layer was formed as the emitting layer and the first electron transporting layer was formed on the first emitting layer without forming the second emitting layer.

Comparative Example 96

The organic EL device of Comparative Example 96 was manufactured in the same manner as that of Example 114 except that a 25-nm-thick second emitting layer was formed on the second hole transporting layer without forming the first emitting layer as shown in Table 25.

TABLE 25

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Example 114 | BH1-83 | BD1 | 5 | BH2 | BD1 | 20 | 9.7 | 247 |
| Example 115 | R-BH3 | BD1 | 5 | BH2 | BD1 | 20 | 8.5 | — |
| Comparative Ex. 95 | BH1-83 | BD1 | 25 | — | — | — | 6.0 | 76 |
| Comparative Ex. 96 | — | — | — | BH2 | BD1 | 25 | 9.1 | 183 |

Manufacture 11 of Organic EL Device

Example 116

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 116 is roughly shown as follows.

ITO(130)/HA1(5)/HT1(80)/HT4(10)/BH1:BD1(5.98%: 2%)/BH2-8:BD1(20.98%:2%)/ET1(10)/ET2(20)/LiF(1)/Al (80)

The numerals in parentheses represent a film thickness (unit: nm).

The numerals (98%:2%) represented by percentage in the same parentheses indicate a ratio (mass %) between the host material (compound BH1) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Example 117

The organic EL device of Example 117 was manufactured in the same manner as that of Example 116 except that the compound BH2-8 (second host material) in the second emitting layer was replaced with the second compound shown in Table 26.

Comparative Example 97

The organic EL device of Comparative Example 97 was manufactured in the same manner as that of Example 116 except that a 25-nm-thick second emitting layer was formed on the second hole transporting layer without forming the first emitting layer, and the second compound (second host material) in the second emitting layer was replaced with the second compound shown in Table 26, as shown in Table 26.

TABLE 26

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 116 | BH1 | BD1 | 5 | BH2-8 | BD1 | 20 | 3.4 | 9.8 | 120 |
| Example 117 | BH1 | BD1 | 5 | BH2-5 | BD1 | 20 | 3.6 | 10.1 | 160 |
| Comparative Ex. 97 | — | — | — | BH2-5 | BD1 | 25 | 3.8 | 8.9 | 110 |

Manufacture 12 of Organic EL Device

Examples 118 and 119

The organic EL devices of Examples 118 and 119 were manufactured in the same manner as that of Example 116 except that the compound BH2-8 (second host material) in the second emitting layer was replaced with the second compounds shown in Table 27.

Comparative Example 98

The organic EL device of Comparative Example 98 was manufactured in the same manner as that of Example 116 except that a 25-nm-thick second emitting layer was formed on the second hole transporting layer without forming the first emitting layer, and the second compound (second host material) in the second emitting layer was replaced with the second compound shown in Table 27.

TABLE 27

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 118 | BH1 | BD1 | 5 | BH2-2 | BD1 | 20 | 3.8 | 10.5 | 200 |
| Example 119 | BH1 | BD1 | 5 | BH2-10 | BD1 | 20 | 3.8 | 10.5 | 240 |
| Comparative Ex. 98 | — | — | — | BH2-10 | BD1 | 25 | 4.0 | 9.8 | 140 |

Example 120

The organic EL device of Example 120 was manufactured in the same manner as that of Example 116 except that the compound BH2-8 (second host material) in the second emitting layer was replaced with the second compound shown in Table 28.

Comparative Example 99

The organic EL device of Comparative Example 99 was manufactured in the same manner as that of Example 116 except that a 25-nm-thick second emitting layer was formed on the second hole transporting layer without forming the first emitting layer, and the second compound (second host material) in the second emitting layer was replaced with the second compound shown in Table 28, as shown in Table 28.

TABLE 28

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 116 | BH1 | BD1 | 5 | BH2-8 | BD1 | 20 | 3.4 | 9.8 | 120 |
| Example 120 | BH1 | BD1 | 5 | BH2-11 | BD1 | 20 | 3.4 | 9.8 | 150 |
| Comparative Ex. 99 | — | — | — | BH2-11 | BD1 | 25 | 3.6 | 7.5 | 100 |

Manufacture 13 of Organic EL Device

Example 121

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

The compound BH1 (first host material (BH)) and a compound BD2 (dopant material (BD)) were co-deposited on the second hole transporting layer such that the ratio of the compound BD2 accounted for 2 mass %, thereby forming a 5-nm-thick first emitting layer.

The compound BH2-2 (second host material (BH)) and the compound BD2 (dopant material (BD)) were co-deposited on the first emitting layer such that the ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 121 is roughly shown as follows.

ITO(130)/HA1(5)/HT3(80)/HT4(10)/BH1:BD2(5.98%:2%)/BH2-2:BD2(20.98%:2%)/ET7(10)/ET2(20)/LiF(1)/Al (80)

The numerals in parentheses represent a film thickness (unit: nm).

The numerals (98%:2%) represented by percentage in the same parentheses indicate a ratio (mass %) between the host material (compound BH1) and the compound BD2 in the first emitting layer, and numerals (98%:2%) represented by percentage in the same parentheses indicate a ratio (mass %) between the host material (compound BH2-2) and the compound BD2 in the second emitting layer. Similar notations apply to the description below.

Example 122

The organic EL device of Example 122 was manufactured in the same manner as that of Example 121 except that the compound BH2-2 (second host material) in the second emitting layer was replaced with the second compound shown in Table 29.

Comparative Example 100

The organic EL device of Comparative Example 100 was manufactured in the same manner as that of Example 121 except that a 25-nm-thick second emitting layer was formed on the second hole transporting layer without forming the first emitting layer, and the second compound (second host material) in the second emitting layer was replaced with the second compound shown in Table 29, as shown in Table 29.

TABLE 29

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 121 | BH1 | BD2 | 5 | BH2-2 | BD2 | 20 | 3.8 | 10.1 | 180 |
| Example 122 | BH1 | BD2 | 5 | BH2-12 | BD2 | 20 | 4.0 | 10.3 | 200 |
| Comparative Ex. 100 | — | — | — | BH2-12 | BD2 | 25 | 4.2 | 8.8 | 110 |

Manufacture 14 of Organic EL Device

Example 123

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT5 was vapor-deposited to form an 80-nm-thick first hole transporting layer (HT).

After the formation of the first hole transporting layer, a compound HT6 was vapor-deposited to form a 10-nm-thick second hole transporting layer (also referred to as an electron blocking layer (EBL)).

A compound BH1-10 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

The compound BH2-2 (second host material (BH)) and the compound BD2 (dopant material (BD)) were co-deposited on the first emitting layer such that the ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 123 is roughly shown as follows.

ITO(130)/HA1(5)/HT5(80)/HT6(10)/BH1-10:BD2(5.98%:2%)/BH2-2:BD2(20.98%:2%)/ET7(10)/ET2(20)/LiF(1)/Al(80)

The numerals in parentheses represent a film thickness (unit: nm).

The numerals (98%:2%) represented by percentage in the same parentheses indicate a ratio (mass %) between the host material (compound BH1-10) and the compound BD2 in the first emitting layer, and numerals (98%:2%) represented by percentage in the same parentheses indicate a ratio (mass %) between the host material (compound BH2-2) and the compound BD2 in the second emitting layer. Similar notations apply to the description below.

Example 124

The organic EL device of Example 124 was manufactured in the same manner as that of Example 123 except that the compound BH2-2 (second host material) in the second emitting layer was replaced with the second compound shown in Table 30.

Comparative Example 101

The organic EL device of Comparative Example 101 was manufactured in the same manner as that of Example 123 except that a 25-nm-thick second emitting layer was formed on the second hole transporting layer without forming the first emitting layer, and the second compound (second host material) in the second emitting layer was replaced with the second compound shown in Table 30, as shown in Table 30.

TABLE 30

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 123 | BH1-10 | BD2 | 5 | BH2-2 | BD2 | 20 | 3.9 | 10.0 | 210 |
| Example 124 | BH1-10 | BD2 | 5 | BH2-13 | BD2 | 20 | 3.8 | 10.3 | 190 |
| Comparative Ex. 101 | — | — | — | BH2-13 | BD2 | 25 | 4.1 | 9.2 | 110 |

Manufacture 15 of Organic EL Device

Example 125

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT7 was vapor-deposited to form a 10-nm-thick second hole transporting layer (also referred to as an electron blocking layer (EBL)).

The compound BH1-10 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 125 is roughly shown as follows.

ITO(130)/HA1(5)/HT3(80)/HT7(10)/BH1-10:BD1(5.98%:2%)/BH2-2:BD1(20.98%:2%)/ET7(10)/ET2(20)/LiF(1)/Al(80)

The numerals in parentheses represent a film thickness (unit: nm).

The numerals (98%:2%) represented by percentage in the same parentheses indicate a ratio (mass %) between the host material (compound BH1-10) and the compound BD1 in the first emitting layer, and numerals (98%:2%) represented by percentage in the same parentheses indicate a ratio (mass %) between the host material (compound BH2-2) and the compound BD1 in the second emitting layer. Similar notations apply to the description below.

Example 126

The organic EL device of Example 126 was manufactured in the same manner as that of Example 125 except that the compound BH2-2 (second host material) in the second emitting layer was replaced with the second compound shown in Table 31.

Comparative Example 102

The organic EL device of Comparative Example 102 was manufactured in the same manner as that of Example 125 except that a 25-nm-thick second emitting layer was formed on the second hole transporting layer without forming the first emitting layer, and the second compound (second host material) in the second emitting layer was replaced with the second compound shown in Table 31, as shown in Table 31.

TABLE 31

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 125 | BH1-10 | BD1 | 5 | BH2-2 | BD1 | 20 | 4.0 | 10.5 | 150 |
| Example 126 | BH1-10 | BD1 | 5 | BH2-14 | BD1 | 20 | 4.0 | 10.8 | 160 |
| Comparative Ex. 102 | — | — | — | BH2-14 | BD1 | 25 | 4.2 | 9.5 | 100 |

Example 127

The organic EL device of Example 127 was manufactured in the same manner as that of Example 125 except that the compound BH2-2 (second host material) in the second emitting layer was replaced with the second compound shown in Table 32.

Comparative Example 103

The organic EL device of Comparative Example 103 was manufactured in the same manner as that of Example 125 except that a 25-nm-thick second emitting layer was formed on the second hole transporting layer without forming the first emitting layer, and the second compound (second host material) in the second emitting layer was replaced with the second compound shown in Table 32, as shown in Table 32.

TABLE 32

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 125 | BH1-10 | BD1 | 5 | BH2-2 | BD1 | 20 | 4.0 | 10.5 | 150 |
| Example 127 | BH1-10 | BD1 | 5 | BH2-15 | BD1 | 20 | 3.9 | 10.3 | 180 |
| Comparative Ex. 103 | — | — | — | BH2-15 | BD1 | 25 | 4.0 | 9.2 | 80 |

Example 128

The organic EL device of Example 128 was manufactured in the same manner as that of Example 125 except that the compound BH2-2 (second host material) in the second emitting layer was replaced with the second compound shown in Table 33.

Comparative Example 104

The organic EL device of Comparative Example 104 was manufactured in the same manner as that of Example 125 except that a 25-nm-thick second emitting layer was formed on the second hole transporting layer without forming the first emitting layer, and the second compound (second host material) in the second emitting layer was replaced with the second compound shown in Table 33, as shown in Table 33.

TABLE 33

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 125 | BH1-10 | BD1 | 5 | BH2-2 | BD1 | 20 | 4.0 | 10.5 | 150 |
| Example 128 | BH1-10 | BD1 | 5 | BH2-16 | BD1 | 20 | 3.8 | 10.5 | 170 |
| Comparative Ex. 104 | — | — | — | BH2-16 | BD1 | 25 | 4.1 | 9.5 | 70 |

Example 129

The organic EL device of Example 129 was manufactured in the same manner as that of Example 125 except that the compound BH2-2 (second host material) in the second emitting layer was replaced with the second compound shown in Table 34.

Comparative Example 105

The organic EL device of Comparative Example 105 was manufactured in the same manner as that of Example 125 except that a 25-nm-thick second emitting layer was formed on the second hole transporting layer without forming the first emitting layer, and the second compound (second host material) in the second emitting layer was replaced with the second compound shown in Table 34, as shown in Table 34.

TABLE 34

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 125 | BH1-10 | BD1 | 5 | BH2-2 | BD1 | 20 | 4.0 | 10.5 | 150 |
| Example 129 | BH1-10 | BD1 | 5 | BH2-17 | BD1 | 20 | 3.7 | 10.6 | 170 |
| Comparative Ex. 105 | — | — | — | BH2-17 | BD1 | 25 | 4.0 | 9.1 | 60 |

Manufacture 16 of Organic EL Device

Example 130

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT7 was vapor-deposited to form a 10-nm-thick second hole transporting layer (also referred to as an electron blocking layer (EBL)).

The compound BH1-10 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET5 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 130 is roughly shown as follows.

ITO(130)/HA1(5)/HT3(80)/HT7(10)/BH1-10:BD1(5.98%:2%)/BH2-8:BD1(20.98%:2%)/ET1(10)/ET5(20)/LiF(1)/Al(80)

The numerals in parentheses represent a film thickness (unit: nm).

The numerals (98%:2%) represented by percentage in the same parentheses indicate a ratio (mass %) between the host material (compound BH1-10) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Example 131

The organic EL device of Example 131 was manufactured in the same manner as that of Example 130 except that the compound BH2-8 (second host material) in the second emitting layer was replaced with the second compound shown in Table 35.

Comparative Example 106

The organic EL device of Comparative Example 106 was manufactured in the same manner as that of Example 130 except that a 25-nm-thick second emitting layer was formed on the second hole transporting layer without forming the first emitting layer, and the second compound (second host material) in the second emitting layer was replaced with the second compound shown in Table 35, as shown in Table 35.

TABLE 35

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 130 | BH1-10 | BD1 | 5 | BH2-8 | BD1 | 20 | 3.4 | 9.5 | 140 |
| Example 131 | BH1-10 | BD1 | 5 | BH2-18 | BD1 | 20 | 3.4 | 10.0 | 150 |
| Comparative Ex. 106 | — | — | — | BH2-18 | BD1 | 25 | 3.6 | 9.0 | 100 |

Example 132

The organic EL device of Example 132 was manufactured in the same manner as that of Example 130 except that the compound BH2-8 (second host material) in the second emitting layer was replaced with the second compound shown in Table 36.

Comparative Example 107

The organic EL device of Comparative Example 107 was manufactured in the same manner as that of Example 130 except that a 25-nm-thick second emitting layer was formed on the second hole transporting layer without forming the first emitting layer, and the second compound (second host material) in the second emitting layer was replaced with the second compound shown in Table 36, as shown in Table 36.

TABLE 36

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 130 | BH1-10 | BD1 | 5 | BH2-8 | BD1 | 20 | 3.4 | 9.5 | 140 |
| Example 132 | BH1-10 | BD1 | 5 | BH2-19 | BD1 | 20 | 3.5 | 10.3 | 140 |
| Comparative Ex. 107 | — | — | — | BH2-19 | BD1 | 25 | 3.6 | 9.2 | 80 |

Example 133

The organic EL device of Example 133 was manufactured in the same manner as that of Example 130 except that the compound BH2-8 (second host material) in the second emitting layer was replaced with the second compound shown in Table 37.

Comparative Example 108

The organic EL device of Comparative Example 108 was manufactured in the same manner as that of Example 130 except that a 25-nm-thick second emitting layer was formed on the second hole transporting layer without forming the first emitting layer, and the second compound (second host material) in the second emitting layer was replaced with the second compound shown in Table 37, as shown in Table 37.

TABLE 37

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 130 | BH1-10 | BD1 | 5 | BH2-8 | BD1 | 20 | 3.4 | 9.5 | 140 |
| Example 133 | BH1-10 | BD1 | 5 | BH2-20 | BD1 | 20 | 3.4 | 9.9 | 160 |
| Comparative Ex. 108 | — | — | — | BH2-20 | BD1 | 25 | 3.7 | 8.8 | 120 |

Manufacture 17 of Organic EL Device

Example 134

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET4 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 134 is roughly shown as follows.

ITO(130)/HA1(5)/HT1(80)/HT2(10)/BH1:BD1(5.98%:2%)/BH2-8:BD1(20.98%:2%)/ET4(10)/ET2(20)/LiF(1)/Al(80)

The numerals in parentheses represent a film thickness (unit: nm).

The numerals (98%:2%) represented by percentage in the same parentheses indicate a ratio (mass %) between the host material (compound BH1) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Example 135

The organic EL device of Example 135 was manufactured in the same manner as that of Example 134 except that the compound BH2-8 (second host material) in the second emitting layer was replaced with the second compound shown in Table 38.

Comparative Example 109

The organic EL device of Comparative Example 109 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 38, as shown in Table 38.

TABLE 38

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 135 | BH1 | BD1 | 5 | BH2-21 | BD1 | 20 | 3.3 | 9.6 | 130 |
| Comparative Ex. 109 | — | — | — | BH2-21 | BD1 | 25 | 3.5 | 8.5 | 80 |

Example 136

The organic EL device of Example 136 was manufactured in the same manner as that of Example 134 except that the compound BH2-8 (second host material) in the second emitting layer was replaced with the second compound shown in Table 39.

Comparative Example 110

The organic EL device of Comparative Example 110 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 39, as shown in Table 39.

TABLE 39

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 136 | BH1 | BD1 | 5 | BH2-22 | BD1 | 20 | 3.4 | 8.3 | 140 |
| Comparative Ex. 110 | — | — | — | BH2-22 | BD1 | 25 | 3.5 | 7.3 | 80 |

Example 137

The organic EL device of Example 137 was manufactured in the same manner as that of Example 134 except that the compound BH2-8 (second host material) in the second emitting layer was replaced with the second compound shown in Table 40.

Comparative Example 111

The organic EL device of Comparative Example 111 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 40, as shown in Table 40.

TABLE 40

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 137 | BH1 | BD1 | 5 | BH2-23 | BD1 | 20 | 3.3 | 8.8 | 130 |
| Comparative Ex. 111 | — | — | — | BH2-23 | BD1 | 25 | 3.4 | 8.0 | 80 |

Example 138

The organic EL device of Example 138 was manufactured in the same manner as that of Example 134 except that the compound BH2-8 (second host material) in the second emitting layer was replaced with the second compound shown in Table 41.

Comparative Example 112

The organic EL device of Comparative Example 112 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 41, as shown in Table 41.

TABLE 41

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 138 | BH1 | BD1 | 5 | BH2-24 | BD1 | 20 | 3.5 | 9.1 | 120 |
| Comparative Ex. 112 | — | — | — | BH2-24 | BD1 | 25 | 3.7 | 7.8 | 90 |

Example 139

The organic EL device of Example 139 was manufactured in the same manner as that of Example 134 except that the compound BH2-8 (second host material) in the second emitting layer was replaced with the second compound shown in Table 42.

Comparative Example 113

The organic EL device of Comparative Example 113 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 42, as shown in Table 42.

TABLE 42

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 139 | BH1 | BD1 | 5 | BH2-25 | BD1 | 20 | 3.4 | 9.4 | 130 |
| Comparative Ex. 113 | — | — | — | BH2-25 | BD1 | 25 | 3.4 | 7.1 | 70 |

Example 140

The organic EL device of Example 140 was manufactured in the same manner as that of Example 143 except that the compound BH2-8 (second host material) in the second emitting layer was replaced with the second compound shown in Table 43.

Comparative Example 114

The organic EL device of Comparative Example 114 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 43, as shown in Table 43.

TABLE 43

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 140 | BH1 | BD1 | 5 | BH2-26 | BD1 | 20 | 3.5 | 9.2 | 130 |
| Comparative Ex. 114 | — | — | — | BH2-26 | BD1 | 25 | 3.4 | 7.5 | 75 |

Example 141

The organic EL device of Example 141 was manufactured in the same manner as that of Example 134 except that the compound BH2-8 (second host material) in the second emitting layer was replaced with the second compound shown in Table 44.

Comparative Example 115

The organic EL device of Comparative Example 115 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 44, as shown in Table 44.

TABLE 44

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 141 | BH1 | BD1 | 5 | BH2-27 | BD1 | 20 | 3.2 | 9.1 | 130 |
| Comparative Ex. 115 | — | — | — | BH2-27 | BD1 | 25 | 3.5 | 7.2 | 80 |

Example 142

The organic EL device of Example 142 was manufactured in the same manner as that of Example 134 except that the compound BH2-8 (second host material) in the second emitting layer was replaced with the second compound shown in Table 45.

Comparative Example 116

The organic EL device of Comparative Example 116 was manufactured in the same manner as that of Example 134 except that a 25-nm-thick second emitting layer was formed on the second hole transporting layer without forming the first emitting layer, and the second compound (second host material) in the second emitting layer was replaced with the second compound shown in Table 45, as shown in Table 45.

TABLE 45

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 134 | BH1 | BD1 | 5 | BH2-8 | BD1 | 20 | 3.3 | 9.8 | 90 |
| Example 142 | BH1 | BD1 | 5 | BH2-28 | BD1 | 20 | 3.3 | 9.0 | 140 |
| Comparative Ex. 116 | — | — | — | BH2-28 | BD1 | 25 | 3.4 | 7.4 | 65 |

Manufacture 18 of Organic EL Device

Example 143

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 143 is roughly shown as follows.

ITO(130)/HA1(5)/HT1(80)/HT2(10)/BH1:BD1(5.98%:2%)/BH2-8:BD1(20.98%:2%)/ET7(10)/ET2(20)/LiF(1)/Al (80)

The numerals in parentheses represent a film thickness (unit: nm).

The numerals (98%:2%) represented by percentage in the same parentheses indicate a ratio (mass %) between the host material (compound BH1) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Example 144

The organic EL device of Example 144 was manufactured in the same manner as that of Example 143 except that the compound BH2-8 (second host material) in the second emitting layer was replaced with the second compound shown in Table 46.

Comparative Example 117

The organic EL device of Comparative Example 117 was manufactured in the same manner as that of Example 143 except that a 25-nm-thick second emitting layer was formed on the second hole transporting layer without forming the first emitting layer, and the second compound (second host material) in the second emitting layer was replaced with the second compound shown in Table 46, as shown in Table 46.

TABLE 46

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Example 143 | BH1 | BD1 | 5 | BH2-8 | BD1 | 20 | 3.5 | 9.0 | 120 |
| Example 144 | BH1 | BD1 | 5 | BH2-29 | BD1 | 20 | 4.0 | 10.1 | 80 |
| Comparative Ex. 117 | — | — | — | BH2-29 | BD1 | 25 | 4.5 | 8.2 | 40 |

Example 145

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound 1 BH-1 (first host material (BH)) and the compound BD1 (dopant material (BD)) were co-deposited on the second hole transporting layer so that a ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 145 is roughly shown as follows.

ITO(130)/HA1(5)/HT1(80)/HT2(10)/1BH-1:BD1 (5.98%:2%)/BH2:BD1 (20.98%:2%)/ET1(10)/ET2(15)/LiF(1)/Al (80)

The numerals in parentheses represent a film thickness (unit: nm).

The numerals (98%:2%) represented by percentage in the same parentheses indicate a ratio (mass %) between the host material (compound 1BH-1 or compound BH2) and the compound BD1 in the first emitting layer or the second emitting layer.

Comparative Example 118

The organic EL device of Comparative Example 118 was manufactured in the same manner as that of Example 145 except that a 25-nm-thick first emitting layer was formed as the emitting layer and the first electron transporting layer was formed on the first emitting layer without forming the second emitting layer, as shown in Table 47.

TABLE 47

| | First Emitting Layer | | | Second Emitting Layer | | | |
|---|---|---|---|---|---|---|---|
| | First Compound | Third Compound | Film Thickness [nm] | Second Compound | Fourth Compound | Film Thickness [nm] | EQE [%] |
| Example 145 | 1BH-1 | BD1 | 5 | BH2 | BD1 | 20 | 10.5 |
| Comparative Ex. 118 | 1BH-1 | BD1 | 25 | — | — | — | 7.5 |
| Comparative Ex. 2 | — | — | — | BH2 | BD1 | 25 | 9.9 |

Manufacture 19 of Organic EL Device

Organic EL devices were manufactured and evaluated as follows.

Example 146

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound BH3-1 (first host material (BH)) and the compound BD2 (dopant material (BD)) were co-deposited on the second hole transporting layer so that a ratio of the compound BD2 accounted for 2 mass %, thereby forming a 5-nm-thick first emitting layer.

A compound BH3-2 (second host material (BH)) and the compound BD2 (dopant material (BD)) were co-deposited on the first emitting layer so that a ratio of the compound BD2 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 146 is roughly shown as follows.

ITO(130)/HA1(5)/HT1(80)/HT2(10)/BH3-1:BD2 (5.98%:2%)/BH3-2:BD2 (20.98%:2%)/ET1(10)/ET2(15)/LiF(1)/Al (80)

The numerals in parentheses represent a film thickness (unit: nm).

The numerals (98%:2%) represented by percentage in the same parentheses indicate a ratio (mass %) between the host material (compound BH3-1 or compound BH3-2) and the compound BD2 in the first emitting layer or the second emitting layer.

Comparative Example 119

The organic EL device of Comparative Example 119 was manufactured in the same manner as that of Example 146 except that a 25-nm-thick first emitting layer was formed as the emitting layer and the first electron transporting layer was formed on the first emitting layer without forming the second emitting layer, as shown in Table 48.

Comparative Example 120

The organic EL device of Comparative Example 120 was manufactured in the same manner as that of Example 146 except that a 25-nm-thick second emitting layer was formed as the emitting layer on the second hole transporting layer without forming the first emitting layer as shown in Table 48.

TABLE 48

| | First Emitting Layer | | | | Second Emitting Layer | | | | | | |
|---|---|---|---|---|---|---|---|---|---|---|---|
| | First Compound | | Third Compound | Film Thickness | Second Compound | | Fourth Compound | Film Thickness | Drive Voltage | EQE | LT95 |
| | Name | $T_1$ [ev] | Name | [nm] | Name | $T_1$ [ev] | Name | [nm] | [V] | [%] | [h] |
| Example 146 | BH3-1 | 2.11 | BD2 | 5 | BH3-2 | 2.08 | BD2 | 20 | 3.4 | 9.5 | 200 |
| Comparative Ex. 119 | BH3-1 | 2.11 | BD2 | 25 | — | — | — | — | 3.8 | 8.2 | 92 |
| Comparative Ex. 120 | — | — | — | — | BH3-2 | 2.08 | BD2 | 25 | 3.4 | 7.1 | 125 |

Example 147

The organic EL device of Example 147 was manufactured in the same manner as that of Example 146 except that the compound BH3-1 (first host material) in the first emitting layer was replaced with the first compound shown in Table 49.

Comparative Example 121

The organic EL device of Comparative Example 121 was manufactured in the same manner as that of Comparative Example 119 except that the compound BH3-1 (first host material) in the first emitting layer was replaced with the first compound shown in Table 49.

TABLE 49

| | First Emitting Layer | | | | Second Emitting Layer | | | | | | |
|---|---|---|---|---|---|---|---|---|---|---|---|
| | First Compound | | Third Compound | Film Thickness | Second Compound | | Fourth Compound | Film Thickness | Drive Voltage | EQE | LT95 |
| | Name | $T_1$ [ev] | Name | [nm] | Name | $T_1$ [ev] | Name | [nm] | [V] | [%] | [h] |
| Example 147 | BH3-3 | 2.23 | BD2 | 5 | BH3-2 | 2.08 | BD2 | 20 | 3.5 | 9.1 | 230 |
| Comparative Ex. 121 | BH3-3 | 2.23 | BD2 | 25 | — | — | — | — | 3.6 | 6.8 | 52 |
| Comparative Ex. 120 | — | — | — | — | BH3-2 | 2.08 | BD2 | 25 | 3.4 | 7.1 | 125 |

Example 148

The organic EL device of Example 148 was manufactured in the same manner as that of Example 146 except that the compound BH3-1 (first host material) in the first emitting layer and the compound BH3-2 in the second emitting layer were respectively replaced with the first compound and the second compound shown in Table 50.

TABLE 50

| | First Emitting Layer | | | | Second Emitting Layer | | | | | |
|---|---|---|---|---|---|---|---|---|---|---|
| | First Compound | | Third | Film | Second Compound | | Fourth | Film | Drive | |
| | Name | $T_1$ [ev] | Compound Name | Thickness [nm] | Name | $T_1$ [ev] | Compound Name | Thickness [nm] | Voltage [V] | EQE [%] |
| Example 148 | BH3-3 | 2.23 | BD2 | 5 | BH3-1 | 2.11 | BD2 | 20 | 3.3 | 10.1 |
| Comparative Ex. 121 | BH3-3 | 2.23 | BD2 | 25 | — | — | — | — | 3.6 | 6.8 |
| Comparative Ex. 119 | BH3-1 | 2.11 | BD2 | 25 | — | — | — | — | 3.8 | 8.2 |

Example 149

The organic EL device of Example 149 was manufactured in the same manner as that of Example 146 except that the compound BH3-1 (first host material) in the first emitting layer and the compound BH3-2 in the second emitting layer were respectively replaced with the first compound and the second compound shown in Table 51.

Comparative Example 122

The organic EL device of Comparative Example 122 was manufactured in the same manner as that of Comparative Example 119 except that the compound BH3-1 (first host material) in the first emitting layer was replaced with the first compound shown in Table 51.

Comparative Example 123

The organic EL device of Comparative Example 123 was manufactured in the same manner as that of Comparative Example 120 except that the compound BH3-2 (first host material) in the second emitting layer was replaced with the second compound shown in Table 51.

TABLE 51

| | First Emitting Layer | | | | Second Emitting Layer | | | | | | |
|---|---|---|---|---|---|---|---|---|---|---|---|
| | First Compound | | Third | Film | Second Compound | | Fourth | Film | Drive | | |
| | Name | $T_1$ [ev] | Compound Name | Thickness [nm] | Name | $T_1$ [ev] | Compound Name | Thickness [nm] | Voltage [V] | EQE [%] | LT95 [h] |
| Example 149 | BH3-4 | 2.27 | BD2 | 5 | BH3-5 | 1.80 | BD2 | 20 | 3.2 | 10.5 | 165 |
| Comparative Ex. 122 | BH3-4 | 2.27 | BD2 | 25 | — | — | — | — | 3.4 | 6.2 | 103 |
| Comparative Ex. 123 | — | — | — | — | BH3-5 | 1.80 | BD2 | 25 | 4.0 | 8.8 | 140 |

Example 150

The organic EL device of Example 150 was manufactured in the same manner as that of Example 146 except that the compound BH3-1 (first host material) in the first emitting layer was replaced with the first compound shown in Table 52.

TABLE 52

| | First Emitting Layer | | | | Second Emitting Layer | | | | | |
|---|---|---|---|---|---|---|---|---|---|---|
| | First Compound | | Third | Film | Second Compound | | Fourth | Film | Drive | |
| | Name | $T_1$ [ev] | Compound Name | Thickness [nm] | Name | $T_1$ [ev] | Compound Name | Thickness [nm] | Voltage [V] | EQE [%] |
| Example 150 | BH3-4 | 2.27 | BD2 | 5 | BH3-2 | 2.08 | BD2 | 20 | 3.4 | 9.5 |
| Comparative Ex. 122 | BH3-4 | 2.27 | BD2 | 25 | — | — | — | — | 3.4 | 6.2 |
| Comparative Ex. 120 | — | — | — | — | BH3-2 | 2.08 | BD2 | 25 | 3.4 | 7.1 |

Example 151

The organic EL device of Example 151 was manufactured in the same manner as that of Example 146 except that the compound BH3-1 (first host material) in the first emitting layer and the compound BH3-2 in the second emitting layer were respectively replaced with the first compound and the second compound shown in Table 53.

TABLE 53

| | First Emitting Layer | | | | Second Emitting Layer | | | | | | |
|---|---|---|---|---|---|---|---|---|---|---|---|
| | First Compound | | Third | Film | Second Compound | | Fourth | Film | Drive | | |
| | Name | $T_1$ [ev] | Compound Name | Thickness [nm] | Name | $T_1$ [ev] | Compound Name | Thickness [nm] | Voltage [V] | EQE [%] | LT95 [h] |
| Example 151 | BH3-4 | 2.27 | BD2 | 5 | BH3-1 | 2.11 | BD2 | 20 | 3.3 | 9.9 | 180 |
| Comparative Ex. 122 | BH3-4 | 2.27 | BD2 | 25 | — | — | — | — | 3.4 | 6.2 | 103 |
| Comparative Ex. 119 | BH3-1 | 2.11 | BD2 | 25 | — | — | — | — | 3.8 | 8.2 | 92 |

Example 152

The organic EL device of Example 152 was manufactured in the same manner as that of Example 146 except that the compound BH3-1 (first host material) in the first emitting layer and the compound BH3-2 in the second emitting layer were respectively replaced with the first compound and the second compound shown in Table 54.

Comparative Example 124

The organic EL device of Comparative Example 124 was manufactured in the same manner as that of Comparative Example 119 except that the compound BH3-1 (first host material) in the first emitting layer was replaced with the first compound shown in Table 54.

TABLE 54

| | First Emitting Layer | | | | Second Emitting Layer | | | | | | |
|---|---|---|---|---|---|---|---|---|---|---|---|
| | First Compound | | Third | Film | Second Compound | | Fourth | Film | Drive | | |
| | Name | $T_1$ [ev] | Compound Name | Thickness [nm] | Name | $T_1$ [ev] | Compound Name | Thickness [nm] | Voltage [V] | EQE [%] | LT95 [h] |
| Example 152 | BH3-6 | 2.35 | BD2 | 5 | BH3-5 | 1.80 | BD2 | 20 | 3.5 | 10.0 | 175 |
| Comparative Ex. 124 | BH3-6 | 2.35 | BD2 | 25 | — | — | — | — | 4.2 | 4.5 | 21 |
| Comparative Ex. 123 | — | — | — | — | BH3-5 | 1.80 | BD2 | 25 | 4.0 | 8.8 | 140 |

Example 153

The organic EL device of Example 153 was manufactured in the same manner as that of Example 146 except that the compound BH3-1 (first host material) in the first emitting layer was replaced with the first compound shown in Table 55.

TABLE 55

| | First Emitting Layer | | | | Second Emitting Layer | | | | | | | |
|---|---|---|---|---|---|---|---|---|---|---|---|---|
| | First Compound | | Third | Film | Second Compound | | Fourth | Film | Drive | | | |
| | Name | T1 [ev] | Compound Name | Thickness [nm] | Name | T1 [ev] | Compound Name | Thickness [nm] | Voltage [V] | EQE [%] | LT95 [h] |
| Example 153 | BH3-6 | 2.35 | BD2 | 5 | BH3-2 | 2.08 | BD2 | 20 | 3.6 | 9.2 | 210 |
| Comparative Ex. 124 | BH3-6 | 2.35 | BD2 | 25 | — | — | — | — | 4.2 | 4.5 | 21 |
| Comparative Ex. 120 | — | — | — | — | BH3-2 | 2.08 | BD2 | 25 | 3.4 | 7.1 | 125 |

Example 154

The organic EL device of Example 154 was manufactured in the same manner as that of Example 146 except that the compound BH3-1 (first host material) in the first emitting layer and the compound BH3-2 in the second emitting layer were respectively replaced with the first compound and the second compound shown in Table 56.

TABLE 56

| | First Emitting Layer | | | | Second Emitting Layer | | | | | | | |
|---|---|---|---|---|---|---|---|---|---|---|---|---|
| | First Compound | | Third | Film | Second Compound | | Fourth | Film | Drive | | | |
| | Name | T1 [ev] | Compound Name | Thickness [nm] | Name | T1 [ev] | Compound Name | Thickness [nm] | Voltage [V] | EQE [%] | LT95 [h] |
| Example 154 | BH3-6 | 2.35 | BD2 | 5 | BH3-1 | 2.11 | BD2 | 20 | 3.6 | 9.8 | 190 |
| Comparative Ex. 124 | BH3-6 | 2.35 | BD2 | 25 | — | — | — | — | 4.2 | 4.5 | 21 |
| Comparative Ex. 119 | BH3-1 | 2.11 | BD2 | 25 | — | — | — | — | 3.8 | 8.2 | 92 |

Example 155

The organic EL device of Example 155 was manufactured in the same manner as that of Example 146 except that the compound BH3-1 (first host material) in the first emitting layer and the compound BH3-2 in the second emitting layer were respectively replaced with the first compound and the second compound shown in Table 57.

Comparative Example 125

The organic EL device of Comparative Example 125 was manufactured in the same manner as that of Comparative Example 120 except that the compound BH3-2 (second host material) in the second emitting layer was replaced with the second compound shown in Table 57.

TABLE 57

| | First Emitting Layer | | | | Second Emitting Layer | | | | | | | | |
|---|---|---|---|---|---|---|---|---|---|---|---|---|---|
| | First Compound | | Third | Film | Second Compound | | Fourth | Film | Drive | | | | |
| | Name | T1 [ev] | Compound Name | Thickness [nm] | Name | T1 [ev] | Compound Name | Thickness [nm] | Voltage [V] | CIE-x | CIE-y | λp [nm] | EQE [%] |
| Example 155 | BH3-7 | 2.20 | BD1 | 5 | BH2 | 1.87 | BD1 | 20 | 3.48 | 0.135 | 0.104 | 460 | 10.4 |
| Comparative Ex. 125 | — | — | — | — | BH2 | 1.87 | BD1 | 25 | 3.61 | 0.134 | 0.104 | 460 | 9.9 |

Manufacture 20 of Organic EL Device

Organic EL devices were manufactured and evaluated as follows.

Example 156

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT1 and the compound HA2 were co-deposited on a surface provided with the transparent electrode line to cover the transparent electrode, thereby forming a 5-nm-thick hole injecting layer (HI). The ratios of the compound HT1 and the compound HA2 in the hole injecting layer were 97 mass % and 3 mass %, respectively.

After the formation of the hole injecting layer, the compound HT1 was vapor-deposited to form an 80-nm-thick first hole transporting layer (HT).

Subsequent to the formation of the first hole transporting layer, a compound HT9 was vapor-deposited to form a 10-nm-thick second hole transporting layer (also referred to as an electron blocking layer (EBL)).

A compound BH1-84 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

A compound BH2-3 (second host material (BH)) and the compound BD2 (dopant material (BD)) were co-deposited on the first emitting layer so that a ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal aluminum (Al) was vapor-deposited on the electron injecting layer to form an 80-nm-thick cathode.

A device arrangement of the organic EL device in Example 156 is roughly shown as follows.

ITO(130)/HT1: HA2(5.97%:3%)/HT1(80)/HT9(10)/BH1-84:BD2(5.98%:2%)/BH2-3:BD2(20.98%:2%)/ET7(10)/ET2(15)/LiF(1)/Al(80)

The numerals in parentheses represent a film thickness (unit: nm).

The numerals (97%:3%) represented by percentage in the same parentheses indicate a ratio (mass %) between the compound HT1 and the compound HA2 in the hole injecting layer. The numerals (98%:2%) represented by percentage in the same parentheses indicate a ratio (mass %) between the host material (compound BH1-84 or compound BH2-3) and the compound BD2 in the first emitting layer or the second emitting layer. Similar notations apply to the description below.

Examples 157 to 160

The organic EL devices of Examples 157 and 158 were manufactured in the same manner as that of Example 156 except that the compound BH1-84 (first host material) in the first emitting layer was replaced with the second compounds shown in Table 58.

The organic EL device of Example 159 was manufactured in the same manner as that of Example 156 except that the compound BH2-3 (second host material) in the second emitting layer was replaced with the second compound shown in Table 58.

The organic EL device of Example 160 was manufactured in the same manner as that of Example 159 except that the compound BH1-84 (first host material) in the first emitting layer was replaced with the first compound shown in Table 58.

Comparative Examples 126 to 128

The organic EL devices of Comparative Examples 126 to 128 were manufactured in the same manner as that of Example 156 except that a 25-nm-thick first emitting layer was formed as the emitting layer, the first electron transporting layer was formed on the first emitting layer without forming the second emitting layer, and the compound BH1-84 (first host material) in the first emitting layer was replaced with the first compound shown in Table 58.

Comparative Example 129

The organic EL device of Comparative Example 129 was manufactured in the same manner as that of Example 156 except that a 25-nm-thick second emitting layer was formed as the emitting layer on the second hole transporting layer without forming the first emitting layer as shown in Table 58.

Comparative Example 130

The organic EL device of Comparative Example 130 was manufactured in the same manner as that of Example 160 except that a 25-nm-thick first emitting layer was formed as the emitting layer, and the first electron transporting layer was formed on the first emitting layer without forming the second emitting layer as shown in Table 58.

Comparative Example 131

The organic EL device of Comparative Example 131 was manufactured in the same manner as that of Example 160 except that a 25-nm-thick second emitting layer was formed as the emitting layer on the second hole transporting layer without forming the first emitting layer as shown in Table 58.

TABLE 58

| | First Emitting Layer | | | | | Second Emitting Layer | | | | | | |
|---|---|---|---|---|---|---|---|---|---|---|---|---|
| | First Compound | | Third Compound | | Film | Second Compound | | Fourth Compound | | Film | | |
| | Name | $T_1$ [ev] | Name | $T_1$ [ev] | Thickness [nm] | Name | $T_1$ [ev] | Name | $T_1$ [ev] | Thickness [nm] | EQE [%] | LT95 [hr] |
| Example 156 | BH1-84 | 2.09 | BD2 | 2.60 | 5 | BH2-3 | 1.87 | BD2 | 2.60 | 20 | 9.6 | 320 |
| Example 157 | BH1-85 | 2.09 | BD2 | 2.60 | 5 | BH2-3 | 1.87 | BD2 | 2.60 | 20 | 9.6 | 250 |
| Example 158 | BH1-86 | 2.09 | BD2 | 2.60 | 5 | BH2-3 | 1.87 | BD2 | 2.60 | 20 | 9.6 | 160 |
| Example 159 | BH1-84 | 2.09 | BD2 | 2.60 | 5 | BH2 | 1.87 | BD2 | 2.60 | 20 | 9.7 | 255 |
| Example 160 | BH1-87 | 2.09 | BD2 | 2.60 | 5 | BH2 | 1.87 | BD2 | 2.60 | 20 | 9.8 | 150 |
| Comparative Ex. 126 | BH1-84 | 2.09 | BD2 | 2.60 | 25 | — | — | — | — | — | 7.2 | 80 |
| Comparative Ex. 127 | BH1-85 | 2.09 | BD2 | 2.60 | 25 | — | — | — | — | — | 7.2 | 75 |
| Comparative Ex. 128 | BH1-86 | 2.09 | BD2 | 2.60 | 25 | — | — | — | — | — | 7.2 | 75 |
| Comparative Ex. 129 | — | — | — | — | — | BH2-3 | 1.87 | BD2 | 2.60 | 25 | 8.5 | 145 |
| Comparative Ex. 130 | BH1-87 | 2.09 | BD2 | 2.60 | 25 | — | — | — | — | — | 7.3 | 75 |
| Comparative Ex. 131 | — | — | — | — | — | BH2 | 1.87 | BD2 | 2.60 | 25 | 8.8 | 78 |

Examples 161 to 166

The organic EL devices of Examples 161 to 166 were manufactured in the same manner as that of Example 156 except that at least one of the compound BH1-84 in the first emitting layer or the compound BH2-3 in the second emitting layer was replaced with the compounds shown in Table 59.

Comparative Example 132

The organic EL device of Comparative Example 132 was manufactured in the same manner as that of Example 156 except that a 25-nm-thick first emitting layer was formed as the emitting layer, the first electron transporting layer was formed on the first emitting layer without forming the second emitting layer, and the compound BH1-84 in the first emitting layer was replaced with the first compound shown in Table 59, as shown in Table 59.

Comparative Example 133

The organic EL device of Comparative Example 133 was manufactured in the same manner as that of Comparative Example 130 except that the compound BH1-87 in the first emitting layer was replaced with the first compound shown in Table 59, as shown in Table 59.

TABLE 59

| | First Emitting Layer | | | | | Second Emitting Layer | | | | | | |
|---|---|---|---|---|---|---|---|---|---|---|---|---|
| | First Compound | | Third Compound | | Film | Second Compound | | Fourth Compound | | Film | | |
| | Name | $T_1$ [ev] | Name | $T_1$ [ev] | Thickness [nm] | Name | $T_1$ [ev] | Name | $T_1$ [ev] | Thickness [nm] | EQE [%] | LT95 [hr] |
| Example 161 | BH4-3 | 2.10 | BD2 | 2.60 | 5 | BH2-3 | 1.87 | BD2 | 2.60 | 20 | 9.8 | 290 |
| Example 162 | BH4-3 | 2.10 | BD2 | 2.60 | 5 | BH2 | 1.87 | BD2 | 2.60 | 20 | 9.9 | 230 |
| Example 163 | BH4-3 | 2.10 | BD2 | 2.60 | 5 | BH1-84 | 2.09 | BD2 | 2.60 | 20 | 9.0 | 250 |
| Example 164 | BH4-3 | 2.10 | BD2 | 2.60 | 5 | BH1-87 | 2.09 | BD2 | 2.60 | 20 | 9.2 | 240 |
| Example 165 | BH4-4 | 2.10 | BD2 | 2.60 | 5 | BH2 | 1.87 | BD2 | 2.60 | 20 | 10.0 | 140 |
| Example 166 | BH4-4 | 2.10 | BD2 | 2.60 | 5 | BH1-87 | 2.09 | BD2 | 2.60 | 20 | 9.5 | 140 |
| Comparative Ex. 132 | BH4-3 | 2.10 | BD2 | 2.60 | 25 | — | — | — | — | — | 8.4 | 110 |
| Comparative Ex. 126 | BH1-84 | 2.09 | BD2 | 2.60 | 25 | — | — | — | — | — | 7.2 | 80 |
| Comparative Ex. 129 | — | — | — | — | — | BH2-3 | 1.87 | BD2 | 2.60 | 25 | 8.5 | 145 |
| Comparative Ex. 133 | BH4-4 | 2.10 | BD2 | 2.60 | 25 | — | — | — | — | — | 8.5 | 60 |
| Comparative Ex. 130 | BH1-87 | 2.09 | BD2 | 2.60 | 25 | — | — | — | — | — | 7.3 | 75 |
| Comparative Ex. 131 | — | — | — | — | — | BH2 | 1.87 | BD2 | 2.60 | 25 | 8.8 | 78 |

Examples 167 to 172

The organic EL devices of Examples 167 to 172 were manufactured in the same manner as that of Example 156 except that at least one of the compound BH1-84 in the first emitting layer or the compound BH2-3 in the second emitting layer was replaced with the compound shown in Table 60.

Comparative Examples 134 and 135

The organic EL devices of Comparative Example 134 and 135 were manufactured in the same manner as that of Example 156 except that a 25-nm-thick first emitting layer was formed as the emitting layer, the first electron transporting layer was formed on the first emitting layer without forming the second emitting layer, and the compound BH1-84 in the first emitting layer was replaced with the first compound, as shown in Table 60.

After the formation of the first hole transporting layer, a compound HT11 was vapor-deposited to form a 5-nm-thick second hole transporting layer (also referred to as an electron blocking layer (EBL)).

A compound BH4-5 (first host material (BH)) and the compound BD2 (dopant material (BD)) were co-deposited on the second hole transporting layer so that a ratio of the compound BD2 accounted for 2 mass %, thereby forming a 5-nm-thick first emitting layer.

A compound BH3-5 (second host material (BH)) and the compound BD2 (dopant material (BD)) were co-deposited on the first emitting layer so that a ratio of the compound BD2 accounted for 2 mass %, thereby forming a 15-nm-thick second emitting layer.

The compound ET9 was vapor-deposited on the second emitting layer to form a 5-nm-thick first electron transporting layer (also referred to as a hole blocking layer (HBL)).

TABLE 60

| | First Emitting Layer | | | | | Second Emitting Layer | | | | | | |
|---|---|---|---|---|---|---|---|---|---|---|---|---|
| | First Compound | | Third Compound | | Film | Second Compound | | Fourth Compound | | Film | | |
| | Name | $T_1$ [ev] | Name | $T_1$ [ev] | Thickness [nm] | Name | $T_1$ [ev] | Name | $T_1$ [ev] | Thickness [nm] | EQE [%] | LT95 [hr] |
| Example 167 | BH4-1 | 2.25 | BD2 | 2.60 | 5 | BH2-3 | 1.87 | BD2 | 2.60 | 20 | 9.2 | 350 |
| Example 168 | BH4-1 | 2.25 | BD2 | 2.60 | 5 | BH2 | 1.87 | BD2 | 2.60 | 20 | 9.5 | 290 |
| Example 169 | BH4-1 | 2.25 | BD2 | 2.60 | 5 | BH4-3 | 2.10 | BD2 | 2.60 | 20 | 9.5 | 270 |
| Example 170 | BH4-1 | 2.25 | BD2 | 2.60 | 5 | BH4-4 | 2.10 | BD2 | 2.60 | 20 | 9.7 | 230 |
| Example 171 | BH4-2 | 2.25 | BD2 | 2.60 | 5 | BH2 | 1.87 | BD2 | 2.60 | 20 | 9.9 | 200 |
| Example 172 | BH4-2 | 2.25 | BD2 | 2.60 | 5 | BH4-4 | 2.10 | BD2 | 2.60 | 20 | 10.0 | 180 |
| Comparative Ex. 134 | BH4-1 | 2.25 | BD2 | 2.60 | 25 | — | — | — | — | — | 8.0 | 157 |
| Comparative Ex. 132 | BH4-3 | 2.10 | BD2 | 2.60 | 25 | — | — | — | — | — | 8.4 | 110 |
| Comparative Ex. 129 | — | — | — | — | — | BH2-3 | 1.87 | BD2 | 2.60 | 25 | 8.5 | 145 |
| Comparative Ex. 135 | BH4-2 | 2.25 | BD2 | 2.60 | 25 | — | — | — | — | — | 8.2 | 80 |
| Comparative Ex. 133 | BH4-4 | 2.10 | BD2 | 2.60 | 25 | — | — | — | — | — | 8.5 | 60 |
| Comparative Ex. 131 | — | — | — | — | — | BH2 | 1.87 | BD2 | 2.60 | 25 | 8.8 | 78 |

Manufacture 21 of Organic EL Device

Organic EL devices were manufactured and evaluated as follows.

Example 173

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HA3 was vapor-deposited on a surface provided with the transparent electrode line to cover the transparent electrode, thereby forming a 10-nm-thick hole injecting layer (HI).

After the formation of the hole injecting layer, a compound HT10 was vapor-deposited to form a 90-nm-thick first hole transporting layer (HT).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal (Al) was vapor-deposited on the electron injecting layer to form a 50-nm-thick cathode.

A device arrangement of the organic EL device in Example 173 is roughly shown as follows.

ITO(130)/HA3(10)/HT10(90)/HT11(5)/BH4-5:BD2 (5.98%:2%)/BH3-5:BD2(15.98%:2%)/ET9(5)/ET2(20)/LiF (1)/Al(50)

The numerals in parentheses represent a film thickness (unit: nm).

The numerals (98%:2%) represented by percentage in the same parentheses indicate a ratio (mass %) between the host material (BH4-5) and the compound BD2 in the first emitting layer. The numerals (98%:2%) represented by percentage in the same parentheses indicate a ratio (mass %) between the host material (compound BH3-5) and the compound BD2 in the second emitting layer.

Example 174

The organic EL device of Example 174 was manufactured in the same manner as that of Example 173 except that the compound BH4-5 (first host material) in the first emitting layer was replaced with the first compound shown in Table 61 and the compounds BD2 in the first emitting layer and the second emitting layer were respectively replaced with the third compound and the fourth compound shown in Table 61.

Reference Example 1

An organic EL device of Reference Example 1 was manufactured in the same manner as that of Example 173 except that the compound BH4-5 (first host material) in the first emitting layer was replaced with the first compound shown in Table 61.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 manufactured by Hitachi High-Technologies Corporation was used.

Singlet Energy $S_1$

A toluene solution of a measurement target compound at a concentration of 10 μmol/L was prepared and put in a quartz cell. An absorption spectrum (ordinate axis: absorption intensity, abscissa axis: wavelength) of the thus-obtained sample was measured at a normal temperature (300K). A tangent was drawn to the fall of the absorption spectrum close to the long-wavelength region, and a wavelength value $\lambda_{edge}$ (nm) at an intersection of the tangent and the abscissa axis was assigned to a conversion equation (F2) below to calculate the singlet energy.

TABLE 61

| | First Emitting Layer | | | | | Second Emitting Layer | | | | | | |
|---|---|---|---|---|---|---|---|---|---|---|---|---|
| | First Compound | | Third Compound | | Film | Second Compound | | Fourth Compound | | Film | | |
| | Name | $T_1$ [ev] | Name | $T_1$ [ev] | Thickness [nm] | Name | $T_1$ [ev] | Name | $T_1$ [ev] | Thickness [nm] | EQE [%] | LT90 [hr] |
| Example 173 | BH4-5 | 2.02 | BD2 | 2.60 | 5 | BH3-5 | 1.80 | BD2 | 2.60 | 15 | 10.4 | 254 |
| Example 174 | BH1-10 | 2.09 | BD4 | 2.45 | 5 | BH3-5 | 1.80 | BD4 | 2.45 | 15 | 10.6 | 255 |
| Reference Ex. 1 | BH1-10 | 2.09 | BD2 | 2.60 | 5 | BH3-5 | 1.80 | BD2 | 2.60 | 15 | 10.5 | 214 |

Evaluation Method of Compounds

Triplet Energy $T_1$

A measurement target compound was dissolved in EPA (diethylether: isopentane:ethanol=5:5:2 in volume ratio) at a concentration of 10 μmol/L, and the obtained solution was encapsulated in a quartz cell to provide a measurement sample. A phosphorescence spectrum (ordinate axis: phosphorescent luminous intensity, abscissa axis: wavelength) of the measurement sample was measured at a low temperature (77K). A tangent was drawn to the rise of the phosphorescence spectrum close to the short-wavelength region. An energy amount was calculated by a conversion equation (F1) below on a basis of a wavelength value $\lambda_{edge}$ [nm] at an intersection of the tangent and the abscissa axis. The calculated energy amount was defined as triplet energy $T_1$. It should be noted that the triplet energy $T_1$ has an error of about plus or minus 0.02 eV depending on measurement conditions.

$$T_1[\text{eV}]=1239.85/\lambda_{edge} \qquad \text{Conversion Equation (F1):}$$

The tangent to the rise of the phosphorescence spectrum close to the short-wavelength region is drawn as follows. While moving on a curve of the phosphorescence spectrum from the short-wavelength region to the local maximum spectral value closest to the short-wavelength region among the local maximum spectral values, a tangent is checked at each point on the curve toward the long-wavelength region of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

$$S_1[\text{eV}]=1239.85/\lambda_{edge} \qquad \text{Conversion Equation (F2):}$$

A spectrophotometer (U3310 manufactured by Hitachi, Ltd.) was used for measuring absorption spectrum.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve fell (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

Measurement values of a singlet energy $S_1$ and a triplet energy $T_1$ of each of the compounds BH1, BH2, BH2-3 and BH4 are shown in Tables.

A singlet energy Si of the compound BD1 was 2.73 eV.

A triplet energy $T_1$ of the compound BD1 was 2.29 eV.

Measurement values of other compounds are shown in Tables.

Stokes Shift (SS) (nm)

A measurement target compound was dissolved in toluene at a concentration of $2.0\times10^{-5}$ mol/L to prepare a measurement sample. The measurement sample was put into a quartz cell and was irradiated with continuous light falling within an ultraviolet-to-visible region at a room temperature (300K) to measure an absorption spectrum (ordinate axis: absorbance, abscissa axis: wavelength). A spectrophotometer U-3900/3900H manufactured by Hitachi High-Tech Science Corporation was used for the absorption spectrum measurement. Moreover, a measurement target compound was dissolved in toluene at a concentration of $4.9\times10^{-6}$ mol/L to prepare a measurement sample. The measurement sample was put into a quartz cell and was irradiated with excited light at a room temperature (300K) to measure fluorescence spectrum (ordinate axis: fluorescence intensity, abscissa axis: wavelength). A spectrophotofluorometer F-7000 manufactured by Hitachi High-Tech Science Corporation was used for the fluorescence spectrum measurement.

A difference between an absorption local-maximum wavelength and a fluorescence local-maximum wavelength was calculated from the absorption spectrum and the fluorescence spectrum to obtain a Stokes shift (SS). A unit of the Stokes shift (SS) was denoted by nm.

A Stokes shift (SS) of the compound BD1 was 14 nm.

Preparation of Toluene Solution

The compound BD1 was dissolved in toluene at a concentration of $4.9\times10^{-6}$ mol/L to prepare a toluene solution of the compound BD1. A toluene solution of the compound BD2 and a toluene solution of the compound BD3 were prepared in the same manner.

Measurement of Fluorescence Main Peak Wavelength (FL-Peak)

Fluorescence main peak wavelength of the toluene solution of the compound BD1 excited at 390 nm was measured using a fluorescence spectrometer (spectrophotofluorometer F-7000 (manufactured by Hitachi High-Tech Science Corporation)). The fluorescence main peak wavelengths of the toluene solutions of the compound BD2 and the compound BD3 were measured in the same manner as the compound BD1.

The fluorescence main peak wavelength of the compound BD1 was 453 nm.

The fluorescence main peak wavelength of the compound BD2 was 455 nm.

The fluorescence main peak wavelength of the compound BD3 was 451 nm.

The invention claimed is:

1. An organic electroluminescence device comprising:

a first emitting layer and a second emitting layer, wherein the first emitting layer comprises a first host material and a first dopant material, the second emitting layer comprises a second host material and a second dopant material, the first host material and the second host material are mutually different, the first dopant material is a compound that emits fluorescence having a main peak wavelength of 500 nm or less, the second dopant material is a compound that emits fluorescence having a main peak wavelength of 500 nm or less, the first dopant material is the same as or different from the second dopant material, and a triplet energy $T_1$(H1) of the first host material and a triplet energy $T_1$(H2) of the second host material satisfy a relationship of a numerical formula (Numerical Formula 1) below, and wherein (i) the triplet energy $T_1$(H1) of the first host material and a triplet energy $T_1$(D1) of the first dopant material satisfy a relationship of a numerical formula (Numerical Formula 2A) below, (ii) a triplet energy $T_1$(D2) of the second dopant material and the triplet energy $T_1$(H2) of the second host material satisfy a relationship of a numerical formula (Numerical Formula 3) below, or (iii) both relationships defined by the numerical formula (Numerical Formula 2A) and the numerical formula (Numerical Formula 3) are satisfied, $$T_1(H1)>T_1(H2) \quad \text{(Numerical Formula 1)},$$

$$T_1(D1)>T_1(H1) \quad \text{(Numerical Formula 2A)}$$

$$T_1(D2)>T_1(H2) \quad \text{(Numerical Formula 3)}.$$

2. The organic electroluminescence device according to claim 1, wherein the triplet energy $T_1$(H1) of the first host material and the triplet energy $T_1$(D1) of the first dopant material satisfy the relationship of the numerical formula (Numerical Formula 2A).

3. The organic electroluminescence device according to claim 1, wherein the triplet energy $T_1$(D2) of the second dopant material and the triplet energy $T_1$(H2) of the second host material satisfy the relationship of the numerical formula (Numerical Formula 3).

4. The organic electroluminescence device according to claim 3, wherein the second dopant material comprises a Stokes shift exceeding 7 nm.

5. The organic electroluminescence device according to claim 1, further comprising:

an anode and a cathode, wherein the first emitting layer is provided between the anode and the cathode, and the second emitting layer is provided between the first emitting layer and the cathode.

6. The organic electroluminescence device according to claim 1, wherein the triplet energy $T_1$(H1) of the first host material and the triplet energy $T_1$(H2) of the second host material satisfy a relationship of a numerical formula (Numerical Formula 5) below, $$T_1(H1)-T_1(H2)>0.03\ \text{eV} \quad \text{(Numerical Formula 5)}.$$

7. The organic electroluminescence device according to claim 1, wherein the first emitting layer comprises a film thickness in a range from 3 nm to 15 nm.

8. The organic electroluminescence device according to claim 1, wherein the second emitting layer comprises a film thickness in a range from 5 nm to 20 nm.

9. The organic electroluminescence device according to claim 1, wherein the first emitting layer and the second emitting layer are in direct contact with each other.

10. The organic electroluminescence device according to claim 1, wherein a triplet energy $T_1$(DX) of one of the first dopant material and the second dopant material, the triplet energy $T_1(H1)$ of the first host material, and the triplet energy $T_1(H2)$ of the second host material satisfy a relationship of a numerical formula (Numerical Formula 10) below, $$2.6\ eV > T_1(DX) > T_1(H1) > T_1(H2) \quad \text{(Numerical Formula 10)}.$$

11. The organic electroluminescence device according to claim 1, wherein a triplet energy $T_1(DX)$ of one of the first dopant material and the second dopant material, and the triplet energy $T_1(H1)$ of the first host material satisfy a relationship of a numerical formula (Numerical Formula 11) below, $$0\ eV < T_1(DX) - T_1(H1) < 0.6\ eV \quad \text{(Numerical Formula 11)}.$$

12. The organic electroluminescence device according to claim 1, wherein the triplet energy $T_1(H1)$ of the first host material satisfies a relationship of a numerical formula (Numerical Formula 12) below, $$T_1(H1) > 2.0\ eV \quad \text{(Numerical Formula 12)}.$$

13. The organic electroluminescence device according to claim 1, wherein the triplet energy $T_1(H1)$ of the first host material satisfies a numerical formula (Numerical Formula 12A) below, $$T_1(H1) > 2.10\ eV \quad \text{(Numerical Formula 12A)}.$$

14. The organic electroluminescence device according to claim 1, wherein the triplet energy $T_1(H1)$ of the first host material satisfies a numerical formula (Numerical Formula 12C) below, $$2.08\ eV > T_1(H1) > 1.87\ eV \quad \text{(Numerical Formula 12C)}.$$

15. The organic electroluminescence device according to claim 1, wherein the triplet energy $T_1(D1)$ of the first dopant material satisfies a relationship of a numerical formula (Numerical Formula 14A) below, $$2.60\ eV > T_1(D1) \quad \text{(Numerical Formula 14A)}.$$

16. The organic electroluminescence device according to claim 1, wherein the triplet energy $T_1(D2)$ of the second dopant material satisfies a relationship of a numerical formula (Numerical Formula 14C) below, $$2.60\ eV > T_1(D2) \quad \text{(Numerical Formula 14C)}.$$

17. The organic electroluminescence device according to claim 1, wherein the triplet energy $T_1(H2)$ of the second host material satisfies a numerical formula (Numerical Formula 13) below, $$T_1(H2) \geq 1.9\ eV \quad \text{(Numerical Formula 13)}.$$

18. The organic electroluminescence device according to claim 1, wherein the first host material comprises, in a molecule, a linking structure comprising a benzene ring and a naphthalene ring linked to each other with a single bond, the benzene ring and the naphthalene ring in the linking structure are each independently fused or not fused with a further monocyclic ring or fused ring, and the benzene ring and the naphthalene ring in the linking structure are further linked to each other by cross-linking at at least one site other than the single bond.

19. The organic electroluminescence device according to claim 18, wherein the cross-linking comprises a double bond.

20. The organic electroluminescence device according to claim 1, wherein the first host material comprises, in a molecule, a biphenyl structure in which a first benzene ring and a second benzene ring are linked to each other with a single bond, and the first benzene ring and the second benzene ring in the biphenyl structure are further linked to each other by cross-linking at at least one site other than the single bond.

21. The organic electroluminescence device according to claim 20, wherein the first benzene ring and the second benzene ring in the biphenyl structure are further linked to each other by the cross-linking at one site other than the single bond.

22. The organic electroluminescence device according to claim 20, wherein the cross-linking comprises a double bond.

23. The organic electroluminescence device according to claim 20, wherein the first benzene ring and the second benzene ring in the biphenyl structure are further linked to each other by the cross-linking at two sites other than the single bond, and the cross-linking does not comprise a double bond.

* * * * *